US012558341B2

(12) United States Patent
Kotian et al.

(10) Patent No.: US 12,558,341 B2
(45) Date of Patent: Feb. 24, 2026

(54) ORAL COMPLEMENT FACTOR D INHIBITORS

(71) Applicant: BioCryst Pharmaceuticals, Inc., Durham, NC (US)

(72) Inventors: Pravin L. Kotian, Hoover, AL (US); Yarlagadda S. Babu, Birmingham, AL (US); Weihe Zhang, Vestavia Hills, AL (US); Peng-Cheng Lu, Vestavia Hills, AL (US); Andrew E. Spaulding, Hoover, AL (US); Wei Lv, Hoover, AL (US); Zhao Dang, Vestavia Hills, AL (US); Krishnan Raman, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 486 days.

(21) Appl. No.: 17/767,796

(22) PCT Filed: Oct. 9, 2020

(86) PCT No.: PCT/US2020/054992

§ 371 (c)(1),
(2) Date: Apr. 8, 2022

(87) PCT Pub. No.: WO2021/072198

PCT Pub. Date: Apr. 15, 2021

(65) Prior Publication Data

US 2025/0186391 A1 Jun. 12, 2025

Related U.S. Application Data

(60) Provisional application No. 62/912,929, filed on Oct. 9, 2019.

(51) Int. Cl.

| | |
|---|---|
| ***A61K 31/343*** | (2006.01) |
| ***A61K 31/381*** | (2006.01) |
| ***A61K 31/404*** | (2006.01) |
| ***A61K 31/4155*** | (2006.01) |
| ***A61K 31/416*** | (2006.01) |
| ***A61K 31/423*** | (2006.01) |
| ***A61K 31/437*** | (2006.01) |
| ***A61K 31/443*** | (2006.01) |

(Continued)

(52) U.S. Cl.

CPC .......... *A61K 31/343* (2013.01); *A61K 31/381* (2013.01); *A61K 31/404* (2013.01); *A61K 31/4155* (2013.01); *A61K 31/416* (2013.01); *A61K 31/423* (2013.01); *A61K 31/437* (2013.01); *A61K 31/443* (2013.01); *A61K 31/496* (2013.01); *A61K 31/5377* (2013.01); *C07D 209/42* (2013.01);

(Continued)

(58) Field of Classification Search

CPC .. A61K 31/343; A61K 31/381; A61K 31/404; A61K 31/4155; A61K 31/416; A61K 31/423; A61K 31/437; A61K 31/443; A61K 31/496; A61K 31/5377; A61K 31/506; C07D 209/42; C07D 231/56; C07D 261/20; C07D 275/04; C07D 307/81; C07D 333/58; C07D 405/04; C07D 405/06; C07D 407/12; C07D 471/04; C07D 493/04; C07D 209/12; C07D 273/04; C07D 333/56; C07D 405/12; C07D 417/12; C07D 491/048; C07D 495/04; C07D 307/80; C07D 401/04; C07D 405/10; C07D 407/14; C07C 217/48; A61P 7/00; A61P 9/00; A61P 13/12; A61P 25/00; A61P 25/28; A61P 27/02

See application file for complete search history.

(56) References Cited

U.S. PATENT DOCUMENTS 4,970,215 A 11/1990 Mohrs et al.
6,277,877 B1 8/2001 Hoover et al.

(Continued)

FOREIGN PATENT DOCUMENTS

AU 2012/203083 A1 6/2012
JP 2015-178457 A 10/2015

(Continued)

OTHER PUBLICATIONS

International Search Report and Written Opinion for International Application No. PCT/US20/54992 dated Feb. 22, 2021.

(Continued)

*Primary Examiner* — Joseph K Mckane
*Assistant Examiner* — Meghan C Heasley
(74) *Attorney, Agent, or Firm* — Foley Hoag LLP; Dana M. Gordon; Laura A. Wzorek

(57) ABSTRACT

Disclosed are compounds of formula (I), and pharmaceutically acceptable salts thereof, which are inhibitors of the complement system. Also provided are pharmaceutical compositions comprising such a compound, and methods of using the compounds and compositions in the treatment or prevention of a disease or condition characterized by aberrant complement system activity.

(I)

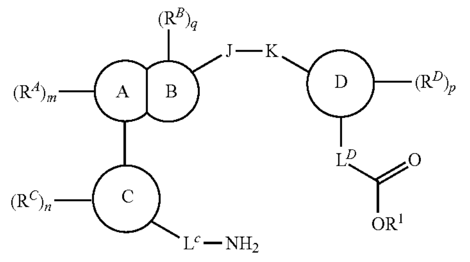

28 Claims, No Drawings

(51) Int. Cl.

| | |
|---|---|
| ***A61K 31/496*** | (2006.01) |
| ***A61K 31/5377*** | (2006.01) |
| ***C07D 209/42*** | (2006.01) |
| ***C07D 231/56*** | (2006.01) |
| ***C07D 261/20*** | (2006.01) |
| ***C07D 275/04*** | (2006.01) |
| ***C07D 307/81*** | (2006.01) |
| ***C07D 333/58*** | (2006.01) |
| ***C07D 405/04*** | (2006.01) |
| ***C07D 405/06*** | (2006.01) |
| ***C07D 407/12*** | (2006.01) |
| ***C07D 471/04*** | (2006.01) |
| ***C07D 493/04*** | (2006.01) |

(52) U.S. Cl.

CPC ......... *C07D 231/56* (2013.01); *C07D 261/20* (2013.01); *C07D 275/04* (2013.01); *C07D 307/81* (2013.01); *C07D 333/58* (2013.01); *C07D 405/04* (2013.01); *C07D 405/06* (2013.01); *C07D 407/12* (2013.01); *C07D 471/04* (2013.01); *C07D 493/04* (2013.01)

(56) References Cited

U.S. PATENT DOCUMENTS

| | | | |
|---|---|---|---|
| 2011/0212940 A1 | 9/2011 | Burli et al. | |
| 2011/0269766 A1 | 11/2011 | Luo et al. | |
| 2012/0022057 A1 | 1/2012 | Zhou et al. | |
| 2013/0225524 A1* | 8/2013 | Chai .................... | A61K 31/506 544/123 |
| 2016/0145247 A1 | 5/2016 | Belanger et al. | |

FOREIGN PATENT DOCUMENTS

| | | |
|---|---|---|
| WO | WO-2008/011560 A2 | 1/2008 |
| WO | WO-2008/021038 A2 | 2/2008 |
| WO | WO-2009/155551 A1 | 12/2009 |
| WO | WO-2010/024903 A1 | 3/2010 |
| WO | WO-2010/080996 A1 | 7/2010 |
| WO | WO-2016/088082 A1 | 6/2016 |
| WO | WO-2017/136395 A1 | 8/2017 |
| WO | WO-2019/057946 A1 | 3/2019 |
| WO | WO-2019/195720 A1 | 10/2019 |
| WO | WO-2021/021909 A1 | 2/2021 |
| WO | WO-2021/072156 A1 | 4/2021 |
| WO | WO-2021/072198 A1 | 4/2021 |

OTHER PUBLICATIONS

Invitation to Pay Additional Fees for International Application No. PCT/US20/54992 dated Dec. 15, 2020.

Zhou et al., "Structure—Activity Relationship Studies of Indole-Based Compounds as Small Molecule HIV-1 Fusion Inhibitors Targeting Glycoprotein 41" Journal of Medicinal Chemistry" vol. 57, p. 5270-5281 (2014).

Extended European Search Report for EP Application No. 20874925.9 dated Feb. 9, 2024.

* cited by examiner

ORAL COMPLEMENT FACTOR D INHIBITORS

RELATED APPLICATIONS

This application is a U.S. National Stage Application of International Application No. PCT/US20/54992, filed Oct. 9, 2020; which claims the benefit of priority to U.S. Provisional Patent Application Ser. No. 62/912,929, filed Oct. 9, 2019.

BACKGROUND OF THE INVENTION

The complement system is a branch of an organism's immune system that enhances the ability of antibodies and phagocytic cells to destroy and remove foreign particles (e.g., pathogens) from the organism. The complement system comprises a set of plasma proteins that act together to attack extracellular forms of pathogens and induce a series of inflammatory responses to help fight infection. Complement activation can occur through several pathways. For example, complement activation can occur spontaneously in response to certain pathogens or by antibody binding to a pathogen. When complement proteins are activated a cascade is triggered by which one complement protein induces the activation of the next protein in the sequence. The activation of a small number of complement proteins at the start of the pathway is hugely amplified by each successive enzymatic reaction, resulting in the rapid generation of a disproportionately large complement response. (Marrides, S. *Pharmacological Reviews* 1998, Vol. 50, pages 59-88). In healthy organisms there are regulatory mechanisms to prevent uncontrolled complement activation.

When activated, complement proteins can bind to a pathogen, opsonizing them for engulfment by phagocytes bearing receptors for complement. Then, small fragments of some complement proteins act as chemoattractants to recruit more phagocytes to the site of complement activation, and also to activate these phagocytes. Next, the complement proteins create holes or pores in the invading organisms, leading to their destruction. While complement plays an important role in protecting the body from foreign organisms, it can also destroy healthy cells and tissue. The inappropriate activation of complement is implicated in a long list of disease pathologies (Morgan, B. *Eur J Clin Invest* 1994, Vol. 24, pages 219-228) affecting the immune, renal, cardiovascular, and neurological systems.

Accordingly, there exists a need to develop further complement inhibitors, which have therapeutic potential in the treatment of numerous disorders.

SUMMARY OF THE INVENTION

In certain aspects, the invention provides compounds having the structure of formula (I), and pharmaceutically acceptable salts thereof:

(I)

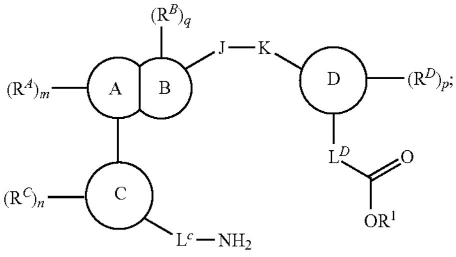

wherein:

ring

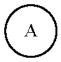

is arylene or heteroarylene;

ring

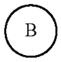

is arylene or heteroarylene;

ring

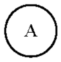

is fused to ring

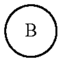

at two and only two adjacent positions;

ring

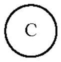

is aryl or heteroaryl;

ring

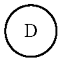

is aryl or heteroaryl;

J represents —$CH_2$—, —NH—, —$CH_2CH_2$—, —C(O)—, —O—, —S—, —S(O)—, —$SO_2$—, —N(alkyl)-, —CH(alkyl)-, —CH(aryl)-, —C(alkyl)$_2$-, —CH(cycloalkyl)-, or

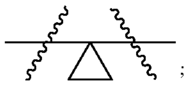;

K represents a bond, —O—, —NH—, —C(O)—, —$CH_2$—, —S—, —S(O)—, —$SO_2$—, —N(alkyl)-, —CH(alkyl)-, or —CH(cycloalkyl)-;

wherein at least one of J and K is a bond, —C(O)—, —$CH_2$—, —$CH_2CH_2$—, —CH(alkyl)-, or —CH (aryl)-;

$L^C$ represents a bond, —$CH_2$—, —CH(alkyl)-, —CH (cycloalkyl)-, —CH(hydroxyalkyl)-, —CH(haloalkyl)-, —$CH_2CH_2$—, —$CF_2$—, —CH(F)—, —CF(alkyl)-, —C(O)—, —$CD_2$-, or —CH(D)-;

$L^D$ represents —$CH_2$—, —$CH_2CH_2$—, —$CF_2$—, —CH(F)—, —$CD_2$-, —CH(D)-, —CH(alkyl)-, —CH(cycloalkyl)-, —$CHNH_2$—, —CH(NH(alkyl))-, —CH(NH(cycloalkyl))-, or a bond;

$R^A$ represents H, halo, hydroxyl, cyano, amino, alkyl, alkoxyl, hydroxyalkyl, optionally substituted aryloxy, (aryloxy)alkyl, (cycloalkyl)alkoxy, (heterocycloalkyl)alkoxy, optionally substituted (heteroaryl)alkoxy, haloalkyl, haloalkoxy, (hydroxy)haloalkyl, alkoxyalkyl, optionally substituted aminoalkyl, optionally substituted alkynyl, optionally substituted aryl, optionally substituted heteroaryl, optionally substituted heteroarylalkyl, optionally substituted cycloalkyl, optionally substituted (cycloalkyl)alkyl, optionally substituted (cycloalkyl)alkenyl, optionally substituted heterocycloalkyl, optionally substituted (heterocycloalkyl)alkyl, —C(O)OH, —C(O)$NH_2$—, —C(O)N$(alkyl)_2$-, —$CH_2$C(O)OH, —$NO_2$, —$CH_2$NH(optionally substituted alkyl), —$CH_2$N(Boc)(optionally substituted alkyl), —$CH_2$NH((cycloalkyl)alkyl), —$CH_2$N(alkyl)(cycloalkyl), —$CH_2$N(alkyl)((cycloalkyl)alkyl), —NH(optionally substituted alkyl), —NH(cycloalkyl), —NH((cycloalkyl)alkyl), —NH((heterocycloalkyl)alkyl), —N$(alkyl)_2$, —N(alkyl)((cycloalkyl)alkyl, —N(alkyl)((heterocycloalkyl)alkyl, —NH(heteroarylalkyl), —$CH_2$O(optionally substituted aryl), —C(O)O(alkyl), —C(O)NH(optionally substituted alkyl), —C(O)NH((cycloalkyl)alkyl), —NHC(O)O(alkyl), or —$CH_2$N$(alkyl)_2$;

$R^B$ represents H, —C(O)O(alkyl), halogen, cyano, amino, —C(O)OH, —$CH_2$C(O)OH, —C(O)$NH_2$, —C(O)NH(cycloalkyl), —C(O)NH(alkyl), —C(O)NH(aryl), —C(O)NH(heteroaryl), —C(O)(alkyl), alkylaminoalkyl, alkylaminocycloalkyl, alkoxyalkyl, hydroxyalkyl, haloalkyl, (hydroxy)haloalkyl, or tosyl, or is optionally substituted alkyl, aryl, heteroaryl, cycloalkyl, (cycloalkyl)alkyl, or heterocycloalkyl;

$R^C$ represents H, halo, —OH, or amino, or is optionally substituted alkoxy, alkyl, cycloalkyl, heterocycloalkyl, or (heteroaryl)alkoxy;

$R^D$ represents H, halo, hydroxyl, cyano, —$NH_2$, —NH(Ac), —NH(alkyl), —N$(alkyl)_2$, —NH(CO)(alkyl), —$CH_2NH_2$, —$CH_2$NHC(O)(alkyl), —C(O)$NH_2$, —C(O)OH, or —NHC(O)O(alkyl), or is optionally substituted alkyl, alkoxyl, cycloalkyl, (cycloalkyl)alkyl, hydroxyalkyl, aminoalkyl, haloalkoxyl, or haloalkyl;

$R^1$ represents H or optionally substituted alkyl; and m, n, p, and q are each independently 0, 1, or 2.

In certain aspects, the invention provides a pharmaceutical composition, comprising a compound of the invention, or a pharmaceutically acceptable salt thereof; and a pharmaceutically acceptable carrier.

In certain aspects, the invention provides methods of treating a disease or condition characterized by aberrant complement system activity, comprising administering to a subject in need thereof a therapeutically effective amount of a compound the invention, or a pharmaceutically acceptable salt thereof. In certain embodiments, the disease or condition characterized by aberrant complement system activity is an immunological disorder. In certain embodiments, the disease or condition characterized by aberrant complement system activity is a disease of the central nervous system. In certain embodiments, the disease or condition characterized by aberrant complement system activity is a neurodegenerative disease or neurological disease. In certain embodiments, the disease or condition characterized by aberrant complement system activity is a renal disease. In certain embodiments, the disease or condition characterized by aberrant complement system activity is a cardiovascular disease. In certain embodiments, the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, and catastrophic antiphospholipid syndrome. In certain other aspects, the disease or condition characterized by aberrant complement system activity is selected from the group consisting of antineutrophil cytoplasmic antibody (ANCA)-associated vasculitis (AAV), warm autoimmune hemolytic anemia, IgA nephropathy, C3 glomerulonephritis, and focal segmental glomerulosclerosis. In further aspects, the the disease or condition characterized by aberrant complement system activity is a hematological disorder. In further aspects, the disease or condition characterized by aberrant complement system activity is an ocular disorder or an eye disorder. In still further aspects, the disease or condition characterized by aberrant complement system activity is macular degeneration, age-related macular degeneration (AMD), macular edema, diabetic macular edema, choroidal neovascularization (CNV), uveitis, Behcet's uveitis, proliferative diabetic retinopathy, non-proliferative diabetic retinopathy, glaucoma, hypertensive retinopathy, a corneal neovascularization disease, post-corneal transplant rejection, a corneal dystrophic disease, an autoimmune dry eye disease, Stevens-Johnson syndrome, Sjogren's syndrome, an environmental dry eye disease, Fuchs' endothelial dystrophy, retinal vein occlusion, or post-operative inflammation.

DETAILED DESCRIPTION

Inhibitors of the complement system are useful in therapeutic methods and compositions suitable for use in treating disorders of the immune, renal, cardiovascular, and neurological systems. Provided herein are compounds of formula (I) and pharmaceutically acceptable salts thereof that are useful in treating or preventing a disease or condition characterized by aberrant activity of the complement system.

Definitions

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium, and alternatively oxygen, nitrogen or sulfur.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ alkyl group. In certain embodiments, the term "alkyl" refers to a $C_1$-$C_6$ alkyl group, for example a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form $-(CH_2)_w-$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "(cycloalkyl)alkyl" as used herein refers to an alkyl group substituted with one or more cycloalkyl groups. An example of cycloalkylalkyl is cyclohexylmethyl group.

The term "heterocycloalkyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2-azobicyclo[3.1.0]hexane. A heterocycloalkyl group is optionally substituted by one or more substituents as described below.

The term "(heterocycloalkyl)alkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

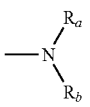 and 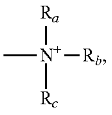

wherein $R_a$, $R_b$, and $R_c$ each independently represent a hydrogen, an alkyl, an alkenyl, $-(CH_2)_x-R_d$, or $R_a$ and $R_b$, taken together with the N atom to which they are attached complete a heterocycle having from 4 to 8 atoms in the ring structure; $R_d$ represents an aryl, a heteroaryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or $-(CH_2)_x-R_d$. In certain embodiments, $R_a$ and $R_b$ are each independently selected from hydrogen, alkyl, alkenyl, alkynyl, aryl, heteroaryl, cycloalkyl, cycloalkenyl, heterocycloalkyl, heterocycloalkenyl, (cycloalkyl)alkyl, (heterocycloalkyl)alkyl, arylalkyl, heteroarylalkyl, alkoxyalkyl, or haloalkyl, any of which may be further substituted (e.g., by halogen, alkyl, alkoxy, hydroxy, and so forth). In certain embodiments, the term "amino" refers to $-NH_2$.

In certain embodiments, the term "alkylamino" refers to —NH(alkyl).

In certain embodiments, the term "dialkylamino" refers to —N(alkyl)$_2$.

The term "amido", as used herein, means —NHC(═O)—, wherein the amido group is bound to the parent molecular moiety through the nitrogen. Examples of amido include alkylamido such as $CH_3C(═O)N(H)$— and $CH_3CH_2C(═O)N(H)$—.

The term "acyl" is a term of art and as used herein refers to any group or radical of the form RCO— where R is any organic group, e.g., alkyl, aryl, heteroaryl, arylalkyl, and heteroarylalkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group, i.e., —$CH_2NH_2$.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

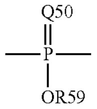

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

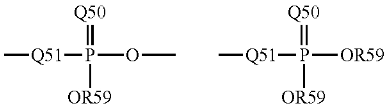

wherein Q50 and R59, each independently, are defined above, and Q51 represents 0, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "azide" or "azido", as used herein, means an —$N_3$ group.

The term "carbonyl" as used herein refers to —C(═O)—.

The term "thiocarbonyl" as used herein refers to —C(═S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—. The term "(alkylthio)alkyl" refers to an alkyl group substituted by an alkylthio group.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, and pyrene. Typically, an aryl group contains from 6-10 carbon ring atoms (i.e., ($C_6$-$C_{10}$)aryl). The aromatic ring may be substituted at one or more ring positions with one or more substituents, such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as triflurom-ethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group.

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" refers to an alkyl group substituted by an alkoxy group.

The term "alkoxycarbonyl" means an alkoxy group, as defined herein, appended to the parent molecular moiety through a carbonyl group, represented by —C(═O)—, as defined herein. Representative examples of alkoxycarbonyl include, but are not limited to, methoxycarbonyl, ethoxycarbonyl, and tert-butoxycarbonyl.

The term “alkylcarbonyl”, as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term “arylcarbonyl”, as used herein, means an aryl group, as defined herein, appended to the parent molecular moiety through a carbonyl group, as defined herein.

Representative examples of arylcarbonyl include, but are not limited to, benzoyl and (2-pyridinyl)carbonyl.

The term “alkylcarbonyloxy” and “arylcarbonyloxy”, as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term “alkenoxy” or “alkenoxyl” means an alkenyl group, as defined herein, appended to the parent molecular moiety through an oxygen atom. Representative examples of alkenoxyl include, but are not limited to, 2-propen-1-oxyl (i.e., $CH_2$═CH—$CH_2$—O—) and vinyloxy (i.e., $CH_2$═CH—O—).

The term “aryloxy” as used herein means an aryl group, as defined herein, appended to the parent molecular moiety through an oxygen atom.

The term “heteroaryloxy” as used herein means a heteroaryl group, as defined herein, appended to the parent molecular moiety through an oxygen atom.

The term “carbocyclyl” as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl).

Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term “cyano” is a term of art and as used herein refers to —CN.

The term “halo” is a term of art and as used herein refers to —F, —Cl, —Br, or —I.

The term “haloalkyl” as used herein refers to an alkyl group, as defined herein, wherein some or all of the hydrogens are replaced with halogen atoms.

The term “hydroxy” is a term of art and as used herein refers to —OH.

The term “hydroxyalkyl”, as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term “silyl”, as used herein, includes hydrocarbyl derivatives of the silyl ($H_3Si$—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term “silyloxy”, as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that “substitution” or “substituted with” includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term “substituted” is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

In certain embodiments, the optional substituents contemplated in this invention include halogen, azide, alkyl, alkenyl, alkynyl, aryl, arylalkyl, heteroaryl, heteroarylalkyl, cycloalkyl, (cycloalkyl)alkyl, heterocyclyl, (heterocyclyl)alkyl, hydroxyl, alkoxyl, amino, aminoalkyl, nitro, sulfhydryl, imino, amido, phosphonate, phosphinate, carbonyl, carboxyl, silyl, ether (e.g., -alkylene-O(alkyl)), alkylthio, sulfonyl, sulfonamido, ketone (e.g., —CO(alkyl)), aldehyde (—C(O)H), ester (e.g., —COO(alkyl)), haloalkyl, hydroxyalkyl, alkoxyalkyl, haloalkoxy, haloalkoxyalkyl, and cyano.

As used herein, the term “optionally substituted” or “substituted or unsubstituted” when it precedes a list of chemical moieties means that the list of chemical moeities that follow are each substituted or unsubstituted. For example, "substituted or unsubstituted aryl, heteroaryl, and cycloalkyl" or "optionally substituted aryl, heteroaryl, and cycloalkyl" means substituted or unsubstituted aryl, substituted or unsubstituted heteroaryl, and substituted or unsubstituted cycloalkyl.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

The term "prodrug" as used herein refers to a compound that can be metabolized in vivo to provide a compound of formula I. Thus prodrugs include compounds that can be prepared by modifying one or more functional groups in a compound of formula I to provide a corresponding compound that can be metabolized in vivo to provide a compound of formula I. Such modifications are known in the art. For example, one or more hydroxyl groups or amine groups in a compound of formula I can be acylated with alkyl-C(=O)— groups or with residues from amino acids to provide a prodrug.

Prodrug forms of a compound bearing various nitrogen-containing functional groups (amino, hydroxyamino, amide, etc.) may include the following types of derivatives, where each $R_p$ group individually may be hydrogen, substituted or unsubstituted alkyl, aryl, alkenyl, alkynyl, heterocycle, alkylaryl, arylalkyl, aralkenyl, aralkynyl, cycloalkyl or cycloalkenyl.

(a) Carboxamides, represented as $—NHC(O)R_p$
(b) Carbamates, represented as $—NHC(O)OR_p$
(c) (Acyloxy)alkyl Carbamates, represented as $NHC(O)OROC(O)R_p$
(d) Enamines, represented as $—NHCR(=CHCO_2R_p)$ or $—NRCR(=CHCONR_pRy)$
(e) Schiff Bases, represented as $—N=CR_pR_p$
(f) Mannich Bases (from carboximide compounds), represented as $RCONHCH_2NR_pR_p$ Preparations of such prodrug derivatives are discussed in various literature sources (examples are: Alexander et al., J. Med. Chem. 1988, 31, 318; Aligas-Martin et al., PCT WO0041531, p. 30).

Prodrug forms of carboxyl-bearing compounds include esters ($—CO_2R_m$) where the $R_m$ group corresponds to any alcohol whose release in the body through enzymatic or hydrolytic processes would be at pharmaceutically acceptable levels. Another prodrug derived from a carboxylic acid form of the disclosure may be a quaternary salt type of structure described by Bodor et al., J. Med. Chem, 1980, 23, 469.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

The present invention provides compounds having the structure of Formula (I), and pharmaceutically acceptable salts thereof:

(I)

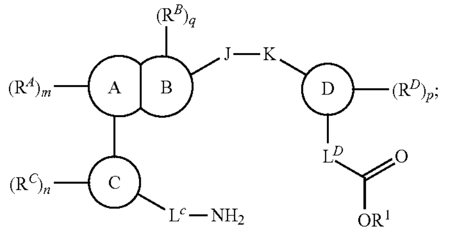

wherein:

ring

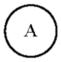

is arylene or heteroarylene;

ring

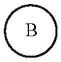

is arylene or heteroarylene;

ring

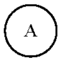

is fused to ring

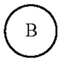

at two and only two adjacent positions;

ring

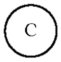

is aryl or heteroaryl;

ring

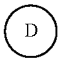

is aryl or heteroaryl;

J represents —$CH_2$—, —NH—, —$CH_2CH_2$—, —C(O)—, —O—, —S—, —S(O)—, —$SO_2$—, —N(alkyl)-, —CH(alkyl)-, —CH(aryl)-, —C$(alkyl)_2$-, —CH(cycloalkyl)-, or Z;

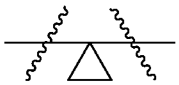

;

K represents a bond, —O—, —NH—, —C(O)—, —$CH_2$—, —S—, —S(O)—, —$SO_2$—, —N(alkyl)-, —CH(alkyl)-, or —CH(cycloalkyl)-;

wherein at least one of J and K is a bond, —C(O)—, —$CH_2$—, —$CH_2CH_2$—, —CH(alkyl)-, or —CH (aryl)-;

$L^C$ represents a bond, —$CH_2$—, —CH(alkyl)-, —CH (cycloalkyl)-, —CH(hydroxyalkyl)-, —CH(haloalkyl)-, —$CH_2CH_2$—, —$CF_2$—, —CH(F)—, —CF(alkyl)-, —C(O)—, —$CD_2$-, or —CH(D)-;

$L^D$ represents —$CH_2$—, —$CH_2CH_2$—, —$CF_2$—, —CH (F)—, —$CD_2$-, —CH(D)-, —CH(alkyl)-, —CH (cycloalkyl)-, —$CHNH_2$—, —CH(NH(alkyl))-, —CH (NH(cycloalkyl))-, or a bond;

$R^A$ represents H, halo, hydroxyl, cyano, amino, alkyl, alkoxyl, hydroxyalkyl, optionally substituted aryloxy, (aryloxy)alkyl, (cycloalkyl)alkoxy, (heterocycloalkyl) alkoxy, optionally substituted (heteroaryl)alkoxy, haloalkyl, haloalkoxy, (hydroxy)haloalkyl, alkoxyalkyl, optionally substituted aminoalkyl, optionally substituted alkynyl, optionally substituted aryl, optionally substituted heteroaryl, optionally substituted heteroarylalkyl, optionally substituted cycloalkyl, optionally substituted (cycloalkyl)alkyl, optionally substituted (cycloalkyl)alkenyl, optionally substituted heterocycloalkyl, optionally substituted (heterocycloalkyl)alkyl, —C(O)OH, —C(O)$NH_2$—, —C(O)N$(alkyl)_2$-, —$CH_2$C(O)OH, —$NO_2$, —$CH_2$NH(optionally substituted alkyl), —$CH_2$N(Boc)(optionally substituted alkyl), —$CH_2$NH((cycloalkyl)alkyl), —$CH_2$N(alkyl) (cycloalkyl), —$CH_2$N(alkyl)((cycloalkyl)alkyl), —NH (optionally substituted alkyl), —NH(cycloalkyl), —NH((cycloalkyl)alkyl), —NH((heterocycloalkyl)alkyl), —N$(alkyl)_2$, —N(alkyl)((cycloalkyl)alkyl, —N(alkyl)((heterocycloalkyl)alkyl, —NH(heteroarylalkyl), —$CH_2$O(optionally substituted aryl), —C(O)O (alkyl), —C(O)NH(optionally substituted alkyl), —C(O)NH((cycloalkyl)alkyl), —NHC(O)O(alkyl), or —$CH_2$N$(alkyl)_2$;

$R^B$ represents H, —C(O)O(alkyl), halogen, cyano, amino, —C(O)OH, —$CH_2$C(O)OH, —C(O)$NH_2$, —C(O)NH (cycloalkyl), —C(O)NH(alkyl), —C(O)NH(aryl), —C(O)NH(heteroaryl), —C(O)(alkyl), alkylaminoalkyl, alkylaminocycloalkyl, alkoxyalkyl, hydroxyalkyl, haloalkyl, (hydroxy)haloalkyl, or tosyl, or is optionally substituted alkyl, aryl, heteroaryl, cycloalkyl, (cycloalkyl)alkyl, or heterocycloalkyl;

$R^C$ represents H, halo, —OH, or amino, or is optionally substituted alkoxy, alkyl, cycloalkyl, heterocycloalkyl, or (heteroaryl)alkoxy;

$R^D$ represents H, halo, hydroxyl, cyano, —$NH_2$, —NH (Ac), —NH(alkyl), —N$(alkyl)_2$, —NH(CO)(alkyl), —$CH_2NH_2$, —$CH_2$NHC(O)(alkyl), —C(O)$NH_2$, —C(O)OH, or —NHC(O)O(alkyl), or is optionally substituted alkyl, alkoxyl, cycloalkyl, (cycloalkyl)alkyl, hydroxyalkyl, aminoalkyl, haloalkoxyl, or haloalkyl;

$R^1$ represents H or optionally substituted alkyl; and m, n, p, and q are each independently 0, 1, or 2.

In certain embodiments of the compound of formula (I):

J represents —$CH_2$—, —NH—, —$CH_2CH_2$—, or —C(O)—;

K represents a bond, —O—, —NH—, or —C(O)—;

wherein if J represents —NH—, then K is a bond or —C(O)—;

$L^C$ represents —$CH_2$—, —CH(alkyl)-, or —CH(hydroxyalkyl)-;

$R^A$ represents H, halo, hydroxyl, alkyl, alkoxyl, hydroxyalkyl, optionally substituted aryloxy, (aryloxy)alkyl, (heterocycloalkyl)alkoxy, optionally substituted aryl, optionally substituted heteroaryl, optionally substituted heterocycloalkyl, optionally substituted (heterocycloalkyl)alkyl, —C(O)OH, —$NO_2$, —$CH_2$NH(optionally substituted alkyl), —$CH_2$NH((cycloalkyl)alkyl), —NH ((cycloalkyl)alkyl, —$CH_2$O(optionally substituted aryl), —C(O)O(alkyl), —C(O)NH(optionally substituted alkyl), —C(O)NH((cycloalkyl)alkyl), —NHC(O)O(alkyl), or —$CH_2N(alkyl)_2$;

$R^B$ represents H, —C(O)O(alkyl), alkyl, —C(O)OH, hydroxyalkyl, tosyl, heterocycloalkyl, —C(O)$N_{12}$, or —C(O)NH(cycloalkyl);

$R^C$ represents H or halo;

$R^D$ represents H or halo, hydroxyl, alkyl, alkoxyl, —$NH_2$, —C(O)$NH_2$, —NHC(O)O(alkyl), or haloalkoxyl; and $R^1$ represents H or alkyl.

In certain embodiments, the compound has the structure of formula (Ia):

(Ia)

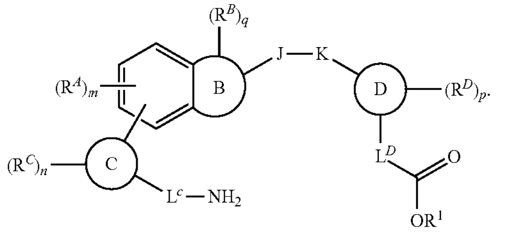

In certain embodiments, the compound has the structure of formula (Ia-1):

(Ia-1)

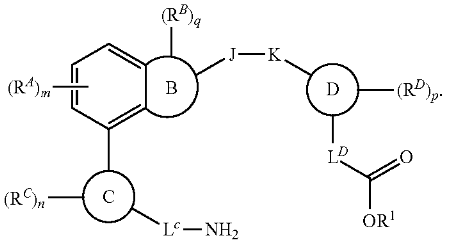

In certain embodiments, the compound has the structure of formula (Ia-2):

(Ia-2)

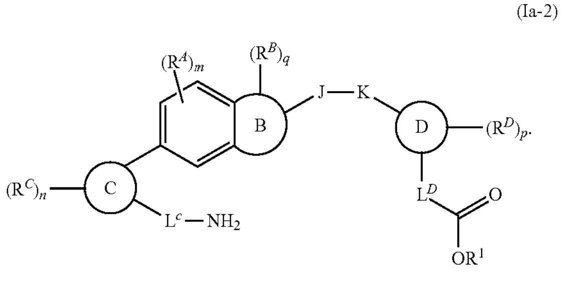

In certain embodiments, the compound has the structure of formula (Ib-1):

(Ib-1)

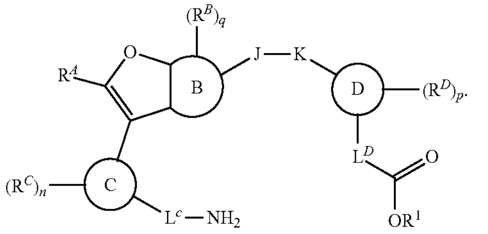

In certain embodiments, the compound has the structure of formula (Ib-2):

(Ib-2)

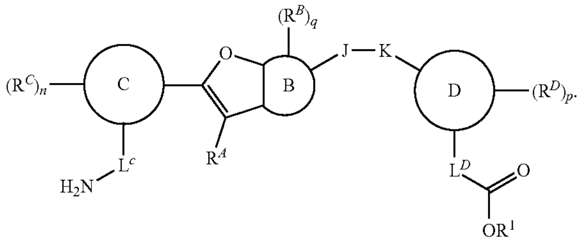

In certain embodiments, the compound has the structure of formula (Ic-1):

(Ic-1)

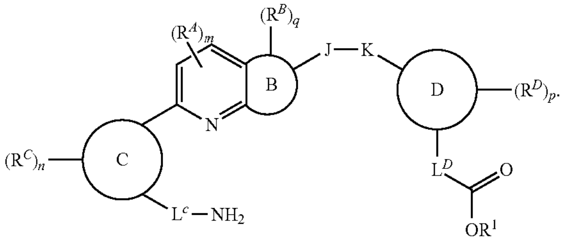

In certain embodiments, the compound has the structure of formula (Id-1):

(Id-1)

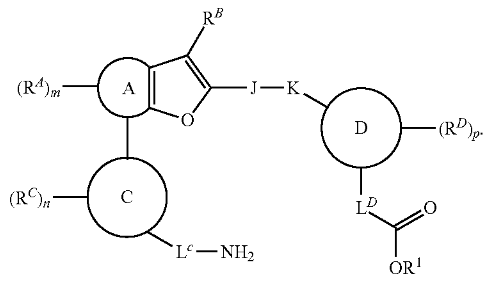

In certain embodiments, the compound has the structure of formula (Id-2):

(Id-2)

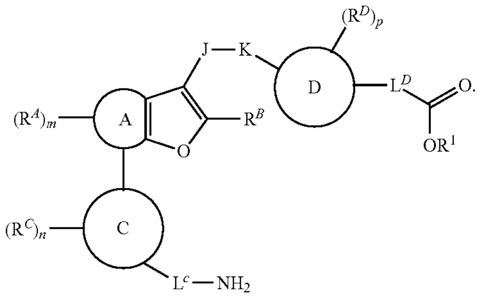

In certain embodiments, the compound has the structure of formula (Ie-1):

(Ie-1)

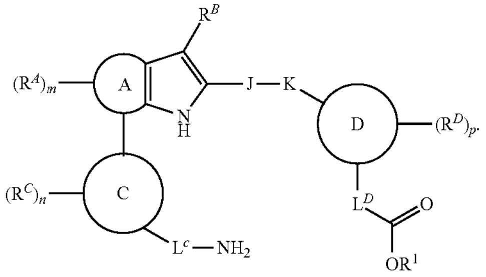

In certain embodiments, the compound has the structure of formula (Ie-2):

(Ie-2)

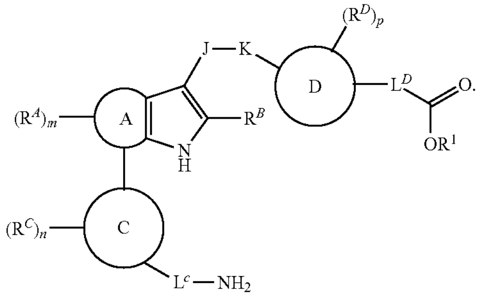

In certain embodiments, the compound has the structure of formula (If-1):

(If-1)

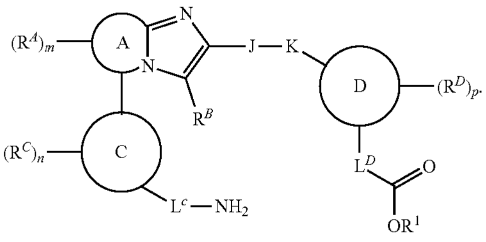

In certain embodiments, the compound has the structure of formula (If-2):

(If-2)

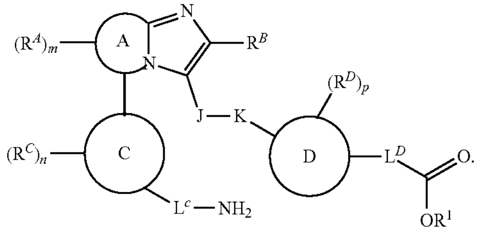

In certain embodiments, the compound has the structure of formula (Ig-1):

(Ig-1)

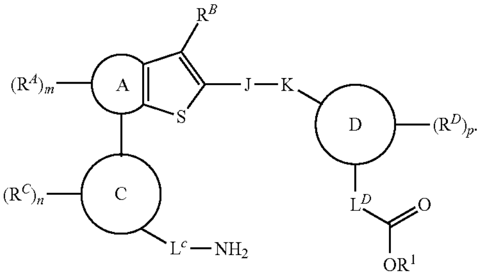

In certain embodiments, the compound has the structure of formula (Ig-2):

(Ig-2)

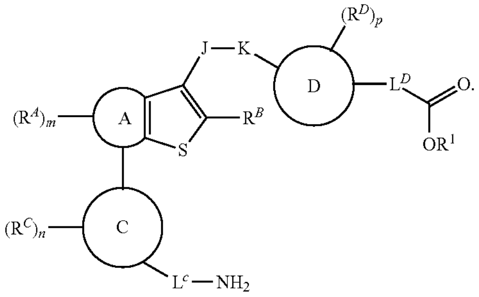

In certain embodiments, the compound has the structure of formula (Ih-1):

(Ih-1)

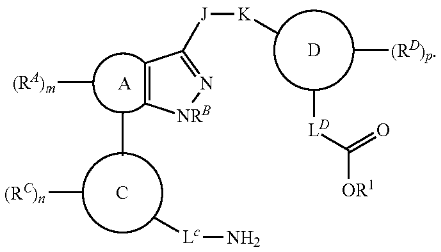

In certain embodiments, the compound has the structure of formula (Ih-2):

(Ih-2)

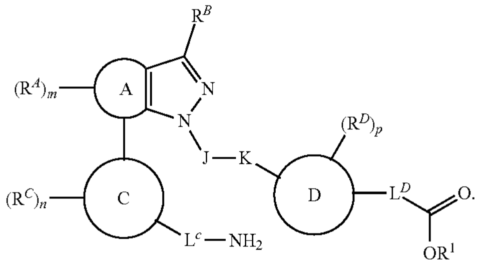

In certain embodiments, the compound has the structure of formula (Ij):

(Ij)

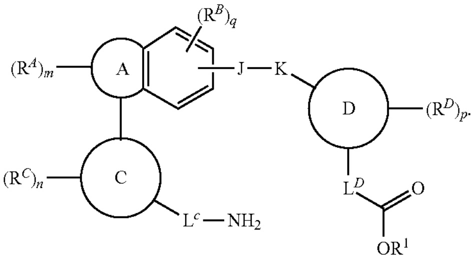

In certain embodiments, the compound has the structure of formula (Ij-1):

(Ij-1)

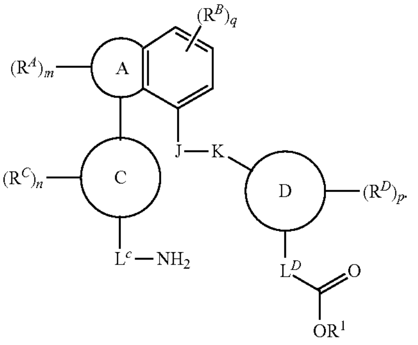

In certain embodiments, the compound has the structure of formula (Ij-2):

(Ij-2)

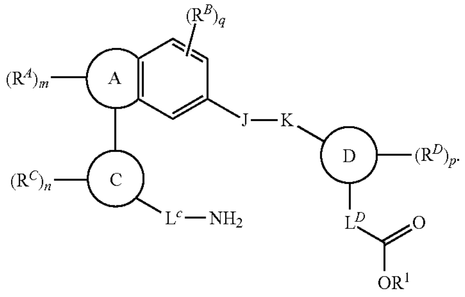

In certain embodiments, the compound has the structure of formula (Ik):

(Ik)

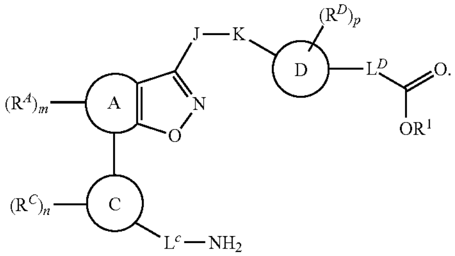

In certain embodiments, the compound has the structure of formula (Im):

(Im)

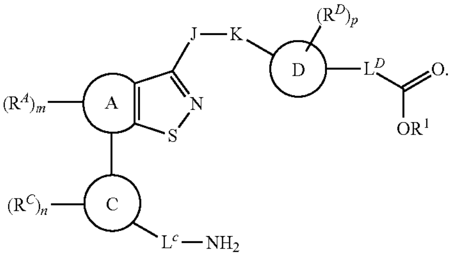

In certain embodiments, the compound has the structure of formula (IIa):

(IIa)

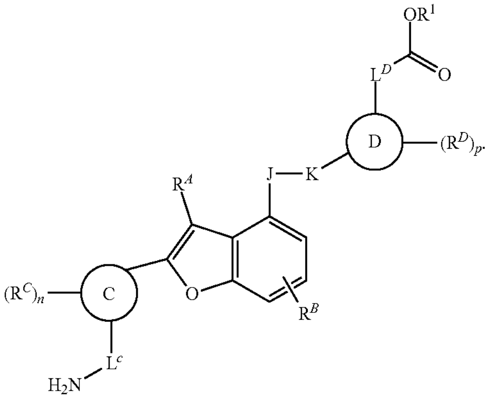

In certain embodiments, the compound has the structure of formula (IIb):

(IIb)

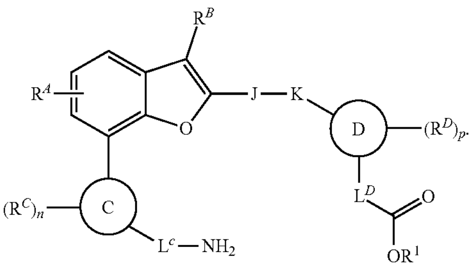

In certain embodiments, the compound has the structure of formula (IIc):

(IIc)

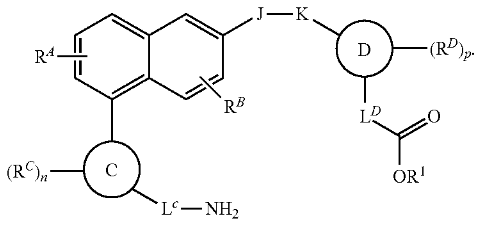

In certain embodiments, the compound has the structure of formula (IId):

(IId)

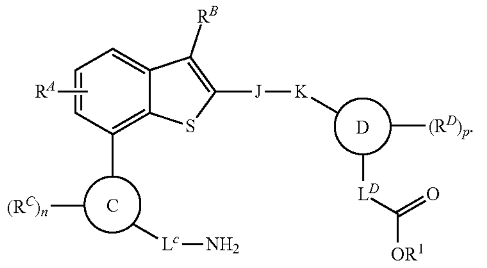

In certain embodiments, the compound has the structure of formula (IIe):

(IIe)

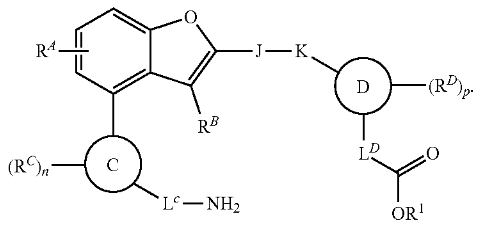

In certain embodiments, the compound has the structure of formula (IIf):

(IIf)

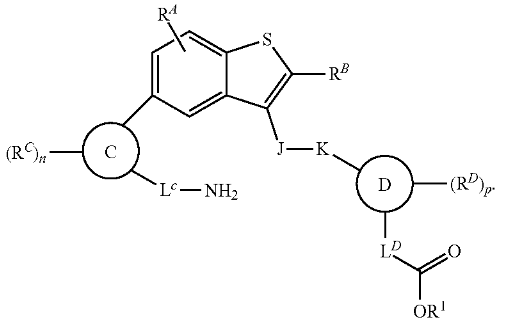

In certain embodiments, the compound has the structure of formula (IIg):

(IIg)

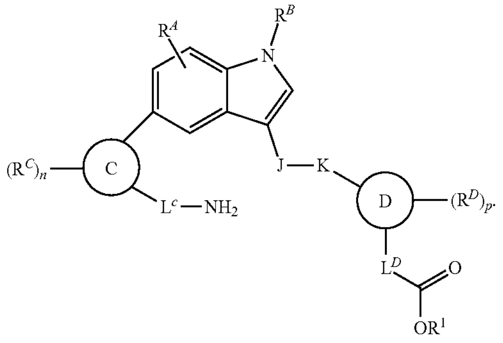

In certain embodiments, the compound has the structure of formula (IIh):

(IIh)

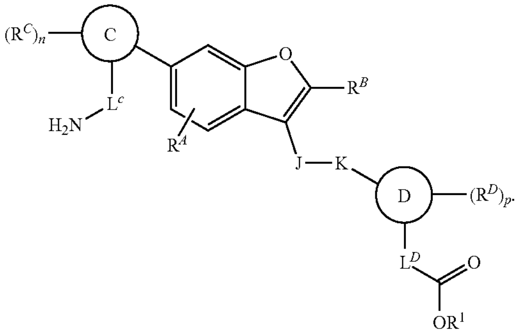

In certain embodiments, the compound has the structure of formula (IIj):

(IIj)

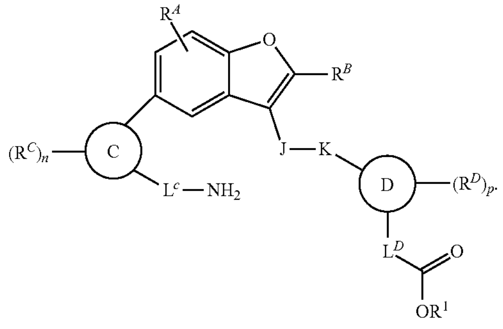

In certain embodiments, the compound has the structure of formula (IIk):

(IIk)

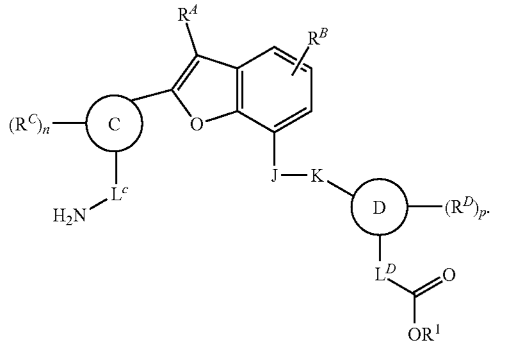

In certain embodiments, the compound has the structure of formula (IIm):

(IIm)

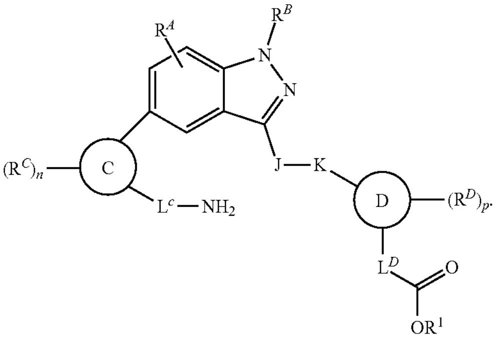

In certain embodiments, the compound has the structure of formula (IIn):

(IIn)

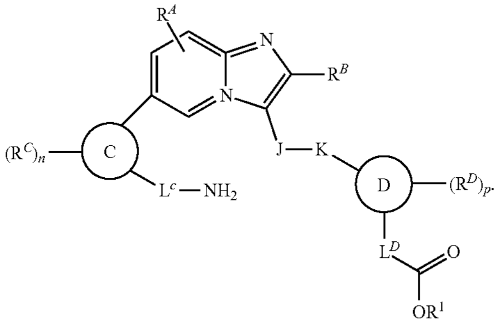

In certain embodiments, the compound has the structure of formula (IIo):

(IIo)

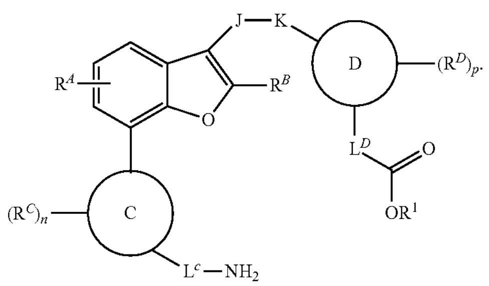

In certain embodiments, the compound has the structure of formula (IIp):

(IIp)

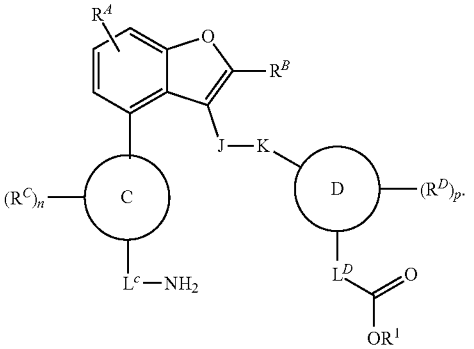

In certain embodiments, the compound has the structure of formula (IIq):

(IIq)

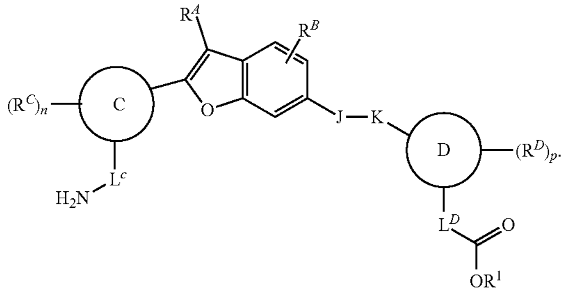

In certain embodiments, the compound has the structure of formula (IIr):

(IIr)

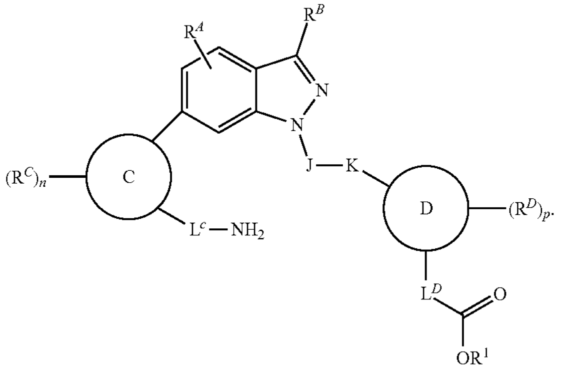

In certain embodiments, the compound has the structure of formula (IIs):

(IIs)

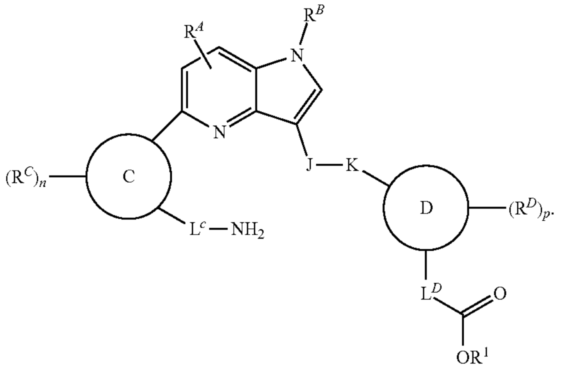

In certain embodiments, the compound has the structure of formula (IIt):

(IIt)

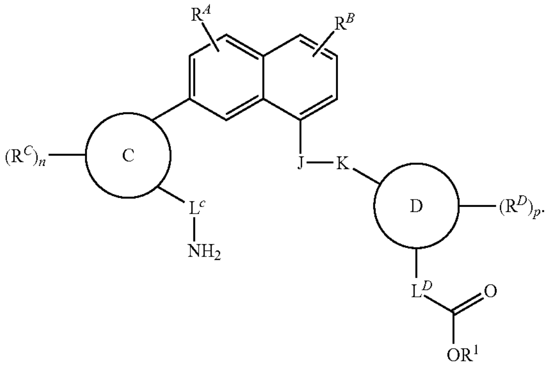

In certain embodiments, the compound has the structure of formula (IIu):

(IIu)

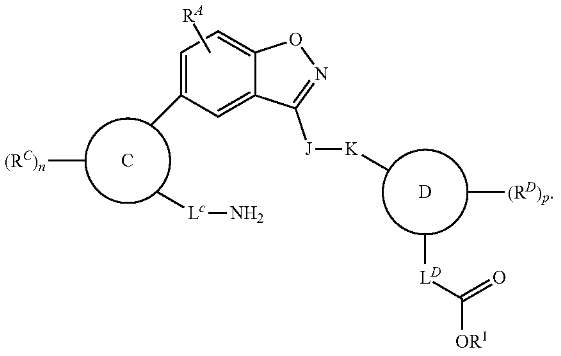

In certain embodiments, the compound has the structure of formula (IIv):

(IIv)

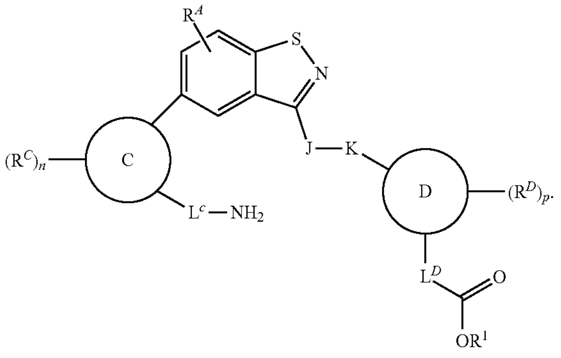

In certain embodiments, the compound has the structure of formula (IIw):

(IIw)

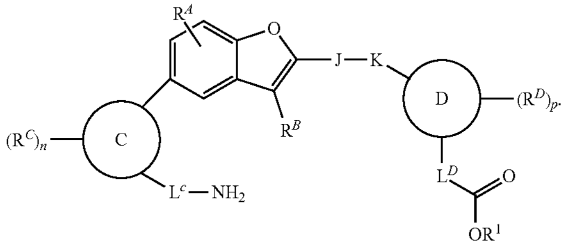

In certain embodiments, the compound has the structure of formula (IIx):

(IIx)

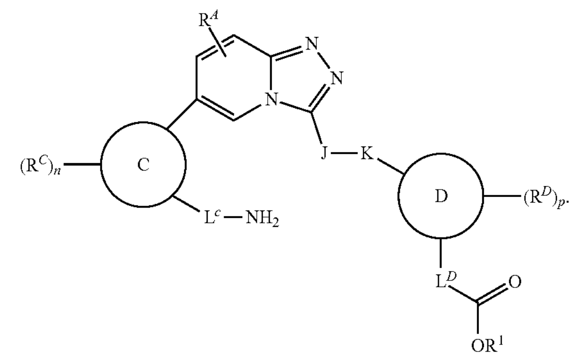

In certain embodiments, the compound has the structure of formula (IIy):

(IIy)

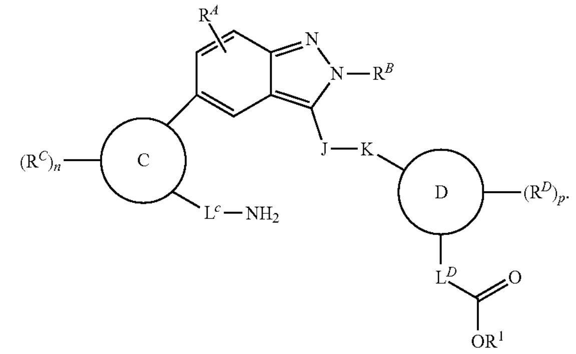

In certain embodiments, the compound has the structure of formula (IIz):

(IIz)

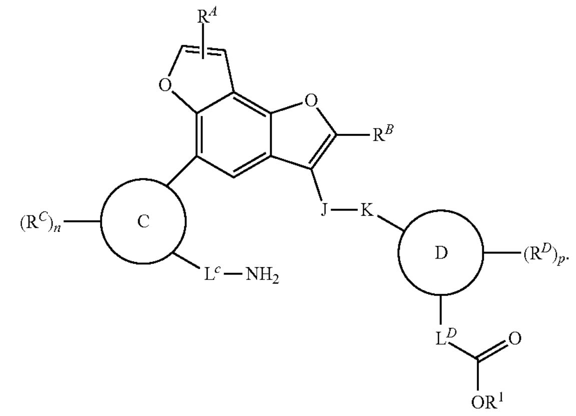

As described above in the definitions, aryl and heteroaryl moieties encompass bicyclic and polycyclic ring structures. Accordingly, in some embodiments, the

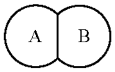

moiety present in formula (I) is a tricyclic ring structure, such as one of the following tricyclic ring

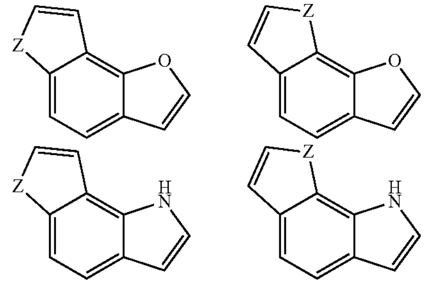

structures:

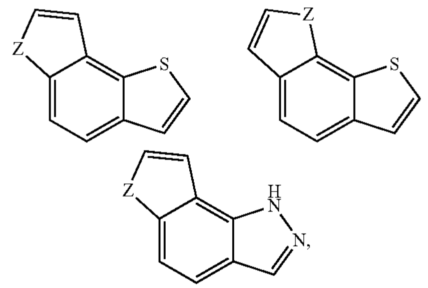

wherein Z is O, NH, —CH—CH—, or —CH—N—. For example, the

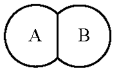

moiety may be a tricyclic ring structure such as any of the following: benzo[1,2-b:3,4-b']difuran, 6H-furo[2,3-e]indole, furo[2,3-f]quinoline, naphtho[1,2-b]furan, furo[3,2-h]quinoline, benzo[2,1-b:3,4-b']difuran, 8H-furo[3,2-g]indole, 1H-furo[2,3-g]indole, 1,6-dihydropyrrolo[2,3-e]indole, 1H-pyrrolo[2,3-f]quinoline, 1H-benzo[g]indole, 1H-pyrrolo[3,2-h]quinoline, 1,8-dihydropyrrolo[3,2-g]indole, 8H-furo[3,2-g]indole, thieno[2,3-e]benzofuran, 6H-thieno[2,3-e]indole, thieno[2,3-f]quinoline, naphtho[1,2-b]thiophene, thieno[3,2-h]quinoline, thieno[3,2-g]benzofuran, 8H-thieno[3,2-g]indole, 1H-furo[2,3-g]indazole, 1,6-dihydropyrrolo[2,3-g]indazole, 1H-pyrazolo[3,4-f]quinoline, 1H-benzo[g]indazole, 1H-pyrazolo[4,3-h]quinoline, 1,8-dihydropyrrolo[3,2-g]indazole, and 1H-furo[3,2-g]indazole. In certain such embodiments, $R^A$ and ring

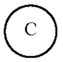

may be attached to the

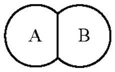

moiety at any open position on ring

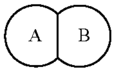

and $R^B$ and -J- may be attached to the

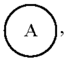, moiety at any open position on ring

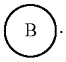.

In any of the foregoing embodiments, ring

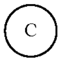

may represent a 6-membered aryl or heteroaryl.

For example, in certain embodiments,

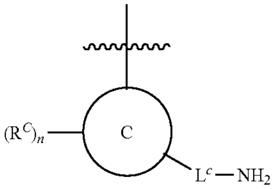

represents

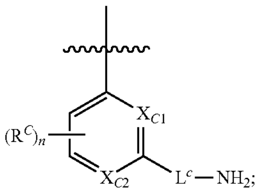

$X_{C1}$ represents CH or N; and $X_{C2}$ represents CH or N.

In certain embodiments,

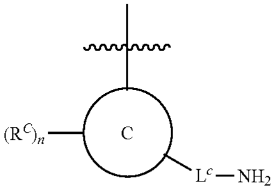

represents

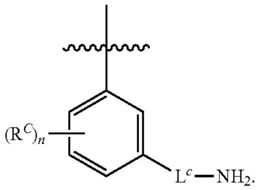

In certain embodiments,

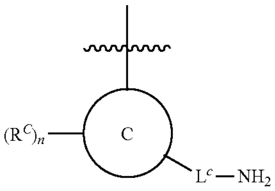

represents

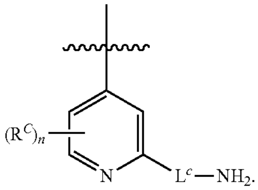

In certain embodiments, $L^C$ represents —$CH_2$—.

In certain embodiments, $R^C$ represents H. Alternatively, $R^C$ may represent halo, preferably F.

In certain embodiments, -J-K— represents —$CH_2$—, —NH—, —$CH_2$—O—, —$CH_2CH_2$—O—, —C(O)—NH—, or —NHC(O)—. Preferably, -J-K— represents —$CH_2$—O— or —C(O)—NH—.

In any of the foregoing embodiments, ring

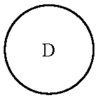

may represent aryl.

For example, in certain embodiments,

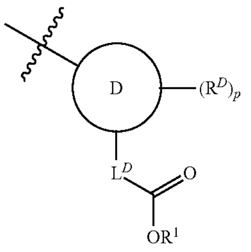

represents

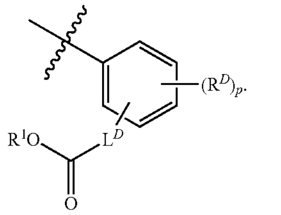

More specifically, in some embodiments,

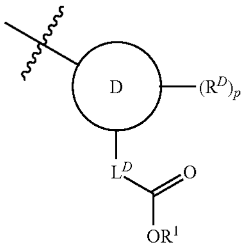

represents

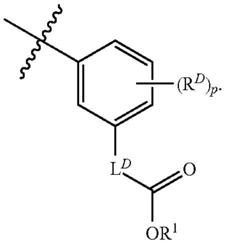

Alternatively, in some embodiments,

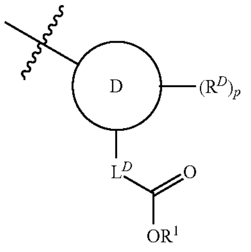

represents

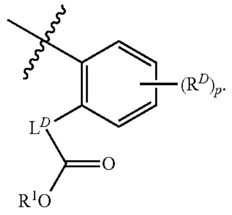

In certain embodiments, $R^1$ is H.

In certain embodiments, $L^D$ represents $—CH_2—$, $—CH_2CH_2—$, or a bond. Preferably, $L^D$ represents $—CH_2—$.

In certain embodiments, $R^D$ represents H, halo, hydroxyl, alkyl, or alkoxyl. Preferably, $R^D$ represents H.

In certain embodiments, $R^B$ represents H, —C(O)O(alkyl), halogen, cyano, amino, —C(O)OH, $—CH_2C(O)OH$, $—C(O)NH_2$, —C(O)NH(cycloalkyl), hydroxyalkyl, haloalkyl, (hydroxy)haloalkyl, or tosyl, or is optionally substituted alkyl, cycloalkyl, or heterocycloalkyl.

In certain embodiments, $R^B$ represents H, alkyl, or —C(O)OH. Preferably, $R^B$ represents H.

In certain embodiments, $R^A$ represents H, alkyl, alkoxyl, or $—CH_2O$(optionally substituted aryl). In some embodiments, $R^A$ represents H.

In certain embodiments, the compound of formula (I) is selected from the following table of compounds, and pharmaceutically acceptable salts thereof:

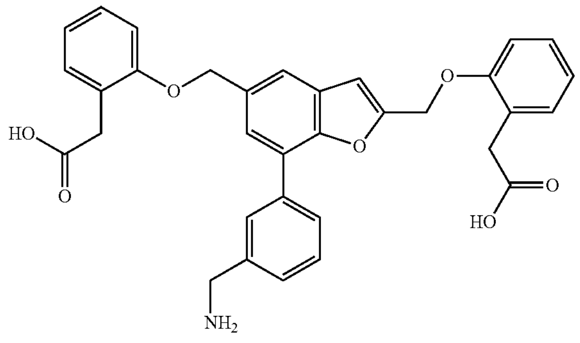

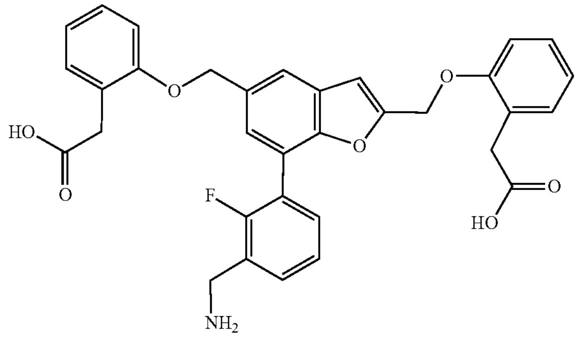

-continued
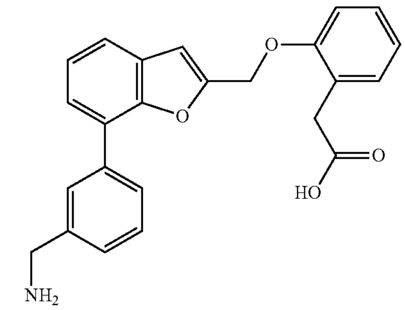
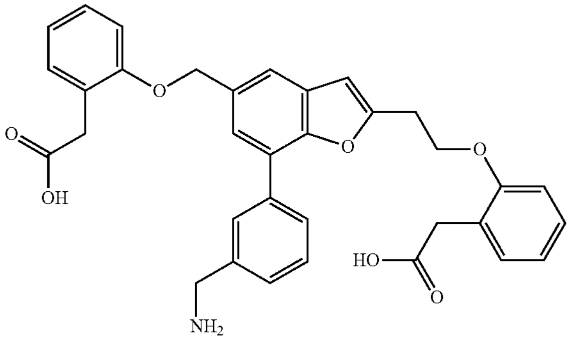
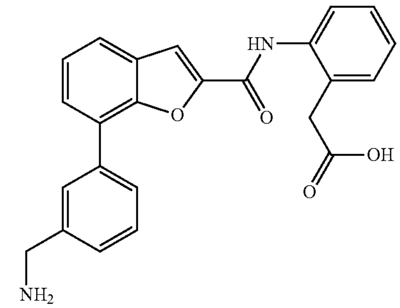
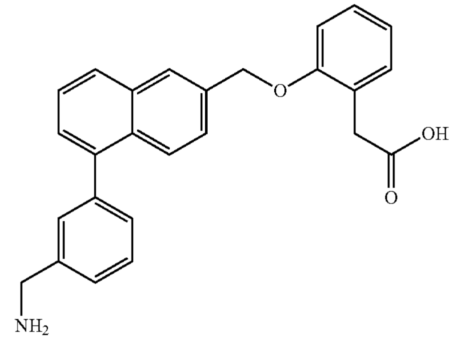
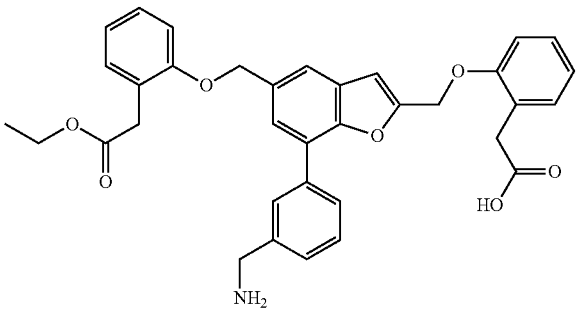
-continued
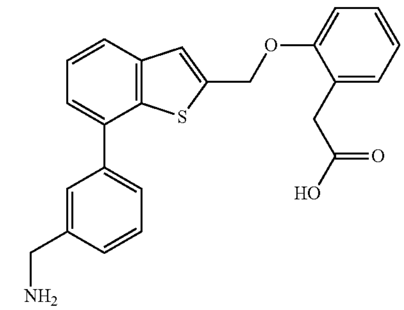
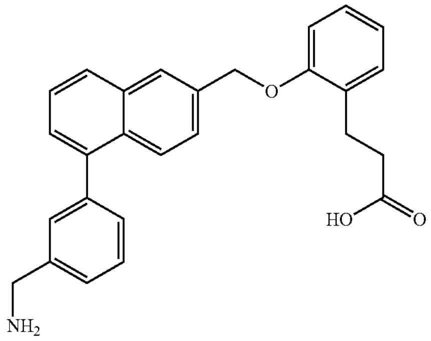
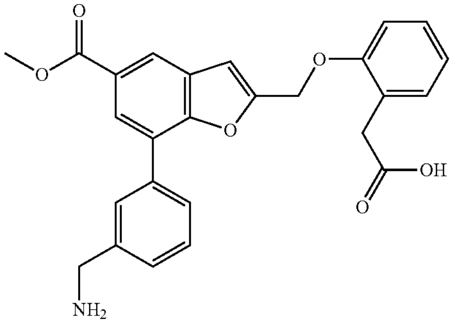
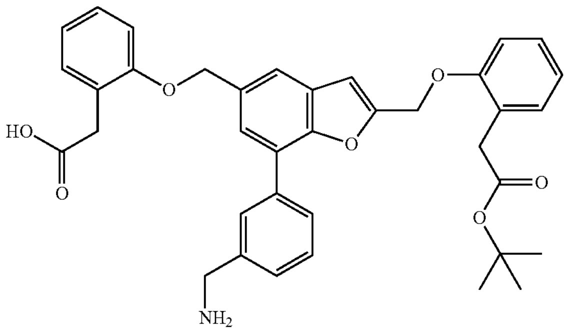
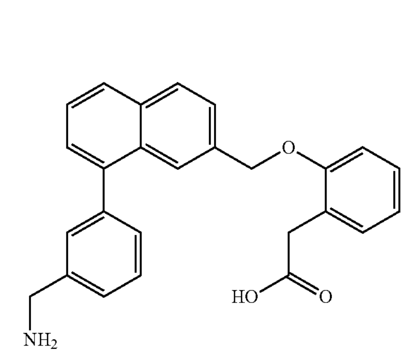

-continued
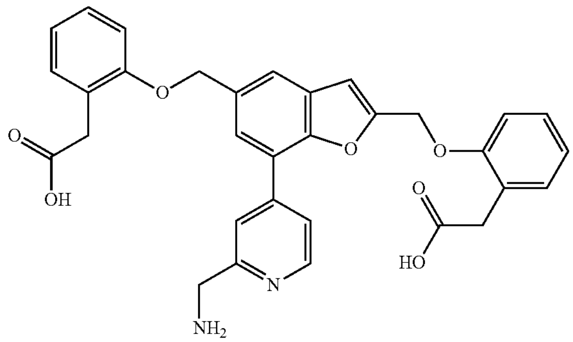
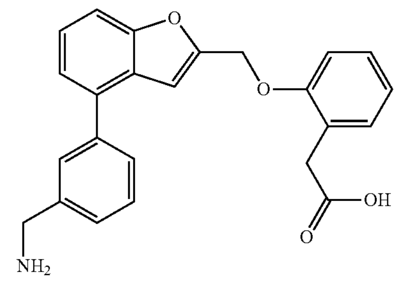
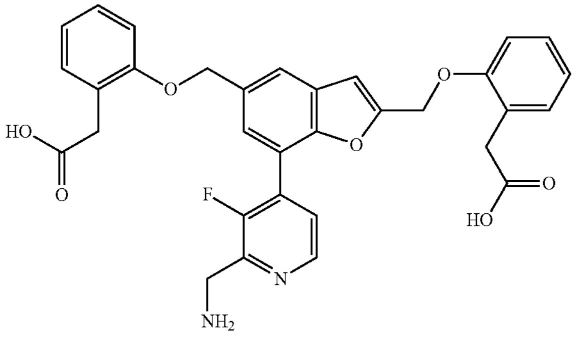
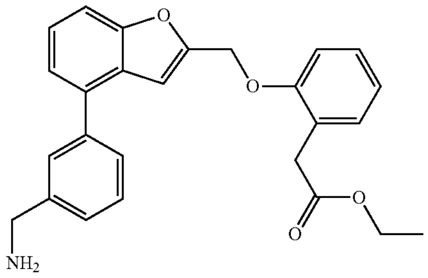
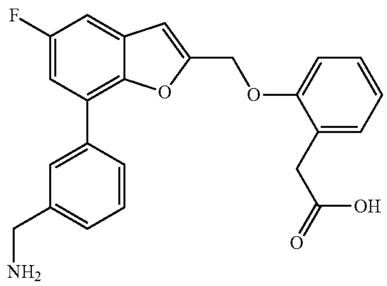
-continued
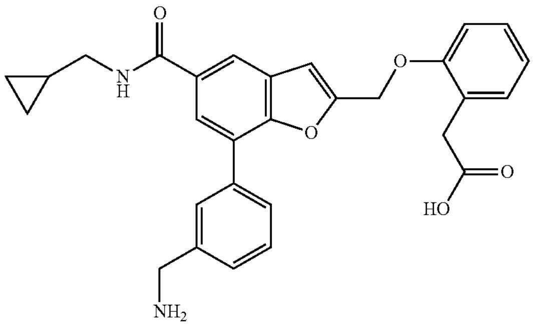
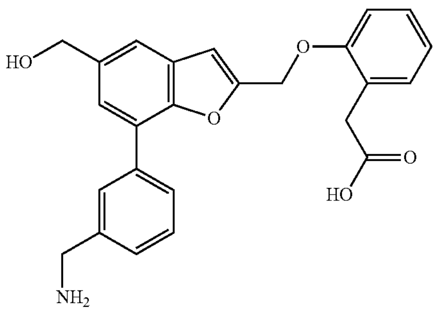
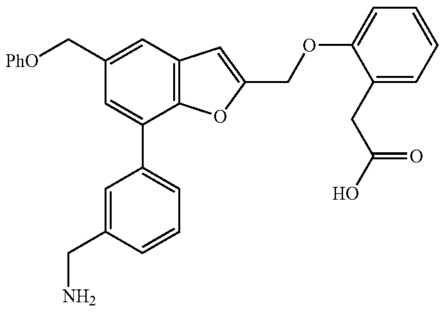
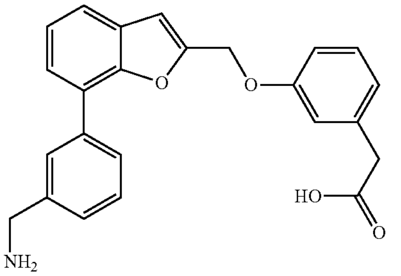
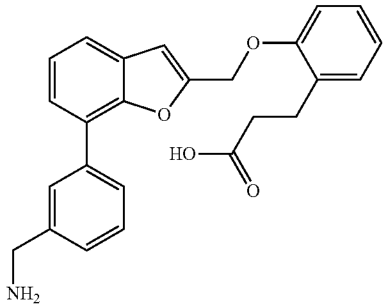

-continued
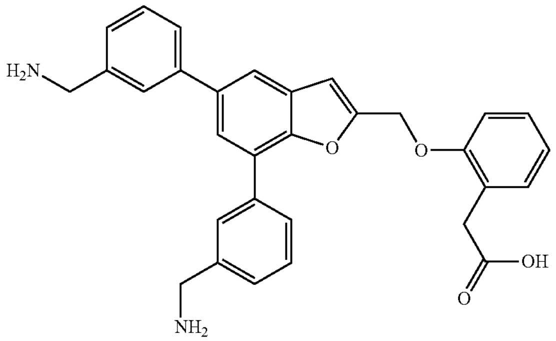
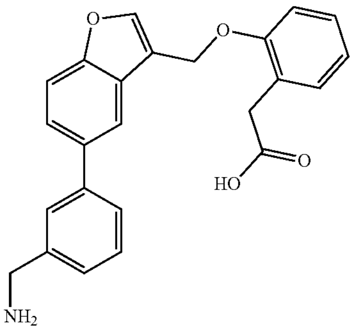
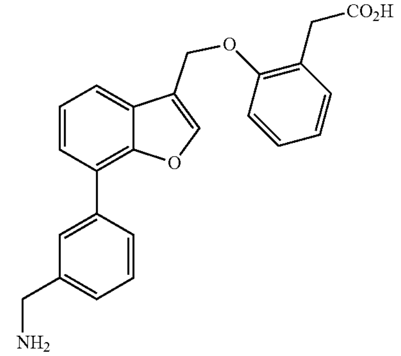
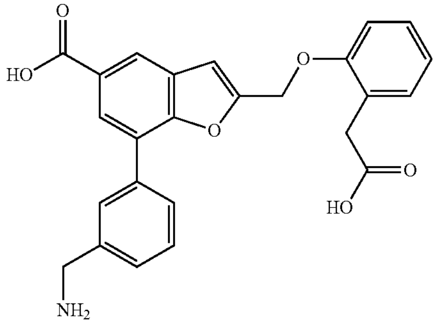
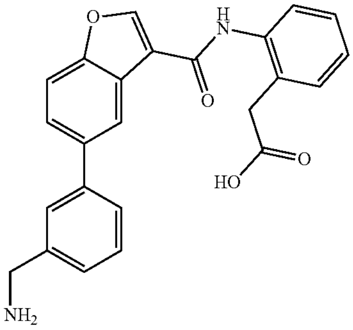
-continued
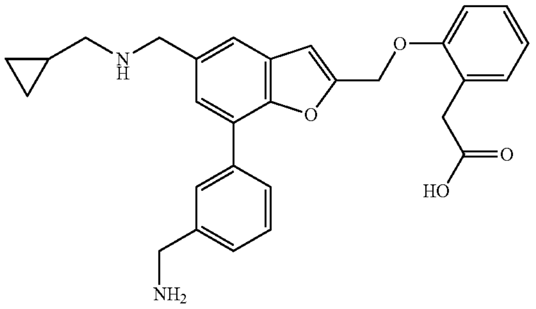
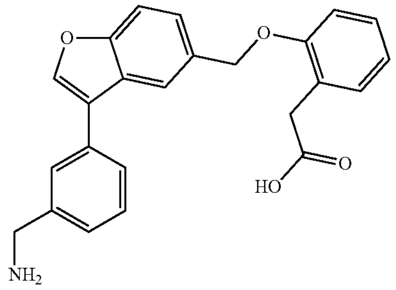
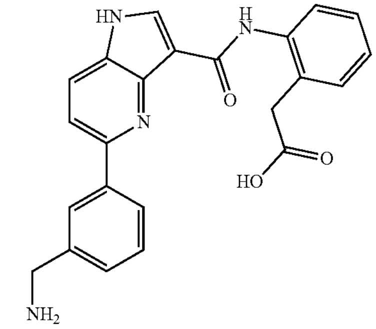
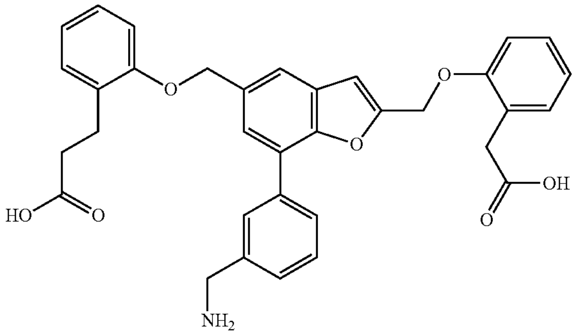
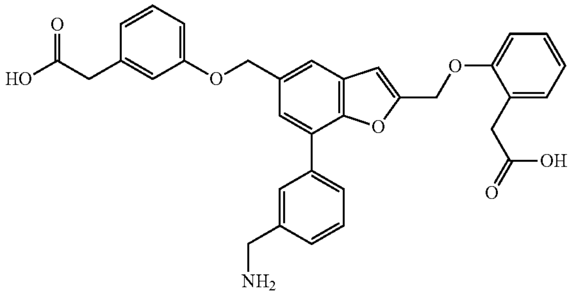

-continued
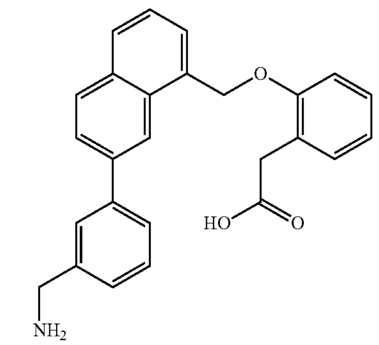
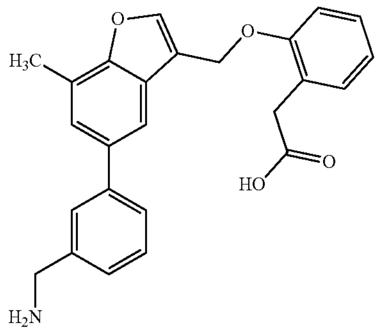
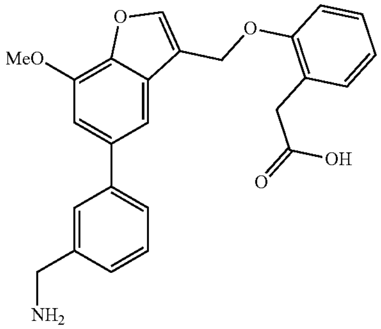
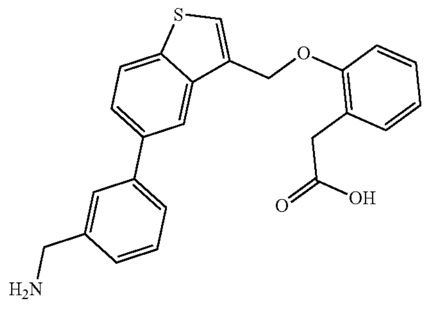
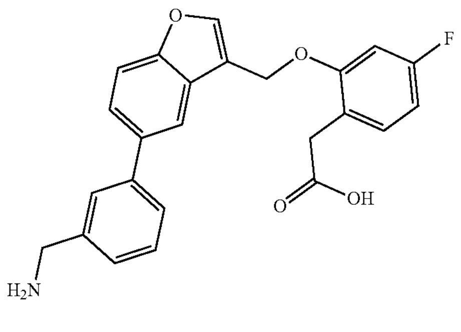
-continued
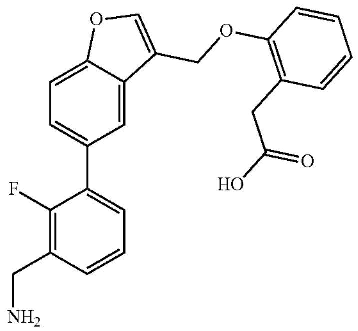
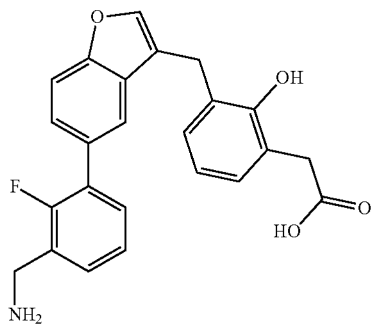
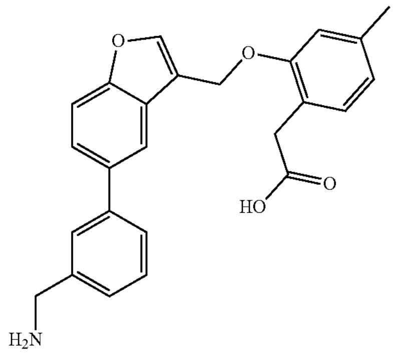
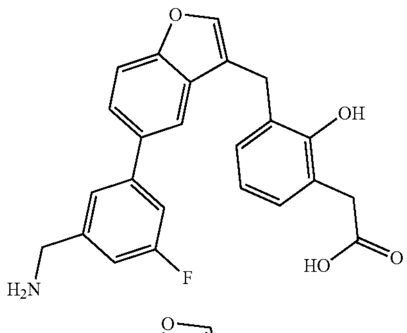
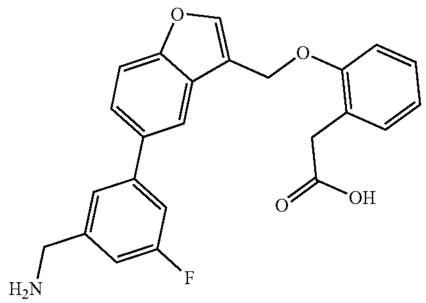

-continued
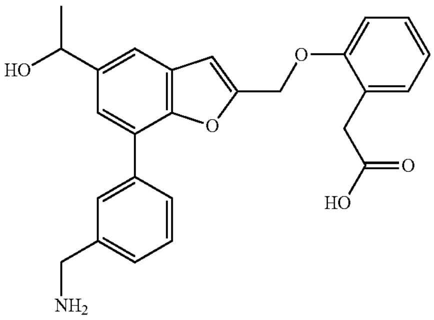
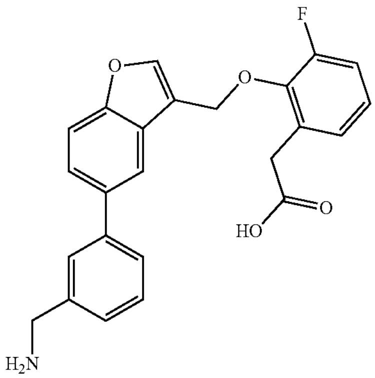
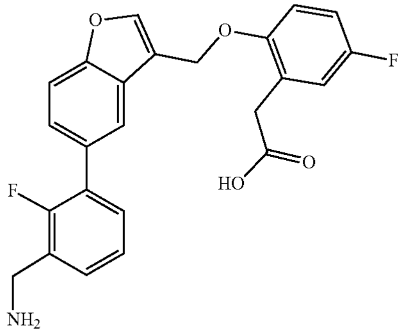
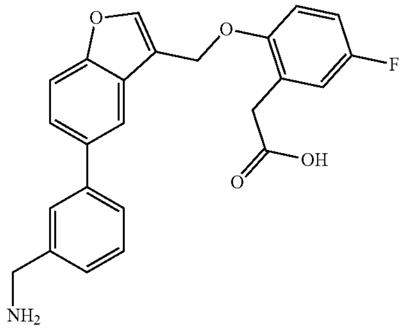
-continued
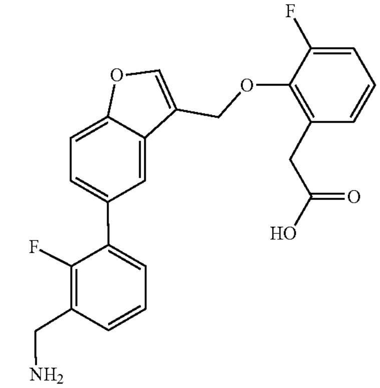
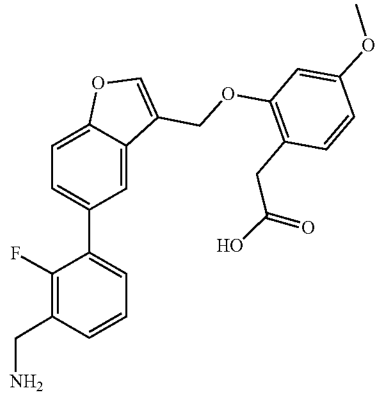
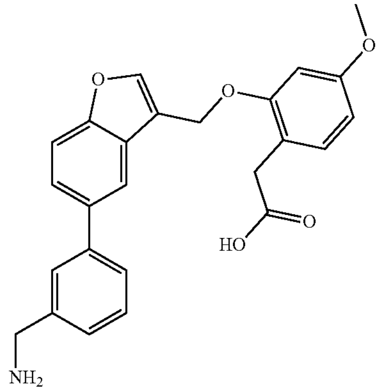
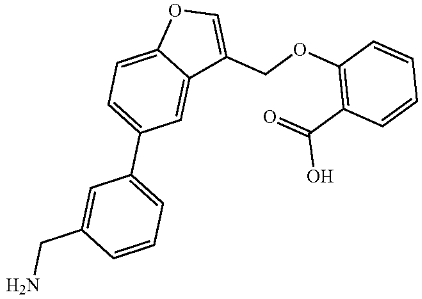

-continued
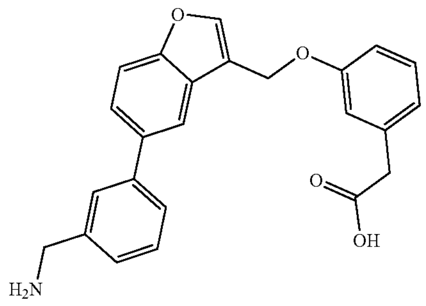
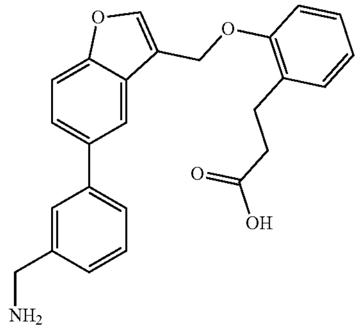
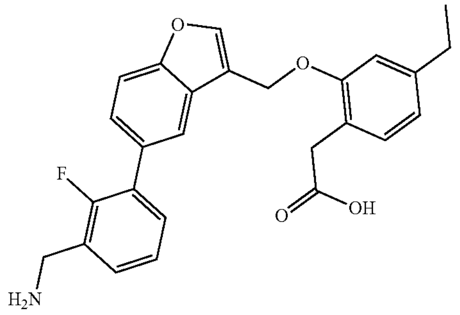
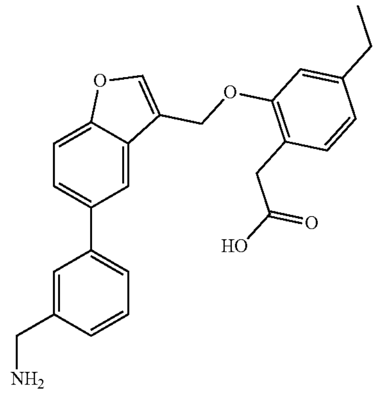
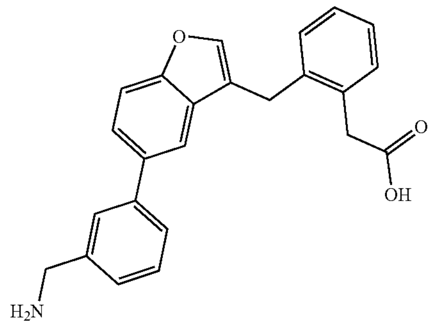
-continued
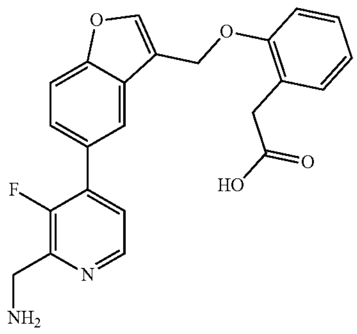
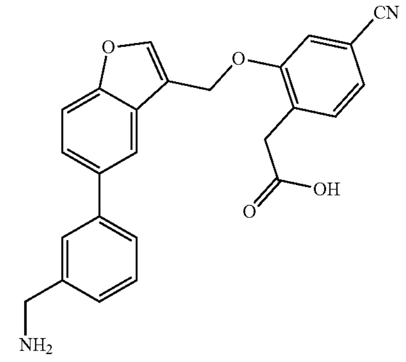
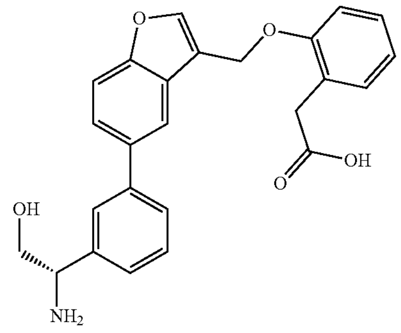
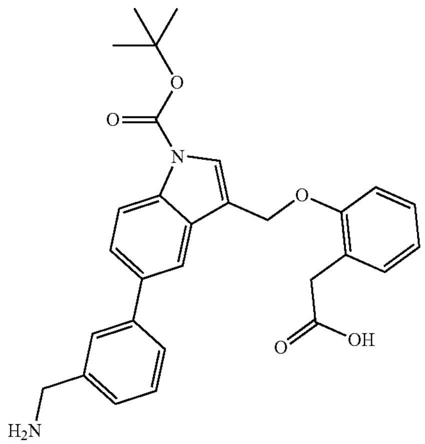

-continued
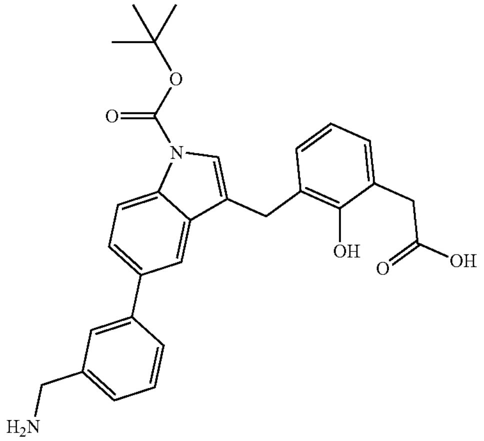
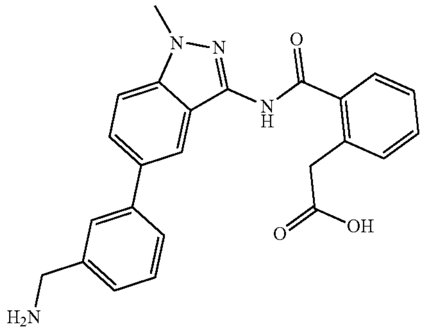
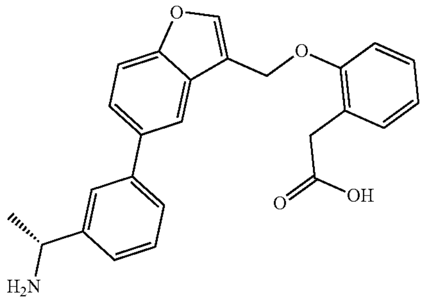
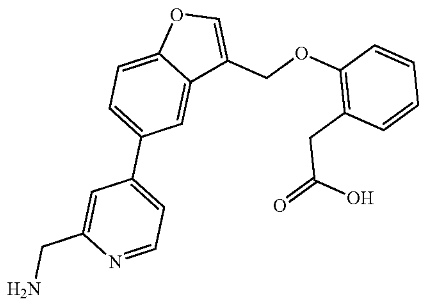
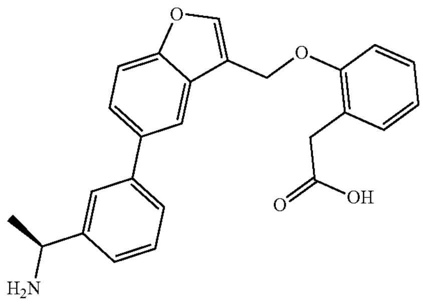
-continued
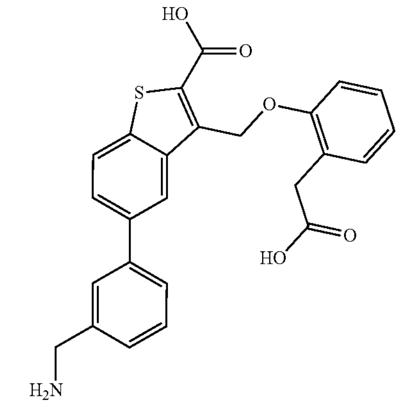
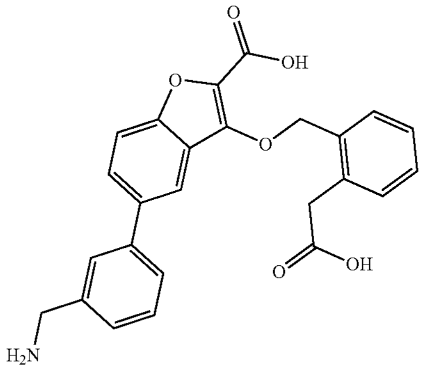
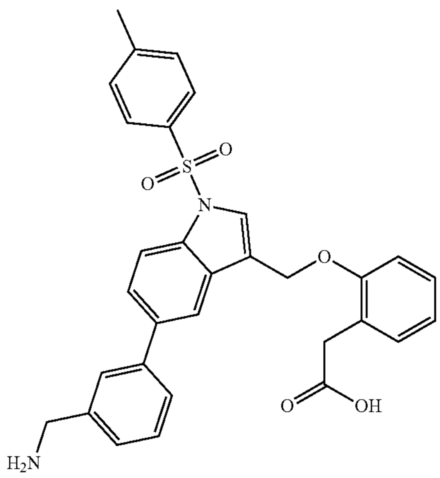
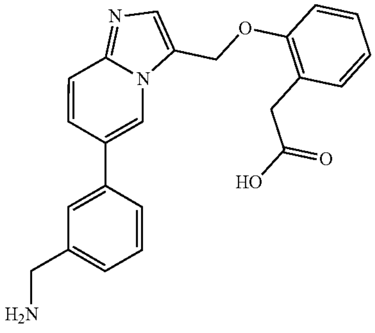

-continued
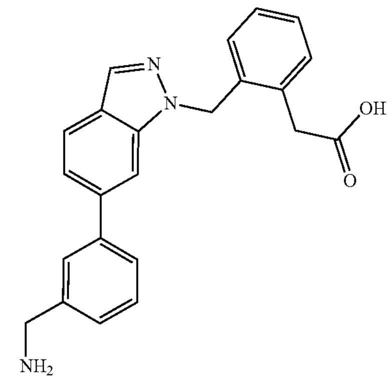
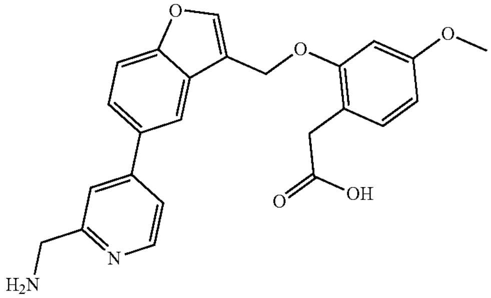
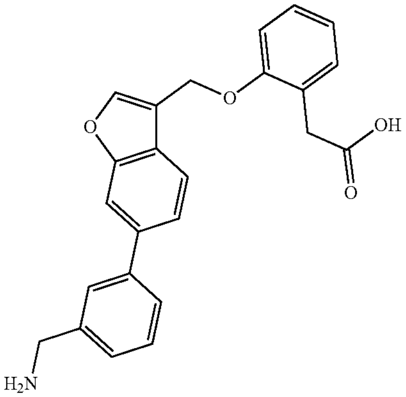
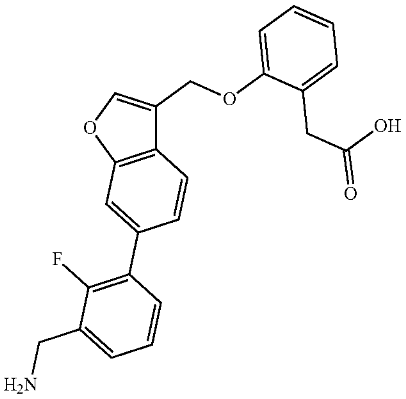
-continued
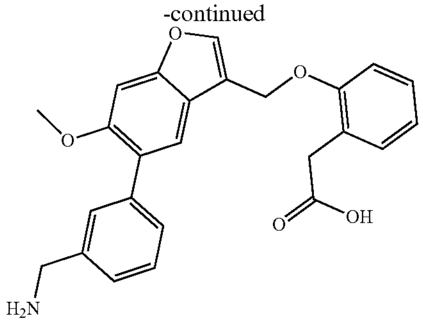
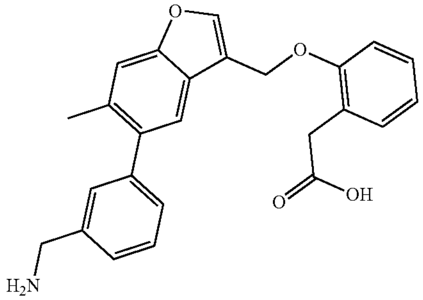
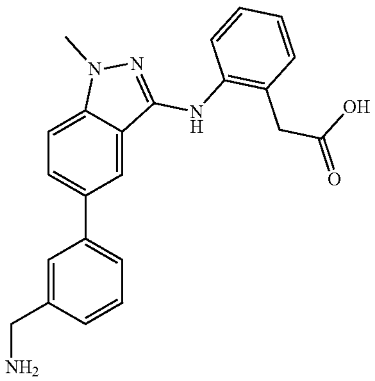
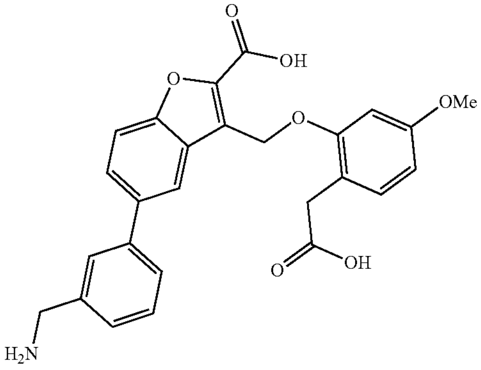
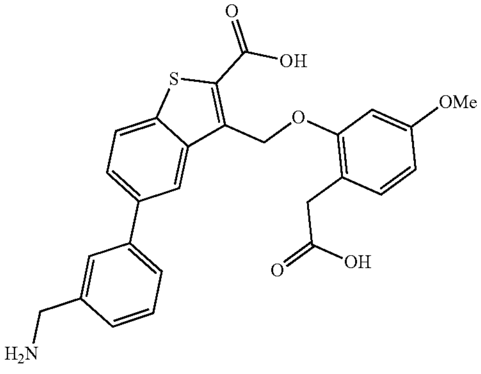

-continued
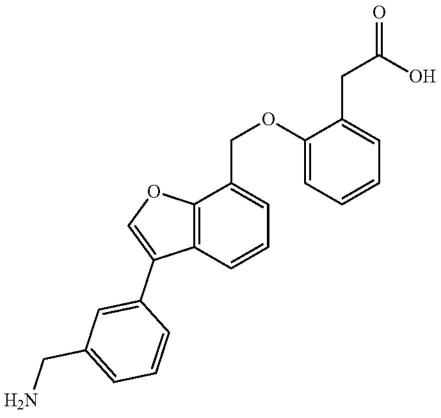
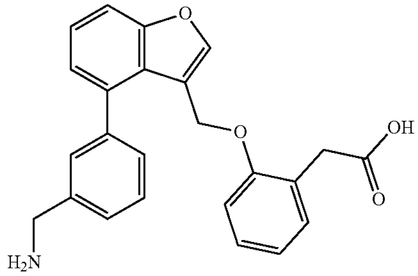
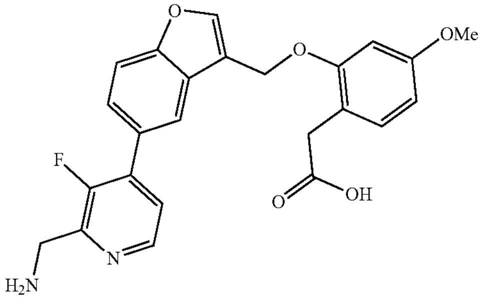
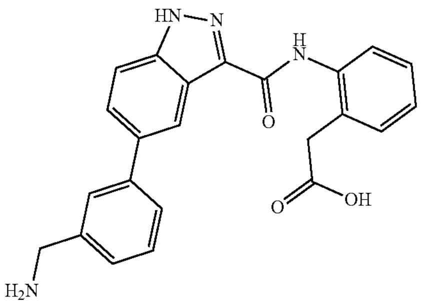
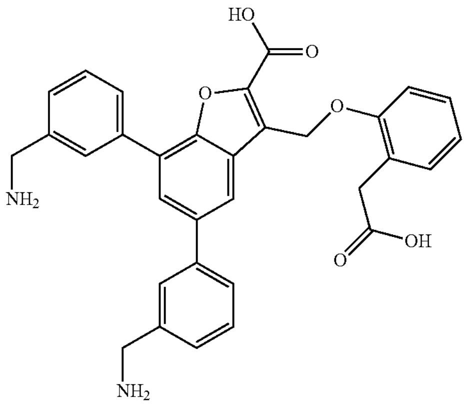
-continued
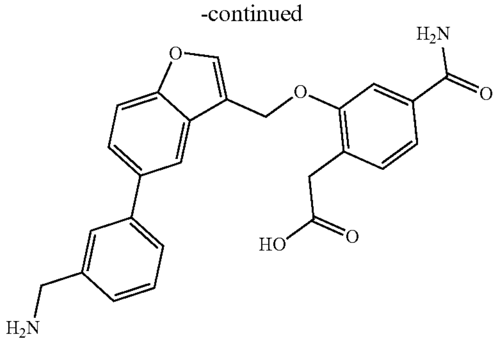
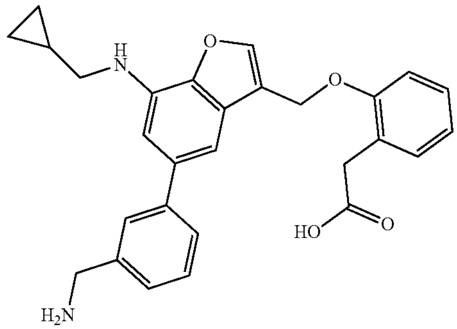
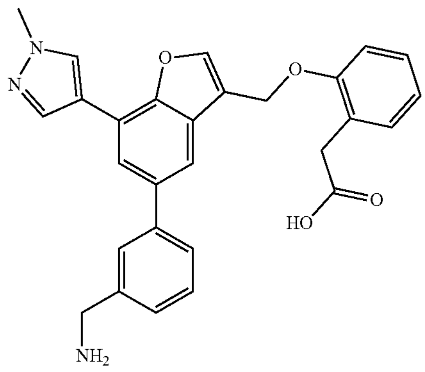
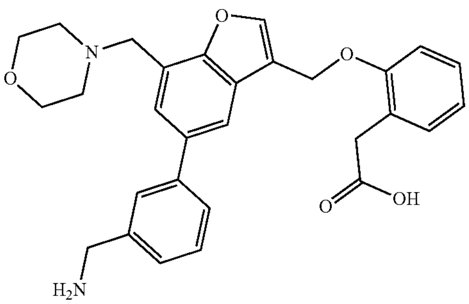
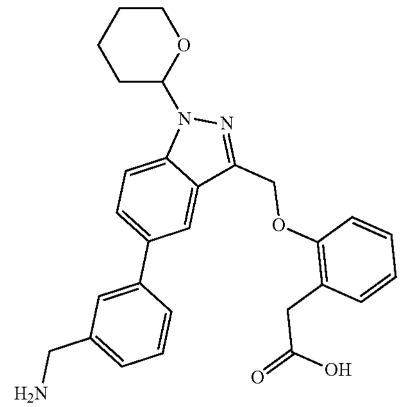

-continued
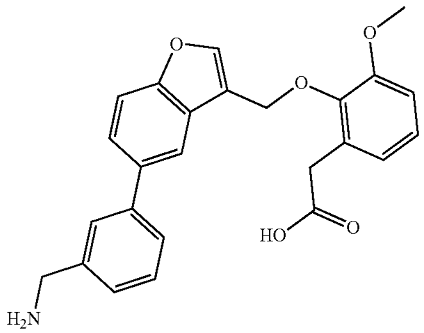
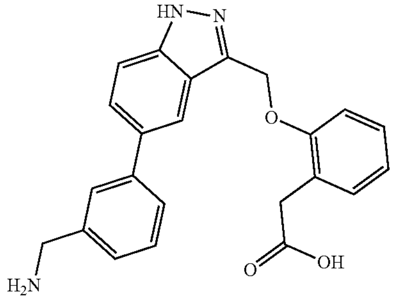
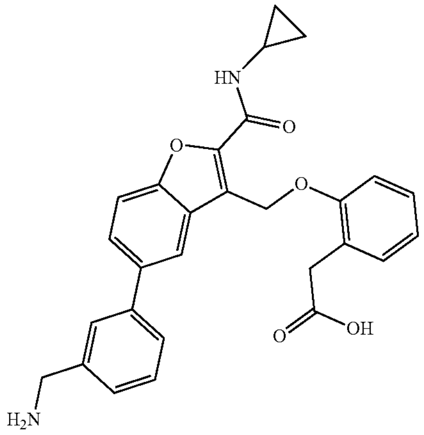
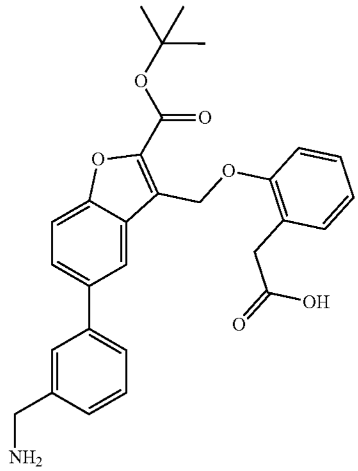
-continued
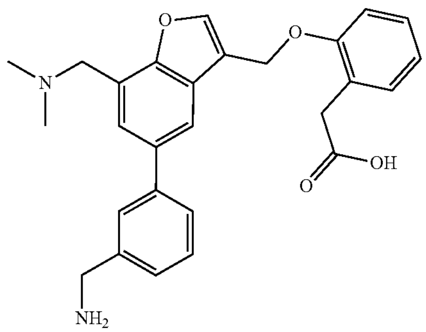
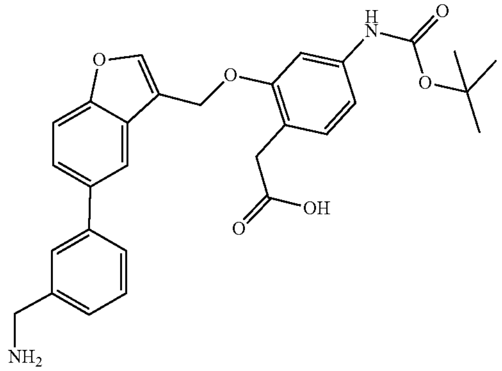
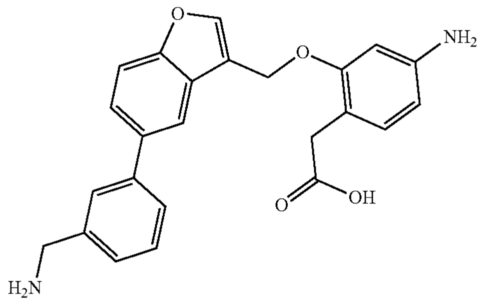
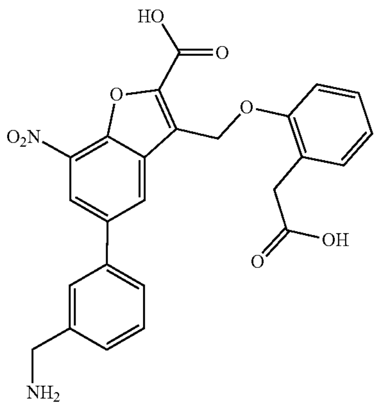

-continued
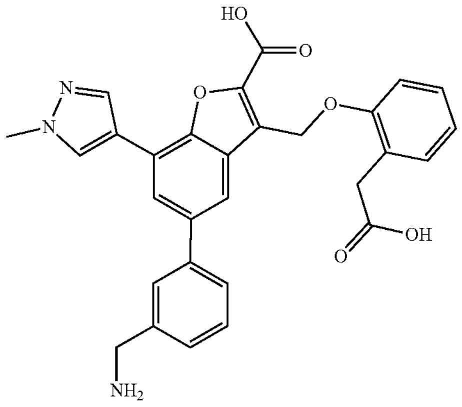
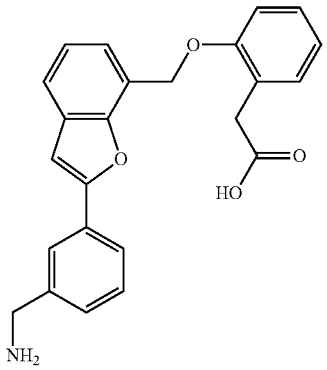
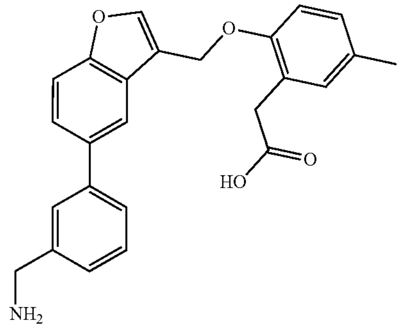
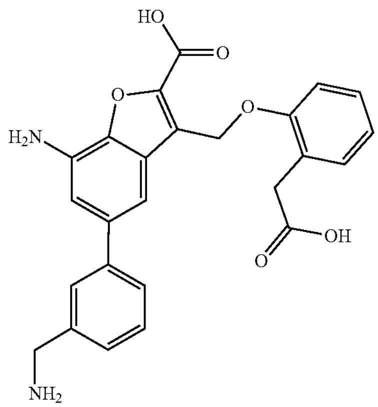
-continued
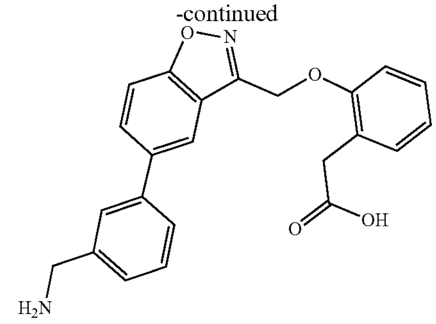
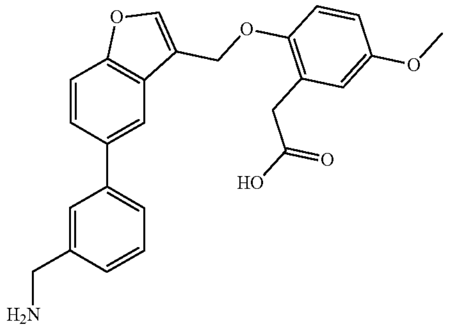
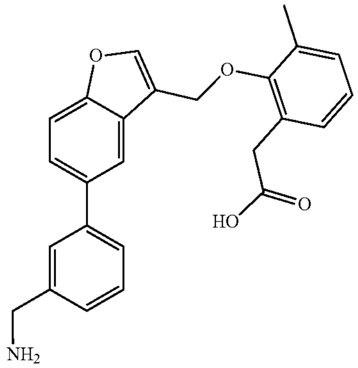
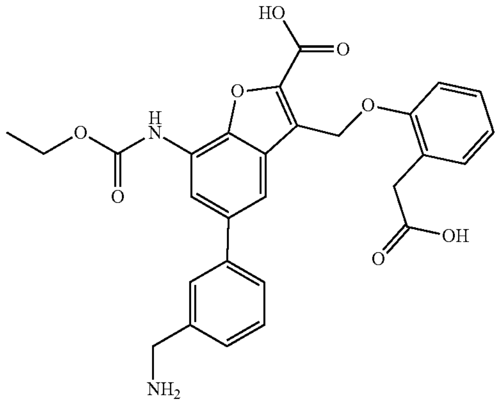
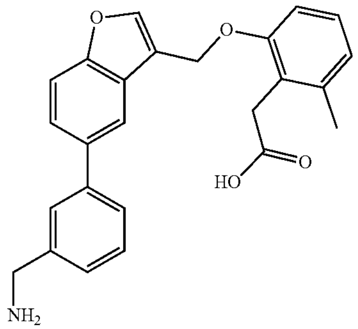

-continued
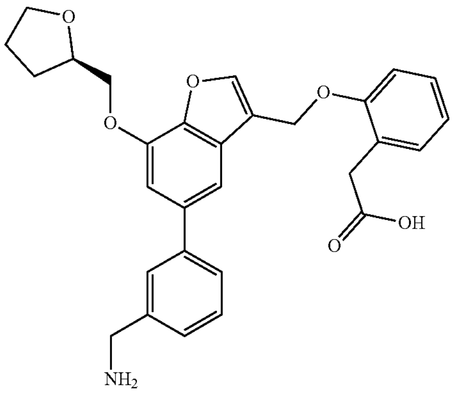
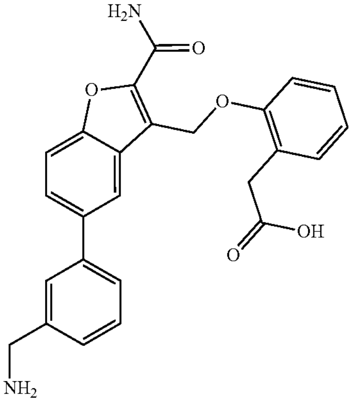
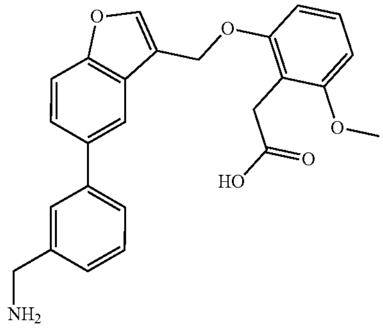
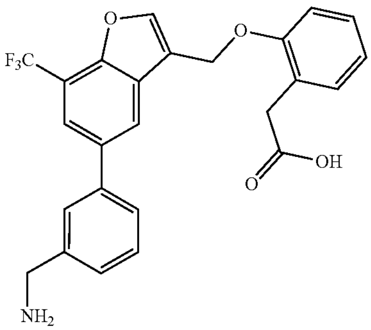
-continued
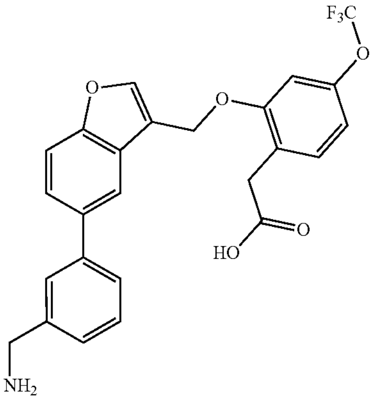
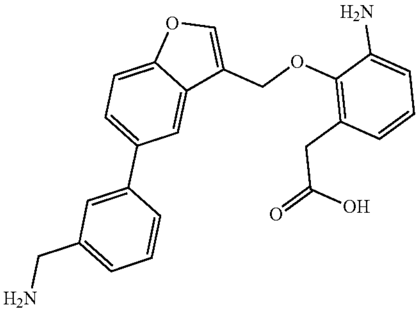
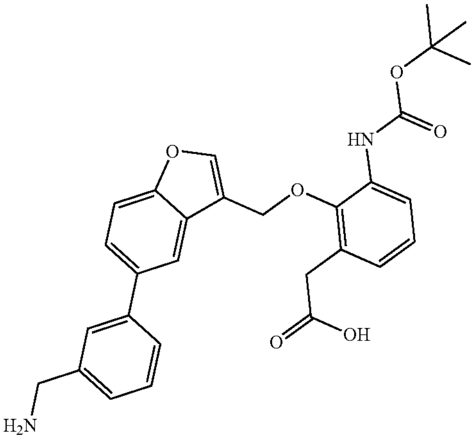
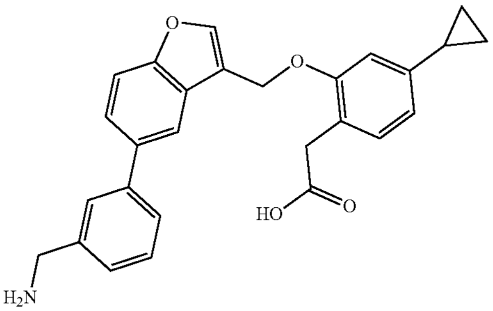

-continued
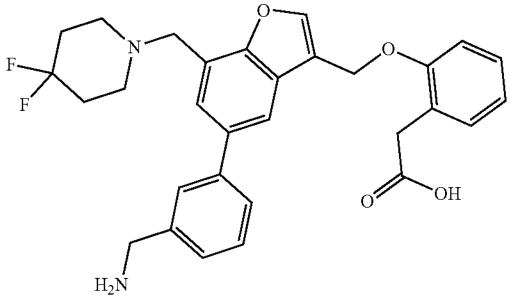
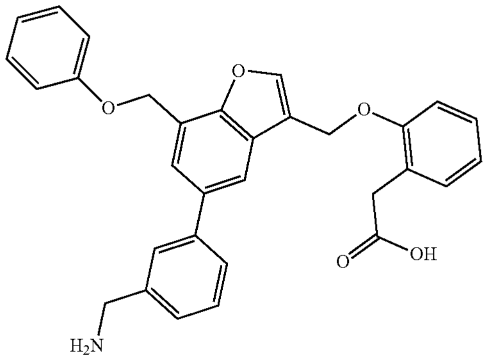
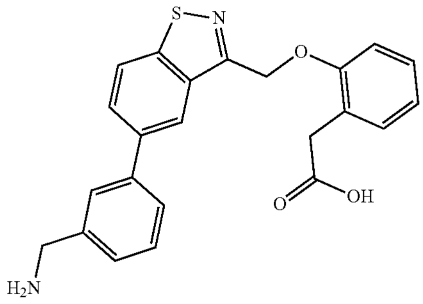
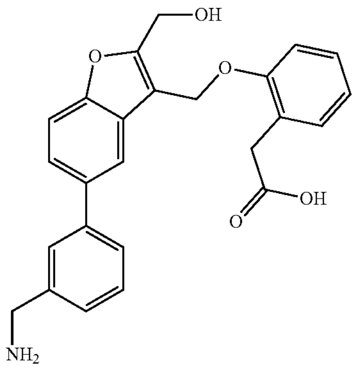
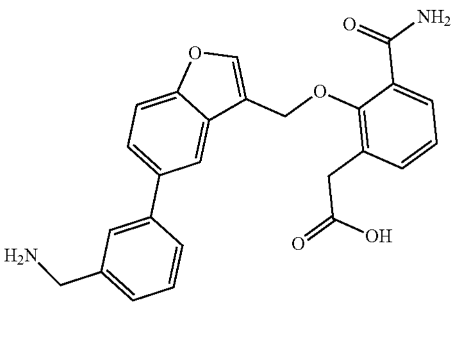
-continued
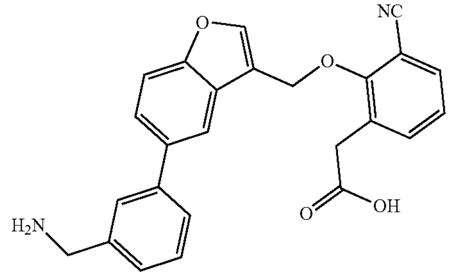
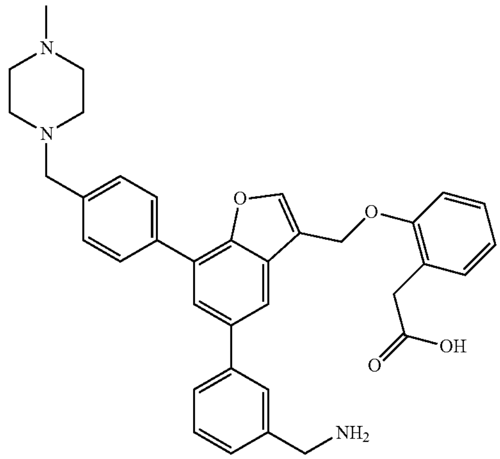
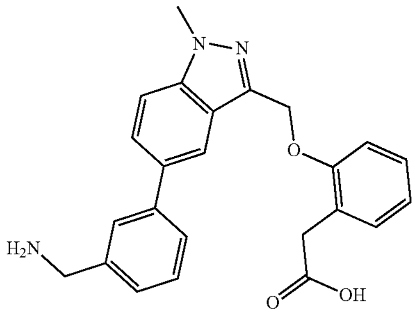
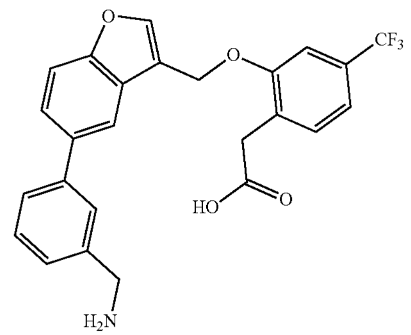
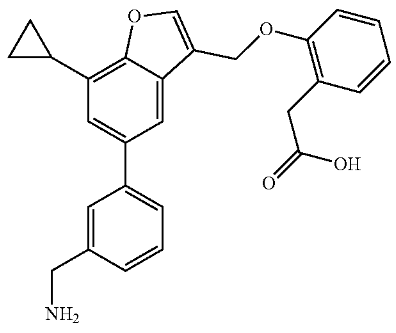

-continued
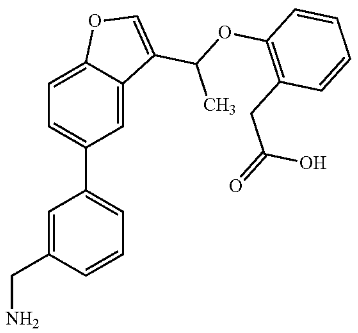
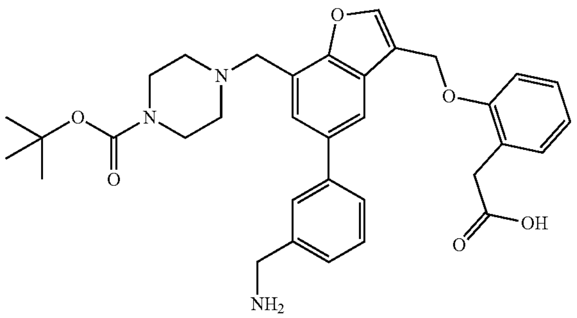
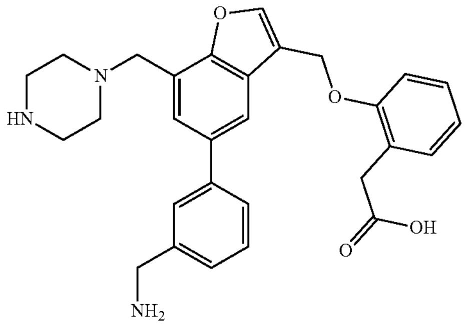
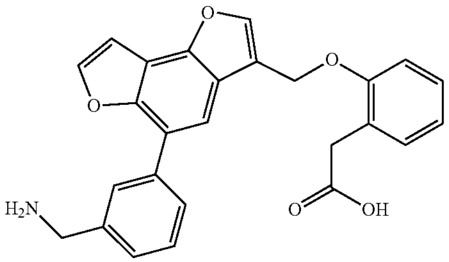
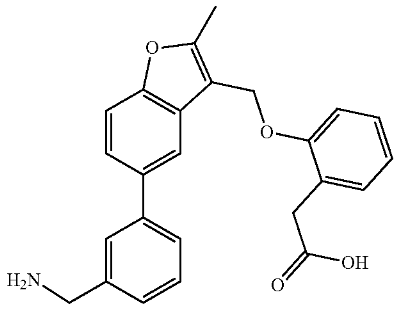
-continued
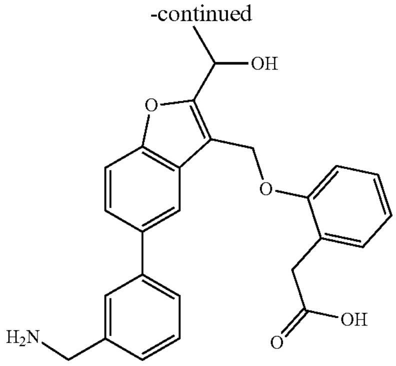
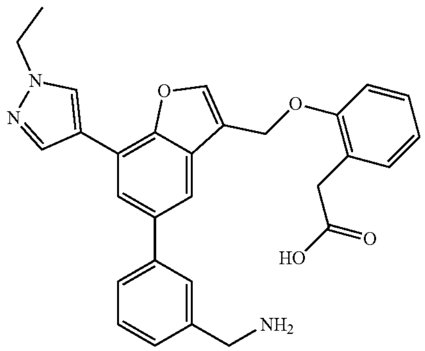
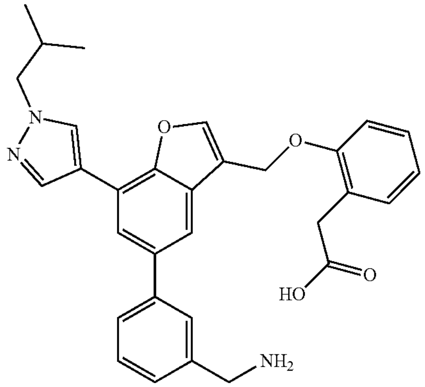
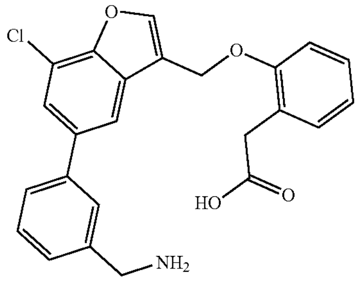
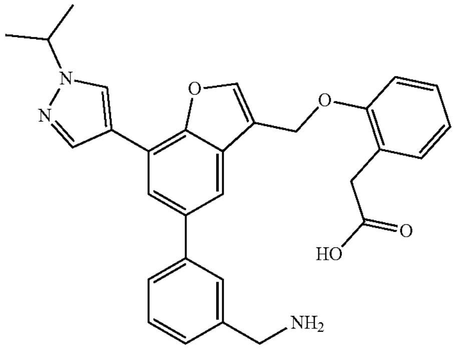

-continued
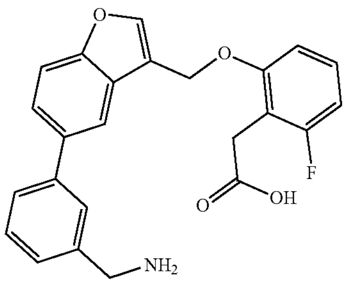
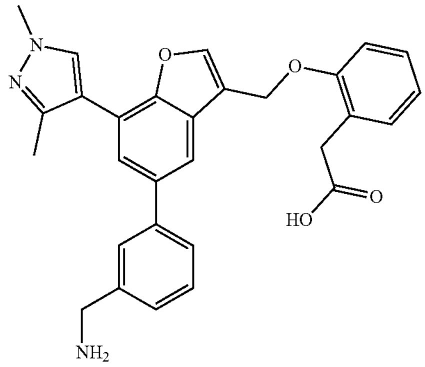
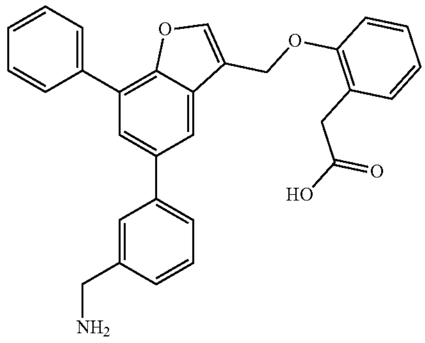
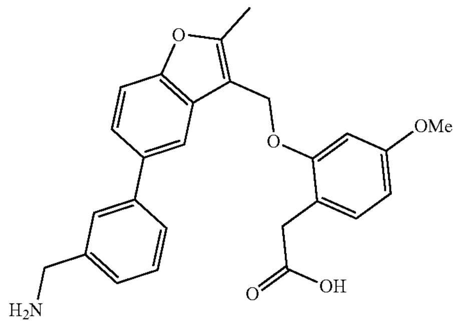
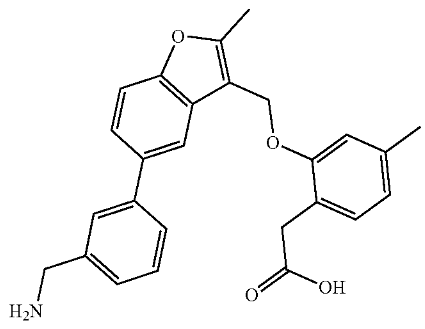
-continued
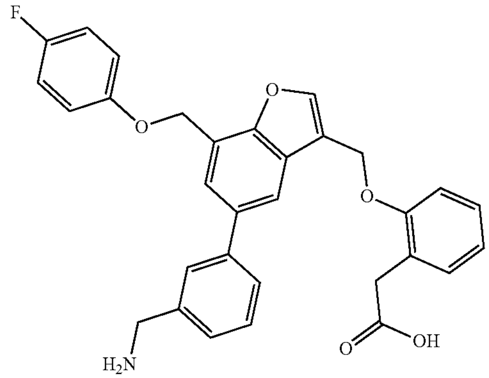
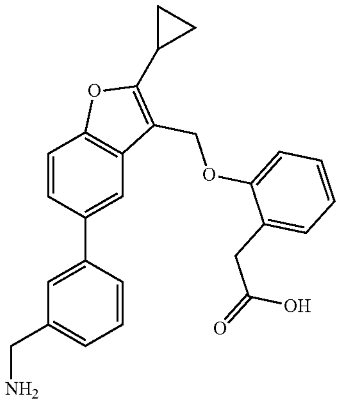
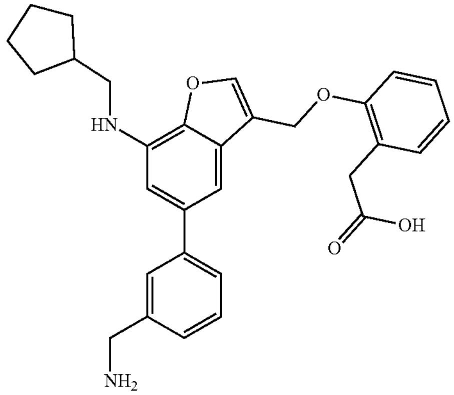
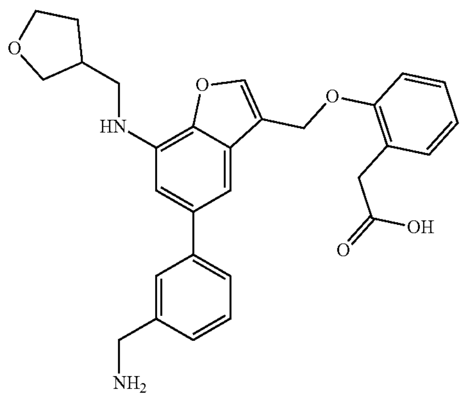

-continued
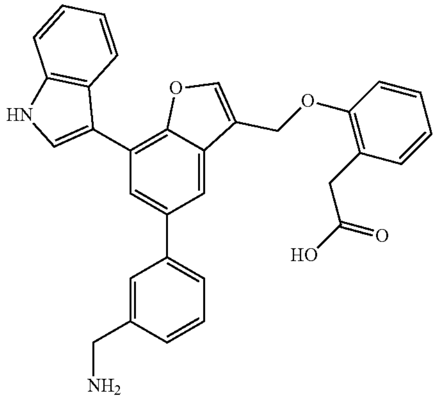
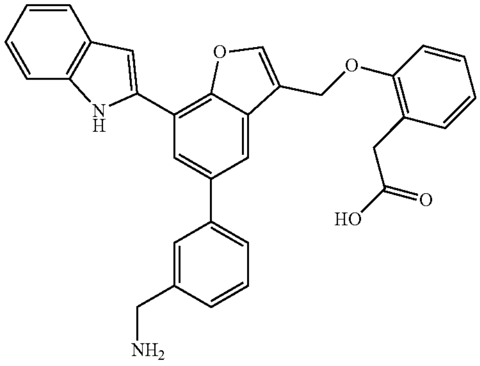
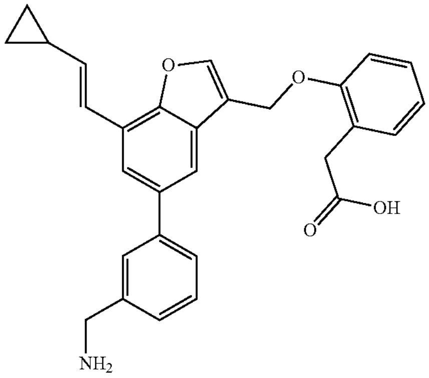
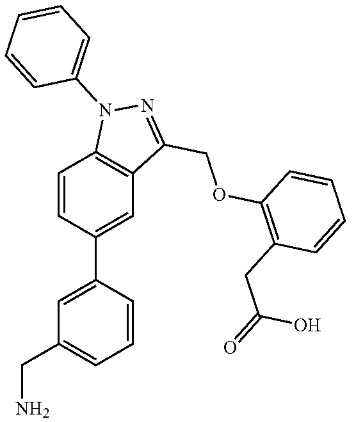
-continued
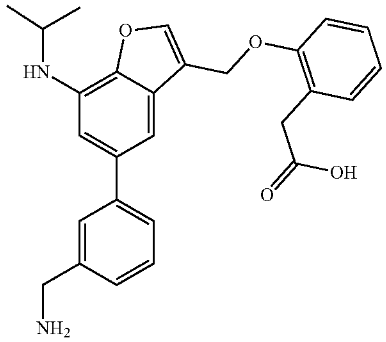
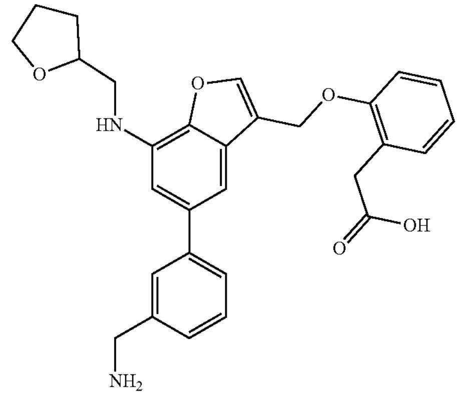
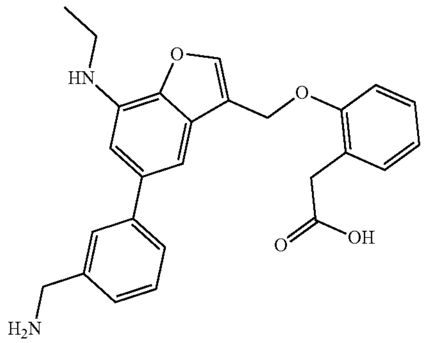
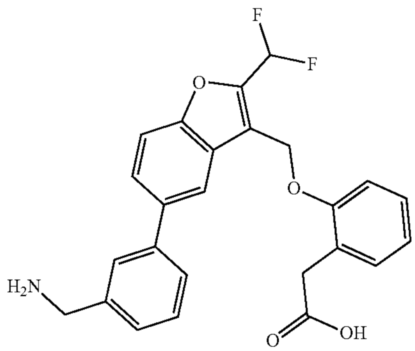

-continued
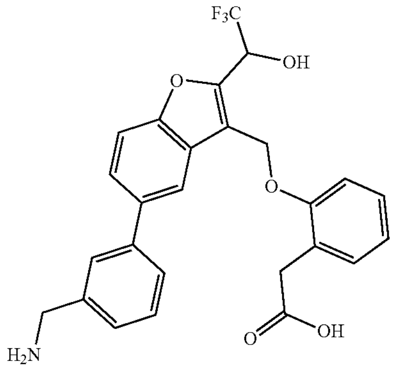
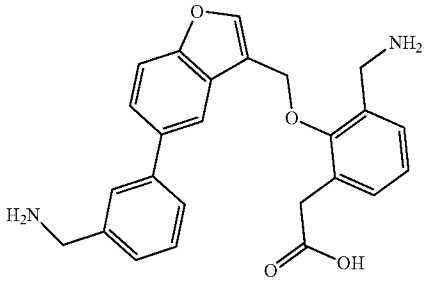
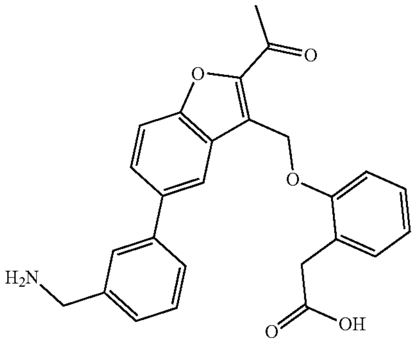
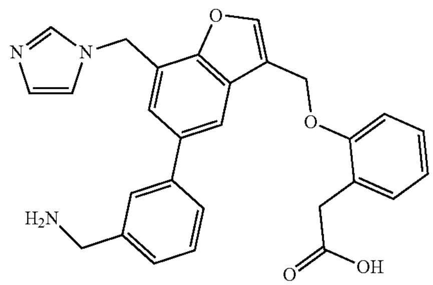
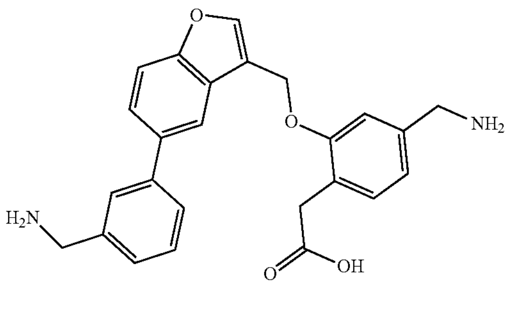
-continued
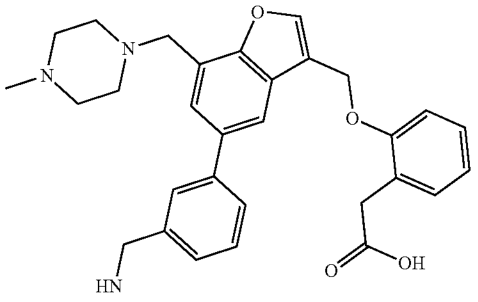
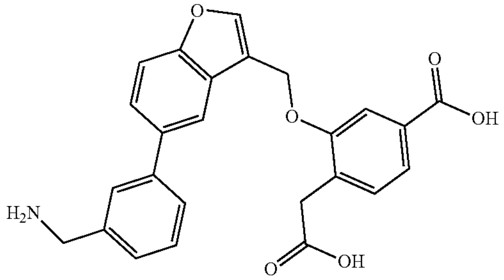
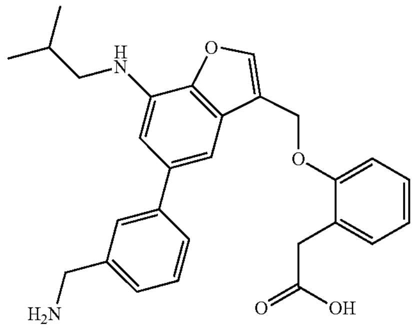
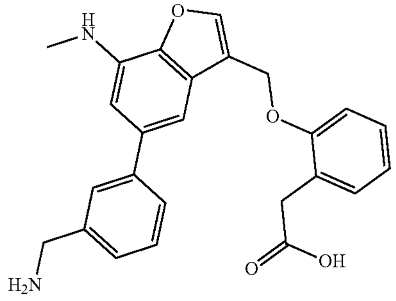
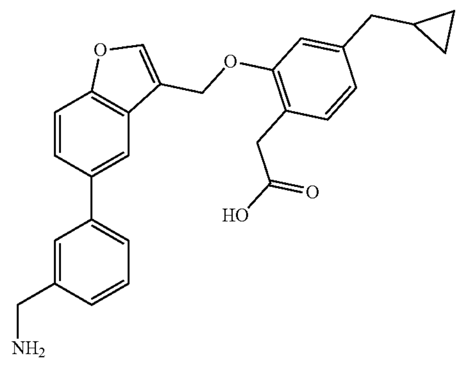

-continued
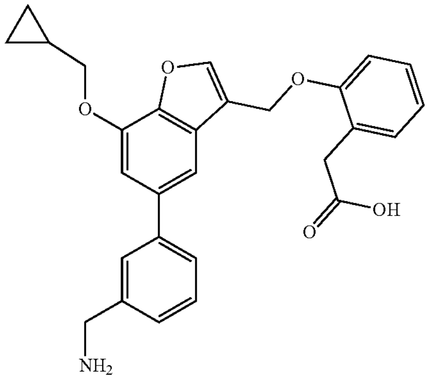
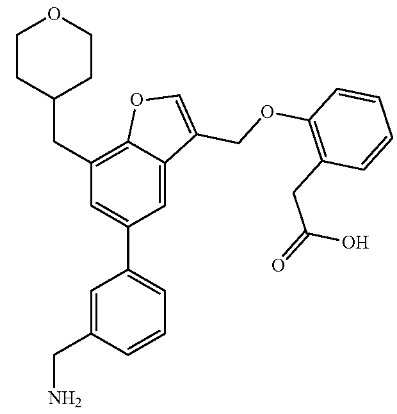
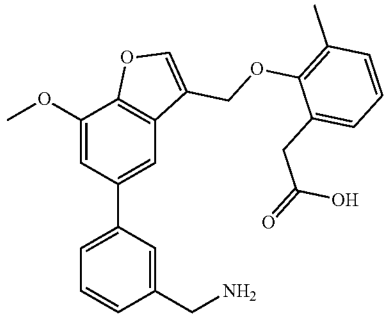
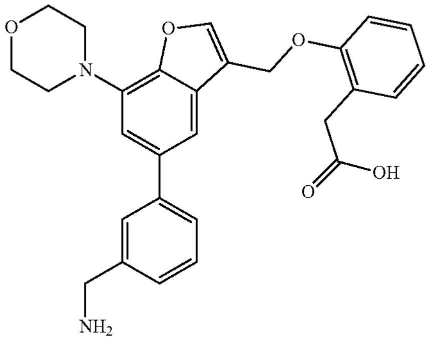
-continued
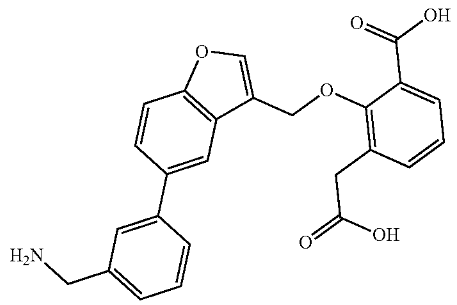
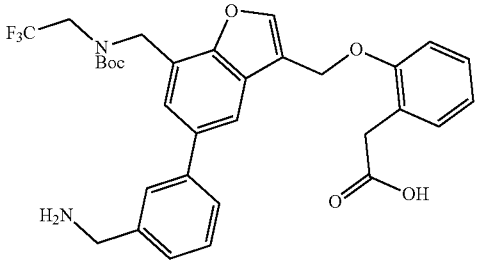
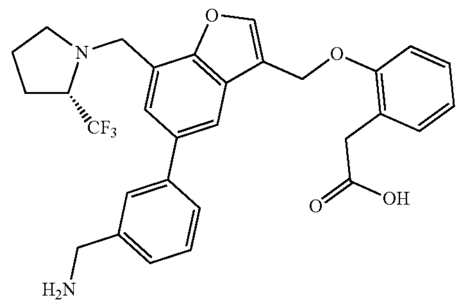
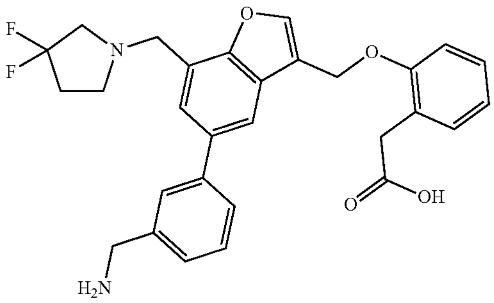
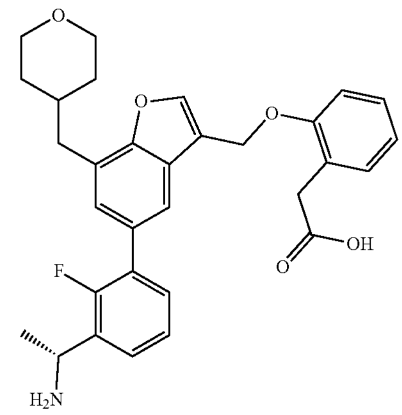

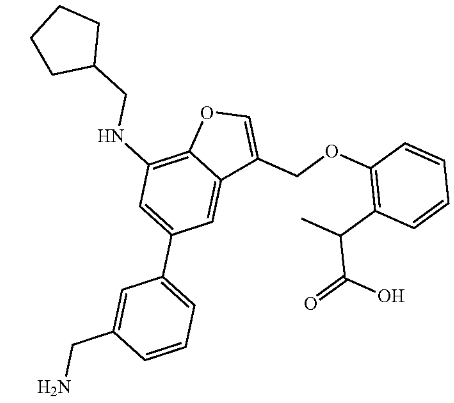
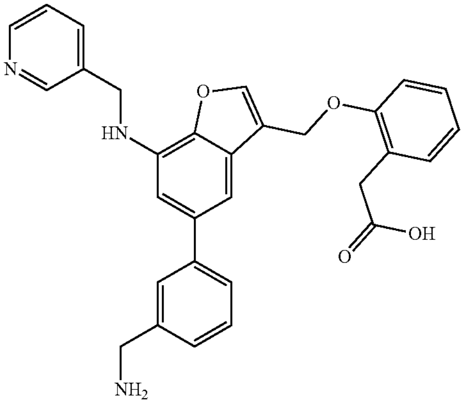
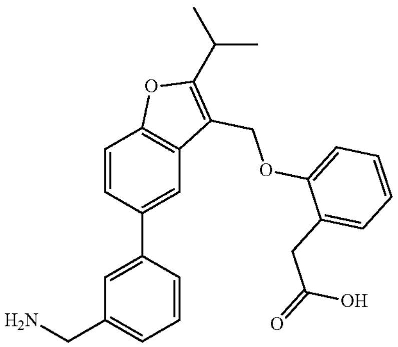
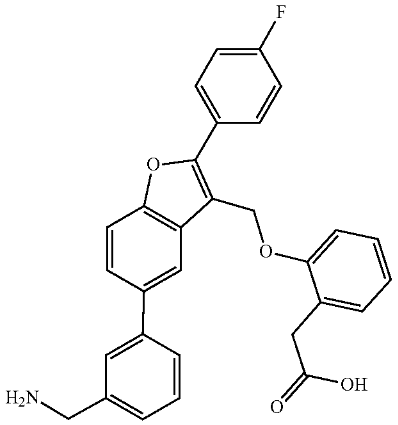
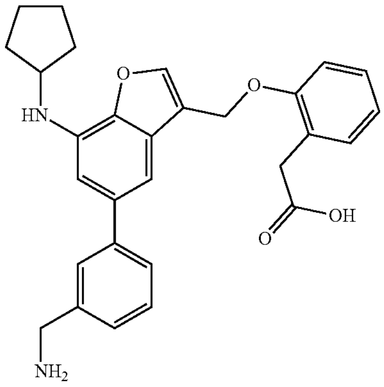
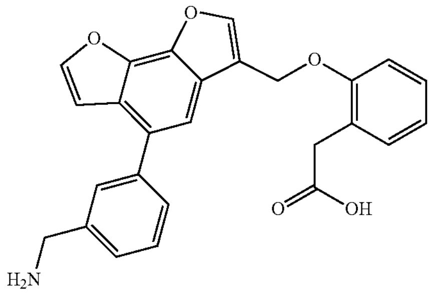
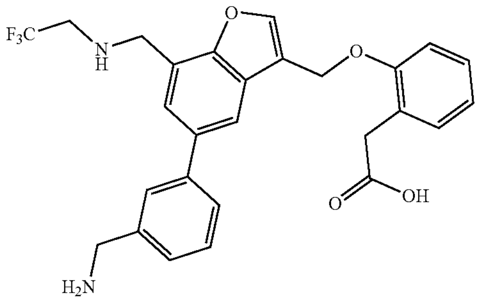
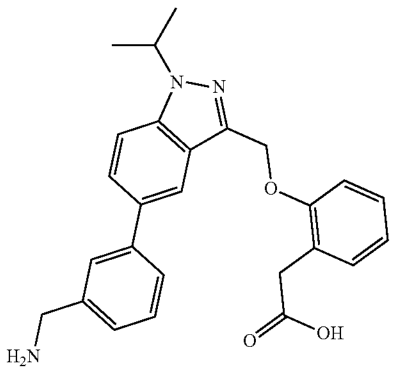

-continued
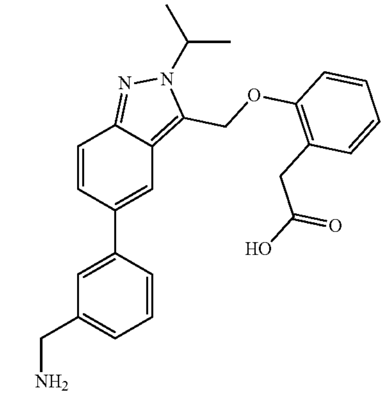
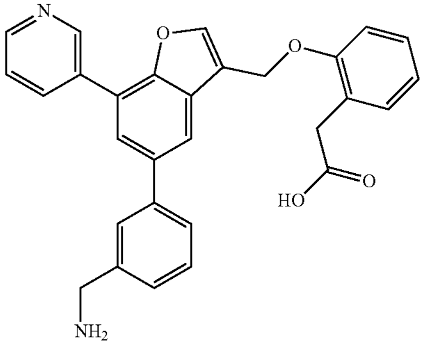
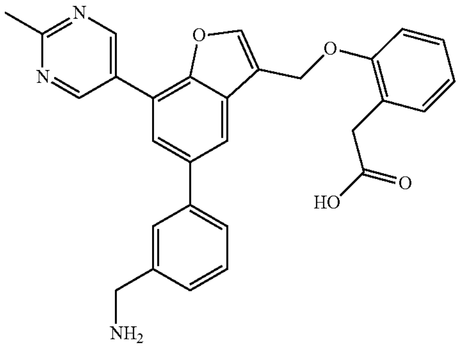
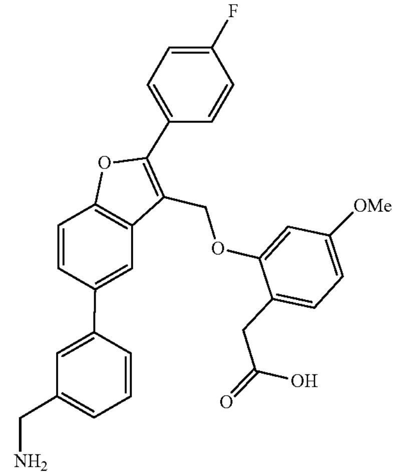
-continued
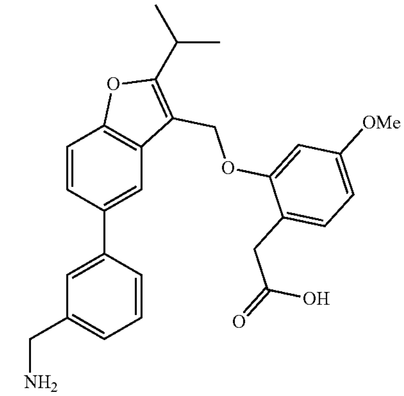
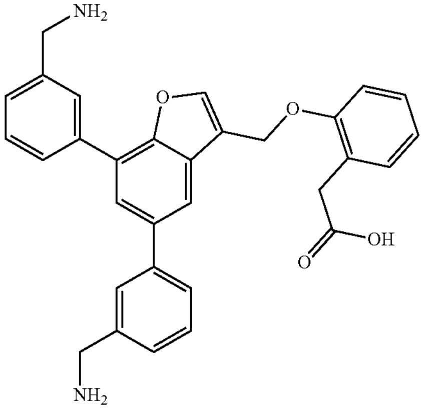
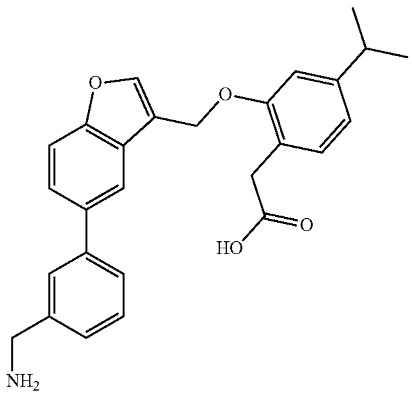
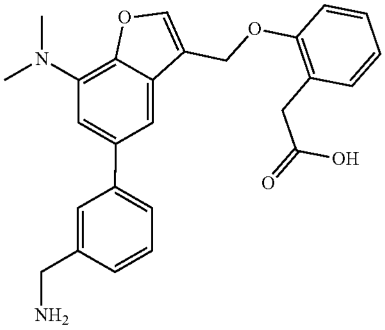

-continued
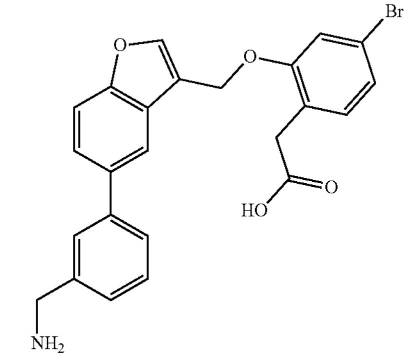
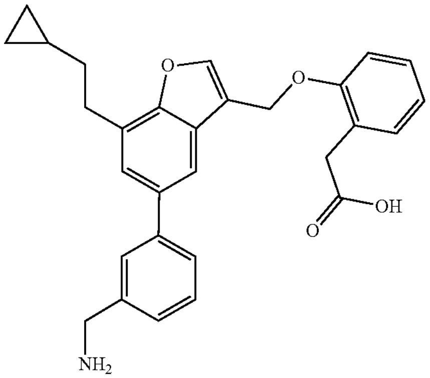
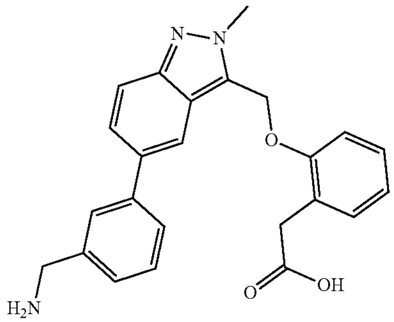
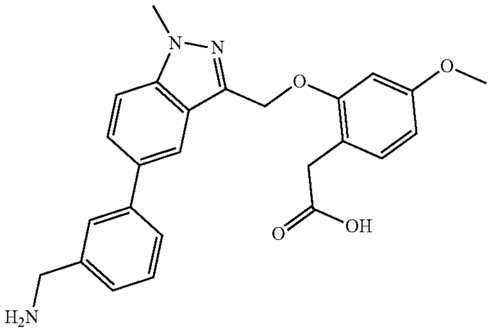
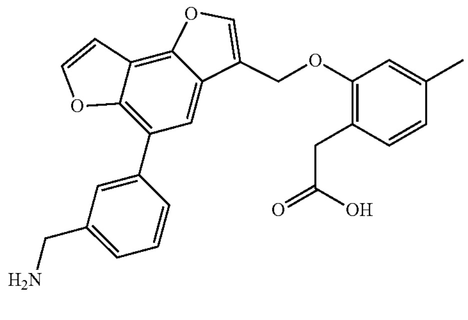
-continued
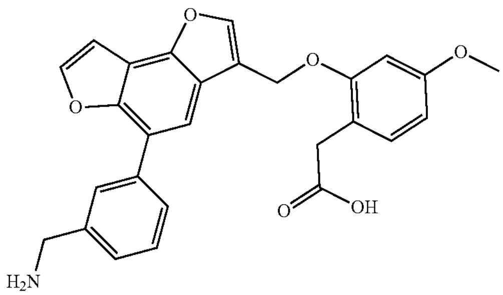
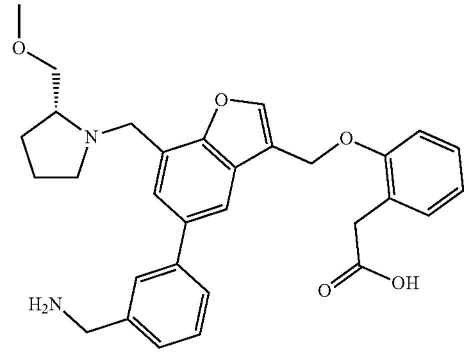
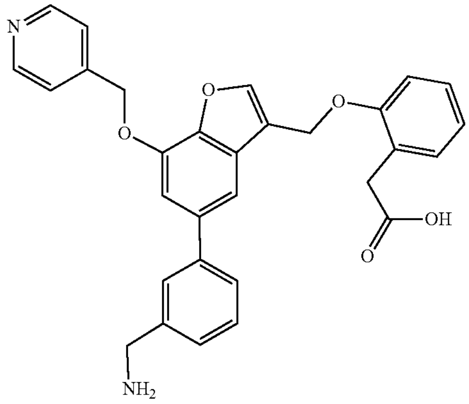
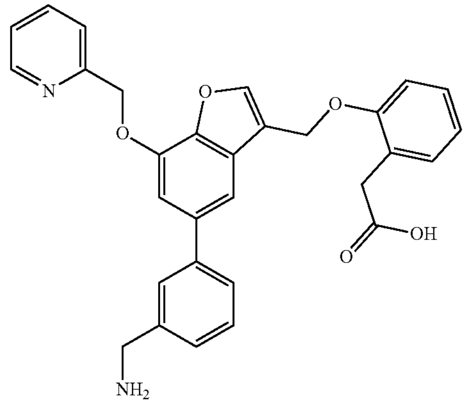

-continued
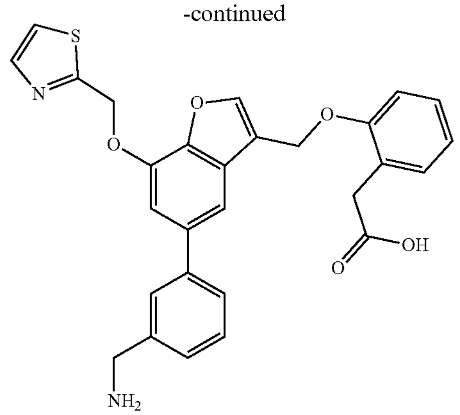
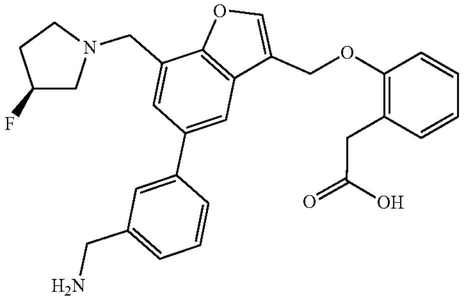
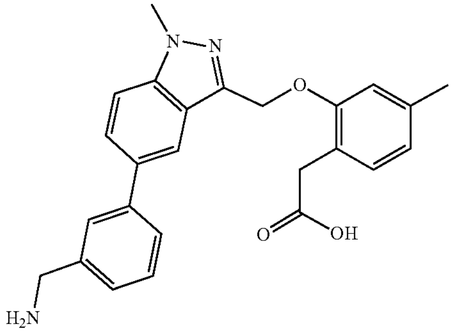
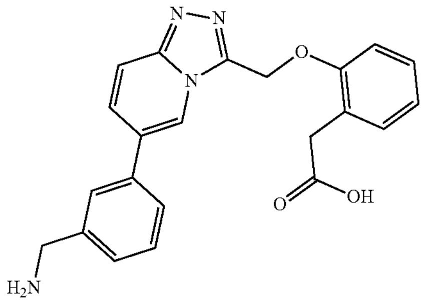
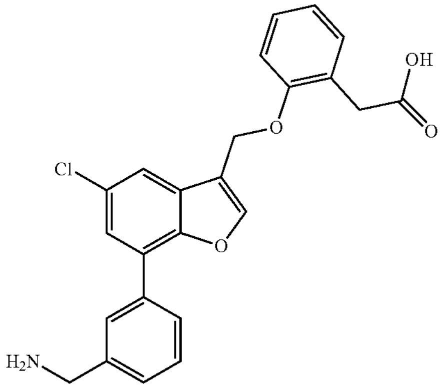
-continued
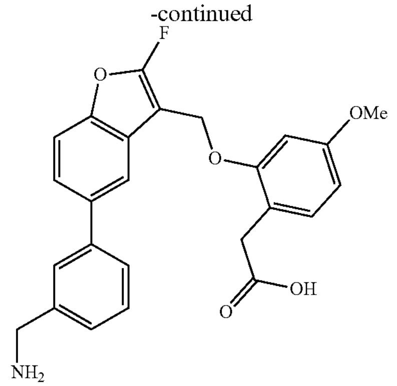
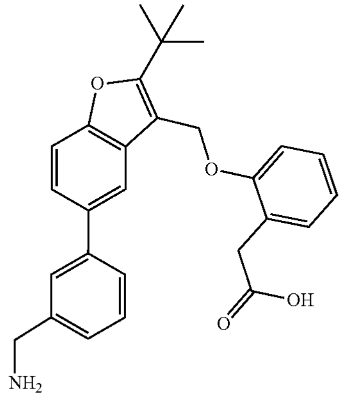
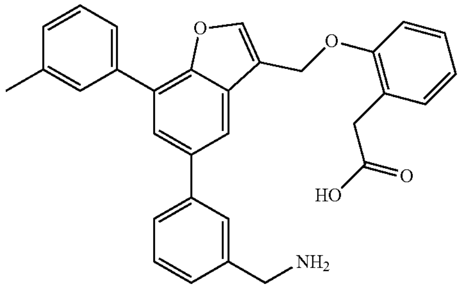
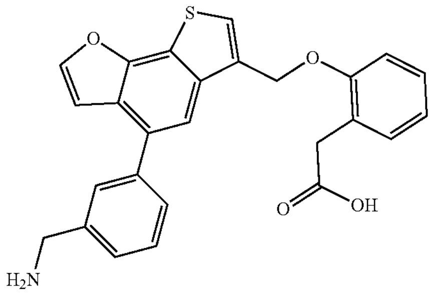
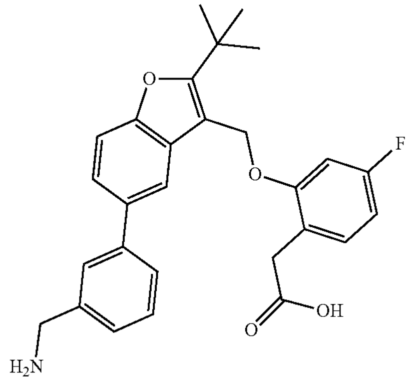

-continued
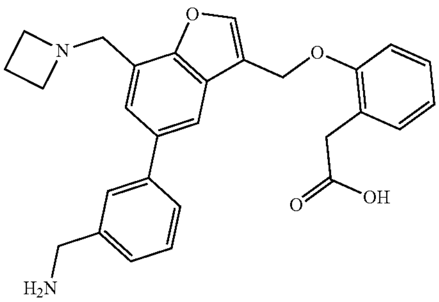
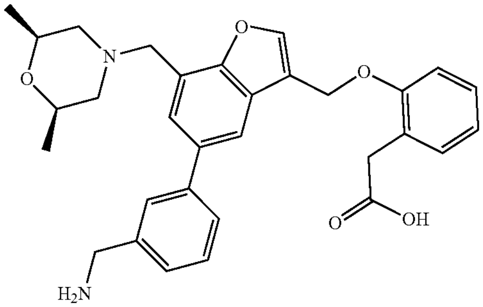
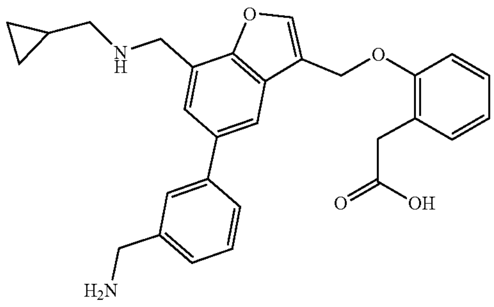
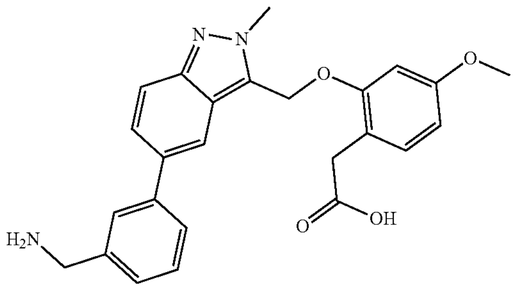
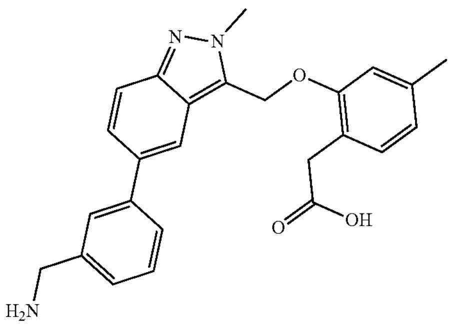
-continued
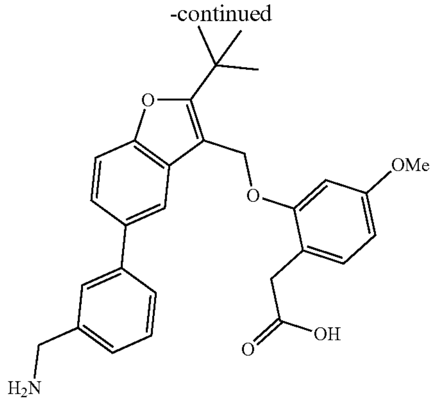
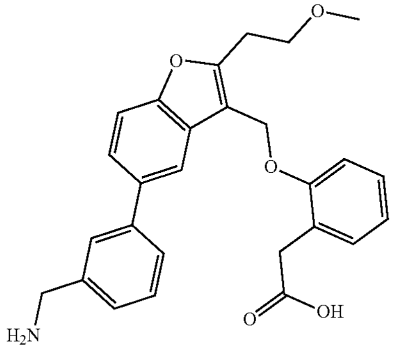
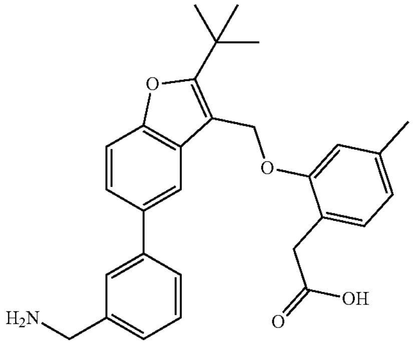
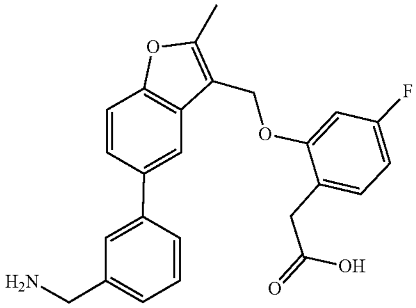
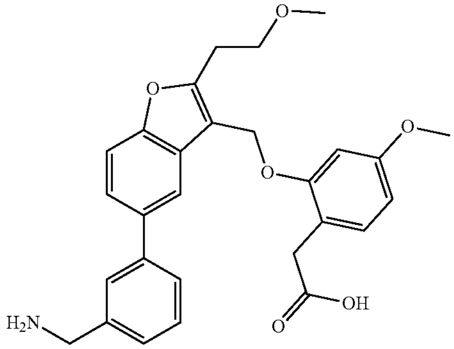

-continued
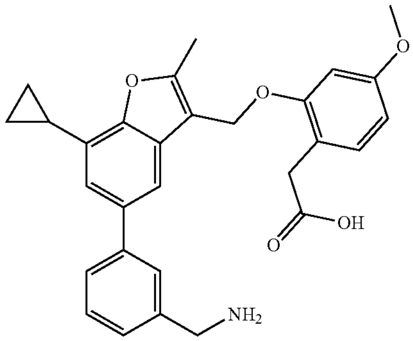
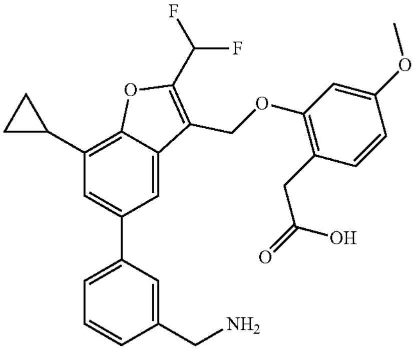
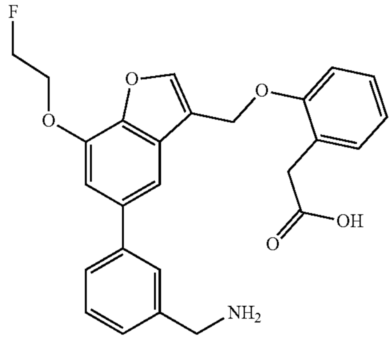
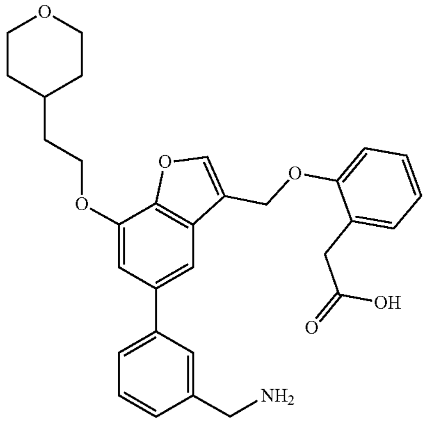
-continued
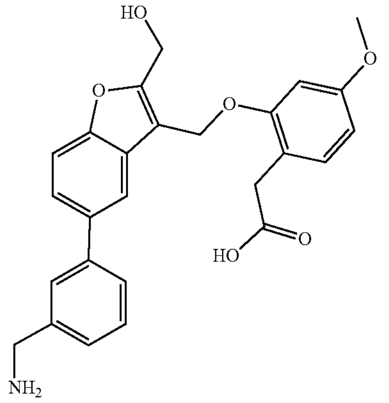
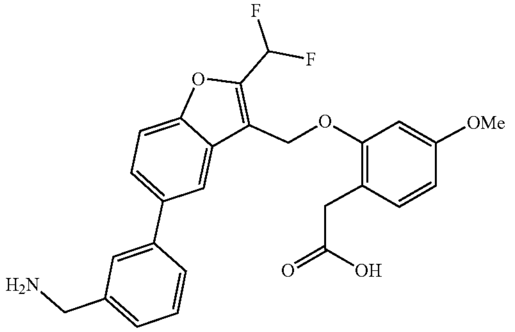
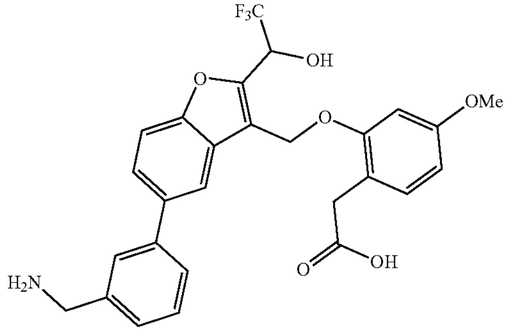
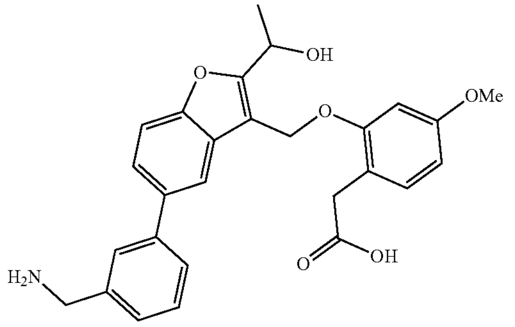
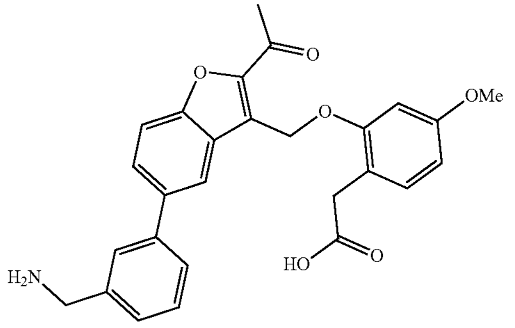

-continued
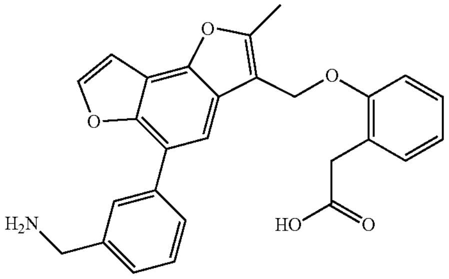
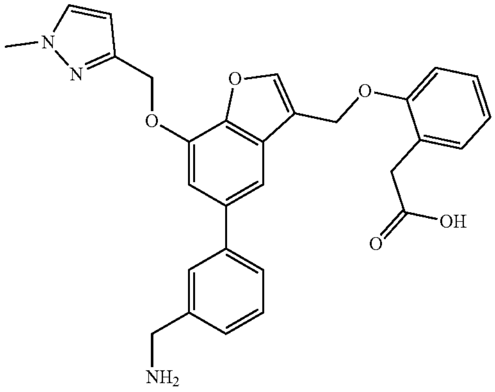
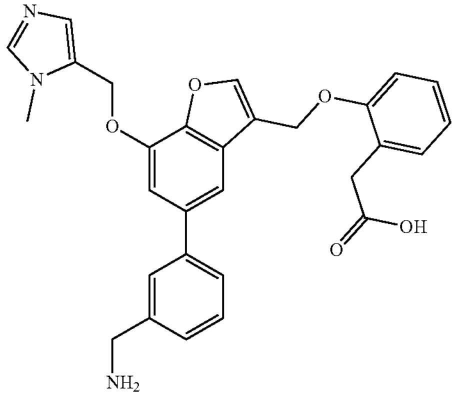
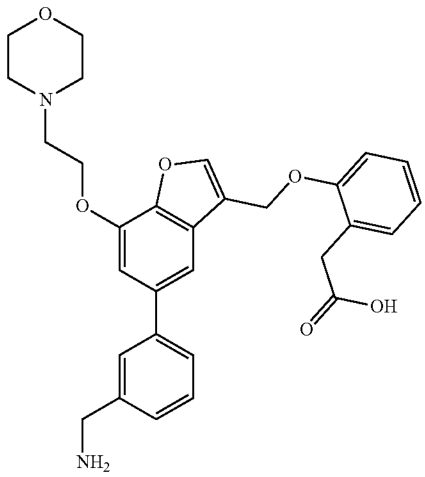
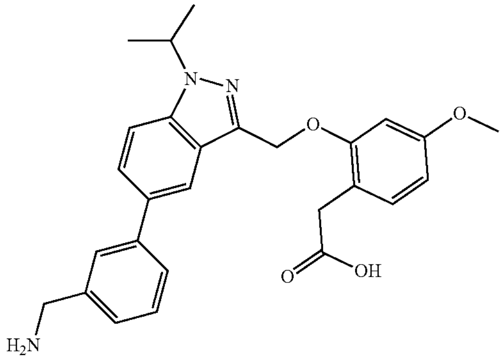
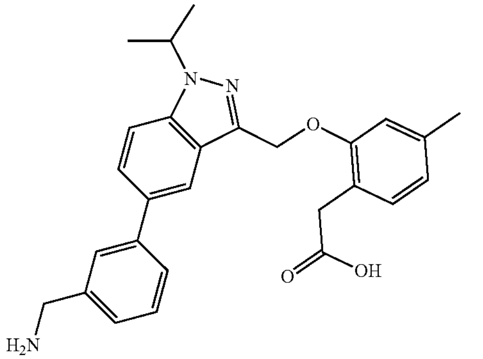
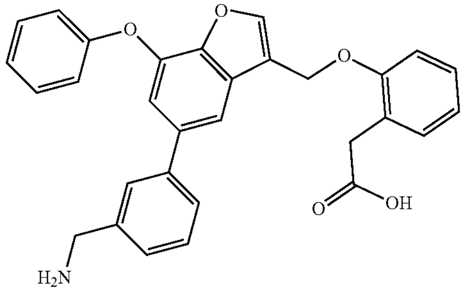
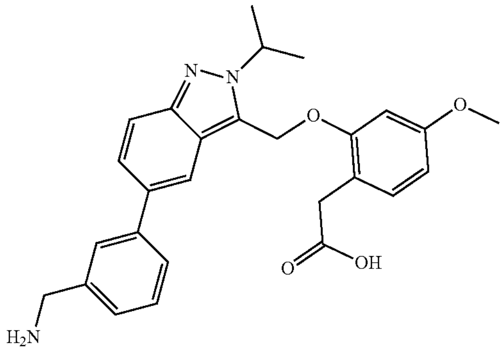
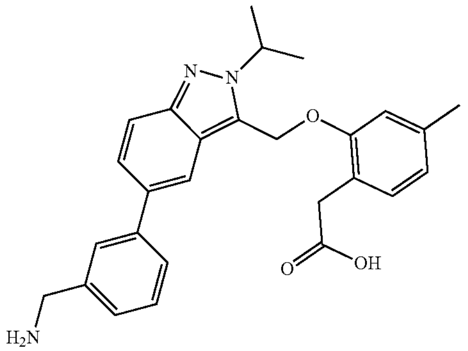

-continued
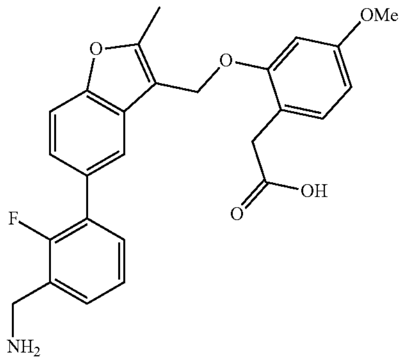
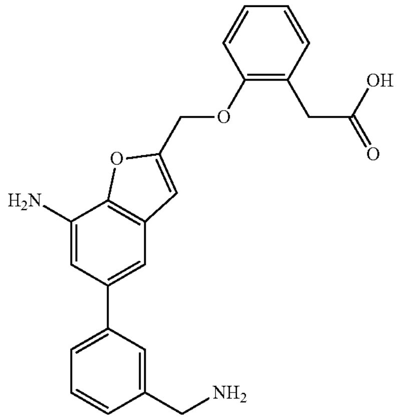
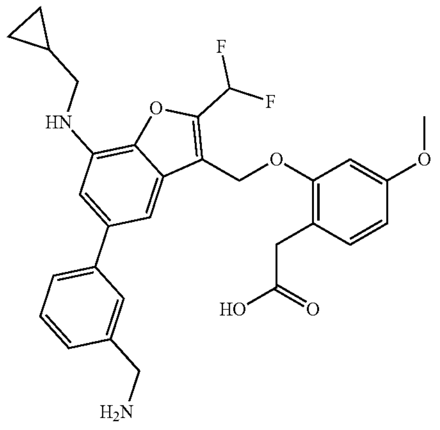
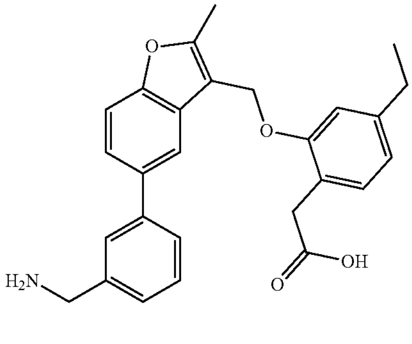
-continued
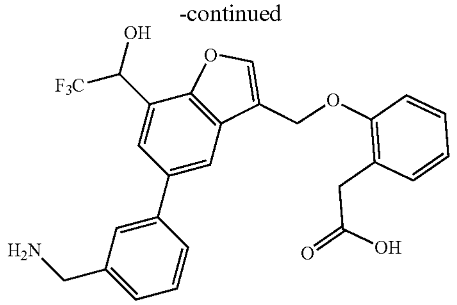
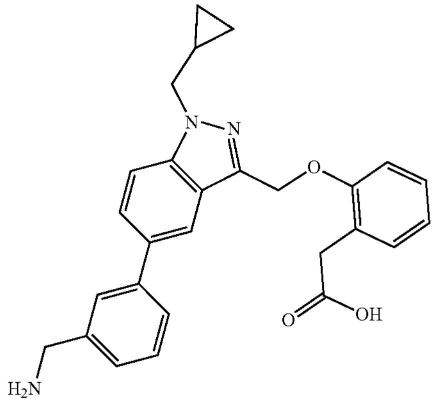
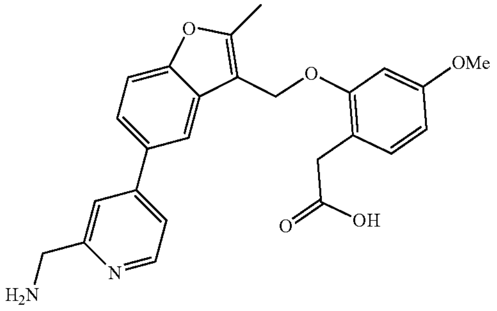
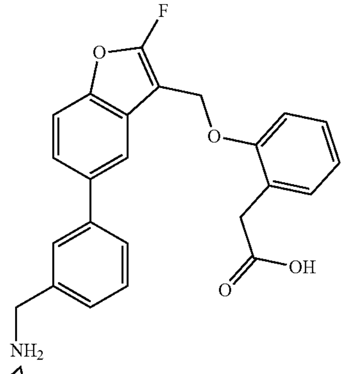
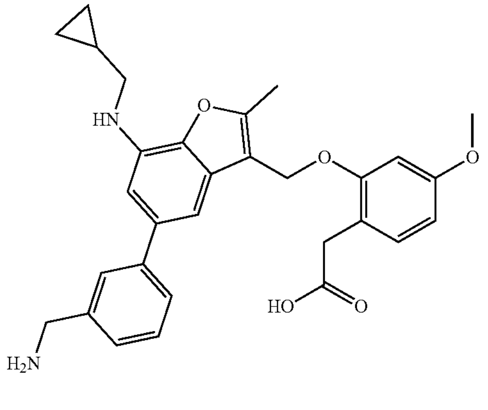

-continued
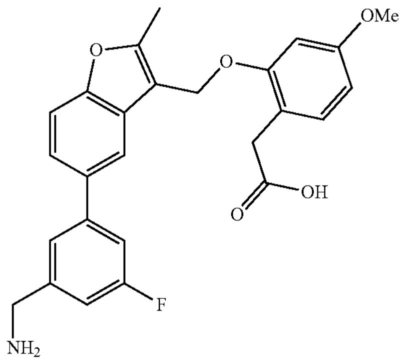
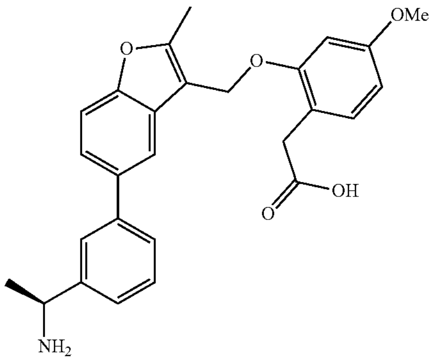
(+)-isomer
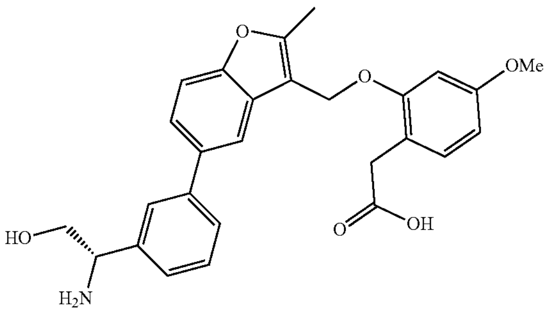
(+)-isomer
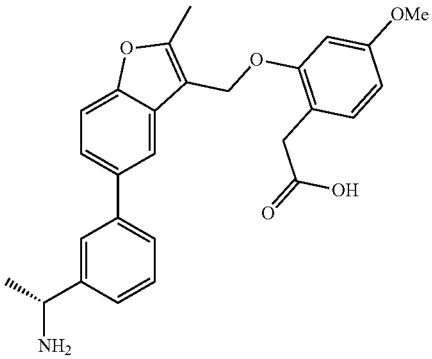
-continued
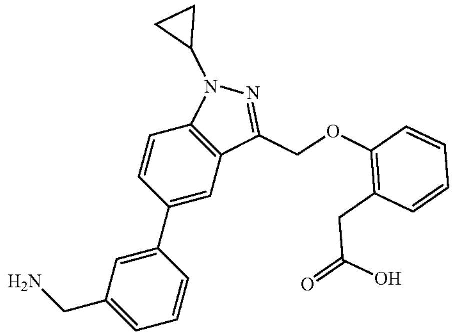
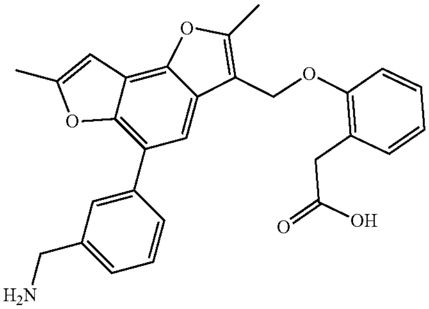
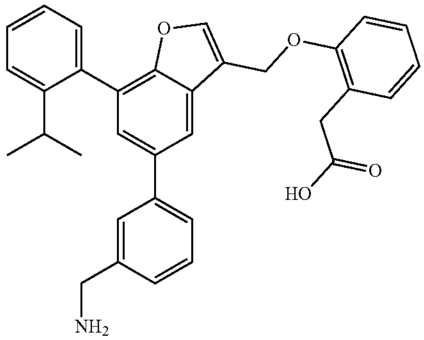
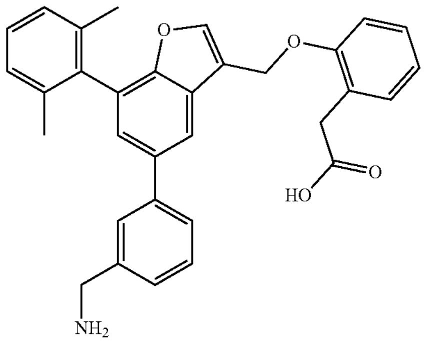
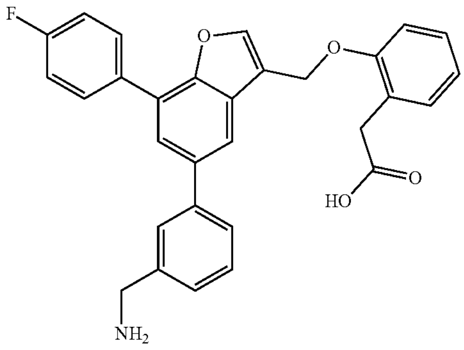

-continued
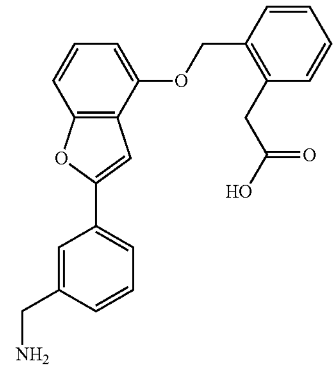
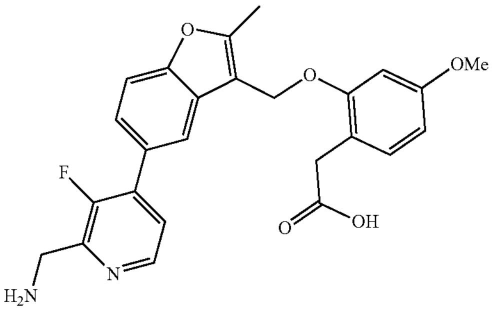
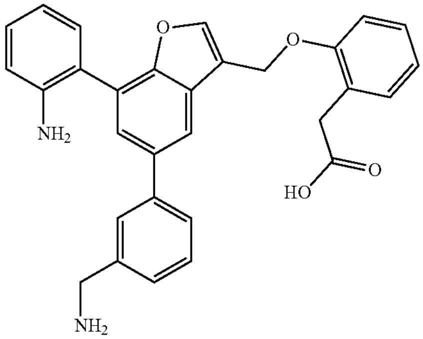
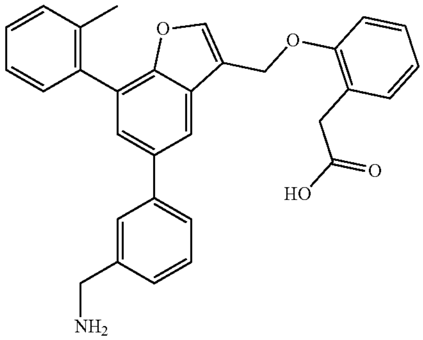
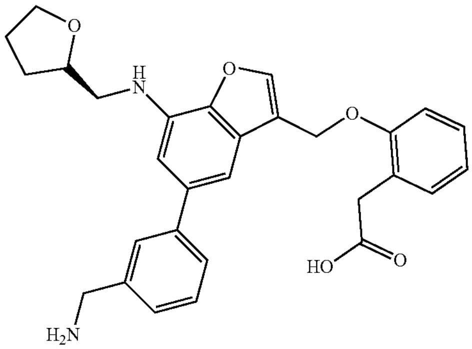
-continued
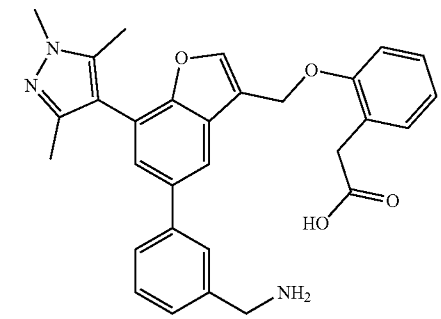
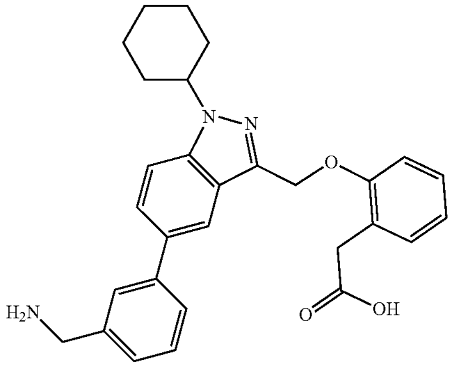
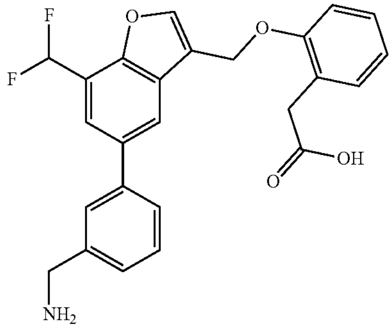
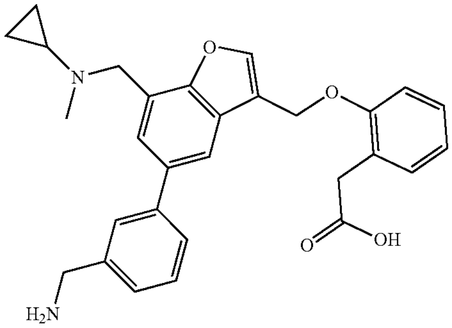
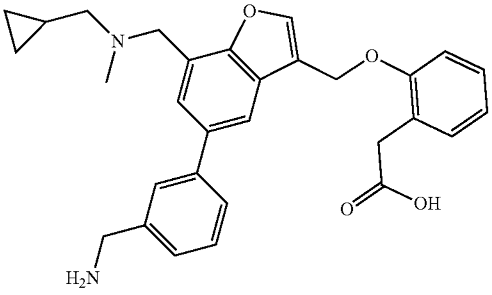

-continued
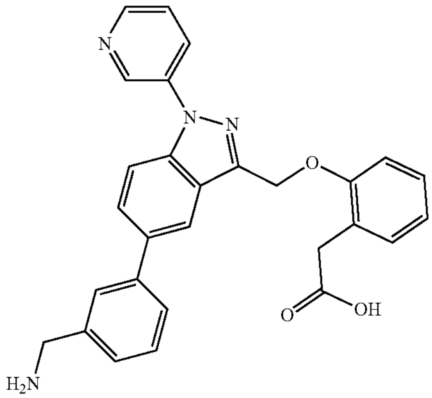
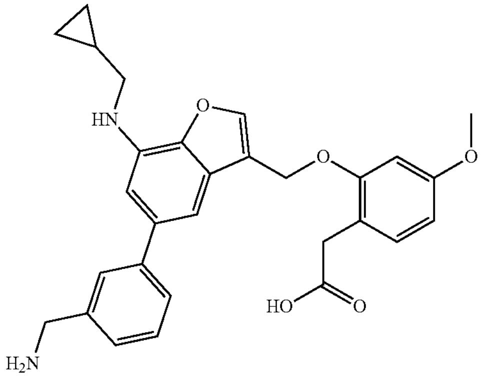
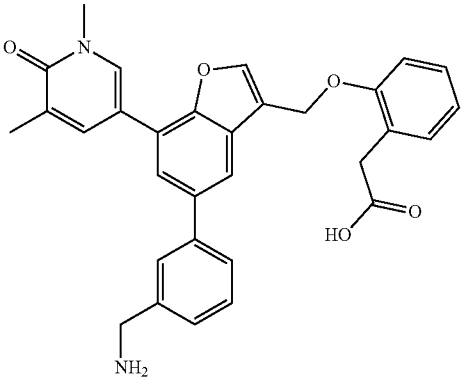
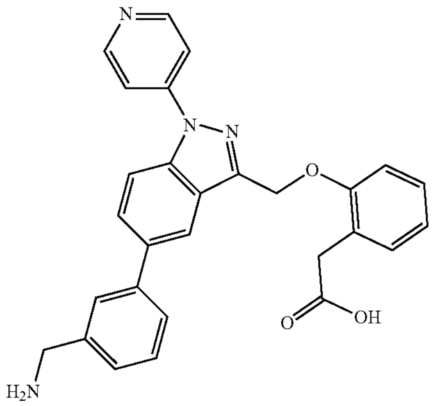
-continued
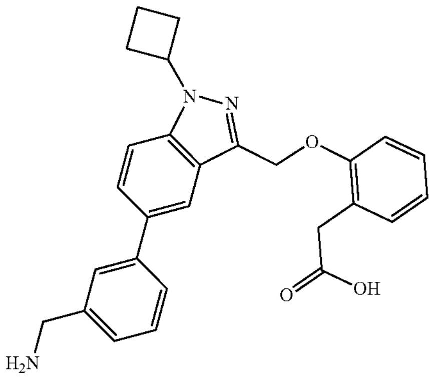
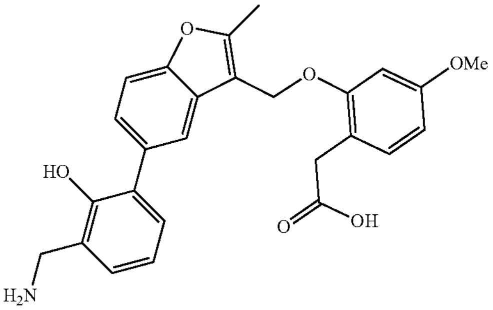
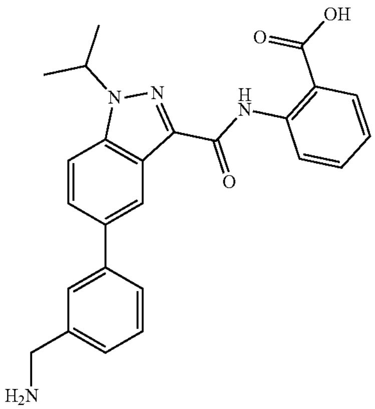
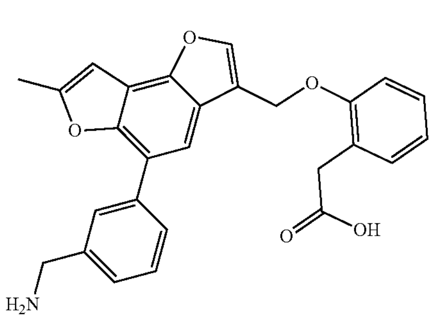

-continued
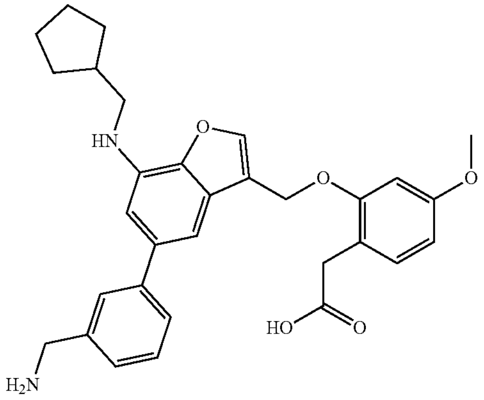
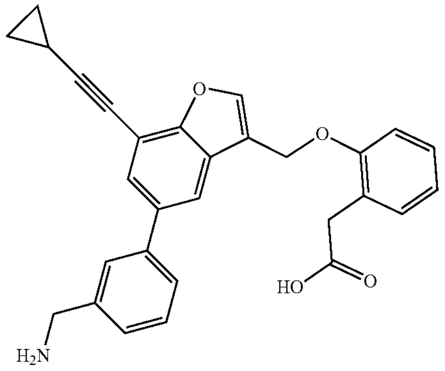
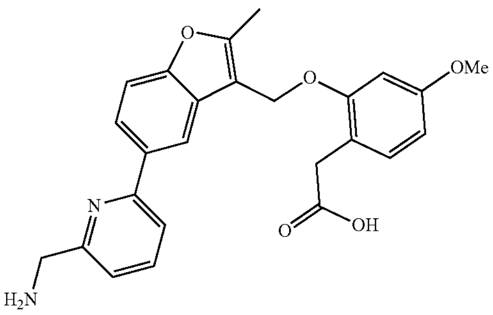
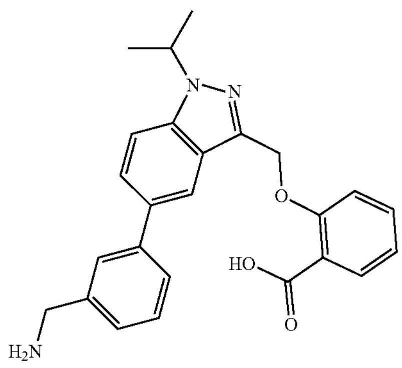
-continued
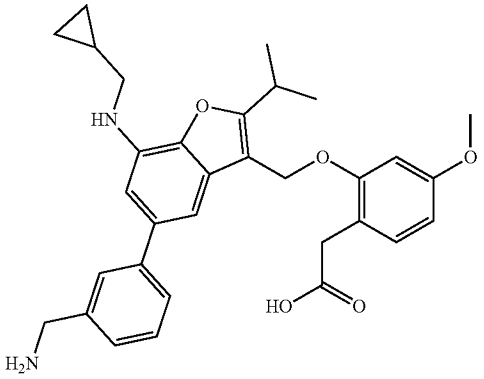
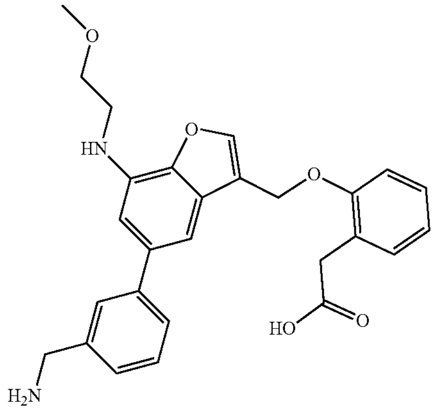
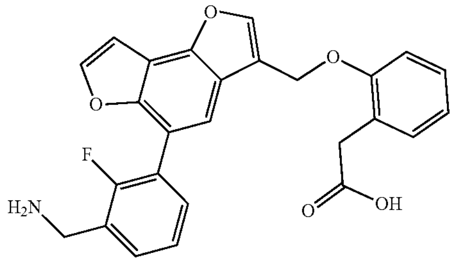
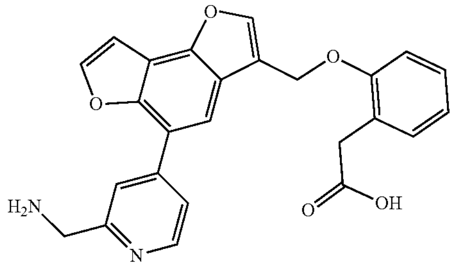
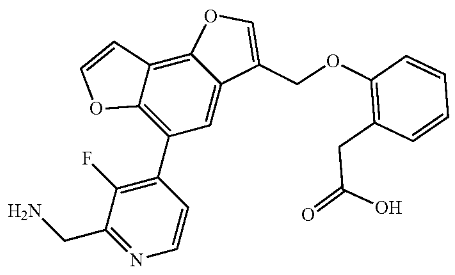

-continued
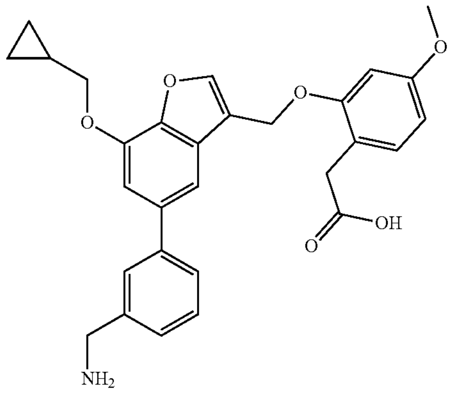
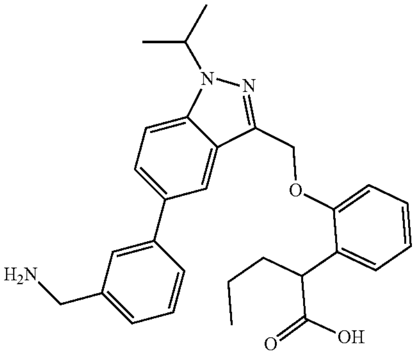
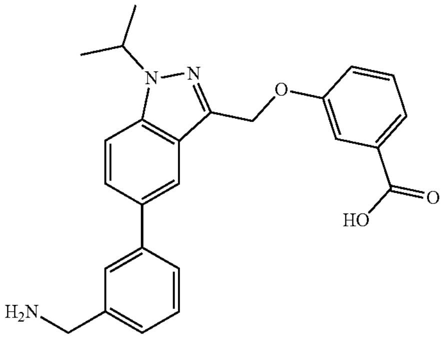
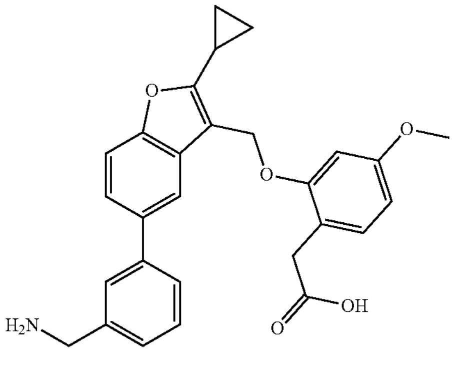
-continued
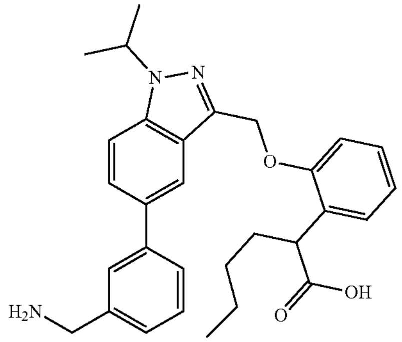
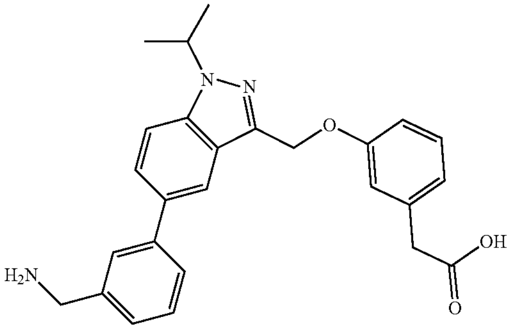
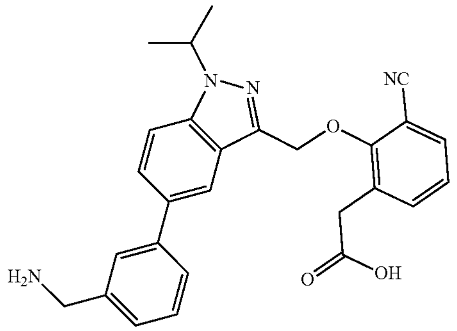
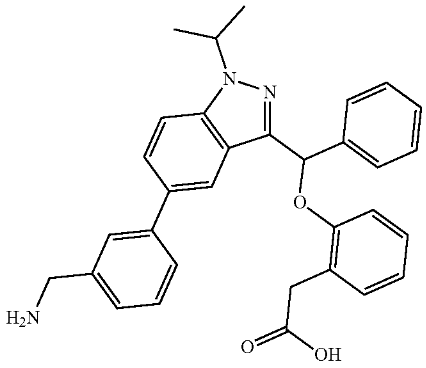
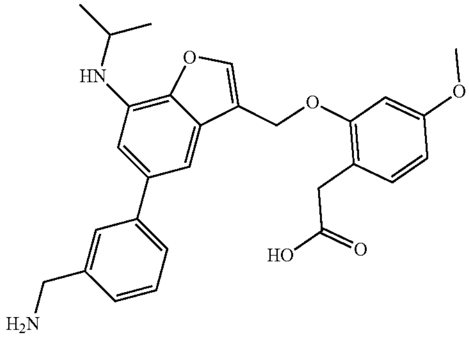

-continued
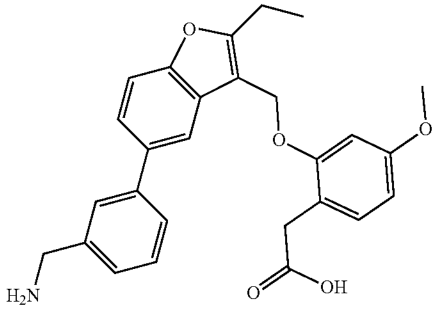
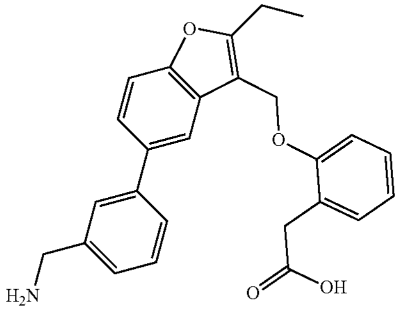
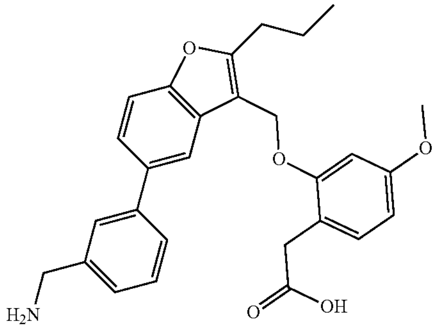
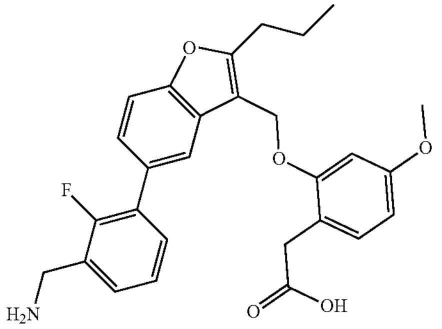
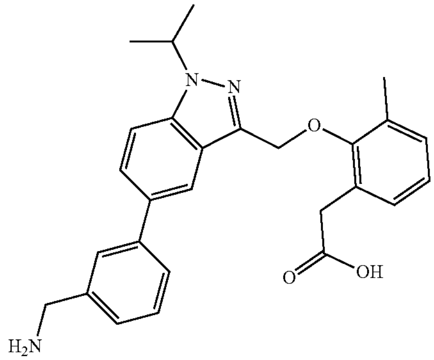
-continued
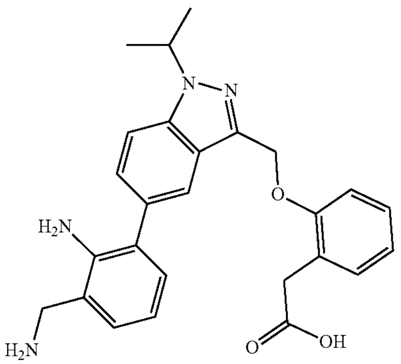
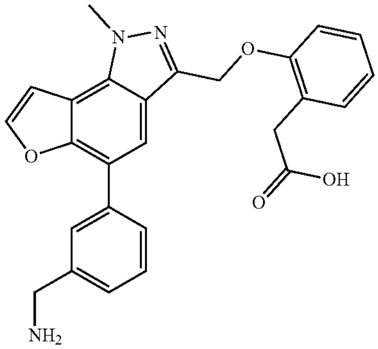
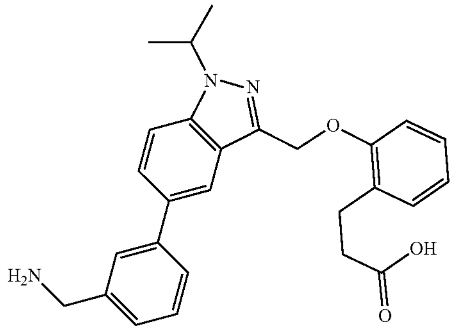
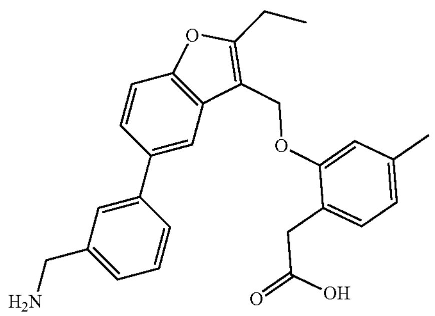
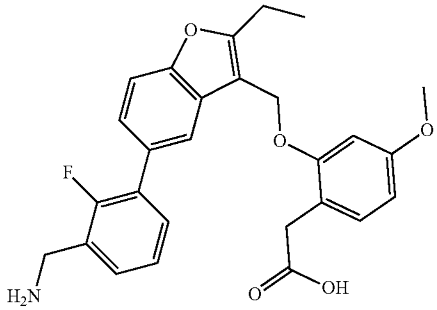

-continued
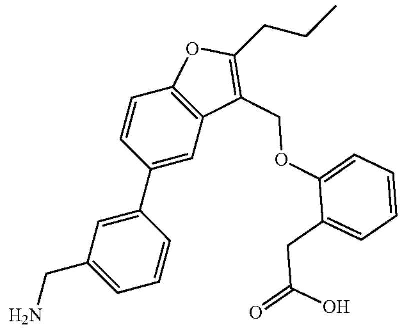
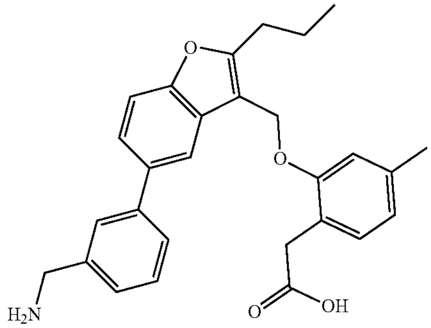
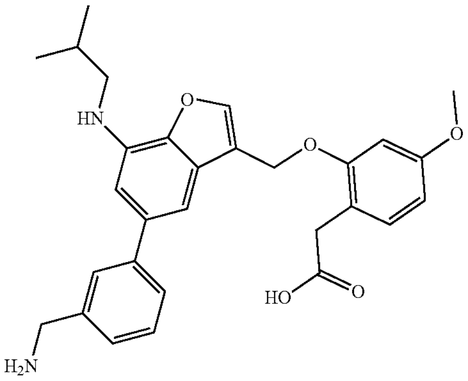
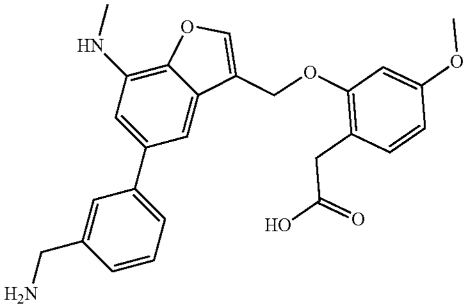
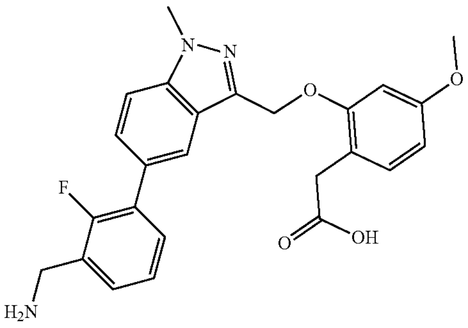
-continued
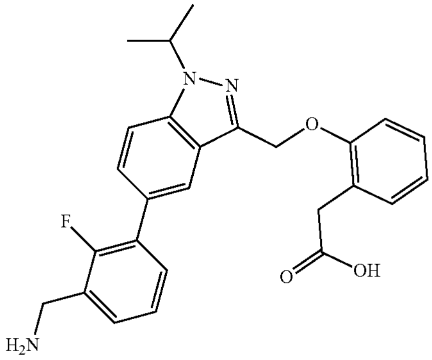
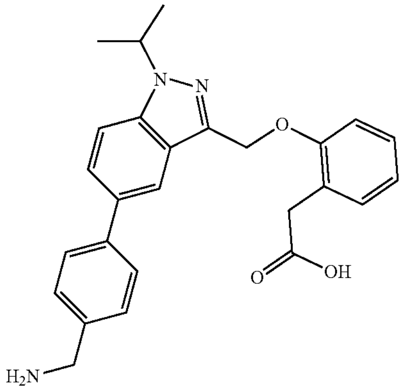
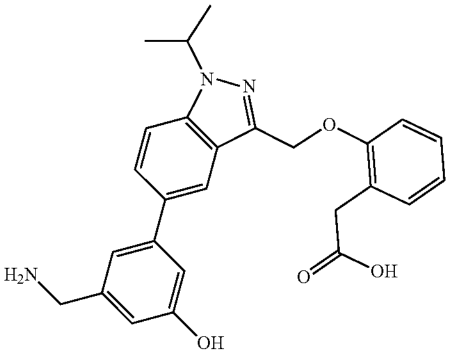
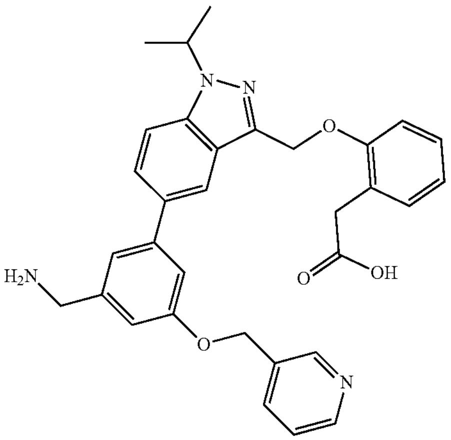

-continued
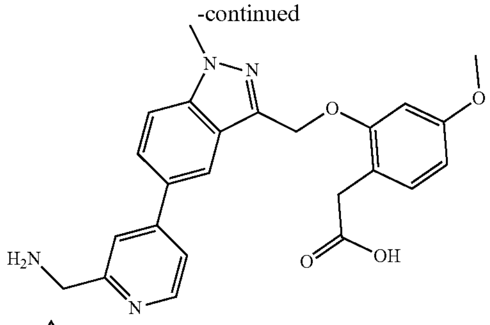
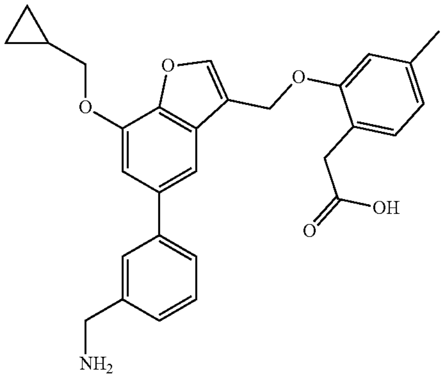
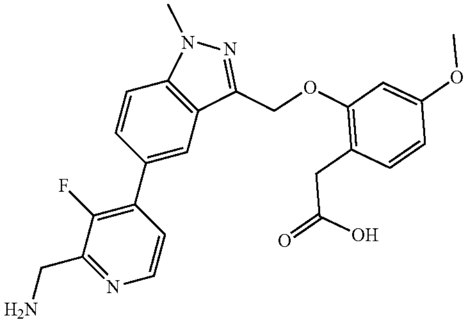
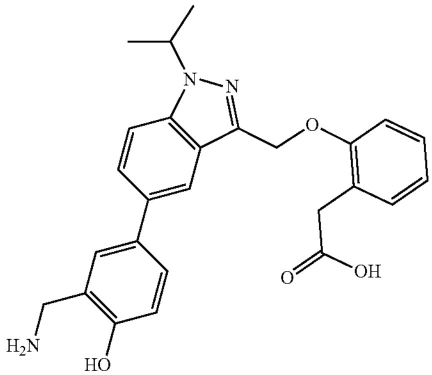
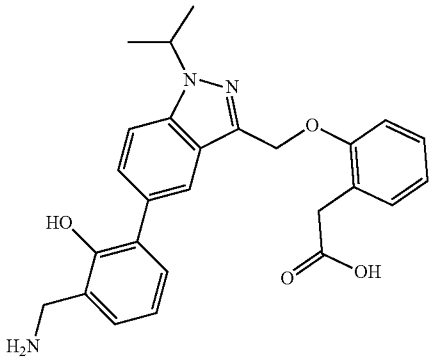
-continued
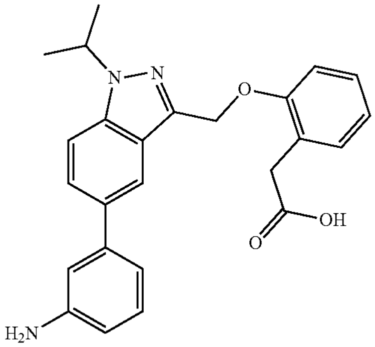
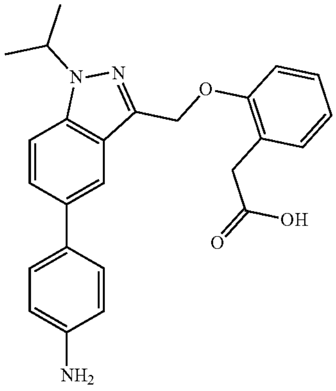
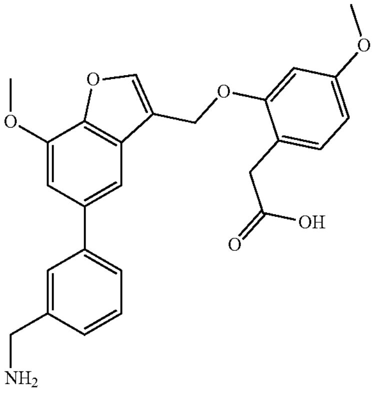
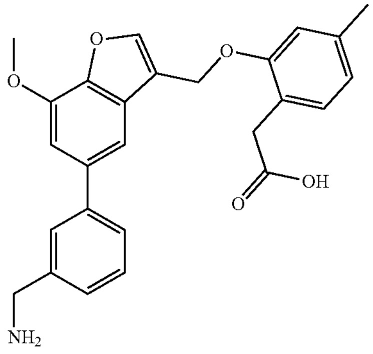

-continued
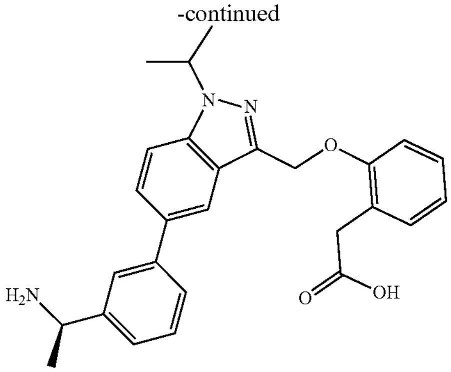
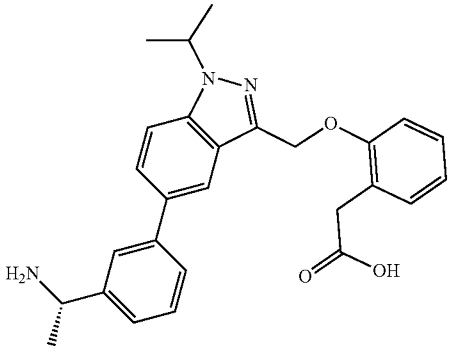
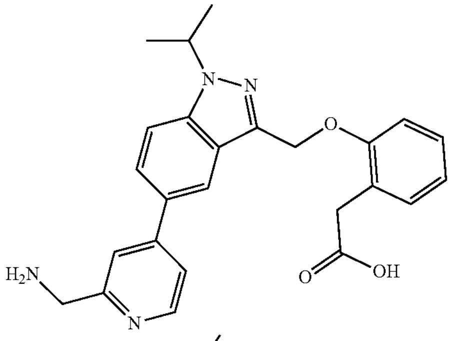
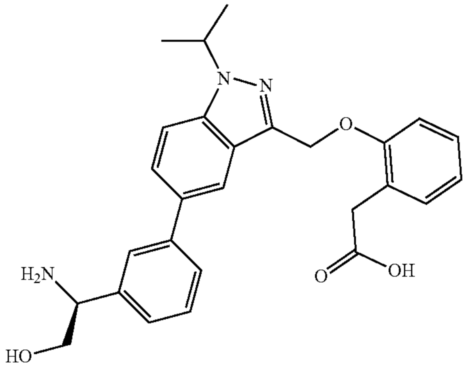
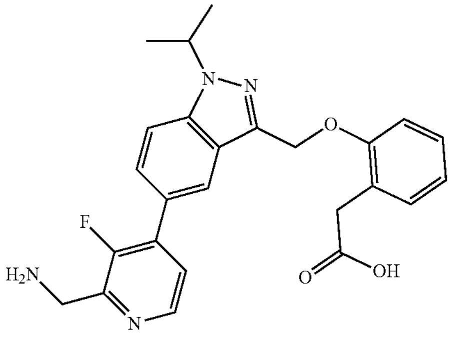
-continued
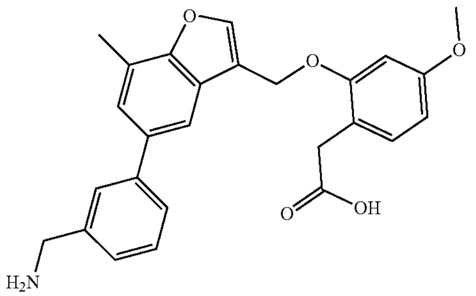
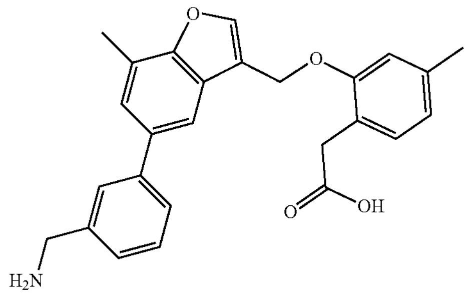
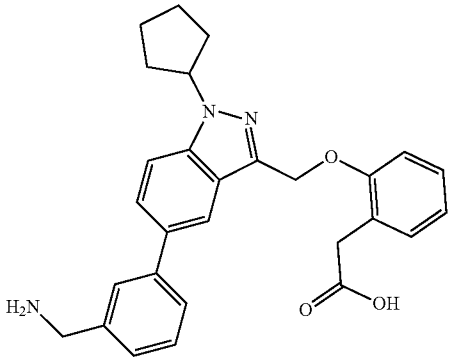
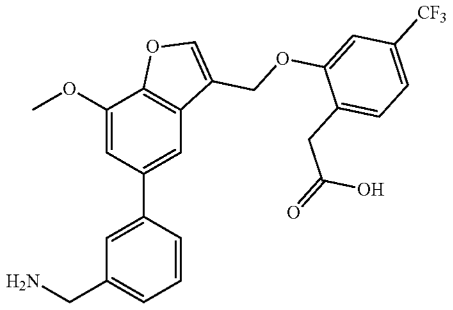
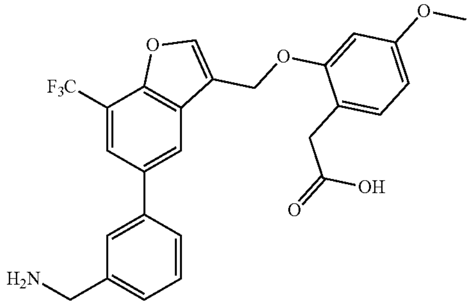

-continued
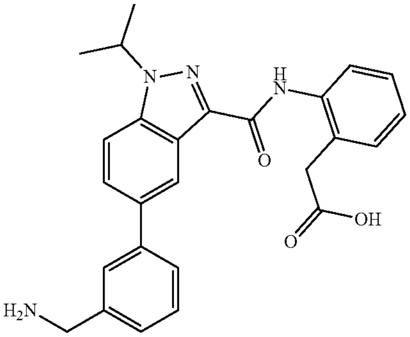
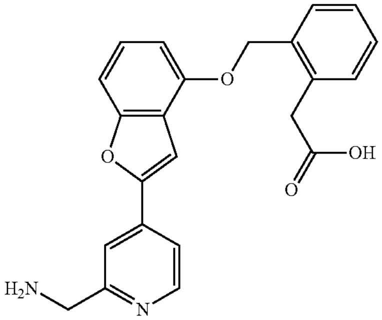
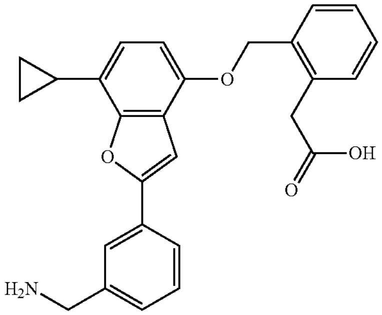
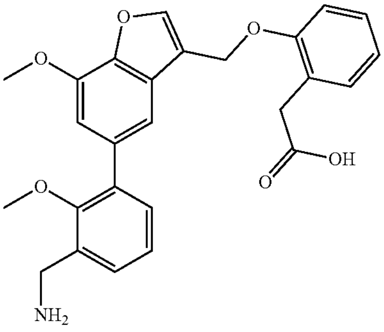
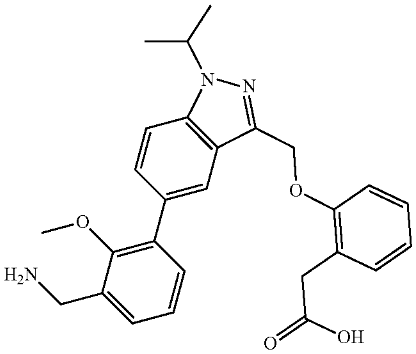
-continued
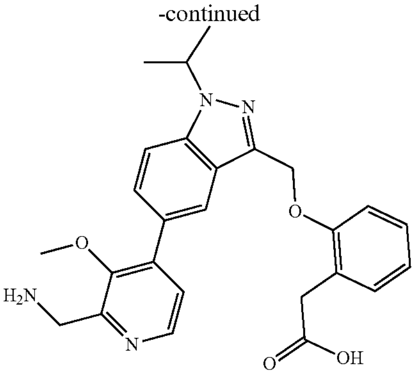
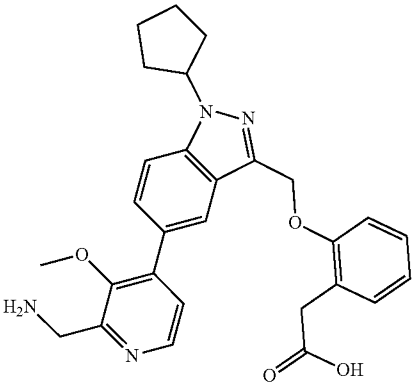
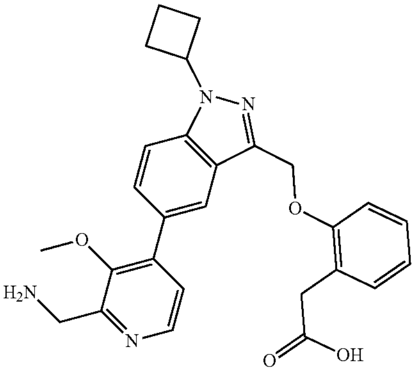
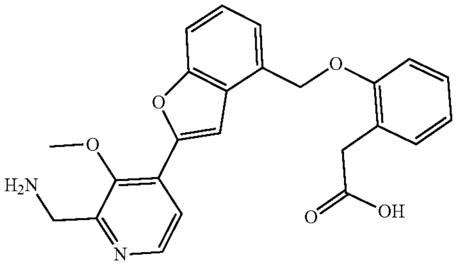
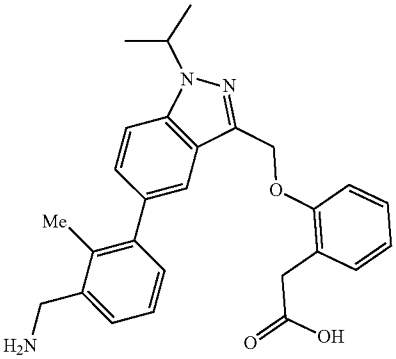

-continued

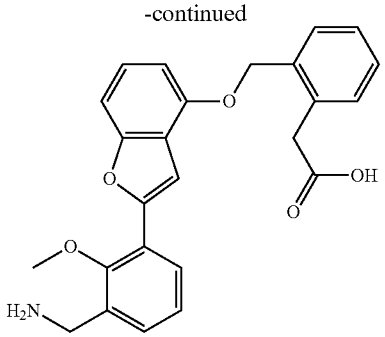

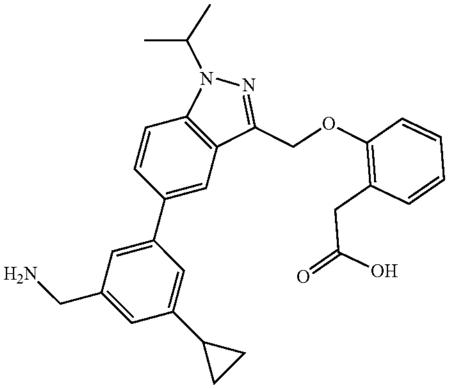

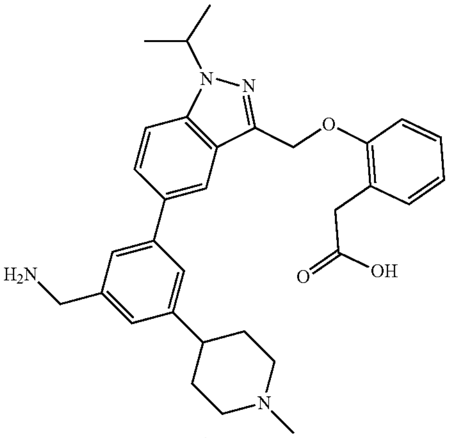

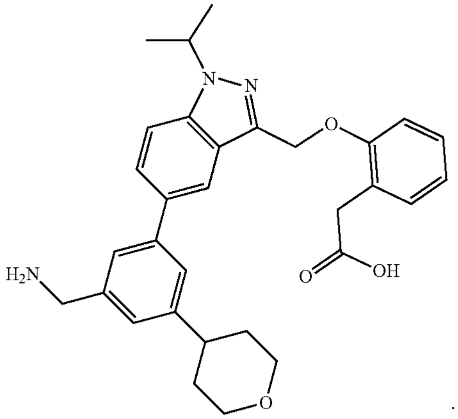

.

Pharmaceutical Compositions

The invention provides pharmaceutical compositions, each comprising one or more compounds of the invention, or pharmaceutically acceptable salts thereof, and a pharmaceutically acceptable carrier. In certain embodiments, the pharmaceutical composition comprises a compound of the invention, or a pharmaceutically acceptable salt thereof, and a pharmaceutically acceptable carrier. In certain embodiments, the pharmaceutical composition comprises a plurality of compounds of the invention, which may include pharmaceutically acceptable salts thereof, and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of a disease or condition characterized by aberrant complement system activity.

Pharmaceutical compositions of the invention can be prepared by combining one or more compounds of the invention with a pharmaceutically acceptable carrier and, optionally, one or more additional pharmaceutically active agents.

Methods of Use

The present invention provides compounds, and pharmaceutically acceptable salts thereof, that are useful for treating or preventing a disease or condition characterized by aberrant complement system activity.

In certain aspects, the invention provides a compound of the invention, or a pharmaceutically acceptable salt thereof, for use as a medicament.

In certain aspects, the invention provides methods of treating or preventing a disease or condition characterized by aberrant complement system activity. The method includes the step of administering to a subject in need thereof a therapeutically effective amount of a compound of the invention, or a pharmaceutically acceptable salt thereof, thereby treating or preventing the disease or condition characterized by aberrant complement system activity. By reducing complement system activity in the subject, the disease or condition characterized by aberrant complement system activity is treated.

Alternatively, in certain aspects, the invention provides a compound of the invention, or a pharmaceutically acceptable salt thereof, for treatment of a disease or condition characterized by aberrant complement system activity.

Alternatively, in certain aspects, the invention provides the use of a compound of the invention, or a pharmaceutically acceptable salt thereof, for the manufacture of a medicament for use in treatment of a disease or condition characterized by aberrant complement system activity.

As used herein, a "disease or condition characterized by aberrant complement system activity" refers to any disease or condition in which it is desirable to reduce complement system activity. For example, it may be desirable to reduce complement system activity in the setting of inappropriate activation or hyperactivation of the complement system.

In certain embodiments, the disease or condition characterized by aberrant complement system activity is an immunological disorder.

In certain embodiments, the disease or condition characterized by aberrant complement system activity is a disease of the central nervous system.

In certain embodiments, the disease or condition characterized by aberrant complement system activity is a renal disease.

In certain embodiments, the disease or condition characterized by aberrant complement system activity is a cardiovascular disease.

In certain embodiments, the disease or condition characterized by aberrant complement system activity is a neurodegenerative disease or neurological disease In certain embodiments, the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, and catastrophic antiphospholipid syndrome.

In certain embodiments, the disease or condition is paroxysmal nocturnal hemoglobinuria.

In certain embodiments, the disease or condition is atypical hemolytic uremic syndrome.

In certain embodiments, the disease or condition is organ transplant rejection.

In certain embodiments, the disease or condition is myasthenia gravis.

In certain embodiments, the disease or condition is neuromyelitis optica.

In certain embodiments, the disease or condition is membranoproliferative glomerulonephritis.

In certain embodiments, the disease or condition is dense-deposit disease.

In certain embodiments, the disease or condition is cold agglutinin disease.

In certain embodiments, the disease or condition is catastrophic antiphospholipid syndrome.

In other embodiments, the disease or condition characterized by aberrant complement system activity is adult respiratory distress syndrome, myocardial infarct, lung inflammation, hyperacute rejection (transplantation rejection), sepsis, cardiopulmonary bypass, burns, asthma, restenosis, multiple organ dysfunction syndrome, Guillain-Barre syndrome, hemorrhagic shock, paroxysmal nocturnal hemoglobinuria, glomerulonephritis, systemic lupus erythematosus, rheumatoid arthritis, infertility, Alzheimer's disease, organ rejection (transplantation), myasthenia gravis, multiple sclerosis, platelet storage, or hemodialysis.

In other embodiments, the disease or condition characterized by aberrant complement system activity is selected from the group consisting of antineutrophil cytoplasmic antibody (ANCA)-associated vasculitis (AAV), warm autoimmune hemolytic anemia, IgA nephropathy, C3 glomerulonephritis, and focal segmental glomerulosclerosis.

In certain embodiments, the disease or condition characterized by aberrant complement system activity is a hematological disorder.

In other embodiments, the disease or condition characterized by aberrant complement system activity is an ocular disorder or an eye disorder.

In certain embodiments, the disease or condition characterized by aberrant complement system activity is macular degeneration, age-related macular degeneration (AMD), macular edema, diabetic macular edema, choroidal neovascularization (CNV), uveitis, Behcet's uveitis, proliferative diabetic retinopathy, non-proliferative diabetic retinopathy, glaucoma, hypertensive retinopathy, a corneal neovascularization disease, post-corneal transplant rejection, a corneal dystrophic disease, an autoimmune dry eye disease, Stevens-Johnson syndrome, Sjogren's syndrome, an environmental dry eye disease, Fuchs' endothelial dystrophy, retinal vein occlusion, or post-operative inflammation.

Formulations, Routes of Administration, and Dosing

The compounds of the invention, and pharmaceutically acceptable salts thereof, can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or pharmaceutically acceptable salt thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention, or pharmaceutically acceptable salts thereof, can be conveniently formulated in unit dosage form; for example, containing 5 to 1000 mg, 10 to 750 mg, or 50 to 500 mg of active ingredient per unit dosage form. In one embodiment, the invention provides a composition comprising a compound of the invention, or pharmaceutically acceptable salts thereof, formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention, or pharmaceutically acceptable salts thereof, can also be administered in combination with other therapeutic agents, for example, other agents that are useful for treating or preventing ischemia, blood loss, or reperfusion injury. In certain embodiments, compounds of the invention, and pharmaceutically acceptable salts thereof, can also be administered in combination with one or more other therapeutic agents that are useful for treating or preventing an ocular disorder or eye disorder.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active ingredient for at least 30 days, and preferably 60 days.

In certain embodiments, a compound of the invention is formulated for intraocular administration, for example direct injection or insertion within or in association with an intraocular medical device. In certain embodiments, a compound of the invention is formulated as an ophthalmic solution. In certain embodiments, a compound of the invention can be administered via ocular delivery, for example, by local ocular administration, including topical, intravitreal, periocular, transscleral, retrobulbar, juxtascleral, suprachoroidal, or sub-tenon administration. A compound of the invention can be administered via ocular delivery either alone or in combination with one or more additional therapeutic agents.

The compounds of the invention may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention to the region of a body which has been treated by interventional technique.

In exemplary embodiment, a compound of the invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No.

4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the compound is coated, adsorbed, placed, or otherwise incorporated into the device by methods known in the art. For example, the compound may be embedded and released from within ("matrix type") or surrounded by and released through ("reservoir type") polymer materials that coat or span the medical device. In the latter example, the compound may be entrapped within the polymer materials or coupled to the polymer materials using one or more the techniques for generating such materials known in the art. In other formulations, the compound may be linked to the surface of the medical device without the need for a coating, for example by means of detachable bonds, and release with time or can be removed by active mechanical or chemical processes. In other formulations, the compound may be in a permanently immobilized form that presents the compound at the implantation site.

In certain embodiments, the compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D, L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable polymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound is formulated for release from the polymer coating into the environment in which the medical device is placed. Preferably, the compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the compound from the polymer coating can be controlled. For example, the diffusion coefficient of the one or more polymer coatings can be modulated to control the release of the compound from the polymer coating. In a variation on this theme, the diffusion coefficient of the one or more polymer coatings can be controlled to modulate the ability of an analyte that is present in the environment in which the medical device is placed (e.g., an analyte that facilitates the breakdown or hydrolysis of some portion of the polymer) to access one or more components within the polymer composition (and for example, thereby modulate the release of the compound from the polymer coating). Yet another embodiment of the invention includes a device having a plurality of polymer coatings, each having a plurality of diffusion coefficients. In such embodiments of the invention, the release of the compound from the polymer coating can be modulated by the plurality of polymer coatings.

In yet another embodiment of the invention, the release of the compound from the polymer coating is controlled by modulating one or more of the properties of the polymer composition, such as the presence of one or more endogenous or exogenous compounds, or alternatively, the pH of the polymer composition. For example, certain polymer compositions can be designed to release a compound in response to a decrease in the pH of the polymer composition.

Kits

The invention also provides a kit, comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to a mammal to treat or prevent a disease or condition characterized by aberrant complement activity. In one embodiment, the mammal is a human.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

Scheme 1

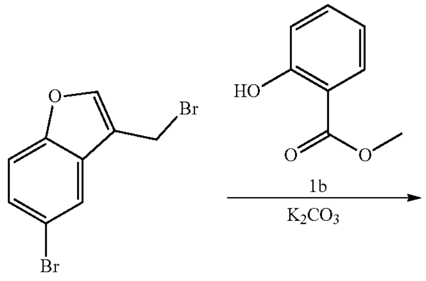

1a

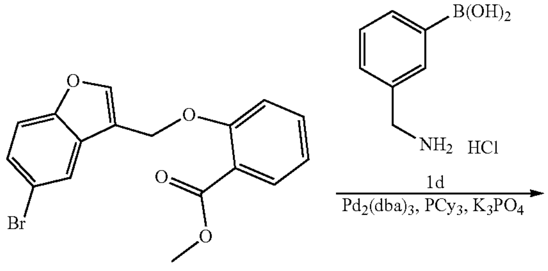

1c

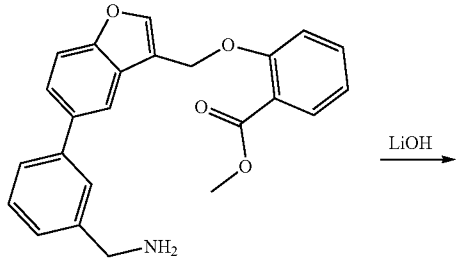

1e

-continued

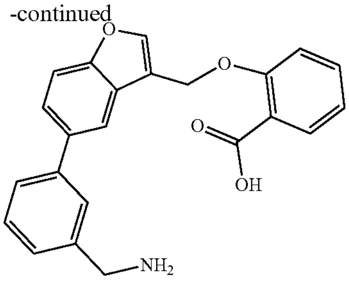

1f

Preparation of 2-((5-(3-(aminomethyl)phenyl)benzofuran-3-yl)methoxy)benzoic acid (1f)

Step-1: Preparation of methyl 2-((5-bromobenzofuran-3-yl)methoxy)benzoate (1c)

To a solution of 5-bromo-3-(bromomethyl)benzofuran (1a) (250 mg, 0.862 mmol; CAS #137242-43-4), potassium carbonate (477 mg, 3.45 mmol) in acetone (3 mL) was added methyl 2-hydroxybenzoate (1b) (157 mg, 1.035 mmol; CAS #119-36-8). The resulting mixture was stirred overnight at room temperature. The suspension was filtered through a pad of Celite and the filtrate was concentrated in vacuum to dryness. The residue obtained was purified by flash column chromatography [silica gel (12 g), eluting with EtOAc in hexane from 0-50%] to afford methyl 2-((5-bromobenzofuran-3-yl)methoxy)benzoate (1c) (301 mg, 97% yield) as a yellow oil; $^1$H NMR (300 MHz, DMSO-$d_6$) δ 8.15 (s, 1H), 7.96 (d, J=2.0 Hz, 1H), 7.65 (dd, J=7.7, 1.8 Hz, 1H), 7.63-7.56 (m, 1H), 7.55 (dd, J=1.9, 1.1 Hz, 1H), 7.54-7.45 (m, 1H), 7.34 (dd, J=8.5, 1.0 Hz, 1H), 7.04 (td, J=7.5, 1.0 Hz, 1H), 5.36 (s, 2H), 3.76 (s, 3H); MS (ES+): 383.00 (M+Na).

Step-2: Preparation of methyl 2-((5-(3-(aminomethyl)phenyl)benzofuran-3-yl)methoxy)benzoate (1e)

To a degassed solution of methyl 2-((5-bromobenzofuran-3-yl)methoxy)benzoate (1c) (300 mg, 0.83 mmol) in dioxane (3 mL) was added 3-(aminomethyl)phenylboronic acid hydrochloride (1d) (234 mg, 1.25 mmol; CAS #352525-94-1), 2M solution of $K_3PO_4$ (0.71 mL, 1.41 mmol), tricyclohexylphosphine (93 mg, 0.33 mmol) and $Pd_2(dba)_3$ (152 mg, 0.17 mmol). The mixture was degassed and filled with argon, then heated at 135° C. for 30 min in microwave. The mixture was diluted with EtOAc and washed with water, brine, filtered and concentrated in vacuum to dryness. The residue obtained was purified by flash chromatography [silica gel (24 g), eluting with DMA-80 in DCM from 0-70%] to give methyl 2-((5-(3-(aminomethyl)phenyl)benzofuran-3-yl)methoxy)benzoate (1e) (108 mg, 34% yield) as a clear oil; $^1$H NMR (300 MHz, DMSO-$d_6$) δ 8.14 (s, 1H), 8.04 (d, J=1.7 Hz, 1H), 7.73-7.63 (m, 4H), 7.63-7.58 (m, 1H), 7.58-7.50 (m, 2H), 7.44-7.37 (m, 2H), 7.33 (dd, J=6.9, 2.0 Hz, 2H), 7.04 (td, J=7.5, 1.0 Hz, 1H), 5.44 (s, 2H), 3.80 (s, 2H), 3.66 (s, 3H); MS (ES+): 388.1 (M+1).

Step-3: Preparation of 2-((5-(3-(aminomethyl)phenyl)benzofuran-3-yl)methoxy)benzoic acid (1f)

To a solution of methyl 2-((5-(3-(aminomethyl)phenyl) benzofuran-3-yl)methoxy)benzoate (1e) (108 mg, 0.28 mmol) in THF (3 mL) was added a solution of lithium hydroxide hydrate (105 mg, 2.49 mmol) in water (1 mL) and stirred at room temperature overnight. The reaction mixture was concentrated to remove organic solvent. The aqueous mixture was acidified to pH 4-5 using 2N HCl and purified by reverse phase column chromatography [C18 column (30 g), eluting with ACN in water (containing 0.1% HCl) from 0-100%] to give 2-((5-(3-(aminomethyl)phenyl)benzofuran-3-yl)methoxy)benzoic acid (1f) (46 mg, 15% yield) hydrochloride salt as a white solid; $^1$H NMR (300 MHz, DMSO-$d_6$) δ 12.68 (s, 1H, $D_2O$ exchangeable), 8.44 (s, 3H, $D_2O$ exchangeable), 8.18 (s, 1H), 8.10 (d, J=1.7 Hz, 1H), 7.87 (t, J=1.8 Hz, 1H), 7.79-7.62 (m, 4H), 7.56-7.44 (m, 3H), 7.35 (d, J=8.3 Hz, 1H), 7.03 (t, J=7.4 Hz, 1H), 5.41 (s, 2H), 4.12 (s, 2H); MS (ES+): 374.1 (M+1); Analysis calculated for $C_{23}H_{19}NO_4 \cdot 1.1HCl \cdot H_2O$: C, 64.02; H, 5.16; Cl, 9.04; N, 3.25. Found: C, 64.27; H, 5.25; Cl, 9.15; N, 3.41.

Scheme 2

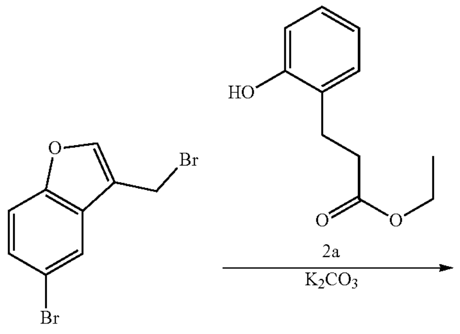

1a

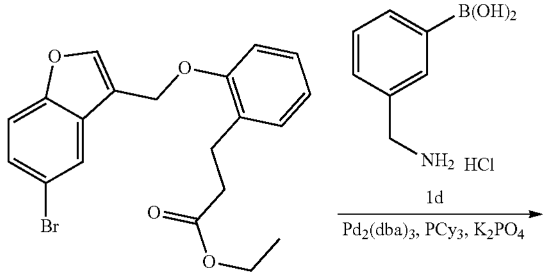

2b

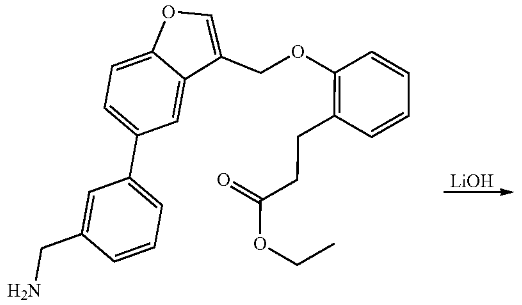

2c

-continued

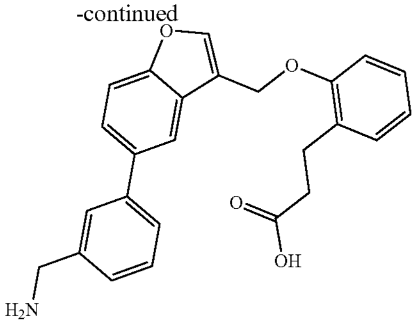

2d

Preparation of 3-(2-((5-(3-(aminomethyl)phenyl) benzofuran-3-yl)methoxy)phenyl)propanoic acid (2d)

Step-1: Preparation of ethyl 3-(2-((5-bromobenzofuran-3-yl)methoxy)phenyl)propanoate (2b)

Compound 2b was prepared according to the procedure reported in step-1 of scheme 1, from 5-bromo-3-(bromomethyl)benzofuran (1a) (250 mg, 0.862 mmol) in acetone (3 mL) using ethyl 3-(2-hydroxyphenyl)propanoate (2a) (201 mg, 1.035 mmol; CAS #: 20921-04-4), $K_2CO_3$ (477 mg, 3.45 mmol) and stirring at room temperature overnight. This gave after workup and purification by flash column chromatography [silica gel (12 g), eluting with EtOAc in hexane from 0-50%] ethyl 3-(2-((5-bromobenzofuran-3-yl) methoxy)phenyl)propanoate (2b) (287 mg, 83% yield) as a yellow oil; $^1$H NMR (300 MHz, DMSO-$d_6$) δ 8.19 (s, 1H), 7.93 (d, J=2.0 Hz, 1H), 7.62 (d, J=8.7 Hz, 1H), 7.51 (dd, J=8.8, 2.1 Hz, 1H), 7.26-7.09 (m, 3H), 6.89 (td, J=7.2, 1.5 Hz, 1H), 5.29 (d, J=1.0 Hz, 2H), 3.99 (q, J=7.1 Hz, 2H), 2.80 (t, J=7.6 Hz, 2H), 2.54-2.51 (m, 2H), 1.10 (t, J=7.1 Hz, 3H); MS (ES+): 425.00 (M+Na).

Step-2: Preparation of ethyl 3-(2-((5-(3-(aminomethyl)phenyl)benzofuran-3-yl)methoxy)phenyl)propanoate (2c)

Compound 2c was prepared according to the procedure reported in step-2 of scheme 1, from ethyl 3-(2-((5-bromobenzofuran-3-yl)methoxy)phenyl)propanoate (2b) (287 mg, 0.712 mmol) in dioxane (3 mL) using 3-(aminomethyl) phenylboronic acid hydrochloride (1d) (200 mg, 1.068 mmol), 2M solution of $K_3PO_4$ (0.605 mL, 1.210 mmol), tricyclohexylphosphine (80 mg, 0.285 mmol), $Pd_2(dba)_3$ (130 mg, 0.142 mmol) and heating at 135° C. for 30 min in a microwave. This gave after workup and purification by flash column chromatography [silica gel (24 g), eluting with DMA-80 in DCM from 0-70%] ethyl 3-(2-((5-(3-(aminomethyl)phenyl)benzofuran-3-yl)methoxy)phenyl)propanoate (2c) (105 mg, 34% yield) as a clear oil; $^1$H NMR (300 MHz, DMSO-$d_6$) δ 8.16 (s, 1H), 7.97 (d, J=1.8 Hz, 1H), 7.71-7.61 (m, 3H), 7.54-7.47 (m, 1H), 7.38 (t, J=7.5 Hz, 1H), 7.34-7.28 (m, 1H), 7.25-7.20 (m, 2H), 7.15 (d, J=7.6 Hz, 1H), 6.93-6.82 (m, 1H), 5.34 (s, 2H), 3.90 (q, J=7.1 Hz, 2H), 3.79 (s, 2H), 2.86-2.77 (m, 2H), 2.58-2.51 (m, 2H), 1.02 (t, J=7.1 Hz, 3H); MS (ES+): 430.2 (M+1).

Step-3: Preparation of 3-(2-((5-(3-(aminomethyl) phenyl)benzofuran-3-yl)methoxy)phenyl)propanoic acid (2d)

Compound 2d was prepared according to the procedure reported in step-3 of scheme 1, from ethyl 3-(2-((5-(3-

(aminomethyl)phenyl)benzofuran-3-yl)methoxy)phenyl) propanoate (2c) (105 mg, 0.244 mmol) in THF (3 mL), using a solution of lithium hydroxide hydrate (135 mg, 3.22 mmol) in water (1 mL) and stirring at room temperature overnight. This gave after workup and purification by reverse phase column chromatography [C18 column (30 g), eluting with ACN in water (containing 0.1% HCl) from 0-100%] 3-(2-((5-(3-(aminomethyl)phenyl)benzofuran-3-yl)methoxy)phenyl)propanoic acid (2d) (22 mg, 8% yield) HCl salt as a white solid; $^1$H NMR (300 MHz, DMSO-$d_6$) δ 12.08 (s, 1H, $D_2O$ exchangeable), 8.43 (s, 3H, $D_2O$ exchangeable), 8.19 (s, 1H), 8.02 (d, J=1.7 Hz, 1H), 7.86 (s, 1H), 7.77-7.65 (m, 3H), 7.56-7.41 (m, 2H), 7.25-7.11 (m, 3H), 6.94-6.84 (m, 1H), 5.34 (s, 2H), 4.10 (s, 2H), 2.80 (t, J=7.7 Hz, 2H), 2.49-2.44 (m, 2H); MS (ES+): 402.1 (M+1).

Scheme 3

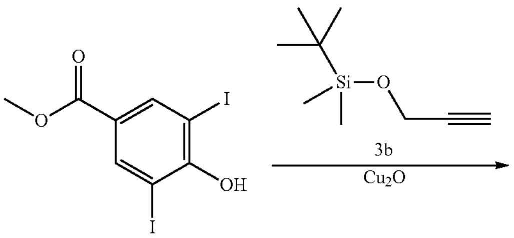

3a

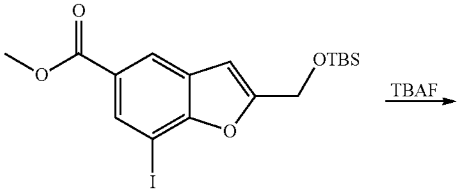

3c

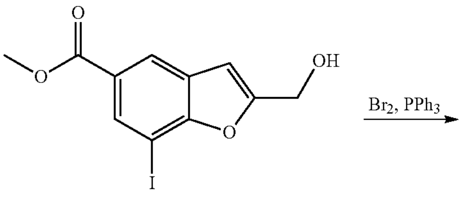

3d

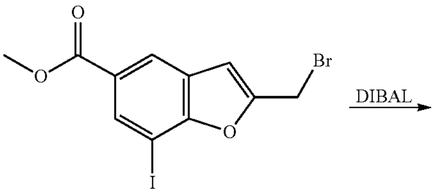

3e

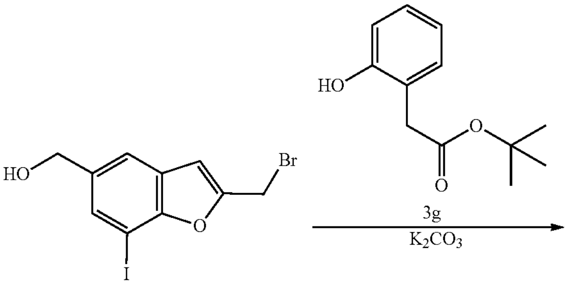

3f

-continued

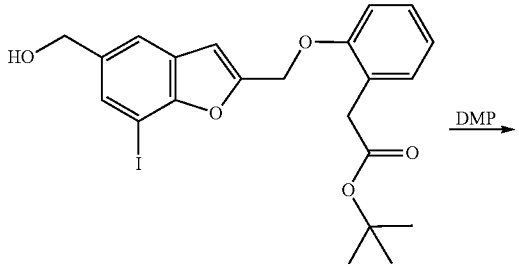

3h

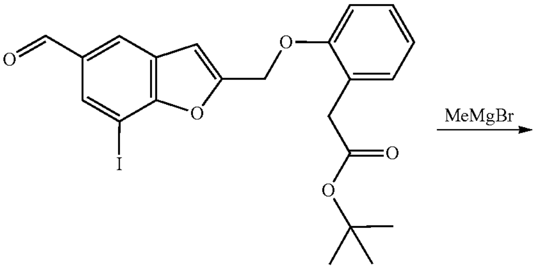

3i

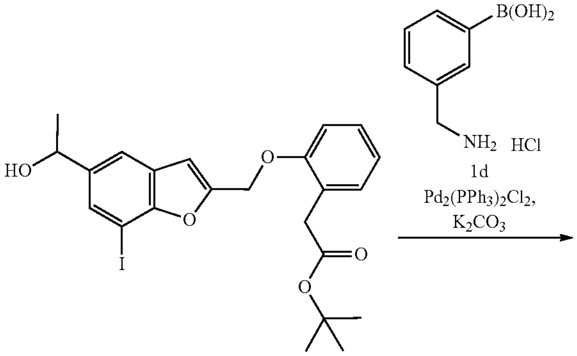

3j

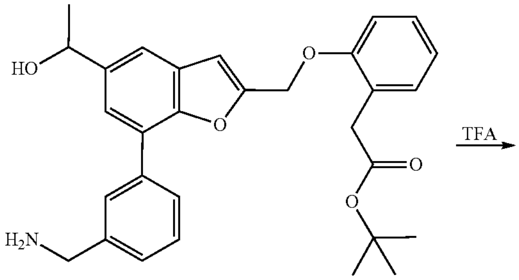

3k

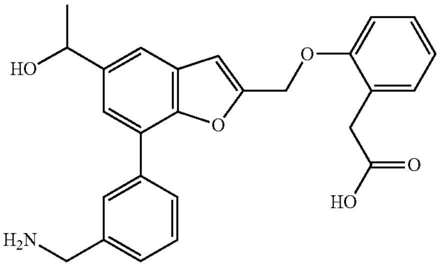

31

Preparation of 2-(2-((7-(3-(aminomethyl)phenyl)-5-(1-hydroxyethyl)benzofuran-2-yl)methoxy)phenyl) acetic acid (3l)

Step-1: Preparation of methyl 2-(((tert-butyldimethylsilyl)oxy)methyl)-7-iodobenzofuran-5-carboxylate (3c)

To a solution of methyl 4-hydroxy-3,5-diiodobenzoate (3a) (5 g, 12.38 mmol; CAS #3337-66-4) in pyridine (10 mL) was added tert-butyldimethyl(prop-2-ynyloxy)silane (3b) (2.11 g, 12.38 mmol; CAS #76782-82-6) and copper(I) oxide (0.89 g, 6.19 mmol). The mixture was degassed and filled with argon stirred for 10 min at room temperature and heated at 125° C. for 4 h in a sealed flask. The reaction was cooled to room temperature, diluted with EtOAc (250 mL), washed with cold 0.02N $KHSO_4$, water, brine, dried, filtered and concentrated in vacuum to dryness. The residue obtained was purified by flash column chromatography [silica gel (80 g), eluting with EtOAc in hexane from 0-70%] to afford methyl 2-(((tert-butyldimethylsilyl)oxy)methyl)-7-iodobenzofuran-5-carboxylate (3c) (3.2 g, 58% yield) as a clear oil; $^1$H NMR (300 MHz, DMSO-$d_6$) δ 8.25 (d, J=1.6 Hz, 1H), 8.19 (d, J=1.6 Hz, 1H), 7.08 (s, 1H), 4.84 (s, 2H), 3.86 (s, 3H), 0.89 (s, 9H), 0.13 (s, 6H); MS (ES+): 469.1 (M+1).

Step-2: Preparation of methyl 2-(hydroxymethyl)-7-iodobenzofuran-5-carboxylate (3d)

To a solution of methyl 2-(((tert-butyldimethylsilyl)oxy) methyl)-7-iodobenzofuran-5-carboxylate (3c) (4.3 g, 9.63 mmol) in THF (60 mL) was added TBAF (3.15 g, 12.04 mmol) at 0° C., stirred at room temperature for 1 h and quenched with saturated $NH_4Cl$. The reaction mixture was extracted with EtOAc and the organic layer was separated, dried, filtered and concentrated under vacuum. The residue obtained was purified by flash column chromatography [silica gel (12 g), eluting with EtOAc in hexane from 0-70%] to give methyl 2-(hydroxymethyl)-7-iodobenzofuran-5-carboxylate (3d) (2.5 g, 78% yield) as a white solid; $^1$H NMR (300 MHz, DMSO-$d_6$) δ 8.25 (d, J=1.6 Hz, 1H), 8.18 (d, J=1.6 Hz, 1H), 7.04 (s, 1H), 5.64 (t, J=5.9 Hz, 1H), 4.62 (d, 2H), 3.87 (s, 3H).

Step-3: Preparation of methyl 2-(bromomethyl)-7-iodobenzofuran-5-carboxylate (3e)

To a stirred solution of triphenylphosphine (1.26 g, 4.82 mmol) in DCM (20 mL) was added bromine (0.25 mL, 4.82 mmol) at 0° C. The reaction mixture was allowed to warm to RT stirred for 10 mins and added methyl 2-(hydroxymethyl)-7-iodobenzofuran-5-carboxylate (3d) (1 g, 3.01 mmol) in DCM (10 mL) over a period of 5 mins. The reaction was stirred for 10 mins quenched with saturated $NaHCO_3$ solution (20 mL), diluted with DCM (50 mL), washed with water, brine, dried, filtered and concentrated in vacuum to dryness. The crude residue obtained was purified by flash column chromatography [silica gel (40 g) eluting with ethyl acetate and hexanes] to afford methyl 2-(bromomethyl)-7-iodobenzofuran-5-carboxylate (3e) (0.72 g, 61% yield) as a white solid; $^1$H NMR (300 MHz, DMSO-$d_6$) δ 8.30 (d, J=1.6 Hz, 1H), 8.25 (d, J=1.6 Hz, 1H), 7.30 (s, 1H), 4.97 (s, 2H), 3.88 (s, 3H).

Step-4: Preparation of (2-(bromomethyl)-7-iodobenzofuran-5-yl)methanol (3f)

To a stirred solution of DIBAL-H (1 M in DCM, 26.6 mL, 26.6 mmol) in toluene (20 mL) was added a solution of methyl 2-(bromomethyl)-7-iodobenzofuran-5-carboxylate (3e) (5 g, 12.66 mmol) in DCM (40 mL) dropwise at 0° C. under a nitrogen atmosphere. The reaction mixture was stirred for 3 h at 0° C. acidified to pH 1 using HCl (1M). The organic phase was separated, washed with water, dried, filtered and concentrated in vacuum to dryness. The residue obtained was purified by flash column chromatography [silica gel (40 g), eluting with EtOAc in hexane from 0-50%] to give (2-(bromomethyl)-7-iodobenzofuran-5-yl)methanol (3f) (2.01 g, 43% yield) as a white solid; $^1$H NMR (300 MHz, DMSO-$d_6$) δ 7.68 (d, J=1.5 Hz, 1H), 7.56 (d, J=1.5 Hz, 1H), 7.15 (s, 1H), 5.30 (s, 1H), 4.94 (s, 2H), 4.54 (s, 2H).

Step-5: Preparation of tert-butyl 2-(2-((5-(hydroxymethyl)-7-iodobenzofuran-2-yl)methoxy)phenyl)acetate (3h)

Compound 3h was prepared according to the procedure reported in step-1 of scheme 1, from (2-(bromomethyl)-7-iodobenzofuran-5-yl)methanol (3f) (1 g, 2.72 mmol) in acetone (15 mL) using tert-butyl 2-(2-hydroxyphenyl)acetate (3g) (0.681 g, 3.27 mmol), potassium carbonate (1.318 g, 9.54 mmol) and heating at 50° C. for 12 h. This gave after workup and purification by flash column chromatography [silica gel (40 g) eluting with ethyl acetate and hexanes from 0-60%] tert-butyl 2-(2-((5-(hydroxymethyl)-7-iodobenzofuran-2-yl)methoxy)phenyl)acetate (3h) (1.02 g, 76% yield) as a white solid; MS (ES+): 517.00 (M+Na).

Step-6: Preparation of tert-butyl 2-(2-((5-formyl-7-iodobenzofuran-2-yl)methoxy)phenyl)acetate (3i)

To a solution of tert-butyl 2-(2-((5-(hydroxymethyl)-7-iodobenzofuran-2-yl)methoxy)phenyl)acetate (3h) (600 mg, 1.21 mmol) in DCM (15 mL) was added Dess-Martin Periodinane (DMP) (1.09 g, 2.43 mmol) at room temperature and stirred at room temperature for 3 h. The reaction mixture was diluted with DCM (100 mL), washed with 1 M $NaHCO_3$ (50 mL), water (50 mL), dried, filtered and concentrated in vacuum to dryness. The residue obtained was purified by flash column chromatography [silica gel (50 g), eluting with ethyl acetate in hexanes from 0 to 50%] to afford tert-butyl 2-(2-((5-formyl-7-iodobenzofuran-2-yl) methoxy)phenyl)acetate (3i) (530 mg, 89% yield) as a white solid; $^1$H NMR (300 MHz, DMSO-$d_6$) δ 10.00 (s, 1H), 8.30-8.18 (m, 2H), 7.33 (s, 1H), 7.29 (ddd, J=8.8, 7.2, 1.7 Hz, 1H), 7.21 (dt, J=7.1, 1.8 Hz, 2H), 6.95 (td, J=7.4, 1.2 Hz, 1H), 5.34 (s, 2H), 3.53 (s, 2H), 1.27 (s, 9H); MS (ES+): 515.00 (M+1).

Step-7: Preparation of tert-butyl 2-(2-((5-(1-hydroxyethyl)-7-iodobenzofuran-2-yl)methoxy)phenyl) acetate (3j)

To a solution of tert-butyl 2-(2-((5-formyl-7-iodobenzofuran-2-yl)methoxy)phenyl)acetate (3i) (1.3 g, 2.64 mmol) in THF (20 mL) was added methyl magnesium bromide (1.4 M in THF, 2.075 mL, 2.90 mmol) at −78° C. and stirred at −78° C. for 1 h. The reaction mixture was quenched with saturated $NH_4Cl$ solution, extracted with EtOAc (3×). The combined organic layers were washed with saturated aqueous $NaHCO_3$, dried, filtered, and concentrated in vacuum to dryness. The residue obtained was purified by flash column chromatography [silica gel (12 g), eluting with EtOAc in hexane from 0-60%] to give tert-butyl 2-(2-((5-(1-hydroxyethyl)-7-iodobenzofuran-2-yl)methoxy)phenyl)acetate (3j) (0.86 g, 64% yield) as a yellow semi-solid; $^1$H NMR (300 MHz, DMSO-$d_6$) δ 7.69 (d, J=1.5 Hz, 1H), 7.58 (d, J=1.5 Hz, 1H), 7.33-7.24 (m, 1H), 7.24-7.15 (m, 2H), 7.12 (s, 1H), 6.94 (td, J=7.3, 1.1 Hz, 1H), 5.30 (s, 1H), 5.28 (s, 2H), 4.85-4.72 (m, 1H), 3.52 (s, 2H), 1.34 (d, J=6.4 Hz, 3H), 1.30 (s, 9H); MS (ES+): 531.00 (M+1).

Step-8: Preparation of tert-butyl 2-(2-((7-(3-(aminomethyl)phenyl)-5-(1-hydroxyethyl)benzofuran-2-yl)methoxy)phenyl)acetate (3k)

To a degassed solution of tert-butyl 2-(2-((5-(1-hydroxyethyl)-7-iodobenzofuran-2-yl)methoxy)phenyl)acetate (3j) (250 mg, 0.49 mmol) in dioxane (5 mL) was added 3-(aminomethyl)phenylboronic acid hydrochloride (1d) (138 mg, 0.738 mmol), bis(triphenylphosphine)palladium(II) chloride (69.0 mg, 0.098 mmol) and a solution of $K_2CO_3$ (170 mg, 1.23 mmol) in water (1 mL). The mixture was degassed, filled with argon, and heated at 100° C. for 3 h in an oil bath. The reaction mixture was cooled to room temperature diluted with EtOAc, washed with water, brine, dried, filtered and concentrated in vacuum to dryness. The residue obtained was purified by flash column chromatography [silica gel (12 g), eluting with DMA-80 in DCM from 0-50%] to give tert-butyl 2-(2-((7-(3-(aminomethyl)phenyl)-5-(1-hydroxyethyl)benzofuran-2-yl)methoxy)phenyl) acetate (3k) (122 mg, 51% yield) as a clear oil; MS (ES+): 488.2 (M+1).

Step-9: Preparation of 2-(2-((7-(3-(aminomethyl) phenyl)-5-(1-hydroxyethyl)benzofuran-2-yl) methoxy)phenyl)acetic acid (3l)

To a solution of tert-butyl 2-(2-((7-(3-(aminomethyl)phenyl)-5-(1-hydroxyethyl)benzofuran-2-yl)methoxy)phenyl) acetate (3k) (122 mg, 0.25 mmol) in DCM (10 mL) was added TFA (0.57 mL, 7.38 mmol). The resulting mixture was stirred at room temperature for 3 h and concentrated to dryness under vacuum. The residue obtained was purified by reverse phase column chromatography [C18 column (30 g), eluting with ACN in water (containing 0.1% HCl) from 0-100%] to give 2-(2-((7-(3-(aminomethyl)phenyl)-5-(1-hydroxyethyl)benzofuran-2-yl)methoxy)phenyl)acetic acid (3l) (44 mg, 21% yield) hydrochloride salt as a white solid; $^1$H NMR (300 MHz, DMSO-$d_6$) δ 12.13 (s, 1H), 8.49 (s, 3H), 7.98-7.87 (m, 2H), 7.63-7.48 (m, 4H), 7.31-7.16 (m, 3H), 7.05 (s, 1H), 6.94 (td, J=7.2, 1.4 Hz, 1H), 5.37-5.23 (m, 3H), 4.95-4.81 (m, 1H), 4.13 (s, 2H), 3.55 (s, 2H), 1.41 (d, J=6.4 Hz, 3H); MS (ES+): 432.1 (M+1); Analysis Calculated for $C_{26}H_{25}NO_5 \cdot 1.1(HCl) \cdot 2(H_2O)$:C, 61.52; H, 5.98; Cl, 7.68; N, 2.76. Found: C, 61.53; H, 5.92; Cl, 7.55; N, 2.94.

Scheme 4

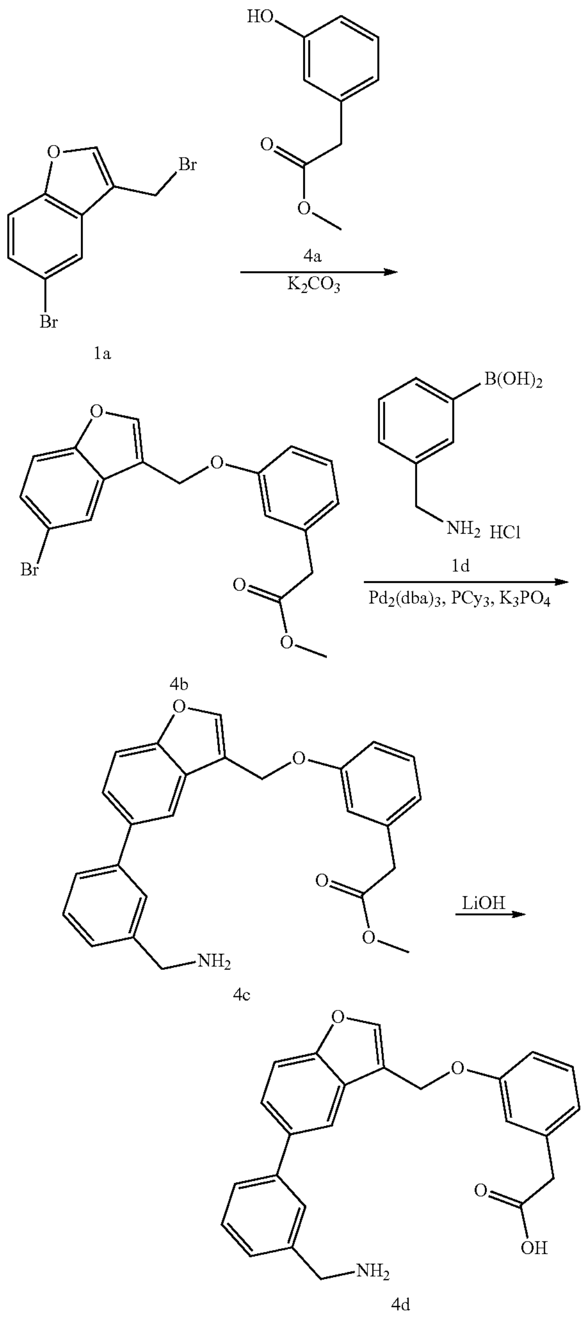

Preparation of 2-(3-((5-(3-(aminomethyl)phenyl) benzofuran-3-yl)methoxy)phenyl)acetic acid (4d)

Step-1: Preparation of methyl 2-(3-((5-bromobenzofuran-3-yl)methoxy)phenyl)acetate (4b)

Compound 4b was prepared according to the procedure reported in step-1 of scheme 1, from 5-bromo-3-(bromomethyl)benzofuran (1a) (250 mg, 0.86 mmol) in acetone (3 mL) using methyl 2-(3-hydroxyphenyl)acetate (4a) (172 mg, 1.035 mmol; CAS #: 42058-59-3), $K_2CO_3$ (477 mg, 3.45 mmol) and stirring overnight at room temperature. This gave after workup and purification by flash column chromatography [silica gel (12 g), eluting with EtOAc in hexane from 0-50%]methyl 2-(3-((5-bromobenzofuran-3-yl)methoxy)phenyl)acetate (4b) (170 mg, 53% yield) as a yellow oil; $^1H$ NMR (300 MHz, DMSO-$d_6$) δ 8.20 (s, 1H), 7.92 (d, J=2.0 Hz, 1H), 7.62 (d, J=8.7 Hz, 1H), 7.51 (dd, J=8.7, 2.1 Hz, 1H), 7.30-7.19 (m, 1H), 7.00-6.94 (m, 2H), 6.87 (dt, J=7.6, 1.2 Hz, 1H), 5.25 (s, 2H), 3.66 (s, 2H), 3.61 (s, 3H); MS (ES+): 397.00 (M+Na).

Step-2: Preparation of methyl 2-(3-((5-(3-(aminomethyl)phenyl)benzofuran-3-yl)methoxy)phenyl)acetate (4c)

Compound 4c was prepared according to the procedure reported in step-2 of scheme 1, from methyl 2-(3-((5-bromobenzofuran-3-yl)methoxy)phenyl)acetate (4b) (170 mg, 0.453 mmol) in dioxane (3 mL) using 3-(aminomethyl)phenylboronic acid hydrochloride (1d) (127 mg, 0.680 mmol), 2 M solution of $K_3PO_4$ (0.385 mL, 0.770 mmol), tricyclohexylphosphine (51 mg, 0.181 mmol), $Pd_2(dba)_3$ (83 mg, 0.091 mmol) and heating at 135° C. for 30 min in a microwave. This gave after workup and purification by flash column chromatography [silica gel (24 g), eluting with DMA-80 in DCM from 0-70%]methyl 2-(3-((5-(3-(aminomethyl)phenyl)benzofuran-3-yl)methoxy)phenyl)acetate (4c) (95 mg, 52% yield) as a clear oil; $^1H$ NMR (300 MHz, DMSO-$d_6$) δ 8.17 (s, 1H), 7.95 (d, J=1.8 Hz, 1H), 7.71-7.63 (m, 3H), 7.54-7.48 (m, 1H), 7.39 (t, J=7.6 Hz, 1H), 7.31 (d, J=7.5 Hz, 1H), 7.27-7.21 (m, 1H), 7.03-6.97 (m, 2H), 6.86 (d, J=7.4 Hz, 1H), 5.31 (s, 2H), 3.79 (s, 2H), 3.65 (s, 2H), 3.59 (s, 3H); MS (ES+): 402.1 (M+1).

Step-3: Preparation of 2-(3-((5-(3-(aminomethyl)phenyl)benzofuran-3-yl)methoxy)phenyl)acetic acid (4d)

Compound 4d was prepared according to the procedure reported in step-3 of scheme 1, from methyl 2-(3-((5-(3-(aminomethyl)phenyl)benzofuran-3-yl)methoxy)phenyl)acetate (4c) (95 mg, 0.237 mmol) in THF (3 mL) using a solution of lithium hydroxide hydrate (57 mg, 1.359 mmol) in water (1 mL) and stirring at room temperature overnight. This gave after workup and purification by reverse phase column chromatography [C18 column (30 g), eluting with ACN in water (containing 0.1% HCl) from 0-100%] 2-(3-((5-(3-(aminomethyl)phenyl)benzofuran-3-yl)methoxy)phenyl)acetic acid (4d) (30 mg, 17% yield) hydrochloride salt as a white solid; $^1H$ NMR (300 MHz, DMSO-$d_6$) δ 12.36 (s, 1H, $D_2O$ exchangeable), 8.40 (s, 3H, $D_2O$ exchangeable), 8.20 (s, 1H), 7.99 (d, J=1.8 Hz, 1H), 7.86 (d, J=2.2 Hz, 1H), 7.77-7.65 (m, 3H), 7.57-7.41 (m, 2H), 7.29-7.20 (m, 1H), 7.04-6.93 (m, 2H), 6.86 (d, J=7.4 Hz, 1H), 5.30 (s, 2H), 4.11 (s, 2H), 3.55 (s, 2H); MS (ES+): 388.1 (M+1); Analysis Calculated for $C_{24}H_{21}NO_4 \cdot (HCl) \cdot 1.5(H_2O)$: C, 63.93; H, 5.59; Cl, 7.86; N, 3.11. Found: C, 64.14; H, 5.61; Cl, 8.08; N, 3.28.

Scheme 5

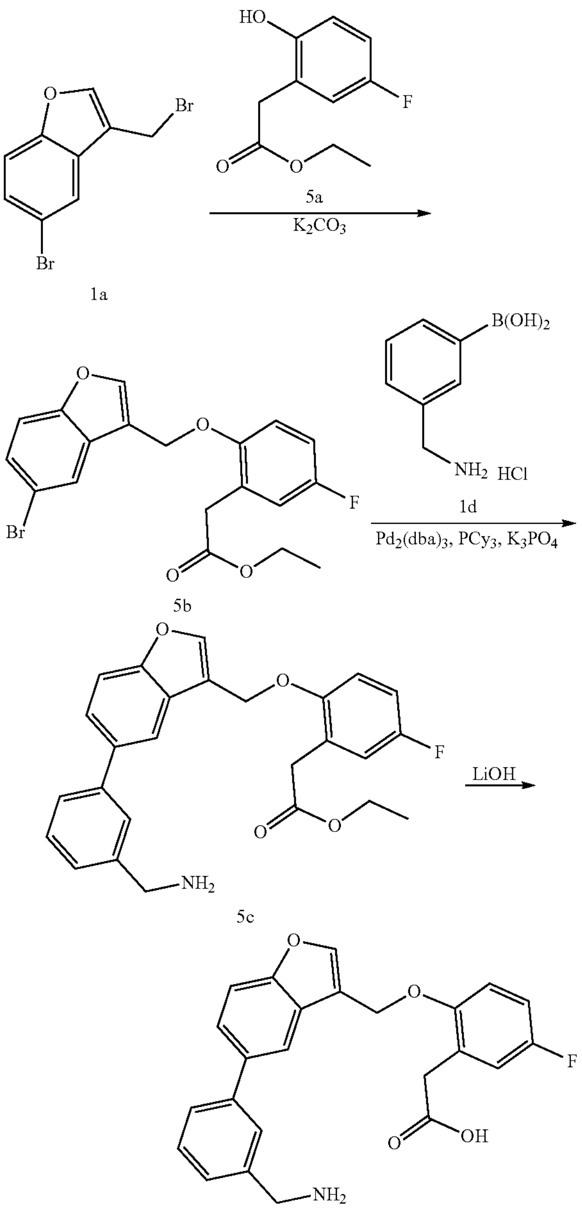

5d

Preparation of 2-(2-((5-(3-(aminomethyl)phenyl)benzofuran-3-yl)methoxy)-5-fluorophenyl)acetic acid (5d)

Step-1: Preparation of ethyl 2-(2-((5-bromobenzofuran-3-yl)methoxy)-5-fluorophenyl)acetate (5b)

Compound 5b was prepared according to the procedure reported in step-1 of scheme 1, from 5-bromo-3-(bromomethyl)benzofuran (1a) (450 mg, 1.552 mmol) in acetone (5 mL) using ethyl 2-(5-fluoro-2-hydroxyphenyl)acetate (5a) (354 mg, 1.785 mmol; CAS #: 1261826-26-9), $K_2CO_3$ (751 mg, 5.43 mmol) and stirring at room temperature overnight. This gave after workup and purification by flash column chromatography [silica gel (12 g), eluting with EtOAc in hexane from 0-50%] ethyl 2-(2-((5-bromobenzofuran-3-yl)methoxy)-5-fluorophenyl)acetate (5b) (610 mg, 97% yield) as a clear oil; $^{1}$H NMR (300 MHz, DMSO-$d_6$) δ 8.13 (s, 1H), 7.84 (d, J=2.0 Hz, 1H), 7.64-7.57 (m, 1H), 7.50 (dd, J=8.8, 2.1 Hz, 1H), 7.23-7.16 (m, 1H), 7.15-7.08 (m, 2H), 5.22 (s, 2H), 3.94 (q, J=7.1 Hz, 2H), 3.57 (s, 2H), 0.98 (t, J=7.1 Hz, 3H); MS (ES+): 397.00 (M+Na).

Step-2: Preparation of ethyl 2-(2-((5-(3-(aminomethyl)phenyl)benzofuran-3-yl)methoxy)-5-fluorophenyl)acetate (5c)

Compound 5c was prepared according to the procedure reported in step-2 of scheme 1, from ethyl 2-(2-((5-bromobenzofuran-3-yl)methoxy)-5-fluorophenyl)acetate (5b) (310 mg, 0.761 mmol) in dioxane (3 mL) using 3-(aminomethyl)phenylboronic acid hydrochloride (1d) (214 mg, 1.142 mmol), 2M solution of $K_3PO_4$ (0.647 mL, 1.294 mmol), tricyclohexylphosphine (85 mg, 0.304 mmol), $Pd_2(dba)_3$ (139 mg, 0.152 mmol) and heating at 135° C. for 30 min in a microwave. This gave after workup and purification by flash column chromatography [silica gel (24 g), eluting with DMA-80 in DCM from 0-70%] ethyl 2-(2-((5-(3-(aminomethyl)phenyl)benzofuran-3-yl)methoxy)-5-fluorophenyl)acetate (5c) (68 mg, 21% yield) as a clear oil; MS (ES+): 434.1 (M+1).

Step-3: Preparation of 2-(2-((5-(3-(aminomethyl)phenyl)benzofuran-3-yl)methoxy)-5-fluorophenyl)acetic acid (5d)

Compound 5d was prepared according to the procedure reported in step-3 of scheme 1, from ethyl 2-(2-((5-(3-(aminomethyl)phenyl)benzofuran-3-yl)methoxy)-5-fluorophenyl)acetate (5c) (68 mg, 0.157 mmol) in THF (3 mL) using a solution of lithium hydroxide hydrate (135 mg, 3.22 mmol) in water (1 mL) and stirring at room temperature overnight. This gave after workup and purification by reverse phase column chromatography [C18 column (30 g), eluting with ACN in water (containing 0.1% HCl) from 0-100%] 2-(2-((5-(3-(aminomethyl)phenyl)benzofuran-3-yl)methoxy)-5-fluorophenyl)acetic acid (5d) (9 mg, 3% yield) HCl salt as a white solid; $^{1}$H NMR (300 MHz, DMSO-$d_6$) δ 12.26 (s, 1H, $D_2O$ exchangeable), 8.33 (s, 3H, $D_2O$ exchangeable), 8.12 (s, 1H), 8.00 (d, J=1.8 Hz, 1H), 7.86 (d, J=1.8 Hz, 1H), 7.77-7.65 (m, 3H), 7.53 (t, J=7.6 Hz, 1H), 7.45 (d, J=7.6 Hz, 1H), 7.26-7.17 (m, 1H), 7.16-7.05 (m, 2H), 5.31 (s, 2H), 4.11 (s, 2H), 3.55 (s, 2H); $^{19}$F NMR (282 MHz, DMSO-$d_6$) δ −123.82; MS (ES+): 406.1 (M+1).

Scheme 6

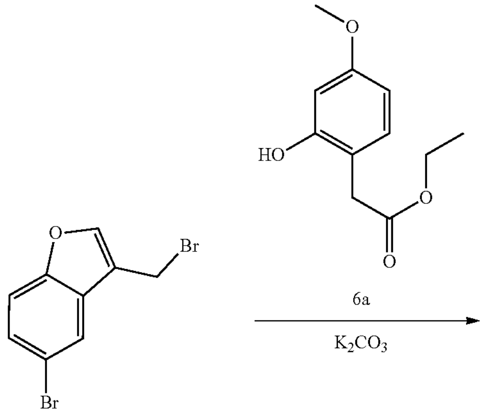

1a

-continued

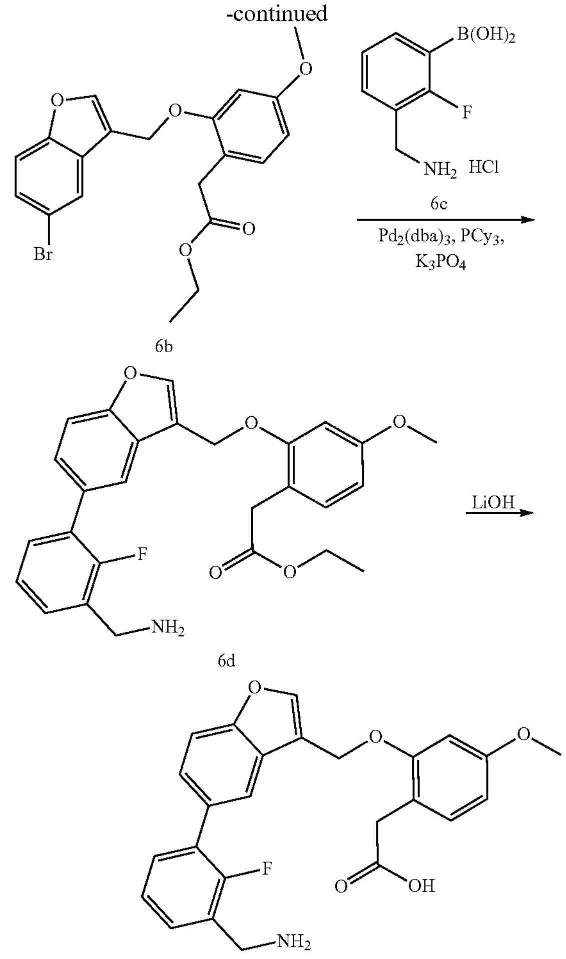

6b

6d

6e

Preparation of 2-(2-((5-(3-(aminomethyl)-2-fluorophenyl)benzofuran-3-yl)methoxy)-4-methoxyphenyl)acetic acid (6e)

Step-1: Preparation of ethyl 2-(2-((5-bromobenzofuran-3-yl)methoxy)-4-methoxyphenyl)acetate (6b)

Compound 6b was prepared according to the procedure reported in step-1 of scheme 1, from 5-bromo-3-(bromomethyl)benzofuran (1a) (400 mg, 1.38 mmol) in acetone (5 mL) using ethyl 2-(2-hydroxy-4-methoxyphenyl)acetate (6a) (334 mg, 1.586 mmol; CAS #: 76322-29-7), $K_2CO_3$ (667 mg, 4.83 mmol) and stirring at room temperature overnight. This gave after workup and purification by flash column chromatography [silica gel (12 g), eluting with EtOAc in hexane from 0-50%] ethyl 2-(2-((5-bromobenzofuran-3-yl)methoxy)-4-methoxyphenyl)acetate (6b) (500 mg, 86% yield) as a white solid; $^{1}$H NMR (300 MHz, DMSO-$d_6$) δ 8.14 (s, 1H), 7.85 (d, J=2.0 Hz, 1H), 7.62 (d, J=8.7 Hz, 1H), 7.51 (dd, J=8.7, 2.1 Hz, 1H), 7.11 (d, J=8.3 Hz, 1H), 6.78 (d, J=2.4 Hz, 1H), 6.51 (dd, J=8.3, 2.4 Hz, 1H), 5.23 (s, 2H), 3.93 (q, J=7.1 Hz, 2H), 3.77 (s, 3H), 3.48 (s, 2H), 0.99 (t, J=7.1 Hz, 3H); MS (ES+): 441.00 (M+Na).

Step-2: Preparation of ethyl 2-(2-((5-(3-(aminomethyl)-2-fluorophenyl)benzofuran-3-yl)methoxy)-4-methoxyphenyl)acetate (6d)

Compound 6d was prepared according to the procedure reported in step-2 of scheme 1, from ethyl 2-(2-((5-bromobenzofuran-3-yl)methoxy)-4-methoxyphenyl)acetate (6b) (250 mg, 0.596 mmol) in dioxane (3 mL) using 3-(aminomethyl)-2-fluorophenylboronic acid hydrochloride (6c) (184 mg, 0.894 mmol), 2M solution of $K_3PO_4$ (0.507 mL, 1.014 mmol), tricyclohexylphosphine (66.9 mg, 0.239 mmol), $Pd_2(dba)_3$ (109 mg, 0.119 mmol) and heating at 135° C. for 30 min in a microwave. This gave after workup and purification by flash column chromatography [silica gel (24 g), eluting with DMA80 in DCM from 0-70%] ethyl 2-(2-((5-(3-(aminomethyl)-2-fluorophenyl)benzofuran-3-yl)methoxy)-4-methoxyphenyl)acetate (6d) (121 mg, 44% yield) as a clear oil; $^1H$ NMR (300 MHz, DMSO-$d_6$) δ 8.14 (s, 1H), 7.79 (s, 1H), 7.70 (d, J=8.5 Hz, 1H), 7.54-7.45 (m, 2H), 7.41 (t, J=7.2 Hz, 1H), 7.25 (t, J=7.5 Hz, 1H), 7.08 (d, J=8.3 Hz, 1H), 6.80 (d, J=2.4 Hz, 1H), 6.49 (dd, J=8.3, 2.3 Hz, 1H), 5.27 (s, 2H), 3.81 (s, 2H), 3.77 (s, 3H), 3.71 (q, J=7.2 Hz, 2H), 3.46 (s, 2H), 0.87 (t, J=7.1 Hz, 3H); MS (ES+): 464.1 (M+1).

Step-3: Preparation of 2-(2-((5-(3-(aminomethyl)-2-fluorophenyl)benzofuran-3-yl)methoxy)-4-methoxyphenyl)acetic acid (6e)

Compound 6e was prepared according to the procedure reported in step-3 of scheme 1, from ethyl 2-(2-((5-(3-(aminomethyl)-2-fluorophenyl)benzofuran-3-yl)methoxy)-4-methoxyphenyl)acetate (6d) (121 mg, 0.261 mmol) in THF (3 mL) using a solution of lithium hydroxide hydrate (75 mg, 1.789 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)-2-fluorophenyl)benzofuran-3-yl)methoxy)-4-methoxyphenyl)acetic acid (6e) (58 mg, 22% yield) HCl salt as a white solid; $^1H$ NMR (300 MHz, DMSO-$d_6$) δ 11.94 (s, 1H, $D_2O$ exchangeable), 8.50 (s, 3H, $D_2O$ exchangeable), 8.15 (s, 1H), 7.88 (t, J=1.5 Hz, 1H), 7.74 (d, J=8.6 Hz, 1H), 7.67-7.48 (m, 3H), 7.37 (t, J=7.7 Hz, 1H), 7.09 (d, J=8.3 Hz, 1H), 6.79 (d, J=2.4 Hz, 1H), 6.50 (dd, J=8.3, 2.4 Hz, 1H), 5.30 (s, 2H), 4.14 (s, 2H), 3.75 (s, 3H), 3.44 (s, 2H); $^{19}F$ NMR (282 MHz, DMSO-$d_6$) δ-122.31; MS (ES+): 436.1 (M+1); Analysis Calculated for $C_{25}H_{22}FNO_5 \cdot 1.1HCl \cdot H_2O$: C, 60.84; H, 5.13; Cl, 7.90; N, 2.84. Found: C, 60.56; H, 5.29; Cl, 7.70; N, 2.86.

Scheme 7

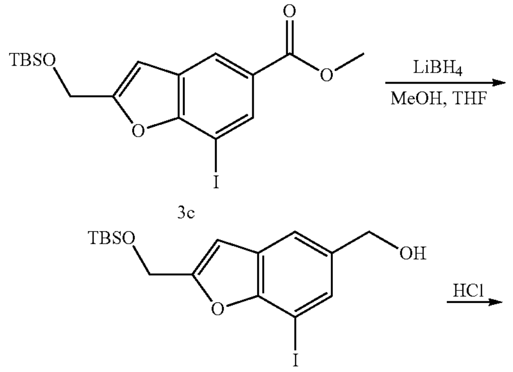

3c

7a

-continued

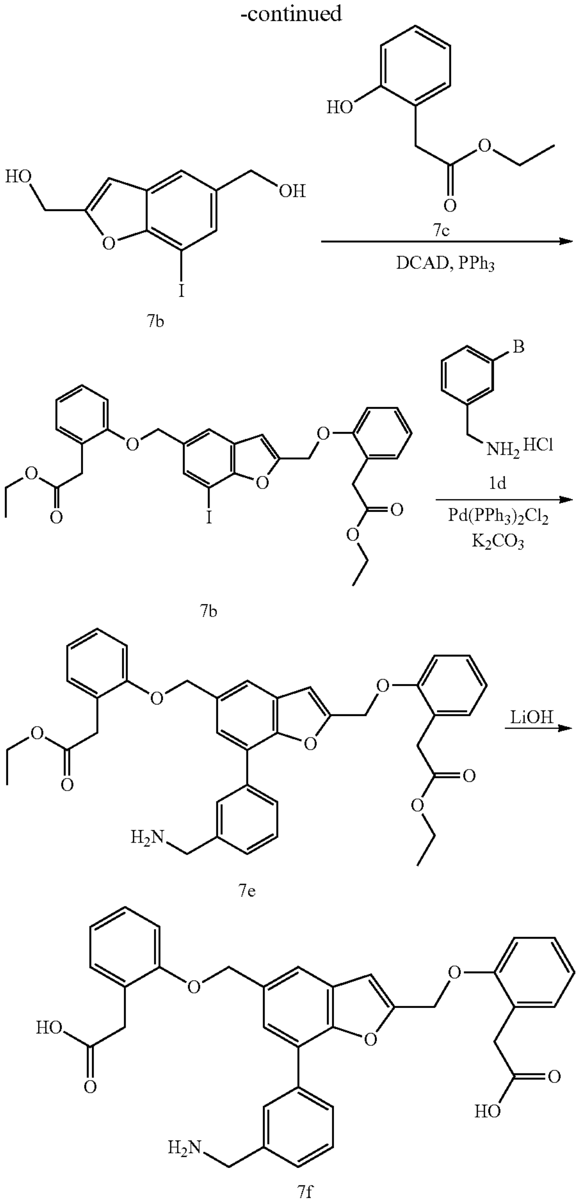

7b

7b

7e

7f

Preparation of 2,2'-((((7-(3-(aminomethyl)phenyl)benzofuran-2,5-diyl)bis(methylene))bis(oxy))bis(2,1-phenylene))diacetic acid (7f)

Step-1: Preparation of (2-(((tert-butyldimethylsilyl)oxy)methyl)-7-iodobenzofuran-5-yl)methanol (7a)

To a solution of methyl 2-(((tert-butyldimethylsilyl)oxy)methyl)-7-iodobenzofuran-5-carboxylate (3c) (268 g, 600 mmol) in THF (1200 mL) at −78° C. was added $LiBH_4$ (600 mL, 1201 mmol, 2 M solution in THF) and MeOH (48.6 mL, 1201 mmol). The reaction mixture was stirred at RT for 6 h, quenched with saturated aqueous $NH_4Cl$ solution and extracted with EtOAc. The organic layer was washed with brine, dried, filtered and concentrated in vacuum and used as such in the next step; $^1H$ NMR (300 MHz, DMSO-$d_6$) δ 7.62 (d, J=1.5 Hz, 1H), 7.52 (d, J=1.4 Hz, 1H), 6.93 (s, 1H), 5.29 (t, J=5.8 Hz, 1H), 4.81 (s, 2H), 4.53 (d, J=5.8 Hz, 2H), 0.89 (s, 9H), 0.12 (s, 6H).

Step-2: Preparation of (7-iodobenzofuran-2,5-diyl)dimethanol (7b)

To a solution of (2-(((tert-butyldimethylsilyl)oxy) methyl)-7-iodobenzofuran-5-yl)methanol (7a) (2 g, 4.78 mmol) in DCM (18 mL) was added HCl (4N in dioxane, 2.39 mL, 9.56 mmol). The reaction mixture was stirred at room temperature for 1 h, concentrated in vacuum and the residue obtained was purified by flash column chromatography [silica gel (40 g), eluting with EtOAc/MeOH (9:1) in hexane from 0-80%] to give (7-iodobenzofuran-2,5-diyl) dimethanol (7b) (1.42 g, 98% yield) as a clear oil; $^1$H NMR (300 MHz, DMSO-$d_6$) δ 7.60 (d, J=1.5 Hz, 1H), 7.55-7.48 (m, 1H), 6.92-6.84 (m, 1H), 5.53 (t, J=5.8 Hz, 1H, $D_2O$ exchangeable), 5.27 (t, J=5.8 Hz, 1H, $D_2O$ exchangeable), 4.58 (dd, J=5.9, 0.9 Hz, 2H), 4.53 (d, J=5.8, 0.7 Hz, 2H).; MS (ES+): 326.9 (M+Na).

Step-3: Preparation of diethyl 2,2'-((((7-iodobenzofuran-2,5-diyl)bis(methylene))bis(oxy))bis(2,1-phenylene))diacetate (7d)

To a solution of (7-iodobenzofuran-2,5-diyl)dimethanol (7b) (500 mg, 1.644 mmol), triphenylphosphine (949 mg, 3.62 mmol) and ethyl 2-(2-hydroxyphenyl)acetate (7c) (652 mg, 3.62 mmol; CAS #41873-65-8) in DCM (30 mL) at 0° C. was added dropwise bis(4-chlorobenzyl)diazene-1,2-dicarboxylate (DCAD) (1.33 g, 3.62 mmol) in DCM (20 mL). The reaction mixture was stirred for 30 min at room temperature. The suspension was filtered over a pad of Celite and the filtrate was concentrated in vacuum and purified by flash column chromatography [silica gel (40 g), eluting with EtOAc in hexane from 0-50%] to give diethyl 2,2'-((((7-iodobenzofuran-2,5-diyl)bis(methylene))bis(oxy))bis(2,1-phenylene))diacetate (7d) (400 mg, 38.7% yield) as a yellow oil; $^1$H NMR (300 MHz, DMSO-$d_6$) δ 7.76 (d, J=1.5 Hz, 1H), 7.69 (d, J=1.5 Hz, 1H), 7.29-7.20 (m, 5H), 7.14 (s, 1H), 7.06 (dd, J=8.3, 1.1 Hz, 1H), 6.99-6.87 (m, 2H), 5.29 (s, 2H), 5.15 (s, 2H), 4.05-3.98 (m, 4H), 3.62 (s, 2H), 3.60 (s, 2H), 1.11-1.01 (m, 6H); MS (ES+): 651.1 (M+Na).

Step-4: Preparation of diethyl 2,2'-((((7-(3-(aminomethyl)phenyl)benzofuran-2,5-diyl)bis(methylene))bis(oxy))bis(2,1-phenylene))diacetate (7e)

Compound 7e was prepared according to the procedure reported in step-8 of Scheme 3, from diethyl 2,2'-((((7-iodobenzofuran-2,5-diyl)bis(methylene))bis(oxy))bis(2,1-phenylene))diacetate (7d) (280 mg, 0.446 mmol) in dioxane (15 mL) using 3-(aminomethyl)phenylboronic acid hydrochloride (1d) (150 mg, 0.802 mmol), bis(triphenylphosphine)palladium(II) chloride (47 mg, 0.067 mmol), a solution of $K_2CO_3$ (185 mg, 1.337 mmol) in water (3 mL) and heating at 100° C. for 3 h. This gave after workup and purification by flash column chromatography [silica gel (12 g), eluting with DMA-80 in DCM from 0-50%]diethyl 2,2'-((((7-(3-(aminomethyl)phenyl)benzofuran-2,5-diyl)bis(methylene))bis(oxy))bis(2,1-phenylene))diacetate (7e) (136 mg, 50% yield) as a yellow oil. $^1$H NMR (300 MHz, DMSO-$d_6$) δ 7.80 (s, 1H), 7.76-7.70 (m, 1H), 7.68-7.66 (m, 1H), 7.66-7.63 (m, 1H), 7.59 (d, J=1.7 Hz, 1H), 7.48-7.39 (m, 3H), 7.29-7.20 (m, 5H), 7.13-7.08 (m, 1H), 7.06 (s, 1H), 6.98-6.87 (m, 2H), 5.30 (s, 2H), 5.24 (s, 2H), 3.95-3.86 (m, 4H), 3.80 (s, 2H), 3.63 (s, 2H), 3.59 (s, 2H), 1.01-0.92 (m, 6H); MS (ES+): 608.3 (M+1).

Step-5: Preparation of 2,2'-((((7-(3-(aminomethyl)phenyl)benzofuran-2,5-diyl)bis(methylene))bis(oxy))bis(2,1-phenylene))diacetic acid (7f)

Compound 7f was prepared according to the procedure reported in step-3 of scheme 1, from diethyl 2,2'-((((7-(3-(aminomethyl)phenyl)benzofuran-2,5-diyl)bis(methylene))bis(oxy))bis(2,1-phenylene))diacetate (7e) (136 mg, 0.224 mmol) in THF (5 mL) using a solution of lithium hydroxide hydrate (47 mg, 1.119 mmol) in water (1 mL) and stirring at room temperature overnight. This gave after workup and purification by reverse phase column chromatography [C18 column (50 g), eluting with ACN in water (containing 0.1% HCl) from 0-100%] 2,2'-((((7-(3-(aminomethyl)phenyl)benzofuran-2,5-diyl)bis(methylene))bis(oxy))bis(2,1-phenylene))diacetic acid (7f) (46 mg, 37% yield) HCl salt as a white solid; $^1$H NMR (300 MHz, DMSO-$d_6$) δ 9.81 (brs, 3H, $D_2O$ exchangeable), 8.03-7.99 (m, 1H), 7.96-7.91 (m, 1H), 7.73 (d, J=1.6 Hz, 1H), 7.67 (d, J=1.7 Hz, 1H), 7.62-7.55 (m, 2H), 7.30-7.19 (m, 5H), 7.12-7.05 (m, 2H), 6.99-6.86 (m, 2H), 5.34 (s, 2H), 5.26 (s, 2H), 4.13 (s, 2H), 3.60 (s, 2H), 3.56 (s, 2H); MS (ES+): 552.2 (M+1); (ES−): 550.2 (M−1); Analysis calculated for $C_{33}H_{29}NO_7 \cdot HCl \cdot 1.25H_2O$: C, 64.92; H, 5.37; Cl, 5.81; N, 2.29. Found: C, 64.84; H, 5.36; Cl, 5.93; N, 2.44.

Scheme 8

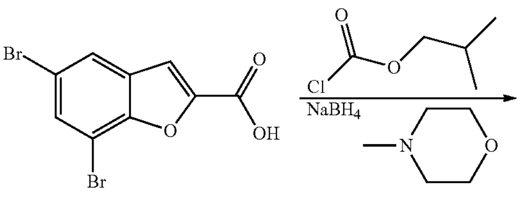

8a

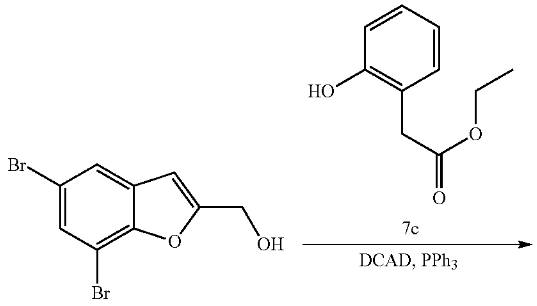

8b

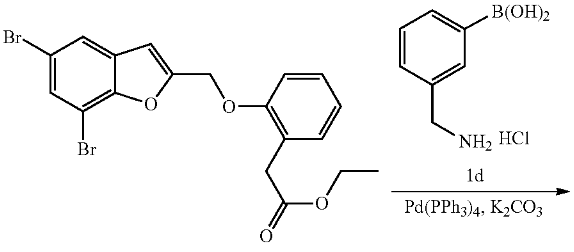

8c

-continued

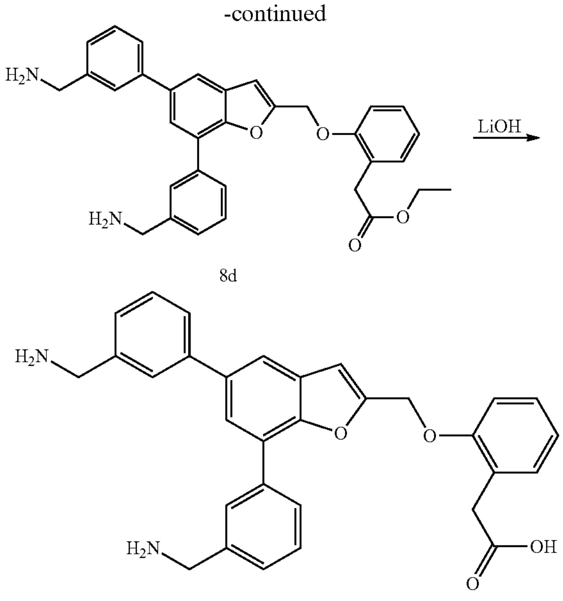

8d

8e

Preparation of 2-(2-((5,7-bis(3-(aminomethyl)phenyl)benzofuran-2-yl)methoxy)phenyl)acetic acid (8e)

Step-1: Preparation of (5,7-dibromobenzofuran-2-yl)methanol (8b)

To a solution of 5,7-dibromobenzofuran-2-carboxylic acid (8a) (850 mg, 2.66 mmol; CAS #: 90415-17-1) and N-Methylmorpholine (0.351 mL, 3.19 mmol) in THF (50 mL) was added isobutyl chloroformate (0.419 mL, 3.19 mmol) at −5° C. and stirred for 30 min. The reaction mixture was filtered over a pad of Celite and the precipitate was washed with THF (3×20 mL). The combined filtrates were cooled to 0° C. and added a solution of $NaBH_4$ (302 mg, 7.97 mmol) in water (2 mL). The mixture was diluted with water (10 mL) and extracted with EtOAc (3×). The combined organics were dried, filtered and concentrated in vacuum. The residue obtained was purified by flash column chromatography [silica gel (24 g), eluting with EtOAc/MeOH (9:1) in hexane from 0-50%] to give (5,7-dibromobenzofuran-2-yl)methanol (8b) (705 mg, 87% yield) as a white solid; $^1$H NMR (300 MHz, DMSO-$d_6$) δ 7.86 (d, J=1.8 Hz, 1H), 7.71 (d, J=1.9 Hz, 1H), 6.88 (d, J=0.9 Hz, 1H), 5.63 (t, J=5.9 Hz, 1H), 4.61 (dd, J=5.9, 0.9 Hz, 2H).

Step-2: Preparation of ethyl 2-(2-((5,7-dibromobenzofuran-2-yl)methoxy)phenyl)acetate (8c)

Compound 8c was prepared according to the procedure reported in step-3 of scheme 7 from (5,7-dibromobenzofuran-2-yl)methanol (8b)(400 mg, 1.307 mmol) in DCM (30 mL) using triphenylphosphine (377 mg, 1.438 mmol), ethyl 2-(2-hydroxyphenyl)acetate (7c) (259 mg, 1.438 mmol), a solution of bis(4-chlorobenzyl) diazene-1,2-dicarboxylate (DCAD) (528 mg, 1.438 mmol) in DCM (20 mL) and stirring at room temperature for 30 min. This gave after workup and purification by flash column chromatography [silica gel (40 g), eluting with EtOAc in hexane from 0-50%] ethyl 2-(2-((5,7-dibromobenzofuran-2-yl)methoxy)phenyl)acetate (8c) (210 mg, 0.449 mmol, 34% yield) as a yellow oil; MS (ES+): 488.90 (M+1).

Step-3: Preparation of ethyl 2-(2-((5,7-bis(3-(aminomethyl)phenyl)benzofuran-2-yl)methoxy)phenyl)acetate (8d)

Compound 8d was prepared according to the procedure reported in step-8 of Scheme 3 from ethyl 2-(2-((5,7-dibromobenzofuran-2-yl)methoxy)phenyl)acetate (8c) (210 mg, 0.449 mmol) in dioxane (10 mL) using 3-(aminomethyl)phenylboronic acid hydrochloride (1d) (210 mg, 1.121 mmol), $Pd(PPh_3)_4$ (104 mg, 0.09 mmol), a solution of $K_2CO_3$ (155 mg, 1.121 mmol) in water (3 mL) and heating at 100° C. for 3 h. This gave after workup and purification by flash column chromatography [silica gel (12 g), eluting with DMA-80 in DCM from 0-50%] ethyl 2-(2-((5,7-bis(3-(aminomethyl)phenyl)benzofuran-2-yl)methoxy)phenyl)acetate (8d) (121 mg, 52% yield) as a clear oil; $^1$H NMR (300 MHz, DMSO-$d_6$) δ 7.89 (d, J=1.8 Hz, 1H), 7.85 (d, J=1.8 Hz, 1H), 7.80-7.72 (m, 3H), 7.69-7.55 (m, 3H), 7.49-7.37 (m, 4H), 7.35-7.28 (m, 2H), 7.28-7.19 (m, 3H), 7.11 (s, 1H), 6.99-6.91 (m, 1H), 5.32 (s, 2H), 3.89 (q, J=7.2 Hz, 2H), 3.83-3.76 (m, 4H), 3.60 (s, 2H), 0.98 (t, J=7.1 Hz, 3H); MS (ES+): 521.2 (M+1).

Step-4: Preparation of 2-(2-((5,7-bis(3-(aminomethyl)phenyl)benzofuran-2-yl)methoxy)phenyl)acetic acid (8e)

Compound 8e was prepared according to the procedure reported in step-3 of scheme 1 from ethyl 2-(2-((5,7-bis(3-(aminomethyl)phenyl)benzofuran-2-yl)methoxy)phenyl)acetate (8d) (121 mg, 0.232 mmol) in THF (3 mL) using a solution of lithium hydroxide hydrate (75 mg, 1.794 mmol) in water (1 mL) and stirring at room temperature overnight. This gave after workup and purification by reverse phase column chromatography [C18 column (30 g), eluting with ACN in water (containing 0.1% HCl) from 0-100%] 2-(2-((5,7-bis(3-(aminomethyl)phenyl)benzofuran-2-yl)methoxy)phenyl)acetic acid (8e) (49 mg, 22% yield) HCl salt as a white solid; $^1$H NMR (300 MHz, DMSO-$d_6$) δ 8.71 (s, 3H, $D_2O$ exchangeable), 8.25 (d, J=1.9 Hz, 1H), 8.15 (d, J=1.8 Hz, 1H), 8.04 (dd, J=7.5, 1.8 Hz, 2H), 7.99 (d, J=1.7 Hz, 1H), 7.83 (dt, J=7.5, 1.7 Hz, 1H), 7.62-7.45 (m, 4H), 7.25 (tt, J=7.5, 1.6 Hz, 3H), 7.15 (s, 1H), 6.95 (td, J=7.0, 1.8 Hz, 1H), 5.36 (s, 2H), 4.15 (d, J=8.6 Hz, 4H), 3.57 (s, 2H); MS (ES+): 493.2 (M+1); (ES−): 491.2 (M−1); Analysis calculated for $C_{31}H_{28}N_2O_4 \cdot 2HCl \cdot H_2O$: C, 63.81; H, 5.53; Cl, 12.15; N, 4.80. Found: C, 63.45; H, 5.43; Cl, 12.09; N, 4.88.

Scheme 9

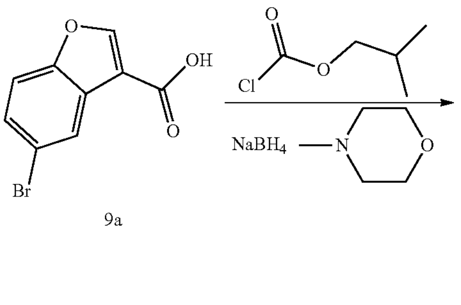

9a

-continued

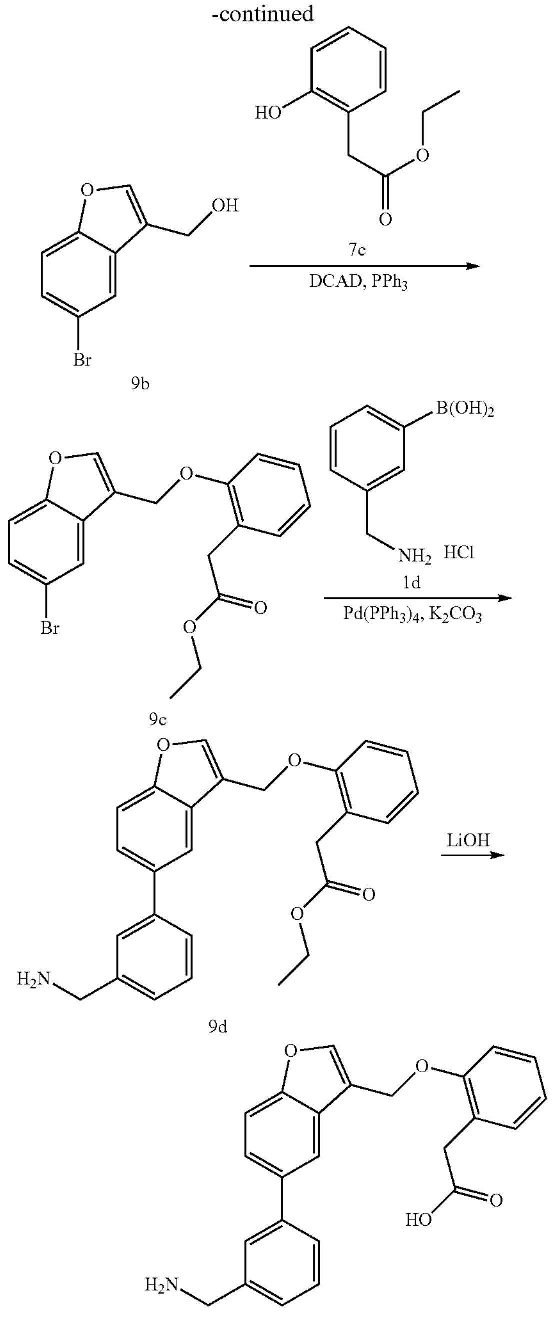

9b 9c 9d 9e

Preparation of 2-(2-((5-(3-(aminomethyl)phenyl) benzofuran-3-yl)methoxy)phenyl)acetic acid (9e)

Step-1: Preparation of (5-bromobenzofuran-3-yl)methanol (9b)

Compound 9b was prepared according to the procedure reported in step-1 of scheme 8, from 5-bromobenzofuran-3-carboxylic acid (9a) (850 mg, 3.53 mmol; CAS #: 461663-79-6) in THE (50 mL) using N-Methylmorpholine (0.465 mL, 4.23 mmol), isobutyl chloroformate (0.556 mL, 4.23 mmol) and a solution of $NaBH_4$ (400 mg, 10.58 mmol) in water (2.0 mL). This gave after workup and purification by flash column chromatography [silica gel (24 g), eluting with EtOAc/MeOH (9:1) in hexane from 0-50%] (5-bromobenzofuran-3-yl)methanol (9b) (705 mg, 88% yield) as a white solid; $^1H$ NMR (300 MHz, DMSO-$d_6$) δ 7.97-7.83 (m, 2H), 7.56 (d, J=8.7 Hz, 1H), 7.45 (dd, J=8.7, 2.1 Hz, 1H), 5.21 (t, J=5.6 Hz, 1H, $D_2O$ exchangeable), 4.61 (dd, J=5.6, 1.1 Hz, 2H).

Step-2: Preparation of ethyl 2-(2-((5-bromobenzofuran-3-yl)methoxy)phenyl)acetate (9c)

Compound 9c was prepared according to the procedure reported in step-3 of scheme 7 from (5-bromobenzofuran-3-yl)methanol (9b) (350 mg, 1.541 mmol) in DCM (30 mL) using triphenylphosphine (445 mg, 1.696 mmol), ethyl 2-(2-hydroxyphenyl)acetate (7c) (306 mg, 1.696 mmol), a solution of bis(4-chlorobenzyl) diazene-1,2-dicarboxylate (DCAD) (623 mg, 1.696 mmol) in DCM (20 mL) and stirring at room temperature for 30 min. This gave after workup and purification by flash column chromatography [silica gel (12 g), eluting with EtOAc in hexane from 0-50%] ethyl 2-(2-((5-bromobenzofuran-3-yl)methoxy)phenyl)acetate (9c) (255 mg, 43% yield) as a clear oil; MS (ES+): 413.00 (M+Na).

Step-3: Preparation of ethyl 2-(2-((5-(3-(aminomethyl)phenyl)benzofuran-3-yl)methoxy)phenyl)acetate (9d)

Compound 9d was prepared according to the procedure reported in step-8 of Scheme 3, from ethyl 2-(2-((5-bromobenzofuran-3-yl)methoxy)phenyl)acetate (9c) (250 mg, 0.642 mmol) in dioxane (10 mL) using 3-(aminomethyl) phenylboronic acid hydrochloride (1d) (181 mg, 0.963 mmol), $Pd(PPh_3)_4$ (111 mg, 0.096 mmol), a solution of $K_2CO_3$ (222 mg, 1.606 mmol) in water (3 mL) and heating at 100° C. for 3 h. This gave after workup and purification by flash column chromatography [silica gel (12 g), eluting with DMA-80 in DCM from 0-50%]ethyl 2-(2-((5-(3-(aminomethyl)phenyl)benzofuran-3-yl)methoxy)phenyl)acetate (9d) as a clear oil (88 mg, 33% yield); MS (ES+): 416.1 (M+1).

Step-4: Preparation of 2-(2-((5-(3-(aminomethyl) phenyl)benzofuran-3-yl)methoxy)phenyl)acetic acid (9e)

Compound 9e was prepared according to the procedure reported in step-3 of scheme 1, from ethyl 2-(2-((5-(3-(aminomethyl)phenyl)benzofuran-3-yl)methoxy)phenyl)acetate (9d) (88 mg, 0.212 mmol) in THF (3 mL) using a solution of lithium hydroxide hydrate (108 mg, 2.57 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)benzofuran-3-yl)methoxy)phenyl)acetic acid (9e) (30 mg, 37% yield) HCl salt as a white solid; $^1H$ NMR (300 MHz, DMSO-$d_6$) δ 8.40 (s, 3H, $D_2O$ exchangeable), 8.13 (s, 1H), 8.01 (d, J=1.7 Hz, 1H), 7.89 (t, J=1.8 Hz, 1H), 7.78-7.64 (m, 3H), 7.52 (t, J=7.6 Hz, 1H), 7.45 (dt, J=7.6, 1.5 Hz, 1H), 7.31-7.17 (m, 3H), 6.93 (td, J=7.3, 1.3 Hz, 1H), 5.32 (s, 2H), 4.11 (s, 2H), 3.54 (s, 2H); MS (ES+): 388.1 (M+1); (ES−): 386.1 (M−1); Analysis calculated for $C_{24}H_{21}NO_4\cdot1.05HCl\cdot0.75H_2O$: C, 65.63; H, 5.40; Cl, 8.48; N, 3.19. Found: C, 66.03; H, 5.25; Cl, 8.50; N, 3.43.

Scheme 10

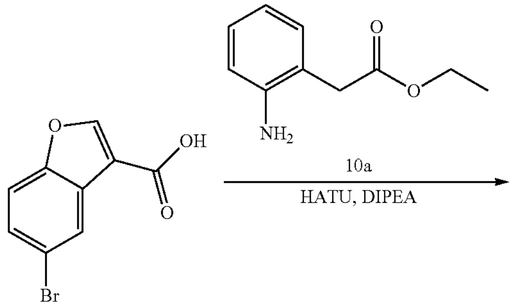

9a

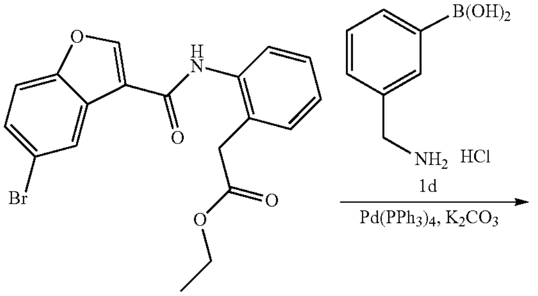

10b

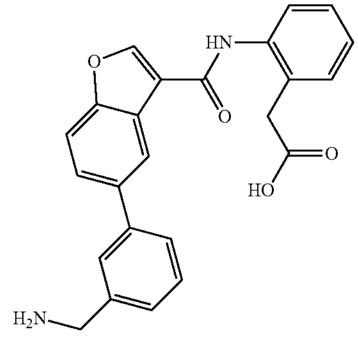

10c

Preparation of 2-(2-(5-(3-(aminomethyl)phenyl) benzofuran-3-carboxamido)phenyl)acetic acid (10c)

Step-1: Preparation of ethyl 2-(2-(5-bromobenzo-furan-3-carboxamido)phenyl)acetate (10b)

To a stirred solution of 5-bromobenzofuran-3-carboxylic acid (9a) (150 mg, 0.622 mmol; CAS #: 461663-79-6)) in DMF (5 mL) was added ethyl 2-(2-aminophenyl)acetate (10a) (139 mg, 0.778 mmol), N-ethyl-N-isopropylpropan-2-amine (DIPEA) (0.272 mL, 1.556 mmol), 2-(3H-[1,2,3] triazolo[4,5-b]pyridin-3-yl)-1,1,3,3-tetramethylisouronium hexafluorophosphate(V) (HATU) (296 mg, 0.778 mmol) and stirred at room temperature for 3 h. The reaction mixture was diluted with EtOAc, washed with water, brine, dried, filtered and concentrated in vacuum. The residue obtained was purified by flash column chromatography [silica gel (12 g), eluting with EtOAc in hexane from 0-100%] to give ethyl 2-(2-(5-bromobenzofuran-3-carboxamido)phenyl)acetate (10b) (225 mg, 90% yield) as a yellow oil; MS (ES+): 402.00 (M+1).

Step-2: Preparation of 2-(2-(5-(3-(aminomethyl) phenyl)benzofuran-3-carboxamido)phenyl)acetic acid (10c)

Compound 10c was prepared according to the procedure reported in step-8 of Scheme 3, from ethyl 2-(2-(5-bromobenzofuran-3-carboxamido)phenyl)acetate (10b) (225 mg, 0.559 mmol) in dioxane (10 mL) using 3-(aminomethyl) phenylboronic acid hydrochloride (1d) (157 mg, 0.839 mmol), $Pd(PPh_3)_4$ (97 mg, 0.084 mmol), a solution of $K_2CO_3$ (193 mg, 1.398 mmol) in water (3 mL) and heating at 100° C. for 3 h. This gave after workup and purification by flash column chromatography [silica gel (12 g), eluting with DMA80 in DCM from 0-50%] followed by reverse phase column chromatography [C18 column (30 g), eluting with ACN in water (containing 0.1% HCl) from 0-100%] 2-(2-(5-(3-(aminomethyl)phenyl)benzofuran-3-carboxamido)phenyl)acetic acid (10c) (35 mg, 16% yield) HCl salt as a white solid; $^1H$ NMR (300 MHz, DMSO-$d_6$) δ 12.32 (s, 1H, $D_2O$ exchangeable), 10.11 (s, 1H, $D_2O$ exchangeable), 8.78 (s, 1H), 8.39 (d, J=1.9 Hz, 4H, 3H $D_2O$ exchangeable), 7.89 (t, J=1.8 Hz, 1H), 7.83 (d, J=8.7 Hz, 1H), 7.76-7.69 (m, 2H), 7.56-7.44 (m, 3H), 7.37-7.29 (m, 2H), 7.23 (td, J=7.4, 1.5 Hz, 1H), 4.12 (s, 2H), 3.71 (s, 2H); MS (ES+): 401.2 (M+1); (ES−): 399.1 (M−1); Analysis calculated for $C_{24}H_{20}N_2O_4 \cdot HCl \cdot H_2O$: C, 63.37; H, 5.10; Cl, 7.79; N, 6.16. Found: C, 62.95; H, 4.73; Cl, 7.53; N, 6.12.

Scheme 11

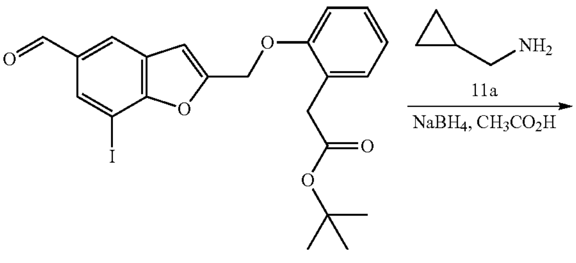

3i

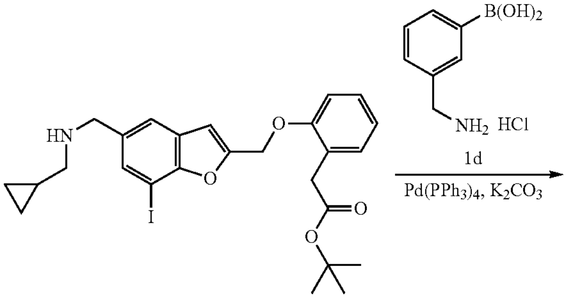

11b

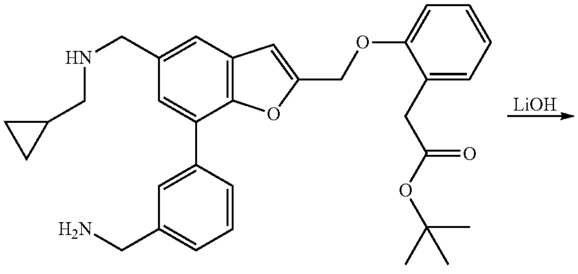

11c

-continued

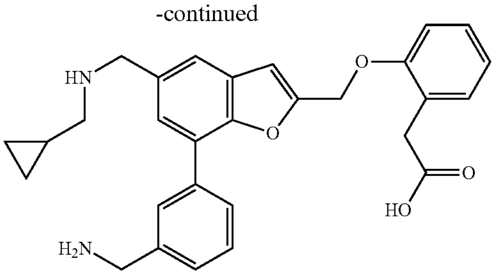

11d

Preparation of 2-(2-((7-(3-(aminomethyl)phenyl)-5-(((cyclopropylmethyl)amino)methyl)benzofuran-2-yl)methoxy)phenyl)acetic acid (11d)

Step-1: Preparation of tert-butyl 2-(2-((5-(((cyclopropylmethyl)amino)methyl)-7-iodobenzofuran-2-yl)methoxy)phenyl)acetate (11b)

To a solution of tert-butyl 2-(2-((5-formyl-7-iodobenzofuran-2-yl)methoxy)phenyl)acetate (3i) (350 mg, 0.711 mmol) in DCM/MeOH (10 mL, 4:1) was added cyclopropylmethanamine (11a) (51 mg, 0.711 mmol), acetic acid (0.081 mL, 1.422 mmol) and stirred at RT for 10 min.

To this was added $NaBH_4$ (54 mg, 1.42 mmol) stirred at room temperature overnight and quenched with saturated $NaHCO_3$ (10 mL). The reaction mixture was extracted with EtOAc (3×). The organic layers were combined dried, filtered and concentrated in vacuum. The residue obtained was purified by flash column chromatography [silica gel (12 g), eluting with EtOAc in hexane from 0 to 60%] to give tert-butyl 2-(2-((5-(((cyclopropylmethyl)amino)methyl)-7-iodobenzofuran-2-yl)methoxy)phenyl)acetate (11b) (140 mg, 360% yield) as a clear oil; $^1H$ NMR (300 MHz, DMSO-$d_6$) δ 7.69 (d, J=1.5 Hz, 1H), 7.56 (d, J=1.5 Hz, 1H), 7.27 (td, J=7.8, 7.2, 1.7 Hz, 1H), 7.22-7.15 (m, 2H), 7.10 (s, 1H), 6.94 (td, J=7.4, 1.1 Hz, 1H), 5.27 (s, 2H), 3.75 (s, 2H), 3.51 (s, 2H), 2.34 (d, J=6.6 Hz, 2H), 1.28 (s, 9H), 0.93-0.81 (m, 1H), 0.44-0.33 (m, 2H), 0.11-0.02 (m, 2H); MS (ES+): 548.10 (M+1).

Step-2: Preparation of tert-butyl 2-(2-((7-(3-(aminomethyl)phenyl)-5-(((cyclopropylmethyl)amino)methyl)benzofuran-2-yl)methoxy)phenyl)acetate (11c)

Compound 11c was prepared according to the procedure reported in step-8 of Scheme 3, from tert-butyl 2-(2-((5-(((cyclopropylmethyl)amino)methyl)-7-iodobenzofuran-2-yl)methoxy)phenyl)acetate (11b) (140 mg, 0.256 mmol) in dioxane (10 mL), using 3-(aminomethyl)phenylboronic acid hydrochloride (1d) (72 mg, 0.384 mmol), $Pd(PPh_3)_4$ (44 mg, 0.038 mmol), a solution of $K_2CO_3$ (88 mg, 0.639 mmol) in water (3 mL) and heating at 100° C. for 3 h. This gave after workup and purification by flash column chromatography [silica gel (12 g), eluting with DMA-80 in DCM from 0-50%] tert-butyl 2-(2-((7-(3-(aminomethyl)phenyl)-5-(((cyclopropylmethyl)amino)methyl)benzofuran-2-yl)methoxy)phenyl)acetate (11c) (76 mg, 56% yield) as a clear oil; MS (ES+): 527.2 (M+1).

Step-3: Preparation of 2-(2-((7-(3-(aminomethyl)phenyl)-5-(((cyclopropylmethyl)amino)methyl)benzofuran-2-yl)methoxy)phenyl)acetic acid (11d)

Compound 11d was prepared according to the procedure reported in step-3 of scheme 1, from tert-butyl 2-(2-((7-(3-(aminomethyl)phenyl)-5-(((cyclopropylmethyl)amino)methyl)benzofuran-2-yl)methoxy)phenyl)acetate (11c) (76 mg, 0.144 mmol) in THF (3 mL) using a solution of lithium hydroxide hydrate (43 mg, 1.023 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((7-(3-(aminomethyl)phenyl)-5-(((cyclopropylmethyl)amino)methyl)benzofuran-2-yl)methoxy)phenyl)acetic acid (11d) (53 mg, 78% yield) HCl salt as a white solid; $^1H$ NMR (300 MHz, DMSO-$d_6$) δ 12.20 (s, 1H, $D_2O$ exchangeable), 9.53 (s, 2H, $D_2O$ exchangeable), 8.59 (s, 3H, $D_2O$ exchangeable), 8.12 (d, J=1.8 Hz, 1H), 8.01-7.90 (m, 2H), 7.84 (d, J=1.6 Hz, 1H), 7.62-7.56 (m, 2H), 7.32-7.18 (m, 3H), 7.13 (s, 1H), 6.94 (td, J=7.2, 1.4 Hz, 1H), 5.35 (s, 2H), 4.28 (s, 2H), 4.13 (s, 2H), 3.56 (s, 2H), 2.83 (s, 2H), 1.23-1.07 (m, 1H), 0.61-0.52 (m, 2H), 0.42-0.31 (m, 2H); MS (ES+): 471.2 (M+1); (ES−): 469.2 (M−1); Analysis calculated for $C_{29}H_{30}N_2O_4·2HCl·1.5H_2O$: C, 61.05; H, 6.18; Cl, 12.43; N, 4.91. Found: C, 61.20; H, 6.12; Cl, 12.16; N, 4.92.

Scheme 12

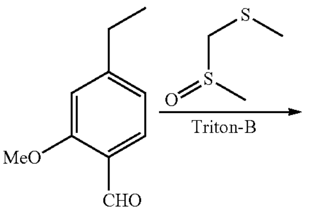

12a

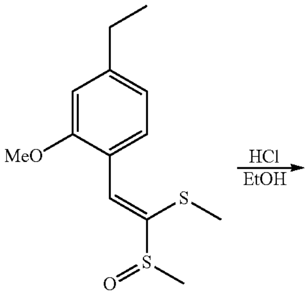

12b

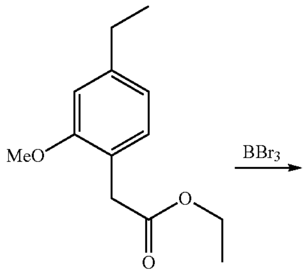

12c

-continued

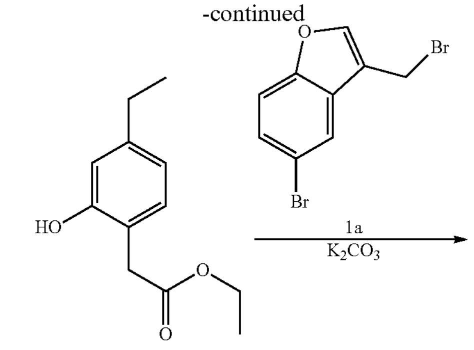

12d

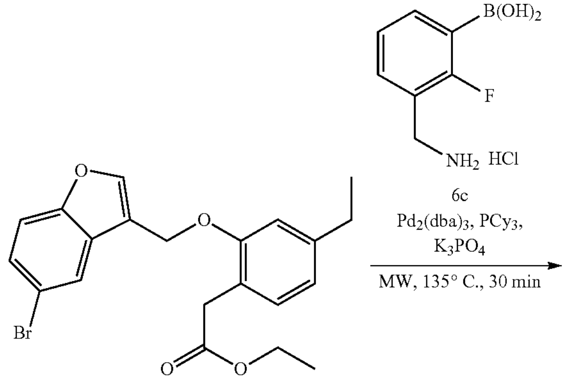

12e

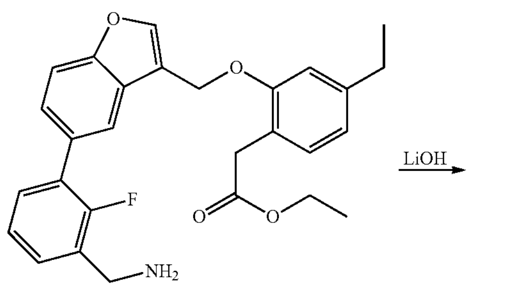

12f

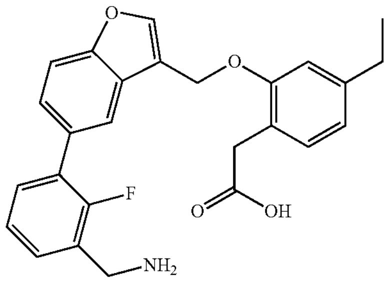

12g

Preparation of 2-(2-((5-(3-(aminomethyl)-2-fluorophenyl)benzofuran-3-yl)methoxy)-4-ethylphenyl) acetic acid (12g)

Step-1: Preparation of (2-(4-ethyl-2-methoxyphenyl)-1-(methylsulfinyl)vinyl)(methyl)sulfane (12b)

A solution of 4-ethyl-2-methoxybenzaldehyde (12a) (1.82 g, 11.08 mmol; CAS #142224-35-9), methyl(methylsulfinylmethyl)sulfane (2.203 g, 17.73 mmol), and Triton B (40% wt. in MeOH) (2.317 g, 5.54 mmol) in THF (20 mL) was heated at 70° C. for 16 h. The reaction mixture was diluted with ethyl acetate (250 mL), washed with brine, dried, filtered and concentrated in vacuum. The residue obtained was purified by flash column chromatography [silica gel (24 g), eluting with EtOAc in hexane from 0-40%] to give (2-(4-ethyl-2-methoxyphenyl)-1-(methylsulfinyl)vinyl)(methyl)sulfane (12b) (2.66 g, 89% yield) as a pale-yellow oil; $^1$H NMR (300 MHz, DMSO-$d_6$) δ 8.01 (d, J=7.9 Hz, 1H), 7.75 (s, 1H), 6.95 (d, J=1.6 Hz, 1H), 6.93-6.83 (m, 1H), 3.84 (s, 3H), 2.71 (s, 3H), 2.64 (q, J=7.6 Hz, 2H), 2.28 (s, 3H), 1.22 (t, J=7.6 Hz, 3H); MS (ES+): 271 (M+1).

Step-2: Preparation of ethyl 2-(4-ethyl-2-methoxyphenyl)acetate (12c)

To a solution of (2-(4-ethyl-2-methoxyphenyl)-1-(methylsulfinyl)vinyl)(methyl)sulfane (12b) (2.66 g, 9.84 mmol) in ethanol (20 mL) was added HCl (4 M HCl in dioxane, 12.30 mL, 49.2 mmol) and heated at 80° C. for 16 h. The reaction mixture was concentrated to remove ethanol, diluted with saturated $NaHCO_3$ (20 mL) and extracted with EtOAc. The organic layer was washed with water, brine, dried, filtered and concentrated in vacuum. The residue obtained was purified by flash column chromatography [silica gel (24 g), eluting with ethyl acetate in hexanes from 0-2%] to afford ethyl 2-(4-ethyl-2-methoxyphenyl)acetate (12c) (1.61 g, 74% yield) as a clear colorless liquid; $^1$H NMR (300 MHz, DMSO-$d_6$) δ 7.06 (d, J=7.5 Hz, 1H), 6.82 (d, J=1.6 Hz, 1H), 6.73 (dd, J=7.5, 1.6 Hz, 1H), 4.05 (q, J=7.1 Hz, 2H), 3.74 (s, 3H), 3.51 (s, 2H), 2.58 (q, J=7.6 Hz, 2H), 1.22-1.13 (m, 6H); MS (ES+): 245 (M+Na).

Step-3: Preparation of ethyl 2-(4-ethyl-2-hydroxyphenyl)acetate (12d)

To a stirred solution of ethyl 2-(4-ethyl-2-methoxyphenyl)acetate (12c) (1.61 g, 7.24 mmol) in DCM (15 mL) was added boron tribromide (10 M in DCM, 14.49 mL, 14.49 mmol) under a nitrogen atmosphere at 0° C. and stirred at 0° C. for 2 h. The reaction mixture was quenched with a saturated solution of $NaHCO_3$ (25 mL) and extracted with EtOAc (3x25 mL). The combined organic layers were washed with water, brine, dried, filtered and concentrated in vacuum. The residue obtained was purified by flash column chromatography [silica gel, eluting with EtOAc in hexane from 0-10%] to give ethyl 2-(4-ethyl-2-hydroxyphenyl)acetate (12d) (472 mg, 31% yield) as a yellow oil; $^1$H NMR (300 MHz, DMSO-$d_6$) δ 9.32 (s, 1H), 6.98 (d, J=7.6 Hz, 1H), 6.62 (d, J=1.7 Hz, 1H), 6.58 (dd, J=7.6, 1.7 Hz, 1H), 4.05 (q, J=7.1 Hz, 2H), 3.48 (s, 2H), 2.49-2.43 (m, 2H), 1.15 (dt, J=10.4, 7.3 Hz, 6H); MS (ES+): 209 (M+1).

Step-4: Preparation of ethyl 2-(2-((5-bromobenzofuran-3-yl)methoxy)-4-ethylphenyl)acetate (12e)

Compound 12e was prepared according to the procedure reported in step-1 of scheme 1, from 5-bromo-3-(bromomethyl)benzofuran (1a) (300 mg, 1.035 mmol) in acetone (5 mL) using ethyl 2-(4-ethyl-2-hydroxyphenyl)acetate (12d) (248 mg, 1.190 mmol), $K_2CO_3$ (500 mg, 3.62 mmol) and stirring overnight at room temperature. This gave after workup and purification by flash column chromatography [silica gel (12 g), eluting with EtOAc in hexane from 0-50%]ethyl 2-(2-((5-bromobenzofuran-3-yl)methoxy)-4-ethylphenyl)acetate (12e) (412 mg, 95% yield) as a yellow oil; $^1$H NMR (300 MHz, DMSO-$d_6$) δ 8.14 (s, 1H), 7.85 (d, J=2.0 Hz, 1H), 7.61 (d, J=8.7 Hz, 1H), 7.50 (dd, J=8.7, 2.1

Hz, 1H), 7.12-7.02 (m, 2H), 6.76 (dd, J=7.6, 1.5 Hz, 1H), 5.23 (s, 2H), 3.93 (q, J=7.1 Hz, 2H), 3.53 (s, 2H), 2.61 (q, J=7.6 Hz, 2H), 1.20 (t, J=7.6 Hz, 3H), 0.98 (t, J=7.1 Hz, 3H).

Step-5: Preparation of ethyl 2-(2-((5-(3-(aminomethyl)-2-fluorophenyl)benzofuran-3-yl)methoxy)-4-ethylphenyl)acetate (12f)

Compound 12f was prepared according to the procedure reported in step-2 of scheme 1, from ethyl 2-(2-((5-bromobenzofuran-3-yl)methoxy)-4-ethylphenyl)acetate (12e) (206 mg, 0.494 mmol) in dioxane (3 mL) using 3-(aminomethyl)-2-fluorophenylboronic acid hydrochloride (6c) (152 mg, 0.740 mmol), a 2 M solution of $K_3PO_4$ (0.420 mL, 0.839 mmol), tricyclohexylphosphine (55 mg, 0.197 mmol), $Pd_2(dba)_3$ (90 mg, 0.099 mmol) and heating at 135° C. for 30 min in a microwave. This gave after workup and purification by flash column chromatography [silica gel (24 g), eluting with DMA-80 in DCM from 0-70%] ethyl 2-(2-((5-(3-(aminomethyl)-2-fluorophenyl)benzofuran-3-yl)methoxy)-4-ethylphenyl)acetate (12f) (79 mg, 35% yield) as a clear oil; MS (ES+): 462.2 (M+1).

Step-6: Preparation of 2-(2-((5-(3-(aminomethyl)-2-fluorophenyl)benzofuran-3-yl)methoxy)-4-ethylphenyl)acetic acid (12g)

Compound 12g was prepared according to the procedure reported in step-3 of scheme 1, from ethyl 2-(2-((5-(3-(aminomethyl)-2-fluorophenyl)benzofuran-3-yl)methoxy)-4-ethylphenyl)acetate (12f) (79 mg, 0.171 mmol) in THF (3 mL) using a solution of lithium hydroxide hydrate (62 mg, 1.481 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)-2-fluorophenyl)benzofuran-3-yl)methoxy)-4-ethylphenyl)acetic acid (12g) (22 mg, 30% yield) HCl salt as a white solid; $^1H$ NMR (300 MHz, DMSO-$d_6$) δ 8.50 (s, 1H, $D_2O$ exchangeable), 8.15 (s, 1H), 7.88 (d, J=1.8 Hz, 1H), 7.75 (d, J=8.6 Hz, 1H), 7.68-7.58 (m, 1H), 7.58-7.50 (m, 2H), 7.37 (t, J=7.7 Hz, 1H), 7.12-7.03 (m, 2H), 6.76 (dd, J=7.6, 1.5 Hz, 1H), 5.30 (s, 2H), 4.15 (s, 2H), 3.47 (s, 2H), 2.60 (q, J=7.6 Hz, 2H), 1.19 (t, J=7.6 Hz, 3H); $^{19}F$ NMR (282 MHz, DMSO-$d_6$) δ −122.31; MS (ES+): 434.2 (M+1); Analysis calculated for $C_{26}H_{24}FNO_4 \cdot HCl \cdot 1.75H_2O$: C, 62.27; H, 5.73; N, 2.79. Found: C, 62.56; H, 5.84; N, 3.04.

Scheme 13

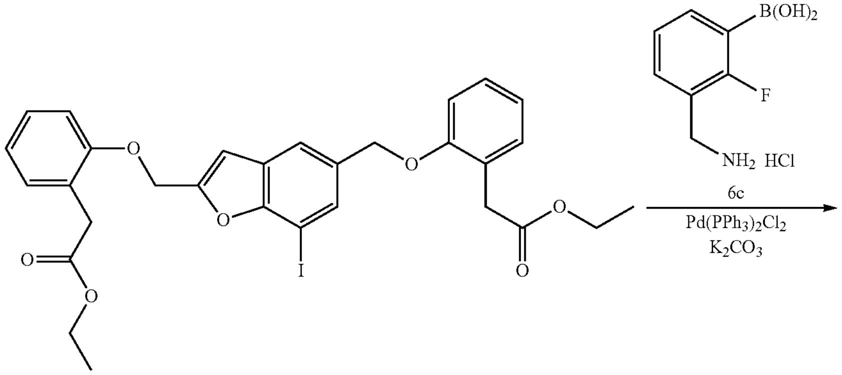

7d

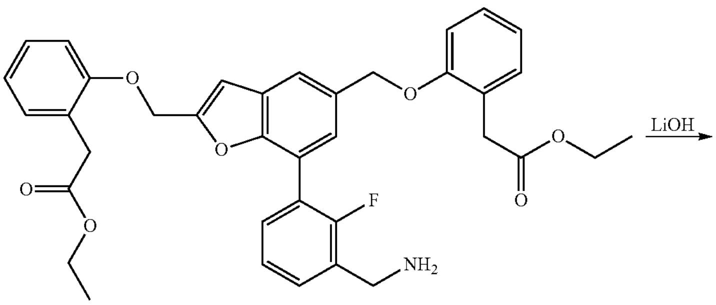

13a

-continued

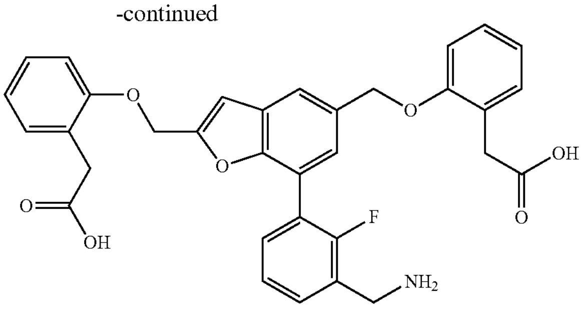

13b

Preparation of 2,2'-((((7-(3-(aminomethyl)-2-fluorophenyl)benzofuran-2,5-diyl)bis(methylene))bis(oxy))bis(2,1-phenylene))diacetic acid (13b)

Step-1: Preparation of diethyl 2,2'-((((7-(3-(aminomethyl)-2-fluorophenyl)benzofuran-2,5-diyl)bis(methylene))bis(oxy))bis(2,1-phenylene))diacetate (13a)

Compound 13a was prepared according to the procedure reported in step-8 of Scheme 3, from diethyl 2,2'-((((7-iodobenzofuran-2,5-diyl)bis(methylene))bis(oxy))bis(2,1-phenylene))diacetate (7d) (290 mg, 0.461 mmol) in dioxane (15 mL) using 3-(aminomethyl)-2-fluorophenylboronic acid (6c) (171 mg, 0.831 mmol), bis(triphenylphosphine)palladium(II) chloride (48.6 mg, 0.069 mmol), a solution of $K_2CO_3$ (191 mg, 1.384 mmol) in water (3 mL) and heating at 100° C. for 3 h. This gave after workup and purification by flash column chromatography [silica gel (12 g), eluting with DMA-80 in DCM from 0-50%]diethyl 2,2'-((((7-(3-(aminomethyl)-2-fluorophenyl)benzofuran-2,5-diyl)bis(methylene))bis(oxy))bis(2,1-phenylene))diacetate (13a) (180 mg, 62% yield) as a yellow oil; MS (ES+): 626.2 (M+1).

Step-2: Preparation of 2,2'-((((7-(3-(aminomethyl)-2-fluorophenyl)benzofuran-2,5-diyl)bis(methylene))bis(oxy))bis(2,1-phenylene))diacetic acid (13b)

Compound 13b was prepared according to the procedure reported in step-3 of scheme 1, from diethyl 2,2'-((((7-(3-(aminomethyl)-2-fluorophenyl)benzofuran-2,5-diyl)bis(methylene))bis(oxy))bis(2,1-phenylene))diacetate (13a) (180 mg, 0.288 mmol) in THF (3 mL) using a solution of lithium hydroxide hydrate (155 mg, 3.69 mmol) in water (1 mL) and stirring overnight at room temperature. This gave after workup and purification by reverse phase column chromatography [C18 column (30 g), eluting with ACN in water (containing 0.1% HCl) from 0-100%] 2,2'-((((7-(3-(aminomethyl)-2-fluorophenyl)benzofuran-2,5-diyl)bis(methylene))bis(oxy))bis(2,1-phenylene))diacetic acid (13b) (34 mg, 21% yield) HCl salt as a white solid; $^1H$ NMR (300 MHz, DMSO-$d_6$) δ 9.73 (s, 1H, $D_2O$ exchangeable), 7.79 (d, J=1.7 Hz, 1H), 7.73-7.64 (m, 2H), 7.50-7.47 (m, 1H), 7.46-7.39 (m, 1H), 7.26-7.15 (m, 5H), 7.13-7.03 (m, 2H), 6.97-6.86 (m, 2H), 5.26 (d, J=3.0 Hz, 4H), 4.17 (s, 2H), 3.58 (s, 2H), 3.54 (s, 2H); $^{19}F$ NMR (282 MHz, DMSO-$d_6$) δ-118.59; MS (ES+): 570.2 (M+1); (ES−): 568.2 (M−1); Analysis calculated for $C_{33}H_{28}FNO_7 \cdot HCl \cdot 1.5H_2O$: C, 62.61; H, 5.09; Cl, 5.60; N, 2.21. Found: C, 62.57; H, 4.96; Cl, 5.80; N, 2.28.

Scheme 14

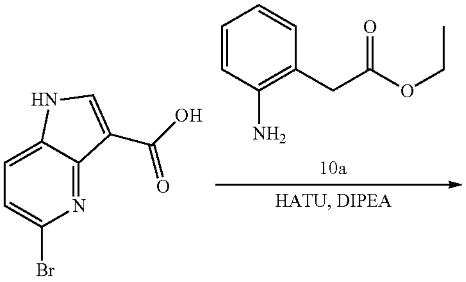

14a

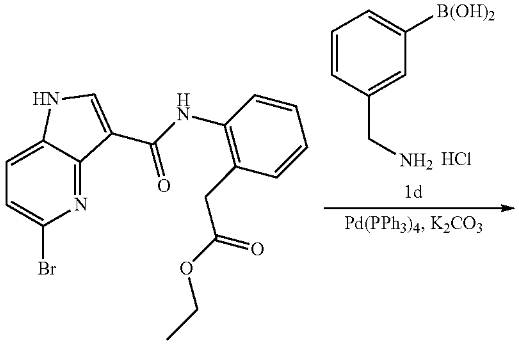

14b

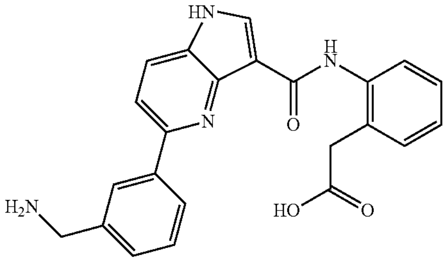

14c

Preparation of 2-(2-(5-(3-(aminomethyl)phenyl)-1H-pyrrolo[3,2-b]pyridine-3-carboxamido)phenyl)acetic acid (14c)

Step-1: Preparation of ethyl 2-(2-(5-bromo-1H-pyrrolo[3,2-b]pyridine-3-carboxamido)phenyl)acetate (14b)

Compound 14b was prepared according to the procedure reported in step-1 of scheme 10, from 5-bromo-1H-pyrrolo

[3,2-b]pyridine-3-carboxylic acid (14a) (350 mg, 1.452 mmol; CAS #: 1167056-46-3) in DMF (5 mL) using ethyl 2-(2-aminophenyl)acetate (10a) (325 mg, 1.815 mmol), N-ethyl-N-isopropylpropan-2-amine (DIPEA) (0.634 mL, 3.63 mmol), 2-(3H-[1,2,3]triazolo[4,5-b]pyridin-3-yl)-1,1,3,3-tetramethylisouronium hexafluorophosphate(V) (HATU) (690 mg, 1.815 mmol) and stirring at room temperature overnight. This gave after workup and purification by flash column chromatography [silica gel (12 g), eluting with EtOAc in hexane from 0-100%] ethyl 2-(2-(5-bromo-1H-pyrrolo[3,2-b]pyridine-3-carboxamido)phenyl)acetate (14b) (140 mg, 24% yield) as a white solid; MS (ES+): 402.00 (M+1).

Step-2: Preparation of 2-(2-(5-(3-(aminomethyl)phenyl)-1H-pyrrolo[3,2-b]pyridine-3-carboxamido)phenyl)acetic acid (14c)

Compound 14c was prepared according to the procedure reported in step-8 of Scheme 3, from ethyl 2-(2-(5-bromo-1H-pyrrolo[3,2-b]pyridine-3-carboxamido)phenyl)acetate (14b) (140 mg, 0.35 mmol) in dioxane (10 mL) using 3-(aminomethyl)phenylboronic acid hydrochloride (1d) (98 mg, 0.522 mmol), $Pd(PPh_3)_4$ (60.3 mg, 0.052 mmol), a solution of $K_2CO_3$ (120 mg, 0.870 mmol) in water (3 mL) and heating at 100° C. for 3 h. This gave after workup and purification by flash column chromatography [silica gel (12 g), eluting with DMA-80 in DCM from 0-50%] followed by reverse phase column chromatography [C18 column (30 g), eluting with ACN in water (containing 0.1% HCl) from 0-100%] 2-(2-(5-(3-(aminomethyl)phenyl)-1H-pyrrolo[3,2-b]pyridine-3-carboxamido)phenyl)acetic acid (14c) (40 mg, 29% yield) HCl salt as a white solid; $^1H$ NMR (300 MHz, DMSO-$d_6$) δ 12.37 (d, J=3.2 Hz, 1H, $D_2O$ exchangeable), 10.54 (s, 1H, $D_2O$ exchangeable), 8.48 (s, 3H, $D_2O$ exchangeable), 8.38 (d, J=3.1 Hz, 1H), 8.21 (s, 1H), 8.17-8.05 (m, 2H), 7.97 (dd, J=8.5, 1.4 Hz, 1H), 7.84 (d, J=8.6 Hz, 1H), 7.62-7.51 (m, 2H), 7.38-7.25 (m, 2H), 7.16 (td, J=7.4, 1.3 Hz, 1H), 4.13 (q, J=5.8 Hz, 2H), 3.78 (s, 2H); MS (ES+): 401.1 (M+1); (ES−): 399.1 (M−1); Analysis calculated for $C_{23}H_{20}N_4O_3 \cdot 2HCl \cdot 2.75H_2O$: C, 52.83; H, 5.30; Cl, 13.56; N, 10.71. Found: C, 53.03; H, 5.19; Cl, 13.21; N, 10.70.

Scheme 15

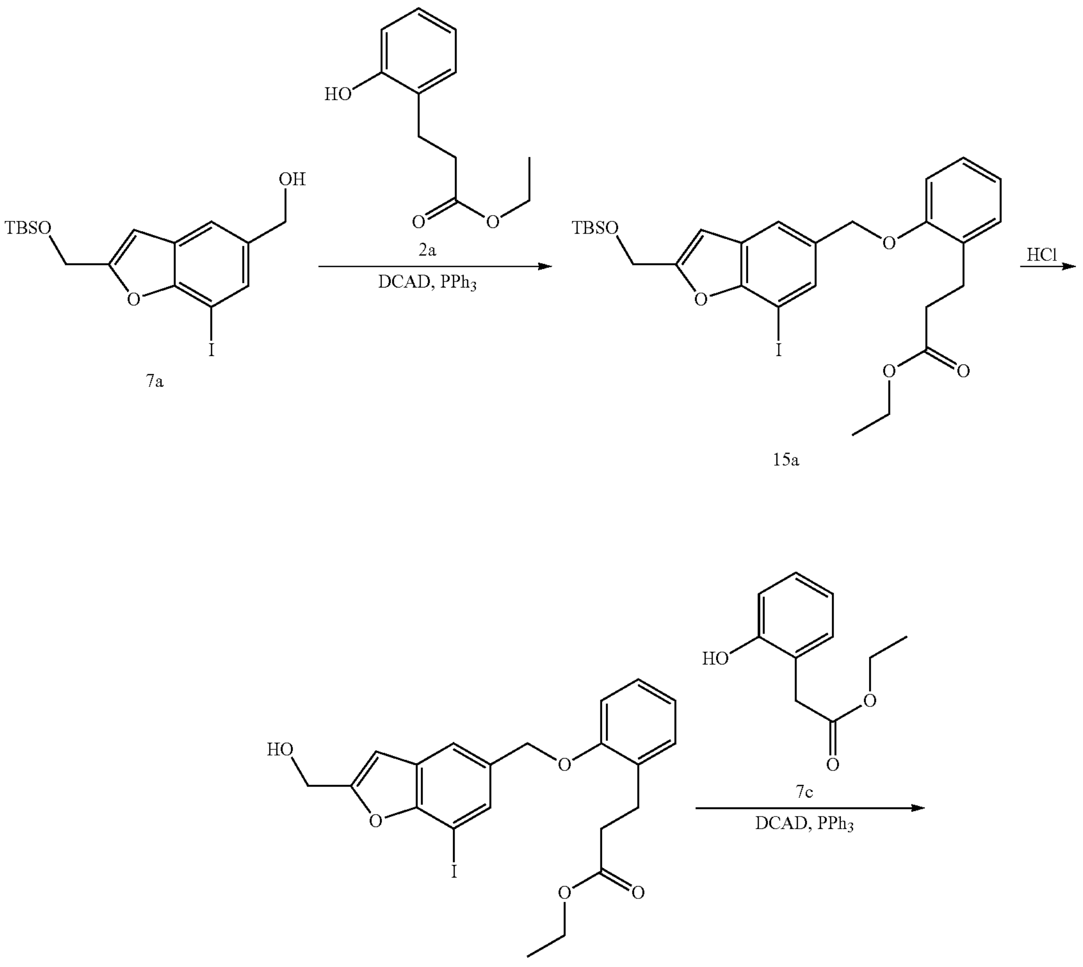

7a
15a
15b

-continued

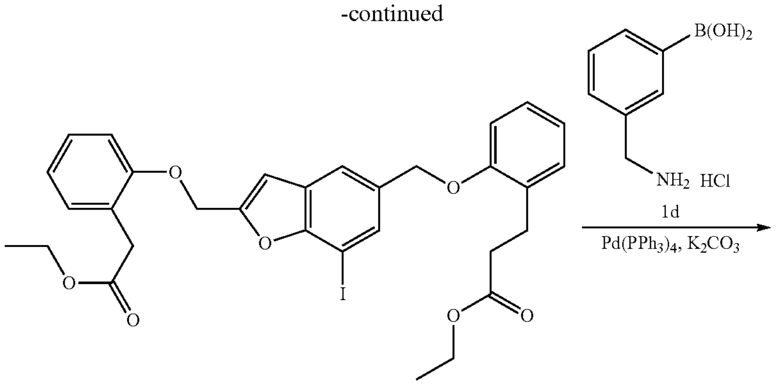

15c

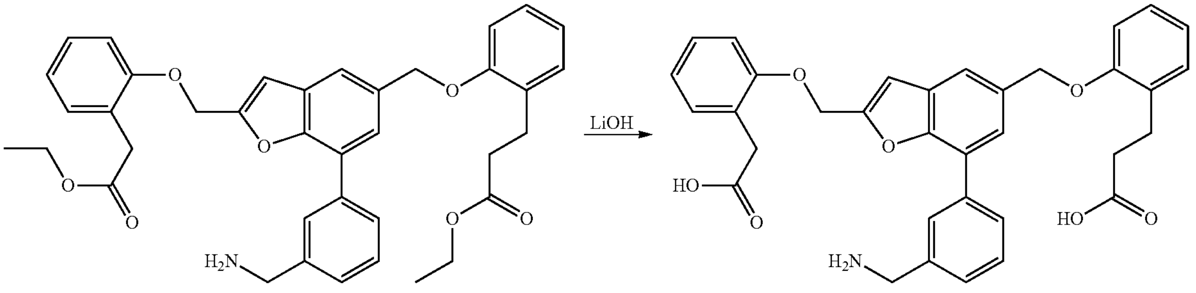

15d 15e

Preparation of 3-(2-((7-(3-(aminomethyl)phenyl)-2-((2-(carboxymethyl)phenoxy)methyl)benzofuran-5-yl)methoxy)phenyl)propanoic acid (15e)

Step-1: Preparation of ethyl 3-(2-((2-(((tert-butyldimethylsilyl)oxy)methyl)-7-iodobenzofuran-5-yl)methoxy)phenyl)propanoate (15a)

Compound 15a was prepared according to the procedure reported in step-3 of scheme 7, from (2-(((tert-butyldimethylsilyl)oxy)methyl)-7-iodobenzofuran-5-yl)methanol (7a) (2 g, 4.78 mmol) in DCM (30 mL) using triphenylphosphine (1.379 g, 5.26 mmol), ethyl 3-(2-hydroxyphenyl)propanoate (2a) (1.021 g, 5.26 mmol), a solution of bis(4-chlorobenzyl) diazene-1,2-dicarboxylate (DCAD) (1.931 g, 5.26 mmol) in DCM (20 mL) and stirring at room temperature for 30 min. This gave after workup and purification by flash column chromatography [silica gel (40 g), eluting with EtOAc in hexane from 0-50%] ethyl 3-(2-((2-(((tert-butyldimethylsilyl)oxy)methyl)-7-iodobenzofuran-5-yl)methoxy)phenyl)propanoate (15a) (1.9 g, 67%) as a yellow oil.

Step-2: Preparation of ethyl 3-(2-((2-(hydroxymethyl)-7-iodobenzofuran-5-yl)methoxy)phenyl)propanoate (15b)

Compound 15b was prepared according to the procedure reported in step-2 of scheme 7, from ethyl 3-(2-((2-(((tert-butyldimethylsilyl)oxy)methyl)-7-iodobenzofuran-5-yl)methoxy)phenyl)propanoate (15a) (1.9 g, 3.20 mmol) in DCM (20 mL) using 4N HCl in dioxane (3.59 mL, 14.34 mmol) and stirring at room temperature for 3 h. This gave after workup and purification by flash column chromatography [silica gel (40 g), eluting with EtOAc in hexane from 0-70%] ethyl 3-(2-((2-(hydroxymethyl)-7-iodobenzofuran-5-yl)methoxy)phenyl)propanoate (15b) (975 mg, 43% yield) as a clear oil; $^1H$ NMR (300 MHz, DMSO-$d_6$) δ 7.75 (d, J=1.5 Hz, 1H), 7.68 (d, J=1.5 Hz, 1H), 7.17 (t, J=7.9 Hz, 2H), 7.04 (d, J=8.0 Hz, 1H), 6.91 (s, 1H), 6.87 (td, J=7.4, 1.1 Hz, 1H), 5.55 (t, J=5.8 Hz, 1H), 5.18 (s, 2H), 4.59 (dd, J=5.9, 0.8 Hz, 2H), 4.07-3.97 (m, 2H), 2.85 (t, J=7.6 Hz, 2H), 2.59-2.53 (m, 2H), 1.22-1.06 (m, 3H).

Step-3: Preparation of ethyl 3-(2-((2-((2-(2-ethoxy-2-oxoethyl)phenoxy)methyl)-7-iodobenzofuran-5-yl)methoxy)phenyl)propanoate (15c)

Compound 15c was prepared according to the procedure reported in step-3 of scheme 7, from ethyl 3-(2-((2-(hydroxymethyl)-7-iodobenzofuran-5-yl)methoxy)phenyl)propanoate (15b) (800 mg, 1.67 mmol) in DCM (30 mL) using triphenylphosphine (481 mg, 1.832 mmol), ethyl 2-(2-hydroxyphenyl)acetate (7c) (330 mg, 1.832 mmol), a solution of bis(4-chlorobenzyl) diazene-1,2-dicarboxylate (DCAD) (673 mg, 1.832 mmol) in DCM (20 mL) and stirring at room temperature for 30 min. This gave after workup and purification by flash column chromatography [silica gel (40 g), eluting with EtOAc in hexane from 0-50%] ethyl 3-(2-((2-((2-(2-ethoxy-2-oxoethyl)phenoxy)methyl)-7-iodobenzofuran-5-yl)methoxy)phenyl)propanoate (15c) (700 mg, 65% yield) as a yellow oil; $^1H$ NMR (300 MHz, DMSO-$d_6$) δ 7.82 (d, J=1.5 Hz, 1H), 7.74 (d, J=1.5 Hz, 1H), 7.29-7.14 (m, 6H), 7.07-7.02 (m, 1H), 6.95 (td, J=7.3, 1.3 Hz, 1H), 6.87 (td, J=7.4, 1.1 Hz, 1H), 5.30 (s, 2H), 5.19 (s, 2H), 4.07-3.96 (m, 4H), 3.61 (s, 2H), 2.87 (t, J=7.6 Hz, 2H), 2.57 (t, J=7.6 Hz, 2H), 1.22-1.10 (m, 6H).

Step-4: Preparation of ethyl 3-(2-((7-(3-(aminomethyl)phenyl)-2-((2-(2-ethoxy-2-oxoethyl)phenoxy)methyl)benzofuran-5-yl)methoxy)phenyl)propanoate (15d)

Compound 15d was prepared according to the procedure reported in step-8 of Scheme 3, from ethyl 3-(2-((2-((2-(2- ethoxy-2-oxoethyl)phenoxy)methyl)-7-iodobenzofuran-5-yl)methoxy)phenyl)propanoate (15c) (400 mg, 0.623 mmol) in dioxane (10 mL) using 3-(aminomethyl)phenylboronic acid hydrochloride (1d) (175 mg, 0.934 mmol), $Pd(PPh_3)_4$ (108 mg, 0.093 mmol), a solution of $K_2CO_3$ (215 mg, 1.556 mmol) in water (3 mL) and heating at 100° C. for 3 h. This gave after workup and purification by flash column chromatography [silica gel (12 g), eluting with DMA-80 in DCM from 0-50%] ethyl 3-(2-((7-(3-(aminomethyl)phenyl)-2-((2-(2-ethoxy-2-oxoethyl)phenoxy)methyl)benzofuran-5-yl)methoxy)phenyl)propanoate (15d) (241 mg, 62% yield) as a clear oil; MS (ES+): 622.2 (M+1); (ES−): 620.2 (M−1).

Step-5: Preparation of 3-(2-((7-(3-(aminomethyl)phenyl)-2-((2-(carboxymethyl)phenoxy)methyl)benzofuran-5-yl)methoxy)phenyl)propanoic acid (15e)

Compound 15e was prepared according to the procedure reported in step-3 of scheme 1, from ethyl 3-(2-((7-(3-(aminomethyl)phenyl)-2-((2-(2-ethoxy-2-oxoethyl)phenoxy)methyl)benzofuran-5-yl)methoxy)phenyl)propanoate (15d) (241 mg, 0.388 mmol) in THF (4 mL) using a solution of lithium hydroxide hydrate (131 mg, 3.11 mmol) in water (1 mL) and stirring at room temperature overnight. This gave after workup and purification by reverse phase column chromatography [C18 column (30 g), eluting with ACN in water (containing 0.1% HCl) from 0-100%] 3-(2-((7-(3-(aminomethyl)phenyl)-2-((2-(carboxymethyl)phenoxy)methyl)benzofuran-5-yl)methoxy)phenyl)propanoic acid (15e) (120 mg, 34% yield) HCl salt as a white solid; $^1H$ NMR (300 MHz, DMSO-$d_6$) δ 9.86 (s, 3H, $D_2O$ exchangeable), 7.99 (d, J=1.9 Hz, 1H), 7.94-7.87 (m, 1H), 7.76 (d, J=1.6 Hz, 1H), 7.68 (d, J=1.6 Hz, 1H), 7.60-7.54 (m, 2H), 7.29-7.15 (m, 5H), 7.13-7.06 (m, 2H), 6.94 (td, J=7.2, 1.5 Hz, 1H), 6.88 (td, J=7.3, 1.2 Hz, 1H), 5.33 (s, 2H), 5.27 (s, 2H), 4.13 (s, 2H), 3.56 (s, 2H), 2.85 (t, J=7.7 Hz, 2H), 2.57-2.51 (m, 2H); MS (ES+): 566.2 (M+1); (ES−): 564.2 (M−1); Analysis calculated for $C_{34}H_{31}NO_7 \cdot HCl \cdot H_2O$: C, 65.86; H, 5.53; Cl, 5.72; N, 2.26. Found: C, 65.84; H, 5.61; Cl, 5.99; N, 2.39.

Scheme 16

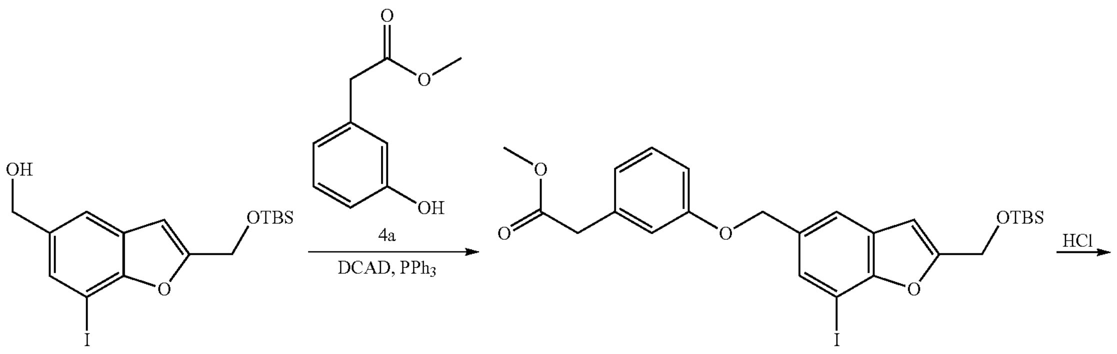

7a 16a

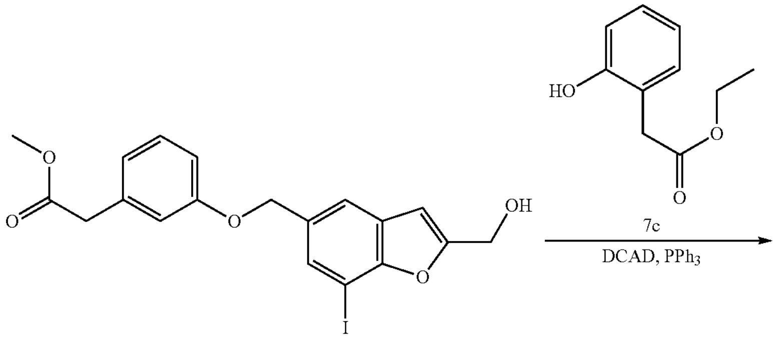

16b

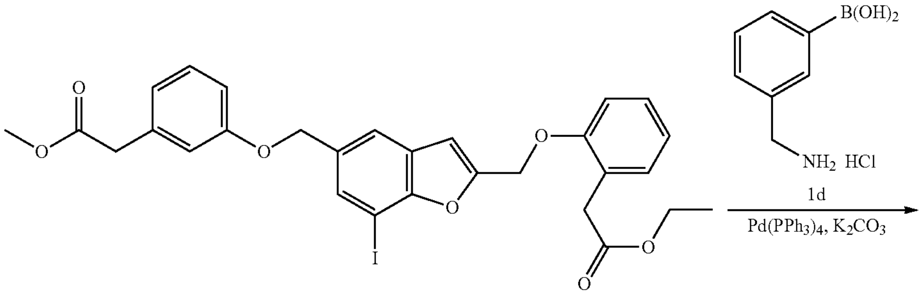

16c

-continued

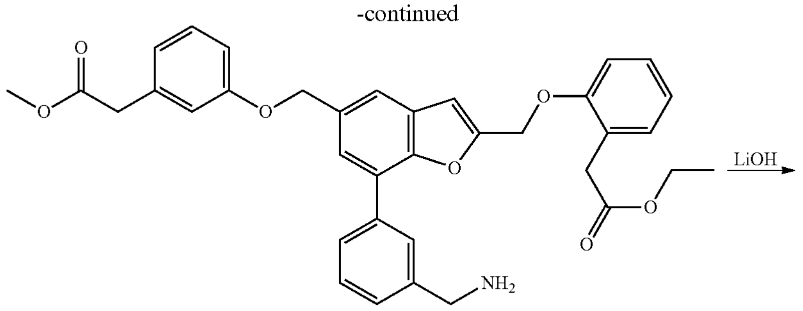

16d

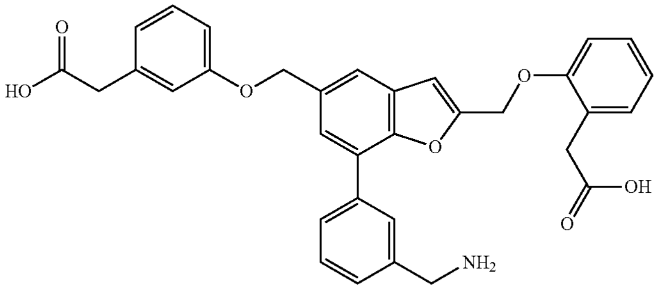

16e

Preparation of 2-(3-((7-(3-(aminomethyl)phenyl)-2-((2-(carboxymethyl)phenoxy)methyl)benzofuran-5-yl)methoxy)phenyl)acetic acid (16e)

Step-1: Preparation of methyl 2-(3-((2-(((tert-butyldimethylsilyl)oxy)methyl)-7-iodobenzofuran-5-yl)methoxy)phenyl)acetate (16a)

Compound 16a was prepared according to the procedure reported in step-3 of scheme 7, from (2-(((tert-butyldimethylsilyl)oxy)methyl)-7-iodobenzofuran-5-yl)methanol (7a) (2 g, 4.78 mmol) in DCM (30 mL) using methyl 2-(3-hydroxyphenyl)acetate (4a) (0.874 g, 5.26 mmol), triphenylphosphine (1.379 g, 5.26 mmol), a solution of bis(4-chlorobenzyl) diazene-1,2-dicarboxylate (DCAD) (1.931 g, 5.26 mmol) in DCM (20 mL) and stirring at room temperature for 90 min. This gave after workup and purification by flash column chromatography [silica gel (40 g), eluting with EtOAc in hexane from 0-50%]methyl 2-(3-((2-(((tert-butyldimethylsilyl)oxy)methyl)-7-iodobenzofuran-5-yl)methoxy)phenyl)acetate (16a) (1.61 g, 59% yield) as a colorless oil; $^1$H NMR (300 MHz, DMSO-$d_6$) δ 7.76 (d, J=1.5 Hz, 1H), 7.69 (d, J=1.5 Hz, 1H), 7.24 (td, J=7.5, 1.3 Hz, 1H), 6.97 (s, 1H), 6.95-6.89 (m, 2H), 6.87-6.80 (m, 1H), 5.12 (s, 2H), 4.82 (s, 2H), 3.64 (s, 2H), 3.60 (s, 3H), 0.89 (s, 9H), 0.13 (s, 6H).

Step-2: Preparation of methyl 2-(3-((2-(hydroxymethyl)-7-iodobenzofuran-5-yl)methoxy)phenyl)acetate (16b)

Compound 16b was prepared according to the procedure reported in step-2 of scheme 7, from methyl 2-(3-((2-(((tert-butyldimethylsilyl)oxy)methyl)-7-iodobenzofuran-5-yl)methoxy)phenyl)acetate (16a) (1.61 g, 2.84 mmol, 59% yield) in DCM (20 mL) using 4N HCl in dioxane (3.59 mL, 14.34 mmol) and stirring at room temperature for 3 h. This gave after workup and purification by flash column chromatography [silica gel (40 g), eluting with EtOAc in hexane from 0-70%]methyl 2-(3-((2-(hydroxymethyl)-7-iodobenzofuran-5-yl)methoxy)phenyl)acetate (16b) (1.05 g, 49% yield) as a colorless oil; $^1$H NMR (300 MHz, DMSO-$d_6$) δ 7.75 (d, J=1.6 Hz, 1H), 7.68 (d, J=1.5 Hz, 1H), 7.25 (td, J=7.4, 1.3 Hz, 1H), 6.96-6.90 (m, 3H), 6.85 (dt, J=7.6, 1.2 Hz, 1H), 5.57 (t, J=5.8 Hz, 1H), 5.13 (s, 2H), 4.63-4.55 (m, 2H), 3.65 (s, 2H), 3.61 (s, 3H).

Step-3: Preparation of ethyl 2-(2-((7-iodo-5-((3-(2-methoxy-2-oxoethyl)phenoxy)methyl)benzofuran-2-yl)methoxy)phenyl)acetate (16c)

Compound 16c was prepared according to the procedure reported in step-3 of scheme 7, from methyl 2-(3-((2-(hydroxymethyl)-7-iodobenzofuran-5-yl)methoxy)phenyl) acetate (16b) in DCM (30 mL) using ethyl 2-(2-hydroxyphenyl)acetate (7c) (373 mg, 2.067 mmol), triphenylphosphine (542 mg, 2.067 mmol), a solution of bis(4-chlorobenzyl) diazene-1,2-dicarboxylate (DCAD) (759 mg, 2.067 mmol) in DCM (20 mL) and stirring at room temperature for 30 min. This gave after workup and purification by flash column chromatography [silica gel (40 g), eluting with EtOAc in hexane from 0-50%] ethyl 2-(2-((7-iodo-5-((3-(2-methoxy-2-oxoethyl)phenoxy)methyl)benzofuran-2-yl)methoxy)phenyl)acetate (16c) (540 mg, 47% yield) as a yellow oil; $^1$H NMR (300 MHz, DMSO-$d_6$) δ 7.81 (d, J=1.5 Hz, 1H), 7.74 (d, J=1.5 Hz, 1H), 7.31-7.19 (m, 4H), 7.15 (s, 1H), 6.99-6.91 (m, 3H), 6.85 (dt, J=7.5, 1.2 Hz, 1H), 5.30 (s, 2H), 5.15 (s, 2H), 4.05-4.01 (m, 2H), 3.65 (s, 3H), 3.61 (d, J=1.6 Hz, 4H), 1.04 (t, J=7.1 Hz, 3H).

Step-4: Preparation of ethyl 2-(2-((7-(3-(aminomethyl)phenyl)-5-((3-(2-methoxy-2-oxoethyl)phenoxy)methyl)benzofuran-2-yl)methoxy)phenyl)acetate (16d)

Compound 16d was prepared according to the procedure reported in step-8 of Scheme 3, from ethyl 2-(2-((7-iodo-5-((3-(2-methoxy-2-oxoethyl)phenoxy)methyl)benzofuran-2- yl)methoxy)phenyl)acetate (16c) (400 mg, 0.651 mmol) in dioxane (10 mL) using 3-(aminomethyl)phenylboronic acid hydrochloride (1d) (183 mg, 0.977 mmol), $Pd(PPh_3)_4$ (113 mg, 0.098 mmol), a solution of $K_2CO_3$ (225 mg, 1.628 mmol) in water (3 mL) and heating at 100° C. for 3 h. This gave after workup and purification by flash column chromatography [silica gel (12 g), eluting with DMA80 in DCM from 0-50%] ethyl 2-(2-((7-(3-(aminomethyl)phenyl)-5-((3-(2-methoxy-2-oxoethyl)phenoxy)methyl)benzofuran-2-yl)methoxy)phenyl)acetate (16d) (223 mg, 58% yield) as a clear oil; $^1$H NMR (300 MHz, DMSO-$d_6$) δ 7.80 (t, J=1.8 Hz, 1H), 7.76-7.70 (m, 2H), 7.63 (d, J=1.7 Hz, 1H), 7.46 (t, J=7.5 Hz, 1H), 7.42-7.37 (m, 1H), 7.29-7.19 (m, 4H), 7.08 (s, 1H), 6.99-6.93 (m, 3H), 6.87-6.82 (m, 1H), 5.30 (s, 2H), 5.23 (s, 2H), 3.88 (q, J=7.1 Hz, 2H), 3.82 (s, 2H), 3.63 (s, 2H), 3.60 (s, 5H), 0.96 (t, J=7.1 Hz, 3H).

Step-5: Preparation of 2-(3-((7-(3-(aminomethyl)phenyl)-2-((2-(carboxymethyl)phenoxy)methyl)benzofuran-5-yl)methoxy)phenyl)acetic acid (16e)

Compound 16e was prepared according to the procedure reported in step-3 of scheme 1, from ethyl 2-(2-((7-(3-(aminomethyl)phenyl)-5-((3-(2-methoxy-2-oxoethyl)phenoxy)methyl)benzofuran-2-yl)methoxy)phenyl)acetate (16d) (223 mg, 0.376 mmol) in THF (4 mL) using a solution of lithium hydroxide hydrate (137 mg, 3.26 mmol) in water (1 mL) and stirring overnight at room temperature. This gave after workup and purification by reverse phase column chromatography [C18 column (30 g), eluting with ACN in water (containing 0.1% HCl) from 0-100%] 2-(3-((7-(3-(aminomethyl)phenyl)-2-((2-(carboxymethyl)phenoxy)methyl)benzofuran-5-yl)methoxy)phenyl)acetic acid (16e) (120 mg, 58% yield) HCl salt as a white solid; $^1$H NMR (300 MHz, DMSO-$d_6$) δ 7.99 (d, J=1.8 Hz, 1H), 7.96-7.88 (m, 1H), 7.75 (d, J=1.6 Hz, 1H), 7.68 (d, J=1.7 Hz, 1H), 7.61-7.53 (m, 2H), 7.30-7.18 (m, 4H), 7.10 (s, 1H), 7.01-6.90 (m, 3H), 6.85 (dt, J=7.5, 1.2 Hz, 1H), 5.33 (s, 2H), 5.22 (s, 2H), 4.13 (s, 2H), 3.56 (s, 2H), 3.55 (s, 2H); MS (ES+): 552.2 (M+1); (ES−): 550.2 (M−1); Analysis calculated for $C_{33}H_{29}NO_7 \cdot HCl \cdot H_2O$: C, 65.40; H, 5.32; Cl, 5.85; N, 2.31. Found: C, 65.50; H, 5.51; Cl, 6.17; N, 2.43.

Scheme 17

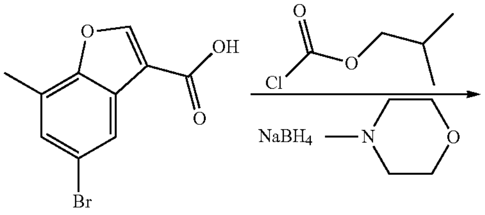

17a

-continued

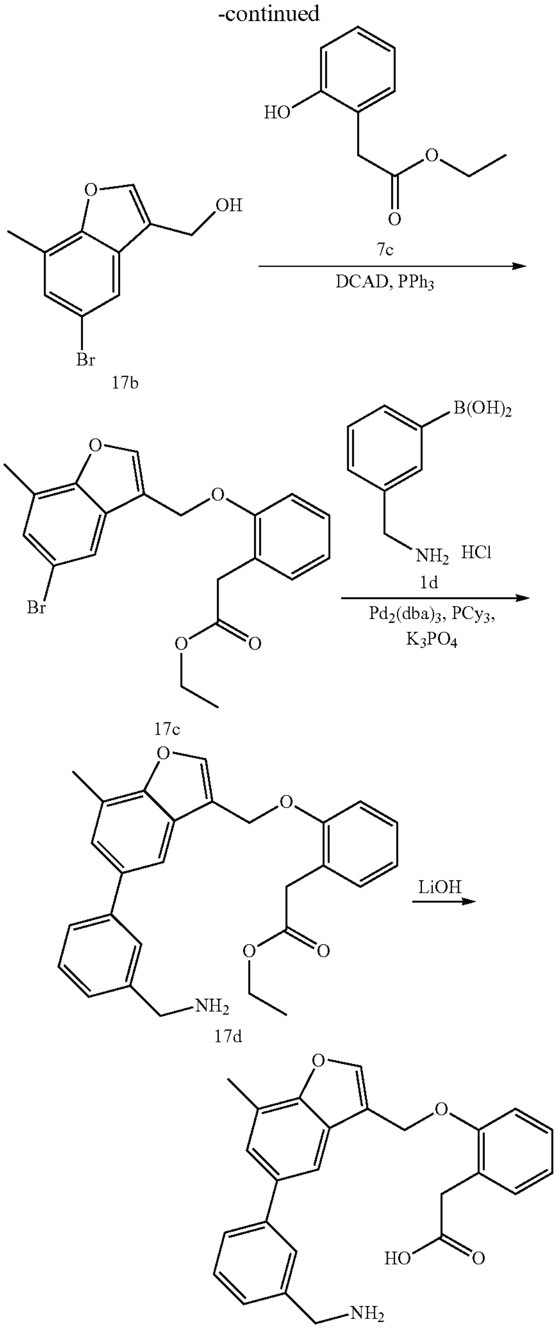

17b, 17c, 17d, 17e

Preparation of 2-(2-((5-(3-(aminomethyl)phenyl)-7-methylbenzofuran-3-yl)methoxy)phenyl)acetic acid (17e)

Step-1: Preparation of (5-bromo-7-methylbenzofuran-3-yl)methanol (17b)

Compound 17b was prepared according to the procedure reported in step-1 of scheme 8, from 5-bromo-7-methylbenzofuran-3-carboxylic acid (17a) (750 mg, 2.94 mmol; CAS #: 1492450-22-2) in THF (20 mL), using N-Methylmorpholine (0.388 mL, 3.53 mmol), isobutyl chloroformate (0.463 mL, 3.53 mmol), a solution of $NaBH_4$ (334 mg, 8.82 mmol)

in water (2.0 mL). This gave after workup and purification by flash column chromatography [silica gel (24 g), eluting with EtOAc/MeOH (9:1) in hexane from 0-50%] (5-bromo-7-methylbenzofuran-3-yl)methanol (17b) (602 mg, 85% yield) as a white solid; $^1$H NMR (300 MHz, DMSO-$d_6$) δ 7.91 (s, 1H), 7.70 (d, J=2.1 Hz, 1H), 7.32 (d, J=2.1 Hz, 1H), 5.19 (t, J=5.6 Hz, 1H), 4.59 (dd, J=5.6, 1.1 Hz, 2H), 2.45 (s, 3H).

Step-2: Preparation of ethyl 2-(2-((5-bromo-7-methylbenzofuran-3-yl)methoxy)phenyl)acetate (17c)

Compound 17c was prepared according to the procedure reported in step-3 of scheme 7, from (5-bromo-7-methylbenzofuran-3-yl)methanol (17b) (286 mg, 1.186 mmol), ethyl 2-(2-hydroxyphenyl)acetate (7c) (235 mg, 1.305 mmol) in DCM (30 mL) using triphenylphosphine (342 mg, 1.305 mmol), a solution of bis(4-chlorobenzyl) diazene-1,2-dicarboxylate (DCAD) (479 mg, 1.305 mmol) in DCM (20 mL) and stirring at room temperature for 30 min. This gave after workup and purification by flash column chromatography [silica gel (12 g), eluting with EtOAc in hexane from 0-50%] ethyl 2-(2-((5-bromo-7-methylbenzofuran-3-yl)methoxy)phenyl)acetate (17c) (242 mg, 51% yield) as a yellow oil; $^1$H NMR (300 MHz, DMSO-$d_6$) δ 8.14 (s, 1H), 7.67 (d, J=2.0 Hz, 1H), 7.37 (dd, J=2.0, 1.0 Hz, 1H), 7.29 (ddd, J=9.0, 7.4, 1.8 Hz, 1H), 7.20 (td, J=8.1, 1.4 Hz, 2H), 6.93 (td, J=7.4, 1.2 Hz, 1H), 5.23 (d, J=0.9 Hz, 2H), 3.95 (q, J=7.1 Hz, 2H), 3.56 (s, 2H), 2.47 (s, 3H), 1.00 (t, J=7.1 Hz, 3H); MS (ES−): 401.10 (M−1).

Step-3: Preparation of ethyl 2-(2-((5-(3-(aminomethyl)phenyl)-7-methylbenzofuran-3-yl)methoxy)phenyl)acetate (17d)

Compound 17d was prepared according to the procedure reported in step-2 of scheme 1, from ethyl 2-(2-((5-bromo-7-methylbenzofuran-3-yl)methoxy)phenyl)acetate (17c) 260 mg, 0.645 mmol) in dioxane (3 mL) using 3-(aminomethyl)phenylboronic acid hydrochloride (1d) (181 mg, 0.967 mmol), 2M solution of $K_3PO_4$ (0.548 mL, 1.096 mmol), tricyclohexylphosphine (54.2 mg, 0.193 mmol) and $Pd_2(dba)_3$ (59.0 mg, 0.064 mmol) and heating at 120° C. for 30 min in microwave. This gave after workup and purification by flash column chromatography [silica gel (12 g), eluting with DMA-80 in DCM from 0-70%] ethyl 2-(2-((5-(3-(aminomethyl)phenyl)-7-methylbenzofuran-3-yl)methoxy)phenyl)acetate (17d) (86 mg, 31% yield) as a colorless oil; MS (ES+): 430.2 (M+1).

Step-4: Preparation of 2-(2-((5-(3-(aminomethyl)phenyl)-7-methylbenzofuran-3-yl)methoxy)phenyl)acetic acid (17e)

Compound 17e was prepared according to the procedure reported in step-3 of scheme 1, from ethyl 2-(2-((5-(3-(aminomethyl)phenyl)-7-methylbenzofuran-3-yl)methoxy)phenyl)acetate (17d) (86 mg, 0.20 mmol) in THF (3 mL) using a solution of lithium hydroxide hydrate (81 mg, 1.934 mmol) in water (1 mL) and stirring overnight at room temperature. This gave after workup and purification by reverse phase column chromatography [C18 column (35 g), eluting with ACN in water (containing 0.1% HCl) from 0-100%] 2-(2-((5-(3-(aminomethyl)phenyl)-7-methylbenzofuran-3-yl)methoxy)phenyl)acetic acid (17e) (27 mg, 34% yield) HCl salt as a white solid; $^1$H NMR (300 MHz, DMSO-$d_6$) δ 12.16 (s, 1H, $D_2O$ exchangeable), 8.41 (s, 3H, $D_2O$ exchangeable), 8.12 (s, 1H), 7.90-7.80 (m, 2H), 7.73 (dt, J=7.6, 1.6 Hz, 1H), 7.57-7.41 (m, 3H), 7.31-7.16 (m, 3H), 6.92 (td, J=7.3, 1.3 Hz, 1H), 5.31 (s, 2H), 4.10 (s, 2H), 3.53 (s, 2H), 2.55 (s, 3H); MS (ES+): 402.1 (M+1); Analysis calculated for $C_{25}H_{23}NO_4 \cdot HCl \cdot H_2O$: C, 65.86; H, 5.75; Cl, 7.78; N, 3.07. Found: C, 65.70; H, 5.65; Cl, 7.82; N, 3.16.

Scheme 18

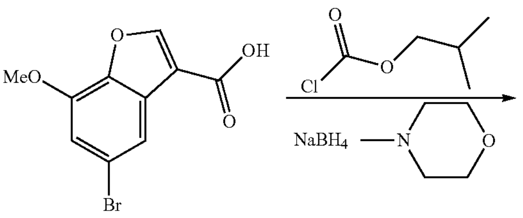

18a

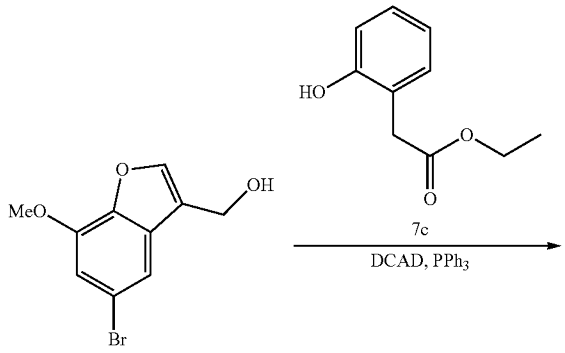

18b

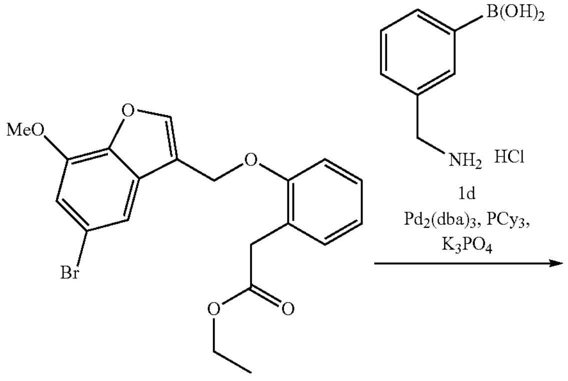

18c

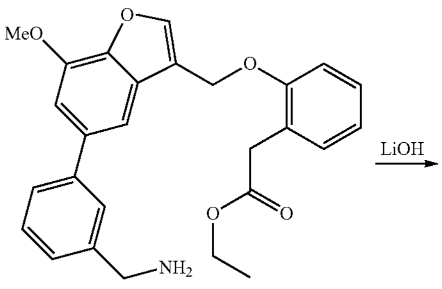

18d

-continued

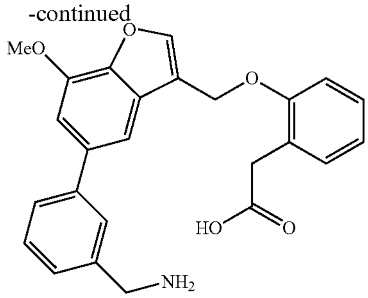

18e

Preparation of 2-(2-((5-(3-(aminomethyl)phenyl)-7-methoxybenzofuran-3-yl)methoxy)phenyl)acetic acid (18e)

Step-1: Preparation of (5-bromo-7-methoxybenzofuran-3-yl)methanol (18b)

Compound 18b was prepared according to the procedure reported in step-1 of scheme 8, from 5-bromo-7-methoxy-benzofuran-3-carboxylic acid (18a) (880 mg, 3.25 mmol; CAS #: 1875597-44-6) in THF (20 mL) using N-Methyl-morpholine (0.428 mL, 3.90 mmol), isobutyl chloroformate (0.512 mL, 3.90 mmol), a solution of $NaBH_4$ (368 mg, 9.74 mmol) in water (2.0 mL). This gave after workup and purification by flash column chromatography [silica gel (24 g), eluting with EtOAc/MeOH (9:1) in hexane from 0-50%] (5-bromo-7-methoxybenzofuran-3-yl)methanol (18b) (458 mg, 55% yield) as a white solid; $^1H$ NMR (300 MHz, DMSO-$d_6$) δ 7.89 (s, 1H), 7.46 (d, J=1.8 Hz, 1H), 7.09 (d, J=1.8 Hz, 1H), 5.20 (t, J=5.6 Hz, 1H), 4.57 (dd, J=5.6, 1.1 Hz, 2H), 3.94 (s, 3H).

Step-2: Preparation of ethyl 2-(2-((5-bromo-7-methoxybenzofuran-3-yl)methoxy)phenyl)acetate (18c)

Compound 18c was prepared according to the procedure reported in step-3 of scheme 7, from (5-bromo-7-methoxy-benzofuran-3-yl)methanol (18b) (600 mg, 2.334 mmol), ethyl 2-(2-hydroxyphenyl)acetate (7c) (463 mg, 2.57 mmol) in DCM (30 mL) using triphenylphosphine (673 mg, 2.57 mmol), a solution of bis(4-chlorobenzyl) diazene-1,2-dicarboxylate (DCAD) (943 mg, 2.57 mmol) in DCM (20 mL) and stirring at room temperature for 30 min. This gave after workup and purification by flash column chromatography [silica gel (12 g), eluting with EtOAc in hexane from 0-50%] ethyl 2-(2-((5-bromo-7-methoxybenzofuran-3-yl)methoxy) phenyl)acetate (18c) (800 mg, 82% yield) as a colorless oil; $^1H$ NMR (300 MHz, DMSO-$d_6$) δ 8.10 (s, 1H), 7.42 (d, J=1.7 Hz, 1H), 7.32-7.24 (m, 1H), 7.24-7.18 (m, 2H), 7.16 (dd, J=5.0, 1.5 Hz, 1H), 6.93 (td, J=7.3, 1.1 Hz, 1H), 5.28-5.14 (m, 2H), 3.97 (d, J=1.8 Hz, 3H), 3.94 (q, J=2.9 Hz, 2H), 3.56 (s, 2H), 1.01 (t, J=7.1 Hz, 3H).

Step-3: Preparation of ethyl 2-(2-((5-(3-(aminomethyl)phenyl)-7-methoxybenzofuran-3-yl)methoxy) phenyl)acetate (18d)

Compound 18d was prepared according to the procedure reported in step-2 of scheme 1, from ethyl 2-(2-((5-bromo-7-methoxybenzofuran-3-yl)methoxy)phenyl)acetate (18c) (369 mg, 0.880 mmol), 3-(aminomethyl)phenylboronic acid hydrochloride (1d) (247 mg, 1.320 mmol) in dioxane (3 mL) using 2M solution of $K_3PO_4$ (0.748 mL, 1.496 mmol), tricyclohexylphosphine (74 mg, 0.264 mmol), $Pd_2(dba)_3$ (81 mg, 0.088 mmol) and heating at 120° C. for 30 min in a microwave. This gave after workup and purification by flash column chromatography [silica gel (12 g), eluting with DMA-80 in DCM from 0-70%] ethyl 2-(2-((5-(3-(aminomethyl)phenyl)-7-methoxybenzofuran-3-yl)methoxy)phenyl) acetate (18d) (122 mg, 31% yield); MS (ES+): 446.2 (M+1).

Step-4: Preparation of 2-(2-((5-(3-(aminomethyl) phenyl)-7-methoxybenzofuran-3-yl)methoxy)phenyl)acetic acid (18e)

Compound 18e was prepared according to the procedure reported in step-3 of scheme 1, from ethyl 2-(2-((5-(3-(aminomethyl)phenyl)-7-methoxybenzofuran-3-yl) methoxy)phenyl)acetate (18d) (122 mg, 0.274 mmol) in THF (3 mL) using a solution of lithium hydroxide hydrate (111 mg, 2.64 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)-7-methoxybenzofuran-3-yl)methoxy)phenyl)acetic acid (18e) (41 mg, 36% yield) HCl salt as a white solid; $^1H$ NMR (300 MHz, DMSO-$d_6$) δ 12.18 (s, 1H, $D_2O$ exchangeable), 8.58 (s, 3H, $D_2O$ exchangeable), 8.09 (s, 1H), 7.98 (s, 1H), 7.77 (dt, J=7.2, 2.0 Hz, 1H), 7.60 (d, J=1.5 Hz, 1H), 7.55-7.42 (m, 2H), 7.36-7.15 (m, 4H), 6.93 (t, J=7.3 Hz, 1H), 5.31 (s, 2H), 4.11 (s, 2H), 4.06 (s, 3H), 3.55 (s, 2H); MS (ES+): 418.1 (M+1); Analysis calculated for $C_{25}H_{23}NO_5 \cdot HCl \cdot H_2O$: C, 63.63; H, 5.55; Cl, 7.51; N, 2.97. Found: C, 63.40; H, 5.59; Cl, 7.67; N, 3.07.

Scheme 19

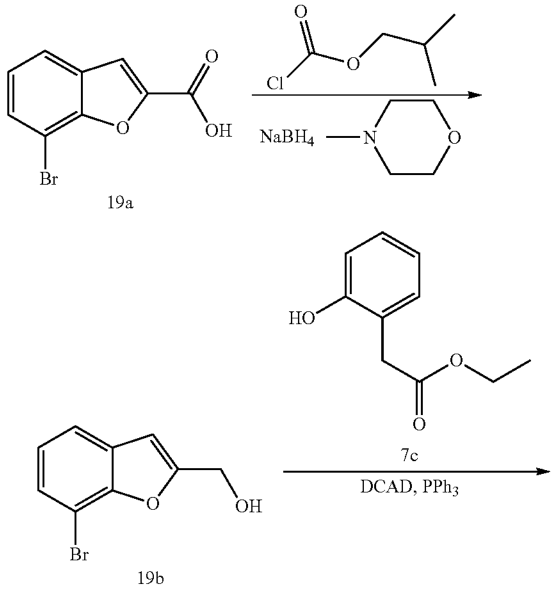

19a

7c

19b

-continued

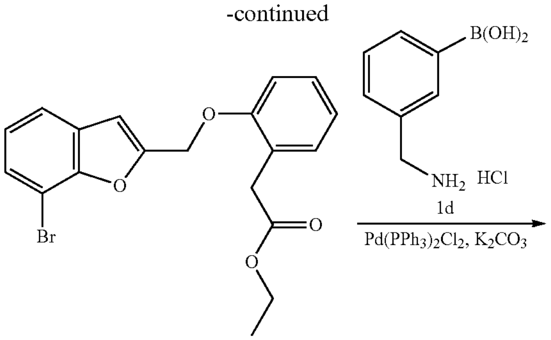

19c

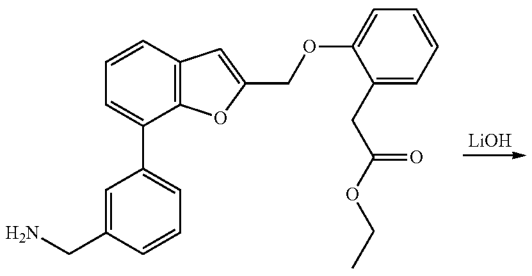

19d

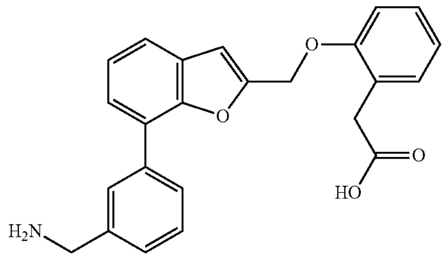

19e

Preparation of 2-(2-((7-(3-(aminomethyl)phenyl) benzofuran-2-yl)methoxy)phenyl)acetic acid (19e)

Step-1: Preparation of (7-bromobenzofuran-2-yl)methanol (19b)

Compound 19b was prepared according to the procedure reported in step-1 of scheme 8, from 7-bromobenzofuran-2-carboxylic acid (19a) (3.5 g, 14.52 mmol; CAS #: 550998-59-9) in THE (50 mL) using N-Methylmorpholine (1.916 mL, 17.42 mmol), isobutyl chloroformate (2.288 mL, 17.42 mmol), a solution of $NaBH_4$ (1.648 g, 43.6 mmol) in water (2.0 mL). This gave after workup and purification by flash column chromatography [silica gel (24 g), eluting with EtOAc/MeOH (9:1) in hexane from 0-50%] (7-bromobenzofuran-2-yl)methanol (19b) (2.2 g, 67% yield) as a yellow solid; $^1H$ NMR (300 MHz, DMSO-$d_6$) δ 7.62 (dd, J=7.7, 1.1 Hz, 1H), 7.50 (dd, J=7.8, 1.1 Hz, 1H), 7.18 (t, J=7.8 Hz, 1H), 6.89 (t, J=0.9 Hz, 1H), 5.57 (t, J=5.9 Hz, 1H, $D_2O$ exchangeable), 4.61 (dd, J=5.9, 0.8 Hz, 2H).

Step-2: Preparation of ethyl 2-(2-((7-bromobenzofuran-2-yl)methoxy)phenyl)acetate (19c)

Compound 19c was prepared according to the procedure reported in step-3 of scheme 7, from (7-bromobenzofuran-2-yl)methanol (19b) (2 g, 9.69 mmol), ethyl 2-(2-hydroxyphenyl)acetate (7c) (1.746 g, 9.69 mmol) in DCM (30 mL) using triphenylphosphine (2.54 g, 9.69 mmol), a solution of bis(4-chlorobenzyl) diazene-1,2-dicarboxylate (DCAD) (3.56 g, 9.69 mmol) in DCM (20 mL) and stirring at room temperature for 30 min. This gave after workup and purification by flash column chromatography [silica gel (40 g), eluting with EtOAc in hexane from 0-50%] ethyl 2-(2-((7-bromobenzofuran-2-yl)methoxy)phenyl)acetate (19c) (1.8 g, 53% yield) as a colorless oil; $^1H$ NMR (300 MHz, DMSO-$d_6$) δ 7.68 (dd, J=7.8, 1.1 Hz, 1H), 7.57 (dd, J=7.8, 1.0 Hz, 1H), 7.32-7.17 (m, 4H), 7.13 (s, 1H), 6.95 (td, J=7.3, 1.3 Hz, 1H), 5.30 (s, 2H), 4.00 (q, J=7.1 Hz, 2H), 3.60 (s, 2H), 1.03 (t, J=7.1 Hz, 3H); MS (ES+): 410.9 (M+Na).

Step-3: Preparation of ethyl 2-(2-((7-(3-(aminomethyl)phenyl)benzofuran-2-yl)methoxy)phenyl)acetate (19d)

Compound 19d was prepared according to the procedure reported in step-8 of Scheme 3, from ethyl 2-(2-((7-bromobenzofuran-2-yl)methoxy)phenyl)acetate (19c) (465 mg, 1.195 mmol) in dioxane (10 mL) using 3-(aminomethyl) phenylboronic acid hydrochloride (1d) (403 mg, 2.150 mmol), bis(triphenylphosphine)palladium(II) chloride (126 mg, 0.179 mmol) and a solution of $K_2CO_3$ (495 mg, 3.58 mmol) in water (3 mL). This gave after workup and purification by flash column chromatography [silica gel (12 g), eluting with DMA80 in DCM from 0-50%] ethyl 2-(2-((7-(3-(aminomethyl)phenyl)benzofuran-2-yl)methoxy)phenyl) acetate (19d) (212 mg, 43% yield) as a yellow oil; MS (ES+): 416.1 (M+1).

Step-4: Preparation of 2-(2-((7-(3-(aminomethyl) phenyl)benzofuran-2-yl)methoxy)phenyl)acetic acid (19e)

Compound 19e was prepared according to the procedure reported in step-3 of scheme 1, from ethyl 2-(2-((7-(3-(aminomethyl)phenyl)benzofuran-2-yl)methoxy)phenyl)acetate (19d) (212 mg, 0.510 mmol) in THF (3 mL) using a solution of lithium hydroxide hydrate (201 mg, 4.78 mmol) in water (1 mL) and stirring at room temperature for 4 h. This gave after workup and purification by reverse phase column chromatography [C18 column (30 g), eluting with ACN in water (containing 0.1% HCl) from 0-100%] 2-(2-((7-(3-(aminomethyl)phenyl)benzofuran-2-yl)methoxy) phenyl)acetic acid (19e) (103 mg, 22% yield) HCl salt as a white solid; $^1H$ NMR (300 MHz, DMSO-$d_6$) δ 8.50 (s, 3H, $D_2O$ exchangeable), 7.97 (s, 1H), 7.92 (dt, J=7.2, 1.8 Hz, 1H), 7.67 (dd, J=7.7, 1.2 Hz, 1H), 7.60-7.53 (m, 3H), 7.38 (t, J=7.6 Hz, 1H), 7.28-7.20 (m, 3H), 7.09 (s, 1H), 6.94 (td, J=7.1, 1.5 Hz, 1H), 5.33 (s, 2H), 4.13 (s, 2H), 3.56 (s, 2H); MS (ES+): 388.1 (M+1); (ES−): 386.1 (M−1); Analysis calculated for $C_{24}H_{21}NO_4·HCl·0.5H_2O$: C, 66.59; H, 5.36; Cl, 8.19; N, 3.24. Found: C, 66.30; H, 5.54; Cl, 8.12; N, 3.27.

Scheme 20
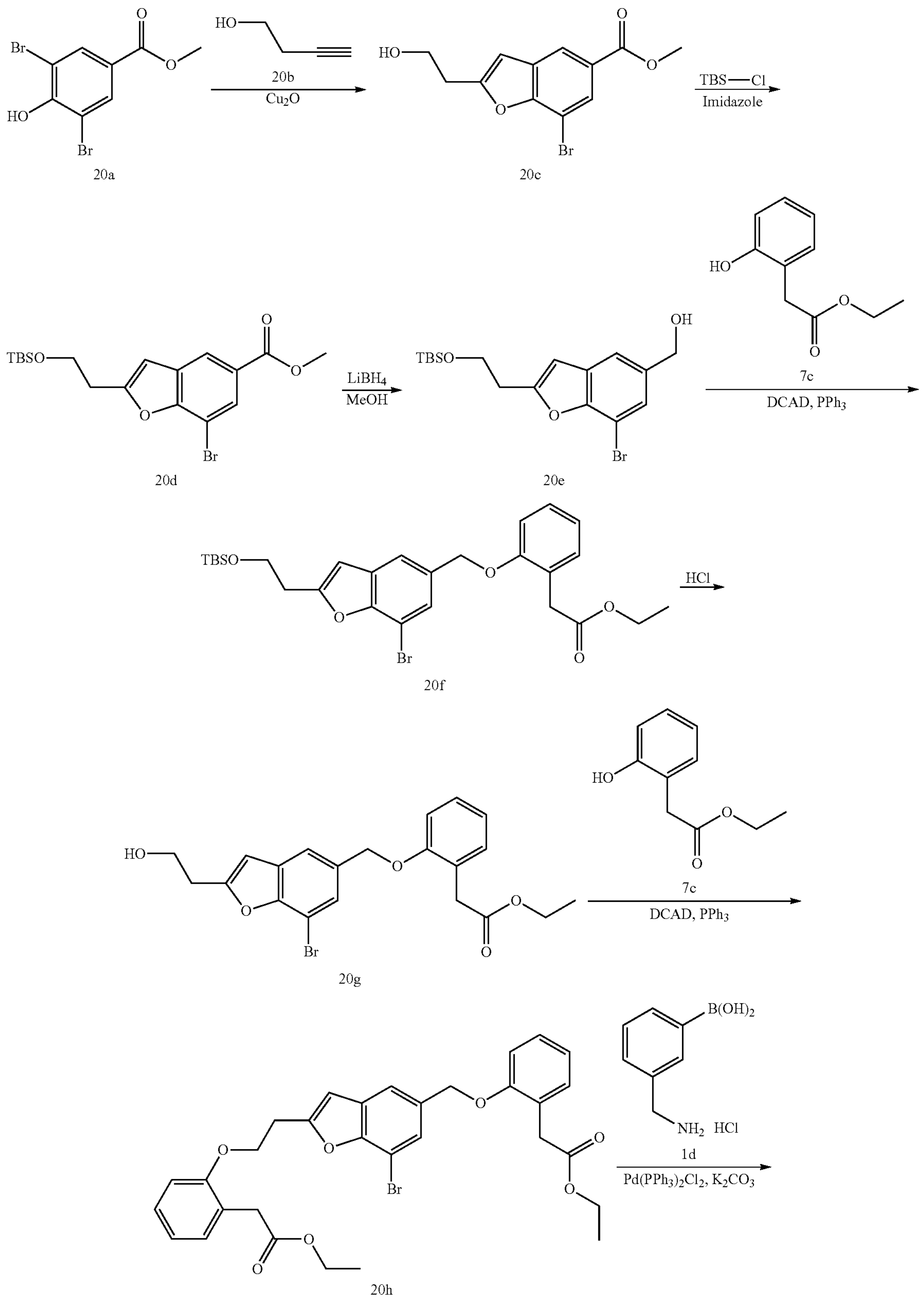
20a 20c 20d 20e 20f 20g 20h

-continued

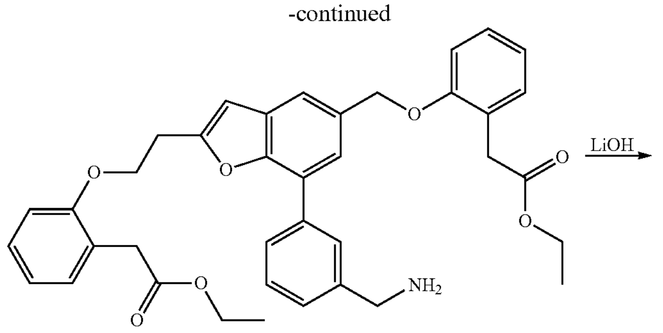

20i

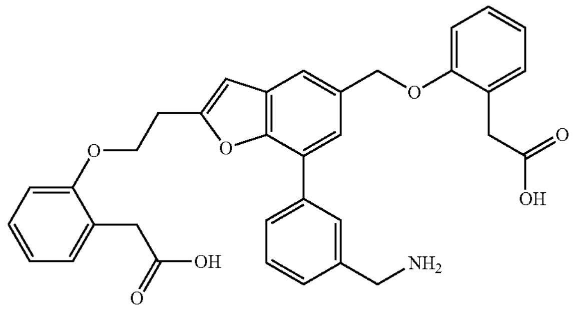

20j

Preparation of 2-(2-((7-(3-(aminomethyl)phenyl)-2-(2-(2-(carboxymethyl)phenoxy)ethyl)benzofuran-5-yl)methoxy)phenyl)acetic acid (20j)

Step-1: Preparation of methyl 7-bromo-2-(2-hydroxyethyl)benzofuran-5-carboxylate (20c)

Compound 20c was prepared according to the procedure reported in step-1 of scheme 3, from methyl 3,5-dibromo-4-hydroxybenzoate (20a) (15 g, 48.4 mmol; CAS #41727-47-3) in pyridine (500 mL) using but-3-yn-1-ol (20b) (3.39 g, 48.4 mmol), copper(I) oxide (3.46 g, 24.20 mmol) and heating at 120° C. for 3 h. This gave after workup and purification by flash column chromatography [silica gel (80 g), eluting with EtOAc in hexane from 0-80%]methyl 7-bromo-2-(2-hydroxyethyl)benzofuran-5-carboxylate (20c) (8.1 g, 56% yield) as a white solid; $^1$H NMR (300 MHz, DMSO-$d_6$) δ 8.21 (d, J=1.6 Hz, 1H), 7.99 (d, J=1.6 Hz, 1H), 6.94-6.90 (m, 1H), 4.95-4.82 (m, 1H, $D_2O$ exchangeable), 3.88 (s, 3H), 3.78 (t, J=6.5 Hz, 2H), 2.99 (td, J=6.4, 1.0 Hz, 2H).

Step-2: Preparation of methyl 7-bromo-2-(2-((tert-butyldimethylsilyl)oxy)ethyl)benzofuran-5-carboxylate (20d)

To a solution of methyl 7-bromo-2-(2-hydroxyethyl)benzofuran-5-carboxylate (20c) (6 g, 20.06 mmol) and imidazole (1.366 g, 20.06 mmol) in anhydrous DCM (120 mL) was added TBS-Cl (3.02 g, 20.06 mmol) at 0° C. The mixture was stirred at 0° C. for 2 h and warmed to room temperature overnight. The reaction mixture was diluted with DCM and water, extracted with DCM (2×). The organic layers were combined washed with water, brine, dried, filtered and concentrated in vacuum. The residue obtained was purified by flash column chromatography [silica gel (80 g), eluting with EtOAc in hexane from 0-50%] to give methyl 7-bromo-2-(2-((tert-butyldimethylsilyl)oxy)ethyl)benzofuran-5-carboxylate (20d) (7.5 g, 90% yield) as a clear oil; $^1$H NMR (300 MHz, DMSO-$d_6$) δ 8.19 (d, J=1.6 Hz, 1H), 7.96 (d, J=1.5 Hz, 1H), 6.93-6.86 (m, 1H), 3.94 (t, J=6.1 Hz, 2H), 3.85 (s, 3H), 3.02 (t, J=6.1 Hz, 2H), 0.78 (s, 9H), −0.05 (s, 6H).

Step-3: Preparation of (7-bromo-2-(2-((tert-butyldimethylsilyl)oxy)ethyl)benzofuran-5-yl)methanol (20e)

Compound 20e was prepared according to the procedure reported in step-1 of scheme 7, from methyl 7-bromo-2-(2-((tert-butyldimethylsilyl)oxy)ethyl)benzofuran-5-carboxylate (20d) (7.32 g, 17.71 mmol) in THF (60 mL) at −78° C. using $LiBH_4$ (3M in THF) (17.71 mL, 53.1 mmol), MeOH (2.149 mL, 53.1 mmol) and stirring at room temperature for 24 h. This gave after workup and purification by flash column chromatography [silica gel (40 g), eluting with EtOAc in hexane from 0-60%] (7-bromo-2-(2-((tert-butyldimethylsilyl)oxy)ethyl)benzofuran-5-yl)methanol (20e) (6.36 g, 93% yield) as a clear oil; $^1$H NMR (300 MHz, DMSO-$d_6$) δ 7.49-7.45 (m, 1H), 7.40-7.37 (m, 1H), 6.75-6.71 (m, 1H), 5.29 (t, J=5.8 Hz, 1H, $D_2O$ exchangeable), 4.54 (d, J=5.8 Hz, 2H), 3.94 (t, J=6.1 Hz, 2H), 2.98 (t, J=6.1 Hz, 2H), 0.79 (s, 9H), −0.04 (s, 6H).

Step-4: Preparation of ethyl 2-(2-((7-bromo-2-(2-((tert-butyldimethylsilyl)oxy)ethyl)benzofuran-5-yl)methoxy)phenyl)acetate (20f)

Compound 20f was prepared according to the procedure reported in step-3 of scheme 7, from (7-bromo-2-(2-((tert-butyldimethylsilyl)oxy)ethyl)benzofuran-5-yl)methanol (20e) (6.11 g, 15.85 mmol), ethyl 2-(2-hydroxyphenyl)acetate (7c) (2.86 g, 15.85 mmol) in DCM (100 mL) using triphenylphosphine (4.16 g, 15.85 mmol), a solution of bis(4-chlorobenzyl) diazene-1,2-dicarboxylate (DCAD) (5.82 g, 15.85 mmol) in DCM (20 mL) and stirring at room temperature for 30 min. This gave after workup and purification by flash column chromatography [silica gel (40 g), eluting with EtOAc in hexane from 0-20%] ethyl 2-(2-((7-bromo-2-(2-((tert-butyldimethylsilyl)oxy)ethyl)benzofuran-5-yl)methoxy)phenyl)acetate (20f) (6.5 g, 75% yield) as a colorless oil; $^1$H NMR (300 MHz, DMSO-$d_6$) δ 7.63 (s, 1H), 7.53 (s, 1H), 7.32-7.22 (m, 2H), 7.10 (d, J=8.1 Hz, 1H), 6.94 (t, J=7.4 Hz, 1H), 6.81 (s, 1H), 5.18 (s, 2H), 4.12-3.90 (m, 4H), 3.65 (s, 2H), 3.03 (t, J=6.1 Hz, 2H), 1.11 (t, J=7.0 Hz, 3H), 0.83 (d, J=0.9 Hz, 9H), 0.00 (s, 6H).

Step-4: Preparation of ethyl 2-(2-((7-bromo-2-(2-hydroxyethyl)benzofuran-5-yl)methoxy)phenyl)acetate (20 g)

Compound 20g was prepared according to the procedure reported in step-2 of scheme 7, from ethyl 2-(2-((7-bromo-2-(2-((tert-butyldimethylsilyl)oxy)ethyl)benzofuran-5-yl)methoxy)phenyl)acetate (20f) (2.3 g, 4.20 mmol) using 4N HCl in dioxane (1.05 mL, 4.2 mmol) in DCM (30 mL) and stirring at room temperature for 3 h. This gave after workup and purification by flash column chromatography [silica gel (40 g), eluting with EtOAc/MeOH (9:1) in hexane from 0-60%] ethyl 2-(2-((7-bromo-2-(2-hydroxyethyl)benzofuran-5-yl)methoxy)phenyl)acetate (20 g) (1.7 g, 93% yield) as a clear oil; MS (ES+): 455.00 (M+Na).

Step-5: Preparation ethyl 2-(2-((7-bromo-2-(2-(2-(2-ethoxy-2-oxoethyl)phenoxy)ethyl)benzofuran-5-yl)methoxy)phenyl)acetate (20h)

Compound 20h was prepared according to the procedure reported in step-3 of scheme 7, from ethyl 2-(2-((7-bromo-2-(2-hydroxyethyl)benzofuran-5-yl)methoxy)phenyl)acetate (20 g) (1.33 g, 3.07 mmol), ethyl 2-(2-hydroxyphenyl)acetate (7c) (0.608 g, 3.38 mmol) in DCM (30 mL) using triphenylphosphine (0.886 g, 3.38 mmol), a solution of bis(4-chlorobenzyl) diazene-1,2-dicarboxylate (DCAD) (1.240 g, 3.38 mmol) in DCM (20 mL) and stirring at room temperature for 30 min. This gave after workup and purification by flash column chromatography [silica gel (40 g), eluting with EtOAc in hexane from 0-50%] ethyl 2-(2-((7-bromo-2-(2-(2-(2-ethoxy-2-oxoethyl)phenoxy)ethyl)benzofuran-5-yl)methoxy)phenyl)acetate (20h) (800 mg, 82% yield) as a colorless oil; MS (ES+): 595.2 (M+1).

Step-6: Preparation of ethyl 2-(2-((7-(3-(aminomethyl)phenyl)-2-(2-(2-(2-ethoxy-2-oxoethyl)phenoxy)ethyl)benzofuran-5-yl)methoxy)phenyl)acetate (20i)

Compound 20i was prepared according to the procedure reported in step-8 of Scheme 3, from ethyl 2-(2-((7-bromo-2-(2-(2-(2-ethoxy-2-oxoethyl)phenoxy)ethyl)benzofuran-5-yl)methoxy)phenyl)acetate (20h) (150 mg, 0.233 mmol) in dioxane (15 mL) using 3-(aminomethyl)phenylboronic acid hydrochloride (1d) (79 mg, 0.420 mmol), bis(triphenylphosphine)palladium(II) chloride (25 mg, 0.035 mmol) a solution of $K_2CO_3$ (97 mg, 0.700 mmol) in water (3 mL) and heating at 100° C. for 3 h. This gave after workup and purification by flash column chromatography [silica gel (12 g), eluting with DMA-80 in DCM from 0-50%] to give ethyl 2-(2-((7-(3-(aminomethyl)phenyl)-2-(2-(2-(2-ethoxy-2-oxoethyl)phenoxy)ethyl)benzofuran-5-yl)methoxy)phenyl)acetate (20i) (101 mg, 70% yield) as a yellow oil; MS (ES+): 622.3 (M+1); (ES−): 656.8 (M+Cl).

Step-7: Preparation of 2-(2-((7-(3-(aminomethyl)phenyl)-2-(2-(2-(carboxymethyl)phenoxy)ethyl)benzofuran-5-yl)methoxy)phenyl)acetic acid (20j)

Compound 20j was prepared according to the procedure reported in step-3 of scheme 1, from ethyl 2-(2-((7-(3-(aminomethyl)phenyl)-2-(2-(2-(2-ethoxy-2-oxoethyl)phenoxy)ethyl)benzofuran-5-yl)methoxy)phenyl)acetate (20i) (101 mg, 0.162 mmol) in THF (4 mL) using a solution of lithium hydroxide hydrate (49 mg, 1.167 mmol) in water (1 mL) and stirring at room temperature overnight. This gave after workup and purification by reverse phase column chromatography [C18 column (30 g), eluting with ACN in water (containing 0.1% HCl) from 0-100%] 2-(2-((7-(3-(aminomethyl)phenyl)-2-(2-(2-(carboxymethyl)phenoxy)ethyl)benzofuran-5-yl)methoxy)phenyl)acetic acid (20j) (45 mg, 34% yield) HCl salt as a white solid; $^1$H NMR (300 MHz, DMSO-$d_6$) δ 7.99 (s, 1H), 7.94 (dt, J=7.1, 1.9 Hz, 1H), 7.66 (d, J=1.6 Hz, 1H), 7.62-7.51 (m, 3H), 7.27-7.14 (m, 4H), 7.13-7.01 (m, 2H), 6.90 (t, J=7.4 Hz, 2H), 6.81 (s, 1H), 5.24 (s, 2H), 4.35 (t, J=6.4 Hz, 2H), 4.12 (s, 2H), 3.59 (s, 2H), 3.48 (s, 2H), 3.30-3.25 (m, 2H); MS (ES+): 566.2 (M+1); (ES−): 564.2 (M−1); Analysis calculated for $C_{34}H_{31}NO_7 \cdot 1.05HCl \cdot H_2O$: C, 65.66; H, 5.52; Cl, 5.99; N, 2.25. Found: C, 65.56; H, 5.61; Cl, 6.06; N, 2.30.

Scheme 21

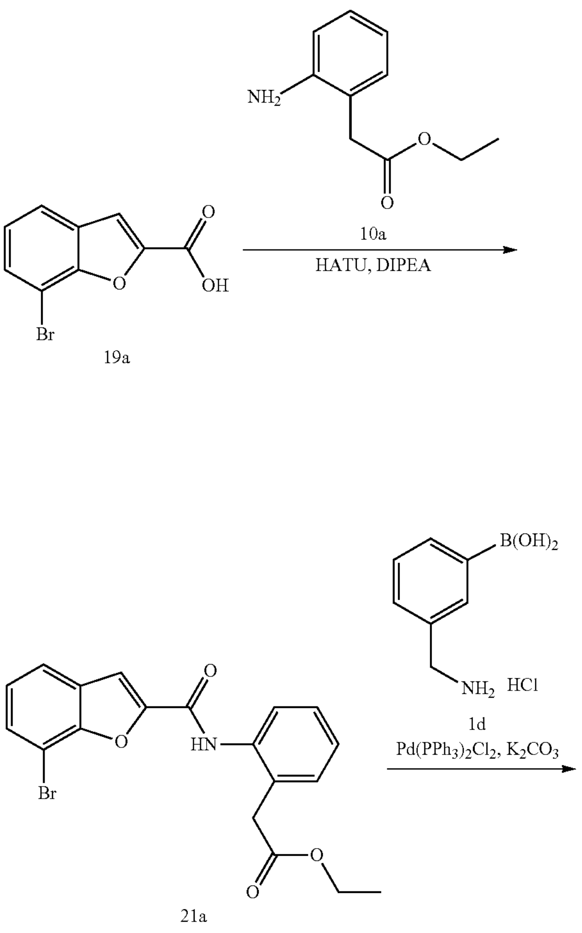

-continued

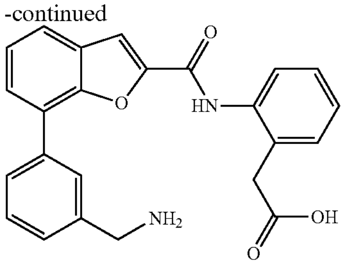

21b

Preparation of 2-(2-(7-(3-(aminomethyl)phenyl) benzofuran-2-carboxamido)phenyl)acetic acid (21b)

Step-1: Preparation of ethyl 2-(2-(7-bromobenzofuran-2-carboxamido)phenyl)acetate (21a)

Compound 21a was prepared according to the procedure reported in step-1 of Scheme 10, from 7-bromobenzofuran-2-carboxylic acid (19a) (750 mg, 3.11 mmol) in DMF (10 mL) using ethyl 2-(2-aminophenyl)acetate (10a) (725 mg, 4.05 mmol), N-ethyl-N-isopropylpropan-2-amine (DIPEA) (1.359 mL, 7.78 mmol), 2-(3H-[1,2,3]triazolo[4,5-b]pyridin-3-yl)-1,1,3,3-tetramethylisouronium hexafluorophosphate(V) (HATU) (1420 mg, 3.73 mmol) and stirring at room temperature for 2 h. This gave after workup and purification by flash column chromatography [silica gel (12 g) eluting with EtOAc in hexane from 0-60%] ethyl 2-(2-(7-bromobenzofuran-2-carboxamido)phenyl)acetate (21a) (1.01 g, 81% yield) as a yellow oil; MS (ES+): 424.00 (M+Na).

Step-2: Preparation of 2-(2-(7-(3-(aminomethyl) phenyl)benzofuran-2-carboxamido)phenyl)acetic acid (21b)

Compound 21b was prepared according to the procedure reported in step-8 of Scheme 3, from ethyl 2-(2-(7-bromobenzofuran-2-carboxamido)phenyl)acetate (21a) (450 mg, 1.119 mmol) in dioxane (10 mL) using 3-(aminomethyl) phenylboronic acid hydrochloride (1d) (377 mg, 2.014 mmol), bis(triphenylphosphine)palladium(II) chloride (118 mg, 0.168 mmol) and a solution of $K_2CO_3$ (464 mg, 3.36 mmol) in water (3 mL). This gave after workup and purification by flash column chromatography [silica gel (12 g), eluting with DMA-80 in DCM from 0-80%] 2-(2-(7-(3-(aminomethyl)phenyl)benzofuran-2-carboxamido)phenyl) acetic acid (21b) (95 mg, 21% yield) as a yellow solid; $^1H$ NMR (300 MHz, DMSO-$d_6$) δ 12.51 (s, 1H, $D_2O$ exchangeable), 10.20 (s, 1H, $D_2O$ exchangeable), 8.54 (s, 3H, $D_2O$ exchangeable), 8.13 (t, J=1.7 Hz, 1H), 8.05 (dt, J=7.3, 1.8 Hz, 1H), 7.87-7.81 (m, 2H), 7.77 (dd, J=7.6, 1.2 Hz, 1H), 7.65-7.54 (m, 3H), 7.50 (t, J=7.7 Hz, 1H), 7.39-7.30 (m, 2H), 7.24 (td, J=7.4, 1.4 Hz, 1H), 4.23-4.09 (m, 2H), 3.73 (s, 2H); MS (ES+): 401.1 (M+1); (ES−); 399.1 (M−1); Analysis calculated for $C_{24}H_{20}N_2O_4$·HCl·$0.75H_2O$: C, 64.00; H, 5.04; Cl, 7.87; N, 6.22. Found: C, 64.06; H, 4.98; Cl, 7.66; N, 6.13.

Scheme 22

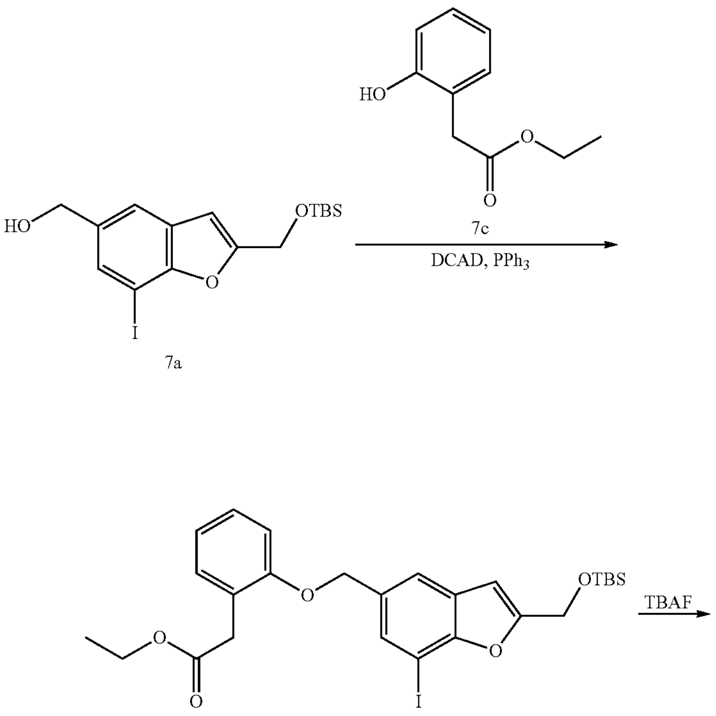

7c
7a
22a

-continued

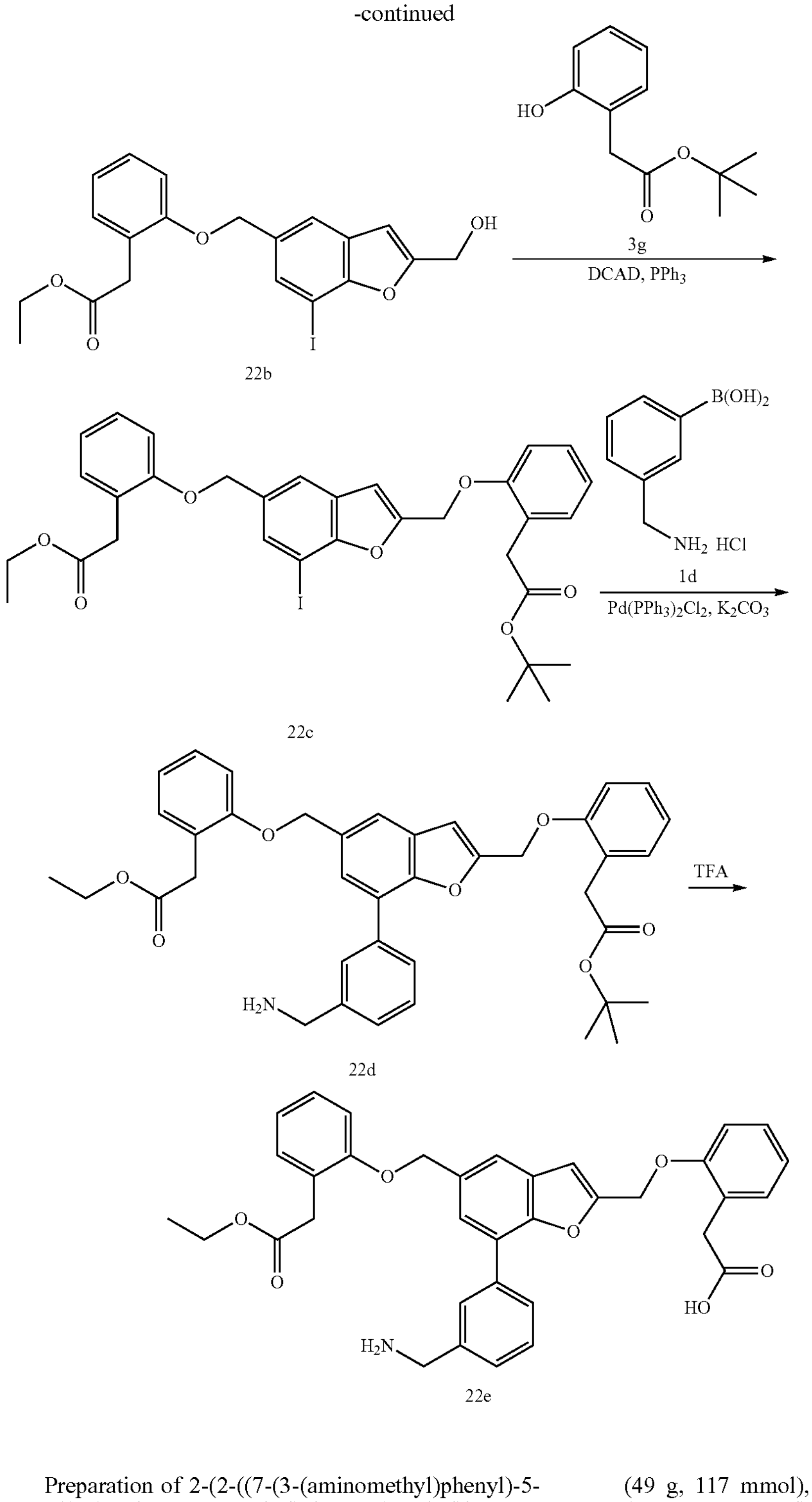

22b

22c

22d

22e

Preparation of 2-(2-((7-(3-(aminomethyl)phenyl)-5-((2-(2-ethoxy-2-oxoethyl)phenoxy)methyl)benzofuran-2-yl)methoxy)phenyl)acetic acid (22e)

Step-1: Preparation of ethyl 2-(2-((2-(((tert-butyldimethylsilyl)oxy)methyl)-7-iodobenzofuran-5-yl)methoxy)phenyl)acetate(22a)

Compound 22a was prepared according to the procedure reported in step-3 of scheme 7, from (2-(((tert-butyldimethylsilyl)oxy)methyl)-7-iodobenzofuran-5-yl)methanol (7a) (49 g, 117 mmol), ethyl 2-(2-hydroxyphenyl)acetate (7c) (27.4 g, 152 mmol) in DCM (450 mL) using triphenylphosphine (39.9 g, 152 mmol), a solution of bis(4-chlorobenzyl) diazene-1,2-dicarboxylate (DCAD) (55.9 g, 152 mmol) in DCM (300 mL) and stirring at room temperature for 30 min. This gave after workup and purification by flash column chromatography [silica gel (330 g), eluting with EtOAc in hexane from 0-8%] ethyl 2-(2-((2-(((tert-butyldimethylsilyl)oxy)methyl)-7-iodobenzofuran-5-yl)methoxy)phenyl)acetate(22a) (44.7 g, 66% yield) as an off white solid; $^1$H NMR (300 MHz, DMSO-d$_6$) δ 7.71 (d, J=1.5 Hz, 1H), 7.64 (d, J=1.5 Hz, 1H), 7.28-7.18 (m, 2H), 7.07 (d, J=8.1 Hz, 1H), 6.96 (s, 1H), 6.95-6.87 (m, 1H), 5.13 (s, 2H), 4.82 (s, 2H), 4.01 (q, J=7.1 Hz, 2H), 3.61 (s, 2H), 1.07 (t, J=7.1 Hz, 3H), 0.89 (s, 9H), 0.12 (s, 6H).

Step-2: Preparation of ethyl 2-(2-((2-(hydroxymethyl)-7-iodobenzofuran-5-yl)methoxy)phenyl)acetate (22b)

Compound 22b was prepared according to the procedure reported in step-2 of scheme 3, from ethyl 2-(2-((2-(((tert-butyldimethylsilyl)oxy)methyl)-7-iodobenzofuran-5-yl)methoxy)phenyl)acetate (22a) (12 g, 20.67 mmol) in THF (180 mL) using TBAF (6.76 g, 25.8 mmol) and stirring at room temperature for 1.5 h. This gave after workup and purification by flash column chromatography [silica gel (220 g), eluting with EtOAc in hexane from 0-45%] ethyl 2-(2-((2-(hydroxymethyl)-7-iodobenzofuran-5-yl)methoxy)phenyl)acetate (22b) (8.78 g, 91% yield) as a white solid; $^1$H NMR (300 MHz, DMSO-$d_6$) δ 7.70 (d, J=1.6 Hz, 1H), 7.63 (d, J=1.6 Hz, 1H), 7.28-7.19 (m, 2H), 7.07 (d, J=8.1 Hz, 1H), 6.96-6.86 (m, 2H), 5.57-5.50 (m, 1H, $D_2O$ exchangeable), 5.14 (s, 2H), 4.60 (d, J=5.8 Hz, 2H), 4.03 (q, J=7.1 Hz, 2H), 3.61 (s, 2H), 1.09 (t, J=7.1 Hz, 3H); MS (ES+): 489.00 (M+Na).

Step-3: Preparation of tert-butyl 2-(2-((5-((2-(2-ethoxy-2-oxoethyl)phenoxy)methyl)-7-iodobenzofuran-2-yl)methoxy)phenyl)acetate (22c)

Compound 22c was prepared according to the procedure reported in step-3 of scheme 7, from ethyl 2-(2-((2-(hydroxymethyl)-7-iodobenzofuran-5-yl)methoxy)phenyl)acetate (22b) (1 g, 2.145 mmol), tert-butyl 2-(2-hydroxyphenyl)acetate (3g) ((0.491 g, 2.359 mmol) in DCM (30 mL) using triphenylphosphine (0.619 g, 2.359 mmol), a solution of bis(4-chlorobenzyl) diazene-1,2-dicarboxylate (DCAD) (0.866 g, 2.359 mmol) in DCM (20 mL) and stirring at room temperature for 30 min. This gave after workup and purification by flash column chromatography [silica gel (40 g), eluting with EtOAc in hexane from 0-50%] tert-butyl 2-(2-((5-((2-(2-ethoxy-2-oxoethyl)phenoxy)methyl)-7-iodobenzofuran-2-yl)methoxy)phenyl)acetate (22c) (650 mg, 46% yield) as a yellow oil; $^1$H NMR (300 MHz, DMSO-$d_6$) δ 7.76 (d, J=1.5 Hz, 1H), 7.68 (d, J=1.5 Hz, 1H), 7.28-7.18 (m, 5H), 7.15 (s, 1H), 7.06 (d, J=7.9 Hz, 1H), 6.98-6.88 (m, 2H), 5.29 (s, 2H), 5.15 (s, 2H), 4.05-3.98 (m, 2H), 3.62 (s, 2H), 3.52 (s, 2H), 1.28 (s, 9H), 1.08 (t, J=7.1 Hz, 3H).

Step-4: Preparation of tert-butyl 2-(2-((7-(3-(aminomethyl)phenyl)-5-((2-(2-ethoxy-2-oxoethyl)phenoxy)methyl)benzofuran-2-yl)methoxy)phenyl)acetate (22d)

Compound 22d was prepared according to the procedure reported in step-8 of Scheme 3, from tert-butyl 2-(2-((5-((2-(2-ethoxy-2-oxoethyl)phenoxy)methyl)-7-iodobenzofuran-2-yl)methoxy)phenyl)acetate (22c) (995 mg, 1.516 mmol) in dioxane (10 mL) using 3-(aminomethyl)phenylboronic acid hydrochloride (1d) (511 mg, 2.73 mmol), bis(triphenylphosphine)palladium(II) chloride (160 mg, 0.227 mmol), a solution of $K_2CO_3$ (628 mg, 4.55 mmol) in water (3 mL) and heating at 100° C. for 3 h. This gave after workup and purification by flash column chromatography [silica gel (40 g), eluting with DMA80 in DCM from 0-50%] tert-butyl 2-(2-((7-(3-(aminomethyl)phenyl)-5-((2-(2-ethoxy-2-oxoethyl)phenoxy)methyl)benzofuran-2-yl)methoxy)phenyl)

acetate (22d) (820 mg, 85% yield) as a yellow oil; $^1$H NMR (300 MHz, DMSO-$d_6$) δ 7.81 (s, 1H), 7.74 (d, J=7.3 Hz, 1H), 7.67 (d, J=1.6 Hz, 1H), 7.58 (d, J=1.7 Hz, 1H), 7.47-7.37 (m, 2H), 7.28-7.17 (m, 5H), 7.13-7.08 (m, 1H), 7.06 (s, 1H), 6.97-6.85 (m, 2H), 5.30 (s, 2H), 5.24 (s, 2H), 3.96-3.87 (m, 2H), 3.82 (s, 2H), 3.63 (s, 2H), 3.52 (s, 2H), 1.22 (s, 9H), 0.99 (t, J=7.1 Hz, 3H); MS (ES+): 636.30 (M+1).

Step-5: Preparation of 2-(2-((7-(3-(aminomethyl)phenyl)-5-((2-(2-ethoxy-2-oxoethyl)phenoxy)methyl)benzofuran-2-yl)methoxy)phenyl)acetic acid (22e)

Compound 22e was prepared according to the procedure reported in step-9 of scheme 3, from tert-butyl 2-(2-((7-(3-(aminomethyl)phenyl)-5-((2-(2-ethoxy-2-oxoethyl)phenoxy)methyl)benzofuran-2-yl)methoxy)phenyl)acetate (22d) (220 mg, 0.346 mmol) in DCM (5 mL) using TFA (0.533 mL, 6.92 mmol) and stirring at room temperature for 2 h. This gave after workup and purification by flash column chromatography [silica gel (12 g), eluting with DMA-80 in DCM from 0-50%] followed by reverse phase column chromatography [C18 (30 g), eluting with ACN in water (containing 0.1% HCl) from 0-100%] 2-(2-((7-(3-(aminomethyl)phenyl)-5-((2-(2-ethoxy-2-oxoethyl)phenoxy)methyl)benzofuran-2-yl)methoxy)phenyl)acetic acid (22e) (21 mg, 10% yield) HCl salt as a white solid; $^1$H NMR (300 MHz, DMSO-$d_6$) δ 12.16 (s, 1H, $D_2O$ exchangeable), 8.38 (s, 3H, $D_2O$ exchangeable), 7.97 (t, J=1.7 Hz, 1H), 7.92 (dt, J=7.3, 1.7 Hz, 1H), 7.71 (d, J=1.6 Hz, 1H), 7.63-7.53 (m, 3H), 7.29-7.19 (m, 5H), 7.14-7.07 (m, 2H), 6.98-6.87 (m, 2H), 5.33 (s, 2H), 5.24 (s, 2H), 4.14 (s, 2H), 3.93 (q, J=7.1 Hz, 2H), 3.63 (s, 2H), 3.56 (s, 2H), 0.99 (t, J=7.1 Hz, 3H); MS (ES+): 580.3 (M+1); (ES−): 578.2 (M−1).

Scheme 23

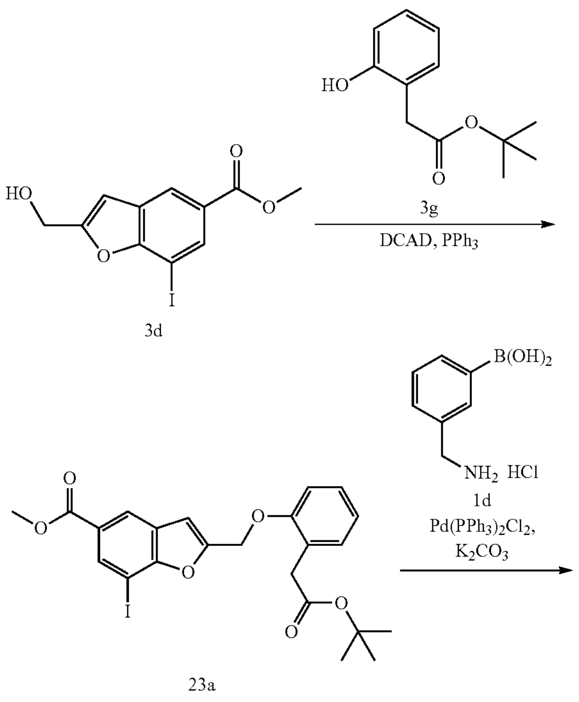

-continued

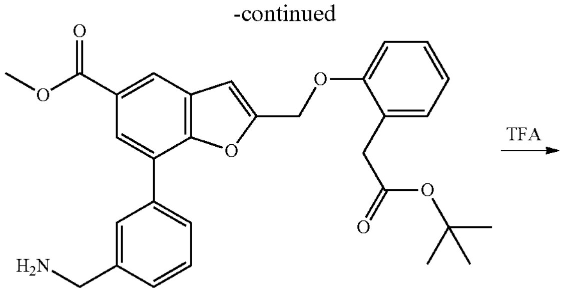

23b

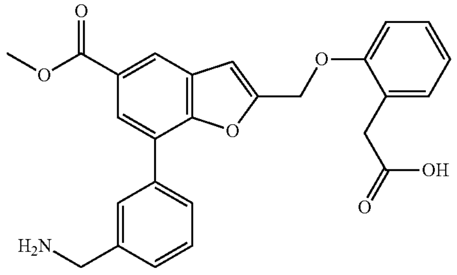

23c

Preparation of 2-(2-((7-(3-(aminomethyl)phenyl)-5-(methoxycarbonyl)benzofuran-2-yl)methoxy)phenyl) acetic acid (23c)

Step-1: Preparation of methyl 2-((2-(2-(tert-butoxy)-2-oxoethyl)phenoxy)methyl)-7-iodobenzofuran-5-carboxylate (23a)

Compound 23a was prepared according to the procedure reported in step-3 of scheme 7, from methyl 2-(hydroxymethyl)-7-iodobenzofuran-5-carboxylate (3d) (670 mg, 2.018 mmol), tert-butyl 2-(2-hydroxyphenyl)acetate (3g) (462 mg, 2.219 mmol) in DCM (30 mL) using triphenylphosphine (582 mg, 2.219 mmol), a solution of bis(4-chlorobenzyl) diazene-1,2-dicarboxylate (DCAD) (815 mg, 2.219 mmol) in DCM (20 mL) and stirring at room temperature for 30 min. This gave after workup and purification by flash column chromatography [silica gel (40 g), eluting with EtOAc in hexane from 0-50%]methyl 2-((2-(2-(tert-butoxy)-2-oxoethyl)phenoxy)methyl)-7-iodobenzofuran-5-carboxylate (23a) (400 mg, 38% yield) as a white solid; $^1$H NMR (300 MHz, DMSO-$d_6$) δ 8.30 (d, J=1.6 Hz, 1H), 8.25 (d, J=1.6 Hz, 1H), 7.32-7.25 (m, 2H), 7.23-7.17 (m, 2H), 6.95 (td, J=7.3, 1.2 Hz, 1H), 5.32 (s, 2H), 3.88 (s, 3H), 3.52 (s, 2H), 1.27 (s, 9H).

Step-2: Preparation of methyl 7-(3-(aminomethyl) phenyl)-2-((2-(2-(tert-butoxy)-2-oxoethyl)phenoxy) methyl)benzofuran-5-carboxylate (23b)

Compound 23b was prepared according to the procedure reported in step-8 of Scheme 3, from methyl 2-((2-(2-(tert-butoxy)-2-oxoethyl)phenoxy)methyl)-7-iodobenzofuran-5-carboxylate (23a) (200 mg, 0.383 mmol), 3-(aminomethyl) phenylboronic acid hydrochloride (1d) (129 mg, 0.689 mmol) in dioxane (10 mL) using bis(triphenylphosphine) palladium(II) chloride (40.3 mg, 0.057 mmol), a solution of $K_2CO_3$ (159 mg, 1.149 mmol) in water (3 mL) and heating at 100° C. for 6 h. This gave after workup and purification by flash column chromatography [silica gel (12 g), eluting with DMA-80 in DCM from 0-50%]methyl 7-(3-(aminomethyl)phenyl)-2-((2-(2-(tert-butoxy)-2-oxoethyl)phenoxy) methyl)benzofuran-5-carboxylate (23b) (160 mg, 0.319 mmol, 83% yield) as a yellow oil; MS (ES+): 502.2 (M+1).

Step-3: Preparation of 2-(2-((7-(3-(aminomethyl) phenyl)-5-(methoxycarbonyl)benzofuran-2-yl) methoxy)phenyl)acetic acid (23c)

Compound 23c was prepared according to the procedure reported in step-9 of scheme 3, from methyl 7-(3-(aminomethyl)phenyl)-2-((2-(2-(tert-butoxy)-2-oxoethyl)phenoxy) methyl)benzofuran-5-carboxylate (23b) (160 mg, 0.319 mmol) in DCM (3 mL) using TFA (0.12 mL, 1.532 mmol) and stirring at room temperature for 4 h. This gave after workup and purification by reverse phase column chromatography [C18 column (30 g), eluting with ACN in water (containing 0.1% HCl) from 0-100%] 2-(2-((7-(3-(aminomethyl)phenyl)-5-(methoxycarbonyl)benzofuran-2-yl) methoxy)phenyl)acetic acid (23c) (41 mg, 24% yield) HCl salt as a white solid; $^1$H NMR (300 MHz, DMSO-$d_6$) δ 12.20 (s, 1H, $D_2O$ exchangeable), 8.63 (s, 3H, $D_2O$ exchangeable), 8.32 (s, J=1.5 Hz, 1H), 8.15 (s, J=1.4 Hz, 1H), 7.99 (s, 1H), 7.96-7.89 (m, 1H), 7.67-7.55 (m, 2H), 7.31-7.19 (m, 4H), 6.95 (t, J=7.2 Hz, 1H), 5.37 (s, 2H), 4.15 (s, 2H), 3.92 (s, 3H), 3.57 (s, 2H); MS (ES+): 446.1 (M+1); (ES−): 444.1 (M−1); Analysis calculated for $C_{26}H_{23}NO_6 \cdot HCl \cdot 1.25H_2O$: C, 61.91; H, 5.30; Cl, 7.03; N, 2.78. Found: C, 61.81; H, 5.26; Cl, 7.13; N, 2.90.

Scheme 24

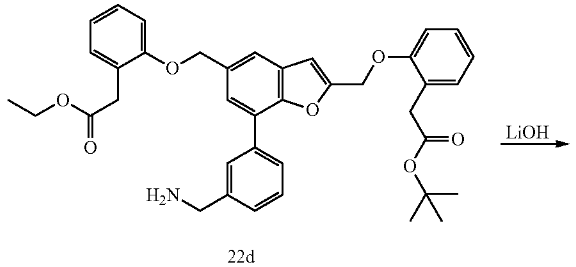

22d

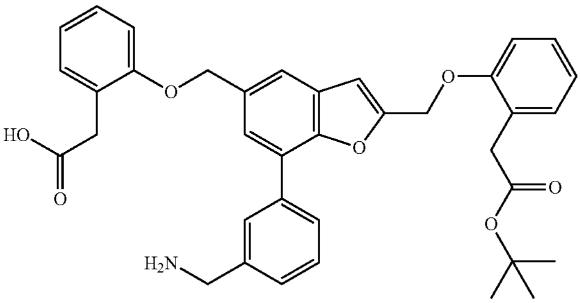

24a

Preparation of 2-(2-((7-(3-(aminomethyl)phenyl)-2-((2-(2-(tert-butoxy)-2-oxoethyl)phenoxy)methyl) benzofuran-5-yl)methoxy)phenyl)acetic acid (24a)

Compound 24a was prepared according to the procedure reported in step-3 of scheme 1, from tert-butyl 2-(2-((7-(3-(aminomethyl)phenyl)-5-((2-(2-ethoxy-2-oxoethyl)phenoxy)methyl)benzofuran-2-yl)methoxy)phenyl)acetate (22d) (210 mg, 0.33 mmol) in THF (5 mL) using a solution of lithium hydroxide hydrate (7.91 mg, 0.33 mmol) in water (1 mL) and stirring at room temperature for 2 h. This gave after workup and purification by reverse phase column chromatography [C18 column (30 g), eluting with ACN in water (containing 0.1% HCl) from 0-100%] 2-(2-((7-(3-(aminomethyl)phenyl)-2-((2-(2-(tert-butoxy)-2-oxoethyl)phenoxy)methyl)benzofuran-5-yl)methoxy)phenyl)acetic acid (24a) (41 mg, 0.067 mmol, 20% yield) HCl salt as a white solid; $^1$H NMR (300 MHz, DMSO-$d_6$) δ 12.21 (s, 1H, $D_2O$ exchangeable), 8.43 (s, 3H, $D_2O$ exchangeable), 7.99-7.95 (m, 1H), 7.74 (s, 1H), 7.68-7.61 (m, 2H), 7.60-7.53 (m, 3H), 7.28-7.19 (m, 4H), 7.09 (d, J=7.2 Hz, 2H), 6.99-6.86 (m, 2H), 5.32 (s, 2H), 5.27 (s, 2H), 4.13 (s, 2H), 3.60 (s, 2H), 3.52 (s, 2H), 1.22 (s, 9H); MS (ES+): 608.3 (M+1); (ES−): 606.2 (M−1); Analysis calculated for $C_{37}H_{37}NO_7 \cdot HCl \cdot 0.25H_2O$: C, 68.51; H, 5.98; Cl, 5.47; N, 2.16. Found: C, 68.59; H, 5.92; Cl, 5.11; N, 2.09.

Scheme 25

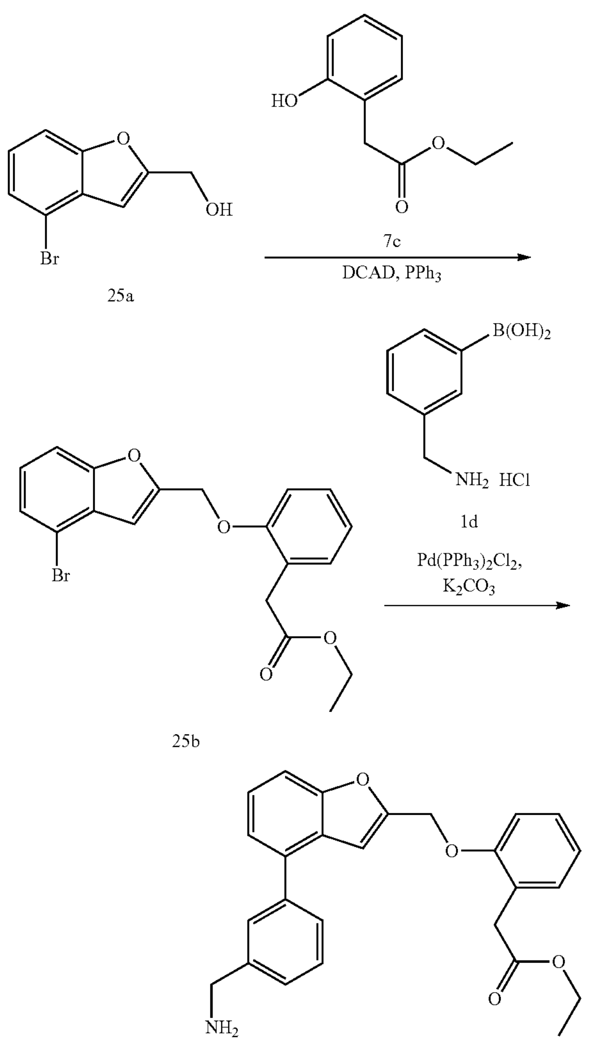

25a

7c

25b

1d

25c

Preparation of ethyl 2-(2-((4-(3-(aminomethyl)phenyl)benzofuran-2-yl)methoxy)phenyl)acetate (25c)

Step-1: Preparation of ethyl 2-(2-((4-bromobenzofuran-2-yl)methoxy)phenyl)acetate (25b)

Compound 25b was prepared according to the procedure reported in step-3 of scheme 7, from (4-bromobenzofuran-2-yl)methanol (25a) (1.5 g, 6.61 mmol; CAS #177735-23-8), ethyl 2-(2-hydroxyphenyl)acetate (7c) (1.190 g, 6.61 mmol) in DCM (30 mL) using triphenylphosphine (1.906 g, 7.27 mmol), a solution of bis(4-chlorobenzyl) diazene-1,2-dicarboxylate (DCAD) (2.67 g, 7.27 mmol) in DCM (20 mL) and stirring at room temperature for 30 min. This gave after workup and purification by flash column chromatography [silica gel (40 g), eluting with EtOAc in hexane from 0-50%] ethyl 2-(2-((4-bromobenzofuran-2-yl)methoxy)phenyl)acetate (25b) (1.5 g, 58% yield) as a colorless oil; $^1$H NMR (300 MHz, DMSO-$d_6$) δ 7.64 (d, J=8.3 Hz, 1H), 7.50 (dd, J=7.7, 1.1 Hz, 1H), 7.33-7.16 (m, 4H), 7.00-6.91 (m, 2H), 5.29 (s, 2H), 4.00 (q, J=7.2 Hz, 2H), 3.60 (s, 2H), 1.06 (t, J=7.1 Hz, 3H).

Step-2: Preparation of ethyl 2-(2-((4-(3-(aminomethyl)phenyl)benzofuran-2-yl)methoxy)phenyl)acetate (25c)

Compound 25c was prepared according to the procedure reported in step-8 of Scheme 3, from ethyl 2-(2-((4-bromobenzofuran-2-yl)methoxy)phenyl)acetate (25b) (1.5 g, 3.85 mmol), 3-(aminomethyl)phenylboronic acid hydrochloride (1d) (1.30 g, 6.94 mmol), in dioxane (20 mL) using bis(triphenylphosphine)palladium(II) chloride (0.541 g, 0.771 mmol), a solution of $K_2CO_3$ (1.598 g, 11.56 mmol) in water (3 mL) and heating at 100° C. for 3 h. This gave after workup and purification by flash column chromatography [silica gel (12 g), eluting with DMA-80 in DCM from 0-50%] followed by reverse phase column chromatography [C18 (30 g), eluting with ACN in water (containing 0.1% HCl) from 0-100%] ethyl 2-(2-((4-(3-(aminomethyl)phenyl)benzofuran-2-yl)methoxy)phenyl)acetate (25c) (502 mg, 31% yield) HCl salt as a white solid; $^1$H NMR (300 MHz, DMSO-$d_6$) δ 8.60 (s, 3H, $D_2O$ exchangeable), 7.81 (s, 1H), 7.69-7.59 (m, 2H), 7.59-7.52 (m, 2H), 7.49-7.39 (m, 2H), 7.32 (s, 1H), 7.28-7.16 (m, 3H), 6.93 (t, J=7.3 Hz, 1H), 5.28 (s, 2H), 4.19-4.07 (m, 2H), 3.97 (q, 2H), 3.58 (s, 2H), 1.02 (t, J=7.1, 1.1 Hz, 3H); MS (ES+): 416.2 (M+1); (ES−): 414.2 (M−1); Analysis calculated for $C_{26}H_{25}NO_4 \cdot HCl \cdot 0.5H_2O$: C, 67.75; H, 5.90; Cl, 7.69; N, 3.04. Found: C, 67.77; H, 5.72; Cl, 7.58; N, 3.09.

Scheme 26

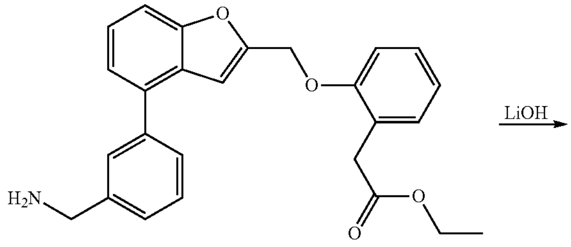

25c

-continued

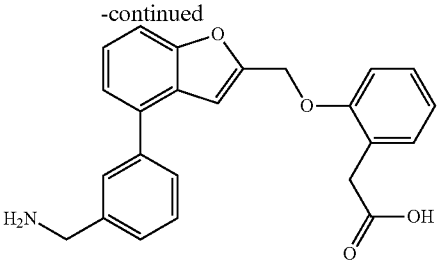

26a

Preparation of 2-(2-((4-(3-(aminomethyl)phenyl) benzofuran-2-yl)methoxy)phenyl)acetic acid (26a)

Compound 26a was prepared according to the procedure reported in step-3 of scheme 1, from ethyl 2-(2-((4-(3-

(aminomethyl)phenyl)benzofuran-2-yl)methoxy)phenyl)acetate (25c) (442 mg, 1.064 mmol) in THF (15 mL) using a solution of lithium hydroxide hydrate (0.323 g, 7.71 mmol) in water (5 mL) and stirring at room temperature overnight. This gave after workup and purification by reverse phase column chromatography [C18 column (30 g), eluting with ACN in water (containing 0.1% HCl) from 0-100%] 2-(2-((4-(3-(aminomethyl)phenyl)benzofuran-2-yl)methoxy) phenyl)acetic acid (26a) (404 mg, 98% yield) HCl salt as a white solid; $^1$H NMR (300 MHz, DMSO-$d_6$) δ 12.19 (s, 1H, $D_2O$ exchangeable), 8.63 (s, 3H, $D_2O$ exchangeable), 7.83 (s, 1H), 7.71-7.60 (m, 2H), 7.57 (d, J=4.8 Hz, 2H), 7.48-7.40 (m, 2H), 7.34 (s, 1H), 7.28-7.16 (m, 3H), 6.93 (t, J=7.3 Hz, 1H), 5.30 (s, 2H), 4.13 (s, 2H), 3.55 (s, 2H); MS (ES+) 388.1 (M+1); (ES−) 386.1 (M−1); Analysis calculated for $C_{24}H_{21}NO_4$·HCl: C, 68.00; H, 5.23; Cl, 8.36; N, 3.30. Found: C, 68.02; H, 5.28; Cl, 8.20; N, 3.31.

Scheme 27

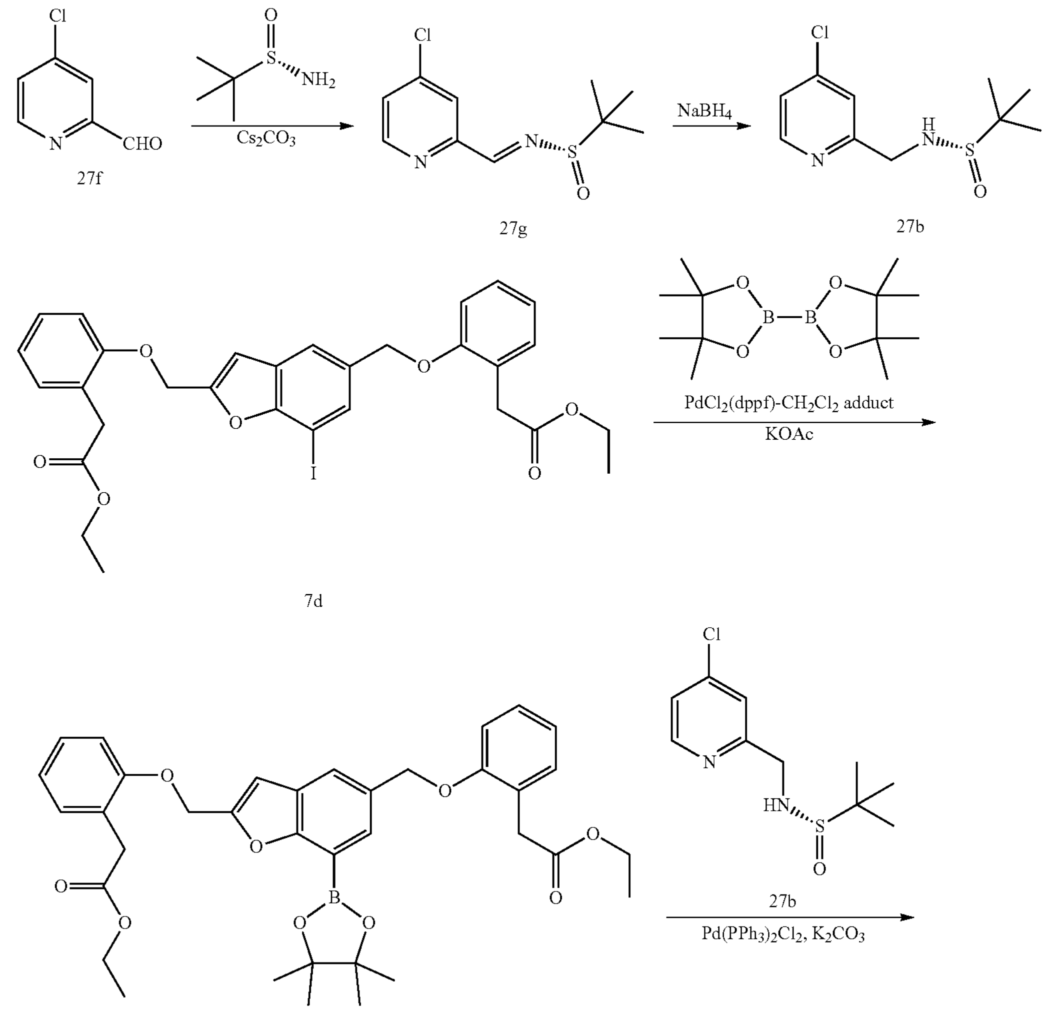

27f, 27g, 27b, 7d, 27a

-continued

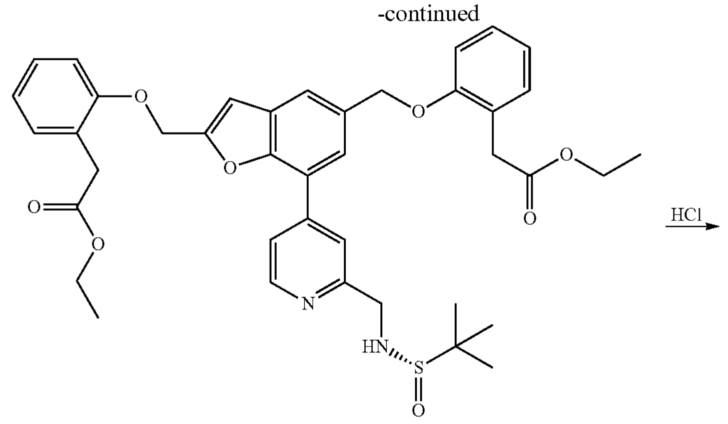

27c

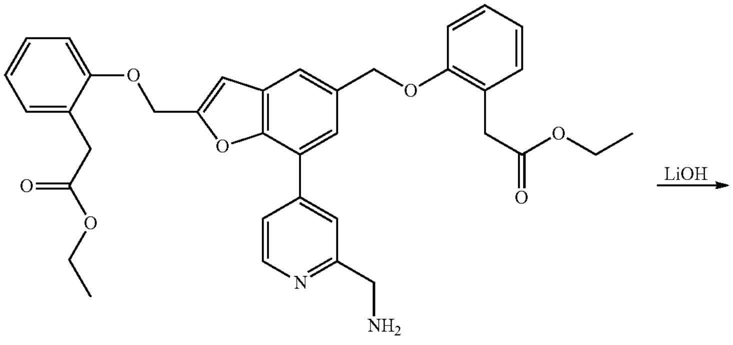

27d

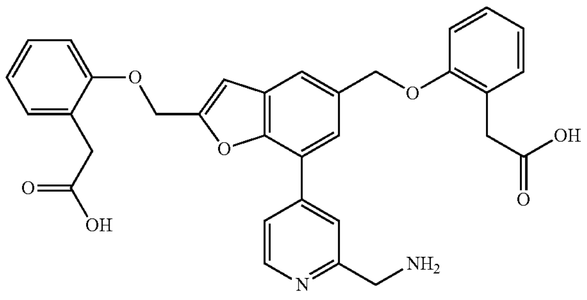

27e

Preparation of 2,2'-((((7-(2-(aminomethyl)pyridin-4-yl)benzofuran-2,5-diyl)bis(methylene))bis(oxy))bis(2,1-phenylene))diacetic acid (27e)

Step-1: Preparation of N-((4-chloropyridin-2-yl)methylene)-2-methylpropane-2-sulfinamide (27g)

To a solution of 4-chloropicolinaldehyde (27f) (15 g, 106 mmol) and $Cs_2CO_3$ (51.8 g, 159 mmol) in DCM (100 mL) was added (S)-2-methylpropane-2-sulfinamide (14.77 g, 122 mmol) and stirred at RT for 1 h. The reaction mixture was diluted with DCM and washed with brine (3×200 mL). The organic layer was dried, filtered and concentrated in vacuo to afford N-((4-chloropyridin-2-yl)methylene)-2-methylpropane-2-sulfinamide (27g) (25.9 g, 100% yield) which was used as such in the next step; $^1$H NMR (300 MHz, DMSO-$d_6$) δ 8.75 (dd, J=5.3, 0.6 Hz, 1H), 8.48 (s, 1H), 8.13 (dd, J=2.1, 0.6 Hz, 1H), 7.76 (dd, J=5.3, 2.1 Hz, 1H), 1.22 (s, 9H).

Step-2: Preparation of (+)-N-((4-chloropyridin-2-yl)methyl)-2-methylpropane-2-sulfinamide (27b)

To a solution of N-((4-chloropyridin-2-yl)methylene)-2-methylpropane-2-sulfinamide (27g) (18.5 g, 76 mmol) in methanol (300 mL) at 0° C. was added $NaBH_4$ (2.86 g, 76 mmol) and stirred for 0.5 h. The reaction was quenched with acetone (20 mL) and concentrated in vacuum. The residue was taken in EtOAc and saturated aqueous $NH_4Cl$. The organic layer was separated, washed with brine, dried, filtered and concentrated under vacuum. The residue obtained was purified by flash column chromatography [silica gel (120 g), eluting with a 9:1 mixture of ethyl acetate and methanol in hexanes] to afford (+)-N-((4-chloropyridin-2-yl)methyl)-2-methylpropane-2-sulfinamide (27b) (15.7 g, 84%) as a white solid. $^1$H NMR (300 MHz, DMSO-$d_6$) δ 8.48 (dd, J=5.3, 0.6 Hz, 1H), 7.58 (dd, J=2.1, 0.7 Hz, 1H), 7.43 (dd, J=5.4, 2.1 Hz, 1H), 5.97 (t, J=6.3 Hz, 1H), 4.29 (dd, J=6.3, 3.3 Hz, 2H), 1.16 (s, 9H); Optical rotation $[\alpha]_D$=+45.4 (0.81, MeOH)

Step-3: Preparation of diethyl 2,2'-((((7-(4,4,5,5-tetramethyl-1,3,2-dioxaborolan-2-yl)benzofuran-2,5-diyl)bis(methylene))bis(oxy))bis(2,1-phenylene)) diacetate (27a)

To a degassed solution of diethyl 2,2'-((((7-iodobenzofuran-2,5-diyl)bis(methylene))bis(oxy))bis(2,1-phenylene)) diacetate (7d) (1.5 g, 2.387 mmol), bis(pinacolato)diboron (BisPin) (1.515 g, 5.97 mmol) and potassium acetate (0.703 g, 7.16 mmol) in anhydrous dioxane (20 mL) was added $PdCl_2(dppf)-CH_2Cl_2$ adduct (0.390 g, 0.477 mmol). The reaction mixture was degassed, filled with argon and heated at 90° C. overnight.

The reaction mixture was diluted with EtOAc (200 mL) and washed with water (100 mL), brine, dried, filtered and concentrated in vacuum. The residue obtained was purified by flash column chromatography [silica gel (40 g), eluting with EtOAc in hexane from 0-40%] to give diethyl 2,2'-((((7-(4,4,5,5-tetramethyl-1,3,2-dioxaborolan-2-yl)benzofuran-2,5-diyl)bis(methylene))bis(oxy))bis(2,1-phenylene)) diacetate (27a) (1.3 g, 87% yield) as a brown oil; MS (ES+): 651.1 (M+Na).

Step-4: Preparation of diethyl 2,2'-((((7-(2-((1,1-dimethylethylsulfinamido)methyl)pyridin-4-yl)benzofuran-2,5-diyl)bis(methylene))bis(oxy))bis(2,1-phenylene))diacetate (27c)

Compound 27c was prepared according to the procedure reported in step-8 of Scheme 3, from diethyl 2,2'-((((7-(4,4,5,5-tetramethyl-1,3,2-dioxaborolan-2-yl)benzofuran-2,5-diyl)bis(methylene))bis(oxy))bis(2,1-phenylene))diacetate (27a) (500 mg, 0.796 mmol), (+)-N-((4-chloropyridin-2-yl)methyl)-2-methylpropane-2-sulfinamide (27b) (294 mg, 1.193 mmol) in dioxane (10 mL) using bis(triphenylphosphine)palladium(II) chloride (84 mg, 0.119 mmol), a solution of $K_2CO_3$ (330 mg, 2.387 mmol) in water (3 mL) and heating at 100° C. for 12 h. This gave after workup and purification by flash column chromatography [silica gel (12 g), eluting with methanol in DCM from 0-5%]diethyl 2,2'-((((7-(2-((1,1-dimethylethylsulfinamido)methyl)pyridin-4-yl)benzofuran-2,5-diyl)bis(methylene))bis(oxy))bis(2,1-phenylene))diacetate (27c) (142 mg, 25% yield) as a gummy solid; MS (ES+): 713.3 (M+1).

Step-5: Preparation of diethyl 2,2'-((((7-(2-(aminomethyl)pyridin-4-yl)benzofuran-2,5-diyl)bis(methylene))bis(oxy))bis(2,1-phenylene))diacetate (27d)

Compound 27d was prepared according to the procedure reported in step-2 of scheme 7, from diethyl 2,2'-((((7-(2-((1,1-dimethylethylsulfinamido)methyl)pyridin-4-yl)benzofuran-2,5-diyl)bis(methylene))bis(oxy))bis(2,1-phenylene)) diacetate (27c) (142 mg, 0.199 mmol) in DCM/THF (100 mL; 1:1) using HCl (4N in dioxane, 0.398 mL, 1.591 mmol) and stirring at room temperature for 30 min. This gave after workup and purification by flash column chromatography [silica gel (24 g), eluting with EtOAc in hexane from 0-100%]methyl diethyl 2,2'-((((7-(2-(aminomethyl)pyridin-4-yl)benzofuran-2,5-diyl)bis(methylene))bis(oxy))bis(2,1-phenylene))diacetate (27d) (89 mg, 18% yield); MS (ES+): 609.3 (M+1).

Step-6: Preparation of 2,2'-((((7-(2-(aminomethyl) pyridin-4-yl)benzofuran-2,5-diyl)bis(methylene))bis (oxy))bis(2,1-phenylene))diacetic acid (27e)

Compound 27e was prepared according to the procedure reported in step-3 of scheme 1, from diethyl 2,2'-((((7-(2-(aminomethyl)pyridin-4-yl)benzofuran-2,5-diyl)bis(methylene))bis(oxy))bis(2,1-phenylene))diacetate (27d) (89 mg, 0.146 mmol) in THE (4 mL) using a solution of lithium hydroxide hydrate (31 mg, 0.731 mmol) in water (1 mL) and stirring at room temperature overnight. This gave after workup and purification by reverse phase column chromatography [C18 column (30 g), eluting with ACN in water (containing 0.1% HCl) from 0-100%] 2,2'-((((7-(2-(aminomethyl)pyridin-4-yl)benzofuran-2,5-diyl)bis(methylene)) bis(oxy))bis(2,1-phenylene))diacetic acid (27e) (29 mg, 36% yield) HCl salt as a white solid; $^1H$ NMR (300 MHz, DMSO-$d_6$) δ 8.79 (d, J=5.3 Hz, 1H), 8.59 (s, 3H, $D_2O$ exchangeable), 8.13 (s, 1H), 8.03 (d, J=5.4 Hz, 1H), 7.85 (s, 2H), 7.24 (dd, J=7.6, 5.7 Hz, 5H), 7.16-7.07 (m, 2H), 6.93 (dt, J=14.4, 7.3 Hz, 2H), 5.37 (s, 2H), 5.29 (s, 2H), 4.32 (s, J=5.5 Hz, 2H), 3.61 (s, 2H), 3.57 (s, 2H); MS (ES+): 553.2 (M+1); (ES−): 551.1 (M−1); Analysis calculated for $C_{32}H_{28}N_2O_7\cdot1.5HCl\cdot1.25H_2O$: C, 61.03; H, 5.12; Cl, 8.44; N, 4.45. Found: C, 60.85; H, 5.29; Cl, 8.64; N, 4.44.

Scheme 28

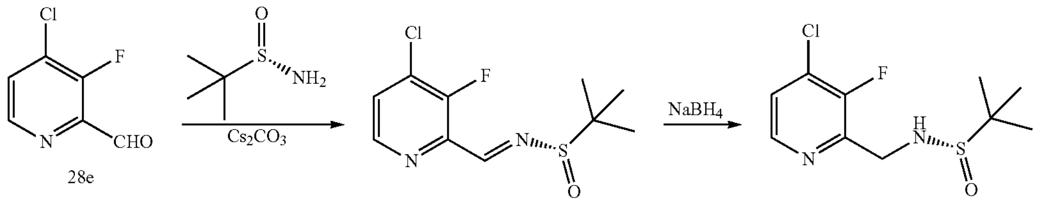

28e

28f

28a

-continued
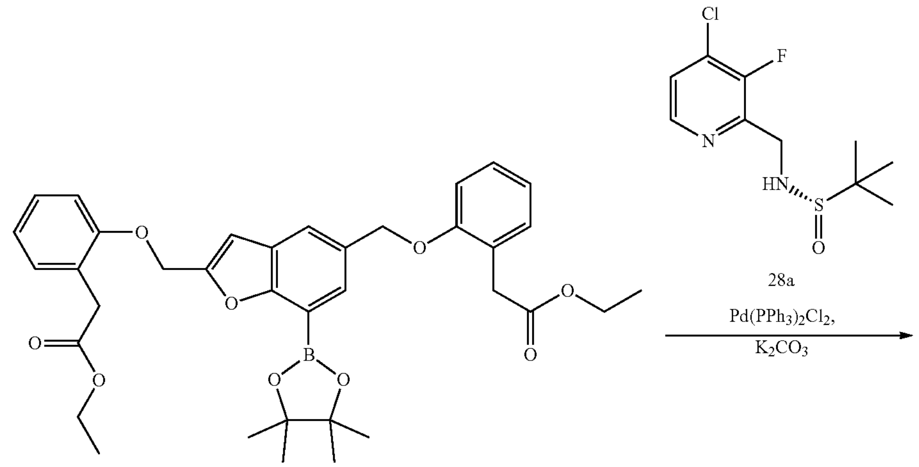
27a
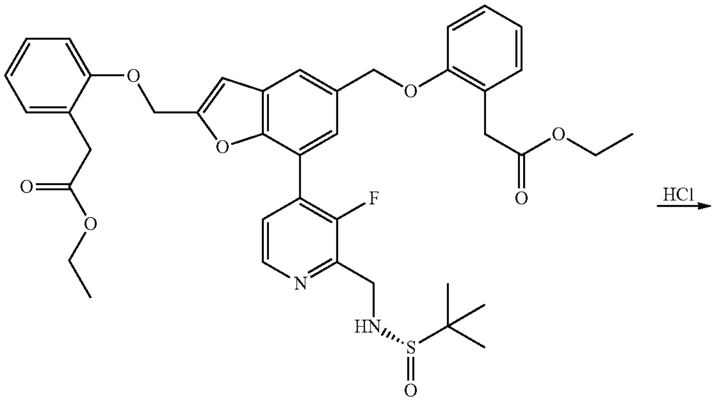
28b
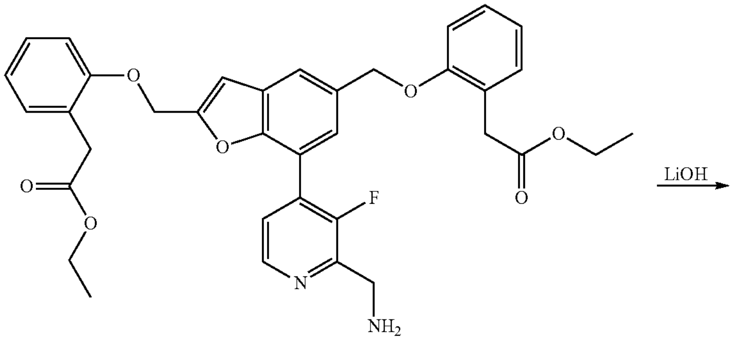
28c
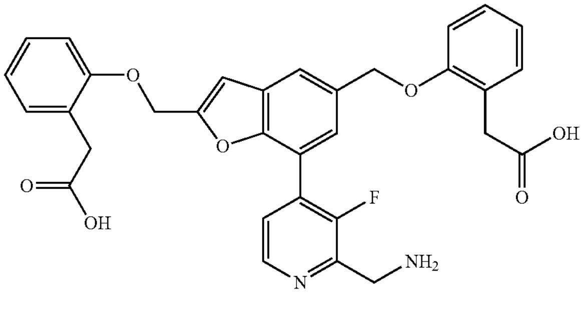
28d

Preparation of 2,2'-((((7-(2-(aminomethyl)-3-fluoropyridin-4-yl)benzofuran-2,5-diyl)bis(methylene))bis(oxy))bis(2,1-phenylene))diacetic acid (28d)

Step-1: Preparation of (S)—N-((4-chloro-3-fluoropyridin-2-yl)methylene)-2-methylpropane-2-sulfinamide (28f)

To a solution of 4-chloro-3-fluoropicolinaldehyde (28e) (6.73 g, 42.2 mmol; CAS #1260878-78-1) and $Cs_2CO_3$ (27.5 g, 84 mmol) in DCM (350 mL) was added (S)-2-methylpropane-2-sulfinamide (5.88 g, 48.5 mmol) and stirred at room temperature for 1 h. The reaction mixture was diluted with DCM and washed with brine (3×200 mL). The organic layer was dried, filtered and concentrated in vacuo to afford (S)—N-((4-chloro-3-fluoropyridin-2-yl)methylene)-2-methylpropane-2-sulfinamide (28f) (11.08 g, 100% yield) which was used in the next reaction without further purification; $^1H$ NMR (300 MHz, DMSO-$d_6$) δ 8.59 (d, J=5.1 Hz, 1H), 8.56 (s, 1H), 7.97 (dd, J=5.6, 5.0 Hz, 1H), 1.21 (s, 9H).

Step-2: Preparation of (+)-N-((4-chloro-3-fluoropyridin-2-yl)methyl)-2-methylpropane-2-sulfinamide (28a)

To a solution of (S)—N-((4-chloro-3-fluoropyridin-2-yl)methylene)-2-methylpropane-2-sulfinamide (28f) (11.08 g, 42.2 mmol) in methanol (211 mL) at 0° C. was added $NaBH_4$ (1.595 g, 42.2 mmol) and stirred for 0.5 h. The reaction was quenched with acetone (20 mL) and concentrated in vacuum. The residue was taken in EtOAc and saturated aqueous $NH_4Cl$.

The organic layer was separated, washed with brine, dried, filtered and concentrated under vacuum. The residue obtained was purified by flash column chromatography [silica gel (120 g), eluting with a 9:1 mixture of ethyl acetate and methanol in hexanes] to afford (+)-N-((4-chloro-3-fluoropyridin-2-yl)methyl)-2-methylpropane-2-sulfinamide (28a) (9.34 g, 84% yield) as a thick clear syrup; $^1H$ NMR (300 MHz, DMSO-$d_6$) δ 8.36 (d, J=5.2 Hz, 1H), 7.72-7.62 (m, 1H), 5.86 (t, J=5.9 Hz, 1H), 4.34 (dd, J=5.9, 2.2 Hz, 2H), 1.09 (s, 9H); Optical rotation $[\alpha]_D$=+53.88 (c=0.49, MeOH)

Step-3: Preparation of diethyl 2,2'-((((7-(2-((1,1-dimethylethylsulfinamido)methyl)-3-fluoropyridin-4-yl)benzofuran-2,5-diyl)bis(methylene))bis(oxy))bis(2,1-phenylene))diacetate (28b)

Compound 28b was prepared according to the procedure reported in step-8 of Scheme 3, from diethyl 2,2'-((((7-(4,4,5,5-tetramethyl-1,3,2-dioxaborolan-2-yl)benzofuran-2,5-diyl)bis(methylene))bis(oxy))bis(2,1-phenylene))diacetate (27a) (800 mg, 1.273 mmol), (+)-N-((4-chloro-3-fluoropyridin-2-yl)methyl)-2-methylpropane-2-sulfinamide (28a) (505 mg, 1.909 mmol) in dioxane (10 mL) using bis(triphenylphosphine)palladium(II) chloride (134 mg, 0.191 mmol), a solution of $K_2CO_3$ (528 mg, 3.82 mmol) in water (3 mL) and heating at 100° C. for 3.5 h. This gave after workup and purification by flash column chromatography [silica gel (12 g), eluting with methanol in DCM from 0-5%]diethyl 2,2'-((((7-(2-((1,1-dimethylethylsulfinamido)methyl)-3-fluoropyridin-4-yl)benzofuran-2,5-diyl)bis(methylene))bis(oxy))bis(2,1-phenylene))diacetate (28b) (136 mg, 15% yield) as a brown gummy solid; MS (ES+): 731.2 (M+1).

Step-2: Preparation of diethyl 2,2'-((((7-(2-(aminomethyl)-3-fluoropyridin-4-yl)benzofuran-2,5-diyl)bis(methylene))bis(oxy))bis(2,1-phenylene))diacetate (28c)

Compound 28c was prepared according to the procedure reported in step-2 of scheme 7, from diethyl 2,2'-((((7-(2-((1,1-dimethylethylsulfinamido)methyl)-3-fluoropyridin-4-yl)benzofuran-2,5-diyl)bis(methylene))bis(oxy))bis(2,1-phenylene))diacetate (28b) (136 mg, 0.186 mmol) in DCM/THF (100 mL; 1:1) using HCl (4N in dioxane, 0.636 mL, 2.55 mmol) and stirring at room temperature for 30 min. This gave after workup and purification by flash column chromatography [silica gel (24 g), eluting with EtOAc in hexane from 0-100%]diethyl 2,2'-((((7-(2-(aminomethyl)-3-fluoropyridin-4-yl)benzofuran-2,5-diyl)bis(methylene))bis(oxy))bis(2,1-phenylene))diacetate (28c) (66 mg, 8% yield); MS (ES+): 627 (M+1).

Step-3: Preparation of 2,2'-((((7-(2-(aminomethyl)-3-fluoropyridin-4-yl)benzofuran-2,5-diyl)bis(methylene))bis(oxy))bis(2,1-phenylene))diacetic acid (28d)

Compound 28d was prepared according to the procedure reported in step-3 of scheme 1, from diethyl 2,2'-((((7-(2-(aminomethyl)-3-fluoropyridin-4-yl)benzofuran-2,5-diyl)bis(methylene))bis(oxy))bis(2,1-phenylene))diacetate (28c) (66 mg, 0.105 mmol) in THE (4 mL) using a solution of lithium hydroxide hydrate (22 mg, 0.527 mmol) in water (1 mL) and stirring at room temperature overnight. This gave after workup and purification by reverse phase column chromatography [C18 column (30 g), eluting with ACN in water (containing 0.1% HCl) from 0-100%] 2,2'-((((7-(2-(aminomethyl)-3-fluoropyridin-4-yl)benzofuran-2,5-diyl)bis(methylene))bis(oxy))bis(2,1-phenylene))diacetic acid (28d) (30 mg, 50% yield) HCl salt as a white solid; $^1H$ NMR (300 MHz, DMSO-$d_6$) δ 8.69-8.55 (m, 4H, 3H $D_2O$ exchangeable), 7.89 (s, 1H), 7.81 (t, J=5.3 Hz, 1H), 7.62 (s, 1H), 7.29-7.15 (m, 5H), 7.14-7.07 (m, 2H), 6.98-6.87 (m, 2H), 5.29 (s, 2H), 5.28 (s, 2H), 4.36 (m, J=5.7 Hz, 2H), 3.59 (s, 2H), 3.55 (s, 2H); $^{19}F$ NMR (282 MHz, DMSO-$d_6$) δ −128.57; MS (ES+): 571.2 (M+1); (ES−): 569.2 (M−1); Analysis calculated for $C_{32}H_{27}FN_2O_7 \cdot 1.35HCl \cdot H_2O$: C, 60.26; H, 4.80; Cl, 7.50; N, 4.39. Found: C, 59.93; H, 4.76; Cl, 7.48; N, 4.41.

Scheme 29

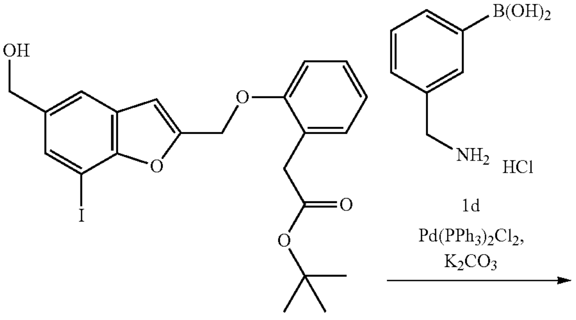

3h

-continued

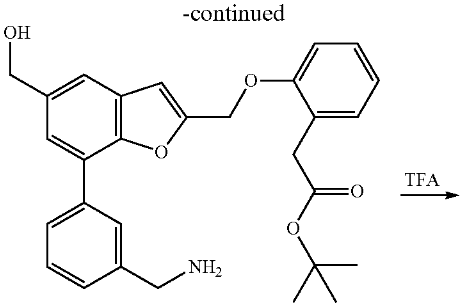

29a

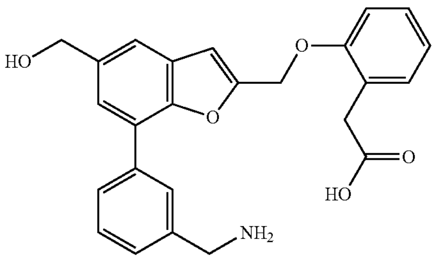

29b

Preparation of 2-(2-((7-(3-(aminomethyl)phenyl)-5-(hydroxymethyl)benzofuran-2-yl)methoxy)phenyl) acetic acid (29b)

Step-1: Preparation of tert-butyl 2-(2-((7-(3-(aminomethyl)phenyl)-5-(hydroxymethyl)benzofuran-2-yl)methoxy)phenyl)acetate (29a)

Compound 29a was prepared according to the procedure reported in step-8 of Scheme 3, from tert-butyl 2-(2-((5-(hydroxymethyl)-7-iodobenzofuran-2-yl)methoxy)phenyl) acetate (3h) (400 mg, 0.809 mmol), 3-(aminomethyl)phenylboronic acid hydrochloride (1d) (228 mg, 1.214 mmol) in dioxane (10 mL) using bis(triphenylphosphine)palladium (II) chloride (114 mg, 0.162 mmol) and a solution of $K_2CO_3$ (280 mg, 2.023 mmol) in water (3 mL) and heating at 100° C. for 3 h. This gave after workup and purification by flash column chromatography [silica gel (12 g), eluting with DMA-80 in DCM from 0-50%] ethyl 2 tert-butyl 2-(2-((7-(3-(aminomethyl)phenyl)-5-(hydroxymethyl)benzofuran-2-yl)methoxy)phenyl)acetate (29a) (286 mg, 75% yield) as a colorless oil; $^1$H NMR (300 MHz, DMSO-$d_6$) δ 7.78 (d, J=1.8 Hz, 1H), 7.71 (dt, J=7.4, 1.7 Hz, 1H), 7.56 (d, J=1.6 Hz, 1H), 7.51-7.45 (m, 1H), 7.45-7.36 (m, 2H), 7.31-7.18 (m, 3H), 7.04 (s, 1H), 6.93 (td, J=7.3, 1.3 Hz, 1H), 5.31-5.20 (m, 3H), 4.64 (d, J=5.1 Hz, 2H), 3.81 (s, 2H), 3.52 (s, 2H), 1.84 (s, 2H), 1.23 (s, 9H); MS (ES+): 474.2 (M+1).

Step-2: Preparation of 2-(2-((7-(3-(aminomethyl)phenyl)-5-(hydroxymethyl)benzofuran-2-yl)methoxy)phenyl)acetic acid (29b)

Compound 29b was prepared according to the procedure reported in step-9 of scheme 3, from tert-butyl 2-(2-((7-(3-(aminomethyl)phenyl)-5-(hydroxymethyl)benzofuran-2-yl)methoxy)phenyl)acetate (29a) (286 mg, 0.604 mmol) in DCM (10 mL) using TFA (0.62 mL, 8.09 mmol) and stirring at room temperature for 3 h. This gave after workup and purification by reverse phase column chromatography [C18 column (30 g), eluting with ACN in water (containing 0.1% HCl) from 0-100%] 2-(2-((7-(3-(aminomethyl)phenyl)-5-(hydroxymethyl)benzofuran-2-yl)methoxy)phenyl)acetic acid(29b) (8 mg, 2% yield) HCl salt as a white solid; $^1$H NMR (300 MHz, DMSO-$d_6$) δ 12.18 (s, 1H, $D_2O$ exchangeable), 8.50 (s, 3H, $D_2O$ exchangeable), 7.96 (s, J=2.3 Hz, 1H), 7.91 (dt, J=6.7, 2.1 Hz, 1H), 7.62-7.49 (m, 4H), 7.30-7.17 (m, 3H), 7.05 (s, 1H), 6.94 (td, J=7.2, 1.4 Hz, 1H), 5.39-5.23 (m, 3H, 1H $D_2O$ exchangeable), 4.64 (d, J=4.3 Hz, 2H), 4.12 (s, 2H), 3.55 (s, 2H); MS (ES+): 418.1 (M+1); (ES−): 416.1 (M−1).

Scheme 30

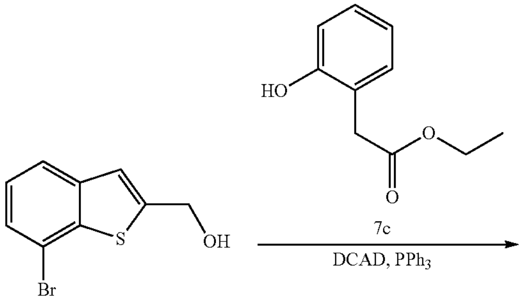

30a

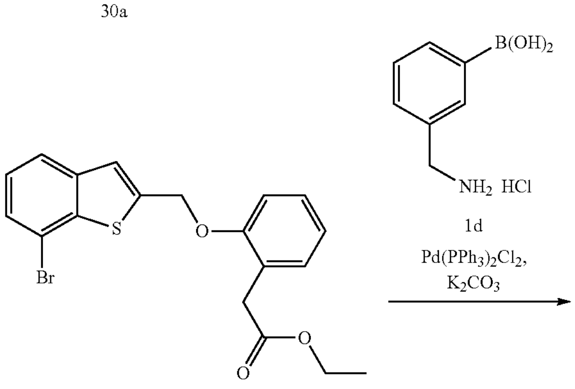

30b

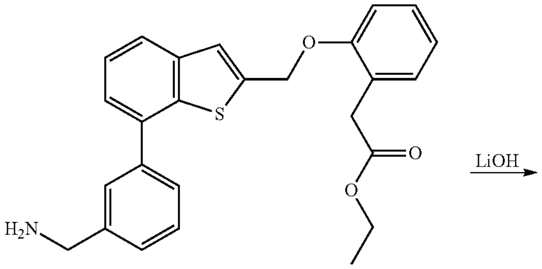

30c

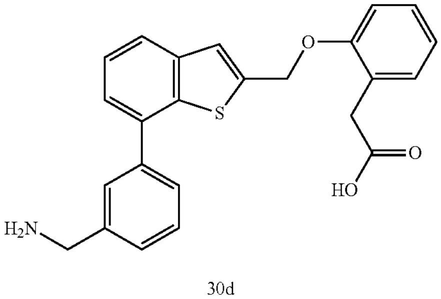

30d

Preparation of 2-(2-((7-(3-(aminomethyl)phenyl)benzo[b]thiophen-2-yl)methoxy)phenyl)acetic acid (30d)

Step-1: Preparation of ethyl 2-(2-((7-bromobenzo[b]thiophen-2-yl)methoxy)phenyl)acetate (30b)

Compound 30b was prepared according to the procedure reported in step-3 of scheme 7, from (7-bromobenzo[b]thiophen-2-yl)methanol (30a) (1.5 g, 6.17 mmol; CAS #1171926-64-9), triphenylphosphine (1.780 g, 6.79 mmol), ethyl 2-(2-hydroxyphenyl)acetate (7c) (1.223 g, 6.79 mmol) in DCM (30 mL) using bis(4-chlorobenzyl) diazene-1,2-dicarboxylate (DCAD) (2.492 g, 6.79 mmol) in DCM (20 mL) and stirring at RT for 30 min. This gave after workup and purification by flash column chromatography [silica gel (40 g), eluting with EtOAc in hexane from 0-50%] ethyl 2-(2-((7-bromobenzo[b]thiophen-2-yl)methoxy)phenyl)acetate (30b) (1.3 g, 52% yield) as a white solid; $^1$H NMR (300 MHz, DMSO-$d_6$) δ 7.88 (dd, J=7.9, 1.0 Hz, 1H), 7.67-7.64 (m, 1H), 7.60 (dd, J=7.7, 0.9 Hz, 1H), 7.35 (t, J=7.8 Hz, 1H), 7.31-7.21 (m, 2H), 7.15 (dd, J=8.3, 1.2 Hz, 1H), 6.95 (td, J=7.4, 1.1 Hz, 1H), 5.44 (d, J=1.0 Hz, 2H), 4.06 (q, J=7.1 Hz, 2H), 3.64 (s, 2H), 1.13 (t, J=7.1 Hz, 3H).

Step-2: Preparation of ethyl 2-(2-((7-(3-(aminomethyl)phenyl)benzo[b]thiophen-2-yl)methoxy)phenyl)acetate (30c)

Compound 30c was prepared according to the procedure reported in step-8 of Scheme 3, from ethyl 2-(2-((7-bromobenzo[b]thiophen-2-yl)methoxy)phenyl)acetate (30b) (400 mg, 0.987 mmol) in dioxane (10 mL) using 3-(aminomethyl)phenylboronic acid hydrochloride (1d) (333 mg, 1.776 mmol), bis(triphenylphosphine)palladium(II) chloride (104 mg, 0.148 mmol), a solution of $K_2CO_3$ (409 mg, 2.96 mmol) in water (3 mL) and heating at 100° C. for 6 h. This gave after workup and purification by flash column chromatography [silica gel (12g), eluting with DMA80 in DCM from 0-50%] ethyl 2-(2-((7-(3-(aminomethyl)phenyl)benzo[b]thiophen-2-yl)methoxy)phenyl)acetate (30c) (98 mg, 23% yield) as a yellow oil; MS (ES+): 432.1 (M+1).

Step-3: Preparation of 2-(2-((7-(3-(aminomethyl)phenyl)benzo[b]thiophen-2-yl)methoxy)phenyl)acetic acid (30d)

Compound 30d was prepared according to the procedure reported in step-3 of scheme 1, from ethyl 2-(2-((7-(3-(aminomethyl)phenyl)benzo[b]thiophen-2-yl)methoxy)phenyl)acetate (30c) (98 mg, 0.227 mmol) in THF (3 mL) using a solution of lithium hydroxide hydrate (166 mg, 3.95 mmol) in water (1 mL) and stirring at room temperature for 4 h. This gave after workup and purification by reverse phase column chromatography [C18 column (30 g), eluting with ACN in water (containing 0.1% HCl) from 0-100%] 2-(2-((7-(3-(aminomethyl)phenyl)benzo[b]thiophen-2-yl)methoxy)phenyl)acetic acid (30d) (49 mg, 12% yield) HCl salt as a white solid; $^1$H NMR (300 MHz, DMSO-$d_6$) δ 9.23 (s, 3H, $D_2O$ exchangeable), 7.82-7.74 (m, 2H), 7.72-7.65 (m, 1H), 7.56-7.50 (m, 3H), 7.48-7.41 (m, 1H), 7.39-7.32 (m, 1H), 7.18-7.09 (m, 2H), 7.06 (dd, J=8.3, 1.2 Hz, 1H), 6.84 (td, J=7.3, 1.2 Hz, 1H), 5.35 (s, 2H), 4.05 (s, 2H), 3.48 (s, 2H); MS (ES+): 404.1 (M+1); (ES−): 402.1 (M−1); Analysis calculated for $C_{24}H_{21}NO_3S \cdot HCl \cdot 0.5H_2O$: C, 64.21; H, 5.16; Cl, 7.90; N, 3.12. Found: C, 64.03; H, 5.21; Cl, 7.72; N, 3.06.

Scheme 31

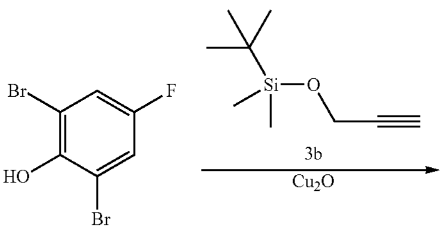

31a

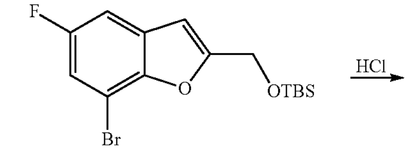

31b

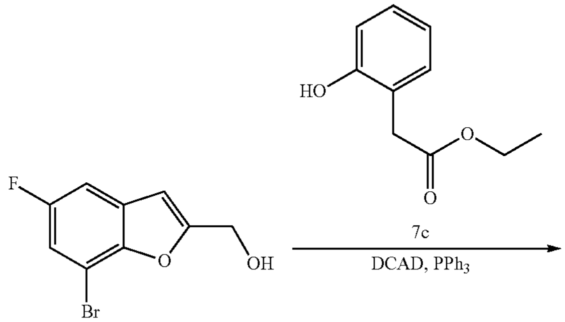

31c

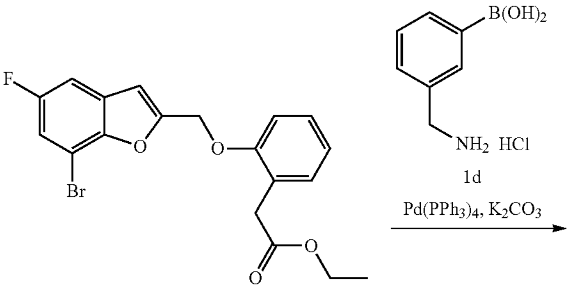

31d

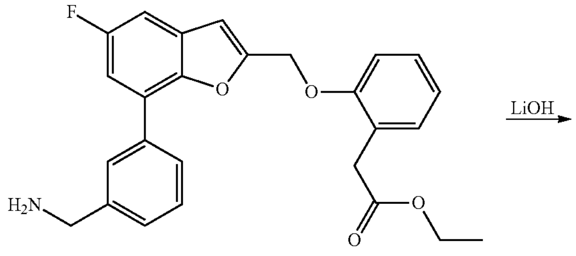

31e

-continued

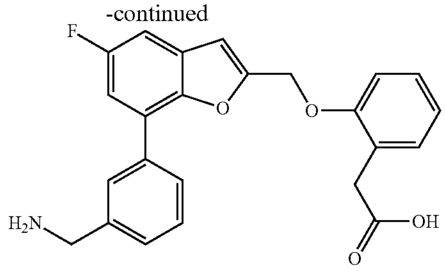

31f

Preparation of 2-(2-((7-(3-(aminomethyl)phenyl)-5-fluorobenzofuran-2-yl)methoxy)phenyl)acetic acid (31f)

Step-1: Preparation of ((7-bromo-5-fluorobenzofuran-2-yl)methoxy)(tert-butyl)dimethylsilane (31b)

Compound 31b was prepared according to the procedure reported in step-1 of scheme 3, from 2,6-dibromo-4-fluorophenol (31a) (5 g, 18.53 mmol; CAS #344-20-7) in pyridine (30 mL) using tert-butyldimethyl(prop-2-ynyloxy)silane (3b) (3.16 g, 18.53 mmol and copper(I) oxide (1.325 g, 9.26 mmol) and stirring at room temperature for 10 min and 125° C. for 6 h. This gave after workup and purification by flash column chromatography [silica gel (80 g), eluting with EtOAc in hexane from 0-70%]((7-bromo-5-fluorobenzofuran-2-yl)methoxy)(tert-butyl)dimethylsilane (31b) (3.6 g, 54% yield) as a clear oil; $^1$H NMR (300 MHz, DMSO-$d_6$) δ 7.51 (s, 1H), 7.48 (s, 1H), 6.93 (s, 1H), 4.83 (s, 2H), 0.89 (d, J=1.3 Hz, 9H), 0.11 (d, J=1.1 Hz, 6H).

Step-2: Preparation of (7-bromo-5-fluorobenzofuran-2-yl)methanol (31c)

Compound 31c was prepared according to the procedure reported in step-5 of scheme 20, from ((7-bromo-5-fluorobenzofuran-2-yl)methoxy)(tert-butyl)dimethylsilane (31b) using HCl (4N in dioxane, 4 mL) in DCM and stirring at room temperature for 1 h. This gave after workup and purification by flash column chromatography [silica gel (80 g), eluting with EtOAc in hexane from 0-70%] (7-bromo-5-fluorobenzofuran-2-yl)methanol (31c) (1.6 g, 35% yield) as a white solid; $^1$H NMR (300 MHz, DMSO-$d_6$) δ 7.49 (d, J=1.1 Hz, 1H), 7.46 (d, J=1.2 Hz, 1H), 6.89 (t, J=0.9 Hz, 1H), 5.60 (t, J=5.8 Hz, 1H, $D_2O$ exchangeable), 4.60 (d, J=5.7 Hz, 2H); $^{19}$F NMR (282 MHz, DMSO-$d_6$) δ −118.70.

Step-3: Preparation of ethyl 2-(2-((7-bromo-5-fluorobenzofuran-2-yl)methoxy)phenyl)acetate (31d)

Compound 31d was prepared according to the procedure reported in step-3 of scheme 7, from (7-bromo-5-fluorobenzofuran-2-yl)methanol (31c) (1.12 g, 4.57 mmol) in DCM (30 mL) using triphenylphosphine (1.319 g, 5.03 mmol), ethyl 2-(2-hydroxyphenyl)acetate (7c) (0.906 g, 5.03 mmol), bis(4-chlorobenzyl) diazene-1,2-dicarboxylate (DCAD) (1.846 g, 5.03 mmol) in DCM (20 mL) and stirring at room temperature for 30 min. This gave after workup and purification by flash column chromatography [silica gel (40 g), eluting with EtOAc in hexane from 0-50%] ethyl 2-(2-((7-bromo-5-fluorobenzofuran-2-yl)methoxy)phenyl)acetate (31d) (1.1 g, 59% yield) as a colorless oil; $^1$H NMR (300 MHz, DMSO-$d_6$) δ 7.56 (d, J=8.8 Hz, 2H), 7.32-7.17 (m, 3H), 7.13 (s, 1H), 6.95 (t, J=7.4 Hz, 1H), 5.31 (s, 2H), 4.00 (q, J=7.1 Hz, 2H), 3.60 (s, 2H), 1.04 (t, J=7.1 Hz, 3H).

Step-4: Preparation of ethyl 2-(2-((7-(3-(aminomethyl)phenyl)-5-fluorobenzofuran-2-yl)methoxy)phenyl)acetate (31e)

Compound 31e was prepared according to the procedure reported in step-8 of Scheme 3, from ethyl 2-(2-((7-bromo-5-fluorobenzofuran-2-yl)methoxy)phenyl)acetate (31d) (420 mg, 1.031 mmol) in dioxane (20 mL) using 3-(aminomethyl)phenylboronic acid hydrochloride (1d) (213 mg, 1.134 mmol), Pd($PPh_3$)$_4$ (238 mg, 0.206 mmol), a solution of $K_2CO_3$ (428 mg, 3.09 mmol) in water (3 mL) and heating at 100° C. for 3 h. This gave after workup and purification by flash column chromatography [silica gel (12 g), eluting with DMA80 in DCM from 0-50%] ethyl 2-(2-((7-(3-(aminomethyl)phenyl)-5-fluorobenzofuran-2-yl)methoxy)phenyl)acetate (31e) (166 mg, 37% yield) as a yellow oil; $^1$H NMR (300 MHz, DMSO-$d_6$) δ 7.82 (s, 1H), 7.77-7.71 (m, 1H), 7.51-7.37 (m, 4H), 7.31-7.17 (m, 3H), 7.06 (s, 1H), 6.94 (t, J=7.3 Hz, 1H), 5.30 (s, 2H), 3.87 (q, 2H), 3.81 (s, 2H), 3.59 (s, 2H), 1.93 (s, 2H), 0.96 (t, J=7.1, 1.1 Hz, 3H); MS (ES+): 434.20 (M+1).

Step-5: Preparation of 2-(2-((7-(3-(aminomethyl)phenyl)-5-fluorobenzofuran-2-yl)methoxy)phenyl)acetic acid (31f)

Compound 31f was prepared according to the procedure reported in step-3 of scheme 1, from ethyl 2-(2-((7-(3-(aminomethyl)phenyl)-5-fluorobenzofuran-2-yl)methoxy)phenyl)acetate (31e) (98 mg, 0.227 mmol) in THF (6 mL) using a solution of lithium hydroxide hydrate (87 mg, 2.063 mmol) in water (2 mL) and stirring at RT overnight. This gave after workup and purification by reverse phase column chromatography [C18 column (30 g), eluting with ACN in water (containing 0.1% HCl) from 0-100%] 2-(2-((7-(3-(aminomethyl)phenyl)-5-fluorobenzofuran-2-yl)methoxy)phenyl)acetic acid (31f) (107 mg, 26% yield) HCl salt as a white solid; $^1$H NMR (300 MHz, DMSO-$d_6$) δ 12.17 (s, 1H, $D_2O$ exchangeable), 8.54 (s, 3H, $D_2O$ exchangeable), 8.02 (s, 1H), 8.00-7.89 (m, 1H), 7.58 (d, J=4.7 Hz, 2H), 7.53-7.41 (m, 2H), 7.30-7.16 (m, 3H), 7.08 (s, 1H), 6.94 (t, J=7.2 Hz, 1H), 5.34 (s, 2H), 4.12 (s, 2H), 3.56 (s, 2H); $^{19}$F NMR (282 MHz, DMSO-$d_6$) δ −119.69; MS (ES+): 406.1 (M+1); (ES−): 404.1 (M−1).

Scheme 32

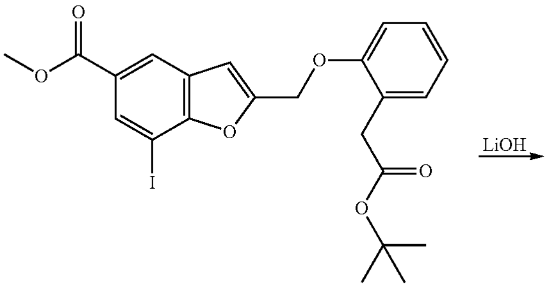

23a

-continued

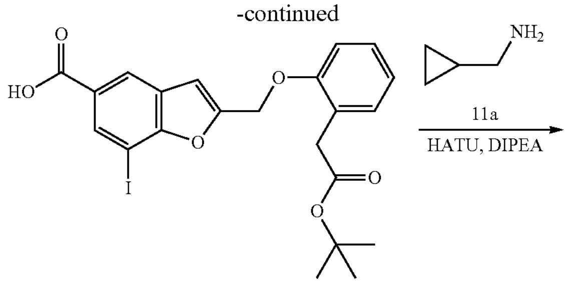

32a

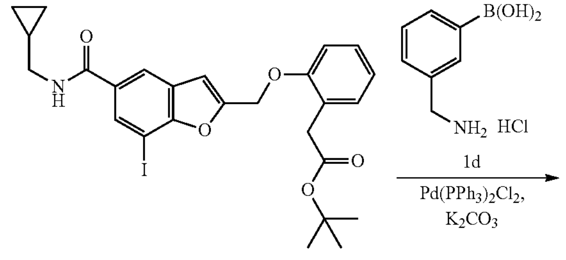

32b

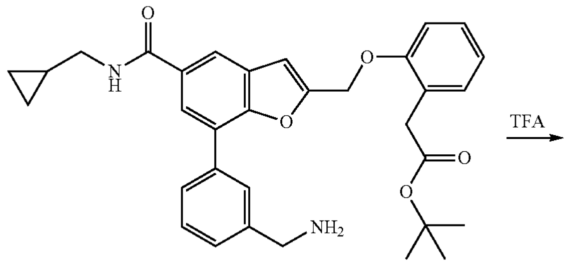

32c

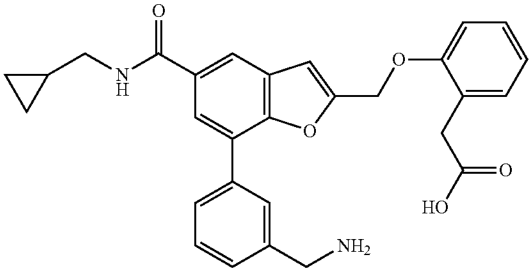

32d

Preparation of 2-(2-((7-(3-(aminomethyl)phenyl)-5-((cyclopropylmethyl)carbamoyl)benzofuran-2-yl)methoxy)phenyl)acetic acid (32d)

Step-1: Preparation of 2-((2-(2-(tert-butoxy)-2-oxoethyl)phenoxy)methyl)-7-iodobenzofuran-5-carboxylic acid (32a)

Compound 32a was prepared according to the procedure reported in step-3 of scheme 1, from methyl 2-((2-(2-(tert-butoxy)-2-oxoethyl)phenoxy)methyl)-7-iodobenzofuran-5-carboxylate (23a) (2.72 g, 5.21 mmol) in THF (10 mL) using a solution of lithium hydroxide hydrate (0.219 g, 5.21 mmol) in water (2 mL) and stirring overnight at room temperature. The reaction mixture was concentrated under vacuum and acidified to pH 4. The aqueous was diluted with EtOAc (200 mL), washed with water, brine, dried, filtered and concentrated. The residue obtained was purified by flash column chromatography [silica gel (80 g), eluting with EtOAc/MeOH (9:1) in hexane from 0-100%] to afford 2-((2-(2-(tert-butoxy)-2-oxoethyl)phenoxy)methyl)-7-iodobenzofuran-5-carboxylic acid (32a) (5.8 g, 11.41 mmol, 66% yield) as a white solid; $^1H$ NMR (300 MHz, DMSO-$d_6$) δ 13.13 (s, 1H), 8.33-8.19 (m, 2H), 7.32-7.23 (m, 2H), 7.20 (dt, J=7.0, 2.0 Hz, 2H), 6.94 (td, J=7.3, 1.2 Hz, 1H), 5.32 (s, 2H), 3.52 (s, 2H), 1.27 (s, 9H).

Step-2: Preparation of tert-butyl 2-(2-((5-((cyclopropylmethyl)carbamoyl)-7-iodobenzofuran-2-yl)methoxy)phenyl)acetate (32b)

Compound 32b was prepared according to the procedure reported in step-1 of scheme 10, from 2-((2-(2-(tert-butoxy)-2-oxoethyl)phenoxy)methyl)-7-iodobenzofuran-5-carboxylic acid (32a) (400 mg, 0.787 mmol) in DMF (10 mL) using cyclopropylmethanamine (11a) (61.6 mg, 0.866 mmol), N-ethyl-N-isopropylpropan-2-amine (DIPEA) (0.344 mL, 1.967 mmol), and 2-(3H-[1,2,3]triazolo[4,5-b]pyridin-3-yl)-1,1,3,3-tetramethylisouronium hexafluorophosphate(V) (HATU) (329 mg, 0.866 mmol) and stirring overnight at room temperature. This gave after workup and purification by flash column chromatography [silica gel (24 g), eluting with EtOAc in hexane from 0-100%] tert-butyl 2-(2-((5-((cyclopropylmethyl)carbamoyl)-7-iodobenzofuran-2-yl)methoxy)phenyl)acetate (32b) (250 mg, 57% yield) as a white solid; MS (ES+): 584.10 (M+Na).

Step-3: Preparation of tert-butyl 2-(2-((7-(3-(aminomethyl)phenyl)-5-((cyclopropylmethyl)carbamoyl)benzofuran-2-yl)methoxy)phenyl)acetate (32c)

Compound 32c was prepared according to the procedure reported in step-8 of Scheme 3, from tert-butyl 2-(2-((5-((cyclopropylmethyl)carbamoyl)-7-iodobenzofuran-2-yl)methoxy)phenyl)acetate (32b) (250 mg, 0.445 mmol) in dioxane (10 mL) using 3-(aminomethyl)phenylboronic acid hydrochloride (1d) (125 mg, 0.668 mmol), bis(triphenylphosphine)palladium(II) chloride (62.5 mg, 0.089 mmol) and a solution of $K_2CO_3$ (154 mg, 1.113 mmol) in water (3 mL). This gave after workup and purification by flash column chromatography [silica gel (12 g), eluting with DMA80 in DCM from 0-50%] tert-butyl 2-(2-((7-(3-(aminomethyl)phenyl)-5-((cyclopropylmethyl)carbamoyl)benzofuran-2-yl)methoxy)phenyl)acetate (32c) (131 mg, 54% yield) as a colorless oil; MS (ES+): 541.3 (M+1), (ES−): 539.2 (M−1)

Step-4: Preparation of 2-(2-((7-(3-(aminomethyl)phenyl)-5-((cyclopropylmethyl)carbamoyl)benzofuran-2-yl)methoxy)phenyl)acetic acid (32d)

Compound 32d was prepared according to the procedure reported in step-9 of scheme 3, from tert-butyl 2-(2-((7-(3-(aminomethyl)phenyl)-5-((cyclopropylmethyl)carbamoyl)benzofuran-2-yl)methoxy)phenyl)acetate (32c) (131 mg, 0.242 mmol) in DCM (15 mL), using TFA (0.343 mL, 4.45 mmol) and stirring at room temperature for 3h. This gave after workup and purification by reverse phase column chromatography [C18 column (30 g), eluting with ACN in water (containing 0.1% HCl) from 0-100%] 2-(2-((7-(3-(aminomethyl)phenyl)-5-((cyclopropylmethyl)carbamoyl)benzofuran-2-yl)methoxy)phenyl)acetic acid (32d) (35 mg, 16% yield) HCl salt as a white solid; $^1H$ NMR (300 MHz, DMSO-$d_6$) δ 12.18 (s, 1H, $D_2O$ exchangeable), 8.78 (t, J=5.7 Hz, 1H), 8.45 (s, 3H, $D_2O$ exchangeable), 8.22-8.12

(m, 2H), 8.07 (d, J=1.7 Hz, 1H), 7.98 (dt, J=7.4, 1.7 Hz, 1H), 7.64-7.52 (m, 2H), 7.31-7.16 (m, 4H), 6.95 (td, J=7.1, 1.5 Hz, 1H), 5.35 (s, 2H), 4.16 (s, 2H), 3.56 (s, 2H), 3.19 (t, J=6.2 Hz, 2H), 1.18-0.99 (m, 1H), 0.50-0.36 (m, 2H), 0.31-0.21 (m, 2H); MS (ES+) 485.2 (M+1); (ES−): 483.2 (M−1); Analysis calculated for $C_{29}H_{28}N_2O_5 \cdot HCl \cdot 1.75H_2O$: C, 63.04; H, 5.93; Cl, 6.42; N, 5.07. Found: C, 63.21; H, 5.95; Cl, 6.37; N, 5.07.

Scheme 33

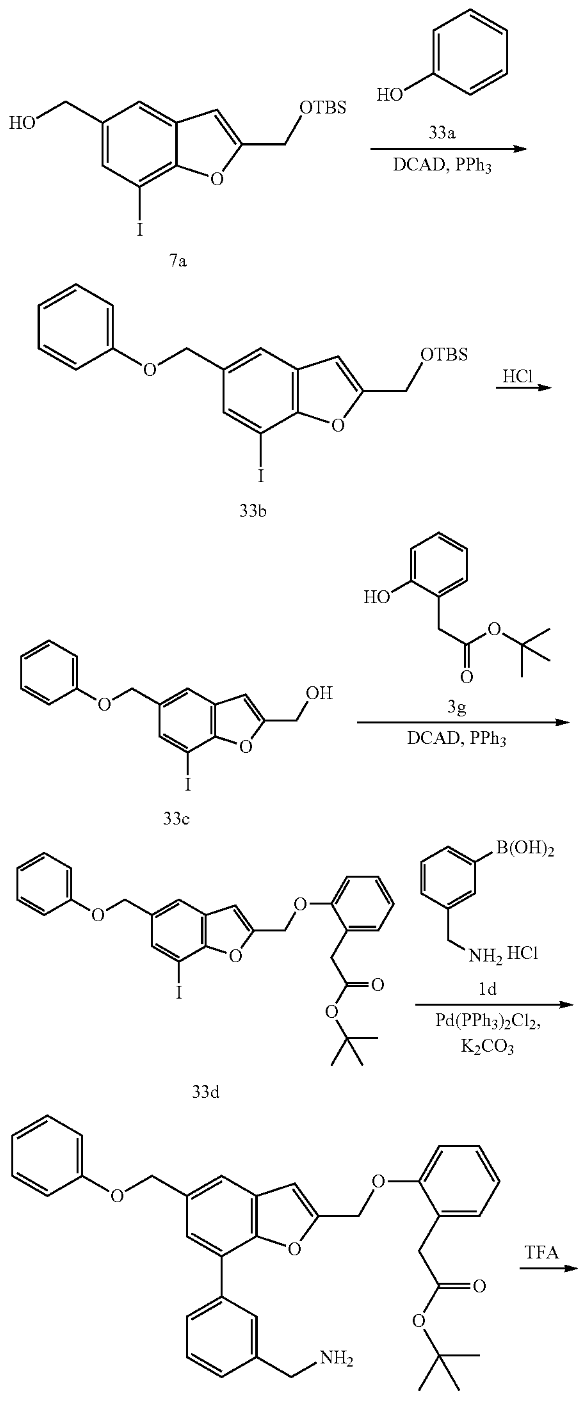

7a

33b

33c

33d

33e

-continued

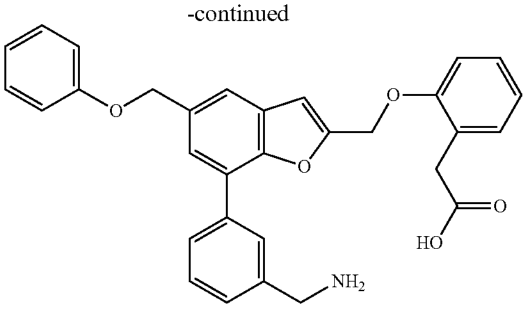

33f

Preparation of 2-(2-((7-(3-(aminomethyl)phenyl)-5-(phenoxymethyl)benzofuran-2-yl)methoxy)phenyl) acetic acid (33f)

Step-1: Preparation of tert-butyl((7-iodo-5-(phenoxymethyl)benzofuran-2-yl)methoxy)dimethylsilane (33b)

Compound 33b was prepared according to the procedure reported in step-3 of scheme 7, from (2-(((tert-butyldimethylsilyl)oxy)methyl)-7-iodobenzofuran-5-yl)methanol (7a) (2 g, 4.78 mmol), triphenylphosphine (1.379 g, 5.26 mmol), phenol (33a) (0.495 g, 5.26 mmol; CAS #108-95-2) in DCM (30 mL) using bis(4-chlorobenzyl) diazene-1,2-dicarboxylate (DCAD) (1.931 g, 5.26 mmol) in DCM (20 mL) and stirring at room temperature for 30 min. This gave after workup and purification by flash column chromatography [silica gel (40 g), eluting with EtOAc in hexane from 0-50%] tert-butyl((7-iodo-5-(phenoxymethyl)benzofuran-2-yl) methoxy)dimethylsilane (33b) (2.1 g, 89% yield) as a yellow oil; $^1$H NMR (300 MHz, DMSO-$d_6$) δ 7.76 (d, J=1.5 Hz, 1H), 7.69 (d, J=1.5 Hz, 1H), 7.41-7.38 (m, 1H), 7.31-7.25 (m, 2H), 7.04-6.99 (m, 2H), 6.95 (d, J=7.8 Hz, 1H), 5.15 (s, 2H), 4.84-4.79 (m, 2H), 0.89 (s, 9H), 0.13 (s, 6H).

Step-2: Preparation of (7-iodo-5-(phenoxymethyl) benzofuran-2-yl)methanol (33c)

Compound 33c was prepared according to the procedure reported in step-2 of scheme 7, from tert-butyl((7-iodo-5-(phenoxymethyl)benzofuran-2-yl)methoxy)dimethylsilane (33b) (2.1 g, 4.25 mmol) using HCl (4N in dioxane, 5.98 mL, 23.90 mmol) in DCM (20 mL) and stirring the reaction mixture at room temperature for 3 h. This gave after workup and purification by flash column chromatography [silica gel (40 g), eluting with EtOAc in hexane from 0-50%](7-iodo-5-(phenoxymethyl)benzofuran-2-yl)methanol (33c) (1.5 g, 83% yield) as a white solid; $^1$H NMR (300 MHz, DMSO-$d_6$) δ 7.74 (d, J=1.6 Hz, 1H), 7.68 (d, J=1.5 Hz, 1H), 7.33-7.24 (m, 2H), 7.06-6.98 (m, 2H), 6.98-6.88 (m, 2H), 5.57 (t, J=5.8 Hz, 1H), 5.16 (s, 2H), 4.60 (dd, J=5.9, 0.8 Hz, 2H); MS (ES+): 403.0 (M+Na).

Step-3: Preparation of tert-butyl 2-(2-((7-iodo-5-(phenoxymethyl)benzofuran-2-yl)methoxy)phenyl) acetate (33d)

Compound 33d was prepared according to the procedure reported in step-3 of scheme 7, from (7-iodo-5-(phenoxymethyl)benzofuran-2-yl)methanol (33c) (400 mg, 1.052 mmol), triphenylphosphine (304 mg, 1.157 mmol), tert-butyl 2-(2-hydroxyphenyl)acetate (3g) (0.241 g, 1.157 mmol) in DCM (30 mL) using bis(4-chlorobenzyl) diazene-1,2-dicarboxylate (DCAD) (425 mg, 1.157 mmol) in DCM (20 mL) and stirring the reaction mixture at room temperature for 30 min. This gave after workup and purification by flash column chromatography [silica gel (40 g), eluting with EtOAc in hexane from 0-50%] tert-butyl 2-(2-((7-iodo-5-(phenoxymethyl)benzofuran-2-yl)methoxy)phenyl)acetate (33d) (220 mg, 37% yield) as a colorless oil.

Step-4: Preparation of tert-butyl 2-(2-((7-(3-(aminomethyl)phenyl)-5-(phenoxymethyl)benzofuran-2-yl)methoxy)phenyl)acetate (33e)

Compound 33e was prepared according to the procedure reported in step-8 of Scheme 3, from tert-butyl 2-(2-((7-iodo-5-(phenoxymethyl)benzofuran-2-yl)methoxy)phenyl) acetate (33d) (220 mg, 0.386 mmol) in dioxane (10 mL) using 3-(aminomethyl)phenylboronic acid hydrochloride (1d) (108 mg, 0.579 mmol), bis(triphenylphosphine)palladium(II) chloride (54.1 mg, 0.077 mmol), a solution of $K_2CO_3$ (133 mg, 0.964 mmol) in water (3 mL) and heating at 100° C. for 3 h. This gave after workup and purification by flash column chromatography [silica gel (12 g), eluting with DMA80 in DCM from 0-50%] tert-butyl 2-(2-((7-(3-(aminomethyl)phenyl)-5-(phenoxymethyl)benzofuran-2-yl) methoxy)phenyl)acetate (33e) (102 mg, 48% yield) as a colorless oil; MS (ES+): 550.2 (M+1).

Step-5: Preparation of 2-(2-((7-(3-(aminomethyl) phenyl)-5-(phenoxymethyl)benzofuran-2-yl) methoxy)phenyl)acetic acid (33f)

Compound 33f was prepared according to the procedure reported in step-9 of scheme 3, from tert-butyl 2-(2-((7-(3-(aminomethyl)phenyl)-5-(phenoxymethyl)benzofuran-2-yl) methoxy)phenyl)acetate (33e) (102 mg, 0.186 mmol) in DCM (5 mL) using TFA (0.297 mL, 3.86 mmol). This gave after workup and purification by reverse phase column chromatography [C18 column (30 g), eluting with ACN in water (containing 0.1% HCl) from 0-100%] 2-(2-((7-(3-(aminomethyl)phenyl)-5-(phenoxymethyl)benzofuran-2-yl) methoxy)phenyl)acetic acid (33f) (14 mg, 7% yield) hydrochloride salt as a white solid; $^1H$ NMR (300 MHz, DMSO-$d_6$) δ 12.12 (s, 1H, $D_2O$ exchangeable), 8.39 (s, 3H, $D_2O$ exchangeable), 7.99-7.90 (m, 2H), 7.75 (d, J=1.6 Hz, 1H), 7.66 (d, J=1.7 Hz, 1H), 7.63-7.51 (m, 2H), 7.35-7.25 (m, 3H), 7.25-7.18 (m, 2H), 7.12-7.01 (m, 3H), 6.94 (td, J=7.2, 1.3 Hz, 2H), 5.33 (s, 2H), 5.24 (s, 2H), 4.13 (s, 2H), 3.55 (s, 2H); MS (ES+): 494.2 (M+1); (ES−): 492.2 (M−1).

Scheme 34

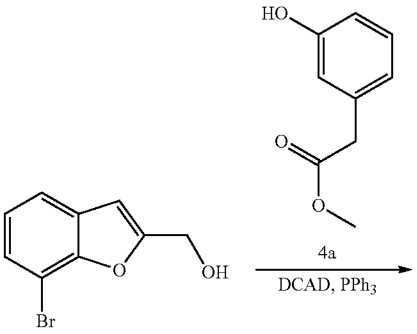

19b

-continued

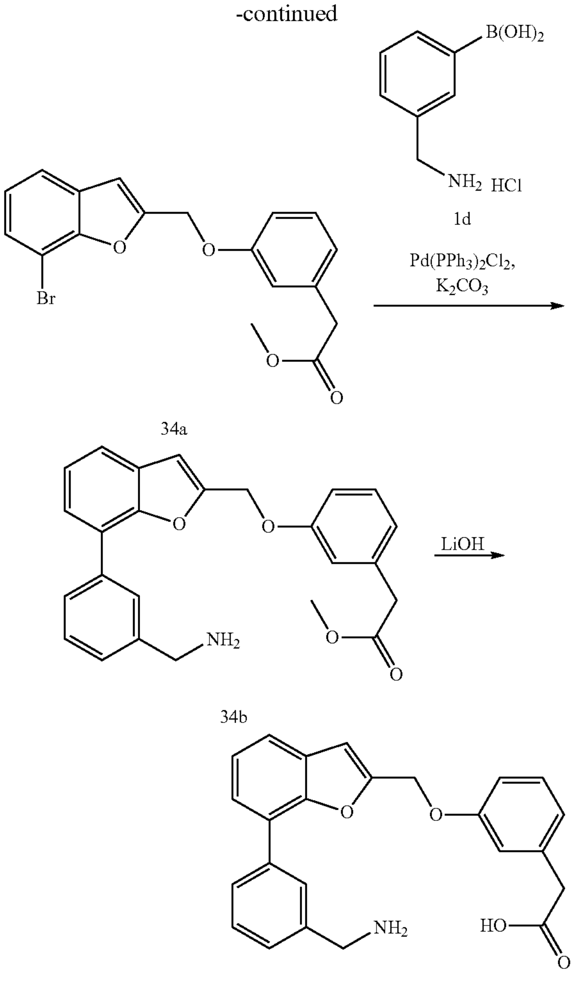

34a

34b

34c

Preparation of 2-(3-((7-(3-(aminomethyl)phenyl) benzofuran-2-yl)methoxy)phenyl)acetic acid (34c)

Step-1: Preparation of methyl 2-(3-((7-bromobenzofuran-2-yl)methoxy)phenyl)acetate (34a)

Compound 34a was prepared according to the procedure reported in step-3 of scheme 7, from (7-bromobenzofuran-2-yl)methanol (19b) (510 mg, 2.246 mmol), triphenylphosphine (648 mg, 2.471 mmol), methyl 2-(3-hydroxyphenyl) acetate (4a) (411 mg, 2.471 mmol) in DCM (30 mL) using bis(4-chlorobenzyl) diazene-1,2-dicarboxylate (DCAD) (907 mg, 2.471 mmol) in DCM (20 mL) and stirring at room temperature for 30 min. This gave after workup and purification by flash column chromatography [silica gel (40 g), eluting with EtOAc in hexane from 0-50%]methyl 2-(3-((7-bromobenzofuran-2-yl)methoxy)phenyl)acetate (34a) (404 mg, 48% yield) as a yellow oil; $^1H$ NMR (300 MHz, DMSO-$d_6$) δ 7.68 (dd, J=7.8, 1.1 Hz, 1H), 7.57 (dd, J=7.8, 1.1 Hz, 1H), 7.30-7.20 (m, 2H), 7.19 (s, 1H), 7.02-6.97 (m, 2H), 6.88 (dt, J=7.6, 1.2 Hz, 1H), 5.29 (s, 2H), 3.66 (s, 2H), 3.60 (s, 3H).

Step-2: Preparation of methyl 2-(3-((7-(3-(aminomethyl)phenyl)benzofuran-2-yl)methoxy)phenyl)acetate (34b)

Compound 34b was prepared according to the procedure reported in step-8 of Scheme 3, from methyl 2-(3-((7-bromobenzofuran-2-yl)methoxy)phenyl)acetate (34a) (400 mg, 1.066 mmol) in dioxane (10 mL) using 3-(aminomethyl) phenylboronic acid hydrochloride (1d) (300 mg, 1.599 mmol), bis(triphenylphosphine)palladium(II) chloride (150 mg, 0.213 mmol) and a solution of $K_2CO_3$ (368 mg, 2.67 mmol) in water (3 mL) and heating at 100° C. for 3 h. This gave after workup and purification by flash column chromatography [silica gel (12g), eluting with DMA80 in DCM from 0-50%]methyl 2-(3-((7-(3-(aminomethyl)phenyl)benzofuran-2-yl)methoxy)phenyl)acetate (34b) (125 mg, 29% yield) as a colorless oil; MS (ES+): 402.1 (M+1).

Step-3: Preparation of 2-(3-((7-(3-(aminomethyl) phenyl)benzofuran-2-yl)methoxy)phenyl)acetic acid (34c)

Compound 34c was prepared according to the procedure reported in step-3 of scheme 1, from methyl 2-(3-((7-(3-(aminomethyl)phenyl)benzofuran-2-yl)methoxy)phenyl)acetate (34b) (125 mg, 0.311 mmol) in THF (4 mL) using a solution of lithium hydroxide hydrate (134 mg, 3.20 mmol) in water (1 mL) and stirring at room temperature overnight. This gave after workup and purification by reverse phase column chromatography [C18 column (30 g), eluting with ACN in water (containing 0.1% HCl) from 0-100%] 2-(3-((7-(3-(aminomethyl)phenyl)benzofuran-2-yl)methoxy) phenyl)acetic acid (34c) (77 mg, 19% yield) HCl salt as a white solid; $^1H$ NMR (300 MHz, DMSO-$d_6$) δ 9.18 (s, 3H, $D_2O$ exchangeable), 7.95 (s, J=1.9 Hz, 1H), 7.89 (dt, J=6.8, 2.0 Hz, 1H), 7.68 (dd, J=7.7, 1.2 Hz, 1H), 7.61-7.51 (m, 3H), 7.38 (t, J=7.6 Hz, 1H), 7.29-7.20 (m, 1H), 7.14 (s, 1H), 7.03-6.92 (m, 2H), 6.87 (dt, J=7.6, 1.2 Hz, 1H), 5.30 (s, 2H), 4.11 (s, 2H), 3.54 (s, 2H); MS (ES+): 388.1 (M+1); (ES−): 386.1 (M−1); Analysis calculated for $C_{24}H_{21}NO_4 \cdot HCl \cdot H_2O$: C, 65.23; H, 5.47; Cl, 8.02; N, 3.17. Found: C, 65.38; H, 5.40; Cl, 7.78; N, 3.13.

Scheme 35

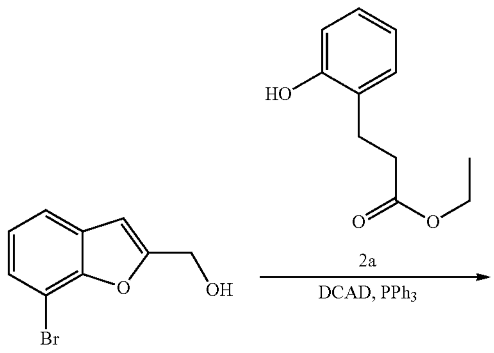

19b

-continued

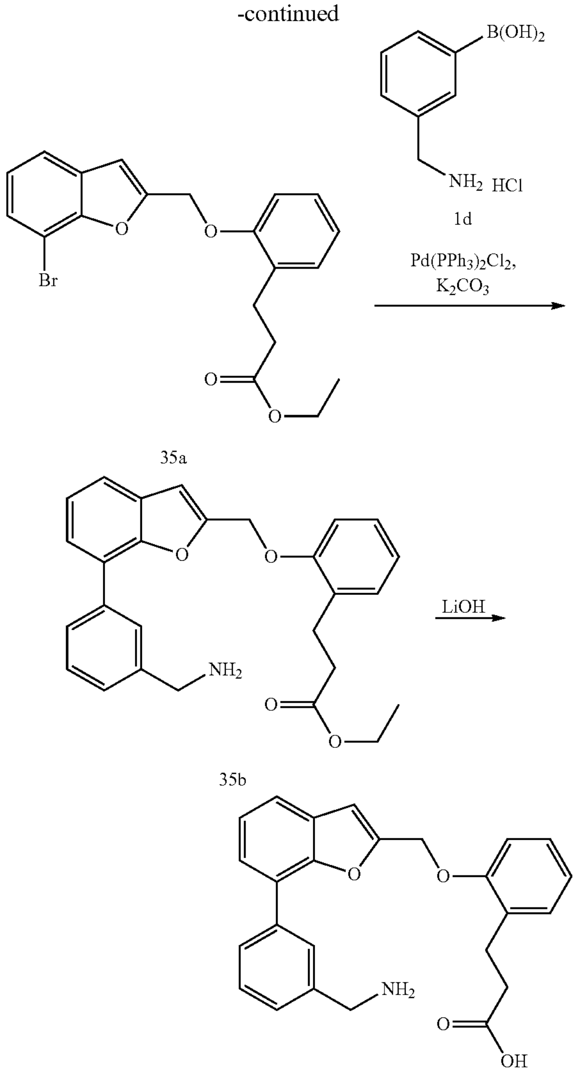

35a

35b

35c

Preparation of 3-(2-((7-(3-(aminomethyl)phenyl) benzofuran-2-yl)methoxy)phenyl)propanoic acid (35c)

Step-1: Preparation of ethyl 3-(2-((7-bromobenzofuran-2-yl)methoxy)phenyl)propanoate (35a)

Compound 35a was prepared according to the procedure reported in step-3 of scheme 7, from (7-bromobenzofuran-2-yl)methanol (19b) (500 mg, 2.202 mmol), triphenylphosphine (635 mg, 2.422 mmol), ethyl 3-(2-hydroxyphenyl) propanoate (2a) (470 mg, 2.422 mmol) in DCM (30 mL) using bis(4-chlorobenzyl) diazene-1,2-dicarboxylate (DCAD) (889 mg, 2.422 mmol) in DCM (20 mL) and stirring at room temperature for 30 min. This gave after workup and purification by flash column chromatography [silica gel (40 g), eluting with EtOAc in hexane from 0-50%] ethyl 3-(2-((7-bromobenzofuran-2-yl)methoxy)phenyl)propanoate (35a)(308 mg, 35% yield) as a colorless oil; $^1H$ NMR (300 MHz, DMSO-$d_6$) δ 7.66 (dd, J=7.8, 1.1 Hz, 1H), 7.55 (dd, J=7.8, 1.0 Hz, 1H), 7.24-7.12 (m, 5H), 6.94-6.86

(m, 1H), 5.36 (s, 2H), 3.99 (q, J=7.1 Hz, 2H), 2.83 (t, J=7.6 Hz, 2H), 2.64-2.53 (m, 2H), 1.09 (t, J=7.1 Hz, 3H).

Step-2: Preparation of ethyl 3-(2-((7-(3-(aminomethyl)phenyl)benzofuran-2-yl)methoxy)phenyl)propanoate (35b)

Compound 35b was prepared according to the procedure reported in step-8 of Scheme 3, from ethyl 3-(2-((7-bromobenzofuran-2-yl)methoxy)phenyl)propanoate (35a) (300 mg, 0.744 mmol) in dioxane (10 mL) using 3-(aminomethyl) phenylboronic acid hydrochloride (1d) (209 mg, 1.116 mmol), bis(triphenylphosphine)palladium(II) chloride (104 mg, 0.149 mmol) and a solution of $K_2CO_3$ (257 mg, 1.860 mmol) in water (3 mL) and heating at 100° C. for 3 h.

This gave after workup and purification by flash column chromatography [silica gel (12g), eluting with DMA80 in DCM from 0-50%] ethyl 3-(2-((7-(3-(aminomethyl)phenyl) benzofuran-2-yl)methoxy)phenyl)propanoate (35b) (155 mg, 49% yield) as a colorless oil; MS (ES+): 430.2 (M+1); (ES−): 428.2 (M−1).

Step-3: Preparation of 3-(2-((7-(3-(aminomethyl) phenyl)benzofuran-2-yl)methoxy)phenyl)propanoic acid (35c)

Compound 35c was prepared according to the procedure reported in step-3 of scheme 1, from ethyl 3-(2-((7-(3-(aminomethyl)phenyl)benzofuran-2-yl)methoxy)phenyl) propanoate (35b) (155 mg, 0.361 mmol) in THF (4 mL) using a solution of lithium hydroxide hydrate (125 mg, 2.98 mmol) in water (1 mL) and stirring at room temperature overnight. This gave after workup and purification by reverse phase column chromatography [C18 column (30 g), eluting with ACN in water (containing 0.1% HCl) from 0-100%] 3-(2-((7-(3-(aminomethyl)phenyl)benzofuran-2-yl)methoxy)phenyl)propanoic acid (35c) (90 mg, 30% yield) HCl salt as a white solid; $^1$H NMR (300 MHz, DMSO-$d_6$) δ 12.11 (s, 1H, $D_2O$ exchangeable), 8.54 (s, 3H, $D_2O$ exchangeable), 7.95 (s, 1H), 7.93-7.88 (m, 1H), 7.68 (dd, J=7.7, 1.2 Hz, 1H), 7.59-7.53 (m, 3H), 7.38 (t, J=7.6 Hz, 1H), 7.23-7.15 (m, 3H), 7.12 (s, 1H), 6.95-6.86 (m, 1H), 5.35 (s, 2H), 4.11 (d, J=4.9 Hz, 2H), 2.81 (t, J=7.7 Hz, 2H), 2.57-2.41 (m, 2H); MS (ES+): 402.1 (M+1); (ES−): 400.2 (M−1); Analysis calculated for $C_{25}H_{23}NO_4 \cdot HCl \cdot 0.75H_2O$: C, 66.52; H, 5.69; Cl, 7.85; N, 3.10. Found: C, 66.97; H, 5.65; Cl, 7.99; N, 3.14.

Scheme 36

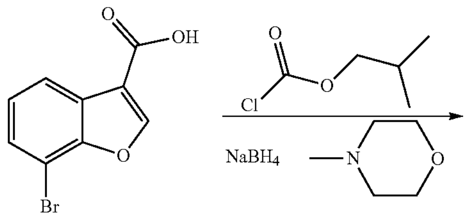

36a

-continued

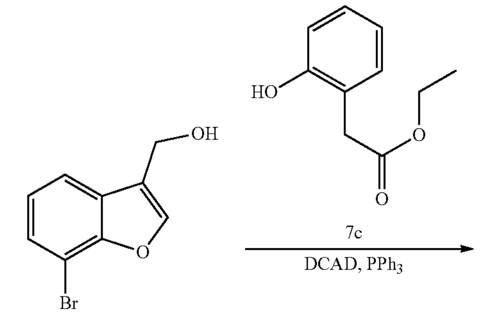

36b

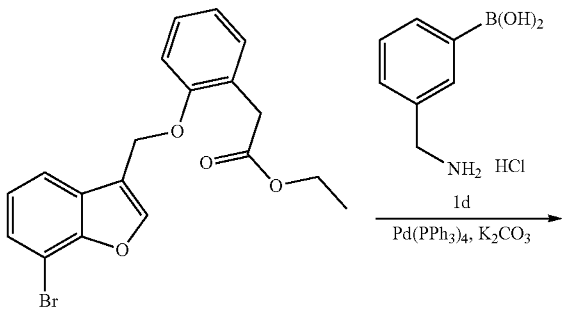

36c

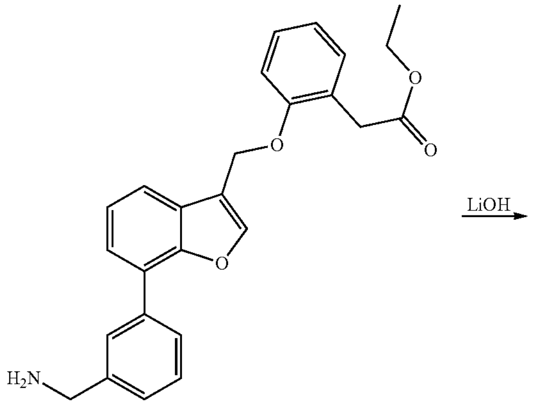

36d

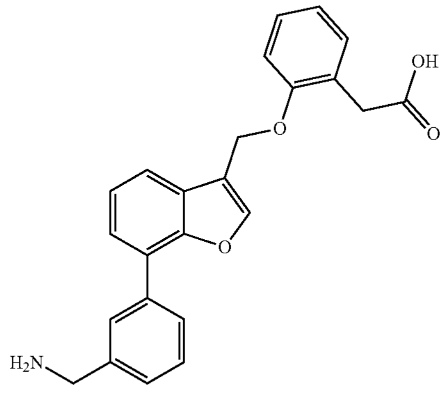

36e

Preparation of 2-(2-((7-(3-(aminomethyl)phenyl) benzofuran-3-yl)methoxy)phenyl)acetic acid (36e)

Step-1: Preparation of (7-bromobenzofuran-3-yl)methanol (36b)

Compound 36b was prepared according to the procedure reported in step-1 of scheme 8, from 7-bromobenzofuran-3-carboxylic acid (36a) (600 mg, 2.489 mmol; CAS #1374574-88-5) using N-Methylmorpholine (0.328 mL, 2.99 mmol), isobutyl chloroformate (0.392 mL, 2.99 mmol) in THF (50 mL) and a solution of $NaBH_4$ (283 mg, 7.47 mmol) in water (2.0 mL). This gave after workup and purification by flash column chromatography [silica gel (24g), eluting with EtOAc/MeOH (9:1) in hexane from 0-50%] (7-bromobenzofuran-3-yl)methanol (36b) (438 mg, 77% yield) as a yellow solid; $^1H$ NMR (300 MHz, DMSO-$d_6$) δ 8.01 (s, 1H), 7.71 (dd, J=7.7, 1.1 Hz, 1H), 7.56 (dd, J=7.8, 1.0 Hz, 1H), 7.22 (t, J=7.7 Hz, 1H), 5.25 (t, J=5.5 Hz, 1H), 4.64 (dd, J=5.5, 1.1 Hz, 2H).

Step-2: Preparation of ethyl 2-(2-((7-bromobenzofuran-3-yl)methoxy)phenyl)acetate (36c)

Compound 36c was prepared according to the procedure reported in step-3 of scheme 7, from (7-bromobenzofuran-3-yl)methanol (36b) (435 mg, 1.916 mmol), triphenylphosphine (553 mg, 2.107 mmol), ethyl 2-(2-hydroxyphenyl) acetate (7c) (380 mg, 2.107 mmol) in DCM (30 mL) using bis(4-chlorobenzyl) diazene-1,2-dicarboxylate (DCAD) (774 mg, 2.107 mmol) in DCM (20 mL) and stirring at room temperature for 30 min. This gave after workup and purification by flash column chromatography [silica gel (40 g), eluting with EtOAc in hexane from 0-50%] ethyl 2-(2-((7-bromobenzofuran-3-yl)methoxy)phenyl)acetate (36c) (260 mg, 35% yield) as a yellow oil; MS (ES+): 389.0 and 391.0 (M+1); (ES−): 387.0 and 390.0 (M−1).

Step-3: Preparation of ethyl 2-(2-((7-(3-(aminomethyl)phenyl)benzofuran-3-yl)methoxy)phenyl)acetate (36d)

Compound 36d was prepared according to the procedure reported in step-8 of scheme 3, from ethyl 2-(2-((7-bromobenzofuran-3-yl)methoxy)phenyl)acetate (36c) (260 mg, 0.668 mmol) using 3-(aminomethyl)phenylboronic acid hydrochloride (1d) (188 mg, 1.002 mmol), $Pd(PPh_3)_4$ (154 mg, 0.134 mmol), a solution of $K_2CO_3$ (231 mg, 1.670 mmol) in water (3 mL) and dioxane (10 mL) and heating at 100° C. for 3 h. This gave after workup and purification by flash column chromatography [silica gel (12 g), eluting with DMA80 in DCM from 0-50%] ethyl 2-(2-((7-(3-(aminomethyl)phenyl)benzofuran-3-yl)methoxy)phenyl)acetate (36d) (82 mg, 30% yield) as a colorless oil; MS (ES+): 416.1 (M+1).

Step-4: Preparation of 2-(2-((7-(3-(aminomethyl) phenyl)benzofuran-3-yl)methoxy)phenyl)acetic acid (36e)

Compound 36e was prepared according to the procedure reported in step-3 of scheme 1, from ethyl 2-(2-((7-(3-(aminomethyl)phenyl)benzofuran-3-yl)methoxy)phenyl)acetate (36d) (82 mg, 0.197 mmol) in THF (3 mL) using a solution of lithium hydroxide hydrate (112 mg, 2.67 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((7-(3-(aminomethyl)phenyl)benzofuran-3-yl)methoxy) phenyl)acetic acid (36e) (5.2 mg, 2% yield) HCl salt as an off white solid; $^1H$ NMR (300 MHz, DMSO-$d_6$) δ 12.17 (s, 1H, $D_2O$ exchangeable), 8.33 (s, 3H, $D_2O$ exchangeable), 8.17 (s, 1H), 7.97 (d, J=1.8 Hz, 1H), 7.90 (dt, J=7.6, 1.7 Hz, 1H), 7.74 (dd, J=7.8, 1.3 Hz, 1H), 7.62-7.51 (m, 3H), 7.43 (t, J=7.6 Hz, 1H), 7.30-7.17 (m, 3H), 6.92 (td, J=7.2, 1.3 Hz, 1H), 5.32 (s, 2H), 4.18-4.08 (m, 2H), 3.53 (s, 2H); MS (ES+): 388.1 (M+1); (ES−): 386.1 (M−1).

Scheme 37

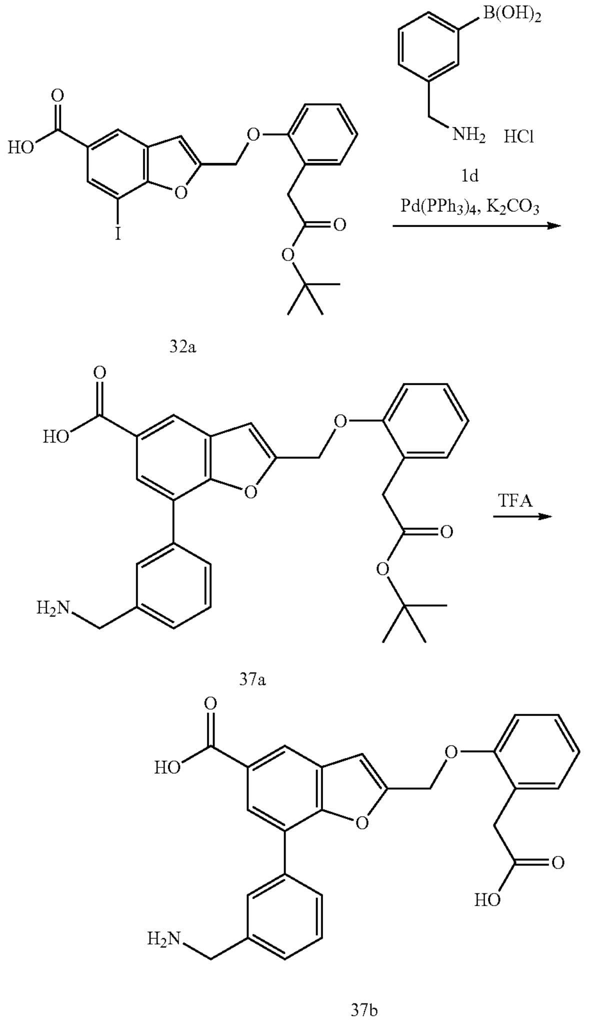

32a

37a

37b

Step-2: Preparation of 7-(3-(aminomethyl)phenyl)-2-((2-(carboxymethyl)phenoxy)methyl)benzofuran-5-carboxylic acid (37b)

Compound 37b was prepared according to the procedure reported in step-9 of scheme 3, from 7-(3-(aminomethyl) phenyl)-2-((2-(2-(tert-butoxy)-2-oxoethyl)phenoxy)methyl) benzofuran-5-carboxylic acid (37a) (103 mg, 0.0.211 mmol) in DCM (10 mL), using TFA (0.379 mL, 4.92 mmol). This gave after workup purification by reverse phase column chromatography [C18 column (30 g), eluting with ACN in water (containing 0.1% HCl) from 0-100%] 7-(3-(aminomethyl)phenyl)-2-((2-(carboxymethyl)phenoxy)methyl)benzofuran-5-carboxylic acid (37b) (48 mg, 23% yield) HCl salt as a white solid; $^1$H NMR (300 MHz, DMSO-$d_6$) δ 12.67 (s, 1H, $D_2O$ exchangeable), 8.47 (s, 3H, $D_2O$ exchangeable), 8.29 (d, J=1.6 Hz, 1H), 8.15 (d, J=1.7 Hz, 1H), 7.99-7.91 (m, 2H), 7.63-7.54 (m, 2H), 7.31-7.18 (m, 4H), 6.95 (td, J=7.1, 1.6 Hz, 1H), 5.36 (s, 2H), 4.15 (s, 2H), 3.56 (s, 2H); MS (ES+): 432.1 (M+1); (ES−): 430.1 (M−1); Analysis calculated for $C_{25}H_{21}NO_6 \cdot 1HCl \cdot 1.75H_2O$: C, 60.12; H, 5.15; Cl, 7.10; N, 2.80. Found: C, 60.42; H, 5.18; Cl, 6.82; N, 2.83.

Scheme 38

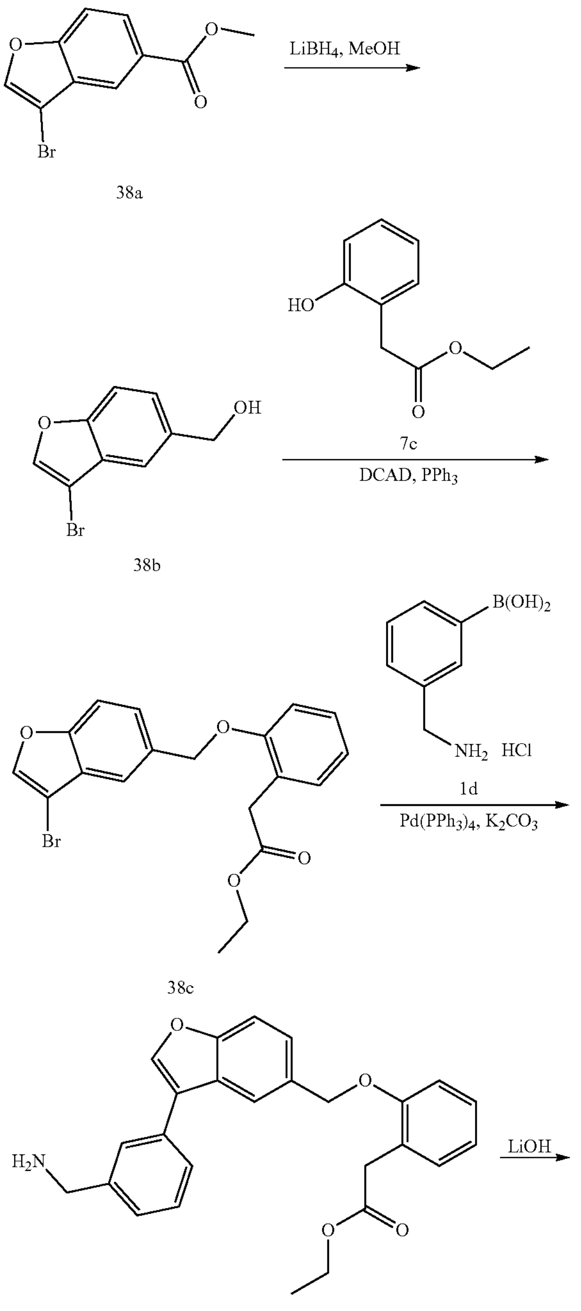

38a

7c

38b

1d

38c

38d

-continued

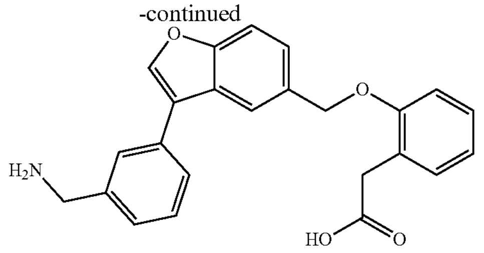

38e

Preparation of 2-(2-((3-(3-(aminomethyl)phenyl)benzofuran-5-yl)methoxy)phenyl)acetic acid (38e)

Step-1: Preparation of (3-bromobenzofuran-5-yl)methanol (38b)

Compound 38b was prepared according to the procedure reported in step-1 of scheme 7, from methyl 3-bromobenzofuran-5-carboxylate (38a) (500 mg, 1.960 mmol; CAS #501892-90-6) in THF (10 mL) using $LiBH_4$ (2.94 mL, 5.88 mmol; 2 M solution in THF) and MeOH (0.238 mL, 5.88 mmol) and stirring at room temperature for 24 h. This gave after workup and purification by flash column chromatography [silica gel (24 g), eluting with EtOAc in hexane from 0-60%] (3-bromobenzofuran-5-yl)methanol (38b) (310 mg, 70% yield) as a white solid; $^1$H NMR (300 MHz, DMSO-$d_6$) δ 8.28 (s, 1H), 7.61 (d, J=8.5 Hz, 1H), 7.50 (dd, J=1.7, 0.8 Hz, 1H), 7.37 (dd, J=8.6, 1.7 Hz, 1H), 5.31 (t, J=5.8 Hz, 1H), 4.62 (d, J=5.7 Hz, 2H); MS (ES+): 226.00 (M+1).

Step-2: Preparation of ethyl 2-(2-((3-bromobenzofuran-5-yl)methoxy)phenyl)acetate (38c)

Compound 38c was prepared according to the procedure reported in step-3 of scheme 7, from (3-bromobenzofuran-5-yl)methanol (38b) (310 mg, 1.365 mmol), triphenylphosphine (394 mg, 1.502 mmol), ethyl 2-(2-hydroxyphenyl)acetate (7c) (271 mg, 1.502 mmol) in DCM (30 mL) using a solution of bis(4-chlorobenzyl) diazene-1,2-dicarboxylate (DCAD, 551 mg, 1.502 mmol) in DCM (20 mL) and stirring at room temperature for 30 min. This gave after workup and purification by flash column chromatography [silica gel (12 g), eluting with EtOAc in hexane from 0-50%] ethyl 2-(2-((3-bromobenzofuran-5-yl)methoxy)phenyl)acetate (38c) (210 mg, 40% yield) as a colorless oil; $^1$H NMR (300 MHz, DMSO-$d_6$) δ 8.33 (s, 1H), 7.70 (d, J=8.5 Hz, 1H), 7.62 (d, J=1.7 Hz, 1H), 7.54-7.42 (m, 1H), 7.25 (m, J=14.9, 7.3, 1.7 Hz, 2H), 7.10 (dd, J=8.2, 1.1 Hz, 1H), 6.91 (td, J=7.4, 1.1 Hz, 1H), 5.23 (s, 2H), 4.01 (q, J=7.1 Hz, 2H), 3.62 (s, 2H), 1.06 (t, J=7.1 Hz, 3H).

Step-3: Preparation of ethyl 2-(2-((3-(3-(aminomethyl)phenyl)benzofuran-5-yl)methoxy)phenyl)acetate (38d)

Compound 38d was prepared according to the procedure reported in step-8 of Scheme 3, from ethyl 2-(2-((3-bromobenzofuran-5-yl)methoxy)phenyl)acetate (38c) (210 mg, 0540 mmol) in dioxane (10 mL) using 3-(aminomethyl)phenylboronic acid hydrochloride (1d) (152 mg, 0.809 mmol), $Pd(PPh_3)_4$ (94 mg, 0.081 mmol), a solution of $K_2CO_3$ (186 mg, 1.349 mmol) in water (3 mL) and heating at 100° C. for 3 h. This gave after workup and purification by flash column chromatography [silica gel (12 g), eluting with DMA80 in DCM from 0-50%] ethyl 2-(2-((3-(3-(aminomethyl)phenyl)benzofuran-5-yl)methoxy)phenyl)acetate (38d) (108 mg, 48% yield) as a clear oil; MS (ES+): 416.1 ((M+1).

Step-4: Preparation of 2-(2-((3-(3-(aminomethyl) phenyl)benzofuran-5-yl)methoxy)phenyl)acetic acid (38e)

Compound 38e was prepared according to the procedure reported in step-3 of scheme 1, ethyl 2-(2-((3-(3-(aminomethyl)phenyl)benzofuran-5-yl)methoxy)phenyl)acetate (38d) (108 mg, 0.260 mmol) in THF (3 mL) using a solution of lithium hydroxide hydrate (68 mg, 1.619 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((3-(3-(aminomethyl)phenyl)benzofuran-5-yl)methoxy)phenyl) acetic acid (38e) (78 mg, 77% yield) HCl salt as a white solid; $^1$H NMR (300 MHz, DMSO-$d_6$) δ 12.20 (s, 1H), 8.62 (s, 3H), 8.43 (s, 1H), 8.21 (s, J=1.7 Hz, 1H), 7.98 (s, J=1.7 Hz, 1H), 7.78 (dt, J=7.1, 1.8 Hz, 1H), 7.68 (d, J=8.5 Hz, 1H), 7.59-7.44 (m, 3H), 7.22 (m, J=7.5 Hz, 2H), 7.10 (d, J=8.1 Hz, 1H), 6.90 (td, J=7.4, 1.1 Hz, 1H), 5.28 (s, 2H), 4.13 (s, 2H), 3.59 (s, 2H); MS (ES+): 388.1 (M+1); (ES−): 386.1 (M−1); Analysis calculated for $C_{24}H_{21}NO_4 \cdot 1.1HCl$: C, 67.42; H, 5.21; Cl, 9.12; N, 3.28. Found: C, 67.61; H, 5.38; Cl, 8.97; N, 3.59.

Scheme 39

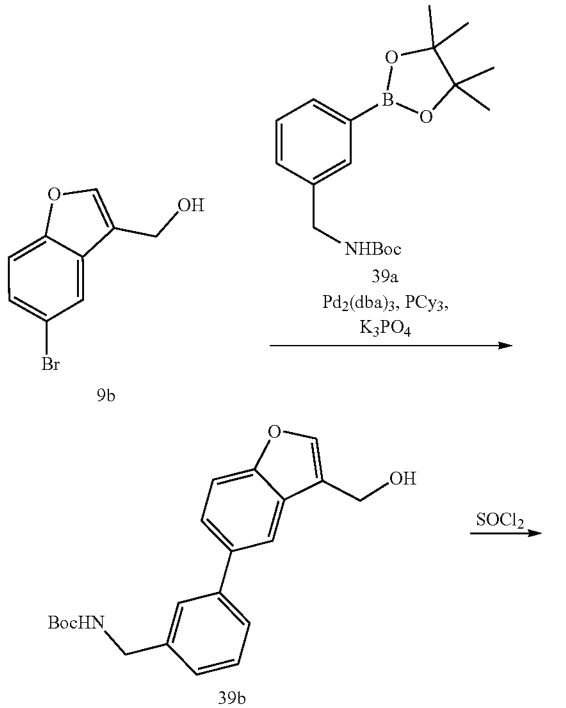

9b

39a

39b

-continued

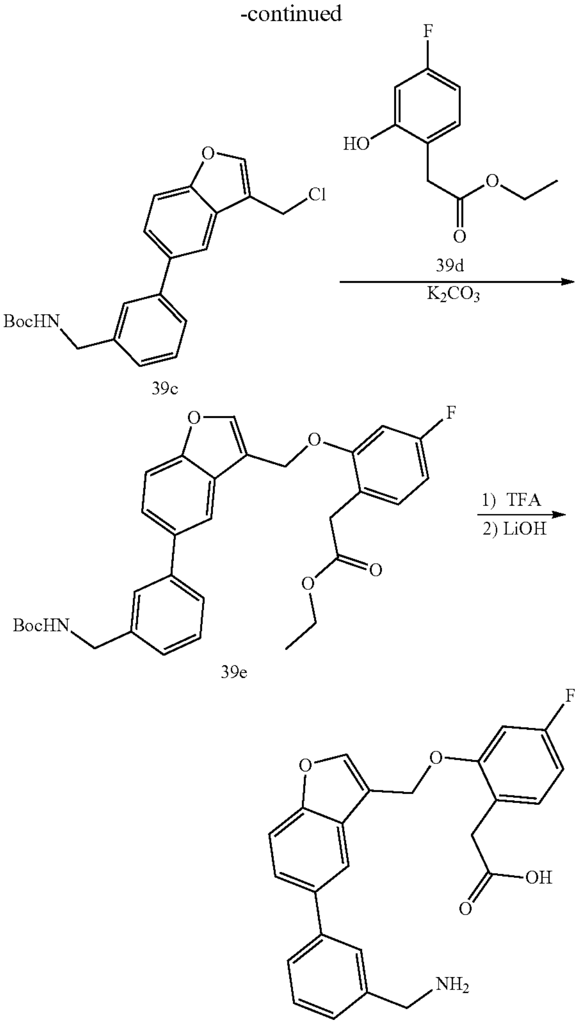

39d

39c

39e

39f

Preparation of 2-(2-((5-(3-(aminomethyl)phenyl) benzofuran-3-yl)methoxy)-4-fluorophenyl)acetic acid (39f)

Step-1: Preparation of tert-butyl 3-(3-(hydroxymethyl)benzofuran-5-yl)benzylcarbamate (39b)

Compound 39b was prepared according to the procedure reported in step-2 of scheme 1, from (5-bromobenzofuran-3-yl)methanol (9b) (6.4 g, 28.2 mmol) in dioxane (100 mL) using tert-butyl 3-(4,4,5,5-tetramethyl-1,3,2-dioxaborolan-2-yl)benzylcarbamate (39a) (12.68 g, 38.1 mmol), 2M solution of $K_3PO_4$ (23.96 mL, 47.9 mmol), tricyclohexylphosphine (2.371 mg, 8.46 mmol), $Pd_2(dba)_3$ (2.58 g, 2.82 mmol) and heating at 110° C. overnight in an oil bath under an argon atmosphere. This gave after workup and purification by column chromatography [silica gel (24 g), eluting with DMA80 in DCM from 0-70%] tert-butyl 3-(3-(hydroxymethyl)benzofuran-5-yl)benzylcarbamate (39b) (7.6 g, 76% yield) as a white solid; H NMR (300 MHz, DMSO-$d_6$) δ 7.95-7.90 (m, 2H), 7.65 (d, J=8.5 Hz, 1H), 7.61-7.52 (m, 3H), 7.52-7.38 (m, 2H), 7.23 (d, J=7.6 Hz, 1H), 5.22 (t, J=5.5 Hz, 1H), 4.68 (dd, J=5.5, 1.1 Hz, 2H), 4.22 (d, J=6.2 Hz, 2H), 1.41 (s, 9H); MS (ES+): 376.10 (M+Na).

Step-2: Preparation of tert-butyl 3-(3-(chloromethyl)benzofuran-5-yl)benzylcarbamate (39c)

To stirred a solution of tert-butyl 3-(3-(hydroxymethyl) benzofuran-5-yl)benzylcarbamate (39b) (1.13 g, 3.20 mmol) in DCM (20 mL) was added at 0° C. thionyl chloride (0.467 mL, 6.39 mmol). The reaction mixture was stirred for 2 h at 0° C., quenched with saturated aqueous $NaHCO_3$ (100 mL) and extracted with DCM (2×100 mL). The combined organics were washed with brine, dried, filtered and concentrated in vacuum to afford tert-butyl 3-(3-(chloromethyl)benzofuran-5-yl)benzylcarbamate (39c) (650 mg, 55% yield) as a thick oil; $^1H$ NMR (300 MHz, DMSO-$d_6$) δ 8.19 (s, 1H), 7.96 (d, J=1.8 Hz, 1H), 7.72 (d, J=8.6 Hz, 1H), 7.64 (dd, J=8.6, 1.9 Hz, 1H), 7.57 (d, J=5.7 Hz, 2H), 7.51-7.40 (m, 2H), 7.25 (d, J=7.5 Hz, 1H), 5.04 (s, 2H), 4.23 (d, J=6.2 Hz, 2H), 1.41 (s, 9H); MS (ES+): 394.10 (M+Na).

Step-3: Preparation of ethyl 2-(2-((5-(3-(((tert-butoxycarbonyl)amino)methyl)phenyl)benzofuran-3-yl)methoxy)-4-fluorophenyl)acetate (39e)

Compound 39e was prepared according to the procedure reported in step-1 of scheme 1, from tert-butyl 3-(3-(chloromethyl)benzofuran-5-yl)benzylcarbamate (39c) (140 mg, 0.376 mmol) in acetone (10 mL) using ethyl 2-(4-fluoro-2-hydroxyphenyl)acetate (39d) (97 mg, 0.489 mmol; CAS #1261751-44-3), $K_2CO_3$ (104 mg, 0.753 mmol) and refluxing for 12 h. This gave after workup and purification by flash column chromatography [silica gel (24 g), eluting with EtOAc/MeOH (9:1) in hexane from 0-80%] ethyl 2-(2-((5-(3-(((tert-butoxycarbonyl)amino)methyl)phenyl)benzofuran-3-yl)methoxy)-4-fluorophenyl)acetate (39e) (145 mg, 72% yield); MS (ES+): 556.2 (M+Na).

Step-4: Preparation of 2-(2-((5-(3-(aminomethyl) phenyl)benzofuran-3-yl)methoxy)-4-fluorophenyl) acetic acid (39f)

To a solution of ethyl 2-(2-((5-(3-(((tert-butoxycarbonyl) amino)methyl)phenyl)benzofuran-3-yl)methoxy)-4-fluorophenyl)acetate (39e) (145 mg, 0.272 mmol) in DCM (10 mL) was added TFA (1.5 mL) and stirred at RT for 2 h. The reaction mixture was concentrated under vacuum added THF (3 mL) and a solution of lithium hydroxide hydrate (63 mg, 1.51 mmol) in water (1 mL) and the resulting mixture was stirred at room temperature overnight. The reaction mixture was concentrated to remove the major organic solvent and the aqueous was acidified to pH 5, purified by reverse phase column chromatography [C18 column (30 g), eluting with ACN in water (containing 0.1% HCl) from 0-100%] to give 2-(2-((5-(3-(aminomethyl)phenyl)benzofuran-3-yl)methoxy)-4-fluorophenyl)acetic acid (39f) (21 mg, 19% yield) HCl salt as a white solid; $^1H$ NMR (300 MHz, DMSO-$d_6$) δ 12.10 (s, 1H, $D_2O$ exchangeable), 8.39 (s, 3H, $D_2O$ exchangeable), 8.15 (s, 1H), 8.01 (d, J=1.7 Hz, 1H), 7.89 (s, J=2.0 Hz, 1H), 7.79-7.65 (m, 3H), 7.52 (t, J=7.6 Hz, 1H), 7.45 (d, J=7.6 Hz, 1H), 7.23 (m, J=8.4, 6.9 Hz, 1H), 7.15 (dd, J=11.4, 2.5 Hz, 1H), 6.76 (td, J=8.5, 2.5 Hz, 1H), 5.34 (s, 2H), 4.11 (s, 2H), 3.51 (s, 2H); $^{19}F$ NMR (282 MHz, DMSO-$d_6$) δ −113.04; MS (ES+): 406.2 (M+1); Analysis calculated for $C_{24}H_{20}FNO_4 \cdot HCl \cdot 1.25H_2O$: C, 62.07; H, 5.10; Cl, 7.63; N, 3.02. Found: C, 62.21; H, 5.00; Cl, 7.97; N, 3.18.

Scheme 40

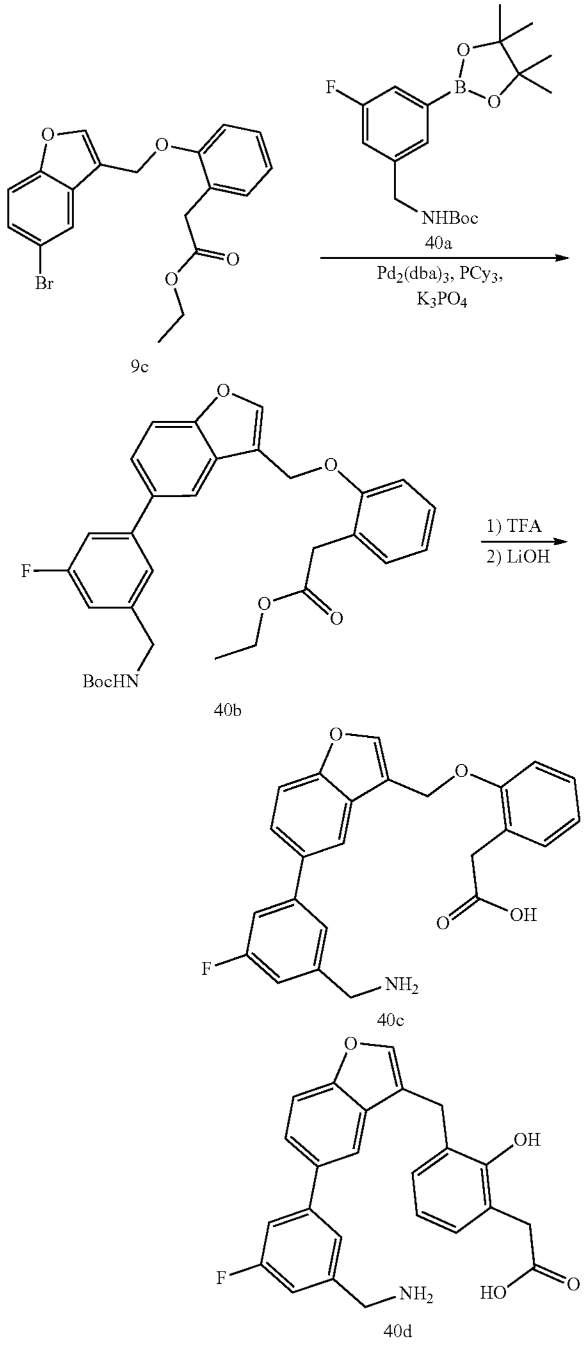

9c, 40a, 40b, 40c, 40d

Preparation of 2-(2-((5-(3-(aminomethyl)-5-fluorophenyl)benzofuran-3-yl)methoxy)phenyl)acetic acid (40c) and 2-(3-((5-(3-(aminomethyl)-5-fluorophenyl)benzofuran-3-yl)methyl)-2-hydroxyphenyl)acetic acid (40d)

Step-1: Preparation of ethyl 2-(2-((5-(3-(((tert-butoxycarbonyl)amino)methyl)-5-fluorophenyl)benzofuran-3-yl)methoxy)phenyl)acetate (40b)

Compound 40b was prepared according to the procedure reported in step-2 of scheme 1, from ethyl 2-(2-((5-bromobenzofuran-3-yl)methoxy)phenyl)acetate (9c) (600 mg, 1.54 mmol) in dioxane (10 mL) using tert-butyl 3-fluoro-5-(4,4,5,5-tetramethyl-1,3,2-dioxaborolan-2-yl)benzylcarbamate (40a) (812 mg, 2.31 mmol), 2M solution of $K_3PO_4$ (1.54 mL, 3.08 mmol), tricyclohexylphosphine (130 mg, 0.46 mmol), $Pd_2(dba)_3$ (212 mg, 0.23 mmol) and heating at 125° C. 40 min in a microwave. This gave after workup and purification by flash column chromatography [silica gel (24 g), eluting with DMA80 in DCM from 0-70%] ethyl 2-(2-((5-(3-(((tert-butoxycarbonyl)amino)methyl)-5-fluorophenyl)benzofuran-3-yl)methoxy)phenyl)acetate (40b) (386 mg, 47% yield) as a colorless oil; MS (ES+): 556.2 (M+Na).

Step-2: Preparation of 2-(2-((5-(3-(aminomethyl)-5-fluorophenyl)benzofuran-3-yl)methoxy)phenyl)acetic acid (40c) and 2-(3-((5-(3-(aminomethyl)-5-fluorophenyl)benzofuran-3-yl)methyl)-2-hydroxyphenyl)acetic acid (40d)

Compound 40c was prepared according to the procedure reported in step-4 of scheme 39, from ethyl 2-(2-((5-(3-(((tert-butoxycarbonyl)amino)methyl)-5-fluorophenyl)benzofuran-3-yl)methoxy)phenyl)acetate (40b) in DCM (10 mL) using TFA (1.19 mL, 15.41 mmol) and stirring at RT for 3 h. The hydrolysis of ester was achieved by using a solution of lithium hydroxide hydrate (135 mg, 3.22 mmol) in water (1 mL) and THF (3 mL) and stirring at room temperature overnight. This gave after workup and purification by reverse phase column chromatography [C18 column (30 g), eluting with ACN in water (containing 0.1% HCl) from 0-100%] 2-(3-((5-(3-(aminomethyl)-5-fluorophenyl)benzofuran-3-yl)methyl)-2-hydroxyphenyl)acetic acid (40d) (37 mg, 6% yield) HCl salt as a white solid; $^1H$ NMR (300 MHz, DMSO-$d_6$) δ 12.21 (s, 1H, $D_2O$ exchangeable), 8.91 (s, 1H, $D_2O$ exchangeable), 8.50 (s, 3H, $D_2O$ exchangeable), 7.93 (s, 1H), 7.77 (s, 1H), 7.68 (d, J=12.5 Hz, 3H), 7.54 (dt, J=10.4, 2.1 Hz, 1H), 7.34 (dt, J=9.6, 1.9 Hz, 1H), 7.00 (ddd, J=14.3, 7.6, 1.7 Hz, 2H), 6.70 (t, J=7.5 Hz, 1H), 4.12 (s, 2H), 4.05 (s, 2H), 3.58 (s, 2H); $^{19}F$ NMR (282 MHz, DMSO-$d_6$) δ-112.67; MS (ES+): 406.1 (M+1); Calculated for $C_{24}H_{23}C_1FNO_5 \cdot HCl \cdot H_2O$: C, 62.68; H, 5.04; Cl, 7.71; N, 3.05. Found: C, 62.71; H, 4.80; Cl, 7.47; N, 3.11. Followed by 2-(2-((5-(3-(aminomethyl)-5-fluorophenyl)benzofuran-3-yl)methoxy)phenyl)acetic acid (40c) (12 mg, 2% yield) HCl salt as a white solid; $^1H$ NMR (300 MHz, DMSO-$d_6$) δ 12.06 (s, 1H, $D_2O$ exchangeable), 8.47 (s, 3H, $D_2O$ exchangeable), 8.14 (s, 1H), 8.07 (s, 1H), 7.78-7.71 (m, 3H), 7.63 (dt, J=10.4, 2.0 Hz, 1H), 7.36 (dt, J=9.5, 1.9 Hz, 1H), 7.31-7.25 (m, 1H), 7.24-7.17 (m, 2H), 6.92 (td, 1H), 5.32 (s, 2H), 4.13 (s, 2H), 3.54 (s, 2H); $^{19}F$ NMR (282 MHz, DMSO-$d_6$) δ −112.69; MS (ES+): 406.1 (M+1).

Scheme 41

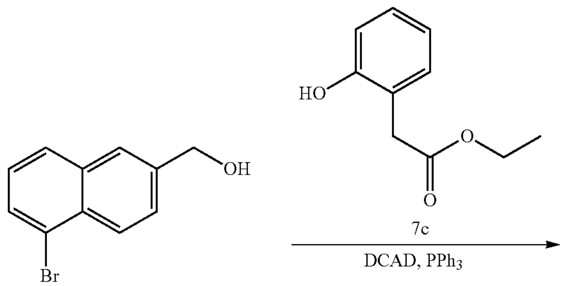

7c

41a

-continued

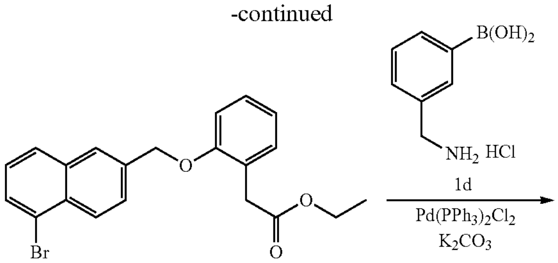

1d

41b

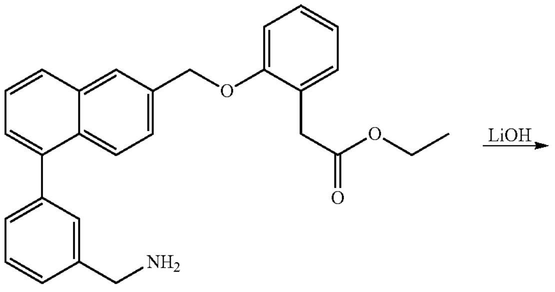

41c

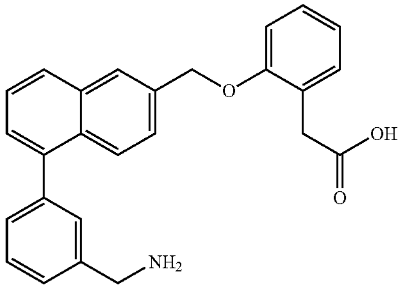

41d

Preparation of 2-(2-((5-(3-(aminomethyl)phenyl)naphthalen-2-yl)methoxy)phenyl)acetic acid (41d)

Step-1: Preparation of ethyl 2-(2-((5-bromonaphthalen-2-yl)methoxy)phenyl)acetate (41b)

Compound 41b was prepared according to the procedure reported in step-3 of scheme 7, from (5-bromonaphthalen-2-yl)methanol (41a) (1 g, 4.22 mmol; CAS #128104-53-0), triphenylphosphine (1.217 g, 4.64 mmol), ethyl 2-(2-hydroxyphenyl)acetate (7c) (0.836 g, 4.64 mmol) in DCM (30 mL) using bis(4-chlorobenzyl) diazene-1,2-dicarboxylate (DCAD) (1.704 g, 4.64 mmol) in DCM (20 mL) and stirring at room temperature for 30 min. This gave after workup and purification by flash column chromatography [silica gel (40 g), eluting with EtOAc in hexane from 0-50%] ethyl 2-(2-((5-bromonaphthalen-2-yl)methoxy)phenyl)acetate (41b) (1.2 g, 71% yield) as a white solid; $^1H$ NMR (300 MHz, DMSO-$d_6$) δ 8.15 (dt, J=8.8, 0.8 Hz, 1H), 8.04 (d, J=1.6 Hz, 1H), 7.96 (dt, J=8.5, 1.0 Hz, 1H), 7.89 (dd, J=7.4, 1.1 Hz, 1H), 7.72 (dd, J=8.8, 1.7 Hz, 1H), 7.47 (dd, J=8.2, 7.4 Hz, 1H), 7.29-7.21 (m, 2H), 7.11 (d, 1H), 6.92 (td, J=7.4, 1.1 Hz, 1H), 5.32 (s, 2H), 4.01 (q, J=7.1 Hz, 2H), 3.67 (s, 2H), 1.06 (t, J=7.1 Hz, 3H); MS (ES−): 397.00 (M−1).

Step-2: Preparation of ethyl 2-(2-((5-(3-(aminomethyl)phenyl)naphthalen-2-yl)methoxy)phenyl)acetate (41c)

Compound 41c was prepared according to the procedure reported in step-8 of Scheme 3, from ethyl 2-(2-((5-bromonaphthalen-2-yl)methoxy)phenyl)acetate (41b) (320 mg, 0.801 mmol) in dioxane (10 mL) using 3-(aminomethyl) phenylboronic acid hydrochloride (1d) (270 mg, 1.443 mmol), $Pd(PPh_3)_2C_{12}$ (84 mg, 0.120 mmol), a solution of $K_2CO_3$ (332 mg, 2.404 mmol) in water (3 mL) and heating at 100° C. for 3 h. This gave after workup and purification by flash column chromatography [silica gel (12 g), eluting with DMA-80 in DCM from 0-50%] ethyl 2-(2-((5-(3-(aminomethyl)phenyl)naphthalen-2-yl)methoxy)phenyl)acetate (41c) (200 mg, 59% yield) as a yellow oil; $^1H$ NMR (300 MHz, DMSO-$d_6$) δ 8.04 (d, J=1.7 Hz, 1H), 7.92 (dt, J=8.3, 1.1 Hz, 1H), 7.84 (d, J=8.8 Hz, 1H), 7.64-7.56 (m, 1H), 7.55-7.49 (m, 1H), 7.47-7.40 (m, 4H), 7.33-7.27 (m, 1H), 7.26-7.21 (m, 2H), 7.15-7.07 (m, 1H), 6.92 (td, J=7.4, 1.1 Hz, 1H), 5.28 (s, 2H), 4.01 (q, J=7.1 Hz, 2H), 3.81 (s, 2H), 3.66 (s, 2H), 1.99 (s, 2H), 1.06 (t, J=7.1 Hz, 3H).

Step-3: Preparation of 2-(2-((5-(3-(aminomethyl) phenyl)naphthalen-2-yl)methoxy)phenyl)acetic acid (41d)

Compound 41d was prepared according to the procedure reported in step-3 of scheme 1, from ethyl 2-(2-((5-(3-(aminomethyl)phenyl)naphthalen-2-yl)methoxy)phenyl)acetate (41c) (200 mg, 0.470 mmol) in THF (3 mL) using a solution of lithium hydroxide hydrate (101 mg, 2.404 mmol) in water (1 mL) and stirring at room temperature for 6 h. This gave after workup and purification by reverse phase column chromatography [C18 column (30 g), eluting with ACN in water from 0-100%] 2-(2-((5-(3-(aminomethyl) phenyl)naphthalen-2-yl)methoxy)phenyl)acetic acid (41d) (57 mg, 18% yield) HCl salt as a white solid; $^1H$ NMR (300 MHz, DMSO-$d_6$) δ 12.18 (s, 1H, $D_2O$ exchangeable), 8.58 (s, 2H, $D_2O$ exchangeable), 8.09 (d, J=1.8 Hz, 1H), 7.97 (d, J=8.2 Hz, 1H), 7.86 (d, J=8.8 Hz, 1H), 7.67-7.53 (m, 5H), 7.53-7.41 (m, 2H), 7.28-7.18 (m, 2H), 7.12-7.03 (m, 1H), 6.90 (td, J=7.4, 1.1 Hz, 1H), 5.31 (s, 2H), 4.13 (s, 2H), 3.61 (s, 2H); MS (ES+): 398.1 (M+1); (ES−): 396.2 (M−1); Analysis calculated for $C_{26}H_{23}NO_3 \cdot HCl \cdot H_2O$: C, 69.10; H, 5.80; N, 3.10. Found: C, 69.13; H, 5.71; N, 3.09.

Scheme 42

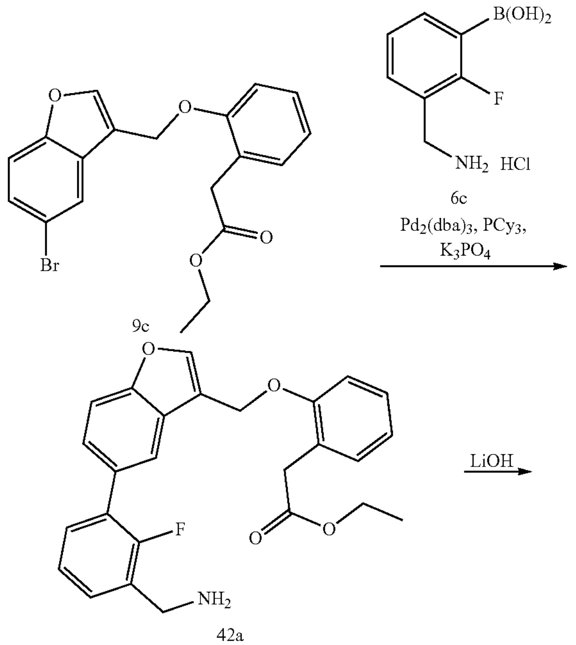

9c

6c

42a

-continued

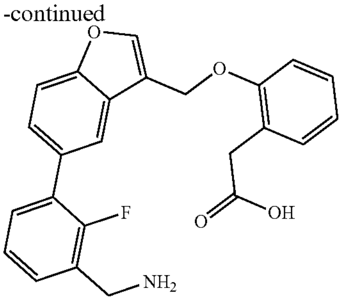

42b

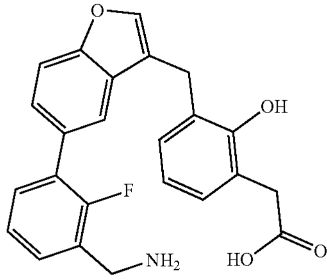

42c

Preparation of 2-(2-((5-(3-(aminomethyl)-2-fluorophenyl)benzofuran-3-yl)methoxy)phenyl)acetic acid (42b) and 2-(3-((5-(3-(aminomethyl)-2-fluorophenyl)benzofuran-3-yl)methyl)-2-hydroxyphenyl)acetic acid (42c)

Step-1: Preparation of ethyl 2-(2-((5-(3-(aminomethyl)-2-fluorophenyl)benzofuran-3-yl)methoxy) phenyl)acetate (42a)

Compound 42a was prepared according to the procedure reported in step-8 of Scheme 3, from ethyl 2-(2-((5-bromobenzofuran-3-yl)methoxy)phenyl)acetate (9c) (300 mg, 0.771 mmol) in dioxane (3 mL) using 3-(aminomethyl)-2-fluorophenylboronic acid hydrochloride (6c) (237 mg, 1.156 mmol), $Pd_2(dba)_3$ (70.6 mg, 0.077 mmol), tricyclohexylphosphine (65 mg, 0.231 mmol), 2 M solution of $K_3PO_4$ (0.655 mL, 1.310 mmol) and heating at 125° C. for 40 min in a microwave. This gave after workup and purification by flash column chromatography [silica gel (24 g), eluting with DMA-80 in DCM from 0-70%] ethyl 2-(2-((5-(3-(aminomethyl)-2-fluorophenyl)benzofuran-3-yl)methoxy)phenyl)acetate (42a) (98 mg, 29% yield) as a colorless oil; MS (ES+): 434.1 (M+1).

Step-2: Preparation of 2-(2-((5-(3-(aminomethyl)-2-fluorophenyl)benzofuran-3-yl)methoxy)phenyl)acetic acid (42b) and 2-(3-((5-(3-(aminomethyl)-2-fluorophenyl)benzofuran-3-yl)methyl)-2-hydroxyphenyl)acetic acid (42c)

Compound 42b was prepared according to the procedure reported in step-3 of scheme 1, from ethyl 2-(2-((5-(3-(aminomethyl)-2-fluorophenyl)benzofuran-3-yl)methoxy) phenyl)acetate (42a) (98 mg, 0.226 mmol) in THF (3 mL) using a solution of lithium hydroxide hydrate (97 mg, 2.312 mmol) in water (1 mL) and stirring at room temperature overnight. This gave after workup and purification by reverse phase column chromatography [C18 column (30 g), eluting with ACN in water (containing 0.1% HCl) from 0-100%] 2-(3-((5-(3-(aminomethyl)-2-fluorophenyl)benzofuran-3-yl)methyl)-2-hydroxyphenyl)acetic acid (42c) (7.5 mg, 2% yield) HCl salt as a white solid; $^{1}H$ NMR (300 MHz, DMSO-$d_6$) δ 12.17 (s, 1H, $D_2O$ exchangeable), 8.40 (s, 3H, $D_2O$ exchangeable), 7.82 (s, 1H), 7.73-7.65 (m, 2H), 7.55 (t, J=7.4 Hz, 2H), 7.46 (dt, J=8.6, 1.8 Hz, 1H), 7.42-7.31 (m, 1H), 6.97 (d, J=7.5 Hz, 2H), 6.69 (t, J=7.5 Hz, 1H), 4.13 (s, 2H), 4.02 (s, 2H), 3.55 (s, 2H); $^{19}F$ NMR (282 MHz, DMSO-$d_6$) δ −122.24; MS (ES+): 406.1 (M+1). Followed by 2-(2-((5-(3-(aminomethyl)-2-fluorophenyl)benzofuran-3-yl)methoxy)phenyl)acetic acid (42b) (21 mg, 7% yield) HCl salt as a white solid; $^{1}H$ NMR (300 MHz, DMSO-$d_6$) δ 8.57 (s, 2H, $D_2O$ exchangeable), 8.15 (s, 1H), 7.88 (s, 1H), 7.75 (d, J=8.6 Hz, 1H), 7.67-7.49 (m, 3H), 7.37 (t, J=7.7 Hz, 1H), 7.31-7.16 (m, 3H), 6.92 (td, J=7.3, 1.3 Hz, 1H), 5.31 (s, 2H), 4.14 (s, 2H), 3.53 (s, 2H); $^{19}F$ NMR (282 MHz, DMSO-$d_6$) δ −122.32; MS (ES+): 406.1 (M+1); Analysis calculated for $C_{24}H_{20}FNO_4·HCl·1.25H_2O$: C, 62.07; H, 5.10; Cl, 7.63; N, 3.02. Found: C, 62.21; H, 4.85; Cl, 7.81; N, 3.11.

Scheme 43

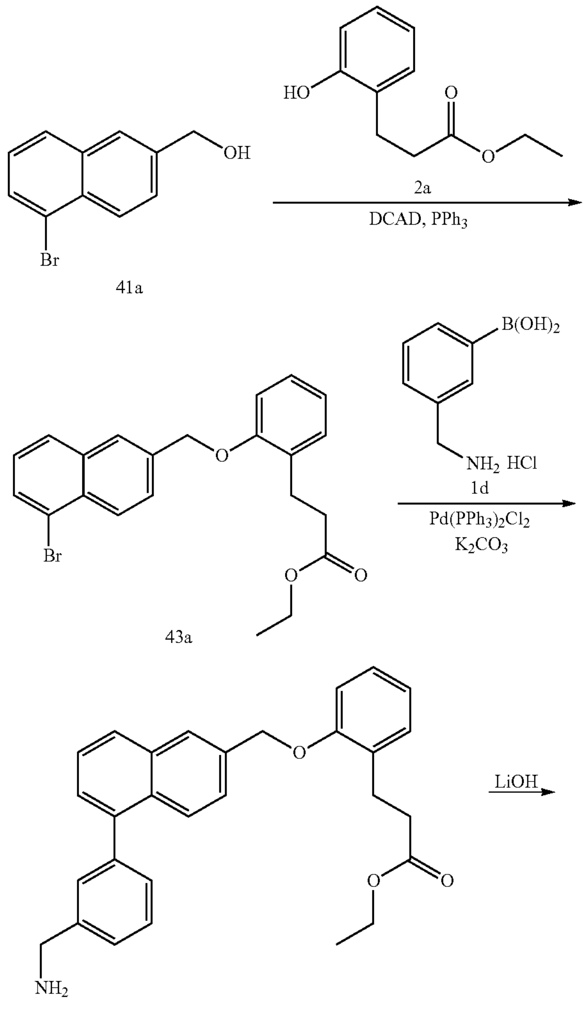

41a

2a

43a

1d

43b

-continued

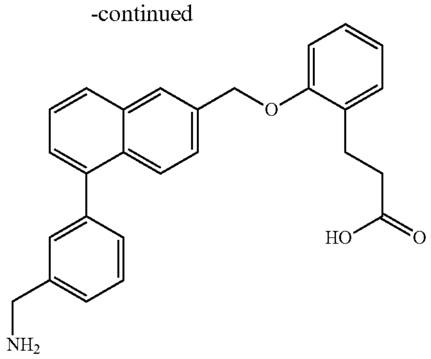

43c

Preparation of 3-(2-((5-(3-(aminomethyl)phenyl)naphthalen-2-yl)methoxy)phenyl)propanoic acid (43c)

Step-1: Preparation of ethyl 3-(2-((5-bromonaphthalen-2-yl)methoxy)phenyl)propanoate (43a)

Compound 43a was prepared according to the procedure reported in step-3 of scheme 7, from (5-bromonaphthalen-2-yl)methanol (41a) (928 mg, 3.91 mmol), triphenylphosphine (1.129 g, 4.30 mmol), ethyl 3-(2-hydroxyphenyl) propanoate (2a) (0.760 g, 3.91 mmol) in DCM (30 mL) using bis(4-chlorobenzyl) diazene-1,2-dicarboxylate (DCAD) (1.580 g, 4.30 mmol) in DCM (20 mL) and stirring at room temperature for 30 min. This gave after workup and purification by flash column chromatography [silica gel (40 g), eluting with EtOAc in hexane from 0-50%] ethyl 3-(2-((5-bromonaphthalen-2-yl)methoxy)phenyl)propanoate (43a) (0.820 g, 51% yield) as a clear oil; $^{1}H$ NMR (300 MHz, DMSO-$d_6$) δ 8.16 (d, 1H), 8.08 (d, J=1.6 Hz, 1H), 7.99 (dt, J=8.5, 1.0 Hz, 1H), 7.89 (dd, J=7.5, 1.1 Hz, 1H), 7.77 (dd, J=8.8, 1.7 Hz, 1H), 7.52-7.42 (m, 1H), 7.22-7.13 (m, 2H), 7.08 (dd, J=8.7, 1.2 Hz, 1H), 6.88 (td, J=7.3, 1.2 Hz, 1H), 5.35 (s, 2H), 4.02 (q, J=7.1 Hz, 2H), 2.92 (t, J=7.6 Hz, 2H), 2.61 (t, J=8.3, 7.0 Hz, 2H), 1.12 (t, J=7.1 Hz, 3H).

Step-2: Preparation of ethyl 3-(2-((5-(3-(aminomethyl)phenyl)naphthalen-2-yl)methoxy)phenyl)propanoate (43b)

Compound 43b was prepared according to the procedure reported in step-8 of Scheme 3, from ethyl 3-(2-((5-bromonaphthalen-2-yl)methoxy)phenyl)propanoate (43a) (345 mg, 0.835 mmol) in dioxane (6 mL) using 3-(aminomethyl) phenylboronic acid hydrochloride (1d) (282 mg, 1.503 mmol), $Pd(PPh_3)_2C_{12}$ (88 mg, 0.125 mmol), a solution of $K_2CO_3$ (346 mg, 2.504 mmol) in water (3 mL) and heating at 100° C. for 3 h. This gave after workup and purification by flash column chromatography [silica gel (12 g), eluting with DMA-80 in DCM from 0-50%] ethyl 3-(2-((5-(3-(aminomethyl)phenyl)naphthalen-2-yl)methoxy)phenyl) propanoate (43b) (146 mg, 40% yield) as a yellow oil; MS (ES+): 440.2 (M+1), (ES−): 438.2 (M−1).

Step-3: Preparation of 3-(2-((5-(3-(aminomethyl)phenyl)naphthalen-2-yl)methoxy)phenyl)propanoic acid (43c)

Compound 43c was prepared according to the procedure reported in step-3 of scheme 1, from ethyl 3-(2-((5-(3-

(aminomethyl)phenyl)naphthalen-2-yl)methoxy)phenyl) propanoate (43b) (146 mg, 0.332 mmol) in THF (3 mL) using a solution of lithium hydroxide hydrate (70.1 mg, 1.669 mmol) in water (1 mL) and stirring overnight at room temperature. This gave after workup and purification by reverse phase column chromatography [C18 column (30 g), eluting with ACN in water (containing 0.1% HCl) from 0-100%] 3-(2-((5-(3-(aminomethyl)phenyl)naphthalen-2-yl)methoxy)phenyl)propanoic acid (43c) (35 mg, 26% yield) HCl salt as a white solid; $^1$H NMR (300 MHz, DMSO-$d_6$) δ 9.00 (s, 2H, $D_2O$ exchangeable), 8.11 (s, 1H), 7.99 (d, J=8.2 Hz, 1H), 7.88 (d, J=8.8 Hz, 1H), 7.67-7.55 (m, 5H), 7.54-7.48 (m, 1H), 7.46 (d, J=7.0 Hz, 1H), 7.23-7.14 (m, 2H), 7.09 (d, J=8.4 Hz, 1H), 6.88 (t, J=7.3 Hz, 1H), 5.33 (s, 2H), 4.13 (s, 2H), 2.88 (t, J=7.7 Hz, 2H), 2.61-2.52 (m, 2H); MS (ES+): 412.2 (M+1); (ES−): 410.2 (M−1).

Scheme 44

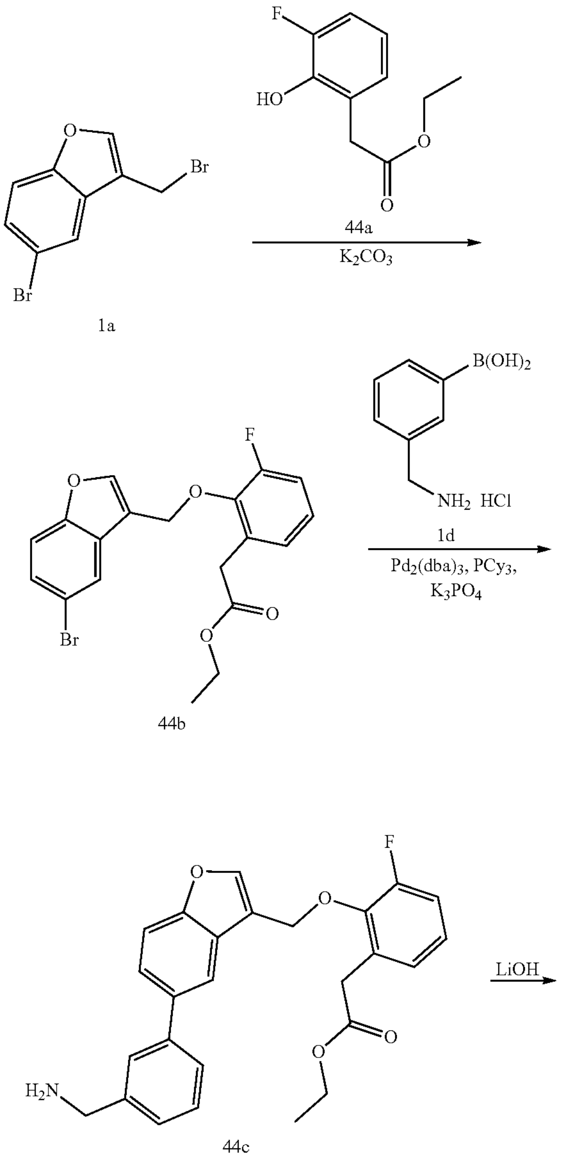

1a, 44a, 44b, 1d, 44c

-continued

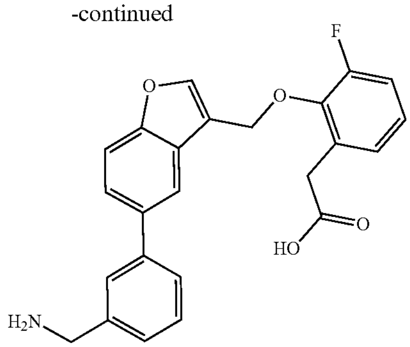

44d

Preparation of 2-(2-((5-(3-(aminomethyl)phenyl) benzofuran-3-yl)methoxy)-3-fluorophenyl)acetic acid (44d)

Step-1: Preparation of ethyl 2-(2-((5-bromobenzofuran-3-yl)methoxy)-3-fluorophenyl)acetate (44b)

Compound 44b was prepared according to the procedure reported in step-1 of scheme 1, from 5-bromo-3-(bromomethyl)benzofuran (1a) (358 mg, 1.235 mmol) in acetone (5 mL) using ethyl 2-(3-fluoro-2-hydroxyphenyl)acetate (44a) (281 mg, 1.420 mmol; CAS #1261451-84-6) and $K_2CO_3$ (597 mg, 4.32 mmol) and stirring overnight at room temperature. This gave after workup and purification by flash column chromatography [silica gel (12 g), eluting with EtOAc in hexane from 0-50%] ethyl 2-(2-((5-bromobenzofuran-3-yl)methoxy)-3-fluorophenyl)acetate (44b)(433 mg, 86% yield) as a yellow oil; MS (ES−): 405.7 (M−1).

Step-2: Preparation of ethyl 2-(2-((5-(3-(aminomethyl)phenyl)benzofuran-3-yl)methoxy)-3-fluorophenyl)acetate (44c)

Compound 44c was prepared according to the procedure reported in step-2 of scheme 1, from ethyl 2-(2-((5-bromobenzofuran-3-yl)methoxy)-3-fluorophenyl)acetate (44b) (200 mg, 0.491 mmol) in dioxane (3 mL) using 3-(aminomethyl)phenylboronic acid hydrochloride (1d) (138 mg, 0.737 mmol), 2M solution of $K_3PO_4$ (0.417 mL, 0.835 mmol), tricyclohexylphosphine (55.1 mg, 0.196 mmol), $Pd_2(dba)_3$ (90 mg, 0.098 mmol) and heating at 135° C. for 30 min in microwave. This gave after workup and purification by flash column chromatography [silica gel (24 g), eluting with DMA-80 in DCM from 0-70%] ethyl 2-(2-((5-(3-(aminomethyl)phenyl)benzofuran-3-yl)methoxy)-3-fluorophenyl)acetate (44c) (56 mg, 26% yield) as a clear oil; MS (ES+): 434.1 (M+1).

Step-3: Preparation of 2-(2-((5-(3-(aminomethyl) phenyl)benzofuran-3-yl)methoxy)-3-fluorophenyl) acetic acid (44d)

Compound 44d was prepared according to the procedure reported in step-3 of scheme 1, from ethyl 2-(2-((5-(3-(aminomethyl)phenyl)benzofuran-3-yl)methoxy)-3-fluorophenyl)acetate (44c) (56 mg, 0.129 mmol) in THF (3 mL) using a solution of lithium hydroxide hydrate (62 mg, 1.473 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)benzofuran-3-yl)methoxy)-3-fluorophenyl)acetic acid (44d) (3.5 mg, 2% yield) HCl salt as a white solid; $^1$H NMR (300 MHz, DMSO-$d_6$) δ 12.33 (s, 1H, $D_2O$ exchangeable), 8.32 (s, 3H, $D_2O$ exchangeable), 8.13 (s, 1H), 7.99 (d, J=1.8 Hz, 1H), 7.85 (t, J=1.8 Hz, 1H), 7.78-7.65 (m, 3H), 7.54 (t, J=7.6 Hz, 1H), 7.46 (d, J=7.5 Hz, 1H), 7.28-7.17 (m, 1H), 7.12-7.04 (m, 2H), 5.27 (s, 2H), 4.12 (s, 2H), 3.57 (s, 2H); $^{19}$F NMR (282 MHz, DMSO-$d_6$) δ −129.52; MS (ES+): 406.1 (M+1).

Scheme 45

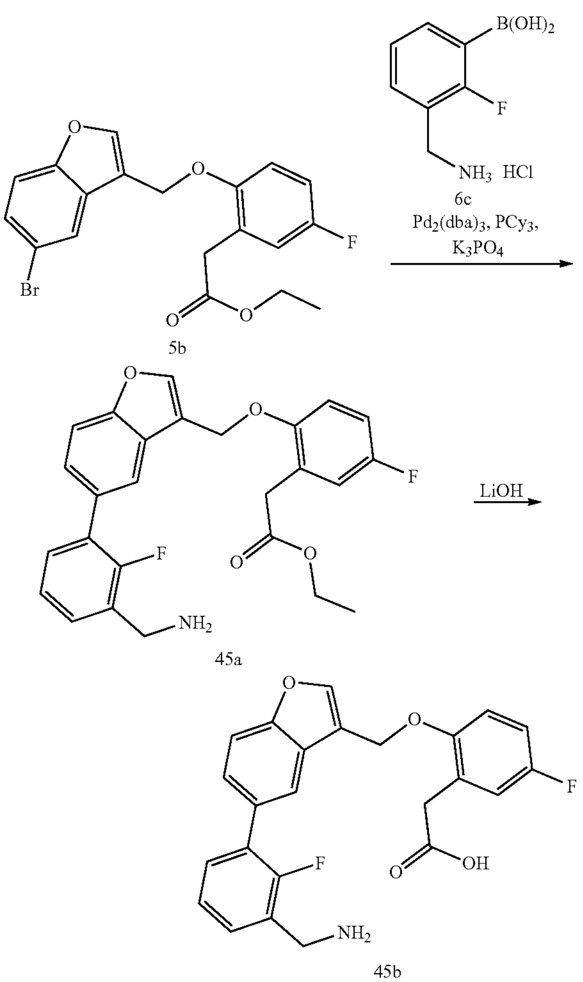

5b

45a

45b

Preparation of 2-(2-((5-(3-(aminomethyl)-2-fluorophenyl)benzofuran-3-yl)methoxy)-5-fluorophenyl) acetic acid (45b)

Step-1: Preparation of ethyl 2-(2-((5-(3-(aminomethyl)-2-fluorophenyl)benzofuran-3-yl)methoxy)-5-fluorophenyl)acetate (45a)

Compound 45a was prepared according to the procedure reported in step-2 of scheme 1, from ethyl 2-(2-((5-bromobenzofuran-3-yl)methoxy)-5-fluorophenyl)acetate (5b) (310 mg, 0.761 mmol) in dioxane (3 mL) using 3-(aminomethyl)-2-fluorophenylboronic acid hydrochloride (6c) (235 mg, 1.142 mmol), 2M solution of $K_3PO_4$ (0.647 mL, 1.294 mmol), tricyclohexylphosphine (85 mg, 0.304 mmol), $Pd_2(dba)_3$ (139 mg, 0.152 mmol) and heating at 135° C. for 30 min in microwave. This gave after workup and purification by column chromatography [silica gel (24 g), eluting with DMA-80 in DCM from 0-70%] ethyl 2-(2-((5-(3-(aminomethyl)-2-fluorophenyl)benzofuran-3-yl)methoxy)-5-fluorophenyl)acetate (45a) (241 mg, 70% yield) as a clear oil; MS (ES+): 452.1 (M+1).

Step-2: Preparation of 2-(2-((5-(3-(aminomethyl)-2-fluorophenyl)benzofuran-3-yl)methoxy)-5-fluorophenyl)acetic acid (45b)

Compound 45b was prepared according to the procedure reported in step-3 of scheme 1, from ethyl 2-(2-((5-(3-(aminomethyl)-2-fluorophenyl)benzofuran-3-yl)methoxy)-5-fluorophenyl)acetate (45a) (241 mg, 0.534 mmol) in THF (3 mL) using a solution of lithium hydroxide hydrate (135 mg, 3.22 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)-2-fluorophenyl)benzofuran-3-yl)methoxy)-5-fluorophenyl)acetic acid (45b) (104 mg, 32% yield) HCl salt as a white solid; $^1$H NMR (300 MHz, DMSO-$d_6$) δ 12.27 (s, 1H, $D_2O$ exchangeable), 8.54 (s, 3H, $D_2O$ exchangeable), 8.14 (s, 1H), 7.87 (d, J=1.5 Hz, 1H), 7.74 (d, J=8.6 Hz, 1H), 7.66-7.49 (m, 3H), 7.37 (t, J=7.7 Hz, 1H), 7.26-7.16 (m, 1H), 7.15-7.05 (m, 2H), 5.29 (s, 2H), 4.14 (s, 2H), 3.55 (s, 2H); $^{19}$F NMR (282 MHz, DMSO-$d_6$) δ −122.36, −123.62; MS (ES+): 424.1 (M+1); Analysis calculated for $C_{24}H_{19}F_2NO_4 \cdot HCl \cdot H_2O$: C, 60.32; H, 4.64; Cl, 7.42; N, 2.93. Found: C, 60.36; H, 4.56; Cl, 7.17; N, 2.94.

Scheme 46

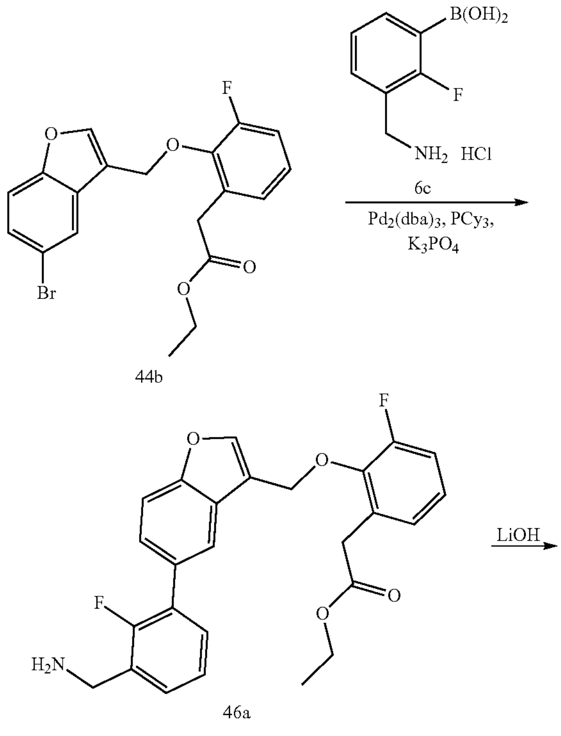

44b

46a

-continued

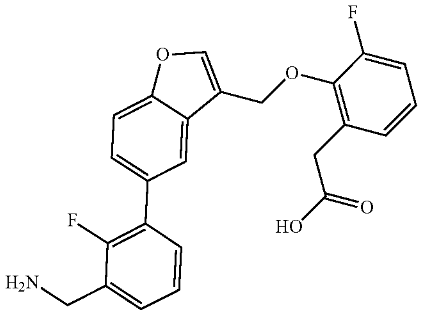

46b

Step-2: Preparation of 2-(2-((5-(3-(aminomethyl)-2-fluorophenyl)benzofuran-3-yl)methoxy)-3-fluorophenyl)acetic acid (46b)

Compound 46b was prepared according to the procedure reported in step-3 of scheme 1, from ethyl 2-(2-((5-(3-(aminomethyl)-2-fluorophenyl)benzofuran-3-yl)methoxy)-3-fluorophenyl)acetate (46a) (86 mg, 0.190 mmol) in THF (3 mL) using a solution of lithium hydroxide hydrate (61.8 mg, 3.22 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)-2-fluorophenyl)benzofuran-3-yl)methoxy)-3-fluorophenyl)acetic acid (46b) (13 mg, 6% yield) HCl salt as a white solid; $^1H$ NMR (300 MHz, DMSO-$d_6$) δ 8.50 (s, 2H, $D_2O$ exchangeable), 8.15 (s, 1H), 7.88 (s, 1H), 7.75 (d, J=8.6 Hz, 1H), 7.65-7.49 (m, 3H), 7.38 (t, J=7.7 Hz, 1H), 7.26-7.17 (m, 1H), 7.12-7.03 (m, 2H), 5.24 (s, 2H), 4.15 (s, 2H), 3.57 (s, 2H); $^{19}F$ NMR (282 MHz, DMSO-$d_6$) δ −122.28, −129.59; MS (ES+): 424.1 (M+1).

Scheme 47

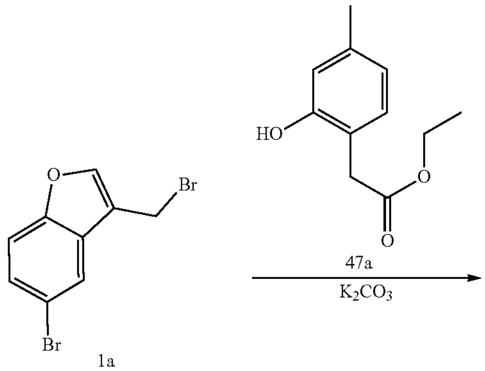

1a

-continued

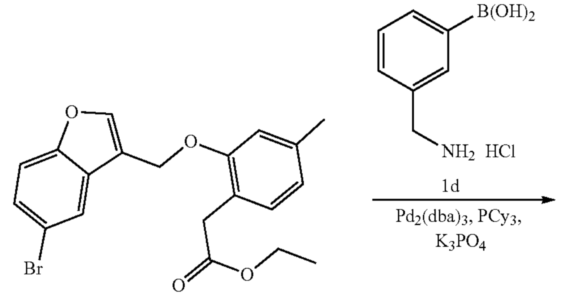

47b

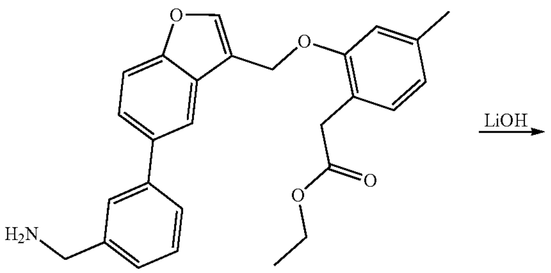

47c

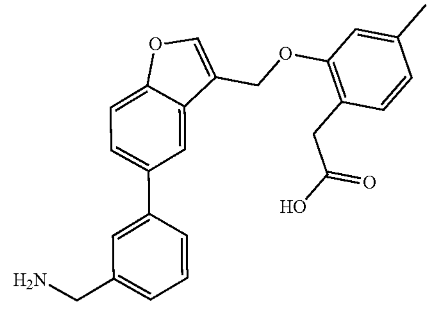

47d

Preparation of 2-(2-((5-(3-(aminomethyl)phenyl)benzofuran-3-yl)methoxy)-4-methylphenyl)acetic acid (47d)

Step-1: Preparation of ethyl 2-(2-((5-bromobenzofuran-3-yl)methoxy)-4-methylphenyl)acetate (47b)

Compound 47b was prepared according to the procedure reported in step-3 of scheme 7, from 5-bromo-3-(bromomethyl)benzofuran (1a) (300 mg, 1.035 mmol) in acetone (5 mL) using ethyl 2-(2-hydroxy-4-methylphenyl)acetate (47a) (221 mg, 1.138 mmol), $K_2CO_3$ (500 mg, 3.62 mmol) and stirring the reaction mixture at room temperature overnight. This gave after workup and purification by flash column chromatography [silica gel (12 g), eluting with EtOAc in hexane from 0-50%] ethyl 2-(2-((5-bromobenzofuran-3-yl)methoxy)-4-methylphenyl)acetate (47b) (383 mg, 92% yield) as a yellow oil; $^1H$ NMR (300 MHz, DMSO-$d_6$) δ 8.14 (s, 1H), 7.85 (d, J=2.1 Hz, 1H), 7.61 (d, J=8.7 Hz, 1H), 7.50 (dd, J=8.7, 2.1 Hz, 1H), 7.08 (d, J=7.5 Hz, 1H), 7.03 (s, 1H), 6.74 (dd, J=7.6, 1.5 Hz, 1H), 5.22 (s, 2H), 3.93 (q, J=7.1 Hz, 2H), 3.51 (s, 2H), 2.32 (s, 3H), 0.98 (t, J=7.1 Hz, 3H); MS (ES+): 425 (M+Na).

Step-2: Preparation of ethyl 2-(2-((5-(3-(aminomethyl)phenyl)benzofuran-3-yl)methoxy)-4-methylphenyl)acetate (47c)

Compound 47c was prepared according to the procedure reported in step-2 of scheme 1, from ethyl 2-(2-((5-bromobenzofuran-3-yl)methoxy)-4-methylphenyl)acetate (47b) (380 mg, 0.94 mmol) in dioxane (3 mL) using 3-(aminomethyl)phenylboronic acid hydrochloride (1d) (309 mg, 1.65 mmol), 2M solution of $K_3PO_4$ (0.942 mL, 1.885 mmol), tricyclohexylphosphine (106 mg, 0.377 mmol), $Pd_2(dba)_3$ (173 mg, 0.188 mmol) and heating at 135° C. for 30 min in a microwave. This gave after workup and purification by flash column chromatography [silica gel (12 g), eluting with DMA-80 in DCM from 0-50%] ethyl 2-(2-((5-(3-(aminomethyl)phenyl)benzofuran-3-yl)methoxy)-4-methylphenyl)acetate (47c) (201 mg, 50% yield) as a clear oil; MS (ES+): 430.2 (M+1).

Step-3: Preparation of 2-(2-((5-(3-(aminomethyl)phenyl)benzofuran-3-yl)methoxy)-4-methylphenyl)acetic acid (47d)

Compound 47d was prepared according to the procedure reported in step-3 of scheme 1, from ethyl 2-(2-((5-(3-(aminomethyl)phenyl)benzofuran-3-yl)methoxy)-4-methylphenyl)acetate (47c) (201 mg, 0.468 mmol) in THF (3 mL) using a solution of lithium hydroxide hydrate (119 mg, 2.83 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)benzofuran-3-yl)methoxy)-4-methylphenyl)acetic acid (47d) HCl salt (93 mg, 25% yield) as a white solid; $^1H$ NMR (300 MHz, DMSO-$d_6$) δ 12.14 (s, 1H, $D_2O$ exchangeable), 8.67-8.44 (bs, 3H, $D_2O$ exchangeable), 8.12 (s, 1H), 8.03 (s, J=1.2 Hz, 1H), 7.92 (s, J=1.9 Hz, 1H), 7.78-7.65 (m, 3H), 7.56-7.44 (m, 2H), 7.08 (m, 2H), 6.78-6.69 (d, 1H), 5.31 (s, 2H), 4.10 (s, 2H), 3.49 (s, 2H), 2.32 (s, 3H); MS (ES+): 402.1 (M+1); Analysis calculated for $C_{25}H_{23}NO_4\cdot HCl\cdot 0.75H_2O$: C, 66.52; H, 5.69; Cl, 7.85; N, 3.10. Found: C, 66.60; H, 5.86; Cl, 8.02; N, 3.27.

Scheme 48

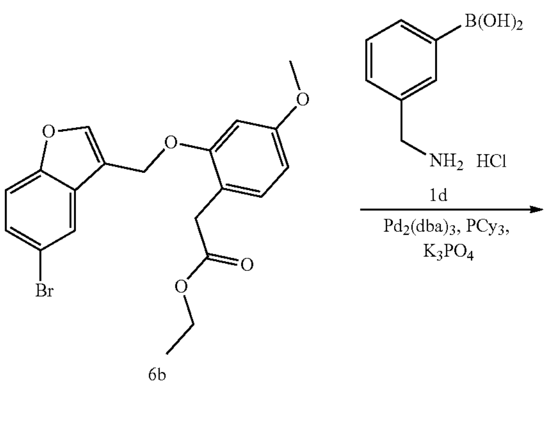

1d

6b

-continued

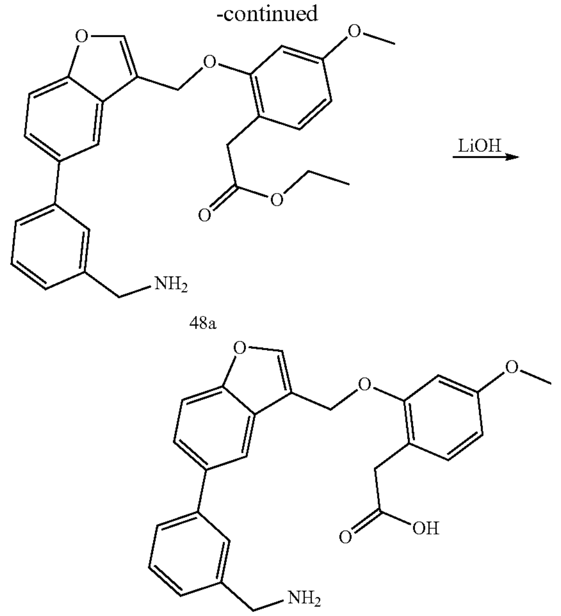

48a

48b

Step-1: Preparation of ethyl 2-(2-((5-(3-(aminomethyl)phenyl)benzofuran-3-yl)methoxy)-4-methoxyphenyl)acetate (48a)

Compound 48a was prepared according to the procedure reported in step-2 of scheme 1, from ethyl 2-(2-((5-bromobenzofuran-3-yl)methoxy)-4-methoxyphenyl)acetate (6b) (250 mg, 0.596 mmol) in dioxane (3 mL) using 3-(aminomethyl)phenylboronic acid hydrochloride (1d) (168 mg, 0.894 mmol), 2M solution of $K_3PO_4$ (0.507 mL, 1.014 mmol), tricyclohexylphosphine (66.9 mg, 0.239 mmol), $Pd_2(dba)_3$ (109 mg, 0.119 mmol) and heating at 135° C. for 30 min in a microwave. This gave after workup and purification by flash column chromatography [silica gel (24 g), eluting with DMA-80 in DCM from 0-70%] ethyl 2-(2-((5-(3-(aminomethyl)phenyl)benzofuran-3-yl)methoxy)-4-methoxyphenyl)acetate (48a) (124 mg, 47% yield) as a clear oil; MS (ES+): 446.1 (M+1).

Step-2: Preparation of 2-(2-((5-(3-(aminomethyl)phenyl)benzofuran-3-yl)methoxy)-4-methoxyphenyl)acetic acid (48b)

Compound 48b was prepared according to the procedure reported in step-3 of scheme 1, from ethyl 2-(2-((5-(3-(aminomethyl)phenyl)benzofuran-3-yl)methoxy)-4-methoxyphenyl)acetate (48a) (124 mg, 0.278 mmol) in THF (3 mL) using a solution of lithium hydroxide hydrate (75 mg, 1.789 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)benzofuran-3-yl)methoxy)-4-methoxyphenyl)acetic acid (48b) (45 mg, 18% yield) HCl salt as a white solid; $^1H$ NMR (300 MHz, DMSO-$d_6$) δ 12.12 (s, 1H, $D_2O$ exchangeable), 8.38 (s, 3H, $D_2O$ exchangeable), 8.12 (s, 1H), 8.02 (d, J=1.8 Hz, 1H), 7.88 (t, J=1.8 Hz, 1H), 7.78-7.65 (m, 3H), 7.57-7.41 (m, 2H), 7.10 (d, J=8.3 Hz, 1H), 6.80 (d, J=2.4 Hz, 1H), 6.50 (dd, J=8.3, 2.4 Hz, 1H), 5.32 (s, 2H), 4.11 (s, 2H), 3.76 (s, 3H), 3.45 (s, 2H); MS (ES+): 418.1 (M+1); Analysis calculated for $C_{25}H_{23}NO_5{\cdot}HCl{\cdot}0.5H_2O$: C, 64.86; H, 5.44; Cl, 7.66; N, 3.03. Found: C, 64.90; H, 5.32; Cl, 7.92; N, 3.16.

Scheme 49

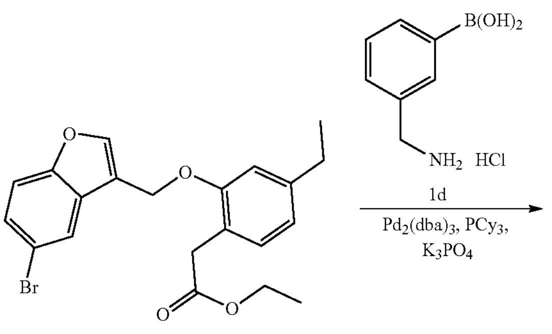

12e

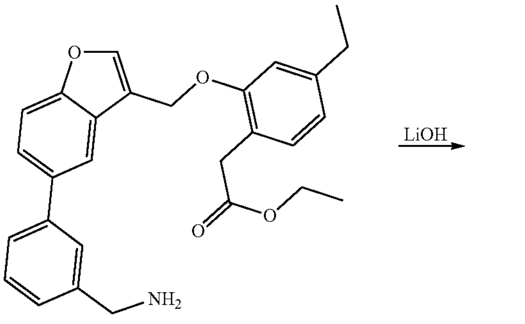

49a

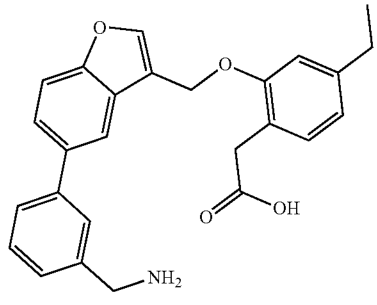

49b

Preparation of 2-(2-((5-(3-(aminomethyl)phenyl)benzofuran-3-yl)methoxy)-4-ethylphenyl)acetic acid (49b)

Step-1: Preparation of ethyl 2-(2-((5-(3-(aminomethyl)phenyl)benzofuran-3-yl)methoxy)-4-ethylphenyl)acetate (49a)

Compound 49a was prepared according to the procedure reported in step-2 of scheme 1, from ethyl 2-(2-((5-bromobenzofuran-3-yl)methoxy)-4-ethylphenyl)acetate (12e) (206 mg, 0.49 mmol) in dioxane (3 mL) using 3-(aminomethyl)phenylboronic acid hydrochloride (1d) (139 mg, 0.74 mmol), 2M solution of $K_3PO_4$ (0.42 mL, 0.84 mmol), tricyclohexylphosphine (55.4 mg, 0.20 mmol), $Pd_2(dba)_3$ (90 mg, 0.099 mmol) and heating at 135° C. for 30 min in a microwave. This gave after workup and purification by column chromatography [silica gel (24 g), eluting with DMA80 in DCM from 0-70%] ethyl 2-(2-((5-(3-(aminomethyl)phenyl)benzofuran-3-yl)methoxy)-4-ethylphenyl)acetate (49a) (88 mg, 0.198 mmol) as a clear oil; $^1$H NMR (300 MHz, DMSO-$d_6$) δ 8.11 (s, 1H), 7.91 (d, J=1.8 Hz, 1H), 7.71-7.59 (m, 3H), 7.53 (d, J=7.5 Hz, 1H), 7.39 (t, J=7.5 Hz, 1H), 7.31 (d, J=7.6 Hz, 1H), 7.09 (dd, J=4.6, 3.0 Hz, 2H), 6.77 (d, J=7.5 Hz, 1H), 5.29 (s, 2H), 3.77 (s, 2H), 3.71 (q, J=7.1 Hz, 2H), 3.51 (s, 2H), 2.62 (q, J=7.6 Hz, 2H), 1.21 (t, J=7.5 Hz, 3H), 0.85 (t, J=7.1 Hz, 3H); MS (ES+): 444.2 (M+1).

Step-2: Preparation of 2-(2-((5-(3-(aminomethyl)phenyl)benzofuran-3-yl)methoxy)-4-ethylphenyl)acetic acid (49b)

Compound 49b was prepared according to the procedure reported in step-3 of scheme 1, from ethyl 2-(2-((5-(3-(aminomethyl)phenyl)benzofuran-3-yl)methoxy)-4-ethylphenyl)acetate (49a) (88 mg, 0.198 mmol) in THF (3 mL) using a solution of lithium hydroxide hydrate (62.1 mg, 1.48 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)benzofuran-3-yl)methoxy)-4-ethylphenyl)acetic acid (49b) (35 mg, 17% yield) HCl salt as a white solid; $^1$H NMR (300 MHz, DMSO-$d_6$) δ 12.06 (s, 1H, $D_2O$ exchangeable), 8.47 (s, 3H, $D_2O$ exchangeable), 8.13 (s, 1H), 8.03 (d, J=1.7 Hz, 1H), 7.90 (t, J=1.7 Hz, 1H), 7.79-7.65 (m, 3H), 7.56-7.42 (m, 2H), 7.12-7.05 (m, 2H), 6.77 (dd, J=7.6, 1.5 Hz, 1H), 5.32 (s, 2H), 4.11 (s, 2H), 3.49 (s, 2H), 2.61 (q, J=7.6 Hz, 2H), 1.20 (t, J=7.6 Hz, 3H); MS (ES+): 416.2 (M+1); Analysis calculated for $C_{26}H_{25}NO_4{\cdot}HCl{\cdot}H_2O$: C, 66.45; H, 6.01; Cl, 7.54; N, 2.98; found: C, 66.77; H, 5.89; Cl, 7.62; N, 3.16.

Scheme 50

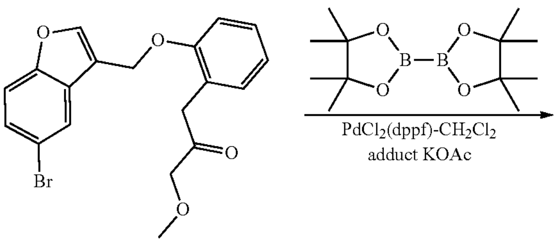

9c

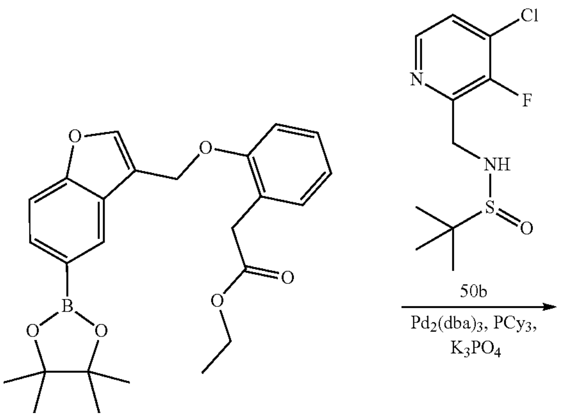

50a

-continued

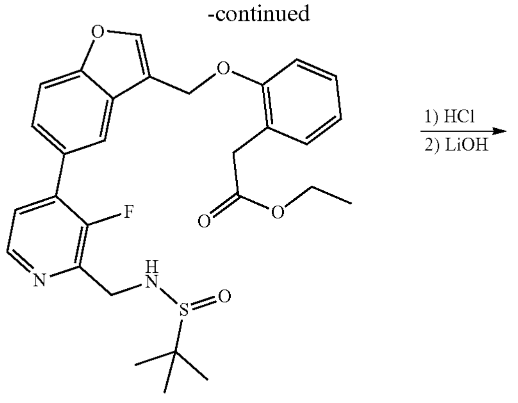

50c

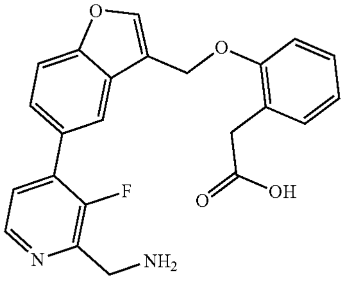

50d

Preparation of 2-(2-((5-(2-(aminomethyl)-3-fluoropyridin-4-yl)benzofuran-3-yl)methoxy)phenyl)acetic acid (50d)

Step-1: Preparation of ethyl 2-(2-((5-(4,4,5,5-tetramethyl-1,3,2-dioxaborolan-2-yl)benzofuran-3-yl)methoxy)phenyl)acetate (50a)

Compound 50a was prepared according to the procedure reported in step-1 of scheme 27 from ethyl 2-(2-((5-bromobenzofuran-3-yl)methoxy)phenyl)acetate (9c) in anhydrous dioxane (15 mL) using BisPin (1 g, 2.57 mmol), potassium acetate (0.756 g, 7.71 mmol), $PdCl_2$(dppf)-$CH_2Cl_2$ adduct (0.315 g, 0.39 mmol) and heating at 90° C. for 6.5 h. This gave after work up and purification by flash column chromatography [silica gel (40 g), eluting with EtOAc in hexane from 0-40%] ethyl 2-(2-((5-(4,4,5,5-tetramethyl-1,3,2-dioxaborolan-2-yl)benzofuran-3-yl)methoxy)phenyl)acetate (50a) (1.01 g, 90% yield) as a clear oil; $^1$H NMR (300 MHz, DMSO-$d_6$) δ 8.13-7.98 (m, 2H), 7.72-7.53 (m, 2H), 7.34-7.14 (m, 3H), 6.94 (td, J=7.3, 1.3 Hz, 1H), 5.29 (d, J=2.4 Hz, 2H), 3.90 (q, J=7.1 Hz, 2H), 3.62-3.50 (m, 2H), 1.31 (s, 12H), 0.99-0.92 (m, 3H).

Step-2: Preparation of ethyl 2-(2-((5-(2-((1,1-dimethylethylsulfinamido)methyl)-3-fluoropyridin-4-yl)benzofuran-3-yl)methoxy)phenyl)acetate (50c)

Compound 50c was prepared according to the procedure reported in step-2 of scheme 1, from ethyl 2-(2-((5-(4,4,5,5-tetramethyl-1,3,2-dioxaborolan-2-yl)benzofuran-3-yl)methoxy)phenyl)acetate (50a) (300 mg, 0.688 mmol) in dioxane (3 mL) using N-((4-chloro-3-fluoropyridin-2-yl)methyl)-2-methylpropane-2-sulfinamide (50b) (273 mg, 1.031 mmol), 2M solution of $K_3PO_4$ (0.584 mL, 1.169 mmol), tricyclohexylphosphine (57.8 mg, 0.206 mmol), $Pd_2(dba)_3$ (63 mg, 0.069 mmol) and heating at 135° C. for 30 min in a microwave. This gave after workup and purification by flash column chromatography [silica gel (24 g), eluting with DMA80 in DCM from 0-70%] ethyl 2-(2-((5-(2-((1,1-dimethylethylsulfinamido)methyl)-3-fluoropyridin-4-yl)benzofuran-3-yl)methoxy)phenyl)acetate (50c) (210 mg, 57% yield)) as a yellow oil; MS (ES+): 539.2 (M+1).

Step-3: Preparation of 2-(2-((5-(2-(aminomethyl)-3-fluoropyridin-4-yl)benzofuran-3-yl)methoxy)phenyl)acetic acid (50d)

Compound 50d was prepared according to the procedure reported in step-4 of scheme 39, from ethyl 2-(2-((5-(2-((1,1-dimethylethylsulfinamido)methyl)-3-fluoropyridin-4-yl)benzofuran-3-yl)methoxy)phenyl)acetate (50c) (210 mg, 0.390 mmol) in DCM (10 mL) using HCl (4 M solution in dioxane, 0.52 mL, 2.063 mmol) and stirring at room temperature for 2 h. The ester was hydrolyzed using a solution of lithium hydroxide hydrate (135 mg, 3.22 mmol) in water (1 mL) and THF (3 mL) and stirring at RT overnight. This gave after workup and purification by reverse phase column chromatography [C18 column (30 g), eluting with ACN in water (containing 0.1% HCl) from 0-100%] 2-(2-((5-(2-(aminomethyl)-3-fluoropyridin-4-yl)benzofuran-3-yl)methoxy)phenyl)acetic acid (50d) (81 mg, 29% yield) HCl salt as a white solid; $^1$H NMR (300 MHz, DMSO-$d_6$) δ 8.61 (t, J=5.7 Hz, 3H, $D_2O$ exchangeable), 8.55 (d, J=5.0 Hz, 1H), 8.21 (s, 1H), 8.05 (d, J=1.5 Hz, 1H), 7.82 (d, J=8.7 Hz, 1H), 7.76 (t, J=5.6 Hz, 1H), 7.67 (dt, J=8.6, 1.8 Hz, 1H), 7.33-7.14 (m, 3H), 6.93 (td, J=7.3, 1.3 Hz, 1H), 5.33 (s, 2H), 4.39-4.28 (m, 2H), 3.54 (s, 2H); $^{19}$F NMR (282 MHz, DMSO-$d_6$) δ −132.79; MS (ES+): 407.1 (M+1); Analysis calculated for $C_{23}H_{19}FN_2O_4 \cdot 1.5HCl \cdot 2.25H_2O$: C, 55.07; H, 5.02; Cl, 10.60; N, 5.58. Found: C, 55.18; H, 4.36; Cl, 10.21; N, 5.64.

Scheme 51

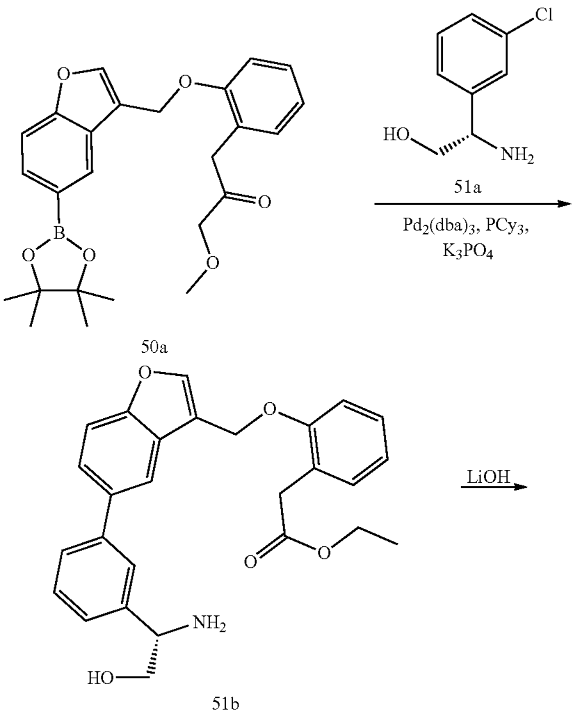

50a

51a

51b

-continued

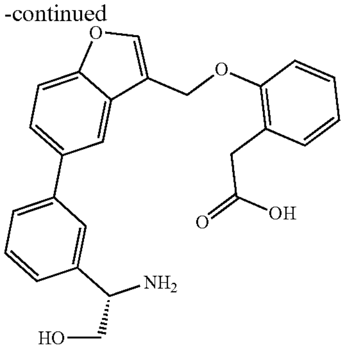

51c

Preparation of (S)-2-(2-((5-(3-(1-amino-2-hydroxyethyl)phenyl)benzofuran-3-yl)methoxy)phenyl)acetic acid (51c)

Step-1: Preparation of (S)-ethyl 2-(2-((5-(3-(1-amino-2-hydroxyethyl)phenyl)benzofuran-3-yl)methoxy)phenyl)acetate (51b)

Compound 51b was prepared according to the procedure reported in step-2 of scheme 1, from ethyl 2-(2-((5-(4,4,5,5-tetramethyl-1,3,2-dioxaborolan-2-yl)benzofuran-3-yl)methoxy)phenyl)acetate (50a) (300 mg, 0.688 mmol) in dioxane (3 mL) using (S)-2-amino-2-(3-chlorophenyl)ethanol (51a) (177 mg, 1.03 mmol; CAS #663611-73-2), 2M solution of $K_3PO_4$ (0.584 mL, 1.17 mmol), tricyclohexylphosphine (57.8 mg, 0.206 mmol), $Pd_2(dba)_3$ (63 mg, 0.069 mmol) and heating at 135° C. for 30 min in a microwave. This gave after workup and purification by flash column chromatography [silica gel (24 g), eluting with DMA-80 in DCM from 0-70%](S)-ethyl 2-(2-((5-(3-(1-amino-2-hydroxyethyl)phenyl)benzofuran-3-yl)methoxy)phenyl)acetate (51b) (162 mg, 53% yield) as a clear oil; MS (ES+): 446.1 (M+1).

Step-2: Preparation of (S)-2-(2-((5-(3-(1-amino-2-hydroxyethyl)phenyl)benzofuran-3-yl)methoxy)phenyl)acetic acid (51c)

Compound 51c was prepared according to the procedure reported in step-3 of scheme 1, from (S)-ethyl 2-(2-((5-(3-(1-amino-2-hydroxyethyl)phenyl)benzofuran-3-yl)methoxy)phenyl)acetate (51b) (162 mg, 0.364 mmol) in THF (3 mL) using a solution of lithium hydroxide hydrate (135 mg, 3.22 mmol) in water (1 mL) and stirring overnight at room temperature. This gave after workup and purification by reverse phase column chromatography [C18 column (30 g), eluting with ACN in water (containing 0.1% HCl) from 0-100%](S)-2-(2-((5-(3-(1-amino-2-hydroxyethyl)phenyl)benzofuran-3-yl)methoxy)phenyl)acetic acid (51c) (82 mg, 29% yield) HCl salt as a white solid; $^1$H NMR (300 MHz, DMSO-$d_6$) δ 12.16 (s, 1H, $D_2O$ exchangeable), 8.68 (s, 3H, $D_2O$ exchangeable), 8.12 (s, 1H), 8.08-8.00 (m, 1H), 7.94 (d, J=2.2 Hz, 1H), 7.78-7.67 (m, 3H), 7.55-7.43 (m, 2H), 7.31-7.16 (m, 3H), 6.93 (td, J=7.2, 1.4 Hz, 1H), 5.62 (s, 1H, $D_2O$ exchangeable), 5.34 (s, 2H), 4.36 (t, J=6.0 Hz, 1H), 3.81 (d, J=5.9 Hz, 2H), 3.56 (s, 2H); MS (ES+): 418.2 (M+1); Analysis calculated for $C_{25}H_{23}NO_5{\cdot}HCl{\cdot}1.5H_2O$: C, 62.43; H, 5.66; Cl, 7.37; N, 2.91. Found: C, 62.41; H, 5.33; Cl, 7.26; N, 2.93; Optical rotation [α]D=+15.56 (c=0.09, MeOH).

Scheme 52

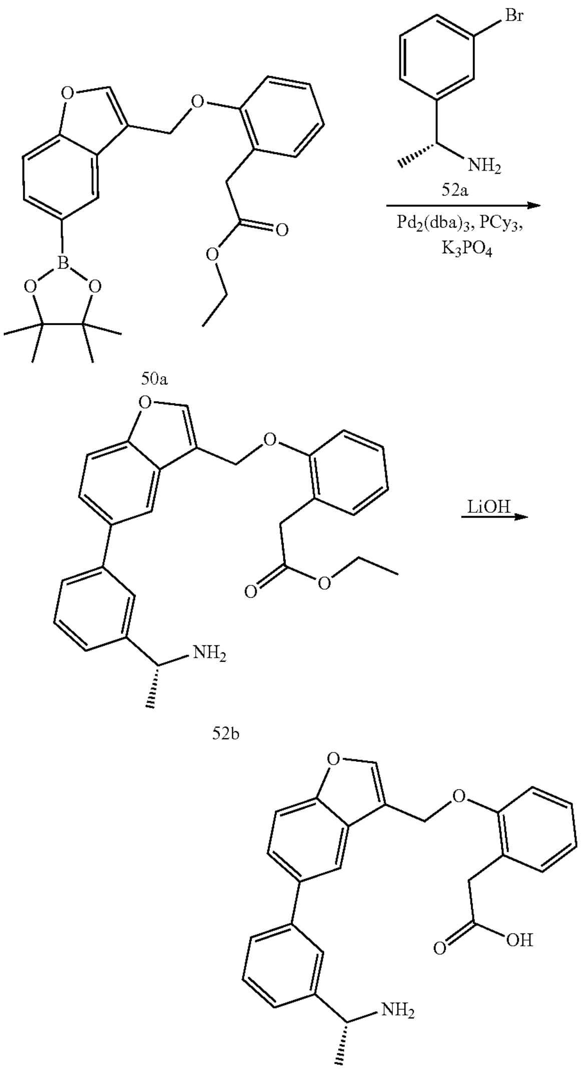

52a

50a

52b

52c

Preparation of (R)-2-(2-((5-(3-(1-aminoethyl)phenyl)benzofuran-3-yl)methoxy)phenyl)acetic acid (52c)

Step-1: Preparation of (R)-ethyl 2-(2-((5-(3-(1-aminoethyl)phenyl)benzofuran-3-yl)methoxy)phenyl)acetate (52b)

Compound 52b was prepared according to the procedure reported in step-2 of scheme 1, from ethyl 2-(2-((5-(4,4,5,5-tetramethyl-1,3,2-dioxaborolan-2-yl)benzofuran-3-yl)methoxy)phenyl)acetate (50a) (350 mg, 0.80 mmol) in dioxane (3 mL) using (R)-1-(3-bromophenyl)ethanamine (52a) (241 mg, 1.20 mmol, CAS #176707-77-0), 2M solution of $K_3PO_4$ (0.68 mL, 1.36 mmol), tricyclohexylphosphine (67.5 mg, 0.24 mmol), $Pd_2(dba)_3$ (73.5 mg, 0.08 mmol) and heating at 135° C. for 30 min in a microwave. This gave after workup and purification by flash column chromatography [silica gel (24 g), eluting with DMA-80 in DCM from 0-70%](R)-ethyl 2-(2-((5-(3-(1-aminoethyl)phenyl)benzofuran-3-yl)methoxy)phenyl)acetate (52b) (166 mg, 48% yield) as a yellow oil; MS (ES+): 430.2 (M+1).

Step-2: Preparation of (R)-2-(2-((5-(3-(1-aminoethyl)phenyl)benzofuran-3-yl)methoxy)phenyl)acetic acid (52c)

Compound 52c was prepared according to the procedure reported in step-3 of scheme 1, from (R)-ethyl 2-(2-((5-(3-(1-aminoethyl)phenyl)benzofuran-3-yl)methoxy)phenyl)acetate (52b) (166 mg, 48% yield) in THF (3 mL) using a solution of lithium hydroxide hydrate (101 mg, 2.41 mmol) in water (1 mL) and stirring overnight at room temperature. This gave after workup and purification by reverse phase column chromatography [C18 column (30 g), eluting with ACN in water (containing 0.1% HCl) from 0-100%](R)-2-(2-((5-(3-(1-aminoethyl)phenyl)benzofuran-3-yl)methoxy)phenyl)acetic acid (52c) (67 mg, 21% yield) HCl salt as a white solid; $^1$H NMR (300 MHz, DMSO-$d_6$) δ 12.17 (s, 1H, $D_2O$ exchangeable), 8.67 (s, 3H, $D_2O$ exchangeable), 8.12 (s, 1H), 8.05 (s, 1H), 7.95 (s, 1H), 7.72 (s, 3H), 7.52 (m, J=4.6 Hz, 2H), 7.33-7.15 (m, 3H), 6.92 (td, J=7.2, 1.4 Hz, 1H), 5.34 (s, 2H), 4.47 (q, J=6.7 Hz, 1H), 3.55 (s, 2H), 1.59 (d, J=6.7 Hz, 3H); MS (ES+): 402.1 (M+1); (ES−): 400.0 (M−1); Analysis calculated for $C_{25}H_{23}NO_4$·HCl·$H_2O$: C, 65.86; H, 5.75; Cl, 7.78; N, 3.07. Found: C, 65.71; H, 5.58 Cl, 7.66; N, 3.08.

Scheme 53

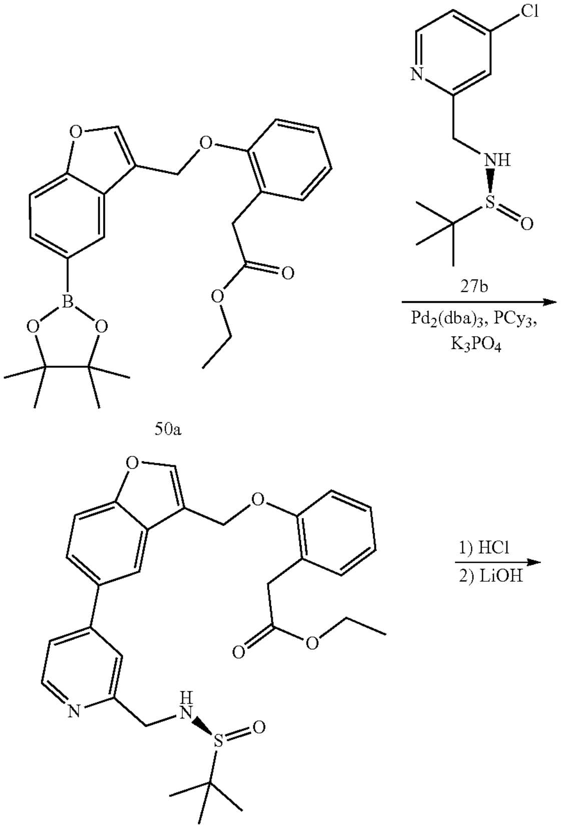

27b

50a

53a

-continued

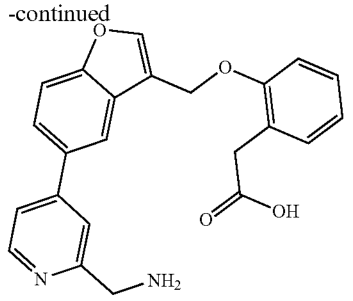

53b

Preparation of 2-(2-((5-(2-(aminomethyl)pyridin-4-yl)benzofuran-3-yl)methoxy)phenyl)acetic acid (53b)

Step-1: Preparation of ethyl 2-(2-((5-(2-((1,1-dimethylethylsulfinamido)methyl)pyridin-4-yl)benzofuran-3-yl)methoxy)phenyl)acetate (53a)

Compound 53a was prepared according to the procedure reported in step-2 of scheme 1, from ethyl 2-(2-((5-(4,4,5,5-tetramethyl-1,3,2-dioxaborolan-2-yl)benzofuran-3-yl)methoxy)phenyl)acetate (50a) 350 mg, 0.80 mmol) in dioxane (3 mL) using (+)-N-((4-chloropyridin-2-yl)methyl)-2-methylpropane-2-sulfinamide (27b) (297 mg, 1.203 mmol), 2 M solution of $K_3PO_4$ (0.68 mL, 1.36 mmol), tricyclohexylphosphine (67.5 mg, 0.24 mmol), $Pd_2(dba)_3$ (73.5 mg, 0.080 mmol) and heating at 135° C. for 30 min in microwave. This gave after workup and purification by column chromatography [silica gel (24 g), eluting with DMA-80 in DCM from 0-70%] ethyl 2-(2-((5-(2-((1,1-dimethylethylsulfinamido)methyl)pyridin-4-yl)benzofuran-3-yl)methoxy)phenyl)acetate (53a) (232 mg, 0.446 mmol, 55% yield) as a clear oil; MS (ES+): 521.2 (M+1).

Step-2: Preparation of 2-(2-((5-(2-(aminomethyl)pyridin-4-yl)benzofuran-3-yl)methoxy)phenyl)acetic acid (53b)

Compound 53b was prepared according to the procedure reported in step-4 of scheme 39, from ethyl 2-(2-((5-(2-((1,1-dimethylethylsulfinamido)methyl)pyridin-4-yl)benzofuran-3-yl)methoxy)phenyl)acetate (53a)) (232 mg, 0.446 mmol) in DCM (10 mL) using HCl (4N in dioxane, 0.60 mL, 2.41 mmol) and stirring at RT for 2 h. The ester was hydrolyzed using a solution of lithium hydroxide hydrate (135 mg, 3.22 mmol) in water (1 mL) and THF (3 mL) and stirring at room temperature overnight. This gave after workup and purification by reverse phase column chromatography [C18 column (30 g), eluting with ACN in water (containing 0.1% HCl) from 0-100%] 2-(2-((5-(2-(aminomethyl)pyridin-4-yl)benzofuran-3-yl)methoxy)phenyl)acetic acid (53b) (81 mg, 47% yield) HCl salt as a white solid; $^1$H NMR (300 MHz, DMSO-$d_6$) δ 8.72 (d, J=5.4 Hz, 1H), 8.55 (s, 3H, $D_2O$ exchangeable), 8.22 (d, J=1.7 Hz, 1H), 8.19 (s, 1H), 8.05 (s, 1H), 7.93-7.87 (m, 1H), 7.86-7.78 (m, 2H), 7.32-7.26 (m, 1H), 7.25-7.19 (m, 2H), 6.94 (td, J=7.3, 1.3 Hz, 1H), 5.35 (s, 2H), 4.36-4.22 (m, 2H), 3.55 (s, 2H); MS (ES+): 389.1 (M+1); Analysis calculated for $C_{23}H_{20}N_2O_4$·1.85HCl·2.5$H_2O$: C, 55.15; H, 5.40; Cl, 13.09; N, 5.59. Found: C, 55.11; H, 5.09; Cl, 13.03; N, 5.63.

Scheme 54

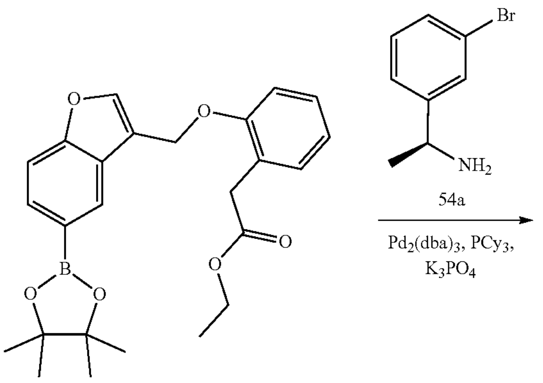

54a

50a

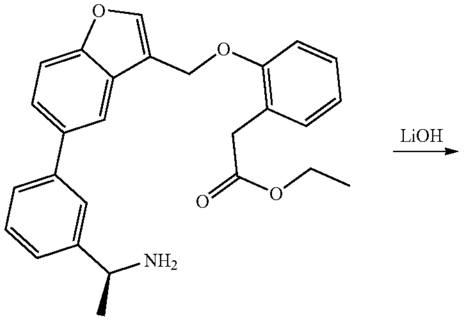

54b

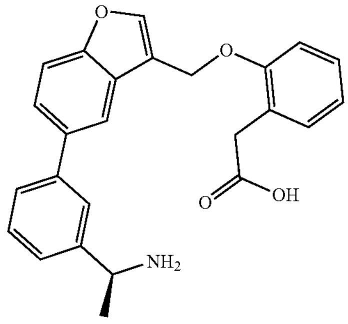

54c

Preparation of (S)-2-(2-((5-(3-(1-aminoethyl)phenyl)benzofuran-3-yl)methoxy)phenyl)acetic acid (54c)

Step-1: Preparation of (S)-ethyl 2-(2-((5-(3-(1-aminoethyl)phenyl)benzofuran-3-yl)methoxy)phenyl) acetate (54b)

Compound 54b was prepared according to the procedure reported in step-2 of scheme 1, from ethyl 2-(2-((5-(4,4,5,5-tetramethyl-1,3,2-dioxaborolan-2-yl)benzofuran-3-yl) methoxy)phenyl)acetate (50a) (350 mg, 0.80 mmol) in dioxane (3 mL) using (S)-1-(3-bromophenyl)ethanamine (54a) (241 mg, 1.20 mmol, CAS #139305-96-7), 2M solution of $K_3PO_4$ (0.68 mL, 1.36 mmol), tricyclohexylphosphine (67.5 mg, 0.24 mmol), $Pd_2(dba)_3$ (73.5 mg, 0.080 mmol) and heating at 135° C. for 30 min in a microwave. This gave after workup and purification by column chromatography [silica gel (24 g), eluting with DMA-80 in DCM from 0-70%](S)-ethyl 2-(2-((5-(3-(1-aminoethyl)phenyl) benzofuran-3-yl)methoxy)phenyl)acetate (54b) (167 mg, 49% yield) as a clear oil; MS (ES+): 430.2 (M+1).

Step-2: Preparation of (S)-2-(2-((5-(3-(1-aminoethyl)phenyl)benzofuran-3-yl)methoxy)phenyl)acetic acid (54c)

Compound 54c was prepared according to the procedure reported in step-3 of scheme 1, (S)-ethyl 2-(2-((5-(3-(1-aminoethyl)phenyl)benzofuran-3-yl)methoxy)phenyl)acetate (54b) (167 mg, 0.389 mmol) in THF (3 mL) using a solution of lithium hydroxide hydrate (135 mg, 3.22 mmol) in water (1 mL) and stirring overnight at room temperature. This gave after workup and purification by reverse phase column chromatography [C18 column (30 g), eluting with ACN in water (containing 0.1% HCl) from 0-100%](S)-2-(2-((5-(3-(1-aminoethyl)phenyl)benzofuran-3-yl)methoxy) phenyl)acetic acid (54c) (52 mg, 16% yield) HCl salt as a white solid; $^1H$ NMR (300 MHz, DMSO-$d_6$) δ 12.11 (s, 1H, $D_2O$ exchangeable), 8.50 (s, 3H, $D_2O$ exchangeable), 8.06 (s, 1H), 7.97 (t, J=1.2 Hz, 1H), 7.86 (s, J=1.9 Hz, 1H), 7.71-7.61 (m, 3H), 7.50-7.39 (m, 2H), 7.24-7.11 (m, 3H), 6.86 (td, J=7.2, 1.4 Hz, 1H), 5.27 (s, 2H), 4.48-4.33 (m, 1H), 3.48 (s, 2H), 1.52 (d, J=6.8 Hz, 3H); MS (ES+): 402.1 (M+1); Analysis calculated for $C_{25}H_{23}NO_4 \cdot HCl \cdot H_2O$: C, 65.86; H, 5.75; Cl, 7.78; N, 3.07. Found: C, 65.76; H, 5.61; Cl, 7.59; N, 3.18.

Scheme 55

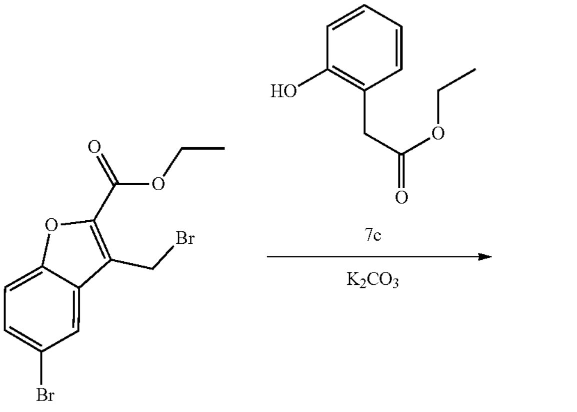

7c

55a

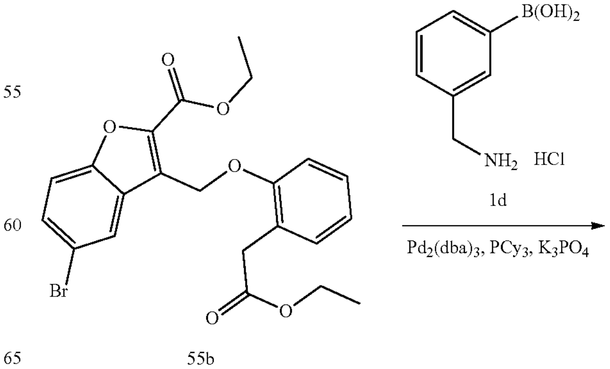

1d

55b

-continued

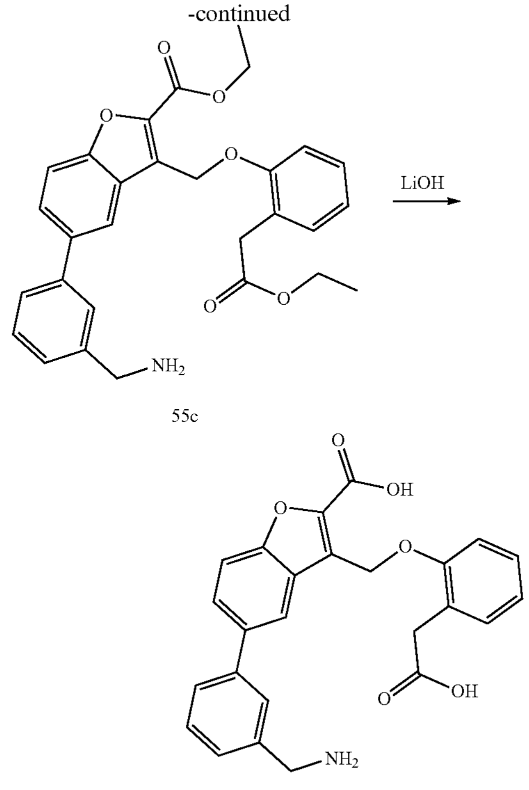

55c

55d

Preparation of 5-(3-(aminomethyl)phenyl)-3-((2-(carboxymethyl)phenoxy)methyl)benzofuran-2-carboxylic acid (55d)

Step-1: Preparation of ethyl 5-bromo-3-((2-(2-ethoxy-2-oxoethyl)phenoxy)methyl)benzofuran-2-carboxylate (55b)

Compound 55b was prepared according to the procedure reported in step-1 of scheme 1, from ethyl 5-bromo-3-(bromomethyl)benzofuran-2-carboxylate (55a) (500 mg, 1.381 mmol; CAS #565192-82-7) in acetone (10 mL) using ethyl 2-(2-hydroxyphenyl)acetate (7c) (286 mg, 1.588 mmol), $K_2CO_3$ (668 mg, 4.83 mmol) and stirring overnight at room temperature. This gave after workup and purification by flash column chromatography [silica gel (12 g), eluting with EtOAc in hexane from 0-50%] ethyl 5-bromo-3-((2-(2-ethoxy-2-oxoethyl)phenoxy)methyl)benzofuran-2-carboxylate (55b) (586 mg, 92% yield) as a clear oil; $^1H$ NMR (300 MHz, DMSO-$d_6$) δ 8.06 (d, J=1.9 Hz, 1H), 7.80-7.69 (m, 2H), 7.34-7.26 (m, 1H), 7.23 (dd, J=7.4, 1.7 Hz, 1H), 7.17 (dd, J=8.3, 1.1 Hz, 1H), 6.95 (td, J=7.4, 1.1 Hz, 1H), 5.59 (s, 2H), 4.39 (q, J=7.1 Hz, 2H), 3.90 (q, J=7.1 Hz, 2H), 3.56 (s, 2H), 1.32 (t, J=7.1 Hz, 3H), 0.95 (t, J=7.1 Hz, 3H).

Step-2: Preparation of ethyl 5-(3-(aminomethyl)phenyl)-3-((2-(2-ethoxy-2-oxoethyl)phenoxy)methyl)benzofuran-2-carboxylate (55c)

Compound 55c was prepared according to the procedure reported in step-2 of scheme 1, from ethyl 5-bromo-3-((2-(2-ethoxy-2-oxoethyl)phenoxy)methyl)benzofuran-2-carboxylate (55b) (250 mg, 0.54 mmol) in dioxane (3 mL) using 3-(aminomethyl)phenylboronic acid hydrochloride (1d) (152 mg, 0.81 mmol), 2 M solution of $K_3PO_4$ (0.46 mL, 0.92 mmol), tricyclohexylphosphine (60.8 mg, 0.22 mmol), $Pd_2(dba)_3$ (99 mg, 0.11 mmol) and heating at 135° C. for 30 min in a microwave. This gave after workup and purification by column chromatography [silica gel (24 g), eluting with DMA-80 in DCM from 0-70%] ethyl 5-(3-(aminomethyl)phenyl)-3-((2-(2-ethoxy-2-oxoethyl)phenoxy)methyl)benzofuran-2-carboxylate (55c) (121 mg, 46% yield) as a clear oil; MS (ES+): 488.2 (M+1).

Step-3: Preparation of 5-(3-(aminomethyl)phenyl)-3-((2-(carboxymethyl)phenoxy)methyl)benzofuran-2-carboxylic acid (55d)

Compound 55d was prepared according to the procedure reported in step-3 of scheme 1, from ethyl 5-(3-(aminomethyl)phenyl)-3-((2-(2-ethoxy-2-oxoethyl)phenoxy)methyl)benzofuran-2-carboxylate (55c) (121 mg, 0.248 mmol) in THF (3 mL) using a solution of lithium hydroxide hydrate (136 mg, 3.25 mmol) in water (1 mL) and stirring overnight at room temperature. This gave after workup and purification by reverse phase column chromatography [C18 column (30 g), eluting with ACN in water (containing 0.1% HCl) from 0-100%] followed by flash column chromatography [silica (12 g), eluting with MeOH in DCM from 0-40%] 5-(3-(aminomethyl)phenyl)-3-((2-(carboxymethyl)phenoxy)methyl)benzofuran-2-carboxylic acid (55d) (52 mg, 22% yield) HCl salt as a white solid; $^1H$ NMR (300 MHz, DMSO-$d_6$) δ 12.52 (s, 1H, $D_2O$ exchangeable), 8.48 (s, 3H, $D_2O$ exchangeable), 8.13 (s, 1H), 7.92-7.81 (m, 3H), 7.73 (dt, J=7.0, 2.0 Hz, 1H), 7.57-7.45 (m, 2H), 7.31-7.14 (m, 3H), 6.97-6.87 (m, 1H), 5.69 (s, 2H), 4.10 (s, 2H), 3.55 (s, 2H); MS (ES+): 432.1 (M+1); Analysis calculated for $C_{25}H_{21}NO_6 \cdot HCl \cdot 2.25H_2O$: C, 59.06; H, 5.25; Cl, 6.97; N, 2.75. Found: C, 58.82; H, 5.13; Cl, 6.78; N, 2.80.

Scheme 56

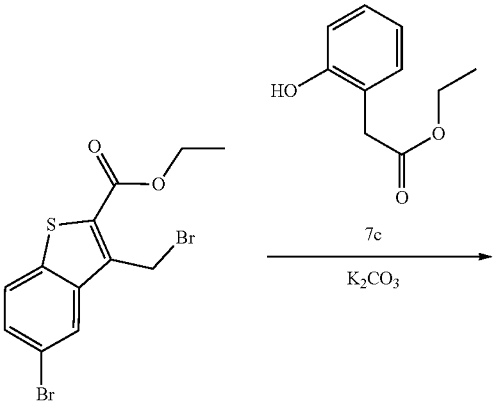

56a

-continued

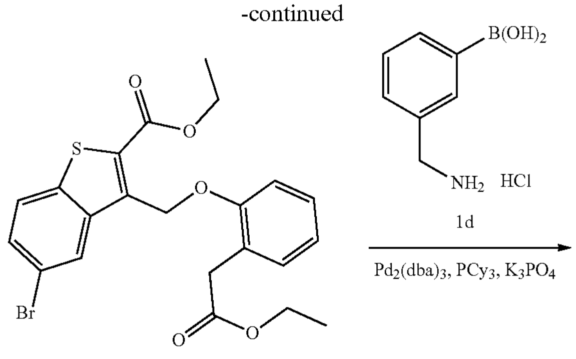

56b

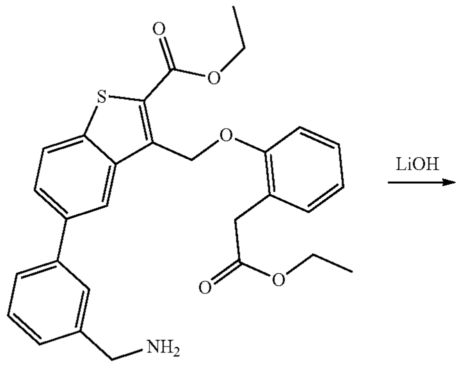

56c

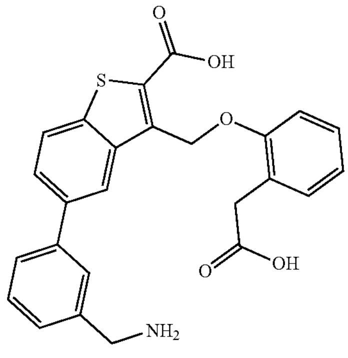

56d

Preparation of 5-(3-(aminomethyl)phenyl)-3-((2-(carboxymethyl)phenoxy)methyl)benzo[b]thiophene-2-carboxylic acid (56d)

Step-1: Preparation of ethyl 5-bromo-3-((2-(2-ethoxy-2-oxoethyl)phenoxy)methyl)benzo[b]thiophene-2-carboxylate (56b)

Compound 56b was prepared according to the procedure reported in step-1 of scheme 1, from ethyl 5-bromo-3-(bromomethyl)benzo[b]thiophene-2-carboxylate (56a) (500 mg, 1.322 mmol; CAS #31310-31-3) in acetone (12 mL) using ethyl 2-(2-hydroxyphenyl)acetate (7c) (274 mg, 1.521 mmol), $K_2CO_3$ (640 mg, 4.63 mmol) and stirring overnight at room temperature. This gave after workup and purification by flash column chromatography [silica gel (12 g), eluting with EtOAc in hexane from 0-50%] ethyl 5-bromo-3-((2-(2-ethoxy-2-oxoethyl)phenoxy)methyl)benzo[b]thiophene-2-carboxylate (56b) (478 mg, 76% yield) as a white solid; $^1$H NMR (300 MHz, DMSO-$d_6$) δ 8.25 (d, J=1.9 Hz, 1H), 8.08 (d, J=8.7 Hz, 1H), 7.73 (dd, J=8.7, 1.9 Hz, 1H), 7.31 (td, J=7.8, 7.3, 1.7 Hz, 1H), 7.25-7.16 (m, 2H), 6.94 (td, J=7.4, 1.2 Hz, 1H), 5.69 (s, 2H), 4.34 (q, J=7.1 Hz, 2H), 3.80 (q, J=7.1 Hz, 2H), 3.46 (s, 2H), 1.27 (t, J=7.1 Hz, 3H), 0.87 (t, J=7.1 Hz, 3H).

Step-2: Preparation of ethyl 5-(3-(aminomethyl)phenyl)-3-((2-(2-ethoxy-2-oxoethyl)phenoxy)methyl)benzo[b]thiophene-2-carboxylate (56c)

Compound 56c was prepared according to the procedure reported in step-2 of scheme 1, from ethyl 5-bromo-3-((2-(2-ethoxy-2-oxoethyl)phenoxy)methyl)benzo[b]thiophene-2-carboxylate (56b) (250 mg, 0.52 mmol) in dioxane (3 mL) using 3-(aminomethyl)phenylboronic acid hydrochloride (1d) (147 mg, 0.786 mmol), 2 M solution of $K_3PO_4$ (0.45 mL, 0.89 mmol), tricyclohexylphosphine (58.7 mg, 0.21 mmol) $Pd_2(dba)_3$ (96 mg, 0.11 mmol) and heating at 135° C. for 30 min in a microwave. This gave after workup and purification by column chromatography [silica gel (24 g), eluting with DMA-80 in DCM from 0-70%] ethyl 5-(3-(aminomethyl)phenyl)-3-((2-(2-ethoxy-2-oxoethyl)phenoxy)methyl)benzo[b]thiophene-2-carboxylate (56c) (88 mg, 33% yield) as a clear oil; MS (ES+): 504.2 (M+1).

Step-3: Preparation of 5-(3-(aminomethyl)phenyl)-3-((2-(carboxymethyl)phenoxy)methyl)benzo[b]thiophene-2-carboxylic acid (56d)

Compound 56d was prepared according to the procedure reported in step-3 of scheme 1, from ethyl 5-(3-(aminomethyl)phenyl)-3-((2-(2-ethoxy-2-oxoethyl)phenoxy)methyl)benzo[b]thiophene-2-carboxylate (56c) (88 mg, 0.175 mmol) in THE (3 mL) using a solution of lithium hydroxide hydrate (135 mg, 3.22 mmol) in water (1 mL) and stirring overnight at room temperature. This gave after workup and purification by reverse phase column chromatography [C18 column (30 g), eluting with ACN in water (containing 0.1% HCl) from 0-100%] followed by flash column chromatography [silica (12 g), eluting with MeOH in DCM from 0-40%] 5-(3-(aminomethyl)phenyl)-3-((2-(carboxymethyl)phenoxy)methyl)benzo[b]thiophene-2-carboxylic acid (56d) (42 mg, 54% yield) as a white solid; $^1$H NMR (300 MHz, DMSO-$d_6$) δ 9.20 (s, 2H, $D_2O$ exchangeable), 8.17 (d, J=1.7 Hz, 1H), 8.04 (s, 1H), 7.94 (d, J=8.4 Hz, 1H), 7.75-7.69 (m, 1H), 7.66 (dd, J=8.4, 1.7 Hz, 1H), 7.49 (t, J=7.6 Hz, 1H), 7.41 (d, J=7.6 Hz, 1H), 7.30 (d, J=8.2 Hz, 1H), 7.19-7.06 (m, 2H), 6.83 (t, J=7.3 Hz, 1H), 5.85 (s, 2H), 4.12 (s, 2H), 3.42 (s, 2H); MS (ES+): 448.1 (M+1); Analysis calculated for $C_{25}H_{21}NO_5S \cdot 1.25H_2O$: C, 63.88; H, 5.04; N, 2.98. Found: C, 63.82; H, 4.88; N, 3.09.

Scheme 57

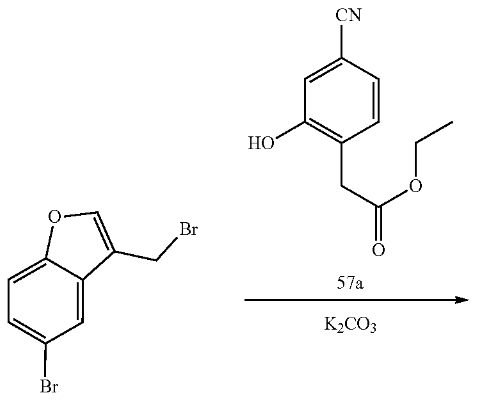

1a

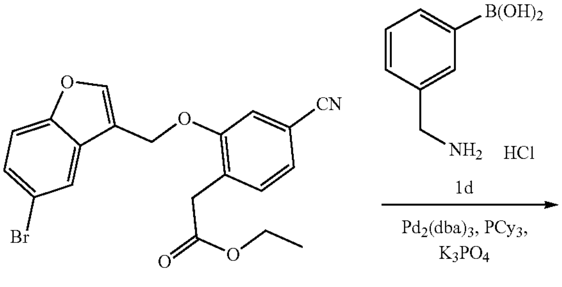

57b

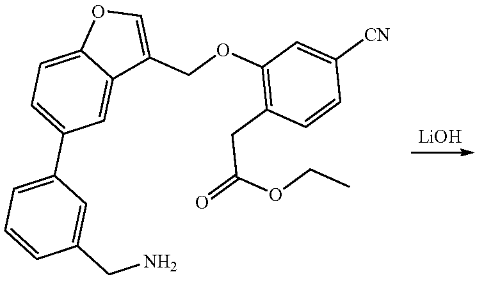

57c

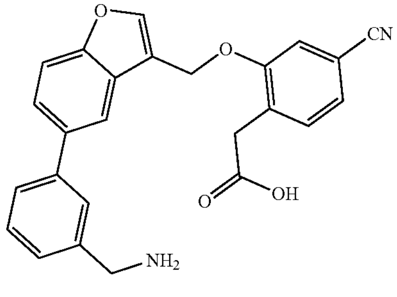

57d

Preparation of 2-(2-((5-(3-(aminomethyl)phenyl) benzofuran-3-yl)methoxy)-4-cyanophenyl)acetic acid (57d)

Step-1: Preparation of ethyl 2-(2-((5-bromobenzofuran-3-yl)methoxy)-4-cyanophenyl)acetate (57b)

Compound 57b was prepared according to the procedure reported in step-1 of scheme 1, from 5-bromo-3-(bromomethyl)benzofuran (1a) (300 mg, 1.035 mmol) in acetone (5 mL) using ethyl 2-(4-cyano-2-hydroxyphenyl)acetate (57a) (244 mg, 1.190 mmol), $K_2CO_3$ (500 mg, 3.62 mmol) and stirring overnight at room temperature. This gave after workup and purification by flash column chromatography [silica gel (12 g), eluting with EtOAc in hexane from 0-50%] ethyl 2-(2-((5-bromobenzofuran-3-yl)methoxy)-4-cyanophenyl)acetate (57b) (235 mg, 55% yield) as a white solid; $^1$H NMR (300 MHz, DMSO-$d_6$) δ 8.19 (s, 1H), 7.86 (d, J=2.0 Hz, 1H), 7.71 (s, 1H), 7.63 (d, J=8.7 Hz, 1H), 7.52 (dd, J=8.8, 2.1 Hz, 1H), 7.45 (s, 2H), 5.33 (s, 2H), 3.93 (q, J=7.1 Hz, 2H), 3.67 (s, 2H), 0.96 (t, J=7.1 Hz, 3H); MS (ES+): 447.9 (M+Cl).

Step-2: Preparation of ethyl 2-(2-((5-(3-(aminomethyl)phenyl)benzofuran-3-yl)methoxy)-4-cyanophenyl)acetate (57c)

Compound 57c was prepared according to the procedure reported in step-2 of scheme 1, from ethyl 2-(2-((5-bromobenzofuran-3-yl)methoxy)-4-cyanophenyl)acetate (57b) (235 mg, 0.57 mmol) in dioxane (3 mL) using 3-(aminomethyl)phenylboronic acid hydrochloride (1d) (159 mg, 0.85 mmol), 2 M solution of $K_3PO_4$ (0.48 mL, 0.96 mmol), tricyclohexylphosphine (63.6 mg, 0.23 mmol), $Pd_2(dba)_3$ (104 mg, 0.11 mmol) and heating at 135° C. for 30 min in a microwave. This gave after workup and purification by column chromatography [silica gel (24 g), eluting with DMA-80 in DCM from 0-70%] ethyl 2-(2-((5-(3-(aminomethyl)phenyl)benzofuran-3-yl)methoxy)-4-cyanophenyl)acetate (57c) (96 mg, 38% yield) as a clear oil; MS (ES+): 441.1 (M+1).

Step-3: Preparation of 2-(2-((5-(3-(aminomethyl) phenyl)benzofuran-3-yl)methoxy)-4-cyanophenyl) acetic acid (57d)

Compound 57d was prepared according to the procedure reported in step-3 of scheme 1, from ethyl 2-(2-((5-(3-(aminomethyl)phenyl)benzofuran-3-yl)methoxy)-4-cyanophenyl)acetate (57c) (96 mg, 0.218 mmol) in THF (3 mL) using a solution of lithium hydroxide hydrate (71 mg, 1.70 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)benzofuran-3-yl)methoxy)-4-cyanophenyl)acetic acid (57d) (15 mg, 6% yield) HCl salt as a white solid; $^1$H NMR (300 MHz, DMSO-$d_6$) δ 12.37 (s, 1H, $D_2O$ exchangeable), 8.36 (s, 3H, $D_2O$ exchangeable), 8.17 (s, 1H), 8.02 (d, J=1.8 Hz, 1H), 7.88 (t, J=1.8 Hz, 1H), 7.79-7.68 (m, 4H), 7.54 (t, J=7.6 Hz, 1H), 7.50-7.42 (m, 3H), 5.43 (s, 2H), 4.12 (s, 2H), 3.65 (s, 2H); MS (ES+): 413.1 (M+1); IR: 2228.9 $cm^1$.

Scheme 58

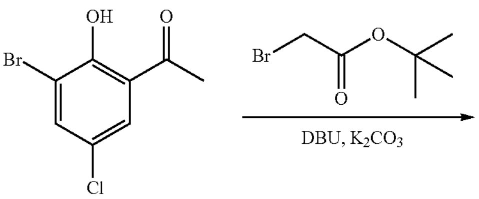

58a

-continued

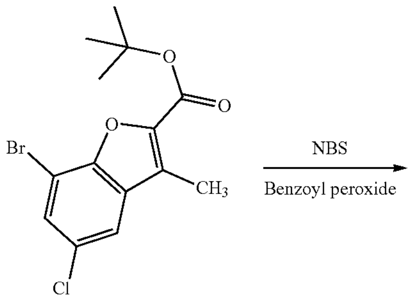

58b

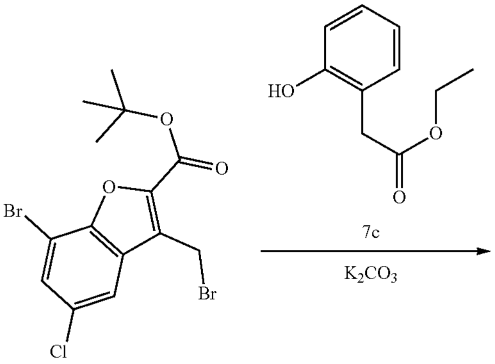

58c

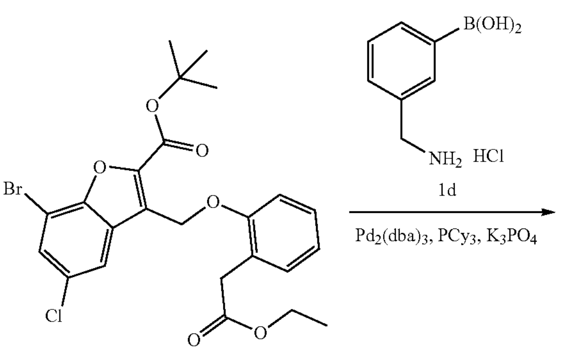

58d

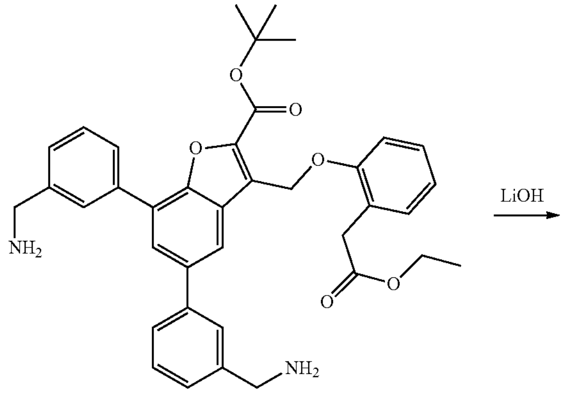

58e

-continued

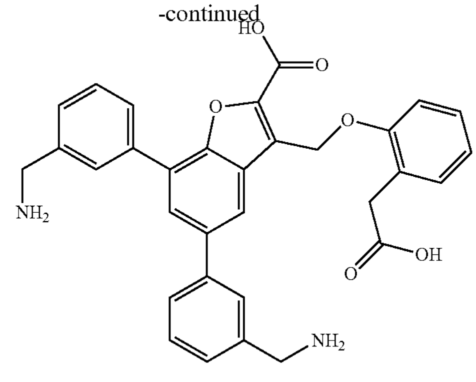

58f

Preparation of 5,7-bis(3-(aminomethyl)phenyl)-3-((2-(carboxymethyl)phenoxy)methyl)benzofuran-2-carboxylic acid (58f)

Step-1: Preparation of tert-butyl 7-bromo-5-chloro-3-methylbenzofuran-2-carboxylate (58b)

To a solution of 1-(3-bromo-5-chloro-2-hydroxyphenyl) ethanone (58a)(5 g, 20.04 mmol; CAS #59443-15-1) in DMF (50 mL) was added tert-butyl 2-bromoacetate (4.30 g, 22.05 mmol), $K_2CO_3$ (4.15 g, 30.1 mmol) and stirred for 2 h at 50° C. To this mixture was added DBU (6.04 mL, 40.1 mmol) heated at 100° C. for 3 h, quenched with a cold solution of 1N HCl (50 mL) and extracted with EtOAc (3×). The Combined organic layers were washed with water, brine, dried, filtered and concentrated in vacuum. The obtained residue was purified by flash column chromatography [silica gel (24 g), eluting with EtOAc in DCM from 0-70%] to give tert-butyl 7-bromo-5-chloro-3-methylbenzofuran-2-carboxylate (58b) (4.1 g, 59% yield) as a white solid; $^1$H NMR (300 MHz, DMSO-$d_6$) δ 7.97 (d, J=1.9 Hz, 1H), 7.87 (d, J=1.9 Hz, 1H), 2.49 (s, 3H), 1.59 (s, 9H).

Step-2: Preparation of tert-butyl 7-bromo-3-(bromomethyl)-5-chlorobenzofuran-2-carboxylate (58c)

To a solution of tert-butyl 7-bromo-5-chloro-3-methylbenzofuran-2-carboxylate (58b) (300 mg, 0.868 mmol) in carbon tetrachloride (10 mL) was added NBS (170 mg, 0.955 mmol) and benzoyl peroxide (31.5 mg, 0.130 mmol). The reaction mixture was heated at reflux for 24 h.

The solid was removed by filtration and washed with $CH_2Cl_2$. The filtrate was concentrated in vacuum and the obtained residue was purified by flash column chromatography [silica gel (12 g), eluting with EtOAc in hexane from 5-10%] to give tert-butyl 7-bromo-3-(bromomethyl)-5-chlorobenzofuran-2-carboxylate (58c) (350 mg, 0.824 mmol, 95% yield) as a clear oil; $^1$HNMR (300 MHz, DMSO-$d_6$) δ 8.11 (d, J=2.0 Hz, 1H), 7.95 (d, J=2.0 Hz, 1H), 5.07 (s, 2H), 1.62 (s, 9H).

Step-3: Preparation of tert-butyl 7-bromo-5-chloro-3-((2-(2-ethoxy-2-oxoethyl)phenoxy)methyl)benzofuran-2-carboxylate (58d)

Compound 58d was prepared according to the procedure reported in step-1 of scheme 1, from tert-butyl 7-bromo-3-(bromomethyl)-5-chlorobenzofuran-2-carboxylate (58c)(3 g, 7.07 mmol) in acetone (30 mL) using ethyl 2-(2-hydroxyphenyl)acetate (7c) (1.464 g, 8.13 mmol), $K_2CO_3$ (3.42 g, 24.73 mmol) and stirring overnight at room temperature. This gave after workup and purification by flash column chromatography [silica gel (12 g), eluting with EtOAc in hexane from 0-50%] tert-butyl 7-bromo-5-chloro-3-((2-(2-ethoxy-2-oxoethyl)phenoxy)methyl)benzofuran-2-carboxylate (58d) (1.7 g, 46% yield) as a yellow oil; H NMR (300 MHz, DMSO-$d_6$) δ 7.97-7.91 (m, 2H), 7.30 (td, J=7.7, 1.7 Hz, 1H), 7.22 (dd, J=7.5, 1.7 Hz, 1H), 7.15 (dd, J=8.3, 1.1 Hz, 1H), 6.95 (td, J=7.4, 1.1 Hz, 1H), 5.54 (s, 2H), 3.89 (q, J=7.1 Hz, 2H), 3.56 (s, 2H), 1.56 (s, 9H), 0.95 (t, J=7.1 Hz, 3H); MS (ES+): 544.90 (M+Na).

Step-4: Preparation of tert-butyl 5,7-bis(3-(aminomethyl)phenyl)-3-((2-(2-ethoxy-2-oxoethyl)phenoxy)methyl)benzofuran-2-carboxylate (58e)

Compound 58e was prepared according to the procedure reported in step-2 of scheme 1, from tert-butyl 7-bromo-5-chloro-3-((2-(2-ethoxy-2-oxoethyl)phenoxy)methyl)benzofuran-2-carboxylate (58d) (500 mg, 0.955 mmol) in dioxane (3 mL) using 3-(aminomethyl)phenylboronic acid hydrochloride (1d) (492 mg, 2.63 mmol), 2 M solution of $K_3PO_4$ (0.811 mL, 1.623 mmol), tricyclohexylphosphine (107 mg, 0.382 mmol), $Pd_2(dba)_3$ (175 mg, 0.191 mmol) and heating at 135° C. for 30 min in a microwave. This gave after workup and purification by column chromatography [silica (24 g), eluting with DMA80 in DCM from 0-70%] tert-butyl 5,7-bis(3-(aminomethyl)phenyl)-3-((2-(2-ethoxy-2-oxoethyl)phenoxy)methyl)benzofuran-2-carboxylate (58e) (85 mg, 14% yield) as a clear oil; MS (ES+): 621.2 (M+1).

Step-5: Preparation of 5,7-bis(3-(aminomethyl)phenyl)-3-((2-(carboxymethyl)phenoxy)methyl)benzofuran-2-carboxylic acid (58f)

Compound 58f was prepared according to the procedure reported in step-3 of scheme 1, from tert-butyl 5,7-bis(3-(aminomethyl)phenyl)-3-((2-(2-ethoxy-2-oxoethyl)phenoxy)methyl)benzofuran-2-carboxylate (58e) (85 mg, 0.137 mmol) in THE (3 mL) using a solution of lithium hydroxide hydrate (120 mg, 2.86 mmol) in water (1 mL) and heating at 60° C. for 1 h. This gave after workup and purification by reverse phase column chromatography [C18 column (30 g), eluting with ACN in water (containing 0.1% HCl) from 0-100%] 5,7-bis(3-(aminomethyl)phenyl)-3-((2-(carboxymethyl)phenoxy)methyl)benzofuran-2-carboxylic acid (58f) HCl salt (37.5 mg, 51% yield) as a white solid; $^1H$ NMR (300 MHz, DMSO-$d_6$) δ 8.55 (s, 6H, $D_2O$ exchangeable), 8.23 (s, 1H), 8.21-8.11 (m, 3H), 8.08 (d, J=7.5 Hz, 1H), 7.85 (d, J=7.4 Hz, 1H), 7.68-7.45 (m, 4H), 7.30-7.17 (m, 3H), 6.93 (t, J=6.7 Hz, 1H), 5.73 (s, 2H), 4.16 (d, J=9.0 Hz, 4H), 3.57 (s, 2H); MS (ES+): 537.1 (M+1); (ES−): 535.1 (M−1); Analysis calculated for $C_{32}H_{28}N_2O_6 \cdot 2HCl \cdot 2.5H_2O$: C, 58.72; H, 5.39; Cl, 10.83; N, 4.28. Found: C, 58.69; H, 5.29; Cl, 10.50; N, 4.62.

Scheme 59

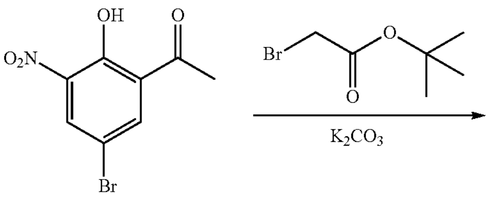

59a

-continued

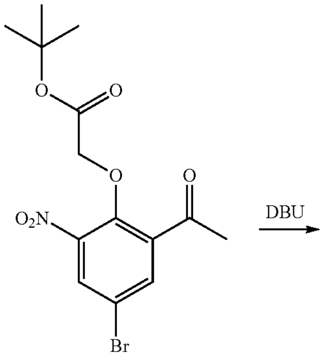

59b

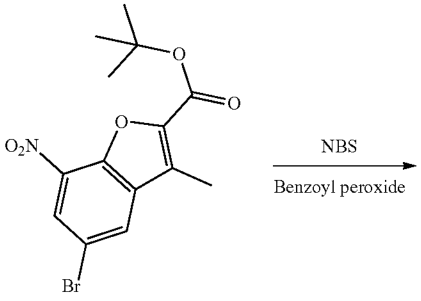

59c

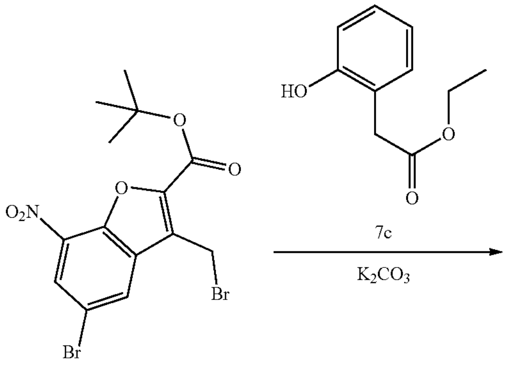

59d

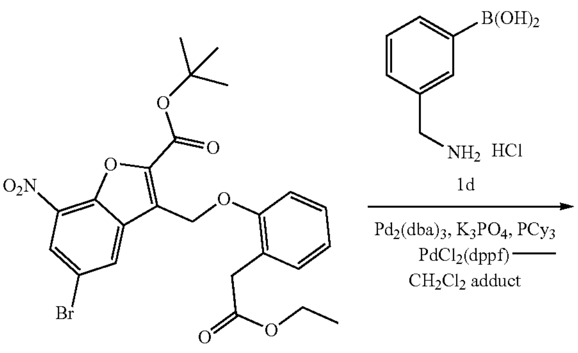

59e

-continued

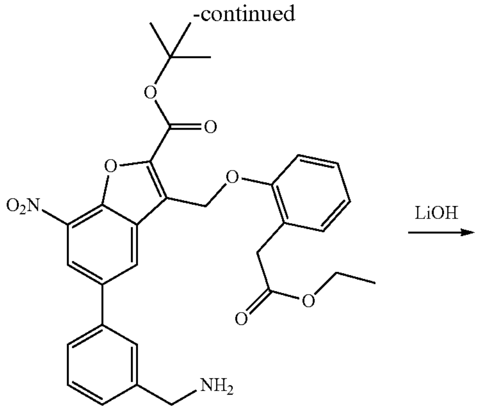

59f

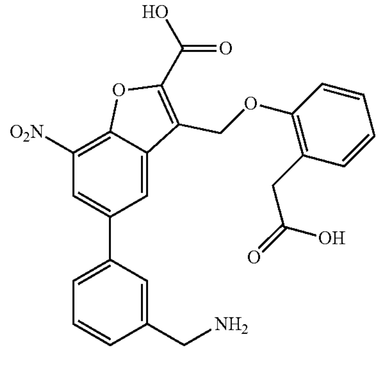

59g

Preparation of 5-(3-(aminomethyl)phenyl)-3-((2-(carboxymethyl)phenoxy)methyl)-7-nitrobenzofuran-2-carboxylic acid (59g)

Step-1: Preparation of tert-butyl 2-(2-acetyl-4-bromo-6-nitrophenoxy)acetate (59b)

To a solution of 1-(5-bromo-2-hydroxy-3-nitrophenyl) ethanone (59a) (5 g, 19.23 mmol; CAS #70978-54-0) in DMF (50 mL) was added tert-butyl 2-bromoacetate (4.50 g, 23.07 mmol), $K_2CO_3$ (3.99 g, 28.8 mmol) and heated for 3 h at 50° C. The reaction mixture was cooled to room temperature, diluted with EtOAc (300 mL), washed with water (3×), brine, dried, filtered and concentrated in vacuum. The obtained residue was purified by flash column chromatography [silica gel (40 g), eluting with EtOAc in hexane from 0-100%] to give tert-butyl 2-(2-acetyl-4-bromo-6-nitrophenoxy)acetate (59b) (5.9 g, 82% yield) as a yellow oil; H NMR (300 MHz, DMSO-$d_6$) δ 8.37 (d, J=2.5 Hz, 1H), 8.13 (d, J=2.5 Hz, 1H), 4.56 (s, 2H), 2.62 (s, 3H), 1.40 (s, 9H).

Step-2: Preparation of tert-butyl 5-bromo-3-methyl-7-nitrobenzofuran-2-carboxylate (59c)

To a solution of tert-butyl 2-(2-acetyl-4-bromo-6-nitrophenoxy)acetate (59b) (2.67 g, 7.14 mmol) in DMF (15 mL) was added DBU (1.613 mL, 10.70 mmol) and heated for 3 h at 120° C. The mixture was cooled to room temperature, diluted with EtOAc (300 mL), washed with water (3×), brine, dried, filtered and concentrated in vacuum. The obtained residue was purified by flash column chromatography [silica gel (40 g), eluting with EtOAc in hexane from 0-100%] to give tert-butyl 5-bromo-3-methyl-7-nitrobenzofuran-2-carboxylate (59c) (1.6 g, 63% yield) as a yellow solid; $^1$H NMR (300 MHz, DMSO-$d_6$) δ 8.58 (d, J=1.9 Hz, 1H), 8.43 (d, J=1.9 Hz, 1H), 2.55 (s, 3H), 1.60 (s, 9H).

Step-3: Preparation of tert-butyl 5-bromo-3-(bromomethyl)-7-nitrobenzofuran-2-carboxylate (59d)

Compound 59d was prepared according to the procedure reported in step-2 of scheme 58, from tert-butyl 5-bromo-3-methyl-7-nitrobenzofuran-2-carboxylate (59c) (500 mg, 1.404 mmol) in carbon tetrachloride (10 mL) using NBS (300 mg, 1.685 mmol), benzoyl peroxide (51.0 mg, 0.211 mmol) and refluxing for 30 h. This gave after workup and purification by flash column chromatography [silica gel (12 g), eluting with EtOAc in hexane from 0-100%] tert-butyl 5-bromo-3-(bromomethyl)-7-nitrobenzofuran-2-carboxylate (59d) (284 mg, 47% yield) as a white solid; $^1$H NMR (300 MHz, DMSO-$d_6$) δ 8.72 (d, J=1.9 Hz, 1H), 8.51 (d, J=1.9 Hz, 1H), 5.13 (s, 2H), 1.63 (s, 9H); MS (ES+): 455.80 (M+Na).

Step-4: Preparation of tert-butyl 5-bromo-3-((2-(2-ethoxy-2-oxoethyl)phenoxy)methyl)-7-nitrobenzofuran-2-carboxylate (59e)

Compound 59e was prepared according to the procedure reported in step-1 of scheme 1, from tert-butyl 5-bromo-3-(bromomethyl)-7-nitrobenzofuran-2-carboxylate (59d) (1 g, 2.29 mmol) in acetone (10 mL) using ethyl 2-(2-hydroxyphenyl)acetate (7c) (0.476 g, 2.64 mmol), $K_2CO_3$ (1.11 g, 8.04 mmol) and stirring overnight at room temperature. This gave after workup and purification by flash column chromatography [silica gel (12 g), eluting with EtOAc in hexane from 0-50%] tert-butyl 5-bromo-3-((2-(2-ethoxy-2-oxoethyl)phenoxy)methyl)-7-nitrobenzofuran-2-carboxylate (59e) (1.05 g, 85% yield) as a clear oil; $^1$H NMR (300 MHz, DMSO-$d_6$) δ 8.54 (d, J=1.9 Hz, 1H), 8.50 (d, J=1.9 Hz, 1H), 7.35-7.26 (m, 1H), 7.26-7.14 (m, 2H), 7.01-6.91 (m, 1H), 5.60 (s, 2H), 3.91 (q, J=7.1 Hz, 2H), 3.53 (s, 2H), 1.57 (s, 9H), 0.98 (t, J=7.1 Hz, 3H); MS (ES+): 555.9 and 558.0 (M+Na).

Step-5: Preparation of tert-butyl 5-(3-(aminomethyl) phenyl)-3-((2-(2-ethoxy-2-oxoethyl)phenoxy) methyl)-7-nitrobenzofuran-2-carboxylate (59f)

Compound 59f was prepared according to the procedure reported in step-8 of scheme 3, from tert-butyl 5-bromo-3-((2-(2-ethoxy-2-oxoethyl)phenoxy)methyl)-7-nitrobenzofuran-2-carboxylate (59e) (295 mg, 0.552 mmol) in dioxane/THF (5 mL, 1:1) using 3-(aminomethyl)phenylboronic acid hydrochloride (1d) (207 mg, 1.104 mmol), 2 M solution of $K_3PO_4$ (1.104 mL, 2.208 mmol), tricyclohexylphosphine (46.4 mg, 0.166 mmol), $Pd_2(dba)_3$ (50.6 mg, 0.055 mmol), $PdCl_2(dppf)$-$CH_2Cl_2$ adduct (45 mg, 0.055 mmol) and heating at 90° C. for 1 h. This gave after workup and purification by flash column chromatography [silica gel (24 g), eluting with DMA-80 in DCM from 0-70%] tert-butyl 5-(3-(aminomethyl)phenyl)-3-((2-(2-ethoxy-2-oxoethyl)phenoxy) methyl)-7-nitrobenzofuran-2-carboxylate (59f) (202 mg, 65% yield) as a yellow semi-solid; $^1$H NMR (300 MHz, DMSO-$d_6$) δ 8.58 (s, 2H), 7.79 (s, 1H), 7.67 (d, J=7.5 Hz, 1H), 7.59-7.53 (m, 1H), 7.53-7.45 (m, 2H), 7.45-7.39 (m, 1H), 7.36-7.27 (m, 1H), 7.26-7.18 (m, 2H), 6.95 (t, J=7.3 Hz, 1H), 5.67 (s, 2H), 3.82 (s, 2H), 3.65 (q, J=6.5, 6.0 Hz, 2H), 3.54 (s, 2H), 1.58 (s, 9H), 0.81 (t, J=7.1 Hz, 3H); MS (ES+): 561.1 (M+1); (ES−): 559.1 (M−1).

Step-6: Preparation of 5-(3-(aminomethyl)phenyl)-3-((2-(carboxymethyl)phenoxy)methyl)-7-nitrobenzofuran-2-carboxylic acid (59g)

Compound 59g was prepared according to the procedure reported in step-3 of scheme 1, from tert-butyl 5-(3-(aminomethyl)phenyl)-3-((2-(2-ethoxy-2-oxoethyl)phenoxy)methyl)-7-nitrobenzofuran-2-carboxylate (59f) (202 mg, 0.360 mmol) in THF (3 mL) using a solution of lithium hydroxide hydrate (70 mg, 1.656 mmol) in water (1 mL) and stirring at 50° C. for 2 h. This gave after workup and purification by reverse phase column chromatography [C18 column (30 g), eluting with ACN in water (containing 0.1% HCl) from 0-100%] 5-(3-(aminomethyl)phenyl)-3-((2-(carboxymethyl)phenoxy)methyl)-7-nitrobenzofuran-2-carboxylic acid (59g) HCl salt (35 mg, 13% yield) as a white solid; $^{1}$H NMR (300 MHz, DMSO-$d_6$) δ 12.32 (s, 1H, $D_2O$ exchangeable), 8.59 (d, J=2.1 Hz, 2H), 8.49 (s, 3H, $D_2O$ exchangeable), 7.99 (s, 1H), 7.89-7.81 (m, 1H), 7.57 (d, J=4.9 Hz, 2H), 7.29-7.16 (m, 3H), 6.93 (td, J=7.1, 1.8 Hz, 1H), 5.73 (s, 2H), 4.14 (s, 2H), 3.52 (s, 2H); MS (ES+): 477.0 (M+1); (ES−): 475.0 (M−1); Analysis calculated for $C_{25}H_{20}N_2O_8 \cdot 0.9HCl \cdot 1.25H_2O$: C, 56.47; H, 4.44; Cl, 6.00; N, 5.27. Found: C, 56.21; H, 4.50; Cl, 5.99; N, 5.11.

Scheme 60

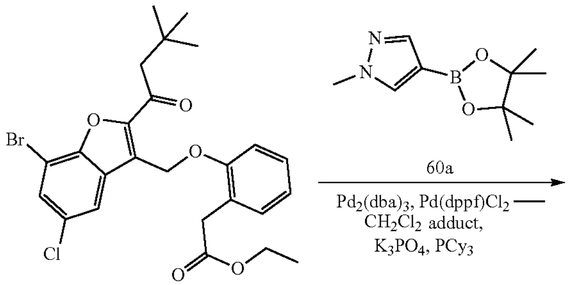

58d

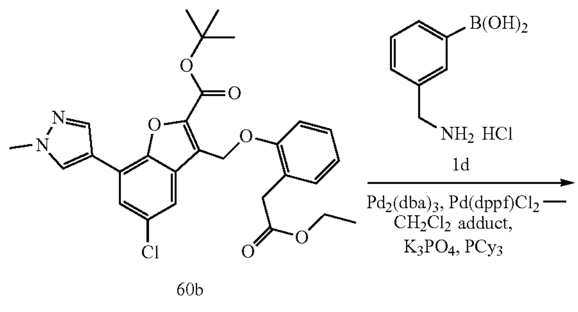

60b

-continued

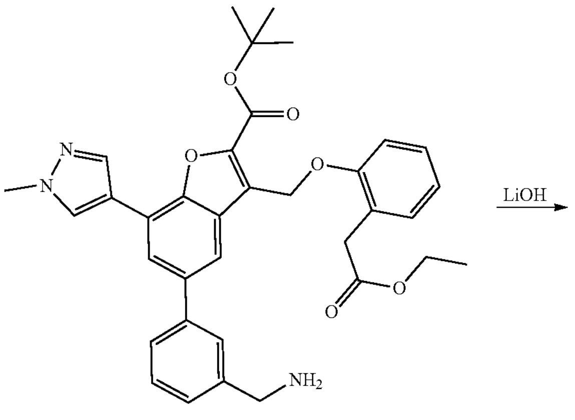

60c

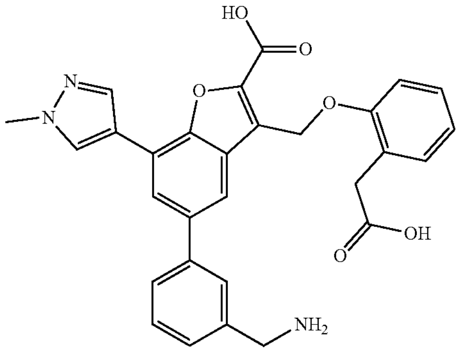

60d

Preparation of 5-(3-(aminomethyl)phenyl)-3-((2-(carboxymethyl)phenoxy)methyl)-7-(1-methyl-1H-pyrazol-4-yl)benzofuran-2-carboxylic acid (60d)

Step-1: Preparation of tert-butyl 5-chloro-3-((2-(2-ethoxy-2-oxoethyl)phenoxy)methyl)-7-(1-methyl-1H-pyrazol-4-yl)benzofuran-2-carboxylate (60b)

Compound 60b was prepared according to the procedure reported in step-8 of scheme 3, from tert-butyl 7-bromo-5-chloro-3-((2-(2-ethoxy-2-oxoethyl)phenoxy)methyl)benzofuran-2-carboxylate (58d) (980 mg, 1.871 mmol) in THF (10 mL) using 1-methyl-4-(4,4,5,5-tetramethyl-1,3,2-dioxaborolan-2-yl)-1H-pyrazole (60a) (1.17 g, 5.61 mmol; CAS #761446-44-0), 2 M solution of $K_3PO_4$ (3.74 mL, 7.48 mmol), tricyclohexylphosphine (105 mg, 0.374 mmol), $Pd_2(dba)_3$ (171 mg, 0.187 mmol), $PdCl_2(dppf)$-$CH_2Cl_2$ adduct (153 mg, 0.187 mmol) and heating at 80° C. for 2 h. This gave after workup and purification by flash column chromatography [silica gel (24 g), eluting with DMA-80 in DCM from 0-70%] tert-butyl 5-chloro-3-((2-(2-ethoxy-2-oxoethyl)phenoxy)methyl)-7-(1-methyl-1H-pyrazol-4-yl)benzofuran-2-carboxylate (60b) (729 mg, 74% yield) as a yellow oil; $^{1}$H NMR (300 MHz, DMSO-$d_6$) δ 8.41 (s, 1H), 8.22 (s, 1H), 7.90 (d, J=2.0 Hz, 1H), 7.71 (d, J=2.0 Hz, 1H), 7.30 (td, J=7.8, 7.4, 1.7 Hz, 1H), 7.25-7.14 (m, 2H), 6.95 (t, J=7.4 Hz, 1H), 5.56 (s, 2H), 3.95 (s, 3H), 3.90 (q, J=7.0 Hz, 2H), 3.56 (s, 2H), 1.59 (s, 9H), 0.95 (t, J=7.1 Hz, 3H); MS (ES+): 525.0 and 527.0 (M+1).

Step-2: Preparation of tert-butyl 5-(3-(aminomethyl)phenyl)-3-((2-(2-ethoxy-2-oxoethyl)phenoxy)methyl)-7-(1-methyl-1H-pyrazol-4-yl)benzofuran-2-carboxylate (60c)

Compound 60c was prepared according to the procedure reported in step-8 of scheme 3, from tert-butyl 5-chloro-3-((2-(2-ethoxy-2-oxoethyl)phenoxy)methyl)-7-(1-methyl-1H-pyrazol-4-yl)benzofuran-2-carboxylate (60b) (361 mg, 0.688 mmol) in dioxane/THF (6 mL, 1:1) using 3-(aminomethyl)phenylboronic acid hydrochloride (1d) (322 mg, 1.719 mmol), 2 M solution of $K_3PO_4$ (1.375 mL, 2.75 mmol), tricyclohexylphosphine (77 mg, 0.275 mmol), $Pd_2(dba)_3$ (94 mg, 0.103 mmol), $PdCl_2(dppf)$-$CH_2Cl_2$ adduct (84 mg, 0.103 mmol) and heating at 125° C. for 4 h. This gave after workup and purification by flash column chromatography [silica gel (24 g), eluting with DMA-80 in DCM from 0-70%] tert-butyl 5-(3-(aminomethyl)phenyl)-3-((2-(2-ethoxy-2-oxoethyl)phenoxy)methyl)-7-(1-methyl-1H-pyrazol-4-yl)benzofuran-2-carboxylate (60c) (156 mg, 38% yield) as a clear oil; MS (ES+): 596.1 (M+1).

Step-3: Preparation of 5-(3-(aminomethyl)phenyl)-3-((2-(carboxymethyl)phenoxy)methyl)-7-(1-methyl-1H-pyrazol-4-yl)benzofuran-2-carboxylic acid (60d)

Compound 60d was prepared according to the procedure reported in step-3 of scheme 1, from tert-butyl 5-(3-(aminomethyl)phenyl)-3-((2-(2-ethoxy-2-oxoethyl)phenoxy)methyl)-7-(1-methyl-1H-pyrazol-4-yl)benzofuran-2-carboxylate (60c) (156 mg, 0.262 mmol,) in THF (3 mL) using a solution of lithium hydroxide hydrate (43 mg, 1.031 mmol) in water (1 mL) and heating for 3 h at 50° C. This gave after workup and purification by reverse phase column chromatography [C18 column (30 g), eluting with ACN in water (containing 0.1% HCl) from 0-100%] followed by flash column chromatography [silica gel (12 g), eluting with MeOH in DCM from 0-40%] 5-(3-(aminomethyl)phenyl)-3-((2-(carboxymethyl)phenoxy)methyl)-7-(1-methyl-1H-pyrazol-4-yl)benzofuran-2-carboxylic acid (60d) (36 mg, 10% yield) HCl salt as a white solid; $^1H$ NMR (300 MHz, DMSO-$d_6$) δ 14.12 (s, 1H, $D_2O$ exchangeable), 12.15 (s, 1H, $D_2O$ exchangeable), 8.46 (s, 1H), 8.36 (s, 3H, $D_2O$ exchangeable), 8.27 (s, 1H), 8.14 (d, J=1.7 Hz, 1H), 8.00-7.93 (m, 2H), 7.82 (d, J=7.6 Hz, 1H), 7.54 (t, J=7.6 Hz, 1H), 7.48 (d, J=7.6 Hz, 1H), 7.30-7.18 (m, 3H), 6.98-6.88 (m, 1H), 5.70 (s, 2H), 4.17-4.08 (m, 2H), 3.98 (s, 3H), 3.55 (s, 2H); MS (ES+): 512.1 (M+1); (ES−): 510.1 (M−1); Analysis calculated for $C_{29}H_{25}N_3O_6 \cdot 1.25HCl \cdot 2.25H_2O$: C, 58.28; H, 5.19; Cl, 7.42; N, 7.03. Found: C, 58.37; H, 5.43; Cl, 7.47; N, 7.02.

Scheme 61

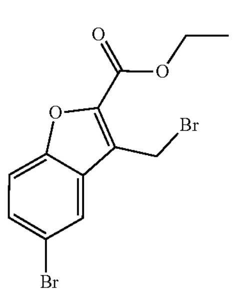

55a

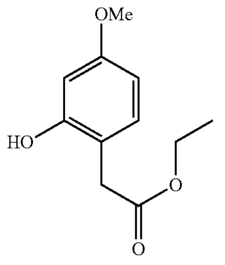

6a

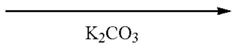

-continued

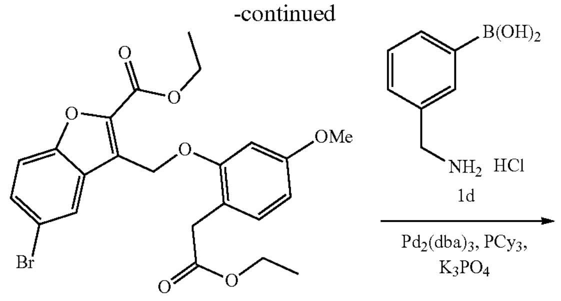

61b

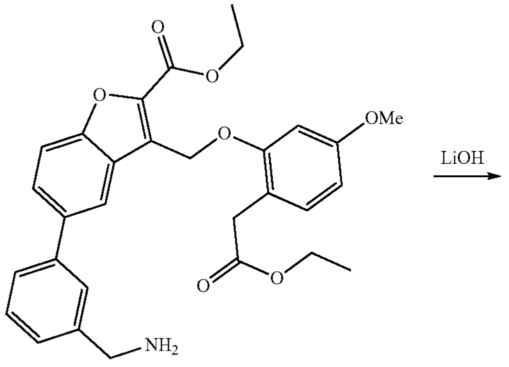

61c

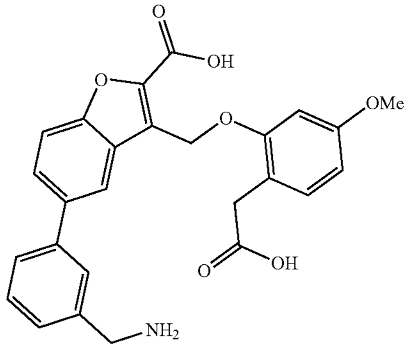

61d

Preparation of 5-(3-(aminomethyl)phenyl)-3-((2-(carboxymethyl)-5-methoxyphenoxy)methyl)benzofuran-2-carboxylic acid (61d)

Step-1: Preparation of ethyl 5-bromo-3-((2-(2-ethoxy-2-oxoethyl)-5-methoxyphenoxy)methyl)benzofuran-2-carboxylate (61b)

Compound 61b was prepared according to the procedure reported in step-1 of scheme 1, from ethyl 5-bromo-3-(bromomethyl)benzofuran-2-carboxylate (55a) (500 mg, 1.381 mmol; CAS #76322-29-7) in acetone (10 mL) using ethyl 2-(2-hydroxy-4-methoxyphenyl)acetate (6a) (334 mg, 1.588 mmol), $K_2CO_3$ (668 mg, 4.83 mmol) and stirring overnight at room temperature. This gave after workup and purification by flash column chromatography [silica gel (12 g), eluting with EtOAc in hexane from 0-50%] ethyl 5-bromo-3-((2-(2-ethoxy-2-oxoethyl)-5-methoxyphenoxy)methyl)benzofuran-2-carboxylate (61b) (320 mg, 47% yield) as a clear oil; $^1H$ NMR (300 MHz, DMSO-$d_6$) δ 8.04

(d, J=1.9 Hz, 1H), 7.79-7.68 (m, 2H), 7.10 (d, J=8.3 Hz, 1H), 6.74 (d, J=2.4 Hz, 1H), 6.51 (dd, J=8.3, 2.4 Hz, 1H), 5.58 (s, 2H), 4.39 (q, J=7.1 Hz, 2H), 3.89 (q, J=7.1 Hz, 2H), 3.75 (s, 3H), 3.46 (s, 2H), 1.32 (t, J=7.1 Hz, 3H), 0.95 (t, J=7.1 Hz, 3H); MS (ES+): 491.0 and 493.1 (M+1).

Step-2: Preparation of ethyl 5-(3-(aminomethyl) phenyl)-3-((2-(2-ethoxy-2-oxoethyl)-5-methoxyphenoxy)methyl)benzofuran-2-carboxylate (61c)

Compound 61c was prepared according to the procedure reported in step-2 of scheme 1, from ethyl 5-bromo-3-((2-(2-ethoxy-2-oxoethyl)-5-methoxyphenoxy)methyl)benzofuran-2-carboxylate (61b) (320 mg, 0.651 mmol) in dioxane (3 mL) using 3-(aminomethyl)phenylboronic acid hydrochloride (1d) (183 mg, 0.977 mmol), 2 M solution of $K_3PO_4$ (0.554 mL, 1.107 mmol), tricyclohexylphosphine (73.1 mg, 0.261 mmol), $Pd_2(dba)_3$ (119 mg, 0.130 mmol) and heating at 135° C. for 30 min in a microwave. This gave after workup and purification by column chromatography [silica gel (24 g), eluting with DMA-80 in DCM from 0-70%] ethyl 5-(3-(aminomethyl)phenyl)-3-((2-(2-ethoxy-2-oxoethyl)-5-methoxyphenoxy)methyl)benzofuran-2-carboxylate (61c) (134 mg, 40% yield) as a clear oil; MS (ES+): 518.1 (M+1).

Step-3: Preparation of 5-(3-(aminomethyl)phenyl)-3-((2-(carboxymethyl)-5-methoxyphenoxy)methyl) benzofuran-2-carboxylic acid (61d)

Compound 61d was prepared according to the procedure reported in step-3 of scheme 1, from ethyl 5-(3-(aminomethyl)phenyl)-3-((2-(2-ethoxy-2-oxoethyl)-5-methoxyphenoxy)methyl)benzofuran-2-carboxylate (61c) (134 mg, 0.259 mmol) in THF (3 mL) using a solution of lithium hydroxide hydrate (168 mg, 4.01 mmol) in water (1 mL) and stirring overnight at RT. This gave after workup and purification by reverse phase column chromatography [C18 column (30 g), eluting with ACN in water (containing 0.1% HCl) from 0-100%] 5-(3-(aminomethyl)phenyl)-3-((2-(carboxymethyl)-5-methoxyphenoxy)methyl) benzofuran-2-carboxylic acid (61d) (16 mg, 5% yield) HCl salt as a white solid; $^1H$ NMR (300 MHz, DMSO-$d_6$) δ 14.14 (s, 1H, $D_2O$ exchangeable), 12.10 (s, 1H, $D_2O$ exchangeable), 8.32 (s, 3H, $D_2O$ exchangeable), 8.13 (s, 1H), 7.85 (d, J=4.3 Hz, 3H), 7.74 (d, J=7.6 Hz, 1H), 7.60-7.43 (m, 2H), 7.08 (d, J=8.3 Hz, 1H), 6.79 (d, J=2.4 Hz, 1H), 6.49 (dd, J=8.3, 2.3 Hz, 1H), 5.69 (s, 2H), 4.12 (s, 2H), 3.73 (s, 3H), 3.45 (s, 2H); MS (ES+): 462.1 (M+1); (ES−): 460.0 (M−1).

Scheme 62

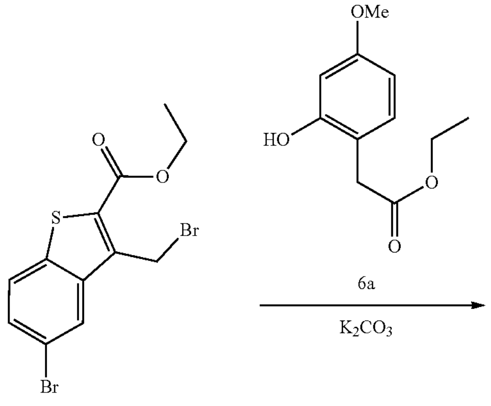

56a

-continued

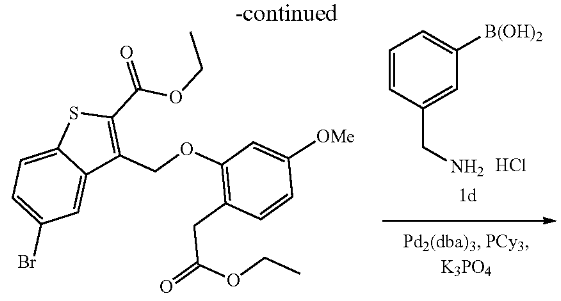

62a

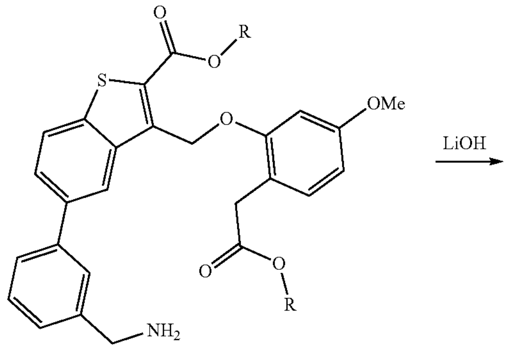

R = Me or Et
62b

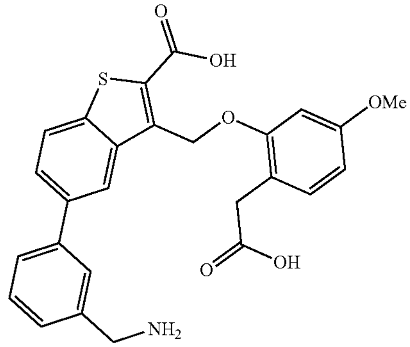

62c

Preparation of 5-(3-(aminomethyl)phenyl)-3-((2-(carboxymethyl)-5-methoxyphenoxy)methyl)benzo [b]thiophene-2-carboxylic acid (62c)

Step-1: Preparation of ethyl 5-bromo-3-((2-(2-ethoxy-2-oxoethyl)-5-methoxyphenoxy)methyl) benzo[b]thiophene-2-carboxylate (62a)

Compound 62a was prepared according to the procedure reported in step-1 of scheme 1, from ethyl 5-bromo-3-(bromomethyl)benzo[b]thiophene-2-carboxylate (56a) (650 mg, 1.719 mmol) in acetone (12 mL) using ethyl 2-(2-hydroxy-4-methoxyphenyl)acetate (6a) (416 mg, 1.977 mmol), $K_2CO_3$ (832 mg, 6.02 mmol) and stirring overnight at room temperature. This gave after workup and purification by flash column chromatography [silica gel (12 g), eluting with EtOAc in hexane from 0-50%] ethyl 5-bromo-3-((2-(2-ethoxy-2-oxoethyl)-5-methoxyphenoxy)methyl) benzo[b]thiophene-2-carboxylate (62a) (375 mg, 43% yield) as a white solid; MS (ES+): 507.0 and 509.0 (M+1).

Step-2: Preparation of ethyl 5-(3-(aminomethyl) phenyl)-3-((2-(2-ethoxy-2-oxoethyl)-5-methoxyphenoxy)methyl)benzo[b]thiophene-2-carboxylate (62b)

Compound 62b was prepared according to the procedure reported in step-2 of scheme 1, from ethyl 5-bromo-3-((2-(2-ethoxy-2-oxoethyl)-5-methoxyphenoxy)methyl)benzo[b] thiophene-2-carboxylate (62a) (375 mg, 0.739 mmol) in dioxane (3 mL) using 3-(aminomethyl)phenylboronic acid hydrochloride (1d) (208 mg, 1.109 mmol), 2 M solution of $K_3PO_4$ (0.628 mL, 1.256 mmol), tricyclohexylphosphine (83 mg, 0.296 mmol), $Pd_2(dba)_3$ (135 mg, 0.148 mmol) and heating at 135° C. for 30 min in a microwave. This gave after workup and purification by flash column chromatography [silica gel (24 g), eluting with DMA-80 in DCM from 0-70%] mixtures containing ethyl 5-(3-(aminomethyl)phenyl)-3-((5-methoxy-2-(2-methoxy-2-oxoethyl)phenoxy) methyl)benzo[b]thiophene-2-carboxylate and methyl/ethyl 5-(3-(aminomethyl)phenyl)-3-((2-(2-ethoxy-2-oxoethyl)-5-methoxyphenoxy)methyl)benzo[b]thiophene-2-carboxylate (62b) (86 mg, 23% yield) as a clear oil, MS (ES+): 520.1 (M+1).

Step-3: Preparation of 5-(3-(aminomethyl)phenyl)-3-((2-(carboxymethyl)-5-methoxyphenoxy)methyl) benzo[b]thiophene-2-carboxylic acid (62c)

Compound 62c was prepared according to the procedure reported in step-3 of scheme 1, from ethyl 5-(3-(aminomethyl)phenyl)-3-((2-(2-ethoxy-2-oxoethyl)-5-methoxyphenoxy)methyl)benzo[b]thiophene-2-carboxylate (62b) (201 mg, 0.468 mmol) in THE (3 mL) using a solution of lithium hydroxide hydrate (119 mg, 2.83 mmol) in water (1 mL) and stirring overnight at room temperature. This gave after workup and purification by reverse phase column chromatography [C18 column (30 g), eluting with ACN in water (containing 0.1% HCl) from 0-100%] 5-(3-(aminomethyl) phenyl)-3-((2-(carboxymethyl)-5-methoxyphenoxy)methyl) benzo[b]thiophene-2-carboxylic acid (62c) (5 mg, 1.4% yield) HCl salt as a white solid; $^1$H NMR (300 MHz, DMSO-$d_6$) δ 14.03 (s, 1H, $D_2O$ exchangeable), 12.05 (s, 1H, $D_2O$ exchangeable), 8.36 (d, J=1.7 Hz, 1H), 8.30 (s, 2H, $D_2O$ exchangeable), 8.19 (d, J=8.5 Hz, 1H), 7.93-7.86 (m, 2H), 7.80 (d, J=7.6 Hz, 1H), 7.60-7.45 (m, 2H), 7.06 (d, J=8.3 Hz, 1H), 6.88 (d, J=2.4 Hz, 1H), 6.48 (dd, J=8.3, 2.4 Hz, 1H), 5.84 (s, 2H), 4.18-4.09 (m, 2H), 3.74 (s, 3H), 3.37 (s, 2H); MS (ES+): 478.0 (M+1); (ES−): 476.0 (M−1).

Scheme 63

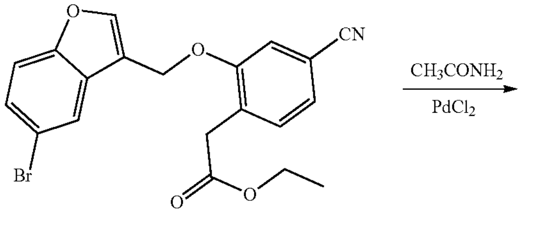

57b

-continued

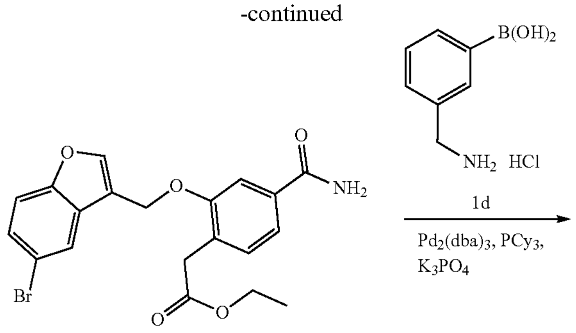

63a

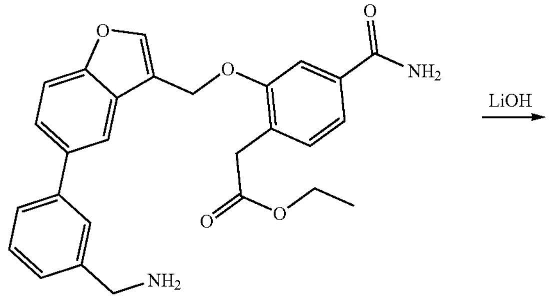

63b

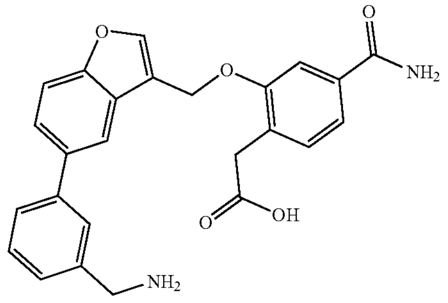

63c

Preparation of 2-(2-((5-(3-(aminomethyl)phenyl) benzofuran-3-yl)methoxy)-4-carbamoylphenyl)acetic acid (63c)

Step-1: Preparation of ethyl 2-(2-((5-bromobenzofuran-3-yl)methoxy)-4-carbamoylphenyl)acetate (63a)

The mixture of acetamide (342 mg, 5.79 mmol), palladium(II) chloride (25.7 mg, 0.145 mmol), and ethyl 2-(2-((5-bromobenzofuran-3-yl)methoxy)-4-cyanophenyl)acetate (57b) (400 mg, 0.966 mmol) in THF (5 mL) and water (0.5 mL) was stirred at room temperature for 13 h. The mixture was diluted with EtOAc, washed with water, brine, dried, filtered and concentrated in vacuum. The obtained residue was purified by flash column chromatography [silica gel (24 g), eluting with EtOAc in hexane from 0-100%] to give ethyl 2-(2-((5-bromobenzofuran-3-yl)methoxy)-4-carbamoylphenyl)acetate (63a) (360 mg, 86% yield) as a white solid; $^1$H NMR (300 MHz, DMSO-$d_6$) δ 8.16 (s, 1H), 8.01 (s, 1H), 7.87 (d, J=2.0 Hz, 1H), 7.68 (d, J=1.6 Hz, 1H), 7.63 (d, J=8.8 Hz, 1H), 7.55-7.45 (m, 2H), 7.43 (s, 1H), 7.30 (d, J=7.8 Hz, 1H), 5.30 (s, 2H), 3.94 (q, J=7.1 Hz, 2H), 3.62 (s, 2H), 0.97 (t, J=7.1 Hz, 3H).

Step-2: Preparation of ethyl 2-(2-((5-(3-(aminomethyl)phenyl)benzofuran-3-yl)methoxy)-4-carbamoylphenyl)acetate (63b)

Compound 63b was prepared according to the procedure reported in step-2 of scheme 1, from ethyl 2-(2-((5-bromobenzofuran-3-yl)methoxy)-4-carbamoylphenyl)acetate (63a) (360 mg, 0.833 mmol) in dioxane (3 mL) using 3-(aminomethyl)phenylboronic acid hydrochloride (1d) (234 mg, 1.249 mmol), 2 M solution of $K_3PO_4$ (0.708 mL, 1.416 mmol), tricyclohexylphosphine (93 mg, 0.333 mmol), $Pd_2(dba)_3$ (153 mg, 0.167 mmol) and heating at 135° C. for 30 min in a microwave. This gave after workup and purification by column chromatography [silica gel (24 g), eluting with DMA80 in DCM from 0-70%] ethyl 2-(2-((5-(3-(aminomethyl)phenyl)benzofuran-3-yl)methoxy)-4-carbamoylphenyl)acetate (63b) (36 mg, 9% yield) as a clear oil; MS (ES+): 459.1 (M+1).

Step-3: Preparation of 2-(2-((5-(3-(aminomethyl)phenyl)benzofuran-3-yl)methoxy)-4-carbamoylphenyl)acetic acid (63c)

Compound 63c was prepared according to the procedure reported in step-3 of scheme 1, from ethyl 2-(2-((5-(3-(aminomethyl)phenyl)benzofuran-3-yl)methoxy)-4-carbamoylphenyl)acetate (63b) (36 mg, 0.079 mmol) in THF (3 mL) using a solution of lithium hydroxide hydrate (34.9 mg, 0.833 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)benzofuran-3-yl)methoxy)-4-carbamoylphenyl)acetic acid (63c) (1.1 mg, 0.307% yield) HCl salt as a white solid; $^1H$ NMR (300 MHz, DMSO-$d_6$) δ 12.24 (s, 1H, $D_2O$ exchangeable), 8.33 (s, 3H, $D_2O$ exchangeable), 8.14 (s, 1H), 8.03 (s, 2H), 7.88 (s, 1H), 7.81-7.62 (m, 4H), 7.56-7.38 (m, 4H), 7.30 (d, J=7.7 Hz, 1H), 5.39 (s, 2H), 4.12 (d, J=5.9 Hz, 2H), 3.60 (s, 2H); MS (ES+): 431.0 (M+1).

Scheme 64

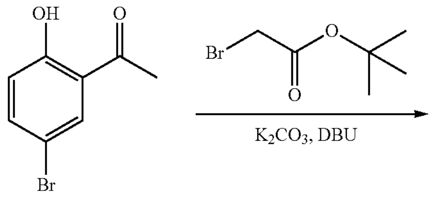

64a

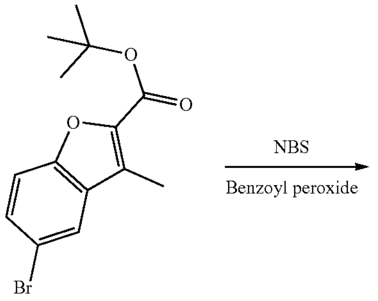

64b

-continued

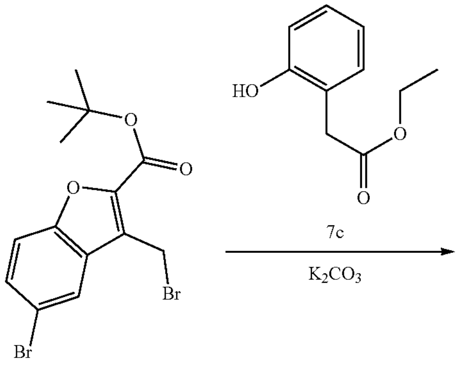

64c

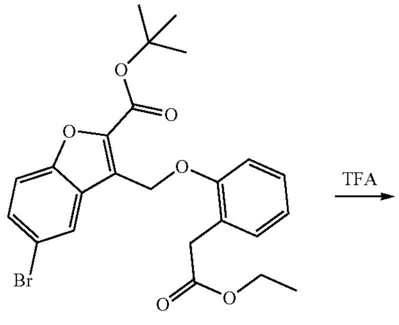

64d

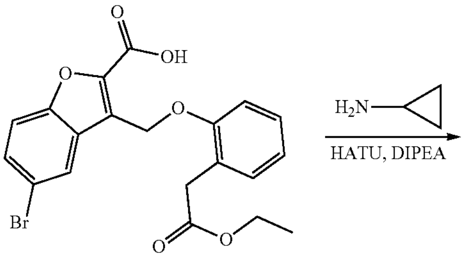

64e

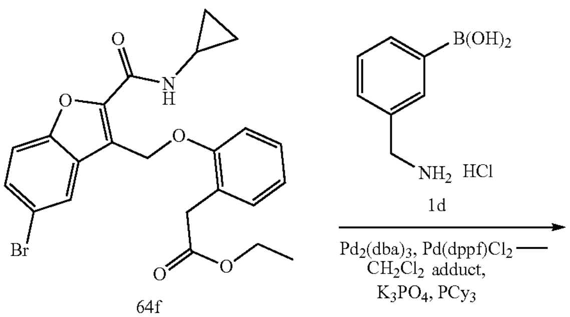

64f

-continued

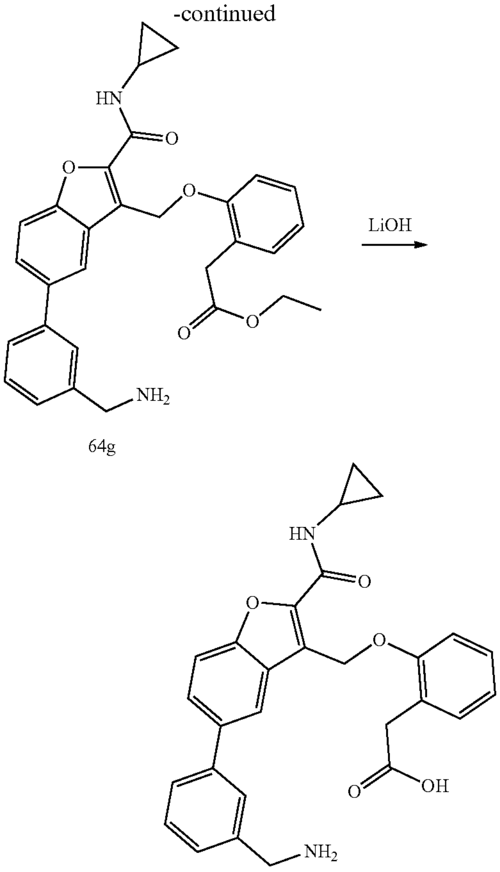

64g

64h

Preparation of 2-(2-((5-(3-(aminomethyl)phenyl)-2-(cyclopropylcarbamoyl)benzofuran-3-yl)methoxy)phenyl)acetic acid (64h)

Step-1: Preparation of tert-butyl 5-bromo-3-methylbenzofuran-2-carboxylate (64b)

Compound 64b was prepared according to the procedure reported in step-1 of scheme 58, from 1-(5-bromo-2-hydroxyphenyl)ethanone (64a) (10 g, 46.5 mmol; CAS #1450-75-5) in DMF(50 mL) using tert-butyl 2-bromoacetate (10.88 g, 55.8 mmol), $K_2CO_3$ (9.64 g, 69.8 mmol), DBU (10.51 mL, 69.8 mmol) and heating at 110° C. for 3 h. This gave after workup and purification by flash column chromatography [silica gel (120 g), eluting with EtOAc in hexane from 0-100%] tert-butyl 5-bromo-3-methylbenzofuran-2-carboxylate (64b) (10.1 g, 70% yield) as a white solid; $^1$H NMR (300 MHz, $CDCl_3$-d) δ 7.73 (d, 1H), 7.50 (dd, J=8.8, 2.0 Hz, 1H), 7.42-7.36 (m, 1H), 2.50 (s, 3H), 1.64 (s, 9H).

Step-2: Preparation of tert-butyl 5-bromo-3-(bromomethyl)benzofuran-2-carboxylate (64c)

Compound 64c was prepared according to the procedure reported in step-2 of scheme 58, from tert-butyl 5-bromo-3-methylbenzofuran-2-carboxylate (64b) (5 g, 16.07 mmol) in carbon tetrachloride (20 mL) using NBS (3.15 g, 17.68 mmol), benzoyl peroxide (0.584 g, 2.410 mmol) and refluxing for 24 h. This gave after workup and purification by flash column chromatography [silica gel (12 g), eluting with EtOAc in hexane from 5-10%] tert-butyl 5-bromo-3-(bromomethyl)benzofuran-2-carboxylate (64c) (5 g, 80% yield) as a white solid; $^1$H NMR (300 MHz, DMSO-$d_6$) δ 8.19 (d, J=1.8 Hz, 1H), 7.79-7.67 (m, 2H), 5.10 (s, 2H), 1.60 (s, 9H).

Step-3: Preparation of tert-butyl 5-bromo-3-((2-(2-ethoxy-2-oxoethyl)phenoxy)methyl)benzofuran-2-carboxylate (64d)

Compound 64d was prepared according to the procedure reported in step-1 of scheme 1, from tert-butyl 5-bromo-3-(bromomethyl)benzofuran-2-carboxylate (64c) (2.5 g, 6.41 mmol) in acetone (30 mL) using ethyl 2-(2-hydroxyphenyl) acetate (7c) (1.328 g, 7.37 mmol), $K_2CO_3$ (3.10 g, 22.43 mmol) and stirring overnight at room temperature. This gave after workup and purification by flash column chromatography [silica gel (12 g), eluting with EtOAc in hexane from 0-50%] tert-butyl 5-bromo-3-((2-(2-ethoxy-2-oxoethyl)phenoxy)methyl)benzofuran-2-carboxylate (64d) (1.4 g, 45% yield) as a yellow oil; $^1$H NMR (300 MHz, DMSO-$d_6$) δ 8.05 (d, J=1.9 Hz, 1H), 7.78-7.65 (m, 2H), 7.36-7.24 (m, 1H), 7.22 (dd, J=7.4, 1.7 Hz, 1H), 7.19-7.13 (m, 1H), 6.95 (td, J=7.4, 1.1 Hz, 1H), 5.55 (s, 2H), 3.90 (q, J=7.0 Hz, 2H), 3.56 (s, 2H), 1.56 (s, 9H), 0.94 (t, J=7.1 Hz, 3H); MS (ES+): 510.90 (M+Na).

Step-4: Preparation of 5-bromo-3-((2-(2-ethoxy-2-oxoethyl)phenoxy)methyl)benzofuran-2-carboxylic acid (64e)

Compound 64e was prepared according to the procedure reported in step-9 of scheme 3, from tert-butyl 5-bromo-3-((2-(2-ethoxy-2-oxoethyl)phenoxy)methyl)benzofuran-2-carboxylate (64d) (2.2 g, 4.50 mmol) in DCM (30 mL) using TFA (1.732 mL, 22.5 mmol) and stirring at room temperature for 6 h. This gave after workup and purification by flash column chromatography [silica gel (40 g), eluting with EtOAc/MeOH in hexane from 0-100%] 5-bromo-3-((2-(2-ethoxy-2-oxoethyl)phenoxy)methyl)benzofuran-2-carboxylic acid (64e)(1.68 g, 86% yield) as a white solid; $^1$H NMR (300 MHz, DMSO-$d_6$) δ 14.17 (s, 1H), 8.00 (d, J=1.9 Hz, 1H), 7.77-7.63 (m, 2H), 7.28 (td, J=7.8, 1.8 Hz, 1H), 7.24-7.12 (m, 2H), 6.94 (td, J=7.4, 1.1 Hz, 1H), 5.59 (s, 2H), 3.90 (q, J=7.1 Hz, 2H), 3.56 (s, 2H), 0.94 (t, J=7.1 Hz, 3H).

Step-5: Preparation of ethyl 2-(2-((5-bromo-2-(cyclopropylcarbamoyl)benzofuran-3-yl)methoxy)phenyl)acetate (64f)

Compound 64f was prepared according to the procedure reported in step-1 of scheme 10, from 5-bromo-3-((2-(2-ethoxy-2-oxoethyl)phenoxy)methyl)benzofuran-2-carboxylic acid (64e) (500 mg, 1.154 mmol) in DMF (30 mL) using cyclopropylamine (0.098 mL, 1.385 mmol), N-ethyl-N-isopropylpropan-2-amine (DIPEA) (0.302 mL, 1.731 mmol), 2-(3H-[1,2,3]triazolo[4,5-b]pyridin-3-yl)-1,1,3,3-tetramethylisouronium hexafluorophosphate(V) (HATU) (527 mg, 1.385 mmol) and stirring overnight at room temperature. This gave after workup and purification by flash column chromatography [silica gel (12 g), eluting with EtOAc in hexane from 0-100%] ethyl 2-(2-((5-bromo-2-(cyclopropylcarbamoyl)benzofuran-3-yl)methoxy)phenyl) acetate (64f) (520 mg, 95% yield) as a clear oil; $^1$H NMR (300 MHz, DMSO-$d_6$) δ 8.95 (d, J=4.6 Hz, 1H), 7.94 (d, J=1.8 Hz, 1H), 7.68-7.57 (m, 2H), 7.27 (td, J=7.7, 7.2, 1.7 Hz, 1H), 7.22-7.13 (m, 2H), 6.92 (td, J=7.3, 1.3 Hz, 1H), 5.65 (s, 2H), 3.94 (q, J=7.1 Hz, 2H), 3.56 (s, 2H), 2.90 (ddt, J=11.5, 7.0, 4.3 Hz, 1H), 0.97 (t, J=7.1 Hz, 3H), 0.74-0.58 (m, 4H).

Step-6: Preparation of ethyl 2-(2-((5-(3-(aminomethyl)phenyl)-2-(cyclopropylcarbamoyl)benzofuran-3-yl)methoxy)phenyl)acetate (64g)

Compound 64g was prepared according to the procedure reported in step-2 of scheme 1, from ethyl 2-(2-((5-bromo-2-(cyclopropylcarbamoyl)benzofuran-3-yl)methoxy)phenyl)acetate (64f) (320 mg, 0.677 mmol) in dioxane/THF (6 mL, Ratio 1:1) using 3-(aminomethyl)phenylboronic acid hydrochloride (1d) (254 mg, 1.355 mmol), 2 M solution of $K_3PO_4$ (1.355 mL, 2.71 mmol), tricyclohexylphosphine (38.0 mg, 0.135 mmol) and $PdCl_2(dppf)$-$CH_2Cl_2$ adduct (55.3 mg, 0.068 mmol), $Pd_2(dba)_3$ (62.0 mg, 0.068 mmol) and heating at 95° C. for 1 h. This gave after workup and purification by flash column chromatography [silica gel (24 g), eluting with DMA-80 in DCM from 0-70%] ethyl 2-(2-((5-(3-(aminomethyl)phenyl)-2-(cyclopropylcarbamoyl)benzofuran-3-yl)methoxy)phenyl)acetate (64g) (181 mg, 54% yield) as a clear oil; $^1$H NMR (300 MHz, DMSO-$d_6$) δ 8.92 (d, J=4.6 Hz, 1H), 8.00 (d, J=1.9 Hz, 1H), 7.77 (dd, J=8.7, 1.9 Hz, 1H), 7.71-7.64 (m, 2H), 7.53 (d, J=7.7 Hz, 1H), 7.40 (t, J=7.5 Hz, 1H), 7.35-7.30 (m, 2H), 7.29-7.23 (m, 2H), 7.22-7.15 (m, 2H), 6.91 (td, J=7.1, 1.7 Hz, 1H), 5.76 (s, 2H), 3.78 (s, 2H), 3.65 (q, J=7.1 Hz, 2H), 3.56 (s, 2H), 2.97-2.85 (m, 1H), 0.81 (t, J=7.1 Hz, 3H), 0.75-0.66 (m, 4H); MS (ES+): 499.1 (M+1).

Step-7: Preparation of 2-(2-((5-(3-(aminomethyl)phenyl)-2-(cyclopropylcarbamoyl)benzofuran-3-yl)methoxy)phenyl)acetic acid (64h)

Compound 64h was prepared according to the procedure reported in step-3 of scheme 1, from ethyl 2-(2-((5-(3-(aminomethyl)phenyl)-2-(cyclopropylcarbamoyl)benzofuran-3-yl)methoxy)phenyl)acetate (64g) (181 mg, 0.363 mmol) in THF (3 mL) using a solution of lithium hydroxide hydrate (85 mg, 2.032 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)-2-(cyclopropylcarbamoyl)benzofuran-3-yl)methoxy)phenyl)acetic acid (64h) (114 mg, 67% yield) HCl salt as an off white solid; $^1$H NMR (300 MHz, DMSO-$d_6$) δ 12.20 (s, 1H, $D_2O$ exchangeable), 8.94 (d, J=4.6 Hz, 1H, $D_2O$ exchangeable), 8.50 (s, 3H, $D_2O$ exchangeable), 8.09 (d, J=1.8 Hz, 1H), 7.88 (d, J=2.1 Hz, 1H), 7.82 (dd, J=8.7, 1.8 Hz, 1H), 7.77-7.66 (m, 2H), 7.58-7.43 (m, 2H), 7.29-7.12 (m, 3H), 6.95-6.84 (m, 1H), 5.75 (s, 2H), 4.10 (q, J=5.8 Hz, 2H), 3.56 (s, 2H), 2.99-2.85 (m, 1H), 0.80-0.63 (m, 4H); MS (ES+): 471.0 (M+1); (ES−): 469.1 (M−1); Analysis calculated for $C_{28}H_{26}N_2O_5 \cdot 1.25HCl \cdot 2.75H_2O$: C, 59.46; H, 5.84; Cl, 7.83; N, 4.95. Found: C, 59.09; H, 5.59; Cl, 7.84; N, 4.88.

Scheme 65

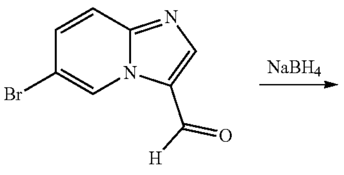

65a

-continued

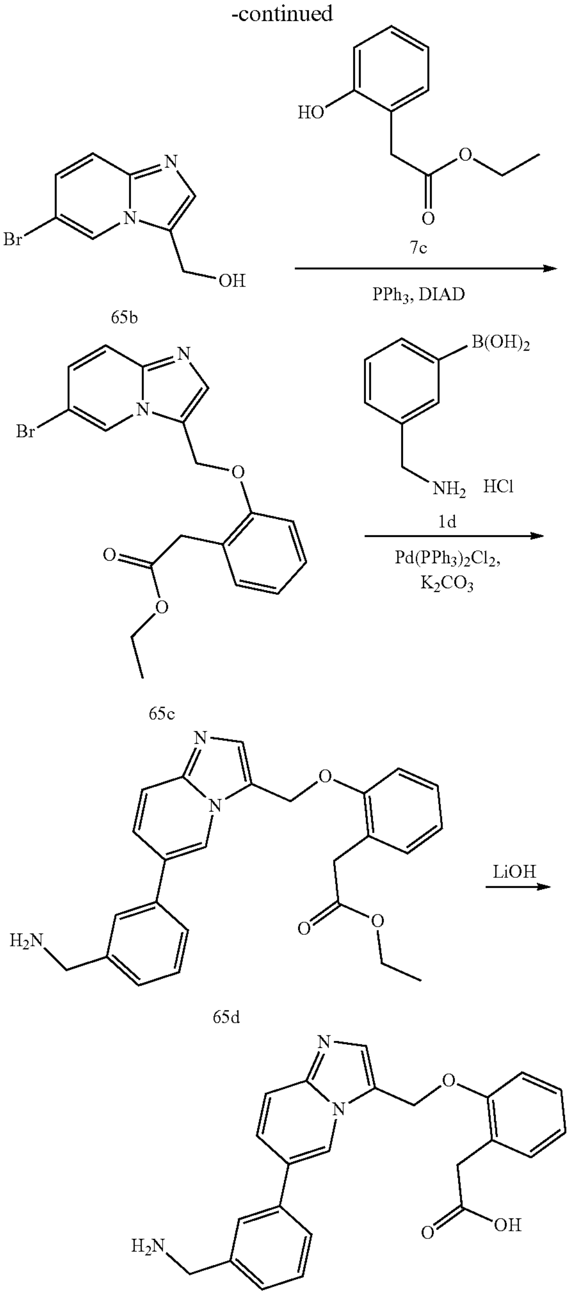

65b, 7c, 65c, 1d, 65d, 65e

Preparation of 2-(2-((6-(3-(aminomethyl)phenyl)imidazo[1,2-a]pyridin-3-yl)methoxy)phenyl)acetic acid (65e)

Step-1: Preparation of (6-bromoimidazo[1,2-a]pyridin-3-yl)methanol (65b)

To a solution of 6-bromoimidazo[1,2-a]pyridine-3-carbaldehyde (65a) (1 g, 4.44 mmol) in THE (30 mL) at 0° C. was added sodium borohydride (0.336 g, 8.89 mmol) over a period of 2 mins. The reaction mixture was stirred at 0° C. for 30 min and allowed to warm to room temperature over a period of 30 min. Reaction was quenched with acetone (1 mL) stirred for 10 mins, diluted with water (10 mL) and concentrated in vacuum. The residue was dissolved in ethyl acetate (100 mL), washed with water (2×20 mL), brine (20 mL), dried, filtered and concentrated in vacuum. The obtained residue was purified by flash column chromatography [silica gel (24 g) eluting with DMA-80 in DCM 0 to 100%] to afford (6-bromoimidazo[1,2-a]pyridin-3-yl) methanol (65b) (0.6 g, 60% yield) as a white solid; $^1$H NMR (300 MHz, DMSO-$d_6$) δ 8.65 (dd, J=1.9, 0.9 Hz, 1H), 7.57 (dd, J=9.6, 0.9 Hz, 1H), 7.54 (s, 1H), 7.38 (dd, J=9.5, 1.9 Hz, 1H), 5.30 (t, J=5.5 Hz, 1H), 4.80 (d, J=5.5 Hz, 2H); MS (ES+): 227.00 (M+1)

Step-2: Preparation of ethyl 2-(2-((6-bromoimidazo[1,2-a]pyridin-3-yl)methoxy)phenyl)acetate (65c)

To a stirred solution of triphenylphosphine (0.381 g, 1.453 mmol), ethyl 2-(2-hydroxyphenyl)acetate (7c) (0.262 g, 1.453 mmol) and (6-bromoimidazo[1,2-a]pyridin-3-yl) methanol (65b) (0.3 g, 1.321 mmol) in THF at 0° C. was added diisopropyl azodicarboxylate (DIAD) (0.283 mL, 1.453 mmol) dropwise and stirred at 0° C. for 10 min. The mixture was concentrated in vacuum and the obtained residue was purified by flash column chromatography [silica gel (24 g), eluting with DMA-80 in DCM from 0-60%] to give ethyl 2-(2-((6-bromoimidazo[1,2-a]pyridin-3-yl) methoxy)phenyl)acetate (65c) (0.35 g, 68% yield) as a yellow solid; $^1$H NMR (300 MHz, DMSO-$d_6$) δ 7.98-7.76 (m, 1H), 7.49-7.13 (m, 6H), 6.94 (t, J=7.4 Hz, 1H), 5.49 (s, 2H), 3.86 (q, J=7.3 Hz, 2H), 3.50 (s, 2H), 0.91 (t, J=7.1 Hz, 3H); MS (ES+): 389.00 (M+1).

Step-3: Preparation of ethyl 2-(2-((6-(3-(aminomethyl)phenyl)imidazo[1,2-a]pyridin-3-yl)methoxy)phenyl)acetate (65d)

Compound 65d was prepared according to the procedure reported in step-8 of Scheme 3, from ethyl 2-(2-((6-bromoimidazo[1,2-a]pyridin-3-yl)methoxy)phenyl)acetate (65c) (0.35 g, 0.899 mmol) in dioxane (6 mL) using 3-(aminomethyl)phenylboronic acid hydrochloride (1d) (0.337 g, 1.798 mmol), bis(triphenylphosphine)palladium(II) chloride (0.095 g, 0.135 mmol), a solution of $K_2CO_3$ (0.373 g, 2.70 mmol) in water (2 mL) and heating at 90° C. for 2 h. This gave after workup and purification by flash column chromatography [silica gel (24 g), eluting with DMA-80 in DCM from 0-50%] ethyl 2-(2-((6-(3-(aminomethyl)phenyl)imidazo[1,2-a]pyridin-3-yl)methoxy)phenyl)acetate (65d) (0.15 g, 40% yield) as a red oil; $^1$H NMR (300 MHz, DMSO-$d_6$) δ 8.59 (d, J=1.8 Hz, 1H), 7.76 (s, 1H), 7.74-7.63 (m, 3H), 7.60 (dt, J=7.4, 1.8 Hz, 1H), 7.42 (t, J=7.5 Hz, 1H), 7.37 (d, J=7.8 Hz, 1H), 7.32-7.28 (m, 2H), 7.21-7.16 (m, 1H), 6.93 (m, 1H), 5.56 (s, 2H), 3.80 (s, 2H), 3.60 (q, J=7.1 Hz, 2H), 3.49 (s, 2H), 0.77 (t, J=7.1 Hz, 3H); MS (ES+): 416.20 (M+1).

Step-4: Preparation of 2-(2-((6-(3-(aminomethyl)phenyl)imidazo[1,2-a]pyridin-3-yl)methoxy)phenyl)acetic acid (65e)

Compound 65e was prepared according to the procedure reported in step-3 of scheme 1, from ethyl 2-(2-((6-(3-(aminomethyl)phenyl)imidazo[1,2-a]pyridin-3-yl)methoxy)phenyl)acetate (65d) (0.15 g, 0.361 mmol) in THF/MeOH (4 mL each) using a solution of lithium hydroxide hydrate (0.061 g, 1.444 mmol) in water (1 mL) and stirring for 15 h at room temperature.

This gave after workup and purification by reverse phase column chromatography [C18 column (50 g), eluting with ACN in water (containing 0.1% HCl) from 0-100%] 2-(2-((6-(3-(aminomethyl)phenyl)imidazo[1,2-a]pyridin-3-yl) methoxy)phenyl)acetic acid (65e) (0.09 g, 64% yield) HCl salt as a white solid; $^1$H NMR (300 MHz, DMSO-$d_6$) δ 12.10 (s, 1H, $D_2O$ exchangeable), 9.18 (s, 1H), 8.65 (s, 3H, $D_2O$ exchangeable), 8.34 (d, J=13.5 Hz, 2H), 8.14 (d, J=9.0 Hz, 2H), 7.89 (dq, J=5.5, 3.7, 2.9 Hz, 1H), 7.60 (d, J=4.8 Hz, 2H), 7.41-7.25 (m, 2H), 7.21 (dd, J=7.3, 1.6 Hz, 1H), 6.97 (td, J=7.2, 1.5 Hz, 1H), 5.72 (s, 2H), 4.14 (q, J=5.8 Hz, 2H), 3.50 (s, 2H); MS (ES+): 388.10 (M+1); Analysis calculated for: $C_{23}H_{21}N_3O_3$·2HCl·2.75$H_2O$. C, 54.18; H, 5.63; Cl, 13.90; N, 8.24. Found: C, 54.12; H, 5.66; Cl, 13.81; N, 8.33.

Scheme 66

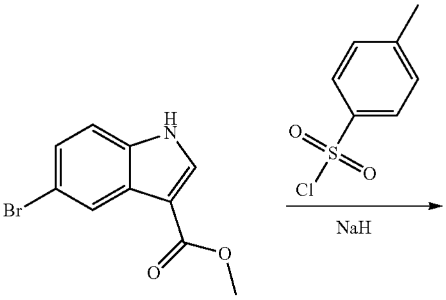

66a

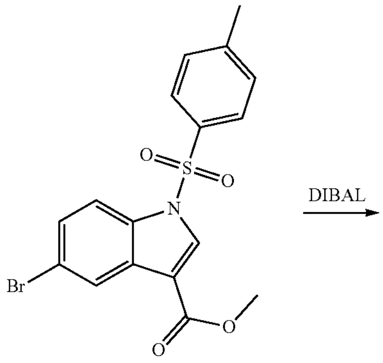

66b

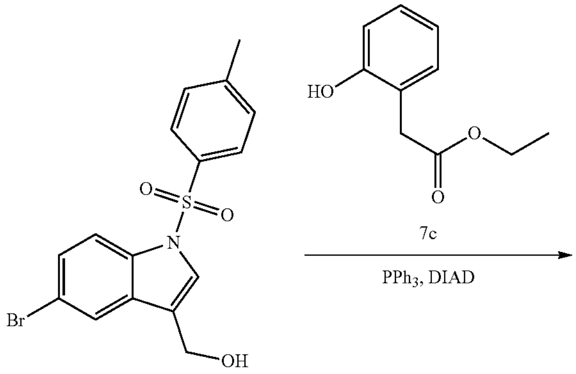

66c

-continued

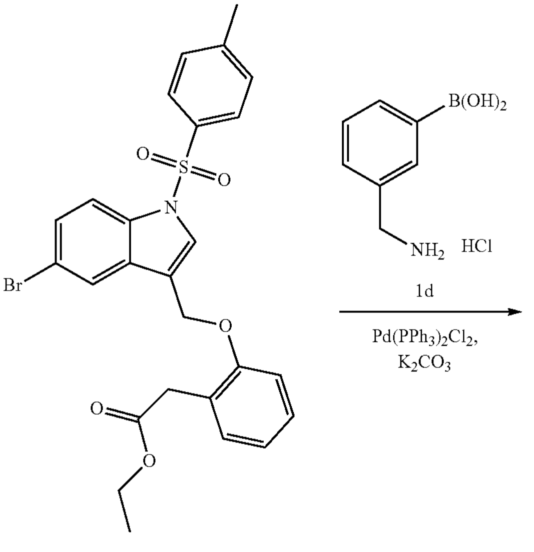

66d

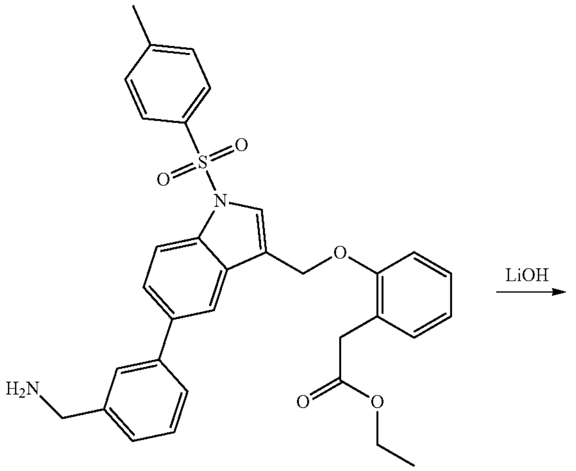

66e

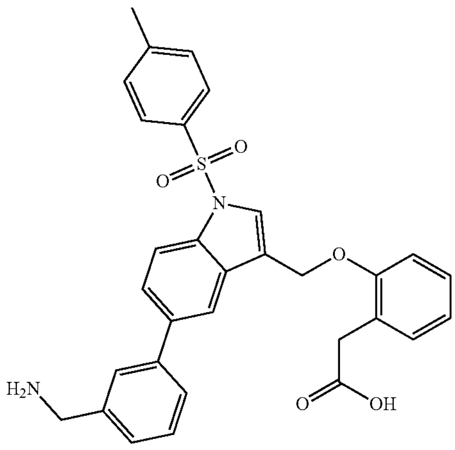

66f

Preparation of 2-(2-((5-(3-(aminomethyl)phenyl)-1-tosyl-1H-indol-3-yl)methoxy)phenyl)acetic acid (66f)

Step-1: Preparation of methyl 5-bromo-1-tosyl-1H-indole-3-carboxylate (66b)

To a solution of methyl 5-bromo-1H-indole-3-carboxylate (66a) (3 g, 11.81 mmol; CAS #773873-77-1) in DMF (30 mL) at 0° C. was added sodium hydride (1.417 g, 35.4 mmol) and the reaction mixture was stirred for 15 min. To this mixture was added 4-methylbenzene-1-sulfonyl chloride (6.75 g, 35.4 mmol) at 0° C. and the reaction was warmed to room temperature overnight. The mixture was poured into EtOAc and acidified with 3M HCl. The organic layer was separated washed with water, brine, dried, filtered and concentrated in vacuum. The obtained residue was purified by flash column chromatography [silica gel (80 g), eluting with EtOAc/MeOH (9:1) in hexane from 0-100%] to give methyl 5-bromo-1-tosyl-1H-indole-3-carboxylate (66b) (3.5 g, 73% yield) as a yellow solid; $^{1}H$ NMR (300 MHz, DMSO-$d_6$) δ 8.49 (s, 1H), 8.14 (d, J=2.0 Hz, 1H), 8.05 (d, J=1.6 Hz, 1H), 8.03 (s, 1H), 7.94 (d, J=8.9 Hz, 1H), 7.58 (dd, J=8.9, 2.0 Hz, 1H), 7.43 (d, J=8.1 Hz, 2H), 3.86 (s, 3H), 2.34 (s, 3H); MS (ES+): 407.90 (M+1).

Step-2: Preparation of (5-bromo-1-tosyl-1H-indol-3-yl)methanol (66c)

Compound 66c was prepared according to the procedure reported in step-4 of scheme 3, from methyl 5-bromo-1-tosyl-1H-indole-3-carboxylate (66b) (0.5 g, 1.225 mmol) using DIBAL-H (1M in DCM, 3.06 mL, 3.06 mmol) and stirring at −78° C. for 1 h. The reaction was quenched by the addition of methanol (15 mL), sodium fluoride (2 g) and Rochelle's salt solution (20 mL). The mixture was diluted with DCM (100 mL) and was stirred vigorously for 1 hour. This gave after workup and purification by flash column chromatography [silica gel (24 g), eluting with EA/MeOH (9:1) in hexane from 0-100%] (5-bromo-1-tosyl-1H-indol-3-yl)methanol (66c) (0.4 g, 86% yield) as a white solid; $^{1}H$ NMR (300 MHz, DMSO-$d_6$) δ 7.91-7.81 (m, 4H), 7.70 (d, J=1.2 Hz, 1H), 7.49 (dd, J=8.8, 2.1 Hz, 1H), 7.40 (q, J=1.6 Hz, 1H), 7.37 (t, J=1.3 Hz, 1H), 5.21 (t, J=5.6 Hz, 1H), 4.58 (dd, J=5.6, 1.1 Hz, 2H), 2.31 (s, 3H); MS (ES+): 401.90 (M+Na).

Step-3: Preparation of ethyl 2-(2-((5-bromo-1-tosyl-1H-indol-3-yl)methoxy)phenyl)acetate (66d)

Compound 66d was prepared according to the procedure reported in step-2 of Scheme 65, from (5-bromo-1-tosyl-1H-indol-3-yl)methanol (66c) (1.1 g, 2.89 mmol) in THF at 0° C. using triphenylphosphine (0.835 g, 3.18 mmol), ethyl 2-(2-hydroxyphenyl)acetate (7c) (0.573 g, 3.18 mmol) and diisopropyl azodicarboxylate (DIAD) (0.619 mL, 3.18 mmol) and stirring at 0° C. for 10 min. This gave after workup and purification by flash column chromatography [silica gel (24 g), eluting with DMA-80 in DCM from 0-60%] ethyl 2-(2-((5-bromo-1-tosyl-1H-indol-3-yl)methoxy)phenyl)acetate (66d) (1.0 g, 64% yield) as a white syrup; MS (ES+): 564.00 (M+Na).

Step-4: Preparation of ethyl 2-(2-((5-(3-(aminomethyl)phenyl)-1-tosyl-1H-indol-3-yl)methoxy)phenyl)acetate (66e)

Compound 66e was prepared according to the procedure reported in step-8 of Scheme 3, from ethyl 2-(2-((5-bromo- 1-tosyl-1H-indol-3-yl)methoxy)phenyl)acetate (66d) (1 g, 1.844 mmol) in dioxane (9 mL) using 3-(aminomethyl) phenylboronic acid hydrochloride (1d) (0.691 g, 3.69 mmol), bis(triphenylphosphine)palladium(II) chloride (0.194 g, 0.277 mmol), a solution of $K_2CO_3$ (0.764 g, 5.53 mmol) in water (3 mL) and heating at 90° C. for 3 h. This gave after workup and purification by flash column chromatography [silica gel (24 g), eluting with DMA-80 in DCM from 0-50%] ethyl 2-(2-((5-(3-(aminomethyl)phenyl)-1-tosyl-1H-indol-3-yl)methoxy)phenyl)acetate (66e) (0.45 g, 43% yield) as a white solid; MS (ES+): 569.20 (M+1).

Step-5: Preparation of 2-(2-((5-(3-(aminomethyl) phenyl)-1-tosyl-1H-indol-3-yl)methoxy)phenyl)acetic acid (66f)

Compound 66f was prepared according to the procedure reported in step-3 of scheme 1, from ethyl 2-(2-((5-(3-(aminomethyl)phenyl)-1-tosyl-1H-indol-3-yl)methoxy)phenyl)acetate (66e) (0.15 g, 0.264 mmol) in THF/MeOH (4 mL, ratio: 1:1) using a solution of lithium hydroxide hydrate (0.044 g, 1.055 mmol) in water (1 mL) and stirring at room temperature for 14 h. This gave after workup and purification by reverse phase column chromatography [C18 column (50 g), eluting with ACN in water (containing 0.1% HCl) from 0-100%] 2-(2-((5-(3-(aminomethyl)phenyl)-1-tosyl-1H-indol-3-yl)methoxy)phenyl)acetic acid (66f) (0.08 g, 56% yield) HCl salt as a white solid; $^1H$ NMR (300 MHz, DMSO-$d_6$) δ 12.19 (s, 1H, $D_2O$ exchangeable), 8.42 (s, 3H, $D_2O$ exchangeable), 8.03 (d, J=8.7 Hz, 1H), 7.98 (d, J=1.7 Hz, 1H), 7.96 (s, 1H), 7.89-7.82 (m, 3H), 7.71 (dd, J=8.6, 1.8 Hz, 2H), 7.54-7.41 (m, 2H), 7.38 (d, J=8.2 Hz, 2H), 7.30-7.12 (m, 3H), 6.92 (td, J=7.3, 1.2 Hz, 1H), 5.33 (s, 2H), 4.09 (s, 2H), 3.54 (s, 2H), 2.32 (s, 3H); MS (ES+): 541.10 (M+1); Analysis calculated for: $C_{31}H_{28}N_2O_5S \cdot HCl \cdot 1.25H_2O$. C, 62.10; H, 5.30; Cl, 5.91; N, 4.67. Found: C, 61.98; H, 5.32; Cl, 5.97; N, 4.75.

Scheme 67

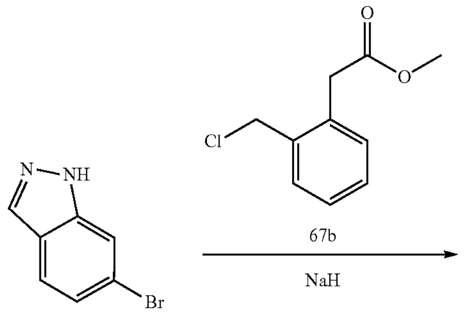

67b

67a

-continued

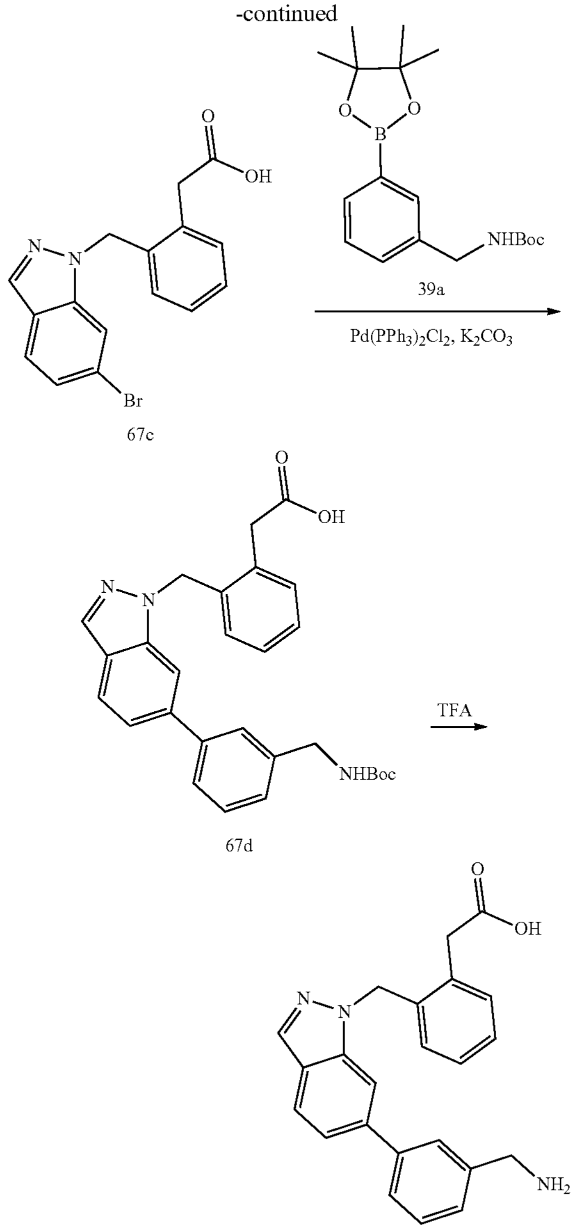

39a

67c

67d

67e

Preparation of 2-(2-((6-(3-(aminomethyl)phenyl)-1H-indazol-1-yl)methyl)phenyl)acetic acid (67e)

Step-1: Preparation of 2-(2-((6-bromo-1H-indazol-1-yl)methyl)phenyl)acetic acid (67c)

To a solution of methyl 2-(2-(chloromethyl)phenyl)acetate (67b) (1008 mg, 5.08 mmol) and 6-bromo-1H-indazole (67a) (500 mg, 2.54 mmol) in DMF (5 mL) was added sodium hydride (203 mg, 5.08 mmol) under an argon atmosphere and stirred at room temperature. Once the reaction was complete the mixture was poured into saturated aqueous ammonium chloride solution. The mixture was extracted with ethyl acetate and the combined organics were washed with brine, dried, filtered, concentrated under vacuum and purified by flash column chromatography [silica gel (24 g) eluting with ethyl acetate in hexanes from 0-50%] to give 2-(2-((6-bromo-1H-indazol-1-yl)methyl)phenyl)acetic acid (67c) (244 mg, 28% yield) as an off-white solid; $^{1}H$ NMR (300 MHz, DMSO-$d_6$) δ 12.54 (s, 1H), 8.19 (d, J=1.0 Hz, 1H), 7.94 (s, 1H), 7.77 (d, J=8.5 Hz, 1H), 7.30-7.22 (m, 2H), 7.13 (td, J=7.3, 1.9 Hz, 2H), 6.60 (d, J=7.5 Hz, 1H), 5.70 (s, 2H), 3.86 (s, 2H).

Step-2: Preparation of 2-(2-((6-(3-(((tert-butoxycarbonyl)amino)methyl)phenyl)-1H-indazol-1-yl)methyl)phenyl)acetic acid (67d)

Compound 67d was prepared according to the procedure reported in step-8 of Scheme 3, from 2-(2-((6-bromo-1H-indazol-1-yl)methyl)phenyl)acetic acid (67c) (244 mg, 0.707 mmol) in dioxane (8 mL) using tert-butyl 3-(4,4,5,5-tetramethyl-1,3,2-dioxaborolan-2-yl)benzylcarbamate (39a) (236 mg, 0.707 mmol), bis(triphenylphosphine)palladium (II) chloride (74.4 mg, 0.106 mmol) and a solution of $K_2CO_3$ (293 mg, 2.121 mmol) in water (3 mL) and heating at 90° C. for 3 h. This gave after workup and purification by flash column chromatography [silica gel (12 g), eluting with DMA-80 in DCM from 0-50%] 2-(2-((6-(3-(((tert-butoxycarbonyl)amino)methyl)phenyl)-1H-indazol-1-yl)methyl)phenyl)acetic acid (67d) (247 mg, 74% yield) as a clear oil; MS (ES+): 472.20 (M+1).

Step-3: Preparation of 2-(2-((6-(3-(aminomethyl)phenyl)-1H-indazol-1-yl)methyl)phenyl)acetic acid (67e)

To a solution of 2-(2-((6-(3-(((tert-butoxycarbonyl)amino)methyl)phenyl)-1H-indazol-1-yl)methyl)phenyl)acetic acid (67d) (247 mg, 0.524 mmol) in DCM (5 mL) was added TFA (5 mL, 0.524 mmol). The resulting mixture was stirred at room temperature and concentrated to dryness under vacuum. The obtained residue was purified by reverse phase column chromatography [C18 column (40 g), eluting with ACN in water (containing 0.1% HCl) from 0-100%] to give 2-(2-((6-(3-(aminomethyl)phenyl)-1H-indazol-1-yl)methyl)phenyl)acetic acid (67e) (21 mg, 11% yield) hydrochloride salt as a solid; $^{1}H$ NMR (300 MHz, DMSO-$d_6$) δ 8.35 (s, 3H, $D_2O$ exchangeable), 8.19 (s, 1H), 7.95 (s, 1H), 7.94-7.89 (m, 2H), 7.75 (d, J=7.5 Hz, 1H), 7.58-7.44 (m, 3H), 7.31-7.23 (m, 1H), 7.23-7.18 (m, 1H), 7.18-7.07 (m, 1H), 6.69 (d, J=7.6 Hz, 1H), 5.78 (s, 2H), 4.11 (s, 2H), 3.90 (s, 2H); MS (ES+): 372.1 (M+1); Analysis calculated for $C_{23}H_{21}N_3O_2$ 1.1HCl·1.6$H_2O$: C, 62.73; H, 5.79; Cl, 8.86; N, 9.54. Found: C, 62.85; H, 5.47; Cl, 8.60; N, 9.63.

Scheme 68

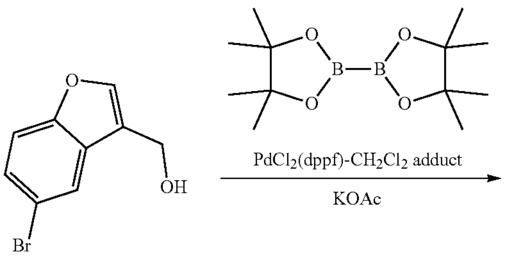

9b

-continued

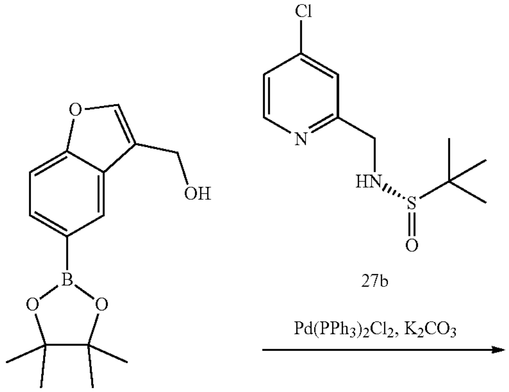

27b

68a

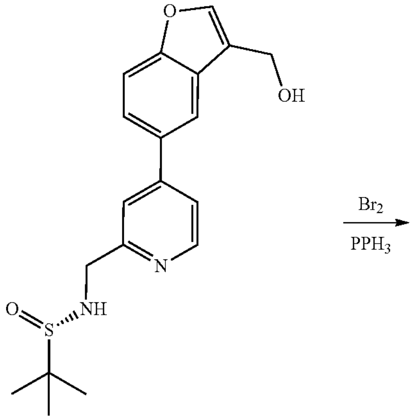

68b

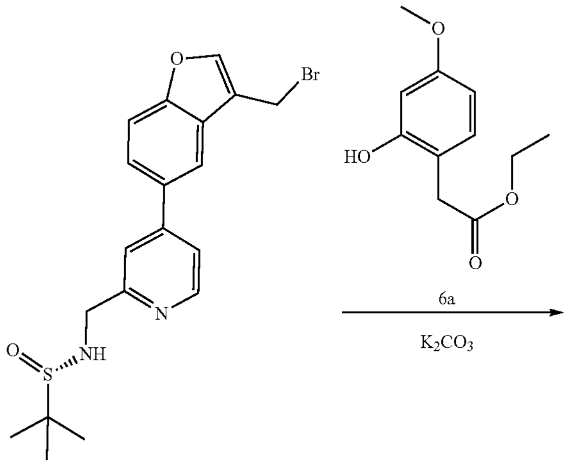

68c

-continued

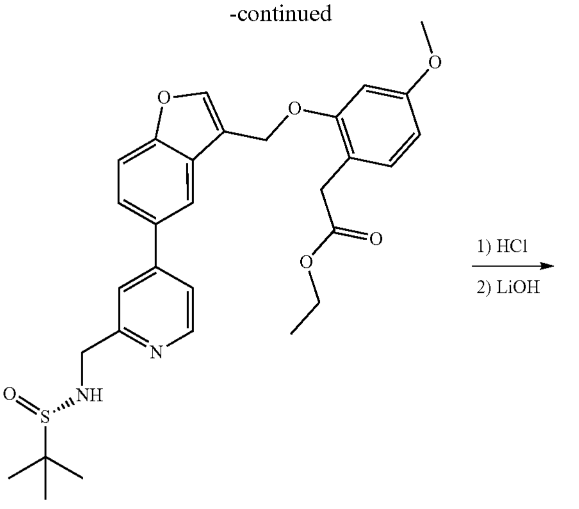

68d

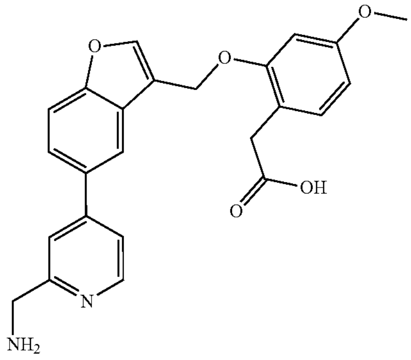

68e

Preparation of 2-(2-((5-(2-(aminomethyl)pyridin-4-yl)benzofuran-3-yl)methoxy)-4-methoxyphenyl) acetic acid (68e)

Step-1: Preparation of (5-(4,4,5,5-tetramethyl-1,3,2-dioxaborolan-2-yl)benzofuran-3-yl)methanol (68a)

Compound 68a was prepared according to the procedure reported in step-1 of scheme 27 from (5-bromobenzofuran-3-yl)methanol (9b) (1.5 g, 6.61 mmol) in anhydrous dioxane (30 mL) using BisPin (2.52 g, 9.91 mmol), potassium acetate (1.945 g, 19.82 mmol), $PdCl_2(dppf)$-$CH_2Cl_2$ adduct (0.539 g, 0.661 mmol) and heating at 90° C. for 16 h. This gave after work up and purification by flash column chromatography [silica gel (40 g), eluting with EtOAc in hexane from 0-40%] (5-(4,4,5,5-tetramethyl-1,3,2-dioxaborolan-2-yl)benzofuran-3-yl)methanol (68a) (1.8 g, 99% yield) as a light brown oil; $^1$H NMR (300 MHz, DMSO-$d_6$) δ 8.07 (d, J=1.0 Hz, 1H), 7.89 (d, J=1.1 Hz, 1H), 7.65-7.52 (m, 2H), 5.21 (t, J=5.5 Hz, 1H), 4.64 (dd, J=5.4, 1.1 Hz, 2H), 1.32 (s, 12H).

Step-2: Preparation of (+)-N-((4-(3-(hydroxymethyl)benzofuran-5-yl)pyridin-2-yl)methyl)-2-methylpropane-2-sulfinamide (68b)

Compound 68b was prepared according to the procedure reported in step-8 of Scheme 3, from (5-(4,4,5,5-tetramethyl-1,3,2-dioxaborolan-2-yl)benzofuran-3-yl)methanol (68a) (900 mg, 3.28 mmol) in dioxane (24 mL) using (+)-N-((4-chloropyridin-2-yl)methyl)-2-methylpropane-2-sulfinamide (27b) (891 mg, 3.61 mmol), bis(triphenylphosphine)palladium(II) chloride (346 mg, 0.492 mmol), a solution of $K_2CO_3$ (1361 mg, 9.85 mmol) in water (3 mL) and heating the reaction mixture at 100° C. for 5 h.

This gave after workup and purification by flash column chromatography [silica gel (40 g), eluting with DMA80 in DCM from 0-30%] to give (+)-N-((4-(3-(hydroxymethyl)benzofuran-5-yl)pyridin-2-yl)methyl)-2-methylpropane-2-sulfinamide (68b) (807 mg, 69% yield) as a brown oil; $^1$H NMR (300 MHz, DMSO-$d_6$) δ 8.57 (d, J=5.2 Hz, 1H), 8.10 (t, J=1.3 Hz, 1H), 7.97 (d, J=1.1 Hz, 1H), 7.85 (d, J=1.8 Hz, 1H), 7.72 (d, J=1.6 Hz, 2H), 7.65 (dd, J=5.3, 1.8 Hz, 1H), 5.98 (t, J=6.1 Hz, 1H), 5.24 (t, J=5.5 Hz, 1H), 4.69 (dd, J=5.5, 1.1 Hz, 2H), 4.35 (dd, J=6.1, 2.9 Hz, 2H), 1.19 (s, 9H); MS (ES+): 359.1 (M+1); Optical rotation $[\alpha]_D$=+30.0 (c=0.1, MeOH).

Step-3: Preparation of N-((4-(3-(bromomethyl)benzofuran-5-yl)pyridin-2-yl)methyl)-2-methylpropane-2-sulfinamide (68c)

To a solution of triphenylphosphine (234 mg, 0.893 mmol) in DCM (3 mL) at 0° C. was added dibromide (0.046 mL, 0.893 mmol) and stirred at room temperature for 10 mins. To this (+)-N-((4-(3-(hydroxymethyl)benzofuran-5-yl)pyridin-2-yl)methyl)-2-methylpropane-2-sulfinamide (68b) (200 mg, 0.558 mmol) in DCM (6 mL) was added over a period of 5 min and stirred at room temperature for 10 mins. The reaction was quenched with a solution of sodium bicarbonate (10 mL), dichloromethane (25 mL). The organic layer was separated washed with water (15 mL), brine (15 mL), dried and concentrated in vacuum. The crude residue was purified by flash column chromatography [silica gel (24 g), eluting with DMA-80 in DCM from 0-40%] to give N-((4-(3-(bromomethyl)benzofuran-5-yl)pyridin-2-yl)methyl)-2-methylpropane-2-sulfinamide (68c) (35 mg, 15% yield) as a pale yellow oil; $^1$H NMR (300 MHz, DMSO-$d_6$) δ 8.59 (d, J=5.1 Hz, 1H), 8.27 (s, 1H), 8.14 (s, 1H), 7.86 (s, 1H), 7.79 (d, J=1.9 Hz, 2H), 7.66 (d, J=5.4 Hz, 1H), 5.99 (t, J=6.0 Hz, 1H), 4.97 (s, 2H), 4.37 (dd, J=6.0, 3.2 Hz, 2H), 1.20 (s, 9H).

Step-4: Preparation of ethyl 2-(2-((5-(2-((1,1-dimethylethylsulfinamido)methyl)pyridin-4-yl)benzofuran-3-yl)methoxy)-4-methoxyphenyl)acetate (68d)

Compound 68d was prepared according to the procedure reported in step-1 of scheme 1, from N-((4-(3-(bromomethyl)benzofuran-5-yl)pyridin-2-yl)methyl)-2-methylpropane-2-sulfinamide (68c) (32 mg, 0.076 mmol) in acetone (2 mL) using ethyl 2-(2-hydroxy-4-methoxyphenyl)acetate (6a) (18.4 mg, 0.087 mmol), $K_2CO_3$ (31.5 mg, 0.228 mmol) and stirring overnight at room temperature. This gave after workup and purification by flash column chromatography [silica gel (12 g), eluting with DMA-80 in DCM from 0-50%] ethyl 2-(2-((5-(2-((1,1-dimethylethylsulfinamido)methyl)pyridin-4-yl)benzofuran-3-yl)methoxy)-4-methoxyphenyl)acetate (68d) (5 mg, 12% yield) as a pale yellow oil; $^1$H NMR (300 MHz, Methanol-$d_4$) δ 8.50 (d, J=5.3 Hz, 1H), 8.04 (d, J=1.9 Hz, 1H), 7.94 (d, J=2.8 Hz, 2H), 7.76 (dd, J=8.6, 1.9 Hz, 1H), 7.69 (dd, J=5.3, 1.8 Hz, 1H), 7.64 (d, J=8.7 Hz, 1H), 7.08 (d, J=8.3 Hz, 1H), 6.76 (d, J=2.4 Hz, 1H), 6.51 (dd, J=8.3, 2.4 Hz, 1H), 5.25 (s, 2H), 4.61 (s, 1H), 4.46 (d, J=3.1 Hz, 2H), 3.81 (s, 3H), 3.69 (q, J=7.1 Hz, 2H), 3.48 (s, 2H), 1.22 (s, 9H), 0.85 (t, J=7.1 Hz, 3H); MS (ES+) 551.2 (M+1).

Step-5: Preparation of 2-(2-((5-(2-(aminomethyl)pyridin-4-yl)benzofuran-3-yl)methoxy)-4-methoxyphenyl)acetic acid (68e)

Compound 68e was prepared according to the procedure reported in step-4 of scheme 39, from ethyl 2-(2-((5-(2-((1,1-dimethylethylsulfinamido)methyl)pyridin-4-yl)benzofuran-3-yl)methoxy)-4-methoxyphenyl)acetate (5 mg, 9.08 µmol) (68d) in THF (0.6 mL) using HCl (4M in 1,4-dioxane, 4.54 µL) and stirring at room temperature for 30 min. The ester was hydrolyzed in THF (0.40 mL), acetonitrile (0.2 mL) using a 1 N solution of lithium hydroxide hydrate (0.082 mL, 0.082 mmol) by stirring at room temperature for 36 h. This gave after workup and purification by reverse phase column chromatography [C18 column (30 g), eluting with ACN in water (containing 0.1% HCl) from 0-100%] 2-(2-((5-(2-(aminomethyl)pyridin-4-yl)benzofuran-3-yl)methoxy)-4-methoxyphenyl)acetic acid (68e) (1.1 mg, 29% yield) HCl salt as a white solid; $^1H$ NMR (300 MHz, Methanol-$d_4$) δ 8.76 (d, J=5.7 Hz, 1H), 8.21 (t, J=2.2 Hz, 2H), 8.09 (dd, J=5.7, 1.8 Hz, 1H), 8.01 (s, 1H), 7.88 (dd, J=8.7, 2.0 Hz, 1H), 7.71 (d, J=8.7 Hz, 1H), 7.11 (d, J=8.3 Hz, 1H), 6.76 (d, J=2.4 Hz, 1H), 6.53 (dd, J=8.3, 2.4 Hz, 1H), 5.31 (s, 2H), 4.47 (s, 1H), 3.80 (s, 3H), 3.53 (s, 2H); MS (ES+): 419.1 (M+1).

Scheme 69

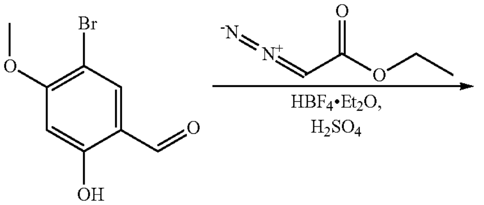

69a

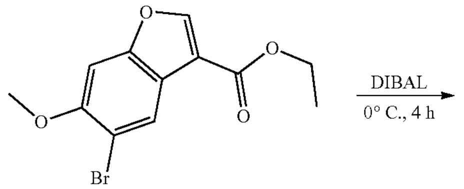

69b

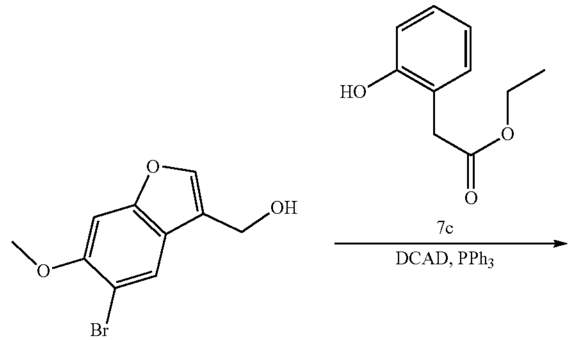

69c

-continued

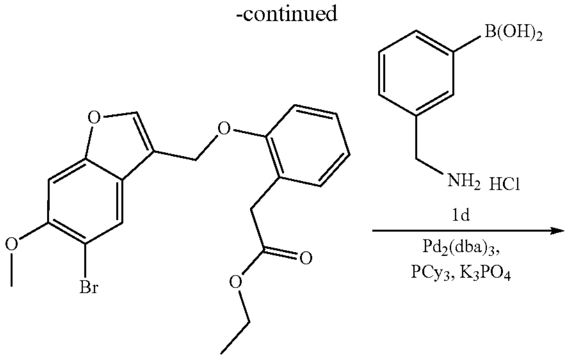

69d

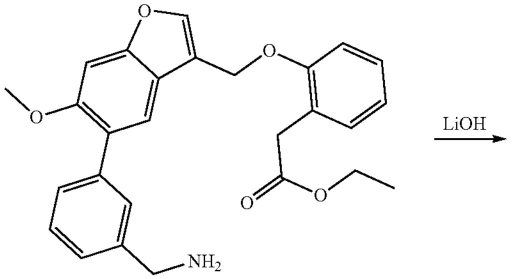

69e

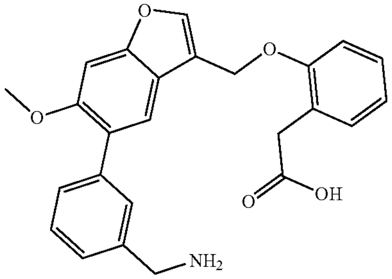

69f

Preparation of 2-(2-((5-(3-(aminomethyl)phenyl)-6-methoxybenzofuran-3-yl)methoxy)phenyl)acetic acid (69f)

Step-1: Preparation of ethyl 5-bromo-6-methoxybenzofuran-3-carboxylate (69b)

To a solution of 5-bromo-2-hydroxy-4-methoxybenzaldehyde (69a) (2.5 g, 10.82 mmol; CAS #57543-36-9) in DCM (25 mL) was added $HBF_4{\cdot}Et_2O$ (0.268 mL, 1.082 mmol), followed by a solution of ethyl diazoacetate (15% in toluene) (11.97 mL, 17.31 mmol; CAS #623-73-4) at RT. [Caution: gas evolved after addition]. The resulting mixture was stirred for 20 min at room temperature and concentrated to dryness to afford a brown thick oil. To the resulting oil was added sulfuric acid (1.442 mL, 27.1 mmol) slowly and the resulting mixture was stirred for 10 min at room temperature. The reaction mixture was diluted with DCM (25 mL), $NaHCO_3$ (6 g) and stirred for 20 h at room temperature. The reaction mixture was concentrated in vacuum and the residue obtained was purified by flash column chromatography [silica gel (40 g), eluting with EtOAc in hexane from 0-50%] followed by reverse-phase column chromatography [C-18 column, 150 g, eluting with 0.1% aqueous HCl in water and acetonitrile from 0-100%] to afford ethyl 5-bromo-6-methoxybenzofuran-3-carboxylate (69b) (0.97 g, 30% yield) as a white solid; $^{1}H$ NMR (300 MHz, DMSO-$d_6$) δ 8.72 (s, 1H), 8.05 (s, 1H), 7.58 (s, 1H), 4.35 (q, J=7.1 Hz, 2H), 3.92 (s, 3H), 1.35 (t, J=7.1 Hz, 3H).

Step-2: Preparation of (5-bromo-6-methoxybenzofuran-3-yl)methanol (69c)

To a stirred solution of ethyl 5-bromo-6-methoxybenzofuran-3-carboxylate (69b) (465 mg, 1.555 mmol) in DCM (2.59 mL) was added a 1.0 M solution of DIBAL in DCM (3.89 mL, 3.89 mmol) at 0° C. under nitrogen. The reaction mixture was stirred at 0° C. for 4 h and diluted with EtOAc (20 mL). The reaction was quenched by successive addition of $H_2O$ (0.16 mL), 15% aqueous NaOH (0.16 mL), $H_2O$ (0.39 mL) at 0° C. and stirred for 15 min at room temperature, followed by addition of anhydrous $MgSO_4$ (0.6 g) and stirring for 15 min. The reaction mixture was filtered, and the residue was washed with EtOAc (20 mL). The filtrate was concentrated in vacuum and residue obtained was purified by flash column chromatography [silica gel (24 g), eluting with EtOAc in hexane from 0-50%] to provide (5-bromo-6-methoxybenzofuran-3-yl)methanol (69c) (233 mg, 58% yield) as a white solid; $^{1}H$ NMR (300 MHz, DMSO-$d_6$) δ 7.89 (s, 1H), 7.81 (d, J=1.1 Hz, 1H), 7.40 (s, 1H), 5.18 (t, J=5.6 Hz, 1H), 4.57 (dd, J=5.7, 1.1 Hz, 2H), 3.89 (s, 3H).

Step-3: Preparation of ethyl 2-(2-((5-bromo-6-methoxybenzofuran-3-yl)methoxy)phenyl)acetate (69d)

Compound 69d was prepared according to the procedure reported in step-2 of Scheme 65, from (5-bromo-6-methoxybenzofuran-3-yl)methanol (69c)(230 mg, 0.895 mmol) using triphenylphosphine (258 mg, 0.984 mmol), a solution of ethyl 2-(2-hydroxyphenyl)acetate (7c)(0.177 g, 0.984 mmol) in DCM (10 mL), a solution of DCAD (361 mg, 0.984 mmol) in DCM (10 mL) at 0° C. and stirring at room temperature for 30 min. This gave after workup and purification by flash column chromatography [silica gel (12 g), eluting with DMA-80 in DCM from 0-50%] ethyl 2-(2-((5-bromo-6-methoxybenzofuran-3-yl)methoxy)phenyl)acetate (69d) (205 mg, 55% yield) as a clear oil; $^{1}H$ NMR (300 MHz, DMSO-$d_6$) δ 8.02 (s, 1H), 7.84 (s, 1H), 7.46 (s, 1H), 7.29 (t, J=7.5 Hz, 1H), 7.23-7.14 (m, 2H), 6.93 (t, J=7.3 Hz, 1H), 5.21 (s, 2H), 3.95 (q, J=7.1 Hz, 2H), 3.90 (s, 3H), 3.56 (s, 2H), 1.00 (t, J=7.1 Hz, 3H).

Step-4: Preparation of ethyl 2-(2-((5-(3-(aminomethyl)phenyl)-6-methoxybenzofuran-3-yl)methoxy)phenyl)acetate (69e)

Compound 69e was prepared according to the procedure reported in step-2 of scheme 1, from ethyl 2-(2-((5-bromo-6-methoxybenzofuran-3-yl)methoxy)phenyl)acetate (69d) (250 mg, 0.596 mmol) in dioxane (2 mL) using 3-(aminomethyl)phenylboronic acid hydrochloride (1d) (134 mg, 0.716 mmol), 2 M solution of $K_3PO_4$ (0.624 mL, 0.811 mmol), tricyclohexylphosphine (40.1 mg, 0.143 mmol), $Pd_2(dba)_3$ (43.7 mg, 0.048 mmol) and heating at 120° C. for 30 min in microwave. This gave after workup and purification by flash column chromatography [silica gel (24 g), eluting with DMA-80 in DCM from 0-50%] ethyl 2-(2-((5-(3-(aminomethyl)phenyl)-6-methoxybenzofuran-3-yl)methoxy)phenyl) acetate (69e) (21 mg, 0.047 mmol, 10% yield); MS (ES+): 446.10 (M+1);

Step-5: Preparation of 2-(2-((5-(3-(aminomethyl)phenyl)-6-methoxybenzofuran-3-yl)methoxy)phenyl) acetic acid (69f)

Compound 69f was prepared according to the procedure reported in step-3 of scheme 1, from ethyl 2-(2-((5-(3-(aminomethyl)phenyl)-6-methoxybenzofuran-3-yl) methoxy)phenyl)acetate (69e) (20 mg, 0.045 mmol) in THF/acetonitrile (0.6 mL; ratio 2:1) using a 1N solution of lithium hydroxide hydrate (0.224 mL, 0.224 mmol) and stirring for 35 h at room temperature. This gave after workup and purification by reverse phase column chromatography [C18 column (50 g), eluting with ACN in water (containing 0.1% HCl) 2-(2-((5-(3-(aminomethyl)phenyl)-6-methoxybenzofuran-3-yl)methoxy)phenyl)acetic acid (69f) (12 mg, 64% yield) HCl salt as a white solid; $^{1}H$ NMR (300 MHz, DMSO-$d_6$) δ 8.26 (s, 3H, $D_2O$ exchangeable), 7.92 (s, 1H), 7.53 (s, 1H), 7.50 (s, 1H), 7.45 (td, J=6.4, 3.4 Hz, 1H), 7.41-7.32 (m, 3H), 7.23-7.06 (m, 3H), 6.84 (td, J=7.3, 1.2 Hz, 1H), 5.19 (s, 2H), 4.01 (s, 2H), 3.75 (s, 3H), 3.46 (s, 2H); MS (ES+): 418.1 (M+1); (ES−): 416.1 (M−1).

Scheme 70

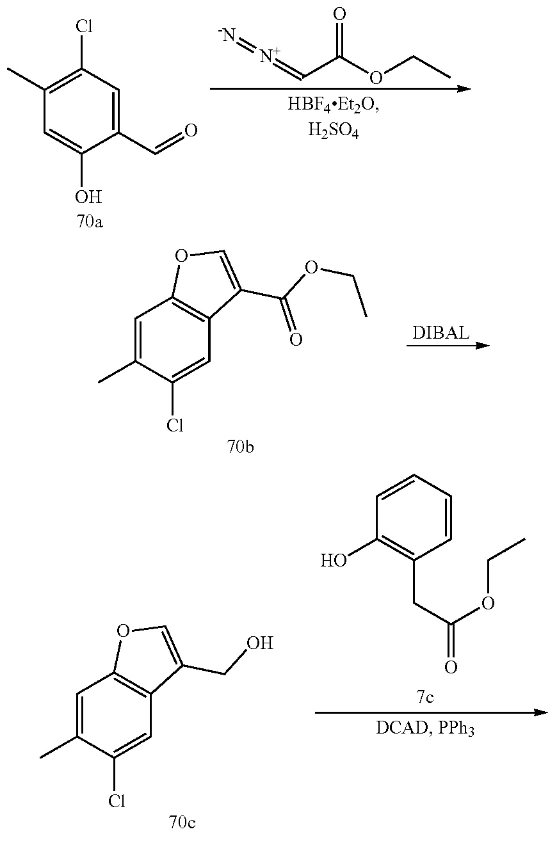

-continued

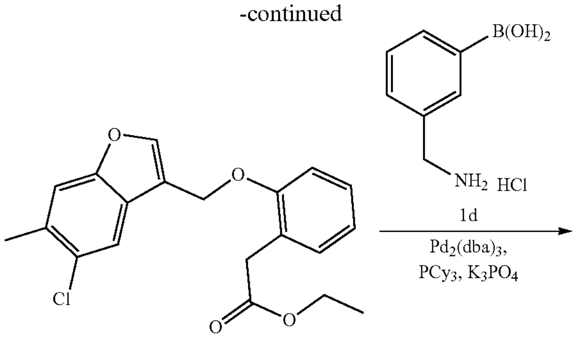

70d

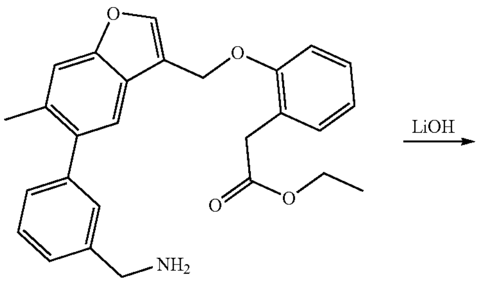

70e

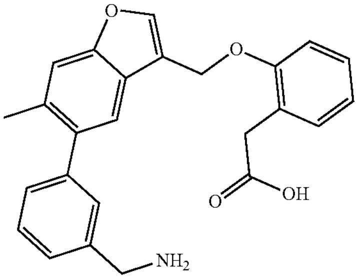

70f

Preparation of 2-(2-((5-(3-(aminomethyl)phenyl)-6-methylbenzofuran-3-yl)methoxy)phenyl)acetic acid (70f)

Step-1: Preparation of ethyl 5-chloro-6-methylbenzofuran-3-carboxylate (70b)

Compound 70b was prepared according to the procedure reported in step-1 of scheme 69, from 5-chloro-2-hydroxy-4-methylbenzaldehyde (70a) (2.5 g, 14.65 mmol; CAS #3328-68-5) in DCM (25 mL) using $HBF_4 \cdot Et_2O$ (0.363 mL, 1.465 mmol), ethyl diazoacetate (15% in toluene) (16.21 mL, 23.45 mmol), sulfuric acid (1.953 mL, 36.6 mmol). This gave after work up and purification [C-18 column (150 g), eluting with ACN in water (containing 0.1% HCl) from 0-100%] ethyl 5-chloro-6-methylbenzofuran-3-carboxylate (70b) (1.3 g, 37% yield) as a white solid; $^1H$ NMR (300 MHz, DMSO-$d_6$) δ 8.78 (s, 1H), 7.92 (s, 1H), 7.80 (s, 1H), 4.36 (q, J=7.1 Hz, 2H), 2.45 (s, 3H), 1.35 (t, J=7.1 Hz, 3H).

Step-2: Preparation of (5-chloro-6-methylbenzofuran-3-yl)methanol (70c)

Compound 70c was prepared according to the procedure reported in step-2 of scheme 69, from ethyl 5-chloro-6-methylbenzofuran-3-carboxylate (70b) (1.25 g, 5.24 mmol) in DCM (8.73 mL) using 1.0 M solution of DIBAL in DCM (13.09 mL, 13.09 mmol) and stirring at 0° C. for 2 h. This gave after work up and purification by flash column chromatography [silica gel (24 g), eluting with EtOAc in hexane from 0-50%] (5-chloro-6-methylbenzofuran-3-yl)methanol (70c) (910 mg, 88% yield) as a white solid; $^1H$ NMR (300 MHz, DMSO-$d_6$) δ 7.86 (d, J=1.1 Hz, 1H), 7.74 (s, 1H), 5.19 (t, J=5.6 Hz, 1H), 4.59 (dd, J=5.6, 1.1 Hz, 2H), 2.42 (s, 3H).

Step-3: Preparation of ethyl 2-(2-((5-chloro-6-methylbenzofuran-3-yl)methoxy)phenyl)acetate (70d)

Compound 70d was prepared according to the procedure reported in step-2 of Scheme 65, from (5-chloro-6-methylbenzofuran-3-yl)methanol (70c) (300 mg, 1.526 mmol) using triphenylphosphine (440 mg, 1.678 mmol), ethyl 2-(2-hydroxyphenyl)acetate (7c) (302 mg, 1.678 mmol) in DCM (10 mL), and DCAD (616 mg, 1.678 mmol) in DCM (10 mL). This gave after workup and purification by flash column chromatography [silica gel (12 g), eluting with DMA-80 in DCM from 0-50%] ethyl 2-(2-((5-chloro-6-methylbenzofuran-3-yl)methoxy)phenyl)acetate (70d) (159 mg, 29% yield) as a clear oil; $^1H$ NMR (300 MHz, DMSO-$d_6$) δ 8.08 (s, 1H), 7.70 (s, 1H), 7.66 (s, 1H), 7.29 (td, J=7.8, 7.4, 1.8 Hz, 1H), 7.20 (ddd, J=9.4, 7.9, 1.4 Hz, 2H), 6.93 (td, J=7.4, 1.2 Hz, 1H), 5.23 (d, J=1.0 Hz, 2H), 3.94 (q, J=7.1 Hz, 2H), 3.56 (s, 2H), 2.43 (s, 3H), 0.99 (t, J=7.1 Hz, 3H).

Step-4: Preparation of ethyl 2-(2-((5-(3-(aminomethyl)phenyl)-6-methylbenzofuran-3-yl)methoxy)phenyl)acetate (70e)

Compound 70e was prepared according to the procedure reported in step-2 of scheme 1, from ethyl 2-(2-((5-chloro-6-methylbenzofuran-3-yl)methoxy)phenyl)acetate (70d) (150 mg, 0.418 mmol) using 3-(aminomethyl)phenylboronic acid hydrochloride (1d) (118 mg, 0.627 mmol), 2 M solution of $K_3PO_4$ (0.547 mL, 0.711 mmol), tricyclohexylphosphine (35.2 mg, 0.125 mmol), $Pd_2(dba)_3$ (38.3 mg, 0.042 mmol) and heating at 120° C. for 30 min in a microwave. This gave after workup and purification by flash column chromatography [silica gel (24 g), eluting with DMA-80 in DCM from 0-50%] ethyl 2-(2-((5-(3-(aminomethyl)phenyl)-6-methylbenzofuran-3-yl)methoxy)phenyl)acetate (70e) (48 mg, 27% yield); MS (ES+): 430.1 (M+1).

Step-5: Preparation of 2-(2-((5-(3-(aminomethyl)phenyl)-6-methylbenzofuran-3-yl)methoxy)phenyl)acetic acid (70f)

Compound 70f was prepared according to the procedure reported in step-3 of scheme 1, from ethyl 2-(2-((5-(3-(aminomethyl)phenyl)-6-methylbenzofuran-3-yl)methoxy)phenyl)acetate (70e) (47 mg, 0.109 mmol) in THF/acetonitrile (1.05 mL; ratio 2:1) using a 1N solution of lithium hydroxide hydrate (0.438 mL, 0.438 mmol) and stirring for 35 h at room temperature. This gave after workup and purification by reverse phase column chromatography [C18 column (50 g), eluting with ACN in water (containing 0.1% HCl) from 0-100%] 2-(2-((5-(3-(aminomethyl)phenyl)-6-methylbenzofuran-3-yl)methoxy)phenyl)acetic acid (70f) (17 mg, 39% yield) HCl salt; $^1H$ NMR (300 MHz, DMSO-$d_6$) δ 12.16 (s, 1H, $D_2O$ exchangeable), 8.39 (s, 3H, $D_2O$ exchangeable), 8.03 (s, 1H), 7.57 (s, 1H), 7.53-7.46 (m, 4H), 7.45-7.34 (m, 1H), 7.29-7.13 (m, 3H), 6.96-6.86 (m, 1H), 5.26 (s, 2H), 4.09 (s, 2H), 3.51 (s, 2H), 2.34 (s, 3H); MS (ES+): 402.1(M+1); (ES−): 400.1 (M−1).

Scheme 71

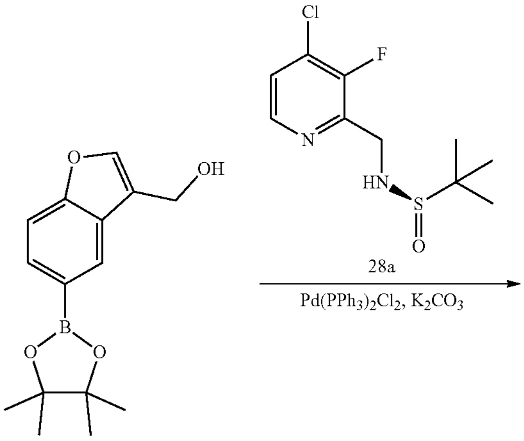

28a

68a

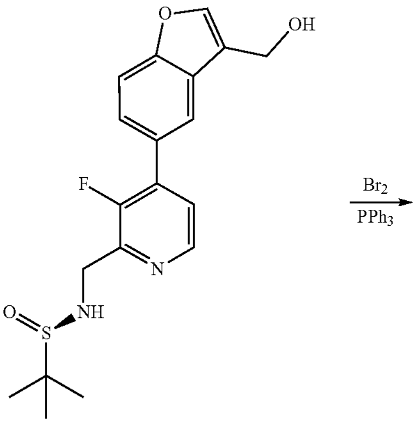

71a

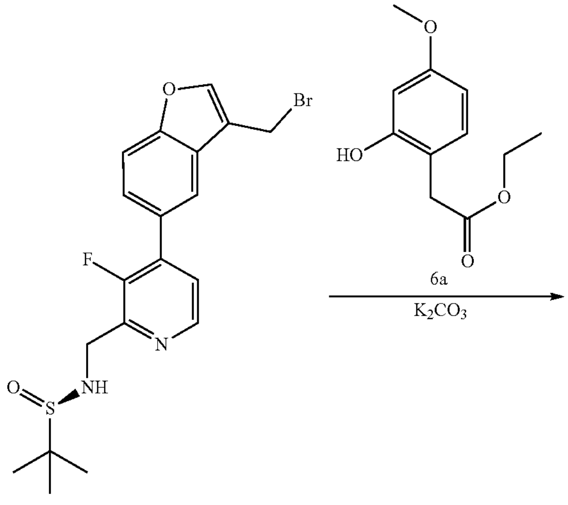

6a

71b

-continued

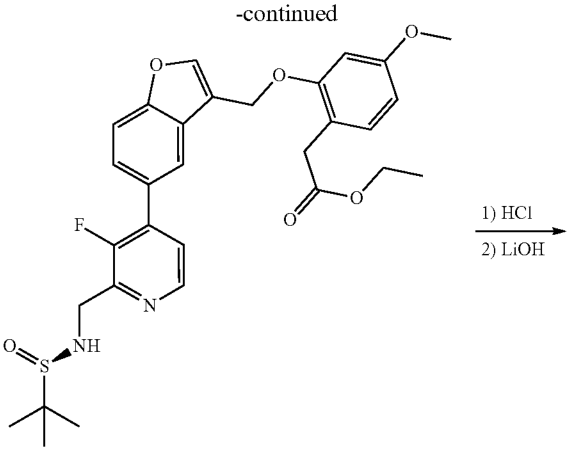

71c

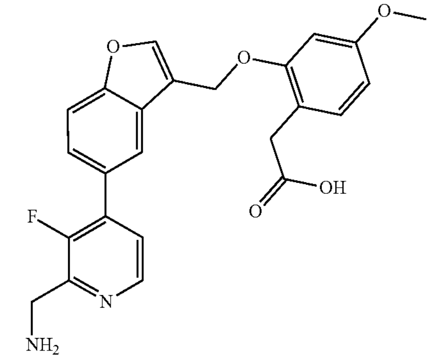

71d

Preparation of 2-(2-((5-(2-(aminomethyl)-3-fluoropyridin-4-yl)benzofuran-3-yl)methoxy)-4-methoxyphenyl)acetic acid (71d)

Step-1: Preparation of N-((3-fluoro-4-(3-(hydroxymethyl)benzofuran-5-yl)pyridin-2-yl)methyl)-2-methylpropane-2-sulfinamide (71a)

Compound 71a was prepared according to the procedure reported in step-8 of Scheme 3, from (5-(4,4,5,5-tetramethyl-1,3,2-dioxaborolan-2-yl)benzofuran-3-yl)methanol (68a) (900 mg, 3.28 mmol) in dioxane (24 mL) using (+)-N-((4-chloro-3-fluoropyridin-2-yl)methyl)-2-methylpropane-2-sulfinamide (28a) (956 mg, 3.61 mmol), bis(triphenylphosphine)palladium(II) chloride (346 mg, 0.492 mmol), a solution of $K_2CO_3$ (1361 mg, 9.85 mmol) in water (3 mL) and heating at 100° C. for 5 h. This gave after workup and purification by flash column chromatography [silica gel (40 g), eluting with DMA-80 in DCM from 0-30%]N-((3-fluoro-4-(3-(hydroxymethyl)benzofuran-5-yl)pyridin-2-yl)methyl)-2-methylpropane-2-sulfinamide (71a) (840 mg, 68% yield) as a brown oil; $^1H$ NMR (300 MHz, DMSO-$d_6$) δ 8.45 (d, J=5.0 Hz, 1H), 8.01-7.95 (m, 2H), 7.74 (d, J=8.6 Hz, 1H), 7.64-7.55 (m, 2H), 5.82 (t, J=5.8 Hz, 1H), 5.24 (t, J=5.5 Hz, 1H), 4.68 (dd, J=5.5, 1.1 Hz, 2H), 4.39 (dd, J=5.9, 2.2 Hz, 2H), 1.12 (s, 9H); MS (ES+) 377.10 (M+1).

Step-2: Preparation of N-((4-(3-(bromomethyl)benzofuran-5-yl)-3-fluoropyridin-2-yl)methyl)-2-methylpropane-2-sulfinamide (71b)

Compound 71b was prepared according to the procedure reported in step-3 of scheme 68, from N-((3-fluoro-4-(3-(hydroxymethyl)benzofuran-5-yl)pyridin-2-yl)methyl)-2-methylpropane-2-sulfinamide (71a) (600 mg, 1.594 mmol) in DCM (5 mL) using dibromine (0.103 mL, 1.992 mmol), triphenylphosphine (523 mg, 1.992 mmol) in DCM (10 mL). This gave after workup and purification by flash column chromatography [silica gel (24 g), eluting with DMA-80 in DCM from 0-40%]N-((4-(3-(bromomethyl)benzofuran-5-yl)-3-fluoropyridin-2-yl)methyl)-2-methylpropane-2-sulfinamide (71b) (210 mg, 30% yield) as a pale yellow oil; $^{1}$H NMR (300 MHz, DMSO-$d_6$) δ 8.47 (d, J=5.1 Hz, 1H), 8.29 (s, 1H), 8.03 (s, 1H), 7.81 (d, J=8.7 Hz, 1H), 7.62 (s, 1H), 7.61 (d, J=1.5 Hz, 1H), 5.83 (t, J=5.8 Hz, 1H), 4.96 (s, 2H), 4.40 (dd, J=5.8, 2.2 Hz, 2H), 1.12 (s, 9H).

Step-3: Preparation of ethyl 2-(2-((5-(2-((1,1-dimethylethylsulfinamido)methyl)-3-fluoropyridin-4-yl)benzofuran-3-yl)methoxy)-4-methoxyphenyl)acetate (71c)

Compound 71c was prepared according to the procedure reported in step-1 of scheme 1, from N-((4-(3-(bromomethyl)benzofuran-5-yl)-3-fluoropyridin-2-yl)methyl)-2-methylpropane-2-sulfinamide (71b) (200 mg, 0.455 mmol) in DMF (3 mL) using ethyl 2-(2-hydroxy-4-methoxyphenyl)acetate (6a) (110 mg, 0.524 mmol), $K_2CO_3$ (189 mg, 1.366 mmol) and stirring overnight at room temperature. This gave after workup and purification by flash column chromatography [silica gel (24 g), eluting with DMA-80 in DCM from 0-50%] ethyl 2-(2-((5-(2-((1,1-dimethylethylsulfinamido)methyl)-3-fluoropyridin-4-yl)benzofuran-3-yl)methoxy)-4-methoxyphenyl)acetate (71c) (10 mg, 4% yield) as a pale yellow oil; MS (ES+): 569.10 (M+1).

Step-4: Preparation of 2-(2-((5-(2-(aminomethyl)-3-fluoropyridin-4-yl)benzofuran-3-yl)methoxy)-4-methoxyphenyl)acetic acid (71d)

Compound 71d was prepared according to the procedure reported in step-4 of scheme 39, from ethyl 2-(2-((5-(2-((1,1-dimethylethylsulfinamido)methyl)-3-fluoropyridin-4-yl)benzofuran-3-yl)methoxy)-4-methoxyphenyl)acetate (71c) (9 mg, 0.016 mmol) in THF (0.45 mL) using HCl (4M in 1,4-dioxane, 7.91 µL, 0.032 mmol) and stirring at room temperature for 30 min. The ester was hydrolyzed in THF (0.30 mL), acetonitrile (0.15 mL) using a solution of lithium hydroxide hydrate (1N, 0.111 mL, 0.111 mmol) and stirring at room temperature for 16 h. This gave after workup and purification by reverse phase column chromatography [C18 column (30 g), eluting with ACN in water (containing 0.1% HCl) from 0-100%] 2-(2-((5-(2-(aminomethyl)-3-fluoropyridin-4-yl)benzofuran-3-yl)methoxy)-4-methoxyphenyl)acetic acid (71d) (1.8 mg, 26% yield) HCl salt as a pale yellow solid; $^{1}$H NMR (300 MHz, Methanol-$d_4$) δ 8.50 (d, J=5.0 Hz, 1H), 8.01 (d, J=1.4 Hz, 1H), 7.97 (s, 1H), 7.73-7.61 (m, 3H), 7.09 (d, J=8.3 Hz, 1H), 6.74 (d, J=2.4 Hz, 1H), 6.51 (dd, J=8.3, 2.4 Hz, 1H), 5.29 (d, J=1.1 Hz, 2H), 4.45-4.37 (m, 2H), 3.79 (s, 3H), 3.51 (s, 2H); $^{19}$F NMR (282 MHz, $CD_3OD$) δ −134.93; MS (ES+): 437.1 (M+1); (ES−): 435.0 (M−1).

Scheme 72

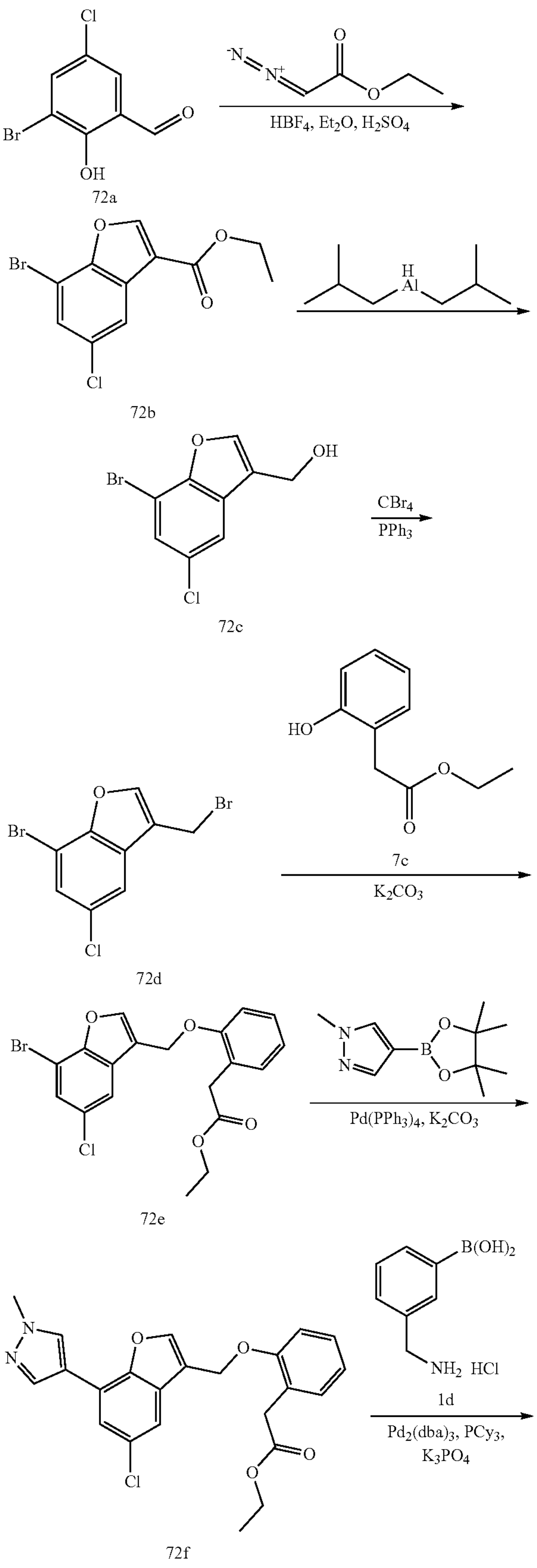

-continued

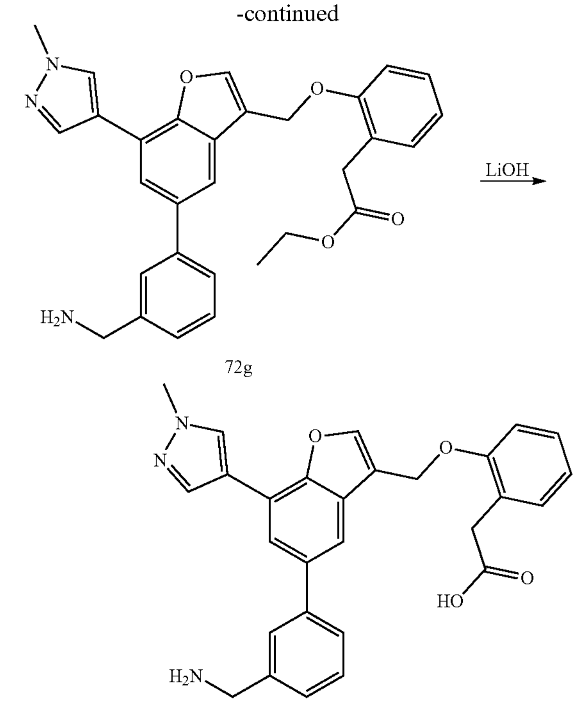

72g

72h

Preparation of 2-(2-((5-(3-(aminomethyl)phenyl)-7-(1-methyl-1H-pyrazol-4-yl)benzofuran-3-yl)methoxy)phenyl)acetic acid (72h)

Step-1: Preparation of ethyl 7-bromo-5-chlorobenzofuran-3-carboxylate (72b)

Compound 72b was prepared according to the procedure reported in step-1 of scheme 69, from 3-bromo-5-chloro-2-hydroxybenzaldehyde (72a) (10 g, 42.5 mmol; CAS #19652-32-5) in DCM (50 mL) using $HBF_4 \cdot Et_2O$ (1.250 g, 4.25 mmol), ethyl diazoacetate (15% in toluene) (47.0 mL, 68.0 mmol), and sulfuric acid (5.66 mL, 106 mmol). This gave after work up and purification by reverse phase column chromatography [C-18 column (40 g), eluting with EtOAc in hexane from 0-50%] ethyl 7-bromo-5-chlorobenzofuran-3-carboxylate (72b) (9.472 g, 74% yield) as a white solid; MS (ES+): 336.30 (M+Cl).

Step-2: Preparation of (7-bromo-5-chlorobenzofuran-3-yl)methanol (72c)

Compound 72c was prepared according to the procedure reported in step-2 of scheme 69, from ethyl 7-bromo-5-chlorobenzofuran-3-carboxylate (72b) (1.25 g, 5.24 mmol) in DCM (50 mL) using 1.0 M solution of DIBAL in DCM (78 mL, 78 mmol) and stirring at 0° C. for 2h. This gave after work up and purification by flash column chromatography [silica gel (24 g), EtOAc in hexane from 0-50%) (7-bromo-5-chlorobenzofuran-3-yl)methanol (72c) (4.52 g, 55% yield) as a white solid; $^1$H NMR (300 MHz, DMSO-$d_6$) δ 8.08 (d, J=1.2 Hz, 1H), 7.80 (d, J=2.0 Hz, 1H), 7.68 (d, J=2.0 Hz, 1H), 5.29 (t, J=5.6 Hz, 1H), 4.60 (dd, J=5.6, 1.1 Hz, 2H).

Step-3: Preparation of 7-bromo-3-(bromomethyl)-5-chlorobenzofuran (72d)

To a solution of (7-bromo-5-chlorobenzofuran-3-yl)methanol (72c) (1 g, 3.82 mmol) was added a solution of $CBr_4$ (2.54 g, 7.65 mmol) in DCM (20 mL) and triphenylphosphine (2.006 g, 7.65 mmol) in DCM (10 mL) at 0° C. over a period of 15 minutes and stirred at 0° C. for 2 h. The reaction was diluted with water (50 mL), extracted with DCM (2×100 mL). The combined organics were dried, filtered, and concentrated in vacuum. The residue obtained was purified by flash column chromatography [silica gel 40 g, eluting with ethyl acetate in hexanes from 0-30%] to furnish 7-bromo-3-(bromomethyl)-5-chlorobenzofuran (72d) (1.046 g, 84% yield) as a white solid; $^1$H NMR (300 MHz, DMSO-$d_6$) δ 8.37 (s, 1H), 7.86 (d, J=2.0 Hz, 1H), 7.76 (d, J=1.9 Hz, 1H), 4.89 (s, 2H).

Step-4: Preparation of ethyl 2-(2-((7-bromo-5-chlorobenzofuran-3-yl)methoxy)phenyl)acetate (72e)

Compound 72e was prepared according to the procedure reported in step-1 of scheme 1, from 7-bromo-3-(bromomethyl)-5-chlorobenzofuran (72d)(1.046 g, 3.22 mmol) in DMF (15 mL) using ethyl 2-(2-hydroxyphenyl)acetate (7c) (0.528 g, 2.93 mmol), $K_2CO_3$ (1.215 g, 8.79 mmol) and stirring overnight at room temperature. This gave after workup and purification by flash column chromatography [silica gel (12 g), eluting with EtOAc in hexane from 0-50%]ethyl 2-(2-((7-bromo-5-chlorobenzofuran-3-yl)methoxy)phenyl)acetate (72e) (872 mg, 70% yield); MS (ES+): 444.90 (M+Na).

Step-5: Preparation of ethyl 2-(2-((5-chloro-7-(1-methyl-1H-pyrazol-4-yl)benzofuran-3-yl)methoxy)phenyl)acetate (72f)

Compound 72f was prepared according to the procedure reported in step-8 of Scheme 3, from ethyl 2-(2-((7-bromo-5-chlorobenzofuran-3-yl)methoxy)phenyl)acetate (72e) (250 mg, 0.590 mmol) in THF (10 mL) using 1-methyl-4-(4,4,5,5-tetramethyl-1,3,2-dioxaborolan-2-yl)-1H-pyrazole (184 mg, 0.885 mmol), $Pd(PPh_3)_4$ (34.1 mg, 0.030 mmol), a solution of $K_2CO_3$ (122 mg, 0.885 mmol) in water (5 mL) and heating at 80° C. for 4 h. This gave after workup and purification by flash column chromatography [silica gel (12 g), eluting with DMA-80 in DCM from 0-50%] followed by purification by reverse phase column chromatography [C18 column (50 g), eluting with ACN in water (containing 0.1% HCl) from 0-100%] ethyl 2-(2-((5-chloro-7-(1-methyl-1H-pyrazol-4-yl)benzofuran-3-yl)methoxy)phenyl)acetate (72f) (100 mg, 40% yield) as a clear gum; $^1$H NMR (300 MHz, DMSO-$d_6$) δ 8.45 (s, 1H), 8.24 (s, 1H), 8.18 (s, 1H), 7.72 (d, J=2.1 Hz, 1H), 7.53 (d, J=2.1 Hz, 1H), 7.30 (td, J=7.8, 7.3, 1.7 Hz, 1H), 7.22 (ddd, J=7.7, 5.5, 3.1 Hz, 2H), 7.00-6.86 (m, 1H), 5.27 (s, 2H), 4.03-3.86 (m, 5H), 3.57 (s, 2H), 0.99 (t, J=7.1 Hz, 3H); MS (ES+): 425.00 (M+1).

Step-6: Preparation of ethyl 2-(2-((5-(3-(aminomethyl)phenyl)-7-(1-methyl-1H-pyrazol-4-yl)benzofuran-3-yl)methoxy)phenyl)acetate (72g)

Compound 72g was prepared according to the procedure reported in step-2 of scheme 1, from ethyl 2-(2-((5-chloro-7-(1-methyl-1H-pyrazol-4-yl)benzofuran-3-yl)methoxy)phenyl)acetate (72f) (97 mg, 0.228 mmol) in dioxane (2 mL)

using 3-(aminomethyl)phenylboronic acid hydrochloride (1d) (53.5 mg, 0.285 mmol), 1.27 M solution of $K_3PO_4$ (0.306 mL, 0.388 mmol), tricyclohexylphosphine (25.6 mg, 0.091 mmol), $Pd_2(dba)_3$ (41.8 mg, 0.046 mmol) and heating at 135° C. for 90 min in a microwave. This gave after workup and purification by column chromatography [silica gel (24 g), eluting with DMA-80 in DCM from 0-100%] ethyl 2-(2-((5-(3-(aminomethyl)phenyl)-7-(1-methyl-1H-pyrazol-4-yl)benzofuran-3-yl)methoxy)phenyl)acetate (72g) (3 mg, 3% yield); MS (ES+): 496.10 (M+1);

Step-7: Preparation of 2-(2-((5-(3-(aminomethyl)phenyl)-7-(1-methyl-1H-pyrazol-4-yl)benzofuran-3-yl)methoxy)phenyl)acetic acid (72h)

Compound 72h was prepared according to the procedure reported in step-3 of scheme 1, from ethyl 2-(2-((5-(3-(aminomethyl)phenyl)-7-(1-methyl-1H-pyrazol-4-yl)benzofuran-3-yl)methoxy)phenyl)acetate (72g) (3 mg, 6.05 μmol) in THF/acetonitrile (0.09 mL; ratio 2:1) using a 1N solution of lithium hydroxide hydrate (0.030 mL, 0.030 mmol) and stirring for 15 h at room temperature. This gave after workup and purification by reverse phase column chromatography [C18 column (30 g), eluting with ACN in water (containing 0.1% HCl) from 0-100%] 2-(2-((5-(3-(aminomethyl)phenyl)-7-(1-methyl-1H-pyrazol-4-yl)benzofuran-3-yl)methoxy)phenyl)acetic acid (72h) (2.1 mg, 74% yield) HCl salt as a solid; $^1H$ NMR (300 MHz, Methanol-$d_4$) δ 8.46 (s, 1H), 8.31 (s, 1H), 8.03 (s, 1H), 7.89 (q, J=1.8 Hz, 2H), 7.87-7.79 (m, 2H), 7.55 (t, J=7.7 Hz, 1H), 7.43 (d, J=7.6 Hz, 1H), 7.33-7.24 (m, 1H), 7.24-7.16 (m, 2H), 6.95 (td, J=7.4, 1.2 Hz, 1H), 5.33 (s, 2H), 4.22 (s, 2H), 4.04 (s, 3H), 3.63 (s, 2H); MS (ES+): 468.1 (M+1).

Scheme 73

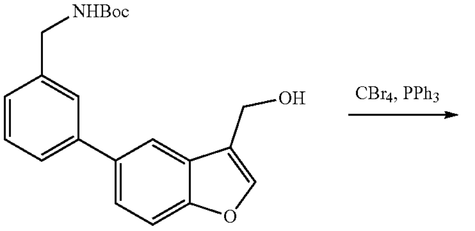

39b

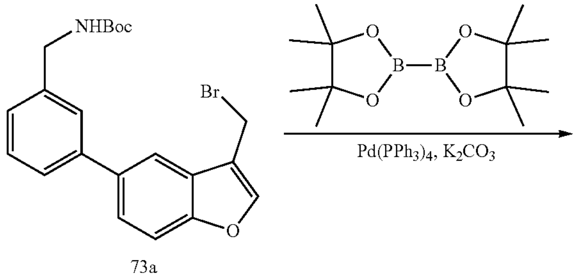

73a

-continued

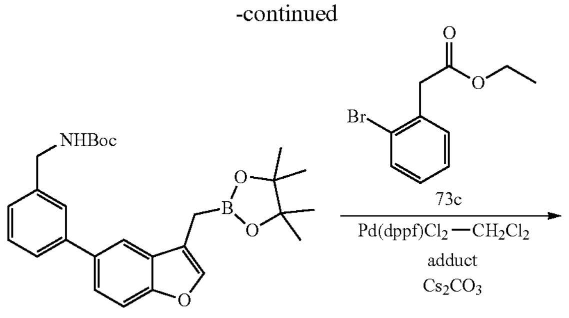

73b

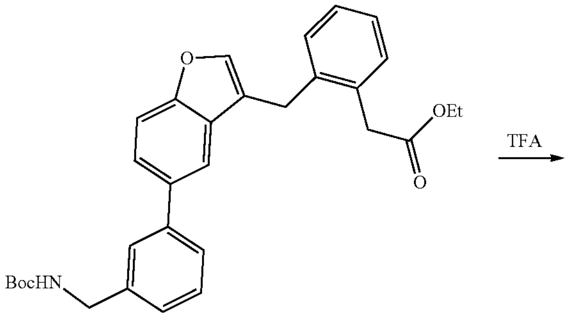

73d

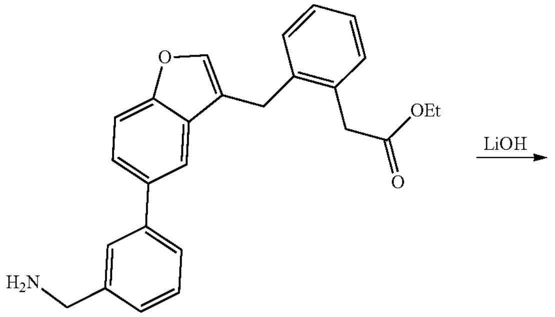

73e

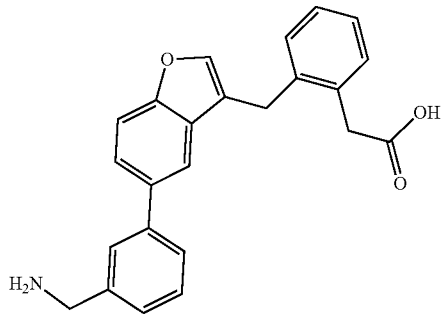

73f

Preparation of 2-(2-((5-(3-(aminomethyl)phenyl)benzofuran-3-yl)methyl)phenyl)acetic acid (73f)

Step-1: Preparation of tert-butyl 3-(3-(bromomethyl)benzofuran-5-yl)benzylcarbamate (73a)

Compound 73a was prepared according to the procedure reported in step-3 of scheme 72, from tert-butyl 3-(3-(hydroxymethyl)benzofuran-5-yl)benzylcarbamate (39b) (500 mg, 1.415 mmol) in DCM (10 mL) using a solution of $CBr_4$ (0.938 g, 2.83 mmol) in DCM (20 mL), triphenylphosphine (742 mg, 2.83 mmol) and stirring at 0° C. for 2 h. This gave after workup and purification by flash column chromatography [silica gel (40 g), eluting with ethyl acetate in hexanes from 0-30%] tert-butyl 3-(3-(bromomethyl)benzofuran-5-yl)benzylcarbamate (73a) (247 mg, 42% yield) as a white solid; $^1$H NMR (300 MHz, DMSO-$d_6$) δ 8.22 (s, 1H), 7.96 (d, J=1.8 Hz, 1H), 7.70 (s, 2H), 7.64 (dd, J=8.6, 1.9 Hz, 1H), 7.58 (d, J=2.0 Hz, 1H), 7.52-7.40 (m, 2H), 7.25 (d, J=7.6 Hz, 1H), 4.96 (s, 2H), 4.23 (d, J=6.2 Hz, 2H), 1.41 (d, J=2.4 Hz, 9H).

Step-2: Preparation of tert-butyl 3-(3-((4,4,5,5-tetramethyl-1,3,2-dioxaborolan-2-yl)methyl)benzofuran-5-yl)benzylcarbamate (73b)

Compound 73b was prepared according to the procedure reported in step-1 of scheme 27, from tert-butyl 3-(3-(bromomethyl)benzofuran-5-yl)benzylcarbamate (73a) (0.247 g, 0.593 mmol) in anhydrous dioxane (23 mL) using BisPin (0.181 g, 0.712 mmol), potassium carbonate (0.246 g, 1.780 mmol), $Pd(PPh_3)_4$ (0.069 g, 0.059 mmol) and heating at 80° C. for 23 h. This gave after work up and purification by flash column chromatography [silica gel (12 g), eluting with EtOAc in hexane from 0-70%] tert-butyl 3-(3-((4,4,5,5-tetramethyl-1,3,2-dioxaborolan-2-yl)methyl)benzofuran-5-yl)benzylcarbamate (73b) (0.118 g, 43% yield) as a solid; MS (ES+): 486.2 (M+Na).

Step-3: Preparation of ethyl 2-(2-((5-(3-(((tert-butoxycarbonyl)amino)methyl)phenyl)benzofuran-3-yl)methyl)phenyl)acetate (73d)

Compound 73d was prepared according to the procedure reported in step-1 of scheme 27, from tert-butyl 3-(3-((4,4,5,5-tetramethyl-1,3,2-dioxaborolan-2-yl)methyl)benzofuran-5-yl)benzylcarbamate (73b) (84 mg, 0.181 mmol) in anhydrous dioxane (3 mL) using ethyl 2-(2-bromophenyl)acetate (73c) (44.1 mg, 0.181 mmol), cesium carbonate (75 mg, 0.544 mmol), $PdCl_2(dppf)-CH_2Cl_2$ adduct (22.21 mg, 0.027 mmol) and heating at 90° C. for 3 h. This gave after work up and purification by flash column chromatography [silica gel (12 g), eluting with DMA-80 in DCM from 0-50%] ethyl 2-(2-((5-(3-(((tert-butoxycarbonyl)amino)methyl)phenyl)benzofuran-3-yl)methyl)phenyl)acetate (73d) (72 mg, 79% yield) as a yellow syrup; MS (ES+): 400.2 (M−Boc+2).

Step-4: Preparation of ethyl 2-(2-((5-(3-(aminomethyl)phenyl)benzofuran-3-yl)methyl)phenyl)acetate (73e)

Compound 73e was prepared according to the procedure reported in step-9 of scheme 3, from ethyl 2-(2-((5-(3-(((tert-butoxycarbonyl)amino)methyl)phenyl)benzofuran-3-yl)methyl)phenyl)acetate (73d) (91 mg, 0.182 mmol) in DCM (8 mL) using TFA (8 mL, 0.182 mmol). The reaction mixture was concentrated in vacuum and used as such in next step; MS (ES+): 400.2 (M+1).

Step-5: Preparation of 2-(2-((5-(3-(aminomethyl)phenyl)benzofuran-3-yl)methyl)phenyl)acetic acid (73f)

Compound 73f was prepared according to the procedure reported in step-3 of scheme 1, from ethyl 2-(2-((5-(3-(aminomethyl)phenyl)benzofuran-3-yl)methyl)phenyl)acetate (73e) (73 mg, 0.183 mmol) in tetrahydrofuran (5 mL), methanol (1 mL) and water (1 mL) using a 1N solution of lithium hydroxide hydrate (17.51 mg, 0.731 mmol) and stirring overnight at room temperature. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methyl)phenyl)acetic acid (73f) (12 mg, 10% yield) HCl salt as a light brown solid; $^1$H NMR (300 MHz, Methanol-$d_4$) δ 7.71-7.63 (m, 3H), 7.57 (d, J=1.8 Hz, 1H), 7.55 (s, 1H), 7.50 (t, J=7.5 Hz, 1H), 7.45-7.43 (m, 1H), 7.39 (d, J=7.6 Hz, 1H), 7.32-7.26 (m, 1H), 7.23-7.18 (m, 3H), 4.17 (s, 2H), 4.13 (s, 2H), 3.74 (s, 2H); MS (ES+): 372.1 (M+1); MS (ES−): 370.0 (M−1).

Scheme 74

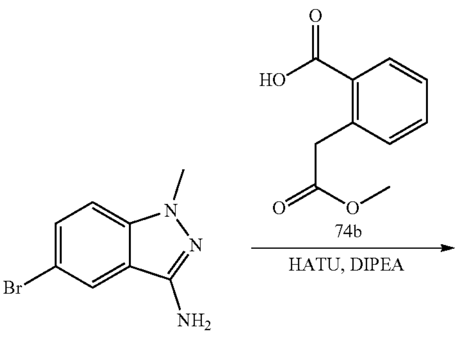

74a

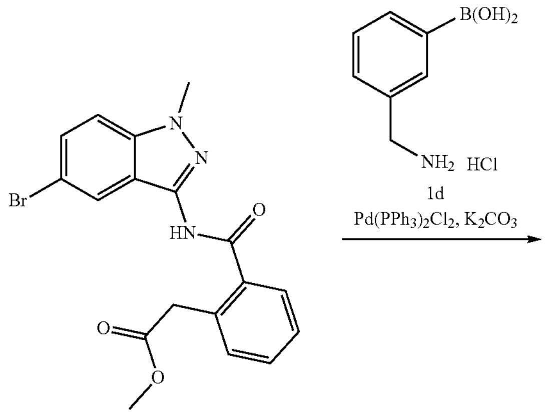

74c

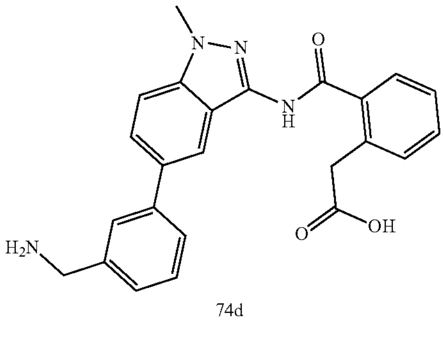

74d

Preparation of 2-(2-((5-(3-(aminomethyl)phenyl)-1-methyl-1H-indazol-3-yl)carbamoyl)phenyl)acetic acid (74d)

Step-1: Preparation of methyl 2-(2-((5-bromo-1-methyl-1H-indazol-3-yl)carbamoyl)phenyl)acetate (74c)

Compound 74c was prepared according to the procedure reported in step-1 of scheme 10, from 5-bromo-1-methyl-1H-indazol-3-amine (74a) (0.4 g, 1.769 mmol; CAS #1000018-06-3) in DMF (5 mL) using 2-(2-methoxy-2-oxoethyl)benzoic acid (74b) (0.344 g, 1.769 mmol; CAS #14736-50-6), N-ethyl-N-isopropylpropan-2-amine (DIPEA) (0.634 mL, 3.63 mmol), 2-(3H-[1,2,3]triazolo[4,5-b]pyridin-3-yl)-1,1,3,3-tetramethylisouronium hexafluorophosphate(V) (HATU) (690 mg, 1.815 mmol) and stirring at room temperature for 16 h. This gave after workup and purification by flash column chromatography [silica gel (24 g), eluting with EtOAc/MeOH (ratio 9:1) in hexane from 0-100%]methyl 2-(2-((5-bromo-1-methyl-1H-indazol-3-yl)carbamoyl)phenyl)acetate (74c) (0.32 g, 45% yield) as a white solid; MS (ES+): 402.00 (M+1).

Step-2: Preparation of 2-(2-((5-(3-(aminomethyl)phenyl)-1-methyl-1H-indazol-3-yl)carbamoyl)phenyl)acetic acid (74d)

Compound 74d was prepared according to the procedure reported in step-8 of Scheme 3, from methyl 2-(2-((5-bromo-1-methyl-1H-indazol-3-yl)carbamoyl)phenyl)acetate (74c) (0.32 g, 0.796 mmol) in dioxane (8 mL) using 3-(aminomethyl)phenylboronic acid hydrochloride (1d) (0.298 g, 1.591 mmol), $Pd(PPh_3)_2C_{12}$ (0.084 g, 0.119 mmol), a solution of $K_2CO_3$ (0.330 g, 2.387 mmol) in water (2 mL) and heating at 90° C. for 3 h. This gave after workup and purification by flash column chromatography [silica gel (12 g), eluting with DMA-80 in DCM from 0-50%] followed by reverse phase column chromatography [C18 column (50 g), eluting with ACN in water (containing 0.1% HCl) from 0-100%] 2-(2-((5-(3-(aminomethyl)phenyl)-1-methyl-1H-indazol-3-yl)carbamoyl)phenyl)acetic acid (74d) (15 mg, 5% yield) HCl salt as a white solid; $^1H$ NMR (300 MHz, DMSO-$d_6$) δ 12.27 (s, 1H, $D_2O$ exchangeable), 10.87 (s, 1H. $D_2O$ exchangeable), 8.32 (s, 3H, $D_2O$ exchangeable), 8.05 (d, J=1.5 Hz, 1H), 7.84-7.81 (m, 1H), 7.78-7.68 (m, 4H), 7.55-7.46 (m, 2H), 7.46-7.36 (m, 3H), 4.15-4.06 (m, 2H), 4.03 (s, 3H), 3.92 (s, 2H); MS (ES+): 415.15 (M+1).

Scheme 75

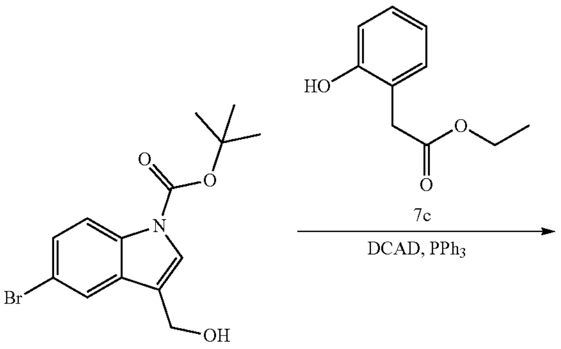

75a

-continued

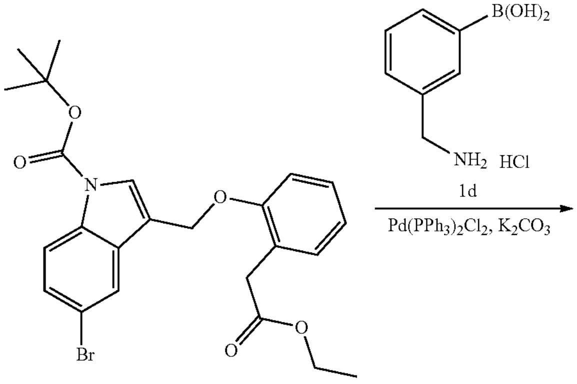

75b

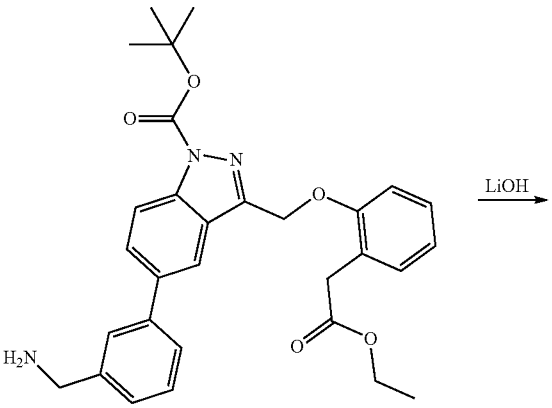

75c

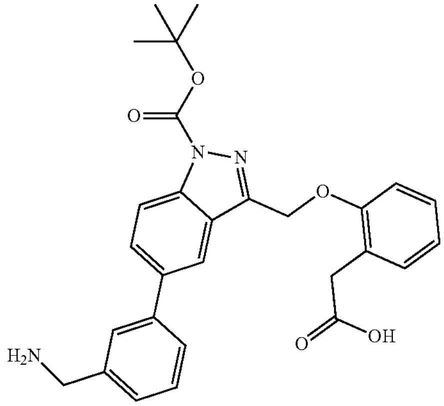

75d

-continued

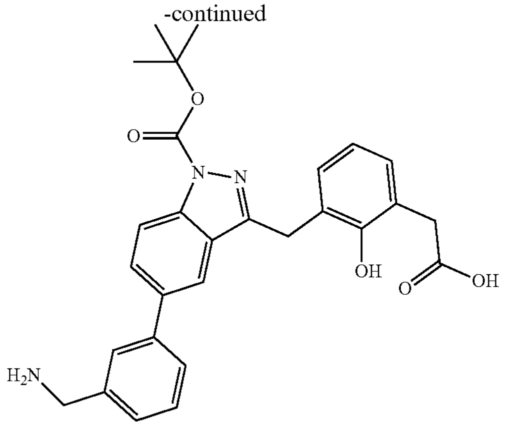

75e

Preparation of 2-(2-((5-(3-(aminomethyl)phenyl)-1-(tert-butoxycarbonyl)-1H-indol-3-yl)methoxy)phenyl)acetic acid (75d) and 2-(3-((5-(3-(aminomethyl)phenyl)-1-(tert-butoxycarbonyl)-1H-indol-3-yl)methyl)-2-hydroxyphenyl)acetic acid (75e)

Step-1: Preparation of tert-butyl 5-bromo-3-((2-(2-ethoxy-2-oxoethyl)phenoxy)methyl)-1H-indole-1-carboxylate (75b)

Compound 75b was prepared according to the procedure reported in step-3 of scheme 7, from tert-butyl 5-bromo-3-(hydroxymethyl)-1H-indole-1-carboxylate (75a) (1 g, 3.07 mmol; CAS #905710-14-7) in DCM (15 mL) using ethyl 2-(2-hydroxyphenyl)acetate (7c)(0.663 g, 3.68 mmol), triphenylphosphine (0.965 g, 3.68 mmol), bis(4-chlorobenzyl) diazene-1,2-dicarboxylate (DCAD) (1.351 g, 3.68 mmol) in DCM (15 mL) and stirring at room temperature for 30 min. This gave after workup and purification by flash column chromatography [silica gel (24 g), eluting with EtOAc/MeOH (Ratio 9:1) in hexane from 0-30%] tert-butyl 5-bromo-3-((2-(2-ethoxy-2-oxoethyl)phenoxy)methyl)-1H-indole-1-carboxylate (75b) (0.58 g, 39% yield) as a white oil; $^1$H NMR (300 MHz, DMSO-$d_6$) δ 8.05-7.97 (m, 1H), 7.85 (d, J=2.1 Hz, 1H), 7.52 (dd, J=8.8, 2.0 Hz, 1H), 7.45 (dd, J=8.8, 1.7 Hz, 1H), 7.30 (td, J=7.7, 7.3, 1.7 Hz, 1H), 7.24-7.17 (m, 2H), 7.06-6.96 (m, 1H), 5.24 (s, 2H), 3.94 (t, J=7.1 Hz, 2H), 3.55 (s, 2H), 1.64 (s, 9H), 0.99 (t, J=7.1 Hz, 3H).

Step-2: Preparation of tert-butyl 5-(3-(aminomethyl)phenyl)-3-((2-(2-ethoxy-2-oxoethyl)phenoxy)methyl)-1H-indole-1-carboxylate (75c)

Compound 75c was prepared according to the procedure reported in step-8 of Scheme 3, from tert-butyl 5-bromo-3-((2-(2-ethoxy-2-oxoethyl)phenoxy)methyl)-1H-indole-1-carboxylate (75b) (0.55 g, 1.126 mmol) in dioxane (10 mL) using 3-(aminomethyl)phenylboronic acid hydrochloride (1d) (0.422 g, 2.252 mmol), bis(triphenylphosphine)palladium(II) chloride (0.119 g, 0.169 mmol), a solution of $K_2CO_3$ (0.467 g, 3.38 mmol) in water (2 mL) and heating the reaction mixture at 90° C. for 3 h. This gave after workup and purification by flash column chromatography [C18 column (50 g), eluting with ACN in water (containing 0.1% HCl) from 0-100%] tert-butyl 5-(3-(aminomethyl)phenyl)-3-((2-(2-ethoxy-2-oxoethyl)phenoxy)methyl)-1H-indole-1-carboxylate (75c)(0.25 g, 43% yield) as a white solid; MS (ES+): 515.20 (M+1).

Step-3: Preparation of 2-(2-((5-(3-(aminomethyl)phenyl)-1-(tert-butoxycarbonyl)-1H-indol-3-yl)methoxy)phenyl)acetic acid (75d) and 2-(3-((5-(3-(aminomethyl)phenyl)-1-(tert-butoxycarbonyl)-1H-indol-3-yl)methyl)-2-hydroxyphenyl)acetic acid (75e)

Compound 75d was prepared according to the procedure reported in step-3 of scheme 1, from tert-butyl 5-(3-(aminomethyl)phenyl)-3-((2-(2-ethoxy-2-oxoethyl)phenoxy)methyl)-1H-indole-1-carboxylate (75c) (0.25 g, 0.486 mmol) in THF/MeOH (4 mL each) using a solution of lithium hydroxide hydrate (0.082 g, 1.943 mmol) in water (1 mL) and stirring for 2 h at room temperature. This gave after workup and purification by reverse phase column chromatography [C18 column (50 g), eluting with ACN in water from 0-100%] 2-(2-((5-(3-(aminomethyl)phenyl)-1-(tert-butoxycarbonyl)-1H-indol-3-yl)methoxy)phenyl)acetic acid (75d) (10 mg, 4% yield) as a white solid; $^1$H NMR (300 MHz, DMSO-$d_6$) δ 8.40 (s, 1H), 8.13 (d, J=8.7 Hz, 1H), 8.05 (d, J=1.8 Hz, 1H), 7.90 (s, 1H), 7.72-7.63 (m, 2H), 7.41 (t, J=7.6 Hz, 1H), 7.28 (d, J=7.6 Hz, 1H), 7.21-7.12 (m, 1H), 7.12-7.05 (m, 2H), 6.85 (td, J=7.3, 1.2 Hz, 1H), 5.19 (s, 2H), 4.03 (s, 2H), 3.32 (s, 2H), 1.66 (s, 9H); MS (ES+): 487.10 (M+1); 509.20 (M+Na); 973.40 (2M+1), followed by 2-(3-((5-(3-(aminomethyl)phenyl)-1-(tert-butoxycarbonyl)-1H-indol-3-yl)methyl)-2-hydroxyphenyl)acetic acid (75e) (10 mg, 4% yield) as a white solid; $^1$H NMR (300 MHz, DMSO-$d_6$) δ 13.94 (s, 1H, $D_2O$ exchangeable), 8.05 (d, J=8.7 Hz, 1H), 7.95 (d, J=1.8 Hz, 1H), 7.74 (d, J=2.8 Hz, 2H), 7.66 (d, J=7.8 Hz, 1H), 7.59 (dd, J=8.8, 1.8 Hz, 1H), 7.45 (t, J=7.7 Hz, 1H), 7.36 (d, J=7.6 Hz, 1H), 6.96 (dd, J=7.6, 1.7 Hz, 1H), 6.79 (dd, J=7.5, 1.7 Hz, 1H), 6.55 (t, J=7.4 Hz, 1H), 4.10 (s, 2H), 4.01 (s, 2H), 3.43 (s, 2H), 1.65 (s, 9H); MS (ES+): 487.20 (M+1).

Scheme 76

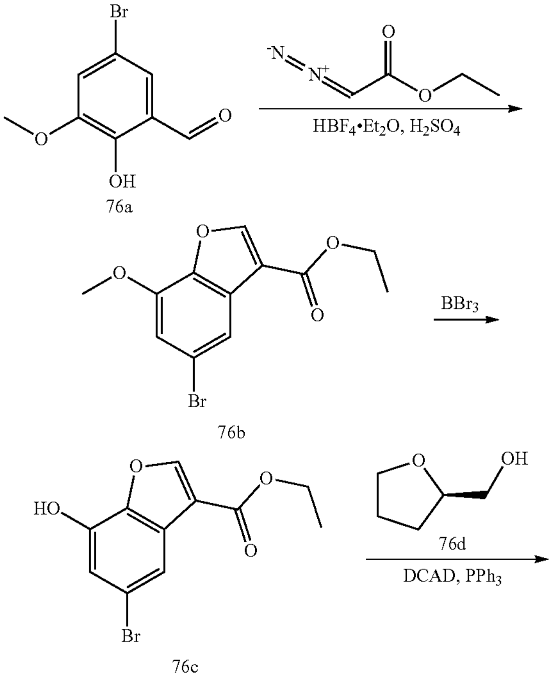

76a

76b

76c

-continued

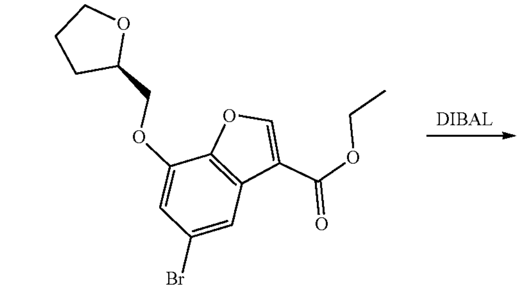

76e

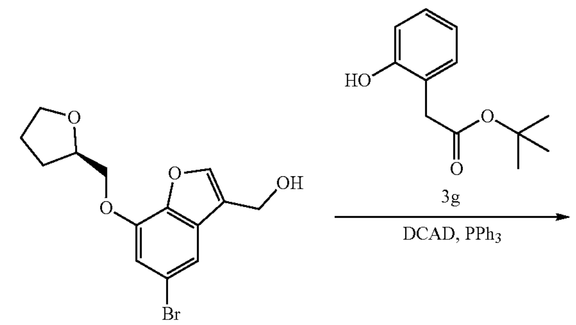

76f

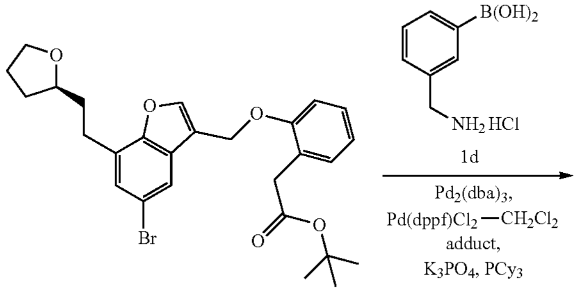

76g

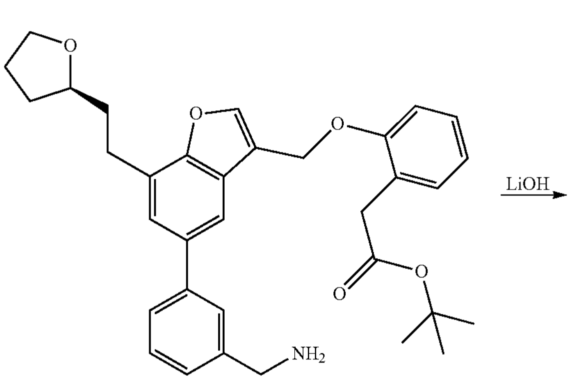

76h

-continued

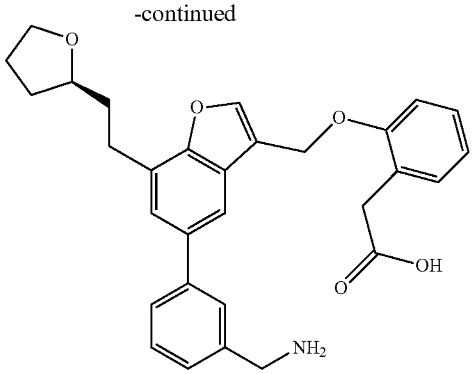

76i

Preparation of (R)-2-(2-((5-(3-(aminomethyl)phenyl)-7-((tetrahydrofuran-2-yl)methoxy)benzofuran-3-yl)methoxy)phenyl)acetic acid (76i)

Step-1: Preparation of ethyl 5-bromo-7-methoxybenzofuran-3-carboxylate (76b)

Compound 76b was prepared according to the procedure reported in step-1 of scheme 69, from 5-bromo-2-hydroxy-3-methoxybenzaldehyde (76a) (10 g, 43.3 mmol; CAS #5034-74-2) in DCM (50 mL) using $HBF_4{\cdot}Et_2O$ (1.071 mL, 4.33 mmol), ethyl diazoacetate (15% in toluene) (62.9 mL, 91 mmol) and concentrated sulfuric acid (1.953 mL, 36.6 mmol). This gave after work up and purification [silica gel (80 g), eluting with EtOAc in hexane from 0-50%] ethyl 5-bromo-7-methoxybenzofuran-3-carboxylate (76b) (5.9 g, 46% yield) as a white solid; $^1H$ NMR (300 MHz, DMSO-$d_6$) δ 8.79 (s, 1H), 7.65 (d, J=1.7 Hz, 1H), 7.24 (d, J=1.8 Hz, 1H), 4.35 (q, J=7.1 Hz, 2H), 3.98 (s, 3H), 1.34 (t, J=7.1 Hz, 3H).

Step-2: Preparation of ethyl 5-bromo-7-hydroxybenzofuran-3-carboxylate (76c)

Compound 76c was prepared according to the procedure reported in step-1 of scheme 69, from ethyl 5-bromo-7-methoxybenzofuran-3-carboxylate (76b) (2 g, 6.69 mmol) in DCM (50 mL) using boron tribromide (1.454 mL, 15.38 mmol) and stirring at −78° C. for 4 h. This gave after workup and purification by flash column chromatography [silica gel (40 g), eluting with EtOAc in hexanes]ethyl 5-bromo-7-hydroxybenzofuran-3-carboxylate (76c) (1.25 g, 66% yield) as a colorless oil; $^1H$ NMR (300 MHz, DMSO-$d_6$) δ 10.93 (s, 1H), 8.77 (s, 1H), 7.51 (d, J=1.9 Hz, 1H), 6.99 (d, J=1.9 Hz, 1H), 4.34 (q, J=7.1 Hz, 2H), 1.34 (t, J=7.1 Hz, 3H).

Step-3: Preparation of (R)-ethyl 5-bromo-7-((tetrahydrofuran-2-yl)methoxy)benzofuran-3-carboxylate (76e)

Compound 76e was prepared according to the procedure reported in step-3 of scheme 7, from ethyl 5-bromo-7-hydroxybenzofuran-3-carboxylate (76c) (510 mg, 1.789 mmol) in DCM (15 mL) using triphenylphosphine (540 mg, 2.057 mmol), (R)-(tetrahydrofuran-2-yl)methanol (76d) (192 mg, 1.878 mmol), a solution of bis(4-chlorobenzyl) diazene-1,2-dicarboxylate (DCAD) (755 mg, 2.057 mmol) in DCM (10 mL) and stirring the reaction mixture at room temperature for 1 h. This gave after workup and purification by flash column chromatography [silica gel (40 g), eluting with EtOAc in hexane from 0-25%](R)-ethyl 5-bromo-7-((tetrahydrofuran-2-yl)methoxy)benzofuran-3-carboxylate (76e) (350 mg, 53% yield) as a white solid; $^1$H NMR (300 MHz, DMSO-$d_6$) δ 8.79 (s, 1H), 7.64 (d, J=1.7 Hz, 1H), 7.27 (d, J=1.8 Hz, 1H), 4.35 (q, J=7.1 Hz, 2H), 4.29-4.09 (m, 3H), 3.85-3.62 (m, 2H), 2.10-1.96 (m, 1H), 1.96-1.79 (m, 2H), 1.79-1.64 (m, 1H), 1.35 (t, J=7.1 Hz, 3H); MS (ES+): 390.90 (M+Na); Optical rotation $[\alpha]_D$=−13.33 (c=0.03, MeOH).

Step-4: Preparation of (R)-(5-bromo-7-((tetrahydrofuran-2-yl)methoxy)benzofuran-3-yl)methanol (76f)

Compound 76f was prepared according to the procedure reported in step-2 of scheme 69, from (R)-ethyl 5-bromo-7-((tetrahydrofuran-2-yl)methoxy)benzofuran-3-carboxylate (76e) (340 mg, 0.921 mmol) in DCM (1.53 mL) using DIBAL (2.302 mmol; 1.0 M solution in DCM) and stirring at 0° C. for 4 h. This gave after work up and purification by flash column chromatography [$SiO_2$ (12 g), EtOAc in hexane](R)-(5-bromo-7-((tetrahydrofuran-2-yl)methoxy)benzofuran-3-yl)methanol (76f) (135 mg, 45% yield) as a white solid; $^1$H NMR (300 MHz, DMSO-$d_6$) δ 7.90 (s, 1H), 7.46 (d, J=1.7 Hz, 1H), 7.12 (d, J=1.8 Hz, 1H), 5.21 (t, J=5.6 Hz, 1H), 4.58 (dd, J=5.6, 1.1 Hz, 2H), 4.29-4.08 (m, 3H), 3.85-3.61 (m, 2H), 2.11-1.63 (m, 4H); MS (ES+): 348.90 (M+Na); Optical rotation [α]D=−30.0 (c=0.02, MeOH).

Step-5: Preparation of (R)-tert-butyl 2-(2-((5-bromo-7-((tetrahydrofuran-2-yl)methoxy)benzofuran-3-yl)methoxy)phenyl)acetate (76g)

Compound 76g was prepared according to the procedure reported in step-3 of scheme 7, from (R)-(5-bromo-7-((tetrahydrofuran-2-yl)methoxy)benzofuran-3-yl)methanol (76f) (130 mg, 0.397 mmol) in DCM (5 mL) using triphenylphosphine (120 mg, 0.457 mmol), tert-butyl 2-(2-hydroxyphenyl)acetate (3g) (91 mg, 0.437 mmol), bis(4-chlorobenzyl) diazene-1,2-dicarboxylate (DCAD) (168 mg, 0.457 mmol) and stirring at room temperature for 1 h. This gave after workup and purification by flash column chromatography [silica gel (80 g), eluting with EtOAc in hexane from 0-25%](R)-tert-butyl 2-(2-((5-bromo-7-((tetrahydrofuran-2-yl)methoxy)benzofuran-3-yl)methoxy)phenyl)acetate (76g) (77 mg, 38% yield) as a colorless gel; $^1$H NMR (300 MHz, DMSO-$d_6$) δ 8.10 (s, 1H), 7.48 (d, J=1.7 Hz, 1H), 7.31-7.23 (m, 1H), 7.21-7.12 (m, 3H), 6.96-6.88 (m, 1H), 5.23 (s, 2H), 4.27-4.08 (m, 3H), 3.84-3.76 (m, 1H), 3.70 (q, J=7.1 Hz, 1H), 3.48 (s, 2H), 2.09-2.01 (m, 1H), 1.94-1.80 (m, 2H), 1.79-1.63 (m, 1H), 1.24 (s, 9H); MS (ES+): 539.00 (M+Na); Optical rotation $[\alpha]_D$=−12.0 (c=0.1, MeOH).

Step-6: Preparation of (R)-tert-butyl 2-(2-((5-(3-(aminomethyl)phenyl)-7-((tetrahydrofuran-2-yl)methoxy)benzofuran-3-yl)methoxy)phenyl)acetate (76h)

Compound 76h was prepared according to the procedure reported in step-2 of scheme 1, from (R)-tert-butyl 2-(2-((5-bromo-7-((tetrahydrofuran-2-yl)methoxy)benzofuran-3-yl)methoxy)phenyl)acetate (76g) (50.7 mg, 0.271 mmol) dioxane/THF (1.5 mL each) using 3-(aminomethyl)phenylboronic acid hydrochloride (1d) (50.7 mg, 0.271 mmol), 2 M solution of $K_3PO_4$ (0.271 mL, 0.541 mmol), tricyclohexylphosphine (11.4 mg, 0.041 mmol), $PdCl_2$(dppf)-$CH_2Cl_2$ adduct (11.05 mg, 0.014 mmol) $Pd_2(dba)_3$ (12.39 mg, 0.014 mmol) and heating at 90° C. for 1 h. This gave after workup and purification by flash column chromatography [silica gel (24 g), eluting with DMA-80 in DCM from 0-50%](R)-tert-butyl 2-(2-((5-(3-(aminomethyl)phenyl)-7-((tetrahydrofuran-2-yl)methoxy)benzofuran-3-yl)methoxy)phenyl)acetate (76h) (47 mg, 64% yield) as a colorless oil; $^1$H NMR (300 MHz, DMSO-$d_6$) δ 8.08 (s, 1H), 7.70-7.63 (m, 1H), 7.58-7.48 (m, 2H), 7.43-7.12 (m, 6H), 6.98-6.84 (m, 1H), 5.29 (s, 2H), 4.25 (q, J=8.8, 8.1 Hz, 3H), 3.91-3.68 (m, 4H), 3.50 (s, 2H), 2.13-1.69 (m, 4H), 1.17 (s, 9H); MS (ES+) 544.2 (M+1).

Step-6: Preparation of (R)-2-(2-((5-(3-(aminomethyl)phenyl)-7-((tetrahydrofuran-2-yl)methoxy)benzofuran-3-yl)methoxy)phenyl)acetic acid (76i)

Compound 76i was prepared according to the procedure reported in step-3 of scheme 1, from (R)-tert-butyl 2-(2-((5-(3-(aminomethyl)phenyl)-7-((tetrahydrofuran-2-yl)methoxy)benzofuran-3-yl)methoxy)phenyl)acetate (76h) (43 mg, 0.079 mmol) in THE (600 μL), MeOH (200 μL) and water (200 μL) using lithium hydroxide hydrate (16.59 mg, 0.395 mmol) and heating at 50° C. for 3 h. This gave after workup and purification by reverse phase column chromatography [C18 column (30 g), eluting with ACN in water (containing 0.1% HCl) from 0-100%](R)-2-(2-((5-(3-(aminomethyl)phenyl)-7-((tetrahydrofuran-2-yl)methoxy)benzofuran-3-yl)methoxy)phenyl)acetic acid (76i) (22 mg, 57% yield) HCl salt as an off white solid; $^1$H NMR (300 MHz, DMSO-$d_6$) δ 12.15 (s, 1H, $D_2O$ exchangeable), 8.35 (s, 3H, $D_2O$ exchangeable), 8.10 (s, 1H), 7.90 (s, 1H), 7.77 (dt, J=7.7, 1.6 Hz, 1H), 7.63-7.39 (m, 3H), 7.34-7.13 (m, 4H), 6.93 (td, J=7.2, 1.2 Hz, 1H), 5.30 (s, 2H), 4.33-4.20 (m, 3H), 4.12 (s, 2H), 3.88-3.77 (m, 1H), 3.77-3.66 (m, 1H), 3.54 (s, 2H), 2.17-1.61 (m, 4H); MS (ES+): 488.1 (M+1); MS (ES−): 486.1 (M−1); Analysis calculated for $C_{29}H_{29}NO_6\cdot HCl\cdot 1.5H_2O$: C, 63.21; H, 6.04; Cl, 6.43; N, 2.54. Found: C, 63.31; H, 5.91; Cl, 6.60; N, 2.55.

Scheme 77

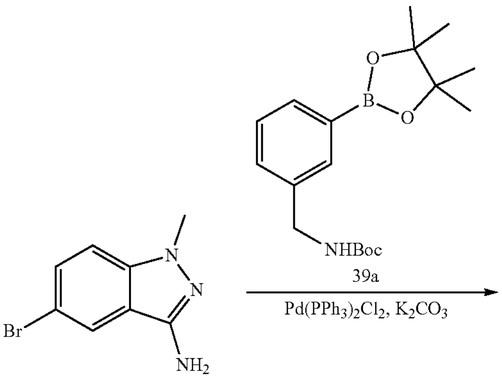

39a

74a

-continued

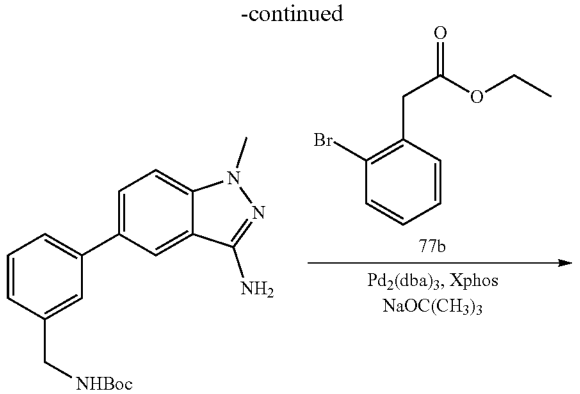

77a

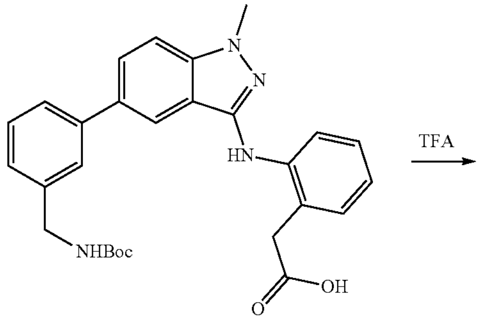

77c

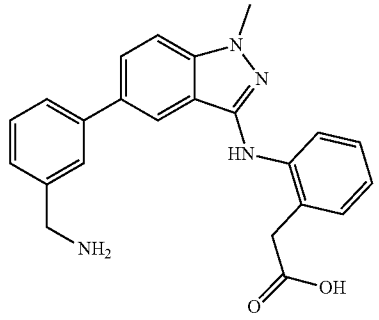

77d

Preparation of 2-(2-((5-(3-(aminomethyl)phenyl)-1-methyl-1H-indazol-3-yl)amino)phenyl)acetic acid (77d)

Step-1: Preparation of tert-butyl 3-(3-amino-1-methyl-1H-indazol-5-yl)benzylcarbamate (77a)

Compound 77a was prepared according to the procedure reported in step-8 of Scheme 3, from 5-bromo-1-methyl-1H-indazol-3-amine (74a) (1 g, 4.42 mmol; CAS #1000018-06-3) in dioxane (10 mL) using tert-butyl 3-(4,4,5,5-tetramethyl-1,3,2-dioxaborolan-2-yl)benzylcarbamate (39a) (1.474 g, 4.42 mmol), bis(triphenylphosphine)palladium(II) chloride (0.466 g, 0.664 mmol), a solution of $K_2CO_3$ (1.834 g, 13.27 mmol) in water (3 mL) and heating at 90° C. for 2 h. This gave after workup and purification by flash column chromatography [silica gel (24 g), eluting with DMA-80 in DCM from 0-100%] tert-butyl 3-(3-amino-1-methyl-1H-indazol-5-yl)benzylcarbamate (77a) (0.42 g, 27% yield) as a yellow syrup; $^1$H NMR (300 MHz, DMSO-$d_6$) δ 7.99 (d, J=1.7 Hz, 1H), 7.61-7.34 (m, 6H), 7.17 (d, J=7.5 Hz, 1H), 5.51 (s, 2H), 4.20 (d, J=6.2 Hz, 2H), 3.74 (s, 3H), 1.40 (s, 9H); MS (ES+): 353.20 (M+1).

Step-2: Preparation of 2-(2-((5-(3-(((tert-butoxycarbonyl)amino)methyl)phenyl)-1-methyl-1H-indazol-3-yl)amino)phenyl)acetic acid (77c)

To a degassed solution of dicyclohexyl(2',4',6'-triisopropylbiphenyl-2-yl)phosphine (XPhos)(0.108 g, 0.227 mmol) in toluene (4.00 mL) and n-Butanol (4.00 mL) was added sodium 2-methylpropan-2-olate (0.164 g, 1.702 mmol) and $Pd_2(dba)_3$ (0.104 g, 0.113 mmol).

The reaction mixture was degassed and heated at 110° C. for 15 min. To this mixture was added tert-butyl 3-(3-amino-1-methyl-1H-indazol-5-yl)benzylcarbamate (77a) (0.2 g, 0.567 mmol) and ethyl 2-(2-bromophenyl)acetate (77b) (0.276 g, 1.135 mmol; CAS #2178-24-7), degassed and filled with Ar. The resulting mixture was heated at 110° C. for 17 h and filtered through a pad of Celite. The filtrate was concentrated in vacuum and the residue obtained was purified by flash column chromatography [silica gel (24 g), eluting with DMA-80 in DCM from 0-100%] to afford 2-(2-((5-(3-(((tert-butoxycarbonyl)amino)methyl)phenyl)-1-methyl-1H-indazol-3-yl)amino)phenyl)acetic acid (77c) (0.1 g, 36% yield) as a yellow solid; $^1$H NMR (300 MHz, DMSO-$d_6$) δ 11.45 (s, 1H), 8.11 (d, J=8.2 Hz, 2H), 7.64 (dd, J=8.8, 1.6 Hz, 1H), 7.58-7.35 (m, 5H), 7.22-7.03 (m, 4H), 6.75 (td, J=7.3, 1.3 Hz, 1H), 4.20 (d, J=6.2 Hz, 2H), 3.91 (s, 3H), 3.17 (s, 2H), 1.40 (s, 9H); MS (ES+): 487.20 (M+1).

Step-3: Preparation of 2-(2-((5-(3-(aminomethyl)phenyl)-1-methyl-1H-indazol-3-yl)amino)phenyl)acetic acid (77d)

Compound 77d was prepared according to the procedure reported in step-9 of scheme 3, from 2-(2-((5-(3-(((tert-butoxycarbonyl)amino)methyl)phenyl)-1-methyl-1H-indazol-3-yl)amino)phenyl)acetic acid (77c) (0.1 g, 0.206 mmol) in DCM (5 mL) using TFA (0.315 mL, 4.11 mmol) and stirring at room temperature for 3 h. This gave after work up and purification by reverse-phase column chromatography [C18 column (50 g), eluting with ACN in water (containing 0.1% HCl) from 0-100%] 2-(2-((5-(3-(aminomethyl)phenyl)-1-methyl-1H-indazol-3-yl)amino)phenyl)acetic acid (77d) (50 mg, 0.129 mmol, 63% yield) HCl salt as a white solid; $^1$H NMR (300 MHz, DMSO-$d_6$) δ 8.38 (s, 3H, $D_2O$ exchangeable), 8.01 (s, 1H), 7.92-7.84 (m, 1H), 7.82 (s, 1H), 7.77-7.59 (m, 4H), 7.51 (dd, J=8.5, 6.7 Hz, 1H), 7.43 (d, J=7.5 Hz, 1H), 7.25-7.14 (m, 2H), 6.89 (t, J=7.4 Hz, 1H), 4.10 (q, J=4.8, 3.7 Hz, 2H), 3.93 (s, 3H), 3.78 (s, 2H); MS (ES+): 387.20 (M+1); MS (ES−): 385.00 (M−1).

Scheme 78

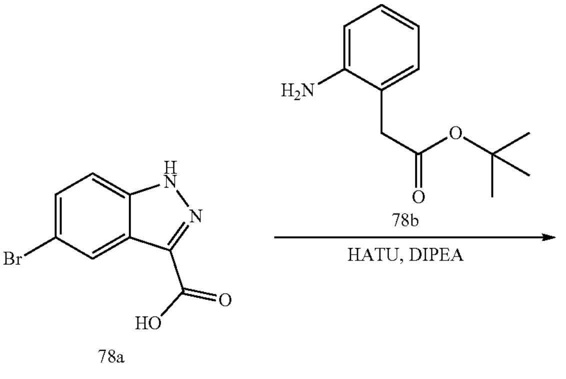

78a

-continued

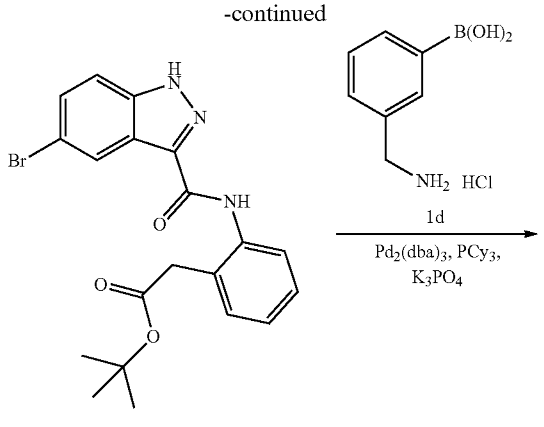

78c

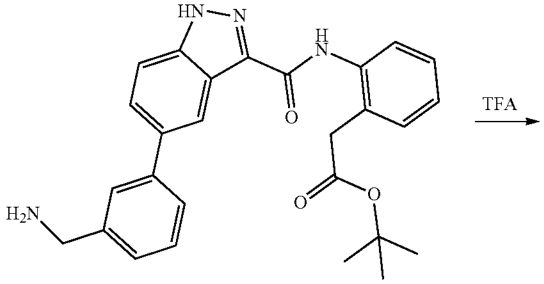

78d

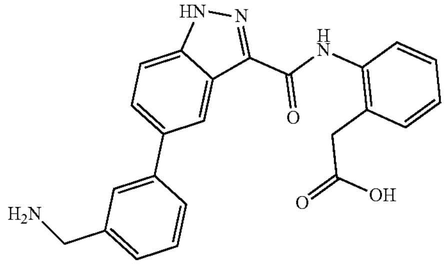

78e

Preparation of 2-(2-(5-(3-(aminomethyl)phenyl)-1H-indazole-3-carboxamido)phenyl)acetic acid (78e)

Step-1: Preparation of tert-butyl 2-(2-(5-bromo-1H-indazole-3-carboxamido)phenyl)acetate (78c)

Compound 78c was prepared according to the procedure reported in step-1 of scheme 10, from 5-bromo-1H-indazole-3-carboxylic acid (78a) (0.3 g, 1.245 mmol; CAS #1077-94-7) in DMF (5 mL), using tert-butyl 2-(2-aminophenyl)acetate (78b) (0.284 g, 1.369 mmol; CAS #98911-34-3), N-ethyl-N-isopropylpropan-2-amine (DIPEA) (0.867 mL, 4.98 mmol), 2-(3H-[1,2,3]triazolo[4,5-b]pyridin-3-yl)-1,1,3,3-tetramethylisouronium hexafluorophosphate(V) (HATU) (710 mg, 1.867 mmol) and stirring for 16 h at room temperature. This gave after workup and purification by flash column chromatography [silica gel (24 g), eluting with MeOH in DCM from 0-100%] tert-butyl 2-(2-(5-bromo-1H-indazole-3-carboxamido)phenyl)acetate (78c) (0.32 g, 60% yield) as a yellow solid; $^1$H NMR (300 MHz, DMSO-$d_6$) δ 14.01 (s, 1H), 9.91 (s, 1H), 8.34 (dd, J=1.9, 0.8 Hz, 1H), 7.70-7.67 (m, 1H), 7.67-7.63 (m, 1H), 7.58 (dd, J=8.9, 1.9 Hz, 1H), 7.37-7.28 (m, 2H), 7.23-7.14 (m, 1H), 3.69 (s, 2H), 1.28 (s, 9H).

MS (ES−): 428.0 (M−1).

Step-2: Preparation of tert-butyl 2-(2-(5-(3-(aminomethyl)phenyl)-1H-indazole-3-carboxamido)phenyl)acetate (78d)

Compound 78d was prepared according to the procedure reported in step-2 of scheme 1, from tert-butyl 2-(2-(5-bromo-1H-indazole-3-carboxamido)phenyl)acetate (78c) (0.22 g, 0.511 mmol) in dioxane (5 mL) using 3-(aminomethyl)phenylboronic acid hydrochloride (1d) (0.144 g, 0.767 mmol), 2 M solution of $K_3PO_4$ (0.579 mL, 0.869 mmol), tricyclohexylphosphine (0.057 g, 0.205 mmol), $Pd_2(dba)_3$ (0.094 g, 0.102 mmol) and heating at 135° C. for 30 min in a microwave. This gave after workup and purification by flash column chromatography [silica gel (24 g), eluting with DMA-80 in DCM from 0-70%] followed by reverse phase column chromatography [C18 column (30 g), eluting with ACN in water (containing 0.1% HCl) from 0-100%] tert-butyl 2-(2-(5-(3-(aminomethyl)phenyl)-1H-indazole-3-carboxamido)phenyl)acetate (78d) (0.12 g, 51% yield) as a white solid; MS (ES+): 457.20 (M+1).

Step-3: Preparation of 2-(2-(5-(3-(aminomethyl)phenyl)-1H-indazole-3-carboxamido)phenyl)acetic acid (78e)

Compound 78e was prepared according to the procedure reported in step-9 of scheme 3, from tert-butyl 2-(2-(5-(3-(aminomethyl)phenyl)-1H-indazole-3-carboxamido)phenyl)acetate (78d) (0.12 g, 0.263 mmol) in DCM (5 mL) using TFA (0.403 mL, 5.26 mmol) and stirring at room temperature overnight. This gave after work up and purification by reverse-phase column chromatography [C18 column (50 g), eluting with ACN in water (containing 0.1% HCl) from 0-100%] 2-(2-(5-(3-(aminomethyl)phenyl)-1H-indazole-3-carboxamido)phenyl)acetic acid (78e) (10 mg, 10% yield) HCl salt as a white solid; $^1$H NMR (300 MHz, DMSO-$d_6$) δ 13.93 (s, 1H, $D_2O$ exchangeable), 12.58 (s, 1H, $D_2O$ exchangeable), 10.03 (s, 1H, $D_2O$ exchangeable), 8.52 (s, 1H), 8.29 (s, 3H, $D_2O$ exchangeable), 7.89 (s, 1H), 7.84-7.64 (m, 4H), 7.55 (t, J=7.6 Hz, 1H), 7.46 (d, J=7.7 Hz, 1H), 7.34 (t, J=7.6 Hz, 2H), 7.24-7.14 (m, 1H), 4.14 (s, 2H), 3.72 (s, 2H); MS (ES+): 401.10(M+1); MS (ES−): 399.10 (M−1).

Scheme 79

Scheme 79

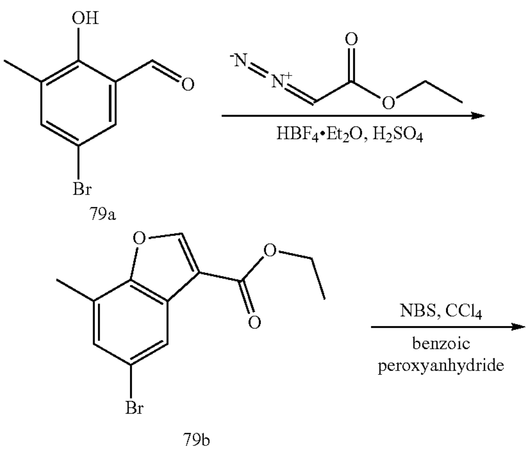

79b

-continued

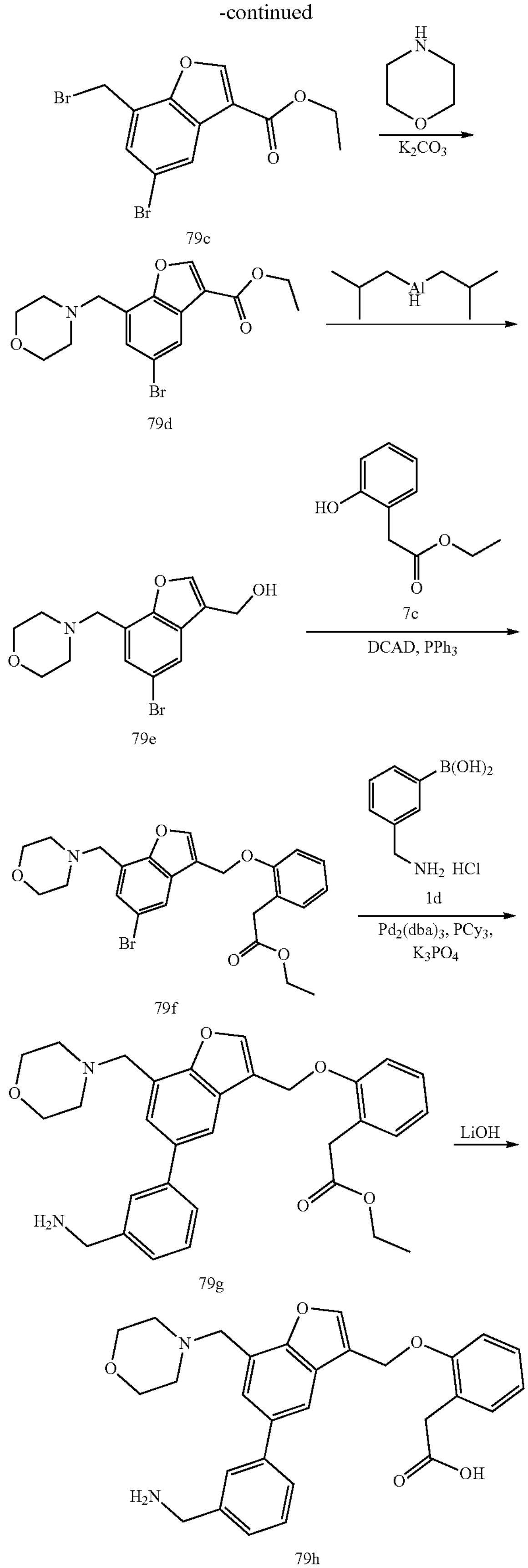

79c, 79d, 79e, 79f, 79g, 79h

Preparation of 2-(2-((5-(3-(aminomethyl)phenyl)-7-(morpholinomethyl)benzofuran-3-yl)methoxy)phenyl)acetic acid (79h)

Step-1: Preparation of ethyl 5-bromo-7-methylbenzofuran-3-carboxylate (79b)

Compound 79b was prepared according to the procedure reported in step-1 of scheme 69, from 5-bromo-2-hydroxy-3-methylbenzaldehyde (79a) (2 g, 9.30 mmol; CAS #33172-56-) in DCM (40 mL) using $HBF_4 \cdot Et_2O$ (0.230 mL, 0.930 mmol), ethyl diazoacetate (15% in toluene) (10.29 mL, 11.32 mmol) and sulfuric acid (1.239 mL, 23.25 mmol). This gave after work up and purification [silica gel (80 g), eluting with EtOAc in hexane from 0-50%] ethyl 5-bromo-7-methylbenzofuran-3-carboxylate (79b) (2.1 g, 80% yield) as a white solid; $^1H$ NMR (300 MHz, DMSO-$d_6$) δ 8.81 (s, 1H), 7.87 (d, J=2.1 Hz, 1H), 7.52-7.34 (m, 1H), 4.34 (q, J=7.1 Hz, 2H), 2.48 (s, 3H), 1.34 (t, J=7.1 Hz, 3H).

MS (ES+): 282.90 (M+1).

Step-2: Preparation of ethyl 5-bromo-7-(bromomethyl)benzofuran-3-carboxylate (79c)

Compound 79c was prepared according to the procedure reported in step-2 of scheme 58, from ethyl 5-bromo-7-methylbenzofuran-3-carboxylate (79b) (0.5 g, 1.766 mmol) in carbon tetrachloride (10 mL) using NBS (0.346 g, 1.943 mmol), benzoic peroxyanhydride (0.064 mg, 0.265 mmol) and heating at reflux for 14 h. This gave after workup and purification by flash column chromatography [silica gel (24 g), eluting with EtOAc in hexane from 0-60%] ethyl 5-bromo-7-(bromomethyl)benzofuran-3-carboxylate (79c) (0.43 g, 68% yield) as a white solid. MS (ES+): 360.80 (M+1).

Step-3: Preparation of ethyl 5-bromo-7-(morpholinomethyl)benzofuran-3-carboxylate (79d)

To a solution of ethyl 5-bromo-7-(bromomethyl)benzofuran-3-carboxylate (79c) (0.32 g, 0.884 mmol) in acetonitrile (5 mL) was added potassium carbonate (0.366 g, 2.65 mmol), morpholine (0.154 g, 1.768 mmol) and stirred under an argon atmosphere at room temperature for 15 h. The reaction mixture was concentrated in vacuum and the residue obtained was purified by flash column chromatography [silica gel (24 g), eluting with DMA-80 in DCM from 0-50%] to give ethyl 5-bromo-7-(morpholinomethyl)benzofuran-3-carboxylate (79d) (0.1 g, 31% yield) as a yellow solid; $^1H$ NMR (300 MHz, DMSO-$d_6$) δ 8.83 (s, 1H), 7.96 (d, J=2.1 Hz, 1H), 7.53 (d, J=2.1 Hz, 1H), 4.35 (q, J=7.1 Hz, 2H), 3.76 (s, 2H), 3.56 (t, J=4.6 Hz, 4H), 2.40 (t, J=4.6 Hz, 4H), 1.34 (t, J=7.1 Hz, 3H); MS (ES+): 368.00 (M+1).

Step-4: Preparation of (5-bromo-7-(morpholinomethyl)benzofuran-3-yl)methanol (79e)

Compound 79e was prepared according to the procedure reported in step-2 of scheme 69, from ethyl 5-bromo-7-(morpholinomethyl)benzofuran-3-carboxylate (79d) (0.35 g, 0.951 mmol) in DCM (10 mL) using 1.0 M solution of DIBAL (2.376 mL, 2.376 mmol) and stirring at −78° C. for 1 h. The residue obtained after workup was used as such for the next step; $^1H$ NMR (300 MHz, DMSO-$d_6$) δ 7.94 (s, 1H), 7.80 (d, J=2.0 Hz, 1H), 7.41 (d, J=2.0 Hz, 1H), 5.21 (t, J=5.6 Hz, 1H), 4.59 (dd, J=5.5, 1.1 Hz, 2H), 3.73 (s, 2H), 3.56 (t, J=4.6 Hz, 4H), 2.39 (t, J=4.7 Hz, 4H); MS (ES+): 326.00 (M+1).

Step-5: Preparation of ethyl 2-(2-((5-bromo-7-(morpholinomethyl)benzofuran-3-yl)methoxy)phenyl) acetate (79f)

Compound 79f was prepared according to the procedure reported in step-2 of Scheme 65, from (5-bromo-7-(morpholinomethyl)benzofuran-3-yl)methanol (79e) (75 mg, 0.23 mmol) in DCM (3 mL) using triphenylphosphine (90 mg, 0.345 mmol), ethyl 2-(2-hydroxyphenyl)acetate (7c) (45.6 mg, 0.253 mmol) and DCAD (127 mg, 0.345 mmol) in DCM (3 mL). This gave after workup and purification by flash column chromatography [silica gel (24 g), eluting with EtOAc/MeOH (9:1) in hexane from 0-30%] ethyl 2-(2-((5-bromo-7-(morpholinomethyl)benzofuran-3-yl)methoxy) phenyl)acetate (79f) (100 mg, 89% yield) as a white oil; MS (ES+): 488.00 (M+1); MS (ES−): 486.00 (M−1).

Step-6: Preparation of ethyl 2-(2-((5-(3-(aminomethyl)phenyl)-7-(morpholinomethyl)benzofuran-3-yl)methoxy)phenyl)acetate (79g)

Compound 79g was prepared according to the procedure reported in step-2 of scheme 1, from ethyl 2-(2-((5-bromo-7-(morpholinomethyl)benzofuran-3-yl)methoxy)phenyl)acetate (79f) (100 mg, 0.205 mmol) in dioxane (4 mL) using 3-(aminomethyl)phenylboronic acid hydrochloride (1d) (77 mg, 0.410 mmol), 1.5 M solution of $K_3PO_4$ (0.232 mL, 0.348 mmol), tricyclohexylphosphine (22.97 mg, 0.082 mmol) and $Pd_2(dba)_3$ (37.5 mg, 0.041 mmol) and heating at 135° C. for 30 min in a microwave. This gave after workup and purification by flash column chromatography [silica gel (24 g), eluting with DMA-80 in DCM from 0-70%]ethyl 2-(2-((5-(3-(aminomethyl)phenyl)-7-(morpholinomethyl) benzofuran-3-yl)methoxy)phenyl)acetate (79g) (30 mg, 29% yield); MS (ES+): 515.2 (M+1).

Step-7: Preparation of 2-(2-((5-(3-(aminomethyl) phenyl)-7-(morpholinomethyl)benzofuran-3-yl) methoxy)phenyl)acetic acid (79h)

Compound 79h was prepared according to the procedure reported in step-3 of scheme 1, from ethyl 2-(2-((5-(3-(aminomethyl)phenyl)-7-(morpholinomethyl)benzofuran-3-yl)methoxy)phenyl)acetate (79g) (30 mg, 0.058 mmol) in THF/MeOH (4 mL; 1:1) using a 1N solution of lithium hydroxide hydrate (19.57 mg, 0.466 mmol) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(morpholinomethyl)benzofuran-3-yl)methoxy)phenyl)acetic acid (79h) (8 mg, 28% yield) HCl salt as a white solid; $^1H$ NMR (300 MHz, DMSO-$d_6$) δ 12.17 (s, 1H, $D_2O$ exchangeable), 11.46 (s, 1H, $D_2O$ exchangeable), 8.45 (s, 3H, $D_2O$ exchangeable), 8.25 (s, 1H), 8.13 (d, J=7.3 Hz, 2H), 7.99 (s, 1H), 7.84 (d, J=7.5 Hz, 1H), 7.62-7.46 (m, 2H), 7.32-7.18 (m, 3H), 6.94 (t, J=7.2 Hz, 1H), 5.35 (s, 2H), 4.68 (s, 2H), 4.11 (q, J=5.7 Hz, 2H), 4.02-3.75 (m, 4H), 3.55 (s, 2H), 3.40-3.19 (m, 4H).; MS (ES+): 487.10 (M+1).

Scheme 80

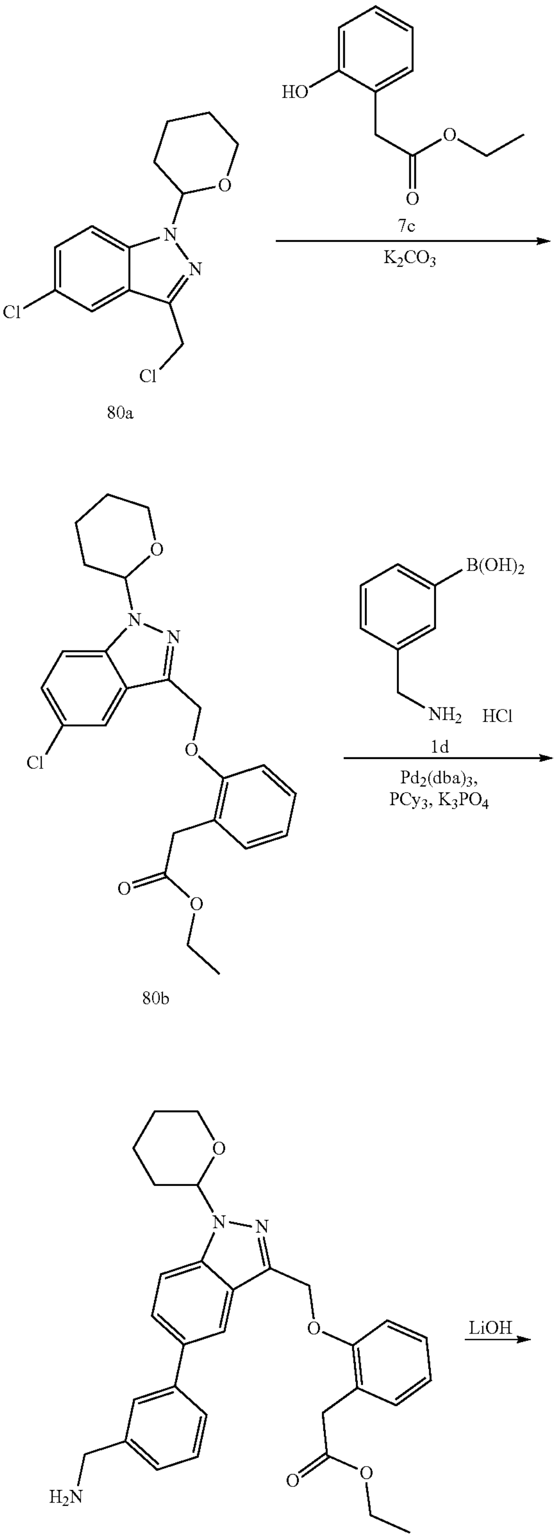

80a

80b

80c

-continued

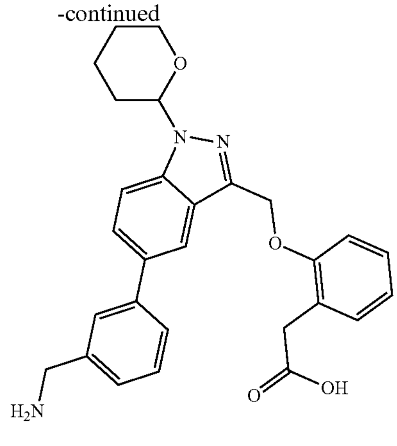

80d

Preparation of 2-(2-((5-(3-(aminomethyl)phenyl)-1-(tetrahydro-2H-pyran-2-yl)-1H-indazol-3-yl)methoxy)phenyl)acetic acid (80d)

Step-1: Preparation of ethyl 2-(2-((5-chloro-1-(tetrahydro-2H-pyran-2-yl)-1H-indazol-3-yl)methoxy)phenyl)acetate (80b)

Compound 80b was prepared according to the procedure reported in step-1 of scheme 1, from 5-chloro-3-(chloromethyl)-1-(tetrahydro-2H-pyran-2-yl)-1H-indazole (80a) (0.58 g, 2.034 mmol; CAS #: 1801253-90-6) in acetonitrile (10 mL) using ethyl 2-(2-hydroxyphenyl)acetate (7c) (0.733 g, 4.07 mmol), $K_2CO_3$ (0.843 g, 6.10 mmol) and stirring overnight at room temperature. This gave after workup and purification by flash column chromatography [silica gel (80 g), eluting with EtOAc in hexane from 0-50%] ethyl 2-(2-((5-chloro-1-(tetrahydro-2H-pyran-2-yl)-1H-indazol-3-yl)methoxy)phenyl)acetate (80b) (0.43 g, 49% yield) as a yellow solid; MS (ES+): 451.00 (M+Na).

Step-2: Preparation of ethyl 2-(2-((5-(3-(aminomethyl)phenyl)-1-(tetrahydro-2H-pyran-2-yl)-1H-indazol-3-yl)methoxy)phenyl)acetate (80c)

Compound 80c was prepared according to the procedure reported in step-2 of scheme 1, from ethyl 2-(2-((5-chloro-1-(tetrahydro-2H-pyran-2-yl)-1H-indazol-3-yl)methoxy)phenyl)acetate (80b) (0.4 g, 0.933 mmol) in dioxane (5 mL) using 3-(aminomethyl)phenylboronic acid hydrochloride (1d) (0.35 g, 1.865 mmol), 2 M solution of $K_3PO_4$ (1.057 mL, 1.585 mmol), tricyclohexylphosphine (0.105 g, 0.373 mmol) $Pd_2(dba)_3$ (0.171 g, 0.187 mmol) and heating at 135° C. for 30 min in a microwave. This gave after workup and purification by flash column chromatography [silica gel (24 g), eluting with DMA-80 in DCM from 0-70%] ethyl 2-(2-((5-(3-(aminomethyl)phenyl)-1-(tetrahydro-2H-pyran-2-yl)-1H-indazol-3-yl)methoxy)phenyl)acetate (80c) (90 mg, 19% yield); MS (ES+): 500.10 (M+1).

Step-3: Preparation of 2-(2-((5-(3-(aminomethyl)phenyl)-1-(tetrahydro-2H-pyran-2-yl)-1H-indazol-3-yl)methoxy)phenyl)acetic acid (80d)

Compound 80d was prepared according to the procedure reported in step-3 of scheme 1, from ethyl 2-(2-((5-(3-(aminomethyl)phenyl)-1-(tetrahydro-2H-pyran-2-yl)-1H-indazol-3-yl)methoxy)phenyl)acetate (80c) (90 mg, 0.18 mmol) in THF/MeOH (4 mL each) using a solution of lithium hydroxide hydrate (60.5 mg, 1.441 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-1-(tetrahydro-2H-pyran-2-yl)-1H-indazol-3-yl)methoxy)phenyl)acetic acid (80d) (20 mg, 23% yield) HCl salt as a white solid; $^1H$ NMR (300 MHz, DMSO-$d_6$) δ 12.12 (s, 1H, $D_2O$ exchangeable), 8.35 (s, 3H, $D_2O$ exchangeable), 8.10 (s, 1H), 7.90-7.84 (m, 2H), 7.84-7.70 (m, 2H), 7.57-7.40 (m, 2H), 7.27 (d, J=4.1 Hz, 2H), 7.21 (d, J=7.4 Hz, 1H), 6.94 (dq, J=8.1, 4.6 Hz, 1H), 5.96-5.86 (m, 1H), 5.45 (s, 2H), 4.11 (q, J=5.8 Hz, 2H), 3.96-3.83 (m, 1H), 3.83-3.69 (m, 1H), 3.53 (s, 2H), 2.48-2.31 (m, 1H), 2.13-1.94 (m, 2H), 1.87-1.68 (m, 1H), 1.68-1.51 (m, 2H); MS (ES+): 472.10 (M+1); MS (ES−): 470.10 (M−1).

Scheme 81

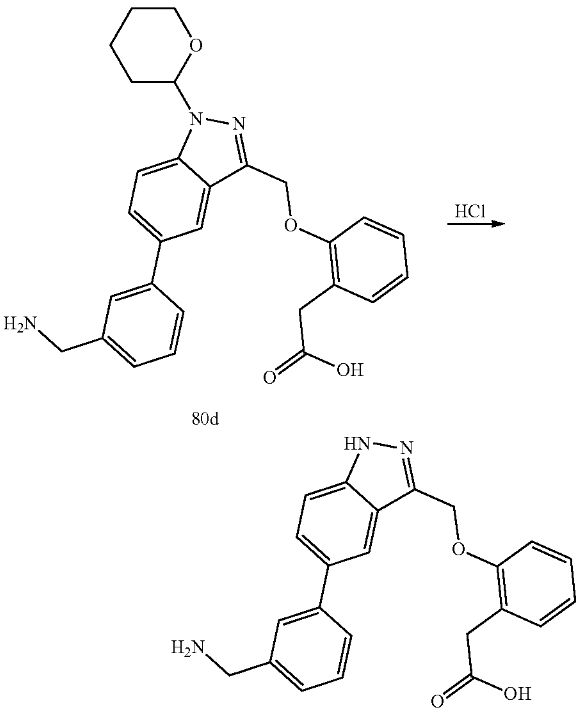

80d

81a

Preparation of 2-(2-((5-(3-(aminomethyl)phenyl)-1H-indazol-3-yl)methoxy)phenyl)acetic acid (81a)

Compound 81a was prepared according to the procedure reported in step-2 of scheme 7, from 2-(2-((5-(3-(aminomethyl)phenyl)-1-(tetrahydro-2H-pyran-2-yl)-1H-indazol-3-yl)methoxy)phenyl)acetic acid (80d) (10 mg, 0.021 mmol) in dioxane (3 mL) using HCl (4 M in dioxane, 0.106 mL, 0.424 mmol) and heating at 90° C. for 3 h. This gave after workup and purification by flash column chromatography [C18 column (50 g), eluting with ACN in water (containing 0.1% HCl) from 0-100%] 2-(2-((5-(3-(aminomethyl)phenyl)-1H-indazol-3-yl)methoxy)phenyl)acetic acid (81a) (2 mg, 24% yield) HCl salt as a white solid; $^1$H NMR (300 MHz, DMSO-$d_6$) δ 13.22 (s, 1H, $D_2O$ exchangeable), 8.25 (s, 2H, $D_2O$ exchangeable), 8.09 (s, 1H), 7.85 (s, 1H), 7.73 (dd, J=7.4, 4.0 Hz, 2H), 7.66 (d, J=8.6 Hz, 1H), 7.51 (t, J=7.7 Hz, 1H), 7.42 (d, J=7.4 Hz, 1H), 7.29-7.24 (m, 2H), 7.20 (d, J=7.3 Hz, 1H), 6.97-6.86 (m, 1H), 6.55 (s, 1H, $D_2O$ exchangeable), 5.46 (s, 2H), 4.13-4.07 (m, 2H), 3.52 (s, 2H); MS (ES+): 388.10 (M+1).

Scheme 82

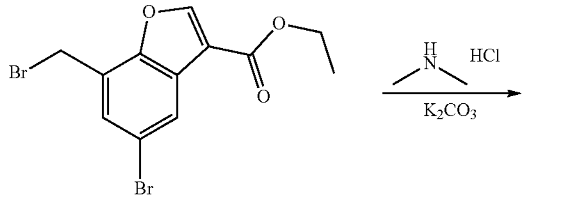

79c

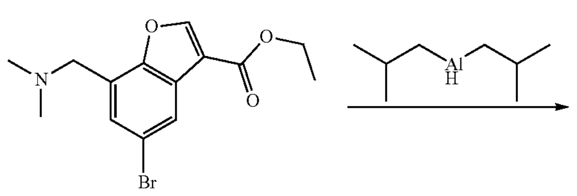

82a

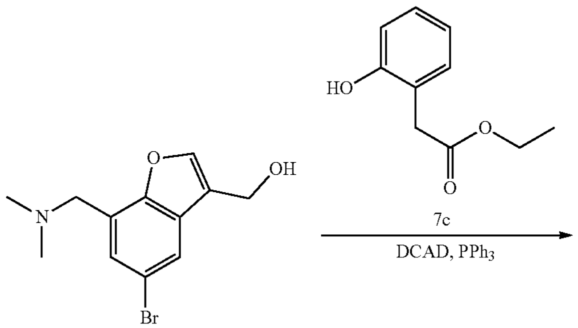

82b

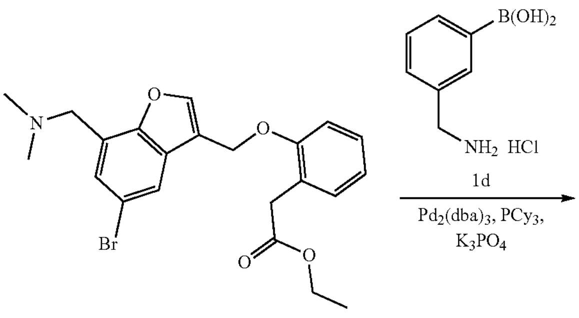

82c

-continued

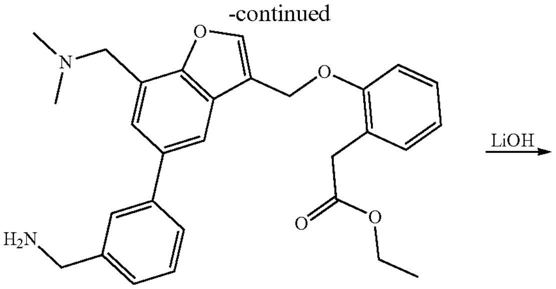

82d

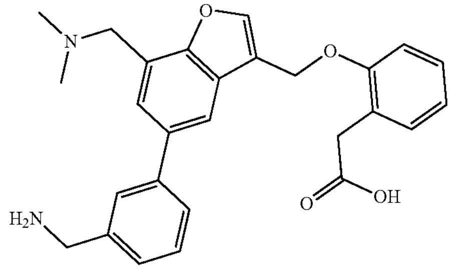

82e

Preparation of 2-(2-((5-(3-(aminomethyl)phenyl)-7-((dimethylamino)methyl)benzofuran-3-yl)methoxy)phenyl)acetic acid (82e)

Step-1: Preparation of ethyl 5-bromo-7-((dimethylamino)methyl)benzofuran-3-carboxylate (82a)

Compound 82a was prepared according to the procedure reported in step-3 of scheme 79, from ethyl 5-bromo-7-(bromomethyl)benzofuran-3-carboxylate (79c) (0.6 g, 1.657 mmol) in acetone (10 mL) using potassium carbonate (0.687 g, 4.97 mmol), dimethylamine hydrochloride (0.405 g, 4.97 mmol) and stirring at room temperature for 15 h. This gave after workup and purification by flash column chromatography [silica gel (24 g), eluting with DMA-80 in DCM from 0-50%] ethyl 5-bromo-7-((dimethylamino)methyl)benzofuran-3-carboxylate (82a) (0.41 g, 76% yield) as a yellow solid; $^1$H NMR (300 MHz, DMSO-$d_6$) δ 8.84 (s, 1H), 7.98 (d, J=2.1 Hz, 1H), 7.53 (d, J=2.1 Hz, 1H), 4.35 (q, J=7.1 Hz, 2H), 3.72 (s, 2H), 2.18 (s, 6H), 1.34 (t, J=7.1 Hz, 3H); MS (ES+): 326.00 (M+1).

Step-2: Preparation of (5-bromo-7-((dimethylamino)methyl)benzofuran-3-yl)methanol (82b)

Compound 82b was prepared according to the procedure reported in step-2 of scheme 69, from ethyl 5-bromo-7-((dimethylamino)methyl)benzofuran-3-carboxylate (82a) (0.4 g, 1.226 mmol) in DCM (10 mL) using a solution of DIBAL (3.07 mL, 3.07 mmol; 1 M in DCM) and stirring at −78° C. for 1 h. The residue obtained after workup was used as such for the next step; MS (ES+): 284.00 (M+1).

Step-3: Preparation of ethyl 2-(2-((5-bromo-7-((dimethylamino)methyl)benzofuran-3-yl)methoxy)phenyl)acetate (82c)

Compound 82c was prepared according to the procedure reported in step-2 of Scheme 65, from (5-bromo-7-((dimethylamino)methyl)benzofuran-3-yl)methanol (82b) (0.13 g, 0.458 mmol) in DCM (10 mL) using triphenylphosphine (0.240 g, 0.915 mmol), ethyl 2-(2-hydroxyphenyl)acetate (7c) (0.091 g, 0.503 mmol), and a solution of DCAD (0.336 mg, 0.915 mmol) in DCM (5 mL). This gave after workup and purification by flash column chromatography [silica gel (24 g), eluting with EtOAc/MeOH (9:1) in hexane from 0-50%]ethyl 2-(2-((5-bromo-7-((dimethylamino)methyl)benzofuran-3-yl)methoxy)phenyl)acetate (82c) (0.13 g, 64% yield) as a white oil; MS (ES+): 446.00 (M+1).

Step-4: Preparation of ethyl 2-(2-((5-(3-(aminomethyl)phenyl)-7-((dimethylamino)methyl)benzofuran-3-yl)methoxy)phenyl)acetate (82d)

Compound 82d was prepared according to the procedure reported in step-2 of scheme 1, from ethyl 2-(2-((5-bromo-7-((dimethylamino)methyl)benzofuran-3-yl)methoxy)phenyl)acetate (82c) (130 mg, 0.291 mmol) in dioxane/THF (4 mL each) using 3-(aminomethyl)phenylboronic acid hydrochloride (1d) (109 mg, 0.583 mmol), 1.5 M solution of $K_3PO_4$ (0.583 mL, 1.165 mmol), tricyclohexylphosphine (16.34 mg, 0.058 mmol), $Pd_2(dba)_3$ (26.7 mg, 0.029 mmol) and heating at 90° C. for 1 h. This gave after workup and purification by flash column chromatography [silica gel (24 g), eluting with DMA-80 in DCM from 0-70%] ethyl 2-(2-((5-(3-(aminomethyl)phenyl)-7-((dimethylamino)methyl)benzofuran-3-yl)methoxy)phenyl)acetate (82d)(65 mg, 47% yield); MS (ES+): 473.15 (M+1).

Step-5: Preparation of 2-(2-((5-(3-(aminomethyl)phenyl)-7-((dimethylamino)methyl)benzofuran-3-yl)methoxy)phenyl)acetic acid (82e)

Compound 82e was prepared according to the procedure reported in step-3 of scheme 1, from ethyl 2-(2-((5-(3-(aminomethyl)phenyl)-7-((dimethylamino)methyl)benzofuran-3-yl)methoxy)phenyl)acetate (82d) (60 mg, 0.127 mmol) in THF/MeOH (4 mL each) using a solution of lithium hydroxide hydrate (21 mg, 0.508 mmol) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-7-((dimethylamino)methyl)benzofuran-3-yl)methoxy)phenyl)acetic acid (82e) (40 mg, 71% yield) HCl salt as a white solid; $^1H$ NMR (300 MHz, DMSO-$d_6$) δ 12.18 (s, 1H, $D_2O$ exchangeable), 10.97 (s, 1H, $D_2O$ exchangeable), 8.47 (s, 3H, $D_2O$ exchangeable), 8.24 (s, 1H), 8.16-8.06 (m, 2H), 7.99 (s, 1H), 7.83 (dt, J=7.4, 1.7 Hz, 1H), 7.62-7.45 (m, 2H), 7.33-7.18 (m, 3H), 7.00-6.88 (m, 1H), 5.35 (s, 2H), 4.63 (s, 2H), 4.11 (s, 2H), 3.55 (s, 2H), 2.80 (s, 6H); MS (ES+): 445.10 (M+1); MS (ES−): 443.10 (M−1); Analysis calculated for $C_{27}H_{28}N_2O_4 \cdot 2.05HCl \cdot 3.5H_2O$: C, 55.69; H, 6.41; Cl, 12.48; N, 4.81. Found: C, 55.91; H, 6.58; Cl, 12.74; N, 5.14.

Scheme 83

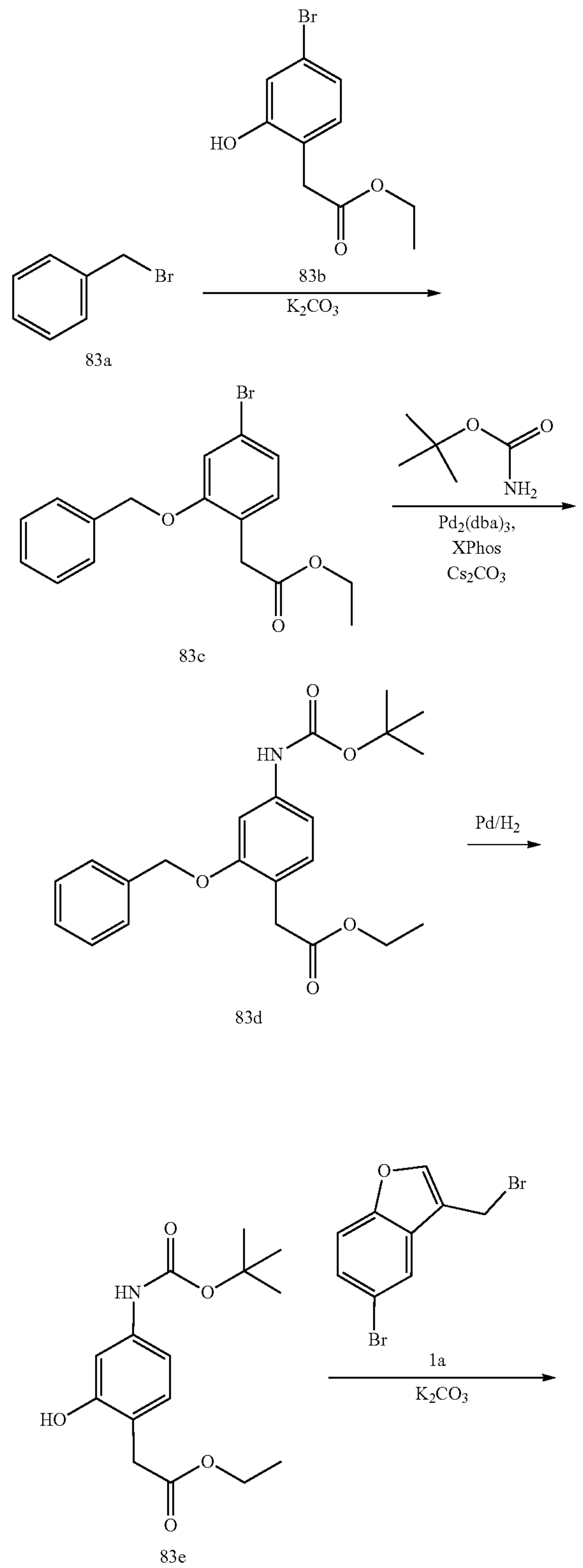

83a

83c

83d

83e

-continued

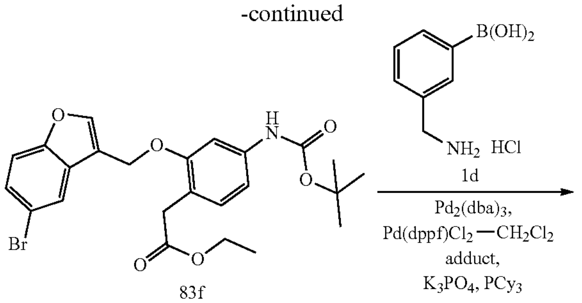

83f

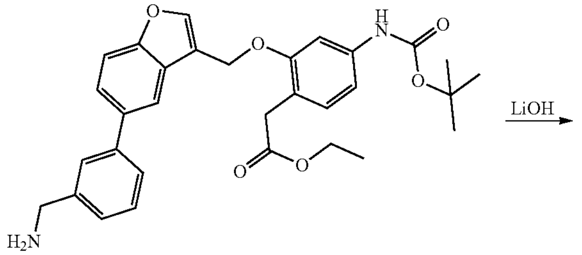

83g

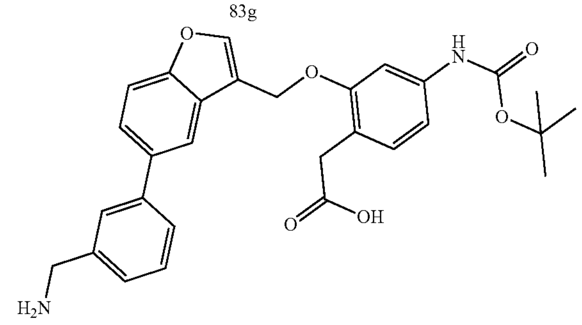

83h

Preparation of 2-(2-((5-(3-(aminomethyl)phenyl) benzofuran-3-yl)methoxy)-4-((tert-butoxycarbonyl) amino)phenyl)acetic acid (83h)

Step-1: Preparation of ethyl 2-(2-(benzyloxy)-4-bromophenyl)acetate (83c)

Compound 83c was prepared according to the procedure reported in step-1 of scheme 1, from (bromomethyl)benzene (83a) (4.95 g, 28.9 mmol; CAS #: 100-39-0) in acetonitrile (50 mL) using ethyl 2-(4-bromo-2-hydroxyphenyl)acetate (83b) (5 g, 19.30 mmol), $K_2CO_3$ (8.0 g, 6.10 mmol) and stirring at room temperature for 16 h. This gave after workup and purification by flash column chromatography [silica gel (40 g), eluting with EtOAc in hexane from 0-80%] ethyl 2-(2-(benzyloxy)-4-bromophenyl)acetate (83c) (6.6 g, 98% yield) as a white solid; $^1$H NMR (300 MHz, DMSO-$d_6$) δ 7.43-7.29 (m, 5H), 7.27 (d, J=1.8 Hz, 1H), 7.19 (d, J=8.0 Hz, 1H), 7.11 (dd, J=8.0, 1.8 Hz, 1H), 5.13 (s, 2H), 4.00 (q, J=7.1 Hz, 2H), 3.60 (s, 2H), 1.09 (t, J=7.1 Hz, 3H); MS (ES+): 370.90 (M+Na).

Step-2: Preparation of ethyl 2-(2-(benzyloxy)-4-((tert-butoxycarbonyl)amino)phenyl)acetate (83d)

Compound 83d was prepared according to the procedure reported in step-2 of scheme 77, from ethyl 2-(2-(benzyloxy)-4-bromophenyl)acetate (83c) (1.5 g, 4.30 mmol) in toluene (25 mL) and n-Butanol (10 mL) using cesium carbonate (4.20 g, 12.89 mmol), $Pd_2(dba)_3$ (0.787 g, 0.859 mmol), XPhos (0.819 g, 1.718 mmol), tert-butyl carbamate (1.006 g, 8.59 mmol) and heating at 110° C. for 17 h. This gave after workup and purification by flash column chromatography [silica gel (40 g), eluting with ethyl acetate in hexane from 0-50%] ethyl 2-(2-(benzyloxy)-4-((tert-butoxycarbonyl)amino)phenyl)acetate (83d) (1.4 g, 85% yield) as a yellow oil; $^1$H NMR (300 MHz, DMSO-$d_6$) δ 9.33 (s, 1H), 7.48-7.33 (m, 5H), 7.29 (d, J=1.9 Hz, 1H), 7.07 (d, J=8.2 Hz, 1H), 6.96 (dd, J=8.1, 1.9 Hz, 1H), 5.02 (s, 2H), 4.05-3.96 (m, 2H), 3.53 (s, 2H), 1.48 (s, 9H), 1.10 (t, J=7.1 Hz, 3H); MS (ES+): 408.10 (M+Na).

Step-3: Preparation of ethyl 2-(4-((tert-butoxycarbonyl)amino)-2-hydroxyphenyl)acetate (83e)

To a solution of ethyl 2-(2-(benzyloxy)-4-((tert-butoxycarbonyl)amino)phenyl)acetate (83d) (1.4 g, 3.63 mmol) in MeOH (30 mL) was added palladium (0.773 g, 0.726 mmol) and hydrogenated for 2 days using a balloon. The reaction mixture was filtered and concentrated in vacuum. The residue obtained was purified by flash column chromatography [silica gel (24 g), eluting with ethyl acetate in hexanes from 0-50%] to afford ethyl 2-(4-((tert-butoxycarbonyl)amino)-2-hydroxyphenyl)acetate (83e) (0.65 g, 61% yield) as a yellow oil; H NMR (300 MHz, DMSO-$d_6$) δ 9.41 (s, 1H), 9.19 (s, 1H), 7.10 (d, J=2.1 Hz, 1H), 6.92 (d, J=8.2 Hz, 1H), 6.75 (dd, J=8.2, 2.1 Hz, 1H), 4.13-3.92 (m, 2H), 3.43 (s, 2H), 1.46 (s, 9H), 1.19-1.14 (m, 3H); MS (ES+): 318.10 (M+Na).

Step-4: Preparation of ethyl 2-(2-((5-bromobenzofuran-3-yl)methoxy)-4-((tert-butoxycarbonyl)amino) phenyl)acetate (83f)

Compound 83f was prepared according to the procedure reported in step-1 of scheme 1, from 5-bromo-3-(bromomethyl)benzofuran (1a) (0.58 g, 2.001 mmol) in DCM (15 mL) using ethyl 2-(4-((tert-butoxycarbonyl)amino)-2-hydroxyphenyl)acetate (83e) (0.65 g, 2.201 mmol), $K_2CO_3$ (0.830 g, 6.00 mmol) and heating at 45° C. for 2 days. This gave after workup and purification by flash column chromatography [silica gel (24 g), eluting with EtOAc in hexane from 0-50%] ethyl 2-(2-((5-bromobenzofuran-3-yl) methoxy)-4-((tert-butoxycarbonyl)amino)phenyl)acetate (83f) (0.43 g, 43% yield) as a yellow solid; $^1$H NMR (300 MHz, DMSO-$d_6$) δ 9.35 (s, 1H), 8.14 (s, 1H), 7.84 (d, J=2.1 Hz, 1H), 7.61 (d, J=8.7 Hz, 1H), 7.50 (dd, J=8.7, 2.0 Hz, 1H), 7.39 (s, 1H), 7.05 (d, J=8.3 Hz, 1H), 7.01-6.91 (m, 1H), 5.16 (s, 2H), 3.92 (q, J=7.1 Hz, 2H), 3.46 (s, 2H), 1.48 (s, 9H), 1.00-0.93 (m, 3H); MS (ES+): 525.95 (M+Na).

Step-5: Preparation of ethyl 2-(2-((5-(3-(aminomethyl)phenyl)benzofuran-3-yl)methoxy)-4-((tert-butoxycarbonyl)amino)phenyl)acetate (83g)

Compound 83g was prepared according to the procedure reported in step-2 of scheme 1, from ethyl 2-(2-((5-bromobenzofuran-3-yl)methoxy)-4-((tert-butoxycarbonyl) amino)phenyl)acetate (83f) (0.43 g, 0.853 mmol) in dioxane/THF (6 mL each) using 3-(aminomethyl)phenylboronic acid hydrochloride (1d) (0.320 g, 1.705 mmol), 2 M solution of $K_3PO_4$ (1.705 mL, 3.41 mmol), tricyclohexylphosphine (0.048 g, 0.171 mmol), $Pd_2(dba)_3$ (0.078 g, 0.085 mmol), $Pd(dppf)Cl_2$—$CH_2Cl_2$ adduct (0.070 g, 0.085 mmol) and heating at 90° C. for 1 h. This gave after workup and purification by flash column chromatography [silica (24 g), eluting with DMA-80 in DCM from 0-70%] ethyl 2-(2-((5-(3-(aminomethyl)phenyl)benzofuran-3-yl)methoxy)-4-((tert-butoxycarbonyl)amino)phenyl)acetate (83g) (0.22 g, 49% yield) as a yellow solid; $^1$H NMR (300 MHz, DMSO-$d_6$) δ 9.36 (s, 1H), 8.12 (s, 1H), 7.89 (d, J=1.7 Hz, 1H), 7.72-7.51 (m, 4H), 7.45-7.29 (m, 3H), 7.07-6.93 (m, 2H), 5.22 (s, 2H), 3.80 (s, 2H), 3.69 (q, J=7.1 Hz, 2H), 3.46 (s, 2H), 1.48 (s, 9H), 0.82 (t, J=7.1 Hz, 3H); MS (ES+): 531.10 (M+1).

Step-6: Preparation of 2-(2-((5-(3-(aminomethyl)phenyl)benzofuran-3-yl)methoxy)-4-((tert-butoxycarbonyl)amino)phenyl)acetic acid (83h)

Compound 83h was prepared according to the procedure reported in step-3 of scheme 1, from ethyl 2-(2-((5-(3-(aminomethyl)phenyl)benzofuran-3-yl)methoxy)-4-((tert-butoxycarbonyl)amino)phenyl)acetate (83g) (60 mg, 0.113 mmol) in THF/MeOH (4 mL each) using a solution of lithium hydroxide hydrate (19 mg, 0.452 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)benzofuran-3-yl)methoxy)-4-((tert-butoxycarbonyl)amino)phenyl)acetic acid (83h) (24 mg, 42% yield) HCl salt as a white solid; $^1$H NMR (300 MHz, DMSO-$d_6$) δ 12.07 (s, 1H, $D_2O$ exchangeable), 9.35 (s, 1H), 8.30 (s, 3H, $D_2O$ exchangeable), 8.14 (s, 1H), 7.98 (d, J=1.8 Hz, 1H), 7.86 (s, 1H), 7.74 (d, J=8.7 Hz, 2H), 7.67 (dd, J=8.7, 1.8 Hz, 1H), 7.52 (t, J=7.6 Hz, 1H), 7.45 (d, J=6.8 Hz, 2H), 7.06 (d, J=8.2 Hz, 1H), 6.95 (dd, J=8.3, 1.8 Hz, 1H), 5.24 (s, 2H), 4.11 (s, 2H), 3.44 (s, 2H), 1.48 (s, 9H); MS (ES+): 503.10 (M+1); MS (ES−): 501.10 (M−1).

Scheme 84

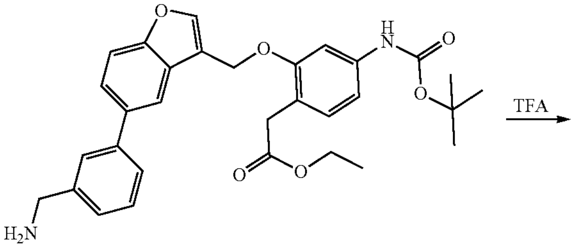

83g

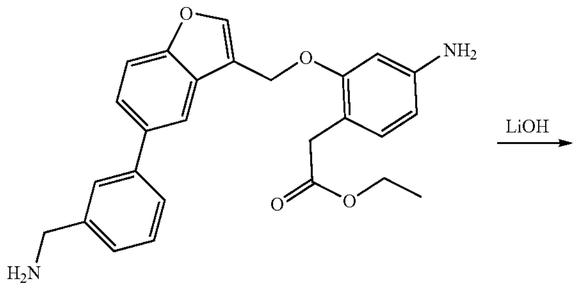

84a

-continued

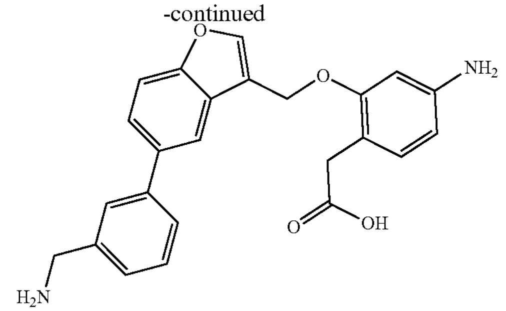

84b

Preparation of 2-(4-amino-2-((5-(3-(aminomethyl)phenyl)benzofuran-3-yl)methoxy)phenyl)acetic acid (84b)

Step-1: Preparation of ethyl 2-(4-amino-2-((5-(3-(aminomethyl)phenyl)benzofuran-3-yl)methoxy)phenyl)acetate (84a)

Compound 84a was prepared according to the procedure reported in step-9 of scheme 3, from ethyl 2-(2-((5-(3-(aminomethyl)phenyl)benzofuran-3-yl)methoxy)-4-((tert-butoxycarbonyl)amino)phenyl)acetate (83g) (160 mg, 0.302 mmol) in DCM (10 mL) using TFA (0.462 mL, 6.03 mmol) and stirring overnight at room temperature. This gave after workup and purification by flash column chromatography [silica gel (24 g), eluting with DMA-80 in DCM from 0-50%] ethyl 2-(4-amino-2-((5-(3-(aminomethyl)phenyl)benzofuran-3-yl)methoxy)phenyl)acetate (84a) (130 mg, 100% yield) as a white solid; $^1$H NMR (300 MHz, DMSO-$d_6$) δ 8.30-8.18 (m, 5H), 8.16 (s, 1H), 7.93 (d, J=1.8 Hz, 1H), 7.82 (s, 1H), 7.75 (d, J=8.4 Hz, 2H), 7.67 (dd, J=8.6, 1.8 Hz, 1H), 7.53 (t, J=7.6 Hz, 1H), 7.44 (d, J=7.2 Hz, 1H), 7.22 (d, J=8.0 Hz, 1H), 7.04 (s, 1H), 6.77 (d, J=8.3 Hz, 1H), 5.29 (s, 2H), 4.12 (d, J=5.7 Hz, 2H), 3.70 (q, J=7.2 Hz, 2H), 3.54 (s, 2H), 0.82 (t, J=7.1 Hz, 3H); MS (ES+): 431.10 (M+1);

Step-2: Preparation of 2-(4-amino-2-((5-(3-(aminomethyl)phenyl)benzofuran-3-yl)methoxy)phenyl)acetic acid (84b)

Compound 84b was prepared according to the procedure reported in step-3 of scheme 1, from ethyl 2-(4-amino-2-((5-(3-(aminomethyl)phenyl)benzofuran-3-yl)methoxy)phenyl)acetate (84a) (130 mg, 0.302 mmol) in THF/MeOH (4 mL each) using a solution of lithium hydroxide hydrate (101 mg, 2.416 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(4-amino-2-((5-(3-(aminomethyl)phenyl)benzofuran-3-yl)methoxy)phenyl)acetic acid (84b) (65 mg, 54% yield) HCl salt as a white solid; $^1$H NMR (300 MHz, DMSO-$d_6$) δ 9.68 (s, 2H, $D_2O$ exchangeable), 8.41 (s, 3H, $D_2O$ exchangeable), 8.18 (s, 1H), 8.00 (d, J=1.7 Hz, 1H), 7.89 (s, 1H), 7.78-7.66 (m, 3H), 7.57-7.43 (m, 2H), 7.22 (d, J=7.9 Hz, 1H), 7.08 (s, 1H), 6.79 (d, J=7.9 Hz, 1H), 5.31 (s, 2H), 4.11 (m, J=5.9 Hz, 2H), 3.52 (s, 2H); MS (ES+): 403.10 (M+1).

Scheme 85

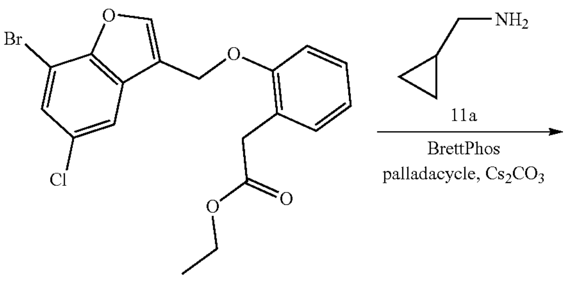

72e

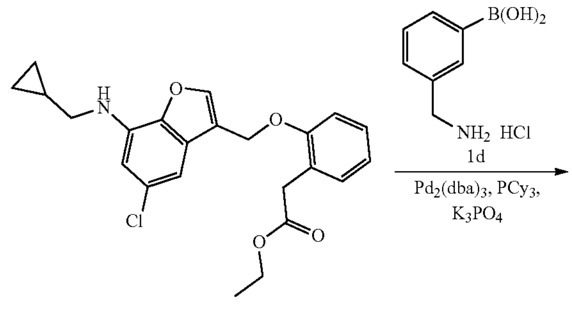

85a

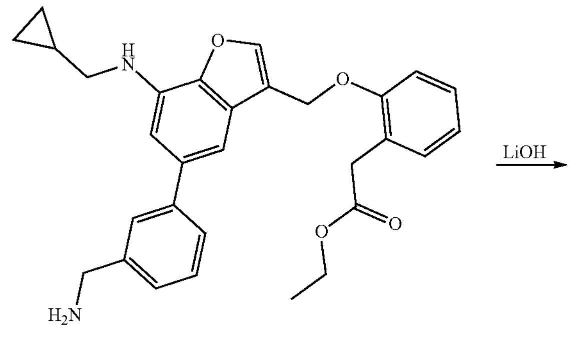

85b

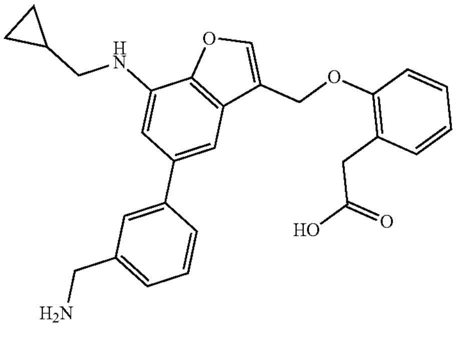

85c

Preparation of 2-(2-((5-(3-(aminomethyl)phenyl)-7-((cyclopropylmethyl)amino)benzofuran-3-yl)methoxy)phenyl)acetic acid (85c)

Step-1: Preparation of ethyl 2-(2-((5-chloro-7-((cyclopropylmethyl)amino)benzofuran-3-yl)methoxy)phenyl)acetate (85a)

Compound 85a was prepared according to the procedure reported in step-8 of Scheme 3, from ethyl 2-(2-((7-bromo-5-chlorobenzofuran-3-yl)methoxy)phenyl)acetate (72e) (200 mg, 0.472 mmol) in acetonitrile (3 mL) using cyclopropylmethanamine (11a) (50 mg, 0.708 mmol), BrettPhos Palladacycle (19 mg, 0.024 mmol), cesium carbonate (461 mg, 1.416 mmol) and heating at 110° C. for 1 h in a microwave. This gave after workup and purification by flash column chromatography [silica gel (12 g), eluting with DMA-80 in DCM from 0-50%] ethyl 2-(2-((5-chloro-7-((cyclopropylmethyl)amino)benzofuran-3-yl)methoxy)phenyl)acetate (85a) (77 mg, 39% yield); $^1$H NMR (300 MHz, DMSO-$d_6$) δ 8.04 (s, 1H), 7.32-7.24 (m, 1H), 7.24-7.14 (m, 2H), 6.92 (t, J=7.3 Hz, 1H), 6.82 (d, J=1.9 Hz, 1H), 6.52 (d, J=2.0 Hz, 1H), 6.11 (t, J=5.9 Hz, 1H), 5.17 (s, 2H), 3.96 (q, J=7.0 Hz, 2H), 3.55 (s, 2H), 3.09 (t, J=6.3 Hz, 2H), 1.18-1.05 (m, 1H), 1.02 (t, J=7.1 Hz, 3H), 0.50-0.38 (m, 2H), 0.29-0.20 (m, 2H); MS (ES+): 414.00 (M+1).

Step-2: Preparation of ethyl 2-(2-((5-(3-(aminomethyl)phenyl)-7-((cyclopropylmethyl)amino)benzofuran-3-yl)methoxy)phenyl)acetate (85b)

Compound 85b was prepared according to the procedure reported in step-2 of scheme 1, from ethyl 2-(2-((5-chloro-7-((cyclopropylmethyl)amino)benzofuran-3-yl)methoxy)phenyl)acetate (85a) (77 mg, 0.186 mmol) in dioxane (2 mL) using 3-(aminomethyl)phenylboronic acid hydrochloride (1d) (52.3 mg, 0.279 mmol), 2 M solution of $K_3PO_4$ (0.158 mL, 0.316 mmol), tricyclohexylphosphine (20.87 mg, 0.074 mmol), $Pd_2(dba)_3$ (34.1 mg, 0.037 mmol) and heating at 120° C. for 30 min. This gave after workup and purification by flash column chromatography [silica gel (24 g), eluting with DMA-80 in DCM from 0-50%] ethyl 2-(2-((5-(3-(aminomethyl)phenyl)-7-((cyclopropylmethyl)amino)benzofuran-3-yl)methoxy)phenyl)acetate (85b) (88 mg, 98% yield); $^1$H NMR (300 MHz, DMSO-$d_6$) δ 8.03 (s, 1H), 7.62 (s, 1H), 7.56-7.48 (m, 1H), 7.37 (t, J=7.7 Hz, 1H), 7.33-7.31 (m, 2H), 7.29-7.26 (m, 1H), 7.26-7.17 (m, 4H), 7.11-7.08 (m, 1H), 6.97-6.88 (m, 1H), 6.82-6.78 (m, 1H), 5.24 (s, 2H), 3.84-3.76 (m, 4H), 3.57 (s, 2H), 3.23-3.13 (m, 2H), 1.21-1.12 (m, 1H), 0.92 (t, J=7.1 Hz, 3H), 0.53-0.43 (m, 2H), 0.31-0.23 (m, 2H); MS (ES+): 485.10 (M+1).

Step-3: Preparation of 2-(2-((5-(3-(aminomethyl)phenyl)-7-((cyclopropylmethyl)amino)benzofuran-3-yl)methoxy)phenyl)acetic acid (85c)

Compound 85c was prepared according to the procedure reported in step-3 of scheme 1, from ethyl 2-(2-((5-(3-(aminomethyl)phenyl)-7-((cyclopropylmethyl)amino)benzofuran-3-yl)methoxy)phenyl)acetate (85b) (88 mg, 0.182 mmol) in THF (2 mL), MeOH (0.2 mL), water (0.2 mL) using a solution of lithium hydroxide hydrate (17.40 mg, 0.726 mmol) and stirring at room temperature for 10 h. This gave after workup and purification by reverse phase column chromatography [C18 column (40 g), eluting with ACN in water (containing 0.1% HCl) from 0-100%] 2-(2-((5-(3-(aminomethyl)phenyl)-7-((cyclopropylmethyl)amino)benzofuran-3-yl)methoxy)phenyl)acetic acid (85c) (6 mg, 7% yield) HCl salt as a white solid; $^1$H NMR (300 MHz, DMSO-$d_6$) δ 8.30 (s, 4H, $D_2O$ exchangeable), 8.04 (s, 1H), 7.79 (s, 1H), 7.69 (d, J=7.7 Hz, 1H), 7.49 (t, J=7.6 Hz, 1H), 7.42 (d, J=7.6 Hz, 1H), 7.32-7.23 (m, 1H), 7.23-7.17 (m, 3H), 6.92 (t, J=7.3 Hz, 1H), 6.84 (d, J=1.7 Hz, 1H), 5.26 (s, 2H), 4.11 (d, J=6.1 Hz, 2H), 3.54 (s, 2H), 3.19 (d, J=6.7 Hz, 2H), 1.27-1.09 (m, 1H), 0.55-0.43 (m, 2H), 0.36-0.22 (m, 2H); MS (ES+): 457.1 (M+1).

Scheme 86

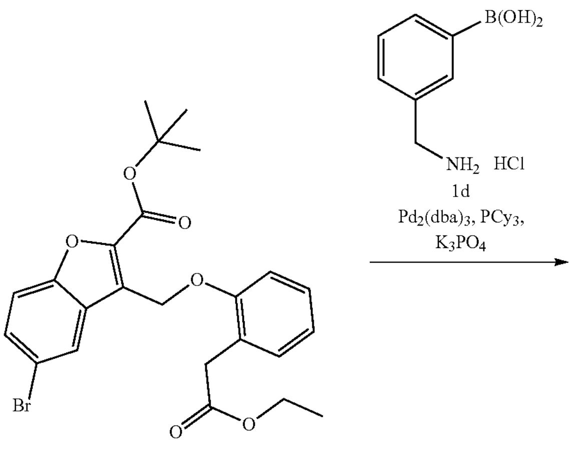

64d

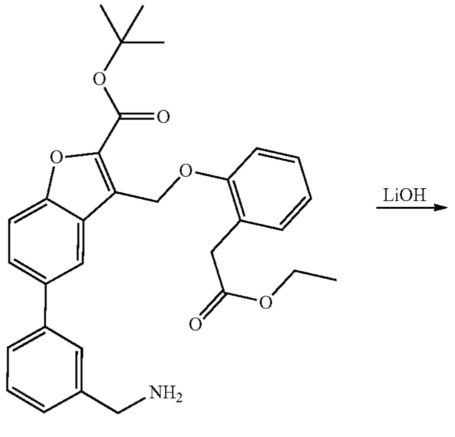

86a

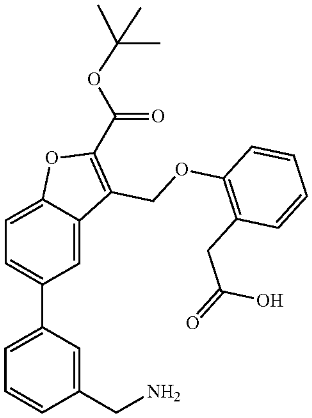

86b

Preparation of 2-(2-((5-(3-(aminomethyl)phenyl)-2-(tert-butoxycarbonyl)benzofuran-3-yl)methoxy)phenyl)acetic acid (86b)

Step-1: Preparation of tert-butyl 5-(3-(aminomethyl)phenyl)-3-((2-(2-ethoxy-2-oxoethyl)phenoxy)methyl)benzofuran-2-carboxylate (86a)

Compound 86a was prepared according to the procedure reported in step-2 of scheme 1, from tert-butyl 5-bromo-3-((2-(2-ethoxy-2-oxoethyl)phenoxy)methyl)benzofuran-2-carboxylate (64d) (350 mg, 0.715 mmol) using 3-(aminomethyl)phenylboronic acid hydrochloride (1d) (268 mg, 1.430 mmol), 2 M solution of $K_3PO_4$ (1.430 mL, 2.86 mmol), tricyclohexylphosphine (40.1 mg, 0.143 mmol), $Pd_2(dba)_3$ (65.5 mg, 0.072 mmol) and heating at 95° C. for 1 h. This gave after workup and purification by flash column chromatography [silica gel (24 g), eluting with DMA-80 in DCM from 0-70%] tert-butyl 5-(3-(aminomethyl)phenyl)-3-((2-(2-ethoxy-2-oxoethyl)phenoxy)methyl)benzofuran-2-carboxylate (86a) (30 mg, 98% yield); $^1H$ NMR (300 MHz, DMSO-$d_6$) δ 8.08 (s, 1H), 7.83 (s, 2H), 7.68 (s, 1H), 7.59-7.50 (m, 2H), 7.31 (q, J=7.6 Hz, 4H), 7.21 (d, J=7.8 Hz, 2H), 6.93 (t, J=7.3 Hz, 1H), 5.62 (s, 2H), 3.80 (s, 2H), 3.66 (q, J=7.2 Hz, 2H), 3.55 (s, 2H), 1.57 (s, 9H), 0.80 (t, J=7.1 Hz, 3H); MS (ES+): 516.1 (M+1).

Step-2: Preparation of 2-(2-((5-(3-(aminomethyl)phenyl)-2-(tert-butoxycarbonyl)benzofuran-3-yl)methoxy)phenyl)acetic acid (86b)

Compound 86b was prepared according to the procedure reported in step-3 of scheme 1, from tert-butyl 5-(3-(aminomethyl)phenyl)-3-((2-(2-ethoxy-2-oxoethyl)phenoxy)methyl)benzofuran-2-carboxylate (86a) (215 mg, 0.417 mmol) in THF (3 mL) using a solution of lithium hydroxide hydrate (30.0 mg, 0.715 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)-2-(tert-butoxycarbonyl)benzofuran-3-yl)methoxy)phenyl)acetic acid (86b) (31 mg, 9% yield) HCl salt as a white solid; $^1H$ NMR (300 MHz, DMSO-$d_6$) δ 12.13 (s, 1H, $D_2O$ exchangeable), 8.40 (s, 3H, $D_2O$ exchangeable), 8.18 (s, 1H), 7.95-7.81 (m, 3H), 7.75 (dd, J=7.4, 1.9 Hz, 1H), 7.56-7.46 (m, 2H), 7.31-7.24 (m, 1H), 7.24-7.16 (m, 2H), 6.93 (t, J=7.3 Hz, 1H), 5.63 (s, 2H), 4.11 (s, 2H), 3.54 (s, 2H), 1.57 (s, 9H); MS (ES+): 488.1 (M+1); (ES−): 486.1 (M−1); Analysis calculated for $C_{29}H_{29}NO_6\cdot HCl\cdot 1.5H_2O$: C, 63.21; H, 6.04; Cl, 6.43; N, 2.54. Found: C, 63.11; H, 5.89; Cl, 6.55; N, 2.58.

Scheme 87

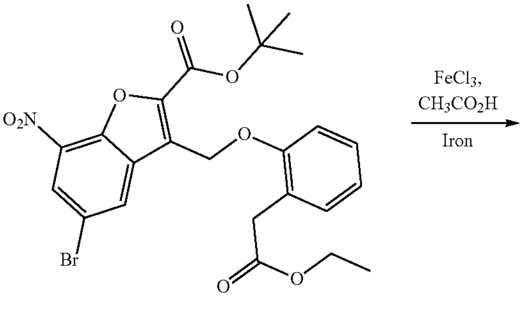

59e

-continued

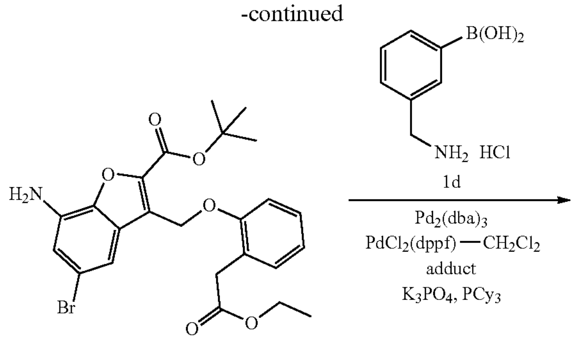

87a

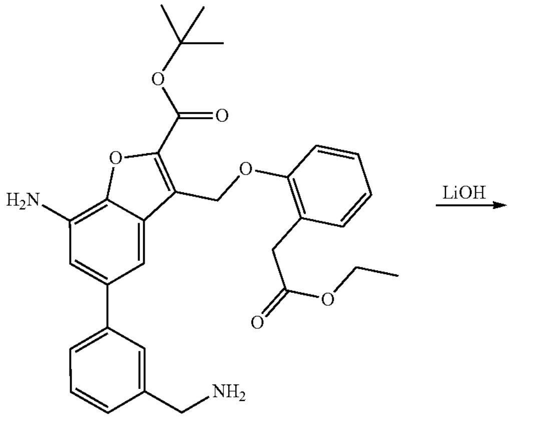

87b

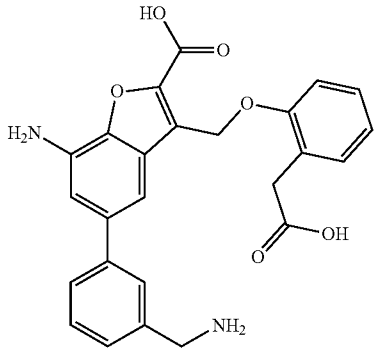

87c

Preparation of 7-amino-5-(3-(aminomethyl)phenyl)-3-((2-(carboxymethyl)phenoxy)methyl)benzofuran-2-carboxylic acid (87c)

Step-1: Preparation of tert-butyl 7-amino-5-bromo-3-((2-(2-ethoxy-2-oxoethyl)phenoxy)methyl) benzofuran-2-carboxylate (87a)

A solution of tert-butyl 5-bromo-3-((2-(2-ethoxy-2-oxoethyl)phenoxy)methyl)-7-nitrobenzofuran-2-carboxylate (59e) (750 mg, 1.404 mmol) and acetic acid (0.321 mL, 5.61 mmol) in absolute ethanol (10 mL) (using a mechanical stirrer) was heated at reflux for 10 min. To this mixture was added iron (627 mg, 11.23 mmol) in portions, followed by ferric chloride hexahydrate (76 mg, 0.281 mmol) and refluxed for 5 h. The mixture was filtered, and the filtrate was diluted with EtOAc and water. The aqueous layer was separated and extracted with ether. The combined organics were dried, filtered and concentrated in vacuum. The residue obtained was purified by flash column chromatography [silica gel (24 g), using EtOAc in hexane from 0-80%] to give tert-butyl 7-amino-5-bromo-3-((2-(2-ethoxy-2-oxoethyl)phenoxy)methyl)benzofuran-2-carboxylate (87a) (625 mg, 88% yield) as a yellow oil; $^1H$ NMR (300 MHz, DMSO-$d_6$) δ 7.28 (td, J=7.7, 1.7 Hz, 1H), 7.21 (dd, J=7.5, 1.7 Hz, 1H), 7.17-7.09 (m, 2H), 6.93 (t, J=7.3 Hz, 1H), 6.85 (d, J=1.8 Hz, 1H), 5.88 (s, 2H), 5.47 (s, 2H), 3.93 (q, J=7.1 Hz, 2H), 3.54 (s, 2H), 1.55 (s, 9H), 0.99 (t, J=7.1 Hz, 3H); MS (ES+): 525.90 (M+Na).

Step-2: Preparation of tert-butyl 7-amino-5-(3-(aminomethyl)phenyl)-3-((2-(2-ethoxy-2-oxoethyl)phenoxy)methyl)benzofuran-2-carboxylate (87b)

Compound 87b was prepared according to the procedure reported in step-2 of scheme 1, from tert-butyl 7-amino-5-bromo-3-((2-(2-ethoxy-2-oxoethyl)phenoxy)methyl)benzofuran-2-carboxylate (87a) (295 mg, 0.585 mmol) in dioxane/THF (5 mL each) using 3-(aminomethyl)phenylboronic acid hydrochloride (1d) (254 mg, 1.355 mmol), 2 M solution of $K_3PO_4$ (1.355 mL, 2.71 mmol), tricyclohexylphosphine (219 mg, 1.170 mmol), $PdCl_2(dppf)$-$CH_2Cl_2$ adduct (47.8 mg, 0.058 mmol), $Pd_2(dba)_3$ (53.6 mg, 0.058 mmol) and heating at 90° C. for 1 h. This gave after workup and purification by flash column chromatography [silica gel (24 g), eluting with DMA-80 in DCM from 0-70%] tert-butyl 7-amino-5-(3-(aminomethyl)phenyl)-3-((2-(2-ethoxy-2-oxoethyl)phenoxy)methyl)benzofuran-2-carboxylate (87b) (197 mg, 64% yield) as a yellow semi-solid; MS (ES+): 531.2 (M+1).

Step-3: Preparation of 7-amino-5-(3-(aminomethyl) phenyl)-3-((2-(carboxymethyl)phenoxy) methyl) benzofuran-2-carboxylic acid (87c)

Compound 87c was prepared according to the procedure reported in step-3 of scheme 1, from tert-butyl 7-amino-5-(3-(aminomethyl)phenyl)-3-((2-(2-ethoxy-2-oxoethyl)phenoxy)methyl)benzofuran-2-carboxylate (87b) (197 mg, 0.371 mmol) in THF (3 mL) using a solution of lithium hydroxide hydrate (73.6 mg, 1.755 mmol) in water (1 mL) and stirring overnight at room temperature. This gave after workup and purification by reverse phase column chromatography [C18 column (30 g), eluting with ACN in water (containing 0.1% HCl) from 0-100%] 7-amino-5-(3-(aminomethyl)phenyl)-3-((2-(carboxymethyl)phenoxy)methyl) benzofuran-2-carboxylic acid (87c) (100 mg, 38% yield) HCl salt as an off white solid; $^1H$ NMR (300 MHz, DMSO-$d_6$) δ 14.08 (brs, 1H, $D_2O$ exchangeable), 11.97 (brs, 1H, $D_2O$ exchangeable), 8.56 (s, 3H, $D_2O$ exchangeable), 7.74 (s, 1H), 7.64-7.54 (m, 1H), 7.52-7.45 (m, 2H), 7.34 (d, J=1.5 Hz, 1H), 7.28-7.13 (m, 3H), 7.11 (s, 1H), 6.97-6.86 (m, 1H), 5.62 (s, 2H), 4.90 (brs, 3H, $D_2O$ exchangeable), 4.07 (q, J=5.8 Hz, 2H), 3.54 (s, 2H); MS (ES+): 447.1 (M+1); (ES−): 445.0 (M−1).

Scheme 88

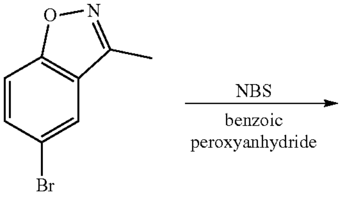

88a

-continued

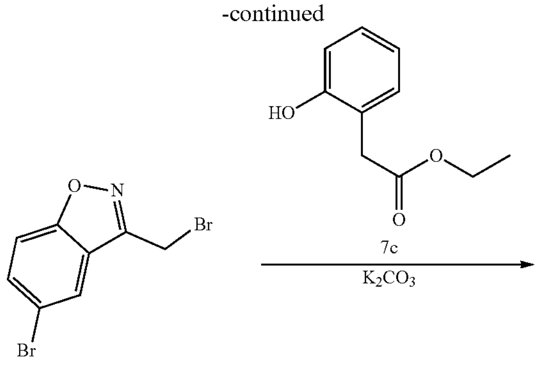

88b

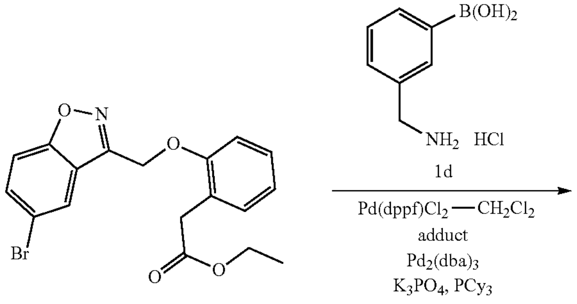

88c

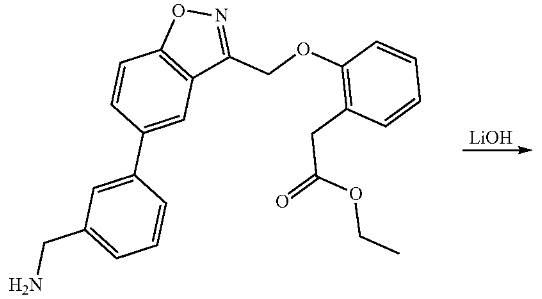

88d

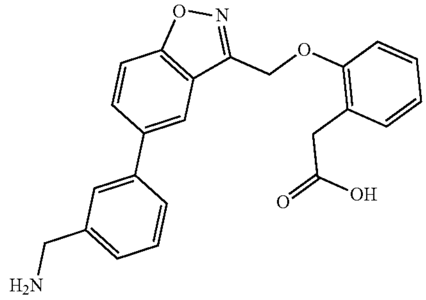

88e

Preparation of 2-(2-((5-(3-(aminomethyl)phenyl)benzo[d]isoxazol-3-yl)methoxy)phenyl)acetic acid (88e)

Step-1: Preparation of 5-bromo-3-(bromomethyl)benzo[d]isoxazole (88b)

Compound 88b was prepared according to the procedure reported in step-2 of scheme 58, from 5-bromo-3-methyl-benzo[d]isoxazole (88a) (0.5 g, 2.358 mmol; CAS #66033-76-9) in carbon tetrachloride (20 mL) using NBS (0.462 g, 2.59 mmol), benzoic peroxyanhydride (0.086 g, 0.354 mmol) and refluxing for 5 days. The reaction mixture was filtered, and the filtrate was concentrated in vacuum to afford 5-bromo-3-(bromomethyl)benzo[d]isoxazole (88b) (0.62 g, 90% yield) which was used as such for the next step without purification.

Step-2: Preparation of ethyl 2-(2-((5-bromobenzo[d]isoxazol-3-yl)methoxy)phenyl)acetate (88c)

Compound 88c was prepared according to the procedure reported in step-2 of Scheme 65, from 5-bromo-3-(bromomethyl)benzo[d]isoxazole (88b) (0.6 g, 2.062 mmol) in DMF (10 mL) using ethyl 2-(2-hydroxyphenyl)acetate (7c) (0.372 g, 2.062 mmol), potassium carbonate (0.855 g, 6.19 mmol) and heating at 70° C. for 15 h. This gave after workup and purification by flash column chromatography [silica gel (24 g), eluting with EtOAc in hexane from 0-50%] ethyl 2-(2-((5-bromobenzo[d]isoxazol-3-yl)methoxy)phenyl)acetate (88c) (20 mg, 2% yield) as a white solid; $^1H$ NMR (300 MHz, DMSO-$d_6$) δ 8.12 (d, J=1.8 Hz, 1H), 7.92-7.78 (m, 2H), 7.32 (t, J=7.7 Hz, 1H), 7.27-7.19 (m, 2H), 6.98 (t, J=7.4 Hz, 1H), 5.56 (s, 2H), 3.93 (q, J=7.1 Hz, 2H), 3.59 (s, 2H), 0.98 (t, J=7.1 Hz, 3H); MS (ES+): 390.00 (M+1); (ES−): 388.85 (M−1).

Step-3: Preparation of ethyl 2-(2-((5-(3-(aminomethyl)phenyl)benzo[d]isoxazol-3-yl)methoxy)phenyl) acetate (88d)

Compound 88d was prepared according to the procedure reported in step-2 of scheme 1, from ethyl 2-(2-((5-bromobenzo[d]isoxazol-3-yl)methoxy)phenyl)acetate (88c) (20 mg, 0.051 mmol) in dioxane/THF (2 mL each) using 3-(aminomethyl)phenylboronic acid hydrochloride (1d) (19.21 mg, 0.103 mmol), 2 M solution of $K_3PO_4$ (0.103 mL, 0.205 mmol), tricyclohexylphosphine (2.87 mg, 10.25 μmol), $PdCl_2$(dppf)-$CH_2Cl_2$ adduct (4.19 mg, 5.13 μmol), $Pd_2(dba)_3$ (4.69 mg, 5.13 μmol) and heating at 90° C. for 1 h. This gave after workup and purification by column chromatography [silica gel (24 g), eluting with DMA-80 in DCM from 0-70%] ethyl 2-(2-((5-(3-(aminomethyl)phenyl)benzo[d]isoxazol-3-yl)methoxy)phenyl)acetate (88d) (10 mg, 47% yield) as a clear oil; MS (ES+): 417.10 (M+1).

Step-4: Preparation of 2-(2-((5-(3-(aminomethyl)phenyl)benzo[d]isoxazol-3-yl)methoxy)phenyl)acetic acid (88e)

Compound 88e was prepared according to the procedure reported in step-3 of scheme 1, from ethyl 2-(2-((5-(3-(aminomethyl)phenyl)benzo[d]isoxazol-3-yl)methoxy)phenyl)acetate (88d) (10 mg, 0.024 mmol) in THF/MeOH (4 mL each) using lithium hydroxide hydrate (8.06 mg, 0.192 mmol) and stirring for 15 h at room temperature. This gave after workup and purification by reverse phase column chromatography [C18 column (50 g), eluting with ACN in water (containing 0.1% HCl) from 0-100%] 2-(2-((5-(3-(aminomethyl)phenyl)benzo[d]isoxazol-3-yl)methoxy)phenyl)acetic acid (88e) (5 mg, 54% yield) HCl salt as a white solid; $^1H$ NMR (300 MHz, DMSO-$d_6$) δ 12.15 (s, 1H, $D_2O$ exchangeable), 8.37 (s, 3H, $D_2O$ exchangeable), 8.21 (d, J=1.7 Hz, 1H), 8.03 (dd, J=8.8, 1.8 Hz, 1H), 7.93 (d, J=8.8 Hz, 1H), 7.90 (s, 1H), 7.77 (dt, J=7.5, 1.7 Hz, 1H), 7.59-7.47 (m, 2H), 7.34-7.19 (m, 3H), 6.97 (td, J=7.2, 1.6 Hz, 1H), 5.62 (s, 2H), 4.11 (d, J=5.5 Hz, 2H), 3.56 (s, 2H). MS (ES+): 389.10 (M+1); MS (ES−): 387.10 (M−1).

Scheme 89
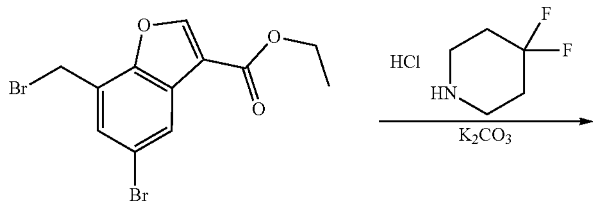
79c
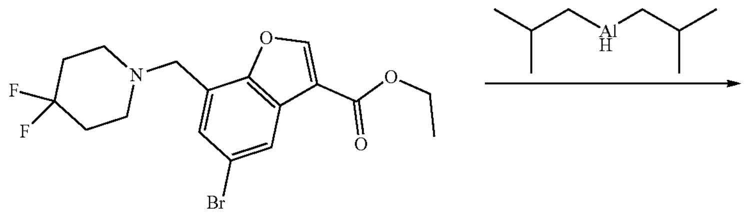
89a
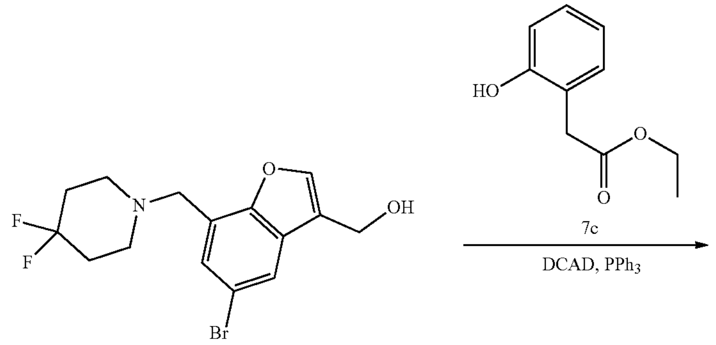
89b
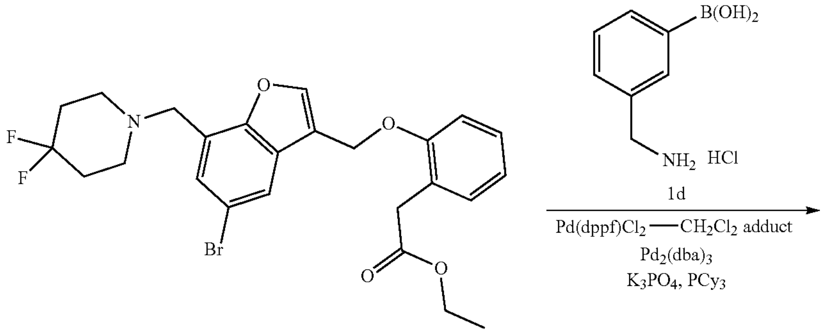
89c
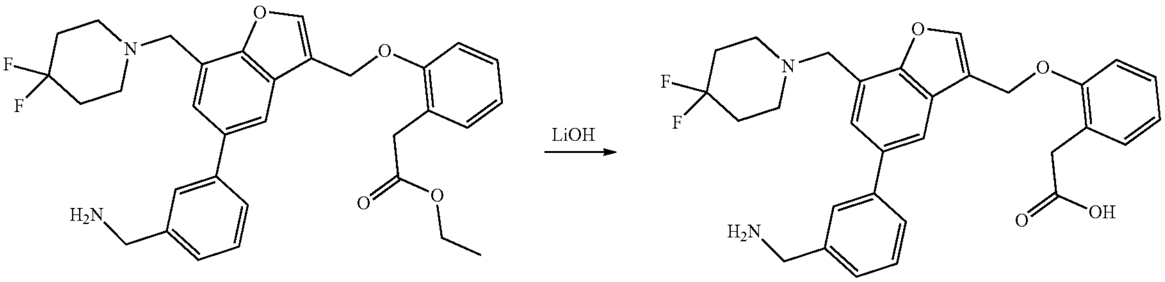
89d
89e Preparation of 2-(2-((5-(3-(aminomethyl)phenyl)-7-((4,4-difluoropiperidin-1-yl)methyl)benzofuran-3-yl)methoxy)phenyl)acetic acid (89e)

Step-1: Preparation of ethyl 5-bromo-7-((4,4-difluoropiperidin-1-yl)methyl)benzofuran-3-carboxylate (89a)

Compound 89a was prepared according to the procedure reported in step-3 of scheme 79, from ethyl 5-bromo-7-(bromomethyl)benzofuran-3-carboxylate (79c) (0.4 g, 1.105 mmol) in DMF (10 mL) using potassium carbonate (0.458 g, 3.31 mmol), 4,4-difluoropiperidine hydrochloride (0.522 g, 3.31 mmol) and stirring at room temperature for 3 h. This gave after workup and purification by flash column chromatography [silica gel (24 g), eluting with EtOAc in hexane from 0-50%] ethyl 5-bromo-7-((4,4-difluoropiperidin-1-yl)methyl)benzofuran-3-carboxylate (89a) (0.36 g, 81% yield) as a yellow solid; $^1H$ NMR (300 MHz, DMSO-$d_6$) δ 8.81 (s, 1H), 7.94 (d, J=2.1 Hz, 1H), 7.53 (d, J=2.1 Hz, 1H), 4.31 (q, J=7.1 Hz, 2H), 3.83 (s, 2H), 2.47-2.45 (m, 4H), 2.00-1.84 (m, 4H), 1.30 (t, J=7.1 Hz, 3H); MS (ES+): 402.00 (M+1).

Step-2: Preparation of (5-bromo-7-((4,4-difluoropiperidin-1-yl)methyl)benzofuran-3-yl)methanol (89b)

Compound 89b was prepared according to the procedure reported in step-2 of scheme 69, from ethyl 5-bromo-7-((4,4-difluoropiperidin-1-yl)methyl)benzofuran-3-carboxylate (89a) (0.36 g, 0.895 mmol) in DCM (10 mL) using a solution of DIBAL (2.238 mL, 2.238 mmol; 1M in DCM) and stirring at −78° C. for 30 min. This gave after workup and purification by flash column chromatography [silica gel (24 g), eluting with DMA-80 in DCM from 0-50%](5-bromo-7-((4,4-difluoropiperidin-1-yl)methyl)benzofuran-3-yl)methanol (89b) (0.28 g, 87% yield) as a white oil; $^1H$ NMR (300 MHz, DMSO-$d_6$) δ 7.94 (s, 1H), 7.80 (d, J=2.0 Hz, 1H), 7.43 (d, J=2.0 Hz, 1H), 5.21 (t, J=5.6 Hz, 1H), 4.59 (dd, J=5.6, 1.0 Hz, 2H), 3.83 (s, 2H), 2.58-2.52 (m, 4H), 2.07-1.85 (m, 4H); MS (ES+): 360.00 (M+1).

Step-3: Preparation of ethyl 2-(2-((5-bromo-7-((4,4-difluoropiperidin-1-yl)methyl)benzofuran-3-yl)methoxy)phenyl)acetate (89c)

Compound 89c was prepared according to the procedure reported in step-2 of Scheme 65, from (5-bromo-7-((4,4-difluoropiperidin-1-yl)methyl)benzofuran-3-yl)methanol (89b) (0.28 g, 0.777 mmol) in DCM (10 mL) using triphenylphosphine (0.408 g, 1.555 mmol), ethyl 2-(2-hydroxyphenyl)acetate (7c)(0.154 g, 0.855 mmol), and a solution of DCAD (0.571 mg, 1.555 mmol) in DCM (5 mL). This gave after workup and purification by flash column chromatography [silica gel (24 g), eluting with EtOAc in hexane from 0-50%] ethyl 2-(2-((5-bromo-7-((4,4-difluoropiperidin-1-yl)methyl)benzofuran-3-yl)methoxy)phenyl)acetate (89c) (0.22 g, 54% yield) as a white oil; $^1H$ NMR (300 MHz, DMSO-$d_6$) δ 8.16 (s, 1H), 7.76 (d, J=2.0 Hz, 1H), 7.48 (d, J=2.0 Hz, 1H), 7.33-7.24 (m, 1H), 7.24-7.14 (m, 2H), 6.96-6.86 (m, 1H), 5.23 (s, 2H), 3.92 (q, J=7.1 Hz, 2H), 3.85 (s, 2H), 3.55 (s, 2H), 2.57-2.52 (m, 4H), 1.99-1.88 (m, 4H), 0.96 (t, J=7.1 Hz, 3H); MS (ES+): 522.00 (M+1).

Step-4: Preparation of ethyl 2-(2-((5-(3-(aminomethyl)phenyl)-7-((4,4-difluoropiperidin-1-yl)methyl)benzofuran-3-yl)methoxy)phenyl)acetate (89d)

Compound 89d was prepared according to the procedure reported in step-2 of scheme 1, from ethyl 2-(2-((5-bromo-7-((4,4-difluoropiperidin-1-yl)methyl)benzofuran-3-yl)methoxy)phenyl)acetate (89c) (0.25 g, 0.479 mmol) in dioxane/THF (4 mL, each) using 3-(aminomethyl)phenylboronic acid hydrochloride (1d) (0.179 g, 0.957 mmol), 2 M solution of $K_3PO_4$ (0.957 mL, 1.914 mmol), tricyclohexylphosphine (0.027 g, 0.096 mmol), $Pd_2(dba)_3$ (0.044 g, 0.048 mmol), $PdCl_2(dppf)$-$CH_2Cl_2$ adduct (0.039 g, 0.048 mmol) and heating at 90° C. for 1 h. This gave after workup and purification by flash column chromatography [silica gel (24 g), eluting with DMA-80 in DCM from 0-70%] ethyl 2-(2-((5-(3-(aminomethyl)phenyl)-7-((4,4-difluoropiperidin-1-yl)methyl)benzofuran-3-yl)methoxy)phenyl)acetate (89d) (0.14 g, 53% yield) as a colorless oil; $^1H$ NMR (300 MHz, DMSO-$d_6$) δ 8.14 (s, 1H), 7.82 (d, J=1.8 Hz, 1H), 7.67 (d, J=2.0 Hz, 1H), 7.59 (d, J=1.8 Hz, 1H), 7.54 (td, J=5.9, 3.0 Hz, 1H), 7.40 (t, J=7.6 Hz, 1H), 7.35-7.29 (m, 2H), 7.29-7.17 (m, 2H), 6.92 (td, J=7.3, 1.2 Hz, 1H), 5.29 (s, 2H), 3.92 (s, 2H), 3.81 (s, 2H), 3.72 (q, J=7.1 Hz, 2H), 3.56 (s, 2H), 2.61-2.54 (m, 4H), 2.06-1.86 (m, 4H), 0.83 (t, J=7.1 Hz, 3H).

Step-5: Preparation of 2-(2-((5-(3-(aminomethyl)phenyl)-7-((4,4-difluoropiperidin-1-yl)methyl)benzofuran-3-yl)methoxy)phenyl)acetic acid (89e)

Compound 89e was prepared according to the procedure reported in step-3 of scheme 1, from ethyl 2-(2-((5-(3-(aminomethyl)phenyl)-7-((4,4-difluoropiperidin-1-yl)methyl)benzofuran-3-yl)methoxy)phenyl)acetate (89d) (140 mg, 0.255 mmol) in THF/MeOH (4 mL each) using a solution of lithium hydroxide hydrate (0.086 g, 2.041 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-7-((4,4-difluoropiperidin-1-yl)methyl)benzofuran-3-yl)methoxy)phenyl)acetic acid (89e) (90 mg, 68% yield) HCl salt as a white solid; $^1H$ NMR (300 MHz, DMSO-$d_6$) δ 12.17 (s, 1H, $D_2O$ exchangeable), 11.69 (s, 1H, $D_2O$ exchangeable), 8.42 (s, 3H, $D_2O$ exchangeable), 8.23 (s, 1H), 8.14 (d, J=16.0 Hz, 2H), 7.99 (s, 1H), 7.86 (d, J=7.5 Hz, 1H), 7.53 (dt, J=14.2, 7.7 Hz, 2H), 7.33-7.25 (m, 1H), 7.25-7.18 (m, 2H), 6.94 (t, J=7.2 Hz, 1H), 5.35 (s, 2H), 4.75 (s, 2H), 4.11 (m, J=5.8 Hz, 2H), 3.56 (s, 2H), 3.51-3.29 (m, 4H), 2.49-2.24 (m, 4H); $^{19}F$ NMR (282 MHz, DMSO-$d_6$) δ −94.92, −100.63; MS (ES+): 521.10 (M+1); MS (ES−): 519.10 (M−1); Analysis calculated for $C_{30}H_{30}F_2N_2O_4 \cdot 2HCl \cdot 2.25H_2O$: C, 56.83; H, 5.80; Cl, 11.18; N, 4.42. Found: C, 56.72; H, 5.46; Cl, 11.33; N, 4.52.

Scheme 90

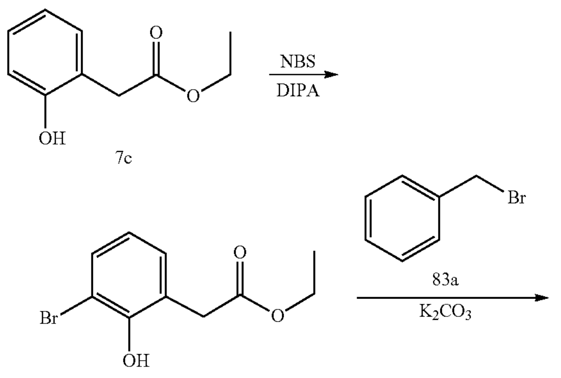

7c

83a

90a

-continued

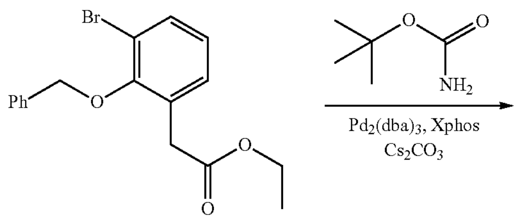

90b

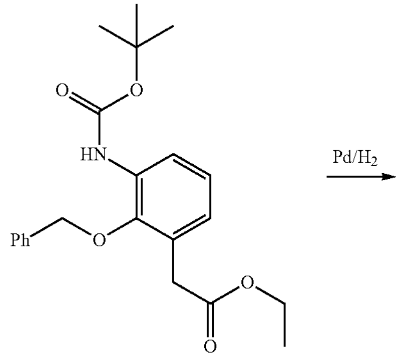

90c

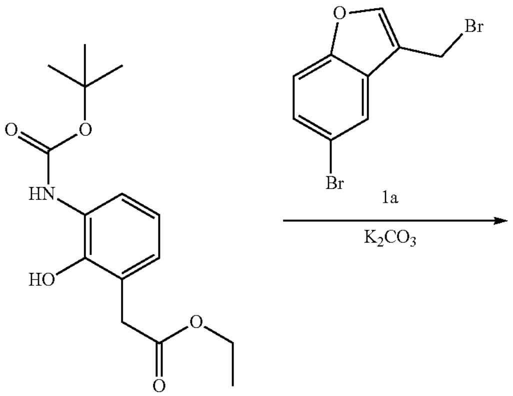

90d

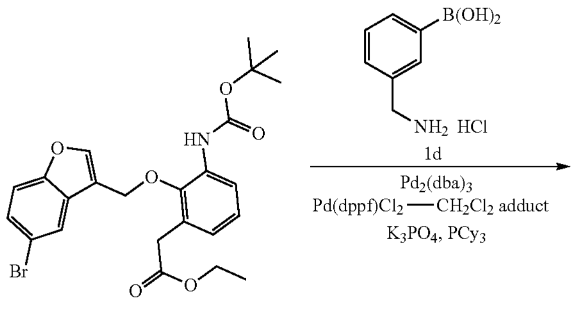

90e

-continued

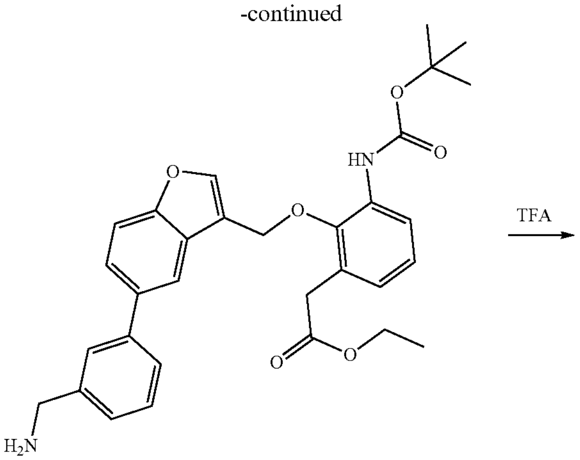

90f

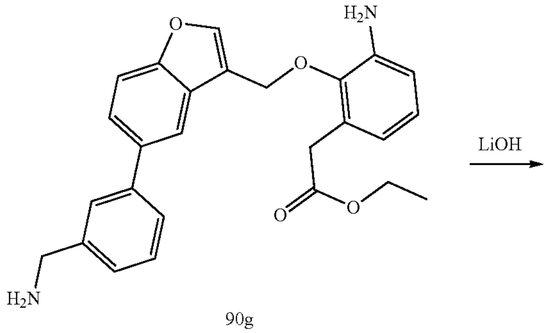

90g

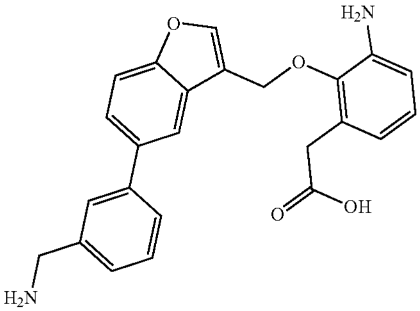

90h

Preparation of 2-(3-amino-2-((5-(3-(aminomethyl)phenyl)benzofuran-3-yl)methoxy)phenyl)acetic acid (90h)

Step-1: Preparation of ethyl 2-(3-bromo-2-hydroxyphenyl)acetate (90a)

To a stirred solution of ethyl 2-(2-hydroxyphenyl)acetate (7c) (6.0 g, 33.29 mmol) in DCM (150 mL) was added diisopropylamine (DIPA) (3.78 g, 37.36 mmol), followed by NBS (2.06 g, 11.57 mmol) (portion wise) at 0° C. The reaction mixture was stirred at room temperature for 1 hour, poured into water (100 mL) and extracted with ethyl acetate (2×250 mL). The organic layers were combined, washed with brine (100 mL), dried, filtered and concentrated in vacuum. The residue obtained was purified by flash column chromatography [silica gel, eluting with EtOAc in n-heptane from 0-15%] to give ethyl 2-(3-bromo-2-hydroxyphenyl)acetate (90a) (5.0 g, 58%) as a white solid. $^{1}$H NMR (300

MHz, DMSO-$d_6$) δ 9.84 (s, 1H), 7.37-7.18 (m, 2H), 6.75 (d, J=8.6 Hz, 1H), 4.06 (q, J=7.1 Hz, 2H), 3.55 (s, 2H), 1.17 (t, J=7.1 Hz, 3H).

Step-2: Preparation of ethyl 2-(2-(benzyloxy)-3-bromophenyl)acetate (90b)

Compound 90b was prepared according to the procedure reported in step-1 of scheme 1, from ethyl 2-(3-bromo-2-hydroxyphenyl)acetate (90a) (23 g, 88.76 mmol) in acetone (460 mL) using (bromomethyl)benzene (83a) (18.21 g, 106.47 mmol), $K_2CO_3$ (36.80 g, 266.27 mmol) and heating at 50° C. for 2 h. This gave after workup and purification by flash column chromatography [silica gel, eluting with EtOAc in n-heptane from 0-15%] ethyl 2-(2-(benzyloxy)-3-bromophenyl)acetate (90b)(12 g, 39% yield) as an off white solid; $^1$H NMR (300 MHz, DMSO-$d_6$) δ 7.48-7.44 (m, 2H), 7.42-7.38 (m, 4H), 7.36-7.18 (m, 1H), 7.02 (d, J=8.4 Hz, 1H), 5.10 (s, 2H), 4.01 (q, J=7.1 Hz, 3H), 3.63 (s, 2H), 1.10 (t, J=7.1 Hz, 3H).

Step-3: Preparation of ethyl 2-(2-(benzyloxy)-3-((tert-butoxycarbonyl)amino)phenyl)acetate (90c)

Compound 90c was prepared according to the procedure reported in step-2 of scheme 77, from ethyl 2-(2-(benzyloxy)-3-bromophenyl)acetate (90b) (0.6 g, 1.718 mmol) in toluene (18.0 mL) and n-Butanol (6.0 mL) using cesium carbonate (5.15 g, 1.679 mmol), $Pd_2(dba)_3$ (0.315 g, 0.344 mmol), XPhos (0.328 g, 0.687 mmol), tert-butyl carbamate (0.403 g, 3.44 mmol) and heating at 110° C. for 17 h. This gave after workup and purification by flash column chromatography [silica gel (40 g), eluting with ethyl acetate in hexane from 0-50%]ethyl 2-(2-(benzyloxy)-3-((tert-butoxycarbonyl)amino)phenyl)acetate (90c) (0.55 g, 83% yield) as a yellow solid; MS (ES+): 408.10 (M+Na).

Step-4: Preparation of ethyl 2-(3-((tert-butoxycarbonyl)amino)-2-hydroxyphenyl)acetate (90d)

Compound 90d was prepared according to the procedure reported in step-3 of scheme 83, from ethyl 2-(2-(benzyloxy)-3-((tert-butoxycarbonyl)amino)phenyl)acetate (90c) (0.55 g, 1.427 mmol) in MeOH (20 mL) using palladium (0.304 g, 0.285 mmol) using a hydrogen filled balloon for 2 days. This gave after workup and purification by flash column chromatography [silica gel (24 g), eluting with ethyl acetate in hexane from 0-50%] ethyl 2-(3-((tert-butoxycarbonyl)amino)-2-hydroxyphenyl)acetate (90d) (0.27 g, 64% yield) as a white solid; $^1$H NMR (300 MHz, DMSO-$d_6$) δ 8.89 (s, 1H), 8.54 (s, 1H), 7.28 (dd, J=8.0, 1.6 Hz, 1H), 6.89 (dd, J=7.6, 1.7 Hz, 1H), 6.75 (t, J=7.7 Hz, 1H), 4.06 (q, J=7.1 Hz, 2H), 3.59 (s, 2H), 1.47 (s, 9H), 1.18 (t, J=7.1 Hz, 3H); MS (ES+): 318.10 (M+Na).

Step-5: Preparation of ethyl 2-(2-((5-bromobenzofuran-3-yl)methoxy)-3-((tert-butoxycarbonyl)amino)phenyl)acetate (90e)

Compound 90e was prepared according to the procedure reported in step-1 of scheme 1, from ethyl 2-(3-((tert-butoxycarbonyl)amino)-2-hydroxyphenyl)acetate (90d) (23.0 mg, 88.76 mmol) in acetone (460 mL) using 5-bromo-3-(bromomethyl)benzofuran (1a) (0.265 g, 0.914 mmol), $K_2CO_3$ (0.379 g, 2.74 mmol) and heating at 70° C. for 2 h. This gave after workup and purification by flash column chromatography [silica gel (12 g), eluting with EtOAc in hexane from 0-50%] ethyl 2-(2-((5-bromobenzofuran-3-yl)methoxy)-3-((tert-butoxycarbonyl)amino)phenyl)acetate (90e) (0.39 g, 85% yield) as a yellow solid; $^1$H NMR (300 MHz, DMSO-$d_6$) δ 8.24 (s, 1H), 8.06 (s, 1H), 7.87 (d, J=2.0 Hz, 1H), 7.61 (d, J=8.7 Hz, 1H), 7.50 (dt, J=7.9, 2.0 Hz, 2H), 7.11-6.98 (m, 2H), 5.00 (s, 2H), 4.00 (q, J=7.1 Hz, 2H), 3.64 (s, 2H), 1.39 (s, 9H), 1.09 (t, J=7.1 Hz, 3H); MS (ES+): 526.00 (M+Na).

Step-6: Preparation of ethyl 2-(2-((5-(3-(aminomethyl)phenyl)benzofuran-3-yl)methoxy)-3-((tert-butoxycarbonyl)amino)phenyl)acetate (90f)

Compound 90f was prepared according to the procedure reported in step-2 of scheme 1, from ethyl 2-(2-((5-bromobenzofuran-3-yl)methoxy)-3-((tert-butoxycarbonyl)amino)phenyl)acetate (90e) (50 mg, 0.099 mmol) in dioxane/THF (4 mL each) using 3-(aminomethyl)phenylboronic acid hydrochloride (1d) (37.2 mg, 0.198 mmol), 2 M solution of $K_3PO_4$ (0.198 mL, 0.397 mmol), tricyclohexylphosphine (5.56 mg, 0.020 mmol), $Pd_2(dba)_3$ (9.08 mg, 9.91 μmol), $Pd(dppf)Cl_2$—$CH_2Cl_2$ adduct (8.10 mg, 9.91 μmol) and heating at 90° C. for 1 h. This gave after workup and purification by flash column chromatography [silica gel (24 g), eluting with DMA80 in DCM from 0-70%] ethyl 2-(2-((5-(3-(aminomethyl)phenyl) benzofuran-3-yl) methoxy)-3-((tert-butoxycarbonyl)amino)phenyl)acetate (90f) (20 mg, 38% yield) as a clear oil; $^1$H NMR (300 MHz, DMSO-$d_6$) δ 9.17 (s, 1H), 8.10 (s, 1H), 7.89 (s, 1H), 7.72-7.66 (m, 2H), 7.66-7.59 (m, 1H), 7.55 (d, J=8.5 Hz, 1H), 7.41 (t, J=7.3 Hz, 1H), 7.37-7.23 (m, 3H), 7.12 (d, J=8.6 Hz, 1H), 5.24 (s, 2H), 4.11 (d, J=5.3 Hz, 2H), 3.75 (q, J=7.1 Hz, 2H), 3.50 (s, 2H), 1.46 (s, 9H), 0.87 (t, J=7.1 Hz, 3H); MS (ES+): 531.10 (M+1).

Step-7: Preparation of ethyl 2-(3-amino-2-((5-(3-(aminomethyl)phenyl)benzofuran-3-yl)methoxy)phenyl)acetate (90 g)

Compound 90g was prepared according to the procedure reported in step-9 of scheme 3, from ethyl 2-(2-((5-(3-(aminomethyl)phenyl)benzofuran-3-yl)methoxy)-3-((tert-butoxycarbonyl)amino)phenyl)acetate (90f) (70 mg, 0.132 mmol) in DCM (5 mL) using TFA (0.202 mL, 2.64 mmol) and stirring at room temperature for 2 h. This gave after workup and purification by flash column chromatography [silica gel (12 g), eluting with DMA-80 in DCM from 0-50%] ethyl 2-(3-amino-2-((5-(3-(aminomethyl)phenyl) benzofuran-3-yl)methoxy)phenyl)acetate (90 g) (56.8 mg, 100% yield) as a yellow oil; $^1$H NMR (300 MHz, DMSO-$d_6$) δ 8.22 (s, 3H), 8.16 (s, 1H), 7.94 (d, J=1.7 Hz, 1H), 7.82 (d, J=1.9 Hz, 1H), 7.75 (d, J=8.5 Hz, 2H), 7.67 (dd, J=8.7, 1.9 Hz, 1H), 7.53 (t, J=7.6 Hz, 1H), 7.44 (d, J=7.5 Hz, 1H), 7.36-7.26 (m, 2H), 7.20 (d, J=2.4 Hz, 1H), 5.33 (s, 2H), 4.12 (d, J=5.8 Hz, 2H), 3.73 (q, J=7.1 Hz, 2H), 0.85 (t, J=7.1 Hz, 3H). MS (ES+): 431.10 (M+1).

Step-8: Preparation of 2-(3-amino-2-((5-(3-(aminomethyl)phenyl)benzofuran-3-yl)methoxy)phenyl)acetic acid (90h)

Compound 90h was prepared according to the procedure reported in step-3 of scheme 1, from ethyl 2-(3-amino-2-((5-(3-(aminomethyl)phenyl)benzofuran-3-yl)methoxy)phenyl)acetate (90 g) (50 mg, 0.116 mmol) in THF/MeOH (4 mL each) using a solution of lithium hydroxide hydrate (39 mg, 0.929 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(3-amino-2-((5-(3-(aminomethyl)phenyl) benzofuran-3-yl)methoxy)phenyl)acetic acid (90h) (25 mg, 54% yield) HCl salt as a yellow solid; $^1$H NMR (300 MHz, DMSO-$d_6$) δ 8.31 (s, 3H, $D_2O$ exchangeable), 8.13 (s, 1H), 8.00 (d, J=1.8 Hz, 1H), 7.86 (s, 1H), 7.74 (d, J=8.6 Hz, 2H), 7.68 (dd, J=8.6, 1.8 Hz, 1H), 7.53 (t, J=7.6 Hz, 1H), 7.45 (d, J=7.6 Hz, 1H), 7.27 (d, J=8.6 Hz, 1H), 7.24-7.10 (m, 2H), 5.34 (s, 2H), 4.12 (s, 2H), 3.58 (s, 2H); MS (ES+): 403.05 (M+1); Analysis calculated for $C_{24}H_{22}N_2O_4·2HCl·2.5H_2O$: C, 55.39; H, 5.62; N, 5.38. Found: C, 55.14; H, 5.53; N, 5.47.

Scheme 91

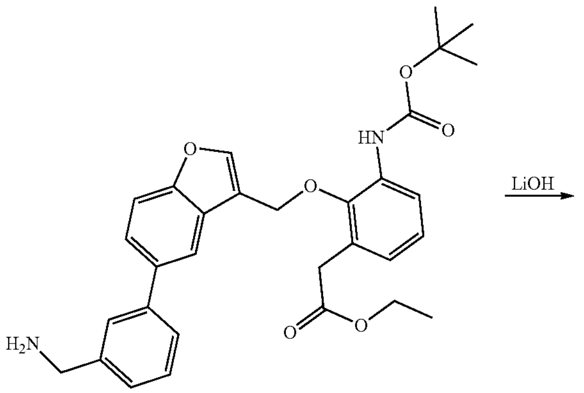

90f

-continued

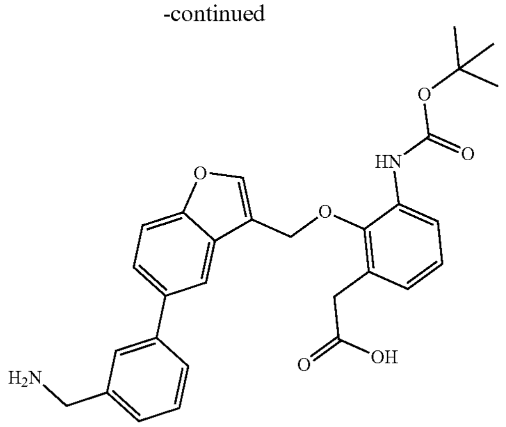

91a

Preparation of 2-(2-((5-(3-(aminomethyl)phenyl) benzofuran-3-yl)methoxy)-3-((tert-butoxycarbonyl) amino)phenyl)acetic acid (91a)

Compound 91a was prepared according to the procedure reported in step-3 of scheme 1, from ethyl 2-(2-((5-(3-(aminomethyl)phenyl)benzofuran-3-yl)methoxy)-3-((tert-butoxycarbonyl)amino)phenyl)acetate (90f) (70 mg, 0.132 mmol) in THF/MeOH (4 mL each) using a solution of lithium hydroxide hydrate (44.3 mg, 1.055 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)benzofuran-3-yl)methoxy)-3-((tert-butoxycarbonyl)amino)phenyl)acetic acid (91a) (33 mg, 50% yield) HCl salt as a white solid; $^1$H NMR (300 MHz, DMSO-$d_6$) δ 12.18 (s, 1H, $D_2O$ exchangeable), 9.17 (s, 1H), 8.34 (s, 3H, $D_2O$ exchangeable), 8.11 (s, 1H), 7.99 (d, J=1.8 Hz, 1H), 7.87 (s, 1H), 7.70 (td, J=10.4, 9.5, 7.2 Hz, 3H), 7.57-7.42 (m, 2H), 7.33 (s, 1H), 7.31-7.22 (m, 1H), 7.11 (d, J=8.9 Hz, 1H), 5.26 (s, 2H), 4.11 (s, 2H), 3.48 (s, 2H), 1.46 (s, 9H); MS (ES+): 503.10 (M+1); MS (ES−): 501.10 (M−1); Analysis calculated for $C_{29}H_{30}N_2O_6·HCl·2H_2O$: C, 60.57; H, 6.14; N, 4.87. Found: C, 60.41; H, 5.75; N, 4.96.

Scheme 92

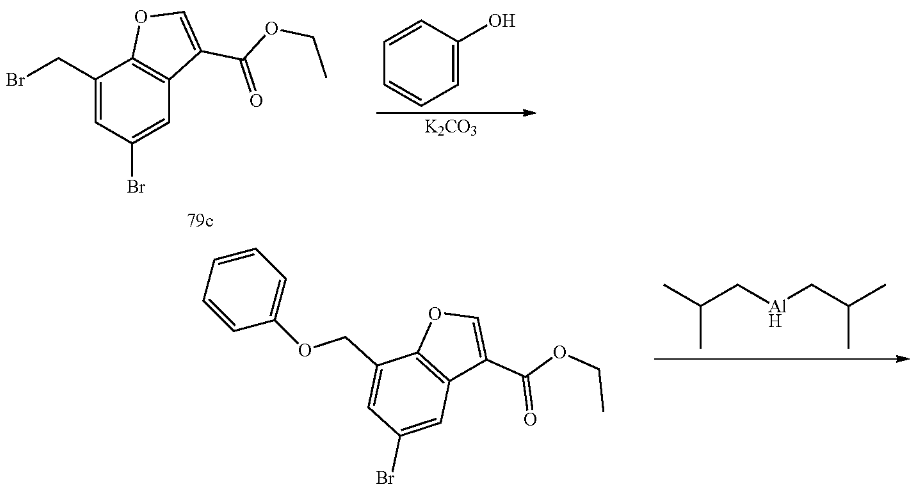

79c

92a

-continued

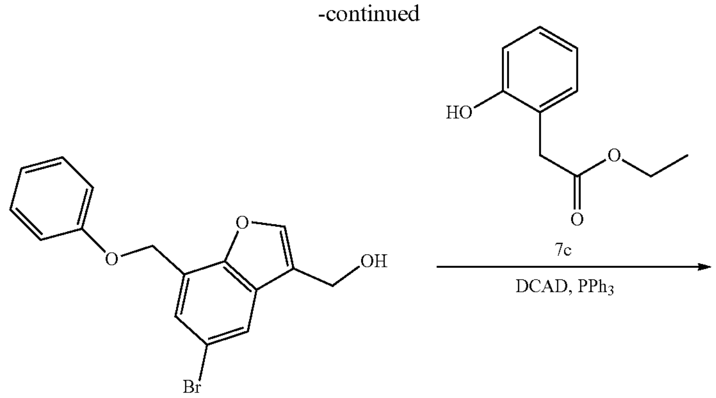

92b

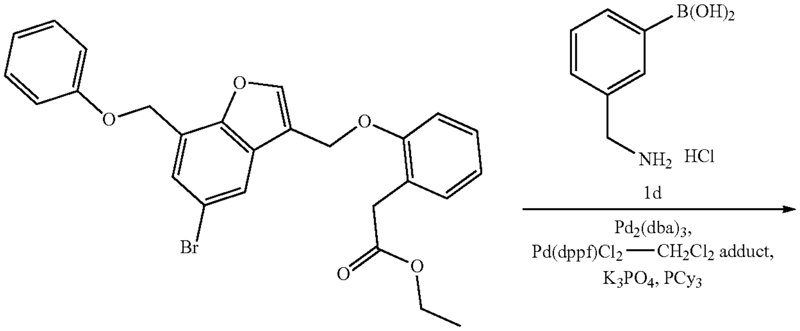

92c

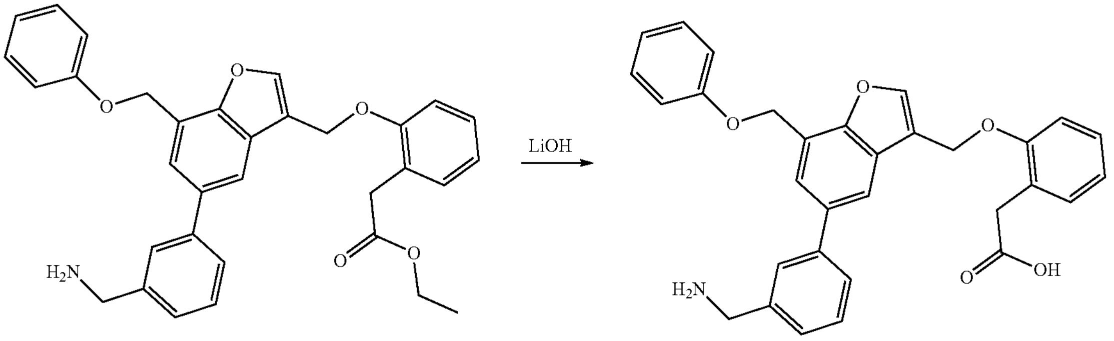

92d 92e

Preparation of 2-(2-((5-(3-(aminomethyl)phenyl)-7-(phenoxymethyl)benzofuran-3-yl)methoxy)phenyl) acetic acid (92e)

Step-1: Preparation of ethyl 5-bromo-7-(phenoxymethyl)benzofuran-3-carboxylate (92a)

Compound 92a was prepared according to the procedure reported in step-3 of scheme 79, from ethyl 5-bromo-7-(bromomethyl)benzofuran-3-carboxylate (79c) (0.4 g, 1.105 mmol) in DMF (10 mL) using potassium carbonate (0.458 g, 3.31 mmol), phenol (0.312 g, 3.31 mmol) and stirring at room temperature for 15 h. This gave after workup and purification by flash column chromatography [silica gel (24 g), eluting with EtOAc in Hexane from 0-50%] ethyl 5-bromo-7-(phenoxymethyl)benzofuran-3-carboxylate (92a) (0.37 g, 89% yield) as a white solid; $^1$H NMR (300 MHz, DMSO-$d_6$) δ 8.90 (s, 1H), 8.06 (d, J=2.0 Hz, 1H), 7.73 (d, J=2.0 Hz, 1H), 7.37-7.26 (m, 2H), 7.11-7.02 (m, 2H), 7.02-6.90 (m, 1H), 5.40 (s, 2H), 4.36 (q, J=7.1 Hz, 2H), 1.35 (t, J=7.1 Hz, 3H); MS (ES+): 396.90 (M+Na).

Step-2: Preparation of (5-bromo-7-(phenoxymethyl) benzofuran-3-yl)methanol (92b)

Compound 92b was prepared according to the procedure reported in step-2 of scheme 69, from ethyl 5-bromo-7-(phenoxymethyl)benzofuran-3-carboxylate (92a) (0.37 g, 0.986 mmol) in DCM (10 mL) using a solution of DIBAL (2.465 mL, 2.465 mmol; 1M in DCM) and stirring at −78° C. for 30 min. This gave after workup and purification by flash column chromatography [silica gel (24 g), eluting with DMA-80 in DCM from 0-50%] (5-bromo-7-(phenoxymethyl)benzofuran-3-yl)methanol (92b) (0.27 g, 82% yield) as a light yellow oil; $^1$H NMR (300 MHz, DMSO-$d_6$) δ 7.99 (s, 1H), 7.89 (d, J=2.0 Hz, 1H), 7.58 (d, J=2.0 Hz, 1H), 7.35-7.26 (m, 2H), 7.09-7.01 (m, 2H), 7.00-6.92 (m, 1H), 5.35 (s, 2H), 5.25 (t, J=5.6 Hz, 1H), 4.62 (dd, J=5.6, 1.1 Hz, 2H); MS (ES+): 354.90 (M+Na).

Step-3: Preparation of ethyl 2-(2-((5-bromo-7-(phenoxymethyl)benzofuran-3-yl)methoxy)phenyl)acetate (92c)

Compound 92c was prepared according to the procedure reported in step-2 of Scheme 65, from (5-bromo-7-(phenoxymethyl)benzofuran-3-yl)methanol (92b) (0.27 g, 0.810 mmol) in DCM (10 mL) using triphenylphosphine (0.425 g, 1.621 mmol), ethyl 2-(2-hydroxyphenyl)acetate (7c)(0.161 g, 0.891 mmol) a solution of DCAD (0.595 g, 1.621 mmol) in DCM (5 mL). This gave after workup and purification by flash column chromatography [silica gel (24 g), eluting with EtOAc in hexane from 0-50%] ethyl 2-(2-((5-bromo-7-(phenoxymethyl)benzofuran-3-yl)methoxy)phenyl)acetate (92c) (0.23 g, 57% yield) as a white oil; $^{1}$H NMR (300 MHz, DMSO-$d_6$) δ 8.20 (s, 1H), 7.85 (d, J=2.0 Hz, 1H), 7.63 (d, J=2.0 Hz, 1H), 7.30 (qd, J=7.1, 1.8 Hz, 3H), 7.20 (td, J=7.2, 1.4 Hz, 2H), 7.09-7.02 (m, 2H), 7.01-6.89 (m, 2H), 5.37 (s, 2H), 5.25 (s, 2H), 3.93 (q, J=7.1 Hz, 2H), 3.56 (s, 2H), 0.98 (t, J=7.1 Hz, 3H); MS (ES+): 495.00 (M+1).

Step-4: Preparation of ethyl 2-(2-((5-(3-(aminomethyl)phenyl)-7-(phenoxymethyl)benzofuran-3-yl)methoxy)phenyl)acetate (92d)

Compound 92d was prepared according to the procedure reported in step-2 of scheme 1, from ethyl 2-(2-((5-bromo-7-(phenoxymethyl)benzofuran-3-yl)methoxy)phenyl)acetate (92c) (0.23 g, 0.464 mmol) in dioxane/THF (4 mL each) using 3-(aminomethyl)phenylboronic acid hydrochloride (1d) (174 mg, 0.929 mmol), 2 M solution of $K_3PO_4$ (0.929 mL, 1.857 mmol), tricyclohexylphosphine (26.0 mg, 0.093 mmol), $PdCl_2$(dppf)-$CH_2Cl_2$ adduct (38.0 mg, 0.046 mmol), $Pd_2(dba)_3$ (43.0 mg, 0.046 mmol) and heating at 90° C. for 1 h. This gave after workup and purification by column chromatography [silica gel (24 g), eluting with DMA-80 in DCM from 0-70%] ethyl 2-(2-((5-(3-(aminomethyl)phenyl)-7-(phenoxymethyl)benzofuran-3-yl)methoxy)phenyl)acetate (92d) (110 mg, 45% yield) as a clear oil; MS (ES+): 522.10 (M+1).

Step-5: Preparation of 2-(2-((5-(3-(aminomethyl)phenyl)-7-(phenoxymethyl)benzofuran-3-yl)methoxy)phenyl)acetic acid (92e)

Compound 92e was prepared according to the procedure reported in step-3 of scheme 1, from ethyl 2-(2-((5-(3-(aminomethyl)phenyl)-7-(phenoxymethyl)benzofuran-3-yl)methoxy)phenyl)acetate (92d) (110 mg, 1.687 mmol) in THF/MeOH (4 mL, each) using a solution of lithium hydroxide hydrate (71 mg, 1.687 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(phenoxymethyl)benzofuran-3-yl)methoxy)phenyl)acetic acid (92e) (55 mg, 53% yield) HCl salt as a white solid; $^{1}$H NMR (300 MHz, DMSO-$d_6$) δ 12.13 (s, 1H, $D_2O$ exchangeable), 8.28 (s, 2H, $D_2O$ exchangeable), 8.19 (s, 1H), 8.01 (d, J=1.8 Hz, 1H), 7.87 (s, 1H), 7.81 (d, J=1.8 Hz, 1H), 7.75 (d, J=7.7 Hz, 1H), 7.54 (t, J=7.6 Hz, 1H), 7.46 (d, J=7.6 Hz, 1H), 7.36-7.24 (m, 3H), 7.22 (d, J=8.0 Hz, 2H), 7.12-7.06 (m, 2H), 6.95 (dt, J=12.0, 7.3 Hz, 2H), 5.44 (s, 2H), 5.34 (s, 2H), 4.12 (s, 2H), 3.54 (s, 2H); MS (ES+): 494.10 (M+1); MS (ES−): 492.10 (M−1); Analysis calculated for $C_{31}H_{27}NO_5\cdot HCl\cdot 0.75H_2O$: C, 68.50; H, 5.47; Cl, 6.52; N, 2.58. Found: C, 68.37; H, 5.33; Cl, 6.78; N, 2.73.

Scheme 93

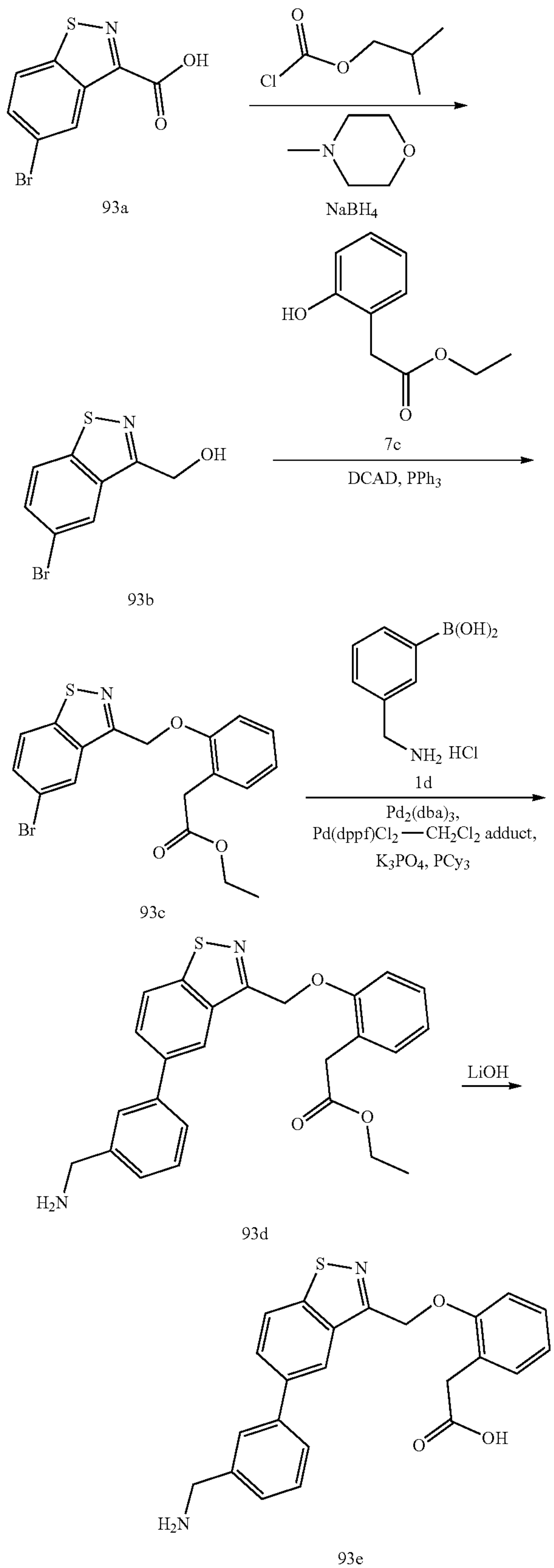

93a

93b

93c

93d

93e

Preparation of 2-(2-((5-(3-(aminomethyl)phenyl)benzo[d]isothiazol-3-yl)methoxy)phenyl)acetic acid (93e)

Step-1: Preparation of (5-bromobenzo[d]isothiazol-3-yl)methanol (93b)

Compound 93b was prepared according to the procedure reported in step-1 of scheme 8, from 5-bromobenzo[d]isothiazole-3-carboxylic acid (93a) (500 mg, 5.81 mmol; CAS #677304-78-8) in THF (20 mL) using N-Methylmorpholine (0.256 mL, 2.325 mmol), isobutyl chloroformate (0.226 mL, 2.325 mmol), a solution of $NaBH_4$ (220 mg, 5.81 mmol) in water (1.0 mL). This gave after workup and purification by flash column chromatography [silica gel (24 g), eluting with EtOAc in hexane from 0-100%] (5-bromobenzo[d]isothiazol-3-yl)methanol (93b) (290 mg, 61% yield) as a yellow solid; $^1H$ NMR (300 MHz, DMSO-$d_6$) δ 8.48 (d, J=1.8 Hz, 1H), 8.18 (d, J=8.6 Hz, 1H), 7.75 (dd, J=8.7, 1.9 Hz, 1H), 5.69 (t, J=6.0 Hz, 1H), 4.88 (d, J=6.0 Hz, 2H).

Step-2: Preparation of ethyl 2-(2-((5-bromobenzo[d]isothiazol-3-yl)methoxy)phenyl)acetate (93c)

Compound 93c was prepared according to the procedure reported in step-3 of scheme 7, from (5-bromobenzo[d]isothiazol-3-yl)methanol (93b) (280 mg, 1.147 mmol) in DCM (10 mL) using triphenylphosphine (602 mg, 2.294 mmol), ethyl 2-(2-hydroxyphenyl)acetate (7c) (227 mg, 1.262 mmol) a solution of bis(4-chlorobenzyl) diazene-1,2-dicarboxylate (DCAD) (842 mg, 2.294 mmol) in DCM (5 mL) and stirring at room temperature for 30 min. This gave after workup and purification by flash column chromatography [silica gel (24 g), eluting with EtOAc in hexane from 0-50%] ethyl 2-(2-((5-bromobenzo[d]isothiazol-3-yl)methoxy)phenyl)acetate (93c) (220 mg, 47% yield) as a light yellow solid; $^1H$ NMR (300 MHz, DMSO-$d_6$) δ 8.39 (d, J=1.8 Hz, 1H), 8.23 (d, J=8.7 Hz, 1H), 7.79 (dd, J=8.7, 1.8 Hz, 1H), 7.32-7.24 (m, 1H), 7.21 (dt, J=8.3, 1.6 Hz, 2H), 6.94 (td, J=7.3, 1.2 Hz, 1H), 5.54 (s, 2H), 3.88 (q, J=7.1 Hz, 2H), 3.56 (s, 2H), 0.94 (t, J=7.1 Hz, 3H); MS (ES+): 427.90 (M+Na).

Step-3: Preparation of ethyl 2-(2-((5-(3-(aminomethyl)phenyl)benzo[d]isothiazol-3-yl)methoxy)phenyl)acetate (93d)

Compound 93d was prepared according to the procedure reported in step-2 of scheme 1, from ethyl 2-(2-((5-bromobenzo[d]isothiazol-3-yl)methoxy)phenyl)acetate (93c) (0.2 g, 0.492 mmol) in dioxane/THF (4 mL each) using 3-(aminomethyl)phenylboronic acid hydrochloride (1d) (185 mg, 0.985 mmol), 2 M solution of $K_3PO_4$ (0.985 mL, 1.969 mmol), tricyclohexylphosphine (28.0 mg, 0.098 mmol), $PdCl_2$(dppf)-$CH_2Cl_2$ adduct (40.0 mg, 0.049 mmol), $Pd_2(dba)_3$ (45.0 mg, 0.049 mmol) and heating at 90° C. for 1 h. This gave after workup and purification by flash column chromatography [silica gel (24 g), eluting with DMA80 in DCM from 0-70%] ethyl 2-(2-((5-(3-(aminomethyl)phenyl)benzo[d]isothiazol-3-yl)methoxy)phenyl)acetate (93d) (120 mg, 56% yield) as a clear oil; $^1H$ NMR (300 MHz, DMSO-$d_6$) δ 8.41 (d, J=1.6 Hz, 1H), 8.32 (d, J=8.5 Hz, 1H), 7.96 (dd, J=8.6, 1.7 Hz, 1H), 7.77 (s, 1H), 7.65 (d, J=7.5 Hz, 1H), 7.42 (dt, J=15.7, 7.6 Hz, 2H), 7.28 (dd, J=7.1, 1.8 Hz, 2H), 7.24-7.17 (m, 1H), 6.98-6.89 (m, 1H), 5.60 (s, 2H), 3.84 (s, 2H), 3.66 (q, J=7.1 Hz, 2H), 3.55 (s, 2H), 0.82 (t, J=7.1 Hz, 3H); MS (ES+): 433.10 (M+1).

Step-4: Preparation of 2-(2-((5-(3-(aminomethyl)phenyl)benzo[d]isothiazol-3-yl)methoxy)phenyl)acetic acid (93e)

Compound 93e was prepared according to the procedure reported in step-3 of scheme 1, from ethyl 2-(2-((5-(3-(aminomethyl)phenyl)benzo[d]isothiazol-3-yl)methoxy)phenyl)acetate (93d) (120 mg, 0.277 mmol) in THF/MeOH (4 mL each) using a solution of lithium hydroxide hydrate (93 mg, 2.219 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)benzo[d]isothiazol-3-yl)methoxy)phenyl)acetic acid (93e) (75 mg, 67% yield) HCl salt as a white solid; $^1H$ NMR (300 MHz, DMSO-$d_6$) δ 12.12 (s, 1H, $D_2O$ exchangeable), 8.52 (d, J=1.6 Hz, 1H), 8.45 (s, 2H, $D_2O$ exchangeable), 8.36 (d, J=8.6 Hz, 1H), 8.03-7.95 (m, 2H), 7.83 (dt, J=7.3, 1.7 Hz, 1H), 7.60-7.48 (m, 2H), 7.28-7.17 (m, 3H), 6.97-6.88 (m, 1H), 5.64 (s, 2H), 4.13 (s, 2H), 3.55 (s, 2H); MS (ES+): 405.10 (M+1); MS (ES−): 403.10 (M−1); Analysis calculated for $C_{23}H_{20}N_2O_3S{\cdot}1.05HCl{\cdot}1.25H_2O$: C, 59.37; H, 5.10; Cl, 8.00; N, 6.02. Found: C, 59.53; H, 5.26; Cl, 8.42; N, 6.02.

Scheme 94

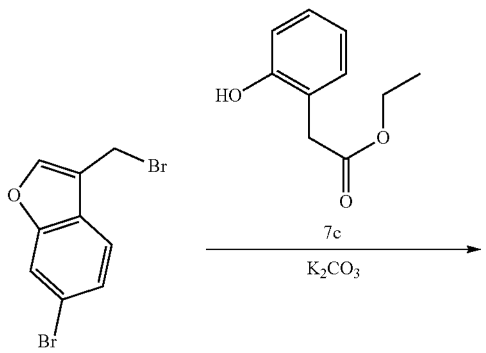

94a

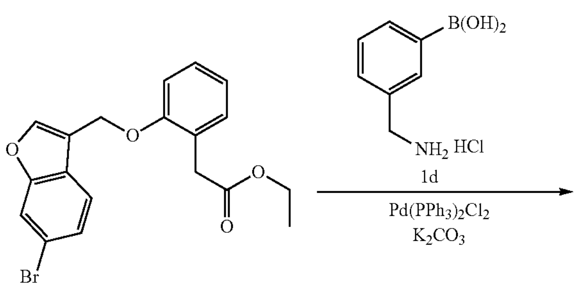

94b

-continued

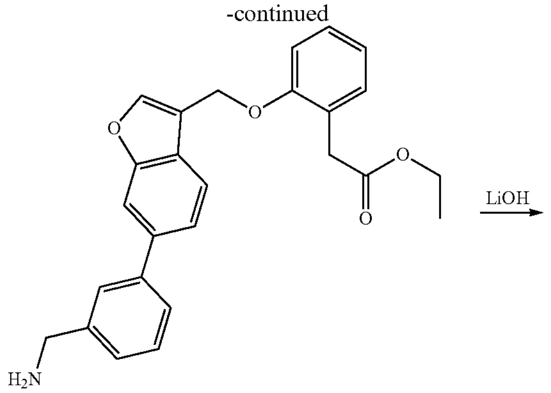

94c

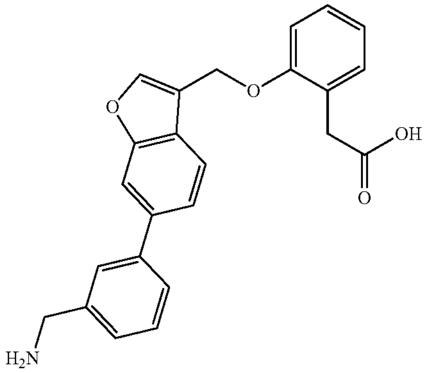

94d

Preparation of 2-(2-((6-(3-(aminomethyl)phenyl) benzofuran-3-yl)methoxy)phenyl)acetic acid (94d)

Step-1: Preparation of ethyl 2-(2-((6-bromobenzofuran-3-yl)methoxy)phenyl)acetate (94b)

Compound 94b was prepared according to the procedure reported in step-3 of scheme 7, from 6-bromo-3-(bromomethyl)benzofuran (94a) (764 mg, 2.63 mmol; CAS #1133005-32-9) in acetone (15 mL) using ethyl 2-(2-hydroxyphenyl)acetate (7c) (617 mg, 3.43 mmol), potassium carbonate (1.275 g, 9.22 mmol) and stirring overnight at room temperature. This gave after workup and purification by flash column chromatography [silica gel (24 g) eluting with ethyl acetate in hexanes from 0-50%] ethyl 2-(2-((6-bromobenzofuran-3-yl)methoxy)phenyl)acetate (94b) (744 mg, 73% yield) as a white yellow solid; $^1$H NMR (300 MHz, DMSO-$d_6$) δ 8.12 (s, 1H), 7.95 (d, J=1.6 Hz, 1H), 7.62 (d, J=8.3 Hz, 1H), 7.48 (dd, J=8.3, 1.7 Hz, 1H), 7.29 (td, J=7.8, 7.3, 1.8 Hz, 1H), 7.24-7.14 (m, 2H), 6.93 (td, J=7.3, 1.2 Hz, 1H), 5.25 (d, J=1.0 Hz, 2H), 3.92 (q, J=7.1 Hz, 2H), 3.56 (s, 2H), 0.99 (t, J=7.1 Hz, 3H).

Step-2: Preparation of ethyl 2-(2-((6-(3-(aminomethyl)phenyl)benzofuran-3-yl)methoxy)phenyl)acetate (94c)

Compound 94c was prepared according to the procedure reported in step-8 of Scheme 3, from ethyl 2-(2-((6-bromobenzofuran-3-yl)methoxy)phenyl)acetate (94b) (257 mg, 0.660 mmol) in dioxane (5 mL) using 3-(aminomethyl) phenylboronic acid hydrochloride (1d) (186 mg, 0.990 mmol), $Pd(PPh_3)_2C_{12}$ (69.5 mg, 0.099 mmol), a solution of $K_2CO_3$ (274 mg, 1.981 mmol) in water (0.5 mL) and heating at 100° C. for 100 min. This gave after workup and purification by flash column chromatography [silica gel (12 g), eluting with DMA-80 in DCM from 0-50%] ethyl 2-(2-((6-(3-(aminomethyl)phenyl)benzofuran-3-yl)methoxy)phenyl) acetate (94c) (110 mg, 40% yield) as a brown oil; MS (ES+): 416.10 (M+1).

Step-3: Preparation of 2-(2-((6-(3-(aminomethyl) phenyl)benzofuran-3-yl)methoxy)phenyl)acetic acid (94d)

Compound 94d was prepared according to the procedure reported in step-3 of scheme 1, from ethyl 2-(2-((6-(3-(aminomethyl)phenyl)benzofuran-3-yl)methoxy)phenyl)acetate (94c) (110 mg, 0.265 mmol) in MeOH/THF (6 mL each) using a solution of lithium hydroxide hydrate (86 mg, 2.05 mmol) in water (2 mL) and stirring overnight at room temperature. This gave after workup and purification by reverse phase column chromatography [C18 column (50 g), eluting with ACN in water (containing 0.1% HCl) from 0-100%] 2-(2-((6-(3-(aminomethyl)phenyl)benzofuran-3-yl)methoxy)phenyl)acetic acid (94d) (48 mg, 47% yield) HCl salt as a white solid; $^1$H NMR (300 MHz, DMSO-$d_6$) δ 12.14 (s, 1H), 8.77-8.36 (m, 3H), 8.23-6.73 (m, 11H), 5.31 (s, 2H), 4.11 (s, 2H), 2.51 (s, 2H); MS (ES+): 388.1 (M+1); Analysis calculated for: $C_{24}H_{20}FNO_4 \cdot HCl \cdot 1.1H_2O$: C, 62.43; H, 5.06; N, 3.03; Cl, 7.68. Found: C, 62.29; H, 4.73; N, 3.05; Cl, 7.50.

Scheme 95

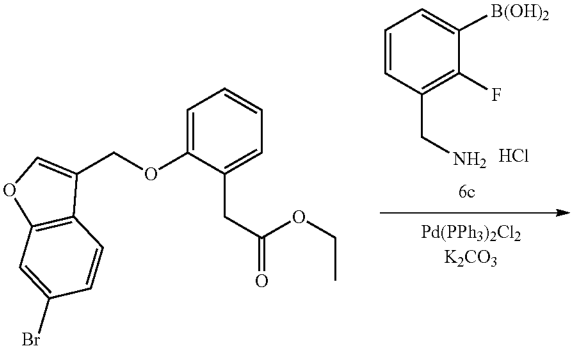

94b

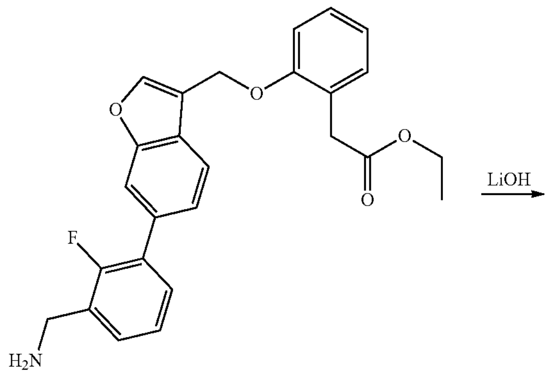

95a

-continued

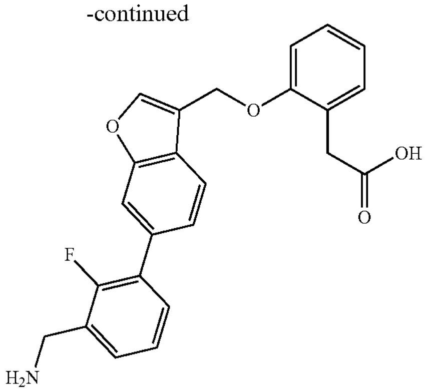

95b

Step-2: Preparation of 2-(2-((6-(3-(aminomethyl)-2-fluorophenyl)benzofuran-3-yl)methoxy)phenyl)acetic acid (95b)

Compound 95b was prepared according to the procedure reported in step-3 of scheme 1, from ethyl 2-(2-((6-(3-(aminomethyl)-2-fluorophenyl)benzofuran-3-yl)methoxy)phenyl)acetate (95a) (170 mg, 0.392 mmol) in THF/MeOH (6 mL each) using a solution of lithium hydroxide hydrate (88 mg, 2.097 mmol) in water (2 mL) and stirring overnight at room temperature. This gave after workup and purification by reverse phase column chromatography [C18 column (50 g), eluting with ACN in water (containing 0.1% HCl) from 0-100%] 2-(2-((6-(3-(aminomethyl)-2-fluorophenyl)benzofuran-3-yl)methoxy)phenyl)acetic acid (95b) (55 mg, 35% yield) HCl salt as a white solid; $^1H$ NMR (300 MHz, DMSO-$d_6$) δ 11.97 (s, 1H), 8.62 (s, 3H), 8.18 (s, 1H), 7.82 (d, J=9.4 Hz, 2H), 7.72-7.55 (m, 2H), 7.50 (d, J=7.9 Hz, 1H), 7.38 (t, J=7.8 Hz, 1H), 7.33-7.09 (m, 3H), 6.93 (t, J=7.2 Hz, 1H), 5.32 (s, 2H), 4.15 (s, 2H), 3.55 (s, 2H); MS (ES+): 406.1 (M+1); Analysis calculated for: $C_{24}H_{20}FNO_4 \cdot HCl \cdot 1H_2O$: C, 62.68; H, 5.04; N, 3.05; Cl, 7.71 Found: C, 62.29; H, 4.73; N, 3.05; Cl, 7.50.

Scheme 96

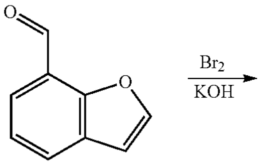

96a

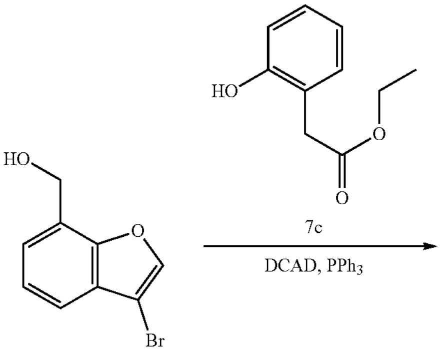

7c

96b

-continued

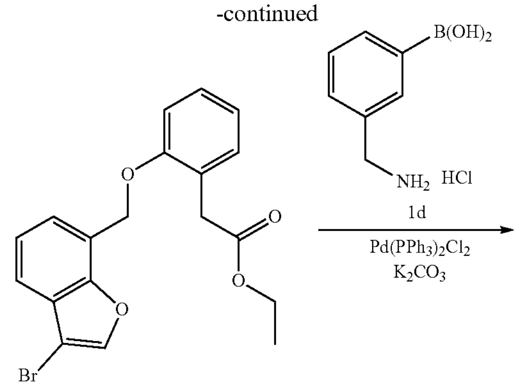

96c

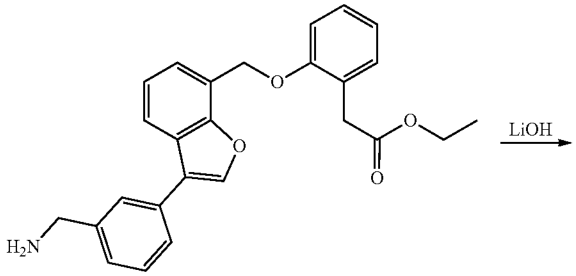

96d

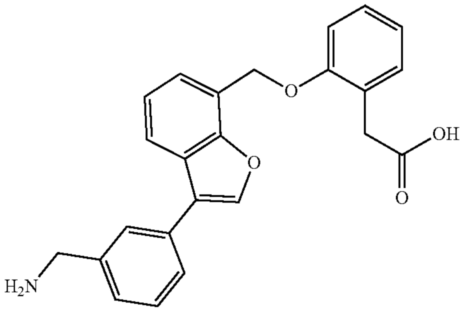

96e

Preparation of 2-(2-((3-(3-(aminomethyl)phenyl)benzofuran-7-yl)methoxy)phenyl)acetic acid (96e)

Step-1: Preparation of (3-bromobenzofuran-7-yl)methanol (96b)

To a solution of benzofuran-7-carbaldehyde (96a)(1.05 g, 7.18 mmol; CAS #95333-14-5) in chloroform (8 mL) at −10° C. was added a solution of bromine (0.374 mL, 7.26 mmol) in $CHCl_3$ (10 mL) and the reaction mixture was stirred for 1 h while allowing it to warm to RT.

The reaction mixture was concentrated under vacuum to afford a white solid, which was dissolved in ethanol (20 mL), added KOH (918 mg, 16.36 mmol) and heated at 70° C. for 90 min. The reaction mixture was filtered, and the solid was washed with EtOAc. The filtrate was concentrated in vacuum and the residue was purified by flash column chromatography [silica gel (24 g), eluting with EtOAc in hexanes from 0-50%] to give (3-bromobenzofuran-7-yl)methanol (96b) (637 mg, 39.0% yield) as a yellow solid. $^1H$ NMR (300 MHz, DMSO-$d_6$) δ 8.31 (s, 1H), 7.51-7.42 (m, 2H), 7.42-7.33 (m, 1H), 5.38 (t, J=5.7 Hz, 1H), 4.80 (d, J=5.7 Hz, 2H); MS (ES+): 226.95 (M+1).

Step-2: Preparation of ethyl 2-(2-((3-bromobenzofuran-7-yl)methoxy)phenyl)acetate (96c)

Compound 96c was prepared according to the procedure reported in step-3 of scheme 7, from (3-bromobenzofuran-7-yl)methanol (96b) (470 mg, 2.070 mmol) in DCM (10 mL) using triphenylphosphine (1.02 g, 3.89 mmol), ethyl 2-(2-hydroxyphenyl)acetate (7c) (733 mg, 4.07 mmol), a solution of bis(4-chlorobenzyl) diazene-1,2-dicarboxylate (DCAD) (1.44 g, 3.92 mmol) in DCM (2 mL). This gave after workup and purification by flash column chromatography [silica gel (24 g), eluting with EtOAc in hexane from 0-50%] ethyl 2-(2-((3-bromobenzofuran-7-yl)methoxy)phenyl)acetate (96c) (557 mg, 69% yield) as a yellow oil; $^1$H NMR (300 MHz, DMSO-$d_6$) δ 8.38 (s, 1H), 7.59-7.49 (m, 2H), 7.45-7.38 (m, 1H), 7.31-7.20 (m, 2H), 7.19-7.10 (m, 1H), 6.93 (td, J=7.4, 1.1 Hz, 1H), 5.40 (s, 2H), 3.92 (q, J=7.1 Hz, 2H), 3.59 (s, 2H), 1.01 (t, J=7.1 Hz, 3H).

Step-3: Preparation of ethyl 2-(2-((3-(3-(aminomethyl)phenyl)benzofuran-7-yl)methoxy)phenyl)acetate (96d)

Compound 96d was prepared according to the procedure reported in step-8 of Scheme 3, from ethyl 2-(2-((3-bromobenzofuran-7-yl)methoxy)phenyl)acetate (96c) (210 mg, 0.540 mmol) in dioxane (5 mL) using 3-(aminomethyl) phenylboronic acid hydrochloride (1d) (152 mg, 0.809 mmol), $Pd(PPh_3)_2C_{12}$ (56.8 mg, 0.081 mmol), a solution of $K_2CO_3$ (224 mg, 1.619 mmol) in water (0.5 mL) and heating at 100° C. for 2.5 h. This gave after workup and purification by flash column chromatography [silica gel (12 g), eluting with MeOH in DCM from 0-20%] ethyl 2-(2-((3-(3-(aminomethyl)phenyl)benzofuran-7-yl)methoxy)phenyl)acetate (96d) (144 mg, 64% yield) as a dark oil; MS (ES+): 416.10 (M+1).

Step-4: Preparation of 2-(2-((3-(3-(aminomethyl)phenyl)benzofuran-7-yl)methoxy)phenyl)acetic acid (96e)

Compound 96e was prepared according to the procedure reported in step-3 of scheme 1, from ethyl 2-(2-((3-(3-(aminomethyl)phenyl)benzofuran-7-yl)methoxy)phenyl)acetate (96d) (143 mg, 0.344 mmol) in MeOH/THF (6 mL each) using a solution of lithium hydroxide hydrate (99 mg, 2.359 mmol) in water (2 mL) and stirring overnight at room temperature. This gave after workup and purification by reverse phase column chromatography [C18 column (50 g), eluting with ACN in water (containing 0.1% HCl) from 0-100%] 2-(2-((3-(3-(aminomethyl)phenyl)benzofuran-7-yl)methoxy)phenyl)acetic acid (96e) (73 mg, 55% yield) HCl salt as a white solid; $^1$H NMR (300 MHz, DMSO-$d_6$) δ 12.18 (s, 1H), 8.57 (s, 3H), 8.46 (s, 1H), 8.07 (d, J=7.8 Hz, 1H), 7.96 (s, 1H), 7.77 (d, J=7.2 Hz, 1H), 7.60-7.47 (m, 3H), 7.38 (t, J=7.6 Hz, 1H), 7.30-7.11 (m, 3H), 6.92 (t, J=7.3 Hz, 1H), 5.46 (s, 2H), 4.12 (s, 2H), 3.58 (s, 2H).

MS (ES+): 388.1 (M+1), 00.00 (M+Na); (ES−): 386.0 (M−1); Analysis calculated for: $C_{24}H_{21}NO_4 \cdot HCl \cdot H_2O$: C, 65.23; H, 5.47; N, 3.17; Cl, 8.02. Found: C, 65.63; H, 5.19; N, 3.28; Cl, 8.13.

Scheme 97

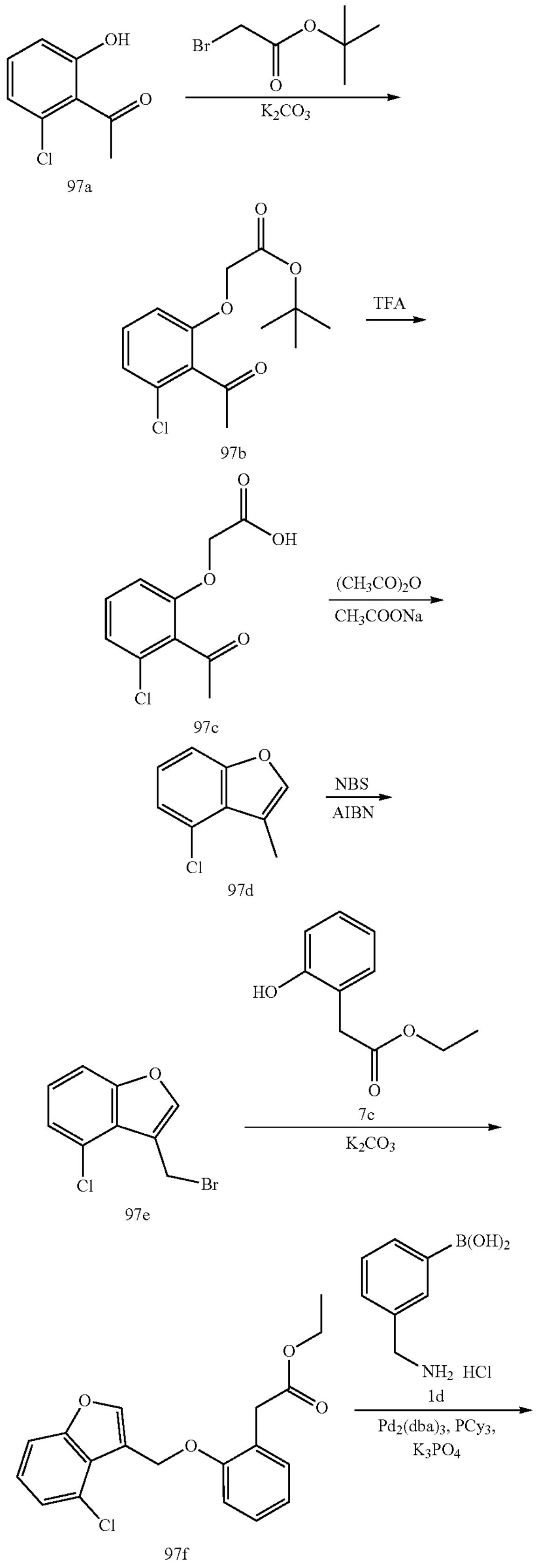

-continued

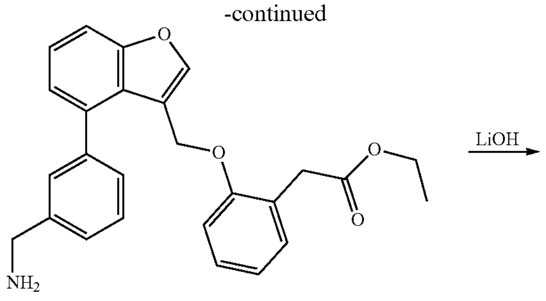

97g

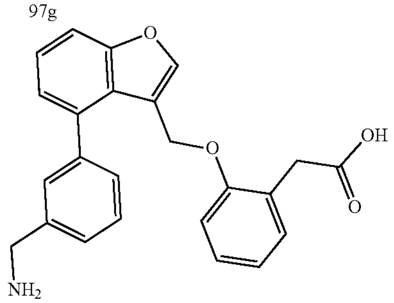

97h

Preparation of 2-(2-((4-(3-(aminomethyl)phenyl) benzofuran-3-yl)methoxy)phenyl)acetic acid (97h)

Step-1: Preparation of tert-butyl 2-(2-acetyl-3-chlorophenoxy)acetate (97b)

Compound 97b was prepared according to the procedure reported in step-1 of scheme 58, from 1-(2-chloro-6-hydroxyphenyl)ethanone (97a) (10 g, 46.5 mmol; CAS #55736-04-4) in acetone (50 mL) using tert-butyl 2-bromoacetate (4.53 g, 23.24 mmol), $K_2CO_3$ (5.68 g, 41.1 mmol) and heating at reflux overnight. This gave after workup tert-butyl 2-(2-acetyl-3-chlorophenoxy)acetate (97b) (5.01 g, 98% yield) as a colorless oil which was used as such in the next step; $^1$H NMR (300 MHz, DMSO-$d_6$) δ 7.38 (t, J=8.3 Hz, 1H), 7.11 (dd, J=8.2, 0.7 Hz, 1H), 7.01 (dd, J=8.5, 0.8 Hz, 1H), 4.80 (s, 2H), 2.50 (s, 3H), 1.42 (s, 9H).

Step-2: Preparation of 2-(2-acetyl-3-chlorophenoxy)acetic acid (97c)

Compound 97c was prepared according to the procedure reported in step-9 of scheme 3, from tert-butyl 2-(2-acetyl-3-chlorophenoxy)acetate (97b) (5.01 g, 17.60 mmol) using TFA (10 mL, 130 mmol) in DCM (20 mL). This gave after workup 2-(2-acetyl-3-chlorophenoxy)acetic acid (97c) (4.02 g, 100% yield) as a gray solid, which was used as such without purification for the next step; MS (ES+): 229.00 (M+1).

Step-3: Preparation of 4-chloro-3-methylbenzofuran (97d)

To a solution of 2-(2-acetyl-3-chlorophenoxy)acetic acid (97c) (4.02 g, 17.58 mmol) and acetic anhydride (40 mL, 424 mmol) was added sodium acetate (2.164 g, 26.4 mmol) and heated overnight at 145° C. The reaction mixture was cooled to 70° C. added ethanol (40 mL) and stirred at 70° C. for 2 h. The reaction mixture was cooled to room temperature diluted with water and extracted with ethyl acetate. The organic phase was separated, washed with 2 N NaOH, water, dried, filtered and concentrated in vacuum. The residue obtained was purified by flash column chromatography [silica gel (24 g), eluting with EtOAc in hexanes from 0-40%] to provide 4-chloro-3-methylbenzofuran (97d) (2.76 g, 94% yield) as colorless oil. (Note: Product is volatile, avoid drying in vacuum. Product can be dried in rotary evaporator at 46° C., 250-300 psi to remove solvent); $^1$H NMR (300 MHz, DMSO-$d_6$) δ 7.86 (q, J=1.4 Hz, 1H), 7.54 (dd, J=6.4, 2.7 Hz, 1H), 7.36-7.22 (m, 2H), 2.38 (d, J=1.4 Hz, 3H).

Step-4: Preparation of 3-(bromomethyl)-4-chlorobenzofuran (97e)

Compound 97e was prepared according to the procedure reported in step-2 of scheme 58, from 4-chloro-3-methylbenzofuran (97d) (567 mg, 3.40 mmol) in carbon tetrachloride (10 mL) using NBS (606 mg, 3.40 mmol), AIBN (55.9 mg, 0.340 mmol) and heating at reflux for 4 h. This gave after workup 3-(bromomethyl)-4-chlorobenzofuran (97e) (836 mg, 100% yield) as a pale-yellow oil, which was used as such in the next step without further purification.

Step-5: Preparation of ethyl 2-(2-((4-chlorobenzofuran-3-yl)methoxy)phenyl)acetate (97f)

Compound 97f was prepared according to the procedure reported in step-3 of scheme 7, from 3-(bromomethyl)-4-chlorobenzofuran (97e) (0.836 g, 3.41 mmol) in acetone (15 mL) using ethyl 2-(2-hydroxyphenyl)acetate (7c) (0.798 g, 4.43 mmol), potassium carbonate (1.647 g, 11.92 mmol) and heating at 50° C. for 12 h. This gave after workup and purification by flash column chromatography [silica gel (24 g) eluting with ethyl acetate and hexanes from 0-50%]ethyl 2-(2-((4-chlorobenzofuran-3-yl)methoxy)phenyl)acetate (97f) (671 mg, 57% yield) as a white yellow solid; $^1$H NMR (300 MHz, DMSO-$d_6$) δ 8.21 (s, 1H), 7.65 (dd, J=5.9, 3.2 Hz, 1H), 7.42-7.33 (m, 2H), 7.30 (td, J=7.8, 7.3, 1.8 Hz, 1H), 7.24-7.15 (m, 2H), 6.94 (td, J=7.3, 1.2 Hz, 1H), 5.31 (s, 2H), 3.88 (q, J=7.1 Hz, 2H), 3.58 (s, 2H), 0.95 (t, J=7.1 Hz, 3H).

Step-6: Preparation of ethyl 2-(2-((4-(3-(aminomethyl)phenyl)benzofuran-3-yl)methoxy)phenyl)acetate (97g)

Compound 97g was prepared according to the procedure reported in step-2 of scheme 1, from ethyl 2-(2-((4-chlorobenzofuran-3-yl)methoxy)phenyl)acetate (97f) (211 mg, 0.612 mmol) in dioxane (4 mL) using 3-(aminomethyl) phenylboronic acid hydrochloride (1d) (139 mg, 0.918 mmol), 2 M solution of $K_3PO_4$ (0.520 mL, 1.040 mmol), tricyclohexylphosphine (68.6 mg, 0.245 mmol), $Pd_2(dba)_3$ (112 mg, 0.122 mmol), heating at 135° C. for 30 min and at 130° C. for 1 h in a microwave. This gave after workup and purification by flash column chromatography [silica gel (12 g), eluting with MeOH in DCM from 0-20%] ethyl 2-(2-((4-(3-(aminomethyl)phenyl)benzofuran-3-yl)methoxy) phenyl)acetate (97g) (205 mg, 81% yield); MS (ES+) 416.10 (M+1).

Step-7: Preparation of 2-(2-((4-(3-(aminomethyl) phenyl)benzofuran-3-yl)methoxy)phenyl)acetic acid (97h)

Compound 97h was prepared according to the procedure reported in step-3 of scheme 1, from ethyl 2-(2-((4-(3-

(aminomethyl)phenyl)benzofuran-3-yl)methoxy)phenyl)acetate (97g) (203 mg, 0.489 mmol) in MeOH/THF (6 mL, ratio 1:1) using a solution of lithium hydroxide hydrate (102 mg, 2.431 mmol) in water (2 mL) and stirring overnight at RT. This gave after workup and purification by reverse phase column chromatography [C18 column (50 g), eluting with ACN in water (containing 0.1% HCl) from 0-100%] 2-(2-((4-(3-(aminomethyl)phenyl)benzofuran-3-yl)methoxy) phenyl)acetic acid (97h) (48 mg, 25% yield) HCl salt as a gray solid; $^1$H NMR (300 MHz, DMSO-$d_6$) δ 12.18 (s, 1H), 8.47 (s, 3H), 8.11 (s, 1H), 7.74-7.05 (m, 9H), 6.85 (t, J=7.4 Hz, 1H), 6.62 (d, J=7.9 Hz, 1H), 4.75 (s, 2H), 3.93 (s, 2H); MS (ES+): 388.1 (M+1); (ES−): 386.0 (M−1); Analysis calculated for: $C_{24}H_{21}NO_4$·HCl·$H_2O$: C, 65.23; H, 5.47; N, 3.17; Cl, 8.02. Found: C, 65.17; H, 5.35; N, 3.20; Cl, 7.93.

Scheme 98

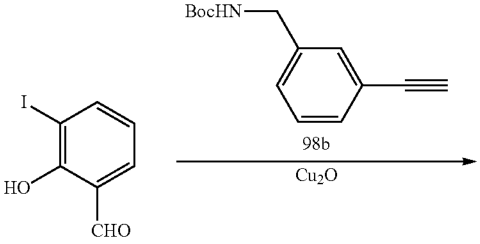

98b

98a

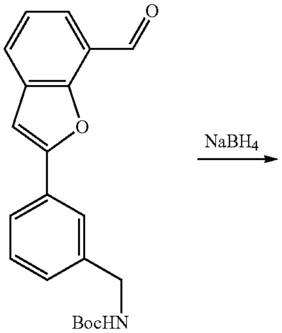

98c

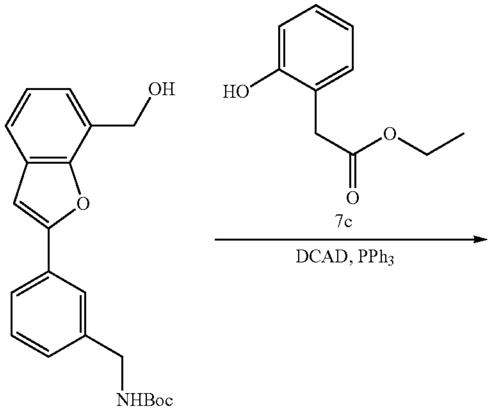

7c

98d

-continued

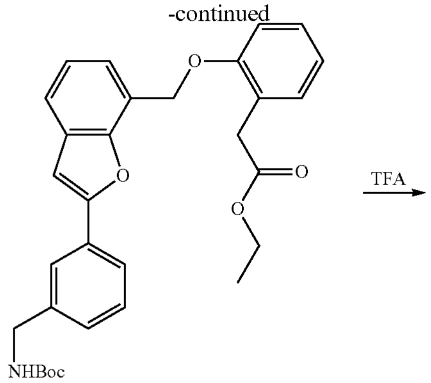

98e

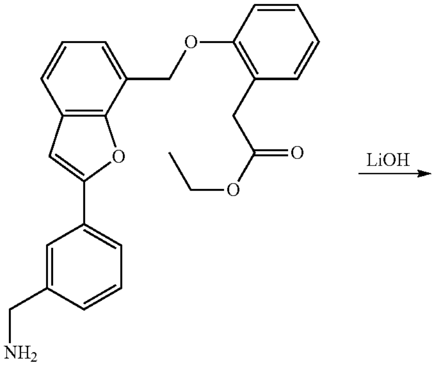

98f

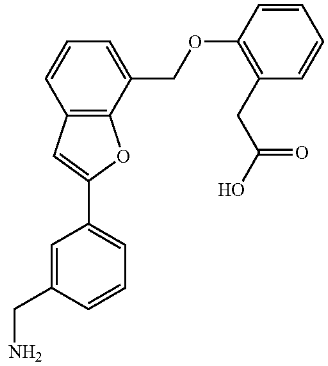

98g

Preparation of 2-(2-((2-(3-(aminomethyl)phenyl) benzofuran-7-yl)methoxy)phenyl)acetic acid (98g)

Step-1: Preparation of tert-butyl 3-(7-formylbenzofuran-2-yl)benzylcarbamate (98c)

Compound 98c was prepared according to the procedure reported in step-1 of scheme 3, from 2-hydroxy-3-iodobenzaldehyde (98a) (257 mg, 1.038 mmol; CAS #23602-64-4) in pyridine (5 mL) using tert-butyl 3-ethynylbenzylcarbamate (98b) (200 mg, 0.865 mmol; CAS #871023-92-6), copper(I) oxide (62 mg, 0.432 mmol) and heating at 125° C. for 3 h. This gave after workup and purification by flash column chromatography [silica gel (12 g), eluting with EtOAc in hexane from 0-70%] tert-butyl 3-(7-formylbenzofuran-2-yl) benzylcarbamate (98c) (220 mg, 72% yield) as a yellow oil; $^1$H NMR (300 MHz, DMSO-$d_6$) δ 10.45 (s, 1H), 8.04 (dd, J=7.7, 1.3 Hz, 1H), 7.93-7.81 (m, 3H), 7.59-7.44 (m, 4H), 7.33 (d, J=7.6 Hz, 1H), 4.24 (d, J=6.2 Hz, 2H), 1.43 (s, 9H); MS (ES+): 374.10 (M+Na).

Step-2: Preparation of tert-butyl 3-(7-(hydroxymethyl)benzofuran-2-yl)benzylcarbamate (98d)

To a solution of tert-butyl 3-(7-formylbenzofuran-2-yl) benzylcarbamate (98c) (220 mg, 0.626 mmol) in THF/MeOH (6 mL each) at 0° C. was added sodium borohydride (89.2 mg, 3.88 mmol) in portions. And allowed to warm to room temperature over 30 min. The reaction was quenched with saturated aqueous $NH_4Cl$ solution, stirred for 10 min and extracted with EtOAc. Organic layer was separated, washed with brine, dried, filtered and concentrated in vacuum. The residue obtained was purified by flash column chromatography [silica gel (12 g), EtOAc in hexanes from 0-80%] to provide tert-butyl 3-(7-(hydroxymethyl)benzofuran-2-yl)benzylcarbamate (98d) (155 mg, 70% yield) as a white foam; $^1$H NMR (300 MHz, DMSO-$d_6$) δ 7.82 (d, J=7.8 Hz, 2H), 7.58-7.43 (m, 3H), 7.41 (s, 1H), 7.36 (d, J=7.2 Hz, 1H), 7.31-7.22 (m, 2H), 5.35 (t, J=5.8 Hz, 1H), 4.88 (d, J=5.7 Hz, 2H), 4.22 (d, J=6.2 Hz, 2H), 1.43 (s, 9H); MS (ES+): 376.1 (M+Na).

Step-3: Preparation of ethyl 2-(2-((2-(3-(((tert-butoxycarbonyl)amino)methyl)phenyl)benzofuran-7-yl)methoxy)phenyl)acetate (98e)

Compound 98e was prepared according to the procedure reported in step-3 of scheme 7, from tert-butyl 3-(7-(hydroxymethyl)benzofuran-2-yl)benzylcarbamate (98d) (155 mg, 0.877 mmol) in DCM (8 mL) using triphenylphosphine (230 mg, 0.877 mmol), ethyl 2-(2-hydroxyphenyl)acetate (7c) (158 mg, 0.877 mmol) a solution of bis(4-chlorobenzyl) diazene-1,2-dicarboxylate (DCAD) (322 mg, 0.877 mmol) in DCM (2 mL) and stirring at room temperature for 1.5 h. This gave after workup and purification by flash column chromatography [silica gel (12 g), eluting with EtOAc in hexane from 0-50%] ethyl 2-(2-((2-(3-(((tert-butoxycarbonyl)amino)methyl)phenyl)benzofuran-7-yl)methoxy)phenyl)acetate (98e) (189 mg, 84% yield) as a yellow oil; $^1$H NMR (300 MHz, DMSO-$d_6$) δ 7.83 (d, J=8.4 Hz, 2H), 7.66 (dd, J=7.7, 1.3 Hz, 1H), 7.53-7.37 (m, 4H), 7.34-7.20 (m, 5H), 6.95 (td, J=7.1, 1.2 Hz, 1H), 5.47 (s, 2H), 4.22 (d, J=6.2 Hz, 2H), 3.91 (q, J=7.1 Hz, 2H), 3.63 (s, 2H), 1.41 (s, 9H), 1.00 (t, J=7.1 Hz, 3H); MS (ES+): 516.85 (M+1).

Step-4: Preparation of ethyl 2-(2-((2-(3-(aminomethyl)phenyl)benzofuran-7-yl)methoxy)phenyl)acetate (98f)

Compound 98f was prepared according to the procedure reported in step-9 of scheme 3, from ethyl 2-(2-((2-(3-(((tert-butoxycarbonyl)amino)methyl)phenyl)benzofuran-7-yl) methoxy)phenyl)acetate (98e) (187 mg, 0.363 mmol) in DCM (5 mL) using TFA (0.559 mL, 0.725 mmol) and stirring at room temperature for 30 min. This gave after workup ethyl 2-(2-((2-(3-(aminomethyl)phenyl)benzofuran-7-yl)methoxy)phenyl)acetate (98f) (151 mg, 100% yield) as a pale-yellow oil, which was used as such for the next step without further purification; MS (ES+): 416.10 (M+1).

Step-5: Preparation of 2-(2-((2-(3-(aminomethyl) phenyl)benzofuran-7-yl)methoxy)phenyl)acetic acid (98g)

Compound 98g was prepared according to the procedure reported in step-3 of scheme 1, from ethyl 2-(2-((2-(3-(aminomethyl)phenyl)benzofuran-7-yl)methoxy)phenyl)acetate (98f) (151 mg, 0.363 mmol) in MeOH/THF (6 mL each) using a solution of lithium hydroxide hydrate (160 mg, 3.81 mmol) in water (2 mL) and stirring overnight at room temperature. This gave after workup and purification by reverse phase column chromatography [C18 column (50 g), eluting with ACN in water (containing 0.1% HCl) from 0-100%] 2-(2-((2-(3-(aminomethyl)phenyl)benzofuran-7-yl)methoxy)phenyl)acetic acid (98g) (120 mg, 85% yield) HCl salt as a white solid; 1H NMR (300 MHz, DMSO-$d_6$) δ 9.20 (s, 3H), 8.19 (s, 1H), 7.97 (d, 1H), 7.67 (d, J=7.7 Hz, 1H), 7.62-7.41 (m, 4H), 7.36-7.14 (m, 4H), 6.94 (t, J=7.2 Hz, 1H), 5.51 (s, 2H), 4.12 (s, 2H), 3.59 (s, 2H); MS (ES+): 388.1 (M+1), 00.00 (M+Na); (ES−): 386.1 (M−1); Analysis calculated for $C_{24}H_{21}NO_4$·HCl·1.5$H_2O$: C, 63.93; H, 5.59; Cl, 7.86; N, 3.11. Found: C, 63.55; H, 5.30; Cl, 8.26; N, 3.36.

Scheme 99

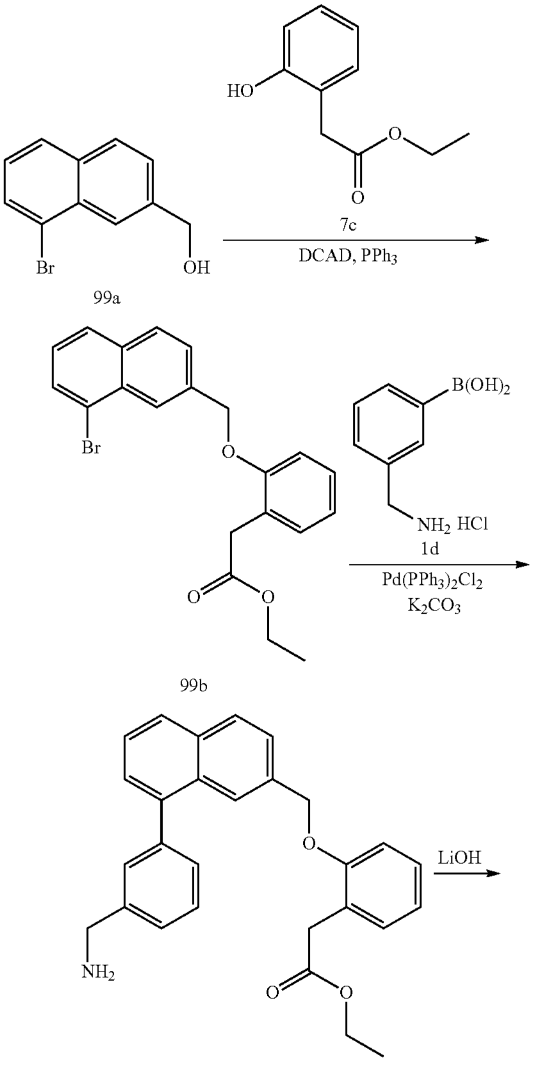

7c, 99a, 1d, 99b, 99c

-continued

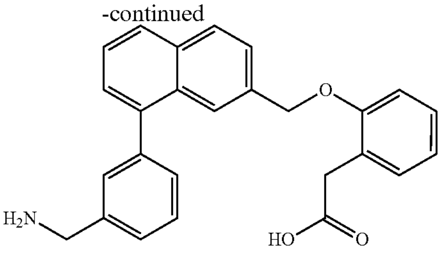

99d

Preparation of 2-(2-((8-(3-(aminomethyl)phenyl)naphthalen-2-yl)methoxy)phenyl)acetic acid (99d)

Step-1: Preparation of ethyl 2-(2-((8-bromonaphthalen-2-yl)methoxy)phenyl)acetate (99b)

Compound 99b was prepared according to the procedure reported in step-3 of scheme 7, from (8-bromonaphthalen-2-yl)methanol (99a) (350 mg, 1.476 mmol; CAS #127810-63-3) in DCM (30 mL) using triphenylphosphine (426 mg, 1.624 mmol), ethyl 2-(2-hydroxyphenyl)acetate (7c) (0.266 g, 1.476 mmol) a solution of bis(4-chlorobenzyl) diazene-1,2-dicarboxylate (DCAD) (596 mg, 1.624 mmol) in DCM (20 mL) and stirring at room temperature for 30 min. This gave after workup and purification by flash column chromatography [silica gel (40 g), eluting with EtOAc in hexane from 0-50%] ethyl 2-(2-((8-bromonaphthalen-2-yl)methoxy)phenyl)acetate (99b) (300 mg, 51% yield) as a colorless oil; $^1$H NMR (300 MHz, DMSO-$d_6$) δ 8.15 (d, J=8.7, 0.7 Hz, 1H), 8.04 (s, 1H), 7.96 (dt, J=8.4, 1.0 Hz, 1H), 7.89 (dd, J=7.4, 1.1 Hz, 1H), 7.72 (dd, J=8.7, 1.7 Hz, 1H), 7.51-7.41 (m, 1H), 7.24 (d, J=7.5 Hz, 2H), 7.11 (dt, J=7.7, 1.1 Hz, 1H), 6.93 (td, J=7.4, 1.1 Hz, 1H), 5.32 (s, 2H), 4.01 (q, J=7.1 Hz, 2H), 3.68 (s, 2H), 1.06 (t, J=7.1 Hz, 3H).

Step-2: Preparation of ethyl 2-(2-((8-(3-(aminomethyl)phenyl)naphthalen-2-yl)methoxy)phenyl)acetate (99c)

Compound 99c was prepared according to the procedure reported in step-8 of Scheme 3, from ethyl 2-(2-((8-bromonaphthalen-2-yl)methoxy)phenyl)acetate (99b) (200 mg, 0.501 mmol) in dioxane (6 mL) using 3-(aminomethyl) phenylboronic acid hydrochloride (1d) (169 mg, 0.902 mmol), bis(triphenylphosphine)palladium(II) chloride (53 mg, 0.075 mmol), a solution of $K_2CO_3$ (208 mg, 1.503 mmol) in water (3 mL) and stirring at 100° C. for 3 h. This gave after workup and purification by flash column chromatography [silica gel (12 g), eluting with DMA-80 in DCM from 0-50%] ethyl 2-(2-((8-(3-(aminomethyl)phenyl)naphthalen-2-yl)methoxy)phenyl)acetate (99c) (82 mg, 39% yield); MS (ES+): 426.2 (M+1).

Step-3: Preparation of 2-(2-((8-(3-(aminomethyl)phenyl)naphthalen-2-yl)methoxy)phenyl)acetic acid (99d)

Compound 99d was prepared according to the procedure reported in step-3 of scheme 1, from ethyl 2-(2-((8-(3-(aminomethyl)phenyl)naphthalen-2-yl)methoxy)phenyl)acetate (99c) (82 mg, 0.193 mmol) in THF (3 mL) using a solution of lithium hydroxide hydrate (21.02 mg, 0.501 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((8-(3-(aminomethyl)phenyl)naphthalen-2-yl)methoxy)phenyl)acetic acid (99d) (25 mg, 13% yield) HCl salt as a white solid; $^1$H NMR (300 MHz, DMSO-$d_6$) δ 12.23 (s, 1H, $D_2O$ exchangeable), 8.56 (s, 3H, $D_2O$ exchangeable), 8.09 (s, 1H), 7.97 (d, J=8.2 Hz, 1H), 7.86 (d, J=8.7 Hz, 1H), 7.67-7.54 (m, 5H), 7.53-7.48 (m, 1H), 7.45 (d, J=7.0 Hz, 1H), 7.26-7.18 (m, 2H), 7.09 (d, J=8.4 Hz, 1H), 6.90 (t, J=7.4 Hz, 1H), 5.31 (s, 2H), 4.13 (s, 2H), 3.61 (s, 2H); MS (ES+): 398.2 (M+1); (ES−): 396.1 (M−1).

Scheme 100

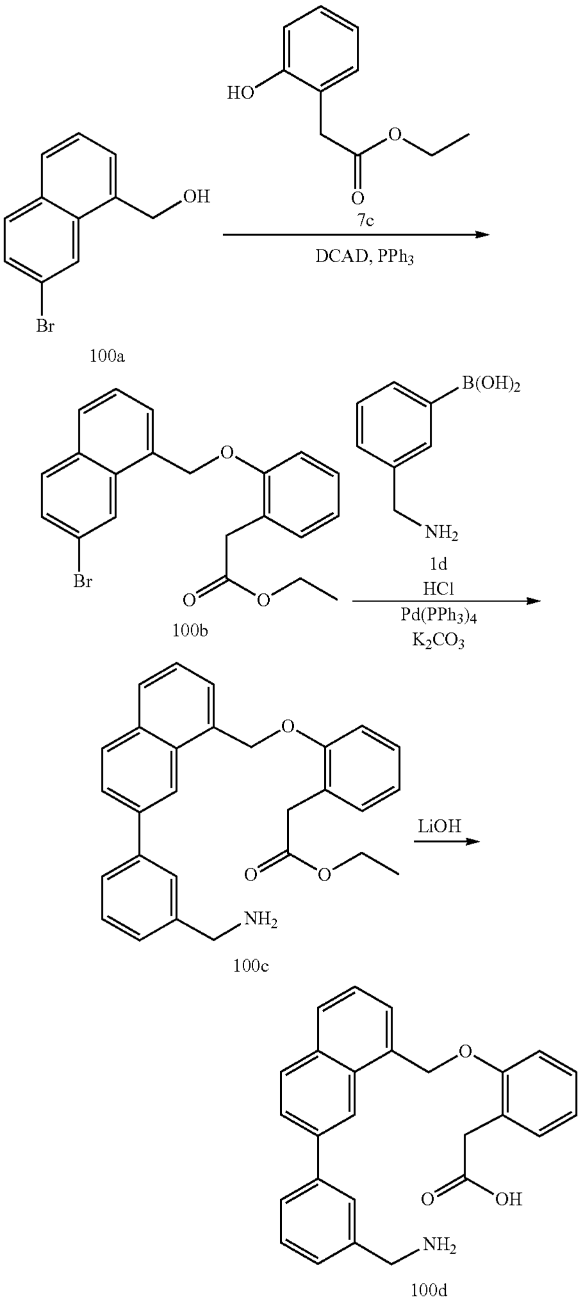

Preparation of 2-(2-((7-(3-(aminomethyl)phenyl)naphthalen-1-yl)methoxy)phenyl)acetic acid (100d)

Step-1: Preparation of ethyl 2-(2-((7-bromonaphthalen-1-yl)methoxy)phenyl)acetate (100b)

Compound 100b was prepared according to the procedure reported in step-3 of scheme 7, from (7-bromonaphthalen-1-yl)methanol (100a) (358 mg, 1.510 mmol; CAS #1058115-75-5) in DCM (30 mL) using triphenylphosphine (436 mg, 1.661 mmol), ethyl 2-(2-hydroxyphenyl)acetate (7c) (0.299 g, 1.661 mmol) a solution of bis(4-chlorobenzyl) diazene-1,2-dicarboxylate (DCAD) (610 mg, 1.661 mmol) in DCM (20 mL) and stirring at room temperature for 30 min. This gave after workup and purification by flash column chromatography [silica gel (12 g), eluting with EtOAc in hexane from 0-50%] ethyl 2-(2-((7-bromonaphthalen-1-yl)methoxy)phenyl)acetate (100b) (381 mg, 63% yield) as a colorless oil; H NMR (300 MHz, DMSO-$d_6$) δ 8.30 (d, J=1.9 Hz, 1H), 7.97 (d, J=8.8 Hz, 2H), 7.76-7.67 (m, 2H), 7.57 (dd, J=8.3, 7.1 Hz, 1H), 7.34-7.28 (m, 2H), 7.26-7.20 (m, 1H), 6.95 (dt, J=7.4, 4.2 Hz, 1H), 5.54 (s, 2H), 3.88 (q, J=7.1 Hz, 2H), 3.58 (s, 2H), 0.95 (t, J=7.1 Hz, 3H); MS (ES+): 421.00 (M+Na).

Step-2: Preparation of ethyl 2-(2-((7-(3-(aminomethyl)phenyl)naphthalen-1-yl)methoxy)phenyl)acetate (100c)

Compound 100c was prepared according to the procedure reported in step-8 of Scheme 3, from ethyl 2-(2-((7-bromonaphthalen-1-yl)methoxy)phenyl)acetate (100b) (380 mg, 0.952 mmol) in dioxane (10 mL) using 3-(aminomethyl) phenylboronic acid hydrochloride (1d) (268 mg, 1.428 mmol), $Pd(PPh_3)_4$ (165 mg, 0.143 mmol), a solution of $K_2CO_3$ (329 mg, 2.379 mmol) in water (3 mL) and stirring at 100° C. for 3 h. This gave after workup and purification by flash column chromatography [silica gel (12 g), eluting with DMA-80 in DCM from 0-50%] ethyl 2-(2-((7-(3-(aminomethyl)phenyl)naphthalen-1-yl)methoxy)phenyl)acetate (100c) (215 mg, 53% yield); MS (ES+): 426.2 (M+1).

Step-3: Preparation of 2-(2-((7-(3-(aminomethyl)phenyl)naphthalen-1-yl)methoxy)phenyl)acetic acid (100d)

Compound 100d was prepared according to the procedure reported in step-3 of scheme 1, from ethyl 2-(2-((7-(3-(aminomethyl)phenyl)naphthalen-1-yl)methoxy)phenyl)acetate (100c) (215 mg, 0.505 mmol) in THF (3 mL) using a solution of lithium hydroxide hydrate (160 mg, 3.81 mmol) in water (1 mL) and stirring overnight at RT. This gave after workup and purification by reverse phase column chromatography [C18 column (30 g), eluting with ACN in water (containing 0.1% HCl) from 0-100%] 2-(2-((7-(3-(aminomethyl)phenyl)naphthalen-1-yl)methoxy)phenyl)acetic acid (100d) (25 mg, 13% yield) HCl salt as a white solid; $^1H$ NMR (300 MHz, DMSO-$d_6$) δ 12.20 (s, 1H, $D_2O$ exchangeable), 8.59 (s, 3H, $D_2O$ exchangeable), 8.39 (d, J=1.7 Hz, 1H), 8.14-8.06 (m, 2H), 7.98-7.91 (m, 2H), 7.90-7.83 (m, 1H), 7.76 (dd, J=7.1, 1.2 Hz, 1H), 7.60-7.48 (m, 3H), 7.35 (dd, J=8.3, 1.2 Hz, 1H), 7.31-7.18 (m, 2H), 6.93 (td, J=7.3, 1.2 Hz, 1H), 5.72 (s, 2H), 4.13 (s, 2H), 3.59 (s, 2H); MS (ES+) 398.1 (M+1); (ES−) 396.1 (M−1).

Scheme 101

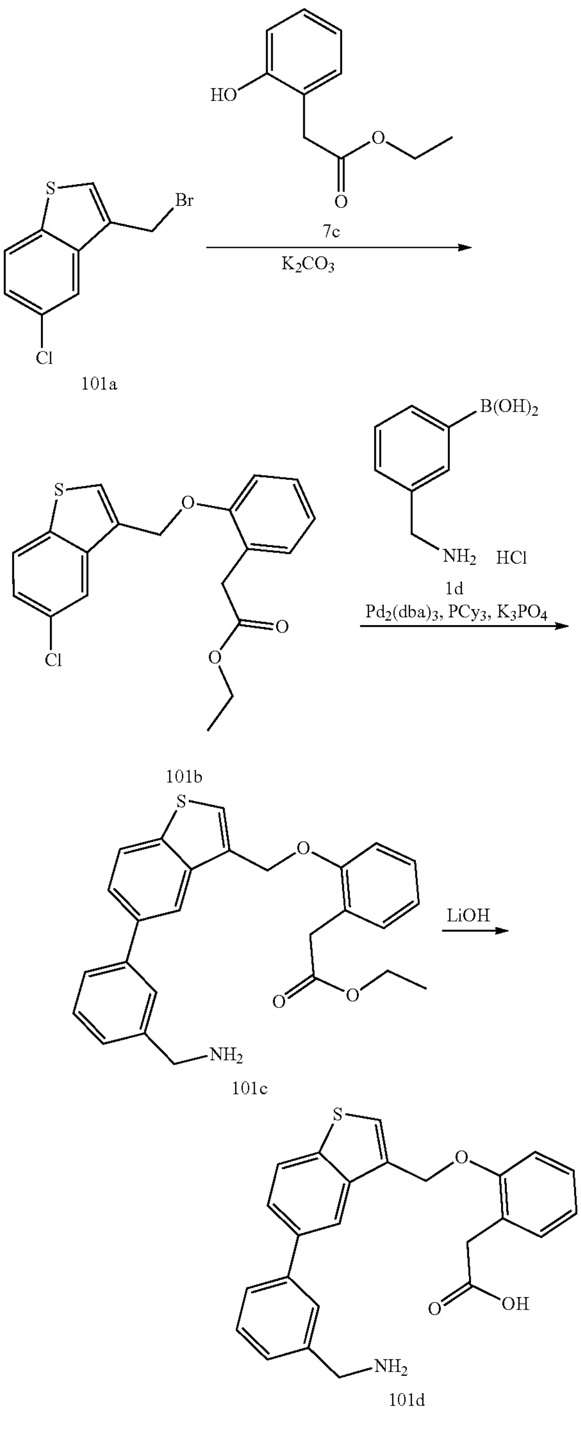

Preparation of 2-(2-((5-(3-(aminomethyl)phenyl)benzo[b]thiophen-3-yl)methoxy)phenyl)acetic acid (101d)

Step-1: Preparation of ethyl 2-(2-((5-chlorobenzo[b]thiophen-3-yl)methoxy)phenyl)acetate (101b)

Compound 101b was prepared according to the procedure reported in step-3 of scheme 7, from 3-(bromomethyl)-5- chlorobenzo[b]thiophene (101a) (2.5 g, 9.56 mmol; CAS #1198-51-2) in DMF (15 mL) using ethyl 2-(2-hydroxyphenyl)acetate (7c) (1.895 g, 10.51 mmol), potassium carbonate (3.96 g, 28.7 mmol) and stirring at room temperature for 2 h. This gave after workup and purification by flash column chromatography [silica gel (40 g), eluting with ethyl acetate and hexanes from 0-50%] ethyl 2-(2-((5-chlorobenzo[b]thiophen-3-yl)methoxy)phenyl)acetate (101b) (1.6 g, 46% yield) as a white solid; MS (ES+): 383.0 (M+Na).

Step-2: Preparation of ethyl 2-(2-((5-(3-(aminomethyl)phenyl)benzo[b]thiophen-3-yl)methoxy)phenyl)acetate (101c)

Compound 101c was prepared according to the procedure reported in step-2 of scheme 1, from ethyl 2-(2-((5-chlorobenzo[b]thiophen-3-yl)methoxy)phenyl)acetate (101b) (450 mg, 1.247 mmol) in dioxane (3 mL) using 3-(aminomethyl)phenylboronic acid hydrochloride (1d) (351 mg, 1.871 mmol), 2M solution of $K_3PO_4$ (1.060 mL, 2.120 mmol), tricyclohexylphosphine (105 mg, 0.374 mmol), $Pd_2(dba)_3$ (114 mg, 0.125 mmol) and heating at 125° C. for 40 min in a microwave. This gave after workup and purification by flash column chromatography [silica gel (24 g), eluting with DMA-80 in DCM from 0-70%] ethyl 2-(2-((5-(3-(aminomethyl)phenyl)benzo[b]thiophen-3-yl)methoxy)phenyl)acetate (101c) (265 mg, 49% yield); MS (ES+): 432.1 (M+1).

Step-3: Preparation of 2-(2-((5-(3-(aminomethyl)phenyl)benzo[b]thiophen-3-yl)methoxy)phenyl)acetic acid (101d)

Compound 101d was prepared according to the procedure reported in step-3 of scheme 1, from ethyl 2-(2-((5-(3-(aminomethyl)phenyl)benzo[b]thiophen-3-yl)methoxy)phenyl)acetate (101c) (265 mg, 0.614 mmol) in THF (3 mL) using a solution of lithium hydroxide hydrate (135 mg, 3.22 mmol) in water (1 mL) and stirring overnight at room temperature. This gave after workup and purification by reverse phase column chromatography [C18 column (30 g), eluting with ACN in water (containing 0.1% HCl) from 0-100%] 2-(2-((5-(3-(aminomethyl)phenyl)benzo[b]thiophen-3-yl)methoxy)phenyl)acetic acid (101d) (177 mg, 35% yield) HCl salt as a white solid; $^1$H NMR (300 MHz, DMSO-$d_6$) δ 8.63 (s, 2H, $D_2O$ exchangeable), 8.28 (d, J=1.7 Hz, 1H), 8.14 (d, J=8.4 Hz, 1H), 8.04 (s, 1H), 7.89-7.71 (m, 3H), 7.58-7.41 (m, 2H), 7.34-7.16 (m, 3H), 6.98-6.86 (m, 1H), 5.47 (s, 2H), 4.12 (s, 2H), 3.59 (s, 2H); MS (ES+) 404.1 (M+1); (ES−) 401.9 (M−1); Analysis calculated for $C_{24}H_{21}NO_3S{\cdot}HCl{\cdot}0.25H_2O$: C, 64.86; H, 5.10; Cl, 7.98; N, 3.15. Found: C, 64.82; H, 5.08; Cl, 8.11; N, 3.25.

Scheme 102

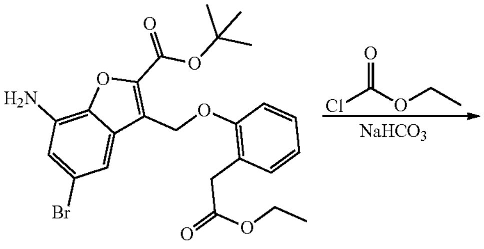

87a

-continued

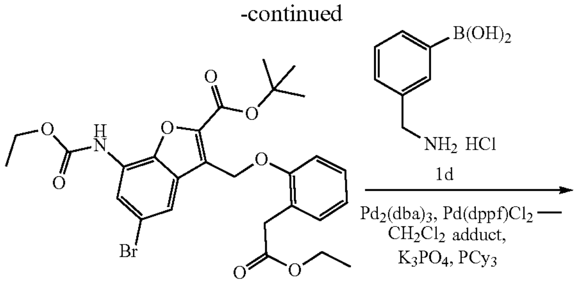

102a

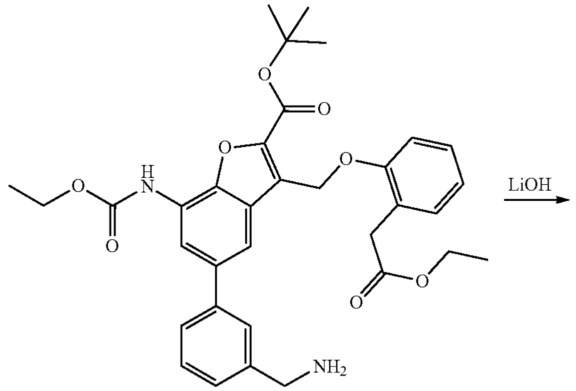

102b

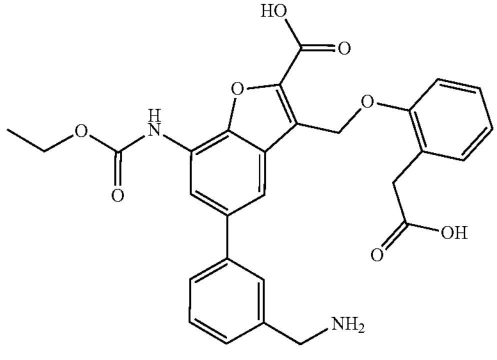

102c

Preparation of 5-(3-(aminomethyl)phenyl)-3-((2-(carboxymethyl)phenoxy)methyl)-7-((ethoxycarbonyl) amino)benzofuran-2-carboxylic acid (102c)

Step-1: Preparation of tert-butyl 5-bromo-3-((2-(2-ethoxy-2-oxoethyl)phenoxy)methyl)-7-((ethoxycarbonyl)amino)benzofuran-2-carboxylate (102a)

To a solution of tert-butyl 7-amino-5-bromo-3-((2-(2-ethoxy-2-oxoethyl)phenoxy)methyl)benzofuran-2-carboxylate (87a) (326 mg, 0.646 mmol) in THF (2 mL) and water (2 mL) at 0° C. was added sodium bicarbonate (81 mg, 0.97 mmol), ethyl chloroformate (0.093 mL, 0.97 mmol) and stirred overnight at room temperature. The reaction mixture was diluted with EtOAc (100 mL), washed with water, brine, dried, filtered and concentrated in vacuum. The residue obtained was purified by flash column chromatography [silica gel (24 g), eluting with EtOAc in hexane from 0-100%] to give tert-butyl 5-bromo-3-((2-(2-ethoxy-2-oxoethyl)phenoxy)methyl)-7-((ethoxycarbonyl)amino)benzofuran-2-carboxylate (102a) (331 mg, 89% yield) as a clear oil; $^1$H NMR (300 MHz, DMSO-$d_6$) δ 10.00 (s, 1H), 7.84 (s, 1H), 7.77 (d, J=1.9 Hz, 1H), 7.33-7.24 (m, 1H), 7.22 (dd, J=7.4, 1.7 Hz, 1H), 7.16 (d, J=8.1 Hz, 1H), 6.95 (t, J=7.4 Hz, 1H), 5.53 (s, 2H), 4.18 (q, J=7.1 Hz, 2H), 3.90 (q, J=7.1 Hz, 2H), 3.55 (s, 2H), 1.56 (s, 9H), 1.27 (t, J=7.1 Hz, 3H), 0.96 (t, J=7.1 Hz, 3H); MS (ES+): 598.00 (M+Na).

Step-2: Preparation of tert-butyl 5-(3-(aminomethyl) phenyl)-3-((2-(2-ethoxy-2-oxoethyl)phenoxy) methyl)-7-((ethoxycarbonyl)amino)benzofuran-2-carboxylate (102b)

Compound 102b was prepared according to the procedure reported in step-2 of scheme 1, from tert-butyl 5-bromo-3-((2-(2-ethoxy-2-oxoethyl)phenoxy)methyl)-7-((ethoxycarbonyl)amino)benzofuran-2-carboxylate (102a) (331 mg, 0.574 mmol) in dioxane/THF (5 mL each) using 3-(aminomethyl)phenylboronic acid hydrochloride (1d) (215 mg, 1.148 mmol), 2 M solution of $K_3PO_4$ (1.148 mL, 2.297 mmol), tricyclohexylphosphine (48.3 mg, 0.172 mmol) $PdCl_2(dppf)\text{-}CH_2Cl_2$ adduct (46.9 mg, 0.057 mmol), $Pd_2(dba)_3$ (52.6 mg, 0.057 mmol) and heating at 90° C. for 1 h. This gave after workup and purification by flash column chromatography [silica gel (24 g), eluting with DMA-80 in DCM from 0-70%] tert-butyl 5-(3-(aminomethyl)phenyl)-3-((2-(2-ethoxy-2-oxoethyl)phenoxy)methyl)-7-((ethoxycarbonyl)amino)benzofuran-2-carboxylate (102b)(186 mg, 54% yield) as a yellow semi-solid; MS (ES+): 603.1 (M+1).

Step-3: Preparation of 5-(3-(aminomethyl)phenyl)-3-((2-(carboxymethyl)phenoxy)methyl)-7-((ethoxycarbonyl)amino)benzofuran-2-carboxylic acid (102c)

Compound 102c was prepared according to the procedure reported in step-3 of scheme 1, from tert-butyl 5-(3-(aminomethyl)phenyl)-3-((2-(2-ethoxy-2-oxoethyl)phenoxy) methyl)-7-((ethoxycarbonyl)amino)benzofuran-2-carboxylate (102b) (186 mg, 0.309 mmol) in THF (3 mL) using a solution of lithium hydroxide hydrate (72.3 mg, 1.723 mmol) in water (1 mL) and stirring at 50° C. for 1 h. This gave after workup and purification by reverse phase column chromatography [C18 column (30 g), eluting with ACN in water (containing 0.1% HCl) from 0-100%] 5-(3-(aminomethyl)phenyl)-3-((2-(carboxymethyl)phenoxy)methyl)-7-((ethoxycarbonyl)amino)benzofuran-2-carboxylic acid (102c) (62 mg, 21% yield) HCl salt as an off white solid; $^1H$ NMR (300 MHz, DMSO-$d_6$) δ 12.63 (brs, 1H, $D_2O$ exchangeable), 9.82 (s, 1H, $D_2O$ exchangeable), 8.44 (s, 3H, $D_2O$ exchangeable), 7.89 (dd, J=12.9, 1.7 Hz, 2H), 7.81 (d, J=2.1 Hz, 1H), 7.72-7.62 (m, 1H), 7.59-7.45 (m, 2H), 7.29-7.14 (m, 3H), 6.92 (td, J=7.2, 1.4 Hz, 1H), 5.67 (s, 2H), 4.17 (q, J=7.1 Hz, 2H), 4.11 (s, 2H), 3.54 (s, 2H), 1.27 (t, J=7.1 Hz, 3H); MS (ES+): 519.1 (M+1); (ES−): 517.1 (M−1); Analysis calculated for $C_{28}H_{26}N_2O_8\cdot HCl\cdot 2H_2O$: C, 56.90; H, 5.29; Cl, 6.00; N, 4.74. Found: C, 57.20; H, 5.34; Cl, 5.82; N, 4.68.

Scheme 103

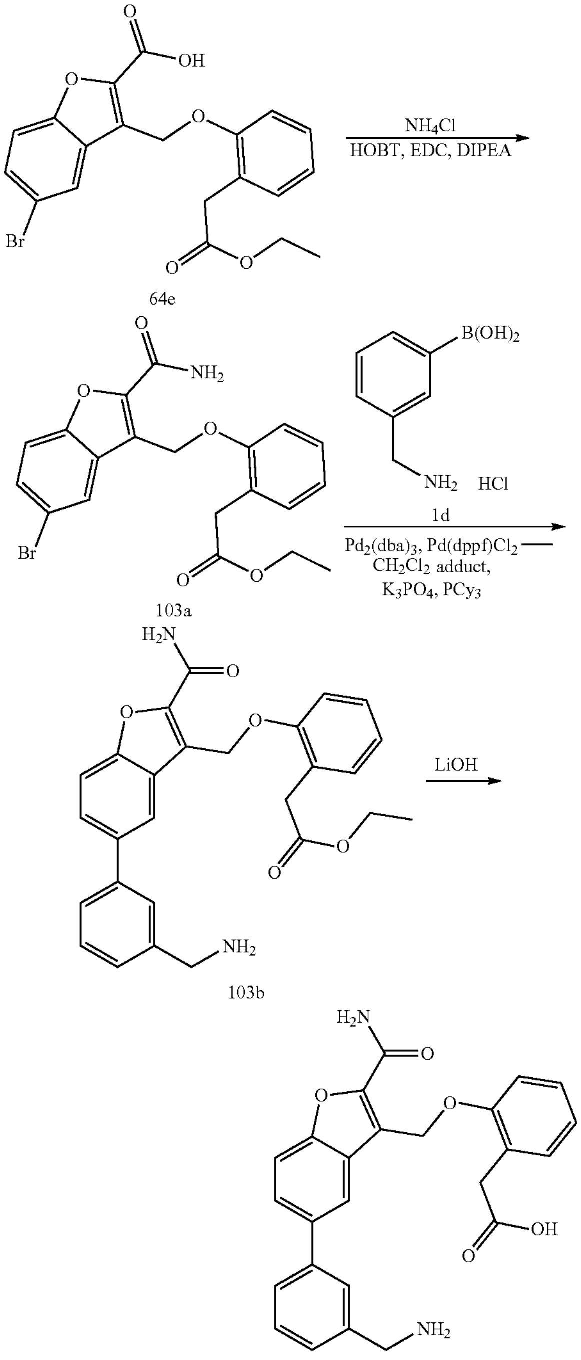

64e

103a

103b

103c

Preparation of 2-(2-((5-(3-(aminomethyl)phenyl)-2-carbamoylbenzofuran-3-yl)methoxy)phenyl)acetic acid (103c)

Step-1: Preparation of ethyl 2-(2-((5-bromo-2-carbamoylbenzofuran-3-yl)methoxy)phenyl)acetate (103a)

To a solution of 5-bromo-3-((2-(2-ethoxy-2-oxoethyl) phenoxy)methyl)benzofuran-2-carboxylic acid (64e) (400 mg, 0.923 mmol) in DMF (5 mL) at room temperature was added hydroxybenzotriazole (HOBT) (156 mg, 1.016 mmol), 1-ethyl-3-(3-dimethylaminopropyl)carbodiimide hydrochloride (EDC) (265 mg, 1.385 mmol), ammonium chloride (99 mg, 1.847 mmol) and DIPEA (0.322 mL, 1.847 mmol) and stirred overnight at room temperature. The reaction mixture was diluted with EtOAc (100 mL), washed with water (3×), brine, dried, filtered and concentrated in vacuum. The residue obtained was purified by flash column chromatography [silica gel (12 g), eluting with EtOAc in hexane from 0-100%] to give ethyl 2-(2-((5-bromo-2-carbamoylbenzofuran-3-yl)methoxy)phenyl)acetate (103a) (410 mg, 88% yield) as a semi-solid; $^1$H NMR (300 MHz, DMSO-$d_6$) δ 8.29 (s, 1H), 7.95 (d, J=2.4 Hz, 2H), 7.68-7.60 (m, 2H), 7.30-7.15 (m, 3H), 6.92 (td, J=7.3, 1.3 Hz, 1H), 5.66 (s, 2H), 3.95 (q, J=7.1 Hz, 2H), 3.57 (s, 2H), 0.98 (t, J=7.1 Hz, 3H).

Step-2: Preparation of ethyl 2-(2-((5-(3-(aminomethyl)phenyl)-2-carbamoylbenzofuran-3-yl)methoxy)phenyl)acetate (103b)

Compound 103b was prepared according to the procedure reported in step-2 of scheme 1, from ethyl 2-(2-((5-bromo-2-carbamoylbenzofuran-3-yl)methoxy)phenyl)acetate (103a) (400 mg, 0.925 mmol) in dioxane/THF (5 mL each) using 3-(aminomethyl)phenylboronic acid hydrochloride (1d) (347 mg, 1.851 mmol), 2 M solution of $K_3PO_4$ (1.851 mL, 3.70 mmol), tricyclohexylphosphine (78.0 mg, 0.278 mmol), $PdCl_2$(dppf)-$CH_2Cl_2$ adduct (76.0 mg, 0.093 mmol), $Pd_2(dba)_3$ (85.0 mg, 0.093 mmol) and heating at 90° C. for 1 h. This gave after workup and purification by flash column chromatography [silica (24 g), eluting with DMA-80 in DCM from 0-70%] ethyl 2-(2-((5-(3-(aminomethyl)phenyl)-2-carbamoylbenzofuran-3-yl)methoxy)phenyl)acetate (103b) (201 mg, 47% yield) as a yellow semi-solid; MS (ES+): 459.1 (M+1).

Step-3: Preparation of 2-(2-((5-(3-(aminomethyl)phenyl)-2-carbamoylbenzofuran-3-yl)methoxy)phenyl)acetic acid (103c)

Compound 103c was prepared according to the procedure reported in step-3 of scheme 1, from ethyl 2-(2-((5-(3-(aminomethyl)phenyl)-2-carbamoylbenzofuran-3-yl)methoxy)phenyl)acetate (103b) (201 mg, 0.438 mmol) in THF (3 mL) using a solution of lithium hydroxide hydrate (116 mg, 2.78 mmol) in water (1 mL) and heating at 50° C. for 1 h.

This gave after workup and purification by reverse phase column chromatography [C18 column (30 g), eluting with ACN in water (containing 0.1% HCl) from 0-100%] 2-(2-((5-(3-(aminomethyl)phenyl)-2-carbamoylbenzofuran-3-yl)methoxy)phenyl)acetic acid (103c) (41 mg, 10% yield) HCl salt as an off white solid; $^1$H NMR (300 MHz, DMSO-$d_6$) δ 12.16 (s, 1H, $D_2O$ exchangeable), 8.43 (s, 3H, $D_2O$ exchangeable), 8.26 (s, 1H, $D_2O$ exchangeable), 8.10 (d, J=1.8 Hz, 1H), 7.95 (s, 1H, $D_2O$ exchangeable), 7.89-7.79 (m, 2H), 7.77-7.69 (m, 2H), 7.57-7.45 (m, 2H), 7.28-7.14 (m, 3H), 6.95-6.85 (m, 1H), 5.75 (s, 2H), 4.11 (d, J=5.4 Hz, 2H), 3.56 (s, 2H); MS (ES+): 431.1 (M+1); (ES−): 429.1 (M−1); Analysis calculated for $C_{25}H_{22}N_2O_5 \cdot HCl \cdot 1.75H_2O$: C, 60.24; H, 5.36; Cl, 7.11; N, 5.62. Found: C, 60.26; H, 5.26; Cl, 7.04; N, 5.53.

Scheme 104

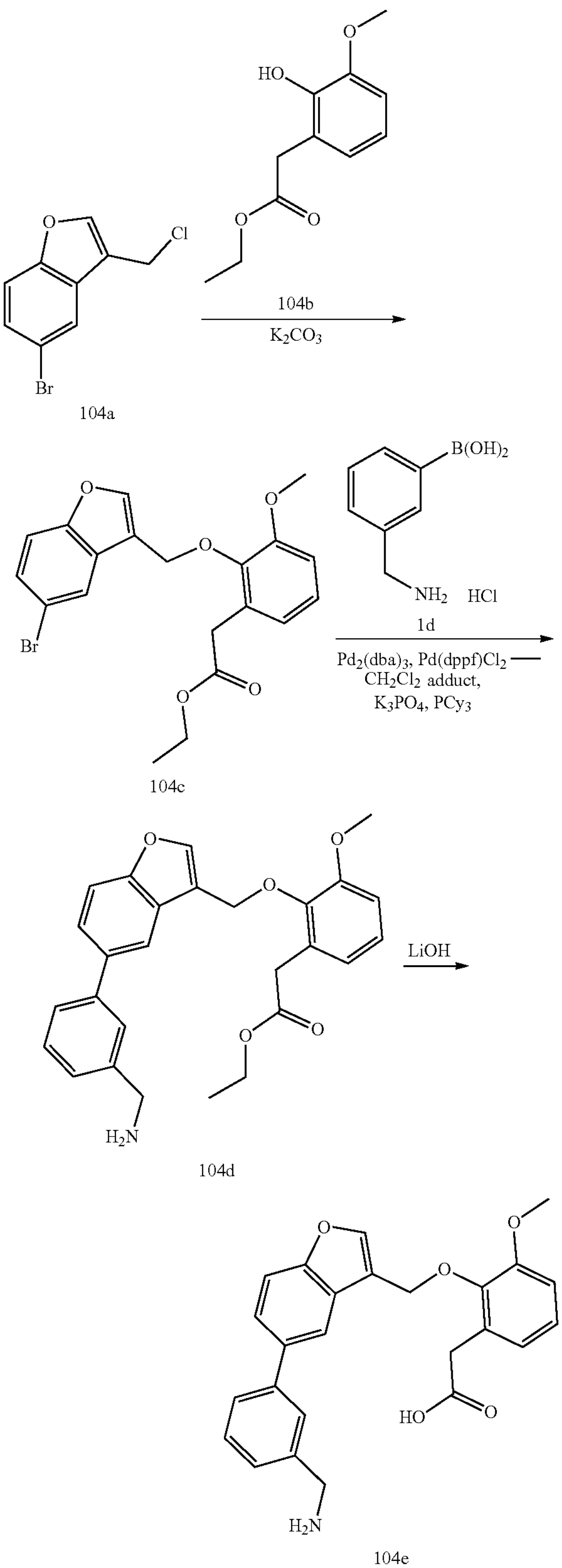

Preparation of 2-(2-((5-(3-(aminomethyl)phenyl)benzofuran-3-yl)methoxy)-3-methoxyphenyl)acetic acid (104e)

Step-1: Preparation of ethyl 2-(2-((5-bromobenzofuran-3-yl)methoxy)-3-methoxyphenyl)acetate (104c)

Compound 104c was prepared according to the procedure reported in step-3 of scheme 7, from 5-bromo-3-(chloromethyl)benzofuran (104a) (500 mg, 2.037 mmol) in DMF (4 mL) using ethyl 2-(2-hydroxy-3-methoxyphenyl)acetate (104b) (0.389; 1.852 mmol CAS #1261620-23-8), potassium carbonate (0.768 g, 5.55 mmol) and stirring overnight at room temperature. This gave after workup and purification by flash column chromatography [silica gel (12 g) eluting with ethyl acetate and hexanes from 0-50%] ethyl 2-(2-((5-bromobenzofuran-3-yl)methoxy)-3-methoxyphenyl)acetate (104c) (633 mg, 82% yield) as a white solid; $^1H$ NMR (300 MHz, DMSO-$d_6$) δ 8.09 (s, 1H), 7.93 (d, J=2.1 Hz, 1H), 7.62 (d, J=8.7 Hz, 1H), 7.51 (dd, J=8.8, 2.1 Hz, 1H), 7.10-7.01 (m, 2H), 6.82 (dd, J=5.5, 3.7 Hz, 1H), 5.13-5.04 (m, 2H), 4.01-3.90 (m, 2H), 3.89 (s, 3H), 3.55 (s, 2H), 1.09 (t, J=7.1 Hz, 3H).

Step-2: Preparation of ethyl 2-(2-((5-(3-(aminomethyl)phenyl)benzofuran-3-yl)methoxy)-3-methoxyphenyl)acetate (104d)

Compound 104d was prepared according to the procedure reported in step-2 of scheme 1, from ethyl 2-(2-((5-bromobenzofuran-3-yl)methoxy)-3-methoxyphenyl)acetate (104c) (633 mg, 1.693 mmol) in dioxane/THF (6 mL each) using 3-(aminomethyl)phenylboronic acid hydrochloride (1d) (635 mg, 3.39 mmol), 2 M solution of $K_3PO_4$ (3.39 mL, 6.77 mmol), tricyclohexylphosphine (95 mg, 0.339 mmol), $PdCl_2(dppf)$-$CH_2Cl_2$ adduct (138 mg, 0.169 mmol), $Pd_2(dba)_3$ (155 mg, 0.169 mmol) and heating at 95° C. for 1 h. This gave after workup and purification by column chromatography [silica gel (24 g), eluting with DMA-80 in DCM from 0-70%] ethyl 2-(2-((5-(3-(aminomethyl)phenyl)benzofuran-3-yl)methoxy)-3-methoxyphenyl)acetate (104d) (167 mg, 22% yield) as a clear oil; $^1H$ NMR (300 MHz, DMSO-$d_6$) δ 8.05 (s, 1H), 7.97 (d, J=1.7 Hz, 1H), 7.71-7.62 (m, 3H), 7.52 (d, J=7.8 Hz, 1H), 7.41 (t, J=7.5 Hz, 1H), 7.32 (d, J=7.6 Hz, 1H), 7.05 (d, J=4.6 Hz, 2H), 6.81 (t, J=4.6 Hz, 1H), 5.17 (s, 2H), 3.95-3.86 (m, 4H), 3.81 (s, 3H), 3.55 (s, 2H), 1.01 (t, J=7.1 Hz, 3H); MS (ES+): 446.10 (M+1).

Step-3: Preparation of 2-(2-((5-(3-(aminomethyl)phenyl)benzofuran-3-yl)methoxy)-3-methoxyphenyl)acetic acid (104e)

Compound 104e was prepared according to the procedure reported in step-3 of scheme 1, from ethyl 2-(2-((5-(3-(aminomethyl)phenyl)benzofuran-3-yl)methoxy)-3-methoxyphenyl)acetate (104d) (167 mg, 0.375 mmol) in THF (2 mL), methanol (0.2 mL) and water (0.2 mL) using lithium hydroxide hydrate (35.9 mg, 1.499 mmol) and stirring at room temperature for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-3-methoxyphenyl)acetic acid (104e) (79 mg, 51% yield) HCl salt as a light brown solid; $^1H$ NMR (300 MHz, DMSO-$d_6$) δ 8.45-8.25 (m, 3H), 8.08 (s, 1H), 8.05 (d, J=1.8 Hz, 1H), 7.86 (s, 1H), 7.77-7.74 (m, 1H), 7.73 (s, 1H), 7.68 (dd, J=8.6, 1.8 Hz, 1H), 7.55 (t, J=7.6 Hz, 1H), 7.47 (d, J=7.6 Hz, 1H), 7.06 (d, J=2.5 Hz, 1H), 7.04 (s, 1H), 6.83 (dd, J=5.7, 3.4 Hz, 1H), 5.17 (s, 2H), 4.13 (s, 2H), 3.89 (s, 3H), 3.51 (s, 2H); MS (ES+): 418.20 (M+1). Analysis calculated for $C_{25}H_{23}NO_5 \cdot HCl \cdot H_2O$: C, 63.63; H, 5.55; Cl, 7.51; N, 2.97. Found: C, 63.85; H, 5.69; Cl, 7.81; N, 3.15.

Scheme 105

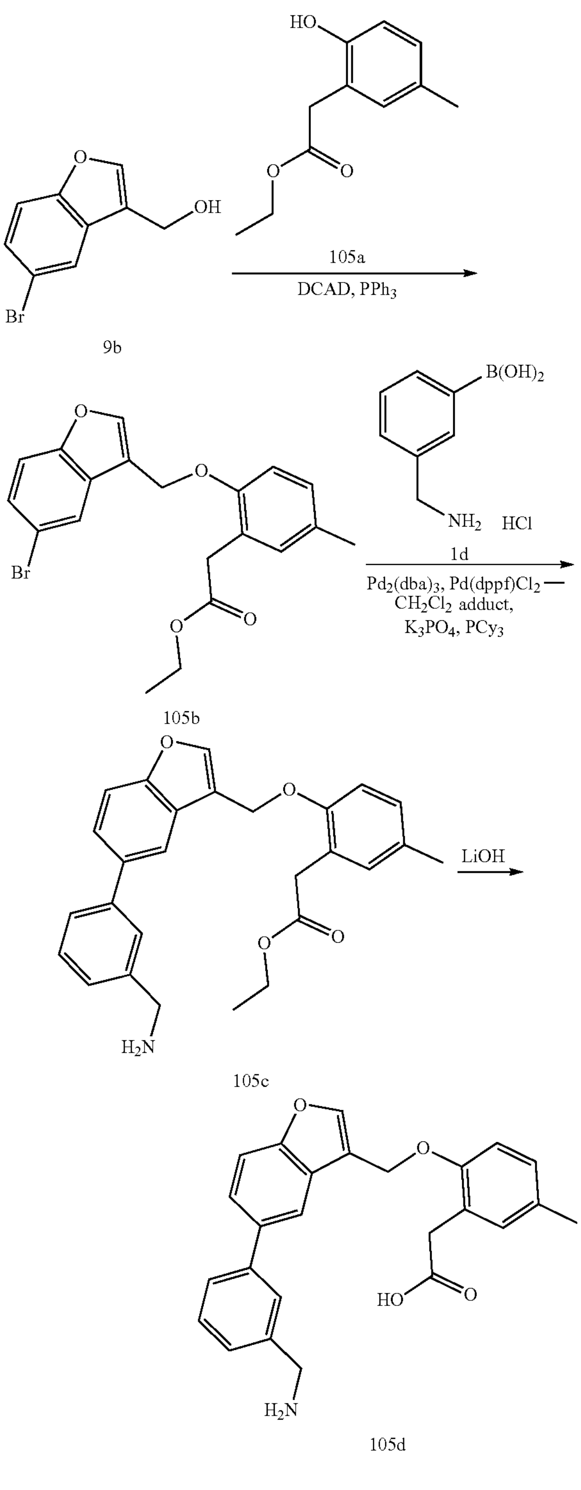

9b

105b

105c

105d

Preparation of 2-(2-((5-(3-(aminomethyl)phenyl) benzofuran-3-yl)methoxy)-5-methylphenyl)acetic acid (105d)

Step-1: Preparation of ethyl 2-(2-((5-bromobenzofuran-3-yl)methoxy)-5-methylphenyl)acetate (105b)

Compound 105b was prepared according to the procedure reported in step-3 of scheme 7, from (5-bromobenzofuran-3-yl)methanol (9b) (250 mg, 1.101 mmol), triphenylphosphine (375 mg, 1.431 mmol), ethyl 2-(2-hydroxy-5-methylphenyl)acetate (105a) (321 mg, 1.652 mmol; CAS #41873-67-0) in DCM (7 mL) using bis(4-chlorobenzyl) diazene-1,2-dicarboxylate (DCAD) (526 mg, 1.431 mmol) in DCM (3 mL) and stirring at room temperature for 3 h. This gave after workup and purification by flash column chromatography [silica gel (12 g), eluting with EtOAc in hexane from 0-50%] ethyl 2-(2-((5-bromobenzofuran-3-yl) methoxy)-5-methylphenyl)acetate (105b)(224 mg, 50% yield) as a white solid; $^1$H NMR (300 MHz, DMSO-$d_6$) δ 8.13 (s, 1H), 7.84 (d, J=2.1 Hz, 1H), 7.61 (d, J=8.7 Hz, 1H), 7.50 (dd, J=8.7, 2.1 Hz, 1H), 7.08 (d, J=1.4 Hz, 2H), 7.02 (s, 1H), 5.24-5.16 (m, 2H), 3.94 (q, J=7.1 Hz, 2H), 3.52 (s, 2H), 2.24 (s, 3H), 0.99 (t, J=7.1 Hz, 3H); MS (ES+): 425.00 (M+Na).

Step-2: Preparation of ethyl 2-(2-((5-(3-(aminomethyl)phenyl)benzofuran-3-yl)methoxy)-5-methylphenyl)acetate (105c)

Compound 105c was prepared according to the procedure reported in step-2 of scheme 1, from ethyl 2-(2-((5-bromobenzofuran-3-yl)methoxy)-5-methylphenyl)acetate (105b) (224 mg, 0.555 mmol) in dioxane/THF (6 mL each) using 3-(aminomethyl)phenylboronic acid hydrochloride (1d) (208 mg, 1.111 mmol), 2 M solution of $K_3PO_4$ (1.111 mL, 2.222 mmol), tricyclohexylphosphine (31.2 mg, 0.111 mmol), $PdCl_2$(dppf)-$CH_2Cl_2$ adduct (45.4 mg, 0.056 mmol), $Pd_2(dba)_3$ (50.9 mg, 0.056 mmol) and heating at 90° C. for 1 h. This gave after workup and purification by flash column chromatography [silica gel (24 g), eluting with DMA-80 in DCM from 0-70%] ethyl 2-(2-((5-(3-(aminomethyl)phenyl) benzofuran-3-yl)methoxy)-5-methylphenyl)acetate (105c) (154 mg, 64% yield) as a colorless oil; $^1$H NMR (300 MHz, DMSO-$d_6$) δ 8.10 (s, 1H), 7.90 (d, J=1.6 Hz, 1H), 7.70-7.64 (m, 3H), 7.59-7.50 (m, 1H), 7.40 (t, 1H), 7.33 (d, 1H), 7.10 (s, 2H), 7.01 (s, 1H), 5.26 (s, 2H), 3.79 (s, 2H), 3.74 (q, 2H), 3.52 (s, 2H), 2.24 (s, 3H), 0.87 (t, J=7.1 Hz, 3H); MS (ES+): 430.10 (M+1).

Step-3: Preparation of 2-(2-((5-(3-(aminomethyl) phenyl)benzofuran-3-yl)methoxy)-5-methylphenyl) acetic acid (105d)

Compound 105d was prepared according to the procedure reported in step-3 of scheme 1, from ethyl 2-(2-((5-(3-(aminomethyl)phenyl)benzofuran-3-yl)methoxy)-5-methylphenyl)acetate (105c) (154 mg, 0.359 mmol) in THF (2 mL, ratio: 10.0), methanol (0.2 mL, ratio: 1.0) and water (0.2 mL, ratio: 1.000) using a solution of lithium hydroxide hydrate (34.3 mg, 1.434 mmol) and stirring at RT for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-5-methylphenyl)acetic acid (105d) (47 mg, 33% yield) HCl salt as a light brown solid; $^1$H NMR (300 MHz, DMSO-$d_6$) δ 12.16 (s, 1H), 8.39 (s, 3H), 8.11 (s, 1H), 8.00 (d, J=1.7 Hz, 1H), 7.88 (s, 1H), 7.77-7.69 (m, 3H), 7.53 (t, J=7.6 Hz, 1H), 7.47 (d, J=8.0 Hz, 1H), 7.13-7.06 (m, 2H), 7.04-7.00 (m, 1H), 5.29 (s, 2H), 4.12 (s, 2H), 3.50 (s, 2H), 2.23 (s, 3H); $^1$HNMR (300 MHz, DMSO/$D_2O$) δ 8.03 (s, 1H), 7.94-7.90 (m, 1H), 7.77 (s, 1H), 7.74-7.64 (m, 3H), 7.52 (t, J=7.6 Hz, 1H), 7.41 (d, J=7.7 Hz, 1H), 7.06 (s, 2H), 6.98 (s, 1H), 5.25 (s, 2H), 4.08 (s, 2H), 3.46 (s, 2H), 2.19 (s, 3H); MS (ES+): 402.10 (M+1); MS (ES−): 400.10 (M−1); Analysis calculated for $C_{25}H_{23}NO_4 \cdot 1HCl \cdot 1H_2O$: C, 65.86; H, 5.75; Cl, 7.78; N, 3.07. Found: C, 65.46; H, 5.59; Cl, 7.84; N, 3.17.

Scheme 106

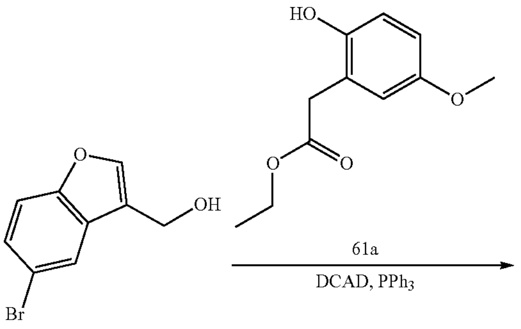

9b

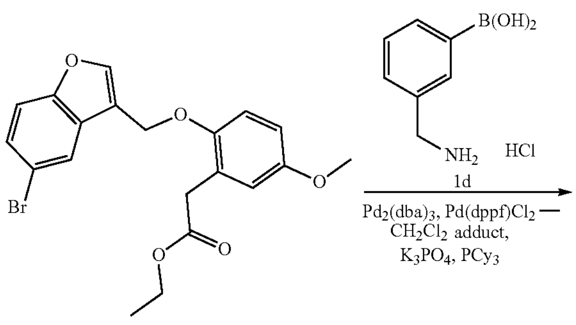

106a

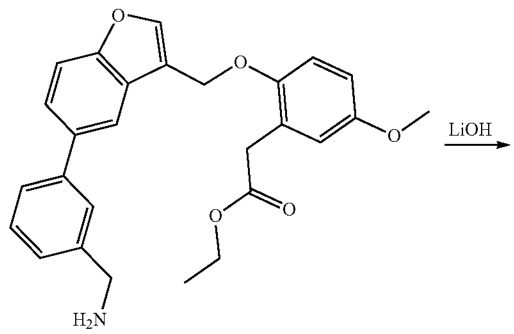

106b

-continued

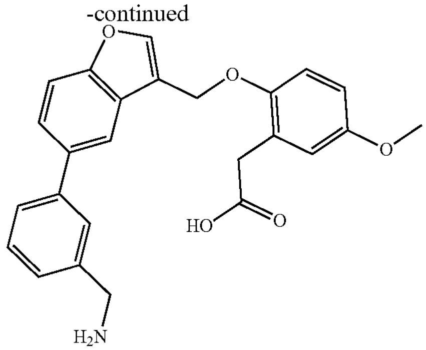

106c

Preparation of 2-(2-((5-(3-(aminomethyl)phenyl)benzofuran-3-yl)methoxy)-5-methoxyphenyl)acetic acid (106c)

Step-1: Preparation of ethyl 2-(2-((5-bromobenzofuran-3-yl)methoxy)-5-methoxyphenyl)acetate (106a)

Compound 106a was prepared according to the procedure reported in step-3 of scheme 7, from (5-bromobenzofuran-3-yl)methanol (9b)(500 mg, 2.202 mmol) in DCM (7 mL) using triphenylphosphine (751 mg, 2.86 mmol), ethyl 2-(2-hydroxy-5-methoxyphenyl)acetate (61a) (964 mg, 3.30 mmol) a solution of bis(4-chlorobenzyl) diazene-1,2-dicarboxylate (DCAD) (1051 mg, 2.86 mmol) in DCM (3 mL) and stirring at room temperature for 3 h. This gave after workup and purification by flash column chromatography [silica gel (12 g), eluting with EtOAc in hexane from 0-50%] ethyl 2-(2-((5-bromobenzofuran-3-yl)methoxy)-5-methoxyphenyl)acetate (106a) (462 mg, 50% yield) as a white solid; $^1$H NMR (300 MHz, DMSO-$d_6$) δ 8.12 (s, 1H), 7.84 (d, J=2.0 Hz, 1H), 7.61 (d, J=8.7 Hz, 1H), 7.50 (dd, J=8.8, 2.1 Hz, 1H), 7.15-7.08 (m, 1H), 6.90-6.79 (m, 2H), 5.17 (s, 2H), 3.95 (q, J=7.1 Hz, 2H), 3.71 (s, 3H), 3.54 (s, 2H), 1.01 (t, J=7.1 Hz, 3H); MS (ES+): 440.90 (M+Na).

Step-2: Preparation of ethyl 2-(2-((5-(3-(aminomethyl)phenyl)benzofuran-3-yl)methoxy)-5-methoxyphenyl)acetate (106b)

Compound 106b was prepared according to the procedure reported in step-2 of scheme 1, from ethyl 2-(2-((5-bromobenzofuran-3-yl)methoxy)-5-methoxyphenyl)acetate (106a) (462 mg, 1.102 mmol) in dioxane/THF (6 mL each) using 3-(aminomethyl)phenylboronic acid hydrochloride (1d) (413 mg, 2.204 mmol), 2 M solution of $K_3PO_4$ (2.204 mL, 4.41 mmol), tricyclohexylphosphine (61.8 mg, 0.220 mmol), $PdCl_2$(dppf)-$CH_2Cl_2$ adduct (90 mg, 0.110 mmol), $Pd_2(dba)_3$ (101 mg, 0.11 mmol) and heating at 90-100° C. for 1 h. This gave after workup and purification by flash column chromatography [silica (24 g), eluting with DMA-80 in DCM from 0-70%] ethyl 2-(2-((5-(3-(aminomethyl)phenyl)benzofuran-3-yl)methoxy)-5-methoxyphenyl)acetate (106b) (319 mg, 67% yield) as a colorless oil; $^1$H NMR (300 MHz, DMSO-$d_6$) δ 8.09 (s, 1H), 7.90 (d, J=1.7 Hz, 1H), 7.73-7.62 (m, 3H), 7.57-7.50 (m, 1H), 7.40 (t, J=7.5 Hz, 1H), 7.32 (d, J=7.3 Hz, 2H), 6.84 (s, 2H), 5.24 (s, 2H), 3.80 (s, 2H), 3.78 (q, 2H), 3.70 (s, 3H), 3.55 (s, 2H), 0.88 (t, J=7.1 Hz, 3H); MS (ES+): 446.10 (M+1).

Step-3: Preparation of 2-(2-((5-(3-(aminomethyl)phenyl)benzofuran-3-yl)methoxy)-5-methoxyphenyl)acetic acid (106c)

Compound 106c was prepared according to the procedure reported in step-3 of scheme 1, from ethyl 2-(2-((5-(3-(aminomethyl)phenyl)benzofuran-3-yl)methoxy)-5-methoxyphenyl)acetate (106b) (319 mg, 0.716 mmol) in THF (2 mL), methanol (0.2 mL) and water (0.2 mL) using a lithium hydroxide hydrate (68.6 mg, 2.86 mmol) and stirring at room temperature for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-5-methoxyphenyl)acetic acid (106c) (125 mg, 40% yield) HCl salt as a light brown solid; $^1$H NMR (300 MHz, DMSO-$d_6$) δ 12.17 (s, 1H), 8.37 (s, 3H), 8.10 (s, 1H), 7.99 (d, J=1.8 Hz, 1H), 7.87 (s, 1H), 7.78-7.63 (m, 3H), 7.52 (t, J=7.6 Hz, 1H), 7.46 (d, J=7.7 Hz, 1H), 7.13 (d, J=9.8 Hz, 1H), 6.86-6.82 (m, 2H), 5.25 (s, 2H), 4.11 (s, 2H), 3.70 (s, 3H), 3.51 (s, 2H); $^1$HNMR (300 MHz, DMSO/$D_2O$) δ 8.02 (s, 1H), 7.90 (s, 1H), 7.77 (s, 1H), 7.73-7.60 (m, 3H), 7.51 (t, J=7.7 Hz, 1H), 7.39 (d, J=7.8 Hz, 1H), 7.11 (d, J=8.7 Hz, 1H), 6.83-6.75 (m, 2H), 5.21 (s, 2H), 4.07 (s, 2H), 3.65 (s, 3H), 3.47 (s, 2H); MS (ES+): 418.1 (M+1); (ES−): 416.1 (M−1); Analysis calculated for $C_{25}H_{23}NO_5$·HCl·$2H_2O$: C, 63.63; H, 5.55; Cl, 7.51; N, 2.97. Found: C, 63.79; H, 5.25; Cl, 7.39; N, 2.93.

Scheme 107

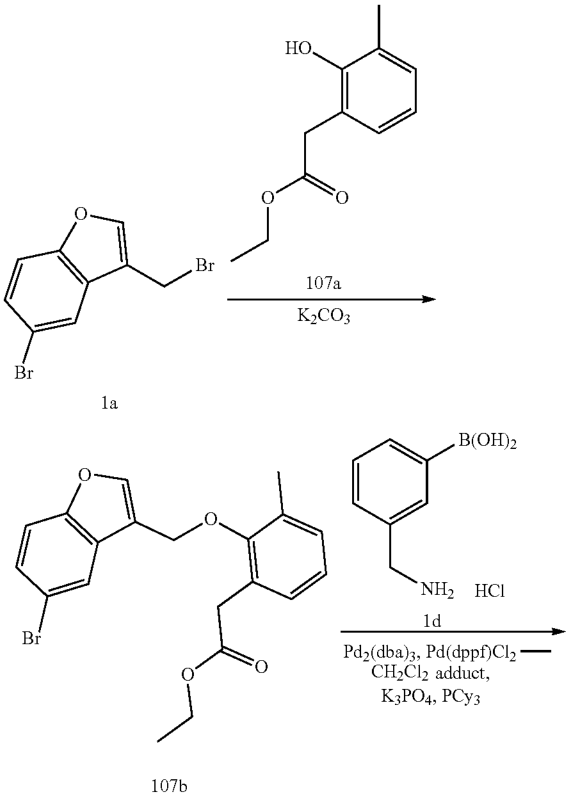

-continued

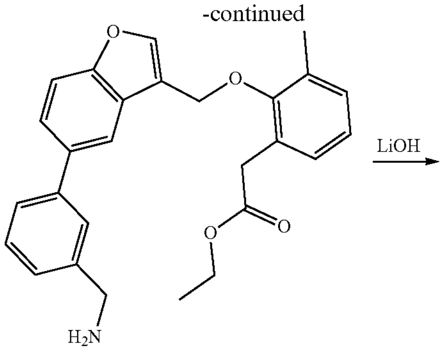

107c

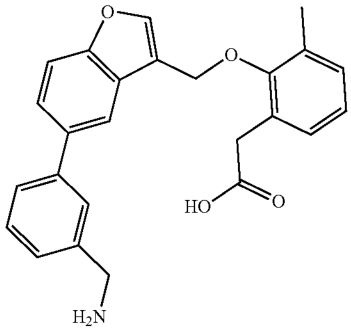

107d

Preparation of 2-(2-((5-(3-(aminomethyl)phenyl)benzofuran-3-yl)methoxy)-3-methylphenyl)acetic acid (107d)

Step-1: Preparation of ethyl 2-(2-((5-bromobenzofuran-3-yl)methoxy)-3-methylphenyl)acetate (107b)

Compound 107b was prepared according to the procedure reported in step-3 of scheme 7, from 5-bromo-3-(bromomethyl)benzofuran (1a) (500 mg, 1.724 mmol) in DMF (3 mL) using ethyl 2-(2-hydroxy-3-methylphenyl)acetate (107a) (0.798 g, 4.43 mmol; CAS #1261620-23-8), potassium carbonate (0.650 g, 4.70 mmol) and stirring overnight at room temperature. This gave after workup and purification by flash column chromatography [silica gel (12 g), eluting with ethyl acetate and hexanes from 0-50%] ethyl 2-(2-((5-bromobenzofuran-3-yl)methoxy)-3-methylphenyl)acetate (107b) (603 mg, 95% yield); $^1$H NMR (300 MHz, DMSO-$d_6$) δ 8.16 (s, 1H), 7.86 (d, J=2.0 Hz, 1H), 7.63 (d, J=8.8 Hz, 1H), 7.51 (dd, J=8.7, 2.1 Hz, 1H), 7.18 (dd, J=7.5, 1.9 Hz, 1H), 7.12 (dd, J=7.6, 1.9 Hz, 1H), 7.05 (d, J=7.4 Hz, 1H), 4.98 (s, 2H), 4.01 (q, J=7.2 Hz, 2H), 3.66 (s, 2H), 2.30 (s, 3H), 1.09 (t, J=7.1 Hz, 3H); MS (ES+): 402.90 (M+1).

Step-2: Preparation of ethyl 2-(2-((5-(3-(aminomethyl)phenyl)benzofuran-3-yl)methoxy)-3-methylphenyl)acetate (107c)

Compound 107c was prepared according to the procedure reported in step-2 of scheme 1, from ethyl 2-(2-((5-bromobenzofuran-3-yl)methoxy)-3-methylphenyl)acetate (107b) (603 mg, 1.438 mmol) in dioxane/THF (6 mL each) using 3-(aminomethyl)phenylboronic acid hydrochloride (1d) (539 mg, 2.88 mmol), 2M solution of $K_3PO_4$ (2.88 mL, 5.75 mmol), tricyclohexylphosphine (81 mg, 0.288 mmol), $PdCl_2$(dppf)-$CH_2Cl_2$ adduct (117 mg, 0.144 mmol), $Pd_2$(dba)$_3$ (132 mg, 0.144 mmol) and heating at 90-100° C. for 1 h. This gave after workup and purification by flash column chromatography [silica gel (24 g), eluting with DMA-80 in DCM from 0-70%] ethyl 2-(2-((5-(3-(aminomethyl)phenyl)benzofuran-3-yl)methoxy)-3-methylphenyl)acetate (107c) (349 mg, 57% yield) as a colorless oil; $^1$H NMR (300 MHz, DMSO-$d_6$) δ 8.13 (s, 1H), 7.92 (s, 1H), 7.75-7.61 (m, 3H), 7.52 (d, J=7.0 Hz, 1H), 7.41 (t, J=7.5 Hz, 1H), 7.33 (d, J=7.4 Hz, 1H), 7.18 (d, J=7.3 Hz, 1H), 7.13 (d, J=7.2 Hz, 1H), 7.04 (t, J=7.4 Hz, 1H), 5.05 (s, 2H), 4.03 (q, J=7.1 Hz, 2H), 3.81 (s, 2H), 3.69 (s, 2H), 2.33 (s, 3H), 1.02 (t, J=7.1 Hz, 3H); MS (ES+): 430.10 (M+1).

Step-3: Preparation of 2-(2-((5-(3-(aminomethyl)phenyl)benzofuran-3-yl)methoxy)-3-methylphenyl)acetic acid (107d)

Compound 107d was prepared according to the procedure reported in step-3 of scheme 1, from ethyl 2-(2-((5-(3-(aminomethyl)phenyl)benzofuran-3-yl)methoxy)-3-methylphenyl)acetate (107c) (349 mg, 0.813 mmol) in THF (2 mL), methanol (0.2 mL) and water (0.2 mL) using lithium hydroxide hydrate (78 mg, 3.25 mmol) and stirring at room temperature for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-3-methylphenyl)acetic acid (107d) (160 mg, 49% yield) HCl salt as a light brown solid; $^1$H NMR (300 MHz, DMSO-$d_6$) δ 12.31 (s, 1H), 8.49 (s, 3H), 8.16 (s, 1H), 8.01 (d, J=1.7 Hz, 1H), 7.87 (d, J=1.7 Hz, 1H), 7.77-7.66 (m, 3H), 7.59-7.44 (m, 2H), 7.22-7.11 (m, 2H), 7.03 (t, J=7.5 Hz, 1H), 5.04 (s, 2H), 4.11 (s, 2H), 3.64 (s, 2H), 2.32 (s, 3H); $^1$H NMR (300 MHz, DMSO-$d_6$/$D_2O$) δ 8.07 (s, 1H), 7.92 (d, J=1.7 Hz, 1H), 7.76 (d, J=1.8 Hz, 1H), 7.74-7.63 (m, 3H), 7.52 (t, J=7.6 Hz, 1H), 7.42 (d, J=7.6 Hz, 1H), 7.15 (dd, J=7.4, 1.9 Hz, 1H), 7.09 (dd, J=7.7, 1.9 Hz, 1H), 7.01 (t, J=7.4 Hz, 1H), 5.00 (s, 2H), 4.09 (s, 2H), 3.59 (s, 2H), 2.28 (s, 3H); MS (ES+): 402.1 (M+1); (ES−): 400.1 (M−1).

Scheme 108

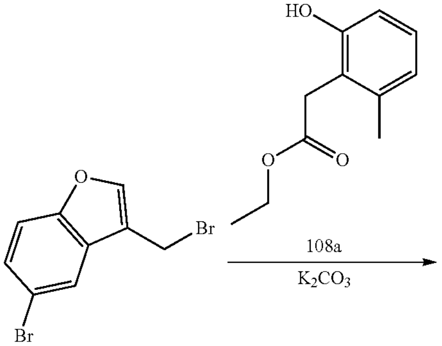

1a

-continued

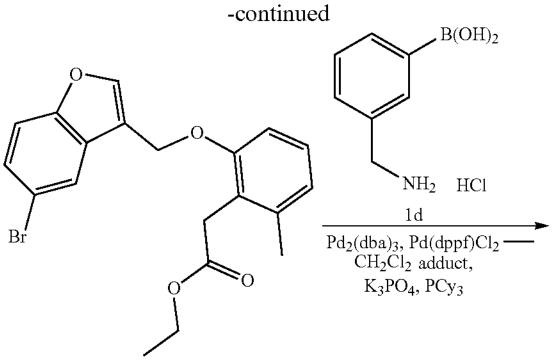

108b

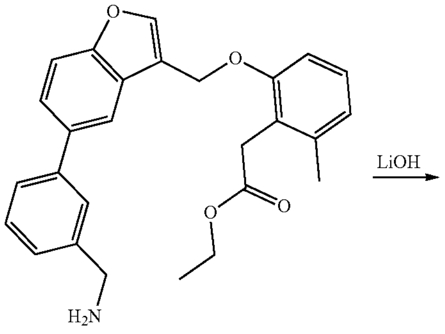

108c

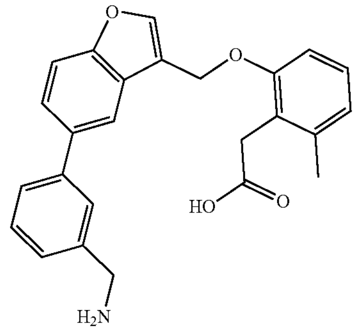

108d

Preparation of 2-(2-((5-(3-(aminomethyl)phenyl)benzofuran-3-yl)methoxy)-6-methylphenyl)acetic acid (108d)

Step-1: Preparation of ethyl 2-(2-((5-bromobenzofuran-3-yl)methoxy)-6-methylphenyl)acetate (108b)

Compound 108b was prepared according to the procedure reported in step-3 of scheme 7, from 5-bromo-3-(bromomethyl)benzofuran (1a) (500 mg, 1.724 mmol) in DMF (3 mL) using ethyl 2-(2-hydroxy-6-methylphenyl)acetate (108a) (0.304 g, 1.568 mmol; CAS #1261862-53-6), potassium carbonate (0.650 g, 4.70 mmol) and stirring overnight at room temperature.

This gave after workup and purification by flash column chromatography [silica gel (12 g), eluting with ethyl acetate and hexanes from 0-50%] ethyl 2-(2-((5-bromobenzofuran-3-yl)methoxy)-6-methylphenyl)acetate (108b)(438 mg, 69% yield); $^1$H NMR (300 MHz, DMSO-$d_6$) δ 8.15 (s, 1H), 7.84 (d, J=2.0 Hz, 1H), 7.62 (d, J=8.7 Hz, 1H), 7.50 (dd, J=8.7, 2.1 Hz, 1H), 7.17 (t, J=7.9 Hz, 1H), 7.04 (d, J=8.2 Hz, 1H), 6.83 (d, J=7.5 Hz, 1H), 5.23 (d, J=1.0 Hz, 2H), 3.97 (q, J=7.1 Hz, 2H), 3.61 (s, 2H), 2.22 (s, 3H), 1.03 (t, J=7.1 Hz, 3H); MS (ES+): 403.00 (M+1), 424.90 (M+Na).

Step-2: Preparation of ethyl 2-(2-((5-(3-(aminomethyl)phenyl)benzofuran-3-yl)methoxy)-6-methylphenyl)acetate (108c)

Compound 108c was prepared according to the procedure reported in step-2 of scheme 1, from ethyl 2-(2-((5-bromobenzofuran-3-yl)methoxy)-6-methylphenyl)acetate (108b)(438 mg, 1.086 mmol) in dioxane/THF (6 mL each) using 3-(aminomethyl)phenylboronic acid hydrochloride (1d) (407 mg, 2.172 mmol), 2 M solution of $K_3PO_4$ (2.172 mL, 4.34 mmol), tricyclohexylphosphine (60.9 mg, 0.217 mmol) $PdCl_2(dppf)$-$CH_2Cl_2$ adduct (89 mg, 0.109 mmol), $Pd_2(dba)_3$ (99 mg, 0.109 mmol) and heating at 90-100° C. for 1 h. This gave after workup and purification by flash column chromatography [silica gel (24 g), eluting with DMA-80 in DCM from 0-70%] ethyl 2-(2-((5-(3-(aminomethyl)phenyl)benzofuran-3-yl)methoxy)-6-methylphenyl)acetate (108c) (374 mg, 80% yield) as a colorless oil; $^1$H NMR (300 MHz, DMSO-$d_6$) δ 8.13 (s, 1H), 7.91 (d, J=1.7 Hz, 1H), 7.74-7.62 (m, 2H), 7.54 (d, J=8.8 Hz, 2H), 7.41 (t, J=7.6 Hz, 1H), 7.37-7.30 (m, 1H), 7.19 (t, 1H), 7.09 (d, J=8.2 Hz, 1H), 6.83 (d, J=7.4 Hz, 1H), 5.29 (s, 2H), 3.82 (s, 2H), 3.76 (q, J=7.1 Hz, 2H), 3.61 (s, 2H), 2.20 (s, 3H), 0.90 (t, J=7.1 Hz, 3H); MS (ES+): 430.10 (M+1).

Step-3: Preparation of 2-(2-((5-(3-(aminomethyl)phenyl)benzofuran-3-yl)methoxy)-6-methylphenyl)acetic acid (108d)

Compound 108d was prepared according to the procedure reported in step-3 of scheme 1, from ethyl 2-(2-((5-(3-(aminomethyl)phenyl)benzofuran-3-yl)methoxy)-6-methylphenyl)acetate (108c) (374 mg, 0.871 mmol) in THF (2 mL), methanol (0.2 mL) and water (0.2 mL) using lithium hydroxide hydrate (83 mg, 3.48 mmol) and stirring at room temperature for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-6-methylphenyl)acetic acid (108d) (103 mg, 30% yield) HCl salt as a light brown solid; $^1$H NMR (300 MHz, DMSO-$d_6$) δ 8.40 (s, 3H), 8.15 (s, 1H), 8.01 (d, J=1.7 Hz, 1H), 7.90-7.85 (m, 1H), 7.77-7.72 (m, 2H), 7.69 (dd, J=8.6, 1.8 Hz, 1H), 7.53 (t, J=7.6 Hz, 1H), 7.51-7.44 (m, 1H), 7.17 (t, J=7.8 Hz, 1H), 7.07 (d, J=8.2 Hz, 1H), 6.83 (d, J=7.4 Hz, 1H), 5.31 (s, 2H), 4.12 (s, 2H), 3.61 (s, 2H), 2.22 (s, 3H); $^1$H NMR (300 MHz, DMSO-$d_6$/$D_2O$) δ 8.07 (d, J=3.8 Hz, 1H), 7.93 (s, 1H), 7.77 (s, 1H), 7.74-7.63 (m, 3H), 7.51 (t, J=7.7 Hz, 1H), 7.45-7.35 (m, 1H), 7.15 (t, J=7.8 Hz, 1H), 7.04 (d, J=8.0 Hz, 1H), 6.82 (d, J=7.4 Hz, 1H), 5.26 (s, 2H), 4.09 (s, 2H), 3.57 (s, 2H), 2.18 (s, 3H); MS (ES+): 402.1 (M+1); (ES−): 400.1 (M−1); Analysis calculated for $C_{25}H_{23}NO_4 \cdot HCl \cdot 1.25H_2O$: C, 65.21; H, 5.80; Cl, 7.70; N, 3.04. found: C, 65.20; H, 5.80; Cl, 8.11; N, 3.03.

Scheme 109

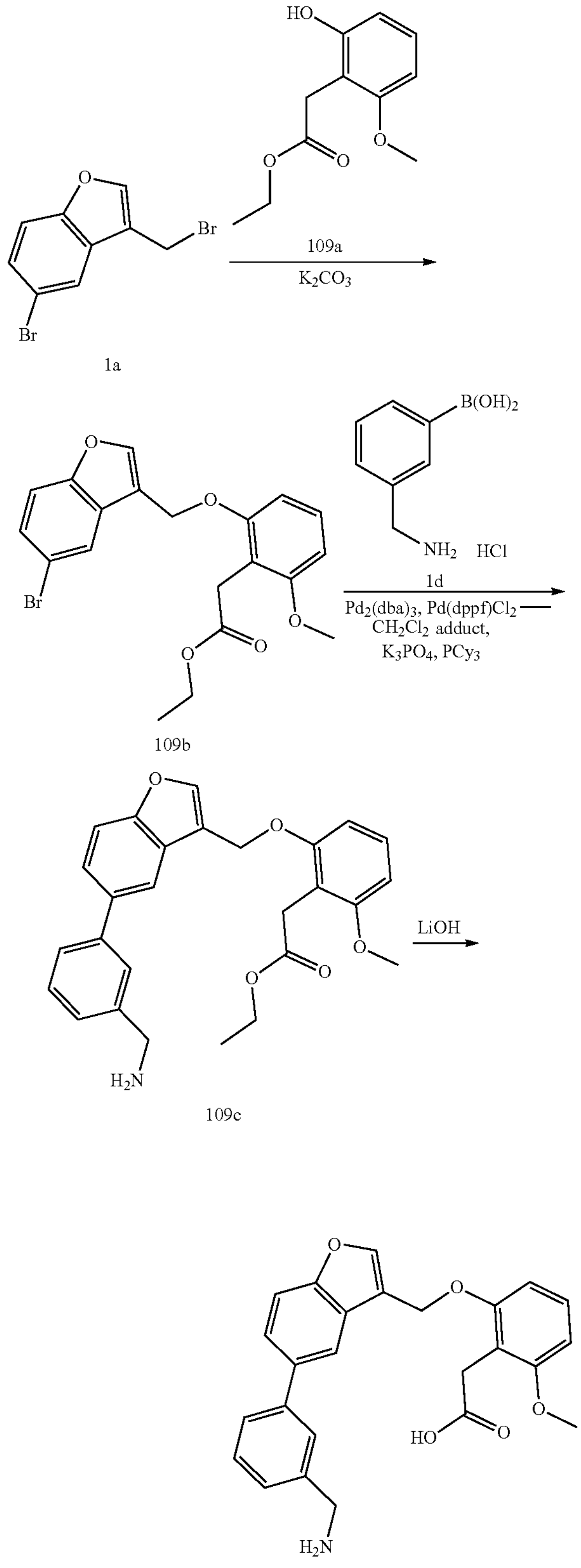

1a

109b

109c

109d

Preparation of 2-(2-((5-(3-(aminomethyl)phenyl) benzofuran-3-yl)methoxy)-6-methoxyphenyl)acetic acid (109d)

Step-1: Preparation of ethyl 2-(2-((5-bromobenzofuran-3-yl)methoxy)-6-methoxyphenyl)acetate (109b)

Compound 109b was prepared according to the procedure reported in step-3 of scheme 7, from 5-bromo-3-(bromomethyl)benzofuran (1a) (500 mg, 1.724 mmol) in DMF (3 mL) using ethyl 2-(2-hydroxy-6-methoxyphenyl)acetate (109a) (0.330 g, 1.568 mmol; CAS #187968-46-3), potassium carbonate (0.650 g, 4.70 mmol) and stirring overnight at room temperature.

This gave after workup and purification by flash column chromatography [silica gel (12 g), eluting with ethyl acetate and hexanes from 0-50%] ethyl 2-(2-((5-bromobenzofuran-3-yl)methoxy)-6-methoxyphenyl)acetate (109b) (422 mg, 64% yield); $^1H$ NMR (300 MHz, DMSO-$d_6$) δ 8.15 (s, 1H), 7.83 (d, J=2.0 Hz, 1H), 7.61 (d, J=8.7 Hz, 1H), 7.50 (dd, J=8.8, 2.1 Hz, 1H), 7.26 (t, J=8.3 Hz, 1H), 6.86 (d, J=8.3 Hz, 1H), 6.69 (d, J=8.3 Hz, 1H), 5.24 (s, 2H), 3.95 (q, J=7.1 Hz, 2H), 3.75 (s, 3H), 3.53 (s, 2H), 1.03 (t, J=7.1 Hz, 3H); MS (ES+): 440.90 (M+Na).

Step-2: Preparation of ethyl 2-(2-((5-(3-(aminomethyl)phenyl)benzofuran-3-yl)methoxy)-6-methoxyphenyl)acetate (109c)

Compound 109c was prepared according to the procedure reported in step-2 of scheme 1, from ethyl 2-(2-((5-bromobenzofuran-3-yl)methoxy)-6-methoxyphenyl)acetate (109b) (422 mg, 1.046 mmol) in dioxane/THF (6 mL each) using 3-(aminomethyl)phenylboronic acid hydrochloride (1d) (392 mg, 2.093 mmol), 2 M solution of $K_3PO_4$ (2.093 mL, 4.19 mmol), tricyclohexylphosphine (58.7 mg, 0.209 mmol), $PdCl_2$(dppf)-$CH_2Cl_2$ adduct (85 mg, 0.105 mmol), $Pd_2(dba)_3$ (96 mg, 0.105 mmol) and heating at 90-100° C. for 1 h. This gave after workup and purification by flash column chromatography [silica (24 g), eluting with DMA-80 in DCM from 0-70%] ethyl 2-(2-((5-(3-(aminomethyl) phenyl)benzofuran-3-yl)methoxy)-6-methoxyphenyl)acetate (109c) (154 mg, 33% yield) as a colorless oil; $^1H$ NMR (300 MHz, DMSO-$d_6$) δ 8.12 (s, 1H), 7.90 (d, J=1.7 Hz, 1H), 7.73-7.62 (m, 3H), 7.58-7.49 (m, 1H), 7.40 (t, J=7.5 Hz, 1H), 7.34-7.29 (m, 1H), 7.26 (d, J=8.4 Hz, 1H), 6.91 (d, J=8.3 Hz, 1H), 6.69 (d, J=8.3 Hz, 1H), 5.31 (s, 2H), 3.80 (d, J=2.0 Hz, 2H), 3.77-3.71 (m, 5H), 3.53 (s, 2H), 0.90 (t, J=7.1 Hz, 3H); MS (ES+): 446.10 (M+1).

Step-3: Preparation of 2-(2-((5-(3-(aminomethyl) phenyl)benzofuran-3-yl)methoxy)-6-methoxyphenyl)acetic acid (109d)

Compound 109d was prepared according to the procedure reported in step-3 of scheme 1, from ethyl 2-(2-((5-(3-(aminomethyl)phenyl)benzofuran-3-yl)methoxy)-6-methoxyphenyl)acetate (109c) (156 mg, 0.350 mmol) in THF (2 mL), methanol (0.2 mL) and water (0.2 mL) using lithium hydroxide hydrate (63.5 mg, 1.401 mmol) and stirring at RT for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-6-methoxyphenyl)acetic acid (109d) (26 mg, 18% yield) HCl salt as a light brown solid; $^1H$ NMR (300 MHz, DMSO-$d_6$) δ 12.10-12.00 (m, 1H), 8.40-8.29 (m, 3H), 8.14 (s, 1H), 7.99 (d, J=1.7 Hz, 1H), 7.86 (s, 1H), 7.77-7.71 (m, 2H), 7.68 (dd, J=8.7, 1.8 Hz, 1H), 7.53 (t, J=7.6 Hz, 1H), 7.46 (d, J=7.6 Hz, 1H), 7.25 (t, J=8.3 Hz, 1H), 6.89 (d, J=8.3 Hz, 1H), 6.68 (d, J=8.3 Hz, 1H), 5.32 (s, 2H), 4.12 (s, 2H), 3.75 (s, 3H), 3.51 (s, 2H); MS (ES+): 418.10 (M+1); (ES−): 416.10 (M−1); Analysis calculated for $C_{25}H_{23}NO_5 \cdot 1HCl \cdot 1H_2O$: C, 63.63; H, 5.55; Cl, 7.51; N, 2.97. Found: C, 63.83; H, 5.44; Cl, 7.81; N, 2.99.

Scheme 110

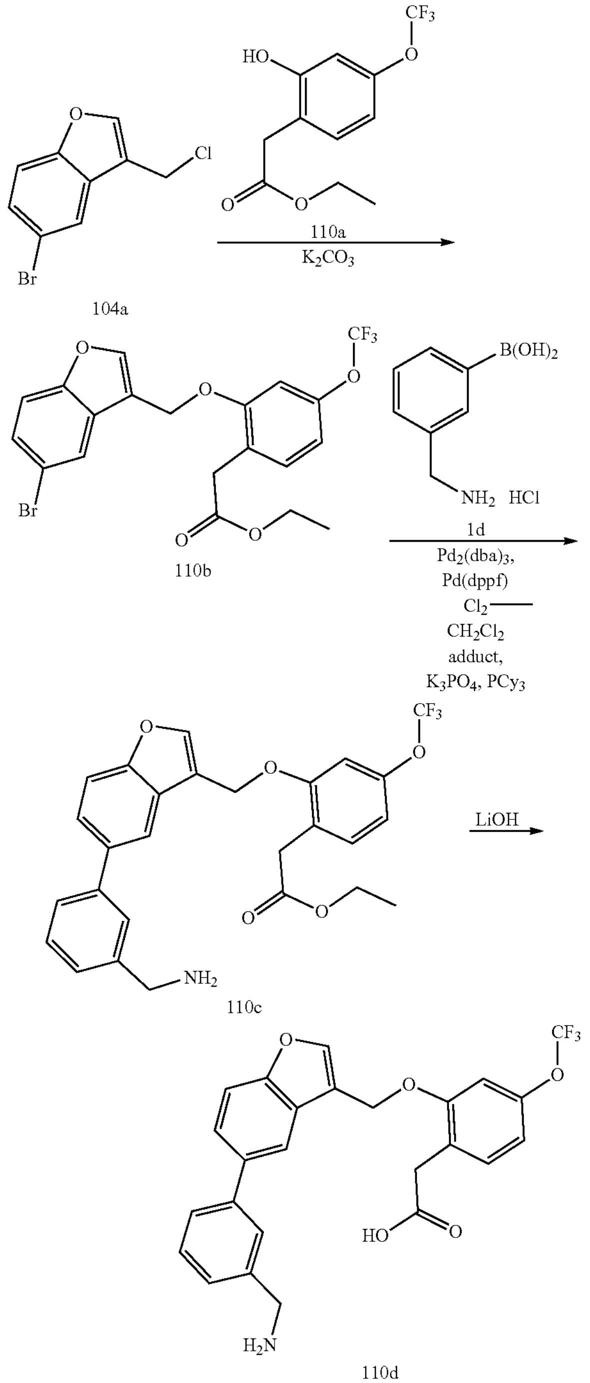

104a, 110b, 110c, 110d

Preparation of 2-(2-((5-(3-(aminomethyl)phenyl)benzofuran-3-yl)methoxy)-4-(trifluoromethoxy)phenyl)acetic acid (110d)

Step-1: Preparation of ethyl 2-(2-((5-bromobenzofuran-3-yl)methoxy)-4-(trifluoromethoxy)phenyl)acetate (110b)

Compound 110b was prepared according to the procedure reported in step-3 of scheme 7, from 5-bromo-3-(chloromethyl)benzofuran (104a) (500 mg, 2.037 mmol) in DMF (4 mL) using ethyl 2-(2-hydroxy-4-(trifluoromethoxy)phenyl)acetate (110a) (0.489 g, 1.852 mmol; CAS #1261673-71-5), potassium carbonate (0.768 g, 5.55 mmol) and stirring overnight at room temperature. This gave after workup and purification by flash column chromatography [silica gel (12 g), eluting with ethyl acetate and hexanes from 0-50%] ethyl 2-(2-((5-bromobenzofuran-3-yl)methoxy)-4-(trifluoromethoxy)phenyl)acetate (110b) (815 mg, 93% yield); $^1H$ NMR (300 MHz, DMSO-$d_6$) δ 8.16 (s, 1H), 7.87 (d, J=2.0 Hz, 1H), 7.63 (d, J=8.8 Hz, 1H), 7.59-7.48 (m, 1H), 7.35 (d, J=8.3 Hz, 1H), 7.24 (d, J=2.3 Hz, 1H), 6.96 (d, 1H), 5.30 (s, 2H), 3.94 (q, J=7.1 Hz, 2H), 3.60 (s, 2H), 0.98 (t, J=7.1 Hz, 3H); $^{19}F$ NMR (282 MHz, DMSO-$d_6$) δ −56.65; MS (ES+): 494.90 (M+Na).

Step-2: Preparation of ethyl 2-(2-((5-(3-(aminomethyl)phenyl)benzofuran-3-yl)methoxy)-4-(trifluoromethoxy)phenyl)acetate (110c)

Compound 110c was prepared according to the procedure reported in step-2 of scheme 1, from ethyl 2-(2-((5-bromobenzofuran-3-yl)methoxy)-4-(trifluoromethoxy)phenyl)acetate (110b) (815 mg, 1.722 mmol) in dioxane/THF (6 mL each) using 3-(aminomethyl)phenylboronic acid hydrochloride (1d) (646 mg, 3.44 mmol), 2 M solution of $K_3PO_4$ (3.44 mL, 6.89 mmol), tricyclohexylphosphine (97 mg, 0.344 mmol), $PdCl_2(dppf)$-$CH_2Cl_2$ adduct (141 mg, 0.172 mmol), $Pd_2(dba)_3$ (158 mg, 0.172 mmol) and heating at 90-100° C. for 1 h. This gave after workup and purification by flash column chromatography [silica gel (24 g), eluting with DMA-80 in DCM from 0-70%] ethyl 2-(2-((5-(3-(aminomethyl)phenyl)benzofuran-3-yl)methoxy)-4-(trifluoromethoxy)phenyl)acetate (110c) (263 mg, 31% yield) as a colorless oil; $^1H$ NMR (300 MHz, DMSO-$d_6$) δ 8.14 (s, 1H), 7.93 (d, J=1.7 Hz, 1H), 7.73-7.64 (m, 3H), 7.60-7.48 (m, 2H), 7.40 (t, J=7.5 Hz, 1H), 7.36-7.31 (m, 1H), 7.29 (d, J=2.3 Hz, 1H), 6.99-6.92 (m, 1H), 5.36 (s, 2H), 3.81 (s, 2H), 3.72 (t, J=7.1 Hz, 2H), 3.59 (s, 2H), 0.85 (t, J=7.1 Hz, 3H); $^{19}F$ NMR (282 MHz, DMSO-$d_6$) δ-56.63; MS (ES+): 500.10 (M+1).

Step-3: Preparation of 2-(2-((5-(3-(aminomethyl)phenyl)benzofuran-3-yl)methoxy)-4-(trifluoromethoxy)phenyl)acetic acid (110d)

Compound 110d was prepared according to the procedure reported in step-3 of scheme 1, from ethyl 2-(2-((5-(3-(aminomethyl)phenyl)benzofuran-3-yl)methoxy)-4-(trifluoromethoxy)phenyl)acetate (110c) (263 mg, 0.527 mmol) in THF (2 mL), methanol (0.2 mL) and water (0.2 mL) using lithium hydroxide hydrate (50.4 mg, 2.106 mmol) and stirring at room temperature for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-4-(trifluoromethoxy)phenyl)acetic acid (110d) (114 mg, 46% yield) HCl salt as a light brown solid; $^1H$ NMR (300 MHz, DMSO-$d_6$) δ 12.23 (s, 1H), 8.37-8.28 (m, 3H), 8.15 (s, 1H), 8.04-8.01 (m, 1H), 7.88 (s, 1H), 7.76 (d, J=8.7 Hz, 2H), 7.69 (dd, J=8.6, 1.8 Hz, 1H), 7.54 (t, J=7.6 Hz, 1H), 7.46 (d, J=7.6 Hz, 1H), 7.34 (d, J=8.3 Hz, 1H), 7.27 (d, J=2.3 Hz, 1H), 6.95 (d, J=8.3 Hz, 1H), 5.38 (s, 2H), 4.12 (s, 2H), 3.57 (s, 2H); $^{19}F$ NMR (282 MHz, DMSO-$d_6$) δ −56.70; MS (ES+) 472.00 (M+1); (ES−): 470.00 (M−1); Analysis calculated for $C_{25}H_{20}F_3NO_5 \cdot 1.1HCl \cdot H_2O$: C, 56.70; H, 4.40; Cl, 7.36; N, 2.65. Found: C, 56.62; H, 4.42; Cl, 7.12; N, 2.72.

Scheme 111

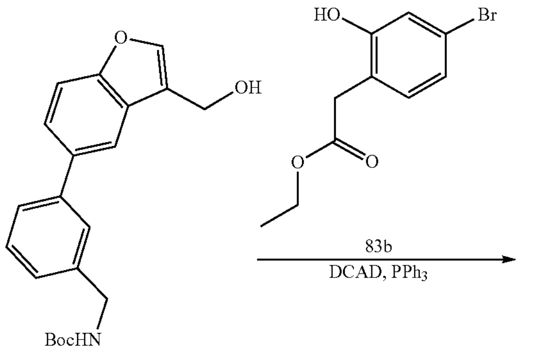

39b

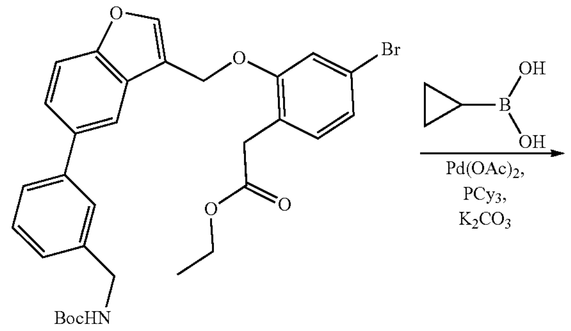

111a

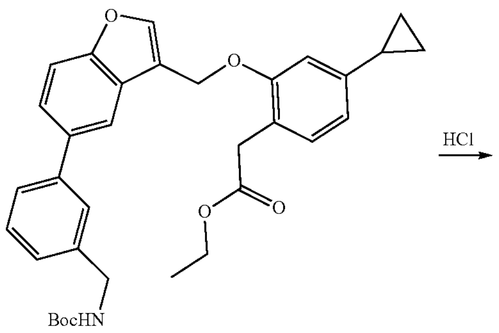

111b

-continued

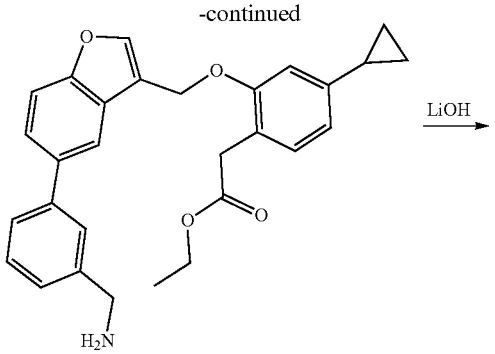

111c

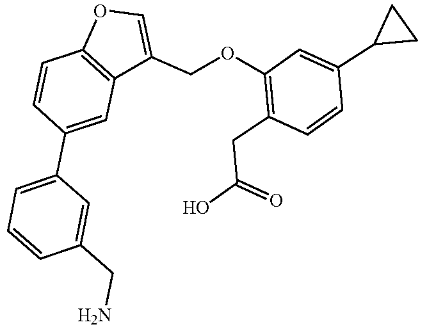

111d

Preparation of 2-(2-((5-(3-(aminomethyl)phenyl) benzofuran-3-yl)methoxy)-4-cyclopropylphenyl) acetic acid (111d)

Step-1: Preparation of ethyl 2-(4-bromo-2-((5-(3-(((tert-butoxycarbonyl)amino)methyl)phenyl) benzofuran-3-yl)methoxy)phenyl)acetate (111a)

Compound 111a was prepared according to the procedure reported in step-3 of scheme 7, from tert-butyl 3-(3-(hydroxymethyl)benzofuran-5-yl)benzylcarbamate (39b) (400 mg, 1.132 mmol) in DCM (7 mL) using triphenylphosphine (386 mg, 1.471 mmol), ethyl 2-(4-bromo-2-hydroxyphenyl) acetate (83b) (440 mg, 1.698 mmol), a solution of bis(4-chlorobenzyl) diazene-1,2-dicarboxylate (DCAD) (540 mg, 1.471 mmol) in DCM (3 mL) and stirring at room temperature for 3 h. This gave after workup and purification by flash column chromatography [silica gel (12 g), eluting with EtOAc in hexane from 0-50%] ethyl 2-(4-bromo-2-((5-(3-(((tert-butoxycarbonyl)amino)methyl)phenyl)benzofuran-3-yl)methoxy)phenyl)acetate (111a) (358 mg, 53% yield) as a white solid; $^1H$ NMR (300 MHz, DMSO-$d_6$) δ 8.13 (s, 1H), 7.89 (d, J=1.8 Hz, 1H), 7.71 (d, J=8.6 Hz, 1H), 7.62 (dd, J=8.5, 1.8 Hz, 1H), 7.59-7.53 (m, 2H), 7.48-7.40 (m, 3H), 7.23 (d, J=7.6 Hz, 1H), 7.21-7.10 (m, 1H), 6.95 (m, 1H), 5.33 (s, 2H), 4.21 (d, J=6.0 Hz, 2H), 3.71 (q, J=7.1 Hz, 2H), 3.54 (s, 2H), 1.39 (s, 9H), 0.87-0.76 (m, 3H); MS (ES+): 616.00 (M+Na).

Step-2: Preparation of ethyl 2-(2-((5-(3-(((tert-butoxycarbonyl)amino)methyl)phenyl)benzofuran-3-yl)methoxy)-4-cyclopropylphenyl)acetate (111b)

To a solution of ethyl 2-(4-bromo-2-((5-(3-(((tert-butoxycarbonyl)amino)methyl)phenyl)benzofuran-3-yl)methoxy) phenyl)acetate (111a) (358 mg, 0.602 mmol) in toluene (5 mL) and water (0.25 mL) were added cyclopropyl boronic acid (67.2 mg, 0.783 mmol), palladium acetate (6.76 mg, 0.030 mmol), tricyclohexylphosphine (152 mg, 0.542 mmol) and potassium carbonate (291 mg, 2.108 mmol) under an argon atmosphere and heated at 80° C. for 1 h. The reaction mixture was cooled and concentrated under vacuum. The obtained residue was purified by flash column chromatography [silica gel, (40 g) eluting with ethyl acetate in hexanes from 0 to 20%] to afford ethyl 2-(2-((5-(3-(((tert-butoxycarbonyl)amino)methyl)phenyl)benzofuran-3-yl)methoxy)-4-cyclopropylphenyl)acetate (111b) (226 mg, 67.5% yield); $^1$H NMR (300 MHz, DMSO-$d_6$) δ 8.12 (s, 1H), 7.89 (d, J=1.8 Hz, 1H), 7.71 (d, J=8.6 Hz, 1H), 7.65-7.56 (m, 3H), 7.53-7.35 (m, 2H), 7.23 (d, J=7.5 Hz, 1H), 7.05 (d, J=7.7 Hz, 1H), 6.91 (d, J=1.6 Hz, 1H), 6.65 (dd, J=7.8, 1.6 Hz, 1H), 5.28 (s, 2H), 4.21 (d, J=6.0 Hz, 2H), 3.72 (q, J=7.1 Hz, 2H), 3.49 (s, 2H), 1.92 (td, J=8.4, 4.2 Hz, 1H), 1.39 (s, 9H), 0.99-0.88 (m, 2H), 0.84 (t, J=7.1 Hz, 3H), 0.73 (dt, J=5.2, 3.0 Hz, 2H); MS (ES+): 578.10 (M+Na).

Step-3: Preparation of ethyl 2-(2-((5-(3-(aminomethyl)phenyl)benzofuran-3-yl)methoxy)-4-cyclopropylphenyl)acetate (111c)

Compound 111c was prepared according to the procedure reported in step-2 of scheme 7, from ethyl 2-(2-((5-(3-(((tert-butoxycarbonyl)amino)methyl)phenyl)benzofuran-3-yl)methoxy)-4-cyclopropylphenyl)acetate (111b) (201 mg, 0.414 mmol) using HCl (4N in dioxane, 0.517 mL, 2.070 mmol) in EtOH (4 mL) and stirring at room temperature for 16 h. This gave after workup ethyl 2-(2-((5-(3-(aminomethyl)phenyl)benzofuran-3-yl)methoxy)-4-cyclopropylphenyl)acetate (111c) (155 mg, 97% yield) which was used as such for the next step; $^1$H NMR (300 MHz, DMSO-$d_6$) δ 8.32 (s, 3H), 8.14 (s, 1H), 7.96 (s, 1H), 7.86 (s, 1H), 7.82-7.71 (m, 2H), 7.68 (d, J=8.6 Hz, 1H), 7.53 (t, J=7.6 Hz, 1H), 7.46 (d, J=7.7 Hz, 1H), 7.06 (d, J=7.7 Hz, 1H), 6.92 (s, 1H), 6.65 (d, J=7.8 Hz, 1H), 5.29 (s, 2H), 4.12 (s, 2H), 3.73 (q, J=7.2 Hz, 2H), 3.48 (s, 2H), 2.00-1.89 (m, 1H), 1.01-0.89 (m, 2H), 0.85 (t, J=7.1 Hz, 3H), 0.80-0.67 (m, 2H); MS (ES+): 456.10 (M+1).

Step-4: Preparation of 2-(2-((5-(3-(aminomethyl)phenyl)benzofuran-3-yl)methoxy)-4-cyclopropylphenyl)acetic acid (111d)

Compound 111d was prepared according to the procedure reported in step-3 of scheme 1, from ethyl 2-(2-((5-(3-(aminomethyl)phenyl)benzofuran-3-yl)methoxy)-4-cyclopropylphenyl)acetate (111c) (155 mg, 0.340 mmol) in THF (2 mL), methanol (0.2 mL) and water (0.2 mL) using lithium hydroxide hydrate (32.6 mg, 1.361 mmol) and stirring at room temperature for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-4-cyclopropylphenyl)acetic acid (111d) (43 mg, 30% yield) HCl salt as a light brown solid; $^1$H NMR (300 MHz, DMSO-$d_6$) δ 12.09 (bs, 1H) 8.30 (bs, 3H), 8.13 (s, 1H), 8.01 (d, J=1.8 Hz, 1H), 7.88 (s, 1H), 7.80-7.72 (m, 2H), 7.72-7.63 (m, 1H), 7.54 (t, J=7.6 Hz, 1H), 7.46 (d, J=7.7 Hz, 1H), 7.06 (d, J=7.7 Hz, 1H), 6.91 (d, J=1.7 Hz, 1H), 6.69-6.61 (m, 1H), 5.32 (s, 2H), 4.12 (s, 2H), 3.47 (s, 2H), 1.98-1.86 (m, 1H), 0.99-0.89 (m, 2H), 0.75-0.64 (m, 2H); MS (ES+): 428.10 (M+1), ES−) 426.1 (M−1); Analysis calculated for $C_{27}H_{25}NO_4$·1.1HCl·1.25$H_2O$: C, 66.17; H, 5.88; Cl, 7.96; N, 2.86. Found: C, 66.18; H, 5.72; Cl, 8.09; N, 3.04.

Scheme 112

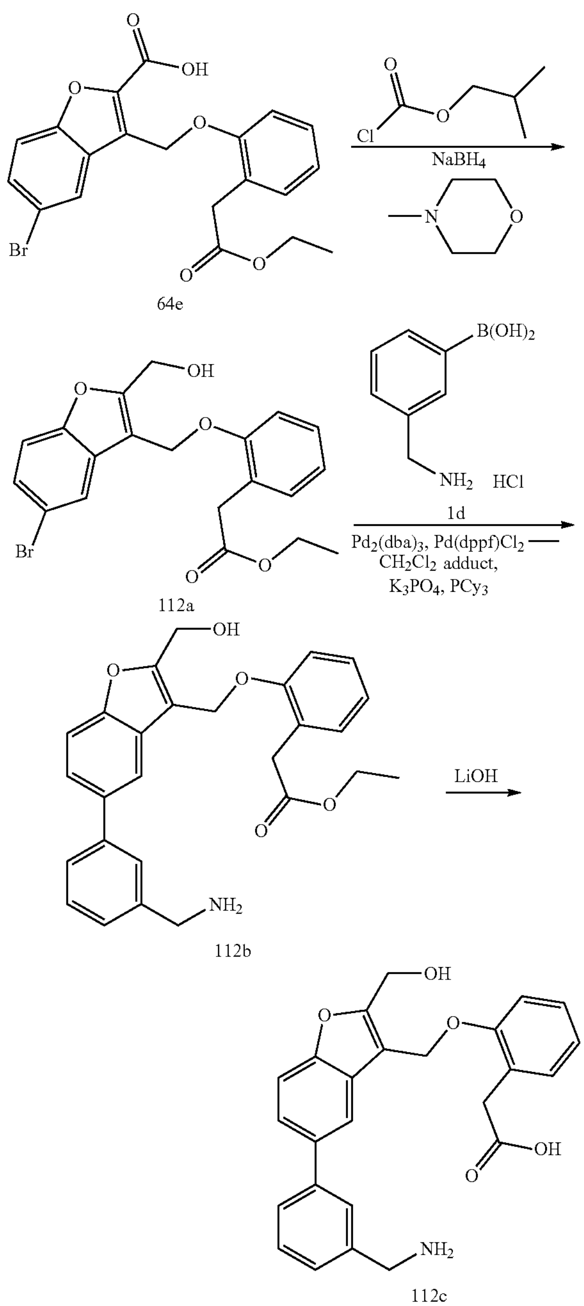

Preparation of 2-(2-((5-(3-(aminomethyl)phenyl)-2-(hydroxymethyl)benzofuran-3-yl)methoxy)phenyl)acetic acid (112c)

Step-1: Preparation of ethyl 2-(2-((5-bromo-2-(hydroxymethyl)benzofuran-3-yl)methoxy)phenyl)acetate (112a)

Compound 112a was prepared according to the procedure reported in step-1 of scheme 8, from 5-bromo-3-((2-(2- ethoxy-2-oxoethyl)phenoxy)methyl)benzofuran-2-carboxylic acid (64e) (5.5 g, 12.69 mmol) in THF (40 mL) using N-Methylmorpholine (1.675 mL, 15.23 mmol), isobutyl chloroformate (2.001 mL, 15.23 mmol) and a solution of $NaBH_4$ (1.441 g, 38.1 mmol) in water (2.0 mL). This gave after workup and purification by flash column chromatography [silica (24 g), eluting with EtOAc/MeOH (9:1) in hexane from 0-50%] ethyl 2-(2-((5-bromo-2-(hydroxymethyl)benzofuran-3-yl)methoxy)phenyl)acetate (112a) (3.8 g, 71% yield) as a colorless oil; $^1H$ NMR (300 MHz, DMSO-$d_6$) δ 7.80 (d, J=2.0 Hz, 1H), 7.58 (d, J=8.7 Hz, 1H), 7.48 (dd, J=8.7, 2.1 Hz, 1H), 7.30 (td, J=7.9, 1.7 Hz, 1H), 7.21 (dd, J=7.4, 1.6 Hz, 2H), 6.97-6.88 (m, 1H), 5.57 (t, J=5.8 Hz, 1H), 5.26 (s, 2H), 4.67 (d, J=5.8 Hz, 2H), 3.92 (t, J=7.1 Hz, 2H), 3.54 (s, 2H), 0.97 (t, J=7.1 Hz, 3H).

Step-2: Preparation of ethyl 2-(2-((5-(3-(aminomethyl)phenyl)-2-(hydroxymethyl)benzofuran-3-yl)methoxy)phenyl)acetate (112b)

Compound 112b was prepared according to the procedure reported in step-2 of scheme 1, from ethyl 2-(2-((5-bromo-2-(hydroxymethyl)benzofuran-3-yl)methoxy)phenyl)acetate (112a) (500 mg, 1.193 mmol) in dioxane/THF (15 mL each) using 3-(aminomethyl)phenylboronic acid hydrochloride (1d) (447 mg, 2.385 mmol), 4 M solution of $K_3PO_4$ (1.193 mL, 4.77 mmol), tricyclohexylphosphine (100 mg, 0.358 mmol), $PdCl_2$(dppf)-$CH_2Cl_2$ adduct (97 mg, 0.119 mmol), $Pd_2(dba)_3$ (109 mg, 0.119 mmol) and heating at 90° C. for 1 h. This gave after workup and purification by flash column chromatography [silica (24 g), eluting with DMA-80 in DCM from 0-70%] ethyl 2-(2-((5-(3-(aminomethyl)phenyl)-2-(hydroxymethyl)benzofuran-3-yl)methoxy)phenyl)acetate (112b) (242 mg, 46% yield) as a yellow semi-solid; MS (ES+): 446.3 (M+1).

Step-3: Preparation of 2-(2-((5-(3-(aminomethyl)phenyl)-2-(hydroxymethyl)benzofuran-3-yl)methoxy)phenyl)acetic acid (112c)

Compound 112c was prepared according to the procedure reported in step-3 of scheme 1, from ethyl 2-(2-((5-(3-(aminomethyl)phenyl)-2-(hydroxymethyl)benzofuran-3-yl)methoxy)phenyl)acetate (112b) (242 mg, 0.543 mmol) in THF (3 mL) using a solution of lithium hydroxide hydrate (150 mg, 3.58 mmol) in water (1 mL) and stirring at 50° C. for 1 h. This gave after workup and purification by reverse phase column chromatography [C18 column (30 g), eluting with ACN in water (containing 0.1% HCl) from 0-100%] 2-(2-((5-(3-(aminomethyl)phenyl)-2-(hydroxymethyl)benzofuran-3-yl)methoxy)phenyl)acetic acid (112c) (74 mg, 15% yield) HCl salt as a white solid; $^1H$ NMR (300 MHz, DMSO-$d_6$) δ 12.12 (s, 1H, $D_2O$ exchangeable), 8.39 (s, 3H, $D_2O$ exchangeable), 7.98 (d, J=1.6 Hz, 1H), 7.87 (s, 1H), 7.73 (dd, J=6.6, 4.7 Hz, 1H), 7.70-7.62 (m, 2H), 7.48 (dt, J=14.5, 7.6 Hz, 2H), 7.27 (dd, J=6.6, 1.7 Hz, 2H), 7.23-7.17 (m, 1H), 6.97-6.88 (m, 1H), 5.56 (s, 1H, $D_2O$ exchangeable), 5.33 (s, 2H), 4.69 (s, 2H), 4.10 (s, 2H), 3.51 (s, 2H); MS (ES+): 418.2 (M+1); (ES−): 416.1 (M−1); Analysis calculated for $C_{25}H_{23}NO_5 \cdot HCl \cdot 0.75H_2O$: C, 64.24; H, 5.50; Cl, 7.58; N, 3.00. Found: C, 64.46; H, 5.32; Cl, 7.78; N, 3.19.

Scheme 113

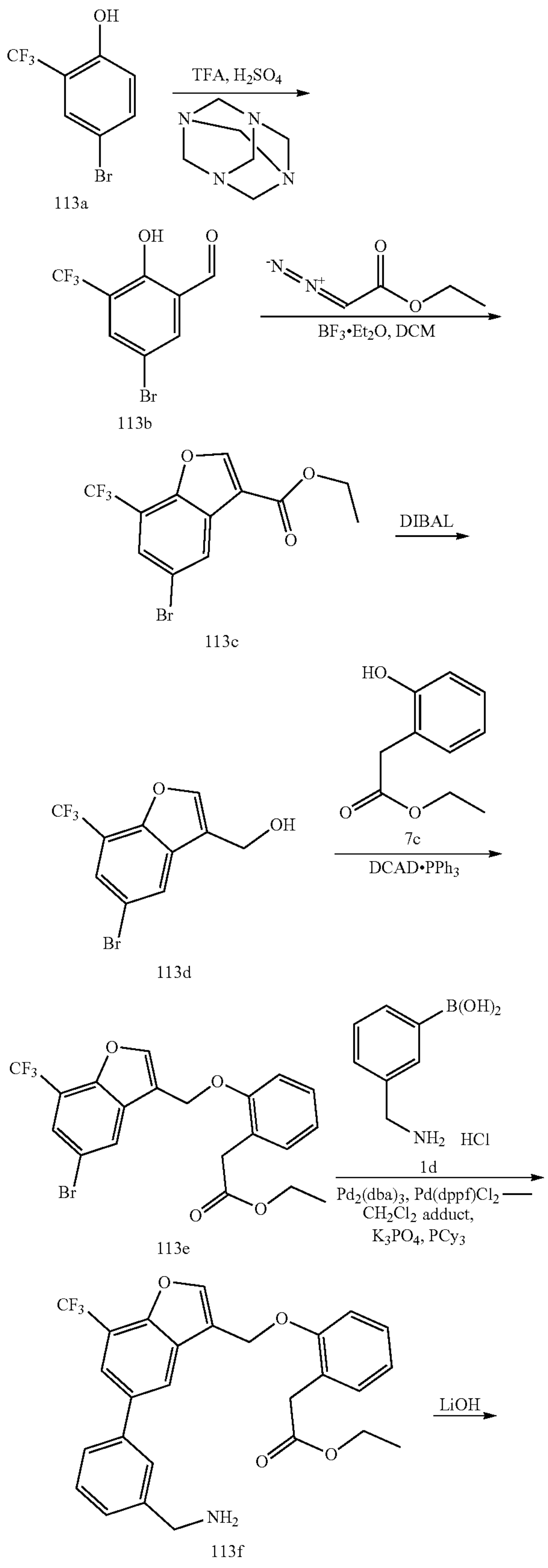

113a
113b
113c
7c
113d
113e
113f

-continued

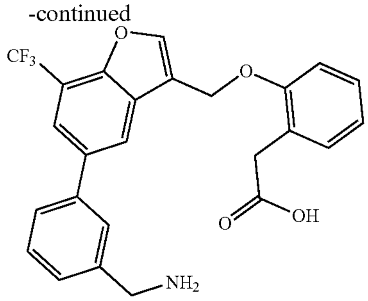

113g

Preparation of 2-(2-((5-(3-(aminomethyl)phenyl)-7-(trifluoromethyl)benzofuran-3-yl)methoxy)phenyl) acetic acid (113g)

Step-1: Preparation of 5-bromo-2-hydroxy-3-(trifluoromethyl)benzaldehyde (113b)

To a stirred solution of 4-bromo-2-(trifluoromethyl) phenol (113a) (2.0 g, 8.30 mmol) in TFA (5.0 mL) was added hexamethylenetetramine (2.32 g, 16.54 mmol) and heated at 90° C. for 24 h. The reaction mixture was cooled to room temperature and poured into a solution of concentrated sulphuric acid (5.0 mL) and water (10 mL), stirred at room temperature for 3 h and diluted with EtOAc (100 mL), water (100 mL). The organic layer was separated concentrated in vacuum and purified by flash column chromatography [silica gel, using 5% EtOAc in heptane] to give 5-bromo-2-hydroxy-3-(trifluoromethyl)benzaldehyde (113b) (1.0 g, 45.4% yield) as a yellow solid; $^1$H NMR (400 MHz, $CDCl_3$) δ 11.61 (s, 1H), 9.89 (s, 1H), 7.88 (s, 1H), 7.86 (s, 1H).

Step-2: Preparation of ethyl 5-bromo-7-(trifluoromethyl)benzofuran-3-carboxylate (113c)

To a stirred solution of 5-bromo-2-hydroxy-3-(trifluoromethyl)benzaldehyde (113b) (1.0 g, 3.717 mmol) in DCM (20 mL) was added boron trifluoride etherate (0.114 mL, 0.371 mmol) at room temperature and stirred for 10 minutes. To this mixture was added dropwise a solution of ethyl diazoacetate (4.52 mL, 5.94 mmol, 15% in toluene. Once gas evolution was ceased, the solvents were evaporated in vacuum and to the oil obtained was added sulphuric acid (0.5 mL) drop wise with vigorous stirring. The acidic reaction mixture was neutralized by slow addition of aqueous saturated $NaHCO_3$ solution (100 mL) and extracted with EtOAc (2×100 mL). The combined organics were washed with brine (2×100 mL), dried, filtered and concentrated in vacuum. The obtained residue was purified by column chromatography [silica gel (mesh size: 320-400), eluting with EtOAc in n-heptane from 0% to 5%] to give ethyl 5-bromo-7-(trifluoromethyl)benzofuran-3-carboxylate (113c) (0.63 g, 50%); $^1$H NMR (300 MHz, $CDCl_3$) δ 8.35 (d, J=2.0 Hz, 1H), 8.26 (s, 1H), 7.68 (s, 1H), 4.37 (q, J=7.1 Hz, 2H), 1.37 (t, J=7.1 Hz, 3H).

Step-3: Preparation of (5-bromo-7-(trifluoromethyl) benzofuran-3-yl)methanol (113d)

To a stirred solution of ethyl 5-bromo-7-(trifluoromethyl) benzofuran-3-carboxylate (113c) (4.0 g, 11.86 mmol) in DCM (100 mL) was added DIBAL (40.0 mL, 5.33 mmol, 1M solution in toluene) drop wise at −65° C. and stirred at −65° C. for 30 mins. The reaction mixture was quenched with MeOH (40 mL) and 1N HCl (50 mL) at −65° C. and warmed to room temperature and extracted with ethyl acetate (2×100 mL). The combined organics were washed with brine (100 mL), dried, filtered and concentrated in vacuum. The obtained residue was purified by column chromatography [silica gel (mesh size: 320-400), eluting with EtOAc in n-heptane from 0%-30%] to give (5-bromo-7-(trifluoromethyl)benzofuran-3-yl)methanol (113d) (1.08 g, 31.03%); $^1$H NMR (300 MHz, DMSO-$d_6$) δ 8.37-8.19 (m, 1H), 8.15 (d, J=1.2 Hz, 1H), 7.84 (d, J=1.9 Hz, 1H), 5.34 (t, J=5.6 Hz, 1H), 4.66 (d, J=5.5 Hz, 2H).

Step-4: Preparation of ethyl 2-(2-((5-bromo-7-(trifluoromethyl)benzofuran-3-yl)methoxy)phenyl)acetate (113e)

Compound 113e was prepared according to the procedure reported in step-3 of scheme 7, from (5-bromo-7-(trifluoromethyl)benzofuran-3-yl)methanol (113d) (500 mg, 1.695 mmol) in DCM (35 mL) using triphenylphosphine (578 mg, 2.203 mmol), ethyl 2-(2-hydroxyphenyl)acetate (7c) (458 mg, 2.54 mmol) a solution of bis(4-chlorobenzyl) diazene-1,2-dicarboxylate (DCAD) (809 mg, 2.203 mmol) in DCM (10 mL) and stirring at room temperature for 3 h. This gave after workup and purification by flash column chromatography [silica (12 g), eluting with EtOAc in hexane from 0-50%] ethyl 2-(2-((5-bromo-7-(trifluoromethyl)benzofuran-3-yl)methoxy)phenyl)acetate (113e) (571 mg, 74% yield) as a white solid; $^1$H NMR (300 MHz, DMSO-$d_6$) δ 8.36 (s, 1H), 8.22 (d, J=1.9 Hz, 1H), 7.91 (s, 1H), 7.37-7.26 (m, 1H), 7.27-7.13 (m, 2H), 7.00-6.86 (m, 1H), 5.30 (s, 2H), 3.91 (q, J=7.1 Hz, 2H), 3.57 (s, 2H), 0.95 (t, J=7.1 Hz, 3H); $^{19}$F NMR (282 MHz, DMSO-$d_6$) δ −59.89; MS (ES+): 478.90 (M+Na).

Step-5: Preparation of ethyl 2-(2-((5-(3-(aminomethyl)phenyl)-7-(trifluoromethyl)benzofuran-3-yl) methoxy)phenyl)acetate (113f)

Compound 113f was prepared according to the procedure reported in step-2 of scheme 1, from ethyl 2-(2-((5-bromo-7-(trifluoromethyl)benzofuran-3-yl)methoxy)phenyl)acetate (113e) (571 mg, 1.249 mmol) in dioxane/THF (6 mL each) using 3-(aminomethyl)phenylboronic acid hydrochloride (1d) (468 mg, 2.498 mmol), 2 M solution of $K_3PO_4$ (2.498 mL, 5.00 mmol), tricyclohexylphosphine (70 mg, 0.250 mmol), $PdCl_2$(dppf)-$CH_2Cl_2$ adduct (102 mg, 0.125 mmol), $Pd_2(dba)_3$ (114 mg, 0.125 mmol) and heating at 90-100° C. for 1 h. This gave after workup and purification by flash column chromatography [silica gel (24 g), eluting with DMA-80 in DCM from 0-70%] ethyl 2-(2-((5-(3-(aminomethyl)phenyl)-7-(trifluoromethyl)benzofuran-3-yl)methoxy) phenyl)acetate (113f) (408 mg, 68% yield); $^1$H NMR (300 MHz, DMSO-$d_6$) δ 8.34 (s, 1H), 8.29-8.20 (m, 1H), 7.94 (s, 1H), 7.75 (s, 1H), 7.66-7.59 (m, 1H), 7.44 (t, J=7.5 Hz, 1H), 7.41-7.36 (m, 1H), 7.36-7.28 (m, 1H), 7.28-7.16 (m, 2H), 6.94 (td, J=7.3, 1.2 Hz, 1H), 5.36 (s, 2H), 3.81 (s, 2H), 3.69 (q, J=7.1 Hz, 2H), 3.56 (s, 2H), 0.82 (t, J=7.1 Hz, 3H); $^{19}$F NMR (282 MHz, DMSO-$d_6$) δ −59.61; MS (ES+): 484.10 (M+1).

Step-6: Preparation of 2-(2-((5-(3-(aminomethyl) phenyl)-7-(trifluoromethyl)benzofuran-3-yl) methoxy)phenyl)acetic acid (113g)

Compound 113g was prepared according to the procedure reported in step-3 of scheme 1, from ethyl 2-(2-((5-(3-

(aminomethyl)phenyl)-7-(trifluoromethyl)benzofuran-3-yl) methoxy)phenyl)acetate (113f) (408 mg, 0.844 mmol) in THF (2 mL, ratio: 10.0), methanol (0.2 mL, ratio: 1.0) and water (0.2 mL, ratio: 1.000) using lithium hydroxide hydrate (81 mg, 3.38 mmol) and stirring at RT for 10 h. This gave after workup and purification by reverse phase column chromatography [C18 column (40 g), eluting with ACN in water (containing 0.1% HCl) from 0-100%] 2-(2-((5-(3-(aminomethyl)phenyl)-7-(trifluoromethyl)benzofuran-3-yl) methoxy)phenyl)acetic acid (113g) (182 mg, 47% yield) HCl salt as a light brown solid; $^1H$ NMR (300 MHz, DMSO-$d_6$) δ 12.04 (s, 1H), 8.36 (s, 1H), 8.34 (s, 1H), 7.98 (d, J=5.0 Hz, 2H), 7.85 (d, J=7.5 Hz, 1H), 7.57 (t, J=7.6 Hz, 1H), 7.51 (d, J=7.7 Hz, 1H), 7.35-7.25 (m, 1H), 7.26-7.18 (m, 2H), 6.95 (t, J=7.3 Hz, 1H), 5.39 (s, 2H), 4.14 (s, 2H), 3.55 (s, 2H); $^1H$ NMR (300 MHz, DMSO-$d_6$/$D_2O$) δ 8.23 (d, J=4.1 Hz, 2H), 7.93 (s, 1H), 7.83 (s, 1H), 7.79 (d, J=8.0 Hz, 1H), 7.55 (t, J=7.7 Hz, 1H), 7.45 (d, J=7.7 Hz, 1H), 7.27 (t, J=8.1 Hz, 1H), 7.19 (s, 1H), 7.17 (s, 1H), 6.93 (t, J=7.4 Hz, 1H), 5.33 (s, 2H), 3.50 (s, 2H); $^{19}F$ NMR (282 MHz, DMSO-$d_6$) δ -59.69; MS (ES+): 456.00 (M+1); (ES-): 454.00 (M-1); Analysis calculated for $C_{25}H_{20}F_3NO_4{\cdot}HCl{\cdot}H_2O$: C, 58.89; H, 4.55; Cl, 6.95; N, 2.75. Found: C, 58.72; H, 4.74; Cl, 6.87; N, 2.71.

Scheme 114

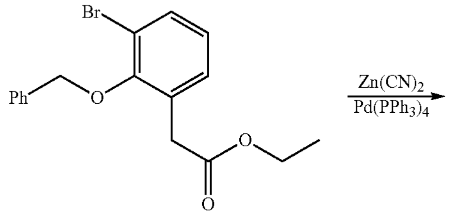

90b

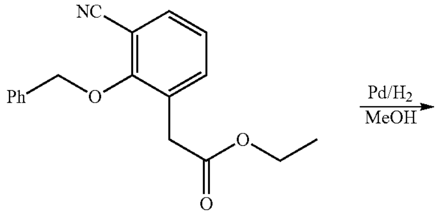

114a

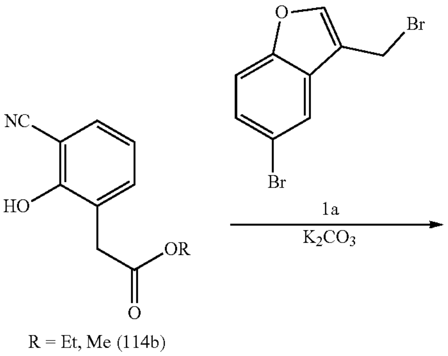

R = Et, Me (114b)

-continued

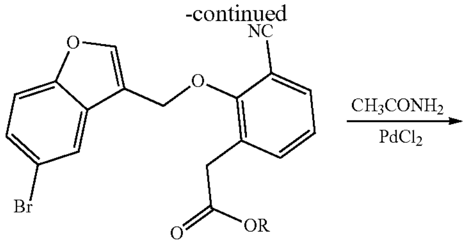

R = Et (114c)
R = Me (114d)

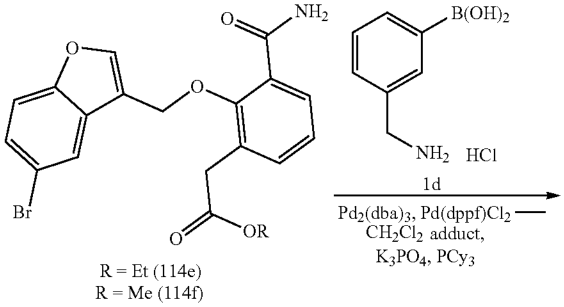

R = Et (114e)
R = Me (114f)

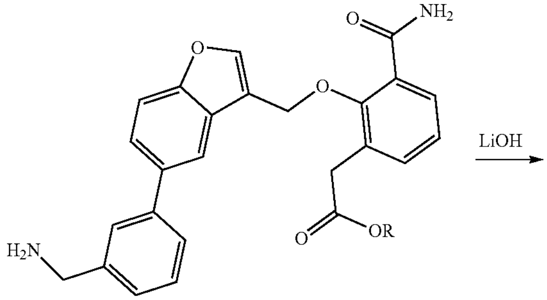

R = Et (114g)
R = Me (114h)

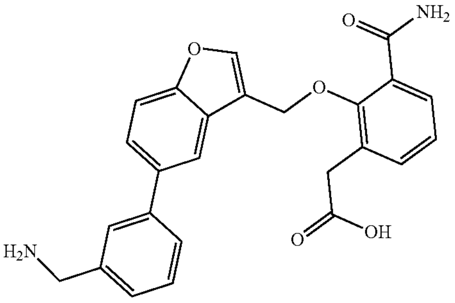

114i

Preparation of 2-(2-((5-(3-(aminomethyl)phenyl) benzofuran-3-yl)methoxy)-3-carbamoylphenyl)acetic acid (114i)

Step-1: Preparation of ethyl 2-(2-(benzyloxy)-3-cyanophenyl)acetate (114a)

A mixture of ethyl 2-(2-(benzyloxy)-3-bromophenyl)acetate (90b) (0.5 g, 1.432 mmol), dicyanozinc (0.504 g, 4.30 mmol), $Pd(PPh_3)_4$ (0.248 g, 0.215 mmol) in anhydrous DMF (10 mL) was heated overnight at 100° C.) under a nitrogen atmosphere. The reaction mixture was cooled to room temperature, diluted with ethyl acetate (100 mL), brine (100 mL) and extracted with ethyl acetate (2×50 mL). The combined organics were washed with brine, dried, filtered and concentrated in vacuum. The residue obtained was purified by column chromatography [silica gel (24 g), eluting with ethyl acetate in hexanes from 0 to 60%] to afford ethyl 2-(2-(benzyloxy)-3-cyanophenyl)acetate (114a) (0.31 g, 73% yield) as a white solid; MS (ES+): 296.10 (M+1).

Step-2: Preparation of ethyl/methyl 2-(3-cyano-2-hydroxyphenyl)acetate (114b)

Compound 114b was prepared according to the procedure reported in step-3 of scheme 83, from ethyl 2-(2-(benzyloxy)-3-cyanophenyl)acetate (114a) (0.31 g, 1.05 mmol) in MeOH (15 mL) using palladium (0.223 g, 0.21 mmol) and hydrogenating for 3 h. This gave after workup and purification [silica gel (12 g), eluting with EtOAc in Hexane from 0-50%] an inseparable mixture of ethyl/methyl 2-(3-cyano-2-hydroxyphenyl)acetate (114b) (60 mg, 28% yield) as a white solid; MS (ES+): 206.00 (M+1) and MS (ES+): 192.10 (M+1).

Step-3: Preparation of ethyl 2-(2-((5-bromobenzofuran-3-yl)methoxy)-3-cyanophenyl)acetate (114c) and methyl 2-(2-((5-bromobenzofuran-3-yl)methoxy)-3-cyanophenyl)acetate (114d)

Compound 114c and 114d were prepared according to the procedure reported in step-1 of scheme 58, from a mixture containing ethyl/methyl 2-(3-cyano-2-hydroxyphenyl)acetate (114b) (425 mg) in DMF (6 mL) using 5-bromo-3-(bromomethyl)benzofuran (1a) (311 mg, 1.072 mmol), $K_2CO_3$ (444 mg, 3.22 mmol) and stirring at room temperature for 15 h. This gave after workup and purification by flash column chromatography [silica gel (24 g), eluting with EtOAc in hexane from 0-50%] ethyl 2-(2-((5-bromobenzofuran-3-yl)methoxy)-3-cyanophenyl)acetate (114c) (0.3 g, 68% yield); MS (ES+): 436.00 (M+Na) and methyl 2-(2-((5-bromobenzofuran-3-yl)methoxy)-3-cyanophenyl)acetate (114d) (0.1 g, 23% yield); MS (ES+): 422.00 (M+Na), (ES−): 398.00 (M−1).

Step-4: Preparation of ethyl 2-(2-((5-bromobenzofuran-3-yl)methoxy)-3-carbamoylphenyl)acetate (114e) and methyl 2-(2-((5-bromobenzofuran-3-yl)methoxy)-3-carbamoylphenyl)acetate (114f)

Compound 114e and 114f were prepared according to the procedure reported in step-1 of scheme 63, from a mixture of ethyl 2-(2-((5-bromobenzofuran-3-yl)methoxy)-3-cyanophenyl)acetate (114c) and methyl 2-(2-((5-bromobenzofuran-3-yl)methoxy)-3-cyanophenyl)acetate (114d) (0.25 g, 0.604 mmol) in THF (5 mL) and water (0.5 mL) using acetamide (0.214 g, 3.62 mmol), palladium(II) chloride (16 mg, 0.091 mmol) and stirring at room temperature for 13 h. This gave after workup and purification by flash column chromatography [silica gel, eluting with EtOAc in hexane from 0-100%] ethyl 2-(2-((5-bromobenzofuran-3-yl)methoxy)-3-carbamoylphenyl)acetate (114e) (0.12 g, 46% yield) MS (ES+): 432.00 (M+1), and methyl 2-(2-((5-bromobenzofuran-3-yl)methoxy)-3-carbamoylphenyl)acetate (114f) (0.08 g, 32% yield); MS (ES+): 440.00 (M+Na).

Step-5: Preparation of ethyl 2-(2-((5-(3-(aminomethyl)phenyl)benzofuran-3-yl)methoxy)-3-carbamoylphenyl)acetate (114g) and methyl 2-(2-((5-(3-(aminomethyl)phenyl)benzofuran-3-yl)methoxy)-3-carbamoylphenyl)acetate (114h)

Compound 114g and 114h were prepared according to the procedure reported in step-2 of scheme 1, from a mixture of ethyl 2-(2-((5-bromobenzofuran-3-yl)methoxy)-3-carbamoylphenyl)acetate (114e) and methyl 2-(2-((5-bromobenzofuran-3-yl)methoxy)-3-carbamoylphenyl)acetate (114f) (0.2 g, 0.463 mmol) in dioxane/THF (4 mL each) using 3-(aminomethyl)phenylboronic acid hydrochloride (1d) (0.173 g, 0.925 mmol), 2 M solution of $K_3PO_4$ (0.925 mL, 1.851 mmol), tricyclohexylphosphine (0.026 g, 0.093 mmol), $PdCl_2(dppf)\text{-}CH_2Cl_2$ adduct (38 mg, 0.046 mmol), $Pd_2(dba)_3$ (42 mg, 0.046 mmol) and heating at 90° C. for 1 h. This gave after workup and purification by flash column chromatography [silica gel (24 g), eluting with DMA-80 in DCM from 0-70%] ethyl 2-(2-((5-(3-(aminomethyl)phenyl)benzofuran-3-yl)methoxy)-3-carbamoylphenyl)acetate (114g) (60 mg, 28% yield); MS (ES+): 459.20 (M+1), (ES−): 457.15 (M−1) and methyl 2-(2-((5-(3-(aminomethyl)phenyl)benzofuran-3-yl)methoxy)-3-carbamoylphenyl)acetate (114h) (40 mg, 19% yield); MS (ES+): 445.20 (M+1), (ES−): 443.15 (M−1).

Step-6: Preparation of 2-(2-((5-(3-(aminomethyl)phenyl)benzofuran-3-yl)methoxy)-3-carbamoylphenyl)acetic acid (114i)

Compound 114i was prepared according to the procedure reported in step-3 of scheme 1, from a mixture of ethyl 2-(2-((5-(3-(aminomethyl)phenyl)benzofuran-3-yl)methoxy)-3-carbamoylphenyl)acetate (114g) and methyl 2-(2-((5-(3-(aminomethyl)phenyl)benzofuran-3-yl)methoxy)-3-carbamoylphenyl)acetate (114h) (100 mg, 0.218 mmol) in THF/MeOH (4 mL each) using a solution of lithium hydroxide hydrate (73.2 mg, 1.745 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)benzofuran-3-yl)methoxy)-3-carbamoylphenyl)acetic acid (114i) (65 mg, 69% yield) HCl salt as a white solid; $^1H$ NMR (300 MHz, DMSO-$d_6$) δ 12.14 (s, 1H), 8.38 (s, 3H, $D_2O$ exchangeable), 8.15 (s, 1H), 8.01 (d, J=1.7 Hz, 1H), 7.87 (d, J=1.8 Hz, 1H, $D_2O$ exchangeable), 7.84 (dd, J=8.4, 2.5 Hz, 2H), 7.78-7.71 (m, 3H), 7.69 (dd, J=8.6, 1.8 Hz, 1H), 7.50 (dt, J=15.6, 7.6 Hz, 2H), 7.27 (d, J=8.6 Hz, 1H), 7.20 (s, 1H), 5.40 (s, 2H), 4.11 (q, J=6.0 Hz, 2H), 3.57 (s, 2H); MS (ES+): 431.20 (M+1); MS (ES−): 429.15 (M−1); Analysis calculated for $C_{25}H_{22}N_2O_5\cdot1.25HCl\cdot2H_2O$: C, 58.64; H, 5.36; Cl, 8.65; N, 5.47. Found: C, 58.68; H, 5.19; Cl, 8.33; N, 5.55.

Scheme 115

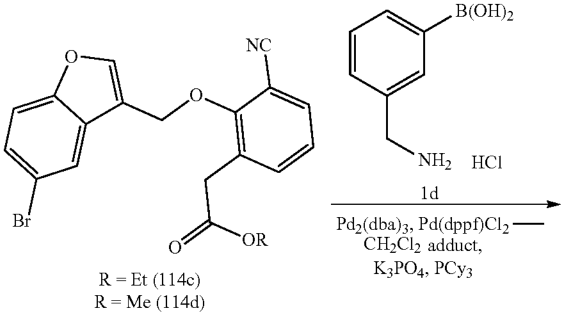

R = Et (114c)
R = Me (114d)

-continued

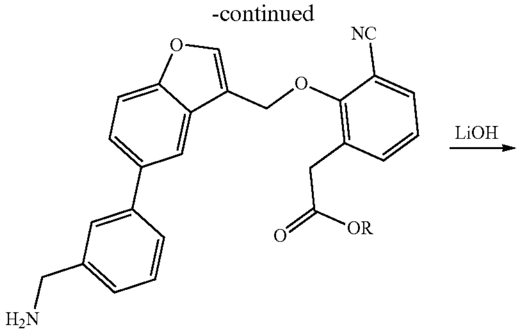

R = Et (115a)
R = Me (115b)

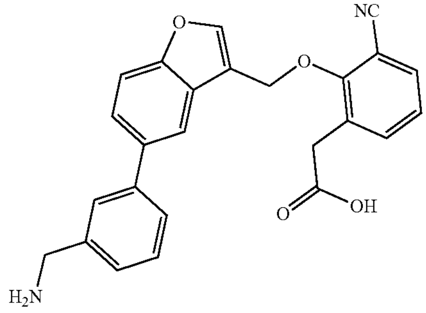

115c

Preparation of 2-(2-((5-(3-(aminomethyl)phenyl) benzofuran-3-yl)methoxy)-3-cyanophenyl)acetic acid (115c)

Step-1: Preparation of ethyl 2-(2-((5-(3-(aminomethyl)phenyl)benzofuran-3-yl)methoxy)-3-cyanophenyl)acetate (115a) and methyl 2-(2-((5-(3-(aminomethyl)phenyl)benzofuran-3-yl)methoxy)-3-cyanophenyl)acetate (115b)

Compound 115a and 115b were prepared according to the procedure reported in step-2 of scheme 1, from a mixture of ethyl 2-(2-((5-bromobenzofuran-3-yl)methoxy)-3-cyanophenyl)acetate (114c) and methyl 2-(2-((5-bromobenzofuran-3-yl)methoxy)-3-cyanophenyl)acetate (114d) (150 mg, 0.362 mmol) in dioxane/THF (4 mL each) using 3-(aminomethyl)phenylboronic acid hydrochloride (1d) (136 mg, 0.724 mmol), 2 M solution of $K_3PO_4$ (0.724 mL, 1.448 mmol), tricyclohexylphosphine (20 mg, 0.072 mmol), $PdCl_2$(dppf)-$CH_2Cl_2$ adduct (30 mg, 0.036 mmol), $Pd_2(dba)_3$ (33 mg, 0.036 mmol) and heating at 90° C. for 1 h. This gave after workup and purification by column chromatography [silica gel (24 g), eluting with DMA-80 in DCM from 0-70%] ethyl 2-(2-((5-(3-(aminomethyl)phenyl)benzofuran-3-yl)methoxy)-3-cyanophenyl)acetate (115a) (60 mg, 38% yield); MS (ES+): 441.20 (M+1); MS (ES−): 439.10 (M−1); and methyl 2-(2-((5-(3-(aminomethyl)phenyl)benzofuran-3-yl)methoxy)-3-cyanophenyl)acetate (115b) (40 mg, 26% yield); MS (ES+): 427.30 (M+1).

Step-1: Preparation of 2-(2-((5-(3-(aminomethyl) phenyl)benzofuran-3-yl)methoxy)-3-cyanophenyl) acetic acid (115c)

Compound 115c was prepared according to the procedure reported in step-3 of scheme 1, from a mixture of ethyl 2-(2-((5-(3-(aminomethyl)phenyl)benzofuran-3-yl)methoxy)-3-cyanophenyl)acetate (115a) and methyl 2-(2-((5-(3-(aminomethyl)phenyl)benzofuran-3-yl)methoxy)-3-cyanophenyl)acetate (115b) (50 mg, 0.114 mmol) in THF/MeOH (4 mL each) using a solution of lithium hydroxide hydrate (38.1 mg, 0.908 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)benzofuran-3-yl)methoxy)-3-cyanophenyl)acetic acid (115c) (8 mg, 17% yield) HCl salt as a white solid; $^1H$ NMR (300 MHz, DMSO-$d_6$) δ 12.36 (s, 1H, $D_2O$ exchangeable), 8.37 (s, 3H, $D_2O$ exchangeable), 8.15 (s, 1H), 8.01 (d, J=1.8 Hz, 1H), 7.87 (s, 1H), 7.81 (dd, J=8.5, 2.2 Hz, 1H), 7.77-7.65 (m, 4H), 7.57-7.36 (m, 3H), 5.45 (s, 2H), 4.11 (s, 2H), 3.60 (s, 2H); MS (ES+): 413.20 (M+1).

Scheme 116

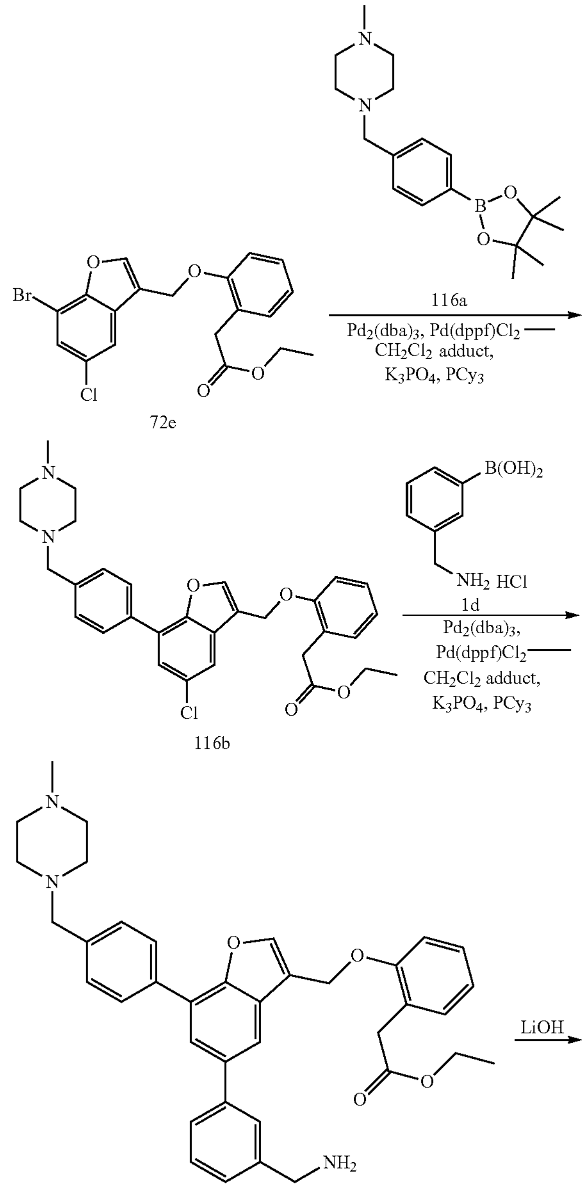

72e

116b

116c

-continued

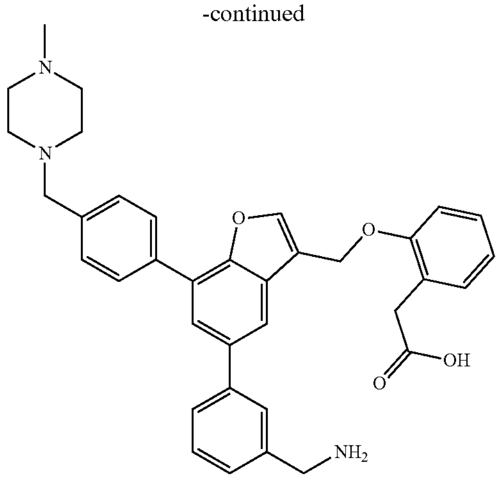

116d

Preparation of 2-(2-((5-(3-(aminomethyl)phenyl)-7-(4-((4-methylpiperazin-1-yl)methyl)phenyl)benzofuran-3-yl)methoxy)phenyl)acetic acid (116d)

Step-1: Preparation of ethyl 2-(2-((5-chloro-7-(4-((4-methylpiperazin-1-yl)methyl)phenyl)benzofuran-3-yl)methoxy)phenyl)acetate (116b)

Compound 116b was prepared according to the procedure reported in step-2 of scheme 1, from ethyl 2-(2-((7-bromo-5-chlorobenzofuran-3-yl)methoxy)phenyl)acetate (72e) (1.3 g, 3.07 mmol) in 2-methyltetrahydrofuran/dioxane (10 mL each) using 1-methyl-4-(4-(4,4,5,5-tetramethyl-1,3,2-dioxaborolan-2-yl)benzyl)piperazine (116a) (1.941 g, 6.14 mmol; CAS #938043-30-2), 2M solution of $K_3PO_4$ (6.14 mL, 12.27 mmol), tricyclohexylphosphine (172 mg, 0.614 mmol) $PdCl_2(dppf)-CH_2Cl_2$ adduct (251 mg, 0.307 mmol), $Pd_2(dba)_3$ (281 mg, 0.307 mmol) and heating at 80° C. for 2 h. This gave after workup and purification by flash column chromatography [silica (80 g), eluting with DMA-80 in DCM from 0-100%] ethyl 2-(2-((5-chloro-7-(4-((4-methylpiperazin-1-yl)methyl)phenyl)benzofuran-3-yl)methoxy)phenyl)acetate (116b) (1.2 g, 73% yield) as a yellow oil; MS (ES+): 533.10 (M+1).

Step-2: Preparation of ethyl 2-(2-((5-(3-(aminomethyl)phenyl)-7-(4-((4-methylpiperazin-1-yl)methyl)phenyl)benzofuran-3-yl)methoxy)phenyl)acetate (116c)

Compound 116c was prepared according to the procedure reported in step-2 of scheme 1, from ethyl 2-(2-((5-chloro-7-(4-((4-methylpiperazin-1-yl)methyl)phenyl)benzofuran-3-yl)methoxy)phenyl)acetate (116b) (910 mg, 1.707 mmol) in dioxane/THF (50 mL each) using 3-(aminomethyl)phenylboronic acid hydrochloride (1d) (640 mg, 3.41 mmol), 4 M solution of $K_3PO_4$ (1.707 mL, 6.83 mmol), tricyclohexylphosphine (191 mg, 0.683 mmol), $PdCl_2(dppf)-CH_2Cl_2$ adduct (139 mg, 0.171 mmol), $Pd_2(dba)_3$ (156 mg, 0.171 mmol) and heating at 115° C. for 4 h. This gave after workup and purification by flash column chromatography [silica gel (24 g), eluting with DMA-80 in DCM from 0-70%] ethyl 2-(2-((5-(3-(aminomethyl)phenyl)-7-(4-((4-methylpiperazin-1-yl)methyl)phenyl)benzofuran-3-yl)methoxy)phenyl)acetate (116c) (456 mg, 44% yield) as a colorless oil; MS (ES+): 604.3 (M+1).

Step-3: Preparation of 2-(2-((5-(3-(aminomethyl)phenyl)-7-(4-((4-methylpiperazin-1-yl)methyl)phenyl)benzofuran-3-yl)methoxy)phenyl)acetic acid (116d)

Compound 116d was prepared according to the procedure reported in step-3 of scheme 1, from ethyl 2-(2-((5-(3-(aminomethyl)phenyl)-7-(4-((4-methylpiperazin-1-yl)methyl)phenyl)benzofuran-3-yl)methoxy)phenyl)acetate (116c) (456 mg, 0.755 mmol) in THF (6 mL) using a solution of lithium hydroxide hydrate (107 mg, 2.56 mmol) in water (1 mL) and stirring at 50° C. for 1 h. This gave after workup and purification by reverse phase column chromatography [C18 column (30 g), eluting with ACN in water (containing 0.1% HCl) from 0-100%] 2-(2-((5-(3-(aminomethyl)phenyl)-7-(4-((4-methylpiperazin-1-yl)methyl)phenyl)benzofuran-3-yl)methoxy)phenyl)acetic acid (116d) (157 mg, 16% yield) HCl salt as a yellow solid; $^1H$ NMR (300 MHz, DMSO-$d_6$) δ 12.25 (s, 1H, $D_2O$ exchangeable), 8.48 (s, 3H, $D_2O$ exchangeable), 8.23 (s, 1H), 8.11-7.99 (m, 4H), 7.95-7.72 (m, 5H), 7.59-7.46 (m, 2H), 7.32-7.19 (m, 3H), 6.95 (td, J=7.1, 1.5 Hz, 1H), 5.38 (s, 2H), 4.43 (d, J=27.9 Hz, 2H), 4.15 (dd, J=10.5, 5.0 Hz, 2H), 3.57 (s, 4H), 3.50-3.32 (m, 4H), 2.81 (s, 4H); $^1H$ NMR (300 MHz, DMSO-$d_6$+$D_2O$) δ 8.20 (s, 1H), 8.07-7.99 (m, 3H), 7.95 (s, 1H), 7.88-7.81 (m, 2H), 7.73 (d, J=7.9 Hz, 2H), 7.55 (t, J=7.6 Hz, 1H), 7.47 (d, J=7.7 Hz, 1H), 7.33-7.18 (m, 3H), 6.94 (t, J=7.3 Hz, 1H), 5.36 (s, 2H), 4.30 (s, 2H), 4.12 (s, 2H), 3.55 (s, 4H), 3.47-3.31 (m, 4H), 3.27-3.10 (m, 2H), 2.85 (s, 3H); MS (ES+): 576.3 (M+1); (ES−): 574.3 (M−1); Analysis calculated for $C_{36}H_{37}N_3O_4·3HCl·4.25H_2O$: C, 56.77; H, 6.42; Cl, 13.96; N, 5.52. Found: C, 56.76; H, 6.15; Cl, 13.73; N, 5.76.

Scheme 117

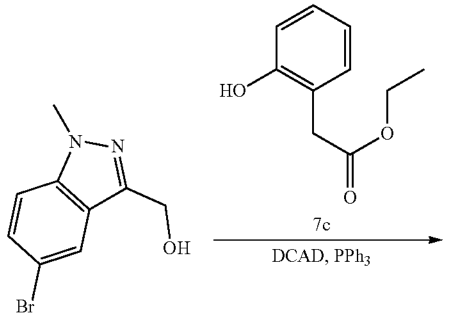

117a

-continued

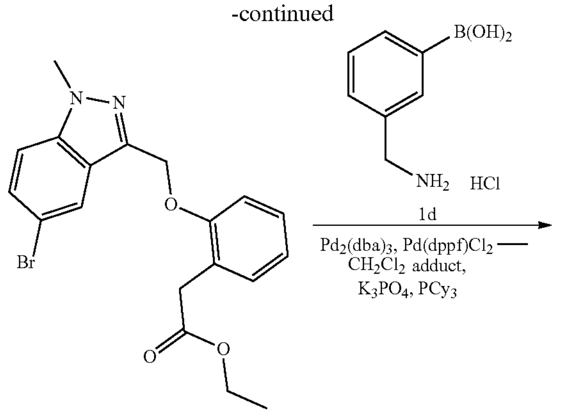

117b

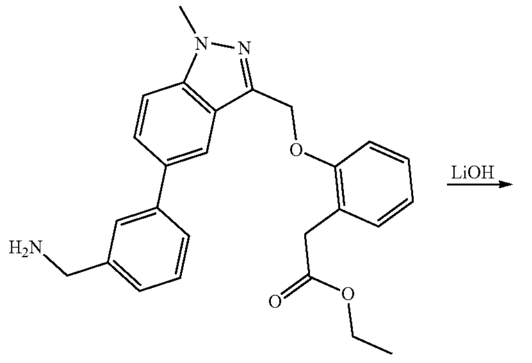

117c

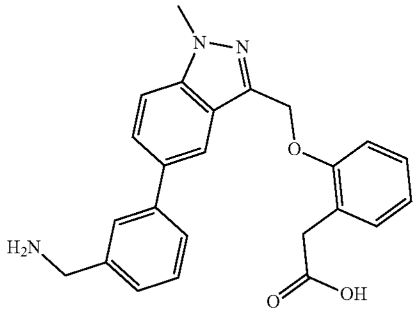

117d

Preparation of 2-(2-((5-(3-(aminomethyl)phenyl)-1-methyl-1H-indazol-3-yl)methoxy)phenyl)acetic acid (117d)

Step-1: Preparation of ethyl 2-(2-((5-bromo-1-methyl-1H-indazol-3-yl)methoxy)phenyl)acetate (117b)

Compound 117b was prepared according to the procedure reported in step-3 of scheme 7, from (5-bromo-1-methyl-1H-indazol-3-yl)methanol (117a) (400 mg, 1.659 mmol; CAS #1352494-93-9) in DCM (10 mL) using triphenylphosphine (870 mg, 3.32 mmol), ethyl 2-(2-hydroxyphenyl) acetate (7c) (329 mg, 1.825 mmol) using a solution of bis(4-chlorobenzyl) diazene-1,2-dicarboxylate (DCAD) (1.218 g, 3.32 mmol) in DCM (5 mL) and stirring at room temperature for 30 min. This gave after workup and purification by flash column chromatography [silica gel (24 g), eluting with EtOAc in hexane from 0-50%] ethyl 2-(2-((5-bromo-1-methyl-1H-indazol-3-yl)methoxy)phenyl)acetate (117b) (250 mg, 37% yield) as a yellow solid; $^1$H NMR (300 MHz, DMSO-$d_6$) δ 7.97-7.93 (m, 1H), 7.66 (d, J=8.9 Hz, 1H), 7.54 (dd, J=8.9, 1.8 Hz, 1H), 7.31-7.17 (m, 3H), 6.92 (td, J=7.2, 1.5 Hz, 1H), 5.36 (s, 2H), 4.05 (s, 3H), 3.91 (q, J=7.1 Hz, 2H), 3.52 (s, 2H), 0.95 (t, J=7.1 Hz, 3H); MS (ES+): 403.10 (M+1).

Step-2: Preparation of ethyl 2-(2-((5-(3-(aminomethyl)phenyl)-1-methyl-1H-indazol-3-yl)methoxy)phenyl)acetate (117c)

Compound 117c was prepared according to the procedure reported in step-2 of scheme 1, from ethyl 2-(2-((5-bromo-1-methyl-1H-indazol-3-yl)methoxy)phenyl)acetate (117b) (250 mg, 0.620 mmol) in dioxane/THF (4 mL each) using 3-(aminomethyl)phenylboronic acid hydrochloride (1d) (232 mg, 1.240 mmol), 2M solution of $K_3PO_4$ (1.240 mL, 2.480 mmol), tricyclohexylphosphine (35 mg, 0.124 mmol), $PdCl_2$(dppf)-$CH_2Cl_2$ adduct (51 mg, 0.062 mmol), $Pd_2$(dba)$_3$ (57 mg, 0.062 mmol) and heating at 90° C. for 1 h. This gave after workup and purification by column chromatography [silica gel (24 g), eluting with DMA-80 in DCM from 0-70%] ethyl 2-(2-((5-(3-(aminomethyl)phenyl)-1-methyl-1H-indazol-3-yl)methoxy)phenyl)acetate (117c) (100 mg, 38% yield); MS (ES+): 430.20 (M+1).

Step-3: Preparation of 2-(2-((5-(3-(aminomethyl)phenyl)-1-methyl-1H-indazol-3-yl)methoxy)phenyl)acetic acid (117d)

Compound 117d was prepared according to the procedure reported in step-3 of scheme 1, from ethyl 2-(2-((5-(3-(aminomethyl)phenyl)-1-methyl-1H-indazol-3-yl)methoxy)phenyl)acetate (117c) (100 mg, 1.863 mmol) in THF/MeOH (4 mL each) using a solution of lithium hydroxide hydrate (78 mg, 1.863 mmol) in water (1 mL) and stirring at room temperature for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-1-methyl-1H-indazol-3-yl)methoxy)phenyl)acetic acid (117d) (65 mg, 70% yield) HCl salt as a white solid; $^1$H NMR (300 MHz, DMSO-$d_6$) δ 11.95 (bs, 1H), 8.34 (bs, 3H), 8.09 (d, J=1.5 Hz, 1H), 7.88 (s, 1H), 7.79 (s, 2H), 7.78-7.72 (m, 1H), 7.51 (t, J=7.6 Hz, 1H), 7.44 (d, J=7.6 Hz, 1H), 7.29-7.25 (m, 2H), 7.20 (d, J=7.4 Hz, 1H), 6.97-6.88 (m, 1H), 5.44 (s, 2H), 4.55-4.12 (m, 2H), 4.10 (s, 3H), 3.51 (s, 2H); MS (ES+): 402.20 (M+1); (ES−) 400.15 (M−1).

Scheme 118

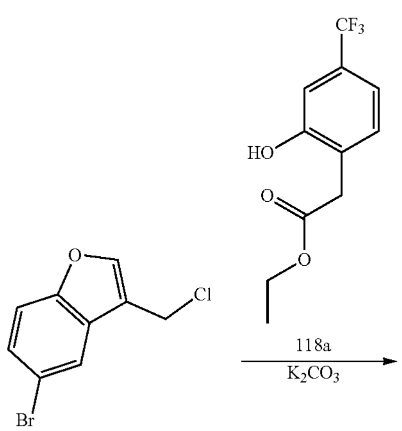

104a

-continued

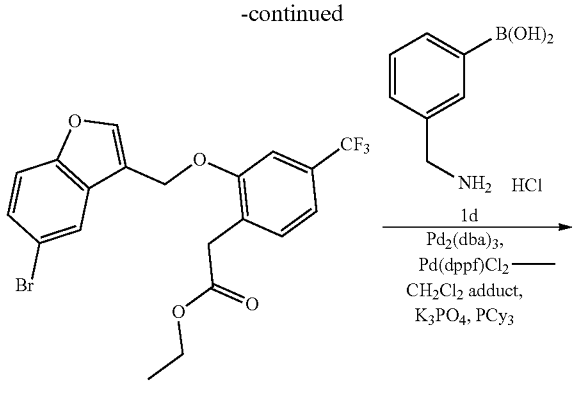

118b

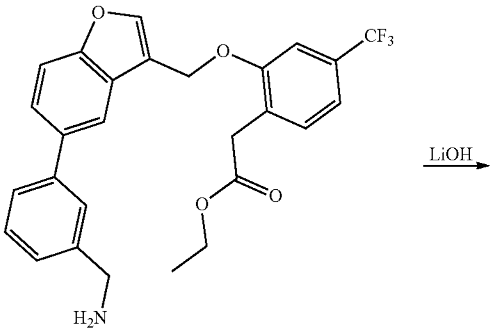

118c

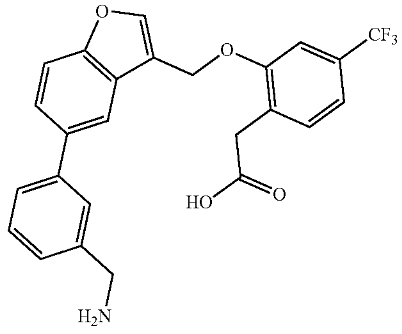

118d

Preparation of 2-(2-((5-(3-(aminomethyl)phenyl)benzofuran-3-yl)methoxy)-4-(trifluoromethyl)phenyl)acetic acid (118d)

Step-1: Preparation of ethyl 2-(2-((5-bromobenzofuran-3-yl)methoxy)-4-(trifluoromethyl)phenyl)acetate (118b)

Compound 118b was prepared according to the procedure reported in step-3 of scheme 7, from 5-bromo-3-(chloromethyl)benzofuran (104a) (500 mg, 2.037 mmol) in DMF (4 mL) using ethyl 2-(2-hydroxy-4-(trifluoromethyl)phenyl) acetate (118a) (0.460 g, 1.852 mmol; CAS #1261500-50-8), potassium carbonate (0.768 g, 5.55 mmol) and stirring overnight at room temperature. This gave after workup and purification by flash column chromatography [silica gel (12 g), eluting with ethyl acetate and hexanes from 0-50%] ethyl 2-(2-((5-bromobenzofuran-3-yl)methoxy)-4-(trifluoromethyl)phenyl)acetate (118b) (630 mg, 74% yield); $^1H$ NMR (300 MHz, DMSO-$d_6$) δ 8.15 (s, 1H), 7.88 (d, J=2.0 Hz, 1H), 7.62 (d, J=8.7 Hz, 1H), 7.53-7.48 (m, 2H), 7.46 (d, J=7.8 Hz, 1H), 7.31 (d, J=8.5 Hz, 1H), 5.35 (s, 2H), 3.93 (q, J=7.1 Hz, 2H), 3.67 (s, 2H), 0.96 (t, J=7.1 Hz, 3H); $^{19}F$ NMR (282 MHz, DMSO-$d_6$) δ −60.74 MS (ES+): 458.00 (M+1).

Step-2: Preparation of ethyl 2-(2-((5-(3-(aminomethyl)phenyl)benzofuran-3-yl)methoxy)-4-(trifluoromethyl)phenyl)acetate (118c)

Compound 118c was prepared according to the procedure reported in step-2 of scheme 1, from ethyl 2-(2-((5-bromobenzofuran-3-yl)methoxy)-4-(trifluoromethyl)phenyl) acetate (118b) (630 mg, 1.378 mmol) in dioxane/THF (6 mL each) using 3-(aminomethyl)phenylboronic acid hydrochloride (1d) (516 mg, 2.76 mmol), 2 M solution of $K_3PO_4$ (2.76 mL, 5.51 mmol), tricyclohexylphosphine (77 mg, 0.276 mmol), $PdCl_2$(dppf)-$CH_2Cl_2$ adduct (113 mg, 0.138 mmol), $Pd_2(dba)_3$ (126 mg, 0.138 mmol) and heating at 90-100° C. for 1 h. This gave after workup and purification by flash column chromatography [silica gel (24 g), eluting with DMA80 in DCM from 0-70%] ethyl 2-(2-((5-(3-(aminomethyl)phenyl)benzofuran-3-yl)methoxy)-4-(trifluoromethyl) phenyl)acetate (118c) (426 mg, 64% yield) as a colorless oil; MS (ES+): 484.10 (M+1).

Step-3: Preparation of 2-(2-((5-(3-(aminomethyl) phenyl)benzofuran-3-yl)methoxy)-4-(trifluoromethyl)phenyl)acetic acid (118d)

Compound 118d was prepared according to the procedure reported in step-3 of scheme 1, from ethyl 2-(2-((5-(3-(aminomethyl)phenyl)benzofuran-3-yl)methoxy)-4-(trifluoromethyl)phenyl)acetate (118c) (213 mg, 0.441 mmol) in THF (2 mL), methanol (0.2 mL) and water (0.2 mL) using lithium hydroxide hydrate (42.2 mg, 1.762 mmol) and stirring at room temperature for 10 h. This gave after workup and purification by reverse phase column chromatography [C18 column (40 g), eluting with ACN in water (containing 0.1% HCl) from 0-100%] 2-(2-((5-(3-(aminomethyl)phenyl) benzofuran-3-yl)methoxy)-4-(trifluoromethyl)phenyl)acetic acid (118d) (58 mg, 29% yield) HCl salt as a light brown solid; $^1H$ NMR (300 MHz, DMSO-$d_6$) δ 12.30 (bs, 1H), 8.32 (bs, 3H), 8.15 (s, 1H), 8.04 (d, J=1.7 Hz, 1H), 7.89 (s, 1H), 7.77 (s, 1H), 7.75 (s, 1H), 7.69 (dd, J=8.6, 1.8 Hz, 1H), 7.57-7.50 (m, 1H), 7.49-7.43 (m, 2H), 7.37-7.27 (m, 1H), 7.12-7.05 (m, 1H), 5.45 (s, 2H), 4.12 (s, 2H), 3.65 (s, 2H); $^{19}F$ NMR (282 MHz, DMSO-$d_6$) δ −60.68; MS (ES+): 456.10 (M+1); Analysis calculated for $C_{25}H_{20}F_3NO_4\cdot0.90HCl\cdot1.50H_2O$: C, 58.27; H, 4.68; Cl, 6.19; N, 2.72. Found: C, 58.43; H, 4.39; Cl, 6.29; N, 2.71.

Scheme 119

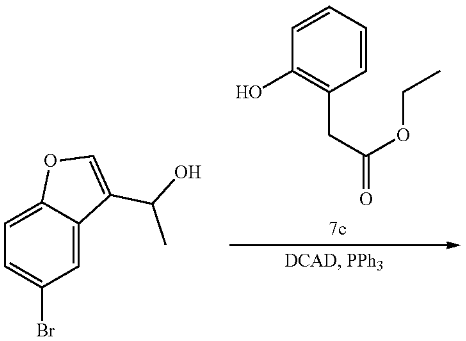

119a

-continued

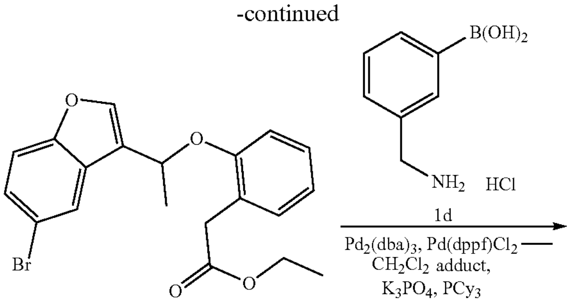

119b

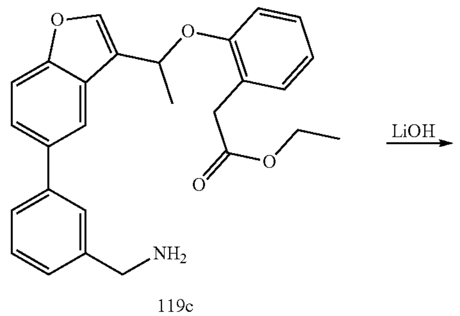

119c

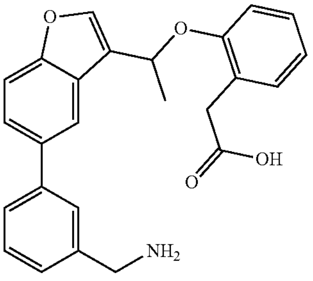

119d

Preparation of 2-(2-(1-(5-(3-(aminomethyl)phenyl) benzofuran-3-yl)ethoxy)phenyl)acetic acid (119d)

Step-1: Preparation of ethyl 2-(2-(1-(5-bromobenzofuran-3-yl)ethoxy)phenyl)acetate (119b)

Compound 119b was prepared according to the procedure reported in step-3 of scheme 7, from 1-(5-bromobenzofuran-3-yl)ethanol (119a) (600 mg, 2.489 mmol; CAS #1782577-22-3), triphenylphosphine (718 mg, 2.74 mmol), ethyl 2-(2-hydroxyphenyl)acetate (7c) (493 mg, 2.74 mmol) in DCM (30 mL) using a solution of bis(4-chlorobenzyl) diazene-1,2-dicarboxylate (DCAD) (1005 mg, 2.74 mmol) in DCM (20 mL) and stirring at RT for 30 min. This gave after workup and purification by flash column chromatography [silica gel (12 g), eluting with EtOAc in hexane from 0-50%] ethyl 2-(2-(1-(5-bromobenzofuran-3-yl)ethoxy)phenyl)acetate (119b) (450 mg, 45% yield) as a colorless oil; MS (ES+): 425.0 and 427.0 (M+Na).

Step-2: Preparation of ethyl 2-(2-(1-(5-(3-(aminomethyl)phenyl)benzofuran-3-yl)ethoxy)phenyl)acetate (119c)

Compound 119c was prepared according to the procedure reported in step-2 of scheme 1, from ethyl 2-(2-(1-(5-bromobenzofuran-3-yl)ethoxy)phenyl)acetate (119b) (450 mg, 1.116 mmol) in dioxane/THF (50 mL, each) using 3-(aminomethyl)phenylboronic acid hydrochloride (1d) (418 mg, 2.232 mmol), 4M solution of $K_3PO_4$ (1.116 mL, 4.46 mmol), tricyclohexylphosphine (125 mg, 0.446 mmol), $PdCl_2(dppf)-CH_2Cl_2$ adduct (137 mg, 0.167 mmol), $Pd_2(dba)_3$ (153 mg, 0.167 mmol) and heating at 100° C. for 2 h. This gave after workup and purification by flash column chromatography [silica gel (24 g), eluting with DMA-80 in DCM from 0-70%] ethyl 2-(2-(1-(5-(3-(aminomethyl)phenyl)benzofuran-3-yl)ethoxy)phenyl)acetate (119c) (227 mg, 47% yield); MS (ES+): 430.2 (M+1).

Step-3: Preparation of 2-(2-(1-(5-(3-(aminomethyl) phenyl)benzofuran-3-yl)ethoxy)phenyl)acetic acid (119d)

Compound 119d was prepared according to the procedure reported in step-3 of scheme 1, from ethyl 2-(2-(1-(5-(3-(aminomethyl)phenyl)benzofuran-3-yl)ethoxy)phenyl)acetate (119c) (227 mg, 0.529 mmol) in THF (3 nmL) using a solution of lithium hydroxide hydrate (70.2 mg, 1.674 mmol) in water (1 mL) and stirring overnight at RT. This gave after workup and purification by reverse phase column chromatography [C18 column (30 g), eluting with ACN in water (containing 0.1% HCl) from 0-100%] 2-(2-(1-(5-(3-(aminomethyl)phenyl)benzofuran-3-yl)ethoxy)phenyl)acetic acid (119d) (100 mg, 38% yield) HCl salt as an off white solid; $^1H$ NMR (300 MHz, DMSO-$d_6$) δ 12.25 (s, 1H, $D_2O$ exchangeable), 8.48 (s, 3H, $D_2O$ exchangeable), 8.08 (d, J=1.7 Hz, 1H), 8.01 (s, 1H), 7.90 (d, J=1.7 Hz, 1H), 7.78-7.63 (m, 3H), 7.57-7.44 (m, 2H), 7.24-7.11 (m, 2H), 7.07 (d, J=7.9 Hz, 1H), 6.86 (td, J=7.4, 1.1 Hz, 1H), 5.89 (q, J=6.3 Hz, 1H), 4.12 (m, J=5.5 Hz, 2H), 3.60 (d, J=2.9 Hz, 2H), 1.71 (d, J=6.3 Hz, 3H); MS (ES+): 402.2 (M+1); (ES−): 400.2 (M−1); Analysis calculated for $C_{25}H_{23}NO_4 \cdot HCl \cdot 1.5H_2O$: C, 64.58; H, 5.85; N, 3.01. Found: C, 64.36; H, 5.61; N, 2.98;

Scheme 120

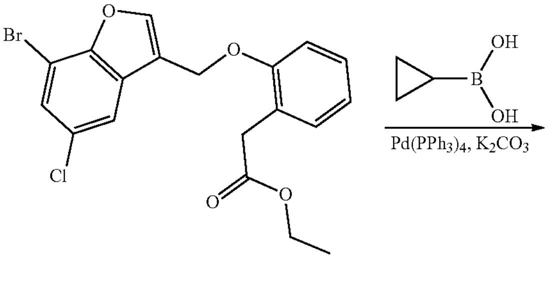

72e

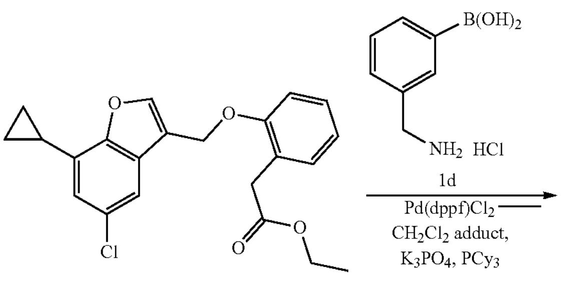

120a

-continued

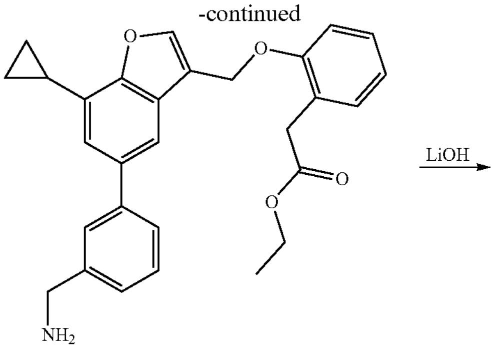

120b

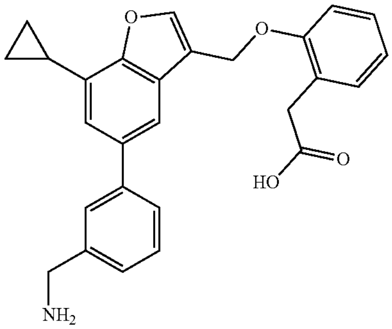

120c

Preparation of 2-(2-((5-(3-(aminomethyl)phenyl)-7-cyclopropylbenzofuran-3-yl)methoxy)phenyl)acetic acid (120c)

Step-1: Preparation of ethyl 2-(2-((5-chloro-7-cyclopropylbenzofuran-3-yl)methoxy)phenyl)acetate (120a)

Compound 120a was prepared according to the procedure reported in step-2 of scheme 111, from ethyl 2-(2-((7-bromo-5-chlorobenzofuran-3-yl)methoxy)phenyl)acetate (72e) (500 mg, 1.180 mmol) in THF (5 mL) using cyclopropylboronic acid (152 mg, 1.770 mmol), $Pd(PPh_3)_4$ (136 mg, 0.118 mmol), a solution of $K_2CO_3$ (245 mg, 1.770 mmol) in water (2.5 mL) and heating at 80° C. for 4 h. This gave after workup and purification by flash column chromatography [silica gel (12 g), eluting with EtOAc in hexanes from 0-50%] ethyl 2-(2-((5-chloro-7-cyclopropylbenzofuran-3-yl)methoxy)phenyl)acetate (120a) (269 mg, 59% yield) as a clear gum; $^1H$ NMR (300 MHz, DMSO-$d_6$) δ 8.16 (s, 1H), 7.46 (d, J=2.1 Hz, 1H), 7.28 (dd, J=7.4, 1.8 Hz, 1H), 7.26-7.13 (m, 2H), 6.99 (d, J=2.1 Hz, 1H), 6.93 (td, J=7.4, 1.2 Hz, 1H), 5.23 (d, J=6.0 Hz, 2H), 3.94 (q, J=7.1 Hz, 2H), 3.56 (d, J=2.9 Hz, 2H), 2.26 (tt, J=8.4, 5.2 Hz, 1H), 1.12-1.02 (m, 2H), 0.99 (t, J=7.1 Hz, 3H), 0.96-0.92 (m, 2H); MS (ES+): 407.10 (M+Na).

Step-2: Preparation of ethyl 2-(2-((5-(3-(aminomethyl)phenyl)-7-cyclopropylbenzofuran-3-yl)methoxy)phenyl)acetate (120b)

Compound 120b was prepared according to the procedure reported in step-2 of scheme 1, from ethyl 2-(2-((5-chloro-7-cyclopropylbenzofuran-3-yl)methoxy)phenyl)acetate (120a) (269 mg, 0.699 mmol) in dioxane/2-MeTHF (12 mL, ratio 2:1) using 3-(aminomethyl)phenylboronic acid hydrochloride (1d) (328 mg, 1.747 mmol), 4 M solution of $K_3PO_4$ (0.699 mL, 2.80 mmol), tricyclohexylphosphine (78 mg, 0.280 mmol), $PdCl_2$(dppf)-$CH_2Cl_2$ adduct (114 mg, 0.140 mmol) and heating at 115° C. for 3 h. This gave after workup and purification by flash column chromatography [silica gel (24 g), eluting with DMA-80 in DCM from 0-70%] ethyl 2-(2-((5-(3-(aminomethyl)phenyl)-7-cyclopropylbenzofuran-3-yl)methoxy)phenyl)acetate (120b) (113 mg, 36% yield); MS (ES+): 456.30 (M+1).

Step-3: Preparation of 2-(2-((5-(3-(aminomethyl)phenyl)-7-cyclopropylbenzofuran-3-yl)methoxy)phenyl)acetic acid (120c)

Compound 120c was prepared according to the procedure reported in step-3 of scheme 1, from ethyl 2-(2-((5-(3-(aminomethyl)phenyl)-7-cyclopropylbenzofuran-3-yl)methoxy)phenyl)acetate (120b) (113 mg, 0.248 mmol) in THF (2 mL), methanol (0.2 mL) and water (0.2 mL) using lithium hydroxide hydrate (23.76 mg, 0.992 mmol) and stirring at RT for 10 h. This gave after workup and purification by reverse phase column chromatography [C18 column (40 g), eluting with ACN in water (containing 0.1% HCl) from 0-100%] 2-(2-((5-(3-(aminomethyl)phenyl)-7-cyclopropylbenzofuran-3-yl)methoxy)phenyl)acetic acid (120c) (56 mg, 53% yield) HCl salt as a light brown solid; $^1H$ NMR (300 MHz, DMSO-$d_6$) δ 12.17 (s, 1H), 8.36 (s, 3H), 8.12 (s, 1H), 7.85 (s, 1H), 7.77 (d, J=1.7 Hz, 1H), 7.75-7.69 (m, 1H), 7.54-7.38 (m, 2H), 7.29-7.18 (m, 4H), 6.92 (t, J=7.2 Hz, 1H), 5.30 (s, 2H), 4.17-4.07 (m, 2H), 3.54 (s, 2H), 2.39-2.26 (m, 1H), 1.20 (d, J=20.1 Hz, 1H), 1.13-0.95 (m, 3H); MS (ES+): 428.2 (M+1); (ES−): 426.2 (M−1).

Scheme 121

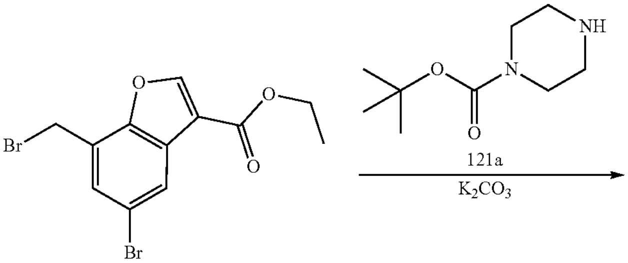

79c

-continued
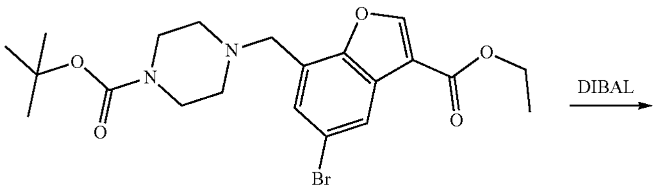
121b
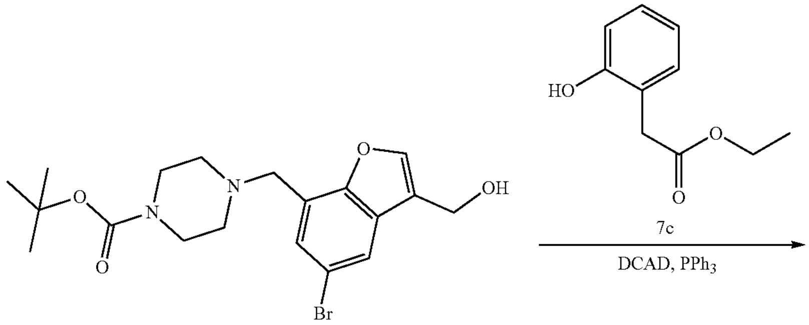
121c
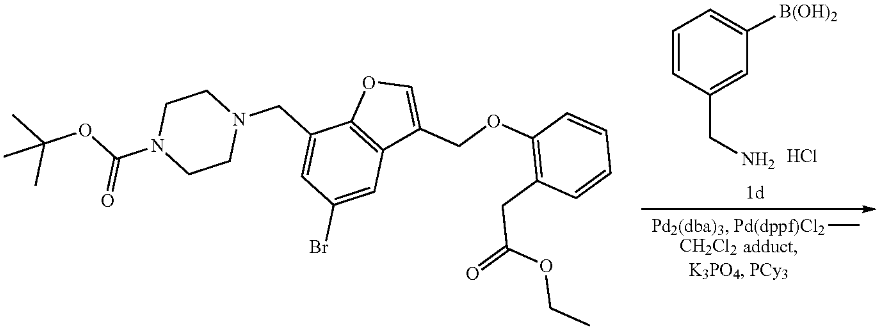
121d
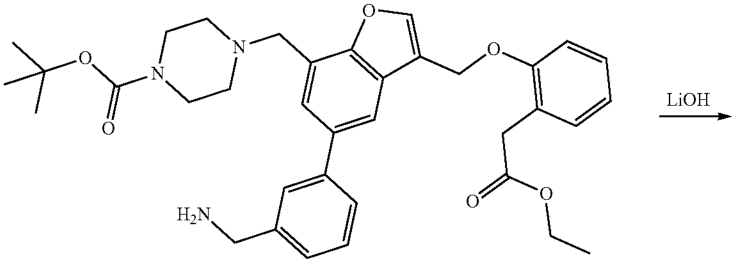
121e
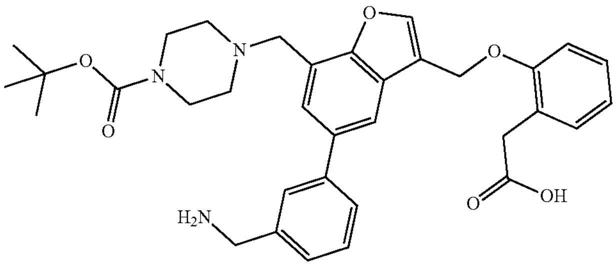
121f Preparation of 2-(2-((5-(3-(aminomethyl)phenyl)-7-((4-(tert-butoxycarbonyl)piperazin-1-yl)methyl)benzofuran-3-yl)methoxy)phenyl)acetic acid (121f)

Step-1: Preparation of tert-butyl 4-((5-bromo-3-(ethoxycarbonyl)benzofuran-7-yl)methyl)piperazine-1-carboxylate (121b)

Compound 121b was prepared according to the procedure reported in step-3 of scheme 79, from ethyl 5-bromo-7-(bromomethyl)benzofuran-3-carboxylate (79c) (1 g, 2.76 mmol) in DMF (15 mL) using tert-butyl piperazine-1-carboxylate (121a) (1.543 g, 8.29 mmol; CAS #57260-71-6) and potassium carbonate (1.145 g, 8.29 mmol) and stirring at RT for 3 h. This gave after workup and purification by flash column chromatography [silica gel (24 g), eluting with EtOAc in hexanes from 0-60%] tert-butyl 4-((5-bromo-3-(ethoxycarbonyl)benzofuran-7-yl)methyl)piperazine-1-carboxylate (121b) (0.63 g, 49% yield) as a yellow solid; MS (ES+) 467.10 (M+1).

Step-2: Preparation of tert-butyl 4-((5-bromo-3-(hydroxymethyl)benzofuran-7-yl)methyl)piperazine-1-carboxylate (121c)

Compound 121c was prepared according to the procedure reported in step-2 of scheme 69, from tert-butyl 4-((5-bromo-3-(ethoxycarbonyl)benzofuran-7-yl)methyl)piperazine-1-carboxylate (121b) (0.63 g, 1.348 mmol) in DCM (10 mL) using DIBAL (2.376 mL, 2.376 mmol; 1M in DCM) and stirring at −78° C. for 30 min. This gave after workup and purification by flash column chromatography [silica gel (12 g), eluting with DMA80 in DCM from 0-100%] tert-butyl 4-((5-bromo-3-(hydroxymethyl)benzofuran-7-yl)methyl)piperazine-1-carboxylate (121c) (0.47 g, 82% yield) as a light yellow oil; MS (ES+) 425.10 (M+1).

Step-3: Preparation of tert-butyl 4-((5-bromo-3-((2-(2-ethoxy-2-oxoethyl)phenoxy)methyl)benzofuran-7-yl)methyl)piperazine-1-carboxylate (121d)

Compound 121d was prepared according to the procedure reported in step-2 of Scheme 65, from tert-butyl 4-((5-bromo-3-(hydroxymethyl)benzofuran-7-yl)methyl)piperazine-1-carboxylate (121c) (0.47 g, 1.105 mmol) using triphenylphosphine (580 mg, 2.210 mmol), ethyl 2-(2-hydroxyphenyl)acetate (7c) (219 mg, 1.216 mmol) in DCM (10 mL), a solution of DCAD (812 mg, 2.210 mmol) in DCM (5 mL) at 0° C. and stirring at RT for 30 min. This gave after workup and purification by flash column chromatography [silica gel (24 g), eluting with EtOAc in hexane from 0-50%] tert-butyl 4-((5-bromo-3-((2-(2-ethoxy-2-oxoethyl)phenoxy)methyl)benzofuran-7-yl)methyl)piperazine-1-carboxylate (121d) (600 mg, 92% yield) as a light yellow solid; MS (ES+): 587.20 (M+1).

Step-4: Preparation of tert-butyl 4-((5-(3-(aminomethyl)phenyl)-3-((2-(2-ethoxy-2-oxoethyl)phenoxy)methyl)benzofuran-7-yl)methyl)piperazine-1-carboxylate (121e)

Compound 121e was prepared according to the procedure reported in step-2 of scheme 1, from tert-butyl 4-((5-bromo-3-((2-(2-ethoxy-2-oxoethyl)phenoxy)methyl)benzofuran-7-yl)methyl)piperazine-1-carboxylate (121d) (600 mg, 1.021 mmol) using 3-(aminomethyl)phenylboronic acid hydrochloride (1d) (383 mg, 2.043 mmol), 2 M solution of $K_3PO_4$ (2.043 mL, 4.09 mmol), tricyclohexylphosphine (57 mg, 0.204 mmol), $Pd_2(dba)_3$ (94 mg, 0.102 mmol) and Pd(dppf)$Cl_2$—$CH_2Cl_2$ adduct (83 mg, 0.102 mmol) and heating at 90° C. for 1 h in microwave. This gave after workup and purification by flash column chromatography [silica gel (24 g), eluting with DMA80 in DCM from 0-70%] tert-butyl 4-((5-(3-(aminomethyl)phenyl)-3-((2-(2-ethoxy-2-oxoethyl)phenoxy)methyl)benzofuran-7-yl)methyl)piperazine-1-carboxylate (121e) (230 mg, 37% yield); MS (ES+): 614.35 (M+1).

Step-5: Preparation of 2-(2-((5-(3-(aminomethyl)phenyl)-7-((4-(tert-butoxycarbonyl)piperazin-1-yl)methyl)benzofuran-3-yl)methoxy)phenyl)acetic acid (121f)

Compound 121f was prepared according to the procedure reported in step-3 of scheme 1, from tert-butyl 4-((5-(3-(aminomethyl)phenyl)-3-((2-(2-ethoxy-2-oxoethyl)phenoxy)methyl)benzofuran-7-yl)methyl)piperazine-1-carboxylate (121e) (75 mg, 0.122 mmol) in THF/MeOH (4 mL each) using a solution of lithium hydroxide hydrate (41 mg, 0.978 mmol) in water (1 mL) and stirring at RT for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-7-((4-(tert-butoxycarbonyl)piperazin-1-yl)methyl)benzofuran-3-yl)methoxy)phenyl)acetic acid (121f) (35 mg, 49% yield) HCl salt as a white solid; $^1H$ NMR (300 MHz, DMSO-$d_6$) δ 12.17 (s, 1H), 11.40 (s, 1H), 8.45 (s, 3H), 8.24 (s, 1H), 8.12 (s, 2H), 7.99 (s, 1H), 7.85 (d, J=7.5 Hz, 1H), 7.59-7.46 (m, 2H), 7.29 (td, J=7.7, 7.1, 1.7 Hz, 1H), 7.22 (dd, J=7.8, 1.5 Hz, 2H), 6.94 (td, J=7.2, 1.3 Hz, 1H), 5.35 (s, 2H), 4.68 (s, 2H), 4.11 (d, J=5.7 Hz, 2H), 4.08-3.94 (m, 2H), 3.56 (s, 2H), 3.42-3.23 (m, 6H), 1.41 (s, 9H); MS (ES+): 586.30 (M+1); MS (ES−): 584.30 (M−1).

Scheme 122

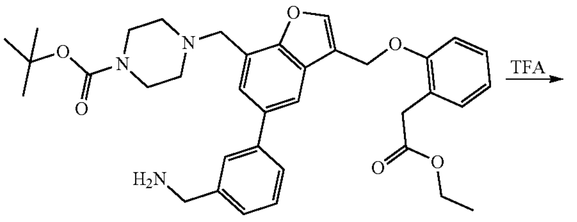

121e

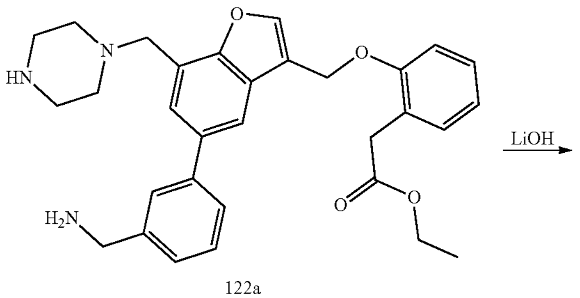

122a

-continued

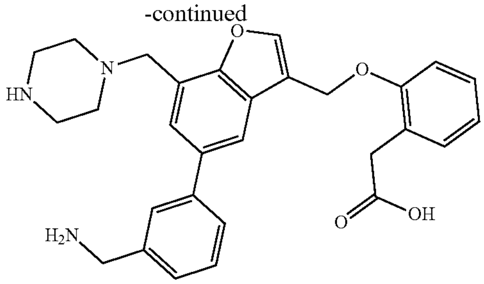

122b

Scheme 123

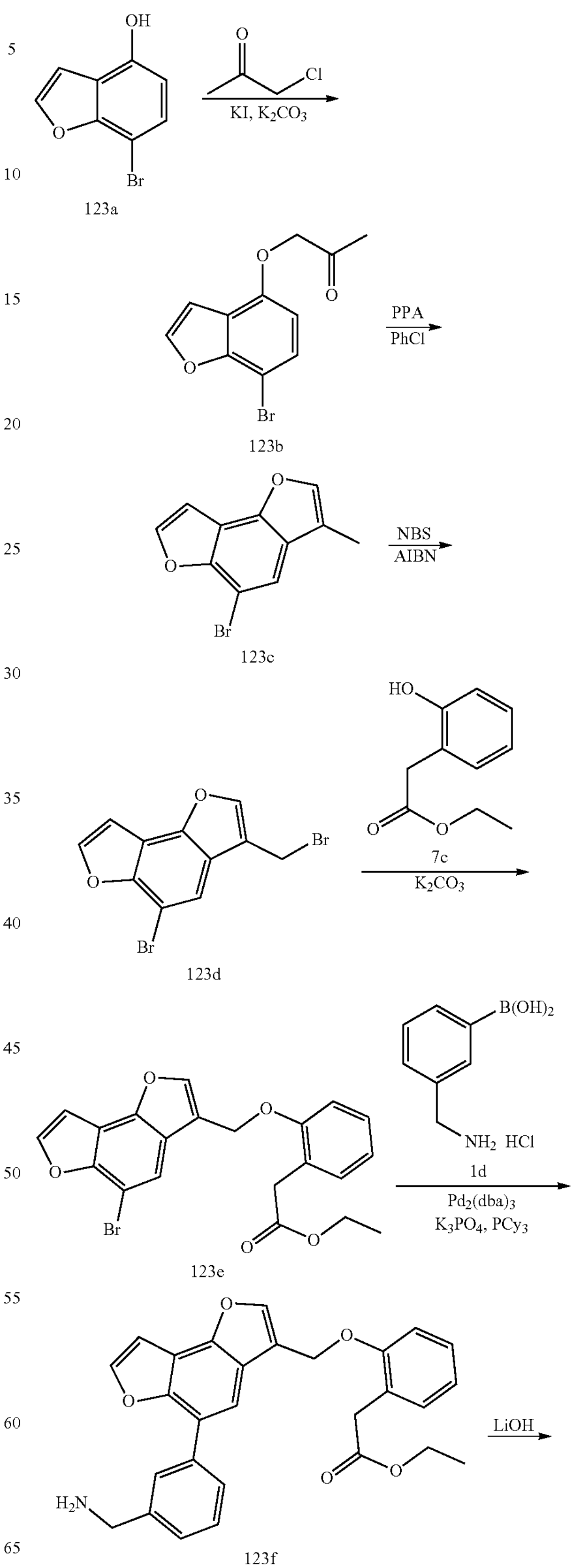

123a, 123b, 123c, 123d, 123e, 123f

Preparation of 2-(2-((5-(3-(aminomethyl)phenyl)-7-(piperazin-1-ylmethyl)benzofuran-3-yl)methoxy)phenyl)acetic acid (122b)

Step-1: Preparation of ethyl 2-(2-((5-(3-(aminomethyl)phenyl)-7-(piperazin-1-ylmethyl)benzofuran-3-yl)methoxy)phenyl)acetate (122a)

Compound 122a was prepared according to the procedure reported in step-9 of scheme 3, from tert-butyl 4-((5-(3-(aminomethyl)phenyl)-3-((2-(2-ethoxy-2-oxoethyl)phenoxy)methyl)benzofuran-7-yl)methyl)piperazine-1-carboxylate (121e) (160 mg, 0.261 mmol) in DCM (5 mL) using TFA (0.399 mL, 5.21 mmol) and stirring at RT for 2 h. This gave after workup and purification by flash column chromatography [silica gel (12 g), eluting with DMA-80 in DCM from 0-50%] ethyl 2-(2-((5-(3-(aminomethyl)phenyl)-7-(piperazin-1-ylmethyl)benzofuran-3-yl)methoxy)phenyl)acetate (122a) (134 mg, 100% yield) as a yellow oil; MS (ES+): 514.30 (M+1).

Step-2: Preparation of 2-(2-((5-(3-(aminomethyl)phenyl)-7-(piperazin-1-ylmethyl)benzofuran-3-yl)methoxy)phenyl)acetic acid (122b)

Compound 122b was prepared according to the procedure reported in step-3 of scheme 1, from ethyl 2-(2-((5-(3-(aminomethyl)phenyl)-7-(piperazin-1-ylmethyl)benzofuran-3-yl)methoxy)phenyl)acetate (122a) (130 mg, 0.253 mmol) in THF/MeOH (4 mL, each) using a solution of lithium hydroxide hydrate (42 mg, 1.012 mmol) in water (1 mL) and stirring at RT for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(piperazin-1-ylmethyl)benzofuran-3-yl)methoxy)phenyl)acetic acid (122b) (60 mg, 49% yield) HCl salt as a white solid; $^1$H NMR (300 MHz, DMSO-$d_6$) δ 12.27 (bs, 1H), 9.55 (bs, 2H), 8.51 (bs, 3H), 8.24 (s, 1H), 8.11 (s, 1H), 8.05 (s, 1H), 7.99 (s, 1H), 7.83 (d, J=7.3 Hz, 1H), 7.58-7.47 (m, 2H), 7.29 (td, J=7.6, 7.0, 1.6 Hz, 1H), 7.25-7.19 (m, 2H), 6.94 (td, J=7.2, 1.4 Hz, 1H), 5.35 (s, 2H), 4.79-4.45 (m, 2H), 4.11 (q, J=5.8 Hz, 2H), 3.74-3.63 (m, 4H), 3.56 (s, 2H), 3.45-3.36 (m, 4H); MS (ES+): 486.25 (M+1).

-continued

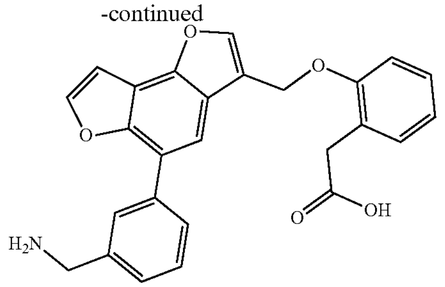

123g

Preparation of 2-(2-((5-(3-(aminomethyl)phenyl)benzo[1,2-b:3,4-b']difuran-3-yl)methoxy)phenyl)acetic acid (123g)

Step-1: Preparation of 1-((7-bromobenzofuran-4-yl)oxy)propan-2-one (123b)

To a solution of 7-bromobenzofuran-4-ol (123a) (529 mg, 2.483 mmol; CAS #405876-51-9) in DMF (6 mL) was added potassium carbonate (1030 mg, 7.45 mmol), 1-chloropropan-2-one (919 mg, 9.93 mmol) KI (412 mg, 2.483 mmol) and heated at 80° C. in a sealed tube overnight. The mixture was diluted with EtOAc, washed with water, brine, dried, filtered and concentrated in vacuum. The residue obtained was purified by flash column chromatography [silica gel (24 g), eluting with EtOAc in hexanes from 0-50%] to afford 1-((7-bromobenzofuran-4-yl)oxy)propan-2-one (123b) (523 mg, 78% yield) as a white yellow solid. $^1$H NMR (300 MHz, DMSO-$d_6$) δ 8.06 (d, J=2.2 Hz, 1H), 7.42 (d, J=8.5 Hz, 1H), 7.11 (d, J=2.2 Hz, 1H), 6.67 (d, J=8.6 Hz, 1H), 4.99 (s, 2H), 2.20 (s, 3H); MS (ES+): 290.90, 292.90 (M+1).

Step-2: Preparation of 5-bromo-3-methylbenzo[1,2-b:3,4-b']difuran (123c)

A mixture of polyphosphoric acid (PPA) (1.7 g) in chlorobenzene (15 mL) was heated to 80° C. and to this mixture was added a solution of 1-((7-bromobenzofuran-4-yl)oxy)propan-2-one (123b) (490 mg, 1.821 mmol) in chlorobenzene (10 mL) drop wise over a period of 10 min and heated with stirring at 80° C. for 2 h and then at 120° C. for 16 h. The reaction mixture was cooled to room temperature and the chlorobenzene solution was decanted from the polyphosphoric acid phase. The remaining residue was washed with MTBE. Combined organics were concentrated in vacuum to provide a dark amber oil, which was purified by flash column chromatography [silica gel (12 g), eluting with EtOAc in hexane from 0-25%] to provide 5-bromo-3-methylbenzo[1,2-b:3,4-b']difuran (123c) (289 mg, 63.2% yield) as a white solid. $^1$H NMR (300 MHz, DMSO-$d_6$) δ 8.22 (d, J=2.2 Hz, 1H), 7.87 (q, J=1.3 Hz, 1H), 7.82 (s, 1H), 7.36 (d, J=2.2 Hz, 1H), 2.26 (d, J=1.3 Hz, 3H).

Step-3: Preparation of 5-bromo-3-(bromomethyl)benzo[1,2-b:3,4-b']difuran (123d)

Compound 123d was prepared according to the procedure reported in step-2 of scheme 58, from 5-bromo-3-methylbenzo[1,2-b:3,4-b']difuran (123c) (312 mg, 1.243 mmol) using NBS (221 mg, 1.243 mmol) and AIBN (20.41 mg, 0.124 mmol) in carbon tetrachloride (10 mL) and refluxing for 6 h. The mixture was cooled to room temperature and filtered. The filtrate was concentrated in vacuum to give 5-bromo-3-(bromomethyl)benzo[1,2-b:3,4-b']difuran (123d) (410 mg, 100% yield) as a yellow solid, which was used as such in the next step without purification.

Step-4: Preparation of ethyl 2-(2-((5-bromobenzo[1,2-b:3,4-b']difuran-3-yl)methoxy)phenyl)acetate (123e)

Compound 123e was prepared according to the procedure reported in step-3 of scheme 7, from 5-bromo-3-(bromomethyl)benzo[1,2-b:3,4-b']difuran (123d) (0.410 g, 1.243 mmol) in acetone (10 mL) using ethyl 2-(2-hydroxyphenyl)acetate (7c) (0.336 g, 1.864 mmol), potassium carbonate (601 mg, 4.35 mmol) and stirring overnight at RT. This gave after workup and purification by flash column chromatography [silica gel (12 g) eluting with ethyl acetate in hexanes from 0-50%] ethyl 2-(2-((5-bromobenzo[1,2-b:3,4-b']difuran-3-yl)methoxy)phenyl)acetate (123e) (231 mg, 43% yield) as a yellow oil; $^1$H NMR (300 MHz, DMSO-$d_6$) δ 8.25 (d, J=2.2 Hz, 1H), 8.18 (s, 1H), 7.84 (s, 1H), 7.41 (d, J=2.2 Hz, 1H), 7.35-7.26 (m, 1H), 7.26-7.16 (m, 2H), 6.94 (t, J=7.3 Hz, 1H), 5.30 (s, 2H), 3.93 (q, J=7.1 Hz, 2H), 3.57 (s, 2H), 0.96 (t, J=7.1 Hz, 3H).

Step-5: Preparation of ethyl 2-(2-((5-(3-(aminomethyl)phenyl)benzo[1,2-b:3,4-b']difuran-3-yl)methoxy)phenyl)acetate (123f)

Compound 123f was prepared according to the procedure reported in step-2 of scheme 1, from ethyl 2-(2-((5-bromobenzo[1,2-b:3,4-b']difuran-3-yl)methoxy)phenyl)acetate (123e) (115 mg, 0.268 mmol) in dioxane/2Me-THF (12 mL, ratio 2:1) using 3-(aminomethyl)phenylboronic acid hydrochloride (1d) (126 mg, 0.670 mmol), 4M solution of $K_3PO_4$ (0.268 mL, 1.072 mmol), tricyclohexylphosphine (30.1 mg, 0.107 mmol), $Pd_2(dba)_3$ (49.1 mg, 0.054 mmol) and heating at 115° C. for 3 h. This gave after workup and purification by flash column chromatography [silica gel (12 g), eluting with DMA-80 in DCM from 0-70%] ethyl 2-(2-((5-(3-(aminomethyl)phenyl)benzo[1,2-b:3,4-b']difuran-3-yl)methoxy)phenyl)acetate (123f) (102 mg, 84% yield) as a yellow oil; MS (ES+): 456.20 (M+1).

Step-6: Preparation of 2-(2-((5-(3-(aminomethyl)phenyl)benzo[1,2-b:3,4-b']difuran-3-yl)methoxy)phenyl)acetic acid (123g)

Compound 123g was prepared according to the procedure reported in step-3 of scheme 1, from ethyl 2-(2-((5-(3-(aminomethyl)phenyl)benzo[1,2-b:3,4-b']difuran-3-yl)methoxy)phenyl)acetate (123f) (102 mg, 0.224 mmol) in MeOH/THF (6 mL each) using a solution of lithium hydroxide hydrate (80 mg, 1.907 mmol) in water (2 mL) and stirring overnight at RT. This gave after workup and purification by reverse phase column chromatography [C18 column (50 g), eluting with ACN in water (containing 0.1% HCl) from 0-100%] 2-(2-((5-(3-(aminomethyl)phenyl)benzo[1,2-b:3,4-b']difuran-3-yl)methoxy)phenyl)acetic acid (123g) (40 mg, 45%% yield) HCl salt as a white solid; $^1$H NMR (300 MHz, DMSO-$d_6$) δ 8.36 (s, 3H), 8.20 (d, J=2.2 Hz, 1H), 8.16 (s, 1H), 7.99 (s, 1H), 7.91 (d, J=7.6 Hz, 1H), 7.82 (s, 1H), 7.64-7.50 (m, 2H), 7.36 (d, J=2.3 Hz, 1H), 7.33-7.16 (m, 3H), 6.93 (t, J=7.2 Hz, 1H), 5.37 (s, 2H), 4.14 (s, 2H), 3.55 (s, 2H); MS (ES+): 428.20 (M+1), (ES−): 426.10 (M−1).

Scheme 124

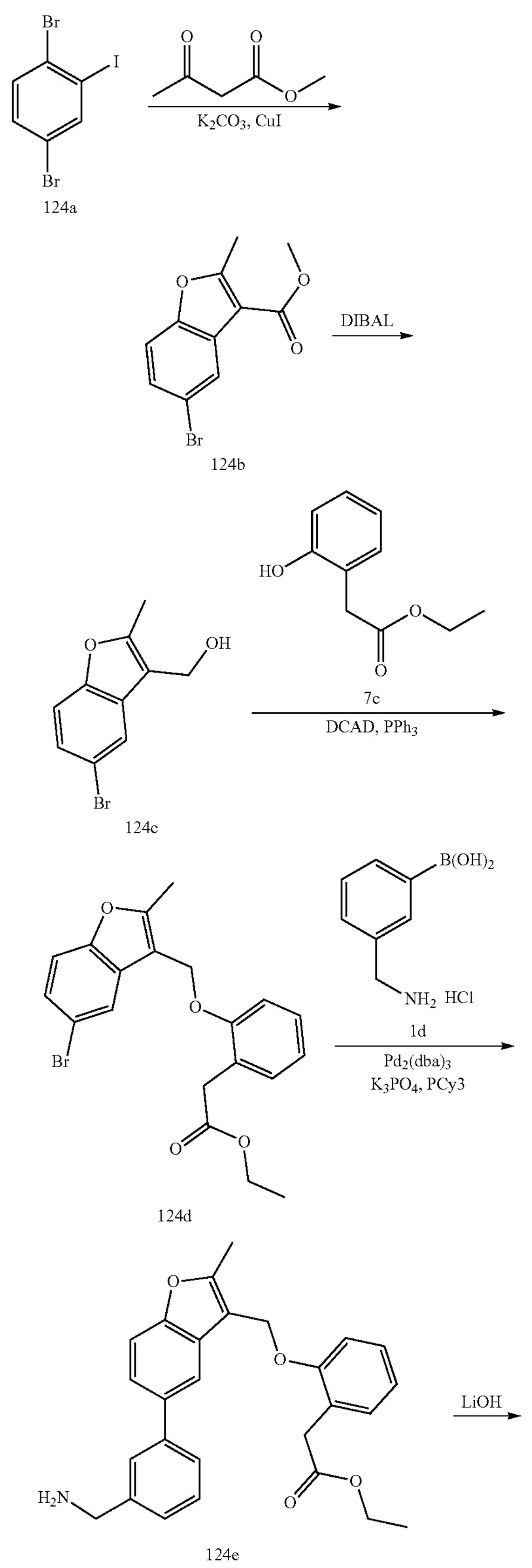

124a 124b 124c 124d 124e

-continued

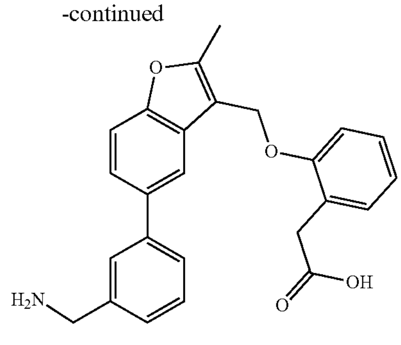

124f

Preparation of 2-(2-((5-(3-(aminomethyl)phenyl)-2-methylbenzofuran-3-yl)methoxy)phenyl)acetic acid (124f)

Step-1: Preparation of methyl 5-bromo-2-methylbenzofuran-3-carboxylate (124b)

To a solution of copper(I) iodide (1.369 g, 7.19 mmol) and potassium carbonate (19.10 g, 138 mmol) in THF (50 mL) was added 1,4-dibromo-2-iodobenzene (124a) (20 g, 55.3 mmol; CAS #89284-52-6) and methyl acetoacetate (8.95 mL, 83 mmol) under an argon atmosphere and stirred at 90° C. for 4 days. The reaction mixture was diluted with EtOAc and extracted with water. The combined organic phases were dried, filtered and concentrated in vacuum. The obtained residue was purified by flash column chromatography [silica gel (80 g), eluting with EtOAc in hexane from 0-100%) to give methyl 5-bromo-2-methylbenzofuran-3-carboxylate (124b) (4.2 g, 28.2% yield) as a white solid; $^1H$ NMR (300 MHz, DMSO-$d_6$) δ 7.96 (d, J=2.1 Hz, 1H), 7.60 (d, J=8.7 Hz, 1H), 7.49 (dd, J=8.7, 2.1 Hz, 1H), 3.89 (s, 3H), 2.73 (s, 3H).

Step-2: Preparation of (5-bromo-2-methylbenzofuran-3-yl)methanol (124c)

Compound 124c was prepared according to the procedure reported in step-4 of scheme 3, from methyl 5-bromo-2-methylbenzofuran-3-carboxylate (124b) (2 g, 7.43 mmol) using DIBAL (18.58 mL, 18.58 mmol; 1M in DCM) and stirring at 0° C. for 2 h. This gave after workup and purification by flash column chromatography [silica gel (24 g), eluting with EtOAc in hexane from 0-100%] (5-bromo-2-methylbenzofuran-3-yl)methanol (124c) (1.48 g, 83% yield) as a white solid; $^1H$ NMR (300 MHz, DMSO-$d_6$) δ 7.79 (d, J=2.0 Hz, 1H), 7.45 (d, J=8.6 Hz, 1H), 7.36 (dd, J=8.6, 2.1 Hz, 1H), 5.06 (t, J=5.6 Hz, 1H), 4.55 (d, J=5.6 Hz, 2H), 2.43 (s, 3H).

Step-3: Preparation of ethyl 2-(2-((5-bromo-2-methylbenzofuran-3-yl)methoxy)phenyl)acetate (124d)

Compound 124d was prepared according to the procedure reported in step-3 of scheme 7, from (5-bromo-2-methylbenzofuran-3-yl)methanol (124c) (750 mg, 3.11 mmol), triphenylphosphine (898 mg, 3.42 mmol), ethyl 2-(2-hydroxyphenyl)acetate (7c) (617 mg, 3.42 mmol) in DCM (20 mL) using bis(4-chlorobenzyl) diazene-1,2-dicarboxylate (DCAD) (1257 mg, 3.42 mmol) in DCM (10 mL). The reaction mixture was stirred at RT for 30 min. This gave after workup and purification by flash column chromatography [silica gel (40 g), eluting with EtOAc in hexane from 0-50%] ethyl 2-(2-((5-bromo-2-methylbenzofuran-3-yl)methoxy)phenyl)acetate (124d) (812 mg, 64.7% yield) as a clear oil; $^1$H NMR (300 MHz, DMSO-$d_6$) δ 7.74 (d, J=2.0 Hz, 1H), 7.51 (d, J=8.7 Hz, 1H), 7.41 (dd, J=8.7, 2.0 Hz, 1H), 7.31 (td, J=7.7, 1.7 Hz, 1H), 7.25-7.16 (m, 2H), 6.93 (td, J=7.4, 1.1 Hz, 1H), 5.18 (s, 2H), 3.92 (q, J=7.1 Hz, 2H), 3.52 (s, 2H), 2.50 (s, 3H), 0.96 (t, J=7.1 Hz, 3H); MS (ES+): 425.1 and 427.0 (M+Na).

Step-4: Preparation of ethyl 2-(2-((5-(3-(aminomethyl)phenyl)-2-methylbenzofuran-3-yl)methoxy)phenyl)acetate (124e)

Compound 124e was prepared according to the procedure reported in step-2 of scheme 1, from ethyl 2-(2-((5-bromo-2-methylbenzofuran-3-yl)methoxy)phenyl)acetate (124d) (400 mg, 0.992 mmol) in dioxane (40 mL) using 3-(aminomethyl)phenylboronic acid hydrochloride (1d) (372 mg, 1.984 mmol), 4 M solution of $K_3PO_4$ (0.992 mL, 3.97 mmol), tricyclohexylphosphine (111 mg, 0.397 mmol) and $Pd_2(dba)_3$ (136 mg, 0.149 mmol) and heating at 100° C. for 2 h. This gave after workup and purification by flash column chromatography [silica gel (24 g), eluting with DMA-80 in DCM from 0-70%] ethyl 2-(2-((5-(3-(aminomethyl)phenyl)-2-methylbenzofuran-3-yl)methoxy)phenyl)acetate (124e) (220 mg, 52% yield) as a yellow oil; $^1$H NMR (300 MHz, DMSO-$d_6$) δ 7.81 (d, J=1.7 Hz, 1H), 7.66 (s, 1H), 7.61-7.51 (m, 3H), 7.38 (t, J=7.6 Hz, 1H), 7.30 (d, J=7.2 Hz, 2H), 7.26 (d, J=1.3 Hz, 1H), 7.24-7.17 (m, 1H), 6.93 (td, J=7.2, 1.3 Hz, 1H), 5.25 (s, 2H), 3.79 (s, 2H), 3.71 (q, J=7.1 Hz, 2H), 3.52 (s, 2H), 2.52 (s, 3H), 0.83 (t, J=7.1 Hz, 3H); MS (ES+): 430.2 (M+1).

Step-5: Preparation of 2-(2-((5-(3-(aminomethyl)phenyl)-2-methylbenzofuran-3-yl)methoxy)phenyl)acetic acid (124f)

Compound 124f was prepared according to the procedure reported in step-3 of scheme 1, from ethyl 2-(2-((5-(3-(aminomethyl)phenyl)-2-methylbenzofuran-3-yl)methoxy)phenyl)acetate (124e) (220 mg, 0.512 mmol) in THF (6 mL) using a solution of lithium hydroxide hydrate (62.4 mg, 1.488 mmol) in water (1 mL) and stirring for 3 h at 50° C. This gave after workup and purification by reverse phase column chromatography [C18 column (30 g), eluting with ACN in water (containing 0.1% HCl) from 0-100%] 2-(2-((5-(3-(aminomethyl)phenyl)-2-methylbenzofuran-3-yl)methoxy)phenyl)acetic acid (124f) (66 mg, 17% yield) HCl salt as a white solid; $^1$H NMR (300 MHz, DMSO-$d_6$) δ 12.09 (s, 1H, $D_2O$ exchangeable), 8.42 (s, 2H, $D_2O$ exchangeable), 7.92 (s, 1H), 7.87 (s, 1H), 7.73 (d, J=7.5 Hz, 1H), 7.66-7.55 (m, 2H), 7.53-7.40 (m, 2H), 7.32-7.23 (m, 2H), 7.23-7.15 (m, 1H), 6.92 (t, J=6.9 Hz, 1H), 5.25 (s, 2H), 4.10 (s, 2H), 3.49 (s, 2H), 2.52 (s, 3H); MS (ES+): 402.2 (M+1), (ES−): 400.2 (M−1).

Scheme 125

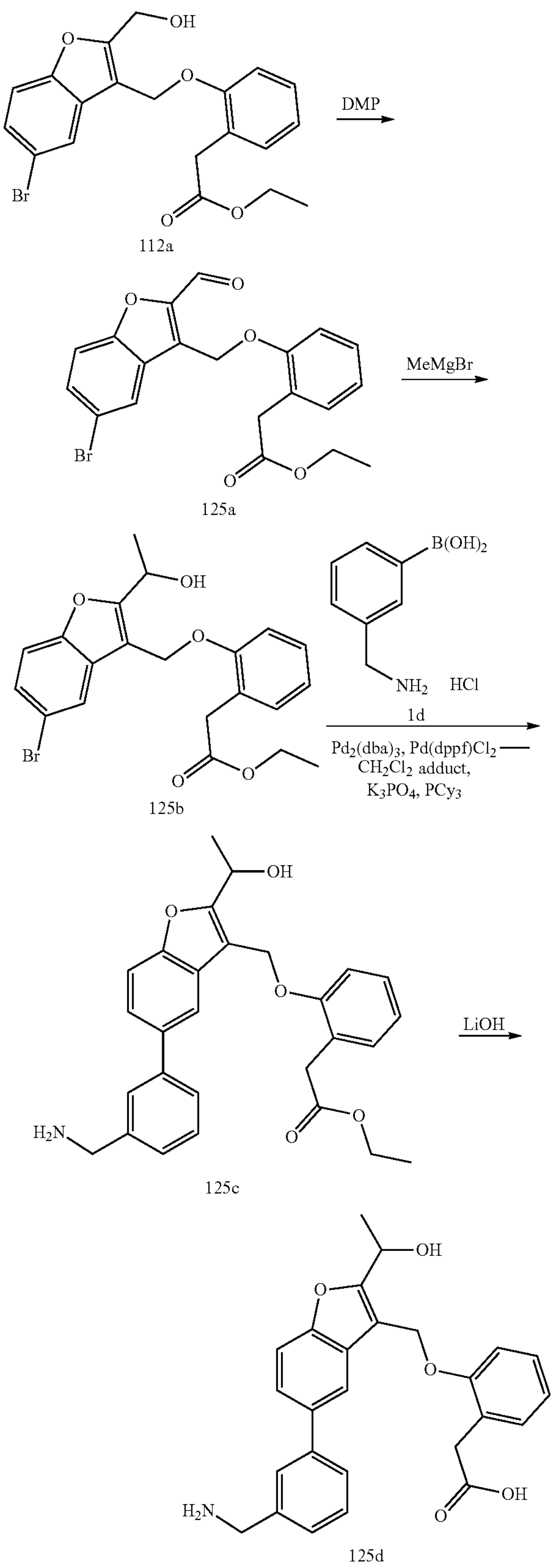

Preparation of 2-(2-((5-(3-(aminomethyl)phenyl)-2-(1-hydroxyethyl)benzofuran-3-yl)methoxy)phenyl) acetic acid (125d)

Step-1: Preparation of ethyl 2-(2-((5-bromo-2-formylbenzofuran-3-yl)methoxy)phenyl)acetate (125a)

To a solution of ethyl 2-(2-((5-bromo-2-(hydroxymethyl) benzofuran-3-yl)methoxy)phenyl)acetate (112a) (2.5 g, 5.96 mmol) in DCM (40 mL) was added Dess-Martin periodinane (DMP) (3.03 g, 7.16 mmol) and stirred at RT for 3 h. The reaction mixture was diluted with DCM, washed with saturated aqueous sodium bicarbonate, dried, filtered, and evaporated in vacuum. The residue obtained was purified by flash column chromatography [silica gel, eluting with EtOAc in hexane from 0-100%] to give ethyl 2-(2-((5-bromo-2-formylbenzofuran-3-yl)methoxy)phenyl)acetate (125a) (1.7 g, 68% yield) as a white solid; $^1$H NMR (300 MHz, DMSO-$d_6$) δ 10.12 (s, 1H), 8.17 (t, J=1.3 Hz, 1H), 7.77 (d, J=1.3 Hz, 2H), 7.32 (ddd, J=8.9, 7.4, 1.7 Hz, 1H), 7.26-7.18 (m, 2H), 6.97 (td, J=7.4, 1.2 Hz, 1H), 5.65 (s, 2H), 3.90 (q, J=7.1 Hz, 2H), 3.58 (s, 2H), 0.97 (t, J=7.1 Hz, 3H).

Step-2: Preparation of ethyl 2-(2-((5-bromo-2-(1-hydroxyethyl)benzofuran-3-yl)methoxy)phenyl)acetate (125b)

Compound 125b was prepared according to the procedure reported in step-7 of scheme 3, from ethyl 2-(2-((5-bromo-2-formylbenzofuran-3-yl)methoxy)phenyl)acetate (125a) (1 g, 2.397 mmol) in THF (20 mL) using methyl magnesium bromide (1.883 mL, 2.64 mmol; 1.4 M in THF) and stirring at 0° C. for 1 h. This gave after work up and purification by flash column chromatography [silica gel, eluting with EtOAc in hexane from 0-100%] ethyl 2-(2-((5-bromo-2-(1-hydroxyethyl)benzofuran-3-yl)methoxy)phenyl)acetate (125b) (825 mg, 79% yield) as a clear oil; $^1$H NMR (300 MHz, DMSO-$d_6$) δ 7.79 (d, J=2.0 Hz, 1H), 7.58 (d, J=8.7 Hz, 1H), 7.46 (dd, J=8.7, 2.1 Hz, 1H), 7.30 (td, J=7.8, 7.2, 1.7 Hz, 1H), 7.25-7.17 (m, 2H), 6.93 (td, J=7.3, 1.2 Hz, 1H), 5.64 (d, J=4.6 Hz, 1H), 5.36-5.21 (m, 2H), 5.16-5.03 (m, 1H), 3.92 (q, J=7.1 Hz, 2H), 3.53 (s, 2H), 1.46 (d, J=6.5 Hz, 3H), 0.96 (t, J=7.1 Hz, 3H); MS (ES+): 455.0 and 457.0 (M+Na).

Step-3: Preparation of ethyl 2-(2-((5-(3-(aminomethyl)phenyl)-2-(1-hydroxyethyl)benzofuran-3-yl) methoxy)phenyl)acetate (125c)

Compound 125c was prepared according to the procedure reported in step-2 of scheme 1, from ethyl 2-(2-((5-bromo-2-(1-hydroxyethyl)benzofuran-3-yl)methoxy)phenyl)acetate (125b) (350 mg, 0.808 mmol) in dioxane (40 mL) using 3-(aminomethyl)phenylboronic acid hydrochloride (1d) (303 mg, 1.616 mmol), 4M solution of $K_3PO_4$ (0.808 mL, 3.23 mmol), tricyclohexylphosphine (91 mg, 0.323 mmol), Pd(dppf) $C_{12}$—$CH_2Cl_2$ adduct (99 mg, 0.121 mmol), $Pd_2(dba)_3$ (111 mg, 0.121 mmol) and heating at 100° C. for 1 h. This gave after workup and purification by column chromatography [silica gel (24 g), eluting with DMA-80 in DCM from 0-70%] ethyl 2-(2-((5-(3-(aminomethyl)phenyl)-2-(1-hydroxyethyl)benzofuran-3-yl)methoxy)phenyl)acetate (125c) (298 mg, 80% yield) as a clear oil, $^1$H NMR (300 MHz, DMSO-$d_6$) δ 7.86 (d, J=1.7 Hz, 1H), 7.68-7.59 (m, 3H), 7.53 (d, J=7.7 Hz, 1H), 7.38 (t, J=7.5 Hz, 1H), 7.34-7.25 (m, 3H), 7.20 (dd, J=7.4, 1.6 Hz, 1H), 6.93 (td, J=7.1, 1.5 Hz, 1H), 5.61 (s, 1H), 5.42-5.28 (m, 2H), 5.12 (q, J=6.5 Hz, 1H), 3.79 (s, 2H), 3.69 (q, J=7.1 Hz, 2H), 3.54 (s, 2H), 2.00 (s, 2H), 1.49 (d, J=6.5 Hz, 3H), 0.83 (t, J=7.1 Hz, 3H); MS (ES+): 460.2 (M+1).

Step-4: Preparation of 2-(2-((5-(3-(aminomethyl) phenyl)-2-(1-hydroxyethyl)benzofuran-3-yl) methoxy)phenyl)acetic acid (125d)

Compound 125d was prepared according to the procedure reported in step-3 of scheme 1, from ethyl 2-(2-((5-(3-(aminomethyl)phenyl)-2-(1-hydroxyethyl)benzofuran-3-yl) methoxy)phenyl)acetate (125c) (298 mg, 0.648 mmol) in THF (6 mL) using a solution of lithium hydroxide hydrate (50.8 mg, 1.212 mmol) in water (1 mL) and stirring at 50° C. for 3 h. This gave after workup and purification by reverse phase column chromatography [C18 column (30 g), eluting with ACN in water (containing 0.1% HCl) from 0-100%] 2-(2-((5-(3-(aminomethyl)phenyl)-2-(1-hydroxyethyl)benzofuran-3-yl)methoxy)phenyl)acetic acid (125d) (187 mg, 54% yield) as a white solid; $^1$H NMR (300 MHz, DMSO-$d_6$) δ 12.11 (s, 1H, $D_2O$ exchangeable), 8.54 (s, 2H, $D_2O$ exchangeable), 7.98 (d, J=1.6 Hz, 1H), 7.90 (d, J=2.2 Hz, 1H), 7.77-7.59 (m, 3H), 7.49 (q, J=7.6 Hz, 2H), 7.33-7.23 (m, 2H), 7.23-7.14 (m, 1H), 6.92 (ddd, J=7.9, 5.4, 3.0 Hz, 1H), 5.63 (s, 1H, $D_2O$ exchangeable), 5.36 (q, J=11.8 Hz, 2H), 5.13 (q, J=6.5 Hz, 1H), 4.09 (s, 2H), 3.51 (s, 2H), 1.48 (d, J=6.5 Hz, 3H); MS (ES+): 432.2 (M+1); (ES−) 430.1 (M−1).

Scheme 126

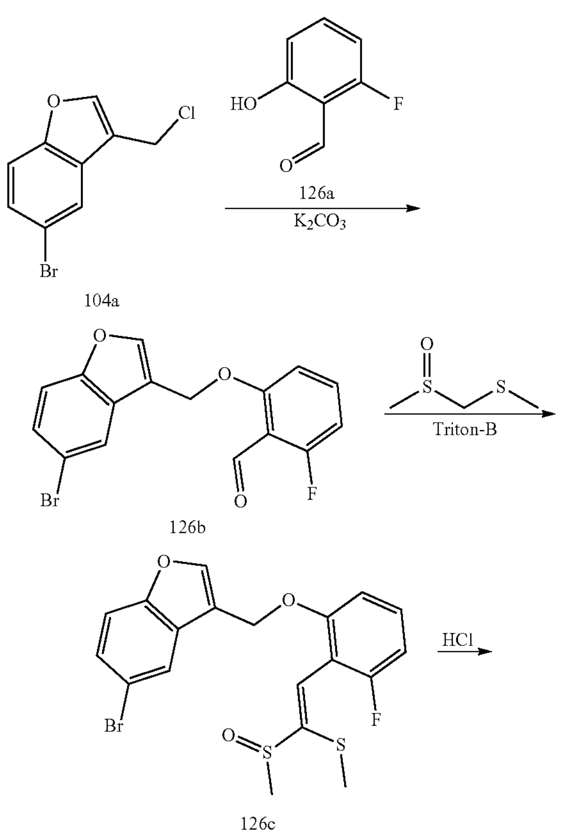

-continued

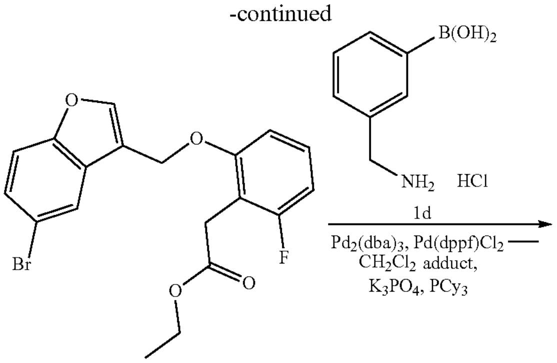

126d

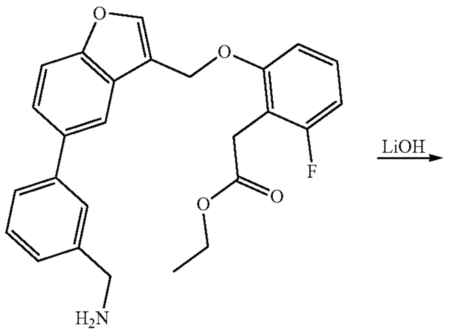

126e

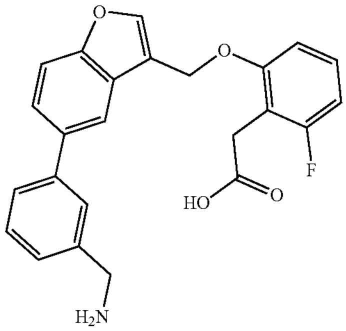

126f

Preparation of 2-(2-((5-(3-(aminomethyl)phenyl) benzofuran-3-yl)methoxy)-6-fluorophenyl)acetic acid (126f)

Step-1: Preparation of 2-((5-bromobenzofuran-3-yl) methoxy)-6-fluorobenzaldehyde (126b)

Compound 126b was prepared according to the procedure reported in step-3 of scheme 7, from 5-bromo-3-(chloromethyl)benzofuran (104a) (1 g, 4.07 mmol) in DMF (8 mL) using 2-fluoro-6-hydroxybenzaldehyde (126a) (519 mg, 3.70 mmol; CAS #38226-10-7) and potassium carbonate (1.535 g, 11.11 mmol) and stirring overnight at RT. This gave after workup and purification by flash column chromatography [silica gel (12 g), eluting with ethyl acetate and hexanes from 0-50%] 2-((5-bromobenzofuran-3-yl) methoxy)-6-fluorobenzaldehyde (126b) (895 mg, 69% yield); $^{1}$H NMR (300 MHz, DMSO-d$_6$) δ 10.32 (d, J=1.3 Hz, 1H), 8.27 (s, 1H), 8.02 (d, J=2.0 Hz, 1H), 7.75-7.66 (m, 1H), 7.63 (d, J=8.7 Hz, 1H), 7.52 (dd, J=8.8, 2.1 Hz, 1H), 7.27 (d, J=8.6 Hz, 1H), 6.93 (dd, J=10.7, 8.4 Hz, 1H), 5.46 (d, J=1.0 Hz, 2H). $^{19}$F NMR (282 MHz, DMSO-d$_6$) δ −115.43.

Step-2: Preparation of 5-bromo-3-((3-fluoro-2-(2-(methylsulfinyl)-2-(methylthio)vinyl)phenoxy) methyl)benzofuran (126c)

Compound 126c was prepared according to the procedure reported in step-1 of scheme 12, from 2-((5-bromobenzofuran-3-yl)methoxy)-6-fluorobenzaldehyde (126b) (895 mg, 2.56 mmol) using methyl(methylsulfinylmethyl)sulfane (0.418 mL, 4.10 mmol) and Triton B (0.582 mL, 1.282 mmol; 40% wt. in MeOH) in THF (10 mL) and refluxing for 12 h. This gave after workup and purification by flash column chromatography [silica gel (24 g), eluting with EtOAc in hexane from 0-40%] 5-bromo-3-((3-fluoro-2-(2-(methylsulfinyl)-2-(methylthio)vinyl)phenoxy)methyl)benzofuran (126c) (515 mg, 44% yield) as a white solid; MS (ES+): 476.90 (M+Na).

Step-3: Preparation of ethyl 2-(2-((5-bromobenzofuran-3-yl)methoxy)-6-fluorophenyl)acetate (126d)

Compound 126d was prepared according to the procedure reported in step-2 of scheme 7, from 5-bromo-3-((3-fluoro-2-(2-(methylsulfinyl)-2-(methylthio)vinyl)phenoxy)methyl) benzofuran (126c) (515 mg, 1.131 mmol) in ethanol (10 mL) using 4M HCl (1.414 mL, 5.65 mmol) and refluxing for 2 h. This gave after workup and purification by flash column chromatography [silica gel (12 g), eluting with EtOAc in hexane]ethyl 2-(2-((5-bromobenzofuran-3-yl)methoxy)-6-fluorophenyl)acetate (126d) (87 mg, 19% yield); MS (ES+): 429.00 (M+Na).

Step-4: Preparation of ethyl 2-(2-((5-(3-(aminomethyl)phenyl)benzofuran-3-yl)methoxy)-6-fluorophenyl)acetate (126e)

Compound 126e was prepared according to the procedure reported in step-2 of scheme 1, from ethyl 2-(2-((5-bromobenzofuran-3-yl)methoxy)-6-fluorophenyl)acetate (126d) (87 mg, 0.208 mmol)) in dioxane/THF (6 mL, each) using 3-(aminomethyl)phenylboronic acid hydrochloride (1d) (78 mg, 0.415 mmol), 2 M solution of K$_3$PO$_4$ (0.415 mL, 0.830 mmol), tricyclohexylphosphine (11.64 mg, 0.042 mmol), Pd(dppf)Cl$_2$—CH$_2$Cl$_2$ adduct (16.95 mg, 0.021 mmol), Pd$_2$(dba)$_3$ (19.0 mg, 0.021 mmol and heating at 95° C. for 1 h. This gave after workup and purification by flash column chromatography [silica gel (24 g), eluting with DMA80 in DCM from 0-70%] ethyl 2-(2-((5-(3-(aminomethyl)phenyl)benzofuran-3-yl)methoxy)-6-fluorophenyl)acetate (126e) (27 mg, 29% yield) as a colorless oil; MS (ES+): 434.20 (M+1).

Step-5: Preparation of 2-(2-((5-(3-(aminomethyl) phenyl)benzofuran-3-yl)methoxy)-6-fluorophenyl) acetic acid (126f)

Compound 126f was prepared according to the procedure reported in step-3 of scheme 1, from ethyl 2-(2-((5-(3-(aminomethyl)phenyl)benzofuran-3-yl)methoxy)-6-fluorophenyl)acetate (126e) (27 mg, 0.067 mmol) in THF (2 mL), methanol (0.2 mL) and water (0.2 mL) using a solution of lithium hydroxide hydrate (6.39 mg, 0.267 mmol) and stirring at RT for 10 h. This gave after workup and purification by reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-6-fluorophenyl)acetic acid (126f) (14 mg, 56% yield) HCl salt as a light brown solid; $^1$H NMR (300 MHz, DMSO-$d_6$) δ 8.33 (s, 3H, $D_2O$ exchangeable), 8.17 (s, 1H), 8.00 (s, 1H), 7.88 (s, 1H), 7.76 (d, J=3.6 Hz, 1H), 7.74 (s, 1H), 7.69 (d, J=8.7 Hz, 1H), 7.53 (t, J=7.7 Hz, 1H), 7.45 (d, J=7.4 Hz, 1H), 7.33 (q, J=8.1 Hz, 1H), 7.11 (d, J=8.3 Hz, 1H), 6.85 (t, J=8.8 Hz, 1H), 5.37 (s, 2H), 4.12 (s, 2H), 3.56 (s, 2H); $^{19}$F NMR (282 MHz, DMSO-$d_6$) δ −116.25; MS (ES+): 406.2 (M+1); (ES−): 404.1(M−1).

Scheme 127

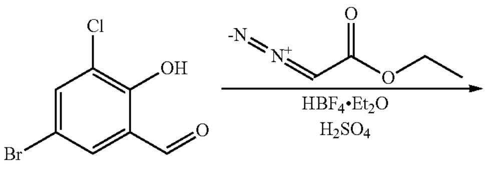

127a

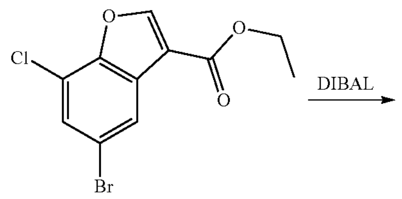

127b

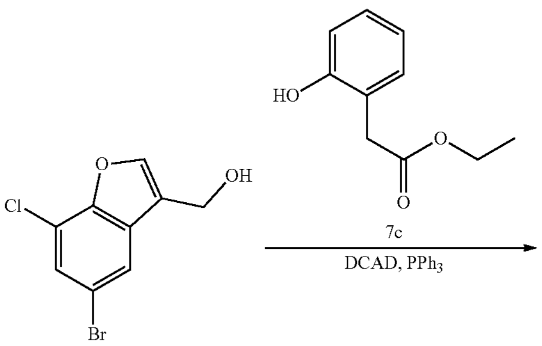

127c

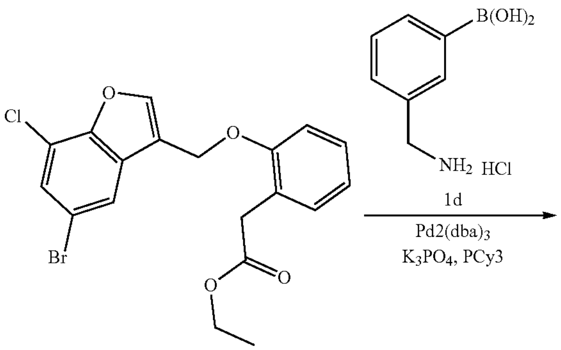

127d

-continued

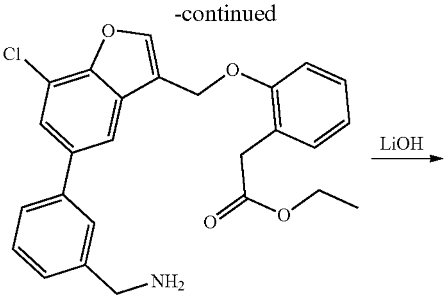

127e

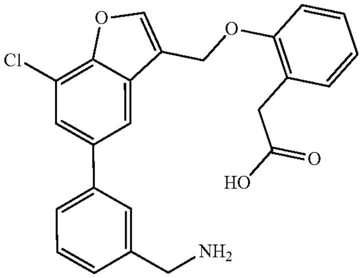

127f

Preparation of 2-(2-((5-(3-(aminomethyl)phenyl)-7-chlorobenzofuran-3-yl)methoxy)phenyl)acetic acid (127f)

Step-1: Preparation of ethyl 5-bromo-7-chlorobenzofuran-3-carboxylate (127b)

Compound 127b was prepared according to the procedure reported in step-1 of scheme 69, from 5-bromo-3-chloro-2-hydroxybenzaldehyde (127a) (36 g, 153 mmol; CAS #19652-33-6) in DCM (200 mL) using $HBF_4 \cdot Et_2O$ (3.78 mL, 15.29 mmol), ethyl diazoacetate (15% in toluene) (169 mL, 245 mmol), sulfuric acid (20.37 mL, 382 mmol) and stirring at RT for 10 min. This gave after work up and purification by flash column chromatography [silica gel (220 g), eluting with EtOAc in hexane from 0-50%] ethyl 5-bromo-7-chlorobenzofuran-3-carboxylate (127b) (22.4 g, 48% yield) as a white solid; $^1$H NMR (300 MHz, DMSO-$d_6$) δ 8.96 (s, 1H), 8.04 (d, J=1.8 Hz, 1H), 7.86 (d, J=1.8 Hz, 1H), 4.37 (q, J=7.1 Hz, 2H), 1.36 (t, J=7.1 Hz, 3H).

Step-2: Preparation of (5-bromo-7-chlorobenzofuran-3-yl)methanol (127c)

Compound 127c was prepared according to the procedure reported in step-2 of scheme 69, from ethyl 5-bromo-7-chlorobenzofuran-3-carboxylate (127b) (22.4 g, 73.8 mmol; CAS #1486842-10-7) in DCM (123 mL) using DIBAL (184 mL, 184 mmol; 1.0 M solution in DCM) and stirring at 0° C. for 4 h. This gave after work up and purification by flash column chromatography [$SiO_2$ (320 g), EtOAc in hexane from 0-50%] (5-bromo-7-chlorobenzofuran-3-yl)methanol (127c) (15.7 g, 81% yield) as a white solid; $^1$H NMR (300 MHz, DMSO-$d_6$) δ 8.07 (d, J=1.2 Hz, 1H), 7.91 (d, J=1.8 Hz, 1H), 7.69 (d, J=1.8 Hz, 1H), 5.31 (t, J=5.6 Hz, 1H), 4.61 (dd, J=5.6, 1.1 Hz, 2H).

Step-3: Preparation of ethyl 2-(2-((5-bromo-7-chlorobenzofuran-3-yl)methoxy)phenyl)acetate (127d)

Compound 127d was prepared according to the procedure reported in step-2 of Scheme 65, from (5-bromo-7-chlorobenzofuran-3-yl)methanol (127c) (10 g, 38.2 mmol) in DCM (300 mL) using triphenylphosphine (11.03 g, 42.1 mmol), ethyl 2-(2-hydroxyphenyl)acetate (7c) (8.27 g, 45.9 mmol), a solution of DCAD (15.45 g, 42.1 mmol) in DCM (240 mL) at 0° C. and stirring at RT for 1 h. This gave after workup and purification by flash column chromatography [silica (220 g), eluting with EtOAc in hexane from 0-25%] ethyl 2-(2-((5-bromo-7-chlorobenzofuran-3-yl)methoxy) phenyl)acetate (127d) (11.5 g, 27% yield) as a white solid; $^1$H NMR (300 MHz, DMSO-$d_6$) δ 8.27 (s, 1H), 7.87 (d, J=1.8 Hz, 1H), 7.74 (d, J=1.8 Hz, 1H), 7.35-7.26 (m, 1H), 7.20 (ddd, J=10.6, 7.9, 1.4 Hz, 2H), 6.94 (td, J=7.4, 1.2 Hz, 1H), 5.31-5.18 (m, 2H), 3.93 (q, J=7.1 Hz, 2H), 3.56 (s, 2H), 0.99 (t, J=7.1 Hz, 3H); MS (ES+): 444.90 (M+Na).

Step-4: Preparation of ethyl 2-(2-((5-(3-(aminomethyl)phenyl)-7-chlorobenzofuran-3-yl)methoxy) phenyl)acetate (127e)

Compound 127e was prepared according to the procedure reported in step-2 of scheme 1, from ethyl 2-(2-((5-bromo-7-chlorobenzofuran-3-yl)methoxy)phenyl)acetate (127d) (2.25 g, 0.5.31 mmol) using 3-(aminomethyl)phenylboronic acid hydrochloride (1d) (1.244 mg, 6.64 mmol), 4 M solution of $K_3PO_4$ (5.31 mL, 21.24 mmol), tricyclohexylphosphine (298 mg, 1.062 mmol), $Pd_2(dba)_3$ (486 mg, 0.531 mmol) and heating at 90° C. for 1.5 h. This gave after workup and purification by flash column chromatography [silica gel (24 g), eluting with DMA80 in DCM from 0-50%] ethyl 2-(2-((5-(3-(aminomethyl)phenyl)-7-chlorobenzofuran-3-yl)methoxy)phenyl)acetate (127e) (1.45 g, 61% yield) as a clear oil; $^1$H NMR (300 MHz, DMSO-$d_6$) δ 8.25 (s, 1H), 7.91 (d, J=1.6 Hz, 1H), 7.77 (d, J=1.6 Hz, 1H), 7.71 (d, J=1.7 Hz, 1H), 7.58 (dt, J=7.5, 1.7 Hz, 1H), 7.45-7.26 (m, 3H), 7.26-7.16 (m, 2H), 6.94 (td, J=7.3, 1.2 Hz, 1H), 5.32 (s, 2H), 3.79 (s, 2H), 3.73 (q, J=7.1 Hz, 2H), 3.56 (s, 2H), 0.86 (t, J=7.1 Hz, 3H); MS (ES+): 450.1 (M+1).

Step-5: Preparation of 2-(2-((5-(3-(aminomethyl) phenyl)-7-chlorobenzofuran-3-yl)methoxy)phenyl) acetic acid (127f)

Compound 127f was prepared according to the procedure reported in step-3 of scheme 1, from ethyl 2-(2-((5-(3-(aminomethyl)phenyl)-7-chlorobenzofuran-3-yl)methoxy) phenyl)acetate (127e) (90 mg, 0.2 mmol) in THF/acetonitrile (1.8 mL; ratio 2:1) using a 1N solution of lithium hydroxide hydrate (0.70 mL, 0.70 mmol) and stirring at RT for 25 h. This gave after workup and purification by reverse phase column chromatography [C18 column (50 g), eluting with ACN in water (containing 0.1% HCl) from 0-100%] 2-(2-((5-(3-(aminomethyl)phenyl)-7-chlorobenzofuran-3-yl)methoxy)phenyl)acetic acid (127f) (72 mg, 85% yield) HCl salt as a white solid; $^1$H NMR (300 MHz, DMSO-$d_6$) δ 12.15 (s, 1H, $D_2O$ exchangeable), 8.45 (s, 3H, $D_2O$ exchangeable), 8.26 (s, 1H), 8.03 (d, J=1.6 Hz, 1H), 7.94 (d, J=2.1 Hz, 1H), 7.84-7.76 (m, 2H), 7.58-7.45 (m, 2H), 7.29 (td, J=7.7, 7.1, 1.7 Hz, 1H), 7.22 (dt, J=8.3, 2.0 Hz, 2H), 6.94 (td, J=7.3, 1.2 Hz, 1H), 5.35 (s, 2H), 4.12 (s, 2H), 3.55 (s, 2H); MS (ES+): 422.1 (M+1); (ES−): 420.1 (M−1).

Scheme 128

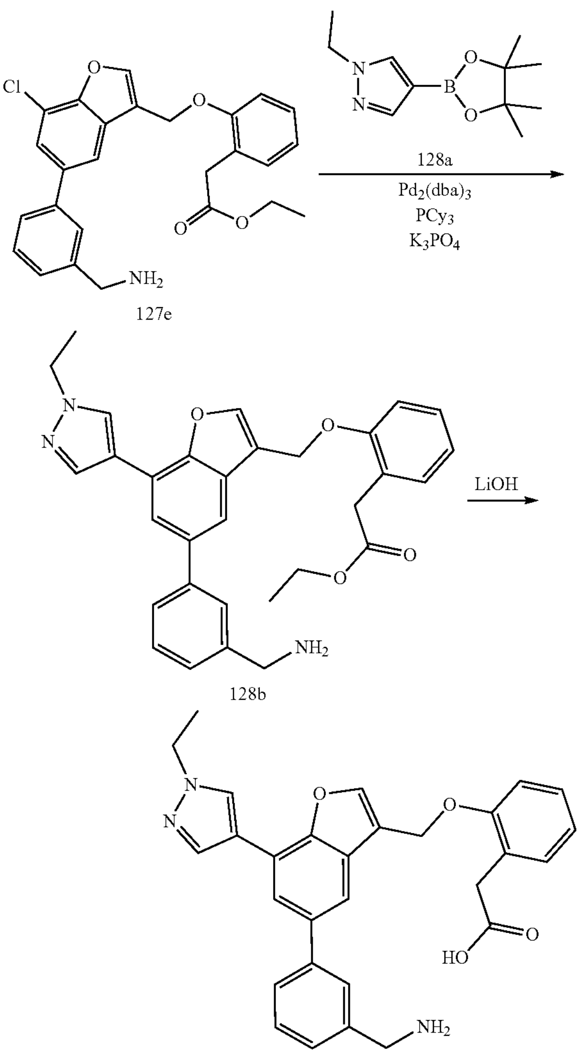

127e

128b

128c

Preparation of 2-(2-((5-(3-(aminomethyl)phenyl)-7-(1-ethyl-1H-pyrazol-4-yl)benzofuran-3-yl)methoxy) phenyl)acetic acid (128c)

Step-1: Preparation of ethyl 2-(2-((5-(3-(aminomethyl)phenyl)-7-(1-ethyl-1H-pyrazol-4-yl)benzofuran-3-yl)methoxy)phenyl)acetate (128b)

Compound 128b was prepared according to the procedure reported in step-2 of scheme 1, from ethyl 2-(2-((5-(3-(aminomethyl)phenyl)-7-chlorobenzofuran-3-yl)methoxy) phenyl)acetate (127e) (400 mg, 0.889 mmol) in dioxane (30 mL) using (2-(1-ethyl-1H-pyrazol-4-yl)-4,5,5-trimethyl-1,3,2-dioxaborolan-4-yl)methylium (128a) (CAS #847818-70-6, 246 mg, 1.111 mmol), 4M solution of $K_3PO_4$ (0.889 mL, 3.56 mmol), tricyclohexylphosphine (49.9 mg, 0.178 mmol), $Pd_2(dba)_3$ (81 mg, 0.089 mmol) and heating at 115° C. for 12h in a oil bath. This gave after workup and purification by flash column chromatography [silica gel (40 g), eluting with DMA-80 in DCM from 0-50%] ethyl 2-(2-((5-(3-(aminomethyl)phenyl)-7-(1-ethyl-1H-pyrazol- 4-yl)benzofuran-3-yl)methoxy)phenyl)acetate (128b) (280 mg, 0.549 mmol, 61.8% yield) as a clear oil; $^1$H NMR (300 MHz, DMSO-$d_6$) δ 8.50 (s, 1H), 8.21 (d, J=4.6 Hz, 2H), 7.91 (d, J=1.7 Hz, 1H), 7.80-7.70 (m, 2H), 7.66-7.59 (m, 1H), 7.42 (t, J=7.5 Hz, 1H), 7.37-7.18 (m, 4H), 6.93 (td, J=7.2, 1.3 Hz, 1H), 5.33 (s, 2H), 4.25 (q, J=7.2 Hz, 2H), 3.82 (s, 2H), 3.76 (q, J=7.1 Hz, 2H), 3.58 (s, 2H), 2.32 (s, 2H), 1.46 (t, J=7.2 Hz, 3H), 0.87 (t, J=7.1 Hz, 3H); MS (ES+): 510.30.

Step-2: Preparation of 2-(2-((5-(3-(aminomethyl)phenyl)-7-(1-ethyl-1H-pyrazol-4-yl)benzofuran-3-yl)methoxy)phenyl)acetic acid (128c)

Compound 128c was prepared according to the procedure reported in step-3 of scheme 1, from ethyl 2-(2-((5-(3-(aminomethyl)phenyl)-7-(1-ethyl-1H-pyrazol-4-yl)benzofuran-3-yl)methoxy)phenyl)acetate (128b) (240 mg, 0.471 mmol) in THF (3.3 mL), acetonitrile (1.65 mL) using a 1 N solution of lithium hydroxide hydrate (1.648 mL, 1.648 mmol) and stirring at room temperature for 25 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(1-ethyl-1H-pyrazol-4-yl)benzofuran-3-yl)methoxy)phenyl)acetic acid (128c) (210 mg, 0.436 mmol, 93% yield) hydrochloride salt as a white solid; $^1$H NMR (300 MHz, DMSO-$d_6$) δ 8.61 (s, 3H), 8.57 (s, 1H), 8.27 (s, 1H), 8.20 (s, 1H), 8.08-8.01 (m, 2H), 7.88 (d, J=1.7 Hz, 1H), 7.83 (dt, J=7.4, 1.7 Hz, 1H), 7.56-7.46 (m, 2H), 7.32-7.17 (m, 3H), 6.94 (td, J=7.2, 1.4 Hz, 1H), 5.36 (s, 2H), 4.25 (q, J=7.3 Hz, 2H), 4.13 (q, J=5.9 Hz, 2H), 3.57 (s, 2H), 1.46 (t, J=7.3 Hz, 3H); MS (ES+): 482.2 (M+1); (ES−): 480.1 (M−1).

Scheme 129

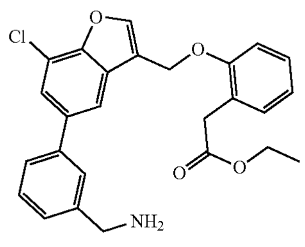

127e

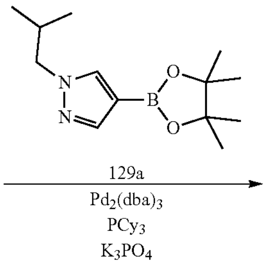

129a

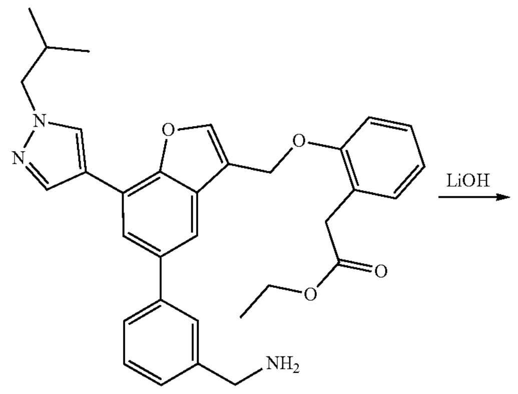

129b

-continued

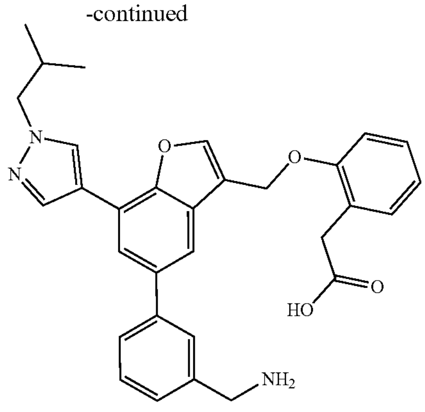

129c

Preparation of 2-(2-((5-(3-(aminomethyl)phenyl)-7-(1-isobutyl-1H-pyrazol-4-yl)benzofuran-3-yl)methoxy)phenyl)acetic acid (129c)

Step-1: Preparation of ethyl 2-(2-((5-(3-(aminomethyl)phenyl)-7-(1-isobutyl-1H-pyrazol-4-yl)benzofuran-3-yl)methoxy)phenyl)acetate (129b)

Compound 129b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (400 mg, 0.889 mmol) in dioxane (30 mL) using 1-isobutyl-4-(4,4,5,5-tetramethyl-1,3,2-dioxaborolan-2-yl)-1H-pyrazole (129a) (CAS #827614-66-4, 277 mg, 1.111 mmol), 4M solution of $K_3PO_4$ (0.889 mL, 3.56 mmol), tricyclohexylphosphine (49.9 mg, 0.178 mmol), $Pd_2(dba)_3$ (81 mg, 0.089 mmol) and heating at 115° C. for 12h in a oil bath. This gave after workup and purification by flash column chromatography [silica gel (40 g), eluting with DMA-80 in DCM from 0-50%] ethyl 2-(2-((5-(3-(aminomethyl)phenyl)-7-(1-isobutyl-1H-pyrazol-4-yl)benzofuran-3-yl)methoxy)phenyl)acetate (129b) (309 mg, 0.575 mmol, 64.6% yield) as a clear oil; $^1$H NMR (300 MHz, DMSO-$d_6$) δ 8.48 (s, 1H), 8.24 (s, 1H), 8.21 (s, 1H), 7.92 (d, J=1.7 Hz, 1H), 7.79-7.71 (m, 2H), 7.66-7.59 (m, 1H), 7.42 (t, J=7.6 Hz, 1H), 7.38-7.17 (m, 4H), 6.93 (td, J=7.2, 1.3 Hz, 1H), 5.33 (s, 2H), 4.03 (q, J=7.1 Hz, 2H), 3.83 (s, 2H), 3.76 (q, J=7.2 Hz, 2H), 3.58 (s, 2H), 2.19 (dq, J=13.5, 6.8 Hz, 1H), 0.94-0.82 (m, 9H); MS (ES+): 538.30 (M+1).

Step-2: Preparation of 2-(2-((5-(3-(aminomethyl)phenyl)-7-(1-isobutyl-1H-pyrazol-4-yl)benzofuran-3-yl)methoxy)phenyl)acetic acid (129c)

Compound 129c was prepared according to the procedure reported in step-3 of scheme 1, from ethyl 2-(2-((5-(3-(aminomethyl)phenyl)-7-(1-isobutyl-1H-pyrazol-4-yl)benzofuran-3-yl)methoxy)phenyl)acetate (129b) (260 mg, 0.484 mmol) in THF (3.4 mL), acetonitrile (1.7 mL) using a 1 N solution of lithium hydroxide hydrate (1.693 mL, 1.693 mmol) and stirring at room temperature for 25 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(1-isobutyl-1H-pyrazol-4-yl)benzofuran-3-yl)methoxy)phenyl)acetic acid (129c) (191 mg, 0.375 mmol, 78% yield) HCl salt as a white solid; $^1$H NMR (300 MHz, DMSO-$d_6$) δ 8.58 (s, 3H), 8.53 (s, 1H), 8.28 (s, 1H), 8.21 (s, 1H), 8.05 (t, J=2.1 Hz, 2H), 7.88 (d, J=1.7 Hz, 1H), 7.84 (dt, J=7.6, 1.6 Hz, 1H), 7.58-7.44 (m, 2H), 7.34-7.17 (m, 3H), 6.94 (td, J=7.2, 1.4 Hz, 1H), 5.36 (s, 2H), 4.13 (q, J=5.8 Hz, 2H), 4.04 (d, J=7.2 Hz, 2H), 3.57 (s, 2H), 2.20 (dt, J=13.6, 6.8 Hz, 1H), 0.90 (d, J=6.6 Hz, 6H); MS (ES+): 510.2 (M+1); (ES−): 508.2 (M−1).

Scheme 130

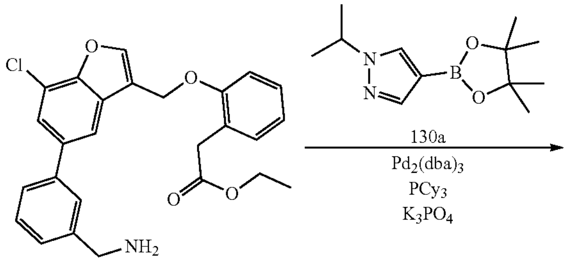

127e

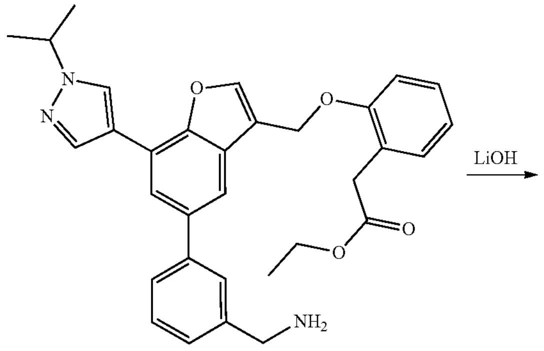

130b

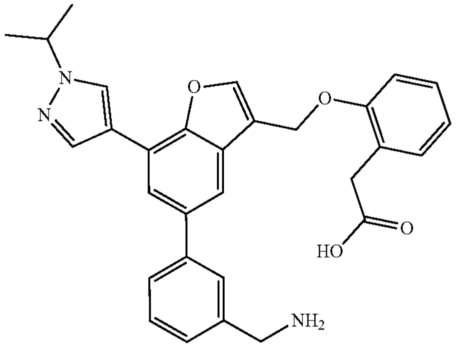

130c

Preparation of 2-(2-((5-(3-(aminomethyl)phenyl)-7-(1-isopropyl-1H-pyrazol-4-yl)benzofuran-3-yl)methoxy)phenyl)acetic acid (130c)

Step-1: Preparation of ethyl 2-(2-((5-(3-(aminomethyl)phenyl)-7-(1-isopropyl-1H-pyrazol-4-yl)benzofuran-3-yl)methoxy)phenyl)acetate (130b)

Compound 130b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (245 mg, 0.545 mmol) in dioxane (20 mL) using 1-isopropyl-4-(4,4,5,5-tetramethyl-1,3,2-dioxaborolan-2-yl)-1H-pyrazole (130a) (CAS #879487-10-2, 161 mg, 0.681 mmol), 4M solution of $K_3PO_4$ (0.545 mL, 2.178 mmol), tricyclohexylphosphine (30.5 mg, 0.109 mmol), $Pd_2(dba)_3$ (49.9 mg, 0.054 mmol) and heating at 115° C. for 12h in an oil bath. This gave after workup and purification by flash column chromatography [silica gel (40 g), eluting with DMA-80 in DCM from 0-50%] ethyl 2-(2-((5-(3-(aminomethyl)phenyl)-7-(1-isopropyl-1H-pyrazol-4-yl)benzofuran-3-yl)methoxy)phenyl)acetate (130b) (172 mg, 60.3% yield) as a clear oil; $^1$H NMR (300 MHz, DMSO-$d_6$) δ 8.51 (s, 1H), 8.21 (s, 2H), 7.92 (d, J=1.7 Hz, 1H), 7.76 (d, J=1.9 Hz, 2H), 7.65 (d, J=7.6 Hz, 1H), 7.44 (t, J=7.6 Hz, 1H), 7.39-7.19 (m, 4H), 6.98-6.88 (m, 1H), 5.33 (s, 2H), 4.63 (p, J=6.9 Hz, 1H), 3.86 (s, 2H), 3.76 (q, J=7.2 Hz, 2H), 3.58 (s, 2H), 1.51 (d, J=6.6 Hz, 6H), 0.87 (t, J=7.1 Hz, 3H); MS (ES+): 524.3 (M+1).

Step-2: Preparation of 2-(2-((5-(3-(aminomethyl)phenyl)-7-(1-isopropyl-1H-pyrazol-4-yl)benzofuran-3-yl)methoxy)phenyl)acetic acid (130c)

Compound 130c was prepared according to the procedure reported in step-3 of scheme 1, from ethyl 2-(2-((5-(3-(aminomethyl)phenyl)-7-(1-isopropyl-1H-pyrazol-4-yl)benzofuran-3-yl)methoxy)phenyl)acetate (130b) (150 mg, 0.286 mmol) in THF (2 mL), acetonitrile (1 mL) using a 1 N solution of lithium hydroxide hydrate (1.003 mL, 1.003 mmol) and stirring at room temperature for 25 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(1-isopropyl-1H-pyrazol-4-yl)benzofuran-3-yl)methoxy)phenyl)acetic acid (130c) (115 mg, 81% yield) hydrochloride salt as a white solid; $^1$H NMR (300 MHz, DMSO-$d_6$) δ 8.51 (d, J=7.8 Hz, 4H), 8.18 (s, 1H), 8.13 (s, 1H), 7.99 (t, J=2.1 Hz, 2H), 7.80 (d, J=1.7 Hz, 1H), 7.78-7.71 (m, 1H), 7.50-7.36 (m, 2H), 7.26-7.12 (m, 3H), 6.86 (td, J=7.2, 1.4 Hz, 1H), 5.29 (s, 2H), 4.55 (p, J=6.6 Hz, 1H), 4.06 (q, J=5.8 Hz, 2H), 3.49 (s, 2H), 1.43 (d, J=6.6 Hz, 6H); MS (ES+): 496.3 (M+1); (ES−): 494.2 (M−1).

Scheme 131

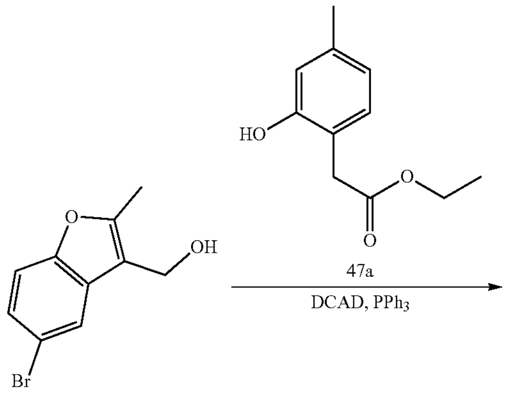

124c

-continued

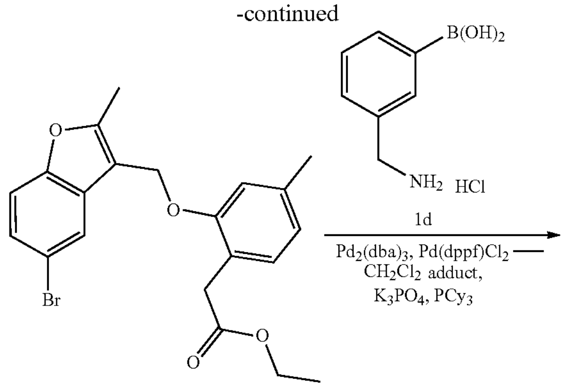

131a

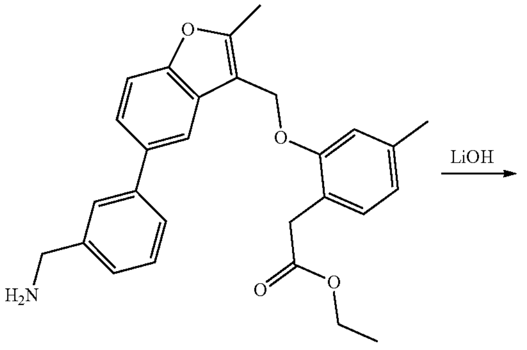

131b

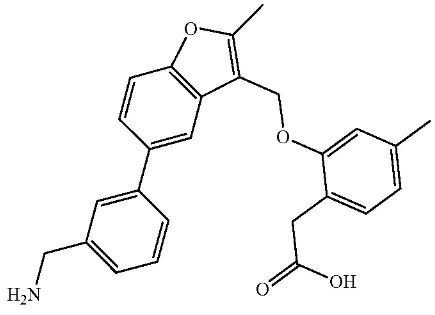

131c

Preparation of 2-(2-((5-(3-(aminomethyl)phenyl)-2-methylbenzofuran-3-yl)methoxy)-4-methylphenyl) acetic acid (131c)

Step-1: Preparation of ethyl 2-(2-((5-bromo-2-methylbenzofuran-3-yl)methoxy)-4-methylphenyl)acetate (131a)

Compound 131a was prepared according to the procedure reported in step-3 of scheme 7, from (5-bromo-2-methylbenzofuran-3-yl)methanol (124c) (355 mg, 1.473 mmol), triphenylphosphine (425 mg, 1.620 mmol), ethyl 2-(2-hydroxy-4-methylphenyl)acetate (47a) (315 mg, 1.620 mmol) in DCM (20 mL) using bis(4-chlorobenzyl) diazene-1,2-dicarboxylate (DCAD) (595 mg, 1.620 mmol) in DCM (10 mL) and stirring the reaction mixture at RT for 30 min. This gave after workup and purification by flash column chromatography [silica (40 g), eluting with EtOAc in hexane from 0-50%] ethyl 2-(2-((5-bromo-2-methylbenzofuran-3-yl)methoxy)-4-methylphenyl)acetate (131a) (338 mg, 55% yield) as a colorless oil; $^1$H NMR (300 MHz, DMSO-$d_6$) δ 7.74 (d, J=2.0 Hz, 1H), 7.51 (d, J=8.6 Hz, 1H), 7.41 (dd, J=8.7, 2.0 Hz, 1H), 7.06 (d, J=7.8 Hz, 2H), 6.82-6.67 (m, 1H), 5.16 (s, 2H), 3.91 (q, J=7.1 Hz, 2H), 3.46 (s, 2H), 2.51 (s, 3H), 2.33 (s, 3H), 0.96 (t, J=7.1 Hz, 3H).

Step-2: Preparation of ethyl 2-(2-((5-(3-(aminomethyl)phenyl)-2-methylbenzofuran-3-yl)methoxy)-4-methylphenyl)acetate (131b)

Compound 131b was prepared according to the procedure reported in step-2 of scheme 1, from ethyl 2-(2-((5-bromo-2-methylbenzofuran-3-yl)methoxy)-4-methylphenyl)acetate (131a) (338 mg, 0.81 mmol) in dioxane (30 mL) using 3-(aminomethyl)phenylboronic acid hydrochloride (1d) (304 mg, 1.62 mmol), 4M solution of $K_3PO_4$ (0.810 mL, 3.24 mmol), tricyclohexylphosphine (68.1 mg, 0.243 mmol), $PdCl_2$(dppf)-$CH_2Cl_2$ adduct (66.1 mg, 0.081 mmol), $Pd_2(dba)_3$ (74.2 mg, 0.081 mmol) and heating at 100° C. for 2 h. This gave after workup and purification by flash column chromatography [silica gel (40 g), eluting with DMA-80 in DCM from 0-100%] ethyl 2-(2-((5-(3-(aminomethyl)phenyl)-2-methylbenzofuran-3-yl)methoxy)-4-methylphenyl) acetate (131b) (255 mg, 71% yield) as a yellow oil; MS (ES+): 444.2 (M+1).

Step-3: Preparation of 2-(2-((5-(3-(aminomethyl) phenyl)-2-methylbenzofuran-3-yl)methoxy)-4-methylphenyl)acetic acid (131c)

Compound 131c was prepared according to the procedure reported in step-3 of scheme 1, from ethyl 2-(2-((5-(3-(aminomethyl)phenyl)-2-methylbenzofuran-3-yl)methoxy)-4-methylphenyl)acetate (131b) (255 mg, 0.575 mmol) in THF (6 mL) using a solution of lithium hydroxide hydrate (34 mg, 0.81 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)-2-methylbenzofuran-3-yl)methoxy)-4-methylphenyl)acetic acid (131c) (134 mg, 40% yield) HCl salt as a white solid; $^1$H NMR (300 MHz, DMSO-$d_6$) δ 11.95 (s, 1H, $D_2O$ exchangeable), 8.46 (s, 2H, $D_2O$ exchangeable), 7.92 (s, 1H), 7.88 (s, 1H), 7.76-7.67 (m, 1H), 7.66-7.55 (m, 2H), 7.55-7.40 (m, 2H), 7.12-7.00 (m, 2H), 6.73 (d, J=7.5 Hz, 1H), 5.23 (s, 2H), 4.09 (s, 2H), 3.43 (s, 2H), 2.52 (s, 3H), 2.32 (s, 3H); MS (ES+): 416.2 (M+1); (ES−): 414.2 (M−1); Analysis calculated for: $C_{26}H_{25}NO_4\cdot HCl\cdot 1.25H_2O$: C, 65.82; H, 6.05; Cl, 7.47; N, 2.95. Found: C, 65.77; H, 6.09; Cl, 7.75; N, 3.08.

Scheme 132

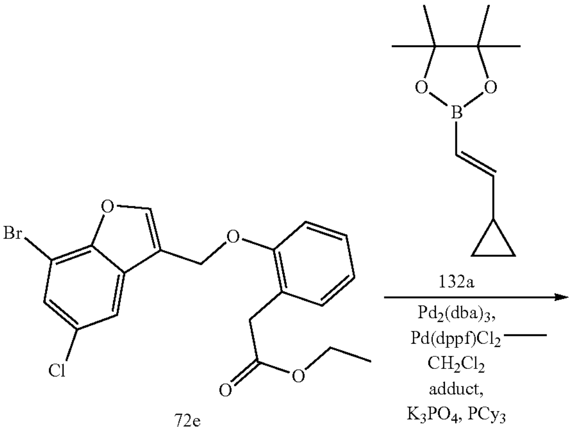

72e

-continued

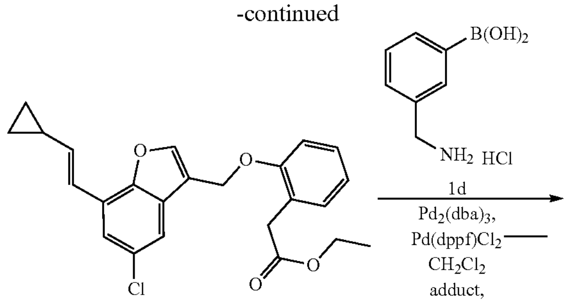

132b

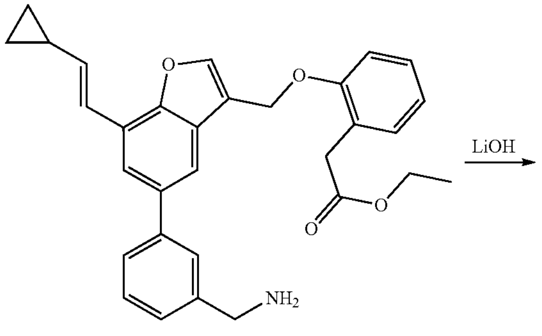

132c

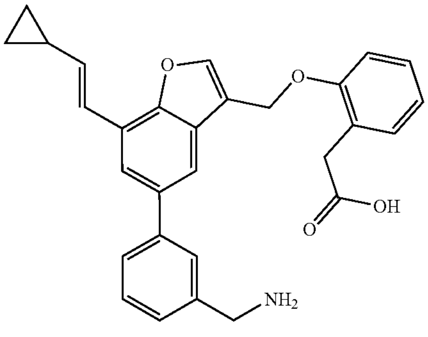

132d

Preparation of (E)-2-(2-((5-(3-(aminomethyl)phenyl)-7-(2-cyclopropylvinyl)benzofuran-3-yl)methoxy)phenyl)acetic acid (132d)

Step-1: Preparation of (E)-ethyl 2-(2-((5-chloro-7-(2-cyclopropylvinyl)benzofuran-3-yl)methoxy)phenyl)acetate (132b)

Compound 132b was prepared according to the procedure reported in step-2 of scheme 1, from ethyl 2-(2-((7-bromo-5-chlorobenzofuran-3-yl)methoxy)phenyl)acetate (72e) (1.5 g, 3.54 mmol) in dioxane (50 mL) using (E)-2-(2-cyclopropylvinyl)-4,4,5,5-tetramethyl-1,3,2-dioxaborolane (132a) (1.031 g, 5.31 mmol CAS #849061-99-0), 4M solution of $K_3PO_4$ (3.54 mL, 14.16 mmol), tricyclohexylphosphine (0.289 g, 0.354 mmol) and $PdCl_2(dppf)$-$CH_2Cl_2$ adduct (0.289 g, 0.354 mmol), $Pd_2(dba)_3$ (0.324, 0.354 mmol) and heating at 80° C. for 2 h. This gave after workup and purification by flash column chromatography [silica gel (80 g), eluting with EtOAc in Hexane from 0-100%](E)-ethyl 2-(2-((5-chloro-7-(2-cyclopropylvinyl)benzofuran-3-yl)methoxy)phenyl)acetate (132b) (1.4 g, 96% yield) as a yellow oil; MS (ES+): 433.1 and 435.1 (M+Na).

Step-2: Preparation of (E)-ethyl 2-(2-((5-(3-(aminomethyl)phenyl)-7-(2-cyclopropylvinyl)benzofuran-3-yl)methoxy)phenyl)acetate (132c)

Compound 132c was prepared according to the procedure reported in step-2 of scheme 1, from (E)-ethyl 2-(2-((5-chloro-7-(2-cyclopropylvinyl)benzofuran-3-yl)methoxy)phenyl)acetate (132b) (1 g, 2.434 mmol) in dioxane (40 mL) using 3-(aminomethyl)phenylboronic acid hydrochloride (1d) (0.912 g, 4.87 mmol), 4M solution of $K_3PO_4$ (2.434 mL, 3.24 mmol), tricyclohexylphosphine (0.205 g, 0.730 mmol), $PdCl_2(dppf)$-$CH_2Cl_2$ adduct (0.199 g, 0.243 mmol), $Pd_2(dba)_3$ (0.223 g, 0.243 mmol) and heating at 100° C. for 2h. This gave after workup and purification by flash column chromatography [silica gel (80 g), eluting with EtOAc in hexane from 0-100%](E)-ethyl 2-(2-((5-(3-(aminomethyl)phenyl)-7-(2-cyclopropylvinyl)benzofuran-3-yl)methoxy)phenyl)acetate (132c) (520 mg, 44% yield) as a yellow oil; MS (ES+): 482.2 (M+1).

Step-3: Preparation of (E)-2-(2-((5-(3-(aminomethyl)phenyl)-7-(2-cyclopropylvinyl)benzofuran-3-yl)methoxy)phenyl)acetic acid (132d)

Compound 132d was prepared according to the procedure reported in step-3 of scheme 1, from (E)-ethyl 2-(2-((5-(3-(aminomethyl)phenyl)-7-(2-cyclopropylvinyl)benzofuran-3-yl)methoxy)phenyl)acetate (132c) (520 mg, 1.080 mmol) in THF (6 mL) using a solution of lithium hydroxide hydrate (0.204 g, 4.87 mmol) in water (1 mL) and stirring overnight at RT.

This gave after workup and purification by reverse phase column chromatography [C18 column (30 g), eluting with ACN in water (containing 0.1% HCl) from 0-100%](E)-2-(2-((5-(3-(aminomethyl)phenyl)-7-(2-cyclopropylvinyl)benzofuran-3-yl)methoxy)phenyl)acetic acid (132d) (72 mg, 7% yield) HCl salt as a white solid; $^1H$ NMR (300 MHz, DMSO-$d_6$) δ 12.12 (s, 1H, $D_2O$ exchangeable), 8.36 (s, 2H, $D_2O$ exchangeable), 8.14 (s, 1H), 7.90 (s, 1H), 7.82 (d, J=1.7 Hz, 1H), 7.76 (d, J=7.7 Hz, 1H), 7.66 (d, J=1.9 Hz, 1H), 7.52 (t, J=7.6 Hz, 1H), 7.45 (d, J=7.6 Hz, 1H), 7.33-7.14 (m, 3H), 6.97-6.87 (m, 1H), 6.78 (d, J=15.9 Hz, 1H), 6.35 (dd, J=16.0, 9.3 Hz, 1H), 5.32 (s, 2H), 4.11 (s, 2H), 3.53 (s, 2H), 1.80-1.62 (m, 1H), 0.95-0.79 (m, 2H), 0.69-0.53 (m, 2H); MS (ES+): 454.2 (M+1); (ES−): 452.1 (M−1); Analysis calculated for $C_{29}H_{27}NO_4 \cdot 0.95HCl \cdot 0.25H_2O$: C, 70.70; H, 5.82; Cl, 6.84; N, 2.84. Found: C, 70.53; H, 5.89; Cl, 6.70; N, 2.87.

Scheme 133

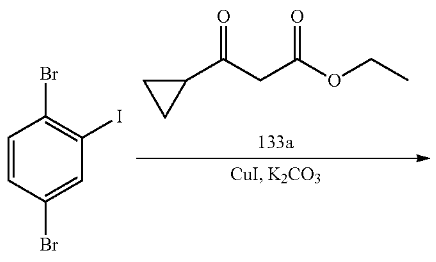

124a

-continued

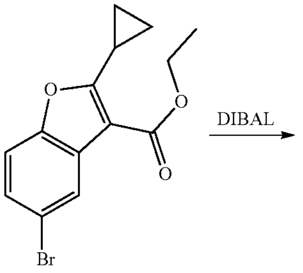

133b

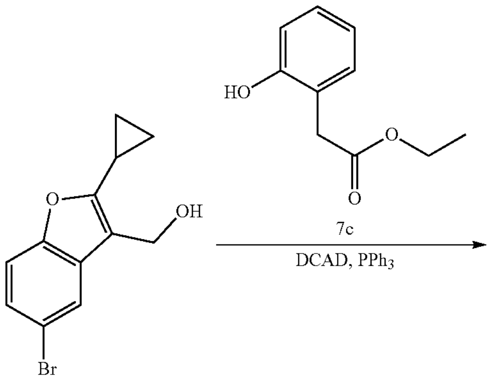

133c

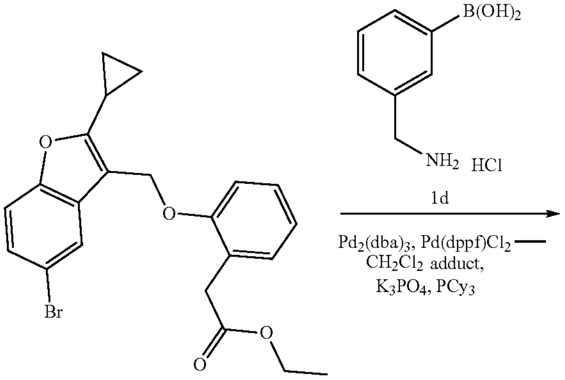

133d

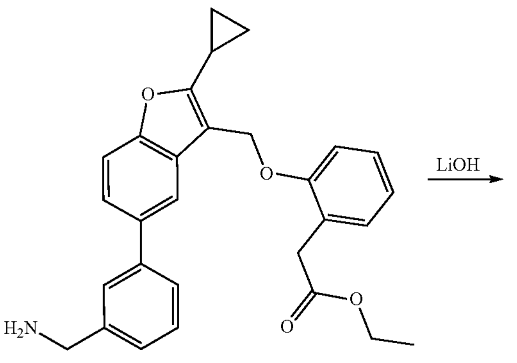

133e

-continued

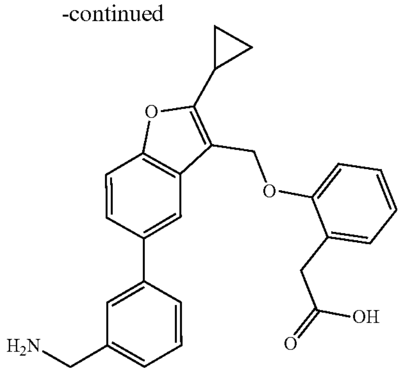

133f

Preparation of 2-(2-((5-(3-(aminomethyl)phenyl)-2-cyclopropylbenzofuran-3-yl)methoxy)phenyl)acetic acid (133f)

Step-1: Preparation of ethyl 5-bromo-2-cyclopropylbenzofuran-3-carboxylate (133b)

Compound 133b was prepared according to the procedure reported in step-1 of scheme 124, from 1,4-dibromo-2-iodobenzene (124a) (20 g, 55.3 mmol) in THF (50 mL) using ethyl 3-cyclopropyl-3-oxopropanoate (133a) (17.27 g, 111 mmol), copper(I) iodide (1.369 g, 7.19 mmol), potassium carbonate (19.10 g, 138 mmol) and stirring at 100° C. for 4 days. This gave after workup and purification by flash column chromatography [silica gel (80 g), eluting with EtOAc in hexane from 0-100%] ethyl 5-bromo-2-cyclopropylbenzofuran-3-carboxylate (133b) (4.3 g, 25% yield) as a light green oil; $^{1}$H NMR (300 MHz, DMSO-$d_6$) δ 7.94 (d, J=2.0 Hz, 1H), 7.52 (d, J=8.7 Hz, 1H), 7.45 (dd, J=8.7, 2.0 Hz, 1H), 4.37 (q, J=7.1 Hz, 2H), 3.05-2.90 (m, 1H), 1.37 (t, J=7.0 Hz, 3H), 1.28-1.18 (m, 4H); MS (ES+): 309.00 (M+1).

Step-2: Preparation of (5-bromo-2-cyclopropylbenzofuran-3-yl)methanol (133c)

Compound 133c was prepared according to the procedure reported in step-4 of scheme 3, from ethyl 5-bromo-2-cyclopropylbenzofuran-3-carboxylate (133b) (4.3 g, 14.57 mmol) in DCM (40 mL) using DIBAL (36.4 mL, 36.4 mmol; 1M in DCM) and stirring at 0° C. for 2 h. This gave after workup and purification by flash column chromatography [silica gel (24 g), eluting with EtOAc in hexane from 0-100%] (5-bromo-2-cyclopropylbenzofuran-3-yl)methanol (133c) (2.3 g, 59% yield) as a white solid; $^{1}$H NMR (300 MHz, DMSO-$d_6$) δ 7.76 (d, J=2.0 Hz, 1H), 7.40 (d, J=8.6 Hz, 1H), 7.32 (dd, J=8.6, 2.1 Hz, 1H), 5.11 (t, J=5.6 Hz, 1H), 4.63 (d, J=5.5 Hz, 2H), 2.31-2.18 (m, 1H), 1.06-0.96 (m, 4H).

Step-3: Preparation of ethyl 2-(2-((5-bromo-2-cyclopropylbenzofuran-3-yl)methoxy)phenyl)acetate (133d)

Compound 133d was prepared according to the procedure reported in step-3 of scheme 7, from (5-bromo-2-cyclopropylbenzofuran-3-yl)methanol (133c) (740 mg, 2.77 mmol), triphenylphosphine (799 mg, 3.05 mmol), ethyl 2-(2-hydroxyphenyl)acetate (7c) (549 mg, 3.05 mmol) in DCM (20 mL) using bis(4-chlorobenzyl) diazene-1,2-dicarboxylate (DCAD) (1119 mg, 3.05 mmol) in DCM (10 mL) and stirring the reaction mixture at RT for 30 min.

This gave after workup and purification by flash column chromatography [silica gel (40 g), eluting with EtOAc in hexane from 0-50%] ethyl 2-(2-((5-bromo-2-cyclopropylbenzofuran-3-yl)methoxy)phenyl)acetate (133d) (650 mg, 55% yield) as a colorless oil; $^1$H NMR (300 MHz, DMSO-$d_6$) δ 7.74 (d, J=2.0 Hz, 1H), 7.51 (d, J=8.7 Hz, 1H), 7.41 (dd, J=8.7, 2.0 Hz, 1H), 7.31 (td, J=7.7, 1.7 Hz, 1H), 7.25-7.16 (m, 2H), 6.93 (td, J=7.4, 1.1 Hz, 1H), 5.18 (s, 2H), 3.92 (q, J=7.1 Hz, 2H), 3.52 (s, 2H), 2.50 (s, 3H), 0.96 (t, J=7.1 Hz, 3H).

Step-4: Preparation of ethyl 2-(2-((5-(3-(aminomethyl)phenyl)-2-cyclopropylbenzofuran-3-yl)methoxy)phenyl)acetate (133e)

Compound 133e was prepared according to the procedure reported in step-2 of scheme 1, from ethyl 2-(2-((5-bromo-2-cyclopropylbenzofuran-3-yl)methoxy)phenyl)acetate (133d) (350 mg, 0.815 mmol) in dioxane (30 mL) using 3-(aminomethyl)phenylboronic acid hydrochloride (1d) (306 mg, 1.631 mmol), 4M solution of $K_3PO_4$ (0.815 mL, 3.26 mmol), tricyclohexylphosphine (68.6 mg, 0.245 mmol) and $PdCl_2$(dppf)-$CH_2Cl_2$ adduct (66.6 mg, 0.082 mmol), $Pd_2(dba)_3$ (74.7 mg, 0.082 mmol) and heating at 100° C. for 2 h. This gave after workup and purification by flash column chromatography [silica gel (40 g), eluting with DMA-80 in DCM from 0-100%] ethyl 2-(2-((5-(3-(aminomethyl)phenyl)-2-cyclopropylbenzofuran-3-yl)methoxy)phenyl)acetate (133e) (156 mg, 42% yield) as a yellow oil; MS (ES+): 456.2 (M+1).

Step-5: Preparation of 2-(2-((5-(3-(aminomethyl)phenyl)-2-cyclopropylbenzofuran-3-yl)methoxy)phenyl)acetic acid (133f)

Compound 133f was prepared according to the procedure reported in step-3 of scheme 1, from ethyl 2-(2-((5-(3-(aminomethyl)phenyl)-2-cyclopropylbenzofuran-3-yl)methoxy)phenyl)acetate (133e) (156 mg, 0.342 mmol) in THF (6 mL) using a solution of lithium hydroxide hydrate (103 mg, 2.45 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)-2-cyclopropylbenzofuran-3-yl)methoxy)phenyl)acetic acid (133f) (45 mg, 13% yield) HCl salt as a white solid; $^1$H NMR (300 MHz, DMSO-$d_6$) δ 12.09 (s, 1H, $D_2O$ exchangeable), 8.42 (s, 3H, $D_2O$ exchangeable), 7.91-7.82 (m, 2H), 7.72 (d, J=7.5 Hz, 1H), 7.56 (s, 2H), 7.53-7.40 (m, 2H), 7.28 (d, J=4.1 Hz, 2H), 7.20 (d, J=7.4 Hz, 1H), 6.97-6.87 (m, 1H), 5.34 (s, 2H), 4.09 (s, 2H), 3.51 (s, 2H), 2.45-2.34 (m, 1H), 1.13-0.94 (m, 4H); MS (ES+): 428.1 (M+1); (ES−): 426.2 (M−1); Analysis calculated for $C_{27}H_{25}NO_4 \cdot 1.05(HCl) \cdot 0.15(H_2O)$: C, 69.22; H, 5.67; Cl, 7.95; N, 2.99. Found: C, 69.17; H, 5.67; Cl, 8.11; N, 3.04.

Scheme 134

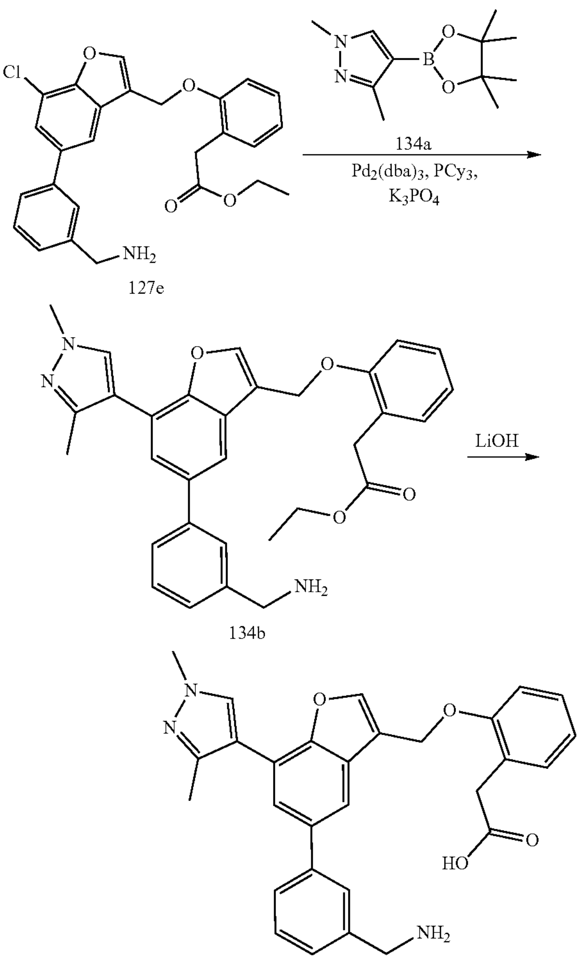

127e

134b

134c

Preparation of 2-(2-((5-(3-(aminomethyl)phenyl)-7-(1,3-dimethyl-1H-pyrazol-4-yl)benzofuran-3-yl)methoxy)phenyl)acetic acid (134c)

Step-1: Preparation of ethyl 2-(2-((5-(3-(aminomethyl)phenyl)-7-(1,3-dimethyl-1H-pyrazol-4-yl)benzofuran-3-yl)methoxy)phenyl)acetate (134b)

Compound 134b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (300 mg, 0.667 mmol) in dioxane (25 mL) using 1,3-dimethyl-4-(4,4,5,5-tetramethyl-1,3,2-dioxaborolan-2-yl)-1H-pyrazole (134a) (184 mg, 0.833 mmol; CAS #1046832-21-6), 4M solution of $K_3PO_4$ (0.667 mL, 2.67 mmol), tricyclohexylphosphine (37.4 mg, 0.133 mmol), $Pd_2(dba)_3$ (61.1 mg, 0.067 mmol) and heating at 125° C. for 9 h in an oil bath. This gave after workup and purification by flash column chromatography [silica gel (40 g), eluting with DMA-80 in DCM from 0-50%] ethyl 2-(2-((5-(3-(aminomethyl)phenyl)-7-(1,3-dimethyl-1H-pyrazol-4-yl)benzofuran-3-yl)methoxy)phenyl)acetate (134b) (33 mg, 10% yield) as a yellow gel; MS (ES+): 510.2 (M+1).

Step-2: Preparation of 2-(2-((5-(3-(aminomethyl) phenyl)-7-(1,3-dimethyl-1H-pyrazol-4-yl)benzo-furan-3-yl)methoxy)phenyl)acetic acid (134c)

Compound 134c was prepared according to the procedure reported in step-3 of scheme 1, from ethyl 2-(2-((5-(3-(aminomethyl)phenyl)-7-(1,3-dimethyl-1H-pyrazol-4-yl) benzofuran-3-yl)methoxy)phenyl)acetate (134b) (30 mg, 0.059 mmol) in THF (0.4 mL), acetonitrile (0.2 mL) using a 1 N solution of lithium hydroxide hydrate (0.206 mL, 0.206 mmol) and stirring at room temperature for 25 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(1,3-dimethyl-1H-pyrazol-4-yl) benzofuran-3-yl)methoxy)phenyl)acetic acid (134c) (23 mg, 81% yield) hydrochloride salt as a white solid; $^1$H NMR (300 MHz, DMSO-$d_6$) δ 8.38 (s, 3H, $D_2O$ exchangeable), 8.17 (d, J=4.8 Hz, 2H), 7.90 (d, J=4.2 Hz, 2H), 7.78 (d, J=7.8 Hz, 1H), 7.67 (s, 1H), 7.59-7.42 (m, 2H), 7.25 (dd, J=15.2, 7.8 Hz, 3H), 6.94 (t, J=7.2 Hz, 1H), 5.35 (s, 2H), 4.13 (q, J=5.7 Hz, 2H), 3.88 (s, 3H), 3.56 (s, 2H), 2.39 (s, 3H); MS (ES+): 482.2 (M+1); (ES−): 480.2 (M−1); Analysis calculated for $C_{29}H_{27}N_3O_4$ $2.5H_2O{\cdot}1.75HCl$: C, 59.00; H, 5.76; N, 7.12. Found: C, 58.69; H, 5.70; N, 7.03.

Scheme 135

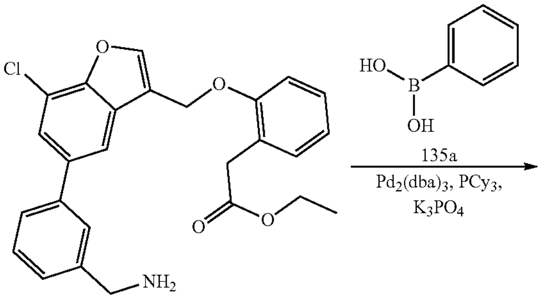

127e

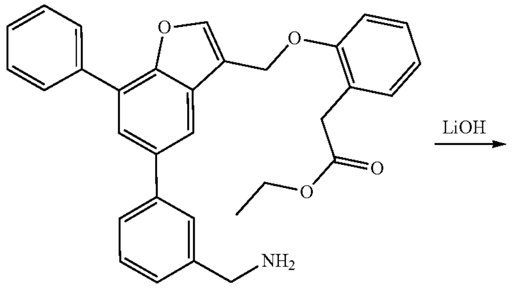

135b

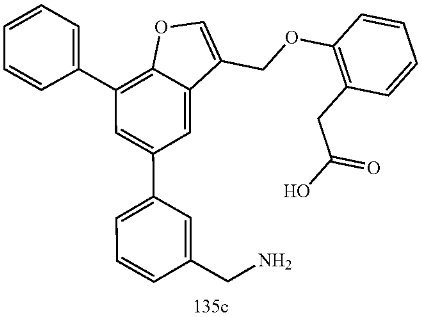

135c

Preparation of 2-(2-((5-(3-(aminomethyl)phenyl)-7-phenylbenzofuran-3-yl)methoxy)phenyl)acetic acid (135c)

Step-1: Preparation of ethyl 2-(2-((5-(3-(aminomethyl)phenyl)-7-phenylbenzofuran-3-yl)methoxy) phenyl)acetate (135b)

Compound 135b was prepared according to the procedure reported in step-2 of scheme 1, from ethyl 2-(2-((5-(3-(aminomethyl)phenyl)-7-chlorobenzofuran-3-yl)methoxy) phenyl)acetate (127e) (150 mg, 0.333 mmol) in dioxane (12 mL) using phenylboronic acid (135a) (50.8 mg, 0.417 mmol; CAS #98-80-6), 4M solution of $K_3PO_4$ (0.333 mL, 1.334 mmol), tricyclohexylphosphine (18.70 mg, 0.067 mmol), $Pd_2(dba)_3$ (30.5 mg, 0.033 mmol) and heating at 115° C. for 12 h in an oil bath. This gave after workup and purification by flash column chromatography [silica gel (24 g), eluting with DMA-80 in DCM from 0-50%] ethyl 2-(2-((5-(3-(aminomethyl)phenyl)-7-phenylbenzofuran-3-yl)methoxy)phenyl)acetate (135b) (152 mg, 93% yield) as a clear oil; $^1$H NMR (300 MHz, DMSO-$d_6$) δ 8.21 (s, 1H), 8.02-7.85 (m, 3H), 7.84-7.74 (m, 2H), 7.71-7.62 (m, 1H), 7.62-7.16 (m, 8H), 6.94 (td, J=7.2, 1.4 Hz, 1H), 5.35 (s, 2H), 3.82 (s, 2H), 3.75 (q, J=7.1 Hz, 2H), 3.58 (s, 2H), 0.87 (t, J=7.1 Hz, 3H); MS (ES+): 492.3 (M+1).

Step-2: Preparation of 2-(2-((5-(3-(aminomethyl) phenyl)-7-phenylbenzofuran-3-yl)methoxy)phenyl) acetic acid (135c)

Compound 135c was prepared according to the procedure reported in step-3 of scheme 1, from ethyl 2-(2-((5-(3-(aminomethyl)phenyl)-7-phenylbenzofuran-3-yl)methoxy) phenyl)acetate (135b) (145 mg, 0.295 mmol) in THF (2.0 mL), acetonitrile (1 mL) using a 1 N solution of lithium hydroxide hydrate (1.032 mL, 1.032 mmol) and stirring at room temperature for 25 h. This gave after workup and purification by reverse phase column chromatography [C18 column (50 g), eluting with ACN in water (containing 0.1% HCl) from 0-100%] 2-(2-((5-(3-(aminomethyl)phenyl)-7-phenylbenzofuran-3-yl)methoxy)phenyl)acetic acid (135c) (85 mg, 62% yield) hydrochloride salt as a white solid; $^1$H NMR (300 MHz, DMSO-$d_6$) δ 8.51 (s, 3H, $D_2O$ exchangeable), 8.22 (s, 1H), 8.07-8.00 (m, 2H), 8.00-7.93 (m, 2H), 7.89-7.82 (m, 2H), 7.63-7.42 (m, 5H), 7.33-7.19 (m, 3H), 6.94 (td, J=7.2, 1.5 Hz, 1H), 5.38 (s, 2H), 4.13 (s, 2H), 3.57 (s, 2H); MS (ES+): 464.2 (M+1); (ES−): 462.1 (M−1); Analysis calculated for $C_{30}H_{25}NO_4{\cdot}HCl$: C, 72.07; H, 5.24; Cl, 7.09; N, 2.80. Found: C, 71.89; H, 5.39; Cl, 7.05; N, 2.71.

Scheme 136

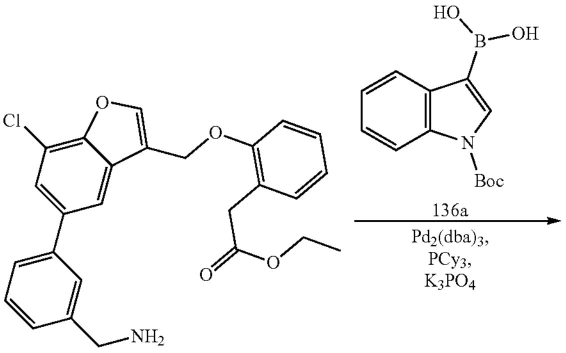

127e

-continued

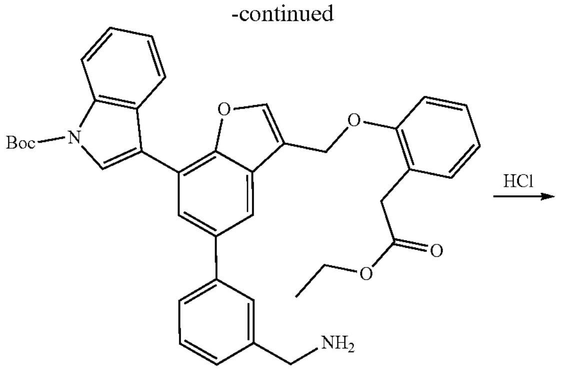

136b

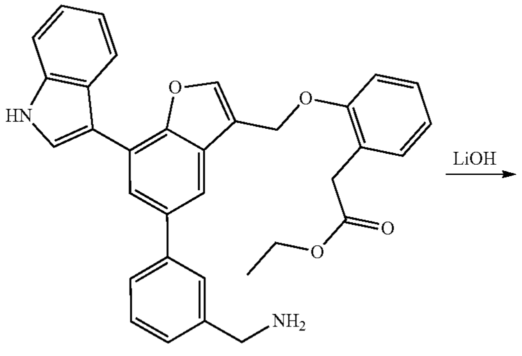

136c

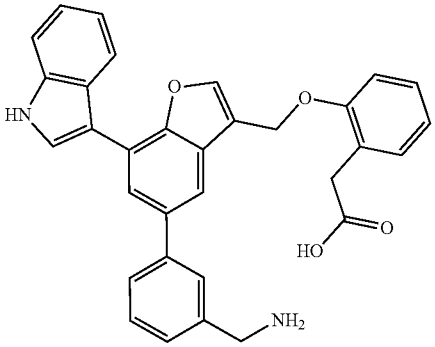

136d

Preparation of 2-(2-((5-(3-(aminomethyl)phenyl)-7-(1H-indol-3-yl)benzofuran-3-yl)methoxy)phenyl) acetic acid (136d)

Step-1: Preparation of tert-butyl 3-(5-(3-(aminomethyl)phenyl)-3-((2-(2-ethoxy-2-oxoethyl)phenoxy) methyl)benzofuran-7-yl)-1H-indole-1-carboxylate (136b)

Compound 136b was prepared according to the procedure reported in step-2 of scheme 1, from ethyl 2-(2-((5-(3-(aminomethyl)phenyl)-7-chlorobenzofuran-3-yl)methoxy) phenyl)acetate (127e) (150 mg, 0.333 mmol) in dioxane (12 mL) using (1-(tert-butoxycarbonyl)-1H-indol-3-yl)boronic acid (136a) (109 mg, 0.417 mmol; CAS #181365-26-4), 4M solution of $K_3PO_4$ (0.333 mL, 1.334 mmol), tricyclohexylphosphine (18.70 mg, 0.067 mmol), $Pd_2(dba)_3$ (30.5 mg, 0.033 mmol) and heating at 115° C. for 12 h in an oil bath. This gave after workup and purification by flash column chromatography [silica gel (24 g), eluting with DMA-80 in DCM from 0-50%] tert-butyl 3-(5-(3-(aminomethyl)phenyl)-3-((2-(2-ethoxy-2-oxoethyl)phenoxy)methyl)benzofuran-7-yl)-1H-indole-1-carboxylate (136b) (160 mg, 76% yield) as a clear oil; $^1$H NMR (300 MHz, DMSO-$d_6$) δ 8.29-8.15 (m, 3H), 7.99-7.90 (m, 2H), 7.87-7.74 (m, 3H), 7.57-7.17 (m, 7H), 6.95 (t, J=7.2 Hz, 1H), 5.36 (s, 2H), 4.02 (s, 2H), 3.76 (q, J=7.1 Hz, 2H), 3.59 (s, 2H), 1.69 (s, 9H), 0.87 (t, J=7.1 Hz, 3H); MS (ES+): 631.3 (M+1).

Step-2: Preparation of ethyl 2-(2-((5-(3-(aminomethyl)phenyl)-7-(1H-indol-3-yl)benzofuran-3-yl) methoxy)phenyl)acetate (136c)

Compound 136c was prepared according to the procedure reported in step-2 of scheme 7, from tert-butyl 3-(5-(3-(aminomethyl)phenyl)-3-((2-(2-ethoxy-2-oxoethyl)phenoxy)methyl)benzofuran-7-yl)-1H-indole-1-carboxylate (136b) (150 mg, 0.238 mmol) using HCl (4N in dioxane) (0.892 mL, 3.57 mmol) and stirring the reaction mixture at RT for 8 h. This gave after workup and purification by flash column chromatography [silica gel (24 g), eluting with DMA-80 in DCM from 0-100%] ethyl 2-(2-((5-(3-(aminomethyl)phenyl)-7-(1H-indol-3-yl)benzofuran-3-yl)methoxy) phenyl)acetate (136c) (55 mg, 44% yield) as a white solid; $^1$H NMR (300 MHz, DMSO-$d_6$) δ 11.61 (s, 1H), 8.20 (s, 1H), 8.00 (d, J=2.5 Hz, 1H), 7.97-7.85 (m, 2H), 7.81-7.73 (m, 2H), 7.66 (d, J=8.1 Hz, 1H), 7.53 (d, J=8.0 Hz, 1H), 7.45 (t, J=7.6 Hz, 1H), 7.41-7.09 (m, 6H), 6.94 (t, J=7.2 Hz, 1H), 5.35 (s, 2H), 3.86 (s, 2H), 3.77 (q, J=7.1 Hz, 2H), 3.59 (s, 2H), 0.89 (t, J=7.1 Hz, 3H); MS (ES+):531.30 (M+1).

Step-3: Preparation of 2-(2-((5-(3-(aminomethyl) phenyl)-7-(1H-indol-3-yl)benzofuran-3-yl)methoxy) phenyl)acetic acid (136d)

Compound 136d was prepared according to the procedure reported in step-3 of scheme 1, from ethyl 2-(2-((5-(3-(aminomethyl)phenyl)-7-(1H-indol-3-yl)benzofuran-3-yl) methoxy)phenyl)acetate (136c) (50 mg, 0.094 mmol) in THF (0.660 mL) and acetonitrile (0.33 mL) using a 1 N solution of lithium hydroxide hydrate (0.330 mL, 0.330 mmol) and stirring at room temperature for 25 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(1H-indol-3-yl)benzofuran-3-yl) methoxy)phenyl)acetic acid (136d) (29 mg, 61% yield) hydrochloride salt as a white solid; $^1$H NMR (300 MHz, DMSO-$d_6$) δ 12.20 (s, 1H, $D_2O$ exchangeable), 11.68 (d, J=2.7 Hz, 1H), 8.45 (s, 3H, $D_2O$ exchangeable), 8.21 (s, 1H), 8.04-7.80 (m, 6H), 7.62-7.46 (m, 3H), 7.35-7.10 (m, 5H), 6.95 (td, J=7.1, 1.6 Hz, 1H), 5.38 (s, 2H), 4.15 (s, 2H), 3.58 (s, 2H); MS (ES+): 503.1 (M+1); (ES−): 501.1 (M−1); Analysis calculated for $C_{32}H_{26}N_2O_4 \cdot 1.25H_2O \cdot HCl$: C, 68.44; H, 5.30; N, 4.99. Found: C, 68.52; H, 5.23; N, 5.09.

Scheme 137

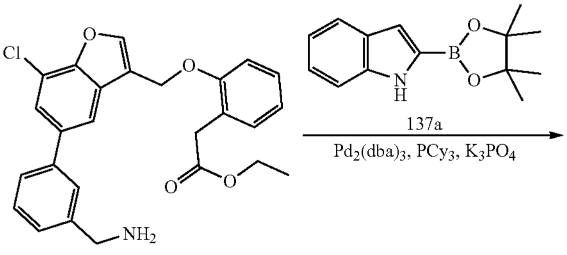

127e

-continued

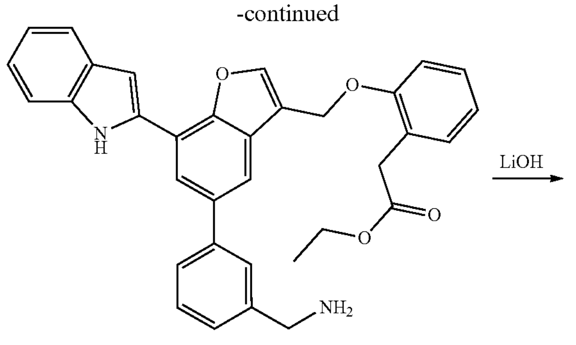

137b

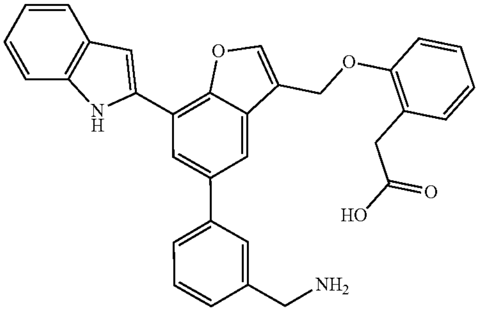

137c

Preparation of 2-(2-((5-(3-(aminomethyl)phenyl)-7-(1H-indol-2-yl)benzofuran-3-yl)methoxy)phenyl) acetic acid (137c)

Step-1: Preparation of ethyl 2-(2-((5-(3-(aminomethyl)phenyl)-7-(1H-indol-2-yl)benzofuran-3-yl) methoxy)phenyl)acetate (137b)

Compound 137b was prepared according to the procedure reported in step-2 of scheme 1, from ethyl 2-(2-((5-(3-(aminomethyl)phenyl)-7-chlorobenzofuran-3-yl)methoxy) phenyl)acetate (127e) (150 mg, 0.333 mmol) in dioxane (12 mL) using 2-(4,4,5,5-tetramethyl-1,3,2-dioxaborolan-2-yl)-1H-indole (137a) (101 mg, 0.417 mmol; CAS #476004-81-6), 4M solution of $K_3PO_4$ (0.333 mL, 1.334 mmol), tricyclohexylphosphine (18.70 mg, 0.067 mmol), $Pd_2(dba)_3$ (30.5 mg, 0.033 mmol) and heating at 115° C. for 12 h in an oil bath. This gave after workup and purification by flash column chromatography [silica gel (24 g), eluting with DMA-80 in DCM from 0-50%] ethyl 2-(2-((5-(3-(aminomethyl)phenyl)-7-(1H-indol-2-yl)benzofuran-3-yl)methoxy) phenyl)acetate (137b) (56 mg, 32% yield) as a pale yellow solid; $^1$H NMR (300 MHz, DMSO-$d_6$) δ 11.79 (s, 1H), 8.30 (s, 1H), 8.21 (d, J=1.7 Hz, 1H), 7.89 (d, J=1.6 Hz, 1H), 7.80 (s, 1H), 7.67 (dd, J=13.8, 8.0 Hz, 2H), 7.54-7.13 (m, 8H), 7.06 (t, J=7.4 Hz, 1H), 6.99-6.89 (m, 1H), 5.37 (s, 2H), 3.85 (s, 2H), 3.75 (dd, J=8.8, 5.5 Hz, 2H), 3.59 (s, 2H), 0.87 (t, J=7.1 Hz, 3H); MS (ES+): 531.3 (M+1).

Step-2: Preparation of Preparation of 2-(2-((5-(3-(aminomethyl)phenyl)-7-(1H-indol-2-yl)benzofuran-3-yl)methoxy)phenyl)acetic acid (137c)

Compound 137c was prepared according to the procedure reported in step-3 of scheme 1, from ethyl 2-(2-((5-(3-(aminomethyl)phenyl)-7-(1H-indol-2-yl)benzofuran-3-yl) methoxy)phenyl)acetate (137b) (50 mg, 0.094 mmol) in THF (0.660 mL), acetonitrile (0.33 mL) using a 1 N solution of lithium hydroxide hydrate (0.330 mL, 0.330 mmol) and stirring at room temperature for 25 h. This gave after workup and purification by reverse phase column chromatography [C18 column (50 g), eluting with ACN in water (containing 0.1% HCl) from 0-100%] 2-(2-((5-(3-(aminomethyl)phenyl)-7-(1H-indol-2-yl)benzofuran-3-yl)methoxy)phenyl) acetic acid (137c) (21 mg, 44% yield) hydrochloride salt as a white solid; $^1$H NMR (300 MHz, DMSO-$d_6$) δ 12.19 (s, 1H, $D_2O$ exchangeable), 11.94 (d, J=2.2 Hz, 1H, $D_2O$ exchangeable), 8.48 (s, 3H, $D_2O$ exchangeable), 8.39 (d, J=1.7 Hz, 1H), 8.30 (s, 1H), 8.13 (d, J=1.8 Hz, 1H), 8.01 (d, J=1.7 Hz, 1H), 7.96-7.85 (m, 1H), 7.65 (d, J=7.8 Hz, 1H), 7.59 (t, J=7.7 Hz, 1H), 7.52 (td, J=5.2, 2.5 Hz, 2H), 7.40-7.34 (m, 1H), 7.34-7.21 (m, 3H), 7.18 (ddd, J=8.2, 7.0, 1.2 Hz, 1H), 7.12-7.01 (m, 1H), 6.95 (td, J=7.1, 1.5 Hz, 1H), 5.40 (s, 2H), 4.17 (m, J=5.7 Hz, 2H), 3.58 (s, 2H); MS (ES+): 503.2 (M+1); (ES−): 501.2 (M−1).

Scheme 138

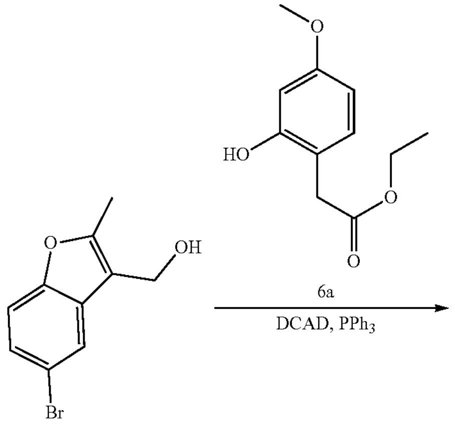

124c

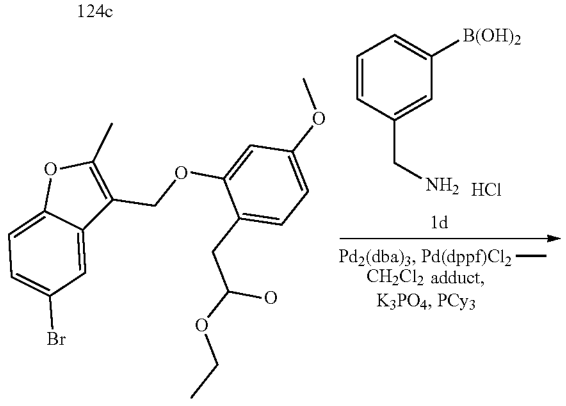

138a

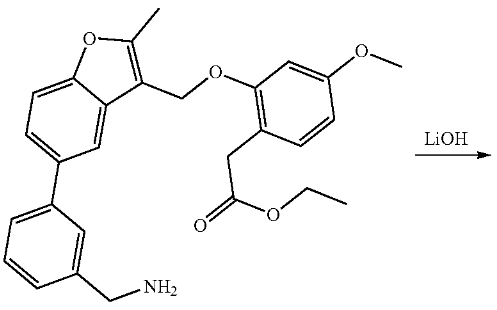

138b

-continued

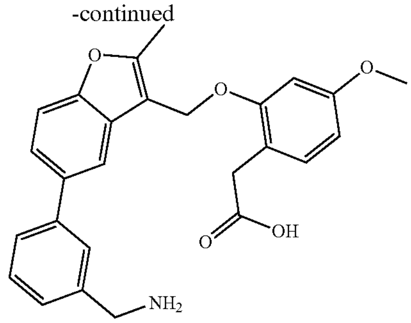

138c

Preparation of 2-(2-((5-(3-(aminomethyl)phenyl)-2-methylbenzofuran-3-yl)methoxy)-4-methoxyphenyl) acetic acid (138c)

Step-1: Preparation of ethyl 2-(2-((5-bromo-2-methylbenzofuran-3-yl)methoxy)-4-methoxyphenyl)acetate (138a)

Compound 138a was prepared according to the procedure reported in step-3 of scheme 7, from (5-bromo-2-methylbenzofuran-3-yl)methanol (124c) (1 g, 4.15 mmol), triphenylphosphine (1.197 g, 4.56 mmol), ethyl 2-(2-hydroxy-4-methoxyphenyl)acetate (6a) (959 mg, 4.56 mmol) in DCM (20 mL) using bis(4-chlorobenzyl) diazene-1,2-dicarboxylate (DCAD) (1.675 g, 4.56 mmol) in DCM (10 mL) and stirring the mixture at RT for 30 min. This gave after workup and purification by flash column chromatography [silica gel (40 g), eluting with EtOAc in hexane from 0-50%] ethyl 2-(2-((5-bromo-2-methylbenzofuran-3-yl)methoxy)-4-methoxyphenyl)acetate (138a) (875 mg, 49% yield) as a clear oil; $^1$H NMR (300 MHz, DMSO-$d_6$) δ 7.75 (d, J=2.0 Hz, 1H), 7.51 (d, J=8.7 Hz, 1H), 7.41 (dd, J=8.7, 2.0 Hz, 1H), 7.09 (d, J=8.3 Hz, 1H), 6.79 (d, J=2.4 Hz, 1H), 6.50 (dd, J=8.3, 2.4 Hz, 1H), 5.18 (s, 2H), 3.91 (q, J=7.1 Hz, 2H), 3.78 (s, 3H), 3.43 (s, 2H), 2.51 (s, 3H), 0.96 (t, J=7.1 Hz, 3H); MS (ES+): 454.6 (M+Na).

Step-2: Preparation of ethyl 2-(2-((5-(3-(aminomethyl)phenyl)-2-methylbenzofuran-3-yl)methoxy)-4-methoxyphenyl)acetate (138b)

Compound 138b was prepared according to the procedure reported in step-2 of scheme 1, from ethyl 2-(2-((5-bromo-2-methylbenzofuran-3-yl)methoxy)-4-methoxyphenyl)acetate (138a) (264 mg, 0.609 mmol) in dioxane (30 mL) using 3-(aminomethyl)phenylboronic acid hydrochloride (1d) (228 mg, 1.219 mmol), 4 M solution of $K_3PO_4$ (0.609 mL, 2.437 mmol), tricyclohexylphosphine (51.3 mg, 0.183 mmol), $Pd_2(dba)_3$ (55.8 mg, 0.061 mmol), $PdCl_2$(dppf)-$CH_2Cl_2$ adduct (49.8 mg, 0.061 mmol) and heating at 100° C. for 2 h. This gave after workup and purification by flash column chromatography [silica gel (40 g), eluting with DMA-80 in DCM from 0-100%] ethyl 2-(2-((5-(3-(aminomethyl)phenyl)-2-methylbenzofuran-3-yl)methoxy)-4-methoxyphenyl)acetate (138b) (165 mg, 59% yield) as a yellow oil; MS (ES+): 460.2 (M+1).

Step-3: Preparation of 2-(2-((5-(3-(aminomethyl) phenyl)-2-methylbenzofuran-3-yl)methoxy)-4-methoxyphenyl)acetic acid (138c)

Compound 138c was prepared according to the procedure reported in step-3 of scheme 1, from ethyl 2-(2-((5-(3-(aminomethyl)phenyl)-2-methylbenzofuran-3-yl)methoxy)-4-methoxyphenyl)acetate (138b) (0.165 g, 0.359 mmol) in THF (6 mL) using a solution of lithium hydroxide hydrate (25.6 mg, 0.609 mmol) in water (1 mL) and stirring for overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)-2-methylbenzofuran-3-yl)methoxy)-4-methoxyphenyl)acetic acid (138c) (84 mg, 32% yield) HCl salt as a white solid; $^1$H NMR (300 MHz, DMSO-$d_6$) δ 8.59 (s, 2H, $D_2O$ exchangeable), 7.95 (s, 1H), 7.90 (s, 1H), 7.72 (dt, J=7.3, 2.0 Hz, 1H), 7.61 (s, 2H), 7.54-7.41 (m, 2H), 7.08 (d, J=8.3 Hz, 1H), 6.83 (d, J=2.4 Hz, 1H), 6.49 (dd, J=8.3, 2.3 Hz, 1H), 5.26 (s, 2H), 4.09 (s, 2H), 3.76 (s, 3H), 3.41 (s, 2H), 2.52 (s, 3H); MS (ES+): 432.2 (M+1); (ES−): 430.2 (M−1); Analysis calculated for $C_{26}H_{25}NO_5 \cdot HCl \cdot H_2O$: C, 64.26; H, 5.81; Cl, 7.30; N, 2.88. Found: C, 64.01; H, 5.75; Cl, 7.16; N, 2.89.

Scheme 139

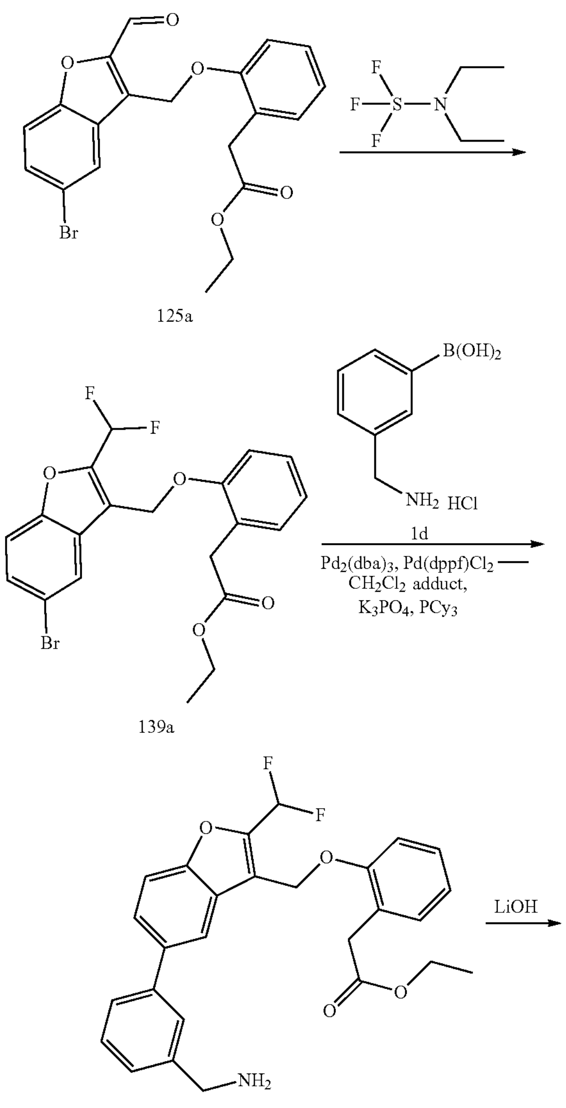

125a

139a

139b

-continued

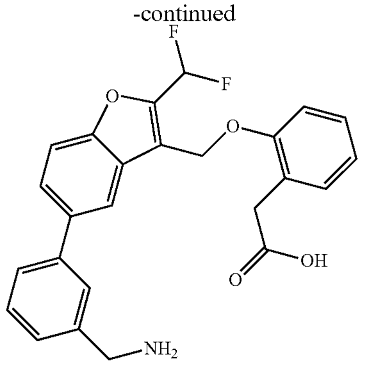

139c

Preparation of 2-(2-((5-(3-(aminomethyl)phenyl)-2-(difluoromethyl)benzofuran-3-yl)methoxy)phenyl) acetic acid (139c)

Step-1: Preparation of ethyl 2-(2-((5-bromo-2-(difluoromethyl)benzofuran-3-yl)methoxy)phenyl)acetate (139a)

To a solution of ethyl 2-(2-((5-bromo-2-formylbenzofuran-3-yl)methoxy)phenyl)acetate (125a) (1 g, 2.397 mmol) in DCM (20 mL) was added diethylamino sulfur trifluoride (DAST) (0.412 mL, 3.12 mmol) and the mixture was stirred at RT for 1h. The reaction mixture was quenched with water, extracted with DCM and the combined organics were dried, filtered, and concentrated in vacuum. The crude residue obtained was purified by flash column chromatography [silica gel, eluting with EtOAc in hexane from 0-100%] to give ethyl 2-(2-((5-bromo-2-(difluoromethyl)benzofuran-3-yl)methoxy)phenyl)acetate (139a) (350 mg, 33% yield) as a white solid; $^1H$ NMR (300 MHz, DMSO-$d_6$) δ 8.02 (d, J=2.0 Hz, 1H), 7.76 (d, J=8.8 Hz, 1H), 7.67 (dd, J=8.7, 2.2 Hz, 1H), 7.51 (s, 1H), 7.33 (ddd, J=9.0, 6.1, 1.7 Hz, 1H), 7.26-7.16 (m, 2H), 6.97 (t, J=7.4 Hz, 1H), 5.41 (s, 2H), 3.91 (q, J=7.1 Hz, 2H), 3.56 (s, 2H), 0.96 (t, J=7.1 Hz, 3H); $^{19}F$ NMR (282 MHz, DMSO-$d_6$) δ −116.14.

Step-2: Preparation of ethyl 2-(2-((5-(3-(aminomethyl)phenyl)-2-(difluoromethyl)benzofuran-3-yl)methoxy)phenyl)acetate (139b)

Compound 139b was prepared according to the procedure reported in step-2 of scheme 1, from ethyl 2-(2-((5-bromo-2-(difluoromethyl)benzofuran-3-yl)methoxy)phenyl)acetate (139a) (350 mg, 0.797 mmol) in dioxane (30 mL) using 3-(aminomethyl)phenylboronic acid hydrochloride (1d) (299 mg, 1.594 mmol), 4 M solution of $K_3PO_4$ (0.797 mL, 3.19 mmol), tricyclohexylphosphine (67.0 mg, 0.239 mmol), $Pd_2(dba)_3$ (73.0 mg, 0.080 mmol), $PdCl_2$(dppf)-$CH_2Cl_2$ adduct (65.1 mg, 0.080 mmol) and heating at 100° C. for 2 h. This gave after workup and purification by flash column chromatography [silica gel (40 g), eluting with DMA-80 in DCM from 0-100%] ethyl 2-(2-((5-(3-(aminomethyl)phenyl)-2-(difluoromethyl)benzofuran-3-yl)methoxy)phenyl)acetate (139b) (252 mg, 68% yield) as a yellow oil; MS (ES+): 466.2 (M+1).

Step-3: Preparation of 2-(2-((5-(3-(aminomethyl)phenyl)-2-(difluoromethyl)benzofuran-3-yl)methoxy)phenyl)acetic acid (139c)

Compound 139c was prepared according to the procedure reported in step-3 of scheme 1, from ethyl 2-(2-((5-(3-(aminomethyl)phenyl)-2-(difluoromethyl)benzofuran-3-yl)methoxy)phenyl)acetate (139b) (252 mg, 0.541 mmol) in THF (3 mL) using a solution of lithium hydroxide hydrate (100 mg, 2.390 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)-2-(difluoromethyl)benzofuran-3-yl)methoxy)phenyl)acetic acid (139c) (188 mg, 54% yield) HCl salt as a white solid; $^1H$ NMR (300 MHz, DMSO-$d_6$) δ 12.16 (s, 1H, $D_2O$ exchangeable), 8.60 (s, 2H, $D_2O$ exchangeable), 8.19 (s, 1H), 7.96 (s, 1H), 7.86 (s, 2H), 7.80-7.69 (m, 1H), 7.59-7.44 (m, 3H, 1H $D_2O$ exchangeable), 7.37-7.19 (m, 3H), 6.96 (t, J=6.8 Hz, 1H), 5.50 (s, 2H), 4.10 (s, 2H), 3.54 (s, 2H); $^{19}F$ NMR (282 MHz, DMSO-$d_6$) δ −115.64; MS (ES+): 438.1 (M+1); (ES−): 436.1 (M−1); Analysis calculated for $C_{25}H_{21}F_2NO_4 \cdot HCl \cdot 0.75H_2O$: C, 61.60; H, 4.86; Cl, 7.27; N, 2.87. Found: C, 61.97; H, 4.76; Cl, 6.87; N, 2.96.

Scheme 140

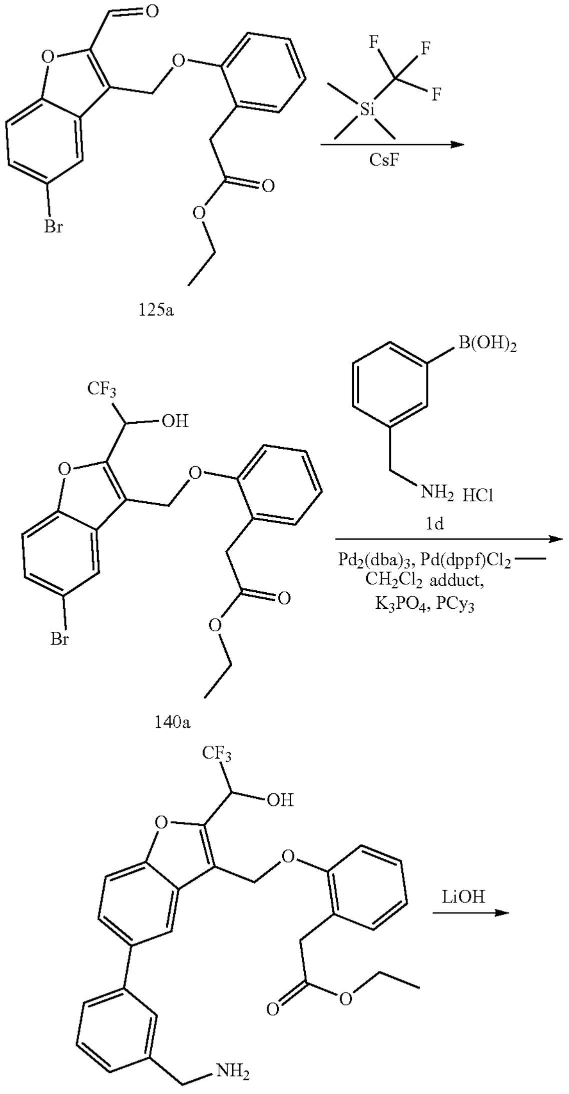

125a

140a

140b

-continued

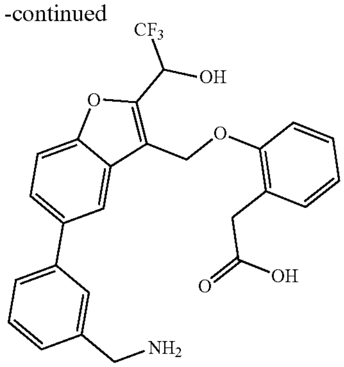

140c

Preparation of 2-(2-((5-(3-(aminomethyl)phenyl)-2-(2,2,2-trifluoro-1-hydroxyethyl)benzofuran-3-yl)methoxy)phenyl)acetic acid (140c)

Step-1: Preparation of ethyl 2-(2-((5-bromo-2-(2,2,2-trifluoro-1-hydroxyethyl)benzofuran-3-yl)methoxy)phenyl)acetate (140a)

To a solution of ethyl 2-(2-((5-bromo-2-formylbenzofuran-3-yl)methoxy)phenyl)acetate (125a) (1 g, 2.397 mmol) in anhydrous THF (20 mL) was added trimethyl (trifluoromethyl)silane (0.443 g, 3.12 mmol) and CsF (0.364 g, 2.397 mmol) at RT under Ar atmosphere and the mixture was sonicated for 20 min to initiate the reaction. The mixture was stirred at RT for 12 h, after which aqueous HCl (1M, 15 mL) was added and the mixture was stirred for additional 15 min. The mixture was then extracted with EtOAc and the organic layer was washed with saturated $NaHCO_3$, brine, dried, filtered and concentrated in vacuo. The residue obtained was purified using flash column chromatography [silica gel (24 g), eluting with EtOAc in hexane from 0-70%] to give ethyl 2-(2-((5-bromo-2-(2,2,2-trifluoro-1-hydroxyethyl)benzofuran-3-yl)methoxy)phenyl)acetate (140a) (550 mg, 47% yield) as a yellow oil; $^1H$ NMR (300 MHz, DMSO-$d_6$) δ 7.88 (d, J=2.0 Hz, 1H), 7.67 (d, J=8.8 Hz, 1H), 7.56 (dd, J=8.8, 2.0 Hz, 1H), 7.36 (d, J=6.2 Hz, 1H), 7.30 (dd, J=7.4, 1.7 Hz, 1H), 7.26-7.16 (m, 2H), 6.95 (td, J=7.3, 1.1 Hz, 1H), 5.77 (p, J=7.0 Hz, 1H), 5.42-5.30 (m, 2H), 3.92 (q, J=7.1 Hz, 2H), 3.55 (s, 2H), 0.94 (t, J=7.1 Hz, 3H).

Step-2: Preparation of ethyl 2-(2-((5-(3-(aminomethyl)phenyl)-2-(2,2,2-trifluoro-1-hydroxyethyl)benzofuran-3-yl)methoxy)phenyl)acetate (140b)

Compound 140b was prepared according to the procedure reported in step-2 of scheme 1, from ethyl 2-(2-((5-bromo-2-(2,2,2-trifluoro-1-hydroxyethyl)benzofuran-3-yl)methoxy)phenyl)acetate (140a) (300 mg, 0.616 mmol) in dioxane (30 mL) using 3-(aminomethyl)phenylboronic acid hydrochloride (1d) (231 mg, 1.231 mmol), 4 M solution of $K_3PO_4$ (0.616 mL, 2.463 mmol), tricyclohexylphosphine (51.8 mg, 0.185 mmol), $Pd_2(dba)_3$ (56.4 mg, 0.062 mmol), $PdCl_2(dppf)$-$CH_2Cl_2$ adduct (50.3 mg, 0.062 mmol) and heating at 100° C. for 2 h. This gave after workup and purification by flash column chromatography [silica gel (40 g), eluting with DMA-80 in DCM from 0-100%] ethyl 2-(2-((5-(3-(aminomethyl)phenyl)-2-(2,2,2-trifluoro-1-hydroxyethyl)benzofuran-3-yl)methoxy)phenyl)acetate (140b) (165 mg, 0.321 mmol) as a yellow oil; MS (ES+): 514.2 (M+1).

Step-3: Preparation of 2-(2-((5-(3-(aminomethyl)phenyl)-2-(2,2,2-trifluoro-1-hydroxyethyl)benzofuran-3-yl)methoxy)phenyl)acetic acid (140c)

Compound 140c was prepared according to the procedure reported in step-3 of scheme 1, from ethyl 2-(2-((5-(3-(aminomethyl)phenyl)-2-(2,2,2-trifluoro-1-hydroxyethyl)benzofuran-3-yl)methoxy)phenyl)acetate (140b) (165 mg, 0.321 mmol) in THF (3 mL) using a solution of lithium hydroxide hydrate (78 mg, 1.847 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)-2-(2,2,2-trifluoro-1-hydroxyethyl)benzofuran-3-yl)methoxy)phenyl)acetic acid (140c) (188 mg, 54% yield) HCl salt as a white solid; $^1H$ NMR (300 MHz, DMSO-$d_6$) δ 12.14 (s, 1H, $D_2O$ exchangeable), 8.44 (s, 3H, $D_2O$ exchangeable), 8.04 (d, J=1.7 Hz, 1H), 7.88 (s, 1H), 7.82-7.69 (m, 3H), 7.57-7.43 (m, 2H), 7.36 (d, J=6.2 Hz, 1H, $D_2O$ exchangeable), 7.33-7.18 (m, 3H), 6.99-6.89 (m, 1H), 5.78 (p, J=6.8 Hz, 1H), 5.50-5.33 (m, 2H), 4.10 (s, 2H), 3.54 (s, 2H); $^{19}F$ NMR (282 MHz, DMSO-$d_6$) δ −75.15; MS (ES+): 486.1 (M+1); (ES−): 484.1 (M−1); Analysis calculated for $C_{26}H_{22}F_3NO_5 \cdot HCl \cdot H_2O$: C, 57.84; H, 4.67; Cl, 6.57; N, 2.59. Found: C, 57.54; H, 4.69; Cl, 6.58; N, 2.71.

Scheme 141

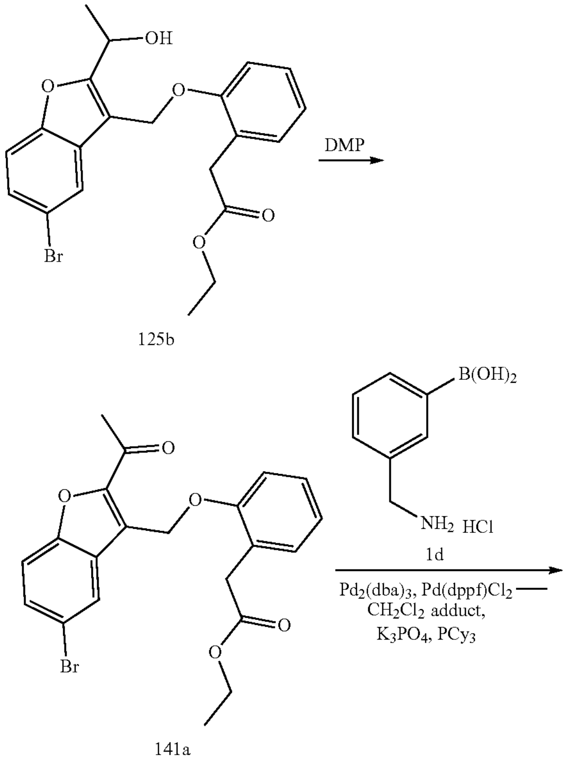

125b

141a

-continued

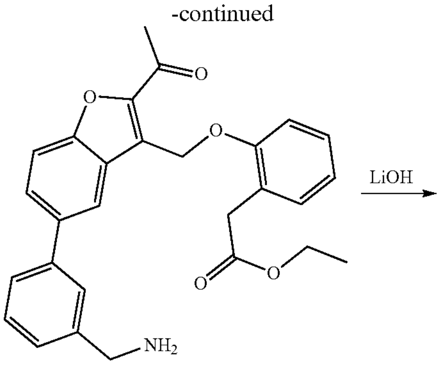

141b

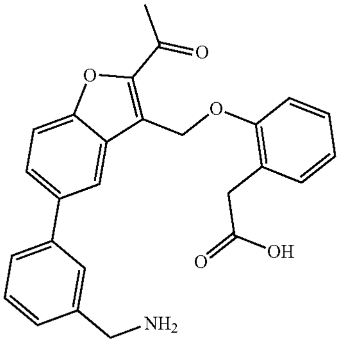

141c

Preparation of 2-(2-((2-acetyl-5-(3-(aminomethyl)phenyl)benzofuran-3-yl)methoxy)phenyl)acetic acid (141c)

Step-1: Preparation of ethyl 2-(2-((2-acetyl-5-bromobenzofuran-3-yl)methoxy)phenyl)acetate (141a)

To a solution of ethyl 2-(2-((5-bromo-2-(1-hydroxyethyl)benzofuran-3-yl)methoxy)phenyl)acetate (125b) (550 mg, 1.269 mmol) in DCM (20 mL) was added Dess-Martin periodinane (DMP) (700 mg, 1.65 mmol) and the mixture was stirred at RT for 3 h. The reaction mixture was diluted with dichloromethane, washed with saturated aqueous sodium bicarbonate, dried, filtered, and concentrated in vacuo. The residue obtained was purified by flash column chromatography [silica gel, eluting with EtOAc in hexane from 0-100%] to give ethyl 2-(2-((2-acetyl-5-bromobenzofuran-3-yl)methoxy)phenyl)acetate (141a) (540 mg, 99% yield) as a white solid; $^1H$ NMR (300 MHz, DMSO-$d_6$) δ 8.06 (d, J=1.8 Hz, 1H), 7.79-7.69 (m, 2H), 7.32-7.18 (m, 2H), 7.16-7.08 (m, 1H), 6.94 (td, J=7.4, 1.1 Hz, 1H), 5.60 (s, 2H), 3.93 (q, J=7.1 Hz, 2H), 3.58 (s, 2H), 2.64 (s, 3H), 0.98 (t, J=7.1 Hz, 3H).

Step-2: Preparation of ethyl 2-(2-((2-acetyl-5-(3-(aminomethyl)phenyl)benzofuran-3-yl)methoxy)phenyl)acetate (141b)

Compound 141b was prepared according to the procedure reported in step-2 of scheme 1, from ethyl 2-(2-((2-acetyl-5-bromobenzofuran-3-yl)methoxy)phenyl)acetate (141a) (400 mg, 0.927 mmol) in dioxane (20 mL) using 3-(aminomethyl)phenylboronic acid hydrochloride (1d) (348 mg, 1.855 mmol), 4 M solution of $K_3PO_4$ (0.927 mL, 3.71 mmol), tricyclohexylphosphine (78 mg, 0.278 mmol), $Pd_2(dba)_3$ (85 mg, 0.093 mmol), $PdCl_2(dppf)-CH_2Cl_2$ adduct (76 mg, 0.093 mmol) and heating at 100° C. for 2 h. This gave after workup and purification by flash column chromatography [silica gel (40 g), eluting with DMA-80 in DCM from 0-100%] ethyl 2-(2-((2-acetyl-5-(3-(aminomethyl)phenyl)benzofuran-3-yl)methoxy)phenyl)acetate (141b) (165 mg, 39% yield) as a yellow oil; MS (ES+): 458.2 (M+1).

Step-3: Preparation of 2-(2-((2-acetyl-5-(3-(aminomethyl)phenyl)benzofuran-3-yl)methoxy)phenyl)acetic acid (141c)

Compound 141c was prepared according to the procedure reported in step-3 of scheme 1, from ethyl 2-(2-((2-acetyl-5-(3-(aminomethyl)phenyl)benzofuran-3-yl)methoxy)phenyl)acetate (141b) (165 mg, 0.361 mmol) in THF (3 mL) using a solution of lithium hydroxide hydrate (117 mg, 2.78 mmol) in water (1 mL) and stirring overnight at RT. This gave after workup and purification using reverse phase column chromatography [C18 column (30 g), eluting with ACN in water (containing 0.1% HCl) from 0-100%] 2-(2-((2-acetyl-5-(3-(aminomethyl)phenyl)benzofuran-3-yl)methoxy)phenyl)acetic acid (141c) (28 mg, 7% yield) HCl salt as a white solid; $^1H$ NMR (300 MHz, DMSO-$d_6$) δ 12.16 (s, 1H, $D_2O$ exchangeable), 8.41 (s, 3H, $D_2O$ exchangeable), 8.19 (s, 1H), 7.96-7.83 (m, 3H), 7.74 (dt, J=7.4, 1.7 Hz, 1H), 7.57-7.43 (m, 2H), 7.29-7.18 (m, 2H), 7.14 (d, J=8.1 Hz, 1H), 6.93 (t, J=7.3 Hz, 1H), 5.68 (s, 2H), 4.11 (s, 2H), 3.55 (s, 2H), 2.66 (s, 3H); MS (ES+): 430.2 (M+1); (ES−): 428.1 (M−1); Analysis calculated for $C_{26}H_{23}NO_5·HCl·1.5H_2O$: C, 63.35; H, 5.52; N, 2.84. Found: C, 63.12; H, 5.38; N, 2.88.

Scheme 142

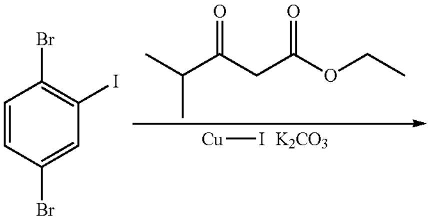

124a

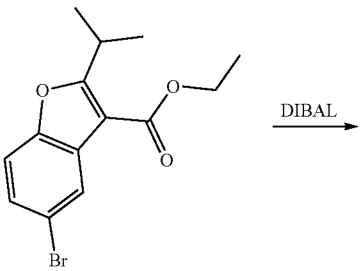

142a

-continued

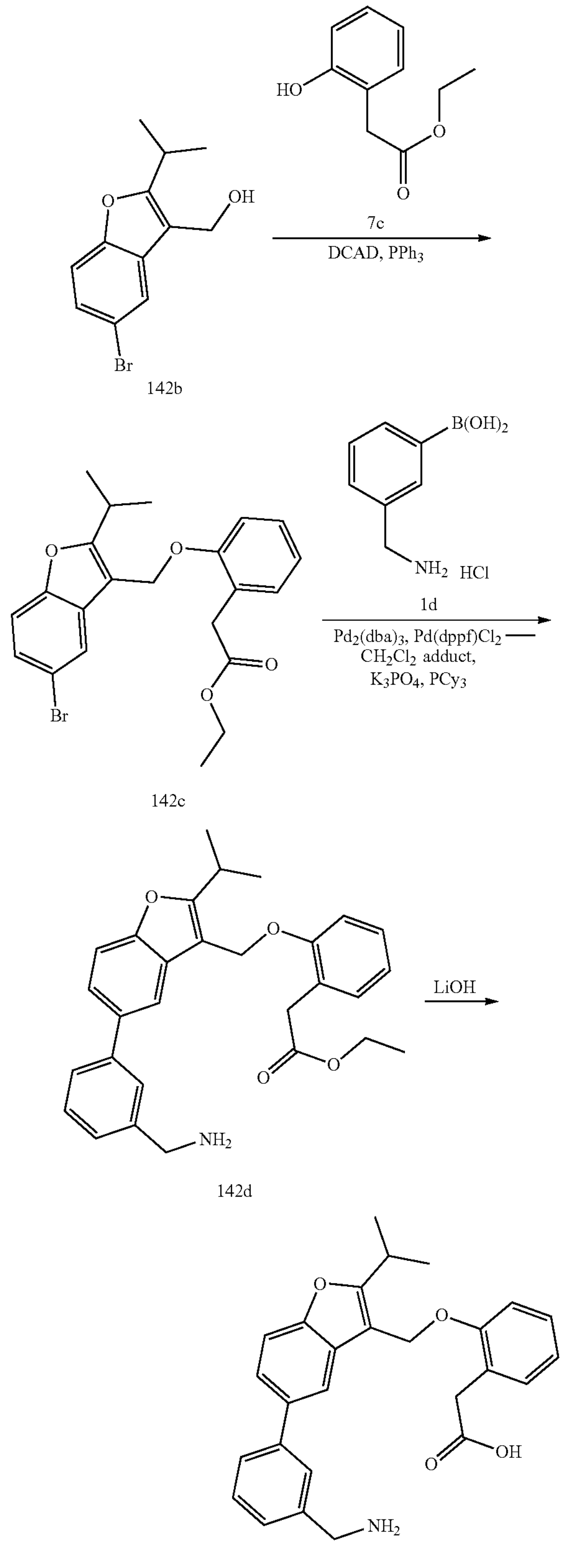

Preparation of 2-(2-((5-(3-(aminomethyl)phenyl)-2-isopropylbenzofuran-3-yl)methoxy)phenyl)acetic acid (142e)

Step-1: Preparation of ethyl 5-bromo-2-isopropylbenzofuran-3-carboxylate (142a)

Compound 142a was prepared according to the procedure reported in step-1 of scheme 124, from 1,4-dibromo-2-iodobenzene (124a) (20 g, 55.3 mmol) in THF (80 mL) using ethyl 4-methyl-3-oxopentanoate (11.37 g, 71.9 mmol), copper(I) iodide (1.369 g, 7.19 mmol), potassium carbonate (19.10 g, 138 mmol) and heating at 100° C. for 2 days under an argon atmosphere. This gave after workup and purification using flash column chromatography [silica gel (80 g), eluting with EtOAc in hexane from 0-100%] ethyl 5-bromo-2-isopropylbenzofuran-3-carboxylate (142a) (1.5 g, 9% yield) as a white solid; $^1$H NMR (300 MHz, DMSO-$d_6$) δ 8.00 (d, J=2.1 Hz, 1H), 7.65 (d, J=8.7 Hz, 1H), 7.52 (dd, J=8.7, 2.1 Hz, 1H), 4.37 (q, J=7.1 Hz, 2H), 3.94 (p, J=6.9 Hz, 1H), 1.40-1.29 (m, 9H).

Step-2: Preparation of (5-bromo-2-isopropylbenzofuran-3-yl)methanol (142b)

Compound 142b was prepared according to the procedure reported in step-4 of scheme 3, from ethyl 5-bromo-2-isopropylbenzofuran-3-carboxylate (142a) (1.5 g, 4.82 mmol) in THE (15 mL) using DIBAL (1.0 M in THF) (12.05 mL, 12.05 mmol) and stirring at 0° C. for 2 h.

This gave after workup and purification by flash column chromatography [silica gel (24 g), eluting with EtOAc in hexane from 0-100%] (5-bromo-2-isopropylbenzofuran-3-yl)methanol (142b) (947 mg, 73% yield) as a white solid; $^1$H NMR (300 MHz, DMSO-$d_6$) δ 7.81 (d, J=2.0 Hz, 1H), 7.48 (d, J=8.6 Hz, 1H), 7.36 (dd, J=8.7, 2.1 Hz, 1H), 5.06 (t, J=5.6 Hz, 1H), 4.56 (d, J=5.6 Hz, 2H), 3.36-3.26 (m, 1H), 1.28 (d, J=6.9 Hz, 6H).

Step-3: Preparation of ethyl 2-(2-((5-bromo-2-isopropylbenzofuran-3-yl)methoxy)phenyl)acetate (142c)

Compound 142c was prepared according to the procedure reported in step-3 of scheme 7, from (5-bromo-2-isopropylbenzofuran-3-yl)methanol (142b) (450 mg, 1.672 mmol), triphenylphosphine (482 mg, 1.839 mmol), ethyl 2-(2-hydroxyphenyl)acetate (7c) (331 mg, 1.839 mmol) in DCM (15 mL) using bis(4-chlorobenzyl) diazene-1,2-dicarboxylate (DCAD) (675 mg, 1.839 mmol) in DCM (10 mL) and stirring at RT for 30 min. This gave after workup and purification by flash column chromatography [silica (40 g), eluting with EtOAc in hexane from 0-50%] ethyl 2-(2-((5-bromo-2-isopropylbenzofuran-3-yl)methoxy)phenyl)acetate (142c) (521 mg, 72% yield) as a clear oil; $^1$H NMR (300 MHz, DMSO-$d_6$) δ 7.78 (d, J=2.0 Hz, 1H), 7.54 (d, J=8.7 Hz, 1H), 7.41 (dd, J=8.7, 2.0 Hz, 1H), 7.34-7.26 (m, 1H), 7.24-7.18 (m, 2H), 6.93 (td, J=7.4, 1.3 Hz, 1H), 5.20 (s, 2H), 3.88 (q, J=7.1 Hz, 2H), 3.50 (s, 2H), 3.45-3.35 (m, 1H), 1.28 (d, J=7.0 Hz, 6H), 0.95 (t, J=7.1 Hz, 3H).

Step-4: Preparation of ethyl 2-(2-((5-(3-(aminomethyl)phenyl)-2-isopropylbenzofuran-3-yl)methoxy)phenyl)acetate (142d)

Compound 142d was prepared according to the procedure reported in step-2 of scheme 1, from ethyl 2-(2-((5-bromo- 2-isopropylbenzofuran-3-yl)methoxy)phenyl)acetate (142c) (500 mg, 1.159 mmol) in dioxane (20 mL) using 3-(aminomethyl)phenylboronic acid hydrochloride (1d) (435 mg, 2.318 mmol), 4 M solution of $K_3PO_4$ (1.159 mL, 4.64 mmol), tricyclohexylphosphine (98 mg, 0.348 mmol), $Pd_2(dba)_3$ (106 mg, 0.116 mmol), $PdCl_2(dppf)$-$CH_2Cl_2$ adduct (95 mg, 0.116 mmol) and heating at 100° C. for 2 h. This gave after workup and purification by flash column chromatography [silica gel (40 g), eluting with DMA-80 in DCM from 0-70%] ethyl 2-(2-((5-(3-(aminomethyl)phenyl)-2-isopropylbenzofuran-3-yl)methoxy)phenyl)acetate (142d) (167 mg, 32% yield) as a yellow oil; MS (ES+): 458.2 (M+1).

Step-5: Preparation of 2-(2-((5-(3-(aminomethyl)phenyl)-2-isopropylbenzofuran-3-yl)methoxy)phenyl)acetic acid (142e)

Compound 142e was prepared according to the procedure reported in step-3 of scheme 1, from ethyl 2-(2-((5-(3-(aminomethyl)phenyl)-2-isopropylbenzofuran-3-yl)methoxy)phenyl)acetate (142d) (167 mg, 0.365 mmol) in THF (3 mL) using a solution of lithium hydroxide hydrate (146 mg, 3.48 mmol) in water (1 mL) and stirring overnight at RT.

This gave after workup and purification by reverse phase column chromatography [C18 column (30 g), eluting with ACN in water (containing 0.1% HCl) from 0-100%] 2-(2-((5-(3-(aminomethyl)phenyl)-2-isopropylbenzofuran-3-yl)methoxy)phenyl)acetic acid (142e) (44 mg, 9% yield) HCl salt as a white solid; $^1$H NMR (300 MHz, DMSO-$d_6$) δ 12.04 (s, 1H, $D_2O$ exchangeable), 8.54 (s, 3H, $D_2O$ exchangeable), 7.99-7.81 (m, 2H), 7.72 (d, J=7.5 Hz, 1H), 7.67-7.57 (m, 2H), 7.55-7.41 (m, 2H), 7.33-7.23 (m, 2H), 7.19 (d, J=7.4 Hz, 1H), 6.96-6.89 (m, 1H), 5.27 (s, 2H), 4.09 (s, 2H), 3.48 (s, 2H), 3.45-3.39 (m, 1H), 1.30 (d, J=6.8 Hz, 6H); MS (ES+): 430.2 (M+1); (ES−): 428.1 (M−1); Analysis calculated for $C_{27}H_{27}NO_4 \cdot 1.15HCl \cdot H_2O$: C, 66.26; H, 6.21; Cl, 8.33; N, 2.86. Found: C, 66.42; H, 5.59; Cl, 8.27; N, 3.15.

Scheme 143

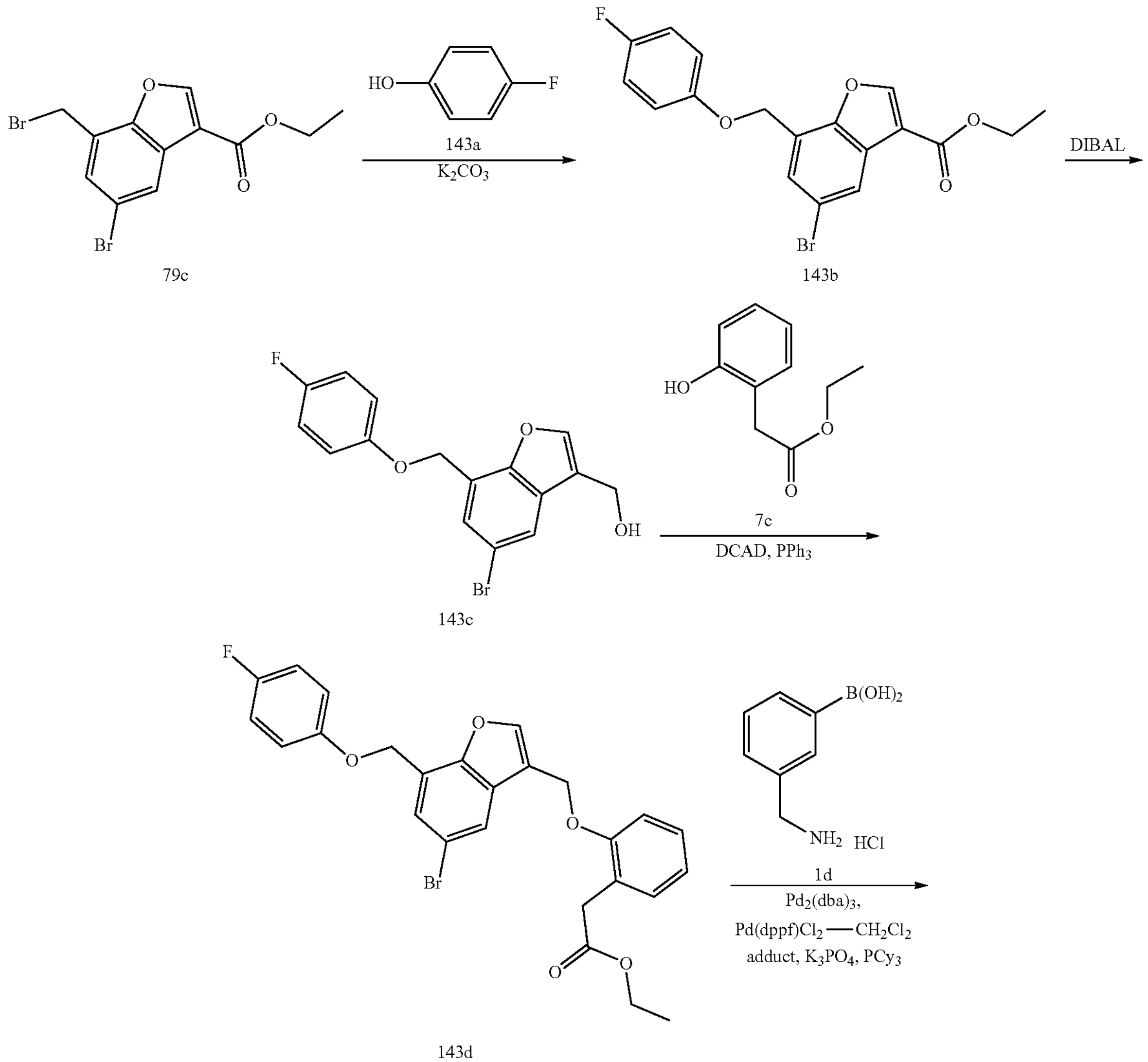

79c

143b

143c

143d

-continued

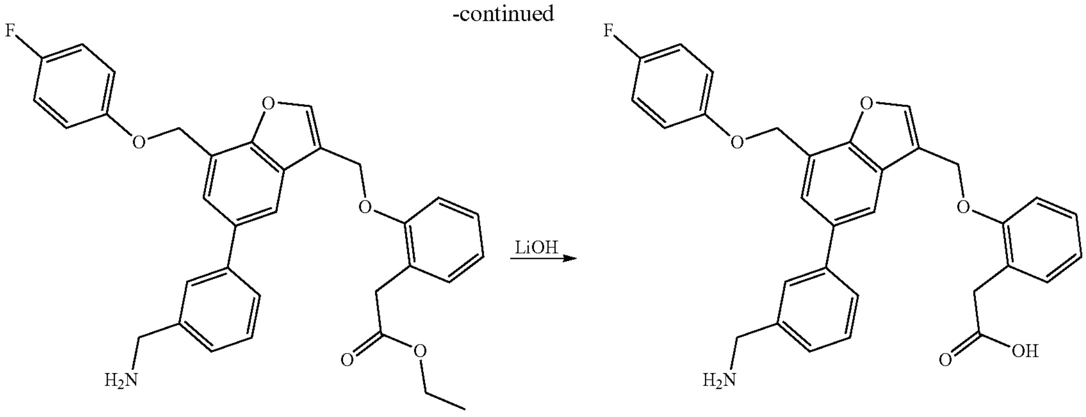

143e

143f

Preparation of 2-(2-((5-(3-(aminomethyl)phenyl)-7-((4-fluorophenoxy)methyl)benzofuran-3-yl)methoxy)phenyl)acetic acid (143f)

Step-1: Preparation of ethyl 5-bromo-7-((4-fluorophenoxy)methyl)benzofuran-3-carboxylate (143b)

Compound 143b was prepared according to the procedure reported in step-1 of scheme 1, from ethyl 5-bromo-7-(bromomethyl)benzofuran-3-carboxylate (79c) (0.5 g, 1.381 mmol) in DMF (10 mL) using 4-fluorophenol (143a) (0.464 g, 4.14 mmol), $K_2CO_3$ (0.573 g, 4.14 mmol) and stirring at RT for 3 h under an Ar atmosphere. This gave after workup and purification by flash column chromatography [silica gel (24 g) eluting with EtOAc in hexane from 0-80%] ethyl 5-bromo-7-((4-fluorophenoxy)methyl)benzofuran-3-carboxylate (143b) (0.36 g, 66% yield) as a yellow solid; $^1H$ NMR (300 MHz, DMSO-$d_6$) δ 8.88 (s, 1H), 8.05 (d, J=2.0 Hz, 1H), 7.72 (d, J=2.0 Hz, 1H), 7.16-7.10 (m, 4H), 5.37 (s, 2H), 4.36 (q, J=7.1 Hz, 2H), 1.35 (t, J=7.2 Hz, 3H); MS (ES+): 393.00 (M+1)

Step-2: Preparation of (5-bromo-7-((4-fluorophenoxy)methyl)benzofuran-3-yl)methanol (143c)

Compound 143c was prepared according to the procedure reported in step-4 of scheme 3, from ethyl 5-bromo-7-((4-fluorophenoxy)methyl)benzofuran-3-carboxylate (143b) (0.35 g, 0.890 mmol) using DIBAL (1.0 M in DCM, 2.225 mL, 2.225 mmol) and stirring at −78° C. for 30 min. This gave after workup and purification by flash column chromatography [silica gel (12 g), eluting with DMA-80 in DCM from 0-100%] (5-bromo-7-((4-fluorophenoxy)methyl)benzofuran-3-yl)methanol (143c) (0.26 mg, 83% yield) as a light yellow oil; $^1H$ NMR (300 MHz, DMSO-$d_6$) δ 7.98 (d, J=4.5 Hz, 1H), 7.89 (d, J=2.0 Hz, 1H), 7.58 (d, J=2.0 Hz, 1H), 7.15-7.08 (m, 4H), 5.33 (s, 2H), 5.29-5.19 (m, 1H), 4.63-4.59 (m, 2H); MS (ES+): 351.00 (M+1).

Step-3: Preparation of ethyl 2-(2-((5-bromo-7-((4-fluorophenoxy)methyl)benzofuran-3-yl)methoxy)phenyl)acetate (143d)

Compound 143d was prepared according to the procedure reported in step-3 of scheme 7, from (5-bromo-7-((4-fluorophenoxy)methyl)benzofuran-3-yl)methanol (143c) (250 mg, 0.712 mmol), triphenylphosphine (373 mg, 1.424 mmol), ethyl 2-(2-hydroxyphenyl)acetate (7c) (141 mg, 0.783 mmol) in DCM (10 mL) using bis(4-chlorobenzyl) diazene-1,2-dicarboxylate (DCAD) (523 mg, 1.424 mmol) in DCM (5 mL) and stirring at RT for 30 min. This gave after workup and purification by flash column chromatography [silica gel (12 g), eluting with EtOAc in hexane from 0-30%] ethyl 2-(2-((5-bromo-7-((4-fluorophenoxy)methyl)benzofuran-3-yl)methoxy)phenyl)acetate (143d) (240 mg, 66% yield) as a light yellow oil; MS (ES+): 535.10 (M+Na).

Step-4, Preparation of ethyl 2-(2-((5-(3-(aminomethyl)phenyl)-7-((4-fluorophenoxy)methyl)benzofuran-3-yl)methoxy)phenyl)acetate (143e)

Compound 143e was prepared according to the procedure reported in step-2 of scheme 1, from ethyl 2-(2-((5-bromo-7-((4-fluorophenoxy)methyl)benzofuran-3-yl)methoxy)phenyl)acetate (143d) (0.24 g, 0.468 mmol) in dioxane (3 mL) and THF (3 mL) using 3-(aminomethyl)phenylboronic acid hydrochloride (1d) (175 mg, 0.935 mmol), 2 M solution of $K_3PO_4$ (0.935 mL, 1.870 mmol), tricyclohexylphosphine (26 mg, 0.094 mmol), $Pd_2(dba)_3$ (43 mg, 0.047 mmol), $Pd(dppf)Cl_2$—$CH_2Cl_2$ adduct (38 mg, 0.047 mmol) and heating at 90° C. for 1.5 h. This gave after workup and purification by flash column chromatography [silica gel (24 g), eluting with DMA-80 in DCM from 0-70%] ethyl 2-(2-((5-(3-(aminomethyl)phenyl)-7-((4-fluorophenoxy)methyl)benzofuran-3-yl)methoxy)phenyl)acetate (143e) (110 mg, 44% yield) as a clear oil; MS (ES+): 540.20 (M+1)

Step-5, Preparation of 2-(2-((5-(3-(aminomethyl)phenyl)-7-((4-fluorophenoxy)methyl)benzofuran-3-yl)methoxy)phenyl)acetic acid (143f)

Compound 143f was prepared according to the procedure reported in step-3 of scheme 1, from ethyl 2-(2-((5-(3-(aminomethyl)phenyl)-7-((4-fluorophenoxy)methyl)benzofuran-3-yl)methoxy)phenyl)acetate (143e) (110 mg, 0.204 mmol) in THF/MeOH (4 mL; 1:1) using a solution of lithium hydroxide hydrate (68.4 mg, 1.631 mmol) in water (1 mL) and stirring at 50° C. for 1.5 h. This gave after workup and purification by reverse phase column chromatography [C18 column (50 g), eluting with ACN in water (containing 0.1% HCl) from 0-100%] 2-(2-((5-(3-(aminomethyl)phenyl)-7-((4-fluorophenoxy)methyl)benzofuran-3-yl)methoxy)phenyl)acetic acid (143f) (40 mg, 38% yield) HCl salt as a white solid; $^1H$ NMR (300 MHz, DMSO-$d_6$)

δ 12.14 (s, 1H, $D_2O$ exchangeable), 8.37 (s, 2H, $D_2O$ exchangeable), 8.18 (s, 1H), 8.02 (d, J=1.8 Hz, 1H), 7.89 (s, 1H), 7.81 (d, J=1.8 Hz, 1H), 7.75 (dt, J=7.6, 1.6 Hz, 1H), 7.50 (dt, J=15.4, 7.6 Hz, 2H), 7.28 (td, J=7.7, 7.1, 1.7 Hz, 1H), 7.24-7.17 (m, 2H), 7.17-7.07 (m, 4H), 6.93 (td, J=7.3, 1.3 Hz, 1H), 5.41 (s, 2H), 5.34 (s, 2H), 4.11 (s, 2H), 3.54 (s, 2H); $^{19}F$ NMR (282 MHz, DMSO-$d_6$) δ −123.45; MS (ES+): 512.20 (M+1); MS (ES−): 510.10 (M−1); Analysis calculated for $C_{31}H_{26}FNO_5 \cdot 1.05HCl \cdot 0.75H_2O$: C, 66.10; H, 5.11; Cl, 6.61; N, 2.49. Found: C, 66.41; H, 5.12; Cl, 6.85; N, 2.57.
Scheme 144
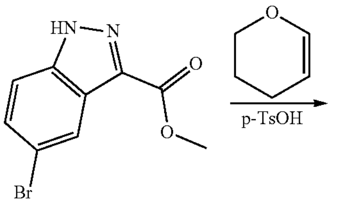
144a
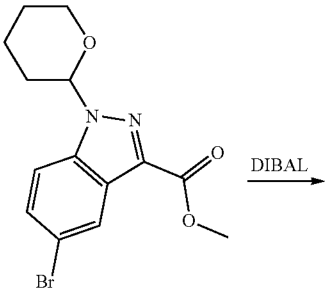
144b
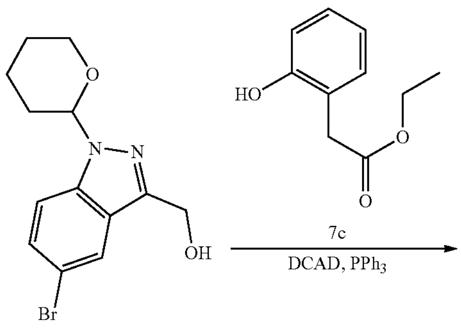
144c
-continued
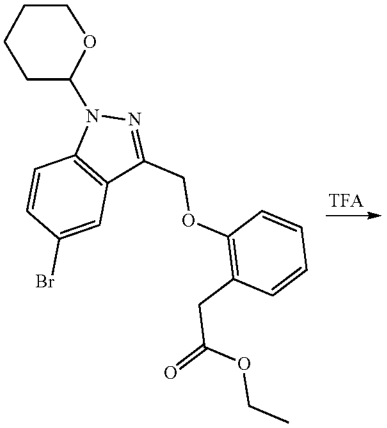
144d
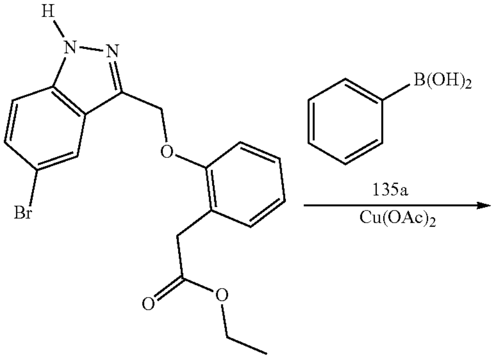
144e
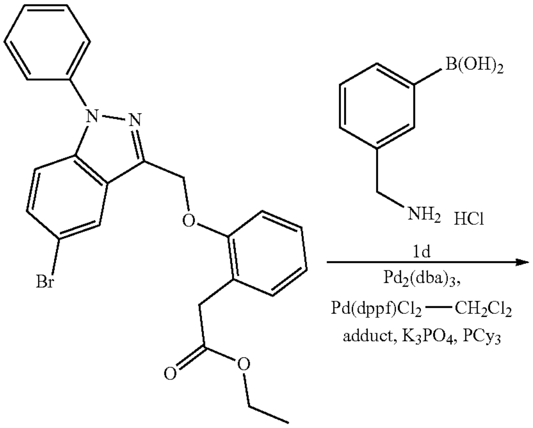
144f -continued

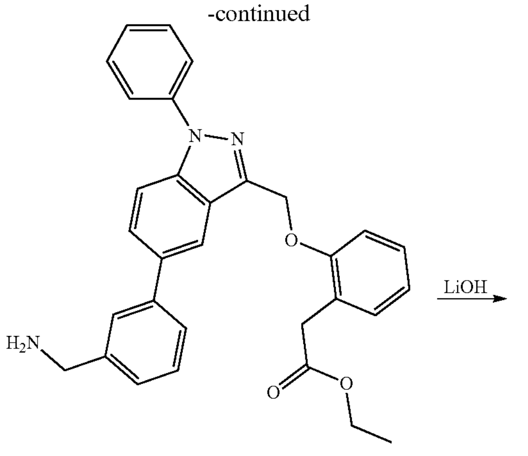

144g

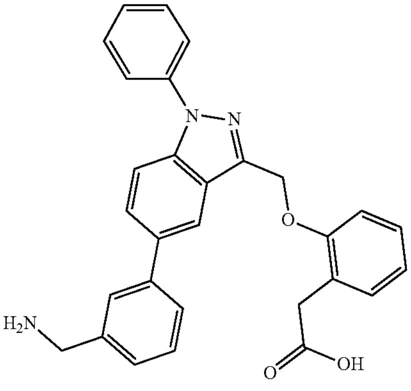

144h

Preparation of 2-(2-((5-(3-(aminomethyl)phenyl)-1-phenyl-1H-indazol-3-yl)methoxy)phenyl)acetic acid (144h)

Step-1: Preparation of methyl 5-bromo-1-(tetrahydro-2H-pyran-2-yl)-1H-indazole-3-carboxylate (144b)

To a solution of methyl 5-bromo-1H-indazole-3-carboxylate (144a) (3 g, 11.76 mmol; CAS #78155-74-5) in DCM (20 mL) and THF (20 mL) was added p-toluenesulphonic acid (p-TsOH) (0.304 g, 1.764 mmol), 3,4-dihydro-2H-pyran (1.610 mL, 17.64 mmol) stirred at RT for 4 h and concentrated in vacuum. The residue obtained was dissolved in methylene chloride (100 mL), washed with a saturated aqueous $Na_2CO_3$, water, brine, dried, filtered and concentrated in vacuum. The resulting oil obtained was purified by flash column chromatography [silica gel (80 g), eluting with EtOAc in hexane from 0-100%] to give methyl 5-bromo-1-(tetrahydro-2H-pyran-2-yl)-1H-indazole-3-carboxylate (144b) (3.6 g, 90% yield) as a white solid; $^1$H NMR (300 MHz, DMSO-$d_6$) δ 8.22 (d, J=1.9 Hz, 1H), 7.89 (d, J=9.0 Hz, 1H), 7.67 (dd, J=9.0, 1.9 Hz, 1H), 6.02 (dd, J=9.5, 2.4 Hz, 1H), 3.94 (s, 3H), 3.88 (dt, J=12.3, 3.7 Hz, 1H), 3.77 (ddd, J=11.4, 7.5, 5.6 Hz, 1H), 2.35 (tdd, J=13.0, 9.6, 4.6 Hz, 1H), 2.02 (dd, J=9.4, 4.2 Hz, 2H), 1.73 (td, J=14.2, 13.7, 7.4 Hz, 1H), 1.60 (h, J=4.0 Hz, 2H); MS (ES+): 361.00 & 363.00 (M+Na).

Step-2: Preparation of (5-bromo-1-(tetrahydro-2H-pyran-2-yl)-1H-indazol-3-yl)methanol (144c)

Compound 144c was prepared according to the procedure reported in step-4 of scheme 3, from methyl 5-bromo-1-(tetrahydro-2H-pyran-2-yl)-1H-indazole-3-carboxylate (144b) (0.6 g, 1.769 mmol) using DIBAL (1.0 M in DCM) (4.42 mL, 4.42 mmol) and stirring at −78° C. for 30 min. This gave after workup and purification using flash column chromatography [silica gel (12 g), eluting with DMA-80 in DCM from 0-100%] (5-bromo-1-(tetrahydro-2H-pyran-2-yl)-1H-indazol-3-yl)methanol (144c) (0.35 g, 64% yield) as a light yellow oil; $^1$H NMR (300 MHz, DMSO-$d_6$) δ 8.07 (d, J=1.8 Hz, 1H), 7.69 (d, J=8.9 Hz, 1H), 7.53 (dd, J=8.9, 1.9 Hz, 1H), 5.80 (dd, J=9.8, 2.4 Hz, 1H), 5.39 (t, J=5.8 Hz, 1H), 4.75 (d, J=5.3 Hz, 2H), 3.92-3.81 (m, 1H), 3.81-3.62 (m, 1H), 2.45-2.25 (m, 1H), 2.12-1.86 (m, 2H), 1.84-1.63 (m, 1H), 1.63-1.45 (m, 2H); MS (ES+): 333.00 (M+Na).

Step-3: Preparation of ethyl 2-(2-((5-bromo-1-(tetrahydro-2H-pyran-2-yl)-1H-indazol-3-yl)methoxy)phenyl)acetate (144d)

Compound 144d was prepared according to the procedure reported in step-3 of scheme 7, from (5-bromo-1-(tetrahydro-2H-pyran-2-yl)-1H-indazol-3-yl)methanol (144c)(2 g, 6.43 mmol), triphenylphosphine (3.37 g, 12.85 mmol), ethyl 2-(2-hydroxyphenyl)acetate (7c) (1.390 g, 7.71 mmol) in DCM (40 mL) using bis(4-chlorobenzyl) diazene-1,2-dicarboxylate (DCAD) (4.72 g, 12.85 mmol) in DCM (20 mL) and stirring at RT for 30 min. This gave after workup and purification using flash column chromatography [silica gel (24 g), eluting with EtOAc in hexane from 0-30%] ethyl 2-(2-((5-bromo-1-(tetrahydro-2H-pyran-2-yl)-1H-indazol-3-yl)methoxy)phenyl)acetate (144d) (2.24 g, 74% yield) as a white oil; MS (ES+): 473.10 (M+1).

Step-4: Preparation of ethyl 2-(2-((5-bromo-1H-indazol-3-yl)methoxy)phenyl)acetate (144e)

Compound 144e was prepared according to the procedure reported in step-9 of scheme 3, from ethyl 2-(2-((5-bromo-1-(tetrahydro-2H-pyran-2-yl)-1H-indazol-3-yl)methoxy)phenyl)acetate (144d) (2 g, 4.23 mmol) in DCM (30 mL) using TFA (3.24 mL, 42.3 mmol) and stirring at RT for 2 h. This gave after workup and purification using flash column chromatography [silica gel (12 g), eluting with DMA-80 in DCM from 0-50%] ethyl 2-(2-((5-bromo-1H-indazol-3-yl)methoxy)phenyl)acetate (144e) (1.44 g, 88% yield) as a yellow oil; $^1$H NMR (300 MHz, DMSO-$d_6$) δ 13.29 (s, 1H), 7.95 (d, J=1.7 Hz, 1H), 7.56-7.51 (m, 1H), 7.48 (dd, J=8.8, 1.7 Hz, 1H), 7.31-7.23 (m, 2H), 7.23-7.16 (m, 1H), 6.92 (td, J=7.1, 1.7 Hz, 1H), 5.38 (s, 2H), 3.91 (q, J=7.1 Hz, 2H), 3.53 (s, 2H), 0.95 (t, J=7.1 Hz, 3H); MS (ES+): 389.05 (M+1).

Step-5: Preparation of ethyl 2-(2-((5-bromo-1-phenyl-1H-indazol-3-yl)methoxy)phenyl)acetate (144f)

To a solution of ethyl 2-(2-((5-bromo-1H-indazol-3-yl)methoxy)phenyl)acetate (144e) (0.46 g, 1.182 mmol) in DCM (10 mL) was added phenylboronic acid (135a) (0.288 g, 2.364 mmol), pyridine (0.191 mL, 2.364 mmol), copper (II) acetate (0.322 g, 1.773 mmol), 4° A molecular sieves (1 g) and was stirred I open air for 24 h at RT. The reaction mixture was filtered through a pad of Celite and the filtrate was concentrated in vacuo. The residue obtained was purified using flash column chromatography [silica gel (24 g), eluting with EtOAc in hexane from 0-50%] to give ethyl 2-(2-((5-bromo-1-phenyl-1H-indazol-3-yl)methoxy)phenyl) acetate (144f) (0.45 g, 82% yield) as a clear oil; MS (ES+): 465.10 & 467.10 (M+1).

Step-6: Preparation of ethyl 2-(2-((5-(3-(aminomethyl)phenyl)-1-phenyl-1H-indazol-3-yl)methoxy) phenyl)acetate (144g)

Compound 144g was prepared according to the procedure reported in step-2 of scheme 1, from ethyl 2-(2-((5-bromo-1-phenyl-1H-indazol-3-yl)methoxy)phenyl)acetate (144f) (0.44 g, 0.946 mmol) in dioxane (4 mL) and THF (4 mL) using 3-(aminomethyl)phenylboronic acid hydrochloride (1d) (354 mg, 1.891 mmol), 2 M solution of $K_3PO_4$ (1.891 mL, 3.78 mmol), tricyclohexylphosphine (53 mg, 0.189 mmol), $Pd_2(dba)_3$ (87 mg, 0.095 mmol), $Pd(dppf)Cl_2$—$CH_2Cl_2$ adduct (77 mg, 0.095 mmol) and heating at 90° C. for 1 h. This gave after workup and purification by flash column chromatography [silica gel (24 g), eluting with DMA-80 in DCM from 0-70%] ethyl 2-(2-((5-(3-(aminomethyl)phenyl)-1-phenyl-1H-indazol-3-yl)methoxy)phenyl) acetate (144g) (0.35 g, 75% yield) as a clear oil; MS (ES+): 492.20 (M+1).

Step-7: Preparation of 2-(2-((5-(3-(aminomethyl) phenyl)-1-phenyl-1H-indazol-3-yl)methoxy)phenyl) acetic acid (144h)

Compound 144h was prepared according to the procedure reported in step-3 of scheme 1, from ethyl 2-(2-((5-(3-(aminomethyl)phenyl)-1-phenyl-1H-indazol-3-yl)methoxy) phenyl)acetate (144g) (0.35 g, 0.712 mmol) in THF/MeOH (4 mL; 1:1) using a solution of lithium hydroxide hydrate (0.120 g, 2.85 mmol) in water (1 mL) and stirring at 50° C. for 1.5 h. This gave after workup and purification using reverse phase column chromatography [C18 column (50 g), eluting with ACN in water (containing 0.1% HCl) from 0-100%] 2-(2-((5-(3-(aminomethyl)phenyl)-1-phenyl-1H-indazol-3-yl)methoxy)phenyl)acetic acid (144h) (150 mg, 46% yield) HCl salt as a white solid; $^1$H NMR (300 MHz, DMSO-$d_6$) δ 12.10 (s, 1H, $D_2O$ exchangeable), 8.48 (s, 2H, $D_2O$ exchangeable), 8.25 (d, J=1.6 Hz, 1H), 7.98 (d, J=8.9 Hz, 1H), 7.95 (s, 1H), 7.92-7.75 (m, 4H), 7.64 (t, J=7.9 Hz, 2H), 7.59-7.40 (m, 3H), 7.36-7.27 (m, 2H), 7.27-7.18 (m, 1H), 6.94 (td, J=7.1, 1.7 Hz, 1H), 5.58 (s, 2H), 4.12 (s, 2H), 3.56 (s, 2H); MS (ES+): 464.20 (M+1); MS (ES−): 462.20 (M−1); Analysis calculated for $C_{29}H_{25}N_3O_3 \cdot 1.2$ HCl. $0.75H_2O$: C, 66.88; H, 5.36; Cl, 8.17; N, 8.07. Found: C, 67.19; H, 5.42; Cl, 7.85; N, 7.98.

Scheme 145

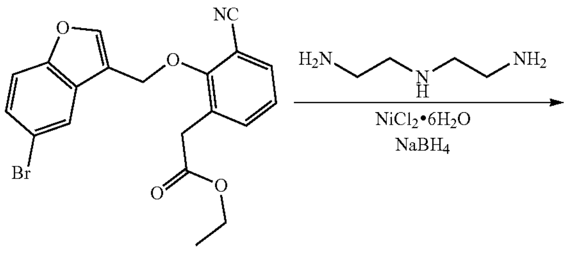

114c

-continued

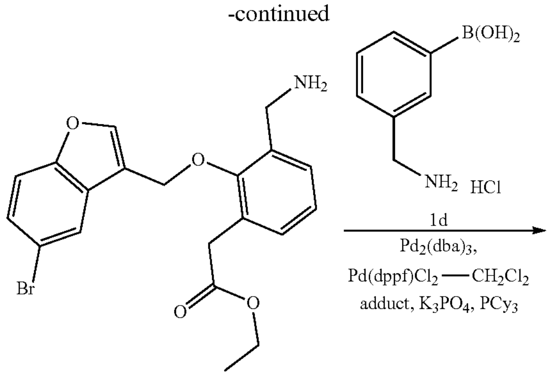

145a

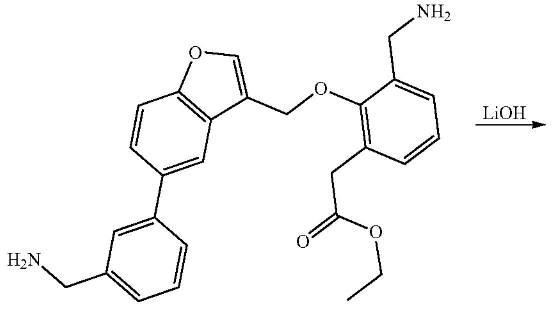

145b

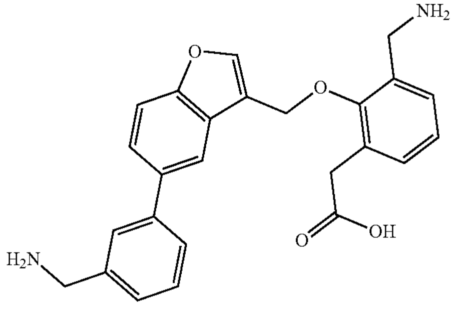

145c

Preparation of 2-(3-(aminomethyl)-2-((5-(3-(aminomethyl)phenyl)benzofuran-3-yl)methoxy)phenyl) acetic acid (145c)

Step-1: Preparation of ethyl 2-(3-(aminomethyl)-2-((5-bromobenzofuran-3-yl)methoxy)phenyl)acetate (145a)

To a stirred solution of ethyl 2-(2-((5-bromobenzofuran-3-yl)methoxy)-3-cyanophenyl)acetate (114c) (0.6 g, 1.448 mmol) in anhydrous methanol (20 mL) at 0° C. was added nickel(II) chloride hexahydrate (0.086 g, 0.362 mmol) followed by sodium borohydride (0.164 g, 4.35 mmol) in small portions over a period of 10 min and stirred at RT for 3 h. The reaction was quenched with N1-(2-aminoethyl)ethane-1,2-diamine (0.313 mL, 2.90 mmol) continued stirring for 1 h and concentrated in vacuum. The residue obtained was taken in ethyl acetate washed with brine and brine layer was extracted with ethyl acetate (2×150 mL). The combined organic layer was dried, filtered and concentrated in vacuum. The residue obtained was purified using flash column chromatography [silica gel (40 g), eluting with MeOH in DCM from 0 to 60%] to furnish ethyl 2-(3-(aminomethyl)-2-((5-bromobenzofuran-3-yl)methoxy)phenyl)acetate (145a) (0.21 g, 35% yield) as a pale yellow wax; MS(+): 418.10 & 420.10 (M+1).

Step-2: Preparation of ethyl 2-(3-(aminomethyl)-2-((5-(3-(aminomethyl)phenyl)benzofuran-3-yl)methoxy)phenyl)acetate (145b)

Compound 145b was prepared according to the procedure reported in step-2 of scheme 1, from ethyl 2-(3-(aminomethyl)-2-((5-bromobenzofuran-3-yl)methoxy)phenyl)acetate (145a) (0.2 g, 0.478 mmol) in dioxane (3 mL) and THF (3 mL) using 3-(aminomethyl)phenylboronic acid hydrochloride (1d) (179 mg, 0.956 mmol), 2 M solution of $K_3PO_4$ (0.956 mL, 1.913 mmol), tricyclohexylphosphine (27 mg, 0.096 mmol), $Pd_2(dba)_3$ (44 mg, 0.048 mmol), Pd(dppf)$Cl_2$—$CH_2Cl_2$ adduct (39 mg, 0.048 mmol) and heating at 90° C. for 1 h. This gave after workup and purification by flash column chromatography [silica gel (12 g), eluting with DMA-80 in DCM from 0-70%] ethyl 2-(3-(aminomethyl)-2-((5-(3-(aminomethyl)phenyl)benzofuran-3-yl)methoxy)phenyl)acetate (145b) (40 mg, 19% yield) as a clear oil; MS (ES+): 445.20 (M+1); 889.40 (2M+1).

Step-3: Preparation of 2-(3-(aminomethyl)-2-((5-(3-(aminomethyl)phenyl)benzofuran-3-yl)methoxy)phenyl)acetic acid (145c)

Compound 145c was prepared according to the procedure reported in step-3 of scheme 1, from ethyl 2-(3-(aminomethyl)-2-((5-(3-(aminomethyl)phenyl)benzofuran-3-yl)methoxy)phenyl)acetate (145b) (40 mg, 0.090 mmol) in THF/MeOH (4 mL; 1:1) using a solution of lithium hydroxide hydrate (15 mg, 0.36 mmol) in water (1 mL) and stirring at 50° C. for 1.5 h. This gave after workup and purification by reverse phase column chromatography [C18 column (50 g), eluting with ACN in water (containing 0.1% HCl) from 0-100%] 2-(3-(aminomethyl)-2-((5-(3-(aminomethyl)phenyl)benzofuran-3-yl)methoxy)phenyl)acetic acid (145c) (15 mg, 40% yield) HCl salt as a white solid; $^1H$ NMR (300 MHz, DMSO-$d_6$) δ 12.45 (s, 1H, $D_2O$ exchangeable), 8.35 (s, 5H, $D_2O$ exchangeable), 8.20 (s, 1H), 8.01 (s, 1H), 7.89 (s, 1H), 7.80-7.67 (m, 3H), 7.53 (t, J=7.6 Hz, 1H), 7.47 (d, J=7.0 Hz, 2H), 7.39 (d, J=7.7 Hz, 1H), 7.24 (t, J=7.5 Hz, 1H), 5.12 (s, 2H), 4.13 (s, 2H), 4.09 (s, 2H), 3.74 (s, 2H); MS (ES+): 417.20 (M+1); 833.30 (2M+1).

Scheme 146

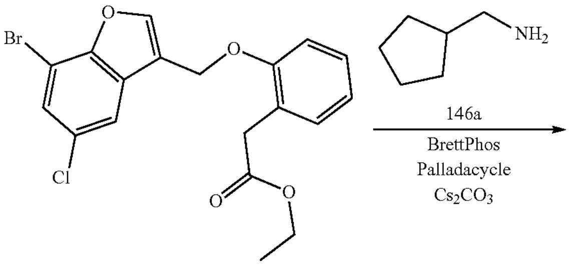

72e

-continued

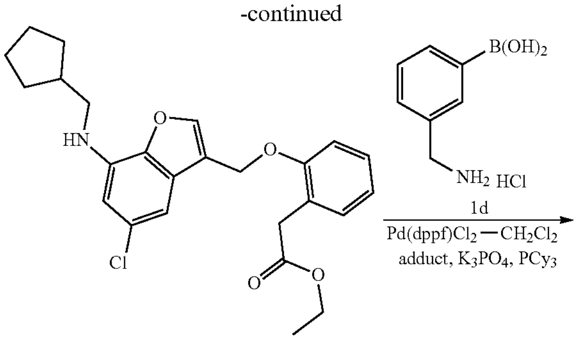

146b

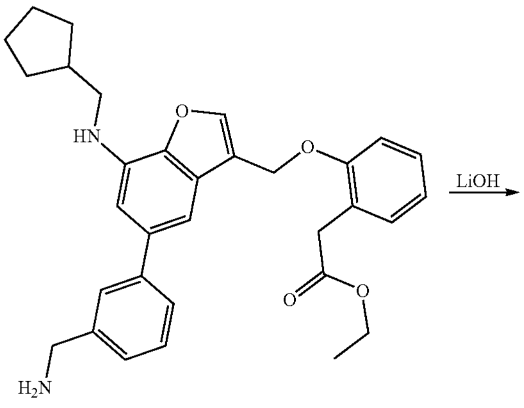

146c

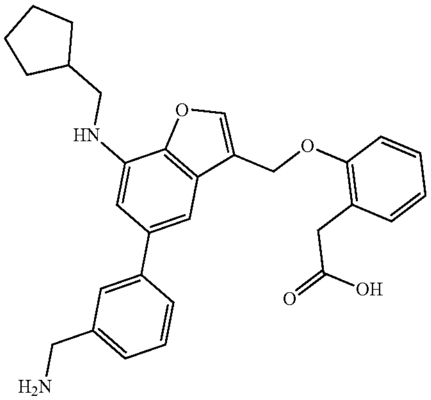

146d

Preparation of 2-(2-((5-(3-(aminomethyl)phenyl)-7-((cyclopentylmethyl)amino)benzofuran-3-yl)methoxy)phenyl)acetic acid (146d)

Step-1: Preparation of ethyl 2-(2-((5-chloro-7-((cyclopentylmethyl)amino)benzofuran-3-yl)methoxy)phenyl)acetate (146b)

To a solution of BrettPhos Palladacycle (0.094 g, 0.118 mmol), cesium carbonate (2.307 g, 7.08 mmol), and cyclopentylmethanamine (146a) (0.351 g, 3.54 mmol) in MeCN (3 mL) was added ethyl 2-(2-((7-bromo-5-chlorobenzofuran-3-yl)methoxy)phenyl)acetate (72e) (1 g, 2.360 mmol). The reaction mixture was degassed and filled with Ar and irradiated at 90° C. for 4 h in microwave. Ethyl acetate (20 mL) was added to the solution, filtered through a pad of Celite and the filtrate was concentrated in vacuo. The residue obtained was purified using flash column chromatography [silica gel (12 g), eluting with EtOAc in hexanes from 0-50%] to give ethyl 2-(2-((5-chloro-7-((cyclopentylmethyl)amino)benzofuran-3-yl)methoxy)phenyl)acetate (146b) (297 mg, 29% yield); $^1$H NMR (300 MHz, DMSO-$d_6$) δ 8.05 (s, 1H), 7.28 (ddd, J=8.2, 7.3, 1.8 Hz, 1H), 7.19 (ddd, J=10.7, 7.8, 1.4 Hz, 2H), 6.92 (td, J=7.4, 1.2 Hz, 1H), 6.81 (d, J=2.0 Hz, 1H), 6.48 (d, J=2.0 Hz, 1H), 6.12 (t, J=5.8 Hz, 1H), 5.17 (s, 2H), 3.96 (q, J=7.1 Hz, 2H), 3.56 (s, 2H), 3.18-3.08 (m, 2H), 2.32-2.15 (m, 1H), 1.82-1.67 (m, 2H), 1.65-1.56 (m, 2H), 1.56-1.45 (m, 2H), 1.35-1.21 (m, 2H), 1.03 (t, J=7.1 Hz, 3H); MS (ES+): 442.20 (M+1).

Step-2: Preparation of ethyl 2-(2-((5-(3-(aminomethyl)phenyl)-7-((cyclopentylmethyl)amino)benzofuran-3-yl)methoxy)phenyl)acetate (146c)

Compound 146c was prepared according to the procedure reported in step-2 of scheme 1, from ethyl 2-(2-((5-chloro-7-((cyclopentylmethyl)amino)benzofuran-3-yl)methoxy)phenyl)acetate (146b) (0.297 g, 0.669 mmol) in dioxane (8 mL) and 2-Me-THF (4 mL) using 3-(aminomethyl)phenylboronic acid hydrochloride (1d) (313 mg, 1.673 mmol), 4 M solution of $K_3PO_4$ (0.669 mL, 2.68 mmol), tricyclohexylphosphine (150 mg, 0.535 mmol), $PdCl_2$(dppf)-$CH_2Cl_2$ adduct(219 mg, 0.268 mmol) and heating at 115° C. for 3 h. This gave after workup ethyl 2-(2-((5-(3-(aminomethyl)phenyl)-7-((cyclopentylmethyl)amino)benzofuran-3-yl)methoxy)phenyl)acetate (146c) as a clear oil which was taken to next step without purification; MS (ES+): 513.30 (M+1).

Step-3: Preparation of 2-(2-((5-(3-(aminomethyl)phenyl)-7-((cyclopentylmethyl)amino)benzofuran-3-yl)methoxy)phenyl)acetic acid (146d)

Compound 146d was prepared according to the procedure reported in step-3 of scheme 1, from ethyl 2-(2-((5-(3-(aminomethyl)phenyl)-7-((cyclopentylmethyl)amino)benzofuran-3-yl)methoxy)phenyl)acetate (146c) (0.669 mmol, from above step-2) in THF (2 mL), methanol (0.2 mL) and water (0.2 mL), using lithium hydroxide monohydrate (64.5 mg, 2.69 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-((cyclopentylmethyl)amino)benzofuran-3-yl)methoxy)phenyl)acetic acid (146d) (65 mg, 20% yield) HCl salt as a light brown solid; $^1$H NMR (300 MHz, DMSO-$d_6$) δ 8.28 (s, 3H, $D_2O$ exchangeable), 8.03 (s, 1H), 7.78 (s, 1H), 7.68 (d, J=7.8 Hz, 1H), 7.50 (t, J=7.6 Hz, 1H), 7.45-7.41 (m, 1H), 7.31-7.24 (m, 1H), 7.24-7.17 (m, 2H), 7.17-7.13 (m, 1H), 6.93 (t, J=7.3 Hz, 1H), 6.80-6.73 (m, 1H), 5.26 (s, 2H), 4.12 (d, J=5.8 Hz, 2H), 3.54 (s, 2H), 3.20 (d, J=7.2 Hz, 2H), 2.39-2.20 (m, 1H), 1.88-1.71 (m, 2H), 1.70-1.45 (m, 4H), 1.41-1.21 (m, 2H); MS (ES+): 485.3 (M+1); Analysis calculated for $C_{30}H_{32}N_2O_4 \cdot 1.5HCl \cdot H_2O$: C, 64.66; H, 6.42; Cl, 9.54; N, 5.03. Found: C, 64.92; H, 6.50; Cl, 9.51; N, 4.89.

Scheme 147

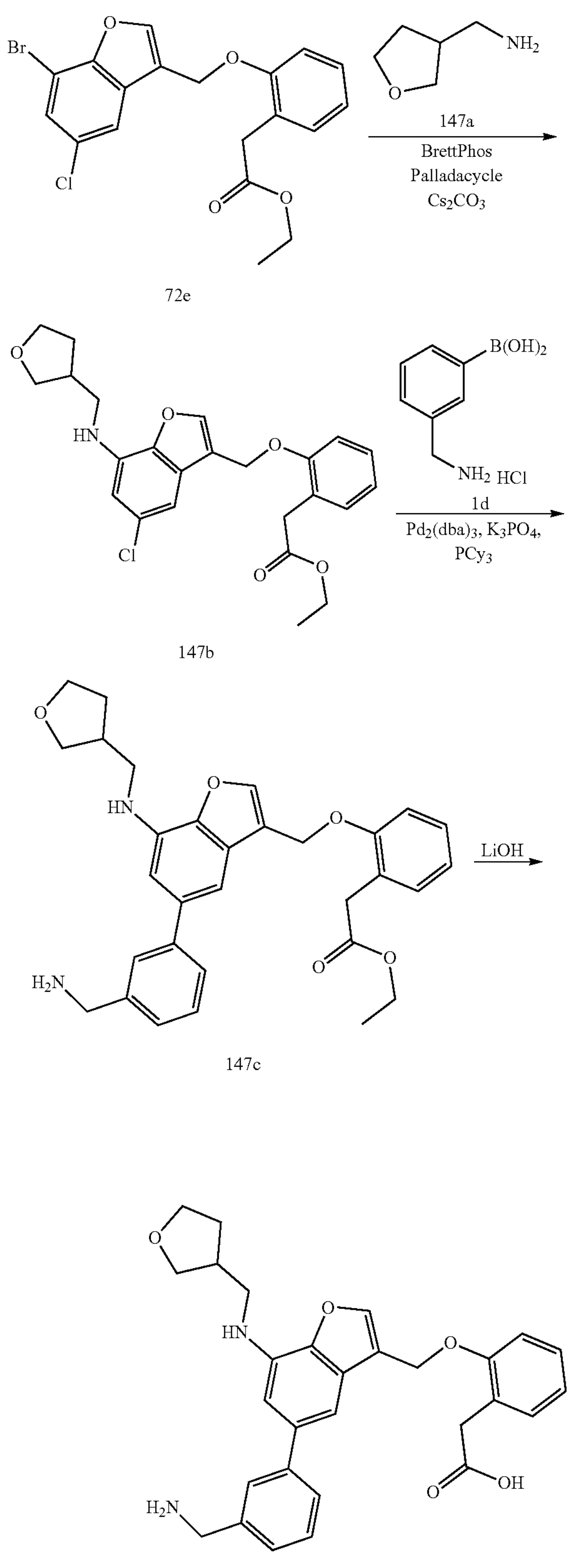

72e

147b

147c

147d

Preparation of 2-(2-((5-(3-(aminomethyl)phenyl)-7-(((tetrahydrofuran-3-yl)methyl)amino)benzofuran-3-yl)methoxy)phenyl)acetic acid (147d)

Step-1: Preparation of ethyl 2-(2-((5-chloro-7-(((tetrahydrofuran-3-yl)methyl)amino)benzofuran-3-yl)methoxy)phenyl)acetate (147b)

Compound 147b was prepared according to the procedure reported in step-1 of scheme 146, from ethyl 2-(2-((7-bromo-5-chlorobenzofuran-3-yl)methoxy)phenyl)acetate (72e) (1 g, 2.36 mmol) in MeCN (3 mL) using (tetrahydrofuran-3-yl)methanamine (147a) (0.358 g, 3.54 mmol), BrettPhos Palladacycle (0.094 g, 0.118 mmol), cesium carbonate (2.307 g, 7.08 mmol) and irradiating at 90° C. for 2 h in microwave. This gave after work up and purification using flash column chromatography [silica gel (12 g), eluting with EtOAc in hexanes from 0-50%] ethyl 2-(2-((5-chloro-7-(((tetrahydrofuran-3-yl)methyl)amino)benzofuran-3-yl)methoxy)phenyl)acetate (147b) (364 mg, 35% yield); MS (ES+): 444.20 (M+1).

Step-2: Preparation of ethyl 2-(2-((5-(3-(aminomethyl)phenyl)-7-(((tetrahydrofuran-3-yl)methyl)amino)benzofuran-3-yl)methoxy)phenyl)acetate (147c)

Compound 147c was prepared according to the procedure reported in step-2 of scheme 1, from ethyl 2-(2-((5-chloro-7-(((tetrahydrofuran-3-yl)methyl)amino)benzofuran-3-yl)methoxy)phenyl)acetate (147b) (0.364 g, 0.82 mmol) in dioxane (8 mL) and 2-Me-THF (4 mL) using 3-(aminomethyl)phenylboronic acid hydrochloride (1d) (384 mg, 2.050 mmol), 4 M solution of $K_3PO_4$ (0.820 mL, 3.28 mmol), tricyclohexylphosphine (184 mg, 0.656 mmol), $Pd_2(dba)_3$ (300 mg, 0.328 mmol) and heating at 115° C. for 16 h. This gave after workup ethyl 2-(2-((5-(3-(aminomethyl)phenyl)-7-(((tetrahydrofuran-3-yl)methyl)amino)benzofuran-3-yl)methoxy)phenyl)acetate (147c) which was used as such for the next step without purification; MS (ES+): 515.20 (M+1).

Step-3: Preparation of 2-(2-((5-(3-(aminomethyl)phenyl)-7-(((tetrahydrofuran-3-yl)methyl)amino)benzofuran-3-yl)methoxy)phenyl)acetic acid (147d)

Compound 147d was prepared according to the procedure reported in step-3 of scheme 1, from ethyl 2-(2-((5-(3-(aminomethyl)phenyl)-7-(((tetrahydrofuran-3-yl)methyl)amino)benzofuran-3-yl)methoxy)phenyl)acetate (147c) (0.82 mmol, from step-2 above) in THF (2 mL), methanol (0.2 mL) and water (0.2 mL), using lithium hydroxide monohydrate (79 mg, 3.28 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(((tetrahydrofuran-3-yl)methyl)amino)benzofuran-3-yl)methoxy)phenyl)acetic acid (147d) (51 mg, 13% yield) HCl salt as a white solid; $^1H$ NMR (300 MHz, DMSO-$d_6$) δ 8.42 (s, 4H, $D_2O$ exchangeable), 8.04 (s, 1H), 7.83 (s, 1H), 7.69 (d, J=7.5 Hz, 1H), 7.53-7.39 (m, 2H), 7.31-7.19 (m, 1H), 7.22-7.18 (m, 3H), 6.93 (t, J=7.3 Hz, 1H), 6.83 (s, 1H), 5.27 (s, 2H), 4.14-4.06 (m, 2H), 3.84-3.72 (m, 2H), 3.64 (q, J=7.6 Hz, 1H), 3.60-3.50 (m, 3H), 3.27 (d, J=7.4 Hz, 2H), 2.75-2.57 (m, 1H), 2.11-1.93 (m, 1H), 1.75-1.60 (m, 1H); MS (ES+): 487.3 (M+1); Analysis calculated for $C_{29}H_{30}N_2O_5$ 1.75HCl 1.25$H_2O$: C, 60.80; H, 6.03; Cl, 10.83; N, 4.89. Found: C, 60.70; H, 6.06; Cl, 10.66; N, 4.83.

Scheme 148

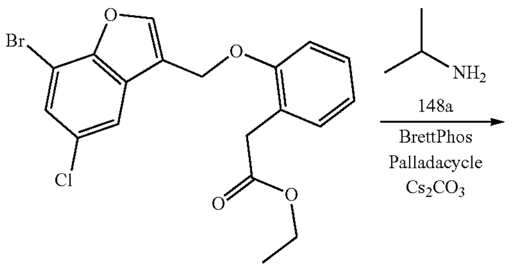

72e

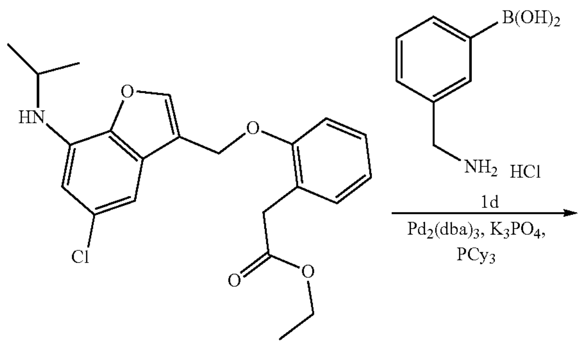

148b

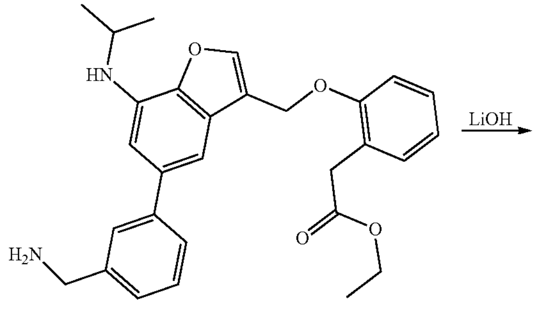

148c

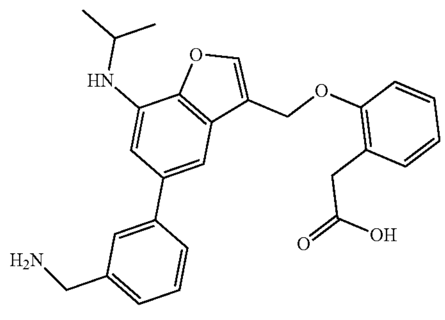

148d

Preparation of 2-(2-((5-(3-(aminomethyl)phenyl)-7-(isopropylamino)benzofuran-3-yl)methoxy)phenyl) acetic acid (148d)

Step-1: Preparation of ethyl 2-(2-((5-chloro-7-(isopropylamino)benzofuran-3-yl)methoxy)phenyl)acetate (148b)

Compound 148b was prepared according to the procedure reported in step-1 of scheme 146, from ethyl 2-(2-((7-bromo-5-chlorobenzofuran-3-yl)methoxy)phenyl)acetate (72e) (1 g, 2.36 mmol) in MeCN (3 mL) using propan-2-amine (148a) (0.209 g, 3.54 mmol), BrettPhos Palladacycle (0.094 g, 0.118 mmol), cesium carbonate (2.307 g, 7.08 mmol) and irradiating at 90° C. for 4 h in microwave. This gave after work up and purification using flash column chromatography [silica gel (12 g), eluting with EtOAc in hexanes from 0-50%] ethyl 2-(2-((5-chloro-7-(isopropylamino)benzofuran-3-yl)methoxy)phenyl)acetate (148b) (211 mg, 22% yield); $^1$H NMR (300 MHz, DMSO-$d_6$) δ 8.04 (s, 1H), 7.36-7.23 (m, 1H), 7.23-7.11 (m, 2H), 6.92 (td, J=7.4, 1.1 Hz, 1H), 6.82 (d, J=1.9 Hz, 1H), 6.51 (d, J=2.0 Hz, 1H), 5.77 (d, J=8.7 Hz, 1H), 5.17 (s, 2H), 3.96 (q, J=7.1 Hz, 2H), 3.86-3.74 (m, 1H), 3.56 (s, 2H), 1.19 (d, J=6.4 Hz, 6H), 1.02 (t, J=7.1 Hz, 3H); MS (ES+): 402.10 (M+1).

Step-2: Preparation of ethyl 2-(2-((5-(3-(aminomethyl)phenyl)-7-(isopropylamino)benzofuran-3-yl) methoxy)phenyl)acetate (148c)

Compound 148c was prepared according to the procedure reported in step-2 of scheme 1, from ethyl 2-(2-((5-chloro-7-(isopropylamino)benzofuran-3-yl)methoxy)phenyl)acetate (148b) (0.211 g, 0.525 mmol) in dioxane (8 mL) and 2-Me-THF (4 mL) using 3-(aminomethyl)phenylboronic acid hydrochloride (1d) (246 mg, 1.313 mmol), 4 M solution of $K_3PO_4$ (0.525 mL, 2.10 mmol), tricyclohexylphosphine (118 mg, 0.420 mmol), $Pd_2(dba)_3$ (192 mg, 0.210 mmol) and heating at 115° C. for 16 h. This gave after workup ethyl 2-(2-((5-(3-(aminomethyl)phenyl)-7-(isopropylamino)benzofuran-3-yl)methoxy)phenyl)acetate (148c) which was used as such for next step without further purification; MS (ES+): 473.20 (M+1).

Step-3: Preparation of 2-(2-((5-(3-(aminomethyl) phenyl)-7-(isopropylamino)benzofuran-3-yl) methoxy)phenyl)acetic acid (148d)

Compound 148d was prepared according to the procedure reported in step-3 of scheme 1, from ethyl 2-(2-((5-(3-(aminomethyl)phenyl)-7-(isopropylamino)benzofuran-3-yl) methoxy)phenyl)acetate (148c) (0.525 mmol, from step-2 above) in THF (2 mL), methanol (0.2 mL) and water (0.2 mL), using lithium hydroxide monohydrate (50.3 mg, 2.099 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl) phenyl)-7-(isopropylamino)benzofuran-3-yl)methoxy) phenyl)acetic acid (148d) (24 mg, 10% yield) HCl salt as a light brown solid; $^1$H NMR (300 MHz, DMSO-$d_6$) δ 8.27 (s, 3H, $D_2O$ exchangeable), 8.04 (s, 1H), 7.79 (s, 2H), 7.69 (d, J=7.6 Hz, 1H), 7.49 (t, J=7.5 Hz, 1H), 7.42 (d, J=7.8 Hz, 1H), 7.32-7.25 (m, 1H), 7.25-7.17 (m, 3H), 6.93 (t, J=7.3 Hz, 1H), 6.84 (s, 1H), 5.26 (s, 2H), 4.16-4.07 (m, 2H), 3.97-3.89 (m, 1H), 3.55 (s, 2H), 1.25 (d, J=6.3 Hz, 6H); MS (ES+): 445.2 (M+1); Analysis calculated for $C_{27}H_{28}N_2O_4 \cdot 1.85HCl \cdot 1.5H_2O$: C, 60.17; H, 6.14; Cl, 12.17; N, 5.20. Found: C, 59.86; H, 5.88; Cl, 12.50; N, 5.02.

Scheme 149

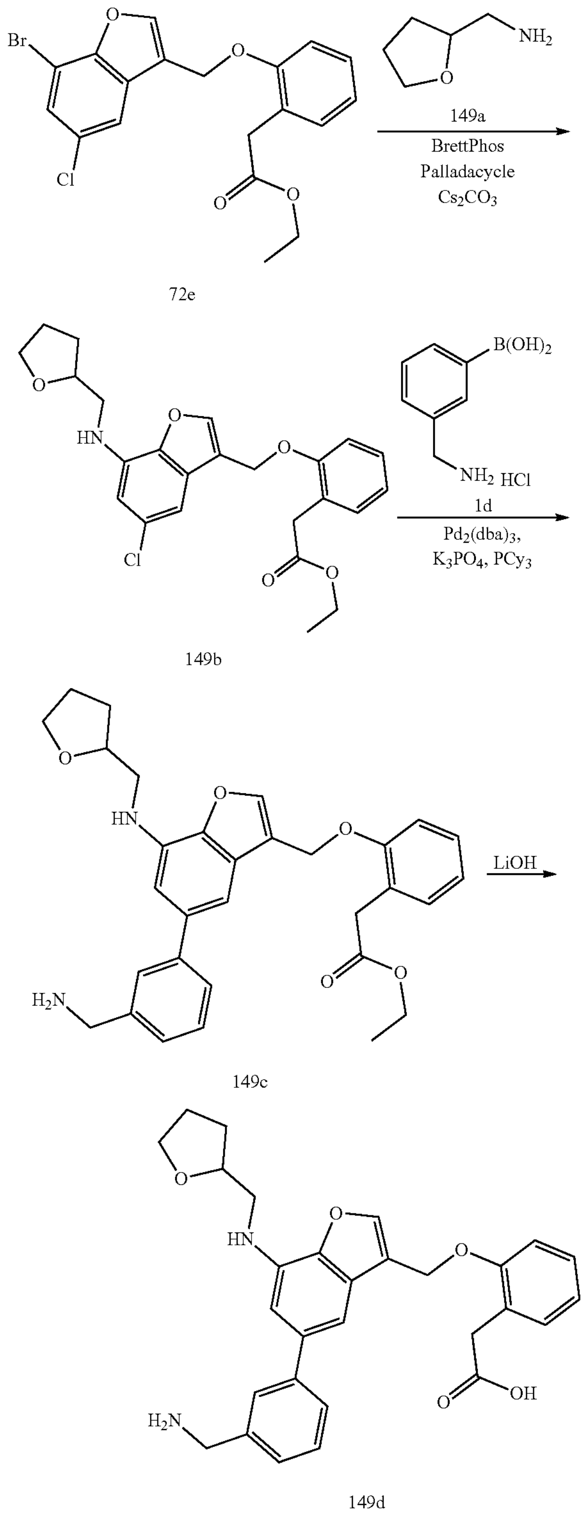

Preparation of 2-(2-((5-(3-(aminomethyl)phenyl)-7-(((tetrahydrofuran-2-yl)methyl)amino)benzofuran-3-yl)methoxy)phenyl)acetic acid (149d)

Step-1: Preparation of ethyl 2-(2-((5-chloro-7-(((tetrahydrofuran-2-yl)methyl)amino)benzofuran-3-yl)methoxy)phenyl)acetate (149b)

Compound 149b was prepared according to the procedure reported in step-1 of scheme 146, from ethyl 2-(2-((7-bromo-5-chlorobenzofuran-3-yl)methoxy)phenyl)acetate (72e) (2 g, 4.72 mmol) in MeCN (3 mL) using (tetrahydrofuran-2-yl)methanamine (149a) (0.955 g, 9.44 mmol), BrettPhos Palladacycle (0.188 g, 0.236 mmol), cesium carbonate (4.61 g, 14.16 mmol) and irradiating at 90° C. for 2 h in microwave. This gave after work up and purification using flash column chromatography [silica gel (12 g), eluting with EtOAc in hexanes from 0-50%] ethyl 2-(2-((5-chloro-7-(((tetrahydrofuran-2-yl)methyl)amino)benzofuran-3-yl)methoxy)phenyl)acetate (149b) (576 mg, 28% yield); $^1$H NMR (300 MHz, DMSO-$d_6$) δ 8.05 (s, 1H), 7.34-7.25 (m, 1H), 7.25-7.16 (m, 2H), 6.92 (td, J=7.4, 1.1 Hz, 1H), 6.84 (d, J=1.9 Hz, 1H), 6.59 (d, J=2.0 Hz, 1H), 5.98 (t, J=6.0 Hz, 1H), 5.17 (s, 2H), 4.09-4.00 (m, 1H), 3.95 (q, J=7.1 Hz, 2H), 3.86-3.70 (m, 1H), 3.70-3.58 (m, 1H), 3.56 (s, 2H), 3.32-3.17 (m, 2H), 1.98-1.75 (m, 2H), 1.72-1.57 (m, 2H), 1.03 (t, J=7.1 Hz, 3H); MS (ES+): 444.20 (M+1).

Step-2: Preparation of ethyl 2-(2-((5-(3-(aminomethyl)phenyl)-7-(((tetrahydrofuran-2-yl)methyl)amino)benzofuran-3-yl)methoxy)phenyl)acetate (149c)

Compound 149c was prepared according to the procedure reported in step-2 of scheme 1, from ethyl 2-(2-((5-chloro-7-(((tetrahydrofuran-2-yl)methyl)amino)benzofuran-3-yl)methoxy)phenyl)acetate (149b) (0.576 g, 1.298 mmol) in dioxane (8 mL) and 2-Me-THF (4 mL) using 3-(aminomethyl)phenylboronic acid hydrochloride (1d) (608 mg, 3.24 mmol), 4 M solution of $K_3PO_4$ (1.298 mL, 5.19 mmol), tricyclohexylphosphine (291 mg, 1.038 mmol), $Pd_2(dba)_3$ (475 mg, 0.519 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-(((tetrahydrofuran-2-yl)methyl)amino)benzofuran-3-yl)methoxy)phenyl)acetate (149c) (165 mg, 25% yield); MS (ES+): 515.30 (M+1).

Step-3: Preparation of 2-(2-((5-(3-(aminomethyl)phenyl)-7-(((tetrahydrofuran-2-yl)methyl)amino)benzofuran-3-yl)methoxy)phenyl)acetic acid (149d)

Compound 149d was prepared according to the procedure reported in step-3 of scheme 1, from ethyl 2-(2-((5-(3-(aminomethyl)phenyl)-7-(((tetrahydrofuran-2-yl)methyl)amino)benzofuran-3-yl)methoxy)phenyl)acetate (149c) (165 mg, 0.321 mmol) in THE (2 mL), methanol (0.2 mL) and water (0.2 mL), using lithium hydroxide monohydrate (30.7 mg, 1.283 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(((tetrahydrofuran-2-yl)methyl)amino)benzofuran-3-yl)methoxy)phenyl)acetic acid (149d) (14 mg, 9% yield) HCl salt as a white solid; $^1$H NMR (300 MHz, DMSO-$d_6$) δ 8.28 (s, 4H, $D_2O$ exchangeable), 8.04 (s, 1H), 7.79 (s, 1H), 7.69 (d, J=7.5 Hz, 1H), 7.50 (t, J=7.7 Hz, 1H), 7.42 (d, J=7.5 Hz, 1H), 7.31-7.23 (m, 1H), 7.23-7.16 (m, 3H), 6.93 (t, J=7.2 Hz, 1H), 6.89-6.85 (m, 1H), 5.26 (s, 2H), 4.17-4.06 (m, 3H), 3.86-3.74 (m, 1H), 3.72-3.61 (m, 1H), 3.54 (s, 2H), 3.38-3.31 (m, 2H), 2.05-1.91 (m, 1H), 1.94-1.77 (m, 2H), 1.76-1.61 (m, 1H); MS (ES+): 487.2 (M+1).

Scheme 150

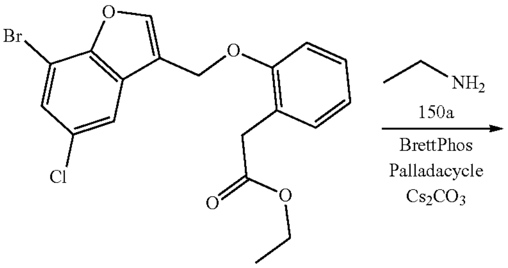

72e

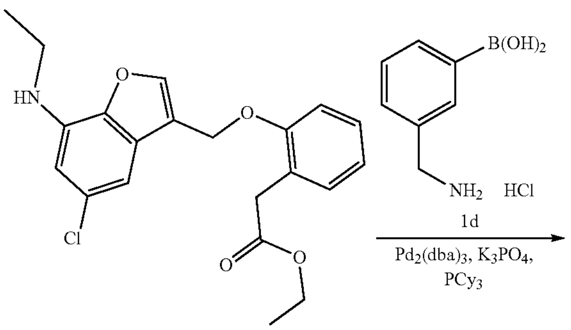

150b

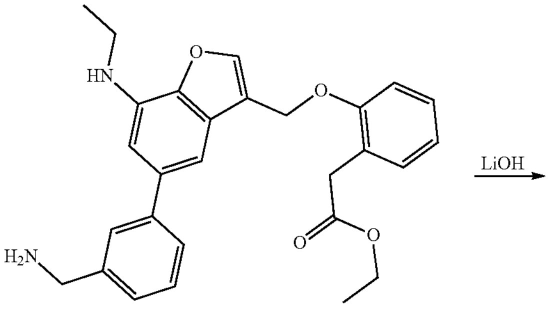

150c

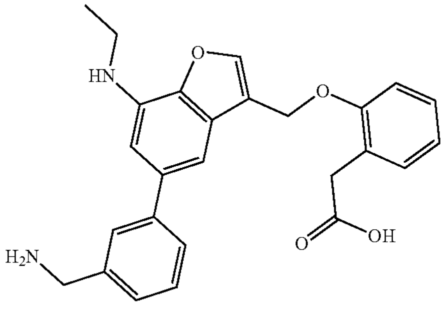

150d

Preparation of 2-(2-((5-(3-(aminomethyl)phenyl)-7-(ethylamino)benzofuran-3-yl)methoxy)phenyl)acetic acid (150d)

Step-1: Preparation of ethyl 2-(2-((5-chloro-7-(ethylamino)benzofuran-3-yl)methoxy)phenyl)acetate (150b)

Compound 150b was prepared according to the procedure reported in step-1 of scheme 146, from ethyl 2-(2-((7-bromo-5-chlorobenzofuran-3-yl)methoxy)phenyl)acetate (72e) (2 g, 4.72 mmol) in MeCN (3 mL) using ethylamine (150a) (3.54 mL, 7.08 mmol), BrettPhos Palladacycle (0.188 g, 0.236 mmol), cesium carbonate (4.61 g, 14.16 mmol) and irradiating at 60° C. for 1 h in microwave. This gave after work up and purification using flash column chromatography [silica gel (12 g), eluting with EtOAc in hexanes from 0-50%] ethyl 2-(2-((5-chloro-7-(ethylamino)benzofuran-3-yl)methoxy)phenyl)acetate (150b) (417 mg, 23% yield); $^1$H NMR (300 MHz, DMSO-$d_6$) δ 8.05 (s, 1H), 7.36-7.23 (m, 1H), 7.23-7.14 (m, 2H), 6.92 (td, J=7.3, 1.1 Hz, 1H), 6.83 (d, J=1.9 Hz, 1H), 6.48 (d, J=2.0 Hz, 1H), 6.07 (t, J=5.7 Hz, 1H), 5.17 (s, 2H), 3.97 (q, J=7.1 Hz, 2H), 3.56 (s, 2H), 3.29-3.15 (m, 2H), 1.19 (t, J=7.1 Hz, 3H), 1.03 (t, J=7.1 Hz, 3H); MS (ES+): 388.10 (M+1).

Step-2: Preparation of ethyl 2-(2-((5-(3-(aminomethyl)phenyl)-7-(ethylamino)benzofuran-3-yl)methoxy)phenyl)acetate (150c)

Compound 150c was prepared according to the procedure reported in step-2 of scheme 1, from ethyl 2-(2-((5-chloro-7-(ethylamino)benzofuran-3-yl)methoxy)phenyl)acetate (150b) (0.417 g, 1.075 mmol) in dioxane (8 mL) and 2-Me-THF (4 mL) using 3-(aminomethyl)phenylboronic acid hydrochloride (1d) (504 mg, 2.69 mmol), 4 M solution of $K_3PO_4$ (1.075 mL, 4.30 mmol), tricyclohexylphosphine (241 mg, 0.860 mmol), $Pd_2(dba)_3$ (394 mg, 0.43 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-(ethylamino)benzofuran-3-yl)methoxy)phenyl)acetate (150c) (137 mg, 28% yield); MS (ES+): 459.20 (M+1).

Step-3: Preparation of 2-(2-((5-(3-(aminomethyl)phenyl)-7-(ethylamino)benzofuran-3-yl)methoxy)phenyl)acetic acid (150d)

Compound 150d was prepared according to the procedure reported in step-3 of scheme 1, from ethyl 2-(2-((5-(3-(aminomethyl)phenyl)-7-(ethylamino)benzofuran-3-yl)methoxy)phenyl)acetate (150c) (137 mg, 0.299 mmol) in THF (2 mL), methanol (0.2 mL) and water (0.2 mL), using lithium hydroxide monohydrate (28.6 mg, 1.195 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(ethylamino)benzofuran-3-yl)methoxy)phenyl)acetic acid (150d) (8 mg, 6% yield) HCl salt as a light brown solid; $^1$H NMR (300 MHz, DMSO-$d_6$) δ 8.32 (s, 4H, $D_2O$ exchangeable), 8.04 (s, 1H), 7.81 (s, 1H), 7.69 (d, J=7.6 Hz, 1H), 7.50 (t, J=7.6 Hz, 1H), 7.42 (d, J=7.6 Hz, 1H), 7.31-7.24 (m, 1H), 7.25-7.14 (m, 3H), 6.93 (t, J=7.2 Hz, 1H), 6.82 (s, 1H), 5.27 (s, 2H), 4.17-4.08 (m, 2H), 3.55 (s, 2H), 3.33 (q, J=7.1 Hz, 2H), 1.26 (t, J=7.1 Hz, 3H); MS (ES+): 431.2 (M+1).

Scheme 151

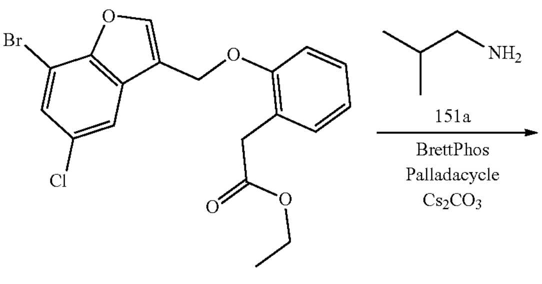

72e

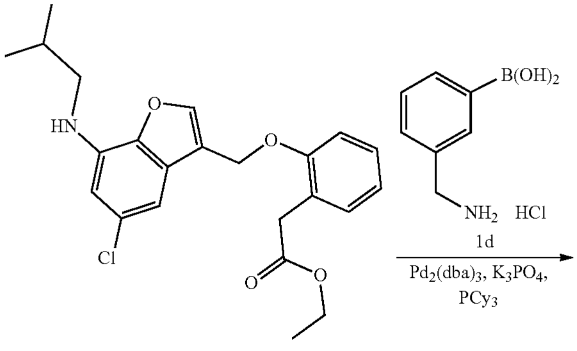

151b

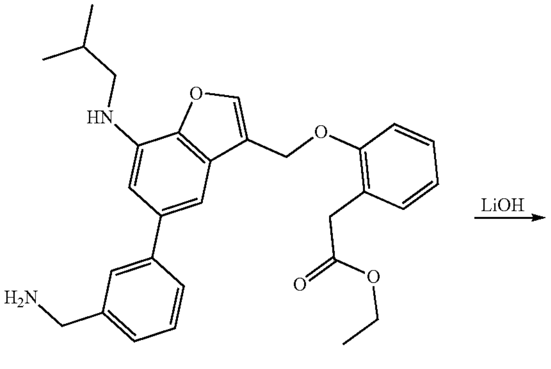

151c

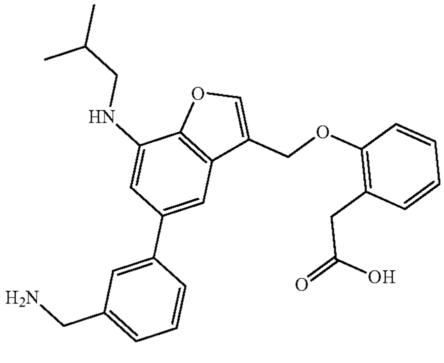

151d

Preparation of 2-(2-((5-(3-(aminomethyl)phenyl)-7-(isobutylamino)benzofuran-3-yl)methoxy)phenyl) acetic acid (151d)

Step-1: Preparation of ethyl 2-(2-((5-chloro-7-(isobutylamino)benzofuran-3-yl)methoxy)phenyl) acetate (151b)

Compound 151b was prepared according to the procedure reported in step-1 of scheme 146, from ethyl 2-(2-((7-bromo-5-chlorobenzofuran-3-yl)methoxy)phenyl)acetate (72e) (2 g, 4.72 mmol) in MeCN (3 mL) using 2-methylpropan-1-amine (151a) (0.704 mL, 7.08 mmol), BrettPhos Palladacycle (0.188 g, 0.236 mmol), cesium carbonate (4.61 g, 14.16 mmol) and irradiating at 60° C. for 1 h in microwave. This gave after work up and purification using flash column chromatography [silica gel (12 g), eluting with EtOAc in hexanes from 0-50%]ethyl 2-(2-((5-chloro-7-(isobutylamino)benzofuran-3-yl)methoxy)phenyl)acetate (151b) (701 mg, 36% yield); $^1H$ NMR (300 MHz, DMSO-$d_6$) δ 8.05 (s, 1H), 7.35-7.25 (m, 1H), 7.25-7.17 (m, 2H), 6.92 (td, J=7.3, 1.1 Hz, 1H), 6.81 (d, J=1.9 Hz, 1H), 6.47 (d, J=1.9 Hz, 1H), 6.17 (t, J=6.0 Hz, 1H), 5.17 (s, 2H), 3.96 (q, J=7.1 Hz, 2H), 3.56 (s, 2H), 3.01 (t, J=6.5 Hz, 2H), 1.98-1.85 (m, 1H), 1.03 (t, J=7.1 Hz, 3H), 0.93 (d, J=6.5 Hz, 6H); MS (ES+): 416.1 (M+1).

Step-2: Preparation of ethyl 2-(2-((5-(3-(aminomethyl)phenyl)-7-(isobutylamino)benzofuran-3-yl) methoxy)phenyl)acetate (151c)

Compound 151c was prepared according to the procedure reported in step-2 of scheme 1, from ethyl 2-(2-((5-chloro-7-(isobutylamino)benzofuran-3-yl)methoxy)phenyl)acetate (151b) (0.701 g, 1.685 mmol) in dioxane (24 mL) using 3-(aminomethyl)phenylboronic acid hydrochloride (1d) (790 mg, 4.21 mmol), 4 M solution of $K_3PO_4$ (1.685 mL, 6.74 mmol), tricyclohexylphosphine (378 mg, 1.348 mmol), $Pd_2(dba)_3$ (617 mg, 0.674 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-(isobutylamino)benzofuran-3-yl)methoxy) phenyl)acetate (151c) (383 mg, 47% yield); MS (ES+): 487.30 (M+1).

Step-3: Preparation of 2-(2-((5-(3-(aminomethyl) phenyl)-7-(isobutylamino)benzofuran-3-yl)methoxy) phenyl)acetic acid (151d)

Compound 151d was prepared according to the procedure reported in step-3 of scheme 1, from ethyl 2-(2-((5-(3-(aminomethyl)phenyl)-7-(isobutylamino)benzofuran-3-yl) methoxy)phenyl)acetate (151c) (383 mg, 0.787 mmol) in THF (2 mL), methanol (0.2 mL) and water (0.2 mL), using lithium hydroxide monohydrate (75 mg, 3.15 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(isobutylamino)benzofuran-3-yl)methoxy)phenyl)acetic acid (151d) (75 mg, 21% yield) HCl salt as a white solid; $^1H$ NMR (300 MHz, DMSO-$d_6$) δ 8.41 (s, 4H, $D_2O$ exchangeable), 8.04 (s, 1H), 7.81 (s, 1H), 7.70-7.65 (m, 1H), 7.50 (d, J=7.6 Hz, 1H), 7.44 (t, J=6.8 Hz, 1H), 7.27 (td, J=7.7, 7.2, 1.7 Hz, 1H), 7.23-7.19 (m, 2H), 7.19-7.15 (m, 1H), 6.97-6.87 (m, 1H), 6.80 (d, J=1.6 Hz, 1H), 5.26 (s, 2H), 4.11 (q, J=5.2, 4.5 Hz, 2H), 3.55 (s, 2H), 3.12 (d, J=6.9 Hz, 2H), 2.07-1.90 (m, 1H), 0.98 (d, J=6.6 Hz, 6H); MS (ES+): 459.3 (M+1); Analysis calculated for $C_{28}H_{30}N_2O_4\cdot1.5HCl\cdot1.25H_2O$: C, 62.77; H, 6.40; Cl, 9.93; N, 5.23. Found: C, 62.65; H, 6.26; Cl, 10.14; N, 5.19.

Scheme 152

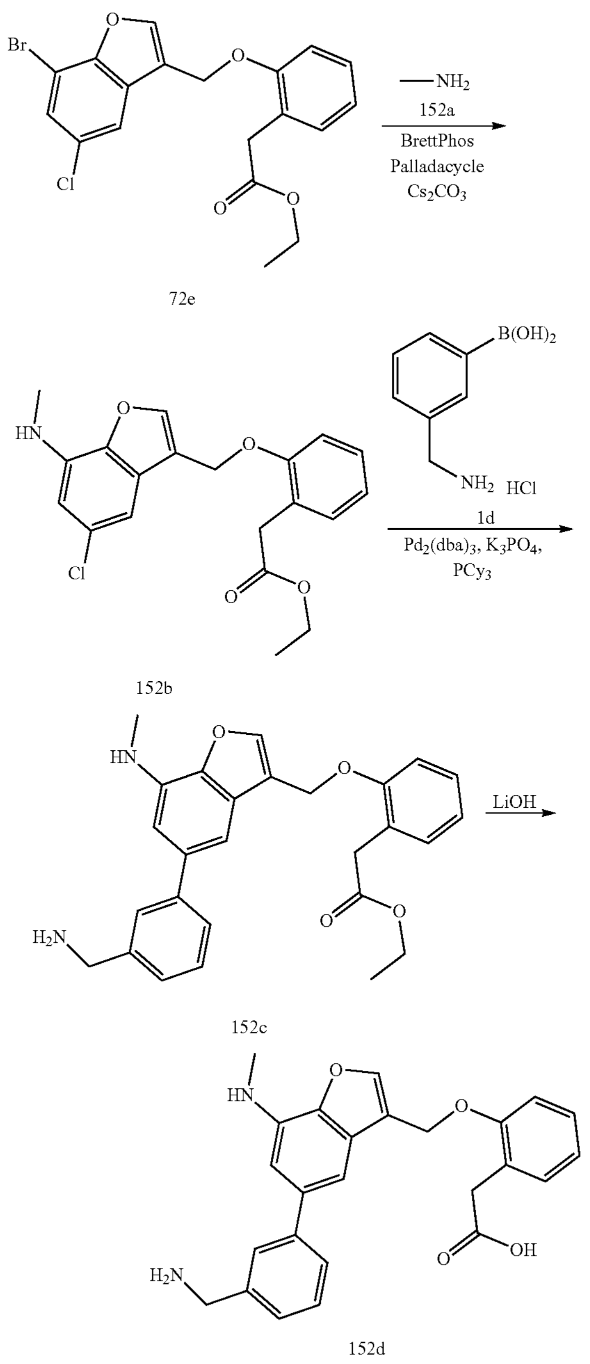

72e

152b

152c

152d

Preparation of 2-(2-((5-(3-(aminomethyl)phenyl)-7-(methylamino)benzofuran-3-yl)methoxy)phenyl) acetic acid (152d)

Step-1: Preparation of ethyl 2-(2-((5-chloro-7-(methylamino)benzofuran-3-yl)methoxy)phenyl) acetate (152b)

Compound 152b was prepared according to the procedure reported in step-1 of scheme 146, from ethyl 2-(2-((7-bromo-5-chlorobenzofuran-3-yl)methoxy)phenyl)acetate (72e) (2 g, 4.72 mmol) in MeCN (3 mL) using methanamine (152a) (3.54 mL, 7.08 mmol), BrettPhos Palladacycle (0.188 g, 0.236 mmol), cesium carbonate (4.61 g, 14.16 mmol) and irradiating at 60° C. for 1 h in microwave. This gave after work up and purification using flash column chromatography [silica gel (12 g), eluting with EtOAc in hexanes from 0-50%] ethyl 2-(2-((5-chloro-7-(methylamino)benzofuran-3-yl)methoxy)phenyl)acetate (152b) (626 mg, 36% yield); $^{1}$H NMR (300 MHz, DMSO-$d_6$) δ 8.05 (s, 1H), 7.33-7.24 (m, 1H), 7.24-7.13 (m, 2H), 6.92 (td, J=7.4, 1.1 Hz, 1H), 6.84 (d, J=1.9 Hz, 1H), 6.42 (d, J=2.0 Hz, 1H), 6.29-6.16 (m, 1H), 5.17 (s, 2H), 3.97 (q, J=7.1 Hz, 2H), 3.56 (s, 2H), 2.81 (d, J=4.9 Hz, 3H), 1.03 (t, J=7.1 Hz, 3H); MS (ES+): 374.10 (M+1).

Step-2: Preparation of ethyl 2-(2-((5-(3-(aminomethyl)phenyl)-7-(methylamino)benzofuran-3-yl) methoxy)phenyl)acetate (152c)

Compound 152c was prepared according to the procedure reported in step-2 of scheme 1, from ethyl 2-(2-((5-chloro-7-(methylamino)benzofuran-3-yl)methoxy)phenyl)acetate (152b) (0.626 g, 1.675 mmol) in dioxane (8 mL) and 2-Me-THF (4 mL) using 3-(aminomethyl)phenylboronic acid hydrochloride (1d) (785 mg, 4.19 mmol), 4 M solution of $K_3PO_4$ (1.675 mL, 6.70 mmol), tricyclohexylphosphine (376 mg, 1.340 mmol), $Pd_2(dba)_3$ (613 mg, 0.670 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-(methylamino)benzofuran-3-yl)methoxy)phenyl)acetate (152c) (326 mg, 44% yield); MS (ES+): 445.20 (M+1).

Step-3: Preparation of 2-(2-((5-(3-(aminomethyl) phenyl)-7-(methylamino)benzofuran-3-yl)methoxy) phenyl)acetic acid (152d)

Compound 152d was prepared according to the procedure reported in step-3 of scheme 1, from ethyl 2-(2-((5-(3-(aminomethyl)phenyl)-7-(methylamino)benzofuran-3-yl) methoxy)phenyl)acetate (152c) (326 mg, 0.733 mmol) in THF (2 mL), methanol (0.2 mL) and water (0.2 mL), using lithium hydroxide monohydrate (70.3 mg, 2.93 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(methylamino)benzofuran-3-yl)methoxy)phenyl)acetic acid (152d) (31 mg, 10% yield) HCl salt as a light brown solid; $^{1}$H NMR (300 MHz, DMSO-$d_6$) δ 8.40 (s, 4H, $D_2O$ exchangeable), 8.04 (s, 1H), 7.84 (s, 1H), 7.71 (d, J=7.4 Hz, 1H), 7.49 (t, J=7.6 Hz, 1H), 7.43 (d, J=7.5 Hz, 1H), 7.33-7.22 (m, 1H), 7.24-7.17 (m, 3H), 6.93 (t, J=7.3 Hz, 1H), 6.78 (d, J=1.6 Hz, 1H), 5.27 (s, 2H), 4.18-4.04 (m, 2H), 3.55 (s, 2H), 2.92 (s, 3H); MS (ES+): 417.2 (M+1); Analysis calculated for $C_{25}H_{24}N_2O_4 \cdot 1.65HCl \cdot 1.75H_2O$: C, 59.09; H, 5.78; Cl, 11.51; N, 5.51. Found: C, 58.99; H, 5.58; Cl, 11.53; N, 5.43.

Scheme 153

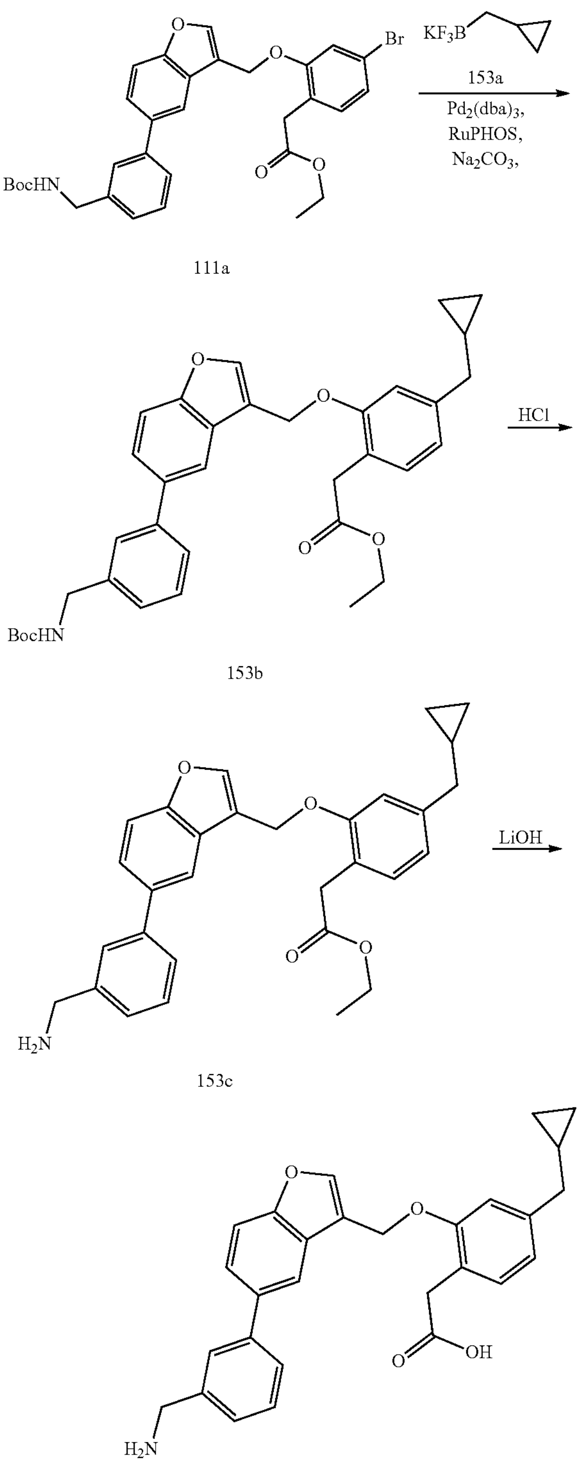

111a

153b

153c

153d

Preparation of 2-(2-((5-(3-(aminomethyl)phenyl) benzofuran-3-yl)methoxy)-4-(cyclopropylmethyl) phenyl)acetic acid (153d)

Step-1: Preparation of ethyl 2-(2-((5-(3-(((tert-butoxycarbonyl)amino)methyl)phenyl)benzofuran-3-yl)methoxy)-4-(cyclopropylmethyl)phenyl)acetate (153b)

Compound 153b was prepared according to the procedure reported in step-2 of scheme 1, from ethyl 2-(4-bromo-2-((5-(3-(((tert-butoxycarbonyl)amino)methyl)phenyl)benzofuran-3-yl)methoxy)phenyl)acetate (111a) (0.491 g, 0.826 mmol) in toluene (10 mL) and water (1 mL) using potassium (cyclopropylmethyl)trifluoroborate (153a) (0.201 g, 1.239 mmol), sodium carbonate (0.35 g, 3.30 mmol), $Pd_2(dba)_3$ (0.038 g, 0.041 mmol), RuPHOS (0.039 g, 0.083 mmol) and heating at 100° C. for 10 h. This gave after workup and purification using flash column chromatography [silica gel (24 g), eluting with EtOAc in hexane from 0-70%]ethyl 2-(2-((5-(3-(((tert-butoxycarbonyl)amino)methyl)phenyl) benzofuran-3-yl)methoxy)-4-(cyclopropylmethyl)phenyl) acetate (153b) (245 mg, 52% yield) as a yellow oil; $^1H$ NMR (300 MHz, DMSO-$d_6$) δ 8.13 (s, 1H), 7.89 (s, 1H), 7.70 (d, J=8.6 Hz, 1H), 7.62 (d, J=1.8 Hz, 1H), 7.57 (s, 3H), 7.42 (d, J=8.0 Hz, 1H), 7.22 (d, J=7.5 Hz, 1H), 7.14-7.05 (m, 2H), 6.79 (dd, J=12.8, 7.7 Hz, 1H), 5.28 (s, 2H), 4.20 (d, J=6.2 Hz, 2H), 4.03 (q, J=7.1 Hz, 2H), 3.51 (s, 2H), 2.60-2.44 (m, 2H), 1.38 (s, 9H), 1.17 (t, J=7.1 Hz, 3H), 1.04-0.90 (m, 1H), 0.49-0.39 (m, 2H), 0.26-0.14 (m, 2H).

Step-2: Preparation of ethyl 2-(2-((5-(3-(aminomethyl)phenyl)benzofuran-3-yl)methoxy)-4-(cyclopropylmethyl)phenyl)acetate (153c)

Compound 153c was prepared according to the procedure reported in step-2 of scheme 7, from ethyl 2-(2-((5-(3-(((tert-butoxycarbonyl)amino)methyl)phenyl)benzofuran-3-yl) methoxy)-4-(cyclopropylmethyl)phenyl)acetate (153b) (254 mg, 0.446 mmol) using HCl (4M in dioxane) (0.557 mL, 2.229 mmol) in EtOH (4 mL) and stirring the reaction mixture at RT for 4 h. This gave after workup ethyl 2-(2-((5-(3-(aminomethyl)phenyl)benzofuran-3-yl)methoxy)-4-(cyclopropylmethyl)phenyl)acetate (153c) which was used as such for step; MS (ES+): 470.30 (M+1).

Step-3: Preparation of 2-(2-((5-(3-(aminomethyl) phenyl)benzofuran-3-yl)methoxy)-4-(cyclopropylmethyl)phenyl)acetic acid (153d)

Compound 153d was prepared according to the procedure reported in step-3 of scheme 1, from ethyl 2-(2-((5-(3-(aminomethyl)phenyl)benzofuran-3-yl)methoxy)-4-(cyclopropylmethyl)phenyl)acetate (153c) (From step-2 above) in THF (2 mL), methanol (0.2 mL) and water (0.2 mL), using lithium hydroxide monohydrate (35.1 mg, 1.465 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-4-(cyclopropylmethyl)phenyl)acetic acid (153d) (32 mg, 20% yield) HCl salt as a white solid; H NMR (300 MHz, DMSO-$d_6$) δ 12.10 (s, 1H, $D_2O$ exchangeable), 8.27 (s, 3H, $D_2O$ exchangeable), 8.14 (s, 1H), 8.01 (d, J=1.8 Hz, 1H), 7.86 (s, 1H), 7.78-7.71 (m, 2H), 7.71-7.63 (m, 1H), 7.53 (t, J=7.7 Hz, 1H), 7.46 (d, 1H), 7.11 (s, 1H), 7.09 (s, 1H), 6.84-6.78 (m, 1H), 5.32 (s, 2H), 4.12 (s, 2H), 3.49 (s, 2H), 2.52-2.47 (m, 2H), 1.05-0.90 (m, 1H), 0.54-0.38 (m, 2H), 0.23-0.13 (m, 2H); MS (ES+): 442.3 (M+1); Analysis calculated for $C_{28}H_{27}NO_4 \cdot HCl \cdot 1.25H_2O$: C, 67.19; H, 6.14; Cl, 7.08; N, 2.80. Found: C, 67.37H, 5.91; Cl, 6.87; N, 2.84.

Scheme 154

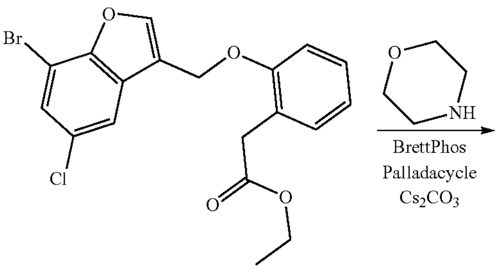

72e

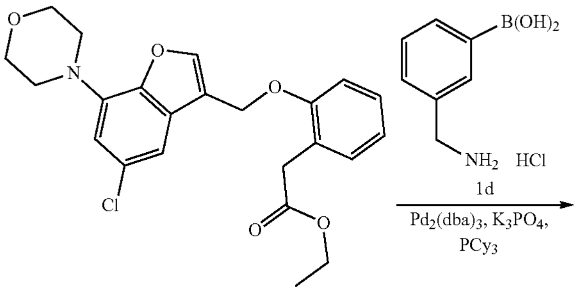

154a

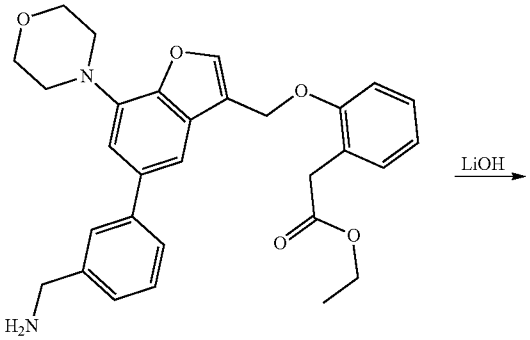

154b

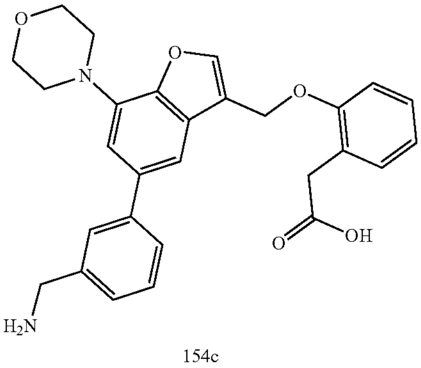

154c

Preparation of 2-(2-((5-(3-(aminomethyl)phenyl)-7-morpholinobenzofuran-3-yl)methoxy)phenyl)acetic acid (154c)

Step-1: Preparation of ethyl 2-(2-((5-chloro-7-morpholinobenzofuran-3-yl)methoxy)phenyl)acetate (154a)

Compound 154a was prepared according to the procedure reported in step-1 of scheme 146, from ethyl 2-(2-((7-bromo-5-chlorobenzofuran-3-yl)methoxy)phenyl)acetate (72e) (1.8 g, 4.25 mmol) in MeCN (3 mL) using morpholine (0.550 mL, 6.37 mmol), BrettPhos Palladacycle (0.169 g, 0.212 mmol), cesium carbonate (4.15 g, 12.75 mmol) and irradiating at 110° C. for 1 h in microwave. This gave after work up and purification using flash column chromatography [silica gel (12 g), eluting with EtOAc in hexanes from 0-50%] ethyl 2-(2-((5-chloro-7-morpholinobenzofuran-3-yl)methoxy)phenyl)acetate (154a) (121 mg, 6.5% yield); MS (ES+): 430.10 (M+1).

Step-2: Preparation of ethyl 2-(2-((5-(3-(aminomethyl)phenyl)-7-morpholinobenzofuran-3-yl)methoxy)phenyl)acetate (154b)

Compound 154b was prepared according to the procedure reported in step-2 of scheme 1, from ethyl 2-(2-((5-chloro-7-morpholinobenzofuran-3-yl)methoxy)phenyl)acetate (154a) (0.121 g, 0.281 mmol) in dioxane (8 mL) and 2-Me-THF (4 mL) using 3-(aminomethyl)phenylboronic acid hydrochloride (1d) (132 mg, 0.704 mmol), 4 M solution of $K_3PO_4$ (0.281 mL, 1.126 mmol), tricyclohexylphosphine (63.1 mg, 0.225 mmol), $Pd_2(dba)_3$ (103 mg, 0.113 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-morpholinobenzofuran-3-yl)methoxy)phenyl)acetate (154b) (26 mg, 18% yield); MS (ES+): 501.30 (M+1).

Step-3: Preparation of 2-(2-((5-(3-(aminomethyl)phenyl)-7-morpholinobenzofuran-3-yl)methoxy)phenyl)acetic acid (154c)

Compound 154c was prepared according to the procedure reported in step-3 of scheme 1, from ethyl 2-(2-((5-(3-(aminomethyl)phenyl)-7-morpholinobenzofuran-3-yl)methoxy)phenyl)acetate (154b) (26 mg, 0.052 mmol) in THF (0.2 mL), methanol (0.02 mL) and water (0.02 mL), using lithium hydroxide monohydrate (4.98 mg, 0.208 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-morpholinobenzofuran-3-yl)methoxy)phenyl)acetic acid (154c) (2.2 mg, 10% yield) HCl salt as a light brown solid; $^1$H NMR (300 MHz, Methanol-$d_4$) δ 7.99 (s, 1H), 7.85 (s, 1H), 7.77 (d, J=7.9 Hz, 1H), 7.74-7.71 (m, 1H), 7.54 (t, J=7.6 Hz, 1H), 7.43 (d, J=7.6 Hz, 1H), 7.40-7.35 (m, 1H), 7.33-7.25 (m, 1H), 7.25-7.15 (m, 2H), 6.95 (t, J=7.4 Hz, 1H), 5.32 (s, 2H), 4.21 (s, 2H), 4.05-3.97 (m, 4H), 3.62 (s, 2H), 3.61-3.57 (m, 4H); MS (ES+): 473.2 (M+1).

Scheme 155

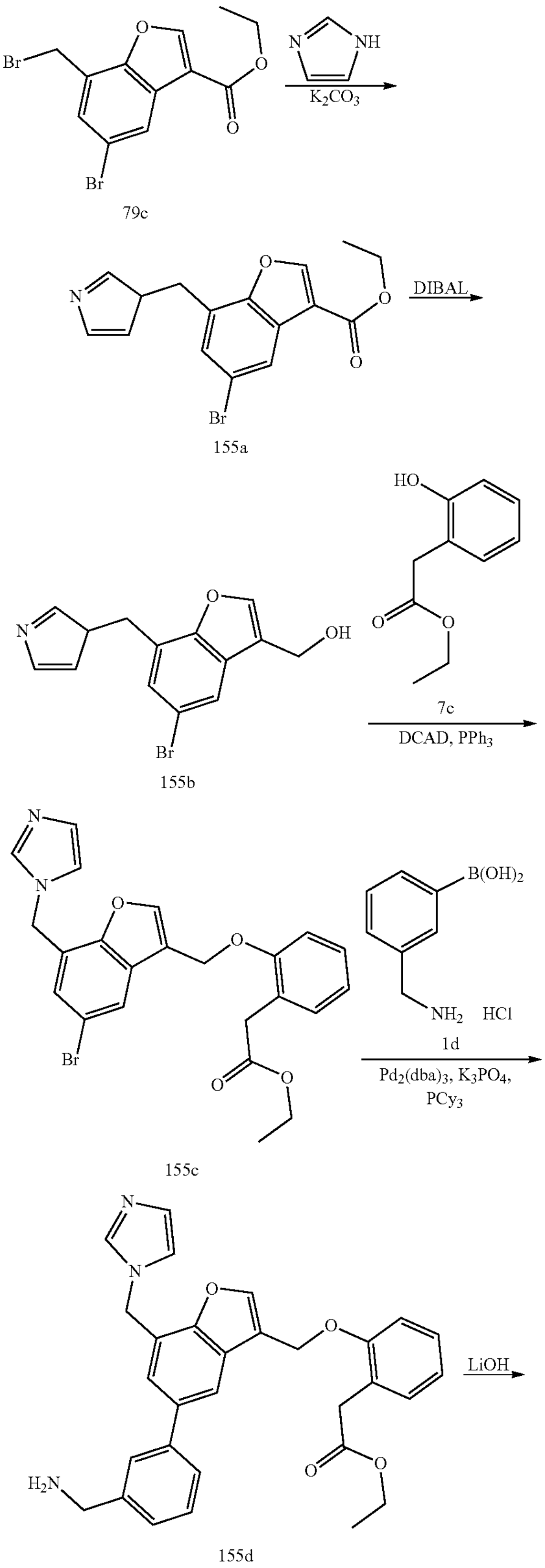

-continued

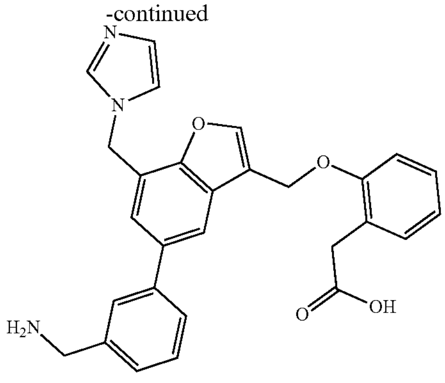

155e

Preparation of 2-(2-((7-((1H-imidazol-1-yl)methyl)-5-(3-(aminomethyl)phenyl)benzofuran-3-yl)methoxy)phenyl)acetic acid (155e)

Step-1: Preparation of ethyl 7-((1H-imidazol-1-yl)methyl)-5-bromobenzofuran-3-carboxylate (155a)

Compound 155a was prepared according to the procedure reported in step-1 of scheme 79, from ethyl 5-bromo-7-(bromomethyl)benzofuran-3-carboxylate (79c) (0.6 g, 1.657 mmol) in DMF (10 mL) using 1H-imidazole (0.338 g, 4.97 mmol), potassium carbonate (0.687 g, 4.97 mmol) and stirring at RT for 15 h. This gave after workup and purification using flash column chromatography [silica gel (24 g), eluting with DMA-80 in DCM from 0-50%] ethyl 7-((1H-imidazol-1-yl)methyl)-5-bromobenzofuran-3-carboxylate (155a) (0.53 g, 92% yield) as a yellow solid; $^1H$ NMR (300 MHz, DMSO-$d_6$) δ 8.90 (s, 1H), 8.02 (d, J=2.0 Hz, 1H), 7.80 (t, J=1.1 Hz, 1H), 7.35 (d, J=2.0 Hz, 1H), 7.24 (t, J=1.3 Hz, 1H), 6.92 (t, J=1.1 Hz, 1H), 5.54 (s, 2H), 4.35 (q, J=7.1 Hz, 2H), 1.34 (t, J=7.1 Hz, 3H); MS (+): 349.05 (M+1).

Step-2: Preparation of (7-((1H-imidazol-1-yl)methyl)-5-bromobenzofuran-3-yl)methanol (155b)

Compound 155b was prepared according to the procedure reported in step-2 of scheme 69, from ethyl 7-((1H-imidazol-1-yl)methyl)-5-bromobenzofuran-3-carboxylate (155a) (0.53 g, 1.518 mmol) in DCM (10 mL) using 1.0 M solution of DIBAL in DCM (3.79 mL, 3.79 mmol) and stirring at −78° C. for 30 min. This gave after workup and purification using flash column chromatography [silica gel (12 g), eluting with DMA-80 in DCM from 0-100%] (7-((1H-imidazol-1-yl)methyl)-5-bromobenzofuran-3-yl)methanol (155b) (0.3 g, 64% yield) as a light yellow oil; $^1H$ NMR (300 MHz, DMSO-$d_6$) δ 7.99 (s, 1H), 7.86 (d, J=2.0 Hz, 1H), 7.79 (s, 1H), 7.27 (d, J=2.0 Hz, 1H), 7.22 (t, J=1.2 Hz, 1H), 6.90 (t, J=1.1 Hz, 1H), 5.48 (s, 2H), 5.24 (t, J=5.6 Hz, 1H), 4.59 (dd, J=5.6, 1.1 Hz, 2H); MS (ES+): 307.00 & 309.00 (M+1).

Step-3: Preparation of ethyl 2-(2-((7-((1H-imidazol-1-yl)methyl)-5-bromobenzofuran-3-yl)methoxy)phenyl)acetate (155c)

Compound 155c was prepared according to the procedure reported in step-2 of scheme 65, from (7-((1H-imidazol-1-yl)methyl)-5-bromobenzofuran-3-yl)methanol (155b) (300 mg, 0.977 mmol) in DCM (10 mL) using triphenylphosphine (90 mg, 0.345 mmol), ethyl 2-(2-hydroxyphenyl) acetate (7c) (194 mg, 1.074 mmol), a solution of DCAD (717 mg, 1.953 mmol) in DCM (5 mL) at 0° C. and stirring at RT for 30 min. This gave after workup and purification using flash column chromatography [silica gel (24 g), eluting with DMA-80 in DCM from 0-60%] ethyl 2-(2-((7-((1H-imidazol-1-yl)methyl)-5-bromobenzofuran-3-yl)methoxy)phenyl)acetate (155c) (250 mg, 55% yield) as a light yellow oil; MS (ES+): 469.10 (M+1).

Step-4: Preparation of ethyl 2-(2-((7-((1H-imidazol-1-yl)methyl)-5-(3-(aminomethyl)phenyl)benzofuran-3-yl)methoxy)phenyl)acetate (155d)

Compound 155d was prepared according to the procedure reported in step-2 of scheme 1, from ethyl 2-(2-((7-((1H-imidazol-1-yl)methyl)-5-bromobenzofuran-3-yl)methoxy)phenyl)acetate (155c) (250 mg, 0.533 mmol) using (3-(aminomethyl)phenyl)boronic acid hydrochloride (1d) (200 mg, 1.065 mmol), 2 M solution of $K_3PO_4$ (1.065 mL, 2.131 mmol), tricyclohexylphosphine (29.9 mg, 0.107 mmol) and $Pd_2(dba)_3$ (48.8 mg, 0.053 mmol) and heating at 90° C. for 1 h. This gave after workup and purification using flash column chromatography [silica gel (12 g), eluting with DMA-80 in DCM from 0-70%] ethyl 2-(2-((7-((1H-imidazol-1-yl)methyl)-5-(3-(aminomethyl)phenyl)benzofuran-3-yl)methoxy)phenyl)acetate (155d) (100 mg, 38% yield); MS (ES+): 496.25 (M+1).

Step-5: Preparation of 2-(2-((7-((1H-imidazol-1-yl)methyl)-5-(3-(aminomethyl)phenyl)benzofuran-3-yl)methoxy)phenyl)acetic acid (155e)

Compound 155e was prepared according to the procedure reported in step-3 of scheme 1, from ethyl 2-(2-((7-((1H-imidazol-1-yl)methyl)-5-(3-(aminomethyl)phenyl)benzofuran-3-yl)methoxy)phenyl)acetate (155d) (100 mg, 0.202 mmol) in THF/MeOH (2 mL each) using a solution of lithium hydroxide hydrate (50.8 mg, 1.211 mmol) in water (1 mL) and heating for 1.5 h at 50° C. This gave after workup and purification by reverse phase column chromatography [C18 column (50 g), eluting with ACN in water (containing 0.1% HCl) from 0-100%] 2-(2-((7-((1H-imidazol-1-yl)methyl)-5-(3-(aminomethyl)phenyl)benzofuran-3-yl)methoxy)phenyl)acetic acid (155e) (65 mg, 69% yield) HCl salt as a white solid; $^1H$ NMR (300 MHz, DMSO-$d_6$) δ 14.90 (s, 1H, $D_2O$ exchangeable), 9.48 (s, 1H), 8.66 (s, 3H, $D_2O$ exchangeable), 8.19 (s, 1H), 8.08 (d, J=1.7 Hz, 1H), 8.02 (s, 1H), 7.91 (t, J=1.7 Hz, 1H), 7.87 (d, J=1.8 Hz, 1H), 7.75 (dt, J=6.7, 2.2 Hz, 1H), 7.71 (t, J=1.7 Hz, 1H), 7.57-7.47 (m, 2H), 7.27 (td, J=7.6, 7.0, 1.7 Hz, 1H), 7.21 (dt, J=8.2, 2.0 Hz, 2H), 6.92 (td, J=7.3, 1.3 Hz, 1H), 5.82 (s, 2H), 5.33 (s, 2H), 4.20-4.02 (m, 2H), 3.54 (s, 2H); MS (ES+): 468.20 (M+1); MS (ES−): 466.10 (M−1); Analysis calculated for $C_{28}H_{25}N_3O_4 \cdot 2HCl \cdot 3.25H_2O$: C, 56.15; H, 5.64; N, 7.02. Found: C, 56.16; H, 5.66; N, 6.82.

Scheme 156

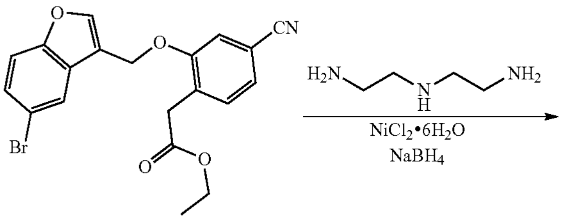

57b

-continued

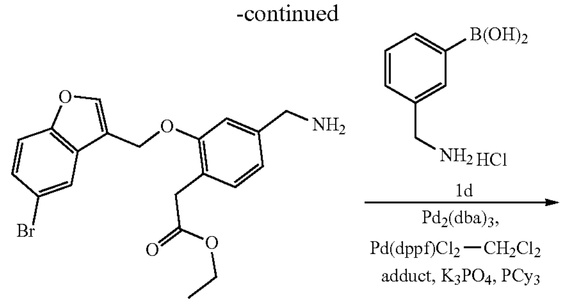

156a

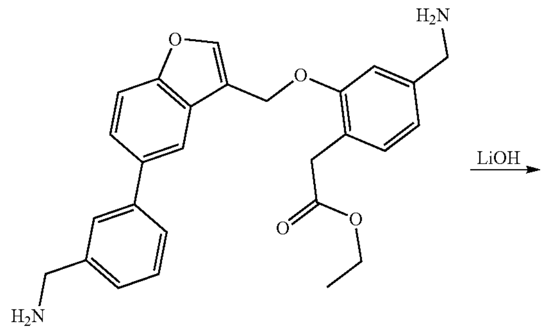

156b

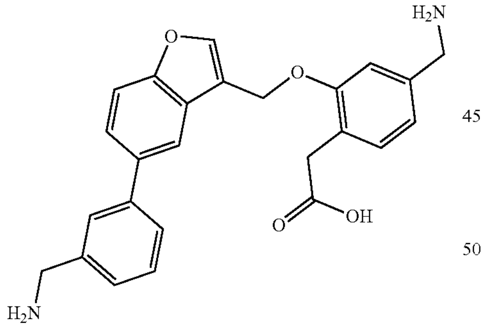

156c

Preparation of 2-(4-(aminomethyl)-2-((5-(3-(aminomethyl)phenyl)benzofuran-3-yl)methoxy)phenyl)acetic acid (156c)

Step-1: Preparation of ethyl 2-(4-(aminomethyl)-2-((5-bromobenzofuran-3-yl)methoxy)phenyl)acetate (156a)

Compound 156a was prepared according to the procedure reported in step-1 of scheme 145, from ethyl 2-(2-((5-bromobenzofuran-3-yl)methoxy)-4-cyanophenyl)acetate (57b) (1 g, 2.414 mmol) in anhydrous methanol (20 mL) using nickel(II) chloride hexahydrate (0.143 g, 0.604 mmol), sodium borohydride (0.274 g, 7.24 mmol), N1-(2-aminoethyl)ethane-1,2-diamine (0.522 mL, 4.83 mmol) and stirring for 1 h. The residue obtained was purified using flash column chromatography [silica gel (40 g), eluting with MeOH in DCM from 0 to 60%)] to furnish ethyl 2-(4-(aminomethyl)-2-((5-bromobenzofuran-3-yl)methoxy)phenyl)acetate (156a)(0.25 g, 25% yield) as a pale yellow wax; MS(+): 418.10 (M+1).

Step-2: Preparation of ethyl 2-(4-(aminomethyl)-2-((5-(3-(aminomethyl)phenyl)benzofuran-3-yl)methoxy)phenyl)acetate (156b)

Compound 156b was prepared according to the procedure reported in step-2 of scheme 1, from ethyl 2-(4-(aminomethyl)-2-((5-bromobenzofuran-3-yl)methoxy)phenyl)acetate (156a) (0.5 g, 1.195 mmol) in dioxane (4 mL) and THF (4 mL) using 3-(aminomethyl)phenylboronic acid hydrochloride (1d) (448 mg, 2.391 mmol), 2 M solution of $K_3PO_4$ (2.391 mL, 4.78 mmol), tricyclohexylphosphine (67 mg, 0.239 mmol), $Pd_2(dba)_3$ (109 mg, 0.120 mmol), $PdCl_2$(dppf)-$CH_2Cl_2$ adduct (98 mg, 0.120 mmol) and heating at 90° C. for 1 h. This gave after workup and purification using flash column chromatography [silica gel (12 g), eluting with DMA-80 in DCM from 0-70%] ethyl 2-(4-(aminomethyl)-2-((5-(3-(aminomethyl)phenyl)benzofuran-3-yl)methoxy)phenyl)acetate (156b) (130 mg, 25% yield) as a clear oil; MS (ES+): 445.20 (M+1).

Step-3: Preparation of 2-(4-(aminomethyl)-2-((5-(3-(aminomethyl)phenyl)benzofuran-3-yl)methoxy)phenyl)acetic acid (156c)

Compound 156c was prepared according to the procedure reported in step-3 of scheme 1, from ethyl 2-(4-(aminomethyl)-2-((5-(3-(aminomethyl)phenyl)benzofuran-3-yl)methoxy)phenyl)acetate (156b) (120 mg, 0.270 mmol) in THF/MeOH (2 mL each) using a solution of lithium hydroxide hydrate (68 mg, 1.62 mmol) in water (1 mL) and heating at 50° C. for 1.5 h. This gave after workup and purification using reverse phase column chromatography [C18 column (50 g), eluting with ACN in water (containing 0.1% HCl) from 0-100%] 2-(4-(aminomethyl)-2-((5-(3-(aminomethyl)phenyl)benzofuran-3-yl)methoxy)phenyl)acetic acid (156c) (90 mg, 80% yield) HCl salt as a white solid; $^1$H NMR (300 MHz, DMSO-$d_6$) δ 12.21 (s, 1H, $D_2O$ exchangeable), 8.61-8.36 (s, 5H, $D_2O$ exchangeable), 8.22 (s, 1H), 8.02 (d, J=1.7 Hz, 1H), 7.92 (s, 1H), 7.79-7.65 (m, 3H), 7.54 (d, J=1.7 Hz, 1H), 7.53-7.44 (m, 2H), 7.23 (d, J=7.7 Hz, 1H), 7.02 (dd, J=7.5, 1.5 Hz, 1H), 5.36 (s, 2H), 4.11 (s, 2H), 4.02 (s, 2H), 3.54 (s, 2H); MS (ES+): 417.20 (M+1); MS (ES−): 415.10 (M−1); Analysis calculated for $C_{25}H_{24}N_2O_4 \cdot 2HCl \cdot 1.5H_2O$: C, 58.15; H, 5.66; Cl, 13.73; N, 5.42. Found: C, 58.08; H, 5.67; Cl, 13.96; N, 5.50.

Scheme 157

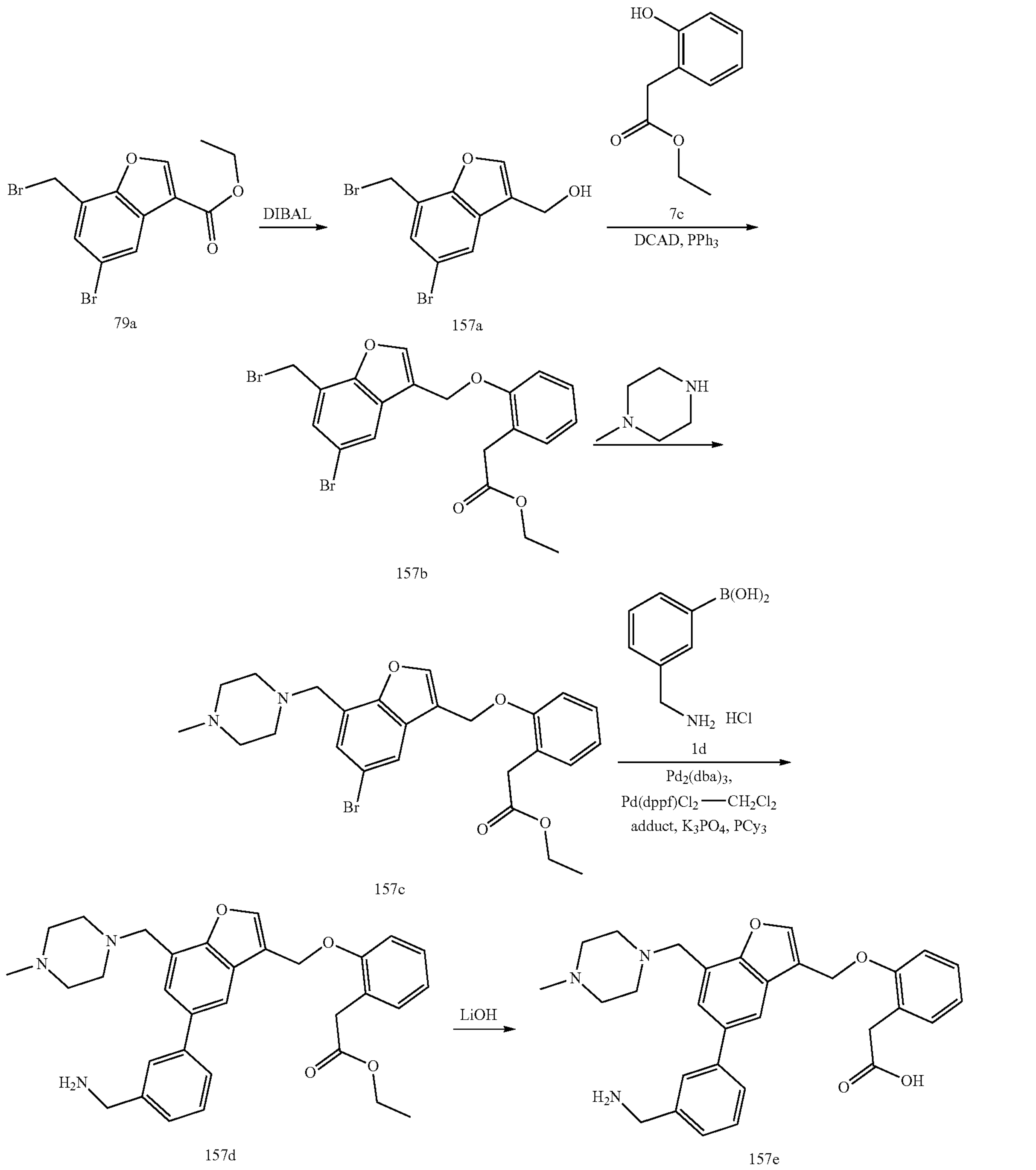

79a 157a 157b 157c 157d 157e

Preparation of 2-(2-((5-(3-(aminomethyl)phenyl)-7-((4-methylpiperazin-1-yl)methyl)benzofuran-3-yl)methoxy)phenyl)acetic acid (157e)

Step-1: Preparation of (5-bromo-7-(bromomethyl)benzofuran-3-yl)methanol (157a)

Compound 157a was prepared according to the procedure reported in step-2 of scheme 69, from ethyl 5-bromo-7-(bromomethyl)benzofuran-3-carboxylate (79c) (500 mg, 1.381 mmol) in DCM (10 mL) using 1.0 M solution of DIBAL in DCM (3.45 mL, 3.45 mmol) and stirring at −78° C. for 30 min. This gave after workup and purification using flash column chromatography [silica gel (12 g), eluting with DMA-80 in DCM from 0-100%] (5-bromo-7-(bromomethyl)benzofuran-3-yl)methanol (157a) (0.38 g, 86% yield); $^1H$ NMR (300 MHz, DMSO-$d_6$) δ 8.02 (s, 1H), 7.88 (d, J=2.0 Hz, 1H), 7.62 (d, J=2.0 Hz, 1H), 5.25 (t, J=5.6 Hz, 1H), 4.90 (s, 2H), 4.60 (d, J=5.1 Hz, 2H); MS (ES+): 318.20 (M+1).

Step-2: Preparation of ethyl 2-(2-((5-bromo-7-(bromomethyl)benzofuran-3-yl)methoxy)phenyl)acetate (157b)

Compound 157b was prepared according to the procedure reported in step-2 of scheme 65, from (5-bromo-7-(bromomethyl)benzofuran-3-yl)methanol (157a) (380 mg, 1.188 mmol) in DCM (10 mL) using triphenylphosphine (327 mg, 1.247 mmol), ethyl 2-(2-hydroxyphenyl)acetate (7c) (225 mg, 1.247 mmol) a solution of DCAD (458 mg, 1.247 mmol) in DCM (5 mL) at 0° C. and stirring at RT for 30 min. This gave after workup and purification using flash column chromatography [silica (24 g), eluting with DMA-80 in DCM from 0-60%] ethyl 2-(2-((5-bromo-7-(bromomethyl)benzofuran-3-yl)methoxy)phenyl)acetate (157b) (300 mg, 52% yield) as a light yellow oil; $^1$H NMR (300 MHz, DMSO-$d_6$) δ 8.23 (s, 1H), 7.83 (d, J=2.0 Hz, 1H), 7.67 (d, J=2.0 Hz, 1H), 7.29 (td, J=7.7, 1.8 Hz, 1H), 7.24-7.15 (m, 2H), 6.97-6.88 (m, 1H), 5.24 (s, 2H), 4.92 (s, 2H), 3.92 (q, J=7.1 Hz, 2H), 3.55 (s, 2H), 0.97 (t, J=7.1 Hz, 3H); MS (ES+): 502.95 (M+Na).

Step-3: Preparation of ethyl 2-(2-((5-bromo-7-((4-methylpiperazin-1-yl)methyl)benzofuran-3-yl)methoxy)phenyl)acetate (157c)

Compound 157c was prepared according to the procedure reported in step-2 of scheme 1, from ethyl 2-(2-((5-bromo-7-(bromomethyl)benzofuran-3-yl)methoxy)phenyl)acetate (157b) (300 mg, 0.622 mmol) in DMF (5 mL) using 1-methylpiperazine (0.187 g, 1.867 mmol) and stirring at RT for 15 h. This gave after work up and purification using flash column chromatography [silica (24 g), eluting with DMA-80 in DCM from 0-50%] ethyl 2-(2-((5-bromo-7-((4-methylpiperazin-1-yl)methyl)benzofuran-3-yl)methoxy)phenyl) acetate (157c) (0.220 g, 71% yield) as a white oil; $^1$H NMR (300 MHz, DMSO-$d_6$) δ 8.15 (s, 1H), 7.74 (d, J=2.0 Hz, 1H), 7.43 (d, J=2.0 Hz, 1H), 7.29 (td, J=7.7, 7.3, 1.7 Hz, 1H), 7.24-7.14 (m, 2H), 6.92 (td, J=7.3, 1.2 Hz, 1H), 5.22 (s, 2H), 3.92 (q, J=7.2 Hz, 2H), 3.74 (s, 2H), 3.55 (s, 2H), 2.48-2.20 (m, 8H), 2.14 (s, 3H), 0.96 (t, J=7.1 Hz, 3H); MS (ES+): 501.10 (M+1); MS (ES−): 499.10 (M−1).

Step-4: Preparation of ethyl 2-(2-((5-(3-(aminomethyl)phenyl)-7-((4-methylpiperazin-1-yl)methyl)benzofuran-3-yl)methoxy)phenyl)acetate (157d)

Compound 157d was prepared according to the procedure reported in step-2 of scheme 1, from ethyl 2-(2-((5-bromo-7-((4-methylpiperazin-1-yl)methyl)benzofuran-3-yl)methoxy)phenyl)acetate (157c) (220 mg, 0.439 mmol) using (3-(aminomethyl)phenyl)boronic acid hydrochloride (1d) (164 mg, 0.878 mmol), 2 M solution of $K_3PO_4$ (0.878 mL, 1.755 mmol), tricyclohexylphosphine (24.61 mg, 0.088 mmol) and $Pd_2(dba)_3$ (40.2 mg, 0.044 mmol), $PdCl_2$(dppf)-$CH_2Cl_2$ adduct (35.8 mg, 0.044 mmol) and heating at 90° C. for 30 min. This gave after workup and purification using flash column chromatography [silica gel (12 g), eluting with DMA-80 in DCM from 0-70%] ethyl 2-(2-((5-(3-(aminomethyl)phenyl)-7-((4-methylpiperazin-1-yl)methyl)benzofuran-3-yl)methoxy)phenyl)acetate (157d) (100 mg, 43% yield); MS (ES+): 528.30 (M+1); 526.30 (M−1).

Step-5: Preparation of 2-(2-((5-(3-(aminomethyl)phenyl)-7-((4-methylpiperazin-1-yl)methyl)benzofuran-3-yl)methoxy)phenyl)acetic acid (157e)

Compound 157e was prepared according to the procedure reported in step-3 of scheme 1, from ethyl 2-(2-((5-(3-(aminomethyl)phenyl)-7-((4-methylpiperazin-1-yl)methyl)benzofuran-3-yl)methoxy)phenyl)acetate (157d) (100 mg, 0.19 mmol) in THF/MeOH (2 mL each) using a solution of lithium hydroxide hydrate (47.7 mg, 1.137 mmol) in water (1 mL) and stirring for 1.5 h at 50° C. This gave after workup and purification using reverse phase column chromatography [C18 column (50 g), eluting with ACN in water (containing 0.1% HCl) from 0-100%] 2-(2-((5-(3-(aminomethyl)phenyl)-7-((4-methylpiperazin-1-yl)methyl)benzofuran-3-yl)methoxy)phenyl)acetic acid (157e) (80 mg, 84% yield) HCl salt as a white solid; $^1$H NMR (300 MHz, DMSO-$d_6$) δ 11.85 (s, 1H, $D_2O$ exchangeable), 8.61 (s, 3H, $D_2O$ exchangeable), 8.23 (s, 1H), 8.13 (s, 1H), 8.09 (s, 1H), 8.01 (s, 1H), 7.88-7.78 (m, 1H), 7.58-7.47 (m, 2H), 7.29 (td, J=7.6, 6.9, 1.6 Hz, 1H), 7.25-7.17 (m, 2H), 6.93 (td, J=7.2, 1.4 Hz, 1H), 5.35 (s, 2H), 4.62 (s, 2H), 4.15-4.05 (m, 2H), 3.72-3.59 (m, 4H), 3.56 (s, 2H), 3.55-3.25 (m, 4H), 2.93-2.64 (s, 3H); MS (ES+): 500.30 (M+1); Analysis calculated for $C_{30}H_{33}N_3O_4 \cdot 3HCl \cdot 3.75H_2O$: C, 53.26; H, 6.48; Cl, 15.72; N, 6.21. Found: C, 53.28; H, 6.33; Cl, 15.93; N, 6.12.

Scheme 158

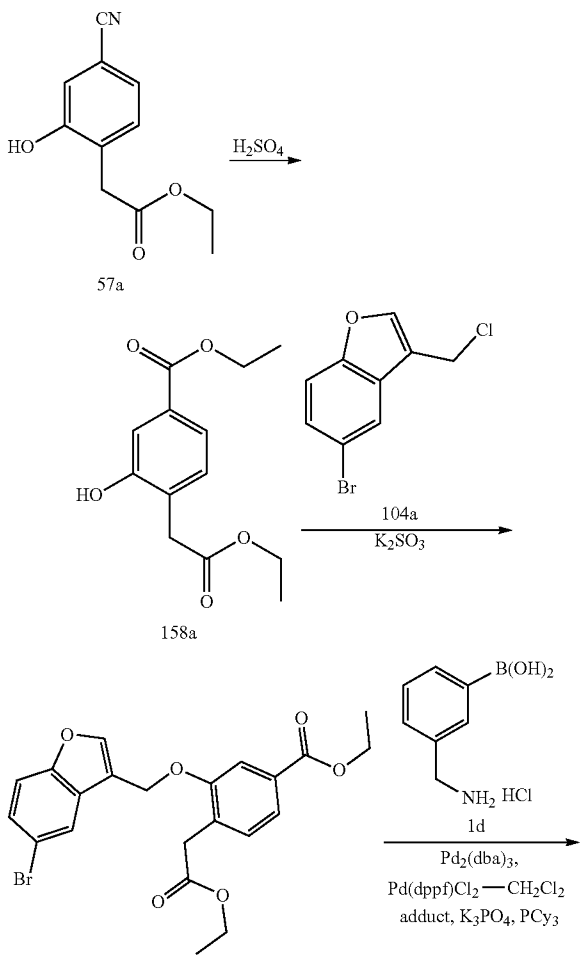

57a

104a

158a

1d

158b

-continued

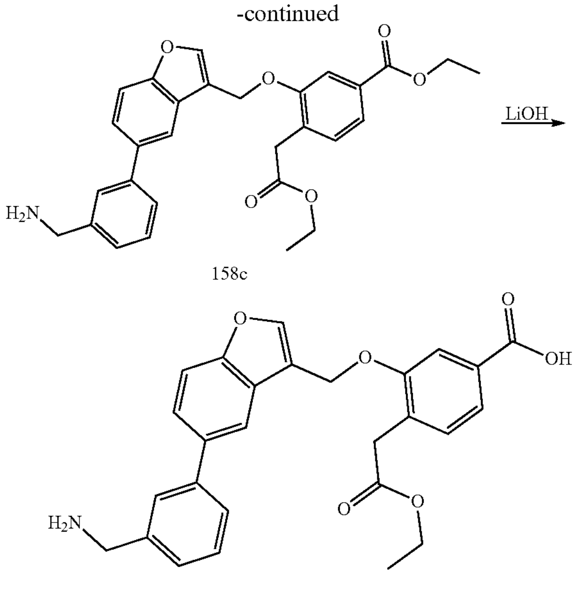

158c

158d

Preparation of 3-((5-(3-(aminomethyl)phenyl)benzofuran-3-yl)methoxy)-4-(carboxymethyl)benzoic acid (158d)

Step-1: Preparation of ethyl 4-(2-ethoxy-2-oxoethyl)-3-hydroxybenzoate (158a)

To a solution of ethyl 2-(4-cyano-2-hydroxyphenyl)acetate (57a) (1 g, 4.87 mmol) in ethanol (20 mL) was added conc. sulfuric acid (2.60 mL, 48.7 mmol) and refluxed for 48 h. The mixture was cooled to RT, diluted with ethyl acetate (240 mL), washed with water (2×75 mL), brine (75 mL), dried, filtered and concentrated in vacuum. The residue obtained was purified using flash column chromatography [silica gel (24 g), eluting with EtOAc in Hexane from 0-80%] to give ethyl 4-(2-ethoxy-2-oxoethyl)-3-hydroxybenzoate (158a) (0.58 g, 47% yield) as a white solid; $^1$H NMR (300 MHz, DMSO-$d_6$) δ 9.97 (s, 1H), 7.41 (d, J=1.7 Hz, 1H), 7.36 (dd, J=7.8, 1.7 Hz, 1H), 7.25 (d, J=7.8 Hz, 1H), 4.28 (q, J=7.1 Hz, 2H), 4.06 (q, J=7.1 Hz, 2H), 3.61 (s, 2H), 1.30 (t, J=7.1 Hz, 3H), 1.17 (t, J=7.1 Hz, 3H).

Step-2: Preparation of ethyl 3-((5-bromobenzofuran-3-yl)methoxy)-4-(2-ethoxy-2-oxoethyl)benzoate (158b)

Compound 158b was prepared according to the procedure reported in step-1 of scheme 1, from ethyl 4-(2-ethoxy-2-oxoethyl)-3-hydroxybenzoate (158a) (580 mg, 2.299 mmol) in DMF (10 mL) using 5-bromo-3-(chloromethyl)benzofuran (104a) (564 mg, 2.299 mmol), $K_2CO_3$ (953 mg, 6.90 mmol) and stirring at RT for 3 h under an Ar atmosphere. This gave after workup and purification using flash column chromatography [silica gel (24 g) eluting with EtOAc in hexane from 0-80%] ethyl 3-((5-bromobenzofuran-3-yl)methoxy)-4-(2-ethoxy-2-oxoethyl)benzoate (158b) (600 mg, 57% yield) as a yellow solid; $^1$H NMR (300 MHz, DMSO-$d_6$) δ 8.13 (s, 1H), 7.90 (d, J=2.0 Hz, 1H), 7.69 (d, J=1.6 Hz, 1H), 7.62 (d, J=8.7 Hz, 1H), 7.57 (dd, J=7.7, 1.5 Hz, 1H), 7.51 (dd, J=8.7, 2.1 Hz, 1H), 7.38 (d, J=7.8 Hz, 1H), 5.33 (s, 2H), 4.33 (q, J=7.1 Hz, 2H), 3.93 (q, J=7.1 Hz, 2H), 3.66 (s, 2H), 1.33 (t, J=7.1 Hz, 3H), 0.97 (t, J=7.1 Hz, 3H); MS (ES+): 483.00 (M+Na).

Step-3: Preparation of ethyl 3-((5-(3-(aminomethyl)phenyl)benzofuran-3-yl)methoxy)-4-(2-ethoxy-2-oxoethyl)benzoate (158c)

Compound 158c was prepared according to the procedure reported in step-2 of scheme 1, from ethyl 3-((5-bromobenzofuran-3-yl)methoxy)-4-(2-ethoxy-2-oxoethyl)benzoate (158b) (0.5 g, 1.084 mmol) in dioxane (4 mL) and THF (4 mL) using 3-(aminomethyl)phenylboronic acid hydrochloride (1d) (406 mg, 2.168 mmol), 2 M solution of $K_3PO_4$ (2.168 mL, 4.34 mmol), tricyclohexylphosphine (61 mg, 0.217 mmol), $Pd_2(dba)_3$ (99 mg, 0.108 mmol), $PdCl_2$(dppf)-$CH_2Cl_2$ adduct (89 mg, 0.108 mmol) and heating at 90° C. for 1 h. This gave after workup and purification using flash column chromatography [silica gel (12 g), eluting with DMA-80 in DCM from 0-70%] ethyl 3-((5-(3-(aminomethyl)phenyl)benzofuran-3-yl)methoxy)-4-(2-ethoxy-2-oxoethyl)benzoate (158c) (200 mg, 38% yield) as a clear oil; $^1$H NMR (300 MHz, DMSO-$d_6$) δ 8.11 (s, 1H), 7.94 (d, J=1.8 Hz, 1H), 7.74-7.70 (m, 1H), 7.70-7.65 (m, 2H), 7.60-7.52 (m, 3H), 7.39 (t, J=7.8 Hz, 2H), 7.31 (d, J=7.6 Hz, 1H), 5.39 (s, 2H), 4.33 (q, J=7.1 Hz, 2H), 3.79 (s, 2H), 3.73 (q, J=7.1 Hz, 2H), 3.66 (s, 2H), 1.33 (t, J=7.1 Hz, 3H), 0.84 (t, J=7.1 Hz, 3H); MS (ES+): 488.20 (M+1).

Step-4: Preparation of 3-((5-(3-(aminomethyl)phenyl)benzofuran-3-yl)methoxy)-4-(carboxymethyl)benzoic acid (158d)

Compound 158d was prepared according to the procedure reported in step-3 of scheme 1, from ethyl 3-((5-(3-(aminomethyl)phenyl)benzofuran-3-yl)methoxy)-4-(2-ethoxy-2-oxoethyl)benzoate (158c) (200 mg, 0.41 mmol) in THF/MeOH (6 mL each) using a solution of lithium hydroxide hydrate (103 mg, 2.461 mmol) in water (2 mL) and heating at 50° C. for 1.5 h. This gave after workup and purification by reverse phase column chromatography [C18 column (50 g), eluting with ACN in water (containing 0.1% HCl) from 0-100%] 3-((5-(3-(aminomethyl)phenyl)benzofuran-3-yl)methoxy)-4-(carboxymethyl)benzoic acid (158d) (120 mg, 68% yield) HCl salt as a white solid; $^1$H NMR (300 MHz, DMSO-$d_6$) δ 8.12 (s, 1H), 8.05 (d, J=1.7 Hz, 1H), 7.93 (s, 1H), 7.79-7.63 (m, 4H), 7.59-7.39 (m, 3H), 7.34 (d, J=7.6 Hz, 1H), 5.40 (s, 2H), 4.10 (s, 2H), 3.62 (s, 2H); MS (ES+): 432.15 (M+1); Analysis calculated for $C_{25}H_{21}NO_6 \cdot HCl \cdot 2.5H_2O$: C, 58.54; H, 5.31; Cl, 6.91; N, 2.73. Found: C, 58.58; H, 5.21; Cl, 6.77; N, 2.74.

Scheme 159

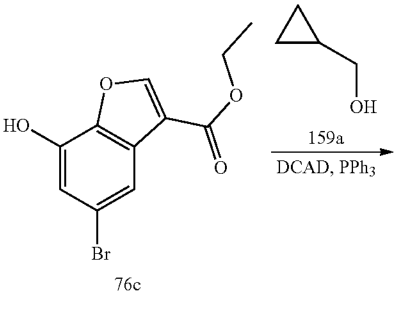

76c

-continued

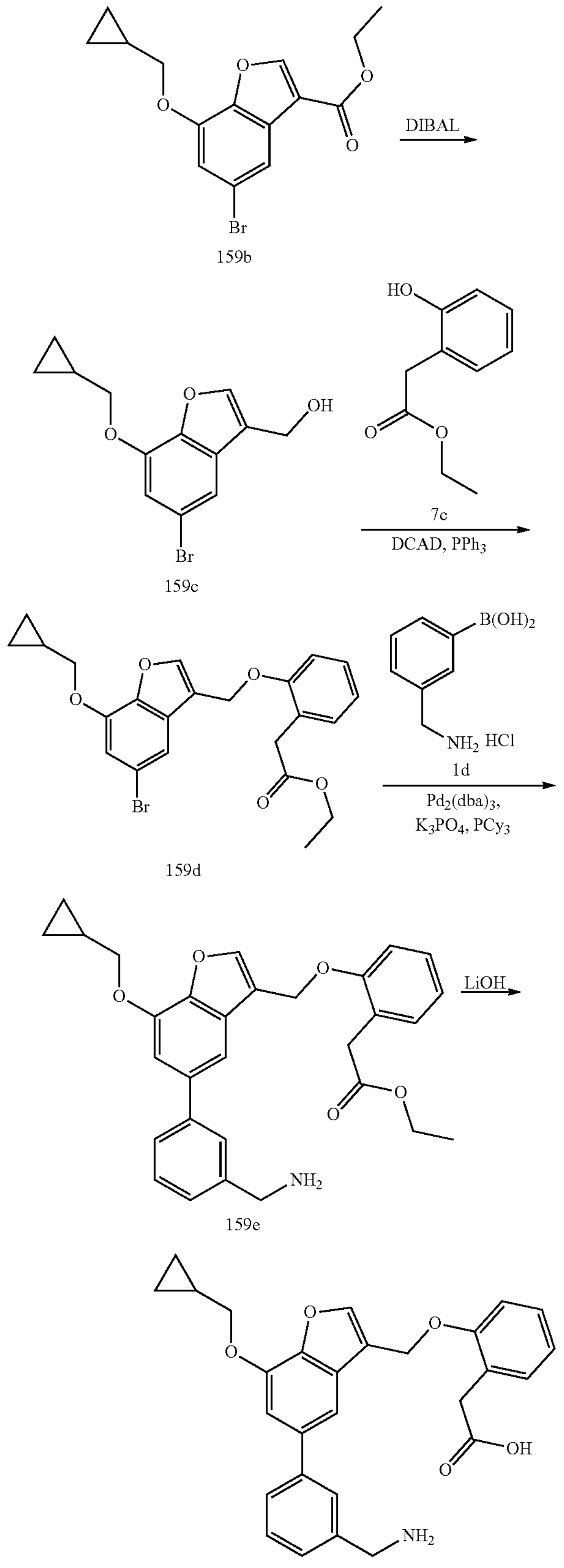

159b, 159c, 159d, 159e, 159f

Preparation of 2-(2-((5-(3-(aminomethyl)phenyl)-7-(cyclopropylmethoxy)benzofuran-3-yl)methoxy)phenyl)acetic acid (159f)

Step-1: Preparation of ethyl 5-bromo-7-(cyclopropylmethoxy)benzofuran-3-carboxylate (159b)

Compound 159b was prepared according to the procedure reported in step-2 of scheme 65, from ethyl 5-bromo-7-hydroxybenzofuran-3-carboxylate (76c) (510 mg, 1.789 mmol) in DCM (15 mL) using triphenylphosphine (540 mg, 2.057 mmol), cyclopropylmethanol (159a) (0.217 mL, 2.68 mmol; CAS #2516-33-8), DCAD (755 mg, 2.057 mmol) in DCM (10 mL) at 0° C. and stirring at RT for 1 h. This gave after workup and purification using flash column chromatography [silica gel (40 g), eluting with EtOAc in hexane from 0-25%] ethyl 5-bromo-7-(cyclopropylmethoxy)benzofuran-3-carboxylate (159b) (404 mg, 67% yield) as a white solid; $^1$H NMR (300 MHz, DMSO-$d_6$) δ 8.78 (s, 1H), 7.63 (d, J=1.7 Hz, 1H), 7.20 (d, J=1.8 Hz, 1H), 4.35 (q, J=7.1 Hz, 2H), 4.06 (d, J=7.1 Hz, 2H), 1.42-1.20 (m, 4H), 0.67-0.54 (m, 2H), 0.40-0.34 (m, 2H); MS (ES+): 339.10 (M+1).

Step-2: Preparation of (5-bromo-7-(cyclopropylmethoxy)benzofuran-3-yl)methanol (159c)

Compound 159c was prepared according to the procedure reported in step-2 of scheme 69, from ethyl 5-bromo-7-(cyclopropylmethoxy)benzofuran-3-carboxylate (159b) (390 mg, 1.15 mmol) in DCM (2.87 mL) using 1.0 M solution of DIBAL in DCM (2.87 mL, 2.87 mmol) and stirring at 0° C. for 2 h. This gave after workup and purification by flash column chromatography [silica gel (12 g), eluting with EtOAc in hexane from 0-50%] (5-bromo-7-(cyclopropylmethoxy)benzofuran-3-yl)methanol (159c) (0.224 g, 66% yield); $^1$H NMR (300 MHz, DMSO-$d_6$) δ 7.89 (s, 1H), 7.44 (d, J=1.7 Hz, 1H), 7.05 (d, J=1.8 Hz, 1H), 5.21 (t, J=5.6 Hz, 1H), 4.58 (dd, J=5.6, 1.1 Hz, 2H), 4.02 (d, J=7.1 Hz, 2H), 1.39-1.17 (m, 1H), 0.67-0.55 (m, 2H), 0.45-0.29 (m, 2H).

Step-3: Preparation of ethyl 2-(2-((5-bromo-7-(cyclopropylmethoxy)benzofuran-3-yl)methoxy)phenyl)acetate (159d)

Compound 159d was prepared according to the procedure reported in step-2 of scheme 65, from (5-bromo-7-(cyclopropylmethoxy)benzofuran-3-yl)methanol (159c) (210 mg, 0.707 mmol) in DCM (5 mL) using triphenylphosphine (213 mg, 0.813 mmol), ethyl 2-(2-hydroxyphenyl)acetate (7c) (140 mg, 0.777 mmol), a solution of DCAD (298 mg, 0.813 mmol) in DCM (5 mL) at 0° C. and stirring at RT for 1 h. This gave after workup and purification using flash column chromatography [silica (40 g), eluting with EtOAc in hexane from 0-25%] ethyl 2-(2-((5-bromo-7-(cyclopropylmethoxy)benzofuran-3-yl)methoxy)phenyl)acetate (159d) (231 mg, 71% yield) as a white solid; $^1$H NMR (300 MHz, DMSO-$d_6$) δ 8.10 (s, 1H), 7.40 (d, J=1.7 Hz, 1H), 7.29 (td, J=7.8, 1.7 Hz, 1H), 7.20 (ddd, J=9.7, 7.9, 1.4 Hz, 2H), 7.10 (d, J=1.7 Hz, 1H), 6.93 (td, J=7.4, 1.1 Hz, 1H), 5.21 (s, 2H), 4.04 (d, J=7.2 Hz, 2H), 3.96 (q, J=7.1 Hz, 2H), 3.56 (s, 2H), 1.35-1.22 (m, 1H), 1.02 (t, J=7.1 Hz, 3H), 0.66-0.54 (m, 2H), 0.41-0.31 (m, 2H); MS (ES+): 481.10 (M+1).

Step-4: Preparation of ethyl 2-(2-((5-(3-(aminomethyl)phenyl)-7-(cyclopropylmethoxy)benzofuran-3-yl)methoxy)phenyl)acetate (159e)

Compound 159e was prepared according to the procedure reported in step-2 of scheme 1, from ethyl 2-(2-((5-bromo- 7-(cyclopropylmethoxy)benzofuran-3-yl)methoxy)phenyl) acetate (159d) (210 mg, 0.457 mmol) using (3-(aminomethyl)phenyl)boronic acid hydrochloride (1d) (107 mg, 0.571 mmol), 4 M solution of $K_3PO_4$ (0.457 mL, 1.829 mmol), tricyclohexylphosphine (25.6 mg, 0.091 mmol), $Pd_2(dba)_3$ (41.9 mg, 0.046 mmol) and heating at 90° C. for 2 h. This gave after workup and purification using flash column chromatography [silica gel (24 g), eluting with DMA-80 in DCM from 0-50%] ethyl 2-(2-((5-(3-(aminomethyl)phenyl)-7-(cyclopropylmethoxy)benzofuran-3-yl) methoxy)phenyl)acetate (159e) (72 mg, 32% yield); $^1H$ NMR (300 MHz, DMSO-$d_6$) δ 8.08 (s, 1H), 7.67 (s, 1H), 7.56 (d, J=7.7 Hz, 1H), 7.46 (d, J=1.4 Hz, 1H), 7.43-7.13 (m, 6H), 6.93 (t, J=7.2 Hz, 1H), 5.28 (s, 2H), 4.12 (d, J=7.1 Hz, 2H), 3.86-3.70 (m, 4H), 3.56 (s, 2H), 1.41-1.26 (m, 1H), 0.89 (t, J=7.1 Hz, 3H), 0.66-0.58 (m, 2H), 0.44-0.35 (m, 2H); MS (ES+): 486.2 (M+1).

Step-5: Preparation of 2-(2-((5-(3-(aminomethyl) phenyl)-7-(cyclopropylmethoxy)benzofuran-3-yl) methoxy)phenyl)acetic acid (159f)

Compound 159f was prepared according to the procedure reported in step-3 of scheme 1, from ethyl 2-(2-((5-(3-(aminomethyl)phenyl)-7-(cyclopropylmethoxy)benzofuran-3-yl)methoxy)phenyl)acetate (159e) (70 mg, 0.144 mmol) in THF (0.9 mL) and acetonitrile (0.45 mL) using a 1N aqueous solution of lithium hydroxide monohydrate (0.432 mL, 0.432 mmol) and stirring for 25 h at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(cyclopropylmethoxy)benzofuran-3-yl) methoxy)phenyl)acetic acid (159f) (51 mg, 77% yield) HCl salt as a white solid; $^1H$ NMR (300 MHz, DMSO-$d_6$) δ 8.51 (s, 3H, $D_2O$ exchangeable), 8.09 (s, 1H), 7.93 (s, 1H), 7.75 (dt, J=7.4, 1.7 Hz, 1H), 7.65-7.38 (m, 3H), 7.32-7.14 (m, 4H), 6.93 (td, J=7.3, 1.2 Hz, 1H), 5.30 (s, 2H), 4.19-4.04 (m, 4H), 3.54 (s, 2H), 1.46-1.19 (m, 1H), 0.72-0.52 (m, 2H), 0.47-0.29 (m, 2H). MS (ES+): 458.2 (M+1); (ES−): 456.2 (M−1); Analysis calculated for $C_{28}H_{27}NO_5 \cdot H_2O \cdot HCl$: C, 65.68; H, 5.91; Cl, 6.92; N, 2.74. Found: C, 65.81; H, 5.85; Cl, 6.65; N, 2.83.

Scheme 160

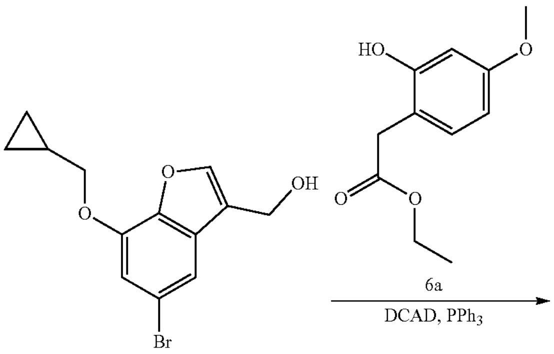

159c

-continued

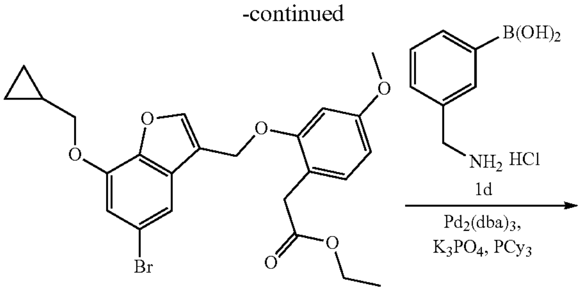

160a

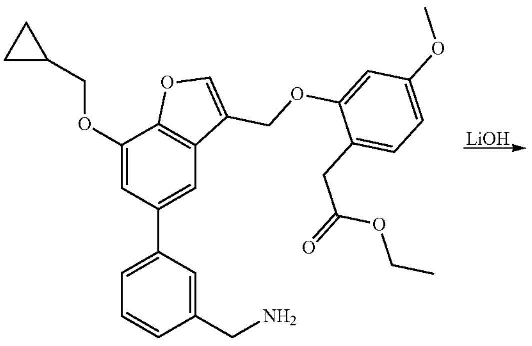

160b

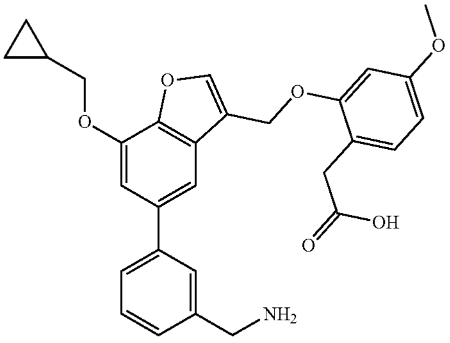

160c

Preparation of 2-(2-((5-(3-(aminomethyl)phenyl)-7-(cyclopropylmethoxy)benzofuran-3-yl)methoxy)-4-methoxyphenyl)acetic acid (160c)

Step-1: Preparation of ethyl 2-(2-((5-bromo-7-(cyclopropylmethoxy)benzofuran-3-yl)methoxy)-4-methoxyphenyl)acetate (160a)

Compound 160a was prepared according to the procedure reported in step-2 of scheme 65, from (5-bromo-7-(cyclopropylmethoxy)benzofuran-3-yl)methanol (159c) (300 mg, 1.01 mmol) in DCM (10 mL) using triphenylphosphine (305 mg, 1.161 mmol), ethyl 2-(2-hydroxy-4-methoxyphenyl) acetate (6a) (233 mg, 1.111 mmol), DCAD (426 mg, 1.161 mmol) in DCM (5 mL) at 0° C. and stirring at RT for 1 h. This gave after workup and purification using flash column chromatography [silica gel (24 g), eluting with EtOAc in hexane from 0-25%] ethyl 2-(2-((5-bromo-7-(cyclopropylmethoxy)benzofuran-3-yl)methoxy)-4-methoxyphenyl)acetate (160a) (220 mg, 45% yield) as a white solid; $^1H$ NMR (300 MHz, DMSO-$d_6$) δ 8.09 (s, 1H), 7.40 (d, J=1.7 Hz, 1H), 7.10 (dd, J=5.0, 3.3 Hz, 2H), 6.77 (d, J=2.4 Hz, 1H), 6.50 (dd, J=8.3, 2.3 Hz, 1H), 5.21 (s, 2H), 4.04 (dd, J=7.1, 2.5 Hz, 2H), 3.95 (q, J=7.1 Hz, 2H), 3.77 (s, 3H), 3.47 (s, 2H), 1.35-1.22 (m, 1H), 1.02 (t, J=7.1 Hz, 3H), 0.68-0.52 (m, 2H), 0.42-0.27 (m, 2H); MS (ES+): 489.1 (M+1).

Step-2: Preparation of ethyl 2-(2-((5-(3-(aminomethyl)phenyl)-7-(cyclopropylmethoxy)benzofuran-3-yl)methoxy)-4-methoxyphenyl)acetate (160b)

Compound 160b was prepared according to the procedure reported in step-2 of scheme 1, from ethyl 2-(2-((5-bromo-7-(cyclopropylmethoxy)benzofuran-3-yl)methoxy)-4-methoxyphenyl)acetate (160a) (210 mg, 0.429 mmol) using (3-(aminomethyl)phenyl)boronic acid hydrochloride (1d) (101 mg, 0.536 mmol), 4 M solution of $K_3PO_4$ (0.429 mL, 1.717 mmol), tricyclohexylphosphine (24.07 mg, 0.086 mmol), $Pd_2(dba)_3$ (39.3 mg, 0.043 mmol) and heating at 105° C. for 3 h. This gave after workup and purification using flash column chromatography [silica gel (24 g), eluting with DMA-80 in DCM from 0-70%] ethyl 2-(2-((5-(3-(aminomethyl)phenyl)-7-(cyclopropylmethoxy)benzofuran-3-yl)methoxy)-4-methoxyphenyl)acetate (160b) (83 mg, 38% yield); $^1H$ NMR (300 MHz, DMSO-$d_6$) δ 8.08 (s, 1H), 7.68 (s, 1H), 7.57 (d, J=7.4 Hz, 1H), 7.46 (d, J=1.4 Hz, 1H), 7.40 (t, J=7.5 Hz, 1H), 7.33 (d, J=7.3 Hz, 1H), 7.17 (d, J=1.5 Hz, 1H), 7.09 (d, J=8.3 Hz, 1H), 6.81 (d, J=2.4 Hz, 1H), 6.50 (dd, J=8.3, 2.4 Hz, 1H), 5.27 (s, 2H), 4.12 (d, J=7.1 Hz, 2H), 3.89-3.68 (m, 7H), 3.47 (s, 2H), 1.39-1.27 (m, 1H), 0.89 (t, J=7.1 Hz, 3H), 0.69-0.57 (m, 2H), 0.40 (dd, J=4.7, 1.7 Hz, 2H); MS (ES+): 516.2 (M+1).

Step-3: Preparation of 2-(2-((5-(3-(aminomethyl)phenyl)-7-(cyclopropylmethoxy)benzofuran-3-yl)methoxy)-4-methoxyphenyl)acetic acid (160c)

Compound 160c was prepared according to the procedure reported in step-3 of scheme 1, from ethyl 2-(2-((5-(3-(aminomethyl)phenyl)-7-(cyclopropylmethoxy)benzofuran-3-yl)methoxy)-4-methoxyphenyl)acetate (160b) (81 mg, 0.157 mmol) in THF (1 mL) and acetonitrile (0.5 mL) using a 1N solution of lithium hydroxide monohydrate (0.471 mL, 0.471 mmol) and stirring for 25 h at RT. This gave after workup and purification using reverse phase column chromatography [C18 column (50 g), eluting with ACN in water (containing 0.1% HCl) from 0-100%] 2-(2-((5-(3-(aminomethyl)phenyl)-7-(cyclopropylmethoxy)benzofuran-3-yl)methoxy)-4-methoxyphenyl)acetic acid (160c) (47 mg, 61% yield) HCl salt as a white solid; $^1H$ NMR (300 MHz, DMSO-$d_6$) δ 12.06 (s, 1H, $D_2O$ exchangeable), 8.30 (s, 2H, $D_2O$ exchangeable), 8.09 (s, 1H), 7.87 (s, 1H), 7.80-7.68 (m, 1H), 7.61-7.40 (m, 3H), 7.23 (d, J=1.5 Hz, 1H), 7.10 (d, J=8.3 Hz, 1H), 6.79 (d, J=2.4 Hz, 1H), 6.51 (dd, J=8.3, 2.4 Hz, 1H), 5.29 (s, 2H), 4.18-4.06 (m, 4H), 3.76 (s, 3H), 3.45 (s, 2H), 1.42-1.26 (m, 1H), 0.70-0.56 (m, 2H), 0.47-0.32 (m, 2H). MS (ES+): 488.2 (M+1); (ES−): 486.2 (M−1); Analysis calculated for $C_{29}H_{29}NO_6H_2O\cdot HCl$: C, 64.26; H, 5.95; Cl, 6.54; N, 2.58. Found: C, 64.35; H, 5.83; Cl, 6.75; N, 2.67.

Scheme 161

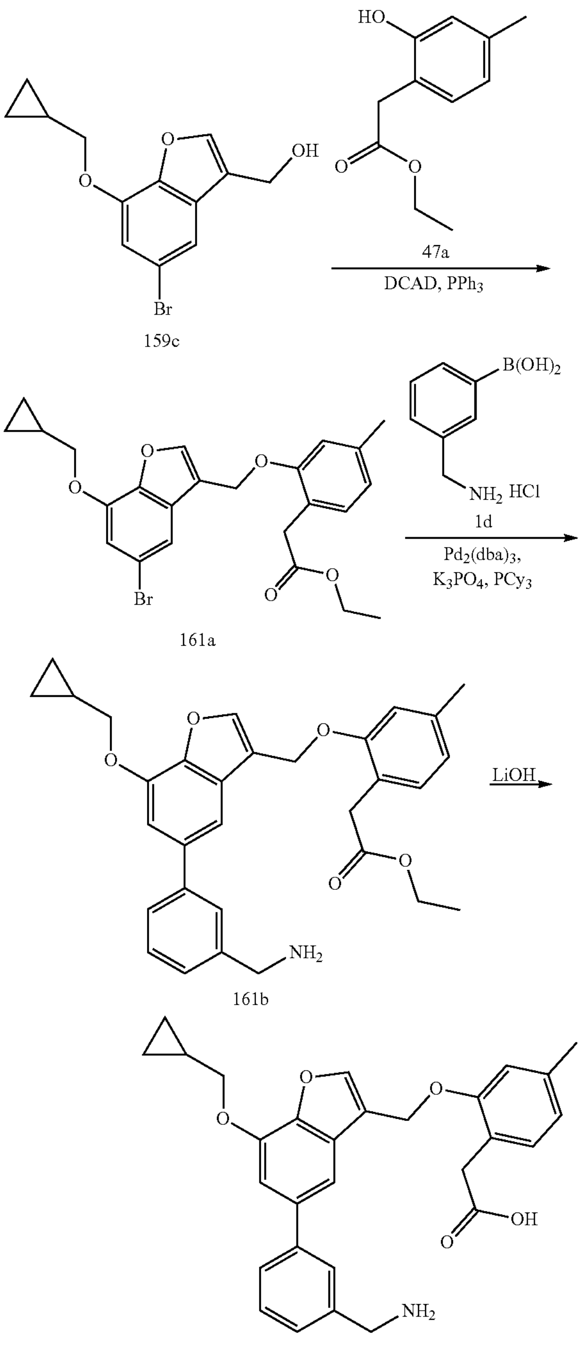

159c, 47a, 161a, 1d, 161b, 161c

Preparation of 2-(2-((5-(3-(aminomethyl)phenyl)-7-(cyclopropylmethoxy)benzofuran-3-yl)methoxy)-4-methylphenyl)acetic acid (161c)

Step-1: Preparation of ethyl 2-(2-((5-bromo-7-(cyclopropylmethoxy)benzofuran-3-yl)methoxy)-4-methylphenyl)acetate (161a)

Compound 161a was prepared according to the procedure reported in step-2 of scheme 65, from (5-bromo-7-(cyclopropylmethoxy)benzofuran-3-yl)methanol (159c) (300 mg, 1.01 mmol) in DCM (10 mL) using triphenylphosphine (305 mg, 1.161 mmol), ethyl 2-(2-hydroxy-4-methylphenyl)acetate (47a) (216 mg, 1.111 mmol), a solution of DCAD (426 mg, 1.161 mmol) in DCM (5 mL) at 0° C. and stirring at RT for 1 h. This gave after workup and purification using flash column chromatography [silica gel (24 g), eluting with EtOAc in hexane from 0-25%] ethyl 2-(2-((5-bromo-7-(cyclopropylmethoxy)benzofuran-3-yl)methoxy)-4-methylphenyl)acetate (161a) (340 mg, 71% yield) as a white solid; $^1$H NMR (300 MHz, DMSO-$d_6$) δ 8.09 (s, 1H), 7.39 (d, J=1.7 Hz, 1H), 7.13-7.05 (m, 2H), 7.02 (s, 1H), 6.74 (d, J=7.5 Hz, 1H), 5.19 (s, 2H), 4.04 (d, J=7.1 Hz, 2H), 3.95 (q, J=7.1 Hz, 2H), 3.50 (s, 2H), 2.32 (s, 3H), 1.37-1.26 (m, 1H), 1.01 (t, J=7.1 Hz, 3H), 0.66-0.53 (m, 2H), 0.46-0.25 (m, 2H); MS (ES+): 473.1 (M+1).

Step-2: Preparation of ethyl 2-(2-((5-(3-(aminomethyl)phenyl)-7-(cyclopropylmethoxy)benzofuran-3-yl)methoxy)-4-methylphenyl)acetate (161b)

Compound 161b was prepared according to the procedure reported in step-2 of scheme 1, from ethyl 2-(2-((5-bromo-7-(cyclopropylmethoxy)benzofuran-3-yl)methoxy)-4-methylphenyl)acetate (161a) (270 mg, 0.57 mmol) using (3-(aminomethyl)phenyl)boronic acid hydrochloride (1d) (134 mg, 0.713 mmol), 4 M solution of $K_3PO_4$ (0.570 mL, 2.282 mmol), tricyclohexylphosphine (48.0 mg, 0.171 mmol), $Pd_2(dba)_3$ (78 mg, 0.086 mmol) and heating at 115° C. for 3 h. This gave after workup and purification using flash column chromatography [silica gel (24 g), eluting with DMA-80 in DCM from 0-70%] ethyl 2-(2-((5-(3-(aminomethyl)phenyl)-7-(cyclopropylmethoxy)benzofuran-3-yl)methoxy)-4-methylphenyl)acetate (161b) (185 mg, 65% yield); $^1$H NMR (300 MHz, DMSO-$d_6$) δ 8.07 (s, 1H), 7.67 (s, 1H), 7.55 (d, J=7.5 Hz, 1H), 7.45 (d, J=1.4 Hz, 1H), 7.39 (t, J=7.5 Hz, 1H), 7.32 (d, J=7.5 Hz, 1H), 7.17 (d, J=1.5 Hz, 1H), 7.10-7.02 (m, 2H), 6.74 (d, J=7.6 Hz, 1H), 5.25 (s, 2H), 4.12 (d, J=7.1 Hz, 2H), 3.88-3.66 (m, 4H), 3.50 (s, 2H), 2.33 (s, 3H), 1.40-1.29 (m, 1H), 0.89 (t, J=7.1 Hz, 3H), 0.72-0.54 (m, 2H), 0.39 (dt, J=6.1, 3.0 Hz, 2H); MS (ES+): 500.20 (M+1).

Step-3: Preparation of 2-(2-((5-(3-(aminomethyl)phenyl)-7-(cyclopropylmethoxy)benzofuran-3-yl)methoxy)-4-methylphenyl)acetic acid (161c)

Compound 161c was prepared according to the procedure reported in step-3 of scheme 1, from ethyl 2-(2-((5-(3-(aminomethyl)phenyl)-7-(cyclopropylmethoxy)benzofuran-3-yl)methoxy)-4-methylphenyl)acetate (161b) (210 mg, 0.420 mmol) in THF (2.5 mL) and acetonitrile (1.25 mL) using a 1N solution of lithium hydroxide monohydrate (1.261 mL, 1.261 mmol) and stirring for 25 h at RT. This gave after workup and purification using reverse phase column chromatography [C18 column (50 g), eluting with ACN in water (containing 0.1% HCl) from 0-100%] 2-(2-((5-(3-(aminomethyl)phenyl)-7-(cyclopropylmethoxy)benzofuran-3-yl)methoxy)-4-methylphenyl)acetic acid (161c) (127 mg, 64% yield) HCl salt as a white solid; $^1$H NMR (300 MHz, DMSO-$d_6$) δ 12.08 (s, 1H, $D_2O$ exchangeable), 8.30 (s, 3H, $D_2O$ exchangeable), 8.09 (s, 1H), 7.87 (s, 1H), 7.76 (d, J=7.5 Hz, 1H), 7.57-7.41 (m, 3H), 7.23 (d, J=1.5 Hz, 1H), 7.13-7.02 (m, 2H), 6.80-6.69 (m, 1H), 5.28 (s, 2H), 4.20-4.06 (m, 4H), 3.48 (s, 2H), 2.32 (s, 3H), 1.44-1.23 (m, 1H), 0.70-0.57 (m, 2H), 0.44-0.34 (m, 2H). MS (ES+): 472.2 (M+1); (ES−): 470.2 (M−1); Analysis calculated for $C_{29}H_{29}NO_5 \cdot 0.5H_2O \cdot HCl$: C, 67.37; H, 6.04; Cl, 6.86; N, 2.71. Found: C, 67.25; H, 6.01; Cl, 7.05; N, 2.80.

Scheme 162

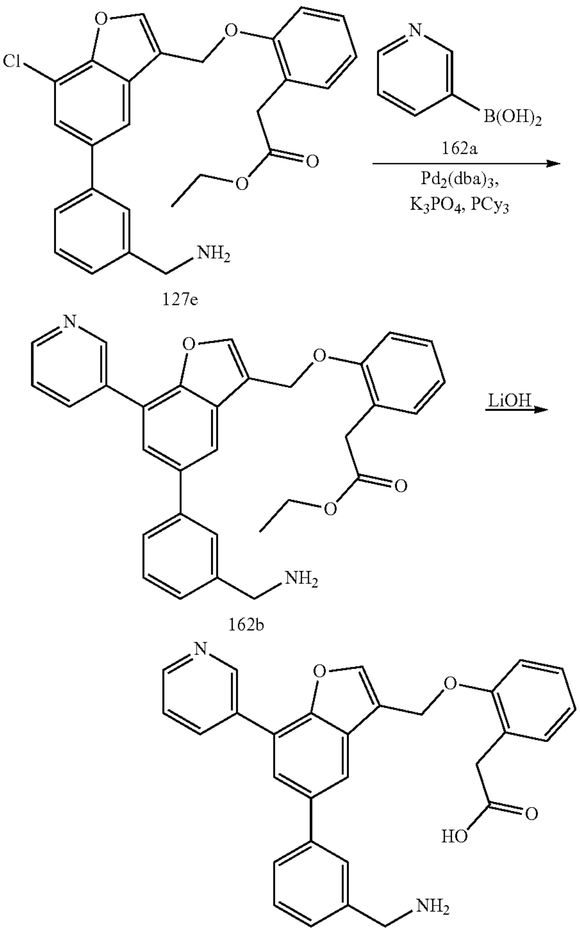

127e

162b

162c

Preparation of 2-(2-((5-(3-(aminomethyl)phenyl)-7-(pyridin-3-yl)benzofuran-3-yl)methoxy)phenyl)acetic acid (162c)

Step-1: Preparation of ethyl 2-(2-((5-(3-(aminomethyl)phenyl)-7-(pyridin-3-yl)benzofuran-3-yl)methoxy) phenyl)acetate (162b)

Compound 162b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (200 mg, 0.445 mmol) using pyridin-3-ylboronic acid (162a) (60.1 mg, 0.489 mmol), 4 M solution of $K_3PO_4$ (0.445 mL, 1.778 mmol), tricyclohexylphosphine (24.93 mg, 0.089 mmol), $Pd_2(dba)_3$ (40.7 mg, 0.044 mmol) and heating at 115° C. for 12 h. This gave after workup and purification using flash column chromatography [silica gel (24 g), eluting with DMA-80 in DCM from 0-50%] ethyl 2-(2-((5-(3-(aminomethyl)phenyl)-7-(pyridin-3-yl)benzofuran-3-yl)methoxy)phenyl)acetate (162b) (75 mg, 34% yield); MS (ES+): 493.20 (M+1).

Step-2: Preparation of 2-(2-((5-(3-(aminomethyl)phenyl)-7-(pyridin-3-yl)benzofuran-3-yl)methoxy)phenyl)acetic acid (162c)

Compound 162c was prepared according to the procedure reported in step-3 of scheme 1, from ethyl 2-(2-((5-(3-(aminomethyl)phenyl)-7-(pyridin-3-yl)benzofuran-3-yl)methoxy)phenyl)acetate (162b) (70 mg, 0.142 mmol) in THF (1 mL) and acetonitrile (0.5 mL) using a 1N solution of lithium hydroxide monohydrate (0.426 mL, 0.426 mmol) and stirring for 25 h at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(pyridin-3-yl)benzofuran-3-yl)methoxy)phenyl)acetic acid (162c) (23 mg, 35% yield) HCl salt as a white solid; $^1H$ NMR (300 MHz, DMSO-$d_6$) δ 9.29 (s, 1H), 8.77 (d, J=5.0 Hz, 1H), 8.62 (d, J=8.0 Hz, 1H), 8.36 (s, 3H, $D_2O$ exchangeable), 8.27 (s, 1H), 8.12 (d, J=1.7 Hz, 1H), 8.05-7.99 (m, 2H), 7.90 (d, J=7.7 Hz, 1H), 7.84-7.73 (m, 1H), 7.57 (t, J=7.6 Hz, 1H), 7.49 (d, J=7.6 Hz, 1H), 7.36-7.18 (m, 3H), 6.95 (td, J=7.1, 1.4 Hz, 1H), 5.39 (s, 2H), 4.19-4.07 (m, 2H), 3.57 (s, 2H). MS (ES+): 465.2 (M+1); (ES−): 463.2 (M−1).

Scheme 163

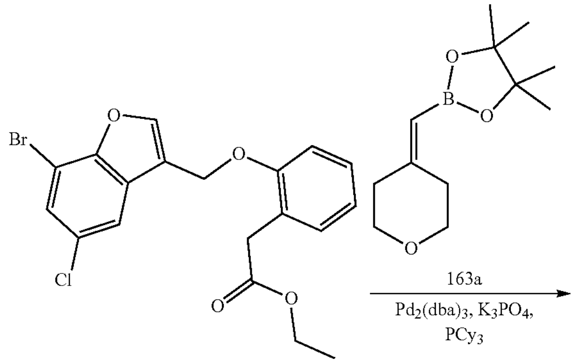

72e

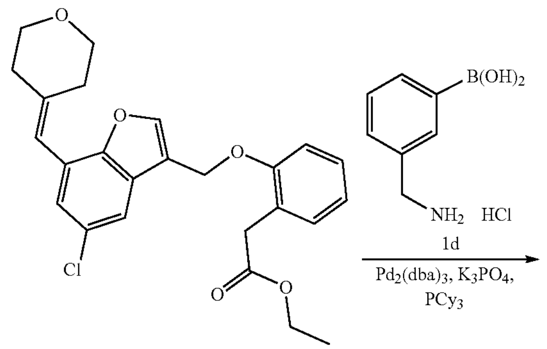

163b

-continued

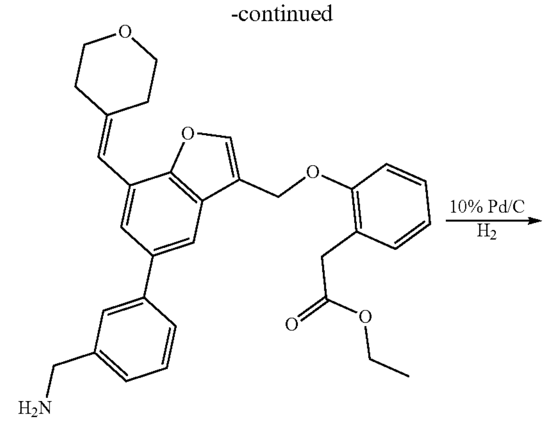

163c

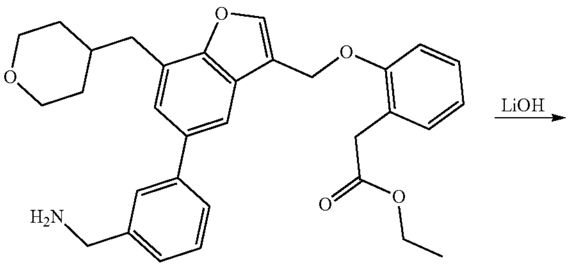

163d

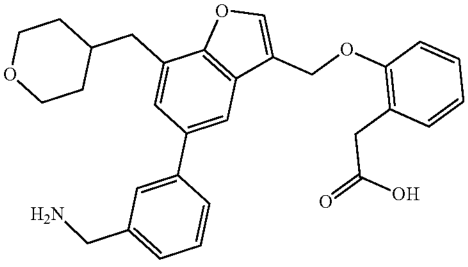

163e

Preparation of 2-(2-((5-(3-(aminomethyl)phenyl)-7-((tetrahydro-2H-pyran-4-yl)methyl)benzofuran-3-yl)methoxy)phenyl)acetic acid (163e)

Step-1: Preparation of ethyl 2-(2-((5-chloro-7-((dihydro-2H-pyran-4(3H)-ylidene)methyl)benzofuran-3-yl)methoxy)phenyl)acetate (163b)

Compound 163b was prepared according to the procedure reported in step-8 of scheme 3, from ethyl 2-(2-((7-bromo-5-chlorobenzofuran-3-yl)methoxy)phenyl)acetate (72e) (0.8 g, 1.888 mmol) in dioxane (30 mL) using 2-((dihydro-2H-pyran-4(3H)-ylidene)methyl)-4,4,5,5-tetramethyl-1,3,2-dioxaborolane (163a) (465 mg, 2.077 mmol; CAS #2304634-36-2), $Pd_2(dba)_3$ (173 mg, 0.189 mmol), $PCy_3$ (106 mg, 0.378 mmol), a 4M solution of $K_3PO_4$ (1.888 mL, 7.55 mmol) and heating at 80° C. for 2 h. This gave after workup and purification using flash column chromatography [silica gel (40 g), eluting with EtOAc in hexane from 0-100%] ethyl 2-(2-((5-chloro-7-((dihydro-2H-pyran-4(3H)-ylidene)methyl)benzofuran-3-yl)methoxy)phenyl)acetate (163b) (0.6 g, 72% yield) as a yellow oil; $^1H$ NMR (300 MHz, DMSO-$d_6$) δ 8.16 (s, 1H), 7.59 (d, J=2.1 Hz, 1H), 7.35-7.10 (m, 4H), 6.93 (td, J=7.4, 1.2 Hz, 1H), 6.48 (s, 1H), 5.24 (s, 2H), 3.93 (q, J=7.1 Hz, 2H), 3.71 (t, J=5.4 Hz, 2H), 3.64-3.51 (m, 4H), 2.40 (dt, J=17.9, 5.4 Hz, 4H), 0.98 (t, J=7.1 Hz, 3H); MS (ES+): 463.20 (M+Na).

Step-2: Preparation of ethyl 2-(2-((5-(3-(aminomethyl)phenyl)-7-((dihydro-2H-pyran-4(3H)-ylidene)methyl)benzofuran-3-yl)methoxy)phenyl)acetate (163c)

Compound 163c was prepared according to the procedure reported in step-2 of scheme 1, from ethyl 2-(2-((5-chloro-7-((dihydro-2H-pyran-4(3H)-ylidene)methyl)benzofuran-3-yl)methoxy)phenyl)acetate (163b) (200 mg, 0.454 mmol) in dioxane (15 mL) using (3-(aminomethyl)phenyl)boronic acid hydrochloride (1d) (102 mg, 0.544 mmol), 4 M solution of $K_3PO_4$ (0.454 mL, 1.814 mmol), tricyclohexylphosphine (25.4 mg, 0.091 mmol), $Pd_2(dba)_3$ (41.5 mg, 0.045 mmol) and heating at 115° C. for 12 h. This gave after workup and purification using flash column chromatography [silica gel (24 g), eluting with DMA-80 in DCM from 0-50%] ethyl 2-(2-((5-(3-(aminomethyl)phenyl)-7-((dihydro-2H-pyran-4(3H)-ylidene)methyl)benzofuran-3-yl)methoxy)phenyl)acetate (163c) (97 mg, 42% yield); MS (ES+): 512.3 (M+1).

Step-3: Preparation of ethyl 2-(2-((5-(3-(aminomethyl)phenyl)-7-((tetrahydro-2H-pyran-4-yl)methyl)benzofuran-3-yl)methoxy)phenyl)acetate (163d)

Compound 163d was prepared according to the procedure reported in step-3 of scheme 83, from ethyl 2-(2-((5-(3-(aminomethyl)phenyl)-7-((dihydro-2H-pyran-4(3H)-ylidene)methyl)benzofuran-3-yl)methoxy)phenyl)acetate (163c) (95 mg, 0.186 mmol) in EtOH (5 mL) using 10% palladium on carbon (20 mg) and hydrogen atmosphere for 4 h. This gave after work up ethyl 2-(2-((5-(3-(aminomethyl)phenyl)-7-((tetrahydro-2H-pyran-4-yl)methyl)benzofuran-3-yl)methoxy)phenyl)acetate (163d) (0.085 g, 89% yield) as a yellow oil; MS (ES+) 514.3 (M+1).

Step-4: Preparation of 2-(2-((5-(3-(aminomethyl)phenyl)-7-((tetrahydro-2H-pyran-4-yl)methyl)benzofuran-3-yl)methoxy)phenyl)acetic acid (163e)

Compound 163e was prepared according to the procedure reported in step-3 of scheme 1, from ethyl 2-(2-((5-(3-(aminomethyl)phenyl)-7-((tetrahydro-2H-pyran-4-yl)methyl)benzofuran-3-yl)methoxy)phenyl)acetate (163d) (80 mg, 0.156 mmol) in THF (1 mL) and acetonitrile (0.5 mL) using 1N solution of lithium hydroxide hydrate (0.467 mL, 0.467 mmol) and stirring for 25 h at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-((tetrahydro-2H-pyran-4-yl)methyl)benzofuran-3-yl)methoxy)phenyl)acetic acid (163e) (45 mg, 60% yield) HCl salt as a white solid; $^1H$ NMR (300 MHz, DMSO-$d_6$) δ 12.14 (s, 1H, $D_2O$ exchangeable), 8.24 (s, 3H, $D_2O$ exchangeable), 8.13 (s, 1H), 7.85 (d, J=1.8 Hz, 2H), 7.75 (d, J=7.7 Hz, 1H), 7.58-7.40 (m, 3H), 7.32-7.17 (m, 3H), 6.97-6.89 (m, 1H), 5.31 (s, 2H), 4.13 (s, 2H), 3.90-3.74 (m, 2H), 3.55 (s, 2H), 3.25 (t, J=11.6 Hz, 2H), 2.87 (d, J=7.2 Hz, 2H), 2.29-1.69 (m, 1H), 1.53 (d, J=12.8 Hz, 2H), 1.40-1.17 (m, 2H); MS (ES+): 486.2 (M+1); (ES−): 484.2 (M−1); Analysis calculated for $C_{30}H_{31}NO_5 \cdot H_2O \cdot HCl$: C, 66.72; H, 6.35; Cl, 6.56; N, 2.59. Found: C, 66.94; H, 6.24; Cl, 6.45; N, 2.61.

Scheme 164

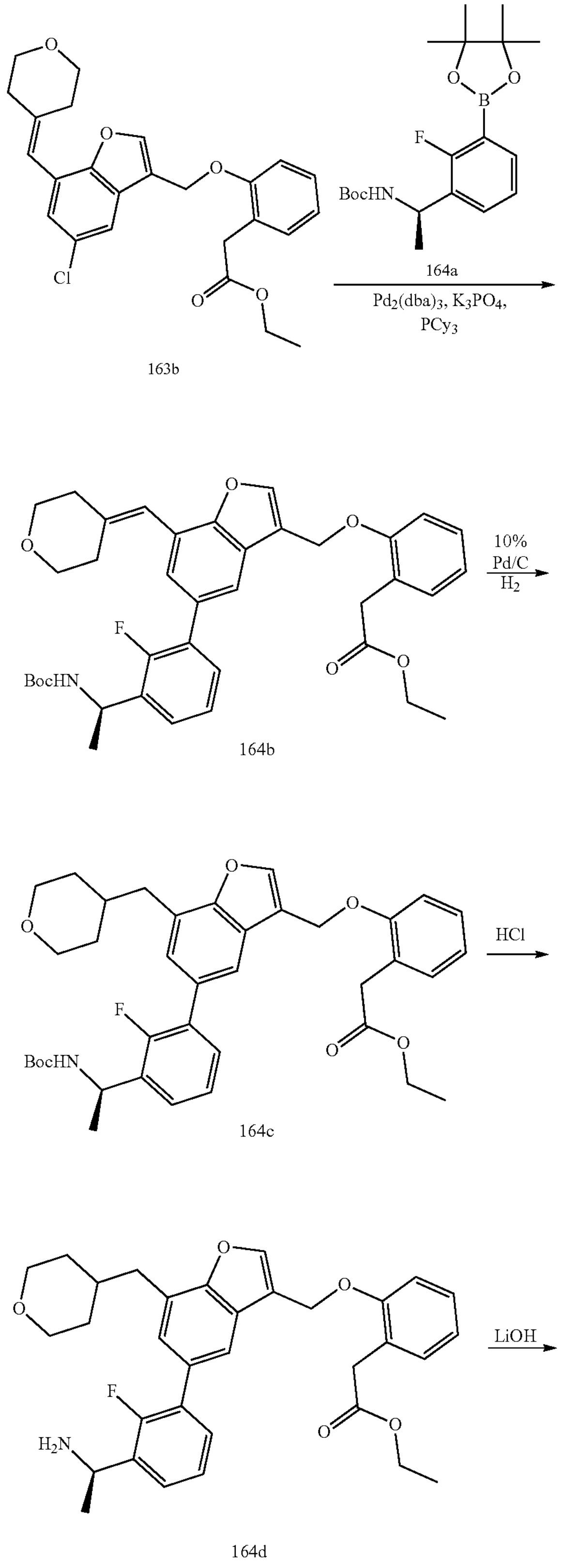

-continued

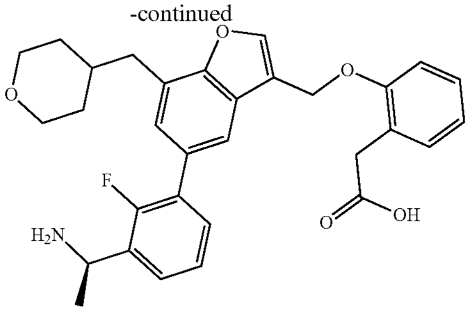

164e

Preparation of (R)-2-(2-((5-(3-(1-aminoethyl)-2-fluorophenyl)-7-((tetrahydro-2H-pyran-4-yl)methyl) benzofuran-3-yl)methoxy)phenyl)acetic acid (164e)

Step-1: Preparation of (R)-ethyl 2-(2-((5-(3-(1-((tert-butoxycarbonyl)amino)ethyl)-2-fluorophenyl)-7-((dihydro-2H-pyran-4(3H)-ylidene)methyl)benzofuran-3-yl)methoxy)phenyl)acetate (164b)

Compound 164b was prepared according to the procedure reported in step-2 of scheme 1, from ethyl 2-(2-((5-chloro-7-((dihydro-2H-pyran-4(3H)-ylidene)methyl)benzofuran-3-yl)methoxy)phenyl)acetate (163b) (200 mg, 0.454 mmol) in dioxane (15 mL) using (R)-tert-butyl (1-(2-fluoro-3-(4,4,5,5-tetramethyl-1,3,2-dioxaborolan-2-yl)phenyl)ethyl)carbamate (164a) (207 mg, 0.567 mmol; CAS #1646556-74-2), 4 M solution of $K_3PO_4$ (0.454 mL, 1.814 mmol), tricyclohexylphosphine (25.4 mg, 0.091 mmol), $Pd_2(dba)_3$ (41.5 mg, 0.045 mmol) and heating at 115° C. for 12 h. This gave after workup and purification using flash column chromatography [silica gel (24 g), eluting with EtOAc in hexane from 0-100%](R)-ethyl 2-(2-((5-(3-(1-((tert-butoxycarbonyl)amino)ethyl)-2-fluorophenyl)-7-((dihydro-2H-pyran-4(3H)-ylidene)methyl)benzofuran-3-yl)methoxy)phenyl)acetate (164b) (225 mg, 77% yield); $^1H$ NMR (300 MHz, DMSO-$d_6$) δ 8.15 (s, 1H), 7.68 (s, 1H), 7.57 (d, J=8.1 Hz, 1H), 7.49-7.34 (m, 2H), 7.34-7.15 (m, 5H), 6.92 (td, J=7.3, 1.3 Hz, 1H), 6.57 (s, 1H), 5.28 (s, 2H), 5.06-4.87 (m, 1H), 3.78-3.51 (m, 8H), 2.45 (d, J=5.1 Hz, 4H), 1.42-1.29 (m, 12H), 0.86 (t, J=7.1 Hz, 3H); MS (ES+): 544.20 (M−Boc+2); Optical rotation: $[\alpha]_D$ (+) 8.608 [$CH_3OH$, 0.395].

Step-2: Preparation of (R)-ethyl 2-(2-((5-(3-(1-((tert-butoxycarbonyl)amino)ethyl)-2-fluorophenyl)-7-((tetrahydro-2H-pyran-4-yl)methyl)benzofuran-3-yl)methoxy)phenyl)acetate (164c)

Compound 164c was prepared according to the procedure reported in step-3 of scheme 83, from (R)-ethyl 2-(2-((5-(3-(1-((tert-butoxycarbonyl)amino)ethyl)-2-fluorophenyl)-7-((dihydro-2H-pyran-4(3H)-ylidene)methyl)benzofuran-3-yl)methoxy)phenyl)acetate (164b) (210 mg, 0.326 mmol) in EtOH (5 mL) using 10% palladium on carbon (50 mg) under hydrogen atmosphere for 4 h. This gave after work up (R)-ethyl 2-(2-((5-(3-(1-((tert-butoxycarbonyl)amino)ethyl)-2-fluorophenyl)-7-((tetrahydro-2H-pyran-4-yl)methyl)benzofuran-3-yl)methoxy)phenyl)acetate (164c) (0.201 g, 95% yield) as a yellow oil; MS (ES+): 546.30 (M−Boc+2).

Step-3: Preparation of (R)-ethyl 2-(2-((5-(3-(1-aminoethyl)-2-fluorophenyl)-7-((tetrahydro-2H-pyran-4-yl)methyl)benzofuran-3-yl)methoxy)phenyl)acetate (164d)

Compound 164d was prepared according to the procedure reported in step-2 of scheme 7, from (R)-ethyl 2-(2-((5-(3-(1-((tert-butoxycarbonyl)amino)ethyl)-2-fluorophenyl)-7-((tetrahydro-2H-pyran-4-yl)methyl)benzofuran-3-yl) methoxy)phenyl)acetate (164c) (190 mg, 0.294 mmol) using HCl (4M HCl in dioxane) (0.368 mL, 1.471 mmol) in EtOH (3 mL) and stirring the reaction mixture at RT for 4 h. This gave after workup and purification using flash column chromatography [silica gel (24 g), eluting with DMA-80 in DCM from 0-100%](R)-ethyl 2-(2-((5-(3-(1-aminoethyl)-2-fluorophenyl)-7-((tetrahydro-2H-pyran-4-yl)methyl)benzofuran-3-yl)methoxy)phenyl)acetate (164d) (90 mg, 56% yield) as a white solid; $^1H$ NMR (300 MHz, DMSO-$d_6$) δ 8.15 (s, 1H), 7.64 (d, J=1.5 Hz, 1H), 7.61-7.52 (m, 1H), 7.44-7.33 (m, 1H), 7.33-7.15 (m, 5H), 6.98-6.86 (m, 1H), 5.27 (s, 2H), 4.34 (q, J=6.7 Hz, 1H), 3.80 (d, J=3.7 Hz, 2H), 3.71 (q, J=7.1 Hz, 2H), 3.55 (s, 2H), 3.30-3.18 (m, 2H), 2.85 (d, J=7.2 Hz, 2H), 1.91 (s, 1H), 1.52 (d, J=12.9 Hz, 2H), 1.39-1.19 (m, 5H), 0.85 (t, J=7.1 Hz, 3H); MS (ES+): 546.30 (M+1).

Step-4: Preparation of (R)-2-(2-((5-(3-(1-aminoethyl)-2-fluorophenyl)-7-((tetrahydro-2H-pyran-4-yl)methyl)benzofuran-3-yl)methoxy)phenyl)acetic acid (164e)

Compound 164e was prepared according to the procedure reported in step-3 of scheme 1, from (R)-ethyl 2-(2-((5-(3-(1-aminoethyl)-2-fluorophenyl)-7-((tetrahydro-2H-pyran-4-yl)methyl)benzofuran-3-yl)methoxy)phenyl)acetate (164d) (80 mg, 0.147 mmol) in THF (1 mL) and acetonitrile (0.5 mL) using a 1N solution of lithium hydroxide hydrate (0.440 mL, 0.440 mmol) and stirring for 25 h at RT. This gave after workup and purification using reverse phase column chromatography [C18 column (30 g), eluting with ACN in water (containing 0.1% HCl) from 0-100%](R)-2-(2-((5-(3-(1-aminoethyl)-2-fluorophenyl)-7-((tetrahydro-2H-pyran-4-yl) methyl)benzofuran-3-yl)methoxy)phenyl)acetic acid (164e) (65 mg, 86% yield) HCl salt as a white solid; $^1H$ NMR (300 MHz, DMSO-$d_6$) δ 8.15 (s, 1H), 7.72 (s, 1H), 7.68-7.55 (m, 2H), 7.41 (t, J=7.7 Hz, 1H), 7.35 (s, 1H), 7.31-7.16 (m, 3H), 6.98-6.87 (m, 1H), 5.30 (s, 2H), 4.71 (q, J=6.8 Hz, 1H), 3.82 (dd, J=10.9, 3.9 Hz, 2H), 3.54 (s, 2H), 3.27-3.15 (m, 2H), 2.86 (d, J=7.1 Hz, 2H), 2.03-1.85 (m, 1H), 1.64-1.43 (m, 5H), 1.39-1.19 (m, 2H); $^{19}F$ NMR (282 MHz, DMSO-$d_6$) δ −123.48; MS (ES+): 518.2 (M+1); (ES−): 516.2 (M−1); Analysis calculated for $C_{31}H_{32}FNO_5 \cdot 0.75H_2O \cdot 1.1HCl$: C, 65.18; H, 6.11; Cl, 6.83; N, 2.45. Found: C, 65.17; H, 6.2; Cl, 6.80; N, 2.53; Optical rotation: $[\alpha]_D$=(+) 9.2 [$CH_3OH$, 0.5].

Scheme 165

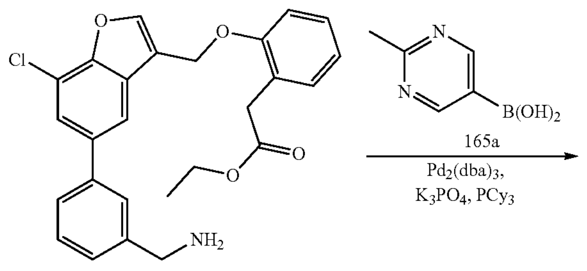

127e

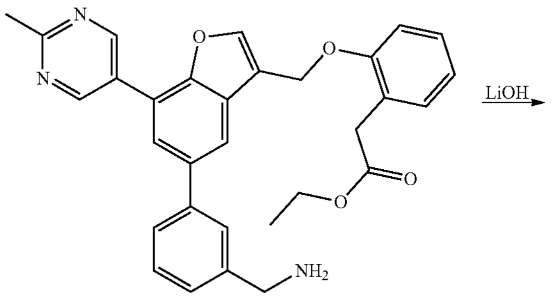

165b

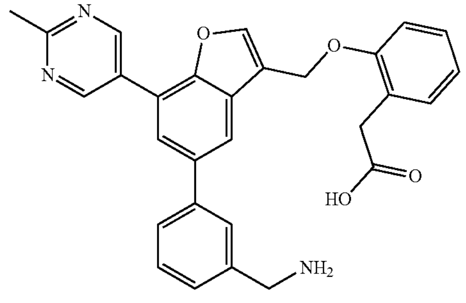

165c

Preparation of 2-(2-((5-(3-(aminomethyl)phenyl)-7-(2-methylpyrimidin-5-yl)benzofuran-3-yl)methoxy)phenyl)acetic acid (165c)

Step-1: Preparation of ethyl 2-(2-((5-(3-(aminomethyl)phenyl)-7-(2-methylpyrimidin-5-yl)benzofuran-3-yl)methoxy)phenyl)acetate (165b)

Compound 165b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (200 mg, 0.445 mmol) in dioxane (15 mL) using (2-methylpyrimidin-5-yl)boronic acid (165a) (67.4 mg, 0.489 mmol; CAS #1034924-06-5), 4 M solution of $K_3PO_4$ (0.454 mL, 1.778 mmol), tricyclohexylphosphine (24.93 mg, 0.089 mmol), $Pd_2(dba)_3$ (40.7 mg, 0.044 mmol) and heating at 115° C. for 12 h. This gave after workup and purification using flash column chromatography [silica gel (40 g), eluting with DMA-80 in DCM from 0-50%] ethyl 2-(2-((5-(3-(aminomethyl)phenyl)-7-(2-methylpyrimidin-5-yl)benzofuran-3-yl)methoxy)phenyl)acetate (165b) (121 mg, 54% yield); MS (ES+): 508.2 (M+1).

Step-2: Preparation of 2-(2-((5-(3-(aminomethyl)phenyl)-7-(2-methylpyrimidin-5-yl)benzofuran-3-yl)methoxy)phenyl)acetic acid (165c)

Compound 165c was prepared according to the procedure reported in step-3 of scheme 1, from ethyl 2-(2-((5-(3-(aminomethyl)phenyl)-7-(2-methylpyrimidin-5-yl)benzofuran-3-yl)methoxy)phenyl)acetate (165b) (125 mg, 0.246 mmol) in THF (1.5 mL) and acetonitrile (0.75 mL) using a 1N solution of lithium hydroxide hydrate (0.739 mL, 0.739 mmol) and stirring for 25 h at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(2-methylpyrimidin-5-yl)benzofuran-3-yl)methoxy)phenyl)acetic acid (165c) (37 mg, 31% yield) HCl salt as a white solid; $^1H$ NMR (300 MHz, DMSO-$d_6$) δ 9.30 (s, 2H), 8.48 (s, 1H), 8.30 (s, 1H), 8.15 (d, J=1.7 Hz, 1H), 7.99 (d, J=1.8 Hz, 1H), 7.89 (d, J=7.7 Hz, 1H), 7.46 (t, J=7.6 Hz, 1H), 7.36-7.31 (m, 1H), 7.22-7.08 (m, 3H), 6.88 (t, J=7.2 Hz, 1H), 5.26 (s, 2H), 4.06 (s, 2H), 3.36 (s, 2H), 2.73 (s, 3H); MS (ES+): 480.2 (M+1); (ES−): 478.2 (M−1); Analysis calculated for $C_{29}H_{25}N_3O_4 \cdot 1.5H_2O \cdot 1.65HCl$: C, 61.46; H, 5.27; Cl, 10.32; N, 7.41. Found: C, 61.18; H, 5.25; Cl, 10.14; N, 7.43.

Scheme 166

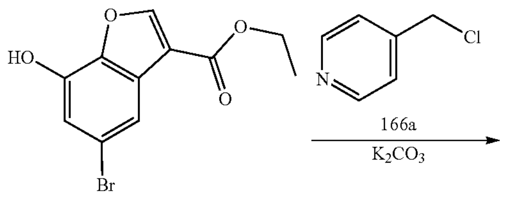

76c

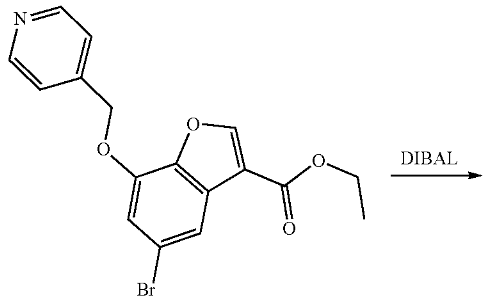

166b

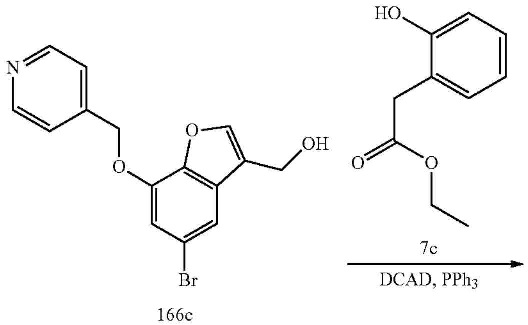

166c

-continued

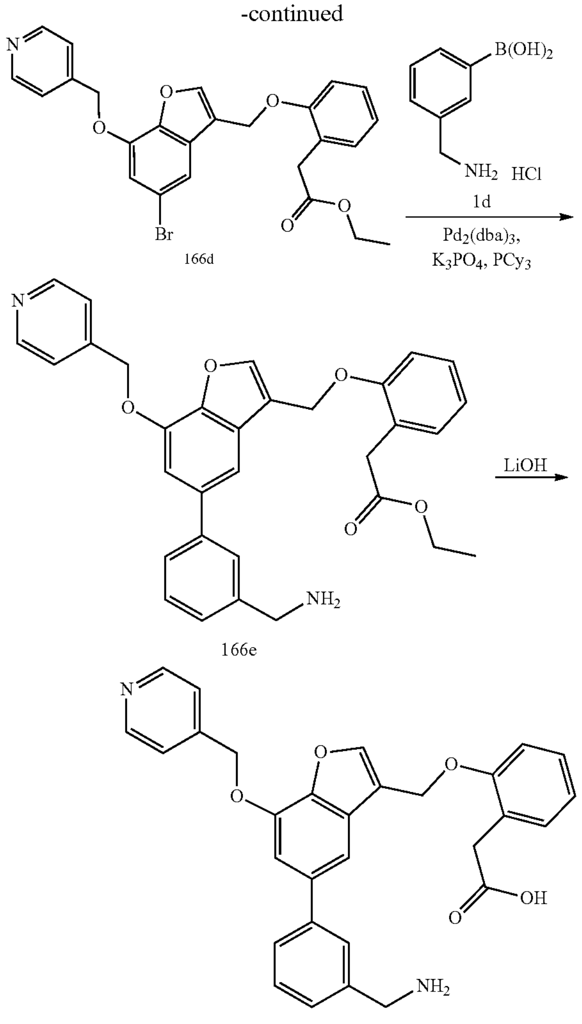

166d

166e

166f

Preparation of 2-(2-((5-(3-(aminomethyl)phenyl)-7-(pyridin-4-ylmethoxy)benzofuran-3-yl)methoxy)phenyl)acetic acid (166f)

Step-1: Preparation of ethyl 5-bromo-7-(pyridin-4-ylmethoxy)benzofuran-3-carboxylate (166b)

Compound 166b was prepared according to the procedure reported in step-1 of scheme 58, from HCl salt of 4-(chloromethyl)pyridine (166a) (288 mg, 1.754 mmol) using $K_2CO_3$ (727 mg, 5.26 mmol) in DMF (5 mL) and stirring at RT for 14 h. This gave after workup ethyl 5-bromo-7-(pyridin-4-ylmethoxy)benzofuran-3-carboxylate (166b) (447 mg, 68% yield) as a pale brown solid; $^1$H NMR (300 MHz, DMSO-$d_6$) δ 8.83 (s, 1H), 8.67-8.58 (m, 2H), 7.69 (d, J=1.7 Hz, 1H), 7.53-7.44 (m, 2H), 7.35 (d, J=1.8 Hz, 1H), 5.44 (s, 2H), 4.36 (q, J=7.1 Hz, 2H), 1.35 (t, J=7.1 Hz, 3H); MS (ES+): 376.1 (M+1).

Step-2: Preparation of ((5-bromo-7-(pyridin-4-ylmethoxy)benzofuran-3-yl)methanol (166c)

Compound 166c was prepared according to the procedure reported in step-2 of scheme 69, from ethyl 5-bromo-7-(pyridin-4-ylmethoxy)benzofuran-3-carboxylate (166b) (420 mg, 1.116 mmol) in DCM (1.86 mL) using 1.0 M solution of DIBAL in DCM (2.79 mL, 2.79 mmol) and stirring at 0° C. for 4 h. This gave after workup and purification by flash column chromatography [silica gel (12 g), eluting with EtOAc in hexane from 0-50%]((5-bromo-7-(pyridin-4-ylmethoxy)benzofuran-3-yl)methanol (166c) (0.22 g, 59% yield); $^1$H NMR (300 MHz, DMSO-$d_6$) δ 8.63-8.59 (m, 2H), 7.94 (d, J=1.3 Hz, 1H), 7.54-7.45 (m, 3H), 7.20 (d, J=1.8 Hz, 1H), 5.41 (s, 2H), 5.23 (t, J=5.6 Hz, 1H), 4.59 (dd, J=5.6, 1.1 Hz, 2H); MS (ES+): 334.0 (M+1).

Step-3: Preparation of ethyl 2-(2-((5-bromo-7-(pyridin-4-ylmethoxy)benzofuran-3-yl)methoxy)phenyl) acetate (166d)

Compound 166d was prepared according to the procedure reported in step-2 of scheme 65, from ((5-bromo-7-(pyridin-4-ylmethoxy)benzofuran-3-yl)methanol (166c) (210 mg, 0.628 mmol) in DCM (5 mL) using triphenylphosphine (190 mg, 0.723 mmol), ethyl 2-(2-hydroxyphenyl)acetate (7c) (125 mg, 0.691 mmol), a solution of DCAD (265 mg, 0.723 mmol) in DCM (5 mL) at 0° C. and stirring at RT for 1 h. This gave after workup and purification using flash column chromatography [silica gel (40 g), eluting with EtOAc in hexane from 0-25%] ethyl 2-(2-((5-bromo-7-(pyridin-4-ylmethoxy)benzofuran-3-yl)methoxy)phenyl)acetate (166d) (305 mg, 98% yield) as a white solid; $^1$H NMR (300 MHz, DMSO-$d_6$) δ 8.66-8.57 (m, 2H), 8.15 (s, 1H), 7.52-7.44 (m, 3H), 7.33-7.25 (m, 1H), 7.25-7.16 (m, 3H), 6.93 (td, J=7.4, 1.1 Hz, 1H), 5.43 (s, 2H), 5.23 (s, 2H), 3.94 (q, J=7.1 Hz, 2H), 3.56 (s, 2H), 0.99 (t, J=7.1 Hz, 3H); MS (ES+): 496.1 (M+1).

Step-4: Preparation of ethyl 2-(2-((5-(3-(aminomethyl)phenyl)-7-(pyridin-4-ylmethoxy)benzofuran-3-yl)methoxy)phenyl)acetate (166e)

Compound 166e was prepared according to the procedure reported in step-2 of scheme 1, from ethyl 2-(2-((5-bromo-7-(pyridin-4-ylmethoxy)benzofuran-3-yl)methoxy)phenyl) acetate (166d) (280 mg, 0.564 mmol) using (3-(aminomethyl)phenyl)boronic acid hydrochloride (1d) (132 mg, 0.705 mmol), 4 M solution of $K_3PO_4$ (0.564 mL, 2.256 mmol), tricyclohexylphosphine (31.6 mg, 0.113 mmol), $Pd_2(dba)_3$ (51.7 mg, 0.056 mmol) and heating at 95° C. for 2 h. This gave after workup and purification using flash column chromatography [silica gel (24 g), eluting with DMA-80 in DCM from 0-50%] ethyl 2-(2-((5-(3-(aminomethyl)phenyl)-7-(pyridin-4-ylmethoxy)benzofuran-3-yl) methoxy)phenyl)acetate (166e) (90 mg, 31% yield); MS (ES+): 523.2 (M+1).

Step-5: Preparation of 2-(2-((5-(3-(aminomethyl) phenyl)-7-(pyridin-4-ylmethoxy)benzofuran-3-yl) methoxy)phenyl)acetic acid (166f)

Compound 166f was prepared according to the procedure reported in step-3 of scheme 1, from ethyl 2-(2-((5-(3-(aminomethyl)phenyl)-7-(pyridin-4-ylmethoxy)benzofuran-3-yl)methoxy)phenyl)acetate (166e) (87 mg, 0.166 mmol) in THF (1 mL) and acetonitrile (0.5 mL) using a 1N solution of lithium hydroxide hydrate (0.499 mL, 0.499 mmol) and stirring for 25 h at RT. This gave after workup and purification using reverse phase column chromatography [C18 column (50 g), eluting with ACN in water (containing 0.1% HCl) from 0-100%] 2-(2-((5-(3-(aminomethyl)phenyl)-7-(pyridin-4-ylmethoxy)benzofuran-3-yl)methoxy)phenyl)

acetic acid (166f) (49 mg, 60% yield) HCl salt as a white solid; $^1$H NMR (300 MHz, DMSO-$d_6$) δ 8.89-8.75 (m, 2H), 8.44 (s, 3H, $D_2O$ exchangeable), 8.16 (s, 1H), 8.01-7.87 (m, 3H), 7.80-7.72 (m, 1H), 7.66 (d, J=1.4 Hz, 1H), 7.57-7.40 (m, 3H), 7.34-7.19 (m, 3H), 6.94 (td, J=7.3, 1.2 Hz, 1H), 5.74 (s, 2H), 5.32 (s, 2H), 4.15-4.07 (m, 2H), 3.55 (s, 2H); MS (ES+): 495.2 (M+1); (ES−): 493.2 (M−1); Analysis calculated for $C_{30}H_{26}N_2O_5 \cdot 2.25H_2O \cdot 2HCl$: C, 59.26; H, 5.39; Cl, 11.66; N, 4.61. Found: C, 59.32; H, 5.26; Cl, 11.77; N, 4.65.

Scheme 167

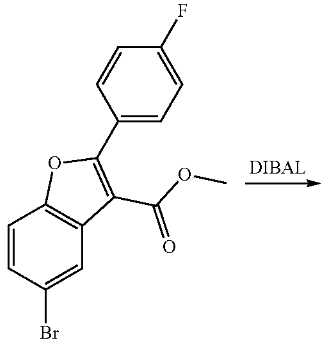

167a

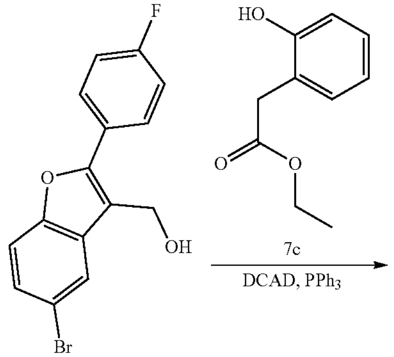

167b

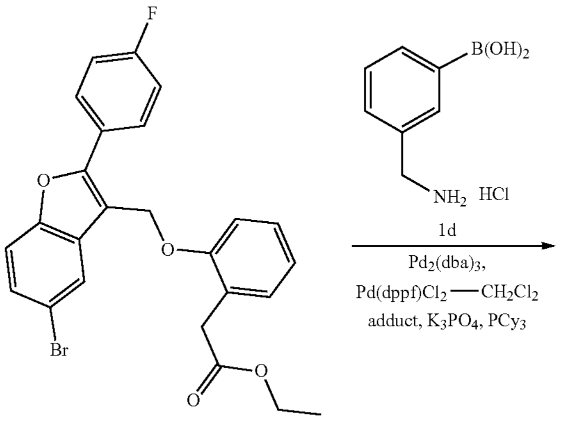

167c

-continued

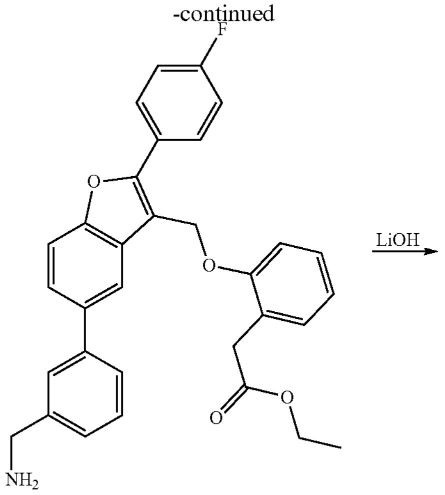

167d

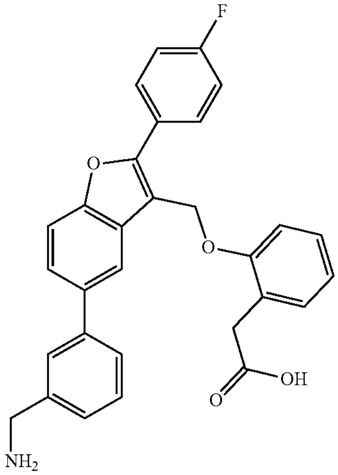

167e

Preparation of 2-(2-((5-(3-(aminomethyl)phenyl)-2-(4-fluorophenyl)benzofuran-3-yl)methoxy)phenyl) acetic acid (167e)

Step-1: Preparation of (5-bromo-2-(4-fluorophenyl) benzofuran-3-yl)methanol (167b)

Compound 167b was prepared according to the procedure reported in step-2 of scheme 69, from methyl 5-bromo-2-(4-fluorophenyl)benzofuran-3-carboxylate (167a) (1.5 g, 4.30 mmol; CAS #1333225-31-2) in THF (40 mL) using 1.0 M solution of DIBAL in THF (10.74 mL, 10.74 mmol) and stirring at 0° C. for 2 h. This gave after workup and purification using flash column chromatography [silica gel (24 g), eluting with EtOAc in hexane from 0-100%] (5-bromo-2-(4-fluorophenyl)benzofuran-3-yl)methanol (167b) (1.01 g, 73% yield); $^1$H NMR (300 MHz, DMSO-$d_6$) δ 7.98 (d, J=2.0 Hz, 1H), 7.95-7.88 (m, 2H), 7.61 (d, J=8.7 Hz, 1H), 7.51-7.38 (m, 3H), 5.43 (t, J=5.5 Hz, 1H), 4.73 (d, J=5.4 Hz, 2H); $^{19}$F NMR (282 MHz, DMSO-$d_6$) δ −111.41.

Step-2: Preparation of ethyl 2-(2-((5-bromo-2-(4-fluorophenyl)benzofuran-3-yl)methoxy)phenyl)acetate (167c)

Compound 167c was prepared according to the procedure reported in step-2 of scheme 65, from (5-bromo-2-(4-fluorophenyl)benzofuran-3-yl)methanol (167b) (450 mg, 1.401 mmol) in DCM (15 mL) using triphenylphosphine (404 mg, 1.541 mmol), ethyl 2-(2-hydroxyphenyl)acetate (7c) (278 mg, 1.541 mmol), a solution of DCAD (566 mg, 1.541 mmol) in DCM (10 mL) and stirring at RT for 30 min. This gave after workup and purification using flash column chromatography [silica gel (40 g), eluting with EtOAc in hexane from 0-50%] ethyl 2-(2-((5-bromo-2-(4-fluorophenyl)benzofuran-3-yl)methoxy)phenyl)acetate (167c) (537 mg, 79% yield) as a white solid; $^1$H NMR (300 MHz, DMSO-$d_6$) δ 7.96 (d, J=2.0 Hz, 1H), 7.89-7.81 (m, 2H), 7.66 (d, J=8.7 Hz, 1H), 7.53 (dd, J=8.7, 2.0 Hz, 1H), 7.45-7.37 (m, 2H), 7.34-7.27 (m, 1H), 7.22 (d, J=7.5, 1.5 Hz, 2H), 6.96 (t, J=7.3, 1.2 Hz, 1H), 5.33 (s, 2H), 3.79 (q, J=7.1 Hz, 2H), 3.50 (s, 2H), 0.85 (t, J=7.1 Hz, 3H); $^{19}$F NMR (282 MHz, DMSO) δ −110.62; MS (ES+): 505.0 and 507.0 (M+Na).

Step-3: Preparation of ethyl 2-(2-((5-(3-(aminomethyl)phenyl)-2-(4-fluorophenyl)benzofuran-3-yl)methoxy)phenyl)acetate (167d)

Compound 167d was prepared according to the procedure reported in step-2 of scheme 1, from ethyl 2-(2-((5-bromo-2-(4-fluorophenyl)benzofuran-3-yl)methoxy)phenyl)acetate (167c) (500 mg, 1.034 mmol) in dioxane (20 mL) using (3-(aminomethyl)phenyl)boronic acid hydrochloride (1d) (388 mg, 2.069 mmol), 4 M solution of $K_3PO_4$ (1.034 mL, 4.14 mmol), tricyclohexylphosphine (87 mg, 0.310 mmol), $Pd_2(dba)_3$ (95 mg, 0.103 mmol), $PdCl_2(dppf)$-$CH_2Cl_2$-adduct (84 mg, 0.103 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(4-fluorophenyl)benzofuran-3-yl)methoxy)phenyl)acetate (167d) (268 mg, 51% yield) as a yellow oil; MS (ES+): 510.2 (M+1); (ES−): 508.2 (M−1).

Step-4: Preparation of 2-(2-((5-(3-(aminomethyl)phenyl)-2-(4-fluorophenyl)benzofuran-3-yl)methoxy)phenyl)acetic acid (167e)

Compound 167e was prepared according to the procedure reported in step-3 of scheme 1, from ethyl 2-(2-((5-(3-(aminomethyl)phenyl)-2-(4-fluorophenyl)benzofuran-3-yl)methoxy)phenyl)acetate (167d) (168 mg, 0.33 mmol) in THF (3 mL) using lithium hydroxide hydrate (130 mg, 3.1 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(4-fluorophenyl)benzofuran-3-yl)methoxy)phenyl)acetic acid (167e) (58 mg, 12% yield) HCl salt as a white solid; $^1$H NMR (300 MHz, DMSO-$d_6$) δ 12.05 (s, 1H, $D_2O$ exchangeable), 8.51 (s, 2H, $D_2O$ exchangeable), 8.10 (d, J=1.7 Hz, 1H), 7.98-7.85 (m, 3H), 7.83-7.67 (m, 3H), 7.56-7.45 (m, 2H), 7.40 (t, J=8.9 Hz, 2H), 7.33-7.17 (m, 3H), 7.01-6.89 (m, 1H), 5.39 (s, 2H), 4.10 (s, 2H), 3.48 (s, 2H); $^{19}$F NMR (282 MHz, DMSO-$d_6$) δ −111.05; MS (ES+): 482.1 (M+1); (ES−): 480.1 (M+1); Analysis calculated for $C_{30}H_{24}FNO_4 \cdot HCl \cdot 0.5H_2O$: C, 68.37; H, 4.97; Cl, 6.73; N, 2.66. Found: C, 68.56; H, 4.84; Cl, 6.95; N, 2.73.

Scheme 168

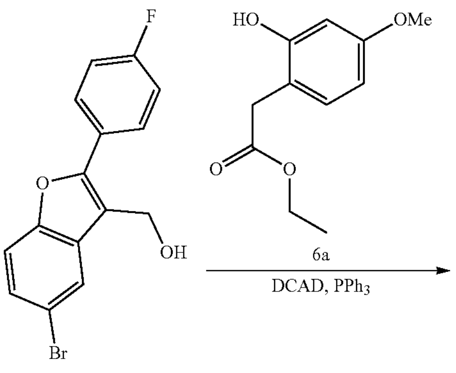

167b

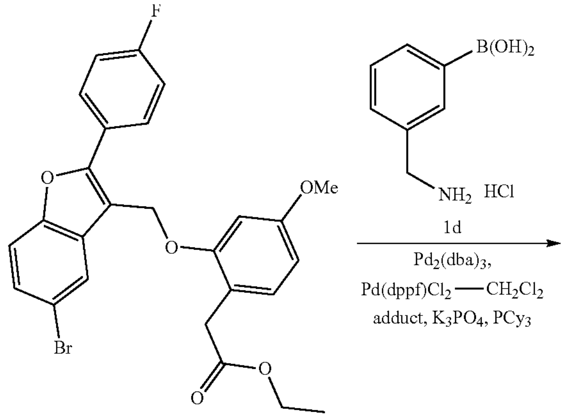

168a

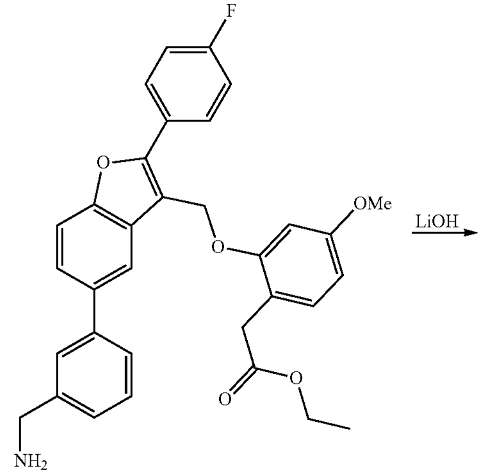

168b

-continued

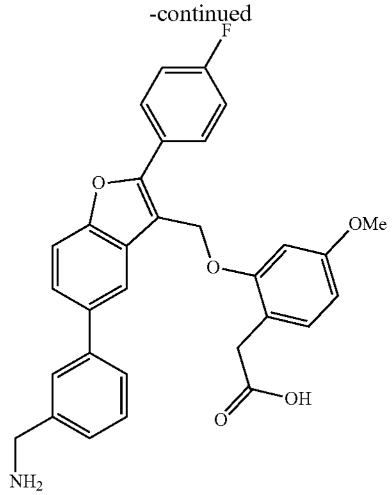

168c

Preparation of 2-(2-((5-(3-(aminomethyl)phenyl)-2-(4-fluorophenyl)benzofuran-3-yl)methoxy)-4-methoxyphenyl)acetic acid (168c)

Step-1: Preparation of ethyl 2-(2-((5-bromo-2-(4-fluorophenyl)benzofuran-3-yl)methoxy)-4-methoxyphenyl)acetate (168a)

Compound 168a was prepared according to the procedure reported in step-2 of scheme 65, from (5-bromo-2-(4-fluorophenyl)benzofuran-3-yl)methanol (167b) (450 mg, 1.401 mmol) in DCM (15 mL) using triphenylphosphine (404 mg, 1.541 mmol), ethyl 2-(2-hydroxy-4-methoxyphenyl)acetate (6a) (324 mg, 1.541 mmol) a solution of DCAD (566 mg, 1.541 mmol) in DCM (10 mL) and stirring at RT for 30 min. This gave after workup and purification using flash column chromatography [silica gel (40 g), eluting with EtOAc in hexane from 0-50%] ethyl 2-(2-((5-bromo-2-(4-fluorophenyl)benzofuran-3-yl)methoxy)-4-methoxyphenyl)acetate (168a) (394 mg, 55% yield) as a white solid; $^1$H NMR (300 MHz, DMSO-$d_6$) δ 7.98 (d, J=2.0 Hz, 1H), 7.90-7.83 (m, 2H), 7.66 (d, J=8.7 Hz, 1H), 7.53 (dd, J=8.7, 2.1 Hz, 1H), 7.42 (t, 2H), 7.10 (d, J=8.3 Hz, 1H), 6.80 (d, J=2.4 Hz, 1H), 6.52 (dd, J=8.3, 2.4 Hz, 1H), 5.35 (s, 2H), 3.84-3.70 (m, 5H), 3.40 (s, 2H), 0.87 (t, J=7.1 Hz, 3H).

Step-2: Preparation of ethyl 2-(2-((5-(3-(aminomethyl)phenyl)-2-(4-fluorophenyl)benzofuran-3-yl)methoxy)-4-methoxyphenyl)acetate (168b)

Compound 168b was prepared according to the procedure reported in step-2 of scheme 1, from ethyl 2-(2-((5-bromo-2-(4-fluorophenyl)benzofuran-3-yl)methoxy)-4-methoxyphenyl)acetate (168a) (390 mg, 0.760 mmol) in dioxane (20 mL) using (3-(aminomethyl)phenyl)boronic acid hydrochloride (1d) (285 mg, 1.519 mmol), 4 M solution of $K_3PO_4$ (0.760 mL, 3.04 mmol), tricyclohexylphosphine (63.9 mg, 0.228 mmol), $Pd_2(dba)_3$ (69.6 mg, 0.076 mmol), $PdCl_2$(dppf)-$CH_2Cl_2$-adduct (62.0 mg, 0.076 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(4-fluorophenyl)benzofuran-3-yl)methoxy)-4-methoxyphenyl)acetate (168b) (155 mg, 38% yield) as a yellow oil; MS (ES+): 540.2 (M+1).

Step-3: Preparation of 2-(2-((5-(3-(aminomethyl)phenyl)-2-(4-fluorophenyl)benzofuran-3-yl)methoxy)-4-methoxyphenyl)acetic acid (168c)

Compound 168c was prepared according to the procedure reported in step-3 of scheme 1, from ethyl 2-(2-((5-(3-(aminomethyl)phenyl)-2-(4-fluorophenyl)benzofuran-3-yl)methoxy)-4-methoxyphenyl)acetate (168b) (155 mg, 0.287 mmol) in THF (3 mL) using lithium hydroxide hydrate (96 mg, 2.279 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(4-fluorophenyl)benzofuran-3-yl)methoxy)-4-methoxyphenyl)acetic acid (168c) (51 mg, 13% yield) HCl salt as a white solid; $^1$H NMR (300 MHz, DMSO-$d_6$) δ 12.00 (s, 1H, $D_2O$ exchangeable), 8.46 (s, 3H, $D_2O$ exchangeable), 8.12 (d, J=1.8 Hz, 1H), 7.96-7.85 (m, 3H), 7.85-7.68 (m, 3H), 7.60-7.32 (m, 4H), 7.10 (d, J=8.3 Hz, 1H), 6.84 (d, J=2.4 Hz, 1H), 6.52 (dd, J=8.3, 2.3 Hz, 1H), 5.40 (s, 2H), 4.11 (s, 2H), 3.73 (s, 3H), 3.37 (s, 2H); $^{19}$F NMR (282 MHz, DMSO-$d_6$) δ −111.07; MS (ES+): 512.2 (M+1); (ES−) 510.1 (M−1); Analysis calculated for $C_{31}H_{26}FNO_5$·HCl: C, 67.94; H, 4.97; Cl, 6.47; N, 2.56. Found: C, 68.00; H, 5.02; Cl, 6.52; N, 2.65.

Scheme 169

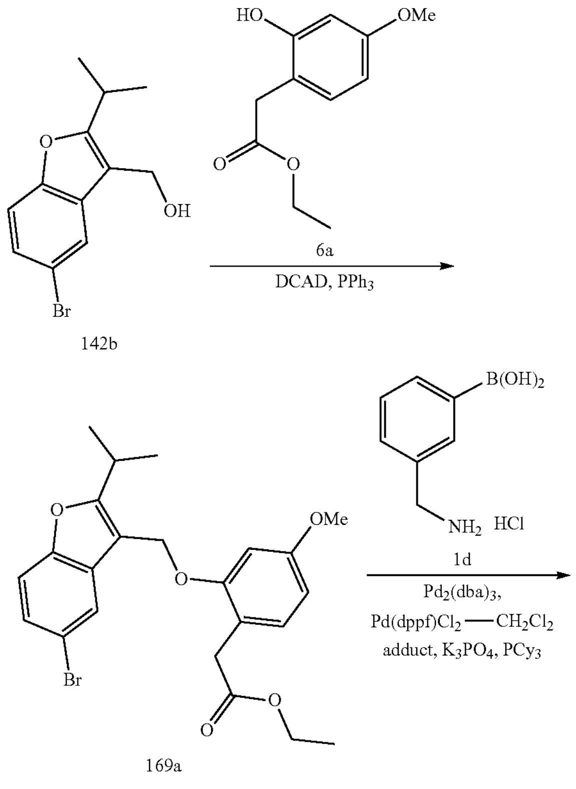

-continued

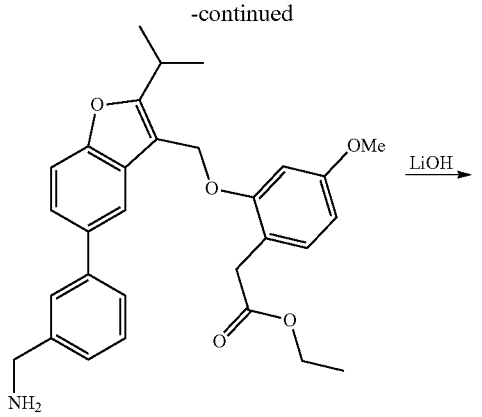

169b

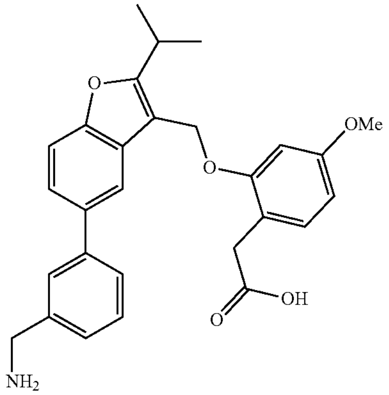

169c

Preparation of 2-(2-((5-(3-(aminomethyl)phenyl)-2-isopropylbenzofuran-3-yl)methoxy)-4-methoxyphenyl)acetic acid (169c)

Step-1: Preparation of ethyl 2-(2-((5-bromo-2-isopropylbenzofuran-3-yl)methoxy)-4-methoxyphenyl) acetate (169a)

Compound 169a was prepared according to the procedure reported in step-2 of scheme 65, from (5-bromo-2-isopropylbenzofuran-3-yl)methanol (142b) (450 mg, 1.672 mmol) in DCM (15 mL) using triphenylphosphine (482 mg, 1.839 mmol), ethyl 2-(2-hydroxy-4-methoxyphenyl)acetate (6a) (387 mg, 1.839 mmol), a solution of DCAD (675 mg, 1.839 mmol) in DCM (10 mL) and stirring at RT for 30 min. This gave after workup and purification using flash column chromatography [silica gel (40 g), eluting with EtOAc in hexane from 0-50%] ethyl 2-(2-((5-bromo-2-isopropylbenzofuran-3-yl)methoxy)-4-methoxyphenyl)acetate (169a) (380 mg, 49% yield) as a clear oil; $^1$H NMR (300 MHz, DMSO-$d_6$) δ 7.79 (d, J=2.0 Hz, 1H), 7.54 (d, J=8.6 Hz, 1H), 7.41 (dd, J=8.6, 2.1 Hz, 1H), 7.08 (d, J=8.3 Hz, 1H), 6.81 (d, J=2.4 Hz, 1H), 6.50 (dd, J=8.3, 2.4 Hz, 1H), 5.20 (s, 2H), 3.88 (q, J=7.1 Hz, 2H), 3.78 (s, 3H), 3.47-3.36 (m, 3H), 1.28 (d, J=6.9 Hz, 6H), 0.95 (t, J=7.1 Hz, 3H).

Step-2: Preparation of ethyl 2-(2-((5-(3-(aminomethyl)phenyl)-2-isopropylbenzofuran-3-yl)methoxy)-4-methoxyphenyl)acetate (169b)

Compound 169b was prepared according to the procedure reported in step-2 of scheme 1, from ethyl 2-(2-((5-bromo- 2-isopropylbenzofuran-3-yl)methoxy)-4-methoxyphenyl) acetate (169a) (380 mg, 0.824 mmol) in dioxane (20 mL) using (3-(aminomethyl)phenyl)boronic acid hydrochloride (1d) (309 mg, 1.647 mmol), 4 M solution of $K_3PO_4$ (0.824 mL, 3.29 mmol), tricyclohexylphosphine (69.3 mg, 0.247 mmol), $Pd_2(dba)_3$ (75 mg, 0.082 mmol), $PdCl_2$(dppf)-$CH_2Cl_2$-adduct (67.3 mg, 0.082 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-isopropylbenzofuran-3-yl)methoxy)-4-methoxyphenyl)acetate (169b) (212 mg, 53% yield) as a yellow oil; MS (ES+): 488.2 (M+1).

Step-3: Preparation of 2-(2-((5-(3-(aminomethyl) phenyl)-2-isopropylbenzofuran-3-yl)methoxy)-4-methoxyphenyl)acetic acid (169c)

Compound 169c was prepared according to the procedure reported in step-3 of scheme 1, from ethyl 2-(2-((5-(3-(aminomethyl)phenyl)-2-isopropylbenzofuran-3-yl) methoxy)-4-methoxyphenyl)acetate (169b) (212 mg, 0.435 mmol) in THF (3 mL) using lithium hydroxide hydrate (104 mg, 2.471 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-isopropylbenzofuran-3-yl)methoxy)-4-methoxyphenyl)acetic acid (169c) (129 mg, 34% yield) HCl salt as a white solid; $^1$H NMR (300 MHz, DMSO-$d_6$) δ 12.02 (s, 1H, $D_2O$ exchangeable), 8.49 (s, 2H, $D_2O$ exchangeable), 7.97 (d, J=1.7 Hz, 1H), 7.89 (t, J=1.7 Hz, 1H), 7.73 (dt, J=7.5, 1.7 Hz, 1H), 7.69-7.57 (m, 2H), 7.53-7.41 (m, 2H), 7.07 (d, J=8.3 Hz, 1H), 6.84 (d, J=2.4 Hz, 1H), 6.50 (dd, J=8.3, 2.3 Hz, 1H), 5.28 (s, 2H), 4.09 (s, 2H), 3.76 (s, 3H), 3.47-3.40 (m, 1H), 3.39 (s, 2H), 1.30 (d, J=6.9 Hz, 6H); MS (ES+) 460.2 (M+1) (ES−) 458.2 (M−1); Analysis calculated for $C_{28}H_{29}NO_5 \cdot HCl \cdot 0.75H_2O$: C, 66.01; H, 6.23; Cl, 6.96; N, 2.75. Found: C, 65.95; H, 5.94; Cl, 7.01; N, 2.83.

Scheme 170

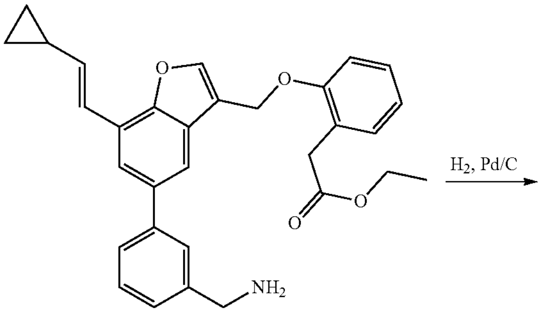

132c

-continued

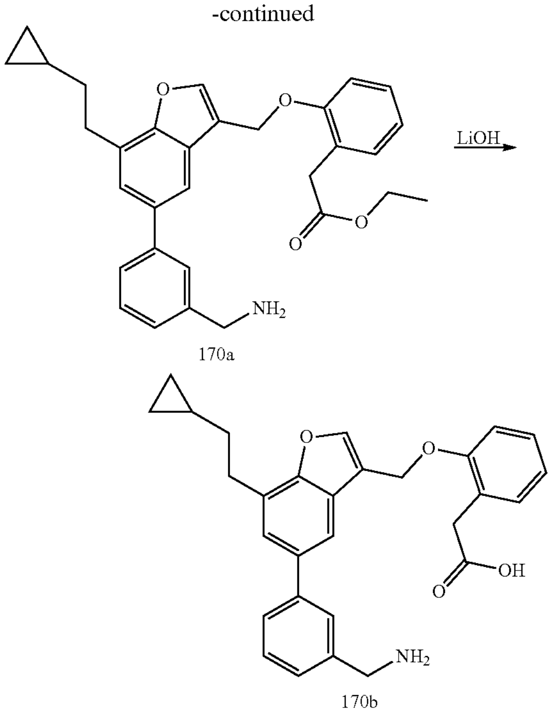

170a

170b

Preparation of 2-(2-((5-(3-(aminomethyl)phenyl)-7-(2-cyclopropylethyl)benzofuran-3-yl)methoxy)phenyl)acetic acid (170b)

Step-1: Preparation of ethyl 2-(2-((5-(3-(aminomethyl)phenyl)-7-(2-cyclopropylethyl)benzofuran-3-yl)methoxy)phenyl)acetate (170a)

Compound 170a was prepared according to the procedure reported in step-3 of scheme 83, from (E)-ethyl 2-(2-((5-(3-(aminomethyl)phenyl)-7-(2-cyclopropylvinyl)benzofuran-3-yl)methoxy)phenyl)acetate (132c) (235 mg, 0.488 mmol) in EtOAc (70 mL) using palladium on carbon (78 mg, 0.073 mmol) and stirring overnight at RT under a hydrogen atmosphere. This gave after work up and purification using flash column chromatography [silica gel (40 g), eluting with EtOAc in hexane from 0-100%] ethyl 2-(2-((5-(3-(aminomethyl)phenyl)-7-(2-cyclopropylethyl)benzofuran-3-yl)methoxy)phenyl)acetate (170a) (0.101 g, 43% yield) as a yellow oil; MS (ES+): 484.2 (M+1).

Step-2: Preparation of 2-(2-((5-(3-(aminomethyl)phenyl)-7-(2-cyclopropylethyl)benzofuran-3-yl)methoxy)phenyl)acetic acid (170b)

Compound 170b was prepared according to the procedure reported in step-3 of scheme 1, from ethyl 2-(2-((5-(3-(aminomethyl)phenyl)-7-(2-cyclopropylethyl)benzofuran-3-yl)methoxy)phenyl)acetate (170a) (101 mg, 0.209 mmol) in THF (3 mL) using lithium hydroxide hydrate (82 mg, 1.952 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(2-cyclopropylethyl)benzofuran-3-yl)methoxy)phenyl)acetic acid (170b) (28 mg, 13% yield) HCl salt as a white solid; $^1H$ NMR (300 MHz, DMSO-$d_6$) δ 12.14 (s, 1H, $D_2O$ exchangeable), 8.36 (s, 3H, $D_2O$ exchangeable), 8.11 (s, 1H), 7.88-7.80 (m, 2H), 7.77-7.70 (m, 1H), 7.56-7.39 (m, 3H), 7.31-7.24 (m, 1H), 7.23-7.16 (m, 2H), 6.97-6.86 (m, 1H), 5.30 (s, 2H), 4.11 (s, 2H), 3.54 (s, 2H), 3.07-2.95 (m, 2H), 1.73-1.57 (m, 2H), 0.85-0.68 (m, 1H), 0.47-0.37 (m, 2H), 0.13-0.01 (m, 2H); MS (ES+) 456.2 (M+1); (ES−) 454.2 (M−1); Analysis calculated for $C_{25}H_{23}NO_4 \cdot HCl \cdot 0.75H_2O$: C, 66.52; H, 5.69; Cl, 7.85; N, 3.10. Found: C, 66.42; H, 5.59; Cl, 8.27; N, 3.15.

Scheme 171

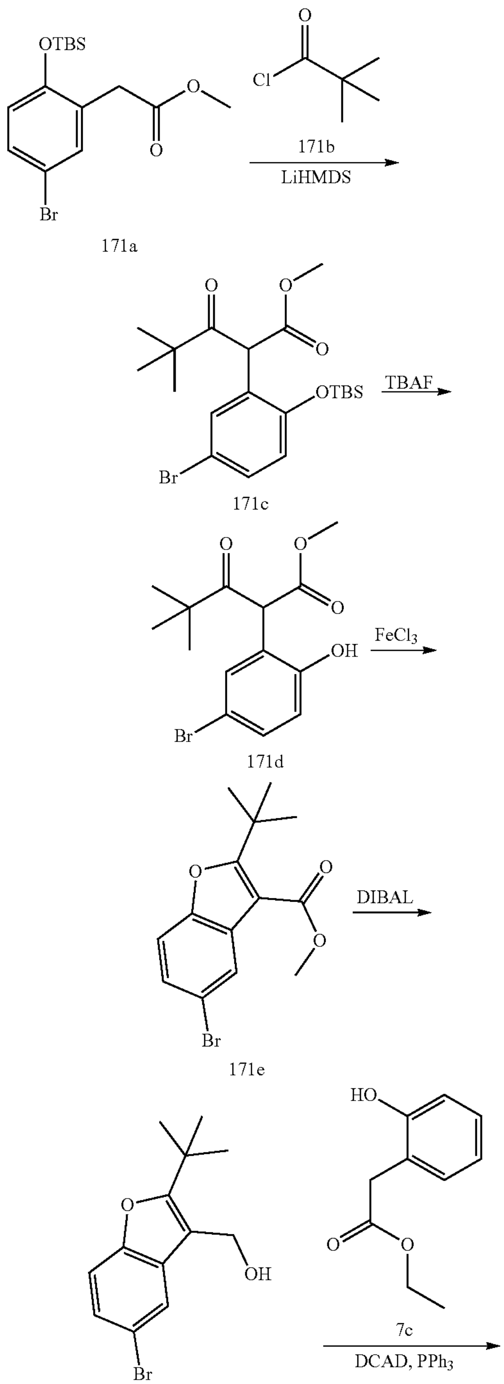

171a

171c

171d

171e

171f

-continued

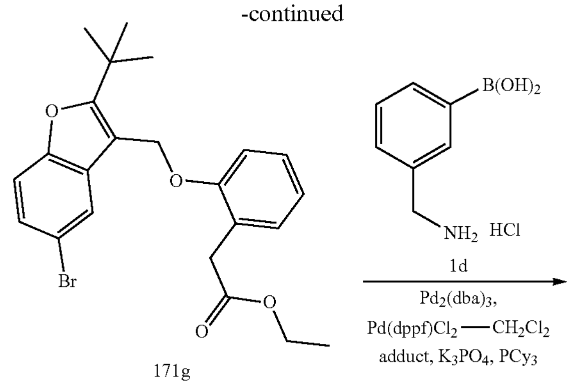

171g

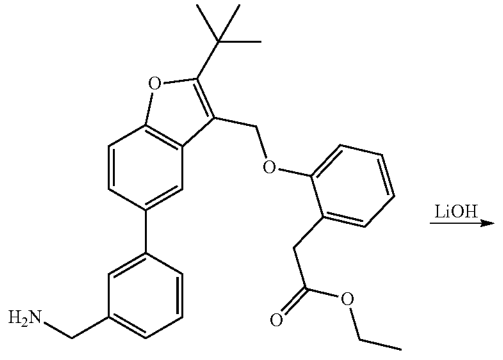

171h

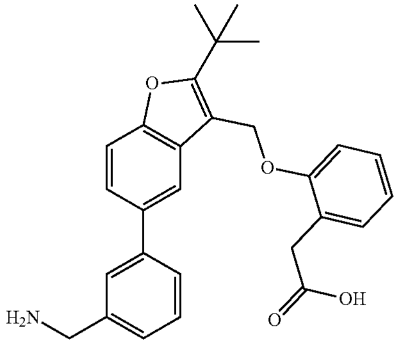

171i

Preparation of 2-(2-((5-(3-(aminomethyl)phenyl)-2-(tert-butyl)benzofuran-3-yl)methoxy)phenyl)acetic acid (171i)

Step-1: Preparation of methyl 2-(5-bromo-2-((tert-butyldimethylsilyl)oxy)phenyl)-4,4-dimethyl-3-oxopentanoate (171c)

To a solution of methyl 2-(5-bromo-2-(tert-butyldimethylsilyloxy)phenyl)acetate (171a) (6 g, 16.70 mmol; CAS #1333225-28-7) in THF (50 mL) at −78° C. was added LiHMDS (1N in THF) (20.04 mL, 20.04 mmol) stirred for 30 min followed by the addition of pivaloyl chloride (171b) (2.315 g, 19.20 mmol) in THF (3 mL). The reaction mixture was stirred at −78° C. for 1 h allowed to warm to 0° C. and stirred for 1 h. The reaction was quenched with HCl (1N), concentrated in vacuo to remove THF and extracted with EtOAc (3×). The combined organic layers were washed with water, brine, dried and concentrated in vacuo. The residue obtained was purified using flash column chromatography [silica gel (80 g), eluting with EtOAc in hexane from 0-100%] to give methyl 2-(5-bromo-2-((tert-butyldimethylsilyl)oxy)phenyl)-4,4-dimethyl-3-oxopentanoate (171c) (7.01 g, 95% yield) as a clear oil, which turned into white solid on standing at RT for a few hours; $^1$H NMR (300 MHz, DMSO-$d_6$) δ 7.24 (dd, J=8.7, 2.6 Hz, 1H), 7.10 (d, J=2.6 Hz, 1H), 6.74 (d, J=8.7 Hz, 1H), 5.44 (s, 1H), 3.46 (s, 3H), 0.88 (s, 9H), 0.81 (s, 9H), 0.12 (s, 3H), −0.00 (s, 3H).

Step-2: Preparation of methyl 2-(5-bromo-2-hydroxyphenyl)-4,4-dimethyl-3-oxopentanoate (171d)

Compound 171d was prepared according to the procedure reported in step-2 of scheme 3, from methyl 2-(5-bromo-2-((tert-butyldimethylsilyl)oxy)phenyl)-4,4-dimethyl-3-oxopentanoate (171c) (7 g, 15.79 mmol) using TBAF (19.73 mL, 19.73 mmol)) in THF (80 mL) and stirring at 0° C. for 1 h. This gave after workup and purification using flash column chromatography [silica gel (40 g), eluting with EtOAc in hexane from 0-100%]methyl 2-(5-bromo-2-hydroxyphenyl)-4,4-dimethyl-3-oxopentanoate (171d) (2.38 g, 46% yield) as a clear oil; $^1$H NMR (300 MHz, DMSO-$d_6$) δ 10.32 (s, 1H), 7.36-7.27 (m, 1H), 7.18 (d, J=2.5 Hz, 1H), 6.89-6.75 (m, 1H), 5.64 (s, 1H), 3.64 (s, 3H), 1.09 (s, 9H); MS (ES+): 329.0 and 331.0 (M+1).

Step-3: Preparation of methyl 5-bromo-2-(tert-butyl)benzofuran-3-carboxylate (171e)

To a solution of methyl 2-(5-bromo-2-hydroxyphenyl)-4,4-dimethyl-3-oxopentanoate (171d) (2.3 g, 6.99 mmol) in DCE (20 mL) was added iron (III) chloride (0.189 g, 0.699 mmol) at RT and stirred for 2 days at RT. The solvent was removed in vacuo and the residue obtained was purified using flash column chromatography [silica gel (24 g), eluting with EtOAc in hexane from 0-100%] to give methyl 5-bromo-2-(tert-butyl)benzofuran-3-carboxylate (171e) (1.7 g, 78% yield) as a white solid; $^1$H NMR (300 MHz, DMSO-$d_6$) δ 8.00 (d, J=2.0 Hz, 1H), 7.63 (d, J=8.7 Hz, 1H), 7.51 (dd, J=8.8, 2.1 Hz, 1H), 3.92 (s, 3H), 1.50 (s, 9H).

Step-4: Preparation of (5-bromo-2-(tert-butyl)benzofuran-3-yl)methanol (171f)

Compound 171f was prepared according to the procedure reported in step-2 of scheme 69, from methyl 5-bromo-2-(tert-butyl)benzofuran-3-carboxylate (171e) (1.5 g, 4.82 mmol) in DCM (20 mL) using 1.0 M solution of DIBAL in DCM (12.05 mL, 12.05 mmol) and stirring at 0° C. for 2 h. This gave after workup and purification using flash column chromatography [silica gel (24 g), eluting with EtOAc in hexane from 0-100%] (5-bromo-2-(tert-butyl)benzofuran-3-yl)methanol (171f) (1.35 g, 99% yield); $^1$H NMR (300 MHz, DMSO-$d_6$) δ 7.83 (d, J=2.0 Hz, 1H), 7.46 (d, J=8.6 Hz, 1H), 7.36 (dd, J=8.6, 2.0 Hz, 1H), 5.07 (t, J=5.4 Hz, 1H), 4.67 (d, J=5.5 Hz, 2H), 1.42 (s, 9H).

Step-5: Preparation of ethyl 2-(2-((5-bromo-2-(tert-butyl)benzofuran-3-yl)methoxy)phenyl)acetate (171g)

Compound 171g was prepared according to the procedure reported in step-2 of scheme 65, from (5-bromo-2-(tert-butyl)benzofuran-3-yl)methanol (171f) (300 mg, 1.059 mmol) in DCM (10 mL) using triphenylphosphine (306 mg, 1.165 mmol), ethyl 2-(2-hydroxyphenyl)acetate (7c) (210 mg, 1.165 mmol), a solution of DCAD (428 mg, 1.165 mmol) in DCM (5 mL) and stirring at RT for 30 min. This gave after workup and purification using flash column chromatography [silica gel (12 g), eluting with EtOAc in hexane from 0-50%] ethyl 2-(2-((5-bromo-2-(tert-butyl)benzofuran-3-yl)methoxy)phenyl)acetate (171g) (390 mg, 83% yield) as a clear oil; $^1$H NMR (300 MHz, DMSO-$d_6$) δ 7.87 (d, J=2.0 Hz, 1H), 7.59 (d, J=8.7 Hz, 1H), 7.47 (dd, J=8.7, 2.0 Hz, 1H), 7.37 (td, J=7.8, 7.2, 1.7 Hz, 1H), 7.32-7.22 (m, 2H), 7.00 (td, J=7.3, 1.2 Hz, 1H), 5.29 (s, 2H), 3.86 (q, J=7.1 Hz, 2H), 3.55 (s, 2H), 1.48 (s, 9H), 0.94 (t, J=7.1 Hz, 3H).

Step-6: Preparation of ethyl 2-(2-((5-(3-(aminomethyl)phenyl)-2-(tert-butyl)benzofuran-3-yl)methoxy)phenyl)acetate (171 h)

Compound 171h was prepared according to the procedure reported in step-2 of scheme 1, from ethyl 2-(2-((5-bromo-2-(tert-butyl)benzofuran-3-yl)methoxy)phenyl)acetate (171g) (390 mg, 0.876 mmol) in dioxane (20 mL) using (3-(aminomethyl)phenyl)boronic acid hydrochloride (1d) (328 mg, 1.751 mmol), 4 M solution of $K_3PO_4$ (0.876 mL, 3.50 mmol), tricyclohexylphosphine (73.7 mg, 0.263 mmol), $Pd_2(dba)_3$ (80 mg, 0.088 mmol), $PdCl_2$(dppf)-$CH_2Cl_2$ adduct (71.5 mg, 0.088 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(tert-butyl)benzofuran-3-yl)methoxy)phenyl)acetate (171 h) (152 mg, 37% yield) as a yellow oil; MS (ES+): 472.3 (M+1).

Step-7: Preparation of 2-(2-((5-(3-(aminomethyl)phenyl)-2-(tert-butyl)benzofuran-3-yl)methoxy)phenyl)acetic acid (171i)

Compound 171i was prepared according to the procedure reported in step-3 of scheme 1, from ethyl 2-(2-((5-(3-(aminomethyl)phenyl)-2-(tert-butyl)benzofuran-3-yl)methoxy)phenyl)acetate (171 h) (152 mg, 0.322 mmol) in THF (3 mL) using lithium hydroxide hydrate (110 mg, 2.63 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(tert-butyl)benzofuran-3-yl)methoxy)phenyl)acetic acid (171i) (84 mg, 22% yield) HCl salt as a white solid; $^1$H NMR (300 MHz, DMSO-$d_6$) δ 8.58 (s, 1H, $D_2O$ exchangeable), 7.95 (s, 1H), 7.89 (s, 1H), 7.77-7.69 (m, 1H), 7.69-7.57 (m, 2H), 7.52-7.37 (m, 2H), 7.35-7.23 (m, 2H), 7.23-7.15 (m, 1H), 6.99-6.85 (m, 1H), 5.30 (s, 2H), 4.08 (s, 2H), 3.47 (s, 2H), 1.45 (s, 9H); MS (ES+): 444.2 (M+1); (ES−): 442.2 (M−1); Analysis calculated for $C_{28}H_{29}NO_4$·HCl·0.5$H_2O$: C, 68.77; H, 6.39; Cl, 7.25; N, 2.86. Found: C, 68.81; H, 6.12; Cl, 7.26; N, 2.98.

Scheme 172

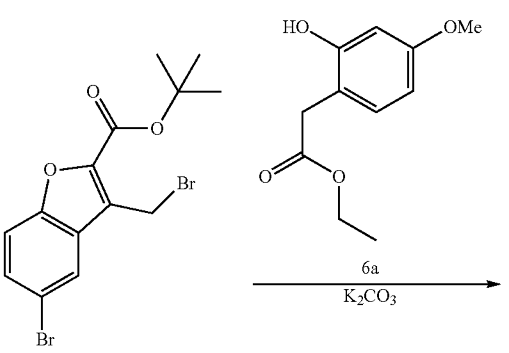

64c

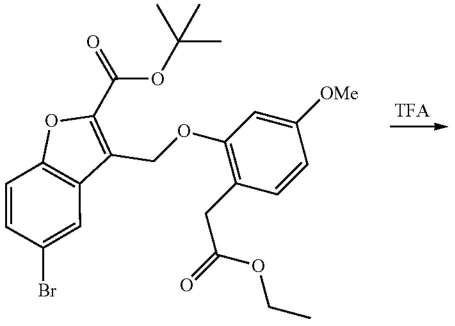

172a

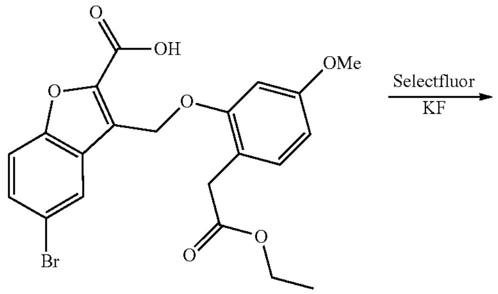

172b

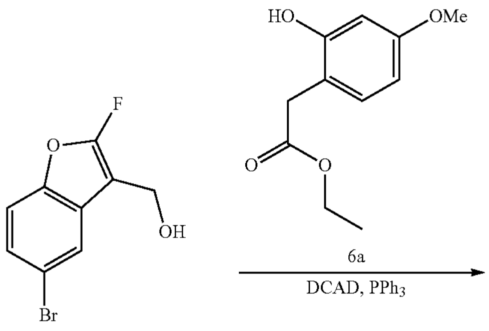

172c

-continued

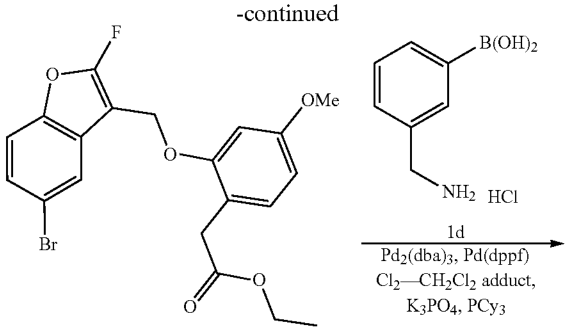

172d

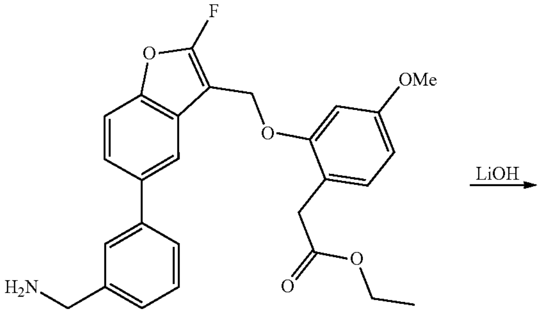

172e

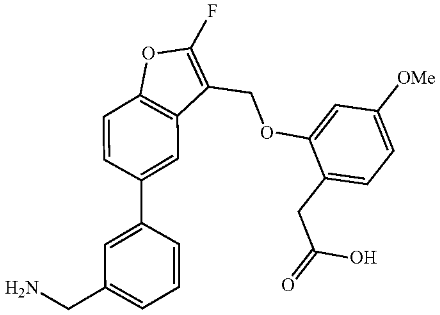

172f

Preparation of 2-(2-((5-(3-(aminomethyl)phenyl)-2-fluorobenzofuran-3-yl)methoxy)-4-methoxyphenyl) acetic acid (172f)

Step-1: Preparation of tert-butyl 5-bromo-3-((2-(2-ethoxy-2-oxoethyl)-5-methoxyphenoxy)methyl)benzofuran-2-carboxylate (172a)

Compound 172a was prepared according to the procedure reported in step-1 of scheme 58, from tert-butyl 5-bromo-3-(bromomethyl)benzofuran-2-carboxylate (64c) (1 g, 2.56 mmol) in acetone (10 mL) using ethyl 2-(2-hydroxy-4-methoxyphenyl)acetate (6a) (0.620 g, 2.95 mmol), $K_2CO_3$ (0.709 g, 5.13 mmol) and stirring overnight at RT. This gave after workup and purification using flash column chromatography [silica gel (24 g), eluting with EtOAc in hexane from 0-50%] tert-butyl 5-bromo-3-((2-(2-ethoxy-2-oxoethyl)-5-methoxyphenoxy)methyl)benzofuran-2-carboxylate (172a) (1.223 g, 92% yield) as a yellow oil; $^1H$ NMR (300 MHz, DMSO-$d_6$) δ 8.04 (d, J=1.9 Hz, 1H), 7.77-7.65 (m, 2H), 7.10 (d, J=8.3 Hz, 1H), 6.74 (d, J=2.4 Hz, 1H), 6.51 (dd, J=8.3, 2.4 Hz, 1H), 5.55 (s, 2H), 3.90 (q, J=7.1 Hz, 2H), 3.75 (s, 3H), 3.47 (s, 2H), 1.56 (s, 9H), 0.95 (t, J=7.1 Hz, 3H); MS (ES+): 542.1 (M+Na).

Step-2: Preparation of 5-bromo-3-((2-(2-ethoxy-2-oxoethyl)-5-methoxyphenoxy)methyl)benzofuran-2-carboxylic acid (172b)

Compound 172b was prepared according to the procedure reported in step-9 of scheme 3, from tert-butyl 5-bromo-3-((2-(2-ethoxy-2-oxoethyl)-5-methoxyphenoxy)methyl)benzofuran-2-carboxylate (172a) (4 g, 7.70 mmol) in DCM (100 mL) using TFA (2.373 mL, 30.8 mmol) and stirring at RT for 2 h. The solid obtained was collected by filtration to give 5-bromo-3-((2-(2-ethoxy-2-oxoethyl)-5-methoxyphenoxy)methyl)benzofuran-2-carboxylic acid (172b) (2 g, 56% yield) as a white solid; $^1H$ NMR (300 MHz, DMSO-$d_6$) δ 14.23 (s, 1H), 8.04-7.97 (m, 1H), 7.76-7.64 (m, 2H), 7.10 (d, J=8.3 Hz, 1H), 6.76 (d, J=2.4 Hz, 1H), 6.50 (dd, J=8.3, 2.4 Hz, 1H), 5.60 (s, 2H), 3.92 (q, J=7.1 Hz, 2H), 3.75 (s, 3H), 3.48 (s, 2H), 0.97 (t, J=7.1 Hz, 3H).

Step-3: Preparation of (5-bromo-2-fluorobenzofuran-3-yl)methanol (172c)

To a solution of 5-bromo-3-((2-(2-ethoxy-2-oxoethyl)-5-methoxyphenoxy)methyl)benzofuran-2-carboxylic acid (172b) (2 g, 4.32 mmol) in DCE/$H_2O$ (30 mL, Ratio: 2:1) was added Selectfluor (3.06 g, 8.63 mmol), potassium fluoride (1.003 g, 17.27 mmol) at RT and the mixture was stirred for 15 h at 70° C. The reaction mixture was diluted with water (100 mL), extracted with DCM (3×), and the combined organics were dried and concentrated in vacuo. The residue obtained was purified using flash column chromatography [silica gel, eluting with EtOAc in hexane from 0-100%] to give (5-bromo-2-fluorobenzofuran-3-yl)methanol (172c) (235 mg, 22% yield) as a white solid; $^1H$ NMR (300 MHz, DMSO-$d_6$) δ 7.88 (d, J=2.1 Hz, 1H), 7.56 (d, J=8.7 Hz, 1H), 7.48 (dd, J=8.7, 2.1 Hz, 1H), 5.28 (t, J=5.8 Hz, 1H), 4.52 (d, J=4.9 Hz, 2H); $^{19}F$ NMR (282 MHz, DMSO-$d_6$) δ −115.15.

Step-4: Preparation of ethyl 2-(2-((5-bromo-2-fluorobenzofuran-3-yl)methoxy)-4-methoxyphenyl)acetate (172d)

Compound 172d was prepared according to the procedure reported in step-2 of scheme 65, from (5-bromo-2-fluorobenzofuran-3-yl)methanol (172c) (230 mg, 0.939 mmol) in DCM (10 mL) using triphenylphosphine (271 mg, 1.032 mmol), ethyl 2-(2-hydroxy-4-methoxyphenyl)acetate (6a) (217 mg, 1.032 mmol), a solution of DCAD (379 mg, 1.032 mmol) in DCM (5 mL) and stirring at RT for 30 min. This gave after workup and purification using flash column chromatography [silica gel (12 g), eluting with EtOAc in hexane from 0-50%] ethyl 2-(2-((5-bromo-2-fluorobenzofuran-3-yl)methoxy)-4-methoxyphenyl)acetate (172d) (202 mg, 49% yield) as a clear oil; $^1H$ NMR (300 MHz, DMSO-$d_6$) δ 7.85 (d, J=2.0 Hz, 1H), 7.61 (d, J=8.7 Hz, 1H), 7.52 (dd, J=8.8, 2.1 Hz, 1H), 7.10 (d, J=8.3 Hz, 1H), 6.78 (d, J=2.4 Hz, 1H), 6.51 (dd, J=8.3, 2.4 Hz, 1H), 5.18 (s, 2H), 3.91 (q, J=7.1 Hz, 2H), 3.78 (s, 3H), 3.45 (s, 2H), 0.98 (t, J=7.1 Hz, 3H).

Step-5: Preparation of ethyl 2-(2-((5-(3-(aminomethyl)phenyl)-2-fluorobenzofuran-3-yl)methoxy)-4-methoxyphenyl)acetate (172e)

Compound 172e was prepared according to the procedure reported in step-2 of scheme 1, from ethyl 2-(2-((5-bromo-2-fluorobenzofuran-3-yl)methoxy)-4-methoxyphenyl)acetate (172d) (200 mg, 0.457 mmol) in dioxane (15 mL) using (3-(aminomethyl)phenyl)boronic acid hydrochloride (1d) (171 mg, 0.915 mmol), 4 M solution of $K_3PO_4$ (0.457 mL, 1.830 mmol), tricyclohexylphosphine (38.5 mg, 0.137 mmol), $Pd_2(dba)_3$ (41.9 mg, 0.046 mmol), $PdCl_2$(dppf)-$CH_2Cl_2$ adduct (37.4 mg, 0.046 mmol) and heating at 110° C. for 5 h. This gave after workup and purification using flash column chromatography [silica gel (40 g), eluting with DMA-80 in DCM from 0-100%] ethyl 2-(2-((5-(3-(aminomethyl)phenyl)-2-fluorobenzofuran-3-yl)methoxy)-4-methoxyphenyl)acetate (172e) (88 mg, 42% yield) as a yellow oil; MS (ES+): 464.2 (M+1).

Step-6: Preparation of 2-(2-((5-(3-(aminomethyl)phenyl)-2-fluorobenzofuran-3-yl)methoxy)-4-methoxyphenyl)acetic acid (172f)

Compound 172f was prepared according to the procedure reported in step-3 of scheme 1, from ethyl 2-(2-((5-(3-(aminomethyl)phenyl)-2-fluorobenzofuran-3-yl)methoxy)-4-methoxyphenyl)acetate (172e) (88 mg, 0.19 mmol) in THF (3 mL) using lithium hydroxide hydrate (57.6 mg, 1.372 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-fluorobenzofuran-3-yl)methoxy)-4-methoxyphenyl)acetic acid (172f) (4 mg, 2% yield) HCl salt as an off white solid; $^1H$ NMR (300 MHz, DMSO-$d_6$) δ 12.02 (s, 1H, $D_2O$ exchangeable), 8.31 (s, 3H, $D_2O$ exchangeable), 7.98 (d, J=1.8 Hz, 1H), 7.86 (s, 1H), 7.78-7.70 (m, 2H), 7.66 (dd, J=8.6, 1.8 Hz, 1H), 7.53 (t, J=7.6 Hz, 1H), 7.49-7.42 (m, 1H), 7.09 (d, J=8.3 Hz, 1H), 6.81 (d, J=2.4 Hz, 1H), 6.56-6.47 (m, 1H), 5.25 (s, 2H), 4.11 (s, 2H), 3.76 (s, 3H), 3.41 (s, 2H); $^{19}F$ NMR (282 MHz, DMSO-$d_6$) δ −113.04; MS (ES+): 436.1 (M+1); (ES−): 434.2 (M−1).

Scheme 173

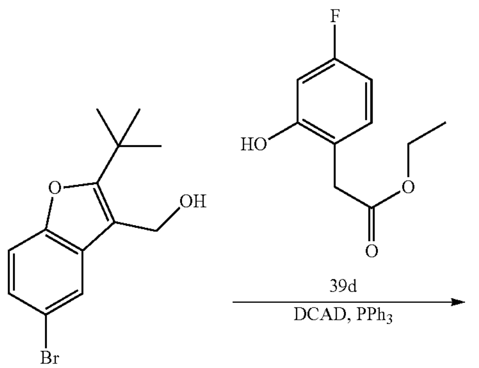

171f

-continued

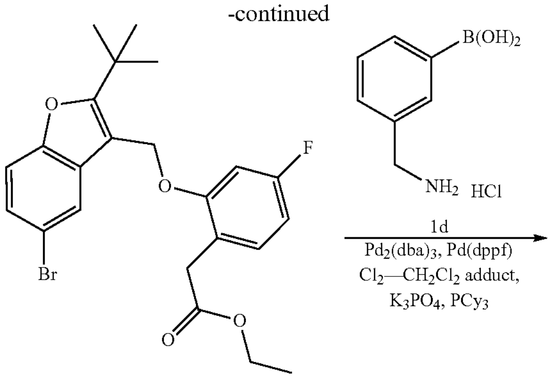

173a

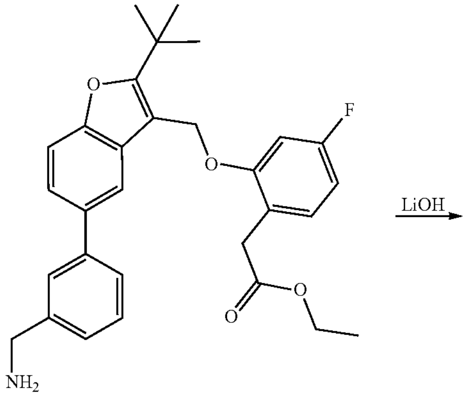

173b

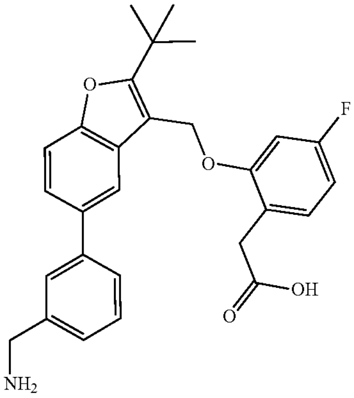

173c

Preparation of 2-(2-((5-(3-(aminomethyl)phenyl)-2-(tert-butyl)benzofuran-3-yl)methoxy)-4-fluorophenyl)acetic acid (173c)

Step-1: Preparation of ethyl 2-(2-((5-bromo-2-(tert-butyl)benzofuran-3-yl)methoxy)-4-fluorophenyl) acetate (173a)

Compound 173a was prepared according to the procedure reported in step-2 of scheme 65, from (5-bromo-2-(tert-butyl)benzofuran-3-yl)methanol (171f) (230 mg, 0.939 mmol) in DCM (10 mL) using triphenylphosphine (271 mg, 1.032 mmol), ethyl 2-(4-fluoro-2-hydroxyphenyl)acetate (39d) (217 mg, 1.032 mmol), a solution of DCAD (379 mg, 1.032 mmol) in DCM (5 mL) and stirring at RT for 30 min. This gave after workup and purification using flash column chromatography [silica gel (12 g), eluting with EtOAc in hexane from 0-50%] ethyl 2-(2-((5-bromo-2-(tert-butyl)benzofuran-3-yl)methoxy)-4-fluorophenyl)acetate (173a) (202 mg, 49% yield) as a clear oil; $^1$H NMR (300 MHz, DMSO-$d_6$) δ 7.84 (d, J=2.0 Hz, 1H), 7.53 (d, J=8.7 Hz, 1H), 7.42 (dd, J=8.7, 2.0 Hz, 1H), 7.27-7.22 (m, 1H), 7.22-7.15 (m, 1H), 6.77 (td, J=8.5, 2.5 Hz, 1H), 5.25 (s, 2H), 3.81 (q, J=7.1 Hz, 2H), 3.47 (s, 2H), 1.42 (s, 9H), 0.88 (t, J=7.1 Hz, 3H); $^{19}$F NMR (282 MHz, DMSO-$d_6$) δ −112.65.

Step-2: Preparation of ethyl 2-(2-((5-(3-(aminomethyl)phenyl)-2-(tert-butyl)benzofuran-3-yl)methoxy)-4-fluorophenyl)acetate (173b)

Compound 173b was prepared according to the procedure reported in step-2 of scheme 1, from ethyl 2-(2-((5-bromo-2-(tert-butyl)benzofuran-3-yl)methoxy)-4-fluorophenyl)acetate (173a) (460 mg, 0.993 mmol) in dioxane (20 mL) using (3-(aminomethyl)phenyl)boronic acid hydrochloride (1d) (372 mg, 1.986 mmol), 4 M solution of $K_3PO_4$ (0.993 mL, 3.97 mmol), tricyclohexylphosphine (84 mg, 0.298 mmol), $Pd_2(dba)_3$ (91 mg, 0.099 mmol), $PdCl_2(dppf)$-$CH_2Cl_2$ adduct (81 mg, 0.099 mmol) and heating at 110° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(tert-butyl)benzofuran-3-yl)methoxy)-4-fluorophenyl)acetate (173b) (212 mg, 44% yield) as a yellow oil; MS (ES+): 490.3 (M+1).

Step-3: Preparation of 2-(2-((5-(3-(aminomethyl)phenyl)-2-(tert-butyl)benzofuran-3-yl)methoxy)-4-fluorophenyl)acetic acid (173c)

Compound 173c was prepared according to the procedure reported in step-3 of scheme 1, from ethyl 2-(2-((5-(3-(aminomethyl)phenyl)-2-(tert-butyl)benzofuran-3-yl)methoxy)-4-fluorophenyl)acetate (173b) (212 mg, 0.433 mmol) in THF (3 mL) using lithium hydroxide hydrate (125 mg, 2.98 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(tert-butyl)benzofuran-3-yl)methoxy)-4-fluorophenyl)acetic acid (173c) (84 mg, 18% yield) HCl salt as a white solid; $^1$H NMR (300 MHz, DMSO-$d_6$) δ 8.51 (s, 2H, $D_2O$ exchangeable), 7.98 (d, J=1.6 Hz, 1H), 7.90 (s, 1H), 7.72 (dt, J=7.5, 1.7 Hz, 1H), 7.69-7.59 (m, 2H), 7.53-7.39 (m, 2H), 7.27-7.16 (m, 2H), 6.76 (td, J=8.4, 2.4 Hz, 1H), 5.32 (s, 2H), 4.09 (s, 2H), 3.43 (s, 2H), 1.45 (s, 9H); $^{19}$F NMR (282 MHz, DMSO-$d_6$) δ −113.00; MS (ES+): 462.2 (M+1), (ES−): 460.2 (M−1); Analysis calculated for $C_{28}H_{28}FNO_4$·HCl·0.75$H_2O$: C, 65.75; H, 6.01; Cl, 6.93; N, 2.74. Found: C, 65.71; H, 5.97; Cl, 7.21; N, 2.86.

Scheme 174

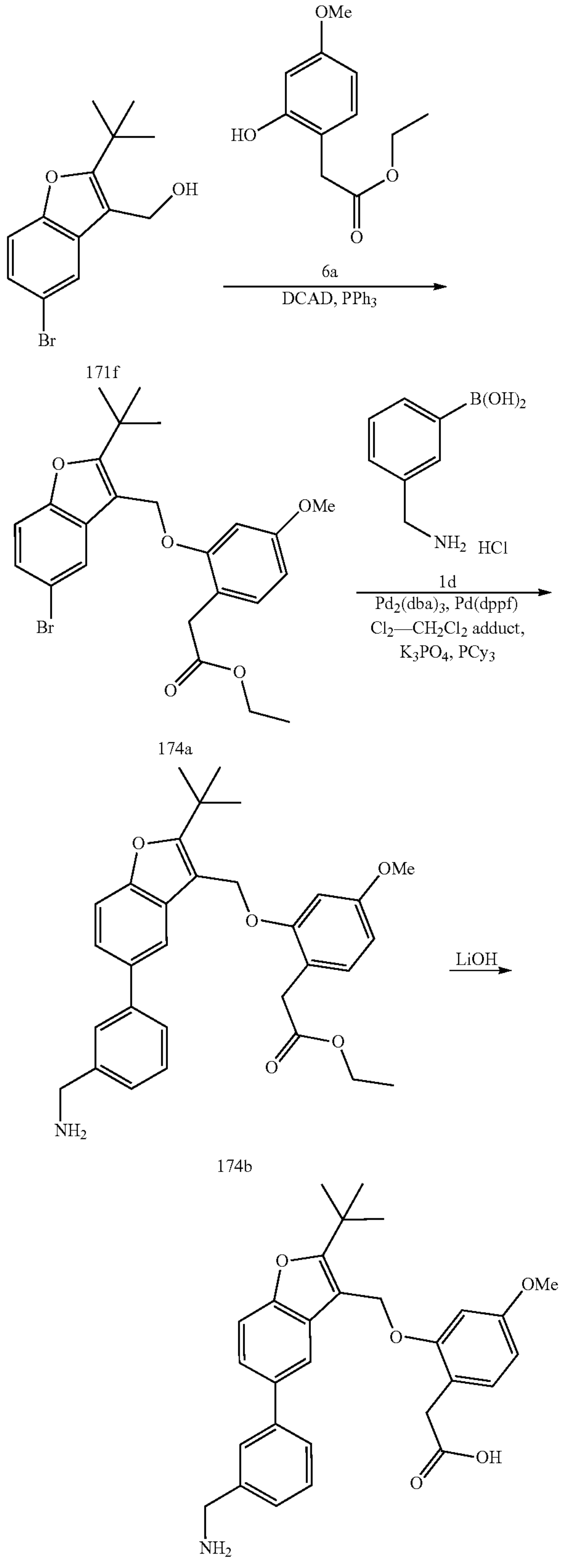

171f

174a

174b

174c

Preparation of 2-(2-((5-(3-(aminomethyl)phenyl)-2-(tert-butyl)benzofuran-3-yl)methoxy)-4-methoxyphenyl)acetic acid (174c)

Step-1: Preparation of ethyl 2-(2-((5-bromo-2-(tert-butyl)benzofuran-3-yl)methoxy)-4-methoxyphenyl) acetate (174a)

Compound 174a was prepared according to the procedure reported in step-2 of scheme 65, from (5-bromo-2-(tert-butyl)benzofuran-3-yl)methanol (171f) (350 mg, 1.236 mmol) in DCM (10 mL) using triphenylphosphine (357 mg, 1.360 mmol), ethyl 2-(2-hydroxy-4-methoxyphenyl)acetate (6a) (286 mg, 1.360 mmol), a solution of DCAD (499 mg, 1.360 mmol) in DCM (5 mL) and stirring at RT for 30 min. This gave after workup and purification using flash column chromatography [silica gel (12 g), eluting with EtOAc in hexane from 0-50%] ethyl 2-(2-((5-bromo-2-(tert-butyl) benzofuran-3-yl)methoxy)-4-methoxyphenyl)acetate (174a) (235 mg, 40% yield) as a clear oil; $^1$H NMR (300 MHz, DMSO-$d_6$) δ 7.84 (d, J=2.0 Hz, 1H), 7.53 (d, J=8.7 Hz, 1H), 7.41 (dd, J=8.6, 2.0 Hz, 1H), 7.10 (d, J=8.3 Hz, 1H), 6.82 (d, J=2.4 Hz, 1H), 6.51 (dd, J=8.3, 2.4 Hz, 1H), 5.23 (s, 2H), 3.85-3.76 (m, 5H), 3.41 (s, 2H), 1.43 (s, 9H), 0.89 (t, J=7.1 Hz, 3H).

Step-2: Preparation of ethyl 2-(2-((5-(3-(aminomethyl)phenyl)-2-(tert-butyl)benzofuran-3-yl) methoxy)-4-methoxyphenyl)acetate (174b)

Compound 174b was prepared according to the procedure reported in step-2 of scheme 1, from ethyl 2-(2-((5-bromo-2-(tert-butyl)benzofuran-3-yl)methoxy)-4-methoxyphenyl) acetate (174a) (230 mg, 0.484 mmol) in dioxane (20 mL) using (3-(aminomethyl)phenyl)boronic acid hydrochloride (1d) (181 mg, 0.968 mmol), 4 M solution of $K_3PO_4$ (0.484 mL, 1.935 mmol), tricyclohexylphosphine (40.7 mg, 0.145 mmol), $Pd_2(dba)_3$ (44.3 mg, 0.048 mmol), $PdCl_2$(dppf)-$CH_2Cl_2$ adduct (39.5 mg, 0.048 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(tert-butyl)benzofuran-3-yl)methoxy)-4-methoxyphenyl)acetate (174b) (121 mg, 50% yield) as a yellow oil; MS (ES+): 502.3 (M+1).

Step-3: Preparation of 2-(2-((5-(3-(aminomethyl) phenyl)-2-(tert-butyl)benzofuran-3-yl)methoxy)-4-methoxyphenyl)acetic acid (174c)

Compound 174c was prepared according to the procedure reported in step-3 of scheme 1, from ethyl 2-(2-((5-(3-(aminomethyl)phenyl)-2-(tert-butyl)benzofuran-3-yl) methoxy)-4-methoxyphenyl)acetate (174b) (121 mg, 0.241 mmol) in THF (3 mL) using lithium hydroxide hydrate (60.9 mg, 1.451 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(tert-butyl)benzofuran-3-yl)methoxy)-4-methoxyphenyl)acetic acid (174c) (50 mg, 22% yield) HCl salt as a white solid; $^1$H NMR (300 MHz, DMSO-$d_6$) δ 8.56 (s, 2H, $D_2O$ exchangeable), 7.99 (s, 1H), 7.92 (s, 1H), 7.75-7.69 (m, 1H), 7.68-7.60 (m, 2H), 7.52-7.42 (m, 2H), 7.10 (d, J=8.3 Hz, 1H), 6.86 (d, J=2.3 Hz, 1H), 6.51 (dd, J=8.3, 2.3 Hz, 1H), 5.31 (s, 2H), 4.09 (s, 2H), 3.78 (s, 3H), 3.38 (s, 2H), 1.46 (s, 9H); MS (ES+): 474.2 (M+1); (ES−): 472.2 (M−1); Analysis calculated for $C_{29}H_{31}NO_5$·HCl·0.75$H_2O$: C, 66.53; H, 6.45; Cl, 6.77; N, 2.68. Found: C, 66.42; H, 6.51; Cl, 7.11; N, 2.83.

Scheme 175

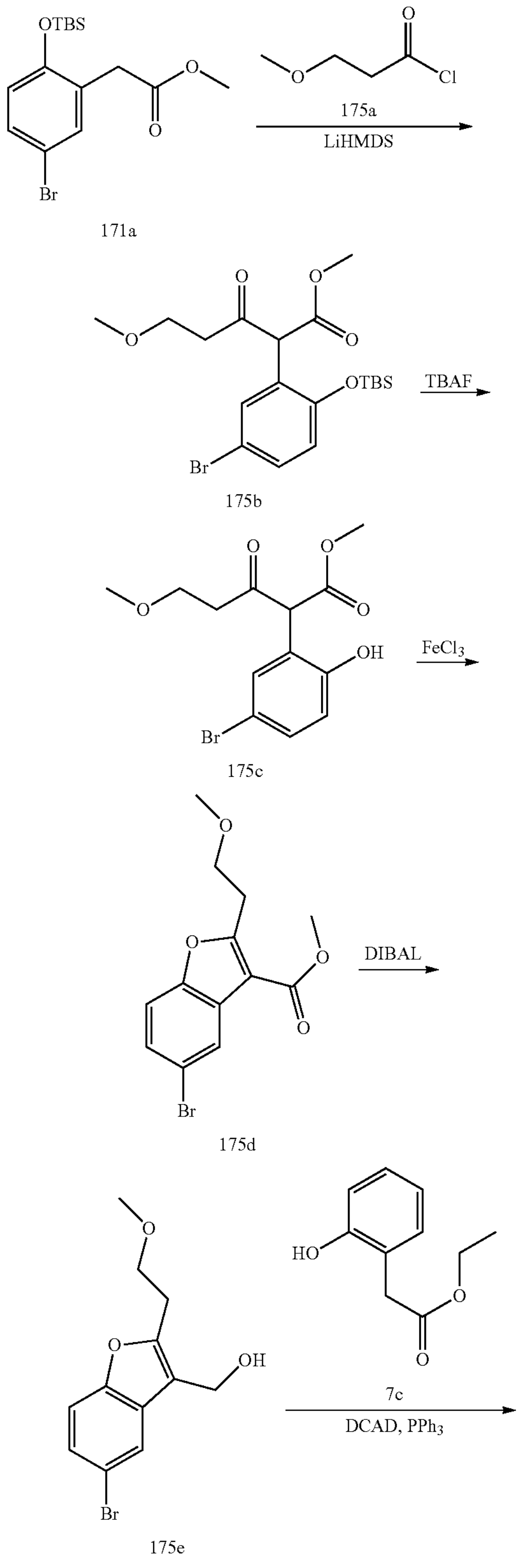

171a

175b

175c

175d

175e

-continued

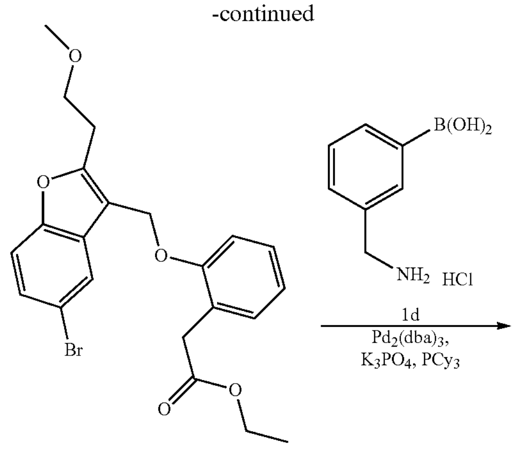

175f

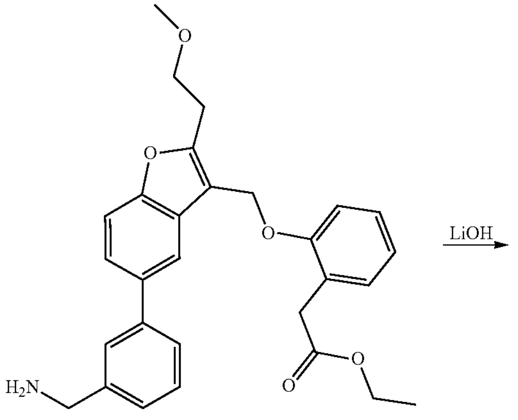

175g

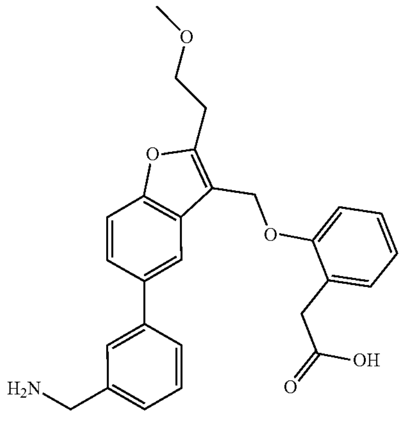

175h

Preparation of 2-(2-((5-(3-(aminomethyl)phenyl)-2-(2-methoxyethyl)benzofuran-3-yl)methoxy)phenyl) acetic acid (175 h)

Step-1: Preparation of methyl 2-(5-bromo-2-((tert-butyldimethylsilyl)oxy)phenyl)-5-methoxy-3-oxo-pentanoate (175b)

Compound 175b was prepared according to the procedure reported in step-1 of scheme 171, from methyl 2-(5-bromo-2-(tert-butyldimethylsilyloxy)phenyl)acetate (171a) (8 g, 22.26 mmol) in THF (60 mL) using LiHMDS (1N in THF) (22.26 mL, 22.26 mmol), 3-methoxypropanoyl chloride (175a) (2.73 g, 22.26 mmol; CAS #4244-59-1) in THF (10 mL) and stirring at −78° C. for 1 h followed by 0° C. for 1 h. This gave after workup and purification using flash column chromatography [silica gel (80 g), eluting with EtOAc in hexane from 0-100%]methyl 2-(5-bromo-2-((tert-butyldimethylsilyl)oxy)phenyl)-5-methoxy-3-oxopentanoate (175b) (5.2 g, 52% yield) as a clear oil; $^1$H NMR (300 MHz, DMSO-$d_6$) δ 7.25 (dd, J=8.6, 2.7 Hz, 1H), 7.18 (d, J=2.6 Hz, 1H), 6.70 (d, J=8.6 Hz, 1H), 3.51 (s, 1H), 3.47 (s, 3H), 3.40-3.32 (m, 1H), 3.32-3.26 (m, 1H), 3.00 (s, 3H), 2.21-2.02 (m, 2H), 0.72 (s, 9H), −0.01 (d, J=5.8 Hz, 6H).

Step-2: Preparation of methyl 2-(5-bromo-2-hydroxyphenyl)-5-methoxy-3-oxopentanoate (175c)

Compound 175c was prepared according to the procedure reported in step-2 of scheme 3, from methyl 2-(5-bromo-2-((tert-butyldimethylsilyl)oxy)phenyl)-5-methoxy-3-oxopentanoate (175b) (5.2 g, 11.67 mmol) using TBAF (14.59 mL, 14.59 mmol)) in THF (80 mL) and stirring at 0° C. for 1 h. This gave after workup methyl 2-(5-bromo-2-hydroxyphenyl)-5-methoxy-3-oxopentanoate (175c) (1.3 g, 34% yield) as a clear oil; MS (ES+): 353.0 and 355.0 (M+Na).

Step-3: Preparation of methyl 5-bromo-2-(2-methoxyethyl)benzofuran-3-carboxylate (175d)

Compound 175d was prepared according to the procedure reported in step-3 of scheme 171, from methyl 2-(5-bromo-2-hydroxyphenyl)-5-methoxy-3-oxopentanoate (175c) (1.3 g, 3.93 mmol) in DCE (20 mL) using iron(III) chloride (0.212 g, 0.785 mmol) and stirring for 2 days at RT. This gave after workup and purification using flash column chromatography [silica gel (24 g), eluting with EtOAc in hexane from 0-100%]methyl 5-bromo-2-(2-methoxyethyl) benzofuran-3-carboxylate (175d) (0.581 g, 47% yield) as an off-white solid; $^1$H NMR (300 MHz, DMSO-$d_6$) δ 8.05 (d, J=2.0 Hz, 1H), 7.69 (d, J=8.7 Hz, 1H), 7.57 (dd, J=8.7, 2.1 Hz, 1H), 3.95 (s, 3H), 3.77 (t, J=6.4 Hz, 2H), 3.46 (t, J=6.4 Hz, 2H), 3.28 (s, 3H); MS (ES+): 335.0 and 337.0 (M+Na).

Step-4: Preparation of (5-bromo-2-(2-methoxyethyl) benzofuran-3-yl)methanol (175e)

Compound 175e was prepared according to the procedure reported in step-2 of scheme 69, from methyl 5-bromo-2-(2-methoxyethyl)benzofuran-3-carboxylate (175d) (0.580 g, 1.852 mmol) in THF (20 mL) using 1.0 M solution of DIBAL in THF (4.63 mL, 4.63 mmol) and stirring at 0° C. for 2 h. This gave after workup and purification using flash column chromatography [silica gel (24 g), eluting with EtOAc in hexane from 0-100%] (5-bromo-2-(2-methoxyethyl)benzofuran-3-yl)methanol (175e) (0.43 g, 81% yield) as a clear oil; $^1$H NMR (300 MHz, DMSO-$d_6$) δ 7.82 (d, J=2.0 Hz, 1H), 7.48 (d, J=8.6 Hz, 1H), 7.38 (dd, J=8.6, 2.1 Hz, 1H), 5.07 (t, J=5.6 Hz, 1H), 4.56 (d, J=5.5 Hz, 2H), 3.63 (t, J=6.6 Hz, 2H), 3.24 (s, 3H), 3.05 (t, J=6.6 Hz, 2H); MS (ES+): 307.0 and 309.0 (M+Na).

Step-5: Preparation of ethyl 2-(2-((5-bromo-2-(2-methoxyethyl)benzofuran-3-yl)methoxy)phenyl) acetate (175f)

Compound 175f was prepared according to the procedure reported in step-2 of scheme 65, from (5-bromo-2-(2-methoxyethyl)benzofuran-3-yl)methanol (175e) (210 mg, 0.736 mmol) in DCM (10 mL) using triphenylphosphine (212 mg, 0.810 mmol), ethyl 2-(2-hydroxyphenyl)acetate (7c) (146 mg, 0.81 mmol), a solution of DCAD (297 mg, 0.810 mmol) in DCM (5 mL) and stirring at RT for 30 min. This gave after workup and purification using flash column chromatography [silica gel (12 g), eluting with EtOAc in hexane from 0-50%] ethyl 2-(2-((5-bromo-2-(2-methoxyethyl)benzofuran-3-yl)methoxy)phenyl)acetate (175f) (210 mg, 64% yield) as a clear oil; MS (ES+): 469.10 (M+Na).

Step-6: Preparation of ethyl 2-(2-((5-(3-(aminomethyl)phenyl)-2-(2-methoxyethyl)benzofuran-3-yl)methoxy)phenyl)acetate (175g)

Compound 175g was prepared according to the procedure reported in step-2 of scheme 1, from ethyl 2-(2-((5-bromo-2-(2-methoxyethyl)benzofuran-3-yl)methoxy)phenyl)acetate (175f) (230 mg, 0.514 mmol) in dioxane (20 mL) using (3-(aminomethyl)phenyl)boronic acid hydrochloride (1d) (193 mg, 1.028 mmol), 4 M solution of $K_3PO_4$ (0.514 mL, 2.057 mmol), tricyclohexylphosphine (57.7 mg, 0.206 mmol), $Pd_2(dba)_3$ (94 mg, 0.103 mmol) and heating at 110° C. for 5 h. This gave after workup and purification using flash column chromatography [silica gel (40 g), eluting with DMA-80 in DCM from 0-100%] ethyl 2-(2-((5-(3-(aminomethyl)phenyl)-2-(2-methoxyethyl)benzofuran-3-yl)methoxy)phenyl)acetate (175g) (122 mg, 50% yield) as a yellow oil; MS (ES+): 474.2 (M+1).

Step-7: Preparation of 2-(2-((5-(3-(aminomethyl)phenyl)-2-(2-methoxyethyl)benzofuran-3-yl)methoxy)phenyl)acetic acid (175 h)

Compound 175h was prepared according to the procedure reported in step-3 of scheme 1, from ethyl 2-(2-((5-(3-(aminomethyl)phenyl)-2-(2-methoxyethyl)benzofuran-3-yl)methoxy)phenyl)acetate (175g) (122 mg, 0.258 mmol) in THF (3 mL) using lithium hydroxide hydrate (64.7 mg, 1.543 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(2-methoxyethyl)benzofuran-3-yl)methoxy)phenyl)acetic acid (175 h) (73 mg, 32% yield) HCl salt as a white solid; $^1H$ NMR (300 MHz, DMSO-$d_6$) δ 12.10 (s, 1H, $D_2O$ exchangeable), 8.46 (s, 2H, $D_2O$ exchangeable), 7.94 (s, 1H), 7.88 (s, 1H), 7.72 (d, J=7.5 Hz, 1H), 7.69-7.58 (m, 2H), 7.54-7.40 (m, 2H), 7.31-7.22 (m, 2H), 7.22-7.14 (m, 1H), 6.96-6.87 (m, 1H), 5.26 (s, 2H), 4.10 (s, 2H), 3.66 (t, J=6.4 Hz, 2H), 3.50 (s, 2H), 3.25 (s, 3H), 3.14 (t, J=6.5 Hz, 2H); MS (ES+): 446.2 (M+1), (ES−): 444.2 (M−1); Analysis calculated for $C_{27}H_{27}NO_5 \cdot 1.1HCl \cdot 0.5H_2O$: C, 65.56; H, 5.93; Cl, 7.88; N, 2.83. Found: C, 65.80; H, 6.01; Cl, 7.78; N, 3.02.

Scheme 176

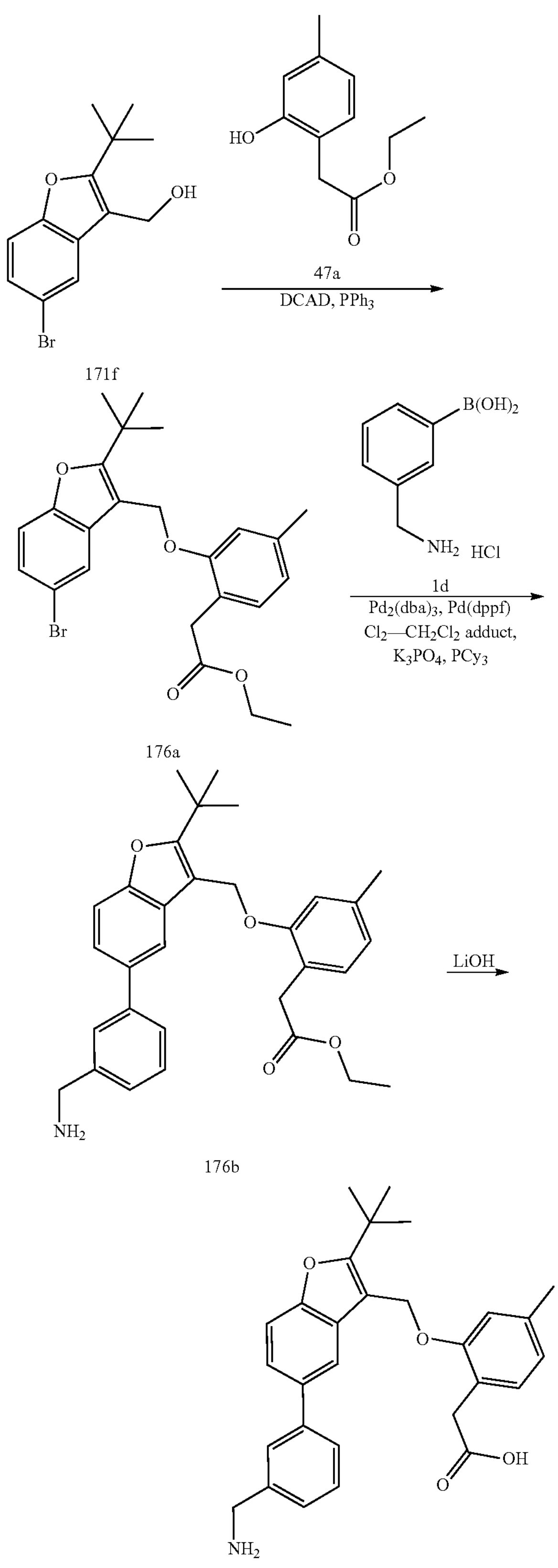

171f

176a

176b

176c

Preparation of 2-(2-((5-(3-(aminomethyl)phenyl)-2-(tert-butyl)benzofuran-3-yl)methoxy)-4-methylphenyl)acetic acid (176c)

Step-1: Preparation of ethyl 2-(2-((5-bromo-2-(tert-butyl)benzofuran-3-yl)methoxy)-4-methylphenyl) acetate (176a)

Compound 176a was prepared according to the procedure reported in step-2 of scheme 65, from (5-bromo-2-(tert-butyl)benzofuran-3-yl)methanol (171f) (350 mg, 1.236 mmol) in DCM (10 mL) using triphenylphosphine (357 mg, 1.360 mmol), ethyl 2-(2-hydroxy-4-methylphenyl)acetate (47a) (264 mg, 1.360 mmol) a solution of DCAD (499 mg, 1.360 mmol) in DCM (5 mL) and stirring at RT for 30 min. This gave after workup and purification using flash column chromatography [silica gel (12 g), eluting with EtOAc in hexane from 0-50%] ethyl 2-(2-((5-bromo-2-(tert-butyl) benzofuran-3-yl)methoxy)-4-methylphenyl)acetate (176a) (300 mg, 53% yield) as a clear oil; $^1H$ NMR (300 MHz, DMSO-$d_6$) δ 7.82 (d, J=2.0 Hz, 1H), 7.53 (d, J=8.7 Hz, 1H), 7.41 (dd, J=8.7, 2.1 Hz, 1H), 7.07 (d, J=7.4 Hz, 2H), 6.75 (d, J=7.5 Hz, 1H), 5.22 (s, 2H), 3.81 (q, J=7.1 Hz, 2H), 3.44 (s, 2H), 2.34 (s, 3H), 1.43 (s, 9H), 0.89 (t, J=7.1 Hz, 3H); MS (ES): 481.1 and 483.1 (M+Na).

Step-2: Preparation of ethyl 2-(2-((5-(3-(aminomethyl)phenyl)-2-(tert-butyl)benzofuran-3-yl) methoxy)-4-methylphenyl)acetate (176b)

Compound 176b was prepared according to the procedure reported in step-2 of scheme 1, from ethyl 2-(2-((5-bromo-2-(tert-butyl)benzofuran-3-yl)methoxy)-4-methylphenyl) acetate (176a) (300 mg, 0.653 mmol) in dioxane (20 mL) using (3-(aminomethyl)phenyl)boronic acid hydrochloride (1d) (245 mg, 1.306 mmol), 4 M solution of $K_3PO_4$ (0.653 mL, 2.61 mmol), tricyclohexylphosphine (54.9 mg, 0.196 mmol), $Pd_2(dba)_3$ (59.8 mg, 0.065 mmol), $PdCl_2$(dppf)-$CH_2Cl_2$ adduct (53.3 mg, 0.065 mmol) and heating at 110° C. for 5 h. This gave after workup and purification using flash column chromatography [silica gel (40 g), eluting with DMA-80 in DCM from 0-100%] ethyl 2-(2-((5-(3-(aminomethyl)phenyl)-2-(tert-butyl)benzofuran-3-yl)methoxy)-4-methylphenyl)acetate (176b) (110 mg, 35% yield) as a yellow oil; MS (ES+): 486.2 (M+1).

Step-3: Preparation of 2-(2-((5-(3-(aminomethyl) phenyl)-2-(tert-butyl)benzofuran-3-yl)methoxy)-4-methylphenyl)acetic acid (176c)

Compound 176c was prepared according to the procedure reported in step-3 of scheme 1, from ethyl 2-(2-((5-(3-(aminomethyl)phenyl)-2-(tert-butyl)benzofuran-3-yl) methoxy)-4-methylphenyl)acetate (176b) (110 mg, 0.227 mmol) in THF (3 mL) using lithium hydroxide hydrate (82 mg, 1.959 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(tert-butyl)benzofuran-3-yl)methoxy)-4-methylphenyl)acetic acid (176c) (80 mg, 27% yield) HCl salt as a white solid; $^1H$ NMR (300 MHz, DMSO-$d_6$) δ 8.52 (s, 2H, $D_2O$ exchangeable), 7.96 (s, 1H), 7.90 (s, 1H), 7.72 (dt, J=7.4, 1.7 Hz, 1H), 7.68-7.58 (m, 2H), 7.53-7.38 (m, 2H), 7.12 (s, 1H), 7.06 (d, J=7.5 Hz, 1H), 6.74 (d, J=7.5 Hz, 1H), 5.28 (s, 2H), 4.08 (s, 2H), 3.41 (s, 2H), 2.33 (s, 3H), 1.45 (s, 9H); MS (ES+): 458.2 (M+1), (ES−): 456.2 (M−1); Calculated for $C_{29}H_{31}NO_4 \cdot HCl \cdot H_2O$: C, 68.02; H, 6.69; Cl, 6.92; N, 2.74. Found: C, 67.80; H, 6.85; Cl, 6.90; N, 2.82.

Scheme 177

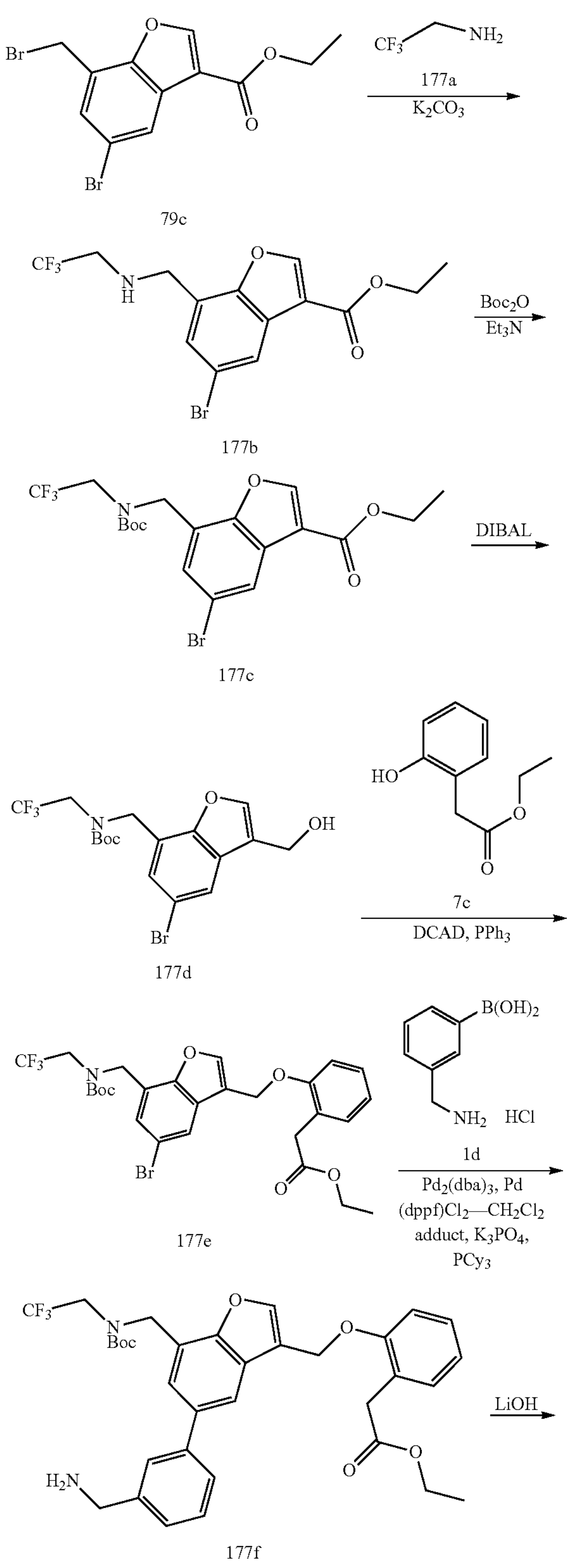

-continued

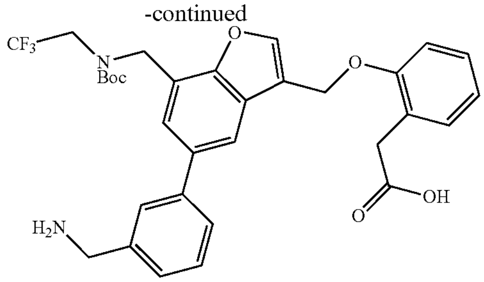

177g

Preparation of 2-(2-((5-(3-(aminomethyl)phenyl)-7-(((tert-butoxycarbonyl)(2,2,2-trifluoroethyl)amino) methyl)benzofuran-3-yl)methoxy)phenyl)acetic acid (177g)

Step-1: Preparation of ethyl 5-bromo-7-(((2,2,2-trifluoroethyl)amino)methyl)benzofuran-3-carboxylate (177b)

Compound 177b was prepared according to the procedure reported in step-1 of scheme 58, from ethyl 5-bromo-7-(bromomethyl)benzofuran-3-carboxylate (79c) (0.5 g, 1.381 mmol) in DMF (10 mL) using 2,2,2-trifluoroethanamine (177a) (0.410 g, 4.14 mmol; CAS #753-90-2), $K_2CO_3$ (0.573 g, 4.14 mmol) and stirring at RT for 3 h. This gave after workup and purification using flash column chromatography [silica gel (24 g), eluting with EtOAc in hexane from 0-80%] ethyl 5-bromo-7-(((2,2,2-trifluoroethyl)amino) methyl)benzofuran-3-carboxylate (177b) (0.2 g, 38% yield) as a white solid; $^1$H NMR (300 MHz, DMSO-$d_6$) δ 8.84 (s, 1H), 7.96 (d, J=2.1 Hz, 1H), 7.63 (d, J=2.0 Hz, 1H), 4.35 (q, J=7.1 Hz, 2H), 4.10 (d, J=6.2 Hz, 2H), 3.33-3.22 (m, 2H), 3.21-3.08 (m, 1H, $D_2O$ exchangeable), 1.35 (t, J=7.1 Hz, 3H); $^{19}$F NMR (282 MHz, DMSO-$d_6$) δ −70.33 (t, J=10.1 Hz); MS (ES+): 380.00 (M+1).

Step-2: Preparation of ethyl 5-bromo-7-(((tert-butoxycarbonyl)(2,2,2-trifluoroethyl)amino)methyl) benzofuran-3-carboxylate (177c)

A solution of ethyl 5-bromo-7-((2,2,2-trifluoroethylamino)methyl)benzofuran-3-carboxylate (177b) (0.7 g, 1.841 mmol) in DCM (15 mL) at 0° C. was treated with triethylamine (0.513 mL, 3.68 mmol) and di-tert-butyl dicarbonate (0.603 g, 2.76 mmol). The reaction was warmed slowly in an ice bath to RT and stirred for 15 h. The mixture was poured into EtOAc, washed with water and brine. The organic layer was dried, filtered and concentrated in vacuo. The obtained residue was purified using flash column chromatography [silica gel (12 g), eluting with EtOAc in hexane from 0-50%] to give ethyl 5-bromo-7-((tert-butoxycarbonyl (2,2,2-trifluoroethyl)amino)methyl)benzofuran-3-carboxylate (177c) (0.58 g, 66% yield) as a white solid; $^1$H NMR (300 MHz, DMSO-$d_6$) δ 8.88 (s, 1H), 8.00 (d, J=2.0 Hz, 1H), 7.39 (d, J=16.8 Hz, 1H), 4.78 (s, 2H), 4.36 (q, J=7.1 Hz, 2H), 4.30-4.08 (m, 2H), 1.43 (s, 3H), 1.35 (t, J=7.1 Hz, 3H), 1.28-1.11 (m, 6H); MS (ES+): 502.05 (M+Na).

Step-3: Preparation of tert-butyl ((5-bromo-3-(hydroxymethyl)benzofuran-7-yl)methyl)(2,2,2-trifluoroethyl)carbamate (177d)

Compound 177d was prepared according to the procedure reported in step-2 of scheme 69, from ethyl 5-bromo-7-(((tert-butoxycarbonyl)(2,2,2-trifluoroethyl)amino)methyl) benzofuran-3-carboxylate (177c) (0.58 g, 1.208 mmol) in DCM (10 mL) using 1.0 M solution of DIBAL in DCM (3.02 mL, 3.02 mmol) and stirring at −78° C. for 30 min. This gave after workup and purification using flash column chromatography [silica gel (24 g), eluting with EtOAc in hexane from 0-100%] tert-butyl ((5-bromo-3-(hydroxymethyl)benzofuran-7-yl)methyl)(2,2,2-trifluoroethyl)carbamate (177d) (0.420 g, 79% yield) as a light yellow oil; MS (ES+): 460.10 (M+Na).

Step-4: Preparation of ethyl 2-(2-((5-bromo-7-(((tert-butoxycarbonyl)(2,2,2-trifluoroethyl)amino) methyl) benzofuran-3-yl)methoxy)phenyl)acetate (177e)

Compound 177e was prepared according to the procedure reported in step-2 of scheme 65, from tert-butyl ((5-bromo-3-(hydroxymethyl)benzofuran-7-yl)methyl)(2,2,2-trifluoroethyl)carbamate (177d) (420 mg, 0.958 mmol) in DCM (10 mL) using triphenylphosphine (503 mg, 1.917 mmol), ethyl 2-(2-hydroxyphenyl)acetate (7c) (190 mg, 1.054 mmol) a solution of DCAD (704 mg, 1.917 mmol) in DCM (5 mL) and stirring at RT for 30 min. This gave after workup and purification using flash column chromatography [silica gel (24 g), eluting with DMA-80 in DCM from 0-60%] ethyl 2-(2-((5-bromo-7-(((tert-butoxycarbonyl)(2,2,2-trifluoroethyl)amino)methyl)benzofuran-3-yl)methoxy)phenyl)acetate (177e) (450 mg, 78% yield) as a light yellow oil; MS (ES+): 622.10 (M+Na); (ES−): 598.10 (M−1).

Step-5: Preparation of ethyl 2-(2-((5-(3-(aminomethyl)phenyl)-7-(((tert-butoxycarbonyl)(2,2,2-trifluoroethyl)amino)methyl)benzofuran-3-yl)methoxy) phenyl)acetate (177f)

Compound 177f was prepared according to the procedure reported in step-2 of scheme 1, from ethyl 2-(2-((5-bromo-7-(((tert-butoxycarbonyl)(2,2,2-trifluoroethyl)amino) methyl)benzofuran-3-yl)methoxy)phenyl)acetate (177e) (450 mg, 0.749 mmol) in dioxane (3 mL) and THF (3 mL) using (3-(aminomethyl)phenyl)boronic acid hydrochloride (1d) (281 mg, 1.499 mmol), 2 M solution of $K_3PO_4$ (1.499 mL, 3.00 mmol), tricyclohexylphosphine (42 mg, 0.150 mmol), $Pd_2(dba)_3$ (68.6 mg, 0.075 mmol), $PdCl_2$(dppf)-$CH_2Cl_2$-adduct (61.2 mg, 0.075 mmol) and heating at 90° C. for 1 h. This gave after workup and purification using flash column chromatography [silica gel (24 g), eluting with DMA-80 in DCM from 0-70%] ethyl 2-(2-((5-(3-(aminomethyl)phenyl)-7-(((tert-butoxycarbonyl)(2,2,2-trifluoroethyl)amino)methyl)benzofuran-3-yl)methoxy)phenyl)acetate (177f) (260 mg, 55% yield) as a clear oil; $^1$H NMR (300 MHz, DMSO-$d_6$) δ 8.14 (s, 1H), 7.83 (s, 1H), 7.63 (s, 1H), 7.48 (t, J=8.9 Hz, 2H), 7.41 (t, J=7.5 Hz, 1H), 7.36-7.26 (m, 2H), 7.25-7.16 (m, 2H), 6.97-6.87 (m, 1H), 5.30 (s, 2H), 4.83 (s, 2H), 4.28-4.10 (m, 2H), 3.79 (s, 2H), 3.73 (q, J=7.1 Hz, 2H), 3.55 (s, 2H), 1.48-1.18 (m, 9H), 0.86 (t, J=7.1 Hz, 3H); MS (ES+): 627.30 (M+1); (ES−): 625.20 (M−1).

Step-6: Preparation of 2-(2-((5-(3-(aminomethyl) phenyl)-7-(((tert-butoxycarbonyl)(2,2,2-trifluoroethyl)amino)methyl)benzofuran-3-yl)methoxy)phenyl)acetic acid (177g)

Compound 177g was prepared according to the procedure reported in step-3 of scheme 1, from ethyl 2-(2-((5-(3-(aminomethyl)phenyl)-7-(((tert-butoxycarbonyl)(2,2,2-trifluoroethyl)amino)methyl)benzofuran-3-yl)methoxy)phenyl)acetate (177f) (90 mg, 0.144 mmol) in THF/MeOH (2 mL each) using lithium hydroxide hydrate (36.2 mg, 0.862 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-7-(((tert-butoxycarbonyl)(2,2,2-trifluoroethyl)amino)methyl)benzofuran-3-yl)methoxy)phenyl)acetic acid (177g) (45 mg, 52% yield) HCl salt as a white solid; $^1$H NMR (300 MHz, DMSO-$d_6$) δ 12.13 (s, 1H, $D_2O$ exchangeable), 8.34 (s, 2H, $D_2O$ exchangeable), 8.15 (s, 1H), 7.93 (s, 1H), 7.83 (s, 1H), 7.68 (d, J=7.6 Hz, 1H), 7.54 (t, J=7.6 Hz, 1H), 7.47 (d, J=7.5 Hz, 2H), 7.31-7.23 (m, 1H), 7.23-7.15 (m, 2H), 6.96-6.88 (m, 1H), 5.32 (s, 2H), 4.84 (s, 2H), 4.31-4.12 (m, 2H), 4.10 (s, 2H), 3.53 (s, 2H), 1.48-1.17 (m, 9H); $^{19}$F NMR (282 MHz, DMSO-$d_6$) δ −69.55; MS (ES+): 599.25 (M+1); (ES−): 597.20 (M−1); Analysis calculated for $C_{32}H_{33}F_3N_2O_6 \cdot 1.05HCl \cdot 1.25H_2O$: C, 58.29; H, 5.59; Cl, 5.64; N, 4.25. Found: C, 58.48; H, 5.48; Cl, 5.85; N, 4.29.

Scheme 178

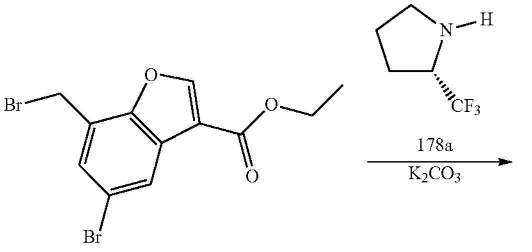

79c

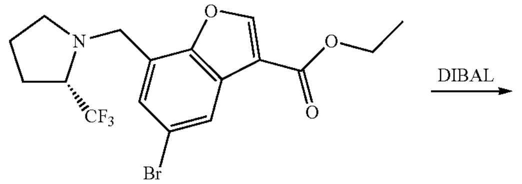

178b

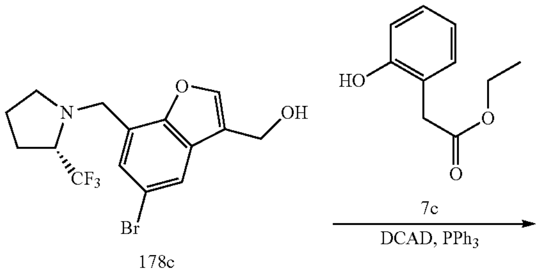

178c

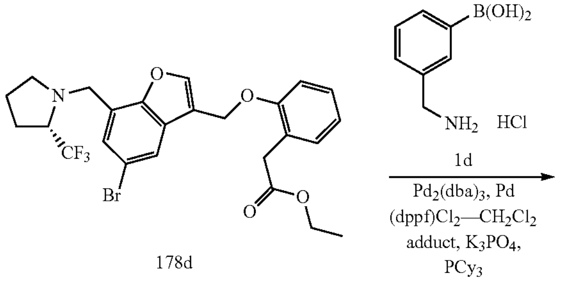

178d

-continued

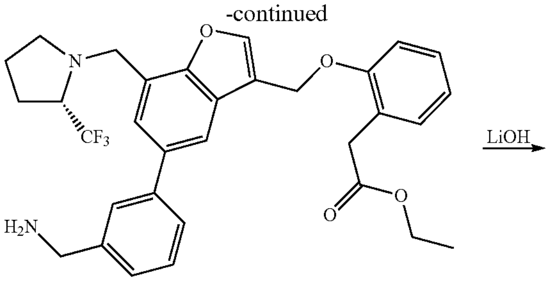

178e

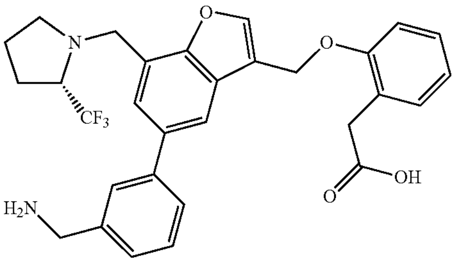

178f

Preparation of (S)-2-(2-((5-(3-(aminomethyl)phenyl)-7-((2-(trifluoromethyl)pyrrolidin-1-yl)methyl)benzofuran-3-yl)methoxy)phenyl)acetic acid (178f)

Step-1: Preparation of (S)-ethyl 5-bromo-7-((2-(trifluoromethyl)pyrrolidin-1-yl)methyl)benzofuran-3-carboxylate (178b)

Compound 178b was prepared according to the procedure reported in step-1 of scheme 58, from ethyl 5-bromo-7-(bromomethyl)benzofuran-3-carboxylate (79c) (0.6 g, 1.657 mmol) in DMF (10 mL) using (S)-2-(trifluoromethyl)pyrrolidine (178a) (0.692 g, 4.97 mmol; CAS #119580-41-5), $K_2CO_3$ (0.687 g, 4.97 mmol) and stirring at RT for 15 h. This gave after workup and purification using flash column chromatography [silica gel (24 g), eluting with EtOAc in hexane from 0-80%](S)-ethyl 5-bromo-7-((2-(trifluoromethyl)pyrrolidin-1-yl)methyl)benzofuran-3-carboxylate (178b) (0.37 g, 53% yield) as a yellow solid; $^1$H NMR (300 MHz, DMSO-$d_6$) δ 8.86 (d, J=2.5 Hz, 1H), 7.98 (d, J=2.2 Hz, 1H), 7.54 (d, J=2.2 Hz, 1H), 4.36 (qd, J=7.1, 2.3 Hz, 2H), 4.31-4.05 (m, 2H), 3.72-3.54 (m, 1H), 2.94-2.83 (m, 1H), 2.48-2.44 (m, 1H), 2.15-1.96 (m, 1H), 1.93-1.59 (m, 3H), 1.35 (td, J=7.1, 2.2 Hz, 3H); $^{19}$F NMR (282 MHz, DMSO-$d_6$) δ −74.91; MS (ES+): 420.00 (M+1).

Step-2: Preparation of (S)—(5-bromo-7-((2-(trifluoromethyl)pyrrolidin-1-yl)methyl)benzofuran-3-yl)methanol (178c)

Compound 178c was prepared according to the procedure reported in step-2 of scheme 69, from (S)-ethyl 5-bromo-7-((2-(trifluoromethyl)pyrrolidin-1-yl)methyl)benzofuran-3-carboxylate (178b) (0.37 g, 0.88 mmol) in DCM (10 mL) using 1.0 M solution of DIBAL in DCM (2.201 mL, 2.201 mmol) and stirring at −78° C. for 30 min. This gave after workup and purification using flash column chromatography [silica gel (24 g), eluting with EtOAc in hexane from 0-100%](S)—(5-bromo-7-((2-(trifluoromethyl)pyrrolidin-1-yl)methyl)benzofuran-3-yl)methanol (178c) (0.28 g, 84% yield) as a light yellow oil; $^1$H NMR (300 MHz, DMSO-$d_6$)

δ 7.94 (s, 1H), 7.80 (d, J=2.0 Hz, 1H), 7.41 (d, J=2.0 Hz, 1H), 5.21 (t, J=5.6 Hz, 1H), 4.59 (dd, J=5.6, 1.1 Hz, 2H), 4.26-4.02 (m, 2H), 3.69-3.50 (m, 1H), 2.87 (t, J=7.1 Hz, 1H), 2.45 (dd, J=9.1, 6.0 Hz, 1H), 2.12-1.95 (m, 1H), 1.90-1.61 (m, 3H); MS (ES+): 378.05 (M+1).

Step-3: Preparation of (S)-ethyl 2-(2-((5-bromo-7-((2-(trifluoromethyl)pyrrolidin-1-yl)methyl)benzofuran-3-yl)methoxy)phenyl)acetate (178d)

Compound 178d was prepared according to the procedure reported in step-2 of scheme 65, from (S)—(5-bromo-7-((2-(trifluoromethyl)pyrrolidin-1-yl)methyl)benzofuran-3-yl) methanol (178c) (280 mg, 0.74 mmol) in DCM (10 mL) using triphenylphosphine (388 mg, 1.481 mmol), ethyl 2-(2-hydroxyphenyl)acetate (7c) (147 mg, 0.814 mmol) a solution of DCAD (544 mg, 1.481 mmol) in DCM (5 mL) and stirring at RT for 30 min. This gave after workup and purification using flash column chromatography [silica gel (24 g), eluting with DMA-80 in DCM from 0-60%](S)-ethyl 2-(2-((5-bromo-7-((2-(trifluoromethyl)pyrrolidin-1-yl) methyl)benzofuran-3-yl)methoxy)phenyl)acetate (178d) (230 mg, 58% yield) as a light yellow oil; $^1$H NMR (300 MHz, DMSO-$d_6$) δ 8.16 (s, 1H), 7.75 (d, J=2.0 Hz, 1H), 7.46 (d, J=2.0 Hz, 1H), 7.29 (td, J=7.8, 7.3, 1.8 Hz, 1H), 7.24-7.14 (m, 2H), 6.92 (td, J=7.3, 1.2 Hz, 1H), 5.23 (s, 2H), 4.31-4.02 (m, 2H), 3.93 (q, J=7.1 Hz, 2H), 3.62 (t, J=8.2 Hz, 1H), 3.55 (s, 2H), 2.88 (t, J=7.6 Hz, 1H), 2.48-2.42 (m, 1H), 2.15-1.95 (m, 1H), 1.92-1.61 (m, 3H), 0.97 (t, J=7.1 Hz, 3H).

Step-4: Preparation of (S)-ethyl 2-(2-((5-(3-(aminomethyl)phenyl)-7-((2-(trifluoromethyl)pyrrolidin-1-yl)methyl)benzofuran-3-yl)methoxy)phenyl)acetate (178e)

Compound 178e was prepared according to the procedure reported in step-2 of scheme 1, from (S)-ethyl 2-(2-((5-bromo-7-((2-(trifluoromethyl)pyrrolidin-1-yl)methyl)benzofuran-3-yl)methoxy)phenyl)acetate (178d) (230 mg, 0.426 mmol) in dioxane (3 mL) and THF (3 mL) using (3-(aminomethyl)phenyl)boronic acid hydrochloride (1d) (160 mg, 0.851 mmol), 2 M solution of $K_3PO_4$ (0.851 mL, 1.703 mmol), tricyclohexylphosphine (23.87 mg, 0.085 mmol), $Pd_2(dba)_3$ (39.0 mg, 0.043 mmol), $PdCl_2(dppf)$-$CH_2Cl_2$-adduct (34.8 mg, 0.043 mmol) and heating at 90° C. for 1 h. This gave after workup and purification using flash column chromatography [silica gel (24 g), eluting with DMA-80 in DCM from 0-70%](S)-ethyl 2-(2-((5-(3-(aminomethyl)phenyl)-7-((2-(trifluoromethyl)pyrrolidin-1-yl) methyl)benzofuran-3-yl)methoxy)phenyl)acetate (178e) (72 mg, 30% yield) as a clear oil; MS (ES+): 567.20 (M+1); (ES−): 565.10 (M−1).

Step-5: Preparation of (S)-2-(2-((5-(3-(aminomethyl)phenyl)-7-((2-(trifluoromethyl)pyrrolidin-1-yl) methyl)benzofuran-3-yl)methoxy)phenyl)acetic acid (178f)

Compound 178f was prepared according to the procedure reported in step-3 of scheme 1, from (S)-ethyl 2-(2-((5-(3-(aminomethyl)phenyl)-7-((2-(trifluoromethyl)pyrrolidin-1-yl)methyl)benzofuran-3-yl)methoxy)phenyl)acetate (178e) (70 mg, 0.124 mmol) in THF/MeOH (2 mL each) using lithium hydroxide hydrate (31.1 mg, 0.741 mmol) in water (1 mL) and stirring at RT for 15 h. This gave after workup and purification using reverse phase column chromatography [C18 column (50 g), eluting with ACN in water (containing 0.1% HCl) from 0-100%](S)-2-(2-((5-(3-(aminomethyl)phenyl)-7-((2-(trifluoromethyl)pyrrolidin-1-yl) methyl)benzofuran-3-yl)methoxy)phenyl)acetic acid (178f) (58 mg, 87% yield) HCl salt as a white solid; $^1$H NMR (300 MHz, DMSO-$d_6$) δ 8.47 (s, 3H, $D_2O$ exchangeable), 8.14 (s, 1H), 7.93 (d, J=1.8 Hz, 1H), 7.87 (s, 1H), 7.75-7.67 (m, 1H), 7.65 (s, 1H), 7.57-7.44 (m, 2H), 7.28 (td, J=7.7, 7.1, 1.7 Hz, 1H), 7.24-7.15 (m, 2H), 6.97-6.86 (m, 1H), 5.32 (s, 2H), 4.43-4.28 (m, 1H), 4.23-4.03 (m, 3H), 3.81-3.63 (m, 1H), 3.55 (s, 2H), 3.04-2.89 (m, 1H), 2.76-2.55 (m, 1H), 2.18-1.95 (m, 1H), 1.94-1.59 (m, 3H); $^{19}$F NMR (282 MHz, DMSO-$d_6$) δ −74.42; MS (ES+): 539.20 (M+1); (ES−): 537.20 (M−1); Analysis calculated for $C_{30}H_{29}F_3N_2O_4 \cdot 2HCl \cdot 2H_2O$: C, 55.65; H, 5.45; Cl, 10.95; N, 4.33. Found: C, 55.49; H, 5.36; Cl, 11.28; N, 4.28; Optical rotation: $[\alpha]_D$=(−) 23.414 [$CH_3OH$, 0.205].

Scheme 179

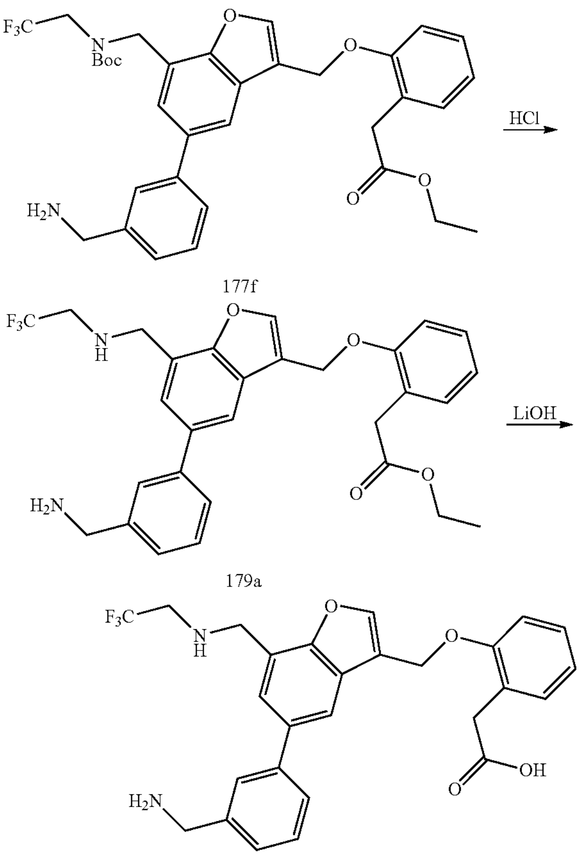

177f

179a

179b

Preparation of 2-(2-((5-(3-(aminomethyl)phenyl)-7-(((2,2,2-trifluoroethyl)amino)methyl)benzofuran-3-yl)methoxy)phenyl)acetic acid (179b)

Step-1: Preparation of ethyl 2-(2-((5-(3-(aminomethyl)phenyl)-7-(((2,2,2-trifluoroethyl)amino) methyl) benzofuran-3-yl)methoxy)phenyl)acetate (179a)

Compound 179a was prepared according to the procedure reported in step-2 of scheme 7, from ethyl 2-(2-((5-(3-

(aminomethyl)phenyl)-7-(((tert-butoxycarbonyl)(2,2,2-trifluoroethyl)amino)methyl)benzofuran-3-yl)methoxy)phenyl)acetate (177f) (170 mg, 0.271 mmol) in EtOH (5 mL) using HCl (4M HCl in dioxane) (0.678 mL, 2.71 mmol) and stirring the reaction mixture at RT for 2 days. This gave after workup and purification using flash column chromatography [silica gel (24 g), eluting with DMA-80 in DCM from 0-50%] ethyl 2-(2-((5-(3-(aminomethyl)phenyl)-7-(((2,2,2-trifluoroethyl)amino)methyl)benzofuran-3-yl)methoxy)phenyl)acetate (179a) (140 mg, 98% yield) as a yellow solid; MS (ES+): 527.20 (M+1); (ES−): 525.15 (M−1).

Step-2: Preparation of 2-(2-((5-(3-(aminomethyl)phenyl)-7-(((2,2,2-trifluoroethyl)amino)methyl) benzofuran-3-yl)methoxy)phenyl)acetic acid (179b)

Compound 179b was prepared according to the procedure reported in step-3 of scheme 1, from ethyl 2-(2-((5-(3-(aminomethyl)phenyl)-7-(((2,2,2-trifluoroethyl)amino)methyl)benzofuran-3-yl)methoxy)phenyl)acetate (179a) (140 mg, 0.266 mmol) in THF/MeOH (2 mL each) using lithium hydroxide hydrate (66.9 mg, 1.595 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-7-(((2,2,2-trifluoroethyl)amino)methyl)benzofuran-3-yl)methoxy)phenyl)acetic acid (179b) (90 mg, 68% yield) HCl salt as a white solid; $^1$H NMR (300 MHz, DMSO-$d_6$) δ 8.44 (s, 3H, $D_2O$ exchangeable), 8.21 (s, 1H), 8.03 (s, 1H), 7.98 (s, 1H), 7.93 (s, 1H), 7.79 (d, J=7.5 Hz, 1H), 7.55 (t, J=7.5 Hz, 1H), 7.49 (d, J=7.7 Hz, 1H), 7.32-7.24 (m, 1H), 7.24-7.17 (m, 2H), 6.93 (td, J=7.2, 1.3 Hz, 1H), 5.34 (s, 2H), 4.45 (s, 2H), 4.14-4.07 (m, 2H), 3.96-3.88 (m, 2H), 3.54 (s, 2H); $^{19}$F NMR (282 MHz, DMSO-$d_6$) δ −67.23; MS (ES+): 499.20 (M+1); MS (ES−): 497.20 (M−1); Analysis calculated for $C_{27}H_{25}F_3N_2O_4$·2HCl·1.5$H_2O$: C, 54.19; H, 5.05; Cl, 11.85; N, 4.68. Found: C, 54.09; H, 5.00; Cl, 11.76; N, 4.66.

Scheme 180

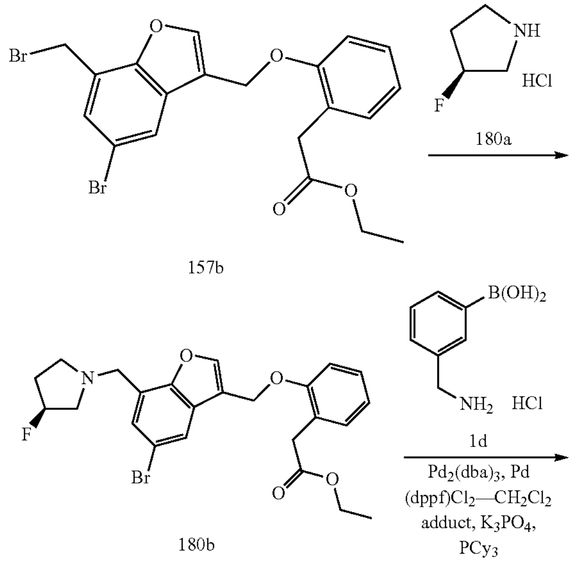

157b

180b

-continued

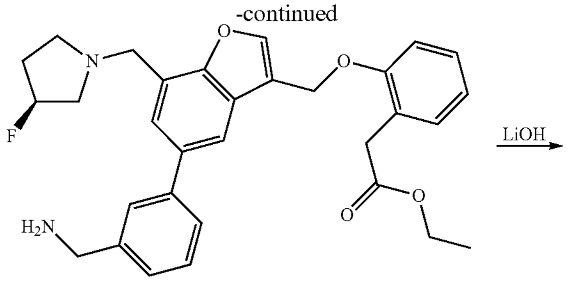

180c

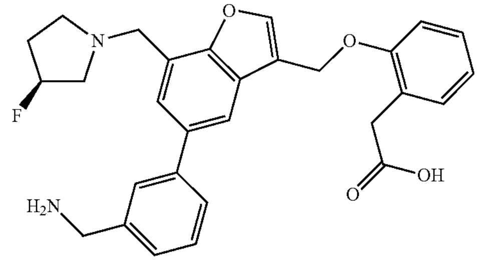

180d

Preparation of (S)-2-(2-((5-(3-(aminomethyl)phenyl)-7-((3-fluoropyrrolidin-11-yl)methyl)benzofuran-3-yl)methoxy)phenyl)acetic acid (180d)

Step-1: Preparation of (S)-ethyl 2-(2-((5-bromo-7-((3-fluoropyrrolidin-1-yl)methyl)benzofuran-3-yl)methoxy)phenyl)acetate (180b)

To a solution of ethyl 2-(2-((5-bromo-7-(bromomethyl)benzofuran-3-yl)methoxy)phenyl)acetate (157b) (270 mg, 0.560 mmol) in DMF (5 mL) was added (S)-3-fluoropyrrolidine hydrochloride (180a) (211 mg, 1.680 mmol; CAS #136725-53-6) and stirred at RT for 15 h under an argon atmosphere. The solvent was removed in vacuo and the residue obtained was purified using flash column chromatography [silica gel (24 g), eluting with DMA-80 in DCM from 0-50%] to give (S)-ethyl 2-(2-((5-bromo-7-((3-fluoropyrrolidin-1-yl)methyl)benzofuran-3-yl)methoxy)phenyl) acetate (180b) (220 mg, 80% yield) as a white oil; MS (ES+): 490.10 (M+1); MS (ES−): 488.05 (M−1).

Step-2: Preparation of (S)-ethyl 2-(2-((5-(3-(aminomethyl)phenyl)-7-((3-fluoropyrrolidin-1-yl) methyl)benzofuran-3-yl)methoxy)phenyl)acetate (180c)

Compound 180c was prepared according to the procedure reported in step-2 of scheme 1, from (S)-ethyl 2-(2-((5-bromo-7-((3-fluoropyrrolidin-1-yl)methyl)benzofuran-3-yl) methoxy)phenyl)acetate (180b) (220 mg, 0.449 mmol) in dioxane (3 mL) and THF (3 mL) using (3-(aminomethyl) phenyl)boronic acid hydrochloride (1d) (168 mg, 0.897 mmol), 2 M solution of $K_3PO_4$ (0.897 mL, 1.795 mmol), tricyclohexylphosphine (25.2 mg, 0.090 mmol), $Pd_2(dba)_3$ (41.1 mg, 0.045 mmol), $PdCl_2$(dppf)-$CH_2Cl_2$-adduct (36.6 mg, 0.045 mmol) and heating at 100° C. for 2 h. This gave after workup and purification using flash column chromatography [silica gel (24 g), eluting with DMA-80 in DCM from 0-70%](S)-ethyl 2-(2-((5-(3-(aminomethyl)phenyl)-7-((3-fluoropyrrolidin-1-yl)methyl)benzofuran-3-yl)methoxy) phenyl)acetate (180c) (90 mg, 38% yield) as a clear oil; MS (ES+): 517.20 (M+1).

Step-3: Preparation of (S)-2-(2-((5-(3-(aminomethyl)phenyl)-7-((3-fluoropyrrolidin-1-yl)methyl)benzofuran-3-yl)methoxy)phenyl)acetic acid (180d)

Compound 180d was prepared according to the procedure reported in step-3 of scheme 1, from (S)-ethyl 2-(2-((5-(3-(aminomethyl)phenyl)-7-((3-fluoropyrrolidin-1-yl)methyl)benzofuran-3-yl)methoxy)phenyl)acetate (180c) (90 mg, 0.174 mmol) in THF/MeOH (2 mL each) using lithium hydroxide hydrate (21.93 mg, 0.523 m) in water (1 mL) and heating at 50° C. for 1 h. This gave after workup and purification using reverse phase column chromatography [C18 column (50 g), eluting with ACN in water (containing 0.1% HCl) from 0-100%](S)-2-(2-((5-(3-(aminomethyl)phenyl)-7-((3-fluoropyrrolidin-1-yl)methyl)benzofuran-3-yl)methoxy)phenyl)acetic acid (180d) (50 mg, 59% yield) HCl salt as a white solid; $^1$H NMR (300 MHz, DMSO-$d_6$) δ 12.19 (s, 1H), 8.49 (s, 3H), 8.25 (s, 1H), 8.14 (m, 2H), 7.99 (s, 1H), 7.82 (m, 1H), 7.61-7.46 (m, 2H), 7.26 (m, 3H), 6.94 (m, 1H), 5.35 (s, 2H), 4.77 (s, 2H), 4.11 (d, J=5.8 Hz, 2H), 3.56 (m, 4H), 3.37 (m, 2H), 2.41-2.02 (m, 2H); $^{19}$F NMR (282 MHz, DMSO-$d_6$) δ −169.21--173.55 (m); MS (ES+): 489.20 (M+1); MS (ES−): 487.20 (M−1); Analysis calculated for $C_{29}H_{29}FN_2O_4$·2HCl·1.75$H_2O$: C, 58.74; H, 5.86; Cl, 11.96; N, 4.72. Found: C, 58.64; H, 5.74; Cl, 12.28; N, 4.73.

Scheme 181

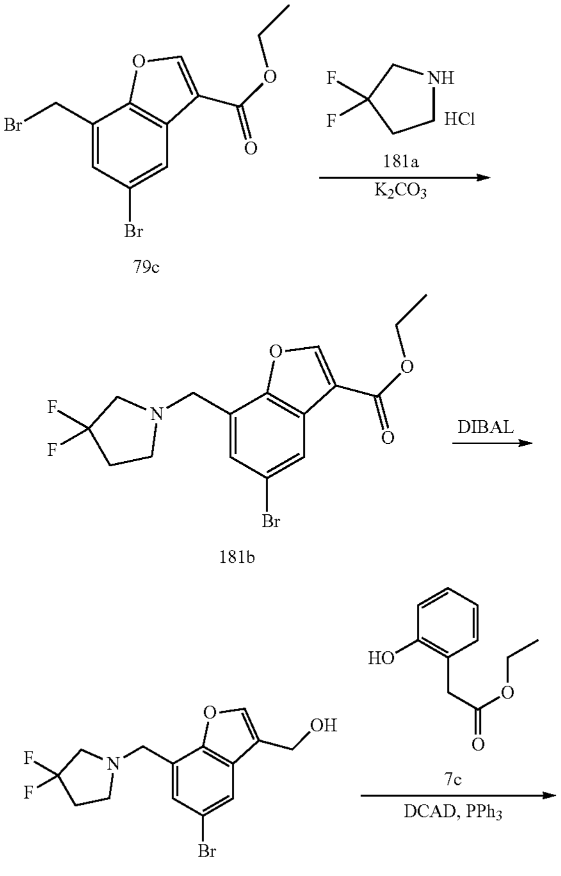

79c, 181b, 181c

-continued

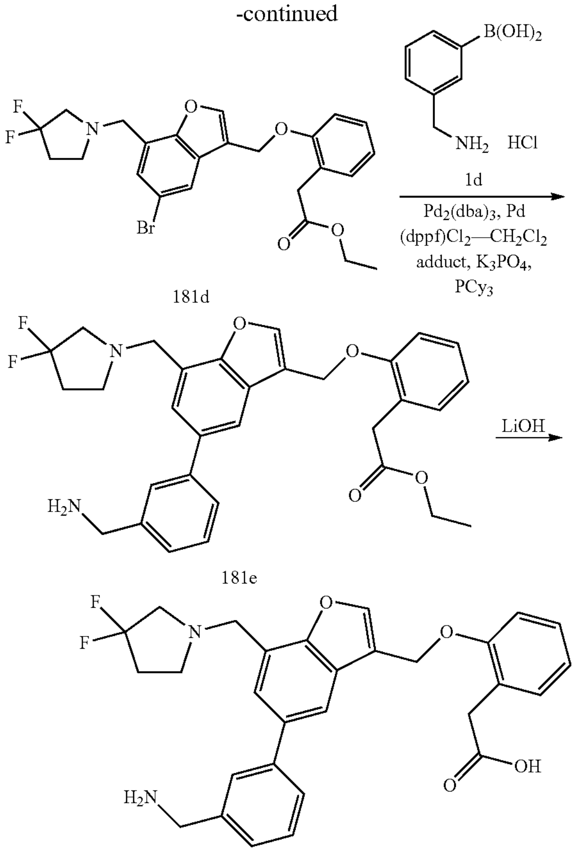

181d, 181e, 181f

Preparation of 2-(2-((5-(3-(aminomethyl)phenyl)-7-((3,3-difluoropyrrolidin-1-yl)methyl)benzofuran-3-yl)methoxy)phenyl)acetic acid (181f)

Step-1: Preparation of ethyl 5-bromo-7-((3,3-difluoropyrrolidin-1-yl)methyl)benzofuran-3-carboxylate (181b)

Compound 181b was prepared according to the procedure reported in step-1 of scheme 58, from ethyl 5-bromo-7-(bromomethyl)benzofuran-3-carboxylate (79c) (0.6 g, 1.657 mmol) in DMF (10 mL) using 3,3-difluoropyrrolidine hydrochloride (181a) (0.714 g, 4.97 mmol; CAS #163457-23-6), $K_2CO_3$ (0.687 g, 4.97 mmol) and stirring at RT for 15 h. This gave after workup and purification using flash column chromatography [silica gel (24 g), eluting with EtOAc in hexane from 0-80%] ethyl 5-bromo-7-((3,3-difluoropyrrolidin-1-yl)methyl)benzofuran-3-carboxylate (181b) (0.46 g, 72% yield) as a yellow solid; $^1$H NMR (300 MHz, DMSO-$d_6$) δ 8.85 (s, 1H), 7.99 (d, J=2.0 Hz, 1H), 7.56 (d, J=2.0 Hz, 1H), 4.35 (q, J=7.1 Hz, 2H), 3.93 (s, 2H), 2.93 (t, J=13.3 Hz, 2H), 2.74 (t, J=6.9 Hz, 2H), 2.25 (tt, J=14.9, 6.9 Hz, 2H), 1.34 (t, J=7.1 Hz, 3H); $^{19}$F NMR (282 MHz, DMSO-$d_6$) δ −90.84; MS (ES+): 388.10 (M+1).

Step-2: Preparation of (5-bromo-7-((3,3-difluoropyrrolidin-1-yl)methyl)benzofuran-3-yl)methanol (181c)

Compound 181c was prepared according to the procedure reported in step-2 of scheme 69, from ethyl 5-bromo-7-((3, 3-difluoropyrrolidin-1-yl)methyl)benzofuran-3-carboxylate (181b) (0.46 g, 1.185 mmol) in DCM (10 mL) using 1.0 M solution of DIBAL in DCM (2.96 mL, 2.96 mmol) and stirring at −78° C. for 30 min. This gave after workup and purification using flash column chromatography [silica gel (24 g), eluting with DMA-80 in DCM from 0-100%](5-bromo-7-((3,3-difluoropyrrolidin-1-yl)methyl)benzofuran-3-yl)methanol (181c) (0.36 g, 88% yield) as a light yellow oil; $^1$H NMR (300 MHz, DMSO-$d_6$) δ 7.95 (d, J=1.3 Hz, 1H), 7.82 (d, J=2.0 Hz, 1H), 7.42 (d, J=2.0 Hz, 1H), 5.22 (t, J=5.6 Hz, 1H), 4.60 (dd, J=5.6, 1.1 Hz, 2H), 3.90 (s, 2H), 2.91 (t, J=13.3 Hz, 2H), 2.73 (t, J=6.9 Hz, 2H), 2.25 (tt, J=15.0, 6.9 Hz, 2H); $^{19}$F NMR (282 MHz, DMSO-$d_6$) δ −90.80; MS (ES+): 346.10 (M+1).

Step-3: Preparation of ethyl 2-(2-((5-bromo-7-((3,3-difluoropyrrolidin-1-yl)methyl)benzofuran-3-yl)methoxy)phenyl)acetate (181d)

Compound 181d was prepared according to the procedure reported in step-2 of scheme 65, from (5-bromo-7-((3,3-difluoropyrrolidin-1-yl)methyl)benzofuran-3-yl)methanol (181c) (360 mg, 1.04 mmol) in DCM (10 mL) using triphenylphosphine (546 mg, 2.080 mmol), ethyl 2-(2-hydroxyphenyl)acetate (7c) (206 mg, 1.144 mmol), DCAD (764 mg, 2.080 mmol) in DCM (5 mL) and stirring at RT for 30 min. This gave after workup and purification using flash column chromatography [silica gel (24 g), eluting with DMA-80 in DCM from 0-60%]ethyl 2-(2-((5-bromo-7-((3,3-difluoropyrrolidin-1-yl)methyl)benzofuran-3-yl)methoxy)phenyl)acetate (181d) (300 mg, 57% yield) as a light yellow oil; $^1$H NMR (300 MHz, DMSO-$d_6$) δ 8.16 (s, 1H), 7.77 (d, J=2.0 Hz, 1H), 7.47 (d, J=2.0 Hz, 1H), 7.33-7.25 (m, 1H), 7.24-7.15 (m, 2H), 6.92 (td, J=7.4, 1.2 Hz, 1H), 5.23 (s, 2H), 3.97-3.84 (m, 4H), 3.55 (s, 2H), 2.92 (t, J=13.3 Hz, 2H), 2.74 (t, J=6.9 Hz, 2H), 2.25 (tt, J=14.9, 6.9 Hz, 2H), 0.96 (t, J=7.1 Hz, 3H); MS (ES+): 508.10 (M+1).

Step-4: Preparation of ethyl 2-(2-((5-(3-(aminomethyl)phenyl)-7-((3,3-difluoropyrrolidin-1-yl)methyl)benzofuran-3-yl)methoxy)phenyl)acetate (181e)

Compound 181e was prepared according to the procedure reported in step-2 of scheme 1, from ethyl 2-(2-((5-bromo-7-((3,3-difluoropyrrolidin-1-yl)methyl)benzofuran-3-yl)methoxy)phenyl)acetate (181d) (300 mg, 0.590 mmol) in dioxane (3 mL) and THF (3 mL) using (3-(aminomethyl)phenyl)boronic acid hydrochloride (1d) (221 mg, 1.18 mmol), 2 M solution of $K_3PO_4$ (1.180 mL, 2.361 mmol), tricyclohexylphosphine (33.1 mg, 0.118 mmol), $Pd_2(dba)_3$ (54 mg, 0.059 mmol), $PdCl_2$(dppf)-$CH_2Cl_2$-adduct (48.2 mg, 0.059 mmol) and heating at 90° C. for 1 h. This gave after workup and purification using flash column chromatography [silica gel (12 g), eluting with DMA-80 in DCM from 0-70%] ethyl 2-(2-((5-(3-(aminomethyl)phenyl)-7-((3,3-difluoropyrrolidin-1-yl)methyl)benzofuran-3-yl)methoxy)phenyl)acetate (181e) (85 mg, 27% yield) as a clear oil; $^1$H NMR (300 MHz, DMSO-$d_6$) δ 8.15 (s, 1H), 7.83 (d, J=1.8 Hz, 1H), 7.67 (s, 1H), 7.61-7.52 (m, 2H), 7.41 (t, J=7.6 Hz, 1H), 7.36-7.27 (m, 2H), 7.27-7.17 (m, 2H), 6.92 (t, J=7.3 Hz, 1H), 5.29 (s, 2H), 3.99 (s, 2H), 3.82 (s, 2H), 3.71 (q, J=7.1 Hz, 2H), 3.55 (s, 2H), 3.03-2.87 (m, 2H), 2.82-2.70 (m, 2H), 2.33-2.20 (m, 2H), 0.83 (t, J=7.1 Hz, 3H); MS (ES+): 535.20 (M+1).

Step-5: Preparation of 2-(2-((5-(3-(aminomethyl)phenyl)-7-((3,3-difluoropyrrolidin-1-yl)methyl)benzofuran-3-yl)methoxy)phenyl)acetic acid (181f)

Compound 181f was prepared according to the procedure reported in step-3 of scheme 1, from ethyl 2-(2-((5-(3-(aminomethyl)phenyl)-7-((3,3-difluoropyrrolidin-1-yl)methyl)benzofuran-3-yl)methoxy)phenyl)acetate (181e) (80 mg, 0.150 mmol) in THF/MeOH (2 mL each) using lithium hydroxide hydrate (37.7 mg, 0.898 mmol) in water (1 mL) and stirring for 15 h at RT. This gave after workup and purification using reverse phase column chromatography [C18 column (50 g), eluting with ACN in water (containing 0.1% HCl) from 0-100%] 2-(2-((5-(3-(aminomethyl)phenyl)-7-((3,3-difluoropyrrolidin-1-yl)methyl)benzofuran-3-yl)methoxy)phenyl)acetic acid (181f) (40 mg, 53% yield) HCl salt as a white solid; $^1$H NMR (300 MHz, DMSO-$d_6$) δ 12.52 (s, 1H, $D_2O$ exchangeable), 8.51 (s, 3H, $D_2O$ exchangeable), 8.23 (s, 1H), 8.10 (s, 2H), 7.98 (s, 1H), 7.82 (d, J=7.1 Hz, 1H), 7.59-7.46 (m, 2H), 7.29 (td, J=7.7, 7.0, 1.6 Hz, 1H), 7.25-7.17 (m, 2H), 6.94 (td, J=7.2, 1.3 Hz, 1H), 5.35 (s, 2H), 4.71 (s, 2H), 4.17-4.06 (m, 2H), 3.97-3.74 (m, 2H), 3.56 (s, 2H), 2.73 (t, J=1.9 Hz, 2H), 2.73-2.51 (m, 2H); $^{19}$F NMR (282 MHz, DMSO-$d_6$) δ −92.38; MS (ES+): 507.20 (M+1); (ES−): 505.20 (M−1); Analysis calculated for $C_{29}H_{28}F_2N_2O_4 \cdot 2.05HCl \cdot 2H_2O$: C, 56.42; H, 5.56; Cl, 11.77; N, 4.54. Found: C, 56.50; H, 5.43; Cl, 12.07; N, 4.56.

Scheme 182

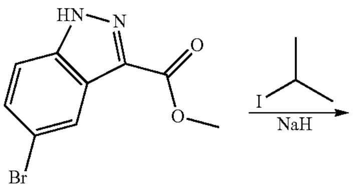

144a

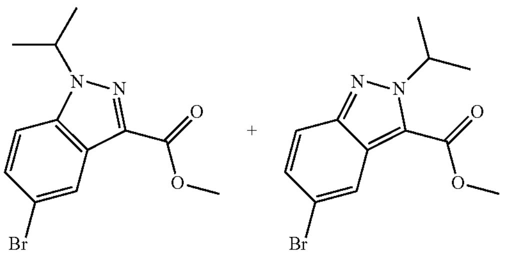

182a

183a

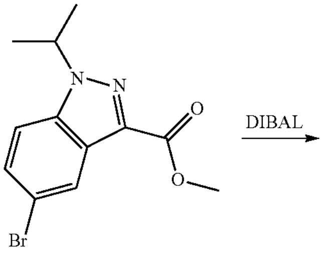

182a

-continued

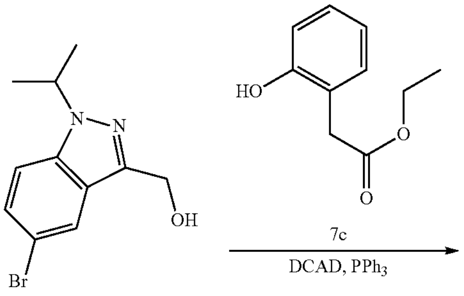

182b

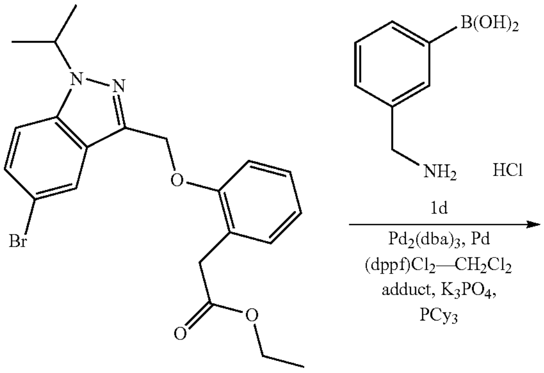

182c

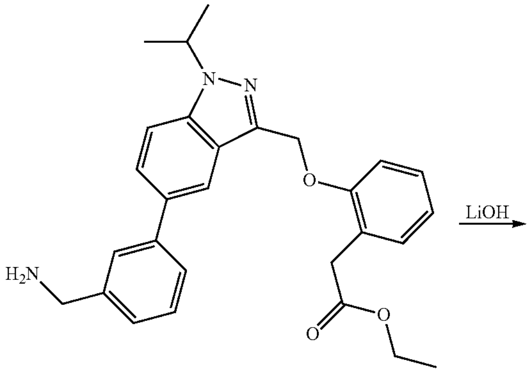

182d

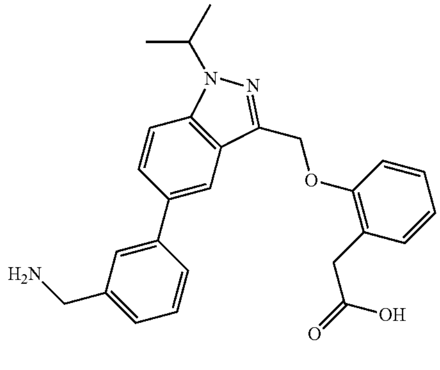

182e

Preparation of 2-(2-((5-(3-(aminomethyl)phenyl)-1-isopropyl-1H-indazol-3-yl)methoxy)phenyl)acetic acid (182e)

Step-1: Preparation of methyl 5-bromo-1-isopropyl-1H-indazole-3-carboxylate (182a) and methyl 5-bromo-2-isopropyl-2H-indazole-3-carboxylate (183a)

Compound 182a and 183a was prepared according to the procedure reported in step-1 of scheme 67, from methyl 5-bromo-1H-indazole-3-carboxylate (144a) (1 g, 3.92 mmol) in DMF (10 mL) using 2-iodopropane (1.187 mL, 11.76 mmol; CAS #75-30-9) and sodium hydride (172 mg, 4.31 mmol). This gave after workup and purification by flash column chromatography [silica gel (40 g), eluting with EtOAc in Hexane from 0-50%]methyl 5-bromo-1-isopropyl-1H-indazole-3-carboxylate (182a) (0.45 g, 39% yield) as a white solid; $^1$H NMR (300 MHz, DMSO-$d_6$) δ 8.27-8.12 (m, 1H), 7.89 (d, J=9.0 Hz, 1H), 7.62 (dd, J=9.0, 1.9 Hz, 1H), 5.24-4.98 (m, J=6.7, 6.1 Hz, 1H), 3.93 (s, 3H), 1.50 (d, J=6.6 Hz, 6H); further elution gave methyl 5-bromo-2-isopropyl-2H-indazole-3-carboxylate (183a) (0.54 g, 46% yield) as a white solid; $^1$H NMR (300 MHz, DMSO-$d_6$) δ 8.16 (d, J=1.9 Hz, 1H), 7.81 (d, J=9.0 Hz, 1H), 7.49 (dd, J=9.1, 1.9 Hz, 1H), 5.84 (hept, J=6.6 Hz, 1H), 3.99 (s, 3H), 1.55 (d, J=6.6 Hz, 6H).

Step-2: Preparation of (5-bromo-1-isopropyl-1H-indazol-3-yl)methanol (182b)

Compound 182b was prepared according to the procedure reported in step-2 of scheme 69, from methyl 5-bromo-1-isopropyl-1H-indazole-3-carboxylate (182a) (0.45 g, 1.514 mmol) in DCM (10 mL) using 1.0 M solution of DIBAL in DCM (3.79 mL, 3.79 mmol) and stirring at −78° C. for 30 min. This gave after workup and purification using flash column chromatography [silica gel (24 g), eluting with DMA-80 in DCM from 0-100%] (5-bromo-1-isopropyl-1H-indazol-3-yl)methanol (182b) (0.35 g, 86% yield) as a light yellow oil; $^1$H NMR (300 MHz, DMSO-$d_6$) δ 8.05 (dd, J=1.9, 0.6 Hz, 1H), 7.72-7.60 (m, 1H), 7.47 (dd, J=8.9, 1.9 Hz, 1H), 5.32 (t, J=5.9 Hz, 1H), 4.94 (hept, J=6.6 Hz, 1H), 4.75 (d, J=5.9 Hz, 2H), 1.44 (d, J=6.6 Hz, 6H); MS (ES+): 269.00 (M+1).

Step-3: Preparation of ethyl 2-(2-((5-bromo-1-isopropyl-1H-indazol-3-yl)methoxy)phenyl)acetate (182c)

Compound 182c was prepared according to the procedure reported in step-2 of scheme 65, from (5-bromo-1-isopropyl-1H-indazol-3-yl)methanol (182b) (350 mg, 1.300 mmol) in DCM (20 mL) using triphenylphosphine (358 mg, 1.365 mmol), ethyl 2-(2-hydroxyphenyl)acetate (7c) (246 mg, 1.365 mmol), DCAD (501 mg, 1.365 mmol) in DCM (10 mL) and stirring at RT for 60 min. This gave after workup and purification using flash column chromatography [silica gel (24 g), eluting with DMA-80 in DCM from 0-60%] ethyl 2-(2-((5-bromo-1-isopropyl-1H-indazol-3-yl)methoxy)phenyl)acetate (182c) (240 mg, 43% yield) as a light yellow oil; $^1$H NMR (300 MHz, DMSO-$d_6$) δ 7.93 (d, J=1.8 Hz, 1H), 7.73 (d, J=8.9 Hz, 1H), 7.52 (dd, J=8.9, 1.9 Hz, 1H), 7.32-7.17 (m, 3H), 6.92 (td, J=7.1, 1.6 Hz, 1H), 5.37 (s, 2H), 5.07-4.93 (m, 1H), 3.91 (q, J=7.1 Hz, 2H), 3.53 (s, 2H), 1.47 (d, J=6.6 Hz, 6H), 0.94 (t, J=7.1 Hz, 3H); MS (ES+): 431.10 (M+1).

Step-4: Preparation of ethyl 2-(2-((5-(3-(aminomethyl)phenyl)-1-isopropyl-1H-indazol-3-yl)methoxy)phenyl)acetate (182d)

Compound 182d was prepared according to the procedure reported in step-2 of scheme 1, from ethyl 2-(2-((5-bromo-1-isopropyl-1H-indazol-3-yl)methoxy)phenyl)acetate (182c) (240 mg, 0.556 mmol) in dioxane (4 mL) and THF (4 mL) using (3-(aminomethyl)phenyl)boronic acid hydrochloride (1d) (209 mg, 1.113 mmol), 2 M solution of $K_3PO_4$ (1.113 mL, 2.226 mmol), tricyclohexylphosphine (31.2 mg, 0.111 mmol), $Pd_2(dba)_3$ (51.0 mg, 0.056 mmol), $PdCl_2$ (dppf)-$CH_2Cl_2$-adduct (45.4 mg, 0.056 mmol) and heating at 90° C. for 1.5 h. This gave after workup and purification using flash column chromatography [silica gel (24 g), eluting with DMA-80 in DCM from 0-70%] ethyl 2-(2-((5-(3-(aminomethyl)phenyl)-1-isopropyl-1H-indazol-3-yl)methoxy)phenyl)acetate (182d) (150 mg, 59% yield) as a clear oil; MS (ES+): 458.25 (M+1).

Step-5: Preparation of 2-(2-((5-(3-(aminomethyl)phenyl)-1-isopropyl-1H-indazol-3-yl)methoxy)phenyl)acetic acid (182e)

Compound 182e was prepared according to the procedure reported in step-3 of scheme 1, from ethyl 2-(2-((5-(3-(aminomethyl)phenyl)-1-isopropyl-1H-indazol-3-yl)methoxy)phenyl)acetate (182d) (150 mg, 0.328 mmol) in THF/MeOH (2 mL each) using lithium hydroxide hydrate (83 mg, 1.967 mmol) in water (1 mL) and stirring for 15 h at RT. This gave after workup and purification using reverse phase column chromatography [C18 column (50 g), eluting with ACN in water (containing 0.1% HCl) from 0-100%] 2-(2-((5-(3-(aminomethyl)phenyl)-1-isopropyl-1H-indazol-3-yl)methoxy)phenyl)acetic acid (182e) (65 mg, 46% yield) HCl salt as a white solid; $^1H$ NMR (300 MHz, DMSO-$d_6$) δ 12.13 (s, 1H, $D_2O$ exchangeable), 8.42 (s, 3H, $D_2O$ exchangeable), 8.08 (s, 1H), 7.88 (s, 1H), 7.84 (d, 1H), 7.80-7.70 (m, 2H), 7.51 (t, J=7.6 Hz, 1H), 7.47-7.39 (m, 1H), 7.32-7.23 (m, 2H), 7.23-7.16 (m, 1H), 6.92 (ddd, J=7.4, 5.9, 2.5 Hz, 1H), 5.45 (s, 2H), 5.11-4.92 (m, 1H), 4.20-3.94 (m, 2H), 3.53 (s, 2H), 1.52 (d, J=6.6 Hz, 6H); MS (ES+): 430.20 (M+1); (ES−): 428.20 (M−1); Analysis calculated for $C_{26}H_{27}N_3O_3 \cdot 1HCl \cdot 0.75H_2O$: C, 65.13; H, 6.20; Cl, 7.39; N, 8.76. Found: C, 65.00; H, 5.71; Cl, 7.35; N, 8.79.

Scheme 183

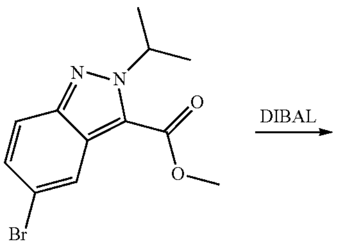

183a

-continued

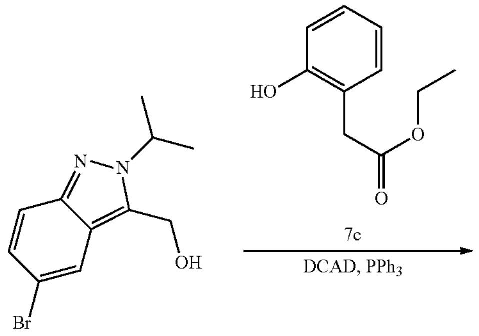

183b

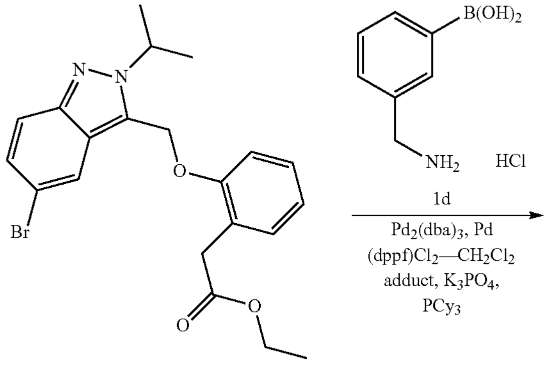

183c

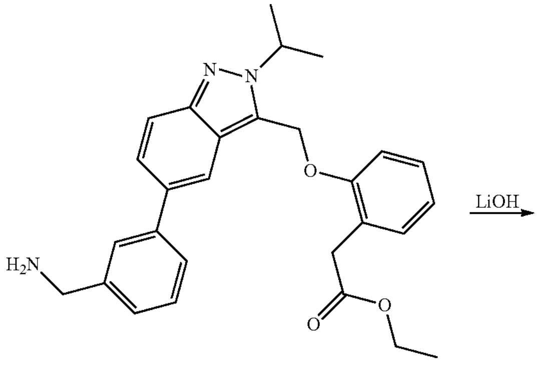

183d

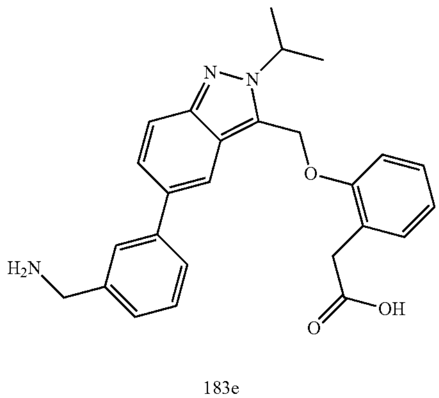 [SMILES: CC(C)n1nc2ccc(-c3cccc(CN)c3)cc2c1COc1ccccc1CC(=O)O]

183e

Preparation of 2-(2-((5-(3-(aminomethyl)phenyl)-2-isopropyl-2H-indazol-3-yl)methoxy)phenyl)acetic acid (183e)

Step-1: Preparation of (5-bromo-2-isopropyl-2H-indazol-3-yl)methanol (183b)

Compound 183b was prepared according to the procedure reported in step-2 of scheme 69, from methyl 5-bromo-2-isopropyl-2H-indazole-3-carboxylate (183a) (0.540 g, 1.817 mmol) in DCM (10 mL) using 1.0 M solution of DIBAL in DCM (4.54 mL, 4.54 mmol) and stirring at −78° C. for 30 min. This gave after workup and purification using flash column chromatography [silica gel (24 g), eluting with DMA-80 in DCM from 0-100%] (5-bromo-2-isopropyl-2H-indazol-3-yl)methanol (183b) (0.46 g, 94% yield) as a light yellow oil; $^1$H NMR (300 MHz, DMSO-$d_6$) δ 8.01 (dd, J=2.0, 0.8 Hz, 1H), 7.57 (dd, J=9.1, 0.8 Hz, 1H), 7.28 (dd, J=9.1, 1.9 Hz, 1H), 5.45 (t, J=5.6 Hz, 1H), 5.01 (h, J=6.5 Hz, 1H), 4.89 (d, J=5.6 Hz, 2H), 1.51 (d, J=6.5 Hz, 6H); MS (ES+): 269.00 (M+1).

Step-2: Preparation of ethyl 2-(2-((5-bromo-2-isopropyl-2H-indazol-3-yl)methoxy)phenyl)acetate (183c)

Compound 183c was prepared according to the procedure reported in step-2 of scheme 65, from (5-bromo-2-isopropyl-2H-indazol-3-yl)methanol (183b) (460 mg, 1.709 mmol) in DCM (20 mL) using triphenylphosphine (471 mg, 1.795 mmol), ethyl 2-(2-hydroxyphenyl)acetate (7c) (323 mg, 1.795 mmol), DCAD (659 mg, 1.795 mmol) in DCM (10 mL) and stirring at RT for 60 min. This gave after workup and purification using flash column chromatography [silica gel (24 g), eluting with DMA-80 in DCM from 0-60%] ethyl 2-(2-((5-bromo-2-isopropyl-2H-indazol-3-yl)methoxy)phenyl)acetate (183c) (140 mg, 19% yield) as a light yellow oil; $^1$H NMR (300 MHz, DMSO-$d_6$) δ 8.13 (dd, J=2.0, 0.7 Hz, 1H), 7.64 (dd, J=9.1, 0.7 Hz, 1H), 7.37-7.25 (m, 3H), 7.22 (dd, J=7.4, 1.6 Hz, 1H), 6.96 (td, J=7.1, 1.6 Hz, 1H), 5.57 (s, 2H), 4.99 (p, J=6.5 Hz, 1H), 3.79 (q, J=7.1 Hz, 2H), 3.51 (s, 2H), 1.53 (d, J=6.5 Hz, 6H), 0.87 (t, J=7.1 Hz, 3H); MS (ES+): 431.10 (M+1).

Step-3: Preparation of ethyl 2-(2-((5-(3-(aminomethyl)phenyl)-2-isopropyl-2H-indazol-3-yl)methoxy)phenyl)acetate (183d)

Compound 183d was prepared according to the procedure reported in step-2 of scheme 1, from ethyl 2-(2-((5-bromo-2-isopropyl-2H-indazol-3-yl)methoxy)phenyl)acetate (183c) (140 mg, 0.325 mmol) in dioxane (3 mL) and THF (3 mL) using (3-(aminomethyl)phenyl)boronic acid hydrochloride (1d) (122 mg, 0.649 mmol), 2 M solution of $K_3PO_4$ (0.649 mL, 1.298 mmol), tricyclohexylphosphine (18.20 mg, 0.065 mmol), $Pd_2(dba)_3$ (29.7 mg, 0.032 mmol), $PdCl_2$(dppf)-$CH_2Cl_2$-adduct (26.5 mg, 0.032 mmol) and heating at 90° C. for 1.5 h. This gave after workup and purification using flash column chromatography [silica gel (24 g), eluting with DMA-80 in DCM from 0-70%] ethyl 2-(2-((5-(3-(aminomethyl)phenyl)-2-isopropyl-2H-indazol-3-yl)methoxy)phenyl)acetate (183d) (60 mg, 40% yield) as a clear oil; MS (ES+): 458.20 (M+1).

Step-4: Preparation of 2-(2-((5-(3-(aminomethyl)phenyl)-2-isopropyl-2H-indazol-3-yl)methoxy)phenyl)acetic acid (183e)

Compound 183e was prepared according to the procedure reported in step-3 of scheme 1, from ethyl 2-(2-((5-(3-(aminomethyl)phenyl)-2-isopropyl-2H-indazol-3-yl)methoxy)phenyl)acetate (183d) (60 mg, 0.131 mmol) in THF/MeOH (2 mL each) using lithium hydroxide hydrate (33 mg, 0.787 mmol) in water (1 mL) and stirring for 15 h at RT. This gave after workup and purification using reverse phase column chromatography [C18 column (50 g), eluting with ACN in water (containing 0.1% HCl) from 0-100%] 2-(2-((5-(3-(aminomethyl)phenyl)-2-isopropyl-2H-indazol-3-yl)methoxy)phenyl)acetic acid (183e) (30 mg, 53% yield) HCl salt as a white solid; $^1$H NMR (300 MHz, DMSO-$d_6$) δ 8.32 (s, 3H, $D_2O$ exchangeable), 8.20 (s, 1H), 7.89 (s, 1H), 7.78 (d, J=9.1 Hz, 2H), 7.65 (dd, J=9.1, 1.6 Hz, 1H), 7.51 (t, J=7.6 Hz, 1H), 7.42 (d, J=7.6 Hz, 1H), 7.38-7.30 (m, 2H), 7.26-7.19 (m, 1H), 6.96 (ddd, J=8.2, 6.0, 2.6 Hz, 1H), 5.63 (s, 2H), 5.11-4.90 (m, 1H), 4.14-4.06 (m, 2H), 3.49 (s, 2H), 1.56 (d, J=6.4 Hz, 6H); MS (ES+): 430.20 (M+1); (ES−): 428.10 (M−1); Analysis calculated for $C_{26}H_{27}N_3O_3 \cdot 1.5HCl \cdot 2.25H_2O$: C, 59.51; H, 6.34; N, 8.01. Found: C, 59.64; H, 6.07; N, 7.96.

Scheme 184

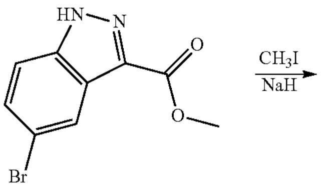

144a

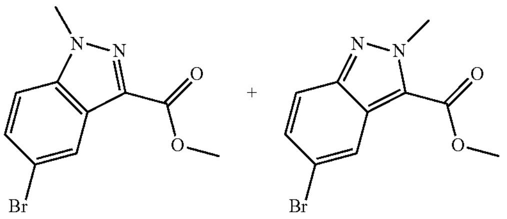

184f 184a

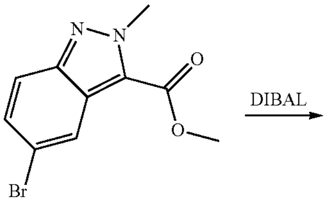

184a

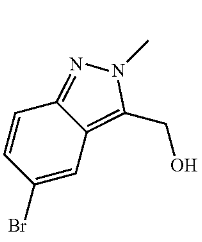

184b

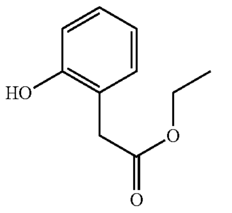

7c

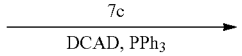

-continued

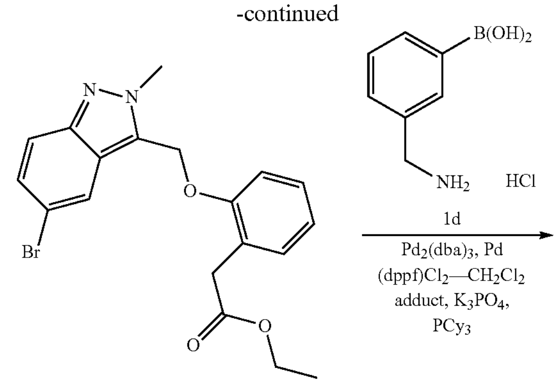

184c

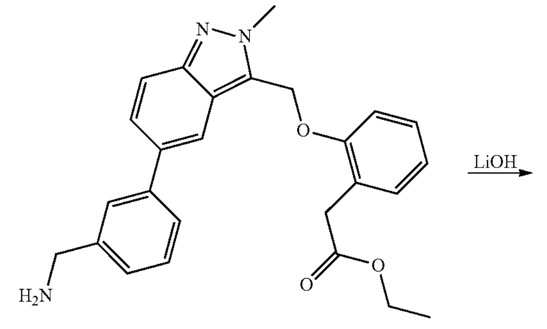

184d

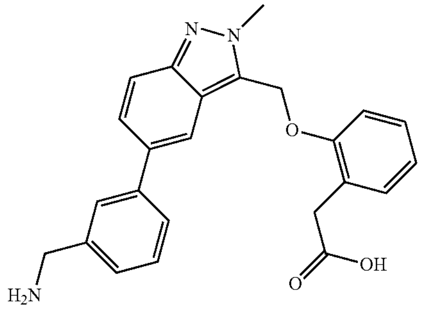

184e

Preparation of 2-(2-((5-(3-(aminomethyl)phenyl)-2-methyl-2H-indazol-3-yl)methoxy)phenyl)acetic acid (184e)

Step-1: Preparation of methyl 5-bromo-2-methyl-2H-indazole-3-carboxylate (184a) and methyl 5-bromo-1-methyl-1H-indazole-3-carboxylate (184f)

Compound 184a and 184f was prepared according to the procedure reported in step-1 of scheme 67, from methyl 5-bromo-1H-indazole-3-carboxylate (144a) (3 g, 11.76 mmol) in DMF (10 mL) using iodomethane (2.197 mL, 35.3 mmol) and sodium hydride (517 mg, 12.94 mmol). This gave after workup and purification by flash column chromatography [silica gel (120 g), eluting with EtOAc in hexane from 0-50%] to give methyl 5-bromo-2-methyl-2H-indazole-3-carboxylate (184a) (1.1 g, 35% yield) as a white solid; $^1$H NMR (300 MHz, DMSO-$d_6$) δ 8.14 (dd, J=1.9, 0.8 Hz, 1H), 7.77 (dd, J=9.0, 0.8 Hz, 1H), 7.49 (dd, J=9.1, 1.9 Hz, 1H), 4.42 (s, 3H), 3.98 (s, 3H) further elution gave methyl 5-bromo-1-methyl-1H-indazole-3-carboxylate (184f) (2.2 g, 70% yield) as a white solid; 1H NMR (300 MHz, DMSO-$d_6$) δ 8.19 (dd, J=1.8, 0.7 Hz, 1H), 7.81 (dd, J=8.9, 0.8 Hz, 1H), 7.65 (dd, J=8.9, 1.9 Hz, 1H), 4.17 (s, 3H), 3.92 (s, 3H).

Step-2: Preparation of (5-bromo-2-methyl-2H-indazol-3-yl)methanol (184b)

Compound 184b was prepared according to the procedure reported in step-2 of scheme 69, from methyl 5-bromo-2-methyl-2H-indazole-3-carboxylate (184a) (1.1 g, 4.09 mmol) in DCM (20 mL) using 1.0 M solution of DIBAL in DCM (10.22 mL, 10.22 mmol) and stirring at −78° C. for 30 min. This gave after workup and purification using flash column chromatography [silica gel (24 g), eluting with DMA-80 in DCM from 0-100%] (5-bromo-2-methyl-2H-indazol-3-yl)methanol (184b) (0.77 g, 78% yield) as a light yellow oil; $^1$H NMR (300 MHz, DMSO-$d_6$) δ 8.02 (d, J=1.9 Hz, 1H), 7.53 (dd, J=9.1, 0.7 Hz, 1H), 7.29 (dd, J=9.1, 1.9 Hz, 1H), 5.44 (t, J=5.6 Hz, 1H), 4.87 (d, J=5.6 Hz, 2H), 4.12 (s, 3H).

Step-3: Preparation of ethyl 2-(2-((5-bromo-2-methyl-2H-indazol-3-yl)methoxy)phenyl)acetate (184c)

Compound 184c was prepared according to the procedure reported in step-2 of scheme 65, from (5-bromo-2-methyl-2H-indazol-3-yl)methanol (184b) (250 mg, 1.037 mmol) in DCM (10 mL) using triphenylphosphine (286 mg, 1.089 mmol), ethyl 2-(2-hydroxyphenyl)acetate (7c) (196 mg, 1.089 mmol), DCAD (400 mg, 1.089 mmol) in DCM (10 mL) and stirring at RT for 30 min. This gave after workup and purification using flash column chromatography [silica gel (24 g), eluting with EtOAc in hexane from 0-80%] ethyl 2-(2-((5-bromo-2-methyl-2H-indazol-3-yl)methoxy)phenyl)acetate (184c) (110 mg, 26% yield) as a light yellow oil; MS (ES+): 403.00 (M+1); 425.00 (M+Na).

Step-4: Preparation of ethyl 2-(2-((5-(3-(aminomethyl)phenyl)-2-methyl-2H-indazol-3-yl)methoxy)phenyl)acetate (184d)

Compound 184d was prepared according to the procedure reported in step-2 of scheme 1, from ethyl 2-(2-((5-bromo-2-methyl-2H-indazol-3-yl)methoxy)phenyl)acetate (184c) (110 mg, 0.273 mmol) in dioxane (2 mL) and THF (2 mL) using (3-(aminomethyl)phenyl)boronic acid hydrochloride (1d) (102 mg, 0.546 mmol), 2 M solution of $K_3PO_4$ (0.546 mL, 1.091 mmol), tricyclohexylphosphine (15.30 mg, 0.055 mmol), $Pd_2(dba)_3$ (24.98 mg, 0.027 mmol), $PdCl_2(dppf)$-$CH_2Cl_2$-adduct (22.28 mg, 0.027 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-2-methyl-2H-indazol-3-yl)methoxy)phenyl)acetate (184d) (80 mg, 68% yield) as a clear oil; MS (ES+): 430.20 (M+1).

Step-5: Preparation of 2-(2-((5-(3-(aminomethyl)phenyl)-2-methyl-2H-indazol-3-yl)methoxy)phenyl)acetic acid (184e)

Compound 184e was prepared according to the procedure reported in step-3 of scheme 1, from ethyl 2-(2-((5-(3-(aminomethyl)phenyl)-2-methyl-2H-indazol-3-yl)methoxy)phenyl)acetate (184d) (80 mg, 0.186 mmol) in THF/MeOH (2 mL each) using lithium hydroxide hydrate (23.45 mg, 0.559 mmol) in water (1 mL) and stirring heating at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-2-methyl-2H-indazol-3-yl)methoxy)phenyl)acetic acid (184e) (40 mg, 54% yield) HCl salt as a white solid; $^1H$ NMR (300 MHz, DMSO-$d_6$) δ 8.37 (s, 3H, $D_2O$ exchangeable), 8.22 (d, J=1.7 Hz, 1H), 7.91 (s, 1H), 7.77 (d, J=7.7 Hz, 1H), 7.73 (d, J=9.0 Hz, 1H), 7.65 (dd, J=9.0, 1.6 Hz, 1H), 7.51 (t, J=7.6 Hz, 1H), 7.43 (d, J=7.6 Hz, 1H), 7.35-7.28 (m, 2H), 7.22 (d, J=7.3 Hz, 1H), 6.99-6.90 (m, 1H), 5.63 (s, 2H), 4.19 (s, 3H), 4.15-4.05 (m, 2H), 3.49 (s, 2H); MS (ES+): 402.20 (M+1); MS (ES−): 400.15 (M−1); Analysis calculated for $C_{24}H_{23}N_3O_3 \cdot 2HCl \cdot 0.5H_2O$: C, 59.63; H, 5.42; Cl, 14.67; N, 8.69. Found: C, 59.96; H, 5.31; Cl, 14.48; N, 8.84.

Scheme 185

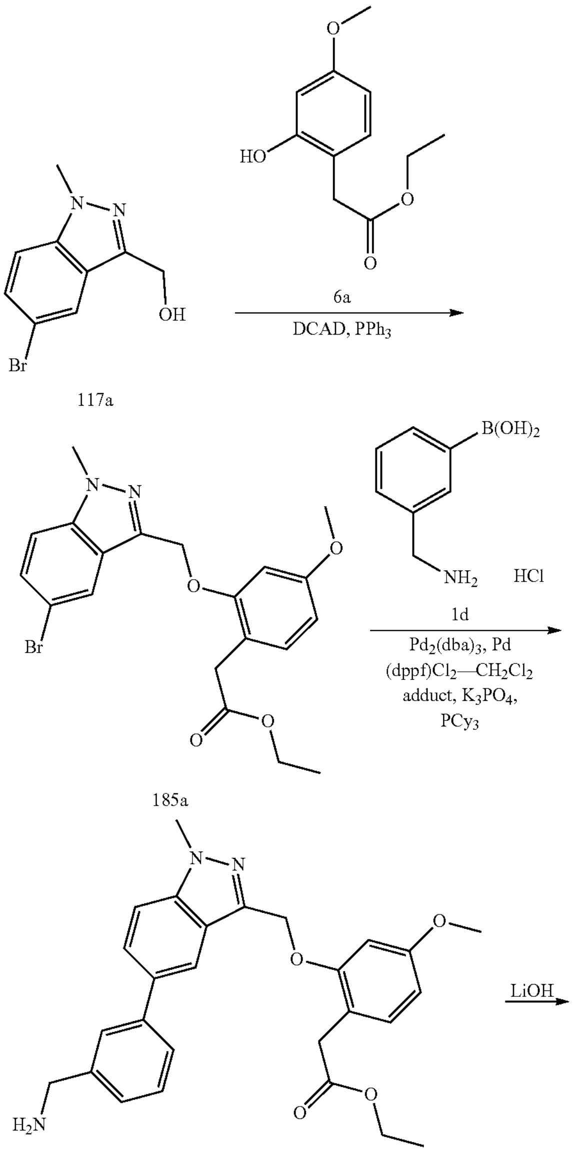

185b

-continued

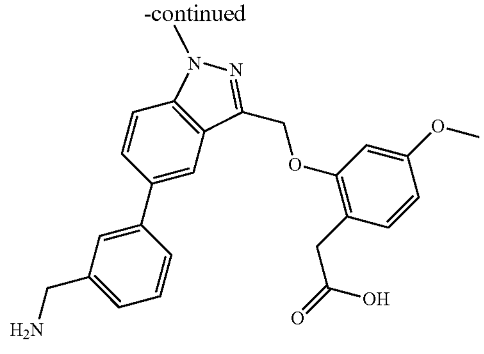

185c

Preparation of 2-(2-((5-(3-(aminomethyl)phenyl)-1-methyl-1H-indazol-3-yl)methoxy)-4-methoxyphenyl)acetic acid (185c)

Step-1: Preparation of ethyl 2-(2-((5-bromo-1-methyl-1H-indazol-3-yl)methoxy)-4-methoxyphenyl)acetate (185a)

Compound 185a was prepared according to the procedure reported in step-2 of scheme 65, from (5-bromo-1-methyl-1H-indazol-3-yl)methanol (117a) (730 mg, 3.03 mmol) in DCM (20 mL) using triphenylphosphine (953 mg, 3.63 mmol), ethyl 2-(2-hydroxy-4-methoxyphenyl)acetate (6a) (668 mg, 3.18 mmol), DCAD (1334 mg, 3.63 mmol) in DCM (10 mL) and stirring at RT for 60 min. This gave after workup and purification using flash column chromatography [silica gel (24 g), eluting with EtOAc in hexane from 0-80%] ethyl 2-(2-((5-bromo-1-methyl-1H-indazol-3-yl)methoxy)-4-methoxyphenyl)acetate (185a) (700 mg, 53% yield) as a white solid; MS (ES+): 433.10 (M+1); (ES−): 431.00 (M−1).

Step-2: Preparation of ethyl 2-(2-((5-(3-(aminomethyl)phenyl)-1-methyl-1H-indazol-3-yl)methoxy)-4-methoxyphenyl)acetate (185b)

Compound 185b was prepared according to the procedure reported in step-2 of scheme 1, from ethyl 2-(2-((5-bromo-1-methyl-1H-indazol-3-yl)methoxy)-4-methoxyphenyl)acetate (185a) (350 mg, 0.808 mmol) in dioxane (4 mL) and THF (4 mL) using (3-(aminomethyl)phenyl)boronic acid hydrochloride (1d) (303 mg, 1.616 mmol), 2 M solution of $K_3PO_4$ (1.616 mL, 3.23 mmol), tricyclohexylphosphine (45.3 mg, 0.162 mmol), $Pd_2(dba)_3$ (74 mg, 0.081 mmol), $PdCl_2$(dppf)-$CH_2Cl_2$-adduct (66 mg, 0.081 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-methyl-1H-indazol-3-yl)methoxy)-4-methoxyphenyl)acetate (185b) (230 mg, 62% yield) as a clear oil; MS (ES+): 460.25 (M+1); (ES−): 458.20 (M−1).

Step-3: Preparation of 2-(2-((5-(3-(aminomethyl)phenyl)-1-methyl-1H-indazol-3-yl)methoxy)-4-methoxyphenyl)acetic acid (185c)

Compound 185c was prepared according to the procedure reported in step-3 of scheme 1, from ethyl 2-(2-((5-(3-

(aminomethyl)phenyl)-1-methyl-1H-indazol-3-yl)methoxy)-4-methoxyphenyl)acetate (185b) (220 mg, 0.479 mmol) in THF/MeOH (2 mL each) using lithium hydroxide hydrate (60.3 mg, 1.436 mmol) in water (1 mL) and stirring at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-1-methyl-1H-indazol-3-yl)methoxy)-4-methoxyphenyl)acetic acid (185c) (85 mg, 41% yield) HCl salt as a white solid; $^1$H NMR (300 MHz, DMSO-$d_6$) δ 12.03 (s, 1H, $D_2O$ exchangeable), 8.41 (s, 3H, $D_2O$ exchangeable), 8.10 (s, 1H), 7.89 (s, 1H), 7.85-7.70 (m, 3H), 7.51 (t, J=7.6 Hz, 1H), 7.45 (d, J=7.7 Hz, 1H), 7.08 (d, J=8.3 Hz, 1H), 6.87 (d, J=2.4 Hz, 1H), 6.49 (dd, J=8.3, 2.4 Hz, 1H), 5.43 (s, 2H), 4.15-4.10 (m, 2H), 4.09 (s, 3H), 3.75 (s, 3H), 3.42 (s, 2H); MS (ES+): 432.15 (M+1); MS (ES−): 430.20 (M−1); Analysis calculated for $C_{25}H_{25}N_3O_4 \cdot 1.05HCl \cdot 1.5H_2O$: C, 60.44; H, 5.89; Cl, 7.49; N, 8.46. Found: C, 60.60; H, 5.77; Cl, 7.79; N, 8.55.

Scheme 186

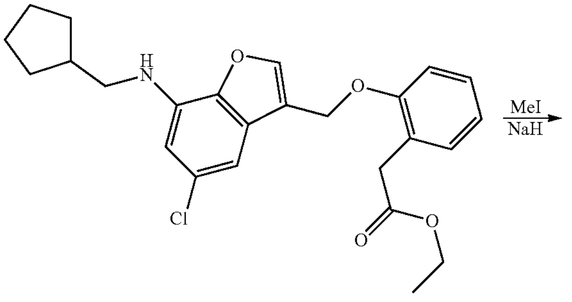

146b

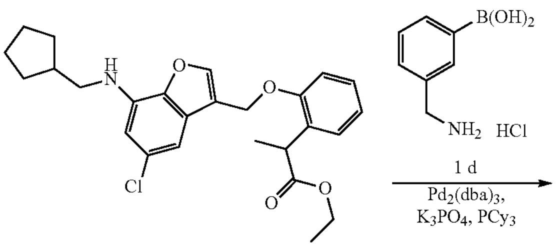

186a

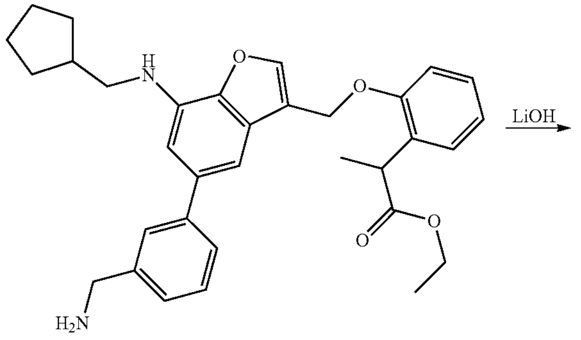

186b

-continued

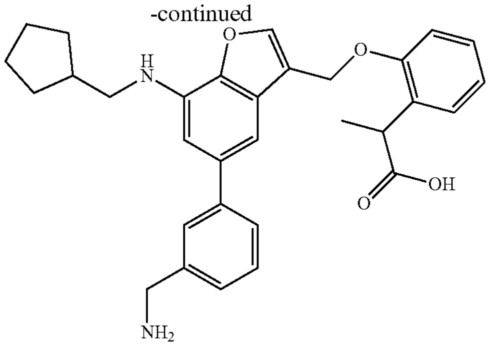

186c

Preparation of 2-(2-((5-(3-(aminomethyl)phenyl)-7-((cyclopentylmethyl)amino)benzofuran-3-yl)methoxy)phenyl)propanoic acid (186c)

Step-1: Preparation of ethyl 2-(2-((5-chloro-7-((cyclopentylmethyl)amino)benzofuran-3-yl)methoxy)phenyl)propanoate (186a)

Compound 186a was prepared according to the procedure reported in step-1 of scheme 67, from ethyl 2-(2-((5-chloro-7-((cyclopentylmethyl)amino)benzofuran-3-yl)methoxy)phenyl)acetate (146b) (227 mg, 0.514 mmol) in DMF (5 mL) using iodomethane (0.096 mL, 1.541 mmol) and sodium hydride (61.6 mg, 1.541 mmol). This gave after workup and purification using flash column chromatography [silica gel (12 g), eluting with EtOAc in Hexane from 0-50%] to give ethyl 2-(2-((5-chloro-7-((cyclopentylmethyl)amino)benzofuran-3-yl)methoxy)phenyl)propanoate (186a) (0.178 g, 76% yield) as a white solid; $^1$H NMR (300 MHz, DMSO-$d_6$) δ 8.06 (s, 1H), 7.31-7.22 (m, 1H), 7.22-7.12 (m, 2H), 6.94 (t, 1H), 6.85 (s, 1H), 6.49 (s, 1H), 6.12 (t, 1H), 5.19 (s, 2H), 4.01-3.87 (m, 3H), 3.10 (t, J=6.6 Hz, 2H), 2.33-2.15 (m, 1H), 1.82-1.66 (m, 2H), 1.66-1.46 (m, 4H), 1.31 (d, 3H), 1.31-1.17 (m, 2H), 1.01 (t, J=7.1, 1.2 Hz, 3H); MS (ES+): 456.2 (M+1).

Step-2: Preparation of ethyl 2-(2-((5-(3-(aminomethyl)phenyl)-7-((cyclopentylmethyl)amino)benzofuran-3-yl)methoxy)phenyl)propanoate (186b)

Compound 186b was prepared according to the procedure reported in step-2 of scheme 1, from ethyl 2-(2-((5-chloro-7-((cyclopentylmethyl)amino)benzofuran-3-yl)methoxy)phenyl)propanoate (186a) (0.178 g, 0.390 mmol) in dioxane (4 mL) and 2-Me-THF (2 mL) using 3-(aminomethyl)phenylboronic acid hydrochloride (1d) (183 mg, 0.976 mmol), 4 M solution of $K_3PO_4$ (0.390 mL, 1.562 mmol), tricyclohexylphosphine (88 mg, 0.312 mmol), $Pd_2(dba)_3$ (143 mg, 0.156 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-((cyclopentylmethyl)amino)benzofuran-3-yl)methoxy)phenyl)propanoate (186b) (129 mg, 63% yield); MS (ES+): 527.3 (M+1).

Step-3: Preparation of 2-(2-((5-(3-(aminomethyl)phenyl)-7-((cyclopentylmethyl)amino)benzofuran-3-yl)methoxy)phenyl)propanoic acid (186c)

Compound 186c was prepared according to the procedure reported in step-3 of scheme 1, from ethyl 2-(2-((5-(3-

(aminomethyl)phenyl)-7-((cyclopentylmethyl)amino)benzofuran-3-yl)methoxy)phenyl)propanoate (186b) (129 mg, 0.245 mmol) in THF (2 mL), methanol (0.2 mL) and water (0.2 mL), using lithium hydroxide monohydrate (23.46 mg, 0.980 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-((cyclopentylmethyl)amino)benzofuran-3-yl)methoxy)phenyl)propanoic acid (186c) (38 mg, 31% yield) HCl salt as a white solid; $^1H$ NMR (300 MHz, DMSO-$d_6$) δ 8.26 (s, 4H), 8.08 (d, J=4.7 Hz, 1H), 7.79 (d, J=12.8 Hz, 1H), 7.75-7.62 (m, 1H), 7.55-7.46 (m, 1H), 7.47-7.37 (m, 1H), 7.33 (d, J=12.8 Hz, 1H), 7.28-7.12 (m, 3H), 7.00-6.94 (m, 1H), 6.83 (d, J=28.2 Hz, 1H), 5.33-5.23 (m, 2H), 4.17-4.03 (m, 2H), 3.97 (q, J=7.8, 7.2 Hz, 1H), 3.07 (s, 2H), 2.33-2.17 (m, 1H), 1.89-1.67 (m, 2H), 1.72-1.43 (m, 4H), 1.37-1.14 (m, 5H); MS (ES+): 499.3 (M+1).

Scheme 187

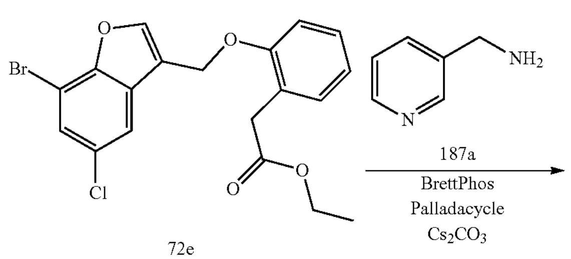

72e

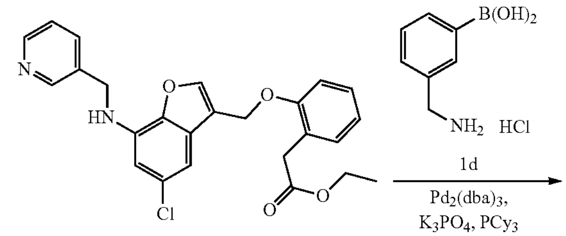

187b

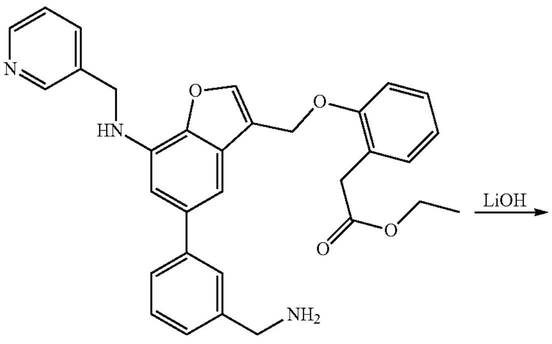

187c

-continued

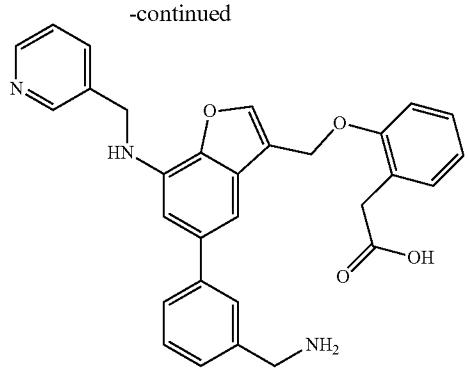

187d

Preparation of 2-(2-((5-(3-(aminomethyl)phenyl)-7-((pyridin-3-ylmethyl)amino)benzofuran-3-yl)methoxy)phenyl)acetic acid (187d)

Step-1: Preparation of ethyl 2-(2-((5-chloro-7-((pyridin-3-ylmethyl)amino)benzofuran-3-yl)methoxy)phenyl)acetate (187b)

Compound 187b was prepared according to the procedure reported in step-1 of scheme 146, from ethyl 2-(2-((7-bromo-5-chlorobenzofuran-3-yl)methoxy)phenyl)acetate (72e) (2 g, 4.72 mmol) in MeCN (3 mL) using pyridine-3-ylmethanamine (187a) (0.721 mL, 7.08 mmol), BrettPhos Palladacycle (0.188 g, 0.236 mmol), cesium carbonate (4.61 g, 14.16 mmol) and irradiating at 90° C. for 2 h in microwave. This gave after work up and purification using flash column chromatography [silica gel (12 g), eluting with DMA-80 in DCM from 0-50%]ethyl 2-(2-((5-chloro-7-((pyridin-3-ylmethyl)amino)benzofuran-3-yl)methoxy)phenyl)acetate (187b) (822 mg, 39% yield); $^1H$ NMR (300 MHz, DMSO-$d_6$) δ 8.63 (d, 1H), 8.51-8.42 (m, 1H), 8.09 (s, 1H), 7.81 (d, J=7.9 Hz, 1H), 7.37 (dd, J=7.8, 4.8 Hz, 1H), 7.32-7.24 (m, 1H), 7.23-7.15 (m, 2H), 6.97-6.89 (m, 2H), 6.85 (d, J=2.0 Hz, 1H), 6.44 (d, J=1.9 Hz, 1H), 5.17 (s, 2H), 4.51 (d, J=6.1 Hz, 2H), 3.93 (q, J=7.1 Hz, 2H), 3.55 (s, 2H), 0.98 (t, J=7.1 Hz, 3H); MS (ES+): 451.10 (M+1).

Step-2: Preparation of ethyl 2-(2-((5-(3-(aminomethyl)phenyl)-7-((pyridin-3-ylmethyl)amino)benzofuran-3-yl)methoxy)phenyl)acetate (187c)

Compound 187c was prepared according to the procedure reported in step-2 of scheme 1, from ethyl 2-(2-((5-chloro-7-((pyridin-3-ylmethyl)amino)benzofuran-3-yl)methoxy)phenyl)acetate (187b)

(0.692 g, 1.535 mmol) in dioxane (8 mL) and 2-Me-THF (4 mL) using 3-(aminomethyl)phenylboronic acid hydrochloride (1d) (719 mg, 3.84 mmol), 4 M solution of $K_3PO_4$ (1.535 mL, 6.14 mmol), tricyclohexylphosphine (344 mg, 1.228 mmol), $Pd_2(dba)_3$ (562 mg, 0.614 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-((pyridin-3-ylmethyl)amino)benzofuran-3-yl)methoxy)phenyl)acetate (187c) (274 mg, 34% yield); MS (ES+): 522.20 (M+1).

Step-3: Preparation of 2-(2-((5-(3-(aminomethyl)phenyl)-7-((pyridin-3-ylmethyl)amino)benzofuran-3-yl)methoxy)phenyl)acetic acid (187d)

Compound 187d was prepared according to the procedure reported in step-3 of scheme 1, from ethyl 2-(2-((5-(3-

(aminomethyl)phenyl)-7-((pyridin-3-ylmethyl)amino)benzofuran-3-yl)methoxy)phenyl)acetate (187c) (274 mg, 0.525 mmol) in THF (2 mL), methanol (0.2 mL) and water (0.2 mL), using lithium hydroxide monohydrate (50.3 mg, 2.101 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-((pyridin-3-ylmethyl)amino)benzofuran-3-yl)methoxy)phenyl)acetic acid (187d) (80 mg, 31% yield) HCl salt as a yellow solid; $^1H$ NMR (300 MHz, DMSO-$d_6$) δ 9.12 (d, J=1.9 Hz, 1H), 8.79 (d, J=5.6 Hz, 1H), 8.71-8.65 (m, 1H), 8.61 (s, 4H, $D_2O$ exchangeable), 8.09 (s, 1H), 8.01 (dd, J=8.1, 5.6 Hz, 1H), 7.89 (s, 1H), 7.64-7.57 (m, 1H), 7.48-7.37 (m, 2H), 7.30-7.23 (m, 2H), 7.23-7.16 (m, 2H), 6.96-6.87 (m, 2H), 5.27 (s, 2H), 4.84 (s, 2H), 4.14-4.01 (m, 2H), 3.54 (s, 2H). MS (ES+): 494.2 (M+1); Analysis calculated for $C_{30}H_{27}N_3O_4 \cdot 2.4HCl \cdot 2H_2O$: C, 58.39; H, 5.46; Cl, 13.79; N, 6.81. Found: C, 58.47; H, 5.41; Cl, 13.69; N, 6.84.

Scheme 188

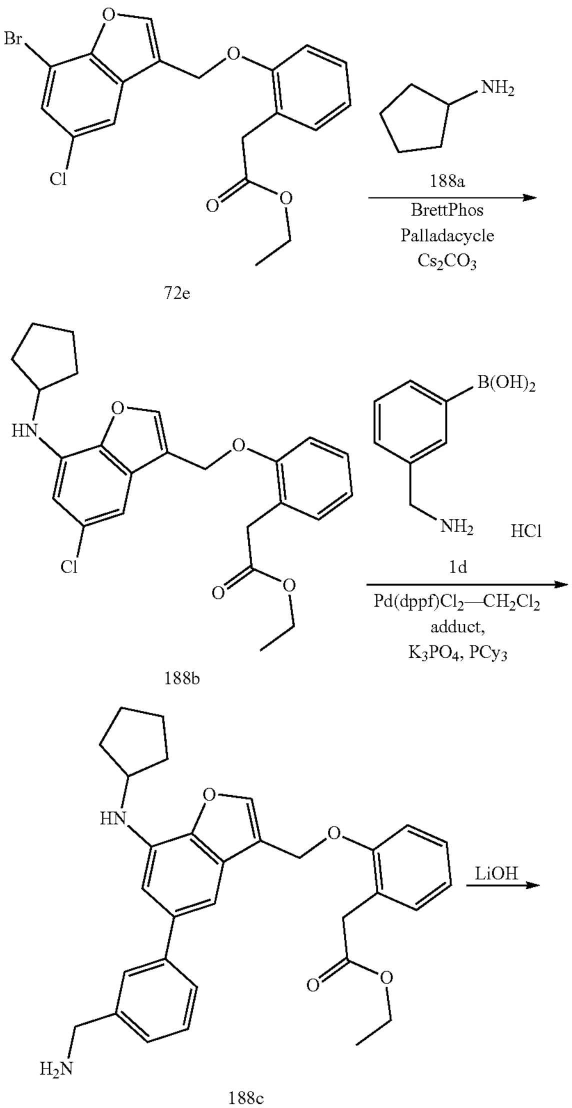

72e

188b

188c

-continued

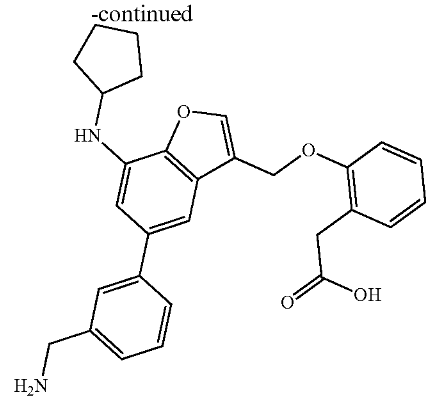

188d

Preparation of 2-(2-((5-(3-(aminomethyl)phenyl)-7-(cyclopentylamino)benzofuran-3-yl)methoxy)phenyl)acetic acid (188d)

Step-1: Preparation of ethyl 2-(2-((5-chloro-7-(cyclopentylamino)benzofuran-3-yl)methoxy)phenyl) acetate (188b)

Compound 188b was prepared according to the procedure reported in step-1 of scheme 146, from ethyl 2-(2-((7-bromo-5-chlorobenzofuran-3-yl)methoxy)phenyl)acetate (72e) (2 g, 4.72 mmol) in MeCN (3 mL) using cyclopentanamine (188a) (0.596 g, 7.08 mmol), BrettPhos Palladacycle (0.188 g, 0.236 mmol), cesium carbonate (4.61 g, 14.16 mmol) and irradiating at 90° C. for 2 h in microwave. This gave after work up and purification using flash column chromatography [silica gel (12 g), eluting with DMA-80 in DCM from 0-50%] ethyl 2-(2-((5-chloro-7-(cyclopentylamino)benzofuran-3-yl)methoxy)phenyl)acetate (188b) (170 mg, 8% yield); $^1H$ NMR (300 MHz, DMSO-$d_6$) δ 8.04 (s, 1H), 7.33-7.23 (m, 1H), 7.23-7.14 (m, 2H), 6.92 (td, J=7.3, 1.1 Hz, 1H), 6.83 (d, J=2.0 Hz, 1H), 6.49 (d, J=2.0 Hz, 1H), 5.95 (d, J=7.0 Hz, 1H), 5.17 (s, 2H), 3.96 (q, J=7.1 Hz, 2H), 3.93-3.85 (m, 1H), 3.56 (s, 2H), 1.98-1.91 (m, 2H), 1.75-1.62 (m, 2H), 1.64-1.50 (m, 4H), 1.03 (t, J=7.1 Hz, 3H); MS (ES+): 428.10 (M+1).

Step-2: Preparation of ethyl 2-(2-((5-(3-(aminomethyl)phenyl)-7-(cyclopentylamino)benzofuran-3-yl)methoxy)phenyl)acetate (188c)

Compound 188c was prepared according to the procedure reported in step-2 of scheme 1, from ethyl 2-(2-((5-chloro-7-(cyclopentylamino)benzofuran-3-yl)methoxy)phenyl)acetate (188b) (0.170 g, 0.397 mmol) in dioxane (6 mL) and 2-Me-THF (3 mL) using 3-(aminomethyl)phenylboronic acid hydrochloride (1d) (186 mg, 0.993 mmol), 4 M solution of $K_3PO_4$ (0.397 mL, 1.589 mmol), tricyclohexylphosphine (89 mg, 0.318 mmol), $Pd_2(dba)_3$ (146 mg, 0.159 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-(cyclopentylamino)benzofuran-3-yl)methoxy)phenyl)acetate (188c) (86 mg, 43% yield); MS (ES+): 499.30 (M+1).

Step-3: Preparation of 2-(2-((5-(3-(aminomethyl)phenyl)-7-(cyclopentylamino)benzofuran-3-yl)methoxy)phenyl)acetic acid (188d)

Compound 188d was prepared according to the procedure reported in step-3 of scheme 1, from ethyl 2-(2-((5-(3-(aminomethyl)phenyl)-7-(cyclopentylamino)benzofuran-3-yl)methoxy)phenyl)acetate (188c) (86 mg, 0.172 mmol) in THF (2 mL), methanol (0.2 mL) and water (0.2 mL), using lithium hydroxide monohydrate (16 mg, 0.69 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(cyclopentylamino)benzofuran-3-yl)methoxy)phenyl)acetic acid (188d) (7 mg, 9% yield) HCl salt as a white solid; $^1H$ NMR (300 MHz, Methanol-$d_4$) δ 8.09 (s, 1H), 7.93 (s, 1H), 7.89 (s, 1H), 7.78 (d, J=7.7 Hz, 1H), 7.61-7.54 (m, 2H), 7.47 (d, J=7.6 Hz, 1H), 7.36-7.24 (m, 1H), 7.25-7.16 (m, 2H), 6.96 (td, J=7.4 Hz, 1H), 5.35 (s, 2H), 4.35-4.22 (m, 1H), 4.22 (s, 2H), 3.63 (s, 2H), 2.20-2.00 (m, 2H), 1.99-1.78 (m, 4H), 1.80-1.63 (m, 2H). MS (ES+): 471.2 (M+1); (ES−): 469.2 (M−1).

Scheme 189

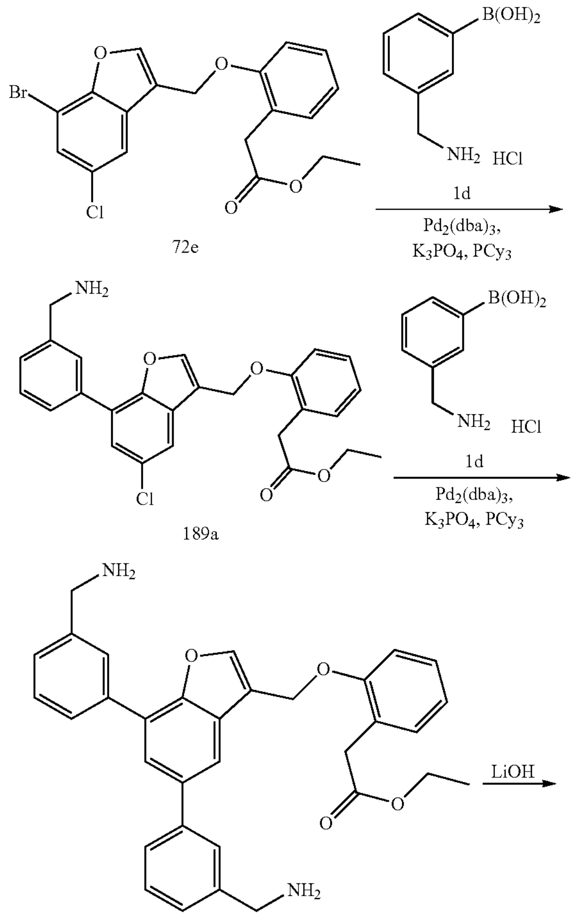

72e

189a

189b

-continued

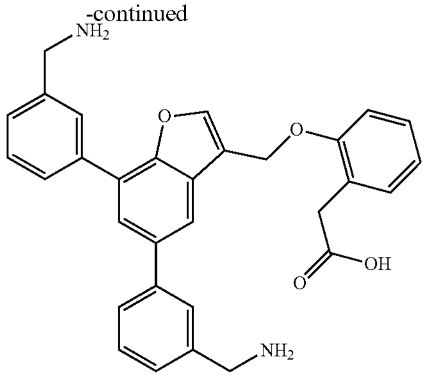

189c

Preparation of 2-(2-((5,7-bis(3-(aminomethyl)phenyl)benzofuran-3-yl)methoxy)phenyl)acetic acid (189c)

Step-1: Preparation of ethyl 2-(2-((7-(3-(aminomethyl)phenyl)-5-chlorobenzofuran-3-yl)methoxy)phenyl)acetate (189a)

Compound 189a was prepared according to the procedure reported in step-2 of scheme 1, from ethyl 2-(2-((7-bromo-5-chlorobenzofuran-3-yl)methoxy)phenyl)acetate (72e) (0.5 g, 1.18 mmol) in dioxane (8 mL) and 2-Me-THF (4 mL) using 3-(aminomethyl)phenylboronic acid hydrochloride (1d) (664 mg, 3.54 mmol), 4 M solution of $K_3PO_4$ (1.180 mL, 4.72 mmol), tricyclohexylphosphine (265 mg, 0.944 mmol), $Pd_2(dba)_3$ (432 mg, 0.472 mmol) and heating at 115° C. for 3 h. This gave after workup and purification using flash column chromatography [silica gel (24 g), eluting with DMA-80 in DCM from 0-70%] ethyl 2-(2-((7-(3-(aminomethyl)phenyl)-5-chlorobenzofuran-3-yl)methoxy)phenyl)acetate (189a) (449 mg, 85% yield); MS (ES+): 450.20 (M+1).

Step-2: Preparation of ethyl 2-(2-((5,7-bis(3-(aminomethyl)phenyl)benzofuran-3-yl)methoxy)phenyl)acetate (189b)

Compound 189b was prepared according to the procedure reported in step-2 of scheme 1, from ethyl 2-(2-((7-(3-(aminomethyl)phenyl)-5-chlorobenzofuran-3-yl)methoxy)phenyl)acetate (189a) (0.225 g, 0.5 mmol) in dioxane (8 mL) and 2-Me-THF (4 mL) using 3-(aminomethyl)phenylboronic acid hydrochloride (1d) (281 mg, 1.5 mmol), 4 M solution of $K_3PO_4$ (0.500 mL, 2.000 mmol), tricyclohexylphosphine (112 mg, 0.400 mmol), $Pd_2(dba)_3$ (183 mg, 0.200 mmol) and heating at 115° C. for 3 h. This gave after workup and purification using flash column chromatography [silica gel (24 g), eluting with DMA-80 in DCM from 0-70%] ethyl 2-(2-((5,7-bis(3-(aminomethyl)phenyl)benzofuran-3-yl)methoxy)phenyl)acetate (189b) (62 mg, 24% yield); MS (ES+): 521.20 (M+1).

Step-3: Preparation of 2-(2-((5,7-bis(3-(aminomethyl)phenyl)benzofuran-3-yl)methoxy)phenyl)acetic acid (189c)

Compound 189c was prepared according to the procedure reported in step-3 of scheme 1, from ethyl 2-(2-((5,7-bis(3-(aminomethyl)phenyl)benzofuran-3-yl)methoxy)phenyl)acetate (189b) (62 mg, 0.119 mmol) in THF (2 mL), methanol (0.2 mL) and water (0.2 mL), using lithium hydroxide monohydrate (11.42 mg, 0.477 mmol) and stirring for 10 h at RT. This gave after workup and purification using reverse phase column chromatography [C18 column (40 g), eluting with ACN in water (containing 0.1% HCl) from 0-100%] 2-(2-((5,7-bis(3-(aminomethyl)phenyl)benzofuran-3-yl) methoxy)phenyl)acetic acid (189c) (20 mg, 34% yield) HCl salt as a yellow solid; $^1$H NMR (300 MHz, Methanol-$d_4$) δ 8.10 (s, 1H), 8.06-7.98 (m, 3H), 7.95 (s, 1H), 7.88-7.86 (m, 1H), 7.85-7.80 (m, 1H), 7.67-7.59 (m, 1H), 7.57-7.50 (m, 2H), 7.45 (d, J=7.5 Hz, 1H), 7.34-7.27 (m, 1H), 7.26-7.16 (m, 2H), 6.96 (t, J=7.2 Hz, 1H), 5.37 (s, 2H), 4.25 (s, 2H), 4.23 (s, 2H), 3.65 (s, 2H); MS (ES+): 493.2 (M+1).

Scheme 190

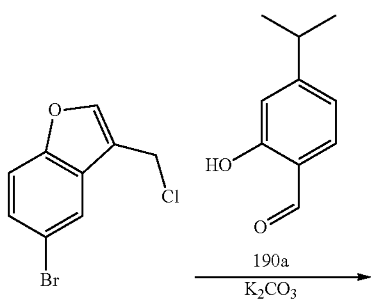

104a

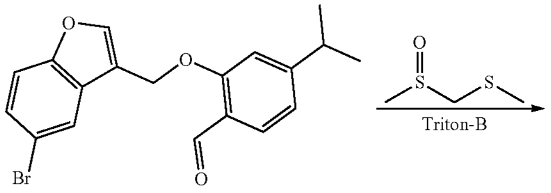

190b

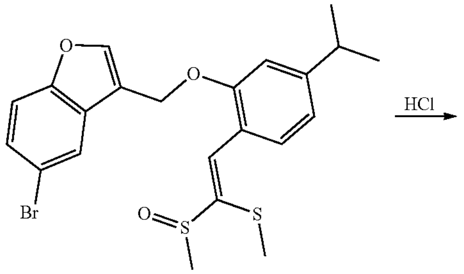

190c

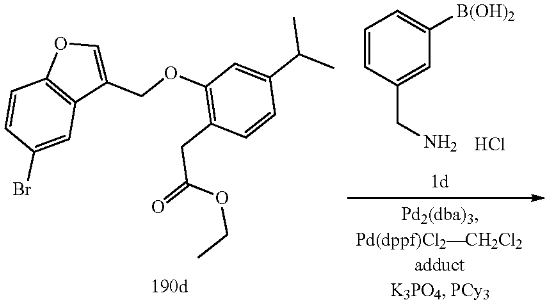

190d

-continued

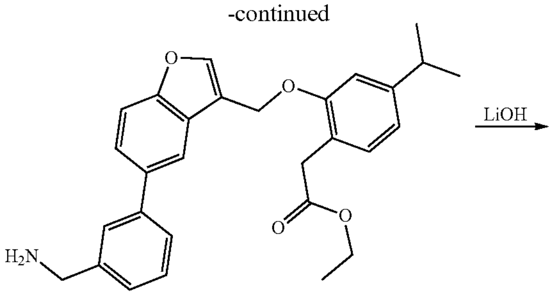

190e

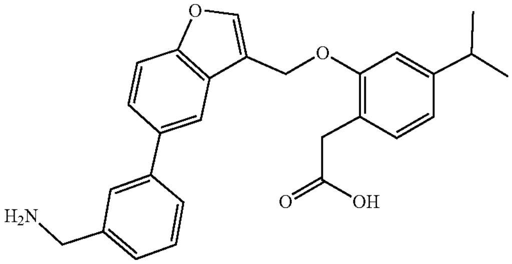

190f

Preparation of 2-(2-((5-(3-(aminomethyl)phenyl) benzofuran-3-yl)methoxy)-4-isopropylphenyl)acetic acid (190f)

Step-1: Preparation of 2-((5-bromobenzofuran-3-yl) methoxy)-4-isopropylbenzaldehyde (190b)

Compound 190b was prepared according to the procedure reported in step-3 of scheme 7, from 5-bromo-3-(chloromethyl)benzofuran (104a) (1 g, 4.07 mmol) in DMF (8 mL) using 2-hydroxy-4-isopropylbenzaldehyde (190a) (608 mg, 3.7 mmol), potassium carbonate (1.535 g, 11.11 mmol) and stirring overnight at RT. This gave after workup and purification using flash column chromatography [silica gel (12 g) eluting with ethyl acetate and hexanes from 0-50%]2-((5-bromobenzofuran-3-yl)methoxy)-4-isopropylbenzaldehyde (190b) (936 mg, 68% yield); $^1$H NMR (300 MHz, DMSO-$d_6$) δ 10.31 (s, 1H), 8.29 (s, 1H), 8.01 (d, J=2.0 Hz, 1H), 7.63 (dd, J=8.4, 5.6 Hz, 2H), 7.50 (dd, J=8.8, 2.1 Hz, 1H), 7.32 (d, J=1.5 Hz, 1H), 7.00 (d, J=8.0 Hz, 1H), 5.47 (s, 2H), 3.05-2.92 (m, 1H), 1.24 (d, J=6.9 Hz, 6H); MS (ES+): 396.0 (M+Na).

Step-2: Preparation of 5-bromo-3-((5-isopropyl-2-(2-(methylsulfinyl)-2-(methylthio)vinyl)phenoxy) methyl)benzofuran (190c)

Compound 190c was prepared according to the procedure reported in step-1 of scheme 12, from 2-((5-bromobenzofuran-3-yl)methoxy)-4-isopropylbenzaldehyde (190b) (936 mg, 2.508 mmol) using methyl(methylsulfinylmethyl)sulfane (0.409 mL, 4.01 mmol), and Triton B (0.57 mL, 1.254 mmol; 40% wt. in MeOH) in THF (10 mL) and refluxing for 12 h. This gave after workup and purification using flash column chromatography [silica gel (12 g), eluting with EtOAc in hexane from 0-50%] 5-bromo-3-((5-isopropyl-2-(2-(methylsulfinyl)-2-(methylthio)vinyl)phenoxy)methyl) benzofuran (190c) (588 mg, 49% yield) as a white solid; H NMR (300 MHz, DMSO-$d_6$) δ 8.17 (s, 1H), 7.97 (d, J=8.0 Hz, 1H), 7.86 (d, J=2.0 Hz, 1H), 7.79 (s, 1H), 7.59 (d, J=8.7

Hz, 1H), 7.48 (dd, J=8.7, 2.1 Hz, 1H), 7.20 (d, J=1.6 Hz, 1H), 6.95 (d, J=8.0, 1.0 Hz, 1H), 5.40 (s, 2H), 3.02-2.84 (m, 1H), 2.68 (s, 3H), 2.24 (s, 3H), 1.24 (d, J=6.9 Hz, 6H).

Step-3: Preparation of ethyl 2-(2-((5-bromobenzofuran-3-yl)methoxy)-4-isopropylphenyl)acetate (190d)

Compound 190d was prepared according to the procedure reported in step-2 of scheme 7, from 5-bromo-3-((5-isopropyl-2-(2-(methylsulfinyl)-2-(methylthio)vinyl)phenoxy) methyl)benzofuran (190c) (588 mg, 1.226 mmol) in ethanol (6 mL) using 4N HCl (1.533 mL, 6.13 mmol) and refluxing the reaction mixture for 2 h. This gave after workup and purification using flash column chromatography [silica gel (12 g), eluting with EtOAc in hexane]ethyl 2-(2-((5-bromobenzofuran-3-yl)methoxy)-4-isopropylphenyl)acetate (190d) (295 mg, 56% yield); $^{1}$H NMR (300 MHz, DMSO-$d_6$) δ 8.15 (s, 1H), 7.87 (d, J=2.0 Hz, 1H), 7.62 (d, J=8.7 Hz, 1H), 7.50 (dd, J=8.8, 2.1 Hz, 1H), 7.10 (d, J=7.7 Hz, 1H), 7.07 (d, J=1.6 Hz, 1H), 6.80 (dd, J=7.7, 1.5 Hz, 1H), 5.28-5.18 (m, 2H), 3.93 (q, J=7.1 Hz, 2H), 3.51 (s, 2H), 2.89 (p, J=6.9 Hz, 1H), 1.23 (d, J=6.9 Hz, 6H), 0.99 (t, J=7.1 Hz, 3H); MS (ES+): 431.10 (M+1).

Step-4: Preparation of ethyl 2-(2-((5-(3-(aminomethyl)phenyl)benzofuran-3-yl)methoxy)-4-isopropylphenyl)acetate (190e)

Compound 190e was prepared according to the procedure reported in step-2 of scheme 1, from ethyl 2-(2-((5-bromobenzofuran-3-yl)methoxy)-4-isopropylphenyl)acetate (190d) (295 mg, 0.684 mmol) using 3-(aminomethyl)phenylboronic acid hydrochloride (1d) (256 mg, 1.368 mmol), 2M solution of $K_3PO_4$ (1.368 mL, 2.74 mmol), tricyclohexylphosphine (38.4 mg, 0.137 mmol), $PdCl_2(dppf)-CH_2Cl_2$ adduct (55.9 mg, 0.068 mmol) and $Pd_2(dba)_3$ (62.6 mg, 0.068 mmol) in dioxane/THF (3 mL each) and heating at 90-100° C. for 1 h. This gave after workup and purification using flash column chromatography [silica gel (24 g), eluting with DMA-80 in DCM from 0-70%] ethyl 2-(2-((5-(3-(aminomethyl)phenyl)benzofuran-3-yl)methoxy)-4-isopropylphenyl)acetate (190e) (202 mg, 65% yield) as a clear oil; MS (ES+): 458.20 (M+1).

Step-5: Preparation of 2-(2-((5-(3-(aminomethyl) phenyl)benzofuran-3-yl)methoxy)-4-isopropylphenyl)acetic acid (190f)

Compound 190f was prepared according to the procedure reported in step-3 of scheme 1, from ethyl 2-(2-((5-(3-(aminomethyl)phenyl)benzofuran-3-yl)methoxy)-4-isopropylphenyl)acetate (190e) (202 mg, 0.441 mmol) in THF (2 mL), methanol (0.2 mL) and water (0.2 mL) using lithium hydroxide monohydrate (42.3 mg, 1.766 mmol) and stirring at RT for 10 h. This gave after workup and purification using reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-4-isopropylphenyl)acetic acid (190f) (101 mg, 53% yield) HCl salt as a light brown solid; $^{1}$H NMR (300 MHz, DMSO-$d_6$) δ 12.14 (s, 1H, $D_2O$ exchangeable), 8.41 (s, 3H, $D_2O$ exchangeable), 8.14 (s, 1H), 8.04 (d, 1H), 7.90 (s, 1H), 7.81-7.72 (m, 2H), 7.69 (dd, J=8.6, 1.8 Hz, 1H), 7.53 (t, J=7.6 Hz, 1H), 7.49-7.45 (m, 1H), 7.15-7.07 (m, 2H), 6.80 (dd, J=7.7, 1.5 Hz, 1H), 5.33 (s, 2H), 4.12 (s, 2H), 3.49 (s, 2H), 2.98-2.83 (m, 1H), 1.23 (d, J=6.9 Hz, 6H); MS (ES+): 430.2 (M+1); Analysis calculated for $C_{27}H_{27}NO_4$·HCl $0.75H_2O$: C, 67.63; H, 6.20; Cl, 7.39; N, 2.92. Found: C, 67.49; H, 5.89; Cl, 7.22; N, 2.94.

Scheme 191

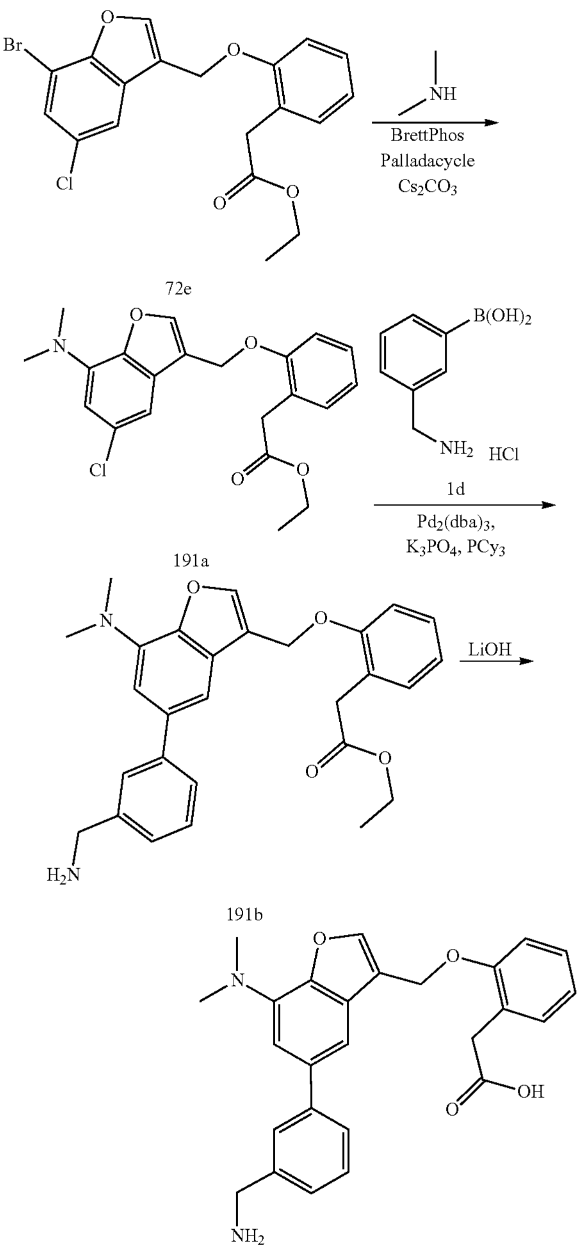

191c

Preparation of 2-(2-((5-(3-(aminomethyl)phenyl)-7-(dimethylamino)benzofuran-3-yl)methoxy)phenyl) acetic acid (191c)

Step-1: Preparation of ethyl 2-(2-((5-chloro-7-(dimethylamino)benzofuran-3-yl)methoxy)phenyl)acetate (191a)

Compound 191a was prepared according to the procedure reported in step-1 of scheme 146, from ethyl 2-(2-((7- bromo-5-chlorobenzofuran-3-yl)methoxy)phenyl)acetate (72e) (2 g, 4.72 mmol) in MeCN (3 mL) using dimethylamine (3.54 mL, 7.08 mmol), BrettPhos Palladacycle (0.188 g, 0.236 mmol), cesium carbonate (4.61 g, 14.16 mmol) and irradiating at 90° C. for 2 h in microwave. This gave after work up and purification using flash column chromatography [silica gel (12 g), eluting with EtOAc in hexanes from 0-50%] ethyl 2-(2-((5-chloro-7-(dimethylamino)benzofuran-3-yl)methoxy)phenyl)acetate (191a) (106 mg, 6% yield); MS (ES+): 388.20 (M+1).

Step-2: Preparation of ethyl 2-(2-((5-(3-(aminomethyl)phenyl)-7-(dimethylamino)benzofuran-3-yl)methoxy)phenyl)acetate (191b)

Compound 191b was prepared according to the procedure reported in step-2 of scheme 1, from ethyl 2-(2-((5-chloro-7-(dimethylamino)benzofuran-3-yl)methoxy)phenyl)acetate (191a) (0.17 g, 0.397 mmol) in dioxane (8 mL) and 2-Me-THF (4 mL) using 3-(aminomethyl)phenylboronic acid hydrochloride (1d) (130 mg, 0.696 mmol), 4 M solution of $K_3PO_4$ (0.278 mL, 1.114 mmol), tricyclohexylphosphine (62.5 mg, 0.223 mmol), $Pd_2(dba)_3$ (102 mg, 0.111 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-(dimethylamino)benzofuran-3-yl)methoxy)phenyl)acetate (191b) (18 mg, 14% yield); MS (ES+): 459.20 (M+1).

Step-3: Preparation of 2-(2-((5-(3-(aminomethyl)phenyl)-7-(dimethylamino)benzofuran-3-yl)methoxy)phenyl)acetic acid (191c)

Compound 191c was prepared according to the procedure reported in step-3 of scheme 1, from ethyl 2-(2-((5-(3-(aminomethyl)phenyl)-7-(dimethylamino)benzofuran-3-yl)methoxy)phenyl)acetate (191b) (18 mg, 0.039 mmol) in THF (0.2 mL), methanol (0.02 mL) and water (0.02 mL) using a solution of lithium hydroxide monohydrate (3.76 mg, 0.157 mmol) and stirring at RT for 10 h. This gave after workup and purification using reverse phase column chromatography [C18 column (40 g), eluting with ACN in water (containing 0.1% HCl) from 0-100%] 2-(2-((5-(3-(aminomethyl)phenyl)-7-(dimethylamino)benzofuran-3-yl)methoxy)phenyl)acetic acid (191c) (3 mg, 18% yield) HCl salt as grey solid; $^1$H NMR (300 MHz, Methanol-$d_4$) δ 8.09 (s, 1H), 7.91 (s, 1H), 7.89 (s, 1H), 7.80 (d, J=7.9 Hz, 1H), 7.63 (s, 1H), 7.57 (t, J=7.7 Hz, 1H), 7.49-7.42 (m, 1H), 7.34-7.26 (m, 1H), 7.26-7.15 (m, 2H), 7.00-6.92 (m, 1H), 5.35 (s, 2H), 4.22 (s, 2H), 3.62 (s, 2H), 3.40 (s, 6H); MS (ES+): 431.2 (M+1).

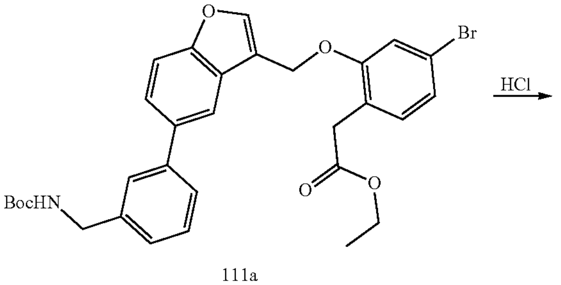

111a

-continued

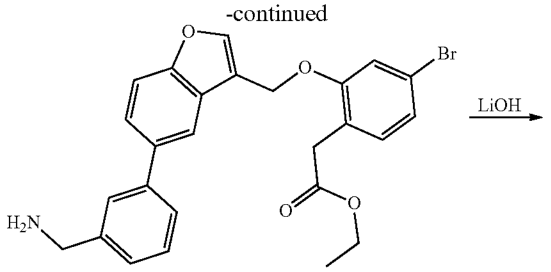

192a

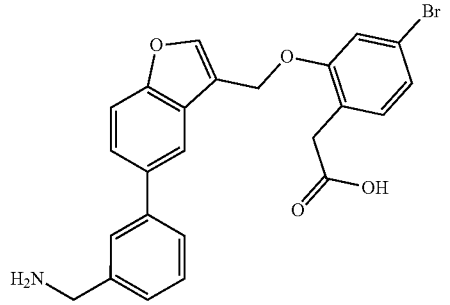

192b

Preparation of 2-(2-((5-(3-(aminomethyl)phenyl)benzofuran-3-yl)methoxy)-4-bromophenyl)acetic acid (192b)

Step-1: Preparation of ethyl 2-(2-((5-(3-(aminomethyl)phenyl)benzofuran-3-yl)methoxy)-4-bromophenyl)acetate (192a)

Compound 192a was prepared according to the procedure reported in step-2 of scheme 7, from ethyl 2-(4-bromo-2-((5-(3-(((tert-butoxycarbonyl)amino)methyl)phenyl)benzofuran-3-yl)methoxy)phenyl)acetate (111a) (200 mg, 0.336 mmol) using HCl (4M HCl in dioxane) (0.421 mL, 1.682 mmol) in EtOH (2 mL) and stirring the reaction mixture at RT for 4 h. This gave after workup ethyl 2-(2-((5-(3-(aminomethyl)phenyl)benzofuran-3-yl)methoxy)-4-bromophenyl)acetate (192a) (154 mg, 93% yield); MS (ES+): 494.10 (M+1).

Step-2: Preparation of 2-(2-((5-(3-(aminomethyl)phenyl)benzofuran-3-yl)methoxy)-4-bromophenyl)acetic acid (192b)

Compound 192b was prepared according to the procedure reported in step-3 of scheme 1, from ethyl 2-(2-((5-(3-(aminomethyl)phenyl)benzofuran-3-yl)methoxy)-4-bromophenyl)acetate (192a) (154 mg, 0.312 mmol) in THF (2 mL), methanol (0.2 mL) and water (0.2 mL), using lithium hydroxide monohydrate (29.8 mg, 1.246 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)benzofuran-3-yl)methoxy)-4-bromophenyl)acetic acid (192b) (37 mg, 26% yield) HCl salt as a light brown solid; $^1$H NMR (300 MHz, DMSO-$d_6$) δ 12.24 (s, 1H, $D_2O$ exchangeable), 8.28 (s, 3H, $D_2O$ exchangeable), 8.13 (s, 1H), 8.02 (d, J=1.8 Hz, 1H), 7.86 (s, 1H), 7.79-7.73 (m, 1H), 7.73-7.65 (m, 1H), 7.54 (t, J=7.6 Hz, 1H), 7.49-7.41 (m, 3H), 7.24-7.12 (m, 2H), 5.37 (s, 2H), 4.13 (s, 2H), 3.53 (s, 2H); MS (ES+):

466.00 (M+1); Analysis calculated for $C_{24}H_{20}BrNO_4 \cdot 1.25HCl \cdot 1.5H_2O$: C, 53.49; H, 4.54; Cl, 8.22; N, 2.60. Found: C, 53.53; H, 4.54; Cl, 8.57; N, 2.74.

Scheme 193

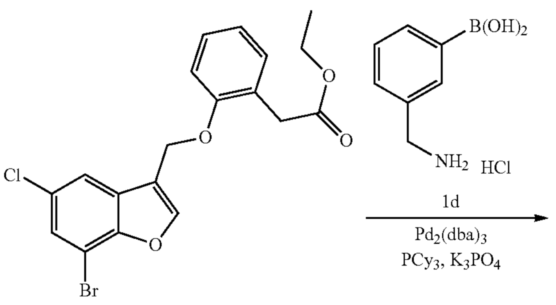

72e

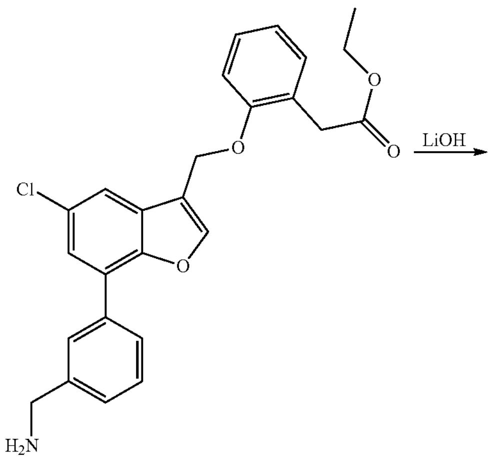

193a

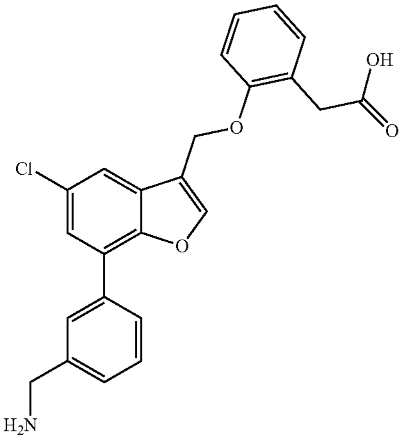

193b

Preparation of 2-(2-((7-(3-(aminomethyl)phenyl)-5-chlorobenzofuran-3-yl)methoxy)phenyl)acetic acid (193b)

Step-1: Preparation of ethyl 2-(2-((7-(3-(aminomethyl)phenyl)-5-chlorobenzofuran-3-yl)methoxy)phenyl)acetate (193a)

Compound 193a was prepared according to the procedure reported in step-2 of scheme 1, from ethyl 2-(2-((7-bromo-5-chlorobenzofuran-3-yl)methoxy)phenyl)acetate (72e) (500 mg, 1.180 mmol) in dioxane/2-methyltetrahydrofuran (12 mL, Ratio: 2:1) using 3-(aminomethyl)phenylboronic acid hydrochloride (1d) (664 mg, 3.54 mmol), 4 M solution of $K_3PO_4$ (1.180 mL, 4.72 mmol), tricyclohexylphosphine (265 mg, 0.944 mmol), $Pd_2(dba)_3$ (432 mg, 0.472 mmol) and heating at 115° C. on a preheated hot block for 3 h. This gave after workup and purification by column chromatography [silica gel (24 g), eluting with DMA-80 in DCM from 0-70%] ethyl 2-(2-((7-(3-(aminomethyl)phenyl)-5-chlorobenzofuran-3-yl)methoxy)phenyl)acetate (193a) (449 mg, 85% yield) as a clear oil; $^1H$ NMR (300 MHz, DMSO-$d_6$) δ 8.25 (s, 1H), 7.83 (s, 1H), 7.71 (d, J=2.1 Hz, 1H), 7.60 (d, J=2.1 Hz, 1H), 7.47 (d, J=7.4 Hz, 1H), 7.43 (d, J=7.7 Hz, 1H), 7.32 (d, J=6.6 Hz, 1H), 7.22 (dt, J=7.2, 2.6 Hz, 3H), 7.00-6.89 (m, 1H), 5.29 (s, 2H), 4.11 (s, 2H), 3.95 (q, J=7.1 Hz, 2H), 3.83 (s, 2H), 1.00 (t, J=7.1 Hz, 3H).

MS (ES+): 450.2 (M+1).

Step-2: Preparation of 2-(2-((7-(3-(aminomethyl)phenyl)-5-chlorobenzofuran-3-yl)methoxy)phenyl)acetic acid (193b)

Compound 193b was prepared according to the procedure reported in step-3 of scheme 1, from ethyl 2-(2-((7-(3-(aminomethyl)phenyl)-5-chlorobenzofuran-3-yl)methoxy)phenyl)acetate (193a) (100 mg, 0.222 mmol) in THF (2 mL), methanol (0.2 mL) and water (0.2 mL), using lithium hydroxide monohydrate (21.29 mg, 0.889 mmol) and stirring for 10 h at RT. This gave after workup and purification using reverse phase column chromatography [C18 column (40 g), eluting with ACN in water (containing 0.1% HCl) from 0-100%] 2-(2-((7-(3-(aminomethyl)phenyl)-5-chlorobenzofuran-3-yl)methoxy)phenyl)acetic acid (193b) (28 mg, 30% yield) HCl salt as a yellow solid; $^1H$ NMR (300 MHz, DMSO-$d_6$) δ 12.17 (s, 1H, $D_2O$ exchangeable), 8.28 (s, 3H, $D_2O$ exchangeable), 8.24 (s, 1H), 8.00-7.97 (m, 2H), 7.95 (s, 1H), 7.83 (d, J=2.1 Hz, 1H), 7.67-7.60 (m, 1H), 7.59-7.52 (m, 1H), 7.33-7.25 (m, 1H), 7.25-7.18 (m, 2H), 6.98-6.85 (m, 1H), 5.33 (s, 2H), 4.16 (s, 2H), 3.55 (s, 2H); MS (ES+): 422.1 (M+1).

Scheme 194

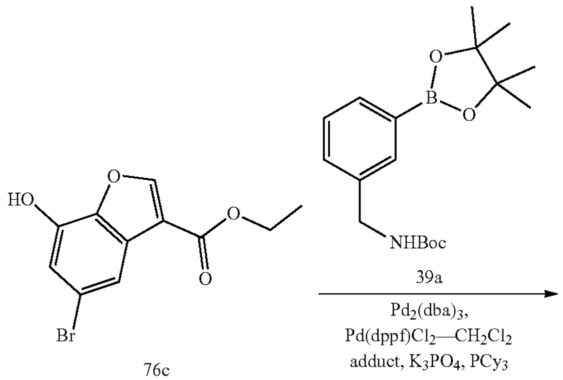

76c

-continued

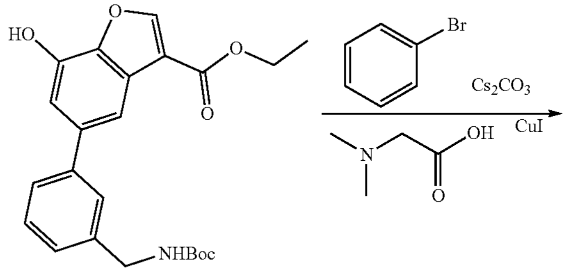

194a

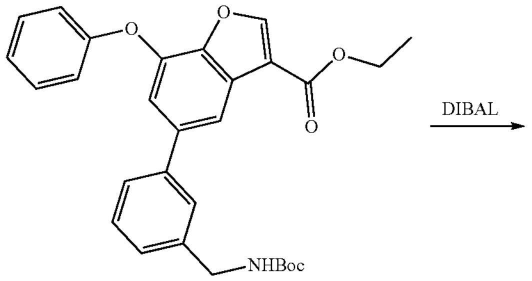

194b

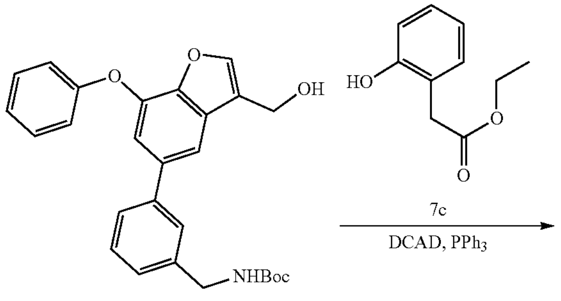

194c

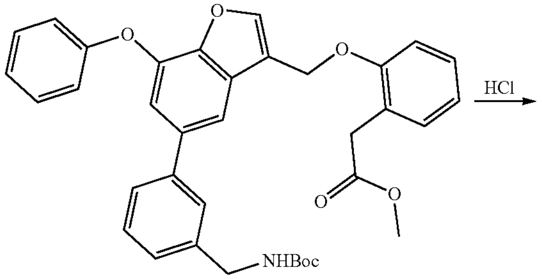

194d

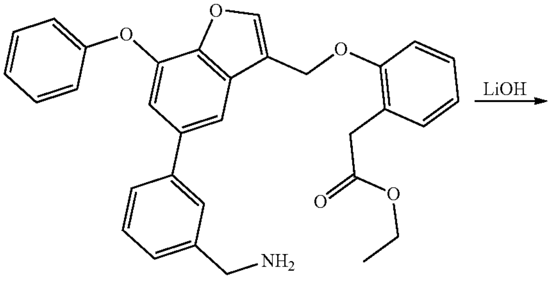

194e

-continued

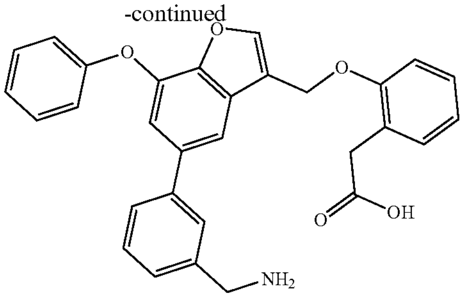

194f

Preparation of 2-(2-((5-(3-(aminomethyl)phenyl)-7-phenoxybenzofuran-3-yl)methoxy)phenyl)acetic acid (194f)

Step-1: Preparation of ethyl 5-(3-(((tert-butoxycarbonyl)amino)methyl)phenyl)-7-hydroxybenzofuran-3-carboxylate (194a)

Compound 194a was prepared according to the procedure reported in step-2 of scheme 1, from ethyl 5-bromo-7-hydroxybenzofuran-3-carboxylate (76c) (5 g, 17.54 mmol) in dioxane (30 mL) and THF (30 mL) using tert-butyl 3-(4,4,5,5-tetramethyl-1,3,2-dioxaborolan-2-yl)benzylcarbamate (39a) (8.77 g, 26.3 mmol), 2 M solution of $K_3PO_4$ (35.1 mL, 70.2 mmol), tricyclohexylphosphine (0.984 g, 3.51 mmol), $Pd_2(dba)_3$ (1.606 g, 1.754 mmol), $PdCl_2(dppf)$-$CH_2Cl_2$-adduct (1.432 g, 1.754 mmol) and heating at 90-100° C. for 1 h. This gave after workup and purification using flash column chromatography [silica gel (80 g), eluting with DMA-80 in DCM from 0-70%] ethyl 5-(3-(((tert-butoxycarbonyl)amino)methyl)phenyl)-7-hydroxybenzofuran-3-carboxylate (194a) (5.463 g, 76% yield) as a clear oil; MS (ES+): 434.20 (M+Na).

Step-2: Preparation of ethyl 5-(3-(((tert-butoxycarbonyl)amino)methyl)phenyl)-7-phenoxybenzofuran-3-carboxylate (194b)

To a solution of $Cs_2CO_3$ (1.188 g, 3.65 mmol) and copper(I) iodide (0.046 g, 0.243 mmol) in dioxane (15 mL) was added ethyl 5-(3-(((tert-butoxycarbonyl)amino)methyl)phenyl)-7-hydroxybenzofuran-3-carboxylate (194a) (1 g, 2.430 mmol), bromobenzene (0.331 mL, 3.16 mmol), and 2-(dimethylamino)acetic acid (0.075 g, 0.729 mmol) and was heated at 100° C. for 3 days under a nitrogen atmosphere. Reaction mixture was diluted with water, acidified, and extracted in EtOAc.

This gave after workup and purification using flash column chromatography [silica gel (24 g), eluting with EtOAc in hexane from 0-75%] ethyl 5-(3-(((tert-butoxycarbonyl)amino)methyl)phenyl)-7-phenoxybenzofuran-3-carboxylate (194b) (730 mg, 62% yield) as a white solid. MS (ES+): 510.20 (M+Na).

Step-3: Preparation of tert-butyl 3-(3-(hydroxymethyl)-7-phenoxybenzofuran-5-yl)benzylcarbamate (194c)

Compound 194c was prepared according to the procedure reported in step-2 of scheme 69, from ethyl 5-(3-(((tert-butoxycarbonyl)amino)methyl)phenyl)-7-phenoxybenzofuran-3-carboxylate (194b) (1.108 g, 2.273 mmol) in DCM (10 mL) using 1.0 M solution of DIBAL in DCM (5.68 mL, 5.68 mmol) and stirring at 0° C. for 2 h. This gave after workup and purification using flash column chromatography [silica gel (24 g), eluting with EtOAc in hexane from 0-50%] tert-butyl 3-(3-(hydroxymethyl)-7-phenoxybenzofuran-5-yl)benzylcarbamate (194c) (0.873 g, 86% yield) as a white solid; MS (ES+): 468.20 (M+Na).

Step-4: Preparation of ethyl 2-(2-((5-(3-(((tert-butoxycarbonyl)amino)methyl)phenyl)-7-phenoxybenzofuran-3-yl)methoxy)phenyl)acetate (194d)

Compound 194d was prepared according to the procedure reported in step-2 of scheme 65, from tert-butyl 3-(3-(hydroxymethyl)-7-phenoxybenzofuran-5-yl)benzylcarbamate (194c) (873 mg, 1.960 mmol) in DCM (20 mL) using triphenylphosphine (668 mg, 2.55 mmol), ethyl 2-(2-hydroxyphenyl)acetate (7c) (529 mg, 2.94 mmol) a solution of DCAD (935 mg, 2.55 mmol) in DCM (7 mL) and stirring at RT for 3 h. This gave after workup and purification using flash column chromatography [silica gel (12 g), eluting with EtOAc in hexane from 0-50%] ethyl 2-(2-((5-(3-(((tert-butoxycarbonyl)amino)methyl)phenyl)-7-phenoxybenzofuran-3-yl)methoxy)phenyl)acetate (194d) (474 mg, 40% yield) as a white solid; $^1H$ NMR (300 MHz, DMSO-$d_6$) δ 9.47 (s, 1H), 8.14 (s, 1H), 7.74 (d, J=1.7 Hz, 1H), 7.53 (s, 2H), 7.44-7.36 (m, 4H), 7.33-7.26 (m, 2H), 7.26-7.18 (m, 2H), 7.10-7.05 (m, 2H), 6.94 (t, J=7.3 Hz, 1H), 6.82-6.75 (m, 1H), 5.30 (s, 2H), 4.18 (d, J=6.2 Hz, 2H), 3.74 (q, J=7.1 Hz, 2H), 3.58 (s, 2H), 1.36 (s, 9H), 0.86 (t, J=7.1 Hz, 3H); MS (ES+): 508.20 (M−Boc+1).

Step-5: Preparation of ethyl 2-(2-((5-(3-(aminomethyl)phenyl)-7-phenoxybenzofuran-3-yl)methoxy)phenyl)acetate (194e)

Compound 194e was prepared according to the procedure reported in step-2 of scheme 7, from ethyl 2-(2-((5-(3-(((tert-butoxycarbonyl)amino)methyl)phenyl)-7-phenoxybenzofuran-3-yl)methoxy)phenyl)acetate (194d) (474 mg, 0.780 mmol) using HCl (4M HCl in dioxane) (0.975 mL, 3.90 mmol) in EtOH (2 mL) and stirring the reaction mixture at RT for 4 h. This gave after workup ethyl 2-(2-((5-(3-(aminomethyl)phenyl)-7-phenoxybenzofuran-3-yl)methoxy)phenyl)acetate (194e) (392 mg, 99% yield); MS (ES+): 508.20 (M+1).

Step-6: Preparation of 2-(2-((5-(3-(aminomethyl)phenyl)-7-phenoxybenzofuran-3-yl)methoxy)phenyl)acetic acid (194f)

Compound 194f was prepared according to the procedure reported in step-3 of scheme 1, from ethyl 2-(2-((5-(3-(aminomethyl)phenyl)-7-phenoxybenzofuran-3-yl)methoxy)phenyl)acetate (194e) (396 mg, 0.78 mmol) in THF (2 mL), methanol (0.2 mL) and water (0.2 mL) using lithium hydroxide monohydrate (74.7 mg, 3.12 mmol) and stirring at RT for 10 h. This gave after workup and purification using reverse phase column chromatography [C18 column (40 g), eluting with ACN in water (containing 0.1% HCl) from 0-100%] 2-(2-((5-(3-(aminomethyl)phenyl)-7-phenoxybenzofuran-3-yl)methoxy)phenyl)acetic acid (194f) (152 mg, 41% yield) HCl salt as a white solid; $^1H$ NMR (300 MHz, DMSO-$d_6$) δ 12.20 (s, 1H, $D_2O$ exchangeable), 8.41 (s, 3H, $D_2O$ exchangeable), 8.13 (s, 1H), 7.89 (d, J=1.6 Hz, 1H), 7.87 (s, 1H), 7.73 (dt, J=7.4, 1.8 Hz, 1H), 7.56-7.44 (m, 2H), 7.44-7.37 (m, 3H), 7.34-7.26 (m, 1H), 7.26-7.20 (m, 2H), 7.18-7.12 (m, 1H), 7.11-7.03 (m, 2H), 6.95 (td, J=7.3, 1.3 Hz, 1H), 5.34 (s, 2H), 4.09 (s, 2H), 3.57 (s, 2H); MS (ES+): 480.70 (M+1); (ES−) 477.8 (M−1); Analysis calculated for $C_{30}H_{25}NO_5$ 1HCl·0.5$H_2O$: C, 68.63; H, 5.18; Cl, 6.75; N, 2.67. Found: C, 68.82; H, 5.10; Cl, 6.86; N, 2.80.

Scheme 195

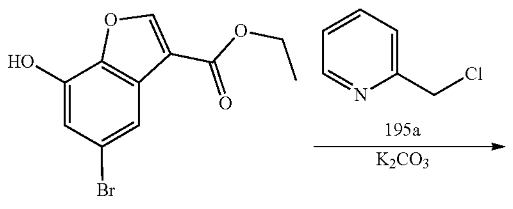

76c

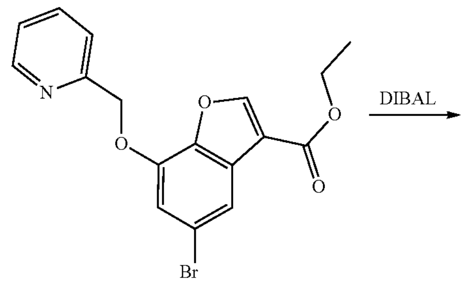

195b

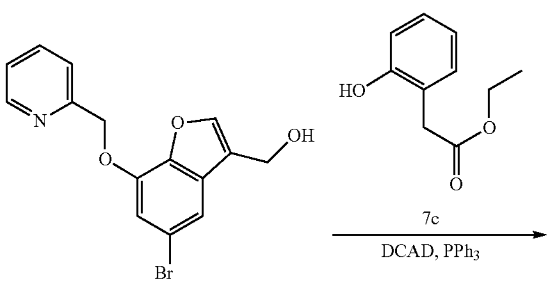

195c

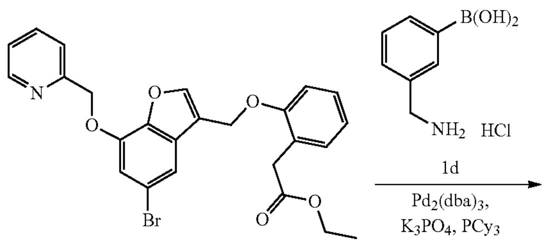

195d

-continued

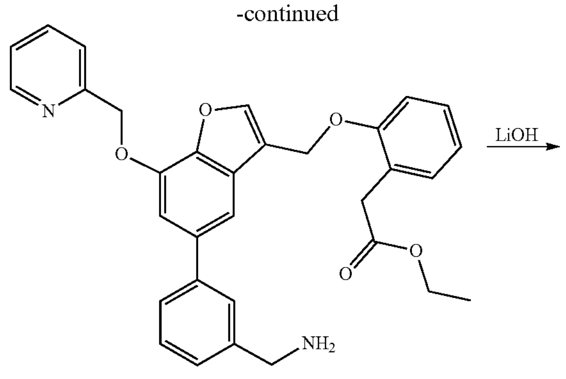

195e

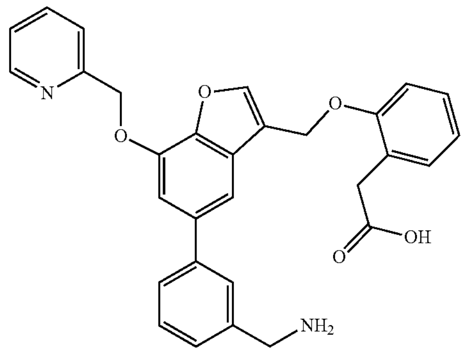

195f

Preparation of 2-(2-((5-(3-(aminomethyl)phenyl)-7-(pyridin-2-ylmethoxy)benzofuran-3-yl)methoxy)phenyl)acetic acid (195f)

Step-1: Preparation of ethyl 5-bromo-7-(pyri din-2-ylmethoxy)benzofuran-3-carboxylate (195b)

Compound 195b was prepared according to the procedure reported in step-1 of scheme 58, from ethyl 5-bromo-7-hydroxybenzofuran-3-carboxylate (76c) (450 mg, 1.578 mmol) in DMF (5 mL) using HCl salt of 2-(chloromethyl) pyridine (195a) (259 mg, 1.578 mmol), $K_2CO_3$ (654 mg, 4.74 mmol) and stirring at RT for 14 h. This gave after workup ethyl 5-bromo-7-(pyridin-2-ylmethoxy)benzofuran-3-carboxylate (195b) (568 mg, 96% yield) as an off-white solid; $^1$H NMR (300 MHz, DMSO-$d_6$) δ 8.82 (s, 1H), 8.62 (ddd, J=4.9, 1.8, 0.9 Hz, 1H), 7.89 (td, J=7.7, 1.8 Hz, 1H), 7.68 (d, J=1.7 Hz, 1H), 7.60 (d, J=8.0 Hz, 1H), 7.45-7.34 (m, 2H), 5.42 (s, 2H), 4.36 (q, J=7.1 Hz, 2H), 1.35 (t, J=7.1 Hz, 3H); MS (ES+): 376.0 (M+1).

Step-2: Preparation of (5-bromo-7-(pyridin-2-ylmethoxy)benzofuran-3-yl)methanol (195c)

Compound 195c was prepared according to the procedure reported in step-2 of scheme 69, from ethyl 5-bromo-7-(pyridin-2-ylmethoxy)benzofuran-3-carboxylate (195b) (500 mg, 1.329 mmol) in DCM (2.66 mL) using 1.0 M solution of DIBAL in DCM (3.99 mL, 3.99 mmol) and stirring at 0° C. for 4 h. This gave after work up and purification using flash column chromatography [silica gel (40 g), eluting with EtOAc/MeOH (ratio 9:1) in hexane from 0-100%] (5-bromo-7-(pyridin-2-ylmethoxy)benzofuran-3-yl)methanol (195c) (0.141 g, 32% yield); $^1$H NMR (300 MHz, DMSO-$d_6$) δ 8.63-8.59 (m, 1H), 7.92 (s, 1H), 7.88 (td, J=7.7, 1.8 Hz, 1H), 7.58 (d, J=7.9 Hz, 1H), 7.49 (d, J=1.7 Hz, 1H), 7.42-7.35 (m, 1H), 7.21 (d, J=1.8 Hz, 1H), 5.39 (s, 2H), 5.22 (t, J=5.6 Hz, 1H), 4.59 (dd, J=5.6, 1.1 Hz, 2H); MS (ES+): 334.0 (M+1).

Step-3: Preparation of ethyl 2-(2-((5-bromo-7-(pyridin-2-ylmethoxy)benzofuran-3-yl)methoxy)phenyl) acetate (195d)

Compound 195d was prepared according to the procedure reported in step-2 of scheme 65, from (5-bromo-7-(pyridin-2-ylmethoxy)benzofuran-3-yl)methanol (195c) (130 mg, 0.389 mmol) in DCM (3 mL) using triphenylphosphine (117 mg, 0.447 mmol), ethyl 2-(2-hydroxyphenyl)acetate (7c) (77 mg, 0.428 mmol) a solution of DCAD (164 mg, 0.447 mmol) in DCM (3 mL) at 0° C. and stirring at RT for 1 h. This gave after workup and purification using flash column chromatography [silica gel (40 g), eluting with EtOAc in hexane from 0-25%] ethyl 2-(2-((5-bromo-7-(pyridin-2-ylmethoxy)benzofuran-3-yl)methoxy)phenyl)acetate (195d) (148 mg, 77% yield) as a white solid; MS (ES+): 496.1 (M+1).

Step-4: Preparation of ethyl 2-(2-((5-(3-(aminomethyl)phenyl)-7-(pyridin-2-ylmethoxy)benzofuran-3-yl)methoxy)phenyl)acetate (195e)

Compound 195e was prepared according to the procedure reported in step-2 of scheme 1, from ethyl 2-(2-((5-bromo-7-(pyridin-2-ylmethoxy)benzofuran-3-yl)methoxy)phenyl) acetate (195d) (140 mg, 0.282 mmol) using (3-(aminomethyl)phenyl)boronic acid hydrochloride (1d) (66.1 mg, 0.353 mmol), 4 M solution of $K_3PO_4$ (0.282 mL, 1.128 mmol), tricyclohexylphosphine (15.82 mg, 0.056 mmol) and $Pd_2(dba)_3$ (25.8 mg, 0.028 mmol) and heating at 105° C. for 2 h. This gave after workup and purification using flash column chromatography [silica gel (24 g), eluting with DMA-80 in DCM from 0-50%] ethyl 2-(2-((5-(3-(aminomethyl)phenyl)-7-(pyridin-2-ylmethoxy)benzofuran-3-yl) methoxy)phenyl)acetate (195e) (73 mg, 50% yield) as a clear oil; MS (ES+): 523.2 (M+1).

Step-5: Preparation of 2-(2-((5-(3-(aminomethyl) phenyl)-7-(pyridin-2-ylmethoxy)benzofuran-3-yl) methoxy)phenyl)acetic acid (195f)

Compound 195f was prepared according to the procedure reported in step-3 of scheme 1, from ethyl 2-(2-((5-(3-(aminomethyl)phenyl)-7-(pyridin-2-ylmethoxy)benzofuran-3-yl)methoxy)phenyl)acetate (195e) (70 mg, 0.134 mmol) in THF (0.8 mL), acetonitrile (0.4 mL) using a 1N solution of lithium hydroxide monohydrate (0.402 mL, 0.402 mmol) and stirring for 25 h at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(pyridin-2-ylmethoxy)benzofuran-3-yl)methoxy) phenyl)acetic acid (195f) (31 mg, 47% yield) HCl salt as a white solid; $^1$H NMR (300 MHz, DMSO-$d_6$) δ 8.71-8.64 (m, 1H), 8.40 (s, 3H, $D_2O$ exchangeable), 8.13 (s, 1H), 8.01 (td, J=7.7, 1.7 Hz, 1H), 7.91 (s, 1H), 7.77-7.71 (m, 2H), 7.63 (d, J=1.5 Hz, 1H), 7.57-7.38 (m, 4H), 7.32-7.16 (m, 3H), 6.97-6.89 (m, 1H), 5.56 (s, 2H), 5.31 (s, 2H), 4.19-4.05 (m, 2H), 3.54 (s, 2H); MS (ES+): 495.2 (M+1), 517.2 (M+Na); (ES−): 493.1 (M−1); Analysis calculated for $C_{30}H_{26}N_2O_5 \cdot 2H_2O \cdot 2HCl$: C, 59.71; H, 5.34; Cl, 11.75; N, 4.64. Found: C, 59.65; H, 5.26; Cl, 11.47; N, 4.77.

Scheme 196

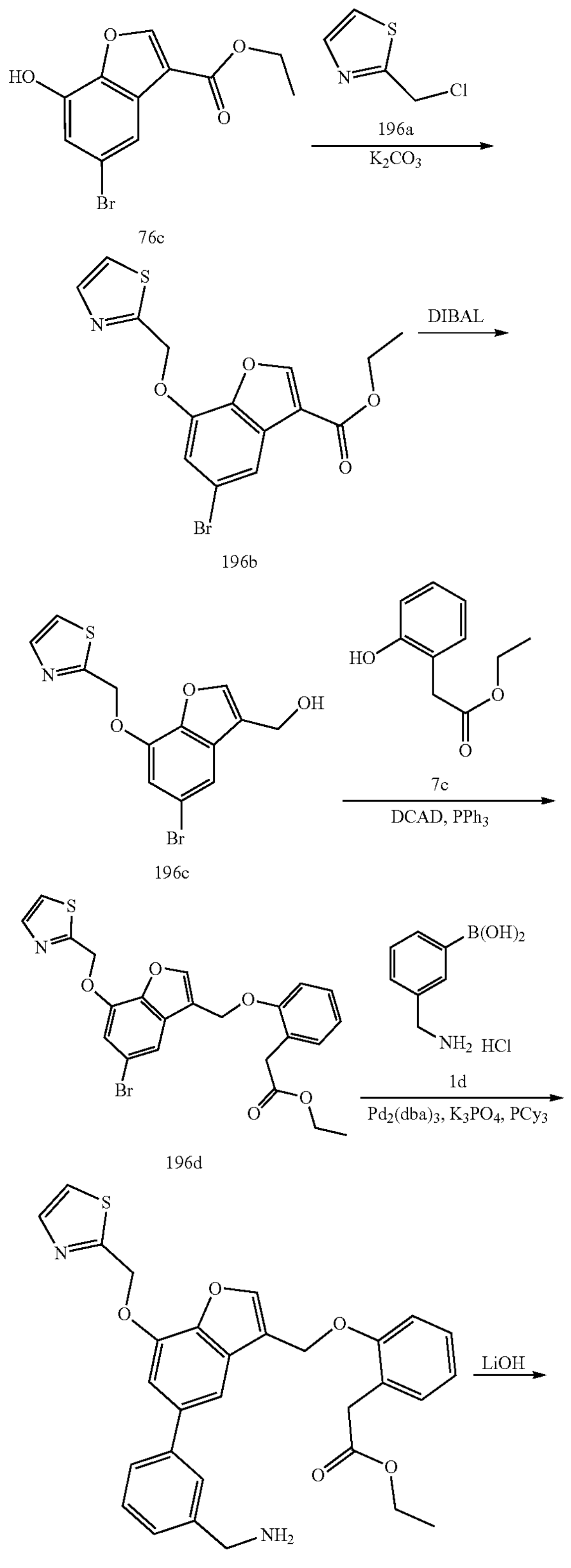

76c

196b

196c

196d

196e

-continued

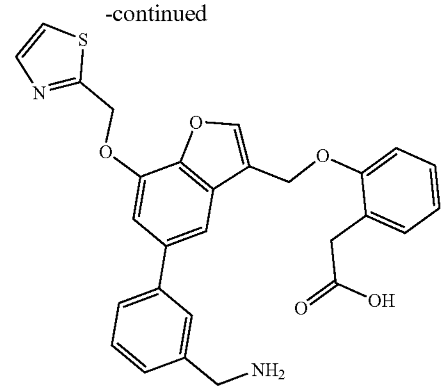

196f

Preparation of 2-(2-((5-(3-(aminomethyl)phenyl)-7-(thiazol-2-ylmethoxy)benzofuran-3-yl)methoxy)phenyl)acetic acid (196f)

Step-1: Preparation of ethyl 5-bromo-7-(thiazol-2-ylmethoxy)benzofuran-3-carboxylate (196b)

Compound 196b was prepared according to the procedure reported in step-1 of scheme 58, from ethyl 5-bromo-7-hydroxybenzofuran-3-carboxylate (76c) (450 mg, 1.578 mmol) in DMF (5 mL) using 2-(chloromethyl)thiazole (196a) (211 mg, 1.578 mmol), $K_2CO_3$ (654 mg, 4.74 mmol) and stirring at RT for 14 h. This gave after workup ethyl 5-bromo-7-(thiazol-2-ylmethoxy)benzofuran-3-carboxylate (196b) (587 mg, 97% yield) as an off-white solid; $^1H$ NMR (300 MHz, DMSO-$d_6$) δ 8.83 (s, 1H), 7.90 (d, J=3.2 Hz, 1H), 7.84 (d, J=3.3 Hz, 1H), 7.70 (d, J=1.7 Hz, 1H), 7.47 (d, J=1.7 Hz, 1H), 5.71 (s, 2H), 4.36 (q, J=7.1 Hz, 2H), 1.35 (t, J=7.1 Hz, 3H); MS (ES+): 381.98 (M+1).

Step-2: Preparation of (5-bromo-7-(thiazol-2-ylmethoxy)benzofuran-3-yl)methanol (196c)

Compound 196c was prepared according to the procedure reported in step-2 of scheme 69, from ethyl 5-bromo-7-(thiazol-2-ylmethoxy)benzofuran-3-carboxylate (196b) (500 mg, 1.308 mmol) in DCM (2.61 mL) using 1.0 M solution of DIBAL in DCM (3.92 mL, 3.92 mmol) and stirring at 0° C. for 4 h. This gave after work up and purification using flash column chromatography [silica gel (40 g), eluting with EtOAc/MeOH (ratio 9:1) in hexane from 0-100%] (5-bromo-7-(thiazol-2-ylmethoxy)benzofuran-3-yl)methanol (196c) (0.243 g, 55% yield) as an off-white solid; $^1H$ NMR (300 MHz, DMSO-$d_6$) δ 7.93 (s, 1H), 7.89 (d, J=3.2 Hz, 1H), 7.83 (d, J=3.2 Hz, 1H), 7.53 (d, J=1.7 Hz, 1H), 7.31 (d, J=1.7 Hz, 1H), 5.67 (s, 2H), 5.23 (t, J=5.6 Hz, 1H), 4.59 (dd, J=5.6, 1.1 Hz, 2H); MS (ES+): 339.9 (M+1).

Step-3: Preparation of ethyl 2-(2-((5-bromo-7-(thiazol-2-ylmethoxy)benzofuran-3-yl)methoxy)phenyl) acetate (196d)

Compound 196d was prepared according to the procedure reported in step-2 of scheme 65, from (5-bromo-7-(thiazol-2-ylmethoxy)benzofuran-3-yl)methanol (196c) (235 mg, 0.691 mmol) in DCM (5 mL) using triphenylphosphine (208 mg, 0.794 mmol), ethyl 2-(2-hydroxyphenyl)acetate (7c) (137 mg, 0.76 mmol) a solution of DCAD (292 mg, 0.794 mmol) in DCM (5 mL) at 0° C. and stirring at RT for 1 h. This gave after workup and purification using flash column chromatography [silica gel (40 g), eluting with EtOAc in hexane from 0-25%] ethyl 2-(2-((5-bromo-7-(thiazol-2-yl-methoxy)benzofuran-3-yl)methoxy)phenyl)acetate (196d) (285 mg, 82% yield) as a white solid; $^1$H NMR (300 MHz, DMSO-$d_6$) δ 8.14 (s, 1H), 7.89 (d, J=3.3 Hz, 1H), 7.83 (d, J=3.2 Hz, 1H), 7.48 (d, J=1.7 Hz, 1H), 7.35 (d, J=1.7 Hz, 1H), 7.33-7.26 (m, 1H), 7.23-7.15 (m, 2H), 6.97-6.88 (m, 1H), 5.69 (s, 2H), 5.22 (s, 2H), 3.94 (q, J=7.1 Hz, 2H), 3.56 (s, 2H), 0.99 (t, J=7.1 Hz, 3H); MS (ES+): 502.0 (M+1).

Step-4: Preparation of ethyl 2-(2-((5-(3-(aminomethyl)phenyl)-7-(pyridin-2-ylmethoxy)benzofuran-3-yl)methoxy)phenyl)acetate (196e)

Compound 196e was prepared according to the procedure reported in step-2 of scheme 1, from ethyl 2-(2-((5-bromo-7-(thiazol-2-ylmethoxy)benzofuran-3-yl)methoxy)phenyl) acetate (196d) (280 mg, 0.557 mmol) using (3-(aminomethyl)phenyl)boronic acid hydrochloride (1d) (131 mg, 0.697 mmol), 4 M solution of $K_3PO_4$ (0.557 mL, 2.229 mmol), tricyclohexylphosphine (31.3 mg, 0.111 mmol), $Pd_2(dba)_3$ (51.0 mg, 0.056 mmol) and heating at 105° C. for 2 h. This gave after workup and purification using flash column chromatography [silica gel (24 g), eluting with DMA-80 in DCM from 0-50%] ethyl 2-(2-((5-(3-(aminomethyl)phenyl)-7-(thiazol-2-ylmethoxy)benzofuran-3-yl) methoxy)phenyl)acetate (196e) (114 mg, 39% yield) as a clear oil; $^1$H NMR (300 MHz, DMSO-$d_6$) δ 8.13 (s, 1H), 7.89 (d, J=3.3 Hz, 1H), 7.82 (d, J=3.2 Hz, 1H), 7.70 (s, 1H), 7.61-7.52 (m, 2H), 7.46-7.26 (m, 4H), 7.26-7.17 (m, 2H), 6.93 (dd, J=7.9, 6.7 Hz, 1H), 5.77 (s, 2H), 5.29 (s, 2H), 3.84 (s, 2H), 3.74 (q, J=7.1 Hz, 2H), 3.56 (s, 2H), 0.86 (t, J=7.1 Hz, 3H); MS (ES+): 529.2 (M+1).

Step-5: Preparation of 2-(2-((5-(3-(aminomethyl) phenyl)-7-(thiazol-2-ylmethoxy)benzofuran-3-yl) methoxy)phenyl)acetic acid (196f)

Compound 196f was prepared according to the procedure reported in step-3 of scheme 1, from ethyl 2-(2-((5-(3-(aminomethyl)phenyl)-7-(thiazol-2-ylmethoxy)benzofuran-3-yl)methoxy)phenyl)acetate (196e) (110 mg, 0.208 mmol) in THF (1.3 mL) and acetonitrile (0.65 mL) using a 1N solution of lithium hydroxide hydrate (0.624 mL, 0.624 mmol) and stirring for 25 h at RT. This gave after workup and purification using reverse phase column chromatography [C18 column (30 g), eluting with ACN in water (containing 0.1% HCl) from 0-100%] 2-(2-((5-(3-(aminomethyl) phenyl)-7-(thiazol-2-ylmethoxy)benzofuran-3-yl)methoxy) phenyl)acetic acid (196f) (61 mg, 59% yield) HCl salt as a white solid; $^1$H NMR (300 MHz, DMSO-$d_6$) δ 8.35 (s, 3H, $D_2O$ exchangeable), 8.14 (s, 1H), 7.92-7.87 (m, 2H), 7.83 (d, J=3.3 Hz, 1H), 7.79-7.74 (m, 1H), 7.65 (d, J=1.4 Hz, 1H), 7.54 (t, J=7.6 Hz, 1H), 7.49-7.43 (m, 2H), 7.28 (td, J=7.7, 7.2, 1.7 Hz, 1H), 7.24-7.17 (m, 2H), 6.94 (td, J=7.3, 1.2 Hz, 1H), 5.78 (s, 2H), 5.31 (s, 2H), 4.19-4.03 (m, 2H), 3.53 (s, 2H); MS (ES+): 501.1 (M+1); (ES−): 499.1 (M−1); Analysis calculated for $C_{28}H_{24}N_2O_5S \cdot 1.25H_2O \cdot 1.15HCl$: C, 59.52; H, 4.93; Cl, 7.22; N, 4.96. Found: C, 59.29; H, 4.60; Cl, 7.07; N, 5.13.

Scheme 197

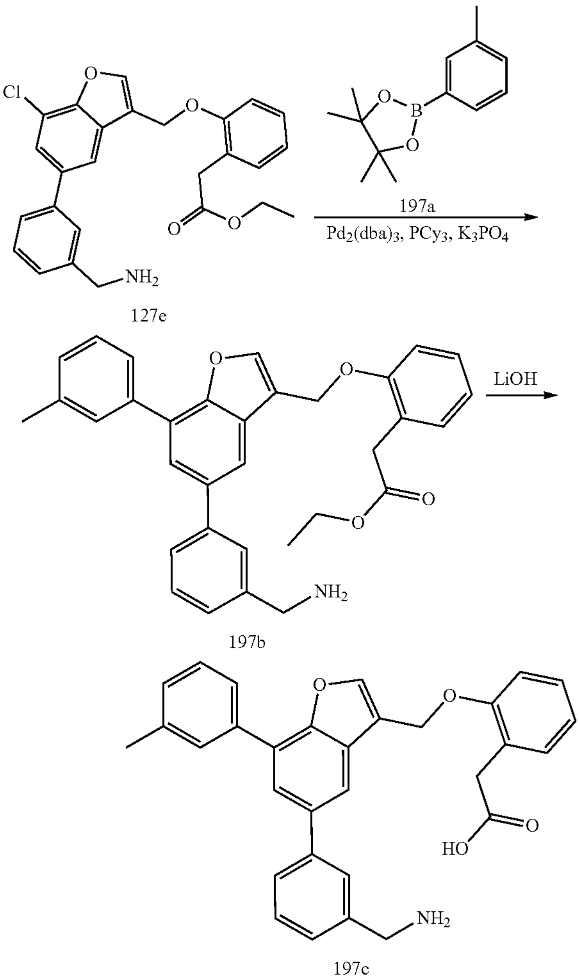

127e

197b

197c

Preparation of 2-(2-((5-(3-(aminomethyl)phenyl)-7-(m-tolyl)benzofuran-3-yl)methoxy)phenyl)acetic acid (197c)

Step-1: Preparation of ethyl 2-(2-((5-(3-(aminomethyl)phenyl)-7-(m-tolyl)benzofuran-3-yl)methoxy) phenyl)acetate (197b)

Compound 197b was prepared according to the procedure reported in step-2 of scheme 1, from ethyl 2-(2-((5-(3-(aminomethyl)phenyl)-7-chlorobenzofuran-3-yl)methoxy) phenyl)acetate (127e) (200 mg, 0.445 mmol) in dioxane (15 mL) using 4,4,5,5-tetramethyl-2-(m-tolyl)-1,3,2-dioxaborolane (197a) (145 mg, 0.667 mmol; CAS #253342-48-2), 4M solution of $K_3PO_4$ (42.2 mg, 0.445 mmol), tricyclohexylphosphine (24.93 mg, 0.089 mmol), $Pd_2(dba)_3$ (40.7 mg, 0.044 mmol) and heating at 115° C. for 12 h in an oil bath. This gave after workup and purification using flash column chromatography [silica gel (40 g), eluting with DMA-80 in DCM from 0-50%] ethyl 2-(2-((5-(3-(aminomethyl)phenyl)-7-(m-tolyl)benzofuran-3-yl)methoxy)phenyl)acetate (197b) (80 mg, 36% yield) as a clear oil; MS (ES+): 506.2 (M+1).

Step-2: Preparation of 2-(2-((5-(3-(aminomethyl)phenyl)-7-(m-tolyl)benzofuran-3-yl)methoxy)phenyl)acetic acid (197c)

Compound 197c was prepared according to the procedure reported in step-3 of scheme 1, from ethyl 2-(2-((5-(3-(aminomethyl)phenyl)-7-(m-tolyl)benzofuran-3-yl)methoxy)phenyl)acetate (197b) (80 mg, 0.158 mmol) in THF (1.0 mL) and acetonitrile (0.5 mL) using a 1 N solution of lithium hydroxide monohydrate (0.475 mL, 0.475 mmol) and stirring at room temperature for 25 h at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(m-tolyl)benzofuran-3-yl)methoxy)phenyl)acetic acid (197c) (25 mg, 33% yield) hydrochloride salt as a white solid; $^1H$ NMR (300 MHz, DMSO-$d_6$) δ 8.40-8.13 (m, 4H, 3H D2O exchangeable), 8.03-7.93 (m, 2H), 7.89-7.80 (m, 2H), 7.75 (s, 1H), 7.72 (s, 1H), 7.55 (t, J=7.7 Hz, 1H), 7.50-7.41 (m, 2H), 7.33-7.27 (m, 2H), 7.27-7.19 (m, 2H), 6.94 (t, J=7.2 Hz, 1H), 5.37 (s, 2H), 4.14 (s, 2H), 3.56 (s, 2H), 2.44 (s, 3H); MS (ES+): 478.2 (M+1); (ES−): 476.2 (M−1).

Scheme 198

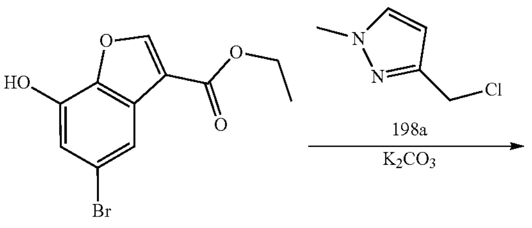

76c

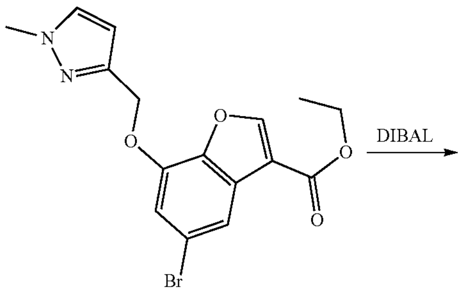

198b

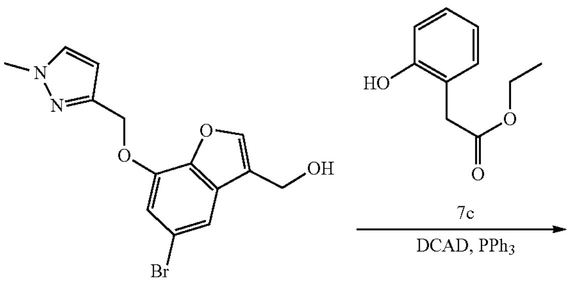

198c

-continued

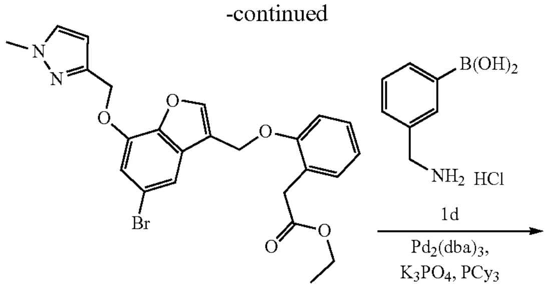

198d

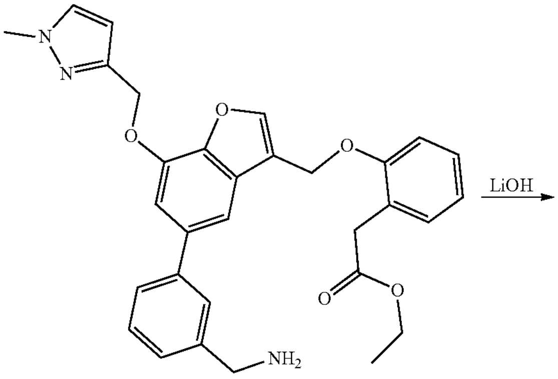

198e

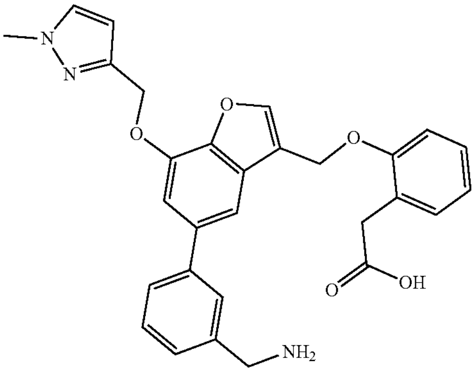

198f

Preparation of 2-(2-((5-(3-(aminomethyl)phenyl)-7-((1-methyl-1H-pyrazol-3-yl)methoxy)benzofuran-3-yl)methoxy)phenyl)acetic acid (198f)

Step-1: Preparation of ethyl 5-bromo-7-((1-methyl-1H-pyrazol-3-yl)methoxy)benzofuran-3-carboxylate (198b)

Compound 198b was prepared according to the procedure reported in step-1 of scheme 58, from ethyl 5-bromo-7-hydroxybenzofuran-3-carboxylate (76c) (205 mg, 0.718 mmol) in DMF (2 mL) using HCl salt of 3-(chloromethyl)-1-methyl-1H-pyrazole (198a) (120 mg, 0.718 mmol), $K_2CO_3$ (298 mg, 2.155 mmol) and stirring at RT for 14 h. This gave after workup ethyl 5-bromo-7-((1-methyl-1H-pyrazol-3-yl)methoxy)benzofuran-3-carboxylate (198b) (247 mg, 91% yield) as an off-white solid; $^1H$ NMR (300 MHz, DMSO-$d_6$) δ 8.77 (s, 1H), 7.70 (d, J=2.2 Hz, 1H), 7.65 (d, J=1.7 Hz, 1H), 7.42 (d, J=1.8 Hz, 1H), 6.37 (d, J=2.2 Hz, 1H), 5.23 (s, 2H), 4.35 (q, J=7.1 Hz, 2H), 3.85 (s, 3H), 1.34 (t, J=7.1 Hz, 3H); MS (ES+): 379.0 (M+1).

Step-2: Preparation of (5-bromo-7-((1-methyl-1H-pyrazol-3-yl)methoxy)benzofuran-3-yl)methanol (198c)

Compound 198c was prepared according to the procedure reported in step-2 of scheme 69, from ethyl 5-bromo-7-((1-methyl-1H-pyrazol-3-yl)methoxy)benzofuran-3-carboxylate (198b) (240 mg, 0.633 mmol) in DCM (1.055 mL) using 1.0 M solution of DIBAL in DCM (1.582 mL, 1.582 mmol) and stirring at 0° C. for 4 h. This gave after work up and purification using flash column chromatography [silica gel (12 g), eluting with EtOAc in hexane from 0-50%] (5-bromo-7-((1-methyl-1H-pyrazol-3-yl)methoxy)benzofuran-3-yl)methanol (198c) (0.102 g, 48% yield); $^1$H NMR (300 MHz, DMSO-$d_6$) δ 7.88 (s, 1H), 7.69 (d, J=2.2 Hz, 1H), 7.46 (d, J=1.7 Hz, 1H), 7.26 (d, J=1.8 Hz, 1H), 6.35 (d, J=2.2 Hz, 1H), 5.26-5.11 (m, 3H), 4.57 (dd, J=5.6, 1.1 Hz, 2H), 3.85 (s, 3H); MS (ES+): 337.0 (M+1).

Step-3: Preparation of ethyl 2-(2-((5-bromo-7-((1-methyl-1H-pyrazol-3-yl)methoxy)benzofuran-3-yl)methoxy)phenyl)acetate (198d)

Compound 198d was prepared according to the procedure reported in step-2 of scheme 65, from (5-bromo-7-((1-methyl-1H-pyrazol-3-yl)methoxy)benzofuran-3-yl)methanol (198c) (100 mg, 0.297 mmol) in DCM (2.5 mL) using triphenylphosphine (89 mg, 0.341 mmol), ethyl 2-(2-hydroxyphenyl)acetate (7c) (58.8 mg, 0.326 mmol) a solution of DCAD (125 mg, 0.341 mmol) in DCM (2.5 mL) at 0° C. and stirring at RT for 1 h. This gave after workup and purification using flash column chromatography [silica gel (24 g), eluting with EtOAc/MeOH (ratio 9:1) in hexane from 0-100%] ethyl 2-(2-((5-bromo-7-((1-methyl-1H-pyrazol-3-yl)methoxy)benzofuran-3-yl)methoxy)phenyl)acetate (198d) (90 mg, 61% yield) as a clear gel; MS (ES+): 499.0 (M+1).

Step-4: Preparation of ethyl 2-(2-((5-(3-(aminomethyl)phenyl)-7-((1-methyl-1H-pyrazol-3-yl)methoxy)benzofuran-3-yl)methoxy)phenyl)acetate (198e)

Compound 198e was prepared according to the procedure reported in step-2 of scheme 1, from ethyl 2-(2-((5-bromo-7-((1-methyl-1H-pyrazol-3-yl)methoxy)benzofuran-3-yl)methoxy)phenyl)acetate (198d) (85 mg, 0.170 mmol) using (3-(aminomethyl)phenyl)boronic acid hydrochloride (1d) (39.9 mg, 0.213 mmol), 4 M solution of $K_3PO_4$ (0.170 mL, 0.681 mmol), tricyclohexylphosphine (9.55 mg, 0.034 mmol), $Pd_2(dba)_3$ (15.59 mg, 0.017 mmol) and heating at 110° C. for 4 h. This gave after workup and purification using flash column chromatography [silica gel (24 g), eluting with DMA-80 in DCM from 0-50%] ethyl 2-(2-((5-(3-(aminomethyl)phenyl)-7-((1-methyl-1H-pyrazol-3-yl)methoxy)benzofuran-3-yl)methoxy)phenyl)acetate (198e) (26 mg, 29% yield) as a clear oil; MS (ES+): 526.2 (M+1).

Step-5: Preparation of 2-(2-((5-(3-(aminomethyl)phenyl)-7-((1-methyl-1H-pyrazol-3-yl)methoxy)benzofuran-3-yl)methoxy)phenyl)acetic acid (198f)

Compound 198f was prepared according to the procedure reported in step-3 of scheme 1, from ethyl 2-(2-((5-(3-(aminomethyl)phenyl)-7-((1-methyl-1H-pyrazol-3-yl)methoxy)benzofuran-3-yl)methoxy)phenyl)acetate (198e) (25 mg, 0.048 mmol) in THF (0.3 mL) and acetonitrile (0.15 mL) using a 1N solution of lithium hydroxide monohydrate (0.143 mL, 0.143 mmol) and stirring for 25 h at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-((1-methyl-1H-pyrazol-3-yl)methoxy)benzofuran-3-yl)methoxy)phenyl)acetic acid (198f) (8 mg, 34% yield) HCl salt as a white solid; $^1$H NMR (300 MHz, Methanol-$d_4$) δ 7.90 (s, 1H), 7.82 (s, 1H), 7.74 (d, J=7.7 Hz, 1H), 7.63 (s, 1H), 7.58-7.49 (m, 2H), 7.41 (d, J=7.7 Hz, 1H), 7.33-7.13 (m, 4H), 6.94 (t, J=7.4 Hz, 1H), 6.49-6.41 (m, 1H), 5.36 (s, 2H), 5.29 (s, 2H), 4.20 (s, 2H), 3.92 (s, 3H), 3.62 (s, 2H); MS (ES+): 498.2 (M+1); (ES−): 496.1 (M−1).

Scheme 199

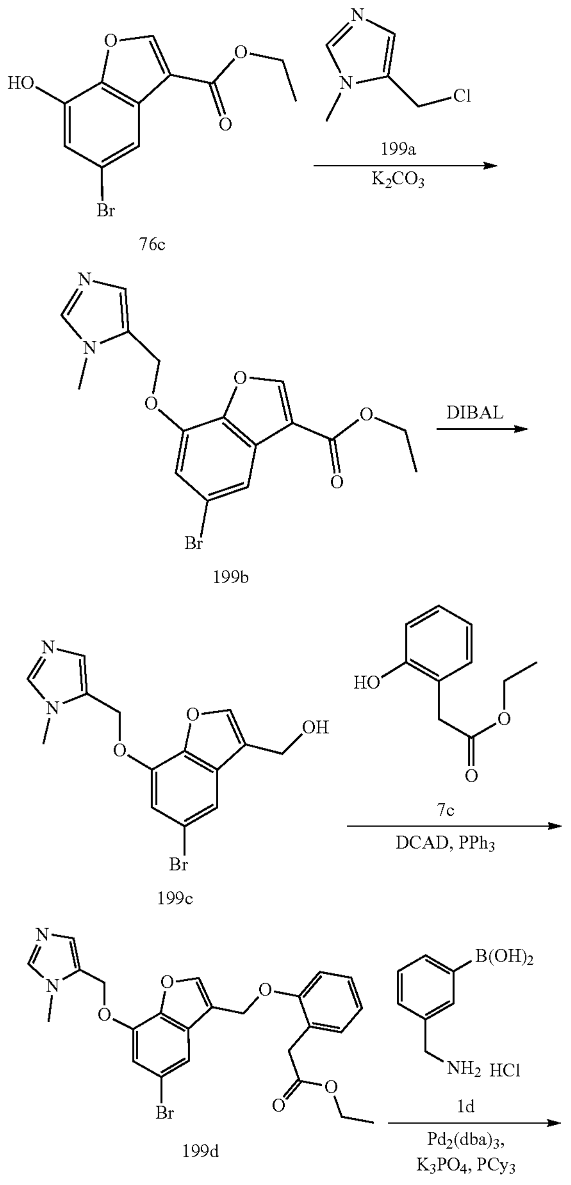

76c

199b

199c

199d

-continued

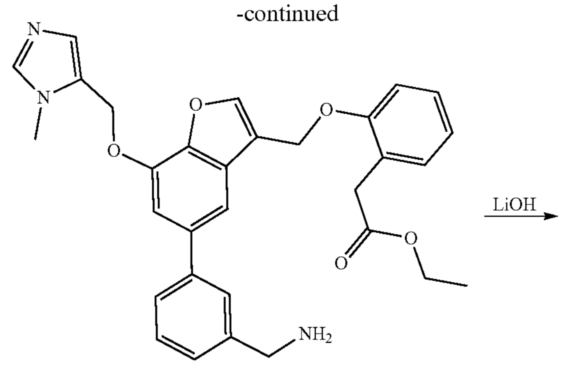

199e

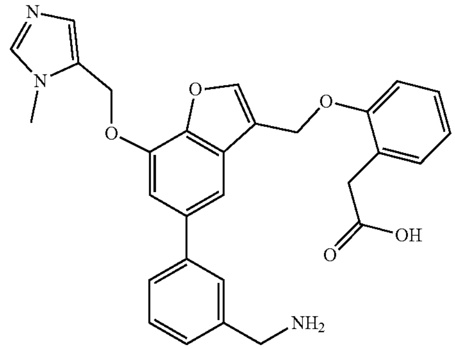

199f

Preparation of 2-(2-((5-(3-(aminomethyl)phenyl)-7-((1-methyl-1H-imidazol-5-yl)methoxy)benzofuran-3-yl)methoxy)phenyl)acetic acid (199f)

Step-1: Preparation of ethyl 5-bromo-7-((1-methyl-1H-imidazol-5-yl)methoxy)benzofuran-3-carboxylate (199b)

Compound 199b was prepared according to the procedure reported in step-1 of scheme 58, from ethyl 5-bromo-7-hydroxybenzofuran-3-carboxylate (76c) (1 g, 3.51 mmol) in DMF (10 mL) using HCl salt of 5-(chloromethyl)-1-methyl-1H-imidazole (199a) (586 mg, 3.51 mmol), $K_2CO_3$ (1.454 g, 10.52 mmol) and stirring at RT for 14 h. This gave after workup ethyl 5-bromo-7-((1-methyl-1H-imidazol-5-yl)methoxy)benzofuran-3-carboxylate (199b) (401 mg, 30% yield) as an off-white solid; $^1H$ NMR (300 MHz, DMSO-$d_6$) δ 8.78 (s, 1H), 7.72-7.64 (m, 2H), 7.47 (d, J=1.8 Hz, 1H), 7.08 (d, J=1.1 Hz, 1H), 5.38 (s, 2H), 4.35 (q, J=7.1 Hz, 2H), 3.67 (s, 3H), 1.34 (t, J=7.1 Hz, 3H); MS (ES+): 379.0 (M+1).

Step-2: Preparation of (5-bromo-7-((1-methyl-1H-imidazol-5-yl)methoxy)benzofuran-3-yl)methanol (199c)

Compound 199c was prepared according to the procedure reported in step-2 of scheme 69, from ethyl 5-bromo-7-((1-methyl-1H-imidazol-5-yl)methoxy)benzofuran-3-carboxylate (199b) (390 mg, 1.028 mmol) in DCM (1.713 mL) using 1.0 M solution of DIBAL in DCM (2.57 mL, 2.57 mmol) and stirring at 0° C. for 4 h. This gave after work up and purification using flash column chromatography [silica gel (12 g), eluting with EtOAc in hexane from 0-50%] (5-bromo-7-((1-methyl-1H-imidazol-5-yl)methoxy)benzofuran-3-yl)methanol (199c) (0.150 g, 43% yield); $^1H$ NMR (300 MHz, DMSO-$d_6$) δ 7.88 (s, 1H), 7.68 (s, 1H), 7.50 (d, J=1.7 Hz, 1H), 7.31 (d, J=1.8 Hz, 1H), 7.06 (d, J=1.1 Hz, 1H), 5.33 (s, 2H), 5.21 (t, J=5.6 Hz, 1H), 4.57 (dd, J=5.6, 1.1 Hz, 2H), 3.67 (s, 3H); MS (ES+): 337.0 (M+1).

Step-3: Preparation of ethyl 2-(2-((5-bromo-7-((1-methyl-1H-imidazol-5-yl)methoxy)benzofuran-3-yl)methoxy)phenyl)acetate (199d)

Compound 199d was prepared according to the procedure reported in step-2 of scheme 65, from (5-bromo-7-((1-methyl-1H-imidazol-5-yl)methoxy)benzofuran-3-yl)methanol (199c) (145 mg, 0.430 mmol) in DCM (3 mL) using triphenylphosphine (130 mg, 0.495 mmol), ethyl 2-(2-hydroxyphenyl)acetate (7c) (85 mg, 0.473 mmol) and DCAD (182 mg, 0.495 mmol) in DCM (3 mL) at 0° C. and stirring at RT for 1 h. This gave after workup and purification using flash column chromatography [silica gel (24 g), eluting with EtOAc/MeOH (ratio 9:1) in hexane from 0-100%] ethyl 2-(2-((5-bromo-7-((1-methyl-1H-imidazol-5-yl)methoxy)benzofuran-3-yl)methoxy)phenyl)acetate (199d)(100 mg, 47% yield) as a clear gel; $^1H$ NMR (300 MHz, DMSO-$d_6$) δ 8.10 (s, 1H), 7.69 (s, 1H), 7.45 (d, J=1.7 Hz, 1H), 7.36 (d, J=1.7 Hz, 1H), 7.33-7.25 (m, 1H), 7.24-7.14 (m, 2H), 7.07 (s, 1H), 6.95-6.89 (m, 1H), 5.35 (s, 2H), 5.21 (s, 2H), 3.95 (q, J=7.2 Hz, 2H), 3.67 (s, 3H), 3.55 (s, 2H), 1.00 (t, J=7.1 Hz, 3H); MS (ES+): 499.0 (M+1).

Step-4: Preparation of ethyl 2-(2-((5-(3-(aminomethyl)phenyl)-7-((1-methyl-1H-imidazol-5-yl)methoxy)benzofuran-3-yl)methoxy)phenyl)acetate (199e)

Compound 199e was prepared according to the procedure reported in step-2 of scheme 1, from ethyl 2-(2-((5-bromo-7-((1-methyl-1H-imidazol-5-yl)methoxy)benzofuran-3-yl)methoxy)phenyl)acetate (199d) (95 mg, 0.190 mmol) using (3-(aminomethyl)phenyl)boronic acid hydrochloride (1d) (44.6 mg, 0.238 mmol), 4 M solution of $K_3PO_4$ (0.190 mL, 0.761 mmol), tricyclohexylphosphine (10.67 mg, 0.038 mmol) and $Pd_2(dba)_3$ (17.42 mg, 0.019 mmol) and heating at 110° C. for 4 h. This gave after workup and purification using flash column chromatography [silica gel (24 g), eluting with DMA-80 in DCM from 0-50%] ethyl 2-(2-((5-(3-(aminomethyl)phenyl)-7-((1-methyl-1H-imidazol-5-yl)methoxy)benzofuran-3-yl)methoxy)phenyl)acetate (199e) (56 mg, 56% yield) as a clear oil; MS (ES+): 526.2 (M+1).

Step-5: Preparation of 2-(2-((5-(3-(aminomethyl)phenyl)-7-((1-methyl-1H-imidazol-5-yl)methoxy)benzofuran-3-yl)methoxy)phenyl)acetic acid (199f)

Compound 199f was prepared according to the procedure reported in step-3 of scheme 1, from ethyl 2-(2-((5-(3-(aminomethyl)phenyl)-7-((1-methyl-1H-imidazol-5-yl)methoxy)benzofuran-3-yl)methoxy)phenyl)acetate (199e) (54 mg, 0.103 mmol) in THF (0.6 mL) and acetonitrile (0.3 mL) using a 1N solution of lithium hydroxide monohydrate (0.308 mL, 0.308 mmol) and stirring for 25 h at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-((1-methyl-1H-imidazol-5-yl)methoxy)benzofuran-3-yl)methoxy)phenyl)acetic acid (199f) (31 mg, 61% yield) HCl salt as a white solid; $^1H$ NMR (300 MHz, DMSO-$d_6$) δ 9.14 (s, 1H), 8.62 (s, 3H, $D_2O$ exchangeable), 8.12 (s, 1H), 8.08 (s, 1H), 7.97 (d, J=1.5 Hz, 1H), 7.82-7.76 (m, 1H), 7.68 (d, J=1.4 Hz, 1H), 7.64 (d, J=1.5 Hz, 1H), 7.57-7.44 (m, 2H), 7.32-7.17 (m, 3H), 6.93 (td, J=7.3, 1.2 Hz, 1H), 5.66 (s, 2H), 5.31 (s, 2H), 4.18-4.05 (m, 2H), 3.97 (s, 3H), 3.54 (s, 2H); MS (ES+): 498.2 (M+1); (ES−): 496.2 (M−1); Analysis calculated for $C_{29}H_{27}N_3O_5 \cdot 3H_2O \cdot 2HCl$: C, 55.77; H, 5.65; Cl, 11.35; N, 6.73. Found: C, 55.62; H, 5.49; Cl, 11.25; N, 6.70.

Scheme 200

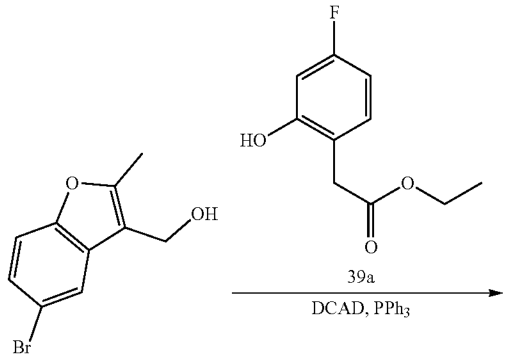

124c

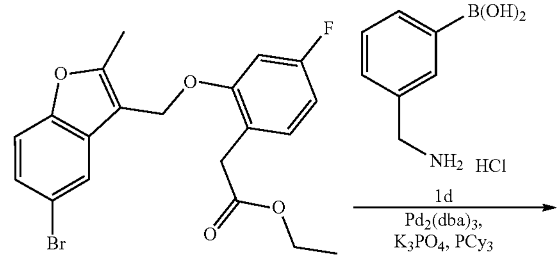

200a

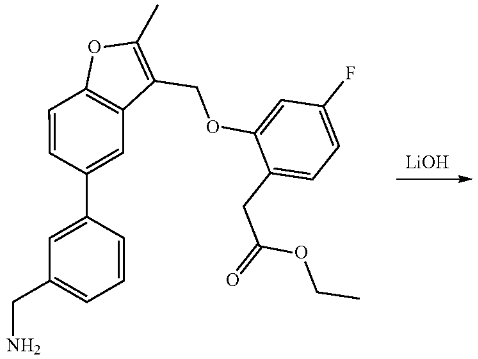

200b

-continued

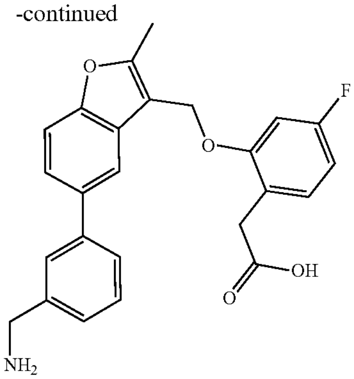

200c

Preparation of 2-(2-((5-(3-(aminomethyl)phenyl)-2-methylbenzofuran-3-yl)methoxy)-4-fluorophenyl) acetic acid (200c)

Step-1: Preparation of ethyl 2-(2-((5-bromo-2-methylbenzofuran-3-yl)methoxy)-4-fluorophenyl)acetate (200a)

Compound 200a was prepared according to the procedure reported in step-3 of scheme 7, from (5-bromo-2-methylbenzofuran-3-yl)methanol (124c) (350 mg, 1.452 mmol) in DCM (10 mL) using triphenylphosphine (419 mg, 1.597 mmol), ethyl 2-(4-fluoro-2-hydroxyphenyl)acetate (39d) (317 mg, 1.597 mmol), bis(4-chlorobenzyl) diazene-1,2-dicarboxylate (DCAD) (586 mg, 1.597 mmol) in DCM (5 mL) and stirring at RT for 30 min. This gave after workup and purification using flash column chromatography [silica gel (12 g), eluting with EtOAc in hexane from 0-50%] ethyl 2-(2-((5-bromo-2-methylbenzofuran-3-yl)methoxy)-4-fluorophenyl)acetate (200a) (380 mg, 62% yield) as a clear oil; $^1H$ NMR (300 MHz, DMSO-$d_6$) δ 7.74 (d, J=2.0 Hz, 1H), 7.52 (d, J=8.7 Hz, 1H), 7.42 (dd, J=8.7, 2.1 Hz, 1H), 7.23 (dd, J=8.4, 6.9 Hz, 1H), 7.14 (dd, J=11.4, 2.5 Hz, 1H), 6.77 (td, J=8.5, 2.5 Hz, 1H), 5.20 (s, 2H), 3.91 (q, J=7.1 Hz, 2H), 3.50 (s, 2H), 2.51 (s, 3H), 0.94 (t, J=7.1 Hz, 3H); $^{19}F$ NMR (282 MHz, DMSO-$d_6$) δ −112.72; MS (ES+): 443.0 and 445.0 (M+Na).

Step-2: Preparation of ethyl 2-(2-((5-(3-(aminomethyl)phenyl)-2-methylbenzofuran-3-yl)methoxy)-4-fluorophenyl)acetate (200b)

Compound 200b was prepared according to the procedure reported in step-2 of scheme 1, from ethyl 2-(2-((5-bromo-2-methylbenzofuran-3-yl)methoxy)-4-fluorophenyl)acetate (200a) (380 mg, 0.902 mmol) in dioxane (20 mL) using 3-(aminomethyl)phenylboronic acid hydrochloride (1d) (338 mg, 1.804 mmol), 4 M solution of $K_3PO_4$ (0.902 mL, 3.61 mmol), tricyclohexylphosphine (101 mg, 0.361 mmol), $Pd_2(dba)_3$ (165 mg, 0.180 mmol) and heating at 110° C. for 5 h. This gave after workup and purification using flash column chromatography [silica gel (40 g), eluting with DMA-80 in DCM from 0-100%] ethyl 2-(2-((5-(3-(aminomethyl)phenyl)-2-methylbenzofuran-3-yl)methoxy)-4-fluorophenyl)acetate (200b) (291.3 mg, 72% yield) as a yellow oil, MS (ES+): 448.2 (M+1).

Step-3: Preparation of 2-(2-((5-(3-(aminomethyl)phenyl)-2-methylbenzofuran-3-yl)methoxy)-4-fluorophenyl)acetic acid (200c)

Compound 200c was prepared according to the procedure reported in step-3 of scheme 1, from ethyl 2-(2-((5-(3-(aminomethyl)phenyl)-2-methylbenzofuran-3-yl)methoxy)-4-fluorophenyl)acetate (200b) (291.3 mg, 0.651 mmol) in THF (3 mL) using a solution of lithium hydroxide hydrate (114 mg, 2.71 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-methylbenzofuran-3-yl)methoxy)-4-fluorophenyl)acetic acid (200c) (113 mg, 30% yield) HCl salt as a white solid; $^1$H NMR (300 MHz, DMSO-$d_6$) δ 12.18 (s, 1H, $D_2O$ exchangeable), 8.55 (s, 2H, $D_2O$ exchangeable), 7.95 (s, 1H), 7.90 (s, 1H), 7.77-7.68 (m, 1H), 7.66-7.56 (m, 2H), 7.53-7.40 (m, 2H), 7.25-7.12 (m, 2H), 6.75 (td, J=8.4, 2.5 Hz, 1H), 5.28 (s, 2H), 4.09 (s, 2H), 3.47 (s, 2H), 2.53 (s, 3H); $^{19}$F NMR (282 MHz, DMSO-$d_6$) δ −113.05; MS (ES+): 420.2 (M+1), (ES−): 418.1 (M−1); Analysis calculated for $C_{25}H_{22}FNO_4$·0.9HCl·1.5$H_2O$: C, 62.65; H, 5.45; Cl, 6.66; N, 2.92. Found: C, 62.84; H, 5.29; Cl, 6.73; N, 2.78.

Scheme 201

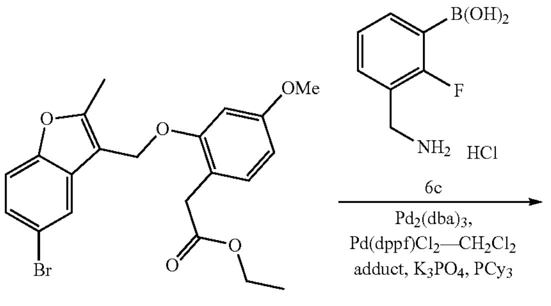

138a

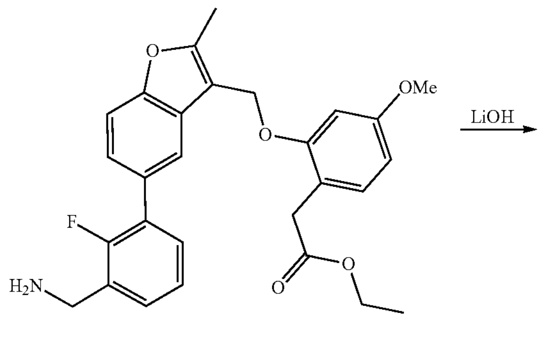

201a

-continued

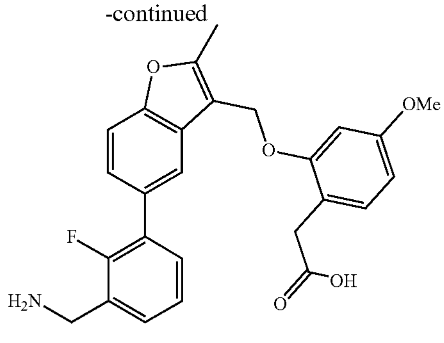

201b

Preparation of 2-(2-((5-(3-(aminomethyl)-2-fluorophenyl)-2-methylbenzofuran-3-yl)methoxy)-4-methoxyphenyl)acetic acid (201b)

Step-1: Preparation of ethyl 2-(2-((5-(3-(aminomethyl)-2-fluorophenyl)-2-methylbenzofuran-3-yl)methoxy)-4-methoxyphenyl)acetate (201a)

Compound 201a was prepared according to the procedure reported in step-2 of scheme 1, from ethyl 2-(2-((5-bromo-2-methylbenzofuran-3-yl)methoxy)-4-methoxyphenyl)acetate (138a) (460 mg, 1.062 mmol) in dioxane/2-Me THF (35 mL; 5:2, v/v) using 3-(aminomethyl)-2-fluorophenylboronic acid hydrochloride (6c) (436 mg, 2.123 mmol), 4 M solution of $K_3PO_4$ (1.062 mL, 4.25 mmol), tricyclohexylphosphine (89 mg, 0.318 mmol), $Pd_2(dba)_3$ (97 mg, 0.106 mmol), $PdCl_2$(dppf)-$CH_2Cl_2$ adduct (87 mg, 0.106 mmol) and heating at 100° C. for 12 h. This gave after workup and purification using flash column chromatography [silica gel (40 g), eluting with DMA-80 in DCM from 0-100%] ethyl 2-(2-((5-(3-(aminomethyl)-2-fluorophenyl)-2-methylbenzofuran-3-yl)methoxy)-4-methoxyphenyl)acetate (201a) (238 mg, 47% yield) as a yellow oil; MS (ES+): 477.7 (M+1).

Step-2: Preparation of 2-(2-((5-(3-(aminomethyl)-2-fluorophenyl)-2-methylbenzofuran-3-yl)methoxy)-4-methoxyphenyl)acetic acid (201b)

Compound 201b was prepared according to the procedure reported in step-3 of scheme 1, from ethyl 2-(2-((5-(3-(aminomethyl)-2-fluorophenyl)-2-methylbenzofuran-3-yl)methoxy)-4-methoxyphenyl)acetate (201a) (0.238 g, 0.498 mmol) in THF (3 mL) using a solution of lithium hydroxide hydrate (44.6 mg, 1.062 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)-2-fluorophenyl)-2-methylbenzofuran-3-yl)methoxy)-4-methoxyphenyl)acetic acid (201b) (118 mg, 25% yield) HCl salt as a white solid; $^1$H NMR (300 MHz, DMSO-$d_6$) δ 8.71 (s, 2H, $D_2O$ exchangeable), 7.79 (s, 1H), 7.68-7.54 (m, 3H), 7.44 (dt, J=8.5, 1.8 Hz, 1H), 7.35 (t, J=7.6 Hz, 1H), 7.07 (d, J=8.3 Hz, 1H), 6.81 (d, J=2.4 Hz, 1H), 6.49 (dd, J=8.3, 2.4 Hz, 1H), 5.24 (s, 2H), 4.12 (s, 2H), 3.75 (s, 3H), 3.40 (s, 2H), 2.53 (s, 3H); $^{19}$F NMR (282 MHz, DMSO-$d_6$) δ −122.38; MS (ES+): 450.7 (M+1); (ES−): 448.8 (M−1); Analysis calculated for $C_{26}H_{24}FNO_5$·HCl·0.75$H_2O$: C, 62.53; H, 5.35; Cl, 7.10; N, 2.80. Found: C, 62.51; H, 5.36; Cl, 6.94; N, 2.84.

Scheme 202

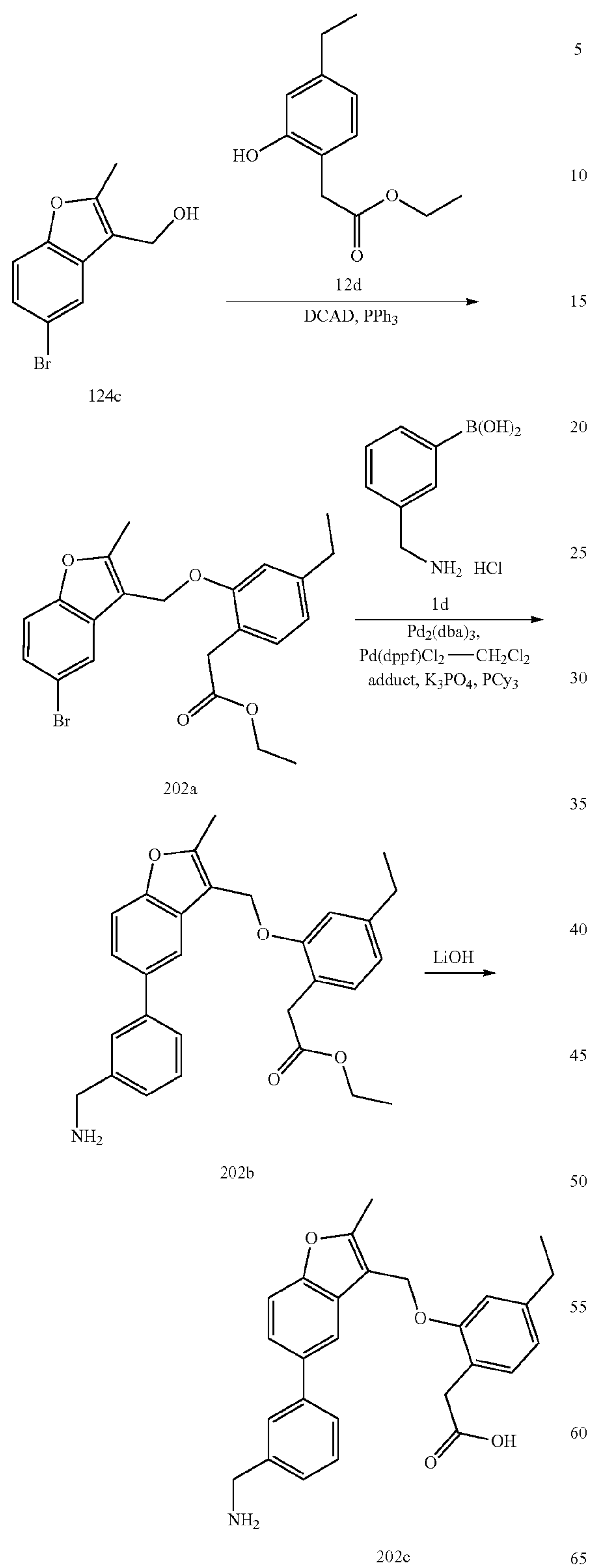

124c

202a

202b

202c

Preparation of 2-(2-((5-(3-(aminomethyl)phenyl)-2-methylbenzofuran-3-yl)methoxy)-4-ethylphenyl) acetic acid (202c)

Step-1: Preparation of ethyl 2-(2-((5-bromo-2-methylbenzofuran-3-yl)methoxy)-4-ethylphenyl)acetate (202a)

Compound 202a was prepared according to the procedure reported in step-3 of scheme 7, from (5-bromo-2-methylbenzofuran-3-yl)methanol (124c) (0.4 g, 1.659 mmol), triphenylphosphine (0.479 mg, 1.825 mmol), ethyl 2-(4-ethyl-2-hydroxyphenyl)acetate (12d) (380 mg, 1.825 mmol) in DCM (20 mL) using bis(4-chlorobenzyl) diazene-1,2-dicarboxylate (DCAD) (670 mg, 1.825 mmol) in DCM (10 mL). The reaction mixture was stirred at RT for 30 min. This gave after workup and purification using flash column chromatography [silica gel (40 g), eluting with EtOAc in hexane from 0-50%] ethyl 2-(2-((5-bromo-2-methylbenzofuran-3-yl)methoxy)-4-ethylphenyl)acetate (202a) (430 mg, 60% yield) as a clear oil; MS (ES+): 452.6 and 454.6 (M+Na).

Step-2: Preparation of ethyl 2-(2-((5-(3-(aminomethyl)phenyl)-2-methylbenzofuran-3-yl)methoxy)-4-ethylphenyl)acetate (202b)

Compound 202b was prepared according to the procedure reported in step-2 of scheme 1, from ethyl 2-(2-((5-bromo-2-methylbenzofuran-3-yl)methoxy)-4-ethylphenyl)acetate (202a) (400 mg, 0.927 mmol) in dioxane (20 mL) using 3-(aminomethyl)phenylboronic acid hydrochloride (1d) (348 mg, 1.855 mmol), 4 M solution of $K_3PO_4$ (0.927 mL, 3.71 mmol), tricyclohexylphosphine (78 mg, 0.278 mmol), $Pd_2(dba)_3$ (85 mg, 0.093 mmol), $PdCl_2(dppf)$-$CH_2Cl_2$ adduct (76 mg, 0.093 mmol) and heating at 100° C. for 12 h. This gave after workup and purification by flash column chromatography [silica gel (40 g), eluting with DMA-80 in DCM from 0-100%] ethyl 2-(2-((5-(3-(aminomethyl)phenyl)-2-methylbenzofuran-3-yl)methoxy)-4-ethylphenyl)acetate (202b) (245 mg, 58% yield) as a yellow oil, MS (ES+): 458.2 (M+1).

Step-3: Preparation of 2-(2-((5-(3-(aminomethyl) phenyl)-2-methylbenzofuran-3-yl)methoxy)-4-ethylphenyl)acetic acid (202c)

Compound 202c was prepared according to the procedure reported in step-3 of scheme 1, from ethyl 2-(2-((5-(3-(aminomethyl)phenyl)-2-methylbenzofuran-3-yl)methoxy)-4-ethylphenyl)acetate (202b) (245 mg, 0.535 mmol) in THF (3 mL) using a solution of lithium hydroxide hydrate (117 mg, 2.78 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)-2-methylbenzofuran-3-yl) methoxy)-4-ethylphenyl)acetic acid (202c) (160 mg, 40% yield) HCl salt as a white solid; $^1H$ NMR (300 MHz, DMSO-$d_6$) δ 12.11 (s, 1H, $D_2O$ exchangeable), 8.62 (s, 3H, $D_2O$ exchangeable), 7.96 (s, 1H), 7.92 (s, 1H), 7.78-7.66 (m, 1H), 7.61 (s, 2H), 7.53-7.44 (m, 2H), 7.12 (s, 1H), 7.07 (d, J=7.6 Hz, 1H), 6.75 (dd, J=7.6, 1.5 Hz, 1H), 5.26 (s, 2H), 4.09 (s, 2H), 3.45 (s, 2H), 2.60 (q, J=7.6 Hz, 2H), 2.52 (s, 3H), 1.19 (t, J=7.5 Hz, 3H); MS (ES+): 430.2 (M+1), (ES−): 428.2 (M−1); Analysis calculated for $C_{27}H_{27}NO_4 \cdot HCl \cdot 0.75H_2O$: C, 67.63; H, 6.20; Cl, 7.39; N, 2.92. Found: C, 67.74; H, 6.13; Cl, 7.06; N, 3.19.

Scheme 203

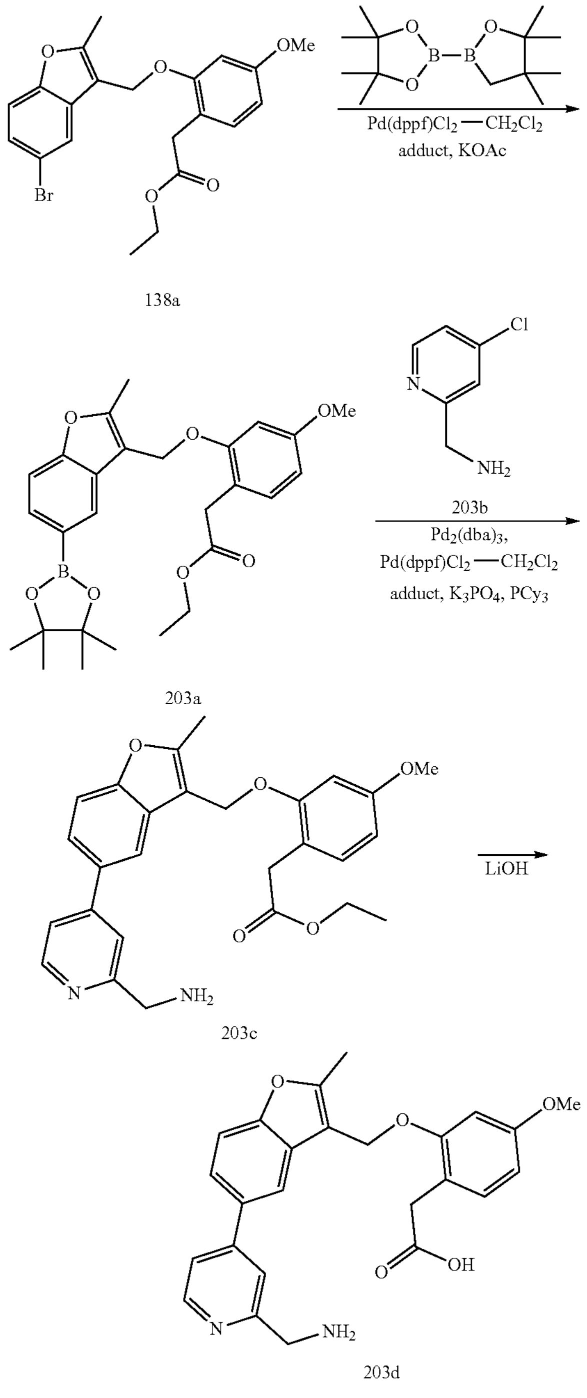

138a

203a

203c

203d

Preparation of 2-(2-((5-(2-(aminomethyl)pyridin-4-yl)-2-methylbenzofuran-3-yl)methoxy)-4-methoxyphenyl)acetic acid (203d)

Step-1: Preparation of ethyl 2-(4-methoxy-2-((2-methyl-5-(4,4,5,5-tetramethyl-1,3,2-dioxaborolan-2-yl)benzofuran-3-yl)methoxy)phenyl)acetate (203a)

Compound 203a was prepared according to the procedure reported in step-1 of scheme 27, from ethyl 2-(2-((5-bromo-2-methylbenzofuran-3-yl)methoxy)-4-methoxyphenyl)acetate (138a) (870 mg, 2.008) in anhydrous dioxane (50 mL) using BisPin (510 mg, 2.008 mmol), potassium acetate (0.690 g, 7.03 mmol), $PdCl_2$(dppf)-$CH_2Cl_2$ adduct (0.164 g, 0.201 mmol) and stirring at 90° C. for 6 h. This gave after work up and purification using flash column chromatography [silica gel (24 g), eluting with EtOAc in hexane from 0-40%] ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (750 mg, 78% yield) as a clear oil; $^1H$ NMR (300 MHz, DMSO-$d_6$) δ 7.94 (s, 1H), 7.58 (dd, J=8.2, 1.2 Hz, 1H), 7.50 (d, J=8.2 Hz, 1H), 7.11-7.05 (m, 1H), 6.83 (d, J=2.3 Hz, 1H), 6.50 (dd, J=8.3, 2.3 Hz, 1H), 5.20 (d, J=8.4 Hz, 2H), 3.85 (q, J=7.1 Hz, 2H), 3.78 (s, 3H), 3.42 (s, 2H), 2.50 (s, 3H), 1.30 (s, 12H), 0.90 (t, J=7.1 Hz, 3H); MS (ES+): 502.7 (M+Na).

Step-2: Preparation of ethyl 2-(2-((5-(2-(aminomethyl)pyridin-4-yl)-2-methylbenzofuran-3-yl)methoxy)-4-methoxyphenyl)acetate (203c)

Compound 203c was prepared according to the procedure reported in step-2 of scheme 1, from ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (300 mg, 0.625 mmol) in dioxane (20 mL) using (4-chloropyridin-2-yl)methanamine (203b) (178 mg, 1.249 mmol), 4 M solution of $K_3PO_4$ (0.625 mL, 2.498 mmol), tricyclohexylphosphine (52.5 mg, 0.187 mmol), $Pd_2(dba)_3$ (114 mg, 0.125 mmol), $PdCl_2$(dppf)-$CH_2Cl_2$ adduct (102 mg, 0.125 mmol) and heating at 110° C. overnight. This gave after workup and purification using flash column chromatography [silica gel (24 g), eluting with DMA-80 in DCM from 0-70%] ethyl 2-(2-((5-(2-(aminomethyl)pyridin-4-yl)-2-methylbenzofuran-3-yl)methoxy)-4-methoxyphenyl)acetate (203c) (47 mg, 16% yield) as a clear oil, MS (ES+): 461.3 (M+1).

Step-3: Preparation of 2-(2-((5-(2-(aminomethyl)pyridin-4-yl)-2-methylbenzofuran-3-yl)methoxy)-4-methoxyphenyl)acetic acid (203d)

Compound 203d was prepared according to the procedure reported in step-3 of scheme 1, from ethyl 2-(2-((5-(2-(aminomethyl)pyridin-4-yl)-2-methylbenzofuran-3-yl)methoxy)-4-methoxyphenyl)acetate (203c) (47 mg, 0.102 mmol) in THF (3 mL) using a solution of lithium hydroxide hydrate (105 mg, 2.498 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(2-(aminomethyl)pyridin-4-yl)-2-methylbenzofuran-3-yl)methoxy)-4-methoxyphenyl)acetic acid (203d) (5 mg, 2% yield) HCl salt as a yellow solid; $^1H$ NMR (300 MHz, DMSO-$d_6$) δ 8.68 (d, J=5.3 Hz, 1H), 8.43 (s, 3H, $D_2O$ exchangeable), 8.10 (d, J=1.7 Hz, 1H), 7.95 (s, 1H), 7.83 (dd, J=5.4, 1.7 Hz, 1H), 7.78-7.68 (m, 2H), 7.09 (d, J=8.3 Hz, 1H), 6.84 (d, J=2.4 Hz, 1H), 6.51 (dd, J=8.3, 2.4 Hz, 1H), 5.28 (s, 2H), 4.27 (s, 2H), 3.77 (s, 3H), 3.41 (s, 2H), 2.55 (s, 3H); MS (ES+) 433.2 (M+1).

Scheme 204

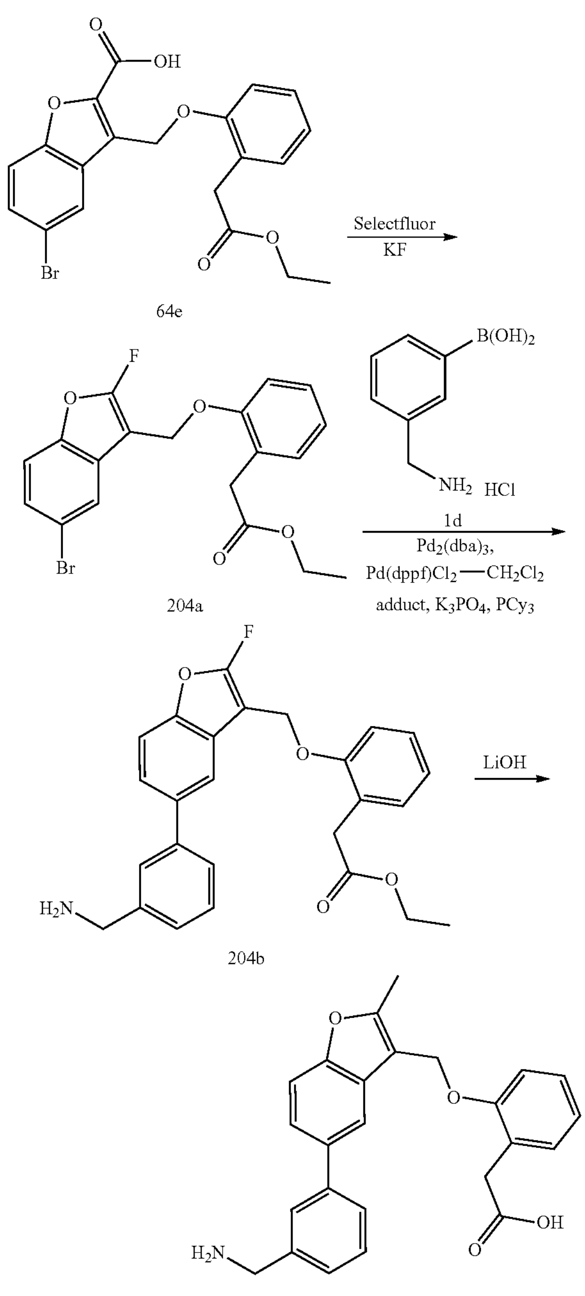

64e

204a

204b

204c

Preparation of 2-(2-((5-(3-(aminomethyl)phenyl)-2-fluorobenzofuran-3-yl)methoxy)phenyl)acetic acid (204c)

Step-1: Preparation of ethyl 2-(2-((5-bromo-2-fluorobenzofuran-3-yl)methoxy)phenyl)acetate (204a)

Compound 204a was prepared according to the procedure reported in step-3 of scheme 7, from 5-bromo-3-((2-(2-ethoxy-2-oxoethyl)phenoxy)methyl)benzofuran-2-carboxylic acid (64e) (2 g, 4.62 mmol) in DCE (20 mL) and $H_2O$ (10 mL) using Selectfluor (3.27 g, 9.23 mmol), potassium fluoride (1.073 g, 18.47 mmol) and heating at 70° C. for 15 h. This gave after workup and purification using flash column chromatography [silica gel, eluting with EtOAc in hexane from 0-100%] ethyl 2-(2-((5-bromo-2-fluorobenzofuran-3-yl)methoxy)phenyl)acetate (204a) (334 mg, 18% yield) as a clear oil; $^1H$ NMR (300 MHz, DMSO-$d_6$) δ 7.84 (d, J=2.0 Hz, 1H), 7.61 (d, J=8.7 Hz, 1H), 7.53 (dd, J=8.8, 2.1 Hz, 1H), 7.35-7.25 (m, 1H), 7.20 (td, J=8.1, 1.4 Hz, 2H), 6.95 (td, J=7.4, 1.2 Hz, 1H), 5.22-5.13 (m, 2H), 3.92 (q, J=7.1 Hz, 2H), 3.56 (s, 2H), 0.98 (t, J=7.1 Hz, 3H); $^{19}F$ NMR (282 MHz, DMSO-$d_6$) δ −112.30.

Step-2: Preparation of ethyl 2-(2-((5-(3-(aminomethyl)phenyl)-2-fluorobenzofuran-3-yl)methoxy)phenyl)acetate (204b)

Compound 204b was prepared according to the procedure reported in step-2 of scheme 1, from ethyl 2-(2-((5-bromo-2-fluorobenzofuran-3-yl)methoxy)phenyl)acetate (204a) (334 mg, 0.820 mmol) in dioxane (20 mL) using 3-(aminomethyl)phenylboronic acid hydrochloride (1d) (307 mg, 1.640 mmol), 4 M solution of $K_3PO_4$ (0.82 mL, 3.28 mmol), tricyclohexylphosphine (69.0 mg, 0.246 mmol), $Pd_2(dba)_3$ (75 mg, 0.082 mmol), $PdCl_2(dppf)$-$CH_2Cl_2$ adduct (67.0 mg, 0.082 mmol) and heating at 100° C. for 2 h. This gave after workup and purification using flash column chromatography [silica gel (40 g), eluting with DMA-80 in DCM from 0-70%] ethyl 2-(2-((5-(3-(aminomethyl)phenyl)-2-fluorobenzofuran-3-yl)methoxy)phenyl)acetate (204b) (90 mg, 25% yield) as a yellow oil; MS (ES+): 434.2 (M+1).

Step-3: Preparation of 2-(2-((5-(3-(aminomethyl)phenyl)-2-fluorobenzofuran-3-yl)methoxy)phenyl)acetic acid (204c)

Compound 204c was prepared according to the procedure reported in step-3 of scheme 1, from ethyl 2-(2-((5-(3-(aminomethyl)phenyl)-2-fluorobenzofuran-3-yl)methoxy)phenyl)acetate (204b) (90 mg, 0.208 mmol) in THF (3 mL) using a solution of lithium hydroxide hydrate (103 mg, 2.461 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-fluorobenzofuran-3-yl)methoxy)phenyl)acetic acid (204c) (18.5 mg, 6% yield) HCl salt as a white solid; $^1H$ NMR (300 MHz, DMSO-$d_6$) δ $^1H$ NMR (300 MHz, DMSO-$d_6$) δ 12.12 (s, 1H, $D_2O$ exchangeable), 8.36 (s, 3H, $D_2O$ exchangeable), 7.98 (d, J=1.8 Hz, 1H), 7.87 (t, J=1.8 Hz, 1H), 7.78-7.71 (m, 2H), 7.67 (dd, J=8.7, 1.8 Hz, 1H), 7.53 (t, J=7.6 Hz, 1H), 7.47 (dt, J=7.7, 1.5 Hz, 1H), 7.34-7.25 (m, 1H), 7.25-7.16 (m, 2H), 6.95 (td, J=7.3, 1.3 Hz, 1H), 5.26 (s, 2H), 4.12 (s, 2H), 3.51 (s, 2H); $^{19}F$ NMR (282 MHz, DMSO-$d_6$) δ −113.16; MS (ES+): 406.2 (M+1); (ES−) 404.1 (M−1).

Scheme 205

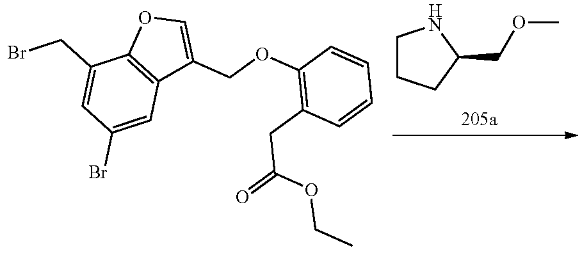

157b

-continued

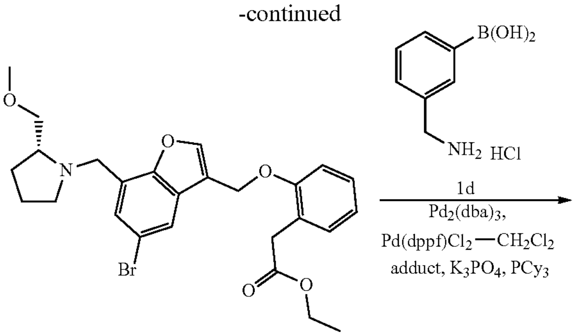

205b

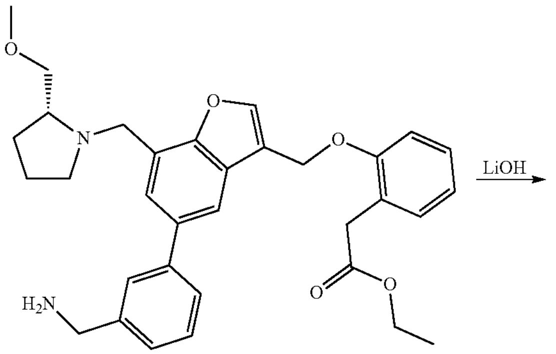

205c

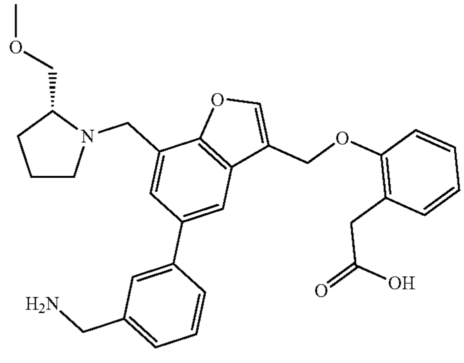

205d

Preparation of (R)-2-(2-((5-(3-(aminomethyl)phenyl)-7-((2-(methoxymethyl)pyrrolidin-1-yl)methyl) benzofuran-3-yl)methoxy)phenyl)acetic acid (205d)

Step-1: Preparation of (R)-ethyl 2-(2-((5-bromo-7-((2-(methoxymethyl)pyrrolidin-1-yl)methyl)benzofuran-3-yl)methoxy)phenyl)acetate (205b)

Compound 205b was prepared according to the procedure reported in step-2 of scheme 1, from ethyl 2-(2-((5-bromo-7-(bromomethyl)benzofuran-3-yl)methoxy)phenyl)acetate (157b) (270 mg, 0.56 mmol) in DMF (5 mL) using (R)-2-(methoxymethyl)pyrrolidine (205a) (0.193 g, 1.68 mmol; CAS #84025-81-0) and stirring at RT for 15 h. This gave after work up and purification using flash column chromatography [silica gel (24 g), eluting with DMA-80 in DCM from 0-50%](R)-ethyl 2-(2-((5-bromo-7-((2-(methoxymethyl)pyrrolidin-1-yl)methyl)benzofuran-3-yl)methoxy)phenyl)acetate (205b) (0.240 g, 83% yield) as a white oil; MS (ES+): 516.10 & 518.10 (M+1); MS (ES−): 514.10 & 516.10 (M−1).

Step-2: Preparation of (R)-ethyl 2-(2-((5-(3-(aminomethyl)phenyl)-7-((2-(methoxymethyl)pyrrolidin-1-yl)methyl)benzofuran-3-yl)methoxy)phenyl)acetate (205c)

Compound 205c was prepared according to the procedure reported in step-2 of scheme 1, from (R)-ethyl 2-(2-((5-bromo-7-((2-(methoxymethyl)pyrrolidin-1-yl)methyl)benzofuran-3-yl)methoxy)phenyl)acetate (205b) (240 mg, 0.465 mmol) using (3-(aminomethyl)phenyl)boronic acid hydrochloride (1d) (174 mg, 0.929 mmol), 2 M solution of $K_3PO_4$ (0.929 mL, 1.859 mmol), tricyclohexylphosphine (26.1 mg, 0.093 mmol), $Pd_2(dba)_3$ (42.6 mg, 0.046 mmol), $PdCl_2(dppf)$-$CH_2Cl_2$ adduct (38.0 mg, 0.046 mmol) and heating at 100° C. for 2 h. This gave after workup and purification using flash column chromatography [silica gel (24 g), eluting with DMA-80 in DCM from 0-70%](R)-ethyl 2-(2-((5-(3-(aminomethyl)phenyl)-7-((2-(methoxymethyl)pyrrolidin-1-yl)methyl)benzofuran-3-yl)methoxy)phenyl)acetate (205c) (190 mg, 75% yield) as a clear oil; MS (ES+): 543.30 (M+1); 565.30 (M+Na); MS (ES−): 541.20 (M−1).

Step-3: Preparation of (R)-2-(2-((5-(3-(aminomethyl)phenyl)-7-((2-(methoxymethyl)pyrrolidin-1-yl)methyl)benzofuran-3-yl)methoxy)phenyl)acetic acid (205d)

Compound 205d was prepared according to the procedure reported in step-3 of scheme 1, from (R)-ethyl 2-(2-((5-(3-(aminomethyl)phenyl)-7-((2-(methoxymethyl)pyrrolidin-1-yl)methyl)benzofuran-3-yl)methoxy)phenyl)acetate (205c) (190 mg, 0.350 mmol) in THF/MeOH (2 mL each) using lithium hydroxide hydrate (44.1 mg, 1.05 mmol) in water (1 mL) and heating at 50° C. for 1 h. This gave after workup and purification using reverse phase column chromatography [C18 column (50 g), eluting with ACN in water (containing 0.1% HCl) from 0-100%](R)-2-(2-((5-(3-(aminomethyl)phenyl)-7-((2-(methoxymethyl)pyrrolidin-1-yl)methyl)benzofuran-3-yl)methoxy)phenyl)acetic acid (205d) (70 mg, 39% yield) HCl salt as a white solid; $^1H$ NMR (300 MHz, DMSO-$d_6$) δ 11.23 (s, 1H, $D_2O$ exchangeable), 8.77 (s, 3H, $D_2O$ exchangeable), 8.24 (s, 1H), 8.20-8.11 (m, 2H), 8.09 (s, 1H), 7.91-7.79 (m, 1H), 7.57-7.47 (m, 2H), 7.32-7.17 (m, 3H), 6.93 (td, J=7.2, 1.5 Hz, 1H), 5.35 (s, 2H), 4.90 (dd, J=13.7, 3.2 Hz, 1H), 4.65 (dd, J=13.6, 7.3 Hz, 1H), 4.10 (q, J=5.9 Hz, 2H), 3.99-3.85 (m, 2H), 3.74-3.63 (m, 1H), 3.57 (s, 2H), 3.42-3.34 (m, 1H), 3.32 (s, 3H), 3.28-3.13 (m, 1H), 2.28-2.11 (m, 1H), 2.08-1.79 (m, 2H), 1.79-1.60 (m, 1H); MS (ES+): 515.30 (M+1); MS (ES−): 513.20 (M−1); Analysis calculated for $C_{31}H_{34}N_2O_5 \cdot 2.25HCl \cdot H_2O$: C, 60.58; H, 6.27; Cl, 12.98; N, 4.56. Found: C, 60.45; H, 6.19; Cl, 12.92; N, 4.52; Optical rotation: $[\alpha]_D$=(−) 4.898 [$CH_3OH$, 0.245].

Scheme 206

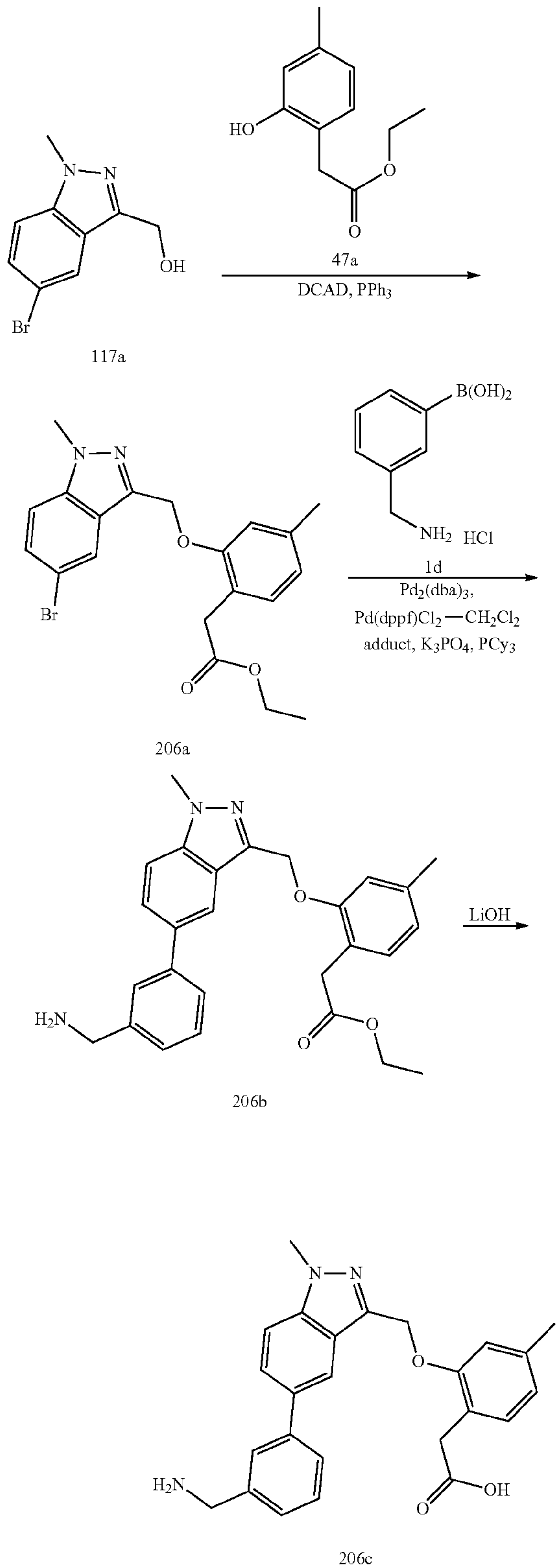

117a, 47a, 206a, 1d, 206b, 206c

Preparation of 2-(2-((5-(3-(aminomethyl)phenyl)-1-methyl-1H-indazol-3-yl)methoxy)-4-methylphenyl)acetic acid (206c)

Step-1: Preparation of ethyl 2-(2-((5-bromo-1-methyl-1H-indazol-3-yl)methoxy)-4-methylphenyl)acetate (206a)

Compound 206a was prepared according to the procedure reported in step-3 of scheme 7, from (5-bromo-1-methyl-1H-indazol-3-yl)methanol (117a) (730 mg, 3.03 mmol), triphenylphosphine (953 mg, 3.63 mmol), ethyl 2-(2-hydroxy-4-methylphenyl)acetate (47a) (618 mg, 3.18 mmol) in DCM (20 mL) using bis(4-chlorobenzyl) diazene-1,2-dicarboxylate (DCAD) (1.334 g, 3.63 mmol) in DCM (10 mL) and stirring at RT for 60 min. This gave after workup and purification using flash column chromatography [silica gel (24 g), eluting with EtOAc in hexane from 0-80%] ethyl 2-(2-((5-bromo-1-methyl-1H-indazol-3-yl)methoxy)-4-methylphenyl)acetate (206a) (660 mg, 52% yield) as a light yellow solid; $^1$H NMR (300 MHz, DMSO-$d_6$) δ 7.95 (dd, J=1.9, 0.7 Hz, 1H), 7.66 (dd, J=8.9, 0.7 Hz, 1H), 7.54 (dd, J=8.9, 1.8 Hz, 1H), 7.11-7.02 (m, 2H), 6.73 (d, J=7.5 Hz, 1H), 5.33 (s, 2H), 4.05 (s, 3H), 3.90 (q, J=7.2 Hz, 2H), 3.46 (s, 2H), 2.31 (s, 3H), 0.94 (t, J=7.1 Hz, 3H); MS (ES+): 417.05 & 419.10 (M+1); 439.00 & 441.10 (M+Na); MS (ES−): 415.00 & 417.10 (M−1).

Step-2: Preparation of ethyl 2-(2-((5-(3-(aminomethyl)phenyl)-1-methyl-1H-indazol-3-yl)methoxy)-4-methylphenyl)acetate (206b)

Compound 206b was prepared according to the procedure reported in step-2 of scheme 1, from ethyl 2-(2-((5-bromo-1-methyl-1H-indazol-3-yl)methoxy)-4-methylphenyl)acetate (206a) (330 mg, 0.791 mmol) in dioxane/THF (4 mL, ratio 1:1) using 3-(aminomethyl)phenylboronic acid hydrochloride (1d) (296 mg, 1.582 mmol), 2M solution of $K_3PO_4$ (1.582 mL, 3.16 mmol), tricyclohexylphosphine (44.4 mg, 0.158 mmol), $PdCl_2$(dppf)-$CH_2Cl_2$ adduct (64.6 mg, 0.079 mmol), $Pd_2(dba)_3$ (72.4 mg, 0.079 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-methyl-1H-indazol-3-yl)methoxy)-4-methylphenyl)acetate (206b) (250 mg, 71% yield); $^1$H NMR (300 MHz, DMSO-$d_6$) δ 7.98 (s, 1H), 7.75 (s, 1H), 7.68 (s, 1H), 7.57-7.51 (m, 2H), 7.38 (t, J=7.5 Hz, 1H), 7.29 (d, J=7.6 Hz, 1H), 7.12 (s, 1H), 7.05 (d, J=7.5 Hz, 1H), 6.73 (d, J=7.5 Hz, 1H), 5.38 (s, 2H), 4.08 (d, J=1.3 Hz, 3H), 3.78 (s, 2H), 3.72-3.61 (m, 2H), 3.45 (s, 2H), 2.32 (s, 3H), 0.78 (td, J=7.1, 1.3 Hz, 3H); MS (ES+): 444.20 (M+1); MS (ES−): 442.10 (M−1).

Step-3: Preparation of 2-(2-((5-(3-(aminomethyl)phenyl)-1-methyl-1H-indazol-3-yl)methoxy)-4-methylphenyl)acetic acid (206c)

Compound 206c was prepared according to the procedure reported in step-3 of scheme 1, from ethyl 2-(2-((5-(3-(aminomethyl)phenyl)-1-methyl-1H-indazol-3-yl)methoxy)-4-methylphenyl)acetate (206b) (250 mg, 0.564 mmol) in THF/MeOH (2 mL each) using a solution of lithium hydroxide hydrate (71 mg, 1.691 mmol) in water (1 mL) and heating at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-1-methyl-1H-indazol-3-yl)methoxy)-4-methylphenyl)acetic acid (206c) (145 mg, 62% yield) HCl salt as a white solid; $^1$H NMR (300 MHz, DMSO-$d_6$) δ 12.03 (s, 1H, $D_2O$ exchangeable), 8.40 (s, 3H, $D_2O$ exchangeable), 8.09 (s, 1H), 7.89 (t, J=1.8 Hz, 1H), 7.84-7.71 (m, 3H), 7.51 (t, J=7.6 Hz, 1H), 7.47-7.40 (m, 1H), 7.12 (s, 1H), 7.06 (d, J=7.5 Hz, 1H), 6.74 (d, J=7.5 Hz, 1H), 5.41 (s, 2H), 4.16-4.04 (m, 5H), 3.45 (s, 2H), 2.31 (s, 3H); MS (ES+): 416.20 (M+1); MS (ES−): 414.20 (M−1); Analysis calculated for $C_{25}H_{25}N_3O_3 \cdot 1.1HCl \cdot H_2O$: C, 63.40; H, 5.98; Cl, 8.23; N, 8.87. Found: C, 63.73; H, 5.83; Cl, 8.28; N, 8.86.

Scheme 207

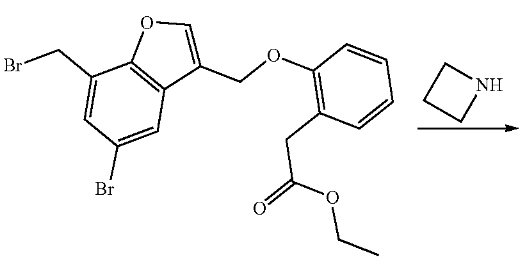

157b

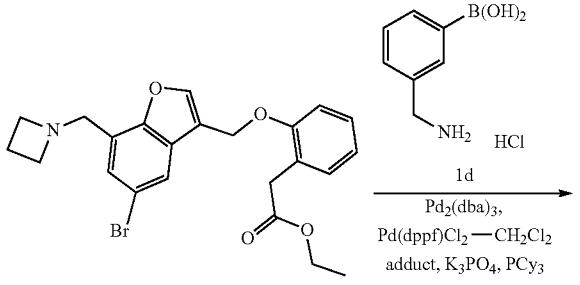

207b

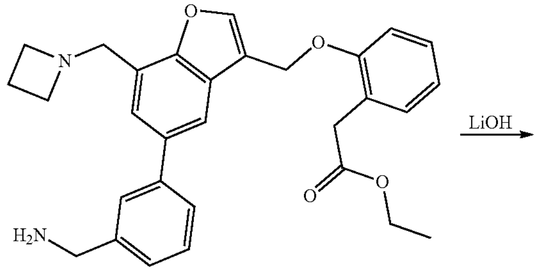

207c

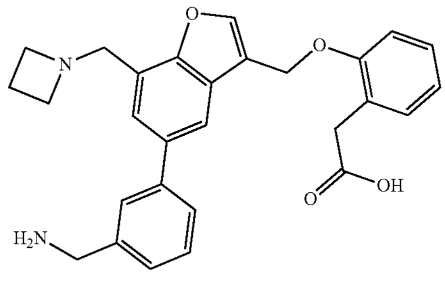

207d

Preparation of 2-(2-((5-(3-(aminomethyl)phenyl)-7-(azetidin-1-ylmethyl)benzofuran-3-yl)methoxy)phenyl)acetic acid (207d)

Step-1: Preparation of ethyl 2-(2-((7-(azetidin-1-ylmethyl)-5-bromobenzofuran-3-yl)methoxy)phenyl)acetate (207b)

Compound 207b was prepared according to the procedure reported in step-2 of scheme 1, from ethyl 2-(2-((5-bromo-7-(bromomethyl)benzofuran-3-yl)methoxy)phenyl)acetate (157b) (300 mg, 0.622 mmol) in DMF (4 mL) using azetidine (207a) (0.107 g, 1.867 mmol) and stirring at RT for 15 h. This gave after work up and purification using flash column chromatography [silica gel (24 g), eluting with DMA-80 in DCM from 0-50%] ethyl 2-(2-((7-(azetidin-1-ylmethyl)-5-bromobenzofuran-3-yl)methoxy)phenyl)acetate (207b) (0.210 g, 74% yield) as a white oil; $^1$H NMR (300 MHz, DMSO-$d_6$) δ 8.14 (s, 1H), 7.71 (d, J=2.0 Hz, 1H), 7.40 (d, J=2.0 Hz, 1H), 7.28 (td, J=7.8, 1.8 Hz, 1H), 7.24-7.15 (m, 2H), 6.92 (td, J=7.3, 1.2 Hz, 1H), 5.22 (s, 2H), 3.93 (q, J=7.1 Hz, 2H), 3.78 (s, 2H), 3.55 (s, 2H), 3.18 (t, J=7.0 Hz, 4H), 1.98 (p, J=6.9 Hz, 2H), 0.97 (t, J=7.1 Hz, 3H); MS (ES+): 458.10 & 460.10 (M+1).

Step-2: Preparation of ethyl 2-(2-((5-(3-(aminomethyl)phenyl)-7-(azetidin-1-ylmethyl)benzofuran-3-yl)methoxy)phenyl)acetate (207c)

Compound 207c was prepared according to the procedure reported in step-2 of scheme 1, from ethyl 2-(2-((7-(azetidin-1-ylmethyl)-5-bromobenzofuran-3-yl)methoxy)phenyl)acetate (207b) (210 mg, 0.458 mmol) in dioxane/THF (4 mL, ratio 1:1), 2 M solution of $K_3PO_4$ (0.916 mL, 1.833 mmol), tricyclohexylphosphine (25.7 mg, 0.092 mmol), $Pd_2(dba)_3$ (42.0 mg, 0.046 mmol), $PdCl_2(dppf)$-$CH_2Cl_2$ adduct (37.4 mg, 0.046 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-7-(azetidin-1-ylmethyl)benzofuran-3-yl)methoxy)phenyl)acetate (207c) (140 mg, 63% yield) as a clear oil; MS (ES+): 485.30 (M+1); 507.20 (M+Na).

Step-3: Preparation of 2-(2-((5-(3-(aminomethyl)phenyl)-7-(azetidin-1-ylmethyl)benzofuran-3-yl)methoxy)phenyl)acetic acid (207d)

Compound 207d was prepared according to the procedure reported in step-3 of scheme 1, from ethyl 2-(2-((5-(3-(aminomethyl)phenyl)-7-(azetidin-1-ylmethyl)benzofuran-3-yl)methoxy)phenyl)acetate (207c) (140 mg, 0.289 mmol) in THF/MeOH (2 mL each) using lithium hydroxide hydrate (36.4 mg, 0.867 mmol) in water (1 mL) and heating at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-7-(azetidin-1-ylmethyl)benzofuran-3-yl)methoxy)phenyl)acetic acid (207d) (105 mg, 80% yield) HCl salt as a white solid; $^1$H NMR (300 MHz, DMSO-$d_6$) δ 11.68 (s, 1H, $D_2O$ exchangeable), 8.54 (s, 2H, $D_2O$ exchangeable), 8.24 (s, 1H), 8.09 (d, J=1.7 Hz, 1H), 8.03-7.92 (m, 2H), 7.81 (dt, J=7.3, 1.9 Hz, 1H), 7.59-7.45 (m, 2H), 7.28 (td, J=7.6, 7.1, 1.7 Hz, 1H), 7.22 (dd, J=7.2, 1.6 Hz, 2H), 6.99-6.86 (m, 1H), 5.34 (s, 2H), 4.71 (s, 2H), 4.21-3.97 (m, 6H), 3.55 (s, 2H), 2.44-2.24 (m, 2H); MS (ES+): 457.20 (M+1); MS (ES−): 455.20 (M−1);

Analysis calculated for $C_{28}H_{28}N_2O_4 \cdot 2HCl \cdot 2.5H_2O$: C, 58.54; H, 6.14; Cl, 12.34; N, 4.88. Found: C, 58.71; H, 5.80; Cl, 12.28; N, 4.86.

Scheme 208

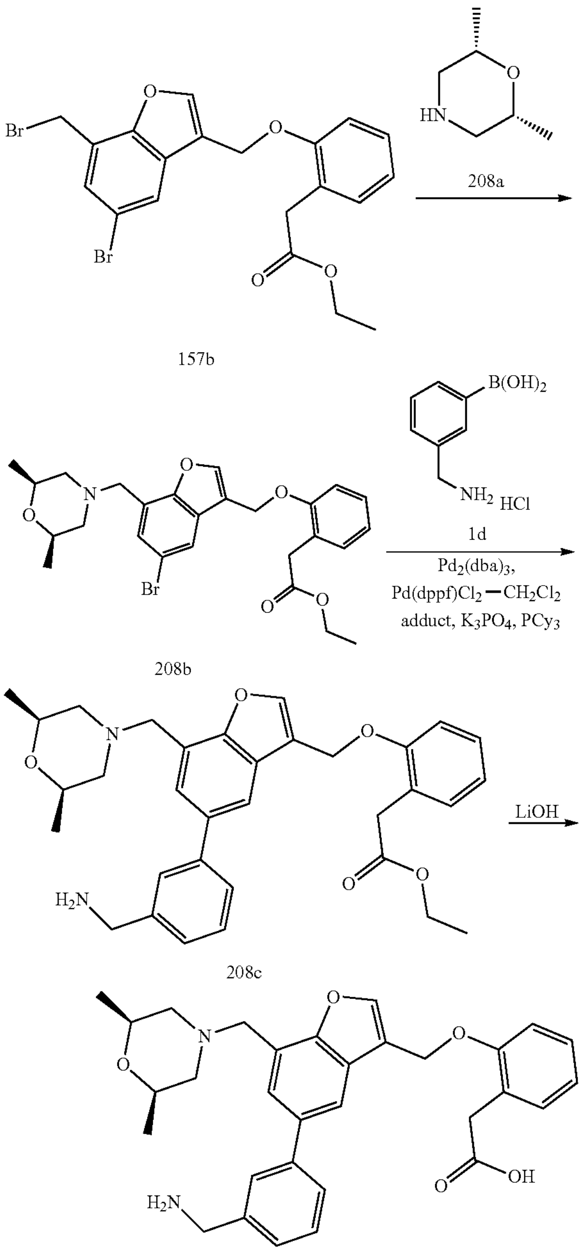

157b

208b

208c

208d

Preparation of 2-(2-((-(3-(aminomethyl)phenyl)-7-((2R,6S)-2,6-dimethylmorpholino)methyl)benzofuran-3-yl)methoxy)phenyl)acetic acid (208d)

Step-1: Preparation of ethyl 2-(2-((5-bromo-7-(((2R,6S)-2,6-dimethylmorpholino)methyl)benzofuran-3-yl)methoxy)phenyl)acetate (208b)

Compound 208b was prepared according to the procedure reported in step-2 of scheme 1, from ethyl 2-(2-((5-bromo-7-(bromomethyl)benzofuran-3-yl)methoxy)phenyl)acetate (157b) (300 mg, 0.622 mmol) in DMF (4 mL) using (2R, 6S)-2,6-dimethylmorpholine (208a)(0.215 g, 1.867 mmol; CAS #6485-55-8) and stirring at RT for 15 h. This gave after work up and purification using flash column chromatography [silica gel (24 g), eluting with DMA-80 in DCM from 0-50%] ethyl 2-(2-((5-bromo-7-(((2R,6S)-2,6-dimethylmorpholino)methyl)benzofuran-3-yl)methoxy)phenyl)acetate (208b) (0.25 g, 78% yield) as a white oil; MS (ES+): 516.10 & 518.10 (M+1); MS (ES−): 514.10 & 516.10 (M−1).

Step-2: Preparation of ethyl 2-(2-((5-(3-(aminomethyl)phenyl)-7-(((2R,6S)-2,6-dimethylmorpholino)methyl)benzofuran-3-yl)methoxy)phenyl)acetate (208c)

Compound 208c was prepared according to the procedure reported in step-2 of scheme 1, from ethyl 2-(2-((5-bromo-7-(((2R,6S)-2,6-dimethylmorpholino)methyl)benzofuran-3-yl)methoxy)phenyl)acetate (208b) (250 mg, 0.484 mmol), 2 M solution of $K_3PO_4$ (0.968 mL, 1.936 mmol), tricyclohexylphosphine (27.2 mg, 0.097 mmol), $Pd_2(dba)_3$ (44.3 mg, 0.048 mmol), $PdCl_2(dppf)$-$CH_2Cl_2$ adduct (39.5 mg, 0.048 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-7-(((2R,6S)-2,6-dimethylmorpholino)methyl)benzofuran-3-yl)methoxy)phenyl)acetate (208c) (140 mg, 53% yield) as a clear oil; MS (ES+): 543.30 (M+1).

Step-3: Preparation of 2-(2-((5-(3-(aminomethyl)phenyl)-7-(((2R,6S)-2,6-dimethylmorpholino)methyl)benzofuran-3-yl)methoxy)phenyl)acetic acid (208d)

Compound 208d was prepared according to the procedure reported in step-3 of scheme 1, from ethyl 2-(2-((5-(3-(aminomethyl)phenyl)-7-(((2R,6S)-2,6-dimethylmorpholino)methyl)benzofuran-3-yl)methoxy)phenyl)acetate (208c) (140 mg, 0.258 mmol) in THF/MeOH (2 mL each) using lithium hydroxide hydrate (32.5 mg, 0.774 mmol) in water (1 mL) and heating at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-7-(((2R,6S)-2,6-dimethylmorpholino)methyl)benzofuran-3-yl)methoxy)phenyl)acetic acid (208d) (70 mg, 53% yield) HCl salt as a white solid; $^1H$ NMR (300 MHz, DMSO-$d_6$) δ 12.20 (s, 1H, $D_2O$ exchangeable), 11.94 (s, 1H, $D_2O$ exchangeable), 8.55 (s, 3H, $D_2O$ exchangeable), 8.24 (s, 2H), 8.13 (s, 1H), 8.02 (s, 1H), 7.89-7.81 (m, 1H), 7.59-7.46 (m, 2H), 7.29 (td, J=7.6, 7.0, 1.7 Hz, 1H), 7.22 (d, J=7.9, 1.5 Hz, 2H), 6.94 (td, J=7.2, 1.3 Hz, 1H), 5.35 (s, 2H), 4.65 (s, 2H), 4.17-3.91 (m, 4H), 3.56 (s, 2H), 3.37-3.27 (m, 2H), 2.95-2.68 (m, 2H), 1.11 (d, J=6.2 Hz, 6H); MS (ES+): 515.20 (M+1); (ES−): 513.20 (M−1); Analysis calculated for $C_{31}H_{34}N_2O_5 \cdot 1.9HCl \cdot 3H_2O$: C, 58.37; H, 6.62; Cl, 10.56; N, 4.39. Found: C, 58.33; H, 6.44; Cl, 10.91; N, 4.36; Optical rotation: $[\alpha]_D$=(+) 1.951 [$CH_3OH$, 0.205].

Scheme 209

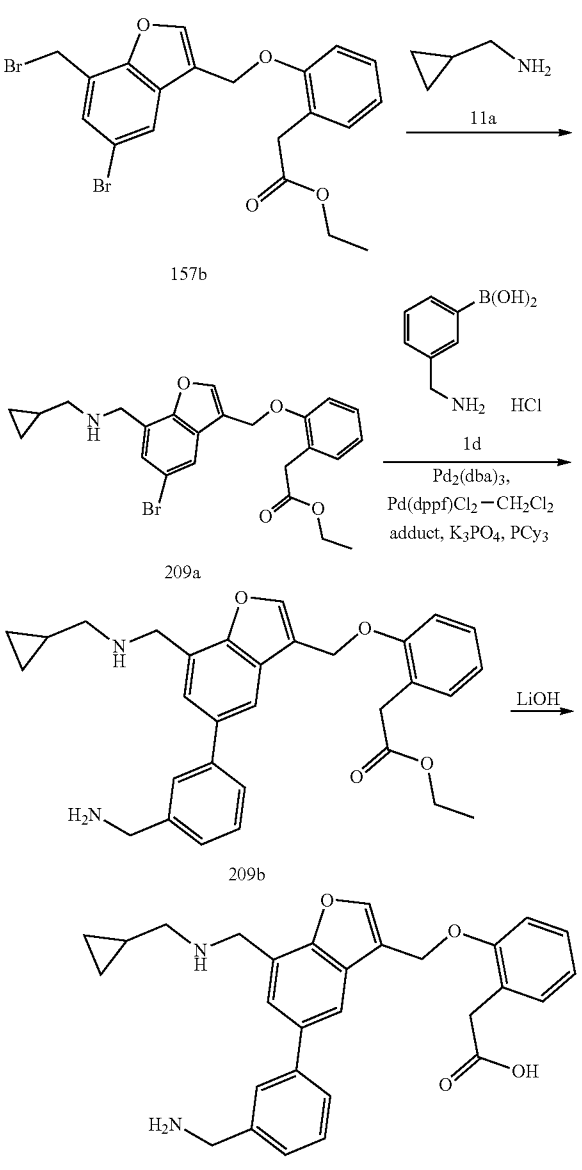

157b

209a

209b

209c

Preparation of 2-(2-((5-(3-(aminomethyl)phenyl)-7-(((cyclopropylmethyl)amino)methyl)benzofuran-3-yl)methoxy)phenyl)acetic acid (209c)

Step-1: Preparation of ethyl 2-(2-((5-bromo-7-(((cyclopropylmethyl)amino)methyl)benzofuran-3-yl)methoxy)phenyl)acetate (209a)

Compound 209a was prepared according to the procedure reported in step-2 of scheme 1, from ethyl 2-(2-((5-bromo-7-(bromomethyl)benzofuran-3-yl)methoxy)phenyl)acetate (157b) (300 mg, 0.622 mmol) in DMF (4 mL) using cyclopropylmethanamine (11a) (0.221 g, 3.11 mmol) and stirring at RT for 15 h. This gave after work up and purification using flash column chromatography [silica gel (24 g), eluting with DMA-80 in DCM from 0-50%] ethyl 2-(2-((5-bromo-7-(((cyclopropylmethyl)amino)methyl)benzofuran-3-yl)methoxy)phenyl)acetate (209a) (0.24 g, 82% yield) as a white oil; $^1H$ NMR (300 MHz, DMSO-$d_6$) δ 8.13 (s, 1H), 7.70 (d, J=2.0 Hz, 1H), 7.53 (d, J=2.0 Hz, 1H), 7.28 (td, J=7.8, 1.8 Hz, 1H), 7.19 (td, J=8.0, 1.4 Hz, 2H), 6.92 (td, J=7.3, 1.2 Hz, 1H), 5.22 (s, 2H), 3.99 (s, 2H), 3.94 (q, J=7.1 Hz, 2H), 3.55 (s, 2H), 2.40 (d, J=6.7 Hz, 2H), 0.98 (t, J=7.1 Hz, 3H), 0.95-0.81 (m, 1H), 0.46-0.33 (m, 2H), 0.17-0.03 (m, 2H); MS (ES+): 472.10 & 474.10 (M+1).

Step-2: Preparation of ethyl 2-(2-((5-(3-(aminomethyl)phenyl)-7-(((cyclopropylmethyl)amino)methyl)benzofuran-3-yl)methoxy)phenyl)acetate (209b)

Compound 209b was prepared according to the procedure reported in step-2 of scheme 1, from ethyl 2-(2-((5-bromo-7-(((cyclopropylmethyl)amino)methyl)benzofuran-3-yl)methoxy)phenyl)acetate (209a) (240 mg, 0.508 mmol), 2 M solution of $K_3PO_4$ (1.016 mL, 2.032 mmol), tricyclohexylphosphine (28.5 mg, 0.102 mmol), $Pd_2(dba)_3$ (46.5 mg, 0.051 mmol), $PdCl_2(dppf)-CH_2Cl_2$ adduct (41.5 mg, 0.051 mmol) and heating at 100° C. for 2 h.

This gave after workup and purification using flash column chromatography [silica gel (24 g), eluting with DMA-80 in DCM from 0-70%] ethyl 2-(2-((5-(3-(aminomethyl)phenyl)-7-(((cyclopropylmethyl)amino)methyl)benzofuran-3-yl)methoxy)phenyl)acetate (209b) (150 mg, 59% yield) as a clear oil; $^1H$ NMR (300 MHz, DMSO-$d_6$) δ 8.11 (s, 1H), 7.76 (d, J=1.8 Hz, 1H), 7.69-7.64 (m, 2H), 7.54 (d, J=7.5 Hz, 1H), 7.39 (t, J=7.5 Hz, 1H), 7.31 (dd, J=8.2, 1.8 Hz, 2H), 7.28-7.16 (m, 3H), 6.92 (td, J=7.3, 1.3 Hz, 1H), 5.29 (s, 2H), 4.06 (s, 2H), 3.80 (s, 2H), 3.73 (q, J=7.1 Hz, 2H), 3.55 (s, 2H), 2.44 (d, J=6.6 Hz, 2H), 0.97-0.89 (m, 1H), 0.86 (t, J=7.1 Hz, 3H), 0.45-0.34 (m, 2H), 0.13-0.03 (m, 2H); MS (ES+): 499.30 (M+1); 521.20 (M+Na).

Step-3: Preparation of 2-(2-((5-(3-(aminomethyl)phenyl)-7-(((cyclopropylmethyl)amino)methyl)benzofuran-3-yl)methoxy)phenyl)acetic acid (209c)

Compound 209c was prepared according to the procedure reported in step-3 of scheme 1, from ethyl 2-(2-((5-(3-(aminomethyl)phenyl)-7-(((cyclopropylmethyl)amino)methyl)benzofuran-3-yl)methoxy)phenyl)acetate (209b) (150 mg, 0.301 mmol) in THF/MeOH (2 mL each) using lithium hydroxide hydrate (37.9 mg, 0.903 mmol) in water (1 mL) and heating at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-7-(((cyclopropylmethyl)amino)methyl)benzofuran-3-yl)methoxy)phenyl)acetic acid (209c) (80 mg, 57% yield) HCl salt as a white solid; $^1H$ NMR (300 MHz, DMSO-$d_6$) δ 12.20 (s, 1H, $D_2O$ exchangeable), 9.71 (s, 2H, $D_2O$ exchangeable), 8.59 (s, 3H, $D_2O$ exchangeable), 8.31-8.15 (m, 2H), 8.15-7.95 (m, 2H), 7.83 (dt, J=7.1, 1.9 Hz, 1H), 7.58-7.47 (m, 2H), 7.28 (td, J=7.6, 7.0, 1.6 Hz, 1H), 7.25-7.17 (m, 2H), 6.93 (td, J=7.2, 1.4 Hz, 1H), 5.35 (s, 2H), 4.49 (t, J=5.8 Hz, 2H), 4.19-4.01 (m, 2H), 3.55 (s, 2H), 3.04-2.87 (m, 2H), 1.30-1.11 (m, 1H), 0.68-0.54 (m, 2H), 0.47-0.37 (m, 2H); MS (ES+): 471.20 (M+1); MS (ES−): 469.20 (M−1); Analysis calculated for $C_{29}H_{30}N_2O_4 \cdot 2HCl \cdot 2H_2O$: C, 60.11; H, 6.26; Cl, 12.23; N, 4.83. Found: C, 60.13; H, 6.12; Cl, 12.12; N, 4.83.

Scheme 210

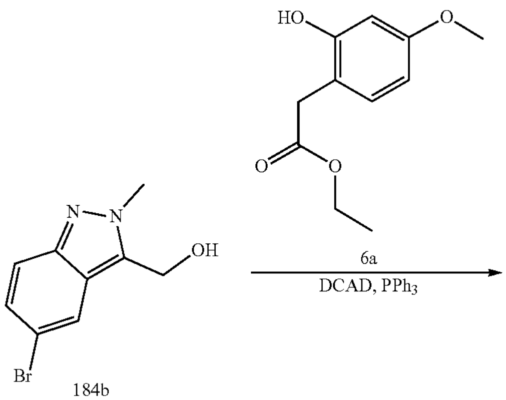

184b

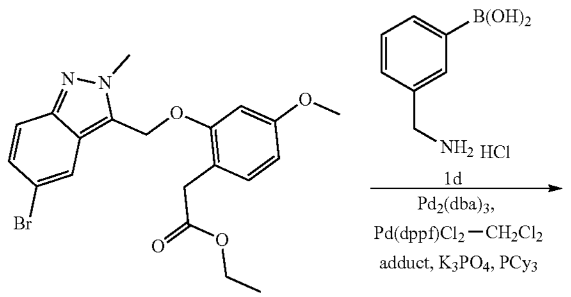

210a

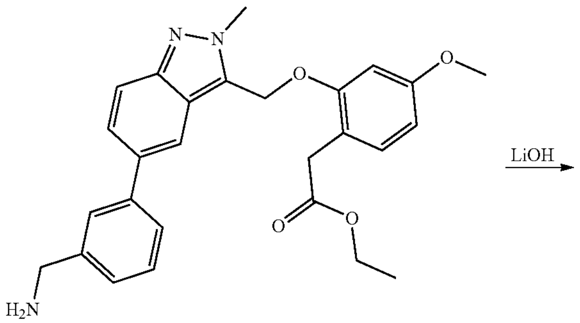

210b

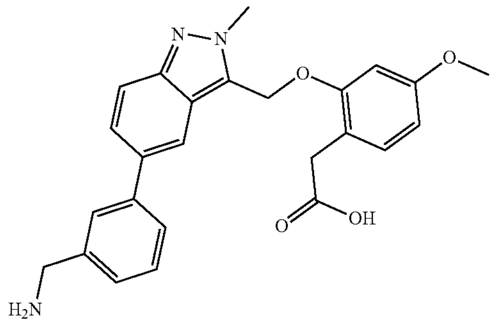

210c

Preparation of 2-(2-((5-(3-(aminomethyl)phenyl)-2-methyl-2H-indazol-3-yl)methoxy)-4-methoxyphenyl)acetic acid (210c)

Step-1: Preparation of ethyl 2-(2-((5-bromo-2-methyl-2H-indazol-3-yl)methoxy)-4-methoxyphenyl)acetate (210a)

Compound 210a was prepared according to the procedure reported in step-2 of scheme 65, from (5-bromo-2-methyl-2H-indazol-3-yl)methanol (184b) (250 mg, 1.037 mmol) in DCM (10 mL) using triphenylphosphine (326 mg, 1.244 mmol), ethyl 2-(2-hydroxy-4-methoxyphenyl)acetate (6a) (229 mg, 1.089 mmol) a solution of DCAD (457 mg, 1.244 mmol) in DCM (10 mL) and stirring at RT for 30 min. This gave after workup and purification using flash column chromatography [silica gel (12 g), eluting with DMA80 in DCM from 0-80%] ethyl 2-(2-((5-bromo-2-methyl-2H-indazol-3-yl)methoxy)-4-methoxyphenyl)acetate (210a) (100 mg, 22% yield) as a light yellow oil; MS (ES+): 433.00 & 435.05 (M+1).

Step-2: Preparation of ethyl 2-(2-((5-(3-(aminomethyl)phenyl)-2-methyl-2H-indazol-3-yl)methoxy)-4-methoxyphenyl)acetate (210b)

Compound 210b was prepared according to the procedure reported in step-2 of scheme 1, from ethyl 2-(2-((5-bromo-2-methyl-2H-indazol-3-yl)methoxy)-4-methoxyphenyl)acetate (210a) (100 mg, 0.231 mmol) in dioxane (2 mL) and THF (2 mL) using (3-(aminomethyl)phenyl)boronic acid hydrochloride (1d) (87 mg, 0.462 mmol), 2 M solution of $K_3PO_4$ (0.462 mL, 0.923 mmol), tricyclohexylphosphine (12.94 mg, 0.046 mmol), $Pd_2(dba)_3$ (21.13 mg, 0.023 mmol), $PdCl_2(dppf)$-$CH_2Cl_2$ adduct (18.85 mg, 0.023 mmol) and heating at 100° C. for 2 h. This gave after workup and purification using flash column chromatography [silica gel (12 g), eluting with DMA-80 in DCM from 0-70%] ethyl 2-(2-((5-(3-(aminomethyl)phenyl)-2-methyl-2H-indazol-3-yl)methoxy)-4-methoxyphenyl)acetate (210b) (80 mg, 75% yield) as a clear oil; MS (ES+): 460.20 (M+1).

Step-3: Preparation of 2-(2-((5-(3-(aminomethyl)phenyl)-2-methyl-2H-indazol-3-yl)methoxy)-4-methoxyphenyl)acetic acid (210c)

Compound 210c was prepared according to the procedure reported in step-3 of scheme 1, from ethyl 2-(2-((5-(3-(aminomethyl)phenyl)-2-methyl-2H-indazol-3-yl)methoxy)-4-methoxyphenyl)acetate (210b) (80 mg, 0.174 mmol) in THF/MeOH (4 mL) using lithium hydroxide hydrate (21.92 mg, 0.522 mmol) in water (1 mL) and stirring at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-2-methyl-2H-indazol-3-yl)methoxy)-4-methoxyphenyl)acetic acid (210c) (55 mg, 73% yield) HCl salt as a white solid; $^1H$ NMR (300 MHz, DMSO-$d_6$) δ 8.36 (s, 3H, $D_2O$ exchangeable), 8.26 (s, 1H), 7.90 (s, 1H), 7.78 (d, J=7.7 Hz, 1H), 7.73 (d, J=9.0 Hz, 1H), 7.65 (dd, J=9.0, 1.6 Hz, 1H), 7.52 (t, J=7.6 Hz, 1H), 7.43 (d, J=7.6 Hz, 1H), 7.10 (d, J=8.3 Hz, 1H), 6.91 (d, J=2.4 Hz, 1H), 6.51 (dd, J=8.3, 2.4 Hz, 1H), 5.65 (s, 2H), 4.19 (s, 3H), 4.16-4.05 (m, 2H), 3.75 (s, 3H), 3.40 (s, 2H); MS (ES+): 432.20 (M+1); MS (ES−): 430.10 (M−1).

Scheme 211

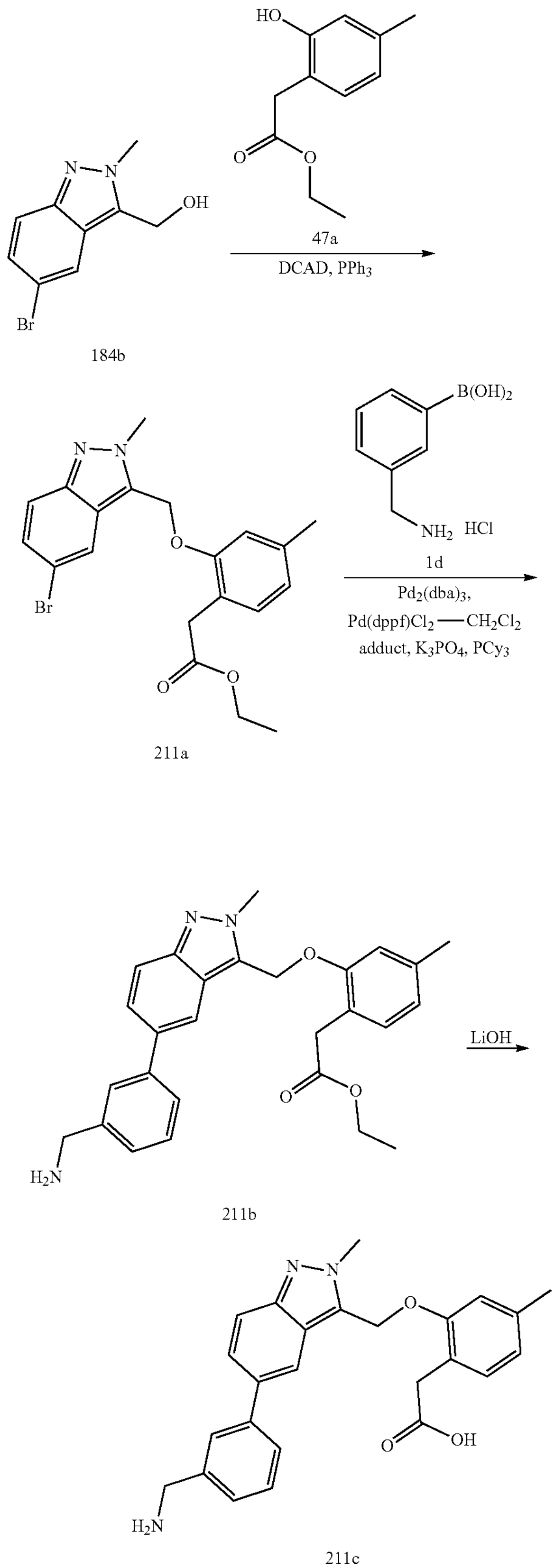

184b

211a

211b

211c

Preparation of 2-(2-((5-(3-(aminomethyl)phenyl)-2-methyl-2H-indazol-3-yl)methoxy)-4-methylphenyl) acetic acid (211c)

Step-1: Preparation of ethyl 2-(2-((5-bromo-2-methyl-2H-indazol-3-yl)methoxy)-4-methylphenyl) acetate (211a)

Compound 211a was prepared according to the procedure reported in step-2 of scheme 65, from (5-bromo-2-methyl-2H-indazol-3-yl)methanol (184b) (250 mg, 1.037 mmol) in DCM (10 mL) using triphenylphosphine (326 mg, 1.244 mmol), ethyl 2-(2-hydroxy-4-methylphenyl)acetate (47a) (211 mg, 1.089 mmol), a solution of DCAD (457 mg, 1.244 mmol) in DCM (10 mL) and stirring at RT for 30 min. This gave after workup and purification using flash column chromatography [silica gel (12 g), eluting with DMA-80 in DCM from 0-80%] ethyl 2-(2-((5-bromo-2-methyl-2H-indazol-3-yl)methoxy)-4-methylphenyl)acetate (211a) (200 mg, 46% yield) as a light yellow oil; MS (ES+): 439.00 & 441.05 (M+Na); MS (ES−): 415.00 (M−1).

Step-2: Preparation of ethyl 2-(2-((5-(3-(aminomethyl)phenyl)-2-methyl-2H-indazol-3-yl)methoxy)-4-methylphenyl)acetate (211b)

Compound 211b was prepared according to the procedure reported in step-2 of scheme 1, from ethyl 2-(2-((5-bromo-2-methyl-2H-indazol-3-yl)methoxy)-4-methylphenyl)acetate (211a) (200 mg, 0.479 mmol) in dioxane (2 mL) and THF (2 mL) using (3-(aminomethyl)phenyl)boronic acid hydrochloride (1d) (180 mg, 0.959 mmol), 2 M solution of $K_3PO_4$ (0.959 mL, 1.917 mmol), tricyclohexylphosphine (26.9 mg, 0.096 mmol), $Pd_2(dba)_3$ (43.9 mg, 0.048 mmol), $PdCl_2(dppf)$-$CH_2Cl_2$ adduct (39.1 mg, 0.048 mmol) and heating at 100° C. for 2 h. This gave after workup and purification using flash column chromatography [silica gel (12 g), eluting with DMA-80 in DCM from 0-70%] ethyl 2-(2-((5-(3-(aminomethyl)phenyl)-2-methyl-2H-indazol-3-yl)methoxy)-4-methylphenyl)acetate (211b) (150 mg, 71% yield) as a clear oil; MS (ES+): 444.20 (M+1).

Step-3: Preparation of 2-(2-((5-(3-(aminomethyl) phenyl)-2-methyl-2H-indazol-3-yl)methoxy)-4-methylphenyl)acetic acid (211c)

Compound 211c was prepared according to the procedure reported in step-3 of scheme 1, from ethyl 2-(2-((5-(3-(aminomethyl)phenyl)-2-methyl-2H-indazol-3-yl) methoxy)-4-methylphenyl)acetate (211b) (150 mg, 0.338 mmol) in THF/MeOH (2 mL each) using lithium hydroxide hydrate (42.6 mg, 1.015 mmol) in water (1 mL) and heating at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-2-methyl-2H-indazol-3-yl)methoxy)-4-methylphenyl)acetic acid (211c) (70 mg, 50% yield) HCl salt as a white solid; $^1H$ NMR (300 MHz, DMSO-$d_6$) δ 8.36 (s, 3H, $D_2O$ exchangeable), 8.24 (s, 1H), 7.91 (s, 1H), 7.78 (d, J=7.7 Hz, 1H), 7.73 (d, J=9.0 Hz, 1H), 7.66 (dd, J=9.1, 1.6 Hz, 1H), 7.52 (t, J=7.7 Hz, 1H), 7.43 (d, J=7.6 Hz, 1H), 7.18 (s, 1H), 7.08 (d, J=7.5 Hz, 1H), 6.76 (d, J=7.7 Hz, 1H), 5.61 (s, 2H), 4.19 (s, 3H), 4.15-4.05 (m, 2H), 3.43 (s, 2H), 2.32 (s, 3H); MS (ES+): 416.20 (M+1); MS (ES−): 414.15 (M−1); Analysis calculated for $C_{25}H_{25}N_3O_3 \cdot 1.3HCl \cdot 2.25H_2O$: C, 59.65; H, 6.17; Cl, 9.16; N, 8.35. Found: C, 59.70; H, 6.08; Cl, 9.28; N, 8.27.

Scheme 212

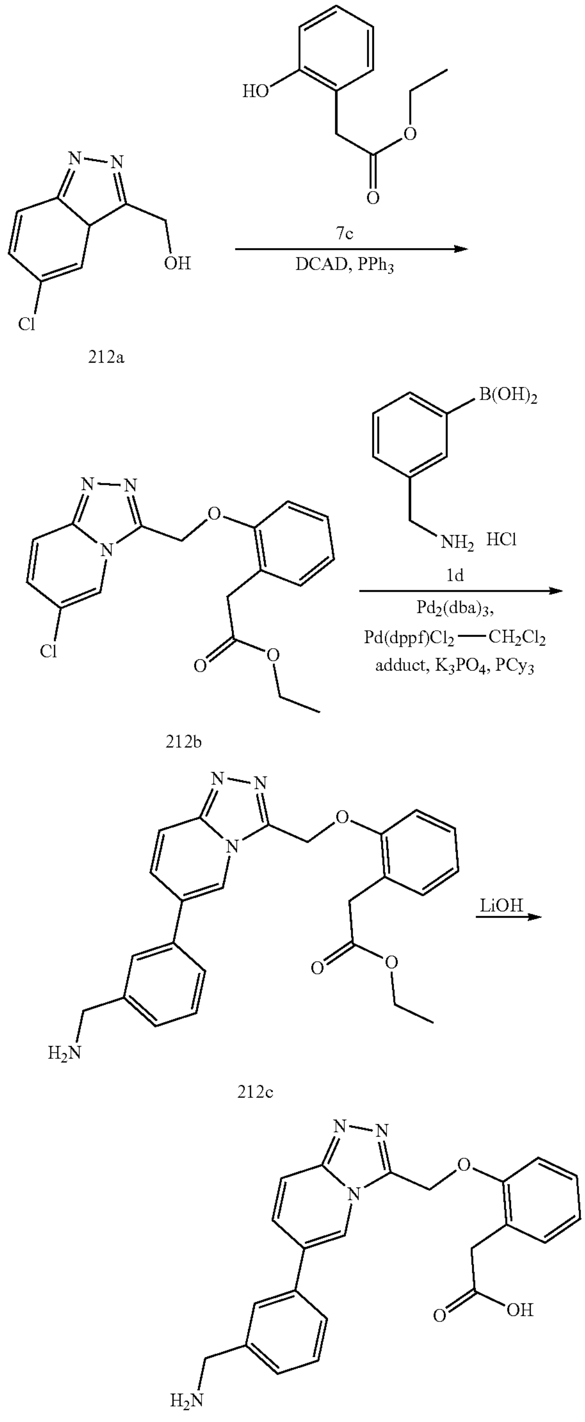

212a

212b

212c

212d

Preparation of 2-(2-((6-(3-(aminomethyl)phenyl)-[1,2,4]triazolo[4,3-a]pyridin-3-yl)methoxy)phenyl)acetic acid (212d)

Step-1: Preparation of ethyl 2-(2-((6-chloro-[1,2,4]triazolo[4,3-a]pyridin-3-yl)methoxy)phenyl)acetate (212b)

Compound 212b was prepared according to the procedure reported in step-2 of scheme 65, from (6-chloro-[1,2,4]triazolo[4,3-a]pyridin-3-yl)methanol (212a) (500 mg, 2.72 mmol; CAS #1781171-55-8) in DCM (20 mL) using triphenylphosphine (857 mg, 3.27 mmol), ethyl 2-(2-hydroxyphenyl)acetate (7c) (515 mg, 2.86 mmol), a solution of DCAD (1200 mg, 3.27 mmol) in DCM (20 mL) and stirring at RT for 30 min. This gave after workup and purification using flash column chromatography [silica gel (24 g), eluting with DMA-80 in DCM from 0-60%] ethyl 2-(2-((6-chloro-[1,2,4]triazolo[4,3-a]pyridin-3-yl)methoxy)phenyl)acetate (212b) (600 mg, 64% yield) as a light yellow oil; $^1H$ NMR (300 MHz, DMSO-$d_6$) δ 8.75 (dd, J=1.9, 1.0 Hz, 1H), 7.92 (dd, J=9.8, 1.0 Hz, 1H), 7.53 (dd, J=9.8, 1.9 Hz, 1H), 7.33-7.28 (m, 2H), 7.21 (d, J=7.4 Hz, 1H), 6.96 (ddd, J=7.4, 5.7, 2.8 Hz, 1H), 5.67 (s, 2H), 3.86 (q, J=7.1 Hz, 2H), 3.52 (s, 2H), 0.93 (t, J=7.1 Hz, 3H); MS (ES+): 346.10 & 348.05 (M+1); MS (ES−): 344.10 & 346.00 (M−1).

Step-2: Preparation of ethyl 2-(2-((6-(3-(aminomethyl)phenyl)-[1,2,4]triazolo[4,3-a]pyridin-3-yl)methoxy)phenyl)acetate (212c)

Compound 212c was prepared according to the procedure reported in step-2 of scheme 1, from ethyl 2-(2-((6-chloro-[1,2,4]triazolo[4,3-a]pyridin-3-yl)methoxy)phenyl)acetate (212b) (400 mg, 1.157 mmol) in dioxane (4 mL) and THF (4 mL) using (3-(aminomethyl)phenyl)boronic acid hydrochloride (1d) (434 mg, 2.314 mmol), 2 M solution of $K_3PO_4$ (2.314 mL, 4.63 mmol), tricyclohexylphosphine (64.9 mg, 0.231 mmol), $Pd_2(dba)_3$ (106 mg, 0.116 mmol), $PdCl_2$(dppf)-$CH_2Cl_2$ adduct (94 mg, 0.116 mmol) and heating at 100° C. for 3 h. This gave after workup and purification using flash column chromatography [silica gel (24 g), eluting with DMA-80 in DCM from 0-70%] ethyl 2-(2-((6-(3-(aminomethyl)phenyl)-[1,2,4]triazolo[4,3-a]pyridin-3-yl)methoxy)phenyl)acetate (212c) (280 mg, 58% yield) as a clear oil; MS (ES+): 417.20 (M+1); MS (ES−): 415.15 (M−1).

Step-3: Preparation of 2-(2-((6-(3-(aminomethyl)phenyl)-[1,2,4]triazolo[4,3-a]pyridin-3-yl)methoxy)phenyl)acetic acid (212d)

Compound 212d was prepared according to the procedure reported in step-3 of scheme 1, from ethyl 2-(2-((6-(3-(aminomethyl)phenyl)-[1,2,4]triazolo[4,3-a]pyridin-3-yl)methoxy)phenyl)acetate (212c) (280 mg, 0.672 mmol) in THF/MeOH (2 mL each) using lithium hydroxide hydrate (169 mg, 4.03 mmol) in water (1 mL) and stirring at RT for 15 h.

This gave after workup and purification using reverse phase column chromatography [C18 column (50 g), eluting with ACN in water (containing 0.1% HCl) from 0-100%] 2-(2-((6-(3-(aminomethyl)phenyl)-[1,2,4]triazolo[4,3-a]pyridin-3-yl)methoxy)phenyl)acetic acid (212d) (125 mg, 48% yield) HCl salt as a white solid; $^1H$ NMR (300 MHz, DMSO-$d_6$) δ 10.25 (s, 2H, $D_2O$ exchangeable), 9.13 (s, 1H), 8.76 (s, 3H, $D_2O$ exchangeable), 8.24 (d, J=9.6 Hz, 1H), 8.20-8.08 (m, 2H), 7.87 (dt, J=7.1, 1.9 Hz, 1H), 7.67-7.52 (m, 2H), 7.38 (d, J=8.2 Hz, 1H), 7.30 (td, J=8.2, 7.7, 1.7 Hz, 1H), 7.21 (dd, J=7.5, 1.7 Hz, 1H), 7.03-6.89 (m, 1H), 5.86 (s, 2H), 4.23-3.96 (m, 2H), 3.51 (s, 2H); MS (ES+): 389.20 (M+1); MS (ES−): 387.10 (M−1); Analysis calculated for $C_{22}H_{20}N_4O_3 \cdot 2.05HCl \cdot 2H_2O$: C, 52.93; H, 5.26; Cl, 14.56; N, 11.22. Found: C, 53.07; H, 5.01; Cl, 14.71; N, 11.32.

Scheme 213

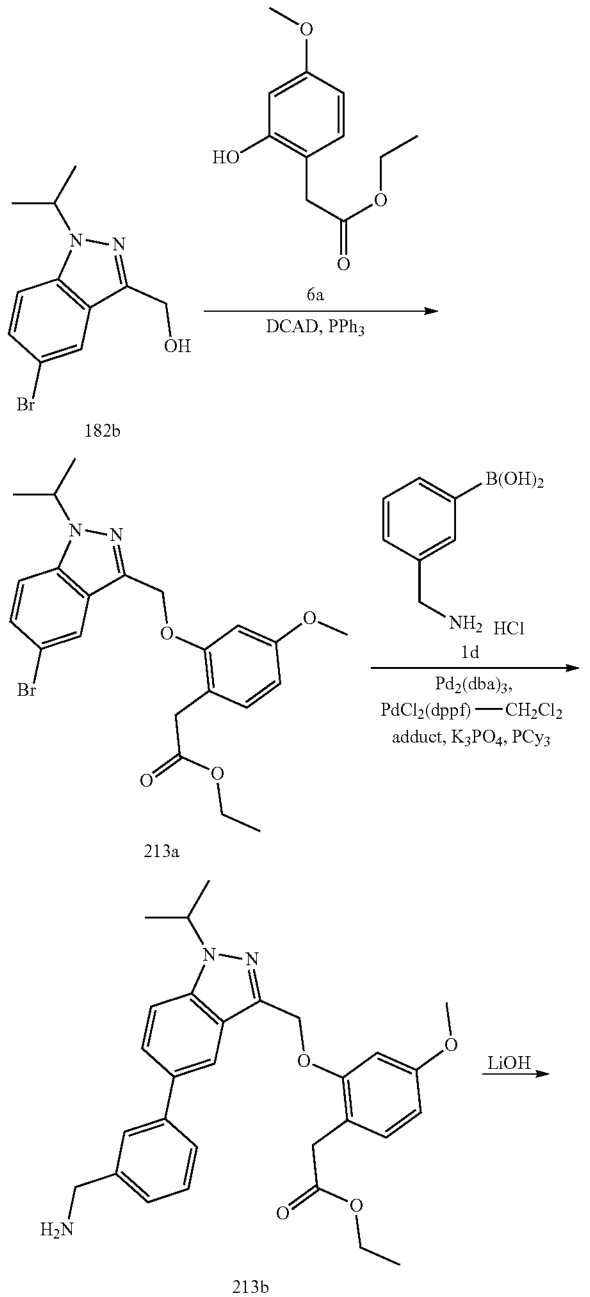

182b

213a

213b

-continued

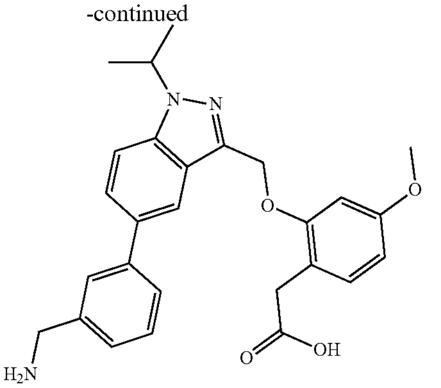

213c

Preparation of 2-(2-((5-(3-(aminomethyl)phenyl)-1-isopropyl-1H-indazol-3-yl)methoxy)-4-methoxyphenyl)acetic acid (213c)

Step-1: Preparation of ethyl 2-(2-((5-bromo-1-isopropyl-1H-indazol-3-yl)methoxy)-4-methoxyphenyl) acetate (213a)

Compound 213a was prepared according to the procedure reported in step-2 of scheme 65, from (5-bromo-1-isopropyl-1H-indazol-3-yl)methanol (182b) (320 mg, 1.189 mmol) in DCM (20 mL) using triphenylphosphine (374 mg, 1.427 mmol), ethyl 2-(2-hydroxy-4-methoxyphenyl)acetate (6a) (262 mg, 1.248 mmol), a solution of DCAD (524 mg, 1.427 mmol) in DCM (10 mL) and stirring at RT for 30 min. This gave after workup and purification using flash column chromatography [silica gel (12 g), eluting with EtOAc in hexane from 0-60%] ethyl 2-(2-((5-bromo-1-isopropyl-1H-indazol-3-yl)methoxy)-4-methoxyphenyl)acetate (213a) (320 mg, 58% yield) as a light yellow oil; MS (ES+): 461.10 & 463.10 (M+1), 483.10 & 485.10 (M+Na); MS (ES−): 459.00 & 461.05 (M−1).

Step-2: Preparation of ethyl 2-(2-((5-(3-(aminomethyl)phenyl)-1-isopropyl-1H-indazol-3-yl) methoxy)-4-methoxyphenyl)acetate (213b)

Compound 213b was prepared according to the procedure reported in step-2 of scheme 1, from ethyl 2-(2-((5-bromo-1-isopropyl-1H-indazol-3-yl)methoxy)-4-methoxyphenyl) acetate (213a) (320 mg, 0.694 mmol) in dioxane (3 mL) and THF (3 mL) using (3-(aminomethyl)phenyl)boronic acid hydrochloride (1d) (260 mg, 1.387 mmol), 2 M solution of $K_3PO_4$ (1.387 mL, 2.77 mmol), tricyclohexylphosphine (38.9 mg, 0.139 mmol), $Pd_2(dba)_3$ (63.5 mg, 0.069 mmol), $PdCl_2(dppf)$-$CH_2Cl_2$ adduct (56.6 mg, 0.069 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-isopropyl-1H-indazol-3-yl)methoxy)-4-methoxyphenyl)acetate (213b) (220 mg, 65% yield) as a clear oil; $^1H$ NMR (300 MHz, DMSO-$d_6$) δ 7.97 (d, J=1.6 Hz, 1H), 7.79 (d, J=8.8 Hz, 1H), 7.72 (dd, J=8.9, 1.6 Hz, 1H), 7.66 (s, 1H), 7.57-7.50 (m, 2H), 7.38 (t, J=7.6 Hz, 1H), 7.30 (d, J=6.5 Hz, 2H), 7.07 (d, J=8.3 Hz, 1H), 6.89 (d, J=2.4 Hz, 1H), 6.48 (dd, J=8.3, 2.3 Hz, 1H), 5.43 (s, 2H), 5.10-4.93 (m, 1H), 3.78 (s, 2H), 3.77 (s, 3H), 3.67 (q, J=7.1 Hz, 2H), 3.45 (s, 2H), 1.51 (d, J=6.6 Hz, 6H), 0.79 (t, J=7.1 Hz, 3H); MS (ES+): 488.30 (M+1); MS (ES−): 486.25 (M−1).

Step-3: Preparation of 2-(2-((5-(3-(aminomethyl)phenyl)-1-isopropyl-1H-indazol-3-yl)methoxy)-4-methoxyphenyl)acetic acid (213c)

Compound 213c was prepared according to the procedure reported in step-3 of scheme 1, from ethyl 2-(2-((5-(3-(aminomethyl)phenyl)-1-isopropyl-1H-indazol-3-yl)methoxy)-4-methoxyphenyl)acetate (213b) (220 mg, 0.451 mmol) in THF/MeOH (2 mL each) using lithium hydroxide hydrate (56.8 mg, 1.354 mmol) in water (1 mL) and stirring at RT for 15 h.

This gave after workup and purification using reverse phase column chromatography [C18 column (50 g), eluting with ACN in water (containing 0.1% HCl) from 0-100%] 2-(2-((5-(3-(aminomethyl)phenyl)-1-isopropyl-1H-indazol-3-yl)methoxy)-4-methoxyphenyl)acetic acid (213c) (85 mg, 41% yield) HCl salt as a white solid; $^1$H NMR (300 MHz, DMSO-$d_6$) δ 12.05 (s, 1H, $D_2O$ exchangeable), 8.38 (s, 3H, $D_2O$ exchangeable), 8.07 (s, 1H), 7.90-7.80 (m, 2H), 7.80-7.71 (m, 2H), 7.51 (t, J=7.6 Hz, 1H), 7.44 (d, J=7.8 Hz, 1H), 7.08 (d, J=8.3 Hz, 1H), 6.89 (d, J=2.4 Hz, 1H), 6.49 (dd, J=8.3, 2.3 Hz, 1H), 5.45 (s, 2H), 5.16-4.94 (m, 1H), 4.16-4.06 (m, 2H), 3.76 (s, 3H), 3.44 (s, 2H), 1.52 (d, J=6.5 Hz, 6H); MS (ES+): 460.20 (M+1); MS (ES−): 458.20 (M−1); Analysis calculated for $C_{27}H_{29}N_3O_4 \cdot HCl \cdot H_2O$: C, 63.09; H, 6.28; Cl, 6.90; N, 8.17. Found: C, 63.20; H, 6.12; Cl, 6.75; N, 8.21.

Scheme 214

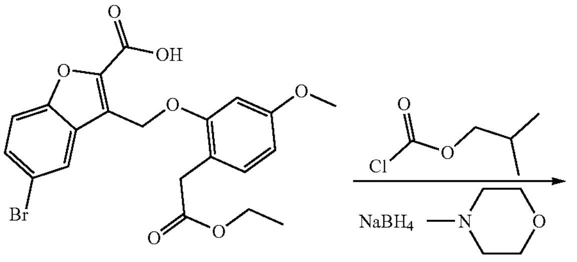

172b

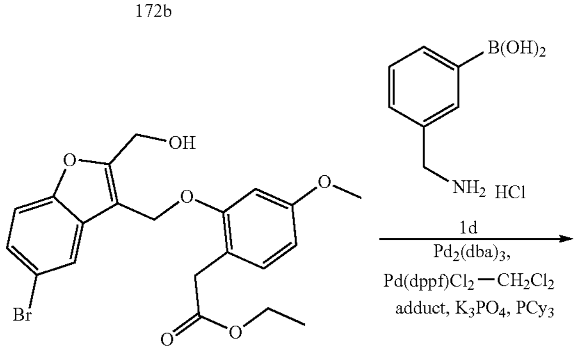

214a

-continued

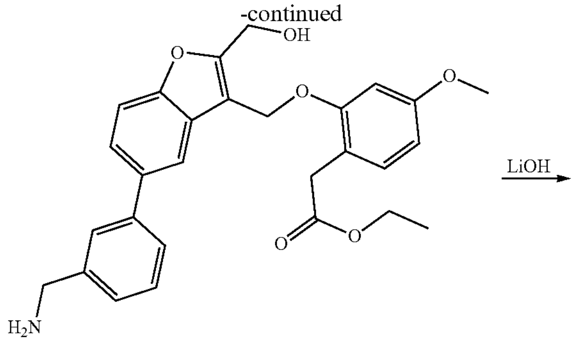

214b

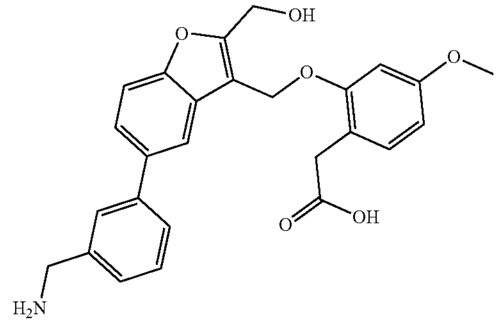

214c

Preparation of 2-(2-((5-(3-(aminomethyl)phenyl)-2-(hydroxymethyl)benzofuran-3-yl)methoxy)-4-methoxyphenyl)acetic acid (214c)

Step-1: Preparation of ethyl 2-(2-((5-bromo-2-(hydroxymethyl)benzofuran-3-yl)methoxy)-4-methoxyphenyl)acetate (214a)

Compound 214a was prepared according to the procedure reported in step-1 of scheme 8, from 5-bromo-3-((2-(2-ethoxy-2-oxoethyl)-5-methoxyphenoxy)methyl)benzofuran-2-carboxylic acid (172b) (1.16 g, 2.504 mmol) using N-Methylmorpholine (0.330 mL, 3.00 mmol), isobutyl chloroformate (0.395 mL, 3.00 mmol) in THF (8 mL) and solution of $NaBH_4$ (0.284 g, 7.51 mmol) in water (2.0 mL). This gave after workup and purification using flash column chromatography [silica (24 g), eluting with EtOAc/MeOH (9:1) in hexane from 0-50%] ethyl 2-(2-((5-bromo-2-(hydroxymethyl)benzofuran-3-yl)methoxy)-4-methoxyphenyl)acetate (214a) (650 mg, 58% yield) as a clear oil; $^1$H NMR (300 MHz, DMSO-$d_6$) δ 7.80 (s, 1H), 7.58 (d, J=8.7 Hz, 1H), 7.48 (d, 1H), 7.09 (d, J=8.3 Hz, 1H), 6.80 (d, J=2.4 Hz, 1H), 6.50 (dd, J=8.3, 2.4 Hz, 1H), 5.58 (t, J=5.8 Hz, 1H), 5.25 (s, 2H), 4.67 (d, J=5.8 Hz, 2H), 3.93 (q, J=7.1 Hz, 2H), 3.78 (s, 3H), 3.45 (s, 2H), 0.97 (t, J=7.1 Hz, 3H).

Step-2: Preparation of ethyl 2-(2-((5-(3-(aminomethyl)phenyl)-2-(hydroxymethyl)benzofuran-3-yl)methoxy)-4-methoxyphenyl)acetate (214b)

Compound 214b was prepared according to the procedure reported in step-2 of scheme 1, from ethyl 2-(2-((5-bromo-2-(hydroxymethyl)benzofuran-3-yl)methoxy)-4-methoxyphenyl)acetate (214a) (500 mg, 1.113 mmol) in dioxane (30 mL) using (3-(aminomethyl)phenyl)boronic acid hydrochloride (1d) (417 mg, 2.226 mmol), 4 M solution of $K_3PO_4$ (1.113 mL, 4.45 mmol), tricyclohexylphosphine (94 mg, 0.334 mmol), $Pd_2(dba)_3$ (102 mg, 0.111 mmol), $PdCl_2$(dppf)-$CH_2Cl_2$ adduct (91 mg, 0.111 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(hydroxymethyl)benzofuran-3-yl)methoxy)-4-methoxyphenyl)acetate (214b) (270 mg, 51% yield) as a brown oil; MS (ES+): 476.2 (M+1).

Step-3: Preparation of 2-(2-((5-(3-(aminomethyl)phenyl)-2-(hydroxymethyl)benzofuran-3-yl)methoxy)-4-methoxyphenyl)acetic acid (214c)

Compound 214c was prepared according to the procedure reported in step-3 of scheme 1, from ethyl 2-(2-((5-(3-(aminomethyl)phenyl)-2-(hydroxymethyl)benzofuran-3-yl)methoxy)-4-methoxyphenyl)acetate (214b) (270 mg, 0.568 mmol) in THF (3 mL) using lithium hydroxide hydrate (140 mg, 3.34 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(hydroxymethyl)benzofuran-3-yl)methoxy)-4-methoxyphenyl)acetic acid (214c) (65 mg, 13% yield) HCl salt as a white solid; $^1H$ NMR (300 MHz, DMSO-$d_6$) δ 12.05 (s, 1H, $D_2O$ exchangeable), 8.41 (s, 3H, $D_2O$ exchangeable), 7.98 (s, 1H), 7.87 (s, 1H), 7.79-7.62 (m, 3H), 7.57-7.43 (m, 2H), 7.08 (d, J=8.3 Hz, 1H), 6.84 (d, J=2.4 Hz, 1H), 6.49 (dd, J=8.3, 2.4 Hz, 1H), 5.58 (t, J=6.0 Hz, 1H, $D_2O$ exchangeable), 5.32 (s, 2H), 4.69 (d, J=4.4 Hz, 2H), 4.10 (s, 2H), 3.76 (s, 3H), 3.42 (s, 2H); MS (ES+): 448.2 (M+1); (ES−): 446.1 (M−1); Analysis calculated for $C_{26}H_{25}NO_6 \cdot HCl \cdot H_2O$: C, 62.21; H, 5.62; Cl, 7.06; N, 2.79. Found: C, 62.59; H, 5.62; Cl, 7.41; N, 3.05.

Scheme 215

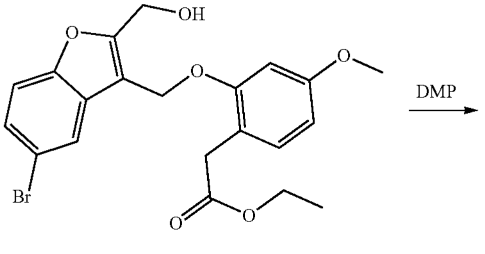

214a

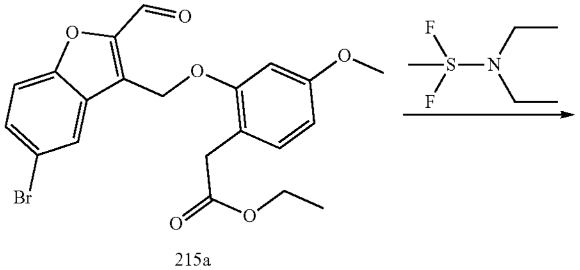

215a

-continued

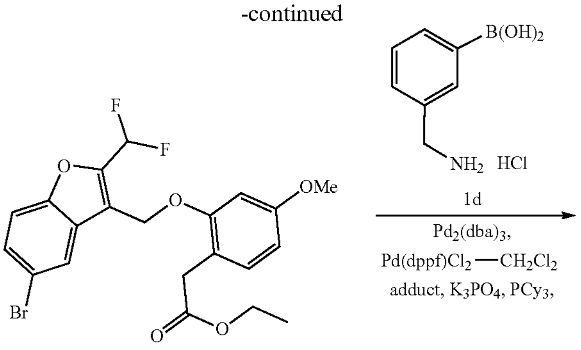

215b

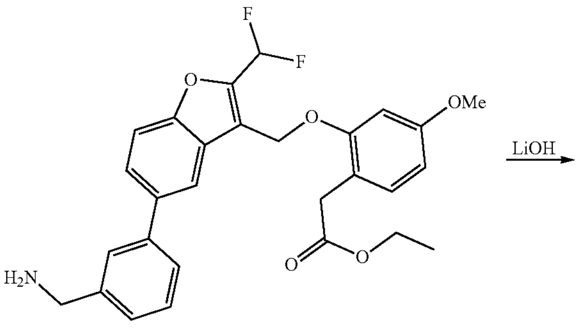

215c

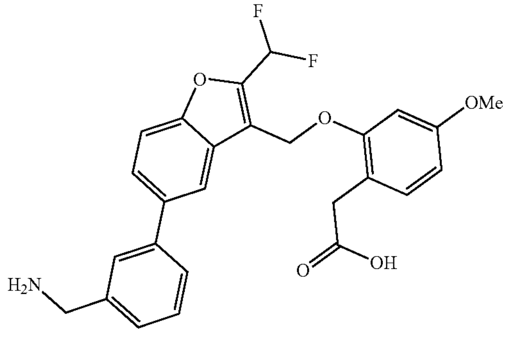

215d

Preparation of 2-(2-((5-(3-(aminomethyl)phenyl)-2-(difluoromethyl)benzofuran-3-yl)methoxy)-4-methoxyphenyl)acetic acid (215d)

Step-1: Preparation of ethyl 2-(2-((5-bromo-2-formylbenzofuran-3-yl)methoxy)-4-methoxyphenyl)acetate (215a)

Compound 215a was prepared according to the procedure reported in step-1 of scheme 141, from ethyl 2-(2-((5-bromo-2-(hydroxymethyl)benzofuran-3-yl)methoxy)-4-methoxyphenyl)acetate (214a) (650 mg, 1.447 mmol) in DCM (10 mL) using Dess-Martin periodinane (DMP) (736 mg, 1.736 mmol) and stirring at RT for 3 h. This gave after workup and purification using flash column chromatography [silica gel, eluting with EtOAc in hexane from 0-100%] ethyl 2-(2-((5-bromo-2-formylbenzofuran-3-yl)methoxy)-4-methoxyphenyl)acetate (215a) (380 mg, 59% yield) as a white solid; $^1H$ NMR (300 MHz, DMSO-$d_6$) δ 10.13 (s, 1H), 8.18 (t, J=1.3 Hz, 1H), 7.77 (d, J=1.3 Hz, 2H), 7.12 (d, J=8.3 Hz, 1H), 6.82 (d, J=2.4 Hz, 1H), 6.54 (dd, J=8.3, 2.4 Hz, 1H), 5.64 (s, 2H), 3.90 (q, J=7.1 Hz, 2H), 3.77 (s, 3H), 3.49 (s, 2H), 0.97 (t, J=7.1 Hz, 3H); MS (ES+): 469.0 (M+Na).

Step-2: Preparation of ethyl 2-(2-((5-bromo-2-(difluoromethyl)benzofuran-3-yl)methoxy)-4-methoxyphenyl)acetate (215b)

Compound 215b was prepared according to the procedure reported in step-1 of scheme 139, from ethyl 2-(2-((5-bromo-2-formylbenzofuran-3-yl)methoxy)-4-methoxyphenyl)acetate (215a) (500 mg, 1.118 mmol) in DCM (20 mL) using diethylamino sulfur trifluoride (DAST, 0.192 mL, 1.453 mmol) and stirring at RT for 1 h. This gave after work up and purification using flash column chromatography [silica gel, eluting with EtOAc in hexane from 0-100%]ethyl 2-(2-((5-bromo-2-(difluoromethyl)benzofuran-3-yl)methoxy)-4-methoxyphenyl)acetate (215b) (150 mg, 29% yield) as a white solid; MS (ES+): 491.00 (M+Na).

Step-3: Preparation of ethyl 2-(2-((5-(3-(aminomethyl)phenyl)-2-(difluoromethyl)benzofuran-3-yl)methoxy)-4-methoxyphenyl)acetate (215c)

Compound 215c was prepared according to the procedure reported in step-2 of scheme 1, from ethyl 2-(2-((5-bromo-2-(difluoromethyl)benzofuran-3-yl)methoxy)-4-methoxyphenyl)acetate (215b) (150 mg, 0.320 mmol) in dioxane (30 mL) using 3-(aminomethyl)phenylboronic acid hydrochloride (1d) (120 mg, 0.639 mmol), 4 M solution of $K_3PO_4$ (0.320 mL, 1.279 mmol), tricyclohexylphosphine (26.9 mg, 0.096 mmol), $Pd_2(dba)_3$ (29.3 mg, 0.032 mmol), $PdCl_2$ (dppf)-$CH_2Cl_2$ adduct (26.1 mg, 0.032 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(difluoromethyl)benzofuran-3-yl)methoxy)-4-methoxyphenyl)acetate (215c) (136 mg, 86% yield) as a yellow oil; MS (ES+): 496.2 (M+1).

Step-4: Preparation of 2-(2-((5-(3-(aminomethyl)phenyl)-2-(difluoromethyl)benzofuran-3-yl)methoxy)-4-methoxyphenyl)acetic acid (215d)

Compound 215d was prepared according to the procedure reported in step-3 of scheme 1, from ethyl 2-(2-((5-(3-(aminomethyl)phenyl)-2-(difluoromethyl)benzofuran-3-yl)methoxy)-4-methoxyphenyl)acetate (215c) (136 mg, 0.274 mmol) in THF (3 mL) using a solution of lithium hydroxide hydrate (40.2 mg, 0.959 mmol) in water (1 mL) and stirring at RT overnight. This gave after workup and purification using reverse phase column chromatography [C18 column (30 g), eluting with ACN in water (containing 0.1% HCl) from 0-100%] 2-(2-((5-(3-(aminomethyl)phenyl)-2-(difluoromethyl)benzofuran-3-yl)methoxy)-4-methoxyphenyl)acetic acid (215d) (35 mg, 23% yield) HCl salt as a white solid; $^1H$ NMR (300 MHz, DMSO-$d_6$) δ 12.10 (s, 1H), 8.34 (s, 3H), 8.16 (s, 1H), 7.97-7.30 (m, 7H), 7.11 (d, J=8.3 Hz, 1H), 6.83 (d, J=2.4 Hz, 1H), 6.53 (dd, J=8.3, 2.4 Hz, 1H), 5.49 (s, 2H), 4.11 (s, 2H), 3.76 (s, 3H), 3.44 (s, 2H); $^{19}F$ NMR (282 MHz, DMSO-$d_6$) δ −115.58, −115.76; MS (ES+): 468.10 (M+1); Analysis calculated for $C_{26}H_{23}F_2NO_5 \cdot 1.1HCl \cdot 0.5H_2O$: C, 60.45; H, 4.90; Cl, 7.55; N, 2.71. Found: C, 60.30; H, 4.90; Cl, 7.35; N, 2.97.

Scheme 216

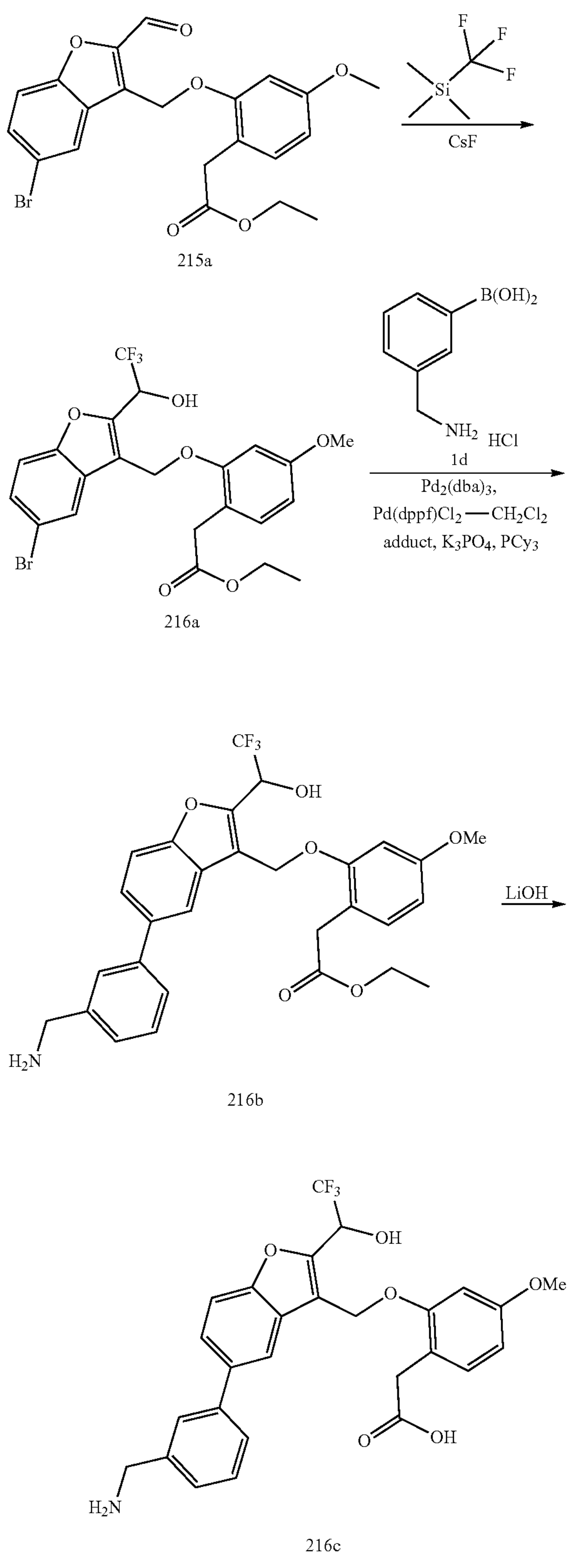

Preparation of 2-(2-((5-(3-(aminomethyl)phenyl)-2-(2,2,2-trifluoro-1-hydroxyethyl)benzofuran-3-yl)methoxy)-4-methoxyphenyl)acetic acid (216c)

Step-1: Preparation of ethyl 2-(2-((5-bromo-2-(2,2,2-trifluoro-1-hydroxyethyl)benzofuran-3-yl)methoxy)-4-methoxyphenyl)acetate (216a)

Compound 216a was prepared according to the procedure reported in step-1 of scheme 140, from ethyl 2-(2-((5-bromo-2-formylbenzofuran-3-yl)methoxy)-4-methoxyphenyl)acetate (215a) (1 g, 2.236 mmol) in anhydrous THF (20 mL) using trimethyl(trifluoromethyl)silane (0.413 g, 2.91 mmol), CsF (0.340 g, 2.236 mmol) and stirring at RT for 12 h. This gave after workup and purification using flash column chromatography [silica gel, eluting with EtOAc in hexane from 0-100%] ethyl 2-(2-((5-bromo-2-(2,2,2-trifluoro-1-hydroxyethyl)benzofuran-3-yl)methoxy)-4-methoxyphenyl)acetate (216a) (800 mg, 69% yield) as a yellow oil; MS (ES+): 539.0 and 541.0 (M+1); (ES−) 515.0 and 517.0 (M−1).

Step-2: Preparation of ethyl 2-(2-((5-(3-(aminomethyl)phenyl)-2-(2,2,2-trifluoro-1-hydroxyethyl)benzofuran-3-yl)methoxy)-4-methoxyphenyl)acetate (216b)

Compound 216b was prepared according to the procedure reported in step-2 of scheme 1, from ethyl 2-(2-((5-bromo-2-(2,2,2-trifluoro-1-hydroxyethyl)benzofuran-3-yl)methoxy)-4-methoxyphenyl)acetate (216a) (800 mg, 1.547 mmol) in dioxane (30 mL) using 3-(aminomethyl)phenylboronic acid hydrochloride (1d) (580 mg, 3.09 mmol), 4 M solution of $K_3PO_4$ (1.547 mL, 6.19 mmol), tricyclohexylphosphine (130 mg, 0.464 mmol), $Pd_2(dba)_3$ (142 mg, 0.155 mmol), $PdCl_2(dppf)$-$CH_2Cl_2$ adduct (126 mg, 0.155 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(2,2,2-trifluoro-1-hydroxyethyl)benzofuran-3-yl)methoxy)-4-methoxyphenyl)acetate (216b) (400 mg, 48% yield) as a yellow oil; MS (ES+): 544.2 (M+1).

Step-3: Preparation of 2-(2-((5-(3-(aminomethyl)phenyl)-2-(2,2,2-trifluoro-1-hydroxyethyl)benzofuran-3-yl)methoxy)-4-methoxyphenyl)acetic acid (216c)

Compound 216c was prepared according to the procedure reported in step-3 of scheme 1, from ethyl 2-(2-((5-(3-(aminomethyl)phenyl)-2-(2,2,2-trifluoro-1-hydroxyethyl)benzofuran-3-yl)methoxy)-4-methoxyphenyl)acetate (216b) (400 mg, 0.736 mmol) in THF (3 mL) using a solution of lithium hydroxide hydrate (195 mg, 4.64 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(2,2,2-trifluoro-1-hydroxyethyl)benzofuran-3-yl)methoxy)-4-methoxyphenyl)acetic acid (216c) (240 mg, 30% yield) HCl salt as a white solid; $^1H$ NMR (300 MHz, DMSO-$d_6$) δ 12.07 (s, 1H, $D_2O$ exchangeable), 8.48 (s, 3H, $D_2O$ exchangeable), 8.05 (s, 1H), 7.90 (s, 1H), 7.84-7.70 (m, 3H), 7.58-7.44 (m, 2H), 7.36 (d, J=6.0 Hz, 1H, $D_2O$ exchangeable), 7.11 (d, J=8.3 Hz, 1H), 6.86 (d, J=2.4 Hz, 1H), 6.53 (dd, J=8.3, 2.3 Hz, 1H), 5.79 (s, 1H), 5.57-5.30 (m, 2H), 4.11 (s, 2H), 3.78 (s, 3H), 3.45 (s, 2H); $^{19}F$ NMR (282 MHz, DMSO) δ −75.10; MS (ES+): 516.0 (M+1); Analysis calculated for $C_{27}H_{24}F_3NO_6 \cdot HCl \cdot 0.75H_2O$: C, 57.35; H, 4.72; Cl, 6.27; N, 2.48. Found: C, 57.56; H, 4.71; Cl, 5.97; N, 2.69.

Scheme 217

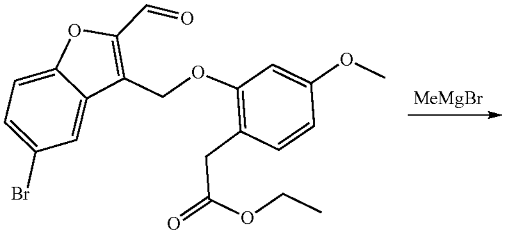

215a

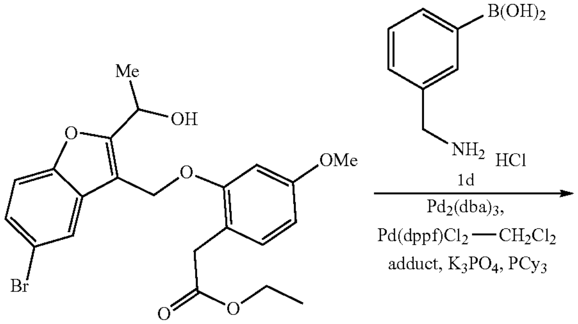

217a

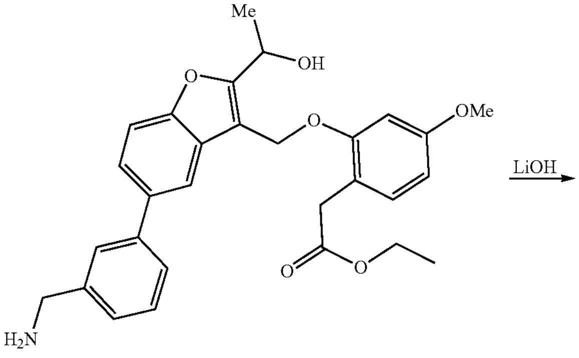

217b

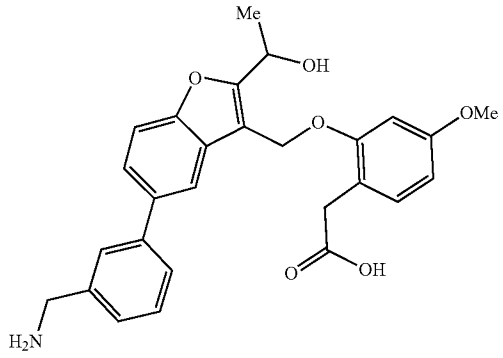

217c

Preparation of 2-(2-((5-(3-(aminomethyl)phenyl)-2-(1-hydroxyethyl)benzofuran-3-yl)methoxy)-4-methoxyphenyl)acetic acid (217c)

Step-1: Preparation of ethyl 2-(2-((5-bromo-2-(1-hydroxyethyl)benzofuran-3-yl)methoxy)-4-methoxyphenyl)acetate (217a)

Compound 217a was prepared according to the procedure reported in step-7 of scheme 3, from ethyl 2-(2-((5-bromo-2-formylbenzofuran-3-yl)methoxy)-4-methoxyphenyl)acetate (215a) (3 g, 6.71 mmol) in THF (100 mL) using methylmagnesium bromide (5.27 mL, 7.38 mmol; 1.4 M in THF) and stirring at 0° C. for 1 h. This gave after work up and purification using flash column chromatography [silica gel, eluting with EtOAc in hexane from 0-100%]ethyl 2-(2-((5-bromo-2-(1-hydroxyethyl)benzofuran-3-yl)methoxy)-4-methoxyphenyl)acetate (217a) (2.4 g, 77% yield) as a clear oil; $^1$H NMR (300 MHz, DMSO-$d_6$) δ 7.79 (d, J=2.0 Hz, 1H), 7.57 (d, J=8.7 Hz, 1H), 7.46 (dd, J=8.7, 2.1 Hz, 1H), 7.09 (d, J=8.3 Hz, 1H), 6.81 (d, J=2.4 Hz, 1H), 6.50 (dd, J=8.3, 2.4 Hz, 1H), 5.63 (d, J=4.7 Hz, 1H), 5.37-5.20 (m, 2H), 5.17-5.02 (m, 1H), 3.92 (q, J=7.1 Hz, 2H), 3.78 (s, 3H), 3.44 (s, 2H), 1.46 (d, J=6.5 Hz, 3H), 0.97 (t, J=7.1 Hz, 3H); MS (ES+): 485.10 and 487.10 (M+Na).

Step-2: Preparation of ethyl 2-(2-((5-(3-(aminomethyl)phenyl)-2-(1-hydroxyethyl)benzofuran-3-yl)methoxy)-4-methoxyphenyl)acetate (217b)

Compound 217b was prepared according to the procedure reported in step-2 of scheme 1, from ethyl 2-(2-((5-bromo-2-(1-hydroxyethyl)benzofuran-3-yl)methoxy)-4-methoxyphenyl)acetate (217a) (500 mg, 1.079 mmol) in dioxane (30 mL) using 3-(aminomethyl)phenylboronic acid hydrochloride (1d) (405 mg, 2.158 mmol), 4 M solution of $K_3PO_4$ (1.079 mL, 4.32 mmol), tricyclohexylphosphine (91 mg, 0.324 mmol), $Pd_2(dba)_3$ (99 mg, 0.108 mmol), $PdCl_2$(dppf)-$CH_2Cl_2$ adduct (88 mg, 0.108 mmol) and heating at 100° C. for 2 h. This gave after workup and purification using flash column chromatography [silica gel (40 g), eluting with DMA-80 in DCM from 0-100%] ethyl 2-(2-((5-(3-(aminomethyl)phenyl)-2-(1-hydroxyethyl)benzofuran-3-yl)methoxy)-4-methoxyphenyl)acetate (217b) (100 mg, 19% yield) as a yellow oil; MS (ES+): 490.2 (M+1).

Step-3: Preparation of 2-(2-((5-(3-(aminomethyl)phenyl)-2-(1-hydroxyethyl)benzofuran-3-yl)methoxy)-4-methoxyphenyl)acetic acid (217c)

Compound 217c was prepared according to the procedure reported in step-3 of scheme 1, from ethyl 2-(2-((5-(3-(aminomethyl)phenyl)-2-(1-hydroxyethyl)benzofuran-3-yl)methoxy)-4-methoxyphenyl)acetate (217b) (100 mg, 0.204 mmol) in THF (3 mL) using a solution of lithium hydroxide hydrate (136 mg, 3.24 mmol) in water (1 mL) and stirring overnight at RT.

This gave after workup and purification using reverse phase column chromatography [C18 column (30 g), eluting with ACN in water (containing 0.1% HCl) from 0-100%] 2-(2-((5-(3-(aminomethyl)phenyl)-2-(1-hydroxyethyl)benzofuran-3-yl)methoxy)-4-methoxyphenyl)acetic acid (217c) (4.8 mg, 1% yield) HCl salt as a white solid; $^1$H NMR (300 MHz, DMSO-$d_6$) δ 12.02 (s, 1H), 8.25 (s, 3H), 7.97 (d, J=1.7 Hz, 1H), 7.85 (s, 1H), 7.77-7.68 (m, 2H), 7.64 (dd, J=8.6, 1.8 Hz, 1H), 7.52 (t, J=7.6 Hz, 1H), 7.44 (d, J=7.6 Hz, 1H), 7.09 (d, J=8.3 Hz, 1H), 6.85 (d, J=2.4 Hz, 1H), 6.57-6.47 (m, 1H), 5.59 (d, J=4.7 Hz, 1H), 5.35 (q, J=11.9 Hz, 2H), 5.20-5.07 (m, 1H), 4.12 (s, 2H), 3.77 (s, 3H), 3.42 (s, 2H), 1.48 (d, J=6.5 Hz, 3H); (ES+): 462.2 (M+1).

Scheme 218

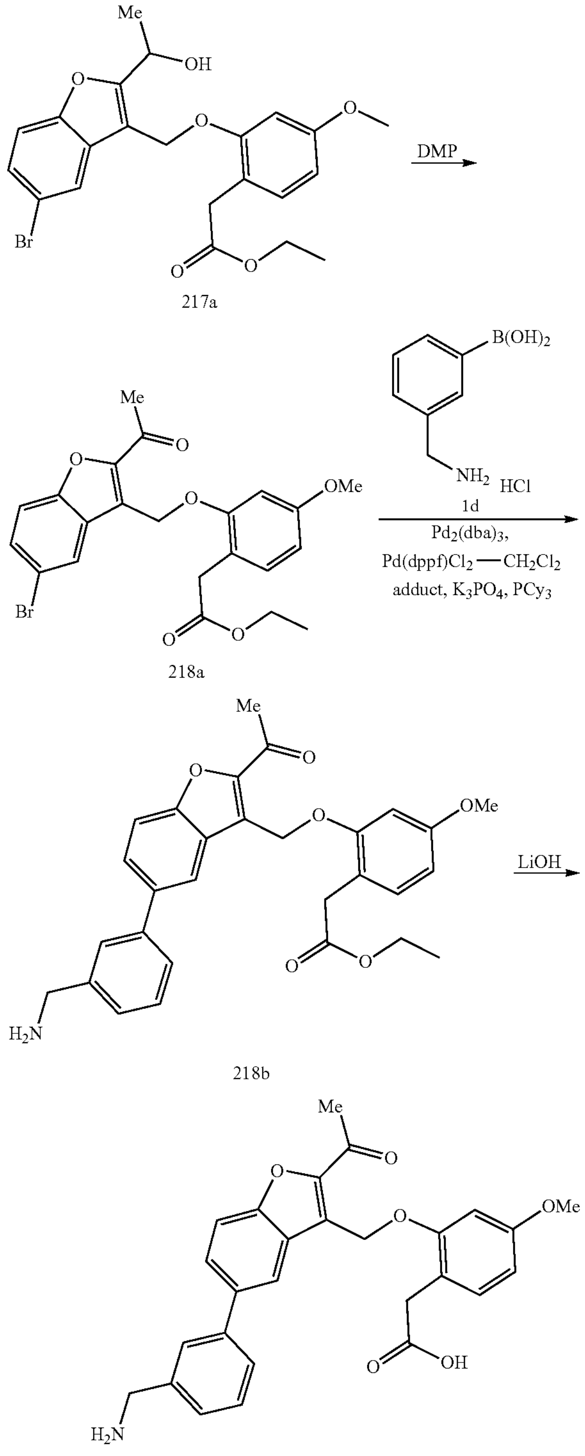

217a

218a

218b

218c

Preparation of 2-(2-((-acetyl-5-(3-(aminomethyl)phenyl)benzofuran-3-yl)methoxy)-4-methoxyphenyl)acetic acid (218c)

Step-1: Preparation of ethyl 2-(2-((2-acetyl-5-bromobenzofuran-3-yl)methoxy)-4-methoxyphenyl)acetate (218a)

Compound 218a was prepared according to the procedure reported in step-1 of scheme 141, from ethyl 2-(2-((5-bromo-2-(1-hydroxyethyl)benzofuran-3-yl)methoxy)-4-methoxyphenyl)acetate (217a) (1.6 g, 3.45 mmol) in DCM (50 mL) using Dess-Martin periodinane (DMP, 2.051 g, 4.83 mmol) and stirring at RT for 3 h. This gave after workup and purification using flash column chromatography [silica gel, eluting with EtOAc in hexane from 0-100%] ethyl 2-(2-((2-acetyl-5-bromobenzofuran-3-yl)methoxy)-4-methoxyphenyl)acetate (218a) (1.3 g, 82% yield) as a white solid; $^1$H NMR (300 MHz, DMSO-$d_6$) δ 8.05 (dd, J=2.0, 0.8 Hz, 1H), 7.81-7.68 (m, 2H), 7.10 (d, J=8.3 Hz, 1H), 6.70 (d, J=2.4 Hz, 1H), 6.50 (dd, J=8.3, 2.4 Hz, 1H), 5.59 (s, 2H), 3.92 (q, J=7.1 Hz, 2H), 3.74 (s, 3H), 3.48 (s, 2H), 2.63 (s, 3H), 0.97 (t, J=7.1 Hz, 3H); (ES+): 483.0 (M+Na).

Step-2: Preparation of ethyl 2-(2-((2-acetyl-5-(3-(aminomethyl)phenyl)benzofuran-3-yl)methoxy)-4-methoxyphenyl)acetate (218b)

Compound 218b was prepared according to the procedure reported in step-2 of scheme 1, from ethyl 2-(2-((2-acetyl-5-bromobenzofuran-3-yl)methoxy)-4-methoxyphenyl)acetate (218a) (500 mg, 1.084 mmol) in dioxane (30 mL) using 3-(aminomethyl)phenylboronic acid hydrochloride (1d) (406 mg, 2.168 mmol), 4 M solution of $K_3PO_4$ (0.320 mL, 1.279 mmol), tricyclohexylphosphine (91 mg, 0.325 mmol), $Pd_2(dba)_3$ (23.07 mg, 0.108 mmol), $PdCl_2(dppf)$-$CH_2Cl_2$ adduct (89 mg, 0.108 mmol) and heating at 100° C. for 2 h. This gave after workup and purification using flash column chromatography [silica gel (40 g), eluting with DMA-80 in DCM from 0-100%] ethyl 2-(2-((2-acetyl-5-(3-(aminomethyl)phenyl)benzofuran-3-yl)methoxy)-4-methoxyphenyl)acetate (218b) (300 mg, 57% yield) as a yellow oil; MS (ES+): 488.2 (M+1).

Step-3: Preparation of 2-(2-((2-acetyl-5-(3-(aminomethyl)phenyl)benzofuran-3-yl)methoxy)-4-methoxyphenyl)acetic acid (218c)

Compound 218c was prepared according to the procedure reported in step-3 of scheme 1, from ethyl 2-(2-((2-acetyl-5-(3-(aminomethyl)phenyl)benzofuran-3-yl)methoxy)-4-methoxyphenyl)acetate (218b) (300 mg, 0.615 mmol) in THF (3 mL) using a solution of lithium hydroxide hydrate (136 mg, 3.25 mmol) in water (1 mL) and stirring overnight at RT.

This gave after workup and purification using reverse phase column chromatography [C18 column (30 g), eluting with ACN in water (containing 0.1% HCl) from 0-100%] 2-(2-((2-acetyl-5-(3-(aminomethyl)phenyl)benzofuran-3-yl)methoxy)-4-methoxyphenyl)acetic acid (218c) (2.5 mg, 0.502% yield) HCl salt as a white solid; $^1$H NMR (300 MHz, DMSO-$d_6$) δ 8.34 (s, 2H), 8.19 (s, 1H), 7.93-7.85 (m, 3H), 7.75 (d, J=7.7 Hz, 1H), 7.53 (t, J=7.6 Hz, 1H), 7.47 (d, J=7.4 Hz, 1H), 7.09 (d, J=8.4 Hz, 1H), 6.72 (d, J=2.4 Hz, 1H), 6.50 (dd, J=8.3, 2.3 Hz, 1H), 5.67 (s, 2H), 4.11 (s, 2H), 3.72 (s, 3H), 3.44 (s, 2H), 2.66 (s, 3H); (ES+): 460.2 (M+1).

Scheme 219

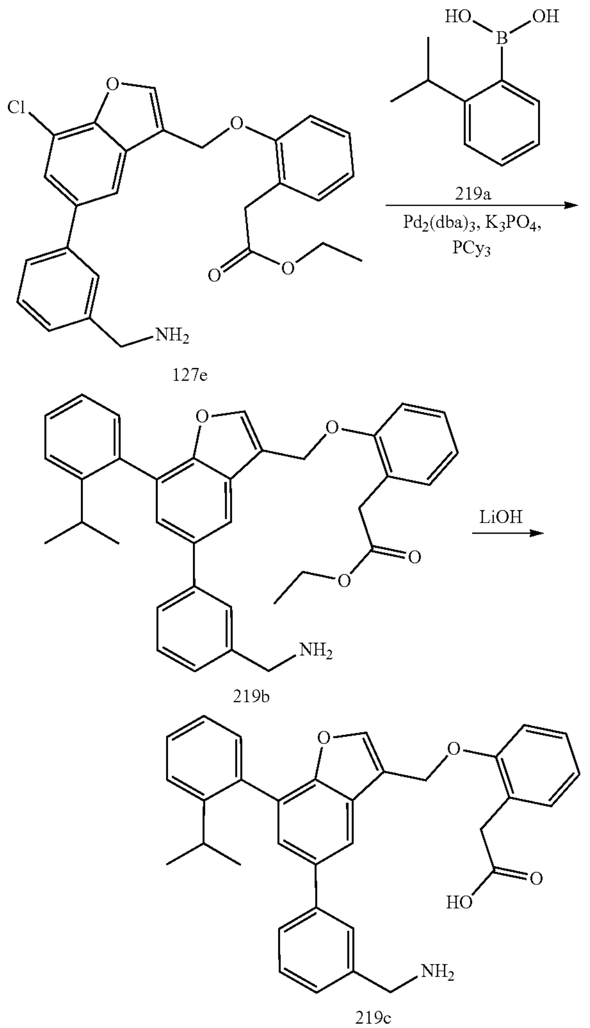

127e

219b

219c

Preparation of 2-(2-((5-(3-(aminomethyl)phenyl)-7-(2-isopropylphenyl)benzofuran-3-yl)methoxy)phenyl)acetic acid (219c)

Step-1: Preparation of ethyl 2-(2-((5-(3-(aminomethyl)phenyl)-7-(2-isopropylphenyl)benzofuran-3-yl)methoxy)phenyl)acetate (219b)

Compound 219b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (350 mg, 0.778 mmol) in dioxane (12 mL) using (2-isopropylphenyl)boronic acid (219a) (159 mg, 0.972 mmol), 4 M solution of $K_3PO_4$ (0.778 mL, 3.11 mmol), tricyclohexylphosphine (43.6 mg, 0.156 mmol), $Pd_2(dba)_3$ (71.2 mg, 0.078 mmol) and heating at 115° C. for 12 h. This gave after workup and purification using flash column chromatography [silica gel (24 g), eluting with DMA-80 in DCM from 0-100%] ethyl 2-(2-((5-(3-(aminomethyl)phenyl)-7-(2-isopropylphenyl)benzofuran-3-yl)methoxy)phenyl)acetate (219b) (120 mg, 29% yield) as a clear oil; (ES+): 534.30 (M+1).

Step-2: Preparation of 2-(2-((5-(3-(aminomethyl)phenyl)-7-(2-isopropylphenyl)benzofuran-3-yl)methoxy)phenyl)acetic acid (219c)

Compound 219c was prepared according to the procedure reported in step-3 of scheme 1, from ethyl 2-(2-((5-(3-(aminomethyl)phenyl)-7-(2-isopropylphenyl)benzofuran-3-yl)methoxy)phenyl)acetate (219b) (120 mg, 0.225 mmol) in THF (3 mL) using a solution of lithium hydroxide hydrate (28.3 mg, 0.675 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(2-isopropylphenyl)benzofuran-3-yl)methoxy)phenyl)acetic acid (219c) (35.7 mg, 31% yield) HCl salt as a white solid; $^1H$ NMR (300 MHz, DMSO-$d_6$) δ 12.15 (s, 1H, $D_2O$ exchangeable), 8.32 (s, 2H, $D_2O$ exchangeable), 8.10 (s, 1H), 8.05 (d, J=1.8 Hz, 1H), 7.92 (s, 1H), 7.81 (d, J=7.6 Hz, 1H), 7.57-7.40 (m, 5H), 7.36-7.28 (m, 3H), 7.24 (t, J=7.8 Hz, 2H), 6.94 (t, J=7.2 Hz, 1H), 5.35 (s, 2H), 4.10 (s, 2H), 3.57 (s, 2H), 2.85-2.69 (m, 1H), 1.12 (d, J=6.8 Hz, 6H); (ES+): 506.20 (M+1).

Scheme 220

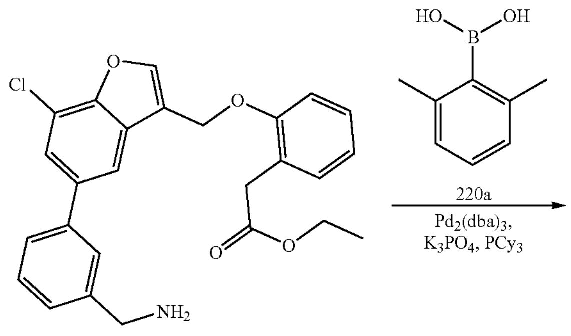

127e

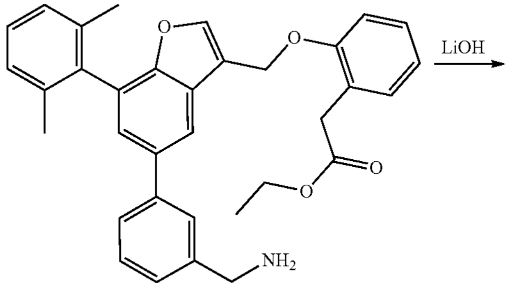

220b

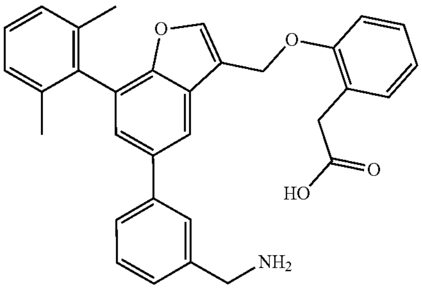

220c

Preparation of 2-(2-((5-(3-(aminomethyl)phenyl)-7-(2,6-dimethylphenyl)benzofuran-3-yl)methoxy)phenyl)acetic acid (220c)

Step-1: Preparation of ethyl 2-(2-((5-(3-(aminomethyl)phenyl)-7-(2,6-dimethylphenyl)benzofuran-3-yl)methoxy)phenyl)acetate (220b)

Compound 220b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (350 mg, 0.778 mmol) in dioxane (12 mL) using (2,6-dimethylphenyl)boronic acid (220a) (146 mg, 0.972 mmol), 4 M solution of $K_3PO_4$ (0.778 mL, 3.11 mmol), tricyclohexylphosphine (43.6 mg, 0.156 mmol), $Pd_2(dba)_3$ (71.2 mg, 0.078 mmol) and heating at 115° C. for 12 h. This gave after workup and purification using flash column chromatography [silica gel (24 g), eluting with DMA-80 in DCM from 0-100%] ethyl 2-(2-((5-(3-(aminomethyl)phenyl)-7-(2,6-dimethylphenyl)benzofuran-3-yl)methoxy)phenyl)acetate (220b) (168 mg, 42% yield) as a clear oil; (ES+): 520.20 (M+1).

Step-2: Preparation of 2-(2-((5-(3-(aminomethyl)phenyl)-7-(2,6-dimethylphenyl)benzofuran-3-yl)methoxy)phenyl)acetic acid (220c)

Compound 220c was prepared according to the procedure reported in step-3 of scheme 1, from ethyl 2-(2-((5-(3-(aminomethyl)phenyl)-7-(2,6-dimethylphenyl)benzofuran-3-yl)methoxy)phenyl)acetate (220b) (168 mg, 0.323 mmol) in THF (3 mL) using a solution of lithium hydroxide hydrate (40.7 mg, 0.970 mmol) in water (1 mL) and stirring for overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(2,6-dimethylphenyl)benzofuran-3-yl)methoxy)phenyl)acetic acid (220c) (34.8 mg, 22% yield) HCl salt as a white solid; $^1H$ NMR (300 MHz, DMSO-$d_6$) δ 12.11 (s, 1H, $D_2O$ Exchangeable), 8.26 (s, 2H, $D_2O$ Exchangeable), 8.06 (s, 2H), 7.94 (s, 1H), 7.82 (dt, J=7.8, 1.6 Hz, 1H), 7.55-7.46 (m, 2H), 7.44 (d, J=7.7 Hz, 1H), 7.33-7.17 (m, 6H), 6.94 (td, J=7.2, 1.4 Hz, 1H), 5.36 (s, 2H), 4.09 (s, 2H), 3.57 (s, 2H), 2.00 (s, 6H); MS (ES+): 492.20 (M+1).

Scheme 221

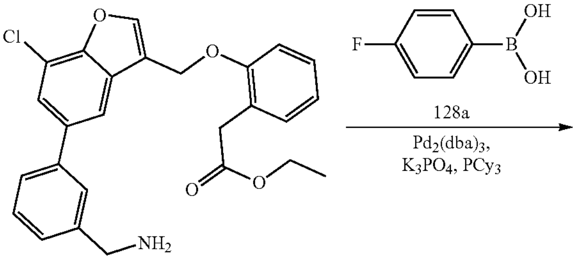

127e

-continued

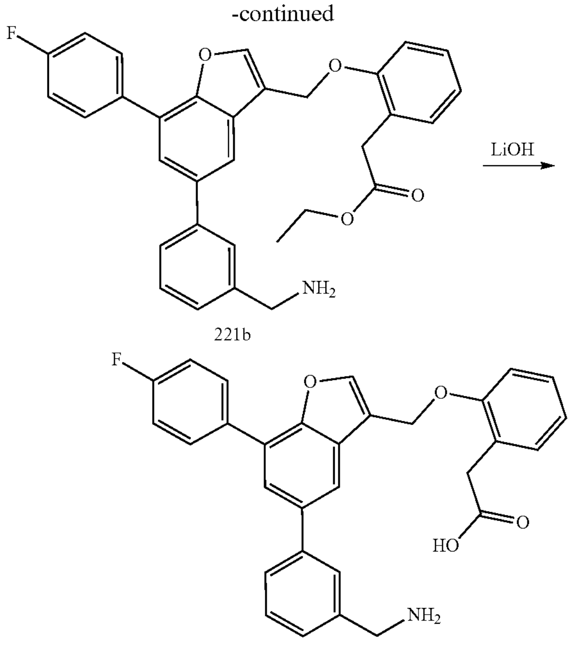

221b

221c

Preparation of 2-(2-((5-(3-(aminomethyl)phenyl)-7-(4-fluorophenyl)benzofuran-3-yl)methoxy)phenyl) acetic acid (221c)

Step-1: Preparation of ethyl 2-(2-((5-(3-(aminomethyl)phenyl)-7-(4-fluorophenyl)benzofuran-3-yl) methoxy)phenyl)acetate (221b)

Compound 221b was prepared according to the procedure reported in step-2 of scheme 1, from ethyl 2-(2-((5-(3-(aminomethyl)phenyl)-7-chlorobenzofuran-3-yl)methoxy) phenyl)acetate (127e) (350 mg, 0.778 mmol) in dioxane (12 mL) using (4-fluorophenyl)boronic acid (221a) (136 mg, 0.972 mmol), 4 M solution of $K_3PO_4$ (0.778 mL, 3.11 mmol), tricyclohexylphosphine (43.6 mg, 0.156 mmol), $Pd_2(dba)_3$ (71.2 mg, 0.078 mmol) and heating at 115° C. for 12 h. This gave after workup and purification using flash column chromatography [silica gel (24 g), eluting with DMA-80 in DCM from 0-50%] ethyl 2-(2-((5-(3-(aminomethyl)phenyl)-7-(4-fluorophenyl)benzofuran-3-yl)methoxy) phenyl)acetate (221b) (375 mg, 95% yield) as a clear oil; (ES+): 510.20 (M+1).

Step-2: Preparation of 2-(2-((5-(3-(aminomethyl) phenyl)-7-(4-fluorophenyl)benzofuran-3-yl) methoxy)phenyl)acetic acid (221c)

Compound 221c was prepared according to the procedure reported in step-3 of scheme 1, from ethyl 2-(2-((5-(3-(aminomethyl)phenyl)-7-(4-fluorophenyl)benzofuran-3-yl) methoxy)phenyl)acetate (221b) (375 mg, 0.736 mmol) in THF (3 mL) using a solution of lithium hydroxide hydrate (93 mg, 2.208 mmol) in water (1 mL) and stirring overnight at RT.

This gave after workup and purification using reverse phase column chromatography [C18 column (30 g), eluting with ACN in water (containing 0.1% HCl) from 0-100%] 2-(2-((5-(3-(aminomethyl)phenyl)-7-(4-fluorophenyl)benzofuran-3-yl)methoxy)phenyl)acetic acid (221c) (325 mg, 92% yield) HCl salt as a white solid; $^1H$ NMR (300 MHz, DMSO-$d_6$) δ 8.44 (s, 2H, $D_2O$ exchangeable), 8.22 (s, 1H), 8.06-7.96 (m, 4H), 7.89-7.79 (m, 2H), 7.54 (t, J=7.6 Hz, 1H), 7.50-7.36 (m, 3H), 7.32-7.18 (m, 3H), 6.93 (td, J=7.2, 1.4 Hz, 1H), 5.36 (s, 2H), 4.12 (s, 2H), 3.55 (s, 2H); $^{19}F$ NMR (282 MHz, DMSO-$d_6$) δ −113.78; MS (ES+): 482.20 (M+1).

Scheme 222

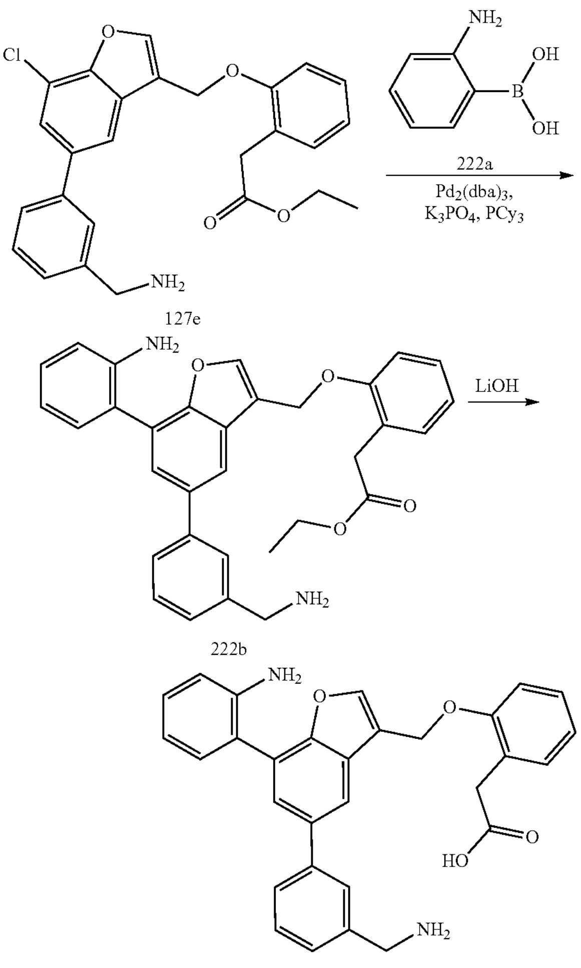

127e

222b

222c

Preparation of 2-(2-((5-(3-(aminomethyl)phenyl)-7-(2-aminophenyl)benzofuran-3-yl)methoxy)phenyl) acetic acid (222c)

Step-1: Preparation of ethyl 2-(2-((5-(3-(aminomethyl)phenyl)-7-(2-aminophenyl)benzofuran-3-yl) methoxy)phenyl)acetate (222b)

Compound 222b was prepared according to the procedure reported in step-2 of scheme 1, from ethyl 2-(2-((5-(3-(aminomethyl)phenyl)-7-chlorobenzofuran-3-yl)methoxy) phenyl)acetate (127e) (280 mg, 0.622 mmol) in dioxane (12 mL) using (2-aminophenyl)boronic acid (222a) (107 mg, 0.778 mmol), 4 M solution of $K_3PO_4$ (0.622 mL, 2.489 mmol), tricyclohexylphosphine (34.9 mg, 0.124 mmol), $Pd_2(dba)_3$ (57.0 mg, 0.062 mmol) and heating at 115° C. for 12 h. This gave after workup and purification using flash column chromatography [silica gel (24 g), eluting with DMA-80 in DCM from 0-50%] ethyl 2-(2-((5-(3-(aminomethyl)phenyl)-7-(2-aminophenyl)benzofuran-3-yl)methoxy)phenyl)acetate (222b) (168 mg, 53% yield) as a clear oil; (ES+): 507.30 (M+1).

Step-2: Preparation of 2-(2-((5-(3-(aminomethyl)phenyl)-7-(2-aminophenyl)benzofuran-3-yl)methoxy)phenyl)acetic acid (222c)

Compound 222c was prepared according to the procedure reported in step-3 of scheme 1, from ethyl 2-(2-((5-(3-(aminomethyl)phenyl)-7-(2-aminophenyl)benzofuran-3-yl)methoxy)phenyl)acetate (222b) (150 mg, 0.296 mmol) in THF (3 mL) using a solution of lithium hydroxide hydrate (37.3 mg, 0.888 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(2-aminophenyl)benzofuran-3-yl)methoxy)phenyl)acetic acid (222c) (2.3 mg, 2% yield) HCl salt as a white solid; $^1$H NMR (300 MHz, DMSO-$d_6$) δ 8.28 (s, 3H, $D_2O$ exchangeable), 8.14 (s, 1H), 8.03 (d, J=1.8 Hz, 1H), 7.94 (s, 1H), 7.83 (d, J=7.4 Hz, 1H), 7.74-7.64 (m, 1H), 7.54 (t, J=7.7 Hz, 1H), 7.45 (d, J=7.7 Hz, 1H), 7.37-7.16 (m, 5H), 6.95 (td, J=7.2, 1.5 Hz, 3H), 5.36 (s, 2H), 4.17-4.06 (m, 2H), 3.58 (s, 2H), 3.47 (s, 2H); (ES+): 479.20 (M+1).

Scheme 223

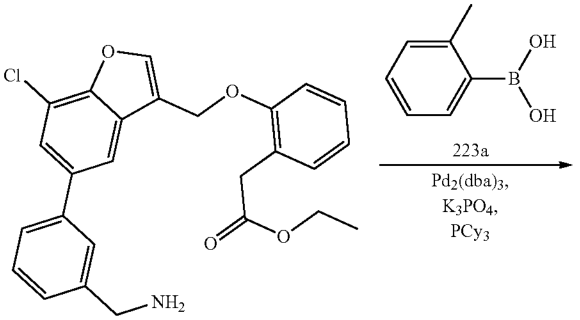

127e

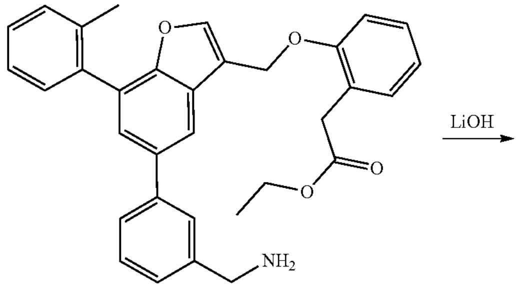

223b

-continued

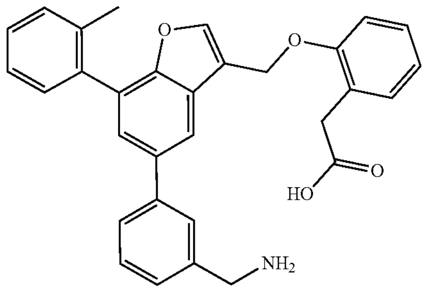

223c

Step-2: Preparation of 2-(2-((5-(3-(aminomethyl)phenyl)-7-(o-tolyl)benzofuran-3-yl)methoxy)phenyl)acetic acid (223c)

Compound 223c was prepared according to the procedure reported in step-3 of scheme 1, from ethyl 2-(2-((5-(3-(aminomethyl)phenyl)-7-(o-tolyl)benzofuran-3-yl)methoxy)phenyl)acetate (223b) (80 mg, 0.158 mmol) in THF (3 mL) using a solution of lithium hydroxide hydrate (19.92 mg, 0.475 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(o-tolyl)benzofuran-3-yl)methoxy)phenyl)acetic acid (223c) (21.9 mg, 29% yield) HCl salt as a white solid; $^1$H NMR (300 MHz, DMSO-$d_6$) δ 12.07 (s, 1H, $D_2O$ exchangeable), 8.40-8.11 (m, 3H, $D_2O$ exchangeable), 8.05 (s, 1H), 7.98 (d, J=1.8 Hz, 1H), 7.92-7.81 (m, 2H), 7.78-7.72 (m, 1H), 7.51 (d, J=1.8 Hz, 1H), 7.47-7.41 (m, 1H), 7.40-7.29 (m, 4H), 7.22-7.12 (m, 3H), 6.87 (td, J=7.3, 1.4 Hz, 1H), 5.29 (s, 2H), 4.04 (s, 2H), 3.49 (s, 2H), 2.12 (s, 3H); MS (ES+): 478.20 (M+1).

Scheme 224

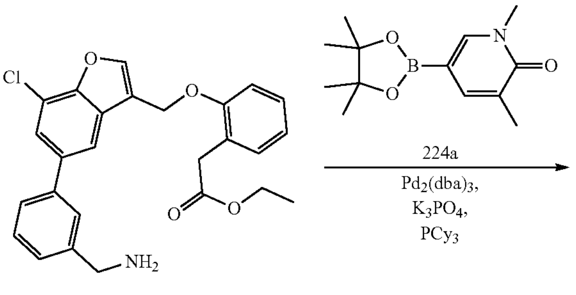

127e

-continued

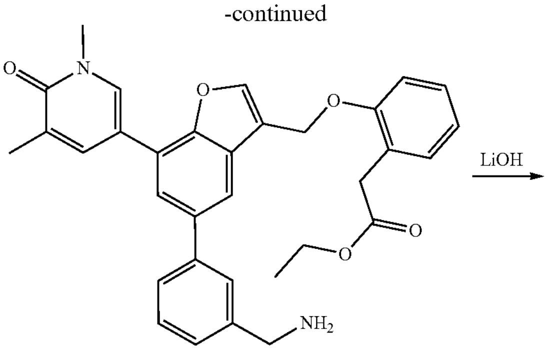

224b

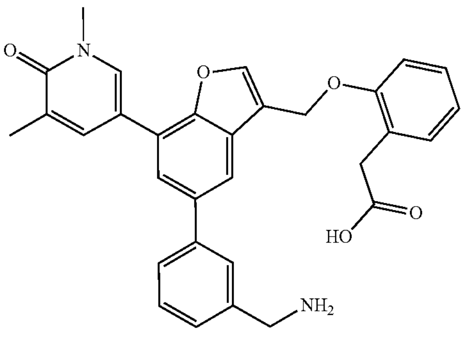

224c

Preparation of 2-(2-((5-(3-(aminomethyl)phenyl)-7-(1,5-dimethyl-6-oxo-1,6-dihydropyridin-3-yl)benzofuran-3-yl)methoxy)phenyl)acetic acid (224c)

Step-1: Preparation of ethyl 2-(2-((5-(3-(aminomethyl)phenyl)-7-(1,5-dimethyl-6-oxo-1,6-dihydropyridin-3-yl)benzofuran-3-yl)methoxy)phenyl)acetate (224b)

Compound 224b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (280 mg, 0.622 mmol) in dioxane (12 mL) using 1,3-dimethyl-5-(4,4,5,5-tetramethyl-1,3,2-dioxaborolan-2-yl)pyridin-2(1H)-one (224a) (194 mg, 0.778 mmol; CAS #1425045-01-7), 4 M solution of $K_3PO_4$ (0.622 mL, 2.489 mmol), tricyclohexylphosphine (34.9 mg, 0.124 mmol), $Pd_2(dba)_3$ (57.0 mg, 0.062 mmol) and heating at 115° C. for 12 h. This gave after workup and purification using flash column chromatography [silica gel (24 g), eluting with DMA-80 in DCM from 0-50%] ethyl 2-(2-((5-(3-(aminomethyl)phenyl)-7-(1,5-dimethyl-6-oxo-1,6-dihydropyridin-3-yl)benzofuran-3-yl)methoxy)phenyl)acetate (224b) (168 mg, 50% yield) as a clear oil; (ES+): 537.30 (M+1).

Step-2: Preparation of 2-(2-((5-(3-(aminomethyl)phenyl)-7-(1,5-dimethyl-6-oxo-1,6-dihydropyridin-3-yl)benzofuran-3-yl)methoxy)phenyl)acetic acid (224c)

Compound 224c was prepared according to the procedure reported in step-3 of scheme 1, from ethyl 2-(2-((5-(3-(aminomethyl)phenyl)-7-(1,5-dimethyl-6-oxo-1,6-dihydropyridin-3-yl)benzofuran-3-yl)methoxy)phenyl)acetate (224b) (117 mg, 0.218 mmol) in THF (3 mL) using a solution of lithium hydroxide hydrate (27.4 mg, 0.654 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-7-(1,5-dimethyl-6-oxo-1,6-dihydropyridin-3-yl)benzofuran-3-yl)methoxy)phenyl)acetic acid (224c) (69 mg, 62% yield) as HCl salt a white solid; $^1H$ NMR (300 MHz, DMSO-$d_6$) δ 12.16 (s, 1H, $D_2O$ exchangeable), 8.38 (s, 3H, $D_2O$ exchangeable), 8.32 (d, J=2.6 Hz, 1H), 8.21 (s, 1H), 8.04-7.97 (m, 2H), 7.94 (d, J=1.7 Hz, 1H), 7.87-7.77 (m, 2H), 7.54 (t, J=7.6 Hz, 1H), 7.47 (d, J=7.9 Hz, 1H), 7.33-7.17 (m, 3H), 6.93 (td, J=7.2, 1.4 Hz, 1H), 5.36 (s, 2H), 4.24-4.06 (m, 2H), 3.59 (s, 3H), 3.55 (s, 2H), 2.14 (s, 3H); (ES+): 509.20 (M+1); 507.20 (M−1); Analysis calculated for $C_{31}H_{28}N_2O_5 \cdot HCl \cdot 2H_2O$: C, 64.08; H, 5.72; Cl, 6.10; N, 4.82. Found: C, 64.14; H, 5.43; Cl, 5.96; N, 4.74.

Scheme 225

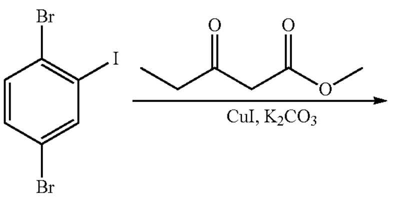

124a

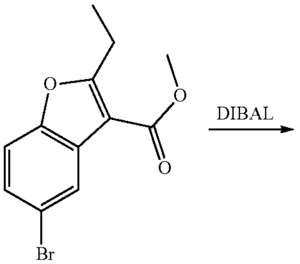

225a

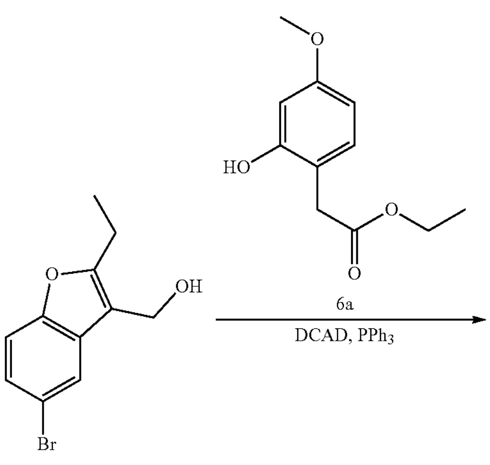

225b

-continued

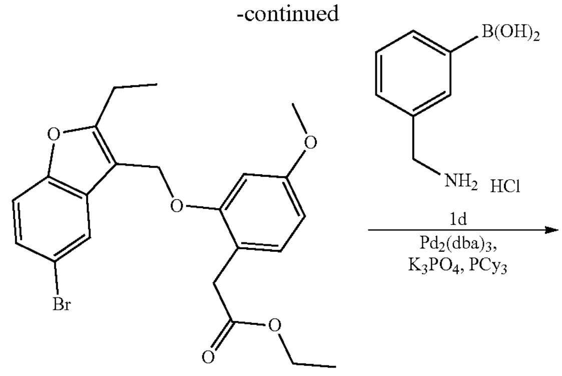

225c

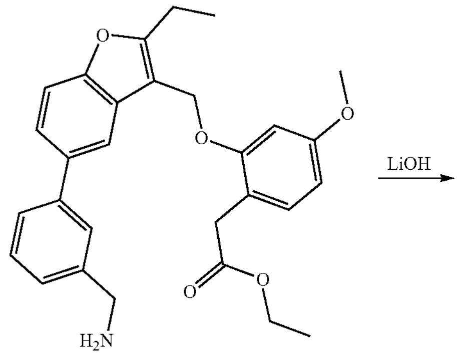

225d

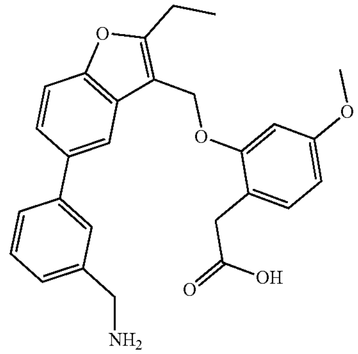

225e

Preparation of 2-(2-((5-(3-(aminomethyl)phenyl)-2-ethylbenzofuran-3-yl)methoxy)-4-methoxyphenyl) acetic acid (225e)

Step-1: Preparation of methyl 5-bromo-2-ethylbenzofuran-3-carboxylate (225a)

Compound 225a was prepared according to the procedure reported in step-1 of scheme 124, from 1,4-dibromo-2-iodobenzene (124a) (25 g, 69.1 mmol) in THF (250 mL) using methyl 3-oxopentanoate (13.01 mL, 104 mmol), copper(I) iodide (2.63 g, 13.82 mmol), potassium carbonate (47.7 g, 345 mmol) and heating at 80° C. for 15 h under an argon atmosphere. This gave after workup and purification using flash column chromatography [silica gel (24 g), eluting with EtOAc in hexane from 0-100%]methyl 5-bromo-2-ethylbenzofuran-3-carboxylate (225a) (880 mg, 5% yield) as a white solid; $^1$H NMR (300 MHz, DMSO-$d_6$) δ 7.99 (d, J=2.1 Hz, 1H), 7.62 (d, J=8.7 Hz, 1H), 7.50 (dd, J=8.7, 2.1 Hz, 1H), 3.90 (s, 3H), 3.17 (q, J=7.6 Hz, 2H), 1.28 (t, J=7.6 Hz, 3H); (ES+): 283.10 (M+1).

Step-2: Preparation of (5-bromo-2-ethylbenzofuran-3-yl)methanol (225b)

Compound 225b was prepared according to the procedure reported in step-4 of scheme 3, from methyl 5-bromo-2-ethylbenzofuran-3-carboxylate (225a) (9.25 g, 32.7 mmol) using DIBAL (1M in DCM) (82 mL, 82 mmol) and stirring at 0° C. for 2 h. This gave after workup and purification using flash column chromatography [silica gel (80 g), eluting with EtOAc in hexane from 0-100%] (5-bromo-2-ethylbenzofuran-3-yl)methanol (225b) (5.011 g, 60% yield) as a white solid; $^1$H NMR (300 MHz, DMSO-$d_6$) δ 7.80 (d, J=2.1 Hz, 1H), 7.48 (d, J=8.6 Hz, 1H), 7.37 (dd, J=8.6, 2.1 Hz, 1H), 5.06 (t, J=5.5 Hz, 1H), 4.55 (d, J=5.2 Hz, 2H), 2.81 (q, J=7.5 Hz, 2H), 1.23 (t, J=7.5 Hz, 3H).

Step-3: Preparation of ethyl 2-(2-((5-bromo-2-ethylbenzofuran-3-yl)methoxy)-4-methoxyphenyl)acetate (225c)

Compound 225c was prepared according to the procedure reported in step-3 of scheme 7, from (5-bromo-2-ethylbenzofuran-3-yl)methanol (225b) (2 g, 7.84 mmol) in DCM (80 mL) using triphenylphosphine (2.262 g, 8.62 mmol), ethyl 2-(2-hydroxy-4-methoxyphenyl)acetate (6a) (1.813 g, 8.62 mmol) using bis(4-chlorobenzyl) diazene-1,2-dicarboxylate (DCAD, 3.17 g, 8.62 mmol) in DCM (10 mL) and stirring at RT for 90 min. This gave after workup and purification using flash column chromatography [silica gel (24 g), eluting with EtOAc in hexane from 0-50%] ethyl 2-(2-((5-bromo-2-ethylbenzofuran-3-yl)methoxy)-4-methoxyphenyl)acetate (225c) (2.5 g, 71% yield) as a clear oil; $^1$H NMR (300 MHz, DMSO-$d_6$) δ 7.77 (d, J=2.0 Hz, 1H), 7.53 (d, J=8.7 Hz, 1H), 7.41 (dd, J=8.7, 2.1 Hz, 1H), 7.09 (d, J=8.3 Hz, 1H), 6.80 (d, J=2.4 Hz, 1H), 6.50 (dd, J=8.3, 2.4 Hz, 1H), 5.19 (s, 2H), 3.90 (q, J=7.1 Hz, 2H), 3.78 (s, 3H), 3.42 (s, 2H), 2.89 (q, J=7.5 Hz, 2H), 1.24 (t, J=7.5 Hz, 3H), 0.96 (t, J=7.1 Hz, 3H); (ES+): 447.00 (M+1).

Step-4: Preparation of ethyl 2-(2-((5-(3-(aminomethyl)phenyl)-2-ethylbenzofuran-3-yl)methoxy)-4-methoxyphenyl)acetate (225d)

Compound 225d was prepared according to the procedure reported in step-2 of scheme 1, from ethyl 2-(2-((5-bromo-2-ethylbenzofuran-3-yl)methoxy)-4-methoxyphenyl)acetate (225c) (250 mg, 0.559 mmol) in dioxane (12 mL) using 3-(aminomethyl)phenylboronic acid hydrochloride (1d) (105 mg, 0.699 mmol), 4 M solution of $K_3PO_4$ (0.559 mL, 2.236 mmol), tricyclohexylphosphine (31.3 mg, 0.112 mmol), $Pd_2(dba)_3$ (51.2 mg, 0.056 mmol) and heating at 115° C. for 12 h. This gave after workup and purification using flash column chromatography [silica gel (12 g), eluting with EtOAc in DCM from 0-100%] ethyl 2-(2-((5-(3-(aminomethyl)phenyl)-2-ethylbenzofuran-3-yl)methoxy)-4-methoxyphenyl)acetate (225d) (75 mg, 28% yield) (ES+): 474.30 (M+1).

Step-5: Preparation of 2-(2-((5-(3-(aminomethyl)phenyl)-2-ethylbenzofuran-3-yl)methoxy)-4-methoxyphenyl)acetic acid (225e)

Compound 225e was prepared according to the procedure reported in step-3 of scheme 1, from ethyl 2-(2-((5-(3-

(aminomethyl)phenyl)-2-ethylbenzofuran-3-yl)methoxy)-4-methoxyphenyl)acetate (225d) (70 mg, 0.148 mmol) in THF (3 mL) using a solution of lithium hydroxide hydrate (18.61 mg, 0.443 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-ethylbenzofuran-3-yl)methoxy)-4-methoxyphenyl)acetic acid (225e) (63.8 mg, 97% yield) HCl salt as a white solid; $^1$H NMR (300 MHz, DMSO-$d_6$) δ 12.05 (s, 1H, $D_2O$ exchangeable), 8.42 (s, 2H, $D_2O$ exchangeable), 7.95 (d, J=1.7 Hz, 1H), 7.88 (s, 1H), 7.73 (dt, J=7.7, 1.6 Hz, 1H), 7.69-7.56 (m, 2H), 7.54-7.38 (m, 2H), 7.08 (d, J=8.3 Hz, 1H), 6.83 (d, J=2.4 Hz, 1H), 6.50 (dd, J=8.3, 2.4 Hz, 1H), 5.26 (s, 2H), 4.10 (s, 2H), 3.76 (s, 3H), 3.39 (s, 2H), 2.91 (q, J=7.5 Hz, 2H), 1.26 (t, J=7.5 Hz, 3H); MS (ES+): 446.20 (M+1); (ES−): 444.20 (M−1).

Scheme 226

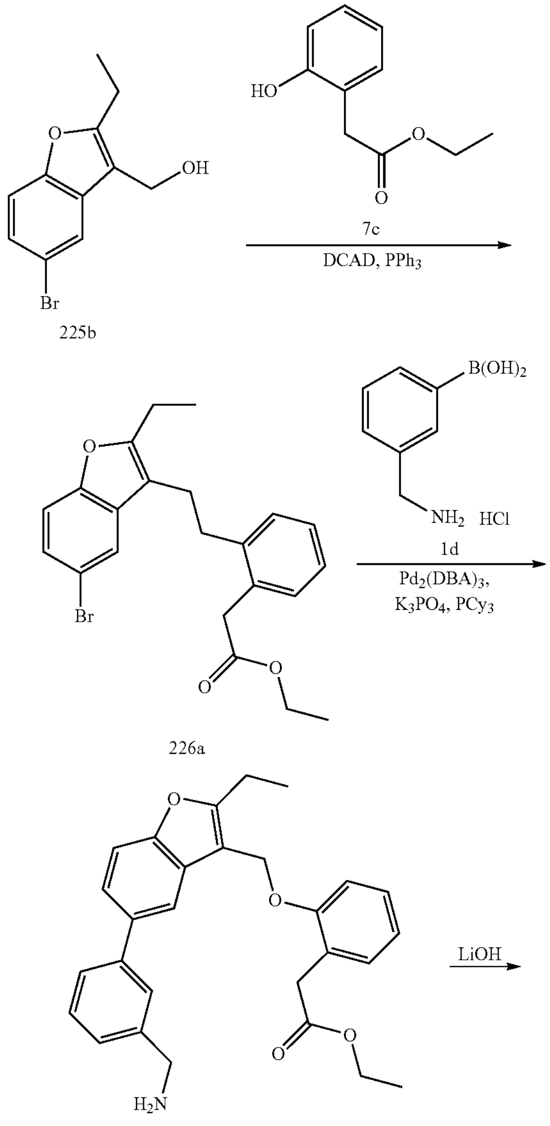

226b

-continued

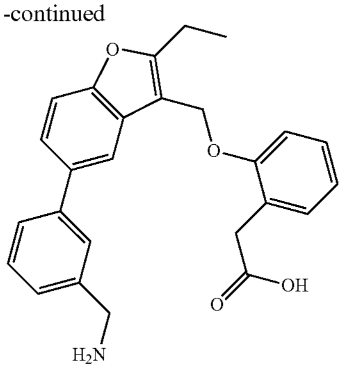

226c

Preparation of 2-(2-((5-(3-(aminomethyl)phenyl)-2-ethylbenzofuran-3-yl)methoxy)phenyl)acetic acid (226c)

Step-1, Preparation of ethyl 2-(2-((5-bromo-2-ethylbenzofuran-3-yl)methoxy)phenyl)acetate (226a)

Compound 226a was prepared according to the procedure reported in step-3 of scheme 7, from (5-bromo-2-ethylbenzofuran-3-yl)methanol (225b) (0.5 g, 1.96 mmol) in DCM (20 mL) using triphenylphosphine (0.565 g, 2.156 mmol), ethyl 2-(2-hydroxyphenyl)acetate (7c) (0.389 g, 2.156 mmol), bis(4-chlorobenzyl) diazene-1,2-dicarboxylate (DCAD, 0.792 g, 2.156 mmol) in DCM (10 mL) and stirring at RT for 30 min. This gave after workup and purification using flash column chromatography [silica gel (40 g), eluting with EtOAc in hexane from 0-50%] ethyl 2-(2-((5-bromo-2-ethylbenzofuran-3-yl)methoxy)phenyl)acetate (226a) (375 mg, 46% yield) as a clear oil; (ES+): 417.10 (M+1).

Step-2: Preparation of ethyl 2-(2-((5-(3-(aminomethyl)phenyl)-2-ethylbenzofuran-3-yl)methoxy)phenyl)acetate (226b)

Compound 226b was prepared according to the procedure reported in step-2 of scheme 1, from ethyl 2-(2-((5-bromo-2-ethylbenzofuran-3-yl)methoxy)phenyl)acetate (226a) (370 mg, 0.887 mmol) in dioxane (12 mL) using 3-(aminomethyl)phenylboronic acid hydrochloride (1d) (167 mg, 1.108 mmol), 4 M solution of $K_3PO_4$ (0.887 mL, 3.55 mmol), tricyclohexylphosphine (49.7 mg, 0.177 mmol), $Pd_2(dba)_3$ (81 mg, 0.089 mmol) and heating at 115° C. for 12 h. This gave after workup and purification using flash column chromatography [silica gel (12 g), eluting with EtOAc in hexane from 0-100%] ethyl 2-(2-((5-(3-(aminomethyl)phenyl)-2-ethylbenzofuran-3-yl)methoxy)phenyl)acetate (226b) (115 mg, 29% yield); (ES+): 444.2 (M+1).

Step-3: Preparation of 2-(2-((5-(3-(aminomethyl)phenyl)-2-ethylbenzofuran-3-yl)methoxy)phenyl)acetic acid (226c)

Compound 226c was prepared according to the procedure reported in step-3 of scheme 1, from ethyl 2-(2-((5-(3-(aminomethyl)phenyl)-2-ethylbenzofuran-3-yl)methoxy)phenyl)acetate (226b) (109 mg, 0.246 mmol) in THF (3 mL) using a solution of lithium hydroxide hydrate (30.9 mg, 0.737 mmol) in water (1 mL) and stirring overnight at RT.

This gave after workup and purification using reverse phase column chromatography [C18 column (30 g), eluting with ACN in water (containing 0.1% HCl) from 0-100%] 2-(2-((5-(3-(aminomethyl)phenyl)-2-ethylbenzofuran-3-yl)methoxy)phenyl)acetic acid (226c) (97.5 mg, 95% yield) HCl salt as a white solid; $^1$H NMR (300 MHz, DMSO-$d_6$) δ 12.08 (s, 1H, $D_2O$ exchangeable), 8.35 (s, 3H, $D_2O$ exchangeable), 7.93 (d, J=1.8 Hz, 1H), 7.86 (s, 1H), 7.73 (dt, J=7.6, 1.7 Hz, 1H), 7.67-7.55 (m, 2H), 7.51 (t, J=7.6 Hz, 1H), 7.44 (d, J=7.5 Hz, 1H), 7.33-7.22 (m, 2H), 7.19 (dd, J=7.4, 1.5 Hz, 1H), 6.92 (td, J=7.0, 1.9 Hz, 1H), 5.26 (s, 2H), 4.10 (s, 2H), 3.49 (s, 2H), 2.90 (q, J=7.5 Hz, 2H), 1.25 (t, J=7.5 Hz, 3H); MS (ES+): 416.20 (M+1); (ES−): 414.10 (M−1).

Scheme 227

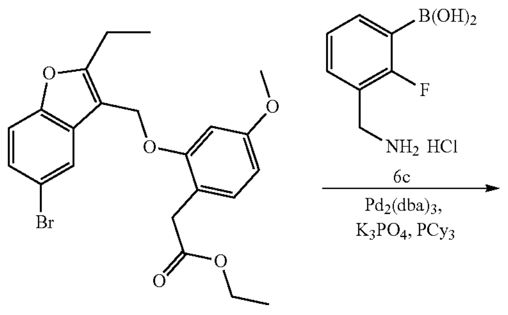

225c

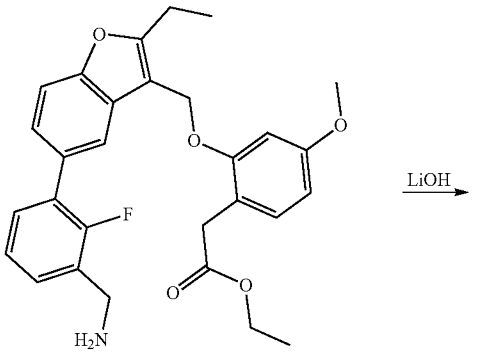

227a

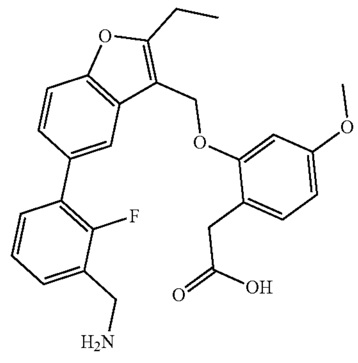

227b

Preparation of 2-(2-((5-(3-(aminomethyl)-2-fluorophenyl)-2-ethylbenzofuran-3-yl)methoxy)-4-methoxyphenyl)acetic acid (227b)

Step-1: Preparation of ethyl 2-(2-((5-(3-(aminomethyl)-2-fluorophenyl)-2-ethylbenzofuran-3-yl)methoxy)-4-methoxyphenyl)acetate (227a)

Compound 227a was prepared according to the procedure reported in step-2 of scheme 1, from ethyl 2-(2-((5-bromo-2-ethylbenzofuran-3-yl)methoxy)-4-methoxyphenyl)acetate (225c) (250 mg, 0.559 mmol) in dioxane (12 mL) using 3-(aminomethyl)-2-fluorophenylboronic acid hydrochloride (6c) (118 mg, 0.699 mmol), 4 M solution of $K_3PO_4$ (0.559 mL, 2.236 mmol), tricyclohexylphosphine (31.3 mg, 0.112 mmol), $Pd_2(dba)_3$ (51.2 mg, 0.056 mmol) and heating at 115° C. for 12 h. This gave after workup and purification using flash column chromatography [silica gel (12 g), eluting with EtOAc in DCM from 0-100%] ethyl 2-(2-((5-(3-(aminomethyl)-2-fluorophenyl)-2-ethylbenzofuran-3-yl)methoxy)-4-methoxyphenyl)acetate (227a) (250 mg, 0.559 mmol); (ES+): 492.20 (M+1).

Step-2: Preparation of 2-(2-((5-(3-(aminomethyl)-2-fluorophenyl)-2-ethylbenzofuran-3-yl)methoxy)-4-methoxyphenyl)acetic acid (227b)

Compound 227b was prepared according to the procedure reported in step-3 of scheme 1, from ethyl 2-(2-((5-(3-(aminomethyl)-2-fluorophenyl)-2-ethylbenzofuran-3-yl)methoxy)-4-methoxyphenyl)acetate (227a)(240 mg, 0.488 mmol) in THF (3 mL) using a solution of lithium hydroxide hydrate (61.5 mg, 1.465 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)-2-fluorophenyl)-2-ethylbenzofuran-3-yl)methoxy)-4-methoxyphenyl)acetic acid (227b) (30 mg, 13% yield) HCl salt as a white solid; $^1$H NMR (300 MHz, DMSO-$d_6$) δ 8.79 (s, 2H, $D_2O$ exchangeable), 7.80 (s, 1H), 7.68-7.49 (m, 3H), 7.44 (dt, J=8.5, 1.9 Hz, 1H), 7.36 (t, J=7.6 Hz, 1H), 7.07 (d, J=8.3 Hz, 1H), 6.81 (d, J=2.4 Hz, 1H), 6.49 (dd, J=8.3, 2.3 Hz, 1H), 5.24 (s, 2H), 4.14 (s, 2H), 3.75 (s, 3H), 3.38 (s, 2H), 2.91 (q, J=7.5 Hz, 2H), 1.26 (t, J=7.5 Hz, 3H); $^{19}$F NMR (282 MHz, DMSO-$d_6$) δ −122.26; (ES+): 464.20 (M+1); (ES−): 462.10 (M−1).

Scheme 228

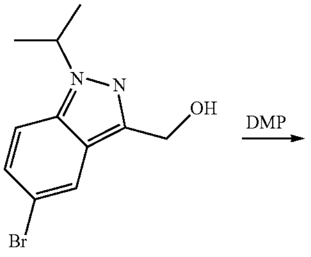

182b

-continued

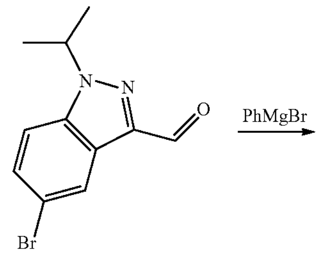

228a

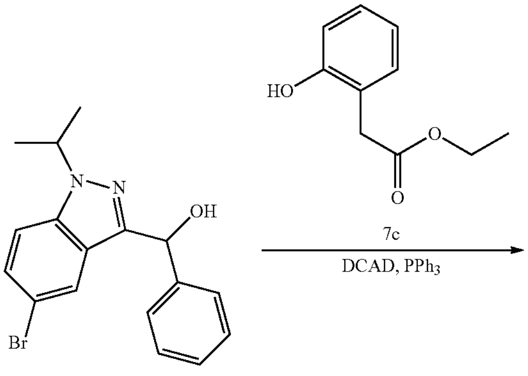

228b

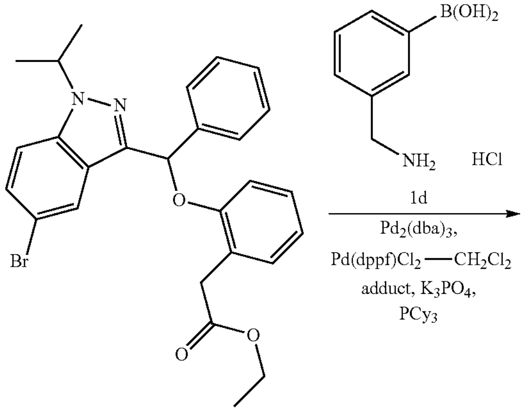

228c

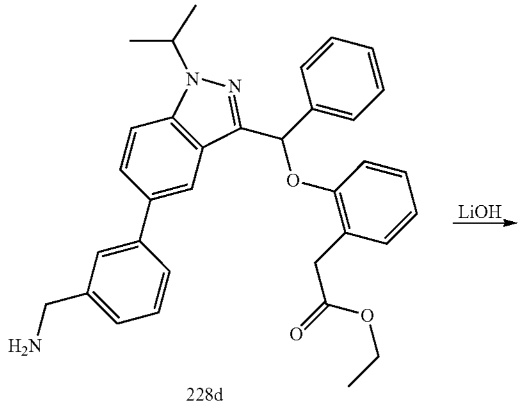

228d

-continued

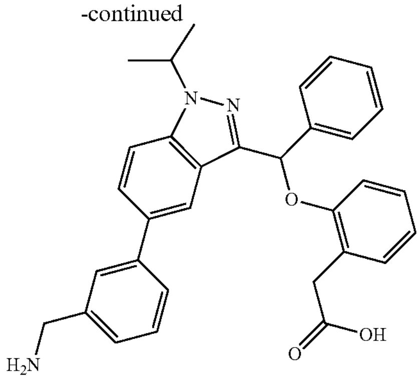

228e

Preparation of 2-(2-((5-(3-(aminomethyl)phenyl)-1-isopropyl-1H-indazol-3-yl)(phenyl)methoxy)phenyl) acetic acid (228e)

Step-1: Preparation of 5-bromo-1-isopropyl-1H-indazole-3-carbaldehyde (228a)

Compound 228a was prepared according to the procedure reported in step-1 of scheme 141, from (5-bromo-1-isopropyl-1H-indazol-3-yl)methanol (182b) (2 g, 7.43 mmol) in DCM (40 mL) using Dess-Martin periodinane (DMP, 3.78 g, 8.92 mmol) and stirring at RT for 3 h.

This gave after workup and purification using flash column chromatography [silica gel, eluting with EtOAc in hexane from 0-100%] 5-bromo-1-isopropyl-1H-indazole-3-carbaldehyde (228a) (1.57 g, 79% yield) as a white solid; $^1$H NMR (300 MHz, DMSO-$d_6$) δ 10.15 (s, 1H), 8.26 (t, J=1.6 Hz, 1H), 8.01-7.87 (m, 1H), 7.68 (dt, J=8.9, 1.6 Hz, 1H), 5.20 (hept, J=6.6 Hz, 1H), 1.54 (d, J=6.6 Hz, 6H); MS (ES+): 267.00 & 269.00 (M+1).

Step-2: Preparation of (5-bromo-1-isopropyl-1H-indazol-3-yl)(phenyl)methanol (228b)

Compound 228b was prepared according to the procedure reported in step-7 of scheme 3, from 5-bromo-1-isopropyl-1H-indazole-3-carbaldehyde (228a) (500 mg, 1.872 mmol) in THF (10 mL) using phenyl magnesium bromide (1M in THF) (0.811 mL, 2.433 mmol) and stirring at −78° C. for 1 h. This gave after work up and purification using flash column chromatography [silica gel (40 g), eluting with EtOAc in hexane from 0-60%] (5-bromo-1-isopropyl-1H-indazol-3-yl)(phenyl)methanol (228b) (520 mg, 80% yield) as a white oil; $^1$H NMR (300 MHz, DMSO-$d_6$) δ 7.80 (d, J=1.8 Hz, 1H), 7.64 (d, J=8.9 Hz, 1H), 7.46-7.38 (m, 3H), 7.32 (dd, J=8.4, 6.8 Hz, 2H), 7.27-7.16 (m, 1H), 6.20 (d, J=4.2 Hz, 1H, $D_2O$ exchangeable), 6.06 (d, J=4.2 Hz, 1H), 4.94 (p, J=6.6 Hz, 1H), 1.46 (dd, J=6.6, 1.9 Hz, 6H); MS (ES+): 345.10 & 347.05 (M+1); (ES−): 343.00 & 345.05 (M−1).

Step-3: Preparation of ethyl 2-(2-((5-bromo-1-isopropyl-1H-indazol-3-yl)(phenyl)methoxy)phenyl) acetate (228c)

Compound 228c was prepared according to the procedure reported in step-3 of scheme 7, from (5-bromo-1-isopropyl- 1H-indazol-3-yl)(phenyl)methanol (228b) (500 mg, 1.448 mmol) in DCM (10 mL) using triphenylphosphine (456 mg, 1.738 mmol), ethyl 2-(2-hydroxyphenyl)acetate (7c) (274 mg, 1.521 mmol), bis(4-chlorobenzyl) diazene-1,2-dicarboxylate (DCAD, 638 mg, 1.738 mmol) in DCM (10 mL) and stirring at RT for 1 h. This gave after workup and purification using flash column chromatography [silica gel (24 g), eluting with EtOAc in hexane from 0-60%] ethyl 2-(2-((5-bromo-1-isopropyl-1H-indazol-3-yl)(phenyl) methoxy)phenyl)acetate (228c) (100 mg, 14% yield) as a white solid; MS (ES+): 507.10 & 509.10 (M+1).

Step-4: Preparation of ethyl 2-(2-((5-(3-(aminomethyl)phenyl)-1-isopropyl-1H-indazol-3-yl)(phenyl) methoxy)phenyl)acetate (228d)

Compound 228d was prepared according to the procedure reported in step-2 of scheme 1, from ethyl 2-(2-((5-bromo-1-isopropyl-1H-indazol-3-yl)(phenyl)methoxy)phenyl)acetate (228c) (100 mg, 0.197 mmol) in dioxane (2 mL) and THF (2 mL) using 3-(aminomethyl)phenylboronic acid hydrochloride (1d) (73.9 mg, 0.394 mmol), 2 M solution of $K_3PO_4$ (0.394 mL, 0.788 mmol), tricyclohexylphosphine (11.05 mg, 0.039 mmol), $Pd_2(dba)_3$ (18.05 mg, 0.020 mmol), $PdCl_2(dppf)$-$CH_2Cl_2$ adduct (16.09 mg, 0.020 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-isopropyl-1H-indazol-3-yl)(phenyl)methoxy)phenyl)acetate (228d) (50 mg, 48% yield) as a clear oil; MS (ES+): 534.30 (M+1); MS (ES−): 532.30 (M−1).

Step-5: Preparation of 2-(2-((5-(3-(aminomethyl) phenyl)-1-isopropyl-1H-indazol-3-yl)(phenyl) methoxy)phenyl)acetic acid (228e)

Compound 228e was prepared according to the procedure reported in step-3 of scheme 1, from ethyl 2-(2-((5-(3-(aminomethyl)phenyl)-1-isopropyl-1H-indazol-3-yl)(phenyl)methoxy)phenyl)acetate (228d) (50 mg, 0.094 mmol) in THF (2 mL) and MeOH (2 mL) using a solution of lithium hydroxide hydrate (23.59 mg, 0.562 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-1-isopropyl-1H-indazol-3-yl)(phenyl)methoxy)phenyl) acetic acid (228e) (5 mg, 11% yield) HCl salt as a white solid; $^1H$ NMR (300 MHz, DMSO-$d_6$) δ 12.20 (s, 1H, $D_2O$ exchangeable), 8.30 (s, 3H, $D_2O$ exchangeable), 7.79 (d, J=8.8 Hz, 1H), 7.72 (d, J=5.0 Hz, 2H), 7.68 (dd, J=8.7, 1.6 Hz, 1H), 7.55 (d, J=7.8 Hz, 1H), 7.48 (t, J=7.6 Hz, 1H), 7.40 (d, J=7.5 Hz, 1H), 7.30-7.23 (m, 5H), 7.23-7.11 (m, 2H), 7.01 (dd, J=7.5, 1.7 Hz, 1H), 6.75 (t, J=7.5 Hz, 1H), 6.39 (s, 1H), 5.14-4.83 (m, 1H), 4.21-3.97 (m, 2H), 3.56 (d, J=3.2 Hz, 2H), 1.49 (dd, J=6.6, 2.6 Hz, 6H); MS (ES+): 506.30 (M+1); (ES−): 504.20 (M−1).

Scheme 229

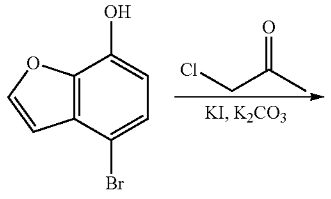

229a

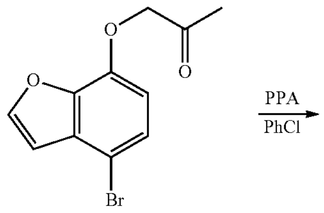

229b

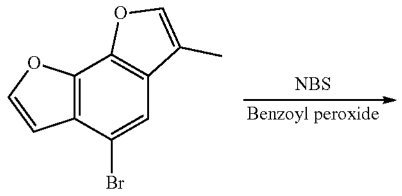

229c

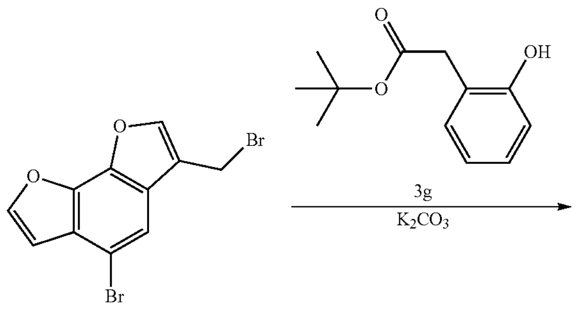

229d

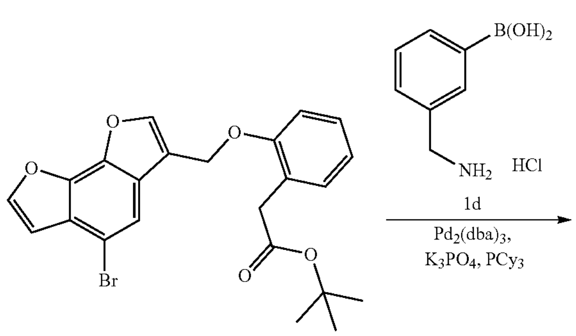

229e

-continued

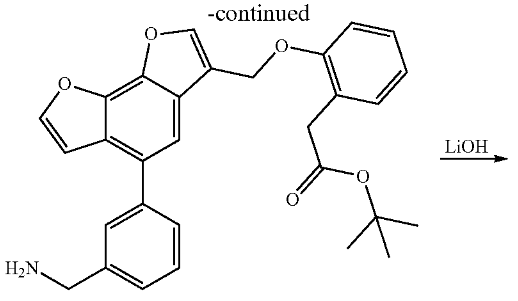

229f

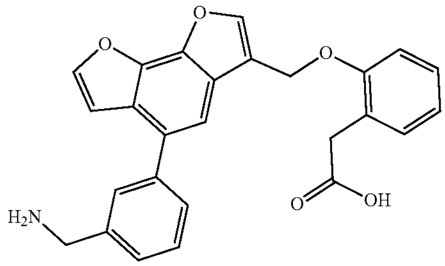

229g

Preparation of 2-(2-((5-(3-(aminomethyl)phenyl) benzo[1,2-b: 6,5-b']difuran-3-yl)methoxy)phenyl) acetic acid (229g)

Step-1: Preparation of 1-((4-bromobenzofuran-7-yl) oxy)propan-2-one (229b)

Compound 229b was prepared according to the procedure reported in step-1 of scheme 123, from 4-bromobenzofuran-7-ol (229a) (550 mg, 2.58 mmol; CAS #1522197-58-5) in DMF (8 mL) using potassium carbonate (1070 mg, 7.75 mmol), 1-chloropropan-2-one (956 mg, 10.33 mmol), KI (429 mg, 2.58 mmol) and heating at 80° C. in a sealed tube overnight. This gave after workup and purification using flash column chromatography [silica gel (24 g), eluting with EtOAc in hexanes from 0-60%] 1-((4-bromobenzofuran-7-yl)oxy)propan-2-one (229b) (548 mg, 79% yield) as a pale yellow oil; $^1$H NMR (300 MHz, DMSO-$d_6$) δ 8.13 (d, J=2.2 Hz, 1H), 7.34 (d, J=8.5 Hz, 1H), 6.91 (d, J=2.2 Hz, 1H), 6.82 (d, J=8.6 Hz, 1H), 5.04 (s, 2H), 2.19 (s, 3H); MS (ES+): 290.9 and 293.0 (M+Na).

Step-2: Preparation of 5-bromo-3-methylbenzo[1,2-b:6,5-b']difuran (229c)

Compound 229c was prepared according to the procedure reported in step-1 of scheme 123, from 1-((4-bromobenzofuran-7-yl)oxy)propan-2-one (229b) (546 mg, 2.029 mmol) in chlorobenzene (8 mL) using polyphosphoric acid (PPA) (2.43 g, 2.029 mmol) in chlorobenzene (16 mL) and stirring at 80° C. for 30 min and then at 120° C. for 16 h. This gave after workup and purification using flash column chromatography [silica gel (12 g) eluting with ethyl acetate in hexanes from 0-25%] 5-bromo-3-methylbenzo[1,2-b:6,5-b'] difuran (229c) (306 mg, 60% yield) as a white solid; $^1$H NMR (300 MHz, DMSO-$d_6$) δ 8.18 (d, J=2.2 Hz, 1H), 7.90 (q, J=1.3 Hz, 1H), 7.77 (s, 1H), 7.07 (d, J=2.2 Hz, 1H), 2.26 (d, J=1.3 Hz, 3H).

Step-3: Preparation of 5-bromo-3-(bromomethyl) benzo[1,2-b:6,5-b']difuran (229d)

Compound 229d was prepared according to the procedure reported in step-2 of scheme 58, from 5-bromo-3-methylbenzo[1,2-b:6,5-b']difuran (229c) (255 mg, 1.016 mmol) using NBS (199 mg, 1.117 mmol), benzoyl peroxide (36.9 mg, 0.152 mmol) in carbon tetrachloride (8 mL) and refluxing overnight. This gave after workup 5-bromo-3-(bromomethyl)benzo[1,2-b:6,5-b']difuran (229d) (335 mg) as a yellow oil and was used as such for the next step; $^1$H NMR (300 MHz, DMSO-$d_6$) δ 8.30 (s, 1H), 8.23 (d, J=2.2 Hz, 1H), 7.88 (s, 1H), 7.11 (d, J=2.2 Hz, 1H), 4.97 (s, 2H).

Step-4: Preparation of tert-butyl 2-(2-((5-bromobenzo[1,2-b:6,5-b']difuran-3-yl)methoxy)phenyl) acetate (229e)

Compound 229e was prepared according to the procedure reported in step-3 of scheme 7, from 5-bromo-3-(bromomethyl)benzo[1,2-b:6,5-b']difuran (229d) (0.332 g, 1.006 mmol) in acetone (10 mL) using tert-butyl 2-(2-hydroxyphenyl)acetate (3g) (0.314 g, 1.509 mmol), potassium carbonate (417 mg, 3.02 mmol) and stirring overnight at RT. This gave after workup and purification using flash column chromatography [silica gel (12 g), eluting with ethyl acetate in hexanes from 0-20%] tert-butyl 2-(2-((5-bromobenzo[1,2-b:6,5-b']difuran-3-yl)methoxy)phenyl)acetate (229e) (310 mg, 67% yield) as a yellow oil; $^1$H NMR (300 MHz, DMSO-$d_6$) δ 8.26-8.17 (m, 2H), 7.86 (s, 1H), 7.32-7.24 (m, 1H), 7.20 (d, J=8.1 Hz, 2H), 7.10 (d, J=2.2 Hz, 1H), 6.98-6.88 (m, 1H), 5.32 (s, 2H), 3.50 (s, 2H), 1.20 (s, 9H).

Step-5: Preparation of tert-butyl 2-(2-((5-(3-(aminomethyl)phenyl)benzo[1,2-b:6,5-b']difuran-3-yl) methoxy)phenyl)acetate (229f)

Compound 229f was prepared according to the procedure reported in step-2 of scheme 1, from tert-butyl 2-(2-((5-bromobenzo[1,2-b:6,5-b']difuran-3-yl)methoxy)phenyl)acetate (229e) (115 mg, 0.251 mmol) in dioxane/2Me-THF (12 mL, ratio 2:1) using 3-(aminomethyl)phenylboronic acid hydrochloride (1d) (118 mg, 0.629 mmol), 4M solution of $K_3PO_4$ (0.251 mL, 1.006 mmol), tricyclohexylphosphine (28.2 mg, 0.101 mmol), $Pd_2(dba)_3$ (46.1 mg, 0.050 mmol) and heating at 115° C. for 3 h. This gave after workup and purification using flash column chromatography [silica gel (12 g), eluting with DMA-80 in DCM from 0-90%] tert-butyl 2-(2-((5-(3-(aminomethyl)phenyl)benzo[1,2-b:6,5-b'] difuran-3-yl)methoxy)phenyl)acetate (229f) (72 mg, 59% yield) as a yellow oil; $^1$H NMR (300 MHz, DMSO-$d_6$) δ 8.19 (s, 1H), 8.16 (d, J=2.2 Hz, 1H), 7.69 (s, 1H), 7.66 (s, 1H), 7.52 (d, J=7.6 Hz, 1H), 7.47 (t, J=7.4 Hz, 1H), 7.39 (d, J=7.3 Hz, 1H), 7.33-7.28 (m, 1H), 7.25 (d, J=8.7 Hz, 1H), 7.22-7.16 (m, 2H), 6.92 (t, J=7.1 Hz, 1H), 5.36 (s, 2H), 3.84 (s, 2H), 3.51 (s, 2H), 1.12 (s, 9H); MS (ES+): 484.2 (M+1).

Step-6: Preparation of 2-(2-((5-(3-(aminomethyl) phenyl)benzo[1,2-b:6,5-b']difuran-3-yl)methoxy) phenyl)acetic acid (229g)

Compound 229g was prepared according to the procedure reported in step-3 of scheme 1, from tert-butyl 2-(2-((5-(3-(aminomethyl)phenyl)benzo[1,2-b:6,5-b']difuran-3-yl) methoxy)phenyl)acetate (229f) (70 mg, 0.145 mmol) in MeOH/THF (3 mL each) using a solution of lithium hydroxide (50 mg, 1.907 mmol) in water (2 mL) and heating for 48 h at 46° C. This gave after workup and purification using reverse phase column chromatography [C18 column (50 g), eluting with ACN in water (containing 0.1% HCl) from 0-100%] 2-(2-((5-(3-(aminomethyl)phenyl)benzo[1,2-b:6,5-b']difuran-3-yl)methoxy)phenyl)acetic acid (229g) (40 mg, 65% yield) HCl salt as a white solid; $^1$H NMR (300 MHz, DMSO-$d_6$) δ 12.17 (s, 1H, $D_2O$ exchangeable), 8.42 (s, 3H, $D_2O$ exchangeable), 8.26-8.12 (m, 2H), 7.83 (s, 1H), 7.76-7.66 (m, 2H), 7.64-7.49 (m, 2H), 7.34 (d, J=2.2 Hz, 1H), 7.31-7.16 (m, 3H), 6.94 (t, J=7.1 Hz, 1H), 5.38 (s, 2H), 4.15 (s, 2H), 3.56 (s, 2H); MS (ES+): 428.2 (M+1); (ES−): 426.1 (M−1); Analysis calculated for: $C_{26}H_{21}NO_5$·1.05 HCl·1.1$H_2O$: C, 64.31; H, 5.03; N, 2.88; Cl, 7.67. Found: C, 64.24; H, 4.96; N, 2.97; Cl, 7.84.

Scheme 230

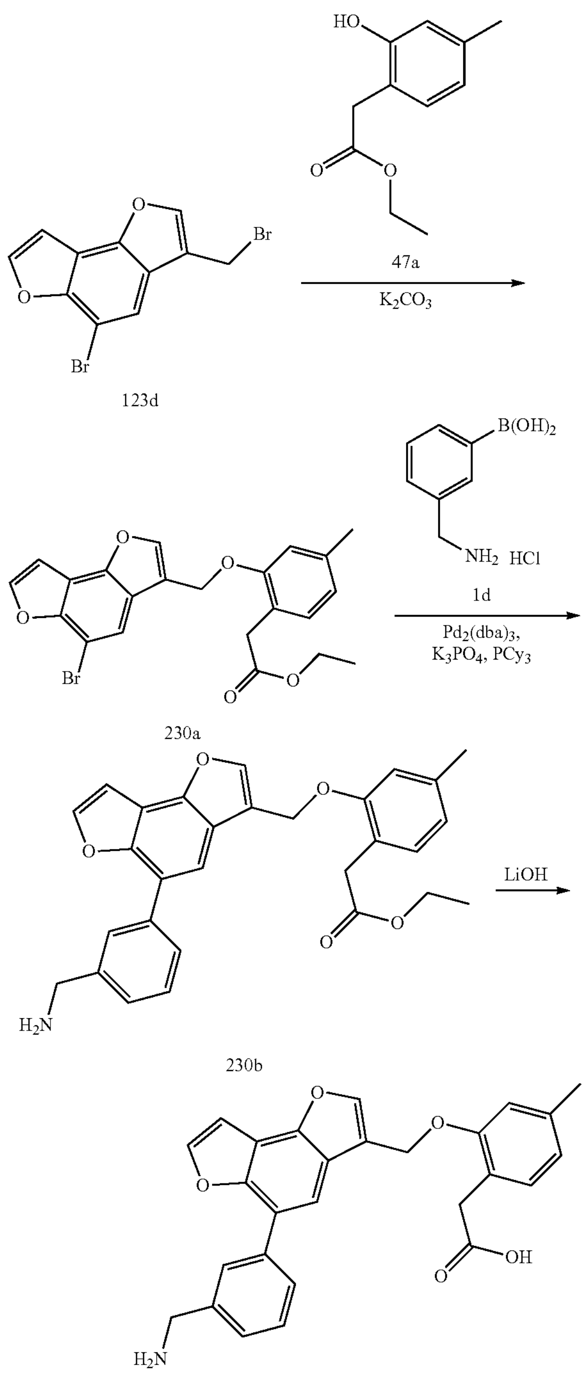

123d

230a

230b

230c

Preparation of 2-(2-((5-(3-(aminomethyl)phenyl) benzo[1,2-b:3,4-b']difuran-3-yl)methoxy)-4-methylphenyl)acetic acid (230c)

Step-1: Preparation of ethyl 2-(2-((5-bromobenzo[1,2-b:3,4-b']difuran-3-yl)methoxy)-4-methylphenyl) acetate (230a)

Compound 230a was prepared according to the procedure reported in step-3 of scheme 7, from 5-bromo-3-(bromomethyl)benzo[1,2-b:3,4-b']difuran (123d) (0.26 g, 0.788 mmol) in acetone (10 mL) using ethyl 2-(2-hydroxy-4-methylphenyl)acetate (47a) (0.230 g, 1.182 mmol), potassium carbonate (381 mg, 2.76 mmol) and stirring overnight at RT. This gave after workup and purification using flash column chromatography [silica gel (12 g), eluting with ethyl acetate in hexanes from 0-30%] ethyl 2-(2-((5-bromobenzo[1,2-b:3,4-b']difuran-3-yl)methoxy)-4-methylphenyl)acetate (230a) (245 mg, 70% yield) as a yellow oil; MS (ES+): 465.0 and 467.0 (M+Na).

Step-2: Preparation of ethyl 2-(2-((5-(3-(aminomethyl)phenyl)benzo[1,2-b:3,4-b']difuran-3-yl) methoxy)-4-methylphenyl)acetate (230b)

Compound 230b was prepared according to the procedure reported in step-2 of scheme 1, from ethyl 2-(2-((5-bromobenzo[1,2-b:3,4-b']difuran-3-yl)methoxy)-4-methylphenyl)acetate (230a) (123 mg, 0.277 mmol) in dioxane/2Me-THF (12 mL, ratio 2:1) using 3-(aminomethyl) phenylboronic acid hydrochloride (1d) (130 mg, 0.694 mmol), 4M solution of $K_3PO_4$ (0.277 mL, 1.11 mmol), tricyclohexylphosphine (31.1 mg, 0.111 mmol), $Pd_2(dba)_3$ (50.8 mg, 0.055 mmol) and heating at 115° C. for 3 h. This gave after workup and purification using flash column chromatography [silica gel (12 g), eluting with DMA-80 in DCM from 0-70%] ethyl 2-(2-((5-(3-(aminomethyl)phenyl) benzo[1,2-b:3,4-b']difuran-3-yl)methoxy)-4-methylphenyl) acetate (230b)(125 mg, 96% yield) as a yellow oil; MS (ES+): 470.2 (M+1).

Step-3: Preparation of 2-(2-((5-(3-(aminomethyl) phenyl)benzo[1,2-b:3,4-b']difuran-3-yl)methoxy)-4-methylphenyl)acetic acid (230c)

Compound 230c was prepared according to the procedure reported in step-3 of scheme 1, from ethyl 2-(2-((5-(3-(aminomethyl)phenyl)benzo[1,2-b:3,4-b']difuran-3-yl) methoxy)-4-methylphenyl)acetate (230b) (125 mg, 0.266 mmol) in MeOH/THF (3 mL each) using a solution of lithium hydroxide monohydrate (44.7 mg, 1.065 mmol) in water (2 mL) and stirring overnight at RT. This gave after workup and purification using reverse phase column chromatography [C18 column (50 g), eluting with ACN in water (containing 0.1% HCl) from 0-100%] 2-(2-((5-(3-(aminomethyl)phenyl)benzo[1,2-b:3,4-b']difuran-3-yl)methoxy)-4-methylphenyl)acetic acid (230c) (45 mg, 38% yield) HCl salt as a white solid; $^1$H NMR (300 MHz, DMSO-$d_6$) δ 12.37 (s, 1H, $D_2O$ exchangeable), 8.53 (s, 3H, $D_2O$ exchangeable), 8.19 (d, J=13.3 Hz, 2H), 8.02 (s, 1H), 7.97-7.76 (m, 2H), 7.59 (s, 2H), 7.36 (s, 1H), 7.08 (s, 2H), 6.75 (d, J=7.5 Hz, 1H), 5.35 (s, 2H), 4.14 (s, 2H), 3.50 (s, 2H), 2.32 (s, 3H); MS (ES+): 442.2 (M+1); (ES−): 440.1 (M−1); Analysis calculated for: $C_{27}H_{23}NO_5$·HCl·$H_2O$: C, 65.39; H, 5.28; N, 2.82; Cl, 7.15. Found: C, 65.47; H, 5.16; N, 2.92; Cl, 7.00.

Scheme 231

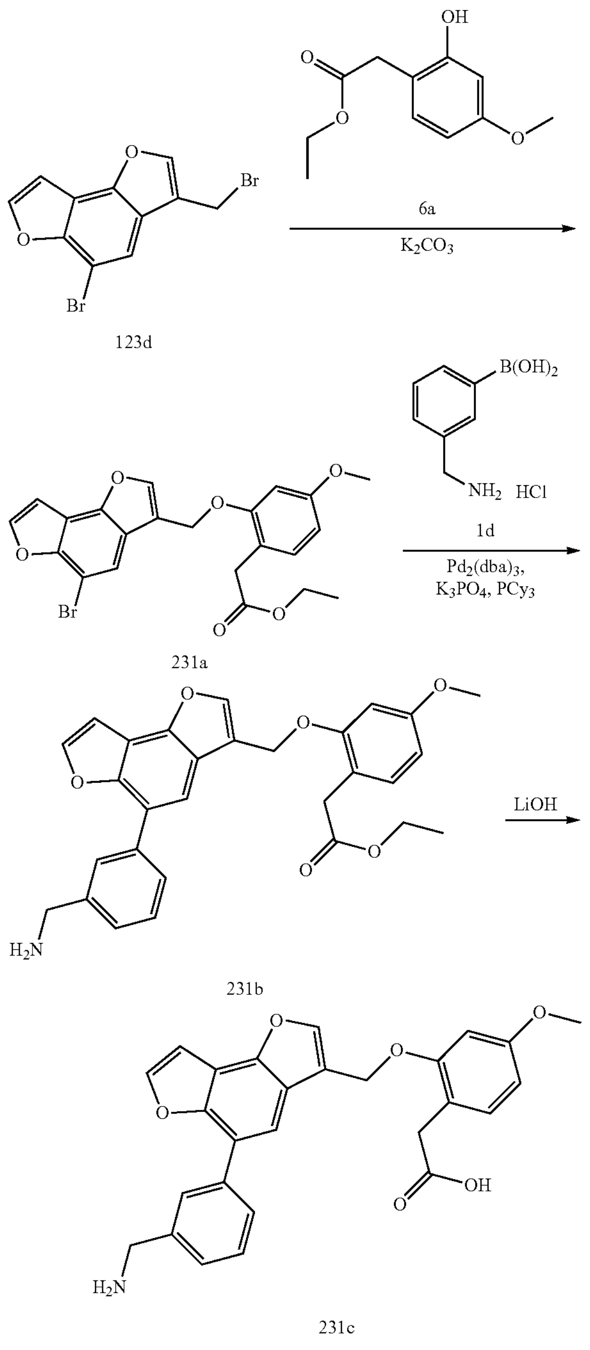

123d

231a

231b

231c

Preparation of 2-(2-((5-(3-(aminomethyl)phenyl)benzo[1,2-b:3,4-b']difuran-3-yl)methoxy)-4-methoxyphenyl)acetic acid (231c)

Step-1: Preparation of ethyl 2-(2-((5-bromobenzo[1,2-b:3,4-b']difuran-3-yl)methoxy)-4-methoxyphenyl)acetate (231a)

Compound 231a was prepared according to the procedure reported in step-3 of scheme 7, from 5-bromo-3-(bromomethyl)benzo[1,2-b:3,4-b']difuran (123d) (0.260 g, 0.788 mmol) in acetone (10 mL) using ethyl 2-(2-hydroxy-4-methoxyphenyl)acetate (6a) (0.248 g, 1.182 mmol), potassium carbonate (381 mg, 2.76 mmol) and stirring overnight at RT. This gave after workup and purification using flash column chromatography [silica gel (12 g), eluting with ethyl acetate in hexanes from 0-40%] ethyl 2-(2-((5-bromobenzo[1,2-b:3,4-b']difuran-3-yl)methoxy)-4-methoxyphenyl)acetate (231a) (276 mg, 76% yield) as a yellow oil; MS (ES+): 481.0 and 483.0 (M+Na)

Step-2: Preparation of ethyl 2-(2-((5-(3-(aminomethyl)phenyl)benzo[1,2-b:3,4-b']difuran-3-yl)methoxy)-4-methoxyphenyl)acetate (231b)

Compound 231b was prepared according to the procedure reported in step-2 of scheme 1, from ethyl 2-(2-((5-bromobenzo[1,2-b:3,4-b']difuran-3-yl)methoxy)-4-methoxyphenyl)acetate (231a) (138 mg, 0.3 mmol) in dioxane/2Me-THF (12 mL, ratio 2:1) using 3-(aminomethyl)phenylboronic acid hydrochloride (1d) (141 mg, 0.751 mmol), 4M solution of $K_3PO_4$ (0.300 mL, 1.202 mmol), tricyclohexylphosphine (33.7 mg, 0.120 mmol), $Pd_2(dba)_3$ (55 mg, 0.06 mmol) and heating at 115° C. for 3 h. This gave after workup and purification using flash column chromatography [silica gel (12 g), eluting with DMA-80 in DCM from 0-70%] ethyl 2-(2-((5-(3-(aminomethyl)phenyl)benzo[1,2-b:3,4-b']difuran-3-yl)methoxy)-4-methoxyphenyl)acetate (231b) (72 mg, 49% yield) as a yellow oil; MS (ES+): 486.2 (M+1).

Step-3: Preparation of 2-(2-((5-(3-(aminomethyl)phenyl)benzo[1,2-b:3,4-b']difuran-3-yl)methoxy)-4-methoxyphenyl)acetic acid (231c)

Compound 231c was prepared according to the procedure reported in step-3 of scheme 1, from ethyl 2-(2-((5-(3-(aminomethyl)phenyl)benzo[1,2-b:3,4-b']difuran-3-yl)methoxy)-4-methoxyphenyl)acetate (231b) (72 mg, 0.148 mmol) in MeOH/THE (3 mL each) using a solution of lithium hydroxide monohydrate (24.89 mg, 0.593 mmol) in water (2 mL) and stirring overnight at RT. This gave after workup and purification using reverse phase column chromatography [C18 column (50 g), eluting with ACN in water (containing 0.1% HCl) from 0-100%] 2-(2-((5-(3-(aminomethyl)phenyl)benzo[1,2-b:3,4-b']difuran-3-yl)methoxy)-4-methoxyphenyl)acetic acid (231c) (40 mg, 59% yield) HCl salt as a yellow solid; $^1H$ NMR (300 MHz, DMSO-$d_6$) δ 12.12 (s, 1H, $D_2O$ exchangeable), 8.58 (s, 3H, $D_2O$ exchangeable), 8.30-8.10 (m, 2H), 8.02 (s, 1H), 7.99-7.78 (m, 2H), 7.58 (d, J=4.7 Hz, 2H), 7.35 (d, J=2.2 Hz, 1H), 7.10 (d, J=8.2 Hz, 1H), 6.82 (d, J=2.4 Hz, 1H), 6.50 (dd, J=8.3, 2.3 Hz, 1H), 5.37 (s, 2H), 4.13 (s, 2H), 3.76 (s, 3H), 3.47 (s, 2H); MS (ES+): 458.2 (M+1); (ES−): 456.1 (M−1); Analysis calculated for: $C_{27}H_{23}NO_6 \cdot HCl \cdot H_2O$: C, 63.34; H, 5.12; Cl, 6.93; N, 2.74. Found: C, 63.57; H, 4.95; N, 2.86; Cl, 7.22.

Scheme 232

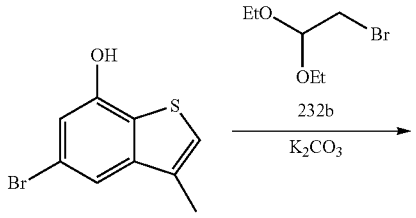

232a

-continued

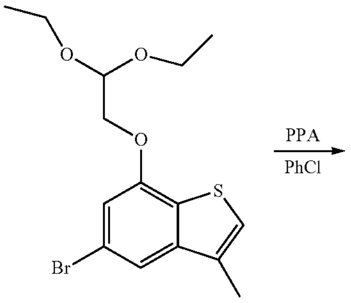

232c

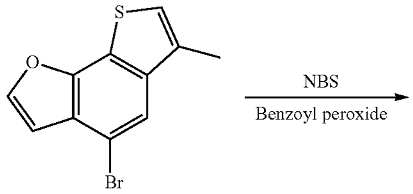

232d

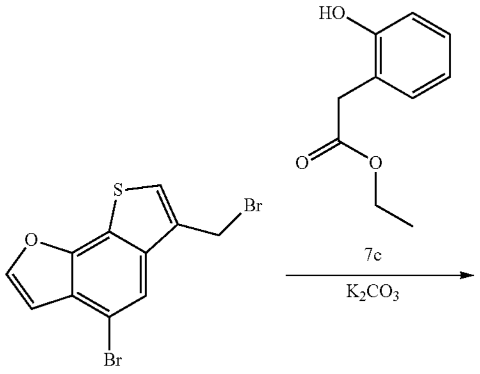

232e

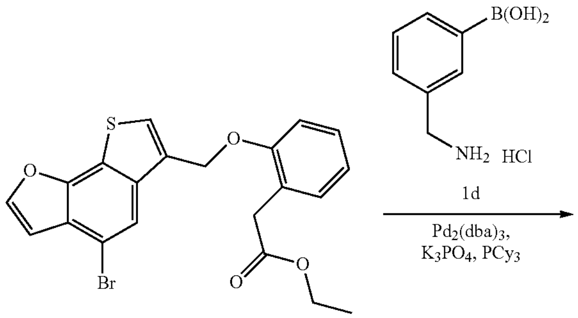

232f

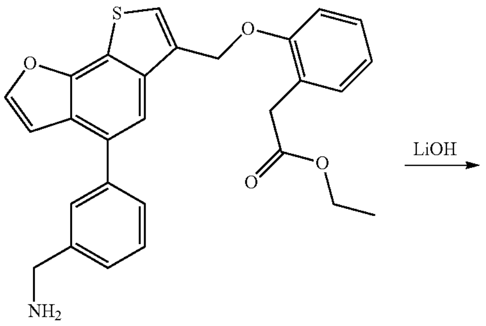

232g

-continued

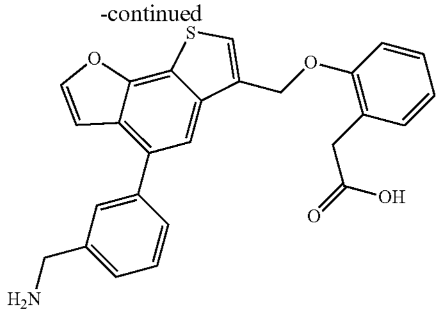

232h

Preparation of 2-(2-((4-(3-(aminomethyl)phenyl)thieno[3,2-g]benzofuran-6-yl)methoxy)phenyl)acetic acid (232 h)

Step-1: Preparation of 5-bromo-7-(2,2-diethoxy-ethoxy)-3-methylbenzo[b]thiophene (232c)

Compound 232c was prepared according to the procedure reported in step-1 of scheme 123, from 5-bromo-3-methyl-benzo[b]thiophen-7-ol (232a) (345 mg, 1.419 mmol; CAS #1936191-94-4) in DMF (8 mL) using potassium carbonate (588 mg, 4.26 mmol), 2-bromo-1,1-diethoxyethane (232b) (559 mg, 2.84 mmol; CAS #2032-35-1) and heating at 120° C. in a sealed tube overnight. This gave after workup and purification using flash column chromatography [silica gel (12 g), eluting with EtOAc in hexanes from 0-20%] 5-bromo-7-(2,2-diethoxyethoxy)-3-methylbenzo[b]thiophene (232c) (499 mg, 98% yield) as a clear yellow oil; MS (ES+): 381.0 and 383.0 (M+Na).

Step-2: Preparation of 4-bromo-6-methylthieno[3,2-g]benzofuran (232d)

Compound 232d was prepared according to the procedure reported in step-1 of scheme 123, from 5-bromo-7-(2,2-diethoxyethoxy)-3-methylbenzo[b]thiophene (232c) (495 mg, 1.378 mmol) in chlorobenzene (6 mL) using polyphosphoric acid (PPA) (880 mg, 1.378 mmol) in chlorobenzene (12 mL) and heating at 80° C. for 90 min followed by heating at 120° C. for 16 h. This gave after workup and purification using flash column chromatography [silica gel (12 g) eluting with ethyl acetate in hexanes from 0-20%] 4-bromo-6-methylthieno[3,2-g]benzofuran (232d) (239 mg, 65% yield) as a white solid; $^1$H NMR (300 MHz, DMSO-$d_6$) δ 8.20 (d, J=2.2 Hz, 1H), 7.92 (s, 1H), 7.49 (q, J=1.2 Hz, 1H), 7.08 (d, J=2.2 Hz, 1H), 2.46 (d, J=1.2 Hz, 3H).

Step-3: Preparation of 4-bromo-6-(bromomethyl)thieno[3,2-g]benzofuran (232e)

Compound 232e was prepared according to the procedure reported in step-2 of scheme 58, from 4-bromo-6-methyl-thieno[3,2-g]benzofuran (232d) (120 mg, 0.449 mmol) in carbon tetrachloride (8 mL) using NBS (88 mg, 0.494 mmol), benzoyl peroxide (16.32 mg, 0.067 mmol) and refluxing for 7 h. This gave after work up 4-bromo-6-(bromomethyl)thieno[3,2-g]benzofuran (232e) (155 mg) as a yellow solid which was used as such for the next step.

Step-4: Preparation of ethyl 2-(2-((4-bromothieno[3,2-g]benzofuran-6-yl)methoxy)phenyl)acetate (232f)

Compound 232f was prepared according to the procedure reported in step-3 of scheme 7, from 4-bromo-6-(bromomethyl)thieno[3,2-g]benzofuran (232e) (0.155 g, 0.448 mmol) in acetone (10 mL) using ethyl 2-(2-hydroxyphenyl)acetate (7c) (0.161 g, 0.896 mmol), potassium carbonate (186 mg, 1.344 mmol) and stirring overnight at RT. This gave after workup and purification using flash column chromatography [silica gel (12 g), eluting with ethyl acetate in hexanes from 0-40%] ethyl 2-(2-((4-bromothieno[3,2-g]benzofuran-6-yl)methoxy)phenyl)acetate (232f) (123 mg, 62% yield) as a white yellow solid; $^1$H NMR (300 MHz, DMSO-$d_6$) δ 8.24 (d, J=2.2 Hz, 1H), 8.03 (s, 1H), 7.88 (s, 1H), 7.36-7.20 (m, 3H), 7.11 (d, J=2.2 Hz, 1H), 6.94 (td, J=7.1, 1.4 Hz, 1H), 5.41 (s, 2H), 3.92 (q, J=7.1 Hz, 2H), 3.59 (s, 2H), 0.95 (t, J=7.1 Hz, 3H).

Step-5: Preparation of ethyl 2-(2-((4-(3-(aminomethyl)phenyl)thieno[3,2-g]benzofuran-6-yl)methoxy)phenyl)acetate (232g)

Compound 232g was prepared according to the procedure reported in step-2 of scheme 1, from ethyl 2-(2-((4-bromothieno[3,2-g]benzofuran-6-yl)methoxy)phenyl)acetate (232f) (120 mg, 0.269 mmol) in dioxane/2Me-THF (12 mL, ratio 2:1) using 3-(aminomethyl)phenylboronic acid hydrochloride (1d) (126 mg, 0.674 mmol), 4M solution of $K_3PO_4$ (0.269 mL, 1.078 mmol), tricyclohexylphosphine (30.2 mg, 0.108 mmol), $Pd_2(dba)_3$ (49.4 mg, 0.054 mmol) and heating at 115° C. for 3 h. This gave after workup and purification using flash column chromatography [silica gel (12 g), eluting with DMA-80 in DCM from 0-90%] ethyl 2-(2-((4-(3-(aminomethyl)phenyl)thieno[3,2-g]benzofuran-6-yl)methoxy)phenyl)acetate (232g) (90 mg, 71% yield) as a yellow foam; MS (ES+): 472.1 (M+1).

Step-6: Preparation of 2-(2-((4-(3-(aminomethyl)phenyl)thieno[3,2-g]benzofuran-6-yl)methoxy)phenyl)acetic acid (232 h)

Compound 232h was prepared according to the procedure reported in step-3 of scheme 1, from ethyl 2-(2-((4-(3-(aminomethyl)phenyl)thieno[3,2-g]benzofuran-6-yl)methoxy)phenyl)acetate (232g) (90 mg, 0.191 mmol) in MeOH/THF (3 mL each) using a solution of lithium hydroxide monohydrate (55 mg, 1.311 mmol) in water (2 mL) and stirring overnight at RT. This gave after workup and purification using reverse phase column chromatography [C18 column (50 g), eluting with ACN in water (containing 0.1% HCl) from 0-100%] 2-(2-((4-(3-(aminomethyl)phenyl)thieno[3,2-g]benzofuran-6-yl)methoxy)phenyl)acetic acid (232 h) (69 mg, 82% yield) HCl salt as a white solid; $^1$H NMR (300 MHz, DMSO-$d_6$) δ 12.29 (s, 1H, $D_2O$ exchangeable), 8.47 (s, 2H, $D_2O$ exchangeable), 8.23 (d, J=2.2 Hz, 1H), 7.95 (s, 1H), 7.90 (s, 1H), 7.85 (s, 1H), 7.77 (d, J=7.3 Hz, 1H), 7.66-7.50 (m, 2H), 7.36 (d, J=2.2 Hz, 1H), 7.30-7.18 (m, 3H), 7.00-6.85 (m, 1H), 5.49 (s, 2H), 4.16 (s, 2H), 3.58 (s, 2H); MS (ES+): 444.1 (M+1); (ES−): 442.1 (M−1); Analysis calculated for: $C_{26}H_{21}NO_4S\cdot HCl\cdot 1.25H_2O$: C, 62.15; H, 4.91; N, 2.79; Cl, 7.06. Found: C, 62.16; H, 4.84; N, 2.85; Cl, 6.97.

Scheme 233

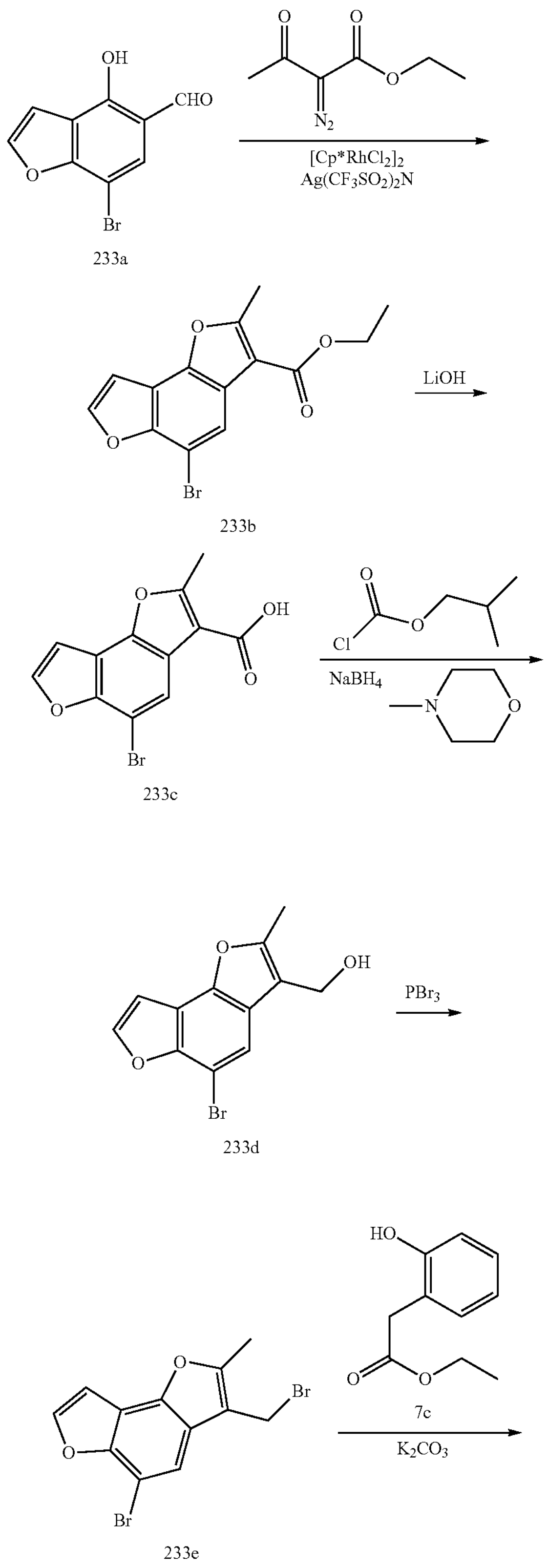

-continued

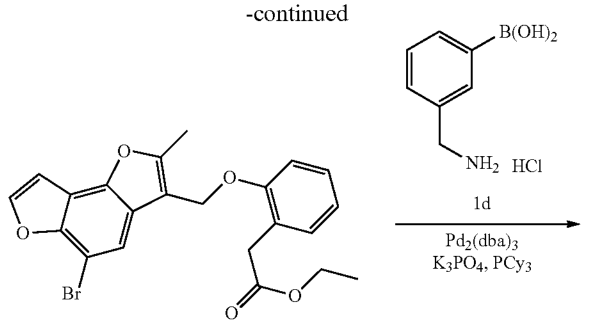

233f

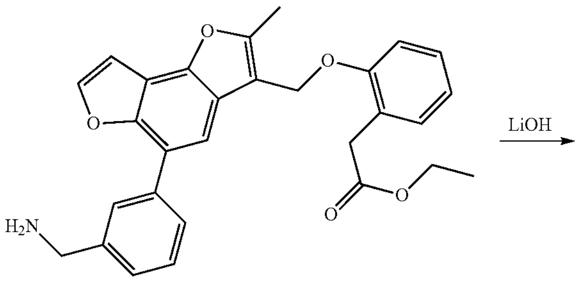

233g

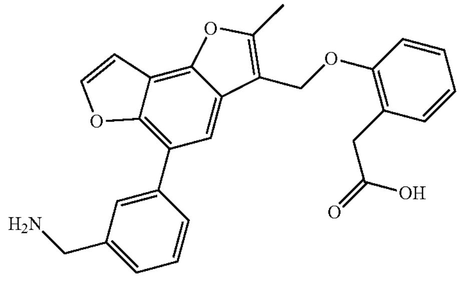

233h

Preparation of 2-(2-((5-(3-(aminomethyl)phenyl)-2-methylbenzo[1,2-b:3,4-b']difuran-3-yl)methoxy) phenyl)acetic acid (233 h)

Step-1: Preparation of ethyl 5-bromo-2-methyl-benzo[1,2-b:3,4-b']difuran-3-carboxylate (233b)

A solution of 7-bromo-4-hydroxybenzofuran-5-carbaldehyde (233a) (509 mg, 2.112 mmol), pentamethylcyclopentadienylrhodium chloride dimer (65.3 mg, 0.106 mmol) in DCE (5 mL), silver bis(trifluoromethanesulfonyl)imide (164 mg, 0.422 mmol), ethyl 2-diazo-3-oxobutanoate (659 mg, 4.22 mmol) was stirred vigorously in a sealed tube at 50° C. overnight. The solvent was removed in vacuo and the residue obtained was purified using flash column chromatography [silica gel (12 g), eluting with EtOAc in hexane from 0-40%] to provide ethyl 5-bromo-2-methylbenzo[1,2-b:3,4-b']difuran-3-carboxylate (233b) (223 mg, 33% yield) as a white solid; $^1$H NMR (300 MHz, DMSO-$d_6$) δ 8.28 (d, J=2.2 Hz, 1H), 8.00 (s, 1H), 7.42 (d, J=2.3 Hz, 1H), 4.39 (q, J=7.1 Hz, 2H), 2.81 (s, 3H), 1.39 (t, J=7.1 Hz, 3H).

Step-2: Preparation of 5-bromo-2-methylbenzo[1,2-b:3,4-b']difuran-3-carboxylic acid (233c)

Compound 233c was prepared according to the procedure reported in step-3 of scheme 1, from ethyl 5-bromo-2-methylbenzo[1,2-b:3,4-b']difuran-3-carboxylate (233b) (200 mg, 0.619 mmol) in MeOH/THF (3 mL each) using a solution of lithium hydroxide (26 mg, 0.619 mmol) in water (2 mL) and stirring overnight at RT. This gave after workup 5-bromo-2-methylbenzo[1,2-b:3,4-b']difuran-3-carboxylic acid (233c) (183 mg), which was used as such in the next step; $^1$H NMR (300 MHz, DMSO-$d_6$) δ 13.22 (s, 1H), 8.26 (d, J=2.2 Hz, 1H), 8.03 (s, 1H), 7.41 (d, J=2.2 Hz, 1H), 2.79 (s, 3H); MS (ES−): 293.0 and 294.9 (M−1).

Step-3: Preparation of (5-bromo-2-methylbenzo[1,2-b:3,4-b']difuran-3-yl)methanol (233d)

Compound 233d was prepared according to the procedure reported in step-1 of scheme 8, from 5-bromo-2-methyl-benzo[1,2-b:3,4-b']difuran-3-carboxylic acid (233c) (183 mg, 0.620 mmol) in THF (10 mL) using N-methylmorpholine (0.082 mL, 0.744 mmol), isobutyl chloroformate (0.098 mL, 0.744 mmol) and $NaBH_4$ (70.4 mg, 1.860 mmol) in water (1 mL).

This gave after workup and purification using flash column chromatography [silica gel (12 g), eluting with EtOAc in hexane from 0-60%] (5-bromo-2-methylbenzo[1,2-b:3,4-b']difuran-3-yl)methanol (233d) (164 mg, 94% yield) as a white solid; $^1$H NMR (300 MHz, DMSO-$d_6$) δ 8.19 (d, J=2.3 Hz, 1H), 7.79 (s, 1H), 7.34 (d, J=2.2 Hz, 1H), 5.10 (t, J=5.6 Hz, 1H), 4.60 (d, J=5.5 Hz, 2H), 2.48 (s, 3H).

Step-4: Preparation of 5-bromo-3-(bromomethyl)-2-methylbenzo[1,2-b:3,4-b']difuran (233e)

Compound 233e was prepared according to the procedure reported in step-3 of scheme 228, from (5-bromo-2-methylbenzo[1,2-b:3,4-b']difuran-3-yl)methanol (233d) (141 mg, 0.502 mmol) in DCM (8 mL) using $PBr_3$ (0.057 mL, 0.602 mmol) and stirring at 60 min. This gave after work up 5-bromo-3-(bromomethyl)-2-methylbenzo[1,2-b:3,4-b']difuran (233e) which was used as such for the next step.

Step-5: Preparation of ethyl 2-(2-((5-bromo-2-methylbenzo[1,2-b:3,4-b']difuran-3-yl)methoxy)phenyl) acetate (233f)

Compound 233f was prepared according to the procedure reported in step-3 of scheme 7, from 5-bromo-3-(bromomethyl)-2-methylbenzo[1,2-b:3,4-b']difuran (233e)(0.173 g, 0.503 mmol) in acetone (10 mL) using ethyl 2-(2-hydroxyphenyl)acetate (7c) (0.181 g, 1.006 mmol), potassium carbonate (209 mg, 1.509 mmol) and stirring at RT for 48 h. This gave after workup and purification using flash column chromatography [silica gel (12 g), eluting with ethyl acetate in hexanes from 0-50%] ethyl 2-(2-((5-bromo-2-methyl-benzo[1,2-b:3,4-b']difuran-3-yl)methoxy)phenyl)acetate (233f) (173 mg, 78% yield) as a yellow oil; $^1$H NMR (300 MHz, DMSO-$d_6$) δ 8.22 (d, J=2.2 Hz, 1H), 7.73 (s, 1H), 7.37 (d, J=2.2 Hz, 1H), 7.35-7.26 (m, 1H), 7.25-7.18 (m, 2H), 6.98-6.88 (m, 1H), 5.24 (s, 2H), 3.90 (q, J=7.1 Hz, 2H), 3.53 (s, 2H), 2.55 (s, 3H), 0.92 (t, J=7.1 Hz, 3H).

Step-6: Preparation of ethyl 2-(2-((5-(3-(aminomethyl)phenyl)-2-methylbenzo[1,2-b:3,4-b']difuran-3-yl)methoxy)phenyl)acetate (233g)

Compound 233g was prepared according to the procedure reported in step-2 of scheme 1, from ethyl 2-(2-((5-bromo-2-methylbenzo[1,2-b:3,4-b']difuran-3-yl)methoxy)phenyl) acetate (233f) (170 mg, 0.383 mmol) in dioxane/2Me-THF (12 mL, ratio 2:1) using 3-(aminomethyl)phenylboronic acid hydrochloride (1d) (180 mg, 0.959 mmol), 4M solution of $K_3PO_4$ (0.383 mL, 1.534 mmol), tricyclohexylphosphine (43.0 mg, 0.153 mmol), $Pd_2(dba)_3$ (70.2 mg, 0.077 mmol) and heating at 115° C. for 3 h. This gave after workup and purification using flash column chromatography [silica gel (12 g), eluting with DMA-80 in DCM from 0-80%] ethyl 2-(2-((5-(3-(aminomethyl)phenyl)-2-methylbenzo[1,2-b:3,4-b']difuran-3-yl)methoxy)phenyl)acetate (233g) (120 mg, 67% yield) as a yellow oil; $^1H$ NMR (300 MHz, DMSO-$d_6$) δ 8.15 (d, J=2.3 Hz, 1H), 7.80 (s, 1H), 7.70 (d, J=7.4 Hz, 1H), 7.63 (s, 1H), 7.45 (t, J=7.5 Hz, 1H), 7.38 (d, J=7.7 Hz, 1H), 7.34-7.23 (m, 3H), 7.23-7.16 (m, 1H), 6.98-6.88 (m, 1H), 5.29 (s, 2H), 3.82 (s, 2H), 3.69 (q, J=7.1 Hz, 2H), 3.52 (s, 2H), 2.57 (s, 3H), 0.80 (t, J=7.1 Hz, 3H); MS (ES+): 470.1 (M+1).

Step-7: Preparation of 2-(2-((5-(3-(aminomethyl)phenyl)-2-methylbenzo[1,2-b:3,4-b']difuran-3-yl)methoxy)phenyl)acetic acid (233 h)

Compound 233h was prepared according to the procedure reported in step-3 of scheme 1, from ethyl 2-(2-((5-(3-(aminomethyl)phenyl)-2-methylbenzo[1,2-b:3,4-b']difuran-3-yl)methoxy)phenyl)acetate (233g) (118 mg, 0.251 mmol) in MeOH/THF (3 mL each) using a solution of lithium hydroxide monohydrate (80 mg, 1.907 mmol) in water (2 mL) and stirring overnight at RT. This gave after workup and purification using reverse phase column chromatography [C18 column (50 g), eluting with ACN in water (containing 0.1% HCl) from 0-100%] 2-(2-((5-(3-(aminomethyl)phenyl)-2-methylbenzo[1,2-b:3,4-b']difuran-3-yl)methoxy)phenyl)acetic acid (233 h) (94 mg, 85% yield) HCl salt as a white solid; $^1H$ NMR (300 MHz, DMSO-$d_6$) δ 12.05 (s, 1H, $D_2O$ exchangeable), 8.71 (s, 3H, $D_2O$ exchangeable), 8.17 (d, J=2.3 Hz, 1H), 7.99 (s, 1H), 7.95-7.83 (m, 1H), 7.75 (s, 1H), 7.63-7.47 (m, 2H), 7.35-7.22 (m, 3H), 7.22-7.13 (m, 1H), 6.99-6.85 (m, 1H), 5.30 (s, 2H), 4.12 (s, 2H), 3.50 (s, 2H), 2.57 (s, 3H); MS (ES+): 442.1 (M+1); (ES−): 440.1 (M−1); Analysis calculated for: $C_{27}H_{23}NO_5 \cdot HCl \cdot 0.5H_2O$: C, 66.60; H, 5.17; N, 2.88; Cl, 7.28. Found: C, 66.35; H, 5.13; N, 2.97; Cl, 7.41.

Scheme 234

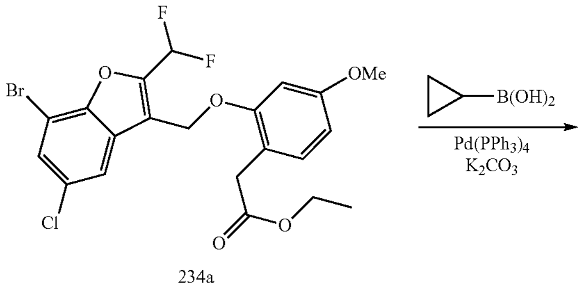

234a

-continued

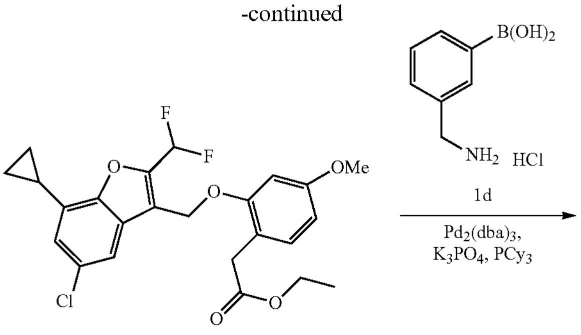

234b

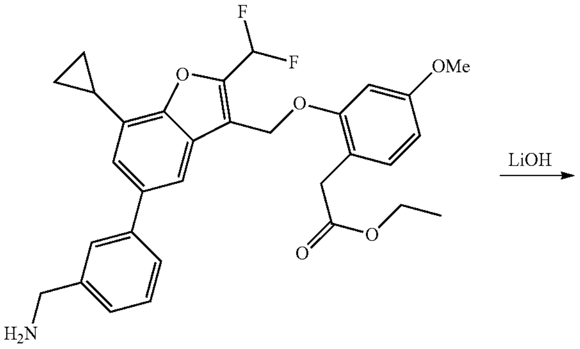

234c

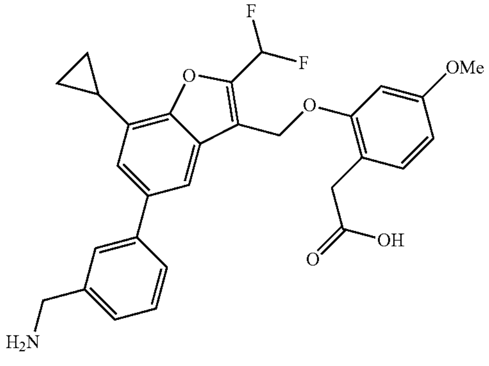

234d

Preparation of 2-(2-((5-(3-(aminomethyl)phenyl)-7-cyclopropyl-2-(difluoromethyl)benzofuran-3-yl)methoxy)-4-methoxyphenyl)acetic acid (234d)

Step-1: Preparation of ethyl 2-(2-((5-chloro-7-cyclopropyl-2-(difluoromethyl)benzofuran-3-yl)methoxy)-4-methoxyphenyl)acetate (234b)

Compound 234b was prepared according to the procedure reported in step-2 of scheme 111, from ethyl 2-(2-((7-bromo-5-chloro-2-(difluoromethyl)benzofuran-3-yl)methoxy)-4-methoxyphenyl)acetate (234a) (250 mg, 0.496 mmol) in THF (2.5 mL) using cyclopropylboronic acid (63.9 mg, 0.744 mmol), $Pd(PPh_3)_4$ (57.4 mg, 0.050 mmol), a solution of $K_2CO_3$ (103 mg, 0.744 mmol) in water (1.25 mL) and heating at 80° C. for 4 h. This gave after workup and purification using flash column chromatography [silica gel (12 g), eluting with EtOAc in hexanes from 0-50%] ethyl 2-(2-((5-chloro-7-cyclopropyl-2-(difluoromethyl)benzofuran-3-yl)methoxy)-4-methoxyphenyl)acetate (234b) (148 mg, 64% yield) as a clear gum; $^1H$ NMR (300 MHz, DMSO-$d_6$) δ 7.63 (d, J=2.1 Hz, 1H), 7.51 (s, 1H), 7.14 (d, J=2.5 Hz, 1H), 7.10 (s, 1H), 6.79 (d, J=2.4 Hz, 1H), 6.54 (dd, J=8.3, 2.3 Hz, 1H), 5.39 (s, 2H), 3.91 (q, J=7.1 Hz, 2H), 3.78 (s, 3H), 3.46 (s, 2H), 2.37-2.19 (m, 1H), 1.13-1.08 (m, 2H), 1.03-0.92 (m, 5H).

Step-2: Preparation of ethyl 2-(2-((5-(3-(aminomethyl)phenyl)-7-cyclopropyl-2-(difluoromethyl)benzofuran-3-yl)methoxy)-4-methoxyphenyl)acetate (234c)

Compound 234c was prepared according to the procedure reported in step-2 of scheme 1, from ethyl 2-(2-((5-chloro-7-cyclopropyl-2-(difluoromethyl)benzofuran-3-yl)methoxy)-4-methoxyphenyl)acetate (234b) (0.148 g, 0.319 mmol) in dioxane (6 mL) and 2-Me-THF (3 mL) using 3-(aminomethyl)phenylboronic acid hydrochloride (1d) (149 mg, 0.797 mmol), 4 M solution of $K_3PO_4$ (0.319 mL, 1.276 mmol), tricyclohexylphosphine (71.5 mg, 0.255 mmol), $Pd_2(dba)_3$ (117 mg, 0.128 mmol) and heating at 115° C. for 16 h. This gave after workup ethyl 2-(2-((5-(3-(aminomethyl)phenyl)-7-cyclopropyl-2-(difluoromethyl)benzofuran-3-yl)methoxy)-4-methoxyphenyl)acetate (234c) (171 mg) and used as such in the next step; MS (ES+): 536.2 (M+1).

Step-3: Preparation of 2-(2-((5-(3-(aminomethyl)phenyl)-7-cyclopropyl-2-(difluoromethyl)benzofuran-3-yl)methoxy)-4-methoxyphenyl)acetic acid (234d)

Compound 234d was prepared according to the procedure reported in step-3 of scheme 1, from ethyl 2-(2-((5-(3-(aminomethyl)phenyl)-7-cyclopropyl-2-(difluoromethyl)benzofuran-3-yl)methoxy)-4-methoxyphenyl)acetate (234c) (171 mg, 0.319 mmol) in THF (2 mL), methanol (0.2 mL) and water (0.2 mL) using lithium hydroxide monohydrate (30.6 mg, 1.277 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-cyclopropyl-2-(difluoromethyl)benzofuran-3-yl)methoxy)-4-methoxyphenyl)acetic acid (234d) (56 mg, 35% yield) HCl salt as a white solid; $^1H$ NMR (300 MHz, DMSO-$d_6$) δ 12.12 (s, 1H, $D_2O$ exchangeable), 8.35 (s, 3H, $D_2O$ exchangeable), 7.93 (d, J=1.7 Hz, 1H), 7.89 (s, 1H), 7.79-7.70 (m, 1H), 7.53 (d, J=7.5 Hz, 1H), 7.50-7.43 (m, 2H), 7.38 (s, 1H), 7.12 (d, J=8.3 Hz, 1H), 6.83 (d, J=2.4 Hz, 1H), 6.54 (dd, J=8.3, 2.4 Hz, 1H), 5.48 (s, 2H), 4.12 (s, 2H), 3.77 (s, 3H), 3.44 (s, 2H), 2.42-2.29 (m, 1H), 1.23-1.09 (m, 2H), 1.09-0.99 (m, 2H); MS (ES+): 508.2 (M+1); Analysis calculated for $C_{29}H_{27}F_2NO_5 \cdot HCl \cdot H_2O$: C, 61.98; H, 5.38; Cl, 6.31; N, 2.49. Found: C, 61.77; H, 5.50; Cl, 6.61; N, 2.64.

Scheme 235

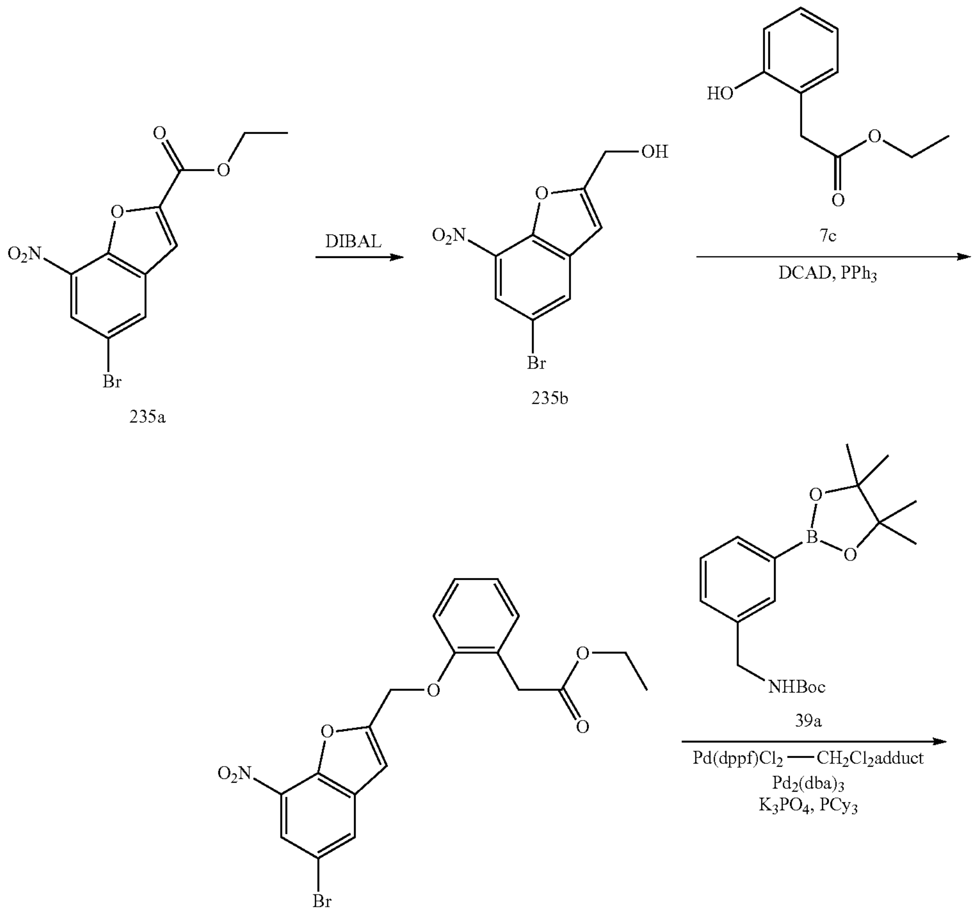

235a

235b

7c

235c

39a

-continued

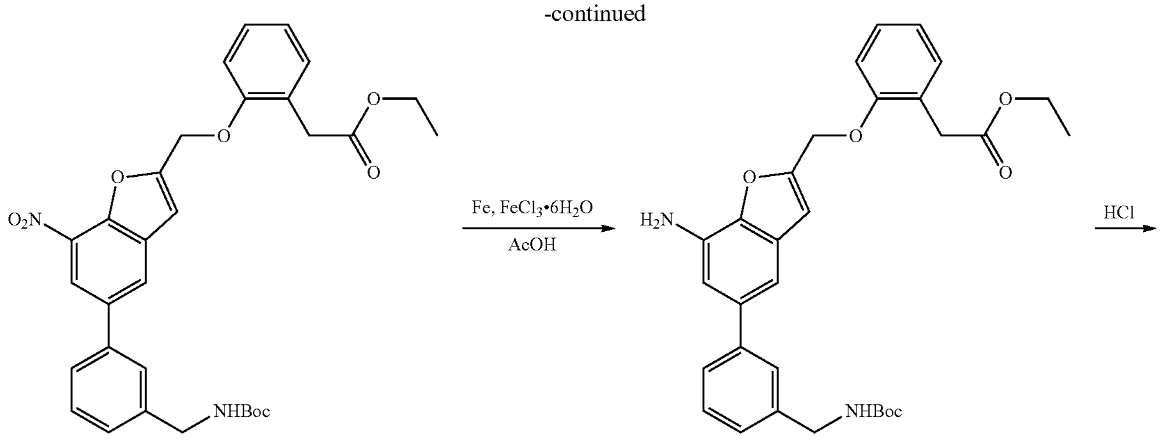

235d 235e

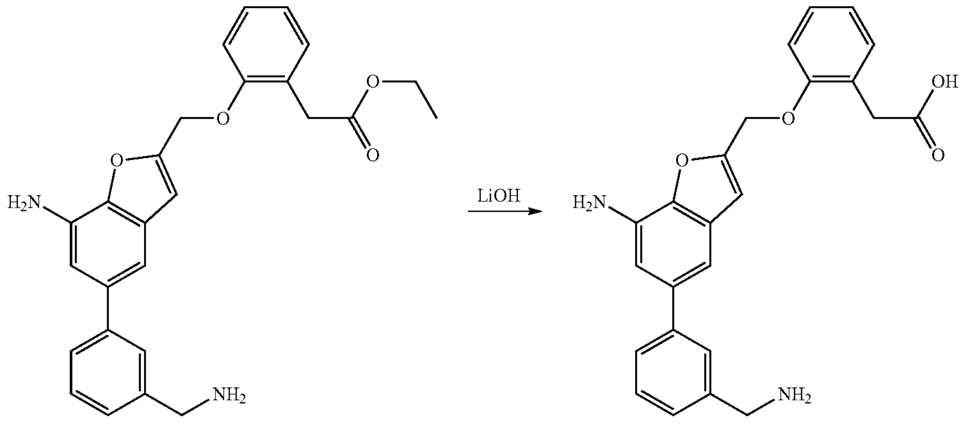

235f 235g

Preparation of 2-(2-((7-amino-5-(3-(aminomethyl)phenyl)benzofuran-2-yl)methoxy)phenyl)acetic acid (235g)

Step-1: Preparation of (5-bromo-7-nitrobenzofuran-2-yl)methanol (235b)

Compound 235b was prepared according to the procedure reported in step-4 of scheme 3, from ethyl 5-bromo-7-nitrobenzofuran-2-carboxylate (235a) (1.968 g, 6.27 mmol; CAS #1221448-66-3) in DCM (20 mL) using DIBAL (1M in DCM) (15.66 mL, 15.66 mmol) and stirring at 0° C. for 2 h. This gave after workup and purification using flash column chromatography [silica gel (120 g), eluting with EtOAc in hexane from 0-50%] (5-bromo-7-nitrobenzofuran-2-yl)methanol (235b) (0.817 g, 48% yield) as a white solid; $^{1}H$ NMR (300 MHz, DMSO-$d_6$) δ 8.33 (d, J=1.9 Hz, 1H), 8.23 (d, J=1.9 Hz, 1H), 7.00 (s, 1H), 5.75 (t, J=5.9 Hz, 1H), 4.68 (d, 2H).

Step-2: Preparation of ethyl 2-(2-((5-bromo-7-nitrobenzofuran-2-yl)methoxy)phenyl)acetate (235c)

Compound 235c was prepared according to the procedure reported in step-2 of scheme 65, from (5-bromo-7-nitrobenzofuran-2-yl)methanol (235b) (817 mg, 3.0 mmol) in DCM (14 mL) using triphenylphosphine (1.024 g, 3.90 mmol), ethyl 2-(2-hydroxyphenyl)acetate (7c) (811 mg, 4.50 mmol) a solution of DCAD (1.433 g, 3.90 mmol) in DCM (6 mL) and stirring at RT for 3 h. This gave after workup and purification using flash column chromatography [silica gel (12 g), eluting with EtOAc in hexane from 0-50%] ethyl 2-(2-((5-bromo-7-nitrobenzofuran-2-yl)methoxy)phenyl)acetate (235c) (915 mg, 70% yield) as a white solid; $^{1}H$ NMR (300 MHz, DMSO-$d_6$) δ 9.47 (s, 1H), 8.42 (d, J=1.9 Hz, 1H), 8.29 (d, J=1.9 Hz, 1H), 7.25-7.20 (m, 2H), 7.12-7.05 (m, 2H), 5.39 (s, 2H), 4.01-3.93 (m, 2H), 3.53 (s, 2H), 1.05 (t, J=7.1 Hz, 3H).

Step-3: Preparation of ethyl 2-(2-((5-(3-(((tert-butoxycarbonyl)amino)methyl)phenyl)-7-nitrobenzofuran-2-yl)methoxy)phenyl)acetate (235d)

Compound 235d was prepared according to the procedure reported in step-2 of scheme 1, from ethyl 2-(2-((5-bromo-7-nitrobenzofuran-2-yl)methoxy)phenyl)acetate (235c) (457 mg, 1.052 mmol) in dioxane (4 mL) and THF (4 mL) using tert-butyl 3-(4,4,5,5-tetramethyl-1,3,2-dioxaborolan-2-yl)benzylcarbamate (39a) (526 mg, 1.579 mmol), 2M solution of $K_3PO_4$ (1.052 mL, 4.21 mmol), tricyclohexylphosphine (59 mg, 0.210 mmol), $Pd_2(dba)_3$ (96 mg, 0.105 mmol), $PdCl_2(dppf)$-$CH_2Cl_2$ adduct (86 mg, 0.105 mmol) and heating at 90-100° C. for 1 h under an argon atmosphere. This gave after workup and purification using flash column chromatography [silica gel (80 g), eluting with DMA-80 in DCM from 0-70%] ethyl 2-(2-((5-(3-(((tert-butoxycarbonyl)

amino)methyl)phenyl)-7-nitrobenzofuran-2-yl)methoxy)phenyl)acetate (235d) (216 g, 37% yield) as a clear oil; MS (ES+): 582.60 (M+Na).

Step-4: Preparation of ethyl 2-(2-((7-amino-5-(3-(((tert-butoxycarbonyl)amino)methyl)phenyl)benzofuran-2-yl)methoxy)phenyl)acetate (235e)

A solution of ethyl 2-(2-((5-(3-(((tert-butoxycarbonyl)amino)methyl)phenyl)-7-nitrobenzofuran-2-yl)methoxy)phenyl)acetate (235d) (216 mg, 0.404 mmol) and acetic acid (0.093 mL, 1.617 mmol) in absolute ethanol (3 mL)) was refluxed for 10 min, followed by addition of iron (181 mg, 3.23 mmol) in portions then followed by ferric chloride hexahydrate (21.85 mg, 0.081 mmol) and heating at reflux for 5 h. The mixture was filtered, and the filtrate was diluted with EtOAc. Water was added and phases separated. The aqueous layer was extracted with ether and the combined organics were dried, filtered and concentrated in vacuo. The residue obtained was purified using flash column chromatography [silica gel (24g), using EtOAc in hexane from 0-80%] to give ethyl 2-(2-((7-amino-5-(3-(((tert-butoxycarbonyl)amino)methyl)phenyl)benzofuran-2-yl)methoxy)phenyl)acetate (235e) (162 mg, 79% yield) as a yellow oil; MS (ES+): 530.70 (M+1).

Step-5: Preparation of ethyl 2-(2-((7-amino-5-(3-(aminomethyl)phenyl)benzofuran-2-yl)methoxy)phenyl)acetate (235f)

Compound 235f was prepared according to the procedure reported in step-2 of scheme 7, from ethyl 2-(2-((7-amino-5-(3-(((tert-butoxycarbonyl)amino)methyl)phenyl)benzofuran-2-yl)methoxy)phenyl)acetate (235e) (162 mg, 0.305 mmol) in EtOH (2 mL) using HCl (4M HCl in dioxane) (0.382 mL, 1.527 mmol) and stirring at RT for 4 h. This gave after workup ethyl 2-(2-((7-amino-5-(3-(aminomethyl)phenyl)benzofuran-2-yl)methoxy)phenyl)acetate (235f) (126 mg), which was used as such for the next step; MS (ES+): 430.80 (M+1).

Step-6: Preparation of 2-(2-((7-amino-5-(3-(aminomethyl)phenyl)benzofuran-2-yl)methoxy)phenyl)acetic acid (235g)

Compound 235g was prepared according to the procedure reported in step-3 of scheme 1, from ethyl 2-(2-((7-amino-5-(3-(aminomethyl)phenyl)benzofuran-2-yl)methoxy)phenyl)acetate (235f) (0.126 g, 0.293 mmol) in THF (2 mL), methanol (0.2 mL) and water (0.2 mL) using lithium hydroxide monohydrate (0.028 g, 1.171 mmol) and stirring for 10 h at RT. This gave after workup and purification using reverse phase column chromatography [C18 column (40 g), eluting with ACN in water (containing 0.1% HCl) from 0-100%] 2-(2-((7-amino-5-(3-(aminomethyl)phenyl)benzofuran-2-yl)methoxy)phenyl)acetic acid (235g) (74 mg, 63% yield) HCl salt as a white solid; $^1H$ NMR (300 MHz, DMSO-$d_6$) δ 8.38 (s, 3H, $D_2O$ exchangeable), 7.77 (s, 1H), 7.60 (d, J=7.7 Hz, 1H), 7.50 (t, J=7.6 Hz, 1H), 7.44 (d, J=7.7 Hz, 1H), 7.27 (d, J=1.7 Hz, 1H), 7.26-7.17 (m, 3H), 7.03-6.99 (m, 2H), 6.95 (td, J=7.2, 1.4 Hz, 1H), 5.28 (s, 2H), 4.14-4.04 (m, 2H), 3.57 (s, 2H); MS (ES+): 403.2 (M+1); (ES−): 401.1 (M−1); Analysis calculated for $C_{24}H_{22}N_2O_4$ 1.75HCl·2.25$H_2O$: C, 56.88; H, 5.62; Cl, 12.24; N, 5.53 Found: C, 56.97; H, 5.37; Cl, 12.38; N, 5.41.

Scheme 236

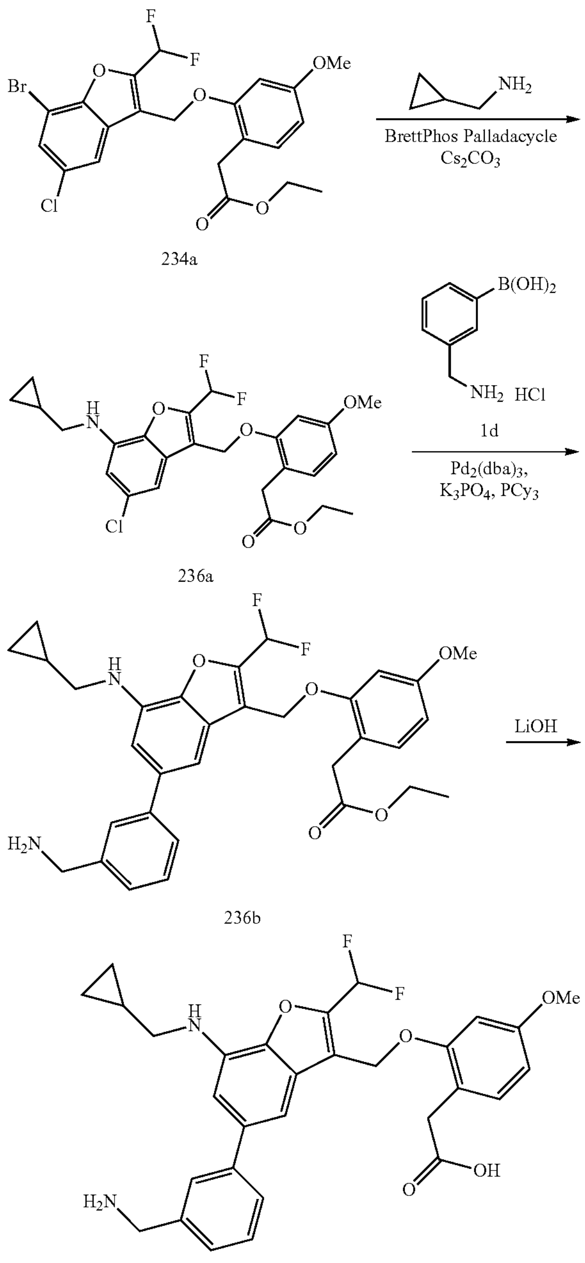

234a

236a

236b

236c

Preparation of 2-(2-((5-(3-(aminomethyl)phenyl)-7-((cyclopropylmethyl)amino)-2-(difluoromethyl)benzofuran-3-yl)methoxy)-4-methoxyphenyl)acetic acid (236c)

Step-1: Preparation of ethyl 2-(2-((5-chloro-7-((cyclopropylmethyl)amino)-2-(difluoromethyl)benzofuran-3-yl)methoxy)-4-methoxyphenyl)acetate (236a)

Compound 236a was prepared according to the procedure reported in step-1 of scheme 146, from ethyl 2-(2-((7-bromo-5-chloro-2-(difluoromethyl)benzofuran-3-yl)

methoxy)-4-methoxyphenyl)acetate (234a) (0.318 g, 0.631 mmol) in MeCN (2 mL) using cyclopropylmethanamine (0.108 mL, 1.263 mmol), BrettPhos Palladacycle (25.2 mg, 0.032 mmol), cesium carbonate (617 mg, 1.894 mmol) and irradiating at 90° C. for 2 h in a microwave. This gave after work up and purification using flash column chromatography [silica gel (12 g), eluting with EtOAc in hexanes from 0-50%] ethyl 2-(2-((5-chloro-7-((cyclopropylmethyl)amino)-2-(difluoromethyl)benzofuran-3-yl)methoxy)-4-methoxyphenyl)acetate (236a) (215 mg, 69% yield); MS (ES+): 493.70 (M+1).

Step-2: Preparation of ethyl 2-(2-((5-(3-(aminomethyl)phenyl)-7-((cyclopropylmethyl)amino)-2-(difluoromethyl)benzofuran-3-yl)methoxy)-4-methoxyphenyl)acetate (236b)

Compound 236b was prepared according to the procedure reported in step-2 of scheme 1, from ethyl 2-(2-((5-chloro-7-((cyclopropylmethyl)amino)-2-(difluoromethyl)benzofuran-3-yl)methoxy)-4-methoxyphenyl)acetate (236a) (0.215 g, 0.435 mmol) in dioxane (4 mL) and 2-Me-THF (2 mL) using 3-(aminomethyl)phenylboronic acid hydrochloride (1d) (204 mg, 1.088 mmol), 4 M solution of $K_3PO_4$ (0.435 mL, 1.741 mmol), tricyclohexylphosphine (98 mg, 0.348 mmol), $Pd_2(dba)_3$ (159 mg, 0.174 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-((cyclopropylmethyl)amino)-2-(difluoromethyl)benzofuran-3-yl)methoxy)-4-methoxyphenyl)acetate (236b) (96 mg, 39% yield); MS (ES+): 564.70 (M+1).

Step-3: Preparation of 2-(2-((5-(3-(aminomethyl)phenyl)-7-((cyclopropylmethyl)amino)-2-(difluoromethyl)benzofuran-3-yl)methoxy)-4-methoxyphenyl)acetic acid (236c)

Compound 236c was prepared according to the procedure reported in step-3 of scheme 1, from ethyl 2-(2-((5-(3-(aminomethyl)phenyl)-7-((cyclopropylmethyl)amino)-2-(difluoromethyl)benzofuran-3-yl)methoxy)-4-methoxyphenyl)acetate (236b) (96 mg, 0.170 mmol) in tetrahydrofuran (2 mL), methanol (0.2 mL) and water (0.2 mL) using a solution of lithium hydroxide monohydrate (16.29 mg, 0.680 mmol) and stirring at RT for 10 h. This gave after workup and purification using reverse phase column chromatography [C18 column (40 g), eluting with ACN in water (containing 0.1% HCl) from 0-100%] 2-(2-((5-(3-(aminomethyl)phenyl)-7-((cyclopropylmethyl)amino)-2-(difluoromethyl)benzofuran-3-yl)methoxy)-4-methoxyphenyl)acetic acid (236c) (59 mg, 65% yield) HCl salt as a white solid; $^1H$ NMR (300 MHz, DMSO-$d_6$) δ 8.35 (s, 4H, $D_2O$ exchangeable), 7.83 (s, 1H), 7.76-7.66 (m, 1H), 7.56-7.41 (m, 3H), 7.30 (d, J=1.5 Hz, 1H), 7.11 (d, J=8.3 Hz, 1H), 6.95 (s, 1H), 6.82 (d, J=2.4 Hz, 1H), 6.53 (dd, J=8.3, 2.3 Hz, 1H), 5.43 (s, 2H), 4.19-4.02 (m, 2H), 3.77 (s, 3H), 3.45 (s, 2H), 3.19 (d, J=6.7 Hz, 2H), 1.30-1.08 (m, 1H), 0.57-0.44 (m, 2H), 0.37-0.23 (m, 2H); $^{19}F$ NMR (282 MHz, DMSO-$d_6$) δ −114.91; MS (ES+): 537.3 (M+1); (ES−): 535.2 (M−1); Calculated for $C_{30}H_{30}F_2N_2O_5 \cdot 1.65HCl \cdot 2.25H_2O$: C, 56.54; H, 5.72; Cl, 9.18; N, 4.40. Found: C, 56.84; H, 5.51; Cl, 9.03; N, 4.16.

Scheme 237

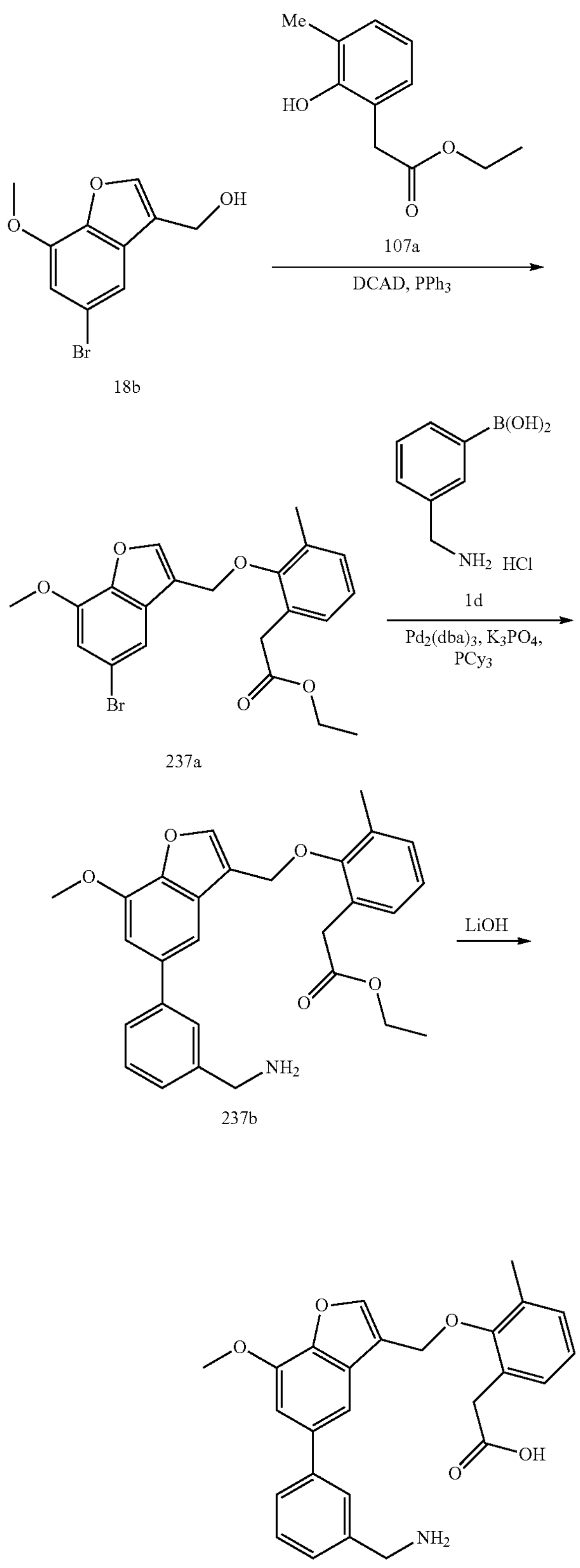

107a
18b
1d
237a
237b
237c

Preparation of 2-(2-((5-(3-(aminomethyl)phenyl)-7-methoxybenzofuran-3-yl)methoxy)-3-methylphenyl) acetic acid (237c)

Step-1: Preparation of ethyl 2-(2-((5-bromo-7-methoxybenzofuran-3-yl)methoxy)-3-methylphenyl) acetate (237a)

Compound 237a was prepared according to the procedure reported in step-3 of scheme 7, from (5-bromo-7-methoxybenzofuran-3-yl)methanol (18b) (0.5 g, 1.945 mmol), triphenylphosphine (0.587 g, 2.237 mmol), ethyl 2-(2-hydroxy-3-methylphenyl)acetate (107a) (0.416 g, 2.139 mmol) in DCM (15 mL) using bis(4-chlorobenzyl) diazene-1,2-dicarboxylate (DCAD, 0.821 g, 2.237 mmol) in DCM (5 mL) and stirring the reaction mixture at RT for 1 h. This gave after workup and purification by flash column chromatography [silica (24 g), eluting with EtOAc in hexane from 0-25%] ethyl 2-(2-((5-bromo-7-methoxybenzofuran-3-yl)methoxy)-3-methylphenyl)acetate (237a) (430 mg, 51% yield) as a clear oil; $^1$H NMR (300 MHz, DMSO-$d_6$) δ 8.11 (s, 1H), 7.43 (d, J=1.8 Hz, 1H), 7.20-6.99 (m, 4H), 4.95 (s, 2H), 4.05-3.94 (m, 5H), 3.65 (s, 2H), 2.30 (s, 3H), 1.10 (t, J=7.1 Hz, 3H); MS (ES+): 433.0 (M+1).

Step-2: Preparation of ethyl 2-(2-((5-(3-(aminomethyl)phenyl)-7-methoxybenzofuran-3-yl)methoxy)-3-methylphenyl)acetate (237b)

Compound 237b was prepared according to the procedure reported in step-2 of scheme 1, from ethyl 2-(2-((5-bromo-7-methoxybenzofuran-3-yl)methoxy)-3-methylphenyl)acetate (237a) (150 mg, 0.346 mmol) in dioxane (12 mL) using 3-(aminomethyl)phenylboronic acid hydrochloride (1d) (81 mg, 0.433 mmol), $K_3PO_4$ (0.346 mL, 1.385 mmol), tricyclohexylphosphine (29.1 mg, 0.104 mmol) and $Pd_2(dba)_3$ (47.6 mg, 0.052 mmol) and heating at 115° C. for 3 h in microwave. This gave after workup and purification by flash column chromatography [silica gel (24 g), eluting with DMA-80 in DCM from 0-70%] ethyl 2-(2-((5-(3-(aminomethyl)phenyl)-7-methoxybenzofuran-3-yl)methoxy)-3-methylphenyl)acetate (237b) (88 mg, 55% yield) as a clear oil; $^1$H NMR (300 MHz, DMSO-$d_6$) δ 8.09 (s, 1H), 7.67 (s, 1H), 7.57-7.30 (m, 4H), 7.25-6.99 (m, 4H), 5.02 (s, 2H), 4.05 (s, 3H), 3.95 (q, J=7.1 Hz, 2H), 3.82 (s, 2H), 3.67 (s, 2H), 2.33 (s, 3H), 1.03 (t, J=7.2 Hz, 3H); MS (ES+): 460.1 (M+1).

Step-3: Preparation of 2-(2-((5-(3-(aminomethyl) phenyl)-7-methoxybenzofuran-3-yl)methoxy)-3-methylphenyl)acetic acid (237c)

Compound 237c was prepared according to the procedure reported in step-3 of scheme 1, from ethyl 2-(2-((5-(3-(aminomethyl)phenyl)-7-methoxybenzofuran-3-yl) methoxy)-3-methylphenyl)acetate (237b) (85 mg, 0.185 mmol) in THF (1.2 mL), acetonitrile (0.6 mL) using a solution of lithium hydroxide (0.555 mL, 0.555 mmol) and stirring at RT for 25 h.

This gave after workup and purification by reverse phase column chromatography [C18 column (50 g), eluting with ACN in water (containing 0.1% HCl) from 0-100%] 2-(2-((5-(3-(aminomethyl)phenyl)-7-methoxybenzofuran-3-yl) methoxy)-3-methylphenyl)acetic acid (237c) (73 mg, 91% yield) HCl salt as a white solid; $^1$H NMR (300 MHz, DMSO-$d_6$) δ 12.31 (s, 1H, $D_2O$ exchangeable), 8.28 (s, 3H, $D_2O$ exchangeable), 8.12 (s, 1H), 7.87 (s, 1H), 7.76 (d, J=7.7 Hz, 1H), 7.60-7.42 (m, 3H), 7.27 (s, 1H), 7.15 (t, J=8.2 Hz, 2H), 7.03 (t, J=7.5 Hz, 1H), 5.02 (s, 2H), 4.14 (s, 2H), 4.06 (s, 3H), 3.63 (s, 2H), 2.31 (s, 3H). MS (ES+): 432.2 (M+1); (ES−): 430.1 (M−1).

Scheme 238

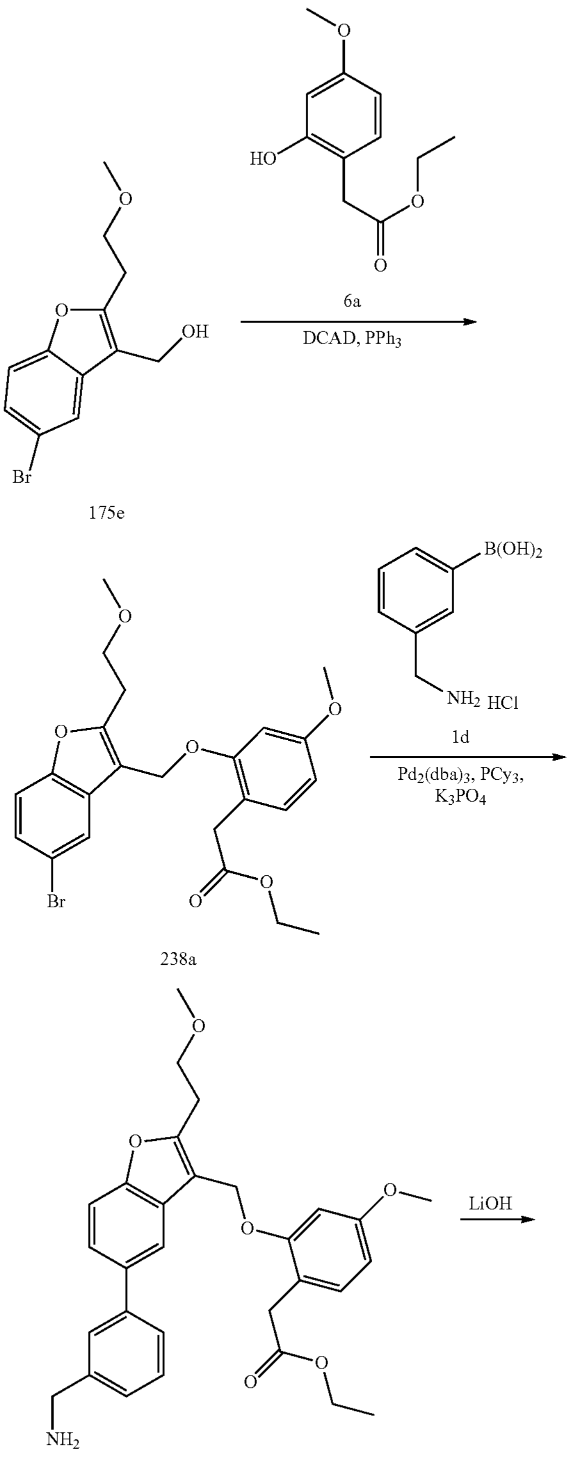

238b

-continued

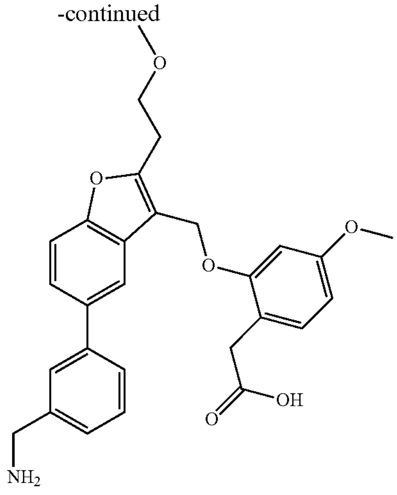

238c

Preparation of 2-(2-((5-(3-(aminomethyl)phenyl)-2-(2-methoxyethyl)benzofuran-3-yl)methoxy)-4-methoxyphenyl)acetic acid (238c)

Step-1: Preparation of ethyl 2-(2-((5-bromo-2-(2-methoxyethyl)benzofuran-3-yl)methoxy)-4-methoxyphenyl)acetate (238a)

Compound 238a was prepared according to the procedure reported in step-2 of scheme 65, from (5-bromo-2-(2-methoxyethyl)benzofuran-3-yl)methanol (175e) (210 mg, 0.736 mmol) in DCM (10 mL) using triphenylphosphine (212 mg, 0.810 mmol), ethyl 2-(2-hydroxy-4-methoxyphenyl)acetate (6a) (170 mg, 0.810 mmol), DCAD (297 mg, 0.810 mmol) in DCM (5 mL) and stirring at RT for 30 min. This gave after workup and purification using flash column chromatography [silica gel (12 g), eluting with EtOAc in hexane from 0-50%] ethyl 2-(2-((5-bromo-2-(2-methoxyethyl)benzofuran-3-yl)methoxy)-4-methoxyphenyl)acetate (238a) (203 mg, 58% yield) as a clear oil; MS (ES+): 498.60 (M+Na).

Step-2: Preparation of ethyl 2-(2-((5-(3-(aminomethyl)phenyl)-2-(2-methoxyethyl)benzofuran-3-yl)methoxy)-4-methoxyphenyl)acetate (238b)

Compound 238b was prepared according to the procedure reported in step-2 of scheme 1, from ethyl 2-(2-((5-bromo-2-(2-methoxyethyl)benzofuran-3-yl)methoxy)-4-methoxyphenyl)acetate (238a) (230 mg, 0.482 mmol) in dioxane (20 mL) using (3-(aminomethyl)phenyl)boronic acid hydrochloride (1d) (181 mg, 0.964 mmol), 4 M solution of $K_3PO_4$ (0.482 mL, 1.927 mmol), tricyclohexylphosphine (54.0 mg, 0.193 mmol), $Pd_2(dba)_3$ (88 mg, 0.096 mmol) and heating at 110° C. for 5 h. This gave after workup and purification using flash column chromatography [silica gel (40 g), eluting with DMA-80 in DCM from 0-100%] ethyl 2-(2-((5-(3-(aminomethyl)phenyl)-2-(2-methoxyethyl)benzofuran-3-yl)methoxy)-4-methoxyphenyl)acetate (238b) (67 mg, 28% yield) as a yellow oil; MS (ES+) 504.2 (M+1).

Step-3: Preparation of 2-(2-((5-(3-(aminomethyl)phenyl)-2-(2-methoxyethyl)benzofuran-3-yl)methoxy)-4-methoxyphenyl)acetic acid (238c)

Compound 238c was prepared according to the procedure reported in step-3 of scheme 1, from ethyl 2-(2-((5-(3-(aminomethyl)phenyl)-2-(2-methoxyethyl)benzofuran-3-yl)methoxy)-4-methoxyphenyl)acetate (238b) (67 mg, 0.133 mmol) in THF (3 mL) using lithium hydroxide hydrate (60.7 mg, 1.445 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-(2-methoxyethyl)benzofuran-3-yl)methoxy)-4-methoxyphenyl)acetic acid (238c) (48 mg, 21% yield) HCl salt as a white solid; $^1H$ NMR (300 MHz, DMSO-$d_6$) δ 12.04 (s, 1H, $D_2O$ exchangeable), 8.52 (s, 2H, $D_2O$ exchangeable), 7.96 (s, 1H), 7.90 (s, 1H), 7.72 (dt, J=7.3, 1.8 Hz, 1H), 7.68-7.59 (m, 2H), 7.53-7.42 (m, 2H), 7.08 (d, J=8.3 Hz, 1H), 6.84 (d, J=2.4 Hz, 1H), 6.50 (dd, J=8.3, 2.3 Hz, 1H), 5.27 (s, 2H), 4.09 (s, 2H), 3.76 (s, 3H), 3.66 (t, J=6.5 Hz, 2H), 3.41 (s, 2H), 3.25 (s, 3H), 3.15 (t, J=6.5 Hz, 2H); MS (ES+): 476.2 (M+1), (ES−): 474.2 (M−1); Calculated for $C_{28}H_{29}NO_6 \cdot HCl \cdot H_2O$: C, 63.45; H, 6.09; Cl, 6.69; N, 2.64. Found: C, 63.29; H, 6.14; Cl, 6.51; N, 2.65.

Scheme 239

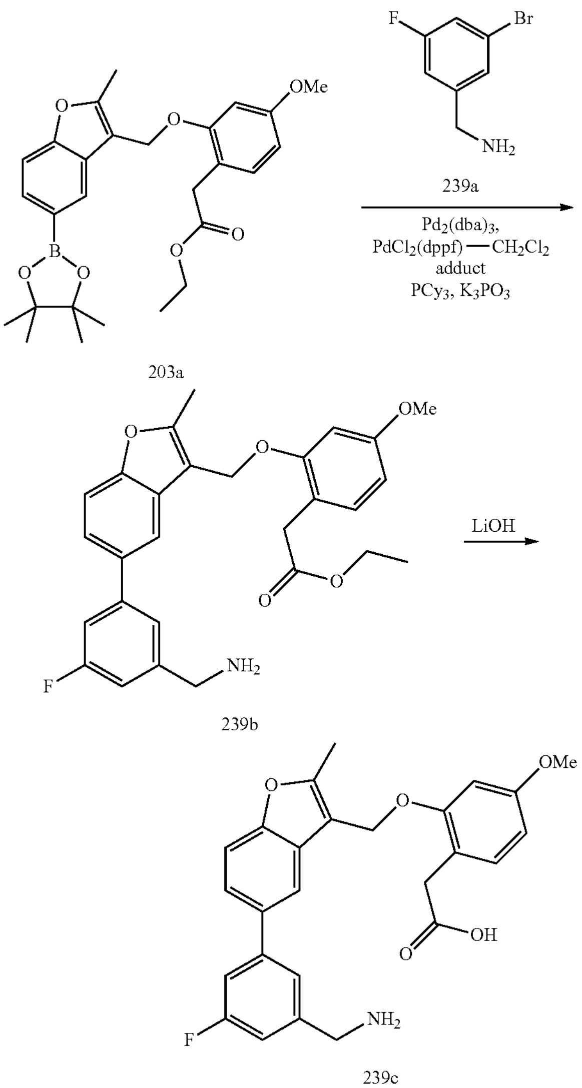

203a

239a

239b

239c

Preparation of 2-(2-((5-(3-(aminomethyl)-5-fluorophenyl)-2-methylbenzofuran-3-yl)methoxy)-4-methoxyphenyl)acetic acid (239c)

Step-1: Preparation of ethyl 2-(2-((5-(3-(aminomethyl)-5-fluorophenyl)-2-methylbenzofuran-3-yl)methoxy)-4-methoxyphenyl)acetate (239b)

Compound 239b was prepared according to the procedure reported in step-2 of scheme 1, from ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (300 mg, 0.625 mmol) in dioxane (20 mL) using (3-bromo-5-fluorophenyl) methanamine (239a) (255 mg, 1.249 mmol), 4 M solution of $K_3PO_4$ (0.625 mL, 2.498 mmol), tricyclohexylphosphine (52.5 mg, 0.187 mmol), $Pd_2(dba)_3$ (114 mg, 0.125 mmol), $PdCl_2(dppf)$-$CH_2Cl_2$ adduct (102 mg, 0.125 mmol) and heating at 110° C. overnight. This gave after workup and purification using flash column chromatography [silica gel (24 g), eluting with DMA-80 in DCM from 0-70%] ethyl 2-(2-((5-(3-(aminomethyl)-5-fluorophenyl)-2-methylbenzofuran-3-yl)methoxy)-4-methoxyphenyl)acetate (239b) (124 mg, 42% yield) as a clear oil; MS (ES+): 478.2 (M+1).

Step-2: Preparation of 2-(2-((5-(3-(aminomethyl)-5-fluorophenyl)-2-methylbenzofuran-3-yl)methoxy)-4-methoxyphenyl)acetic acid (239c)

Compound 239c was prepared according to the procedure reported in step-3 of scheme 1, from ethyl 2-(2-((5-(3-(aminomethyl)-5-fluorophenyl)-2-methylbenzofuran-3-yl)methoxy)-4-methoxyphenyl)acetate (239b) (124 mg, 0.260 mmol) in THF (3 mL) using lithium hydroxide hydrate (105 mg, 2.498 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)-5-fluorophenyl)-2-methylbenzofuran-3-yl)methoxy)-4-methoxyphenyl)acetic acid (239c) (54 mg, 19% yield) HCl salt as a white solid; $^1H$ NMR (300 MHz, DMSO-$d_6$) δ 8.50 (s, 2H, $D_2O$ exchangeable), 7.99 (s, 1H), 7.76 (s, 1H), 7.67-7.54 (m, 3H), 7.34 (dt, J=9.7, 1.8 Hz, 1H), 7.08 (d, J=8.3 Hz, 1H), 6.83 (d, J=2.4 Hz, 1H), 6.49 (dd, J=8.3, 2.4 Hz, 1H), 5.26 (s, 2H), 4.12 (s, 2H), 3.76 (s, 3H), 3.39 (s, 2H), 2.52 (s, 3H); $^{19}F$ NMR (282 MHz, DMSO-$d_6$) δ −112.74. MS (ES+) 450.2 (M+1), (ES−) 448.1 (M−1); Calculated for $C_{26}H_{24}FNO_5 \cdot HCl \cdot 0.5H_2O$: C, 63.09; H, 5.29; Cl, 7.16; N, 2.83. Found: C, 63.08; H, 5.24; Cl, 7.30; N, 2.93.

Scheme 240

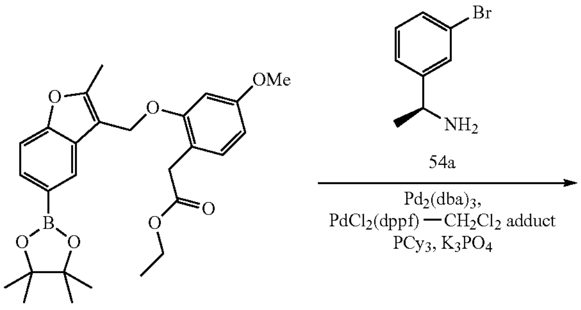

54a

203a

-continued

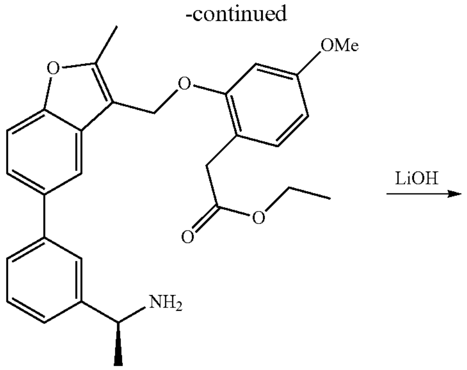

240a

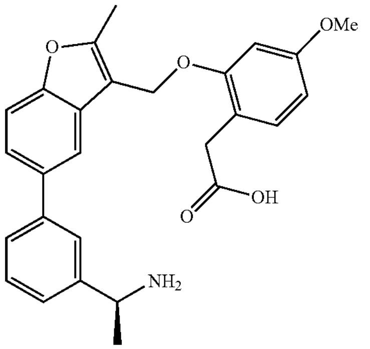

240b

Preparation of (S)-2-(2-((5-(3-(1-aminoethyl)phenyl)-2-methylbenzofuran-3-yl)methoxy)-4-methoxyphenyl)acetic acid (240b)

Step-1: Preparation of (S)-ethyl 2-(2-((5-(3-(1-aminoethyl)phenyl)-2-methylbenzofuran-3-yl)methoxy)-4-methoxyphenyl)acetate (240a)

Compound 240a was prepared according to the procedure reported in step-2 of scheme 1, from ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (300 mg, 0.625 mmol) in dioxane (20 mL) using (S)-1-(3-bromophenyl)ethanamine (54a) (250 mg, 1.249 mmol), 4 M solution of $K_3PO_4$ (10.625 mL, 2.498 mmol), tricyclohexylphosphine (52.5 mg, 0.187 mmol), $Pd_2(dba)_3$ (114 mg, 0.125 mmol), $PdCl_2(dppf)$-$CH_2Cl_2$ adduct (102 mg, 0.125 mmol) and heating at 110° C. for 2 h. This gave after workup and purification using flash column chromatography [silica gel (24 g), eluting with DMA-80 in DCM from 0-70%](S)-ethyl 2-(2-((5-(3-(1-aminoethyl)phenyl)-2-methylbenzofuran-3-yl)methoxy)-4-methoxyphenyl)acetate (240a) (147 mg, 50% yield) as a clear oil; MS (ES+) 474.2 (M+1).

Step-2: Preparation of (S)-2-(2-((5-(3-(1-aminoethyl)phenyl)-2-methylbenzofuran-3-yl)methoxy)-4-methoxyphenyl)acetic acid (240b)

Compound 240b was prepared according to the procedure reported in step-3 of scheme 1, from (S)-ethyl 2-(2-((5-(3-(1-aminoethyl)phenyl)-2-methylbenzofuran-3-yl)methoxy)-4-methoxyphenyl)acetate (240a) (147 mg, 0.310 mmol) in THF (3 mL) using lithium hydroxide hydrate (105 mg, 2.498 mmol) in water (1 mL) and stirring overnight at RT. This gave after workup and purification using reverse phase column chromatography [C18 column (30 g), eluting with ACN in water (containing 0.1% HCl) from 0-100%](S)-2-(2-((5-(3-(1-aminoethyl)phenyl)-2-methylbenzofuran-3-yl)methoxy)-4-methoxyphenyl)acetic acid (240b) (88 mg, 32% yield) HCl salt as a white solid; $^{1}$H NMR (300 MHz, DMSO-$d_6$) δ 12.07 (s, 1H, $D_2O$ exchangeable), 8.71 (s, 3H, $D_2O$ exchangeable), 7.97 (d, J=12.5 Hz, 2H), 7.76-7.66 (m, 1H), 7.66-7.56 (m, 2H), 7.50 (d, J=4.8 Hz, 2H), 7.08 (d, J=8.3 Hz, 1H), 6.84 (d, J=2.4 Hz, 1H), 6.49 (dd, J=8.3, 2.3 Hz, 1H), 5.28 (s, 2H), 4.52-4.38 (m, 1H), 3.76 (s, 3H), 3.42 (s, 2H), 2.52 (s, 3H), 1.59 (d, J=6.7 Hz, 3H); MS (ES+) 446.2 (M+1); (ES−) 444.2 (M−1); Analysis calculated for $C_{27}H_{27}NO_5 \cdot 1.1HCl \cdot 0.25H_2O$: C, 66.17; H, 5.88; Cl, 7.96; N, 2.86. Found: C, 66.12; H, 5.89; Cl, 7.99; N, 3.00. Optical rotation $[\alpha]_D$=(+) 3.265 [$CH_3OH$, 0.245].

Scheme 241

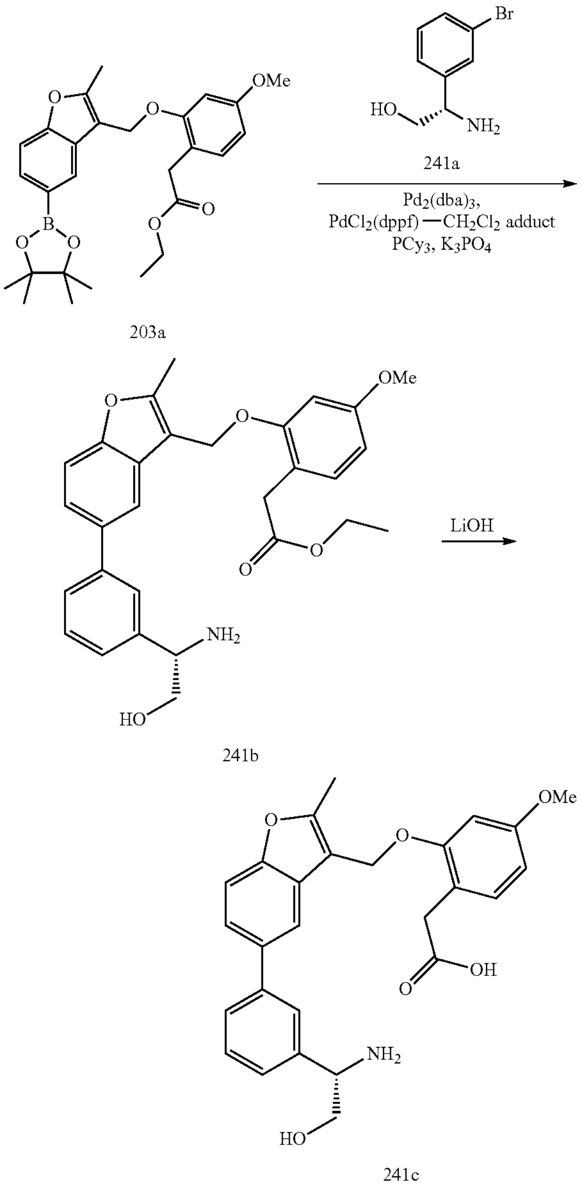

241a

203a

241b

241c

Preparation of (S)-2-(2-((5-(3-(1-amino-2-hydroxyethyl)phenyl)-2-methylbenzofuran-3-yl)methoxy)-4-methoxyphenyl)acetic acid (241c)

Step-1: Preparation of (S)-ethyl 2-(2-((5-(3-(1-amino-2-hydroxyethyl)phenyl)-2-methylbenzofuran-3-yl)methoxy)-4-methoxyphenyl)acetate (241b)

Compound 241b was prepared according to the procedure reported in step-2 of scheme 1, from ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (300 mg, 0.625 mmol) in dioxane (20 mL) using (S)-2-amino-2-(3-bromophenyl)ethanol (241a) (270 mg, 1.249 mmol), 4 M solution of $K_3PO_4$ (0.625 mL, 2.498 mmol), tricyclohexylphosphine (52.5 mg, 0.187 mmol), $Pd_2(dba)_3$ (114 mg, 0.125 mmol), $PdCl_2(dppf)$-$CH_2Cl_2$ adduct (102 mg, 0.125 mmol) and heating at 110° C. overnight. This gave after workup and purification using flash column chromatography [silica gel (24 g), eluting with DMA-80 in DCM from 0-70%](S)-ethyl 2-(2-((5-(3-(1-amino-2-hydroxyethyl)phenyl)-2-methylbenzofuran-3-yl)methoxy)-4-methoxyphenyl)acetate (241b) (143 mg, 47% yield) as a clear oil; MS (ES+): 490.2 (M+1).

Step-2: Preparation of (S)-2-(2-((5-(3-(1-amino-2-hydroxyethyl)phenyl)-2-methylbenzofuran-3-yl)methoxy)-4-methoxyphenyl)acetic acid (241c)

Compound 241c was prepared according to the procedure reported in step-3 of scheme 1, from (S)-ethyl 2-(2-((5-(3-(1-amino-2-hydroxyethyl)phenyl)-2-methylbenzofuran-3-yl)methoxy)-4-methoxyphenyl)acetate (241b) (143 mg, 0.292 mmol) in THF (3 mL) using lithium hydroxide hydrate (105 mg, 2.498 mmol) in water (1 mL) and stirring overnight at RT. This gave after workup and purification using reverse phase column chromatography [C18 column (30 g), eluting with ACN in water (containing 0.1% HCl) from 0-100%](S)-2-(2-((5-(3-(1-amino-2-hydroxyethyl)phenyl)-2-methylbenzofuran-3-yl)methoxy)-4-methoxyphenyl)acetic acid (241c) (81 mg, 28% yield) HCl salt as a white solid; $^{1}$H NMR (300 MHz, DMSO-$d_6$) δ 12.04 (s, 1H, $D_2O$ exchangeable), 8.58 (s, 3H, $D_2O$ exchangeable), 8.02-7.86 (m, 2H), 7.73 (dt, J=7.4, 1.7 Hz, 1H), 7.66-7.56 (m, 2H), 7.55-7.40 (m, 2H), 7.08 (d, J=8.3 Hz, 1H), 6.83 (d, J=2.4 Hz, 1H), 6.49 (dd, J=8.3, 2.4 Hz, 1H), 5.60 (s, 1H, $D_2O$ exchangeable), 5.27 (s, 2H), 4.35 (t, J=6.1 Hz, 1H), 3.79 (s, 2H), 3.76 (s, 3H), 3.41 (s, 2H), 2.52 (s, 3H); MS (ES+): 462.2 (M+1); (ES−): 460.2 (M−1); Analysis calculated for $C_{27}H_{27}NO_{6 \cdot 1.05}HCl \cdot 0.5H_2O$: C, 63.74; H, 5.75; Cl, 7.32; N, 2.75. Found: C, 63.92; H, 5.63; Cl, 7.22; N, 2.97; Optical rotation $[\alpha]_D$=(+) 8.627 [$CH_3OH$, 0.255].

Scheme 242

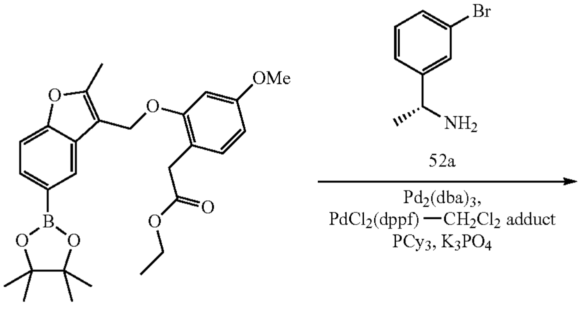

52a

203a

-continued

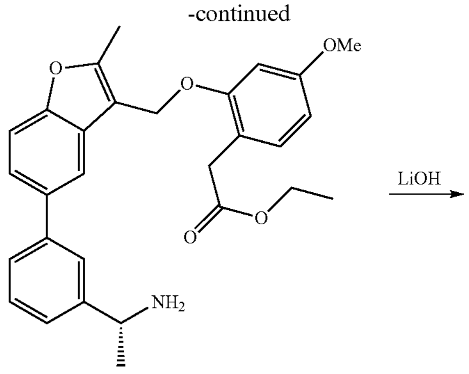

242a

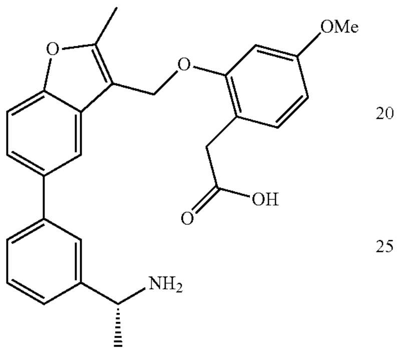

242b

Preparation of (R)-2-(2-((5-(3-(1-aminoethyl)phenyl)-2-methylbenzofuran-3-yl)methoxy)-4-methoxyphenyl)acetic acid (242b)

Step-1: Preparation of (R)-ethyl 2-(2-((5-(3-(1-aminoethyl)phenyl)-2-methylbenzofuran-3-yl)methoxy)-4-methoxyphenyl)acetate (242a)

Compound 242a was prepared according to the procedure reported in step-2 of scheme 1, from ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (300 mg, 0.625 mmol) in dioxane (20 mL) using (R)-1-(3-bromophenyl)ethanamine (52a) (250 mg, 1.249 mmol), 4 M solution of $K_3PO_4$ (0.625 mL, 2.498 mmol), tricyclohexylphosphine (52.5 mg, 0.187 mmol), $Pd_2(dba)_3$ (114 mg, 0.125 mmol), $PdCl_2(dppf)$-$CH_2Cl_2$-adduct (102 mg, 0.125 mmol) and heating at 110° C. for 2 h. This gave after workup and purification using flash column chromatography [silica gel (24 g), eluting with DMA-80 in DCM from 0-70%](R)-ethyl 2-(2-((5-(3-(1-aminoethyl)phenyl)-2-methylbenzofuran-3-yl)methoxy)-4-methoxyphenyl)acetate (242a) (102 mg, 35% yield) as a yellow oil; MS (ES+): 474.2 (M+1).

Step-2: Preparation of (R)-2-(2-((5-(3-(1-aminoethyl)phenyl)-2-methylbenzofuran-3-yl)methoxy)-4-methoxyphenyl)acetic acid (242b)

Compound 242b was prepared according to the procedure reported in step-3 of scheme 1, from (R)-ethyl 2-(2-((5-(3-(1-aminoethyl)phenyl)-2-methylbenzofuran-3-yl)methoxy)-4-methoxyphenyl)acetate (242a) (102 mg, 0.215 mmol) in THF (3 mL) using lithium hydroxide hydrate (105 mg, 2.498 mmol) in water (1 mL) and stirring overnight at RT. This gave after workup and purification using reverse phase column chromatography [C18 column (30 g), eluting with ACN in water (containing 0.1% HCl) from 0-100%](R)-2-(2-((5-(3-(1-aminoethyl)phenyl)-2-methylbenzofuran-3-yl)methoxy)-4-methoxyphenyl)acetic acid (242b) (57 mg, 20% yield) HCl salt as a white solid; $^1H$ NMR (300 MHz, DMSO-$d_6$) δ 12.06 (s, 1H, $D_2O$ exchangeable), 8.57 (s, 3H, $D_2O$ exchangeable), 7.97 (s, 1H), 7.92 (s, 1H), 7.73 (dt, J=7.1, 1.9 Hz, 1H), 7.62 (d, J=1.2 Hz, 2H), 7.55-7.45 (m, 2H), 7.08 (d, J=8.3 Hz, 1H), 6.84 (d, J=2.4 Hz, 1H), 6.50 (dd, J=8.3, 2.3 Hz, 1H), 5.28 (s, 2H), 4.55-4.39 (m, 1H), 3.76 (s, 3H), 3.42 (s, 2H), 2.53 (s, 3H), 1.58 (d, J=6.7 Hz, 3H); MS (ES+): 446.2 (M+1); (ES−): 444.2 (M−1).

Scheme 243

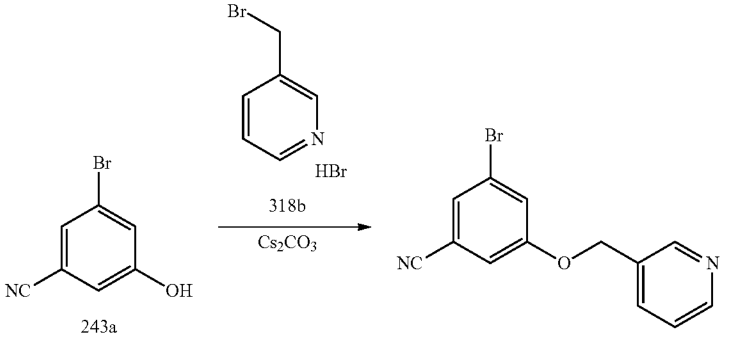

243a

243b

-continued
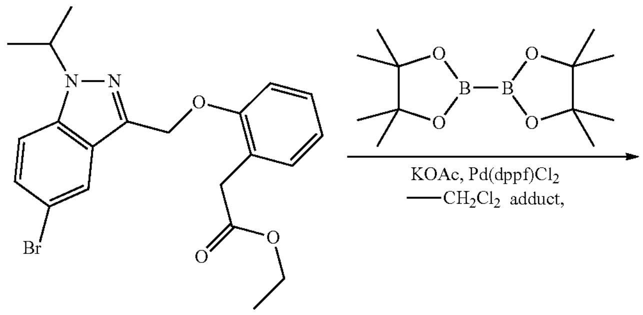
182c
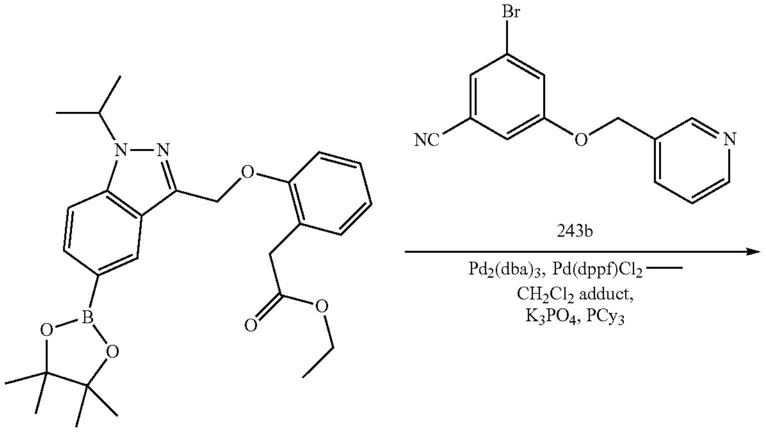
243c
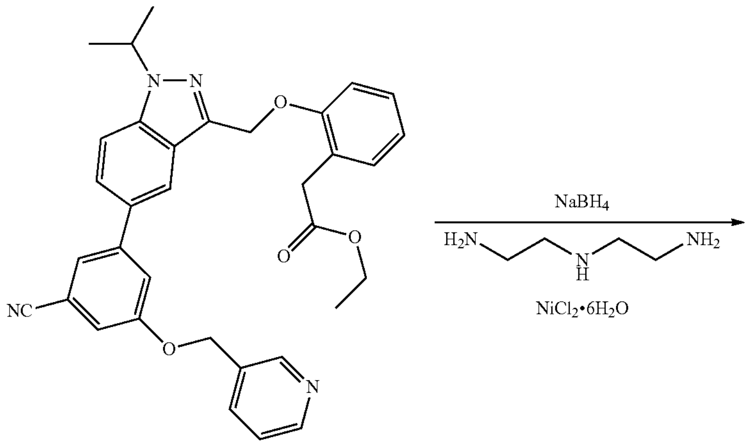
243d

-continued

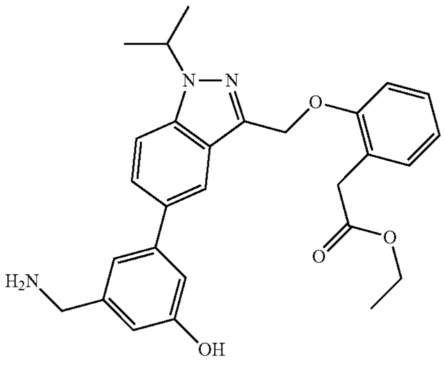

243e and

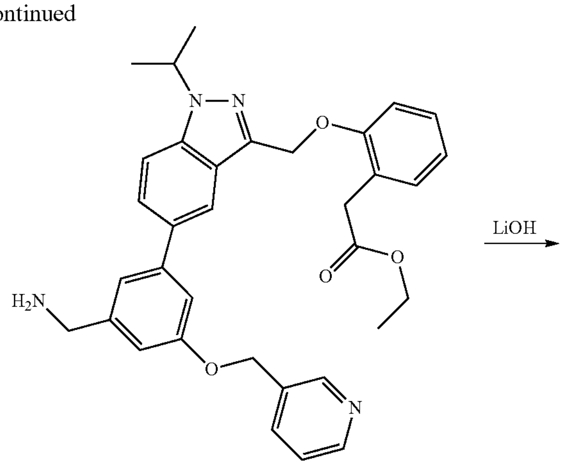

243f

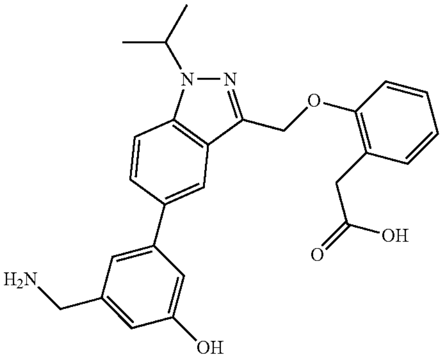

243g and

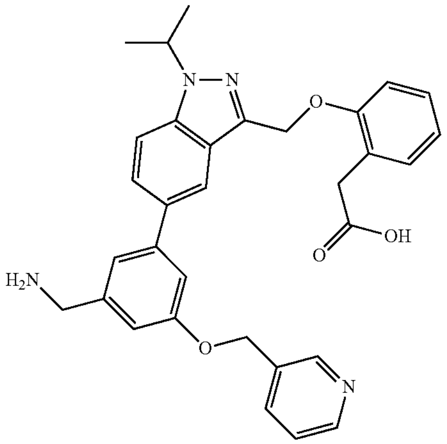

243h

Preparation of 2-(2-((5-(3-(aminomethyl)-5-hydroxyphenyl)-1-isopropyl-1H-indazol-3-yl)methoxy)phenyl)acetic acid (243g) and 2-(2-((5-(3-(aminomethyl)-5-(pyridin-3-ylmethoxy)phenyl)-1-isopropyl-1H-indazol-3-yl)methoxy)phenyl)acetic acid (243 h)

Step-1: Preparation of 3-bromo-5-(pyridin-3-ylmethoxy)benzonitrile (243b)

Compound 243b was prepared according to the procedure reported in step-3 of scheme 7, from 3-bromo-5-hydroxybenzonitrile (243a) (1 g, 5.05 mmol; CAS #770718-92-8) in DMF (15 mL) using 3-(bromomethyl)pyridine hydrobromide (318b) (1.277 g, 5.05 mmol), cesium carbonate (4.94 g, 15.15 mmol) and stirring for 15 h at RT. This gave after workup and purification using flash column chromatography [silica gel (40 g), eluting with EtOAc in Hexane from 0-80%] 3-bromo-5-(pyridin-3-ylmethoxy)benzonitrile (243b) (1.3 g, 89% yield) as a white solid; $^1$H NMR (300 MHz, DMSO-$d_6$) δ 8.68 (d, J=2.2 Hz, 1H), 8.57 (dd, J=4.8, 1.7 Hz, 1H), 7.88 (dt, J=7.9, 2.0 Hz, 1H), 7.74 (t, J=1.5 Hz, 1H), 7.67 (t, J=2.0 Hz, 1H), 7.62 (dd, J=2.4, 1.3 Hz, 1H), 7.45 (ddd, J=7.9, 4.8, 0.9 Hz, 1H), 5.25 (s, 2H); MS (ES+): 289.00 & 291.00 (M+1).

Step-2: Preparation of ethyl 2-(2-((1-isopropyl-5-(4,4,5,5-tetramethyl-1,3,2-dioxaborolan-2-yl)-1H-indazol-3-yl)methoxy)phenyl)acetate (243c)

Compound 243c was prepared according to the procedure reported in step-1 of scheme 27, from ethyl 2-(2-((5-bromo-1-isopropyl-1H-indazol-3-yl)methoxy)phenyl)acetate (182c) (570 mg, 1.322 mmol) in anhydrous dioxane (10 mL) using BisPin (671 mg, 2.64 mmol), potassium acetate (324 mg, 3.30 mmol), $PdCl_2$(dppf)-$CH_2Cl_2$ adduct (64.8 mg, 0.079 mmol) and heating at 100° C. for 3 h. This gave after work up and purification using flash column chromatography [silica gel (12 g), eluting with EtOAc in hexane from 0-40%] ethyl 2-(2-((1-isopropyl-5-(4,4,5,5-tetramethyl-1,3,2-dioxaborolan-2-yl)-1H-indazol-3-yl)methoxy)phenyl)acetate (243c) (500 mg, 79% yield) as a clear oil; MS (ES+): 479.30 (M+1); 501.30 (M+Na); MS (ES−): 477.15 (M−1).

Step-3: Preparation of ethyl 2-(2-((5-(3-cyano-5-(pyridin-3-ylmethoxy)phenyl)-1-isopropyl-1H-indazol-3-yl)methoxy)phenyl)acetate (243d)

Compound 243d was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (2 mL) and THF (2 mL) using 3-bromo- 5-(pyridin-3-ylmethoxy)benzonitrile (243b) (181 mg, 0.627 mmol), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2(dppf)$-$CH_2Cl_2$ adduct (34.1 mg, 0.042 mmol) and heating at 100° C. for 2 h. This gave after workup and purification using flash column chromatography [silica gel (12 g), eluting with EtOAc/MeOH (9:1) in hexane from 0-100%]ethyl 2-(2-((5-(3-cyano-5-(pyridin-3-ylmethoxy)phenyl)-1-isopropyl-1H-indazol-3-yl)methoxy)phenyl)acetate (243d) (200 mg, 85% yield) as a clear oil; $^1H$ NMR (300 MHz, DMSO-$d_6$) δ 8.71 (d, J=2.1 Hz, 1H), 8.57 (dd, J=4.8, 1.7 Hz, 1H), 8.11 (s, 1H), 7.91 (dt, J=7.8, 2.0 Hz, 1H), 7.82 (q, J=1.7 Hz, 3H), 7.74-7.68 (m, 1H), 7.54 (dd, J=2.4, 1.3 Hz, 1H), 7.44 (dd, J=7.9, 4.8 Hz, 1H), 7.29 (d, J=3.9 Hz, 2H), 7.19 (d, J=7.4 Hz, 1H), 6.92 (dt, J=8.0, 4.0 Hz, 1H), 5.43 (s, 2H), 5.31 (s, 2H), 5.05 (p, J=6.5 Hz, 1H), 3.66 (q, J=7.1 Hz, 2H), 3.53 (s, 2H), 1.51 (d, J=6.6 Hz, 6H), 0.76 (t, J=7.1 Hz, 3H); MS (ES+): 561.25 (M+1).

Step-4: Preparation of ethyl 2-(2-((5-(3-(aminomethyl)-5-hydroxyphenyl)-1-isopropyl-1H-indazol-3-yl)methoxy)phenyl)acetate (243e) and ethyl 2-(2-((5-(3-(aminomethyl)-5-(pyridin-3-ylmethoxy)phenyl)-1-isopropyl-1H-indazol-3-yl)methoxy)phenyl)acetate (243f)

Compound 243e was prepared according to the procedure reported in step-2 of scheme 1, from ethyl 2-(2-((5-(3-cyano-5-(pyridin-3-ylmethoxy)phenyl)-1-isopropyl-1H-indazol-3-yl)methoxy)phenyl)acetate (243d) (200 mg, 0.357 mmol) in anhydrous ethanol (10 mL) using nickel(II) chloride hexahydrate (42.4 mg, 0.178 mmol), sodium borohydride (40.5 mg, 1.070 mmol), N1-(2-aminoethyl)ethane-1,2-diamine (0.077 mL, 0.713 mmol) and stirring for 1 h. The residue obtained was purified using flash column chromatography [silica gel (24 g), eluting with DMA-80 in DCM from 0 to 60%] to provide a mixture of ethyl 2-(2-((5-(3-(aminomethyl)-5-hydroxyphenyl)-1-isopropyl-1H-indazol-3-yl)methoxy)phenyl)acetate (243e) and ethyl 2-(2-((5-(3-(aminomethyl)-5-(pyridin-3-ylmethoxy)phenyl)-1-isopropyl-1H-indazol-3-yl)methoxy)phenyl)acetate (243f) (100 mg) as a white solid; MS (ES+): 474.20, 565.30 (M+1).

Step-5: Preparation of 2-(2-((5-(3-(aminomethyl)-5-hydroxyphenyl)-1-isopropyl-1H-indazol-3-yl)methoxy)phenyl)acetic acid (243g) and 2-(2-((5-(3-(aminomethyl)-5-(pyridin-3-ylmethoxy)phenyl)-1-isopropyl-1H-indazol-3-yl)methoxy)phenyl)acetic acid (243 h)

Compounds 243g and 243 h were prepared according to the procedure reported in step-3 of scheme 1, from above mixture (step-3) of ethyl 2-(2-((5-(3-(aminomethyl)-5-hydroxyphenyl)-1-isopropyl-1H-indazol-3-yl)methoxy)phenyl)acetate (243e) and ethyl 2-(2-((5-(3-(aminomethyl)-5-(pyridin-3-ylmethoxy)phenyl)-1-isopropyl-1H-indazol-3-yl)methoxy)phenyl)acetate (243f) (100 mg) in THF (2 mL) and MeOH (2 mL) using a solution of lithium hydroxide hydrate (22.29 mg, 0.531 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-5-hydroxyphenyl)-1-isopropyl-1H-indazol-3-yl)methoxy)phenyl)acetic acid (243g) (18 mg, 23% yield) HCl salt as a white solid; $^1H$ NMR (300 MHz, DMSO-$d_6$) δ 12.07 (s, 1H, $D_2O$ exchangeable), 9.76 (s, 1H, $D_2O$ exchangeable), 8.21 (s, 3H, $D_2O$ exchangeable), 8.00 (d, J=1.4 Hz, 1H), 7.82 (d, J=8.8 Hz, 1H), 7.67 (dd, J=8.8, 1.6 Hz, 1H), 7.32-7.22 (m, 3H), 7.20 (d, J=7.2 Hz, 1H), 7.09 (d, J=1.9 Hz, 1H), 6.92 (ddd, J=7.6, 5.6, 2.8 Hz, 1H), 6.83 (t, J=1.9 Hz, 1H), 5.44 (s, 2H), 5.11-4.93 (m, 1H), 4.01 (s, 2H), 3.52 (s, 2H), 1.51 (d, J=6.6 Hz, 6H); MS (ES+): 446.20 (M+1); (ES−): 444.20 (M−1); and 2-(2-((5-(3-(aminomethyl)-5-(pyridin-3-ylmethoxy)phenyl)-1-isopropyl-1H-indazol-3-yl)methoxy)phenyl)acetic acid (243 h) (15 mg, 16% yield) HCl salt as a white solid; $^1H$ NMR (300 MHz, DMSO-$d_6$) δ 8.85 (d, J=2.1 Hz, 1H), 8.71 (dd, J=5.2, 1.6 Hz, 1H), 8.36 (s, 3H, $D_2O$ exchangeable), 8.22 (d, J=8.0 Hz, 1H), 8.08 (s, 1H), 7.84 (d, J=8.9 Hz, 1H), 7.79-7.67 (m, 2H), 7.48 (s, 1H), 7.45-7.38 (m, 1H), 7.31-7.24 (m, 2H), 7.24-7.16 (m, 2H), 6.97-6.86 (m, 1H), 5.45 (s, 2H), 5.35 (s, 2H), 5.13-4.93 (m, 1H), 4.12-4.05 (m, 2H), 3.53 (s, 2H), 1.52 (d, J=6.6 Hz, 6H); MS (ES+): 537.30 (M+1); (ES−): 535.20 (M−1).

Scheme 244

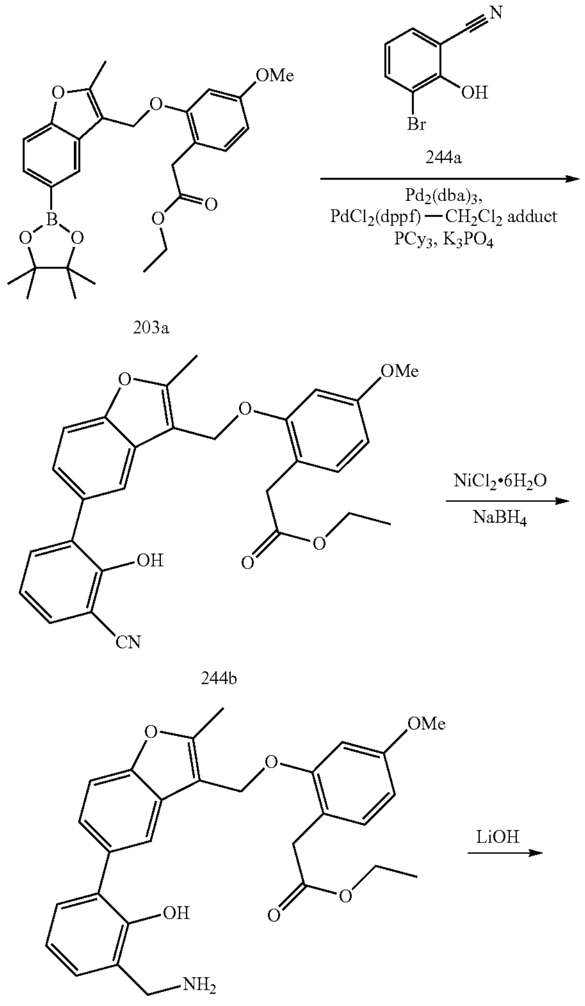

244a

203a

244b

244c

-continued

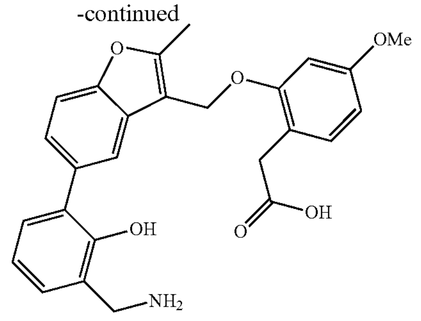

244d

Preparation of 2-(2-((5-(3-(aminomethyl)-2-hydroxyphenyl)-2-methylbenzofuran-3-yl)methoxy)-4-methoxyphenyl)acetic acid (244d)

Step-1: Preparation of ethyl 2-(2-((5-(3-cyano-2-hydroxyphenyl)-2-methylbenzofuran-3-yl)methoxy)-4-methoxyphenyl)acetate (244b)

Compound 244b was prepared according to the procedure reported in step-2 of scheme 1, from ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (350 mg, 0.729 mmol) in dioxane (20 mL) using 3-bromo-2-hydroxybenzonitrile (244a) (289 mg, 1.457 mmol; CAS #13073-28-4), 4 M solution of $K_3PO_4$ (0.729 mL, 2.91 mmol), tricyclohexylphosphine (61.3 mg, 0.219 mmol), $Pd_2(dba)_3$ (133 mg, 0.146 mmol), $PdCl_2(dppf)$-$CH_2Cl_2$ adduct (119 mg, 0.146 mmol) and heating at 110° C. overnight. This gave after workup and purification using flash column chromatography [silica gel (24 g), eluting with DMA-80 in DCM from 0-70%] ethyl 2-(2-((5-(3-cyano-2-hydroxyphenyl)-2-methylbenzofuran-3-yl)methoxy)-4-methoxyphenyl)acetate (244b) (180 mg, 52% yield) as a yellow oil; MS (ES+): 494.20 (M+Na).

Step-2: Preparation of ethyl 2-(2-((5-(3-(aminomethyl)-2-hydroxyphenyl)-2-methylbenzofuran-3-yl)methoxy)-4-methoxyphenyl)acetate (244c)

Compound 244c was prepared according to the procedure reported in step-2 of scheme 145, from ethyl 2-(2-((5-(3-cyano-2-hydroxyphenyl)-2-methylbenzofuran-3-yl)methoxy)-4-methoxyphenyl)acetate (244b) (180 mg, 0.382 mmol) in EtOH (5 mL) using nickel(II) chloride hexahydrate (91 mg, 0.382 mmol), sodium borohydride (87 mg, 2.291 mmol) and stirring at 0° C. This gave after workup and purification using flash column chromatography [silica gel (40 g), eluting with DMA-80 in DCM from 0-100%] ethyl 2-(2-((5-(3-(aminomethyl)-2-hydroxyphenyl)-2-methylbenzofuran-3-yl)methoxy)-4-methoxyphenyl)acetate (244c) (86 mg, 47% yield) as a clear oil; MS (ES+): 476.2 (M+1).

Step-3: Preparation of 2-(2-((5-(3-(aminomethyl)-2-hydroxyphenyl)-2-methylbenzofuran-3-yl)methoxy)-4-methoxyphenyl)acetic acid (244d)

Compound 244d was prepared according to the procedure reported in step-3 of scheme 1, from ethyl 2-(2-((5-(3-(aminomethyl)-2-hydroxyphenyl)-2-methylbenzofuran-3-yl)methoxy)-4-methoxyphenyl)acetate (244c) (86 mg, 0.181 mmol) in THF (3 mL) using lithium hydroxide hydrate (48.1 mg, 1.145 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)-2-hydroxyphenyl)-2-methylbenzofuran-3-yl)methoxy)-4-methoxyphenyl)acetic acid (244d) (30 mg, 18% yield) HCl salt as a white solid; $^1H$ NMR (300 MHz, DMSO-$d_6$) δ 11.90 (s, 1H, $D_2O$ exchangeable), 8.34 (s, 3H, $D_2O$ exchangeable), 7.69 (d, J=1.7 Hz, 1H), 7.56 (d, J=8.5 Hz, 1H), 7.42-7.25 (m, 3H), 7.07 (d, J=8.3 Hz, 1H), 7.00 (t, J=7.6 Hz, 1H), 6.80 (d, J=2.4 Hz, 1H), 6.48 (dd, J=8.3, 2.3 Hz, 1H), 5.22 (s, 2H), 4.06 (s, 2H), 3.75 (s, 3H), 3.39 (s, 2H), 2.52 (s, 3H); MS (ES+): 448.2 (M+1); (ES−): 446.1 (M−1); Analysis calculated for $C_{26}H_{25}NO_6 \cdot HCl \cdot H_2O$: C, 62.21; H, 5.62; N, 2.79. Found: C, 62.31; H, 5.48; N, 3.03.

Scheme 245

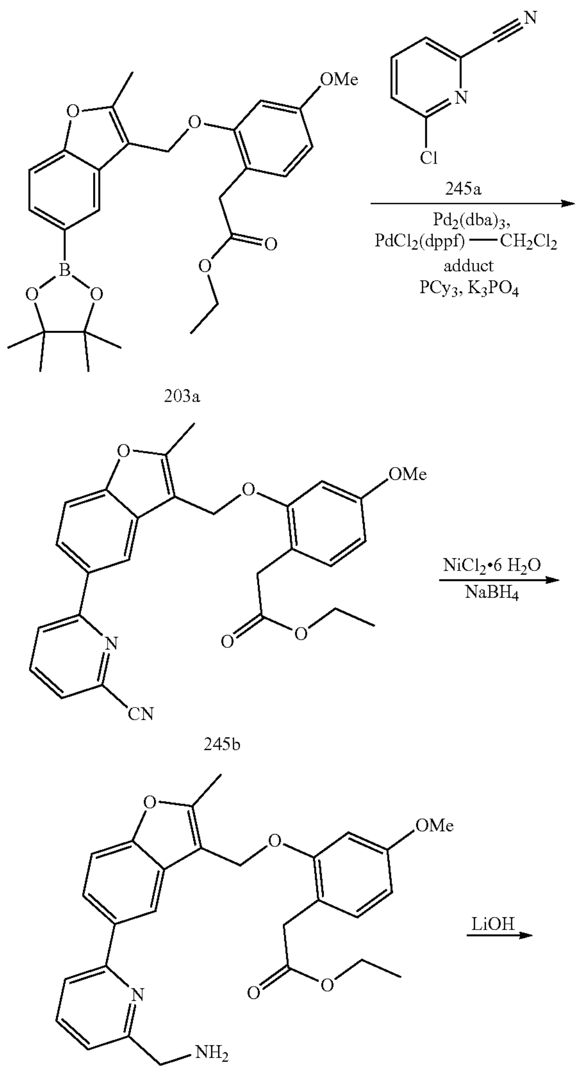

203a, 245a, 245b, 245c

-continued

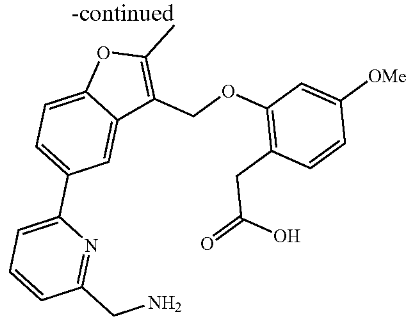

245d

Preparation of 2-(2-((5-(6-(aminomethyl)pyridin-2-yl)-2-methylbenzofuran-3-yl)methoxy)-4-methoxyphenyl)acetic acid (245d)

Step-1: Preparation of ethyl 2-(2-((5-(6-cyanopyridin-2-yl)-2-methylbenzofuran-3-yl)methoxy)-4-methoxyphenyl)acetate (245b)

Compound 245b was prepared according to the procedure reported in step-2 of scheme 1, from ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (400 mg, 0.833 mmol) in dioxane (20 mL) using 6-chloropicolino nitrile (245a) (231 mg, 1.665 mmol; CAS #33252-29-8), 4 M solution of $K_3PO_4$ (0.833 mL, 3.33 mmol), tricyclohexylphosphine (70.1 mg, 0.250 mmol), $Pd_2(dba)_3$ (153 mg, 0.167 mmol), $PdCl_2(dppf)$-$CH_2Cl_2$ adduct (136 mg, 0.167 mmol) and heating at 110° C. overnight. This gave after workup and purification using flash column chromatography [silica gel (24 g), eluting with DMA-80 in DCM from 0-70%] ethyl 2-(2-((5-(6-cyanopyridin-2-yl)-2-methylbenzofuran-3-yl)methoxy)-4-methoxyphenyl)acetate (245b) (320 mg, 84% yield) as a yellow oil; MS (ES+): 479.20 (M+Na).

Step-2: Preparation of ethyl 2-(2-((5-(6-(aminomethyl)pyridin-2-yl)-2-methylbenzofuran-3-yl)methoxy)-4-methoxyphenyl)acetate (245c)

Compound 245c was prepared according to the procedure reported in step-2 of scheme 145, from ethyl 2-(2-((5-(6-cyanopyridin-2-yl)-2-methylbenzofuran-3-yl)methoxy)-4-methoxyphenyl)acetate (245b) (320 mg, 0.701 mmol) in ethanol (5 mL) using nickel(II) chloride hexahydrate (167 mg, 0.701 mmol) and sodium borohydride (159 mg, 4.21 mmol) and stirring at 0° C. This gave after workup and purification using flash column chromatography [silica gel (24 g), eluting with DMA-80 in DCM from 0-100%] ethyl 2-(2-((5-(6-(aminomethyl)pyridin-2-yl)-2-methylbenzofuran-3-yl)methoxy)-4-methoxyphenyl)acetate (245c) (122 mg, 38% yield) as a clear oil, MS (ES+): 461.2 (M+1).

Step-3: Preparation of 2-(2-((5-(6-(aminomethyl)pyridin-2-yl)-2-methylbenzofuran-3-yl)methoxy)-4-methoxyphenyl)acetic acid (245d)

Compound 245d was prepared according to the procedure reported in step-3 of scheme 1, from ethyl 2-(2-((5-(6-(aminomethyl)pyridin-2-yl)-2-methylbenzofuran-3-yl)methoxy)-4-methoxyphenyl)acetate (245c) (122 mg, 0.265 mmol) in THF (3 mL) using lithium hydroxide hydrate (88 mg, 2.103 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(6-(aminomethyl)pyridin-2-yl)-2-methylbenzofuran-3-yl)methoxy)-4-methoxyphenyl)acetic acid (245d) (25 mg, 8% yield) HCl salt as a white solid; $^1$H NMR (300 MHz, DMSO-$d_6$) δ 8.98-8.31 (m, 3H, 2H is $D_2O$ exchangeable), 8.23 (dd, J=8.7, 1.8 Hz, 1H), 8.03 (d, J=7.9 Hz, 1H), 7.93 (t, J=7.7 Hz, 1H), 7.63 (d, J=8.6 Hz, 1H), 7.41 (d, J=7.5 Hz, 1H), 7.08 (d, J=8.3 Hz, 1H), 6.84 (d, J=2.4 Hz, 1H), 6.49 (dd, J=8.3, 2.4 Hz, 1H), 5.29 (s, 2H), 4.26 (s, 2H), 3.76 (s, 3H), 3.41 (s, 2H), 2.52 (s, 3H); MS (ES+): 433.2 (M+1); (ES−): 431.1 (M−1); Analysis calculated for $C_{25}H_{24}N_2O_5 \cdot HCl \cdot 1.5H_2O$: C, 60.54; H, 5.69; N, 5.65. Found: C, 60.69; H, 5.35; N, 5.59.

Scheme 246

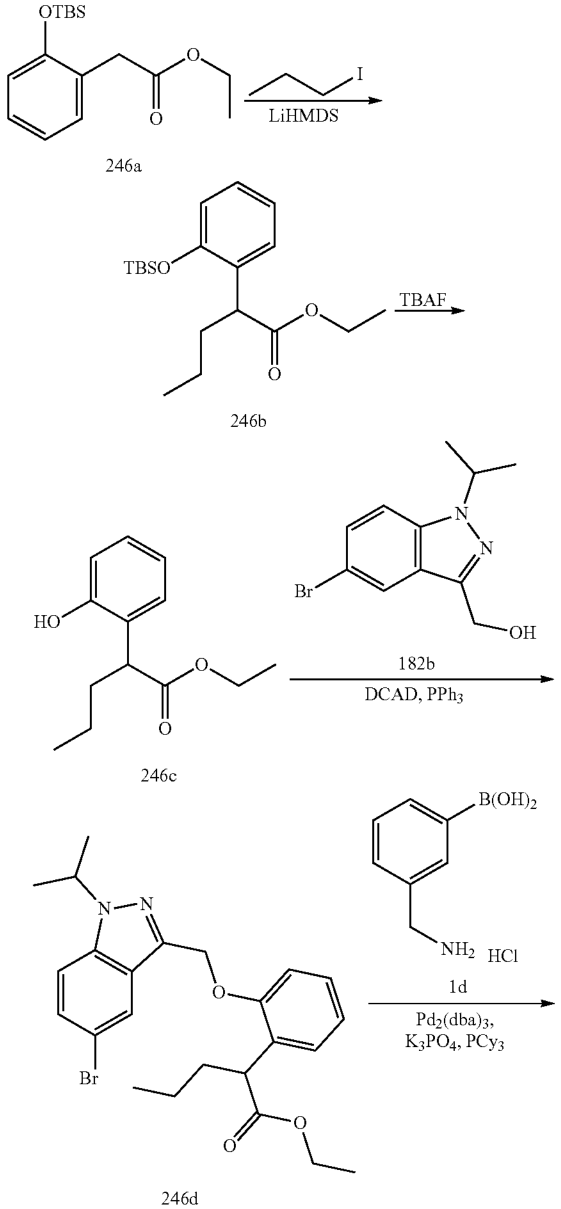

-continued

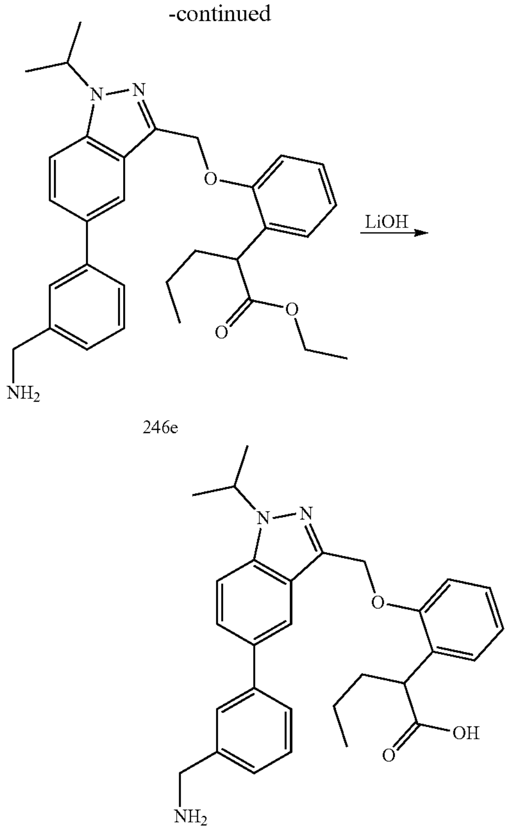

246e

246f

Preparation of 2-(2-((5-(3-(aminomethyl)phenyl)-1-isopropyl-1H-indazol-3-yl)methoxy)phenyl)pentanoic acid (246f)

Step-1: Preparation of ethyl 2-(2-((tert-butyldimethylsilyl)oxy)phenyl)pentanoate (246b)

To a solution of ethyl 2-(2-(tert-butyldimethylsilyloxy)phenyl)acetate (246a) (5 g, 16.98 mmol; CAS #1197814-14-4) in THF (50 mL) was added LiHMDS (1N in THF) (20.38 mL, 20.38 mmol) at −78° C. stirred for 30 min, followed by the addition of a solution of 1-iodopropane (2.89 g, 16.98 mmol) in THF (3 mL) stirred at −78° C. for 1 h and at 0° C. for 1 h. The reaction was quenched with HCl (1 N), concentrated in vacuo and extracted with EtOAc (3×). The combined organics were washed with water, brine, dried, filtered and concentrated in vacuo. The residue obtained was purified using flash column chromatography [silica gel (80 g), eluting with EtOAc in hexane from 0-100%] to give ethyl 2-(2-((tert-butyldimethylsilyl)oxy)phenyl)pentanoate (246b) (5 g, 87% yield) as a clear oil; MS (ES+): 337.2 (M+1); 359.2 (M+Na).

Step-2: Preparation of ethyl 2-(2-hydroxyphenyl)pentanoate (246c)

Compound 246c was prepared according to the procedure reported in step-2 of scheme 3, from ethyl 2-(2-((tert-butyldimethylsilyl)oxy)phenyl)pentanoate (246b) (5 g, 14.86 mmol) using TBAF (5.83 g, 22.29 mmol) in THF (50 mL) and stirring 1 h at 0° C. This gave after workup and purification using flash column chromatography [silica gel (80 g), eluting with EtOAc in hexane from 0-100%] ethyl 2-(2-hydroxyphenyl)pentanoate (246c) (3.1 g, 94% yield) as a clear oil; $^1$H NMR (300 MHz, DMSO-$d_6$) δ 9.49 (s, 1H), 7.13-6.97 (m, 2H), 6.83-6.67 (m, 2H), 4.07-3.98 (m, 2H), 3.90 (t, J=7.5 Hz, 1H), 1.92-1.78 (m, 1H), 1.67-1.53 (m, 1H), 1.25-1.17 (m, 2H), 1.11 (t, J=7.1 Hz, 3H), 0.88-0.85 (m, 3H).

Step-3: Preparation of ethyl 2-(2-((5-bromo-1-isopropyl-1H-indazol-3-yl)methoxy)phenyl)pentanoate (246d)

Compound 246d was prepared according to the procedure reported in step-3 of scheme 7, from (5-bromo-1-isopropyl-1H-indazol-3-yl)methanol (182b) (500 mg, 1.858 mmol) in DCM (20 mL) using ethyl 2-(2-hydroxyphenyl)pentanoate (246c) (454 mg, 2.044 mmol), triphenylphosphine (536 mg, 2.044 mmol), bis(4-chlorobenzyl) diazene-1,2-dicarboxylate (DCAD, 750 mg, 2.044 mmol) in DCM (10 mL) and stirring at RT for 30 min. This gave after workup and purification using flash column chromatography [silica gel (40 g), eluting with EtOAc in hexane from 0-50%] ethyl 2-(2-((5-bromo-1-isopropyl-1H-indazol-3-yl)methoxy)phenyl)pentanoate (246d) (300 mg, 34% yield) as a clear oil; $^1$H NMR (300 MHz, DMSO-$d_6$) δ 8.03 (d, J=1.8 Hz, 1H), 7.78 (d, J=8.9 Hz, 1H), 7.56 (dd, J=8.9, 1.8 Hz, 1H), 7.36-7.19 (m, 3H), 7.05-6.93 (m, 1H), 5.54-5.37 (m, 2H), 5.15-4.99 (m, 1H), 4.04-3.87 (m, 3H), 1.95-1.79 (m, 1H), 1.66-1.55 (m, 1H), 1.52 (dd, J=6.6, 2.8 Hz, 6H), 1.27-1.09 (m, 2H), 1.04 (t, J=7.1 Hz, 3H), 0.82 (t, J=7.3 Hz, 3H); MS (ES+): (M+1).

Step-4: Preparation of ethyl 2-(2-((5-(3-(aminomethyl)phenyl)-1-isopropyl-1H-indazol-3-yl)methoxy)phenyl)pentanoate (246e)

Compound 246e was prepared according to the procedure reported in step-2 of scheme 1, from ethyl 2-(2-((5-bromo-1-isopropyl-1H-indazol-3-yl)methoxy)phenyl)pentanoate (246d) (300 mg, 0.634 mmol) in dioxane (20 mL) using (3-(aminomethyl)phenyl)boronic acid hydrochloride (1d) (238 mg, 1.267 mmol), 4 M solution of $K_3PO_4$ (0.634 mL, 2.53 mmol), tricyclohexylphosphine (53.3 mg, 0.190 mmol), $Pd_2(dba)_3$ (58.0 mg, 0.063 mmol) and heating at 110° C. for 3 h. This gave after workup and purification using flash column chromatography [silica gel (40 g), eluting with DMA-80 in DCM from 0-100%] ethyl 2-(2-((5-(3-(aminomethyl)phenyl)-1-isopropyl-1H-indazol-3-yl)methoxy)phenyl)pentanoate (246e) (166 mg, 52% yield) as a yellow oil; (ES+): 500.3 (M+1).

Step-5: Preparation of 2-(2-((5-(3-(aminomethyl)phenyl)-1-isopropyl-1H-indazol-3-yl)methoxy)phenyl)pentanoic acid (246f)

Compound 246f was prepared according to the procedure reported in step-3 of scheme 1, from ethyl 2-(2-((5-(3-(aminomethyl)phenyl)-1-isopropyl-1H-indazol-3-yl)methoxy)phenyl)pentanoate (246e) (166 mg, 0.332 mmol) in THF (3 mL) using a solution of lithium hydroxide hydrate (80 mg, 1.901 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-1-isopropyl-1H-indazol-3-yl)methoxy)phenyl)pentanoic acid (246f) (74 mg, 25% yield) HCl salt as a white solid; $^1H$ NMR (300 MHz, DMSO-$d_6$) δ 12.17 (s, 1H, $D_2O$ exchangeable), 8.49 (s, 3H, $D_2O$ exchangeable), 8.11 (s, 1H), 7.90-7.82 (m, 2H), 7.78 (dd, J=8.9, 1.6 Hz, 1H), 7.71 (dt, J=7.2, 1.8 Hz, 1H), 7.53-7.40 (m, 2H), 7.33-7.17 (m, 3H), 6.95 (td, J=7.3, 1.4 Hz, 1H), 5.53-5.38 (m, 2H), 5.13-4.97 (m, 1H), 4.15-4.01 (m, 2H), 3.92 (t, J=7.5 Hz, 1H), 1.85-1.69 (m, 1H), 1.58-1.39 (m, 7H), 1.16-0.87 (m, 2H), 0.58 (t, J=7.3 Hz, 3H); MS (ES+) 472.3 (M+1); (ES−) 470.3 (M−1).

Scheme 247

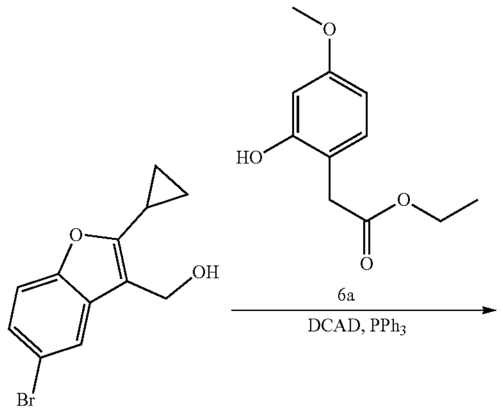

133c

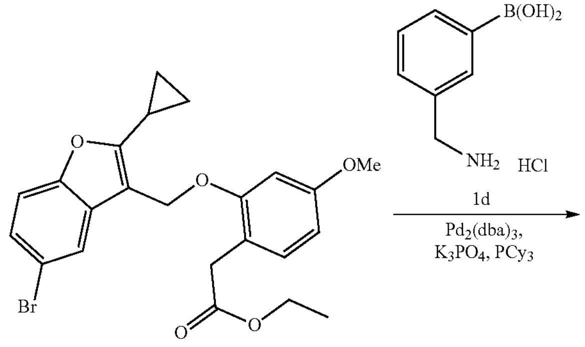

247a

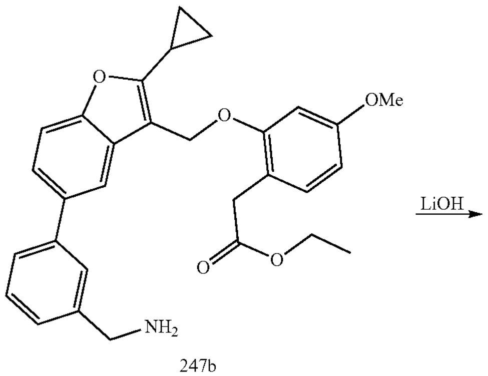

247b

-continued

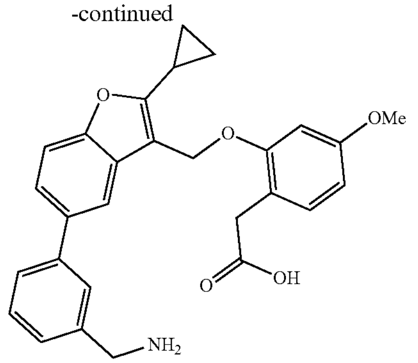

247c

Preparation of 2-(2-((5-(3-(aminomethyl)phenyl)-2-cyclopropylbenzofuran-3-yl)methoxy)-4-methoxyphenyl)acetic acid (247c)

Step-1: Preparation of ethyl 2-(2-((5-bromo-2-cyclopropylbenzofuran-3-yl)methoxy)-4-methoxyphenyl)acetate (247a)

Compound 247a was prepared according to the procedure reported in step-3 of scheme 7, from (5-bromo-2-cyclopropylbenzofuran-3-yl)methanol (133c) (500 mg, 1.872 mmol) in DCM (20 mL) using ethyl 2-(2-hydroxy-4-methoxyphenyl)acetate (6a) (433 mg, 2.059 mmol), triphenylphosphine (540 mg, 2.059 mmol), bis(4-chlorobenzyl) diazene-1,2-dicarboxylate (DCAD, 756 mg, 2.059 mmol) in DCM (10 mL) and stirring the reaction mixture at RT for 30 min. This gave after workup and purification using flash column chromatography [silica gel (40 g), eluting with EtOAc in hexane from 0-50%] ethyl 2-(2-((5-bromo-2-cyclopropylbenzofuran-3-yl)methoxy)-4-methoxyphenyl)acetate (247a) (300 mg, 35% yield) as a clear oil; $^1H$ NMR (300 MHz, DMSO-$d_6$) δ 7.69 (d, J=2.0 Hz, 1H), 7.44 (d, J=8.6 Hz, 1H), 7.36 (dd, J=8.6, 1.9 Hz, 1H), 7.09 (d, J=8.3 Hz, 1H), 6.83 (d, J=2.4 Hz, 1H), 6.50 (dd, J=8.3, 2.3 Hz, 1H), 5.27 (s, 2H), 3.92 (q, J=7.1 Hz, 2H), 3.78 (s, 3H), 3.44 (s, 2H), 2.46-2.35 (m, 1H), 1.10-1.03 (m, 4H), 0.96 (t, J=7.2 Hz, 3H); MS (ES+): 481.1 and 483.1 (M+Na); (ES−): 457.0 and 459.1 (M−1).

Step-2: Preparation of ethyl 2-(2-((5-(3-(aminomethyl)phenyl)-2-cyclopropylbenzofuran-3-yl)methoxy)-4-methoxyphenyl)acetate (247b)

Compound 247b was prepared according to the procedure reported in step-2 of scheme 1, from ethyl 2-(2-((5-bromo-2-cyclopropylbenzofuran-3-yl)methoxy)-4-methoxyphenyl)acetate (247a) (220 mg, 0.479 mmol) in dioxane (20 mL) using 3-(aminomethyl)phenylboronic acid hydrochloride (1d) (180 mg, 0.958 mmol), 4M solution of $K_3PO_4$ (0.479 mL, 1.916 mmol), tricyclohexylphosphine (53.7 mg, 0.192 mmol), $Pd_2(dba)_3$ (65.8 mg, 0.072 mmol) and heating at 100° C. for 12 h. This gave after workup and purification using flash column chromatography [silica gel (40 g), eluting with DMA-80 in DCM from 0-100%] ethyl 2-(2-((5-(3-(aminomethyl)phenyl)-2-cyclopropylbenzofuran-3-yl)

methoxy)-4-methoxyphenyl)acetate (247b) (86 mg, 37% yield) as a yellow oil; MS (ES+): 486.3 (M+1).

Step-3: Preparation of 2-(2-((5-(3-(aminomethyl) phenyl)-2-cyclopropylbenzofuran-3-yl)methoxy)-4-methoxyphenyl)acetic acid (247c)

Compound 247c was prepared according to the procedure reported in step-3 of scheme 1, from ethyl 2-(2-((5-(3-(aminomethyl)phenyl)-2-cyclopropylbenzofuran-3-yl) methoxy)-4-methoxyphenyl)acetate (247b) (86 mg, 0.177 mmol) in THF (3 mL) using a solution of lithium hydroxide hydrate (60.3 mg, 1.437 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-cyclopropylbenzofuran-3-yl)methoxy)-4-methoxyphenyl)acetic acid (247c) (24 mg, 11% yield) HCl salt as a white solid; $^1$H NMR (300 MHz, DMSO-$d_6$) δ 12.04 (s, 1H, $D_2O$ exchangeable), 8.43 (s, 3H, $D_2O$ exchangeable), 7.88 (dt, J=9.3, 1.5 Hz, 2H), 7.72 (dt, J=7.5, 1.7 Hz, 1H), 7.54-7.59 (m, 2H), 7.52-7.42 (m, 2H), 7.08 (d, J=8.3 Hz, 1H), 6.87 (d, J=2.4 Hz, 1H), 6.49 (dd, J=8.3, 2.4 Hz, 1H), 5.35 (s, 2H), 4.09 (s, 2H), 3.76 (s, 3H), 3.42 (s, 2H), 2.45-2.37 (m, 1H), 1.11-0.99 (m, 4H); MS (ES+): 458.2 (M+1); (ES−): 456.1 (M−1).

Scheme 248

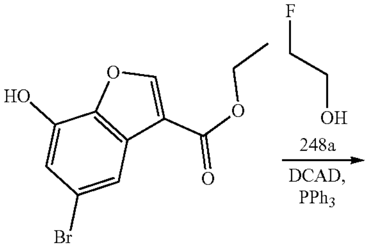

76c

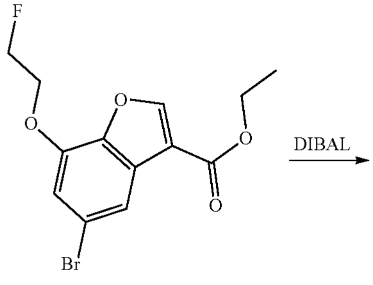

248b

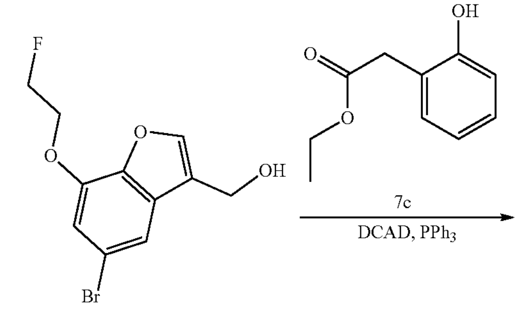

248c

-continued

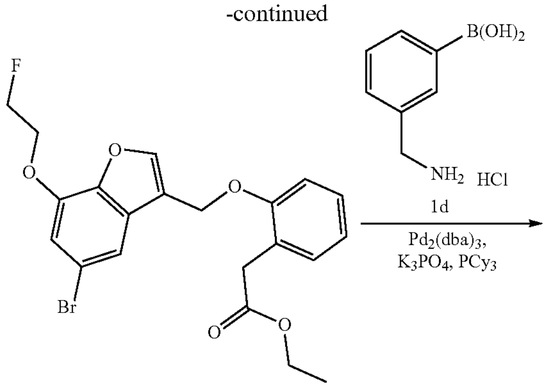

248d

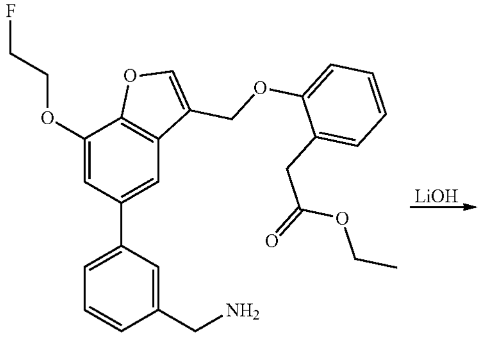

248e

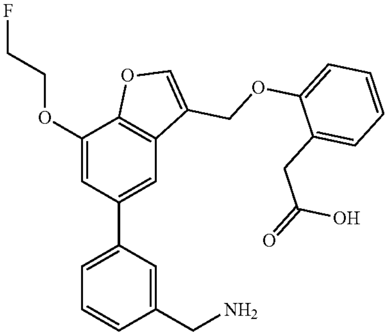

248f

Preparation of 2-(2-((5-(3-(aminomethyl)phenyl)-7-(2-fluoroethoxy)benzofuran-3-yl)methoxy)phenyl) acetic acid (248f)

Step-1: Preparation of ethyl 5-bromo-7-(2-fluoroethoxy)benzofuran-3-carboxylate (248b)

Compound 248b was prepared according to the procedure reported in step-3 of scheme 7, from ethyl 5-bromo-7-hydroxybenzofuran-3-carboxylate (76c) (500 mg, 1.754 mmol) in DCM (15 mL) using 2-fluoroethanol (248a) (169 mg, 2.63 mmol; CAS #371-62-0), triphenylphosphine (529 mg, 2.017 mmol), bis(4-chlorobenzyl) diazene-1,2-dicarboxylate (DCAD, 741 mg, 2.017 mmol) in DCM (10 mL) and stirring at RT for 1 h. This gave after workup and purification using flash column chromatography [silica gel (40 g), eluting with EtOAc in hexane from 0-25%] ethyl 5-bromo-7-(2-fluoroethoxy)benzofuran-3-carboxylate (248b) (160 mg, 28% yield) as a white solid; $^1$H NMR (300 MHz, DMSO-$d_6$) δ 8.81 (s, 1H), 7.68 (d, J=1.8 Hz, 1H), 7.30

(d, J=1.8 Hz, 1H), 4.95-4.86 (m, 1H), 4.79-4.68 (m, 1H), 4.59-4.51 (m, 1H), 4.47-4.41 (m, 1H), 4.35 (q, J=7.1 Hz, 2H), 1.35 (t, J=7.1 Hz, 3H); MS (ES+): 331.0 (M+1).

Step-2: Preparation of (5-bromo-7-(2-fluoroethoxy)benzofuran-3-yl)methanol (248c)

Compound 248c was prepared according to the procedure reported in step-2 of scheme 69, from ethyl 5-bromo-7-(2-fluoroethoxy)benzofuran-3-carboxylate (248b) (420 mg, 1.268 mmol)) in DCM (2.113 mL, ratio 1) using 1.0 M solution DIBAL in DCM (3.17 mL, 3.17 mmol) and stirring at 0° C. for 4 h. This gave after work up and purification using flash column chromatography [silica gel (12 g), EtOAc in hexane from 0-100%] (5-bromo-7-(2-fluoroethoxy)benzofuran-3-yl)methanol (248c) (245 mg, 67% yield) as a white solid; $^{1}$H NMR (300 MHz, DMSO-$d_6$) δ 7.91 (s, 1H), 7.50 (d, J=1.7 Hz, 1H), 7.15 (d, J=1.8 Hz, 1H), 5.22 (t, J=5.6 Hz, 1H), 4.92-4.83 (m, 1H), 4.77-4.68 (m, 1H), 4.58 (dd, J=5.6, 1.1 Hz, 2H), 4.52 (dd, J=4.9, 2.7 Hz, 1H), 4.41 (dd, J=5.0, 2.5 Hz, 1H).

Step-3: Preparation of ethyl 2-(2-((5-bromo-7-(2-fluoroethoxy)benzofuran-3-yl)methoxy)phenyl)acetate (248d)

Compound 248d was prepared according to the procedure reported in step-3 of scheme 7, from (5-bromo-7-(2-fluoroethoxy)benzofuran-3-yl)methanol (248c) (219 mg, 0.757 mmol) in DCM (5 mL) using ethyl 2-(2-hydroxyphenyl) acetate (7c) (150 mg, 0.832 mmol), triphenylphosphine (228 mg, 0.870 mmol), bis(4-chlorobenzyl) diazene-1,2-dicarboxylate (DCAD, 320 mg, 0.870 mmol) in DCM (5 mL) and stirring at RT for 1 h. This gave after workup and purification using flash column chromatography [silica gel (40 g), eluting with EtOAc in hexane from 0-25%] ethyl 2-(2-((5-bromo-7-(2-fluoroethoxy)benzofuran-3-yl)methoxy)phenyl)acetate (248d) (100 mg, 29% yield) as a colorless gel; $^{1}$H NMR (300 MHz, DMSO-$d_6$) δ 8.12 (s, 1H), 7.45 (d, J=1.7 Hz, 1H), 7.34-7.24 (m, 1H), 7.23-7.15 (m, 3H), 6.93 (td, J=7.3, 1.1 Hz, 1H), 5.22 (s, 2H), 4.94-4.80 (m, 1H), 4.79-4.66 (m, 1H), 4.58-4.48 (m, 1H), 4.43 (dd, J=4.8, 2.6 Hz, 1H), 3.96 (q, J=7.1 Hz, 2H), 3.55 (d, J=8.8 Hz, 2H), 1.01 (t, J=7.1 Hz, 3H); MS (ES+): 473.0/475.0 (M+Na).

Step-4: Preparation of ethyl 2-(2-((5-(3-(aminomethyl)phenyl)-7-(2-fluoroethoxy)benzofuran-3-yl)methoxy)phenyl)acetate (248e)

Compound 248e was prepared according to the procedure reported in step-2 of scheme 1, from ethyl 2-(2-((5-bromo-7-(2-fluoroethoxy)benzofuran-3-yl)methoxy)phenyl)acetate (248d) (95 mg, 0.211 mmol) in dioxane (7 mL) using 3-(aminomethyl)phenylboronic acid hydrochloride (1d) (49.3 mg, 0.263 mmol), 4M solution of $K_3PO_4$ (0.211 mL, 0.842 mmol), tricyclohexylphosphine (11.81 mg, 0.042 mmol), $Pd_2(dba)_3$ (19.28 mg, 0.021 mmol) and heating at 110° C. for 4 h. This gave after workup and purification using flash column chromatography [silica gel (24 g), eluting with DMA-80 in DCM from 0-50%] ethyl 2-(2-((5-(3-(aminomethyl)phenyl)-7-(2-fluoroethoxy)benzofuran-3-yl)methoxy)phenyl)acetate (248e) (44 mg, 44% yield) as a colorless oil; $^{1}$H NMR (300 MHz, DMSO-$d_6$) δ 8.10 (s, 1H), 7.70 (s, 1H), 7.59 (d, J=7.6 Hz, 1H), 7.51 (d, J=1.5 Hz, 1H), 7.41 (t, J=7.5 Hz, 1H), 7.37-7.17 (m, 5H), 6.93 (t, J=7.2 Hz, 1H), 5.28 (s, 2H), 4.93 (d, J=4.7 Hz, 1H), 4.76 (s, 1H), 4.62

(s, 1H), 4.51 (s, 1H), 3.82 (s, 2H), 3.76 (q, J=7.1 Hz, 2H), 3.56 (s, 2H), 0.89 (t, J=7.1 Hz, 3H); MS (ES+): 478.2 (M+1).

Step-5: Preparation of 2-(2-((5-(3-(aminomethyl)phenyl)-7-(2-fluoroethoxy)benzofuran-3-yl)methoxy)phenyl)acetic acid (248f)

Compound 248f was prepared according to the procedure reported in step-3 of scheme 1, from ethyl 2-(2-((5-(3-(aminomethyl)phenyl)-7-(2-fluoroethoxy)benzofuran-3-yl)methoxy)phenyl)acetate (248e) (40 mg, 0.084 mmol) in THF (0.5 mL), acetonitrile (0.25 mL) using lithium hydroxide monohydrate, 1N (0.251 mL, 0.251 mmol) and stirring at RT for 25 h. This gave after workup and purification using reverse phase column chromatography [C18 column (30 g), eluting with ACN in water (containing 0.1% HCl) from 0-100%] 2-(2-((5-(3-(aminomethyl)phenyl)-7-(2-fluoroethoxy)benzofuran-3-yl)methoxy)phenyl)acetic acid (248f) (19 mg, 51% yield) HCl salt as an off white solid; $^{1}$H NMR (300 MHz, DMSO-$d_6$) δ 12.17 (s, 1H, $D_2O$ exchangeable), 8.48 (s, 2H, $D_2O$ exchangeable), 8.11 (s, 1H), 7.95 (s, 1H), 7.78 (dt, J=7.5, 1.6 Hz, 1H), 7.62 (d, J=1.5 Hz, 1H), 7.59-7.42 (m, 2H), 7.34 (d, J=1.5 Hz, 1H), 7.32-7.14 (m, 3H), 6.93 (td, J=7.3, 1.2 Hz, 1H), 5.31 (s, 2H), 4.99-4.89 (m, 1H), 4.78 (dd, J=4.9, 2.6 Hz, 1H), 4.68-4.61 (m, 1H), 4.56-4.51 (m, 1H), 4.11 (s, 2H), 3.55 (s, 2H); $^{19}$F NMR (282 MHz, DMSO-$d_6$) δ 15.07.

MS (ES+): 450.1 (M+1); (ES−): 448.2 (M−1).

Scheme 249

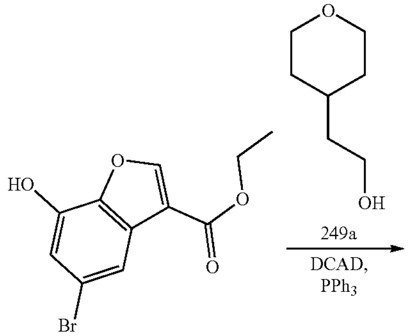

76c

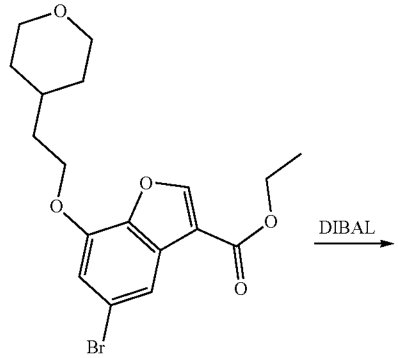

249b

-continued

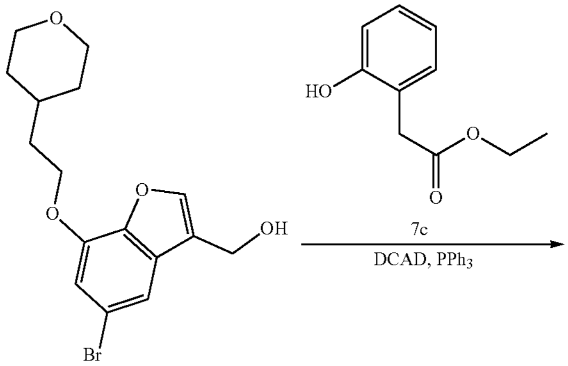

249c

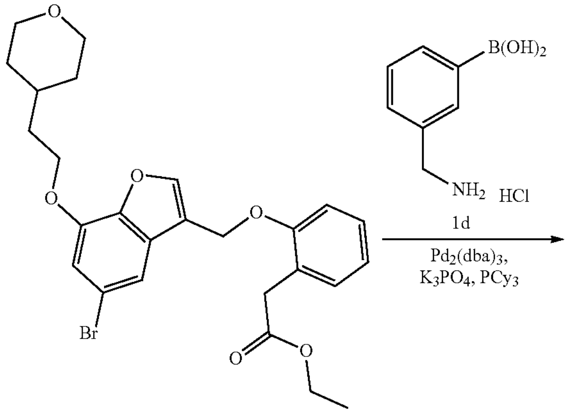

249d

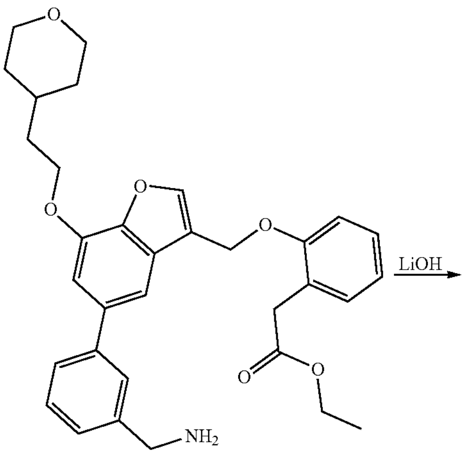

249e

-continued

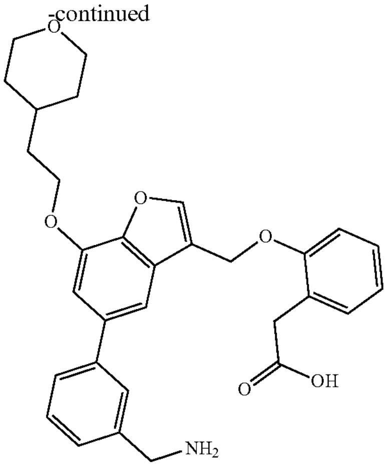

249f

Preparation of 2-(2-((-(3-(aminomethyl)phenyl)-7-(2-(tetrahydro-2H-pyran-4-yl)ethoxy)benzofuran-3-yl)methoxy)phenyl)acetic acid (249f)

Step-1: Preparation of ethyl 5-bromo-7-(2-(tetrahydro-2H-pyran-4-yl)ethoxy)benzofuran-3-carboxylate (249b)

Compound 249b was prepared according to the procedure reported in step-3 of scheme 7, from ethyl 5-bromo-7-hydroxybenzofuran-3-carboxylate (76c) (1 g, 3.51 mmol) in DCM (30 mL) using 2-(tetrahydro-2H-pyran-4-yl)ethanol (249a) (571 mg, 4.38 mmol; CAS #4677-18-3), triphenylphosphine (1.058 g, 4.03 mmol), bis(4-chlorobenzyl) diazene-1,2-dicarboxylate (DCAD, 1.481 g, 4.03 mmol) in DCM (20 mL) and stirring the reaction mixture at RT for 1 h. This gave after workup and purification using flash column chromatography [silica gel (40 g), eluting with EtOAc in hexane from 0-25%] ethyl 5-bromo-7-(2-(tetrahydro-2H-pyran-4-yl)ethoxy)benzofuran-3-carboxylate (249b) (1.3 g, 93% yield) as a white solid; $^1$H NMR (300 MHz, DMSO-$d_6$) δ 8.78 (s, 1H), 7.63 (d, J=1.7 Hz, 1H), 7.27 (d, J=1.8 Hz, 1H), 4.35 (q, J=7.1 Hz, 2H), 4.25 (t, J=6.0 Hz, 2H), 3.84 (ddd, J=11.2, 4.6, 1.8 Hz, 2H), 3.29 (td, J=11.7, 10.8, 2.6 Hz, 2H), 1.81-1.61 (m, 5H), 1.34 (t, J=7.1 Hz, 3H), 1.28-1.20 (m, 2H); MS (ES+): 419.1/421.1 (M+Na).

Step-2: Preparation of (5-bromo-7-(2-(tetrahydro-2H-pyran-4-yl)ethoxy)benzofuran-3-yl)methanol (249c)

Compound 249c was prepared according to the procedure reported in step-2 of scheme 69, from ethyl 5-bromo-7-(2-(tetrahydro-2H-pyran-4-yl)ethoxy)benzofuran-3-carboxylate (249b) (1.25 g, 3.15 mmol)) in DCM (5.25 mL) using 1.0 M solution DIBAL in DCM (7.87 mL, 7.87 mmol) and stirring at 0° C. for 4 h. This gave after work up and purification using flash column chromatography [silica gel (24 g), eluting with EtOAc in hexane from 0-100%] (5-bromo-7-(2-(tetrahydro-2H-pyran-4-yl)ethoxy)benzofuran-3-yl)methanol (249c) (892 mg, 80% yield) as a clear gel; $^1$H NMR (300 MHz, DMSO-$d_6$) δ 7.89 (s, 1H), 7.45 (d, J=1.7 Hz, 1H), 7.12 (d, J=1.8 Hz, 1H), 5.21 (t, J=5.6 Hz, 1H), 4.57 (dd, J=5.6, 1.1 Hz, 2H), 4.22 (t, J=6.1 Hz, 2H), 3.84 (ddd, J=11.2, 4.5, 1.7 Hz, 2H), 3.32-3.23 (m, 2H), 1.80-1.59 (m, 5H), 1.25 (ddd, J=18.5, 8.7, 4.0 Hz, 2H); MS (ES+): 377.1/379.0 (M+Na).

Step-3: Preparation of ethyl 2-(2-((5-bromo-7-(2-(tetrahydro-2H-pyran-4-yl)ethoxy)benzofuran-3-yl) methoxy)phenyl)acetate (249d)

Compound 249d was prepared according to the procedure reported in step-3 of scheme 7, from (5-bromo-7-(2-(tetrahydro-2H-pyran-4-yl)ethoxy)benzofuran-3-yl)methanol (249c) (269 mg, 0.757 mmol) in DCM (5 mL) using ethyl 2-(2-hydroxyphenyl)acetate (7c) (150 mg, 0.832 mmol), triphenylphosphine (228 mg, 0.870 mmol), bis(4-chlorobenzyl) diazene-1,2-dicarboxylate (DCAD, 320 mg, 0.870 mmol) in DCM (5 mL) stirring at RT for 1 h. This gave after workup and purification using flash column chromatography [silica gel (40 g), eluting with EtOAc in hexane from 0-25%] ethyl 2-(2-((5-bromo-7-(2-(tetrahydro-2H-pyran-4-yl) ethoxy)benzofuran-3-yl)methoxy)phenyl)acetate (249d) (200 mg, 51% yield) as a colorless gel; $^1$H NMR (300 MHz, $DMSO-d_6$) δ 8.10 (s, 1H), 7.40 (d, J=1.7 Hz, 1H), 7.33-7.25 (m, 1H), 7.23-7.15 (m, 3H), 6.93 (td, J=7.3, 1.1 Hz, 1H), 5.21 (s, 2H), 4.24 (t, J=6.0 Hz, 2H), 3.95 (q, J=7.1 Hz, 2H), 3.88-3.79 (m, 2H), 3.56 (s, 2H), 3.32-3.22 (m, 2H), 1.85-1.59 (m, 5H), 1.38-1.18 (m, 2H), 1.01 (t, J=7.1 Hz, 3H); MS (ES+): 517.1/519.1 (M+1).

Step-4: Preparation of ethyl 2-(2-((5-(3-(aminomethyl)phenyl)-7-(2-(tetrahydro-2H-pyran-4-yl) ethoxy)benzofuran-3-yl)methoxy)phenyl)acetate (249e)

Compound 249e was prepared according to the procedure reported in step-2 of scheme 1, from ethyl 2-(2-((5-bromo-7-(2-(tetrahydro-2H-pyran-4-yl)ethoxy)benzofuran-3-yl) methoxy)phenyl)acetate (249d) (195 mg, 0.377 mmol) in dioxane (12 mL) using 3-(aminomethyl)phenylboronic acid hydrochloride (1d) (88 mg, 0.471 mmol), 4M solution of $K_3PO_4$ (0.377 mL, 1.508 mmol), tricyclohexylphosphine (21.14 mg, 0.075 mmol), $Pd_2(dba)_3$ (34.5 mg, 0.038 mmol) and heating at 110° C. for 4 h. This gave after workup and purification using flash column chromatography [silica gel (24 g), eluting with DMA-80 in DCM from 0-50%] ethyl 2-(2-((5-(3-(aminomethyl)phenyl)-7-(2-(tetrahydro-2H-pyran-4-yl)ethoxy)benzofuran-3-yl)methoxy)phenyl)acetate (249e) (154 mg, 75% yield) as a colorless oil; $^1$H NMR (300 MHz, $DMSO-d_6$) δ 8.09 (s, 1H), 7.68 (s, 1H), 7.60-7.52 (m, 1H), 7.47 (d, J=1.4 Hz, 1H), 7.39 (t, J=7.5 Hz, 1H), 7.35-7.26 (m, 2H), 7.26-7.18 (m, 3H), 6.93 (td, J=7.3, 1.2 Hz, 1H), 5.28 (s, 2H), 4.33 (t, J=5.9 Hz, 2H), 3.90-3.69 (m, 6H), 3.56 (s, 2H), 3.33-3.24 (m, 2H), 1.86-1.60 (m, 5H), 1.31-1.22 (m, 2H), 0.89 (t, J=7.1 Hz, 3H); MS (ES+): 544.2 (M+1).

Step-5: Preparation of 2-(2-((5-(3-(aminomethyl) phenyl)-7-(2-(tetrahydro-2H-pyran-4-yl)ethoxy)benzofuran-3-yl)methoxy)phenyl)acetic acid (249f)

Compound 249f was prepared according to the procedure reported in step-3 of scheme 1, from ethyl 2-(2-((5-(3-(aminomethyl)phenyl)-7-(2-(tetrahydro-2H-pyran-4-yl) ethoxy)benzofuran-3-yl)methoxy)phenyl)acetate (249e) (150 mg, 0.276 mmol) in THE (1.66 mL), acetonitrile (0.83 mL) using lithium hydroxide monohydrate, 1N (0.828 mL, 0.828 mmol) and stirring at RT for 25 h. This gave after workup and purification using reverse phase column chromatography [C18 column (30 g), eluting with ACN in water (containing 0.1% HCl) from 0-100%] 2-(2-((5-(3-(aminomethyl)phenyl)-7-(2-(tetrahydro-2H-pyran-4-yl)ethoxy)benzofuran-3-yl)methoxy)phenyl)acetic acid (249f) (87 mg, 61% yield) HCl salt as a white solid; $^1$H NMR (300 MHz, $DMSO-d_6$) δ 12.18 (s, 1H, $D_2O$ exchangeable), 8.52 (s, 2H, $D_2O$ exchangeable), 8.09 (s, 1H), 7.95 (s, 1H), 7.77 (dt, J=7.4, 1.7 Hz, 1H), 7.58 (d, J=1.4 Hz, 1H), 7.55-7.43 (m, 2H), 7.34-7.15 (m, 4H), 6.99-6.86 (m, 1H), 5.30 (s, 2H), 4.35 (t, J=5.9 Hz, 2H), 4.11 (s, 2H), 3.85 (dd, J=11.4, 4.5, 1.8 Hz, 2H), 3.54 (s, 2H), 3.33-3.22 (m, 2H), 1.88-1.60 (m, 5H), 1.39-1.16 (m, 2H). MS (ES+): 516.2 (M+1); (ES−): 514.2 (M−1); Analysis calculated for $C_{31}H_{33}NO_6 \cdot 0.5H_2O \cdot HCl$ C, 66.36; H, 6.29; Cl, 6.32; N, 2.50. Found: C, 66.08; H, 6.03; Cl, 6.08; N, 2.49.

Scheme 250

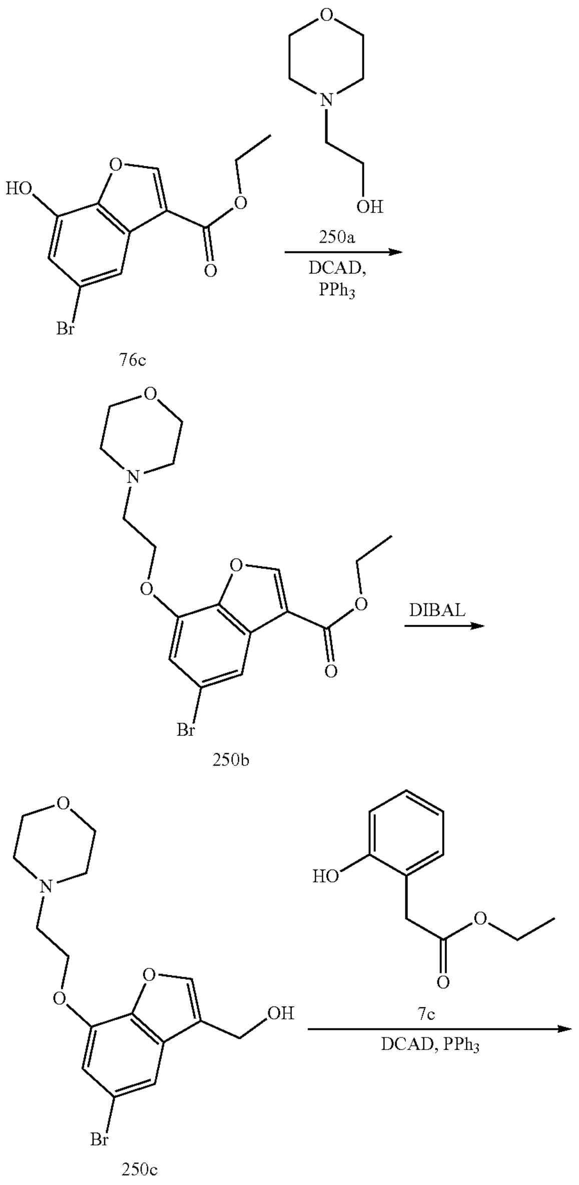

-continued

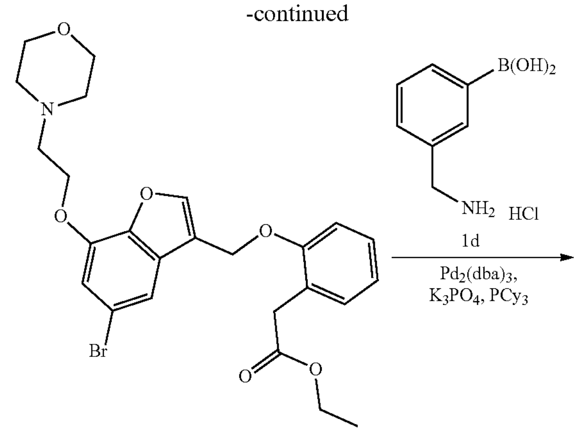

250d

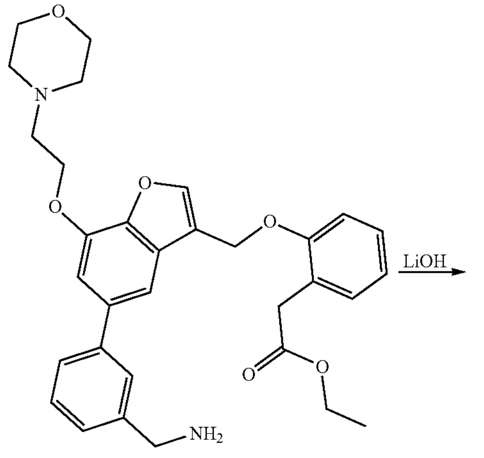

250e

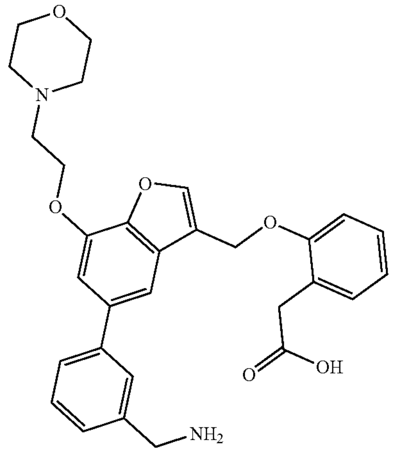

250f

Preparation of 2-(2-((5-(3-(aminomethyl)phenyl)-7-(2-morpholinoethoxy)benzofuran-3-yl)methoxy) phenyl)acetic acid (250f)

Step-1: Preparation of ethyl 5-bromo-7-(2-morpholinoethoxy)benzofuran-3-carboxylate (250b)

Compound 250b was prepared according to the procedure reported in step-3 of scheme 7, from ethyl 5-bromo-7-hydroxybenzofuran-3-carboxylate (76c) (1 g, 3.51 mmol) in DCM (30 mL) using 2-morpholinoethanol (250a) (920 mg, 7.02 mmol; CAS #622-40-2), triphenylphosphine (1.058 g, 4.03 mmol), bis(4-chlorobenzyl) diazene-1,2-dicarboxylate (DCAD, 1.481 g, 4.03 mmol) in DCM (20 mL) and stirring the reaction mixture at RT for 1 h. This gave after workup and purification using flash column chromatography [silica gel (40 g), eluting with EtOAc in hexane from 0-25%] ethyl 5-bromo-7-(2-morpholinoethoxy)benzofuran-3-carboxylate (250b) (0.9 g, 64% yield) as a white solid; $^1H$ NMR (300 MHz, DMSO-$d_6$) δ 8.79 (s, 1H), 7.64 (t, J=1.8 Hz, 1H), 7.30 (d, J=1.8 Hz, 1H), 4.42-4.27 (m, 4H), 3.62-3.53 (m, 4H), 2.76 (t, J=5.5 Hz, 2H), 2.50 (s, 4H), 1.35 (t, J=7.1 Hz, 3H); MS (ES+): 398.1/400.1 (M+1).

Step-2: Preparation of (5-bromo-7-(2-morpholinoethoxy)benzofuran-3-yl)methanol (250c)

Compound 250c was prepared according to the procedure reported in step-2 of scheme 69, from ethyl 5-bromo-7-(2-morpholinoethoxy)benzofuran-3-carboxylate (250b) (0.85 g, 2.134 mmol) in DCM (3.56 mL) using 1.0 M solution DIBAL in DCM (5.34 mL, 5.34 mmol) and stirring at 0° C. for 4 h. This gave after work up and purification using flash column chromatography [silica gel (24 g), eluting with EtOAc in hexane from 0-50%] (5-bromo-7-(2-morpholinoethoxy)benzofuran-3-yl)methanol (250c) (0.7 g, 92% yield) as a clear gel; $^1H$ NMR (300 MHz, DMSO-$d_6$) δ 7.90 (d, J=1.1 Hz, 1H), 7.46 (d, J=1.7 Hz, 1H), 7.14 (d, J=1.8 Hz, 1H), 5.21 (t, J=5.6 Hz, 1H), 4.58 (dd, J=5.6, 1.1 Hz, 2H), 4.29 (t, J=5.6 Hz, 2H), 3.67-3.50 (m, 4H), 2.75 (t, J=5.6 Hz, 2H), 2.51 (d, J=1.9 Hz, 4H); MS (ES+): 356.1/358.1 (M+1).

Step-3: Preparation of ethyl 2-(2-((5-bromo-7-(2-morpholinoethoxy)benzofuran-3-yl)methoxy)phenyl)acetate (250d)

Compound 250d was prepared according to the procedure reported in step-3 of scheme 7, from (5-bromo-7-(2-morpholinoethoxy)benzofuran-3-yl)methanol (250c) (270 mg, 0.757 mmol) in DCM (5 mL) using ethyl 2-(2-hydroxyphenyl)acetate (7c) (150 mg, 0.832 mmol), triphenylphosphine (228 mg, 0.870 mmol), bis(4-chlorobenzyl) diazene-1,2-dicarboxylate (DCAD, 320 mg, 0.870 mmol) in DCM (5 mL) and stirring at RT for 1 h. This gave after workup and purification using flash column chromatography [silica gel (24 g), eluting with EtOAc/MeOH (ratio 9:1) in hexane from 0-100%] ethyl 2-(2-((5-bromo-7-(2-morpholinoethoxy)benzofuran-3-yl)methoxy)phenyl)acetate (250d) (290 mg, 74% yield) as a colorless gel; $^1H$ NMR (300 MHz, DMSO-$d_6$) δ 8.15 (s, 1H), 7.50 (d, J=1.7 Hz, 1H), 7.32-7.25 (m, 2H), 7.24-7.14 (m, 2H), 6.93 (td, J=7.3, 1.1 Hz, 1H), 5.23 (s, 2H), 4.66 (d, J=5.5 Hz, 2H), 3.97 (q, J=7.1 Hz, 4H), 3.76 (t, J=12.2 Hz, 2H), 3.65 (s, 2H), 3.56 (s, 4H), 3.25 (d, J=11.5 Hz, 2H), 1.03 (t, J=7.1 Hz, 3H); MS (ES+): 518.1/520.1 (M+1).

Step-4: Preparation of ethyl 2-(2-((5-(3-(aminomethyl)phenyl)-7-(2-morpholinoethoxy)benzofuran-3-yl)methoxy)phenyl)acetate (250e)

Compound 250e was prepared according to the procedure reported in step-2 of scheme 1, from ethyl 2-(2-((5-bromo-7-(2-morpholinoethoxy)benzofuran-3-yl)methoxy)phenyl) acetate (250d) (110 mg, 0.212 mmol) in dioxane (7 mL) using 3-(aminomethyl)phenylboronic acid hydrochloride (1d) (49.7 mg, 0.265 mmol), 4M solution of $K_3PO_4$ (0.212 mL, 0.849 mmol), tricyclohexylphosphine (11.90 mg, 0.042 mmol), $Pd_2(dba)_3$ (19.43 mg, 0.021 mmol) and heating at 110° C. for 4 h. This gave after workup and purification using flash column chromatography [silica gel (24 g), eluting with DMA-80 in DCM from 0-100%] ethyl 2-(2-((5-(3-(aminomethyl)phenyl)-7-(2-morpholinoethoxy)benzofuran-3-yl)methoxy)phenyl)acetate (250e) (15 mg, 13% yield) as a white solid; MS (ES+): 545.3 (M+1).

Step-5: Preparation of 2-(2-((5-(3-(aminomethyl)phenyl)-7-(2-morpholinoethoxy)benzofuran-3-yl)methoxy)phenyl)acetic acid (250f)

Compound 250f was prepared according to the procedure reported in step-3 of scheme 1, from ethyl 2-(2-((5-(3-(aminomethyl)phenyl)-7-(2-morpholinoethoxy)benzofuran-3-yl)methoxy)phenyl)acetate (250e) (14 mg, 0.026 mmol) in THF (0.2 mL), acetonitrile (0.1 mL) using lithium hydroxide monohydrate, 1N (0.103 mL, 0.103 mmol) and stirring at RT for 25 h. This gave after workup and purification using reverse phase column chromatography [C18 column (30 g), eluting with ACN in water (containing 0.1% HCl) from 0-100%] 2-(2-((5-(3-(aminomethyl)phenyl)-7-(2-morpholinoethoxy)benzofuran-3-yl)methoxy)phenyl)acetic acid (250f) (7 mg, 53% yield) HCl salt as a white solid; $^1H$ NMR (300 MHz, Methanol-$d_4$) δ 7.95 (s, 1H), 7.92 (t, J=1.8 Hz, 1H), 7.78 (dt, J=7.7, 1.4 Hz, 1H), 7.64 (d, J=1.4 Hz, 1H), 7.53 (t, J=7.7 Hz, 1H), 7.43 (d, J=7.6 Hz, 1H), 7.38 (d, J=1.5 Hz, 1H), 7.28 (td, J=7.8, 7.4, 1.7 Hz, 1H), 7.24-7.14 (m, 2H), 6.94 (td, J=7.4, 1.1 Hz, 1H), 5.31 (s, 2H), 4.78 (t, J=4.8 Hz, 2H), 4.21 (s, 2H), 4.10 (dd, J=13.1, 3.6 Hz, 2H), 3.90 (ddd, J=13.3, 11.6, 2.1 Hz, 2H), 3.80-3.67 (m, 4H), 3.61 (s, 2H), 3.46-3.33 (m, 2H); MS (ES+): 517.2 (M+1).

Scheme 251

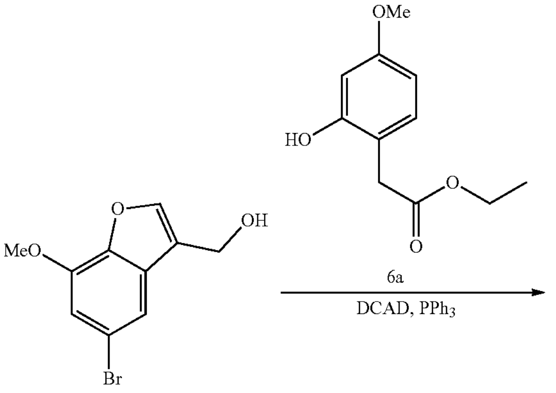

18b

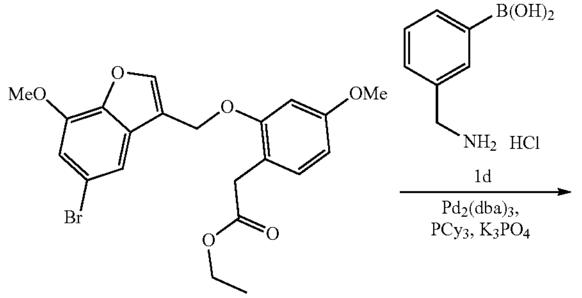

251a

-continued

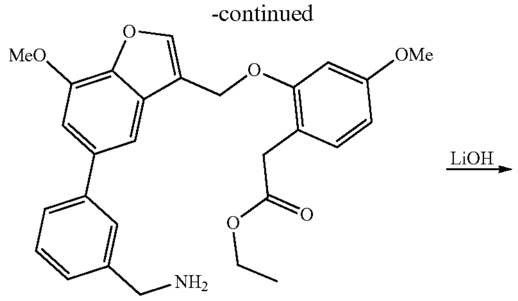

251b

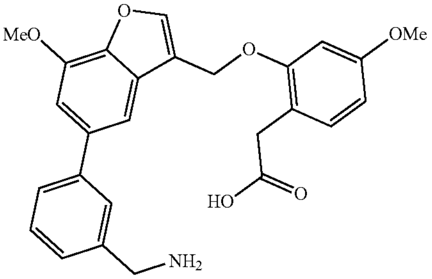

251c

Preparation of 2-(2-((5-(3-(aminomethyl)phenyl)-7-methoxybenzofuran-3-yl)methoxy)-4-methoxyphenyl)acetic acid (251c)

Step-1: Preparation of ethyl 2-(2-((5-bromo-7-methoxybenzofuran-3-yl)methoxy)-4-methoxyphenyl)acetate (251a)

Compound 251a was prepared according to the procedure reported in step-3 of scheme 7, from (5-bromo-7-methoxybenzofuran-3-yl)methanol (18b) (300 mg, 1.167 mmol) in DCM (10 mL) using ethyl 2-(2-hydroxy-4-methoxyphenyl) acetate (6a) (270 mg, 1.284 mmol), triphenylphosphine (352 mg, 1.342 mmol), bis(4-chlorobenzyl) diazene-1,2-dicarboxylate (DCAD, 493 mg, 1.342 mmol) in DCM (5 mL) and stirring at RT for 1 h. This gave after workup and purification using flash column chromatography [silica gel (24 g), eluting with EtOAc in hexane from 0-25%] ethyl 2-(2-((5-bromo-7-methoxybenzofuran-3-yl)methoxy)-4-methoxyphenyl)acetate (251a) (370 mg, 71% yield) as a white solid; MS (ES+): 449.0/451.0 (M+1); 471.0/473.0 (M+Na).

Step-2: Preparation of ethyl 2-(2-((5-(3-(aminomethyl)phenyl)-7-methoxybenzofuran-3-yl)methoxy)-4-methoxyphenyl)acetate (251b)

Compound 251b was prepared according to the procedure reported in step-2 of scheme 1, from ethyl 2-(2-((5-bromo-7-methoxybenzofuran-3-yl)methoxy)-4-methoxyphenyl)acetate (251a) (300 mg, 0.668 mmol) in dioxane (22 mL) using 3-(aminomethyl)phenylboronic acid hydrochloride (1d) (156 mg, 0.835 mmol), 4M solution of $K_3PO_4$ (0.668 mL, 2.67 mmol), tricyclohexylphosphine (0.056 g, 0.200 mmol), $Pd_2(dba)_3$ (92 mg, 0.100 mmol) and heating at 110° C. for 3 h. This gave after workup and purification using flash column chromatography [silica gel (24 g), eluting with DMA-80 in DCM from 0-70%] ethyl 2-(2-((5-(3-(aminomethyl)phenyl)-7-methoxybenzofuran-3-yl)methoxy)-4-methoxyphenyl)acetate (251b) (150 mg, 47% yield) as a colorless oil; $^1H$ NMR (300 MHz, DMSO-$d_6$) δ 8.08 (s, 1H), 7.69 (s, 1H), 7.57 (d, J=7.7 Hz, 1H), 7.47 (d, J=1.5 Hz, 1H), 7.40 (t, J=7.5 Hz, 1H), 7.33 (d, J=7.5 Hz, 1H), 7.21 (d, J=1.5 Hz, 1H), 7.09 (d, J=8.3 Hz, 1H), 6.81 (d, J=2.4 Hz, 1H), 6.50 (dd, J=8.3, 2.4 Hz, 1H), 5.27 (s, 2H), 4.04 (s, 3H), 3.84-3.66 (m, 7H), 3.47 (s, 2H), 0.89 (t, J=7.1 Hz, 3H); MS (ES+): 476.2 (M+1).

Step-3: Preparation of 2-(2-((5-(3-(aminomethyl) phenyl)-7-methoxybenzofuran-3-yl)methoxy)-4-methoxyphenyl)acetic acid (251c)

Compound 251c was prepared according to the procedure reported in step-3 of scheme 1, from ethyl 2-(2-((5-(3-(aminomethyl)phenyl)-7-methoxybenzofuran-3-yl) methoxy)-4-methoxyphenyl)acetate (251b) (140 mg, 0.294 mmol) in THF (1.8 mL), acetonitrile (0.9 mL) using lithium hydroxide monohydrate, 1N (0.883 mL, 0.883 mmol) and stirring at RT for 25 h. This gave after workup and purification using reverse phase column chromatography [C18 column (50 g), eluting with ACN in water (containing 0.1% HCl) from 0-100%] 2-(2-((5-(3-(aminomethyl)phenyl)-7-methoxybenzofuran-3-yl)methoxy)-4-methoxyphenyl)acetic acid (251c) (111 mg, 84% yield) HCl salt as a white solid; $^1H$ NMR (300 MHz, DMSO-$d_6$) δ 8.38 (s, 2H, $D_2O$ exchangeable), 8.09 (s, 1H), 7.91 (s, 1H), 7.77 (dt, J=7.7, 1.5 Hz, 1H), 7.58 (d, J=1.5 Hz, 1H), 7.53 (t, J=7.6 Hz, 1H), 7.49-7.42 (m, 1H), 7.28 (d, J=1.5 Hz, 1H), 7.10 (d, J=8.3 Hz, 1H), 6.79 (d, J=2.4 Hz, 1H), 6.51 (dd, J=8.3, 2.4 Hz, 1H), 5.29 (s, 2H), 4.12 (s, 2H), 4.05 (s, 3H), 3.76 (s, 3H), 3.45 (s, 2H). MS (ES+): 448.2 (M+1); (ES−): 446.1 (M−1); Analysis calculated for $C_{26}H_{25}NO_6 \cdot 0.75H_2O \cdot HCl$: C, 62.78; H, 5.57; Cl, 7.13; N, 2.82. Found: C, 62.73; H, 5.59; Cl, 6.91; N, 2.88.

Scheme 252

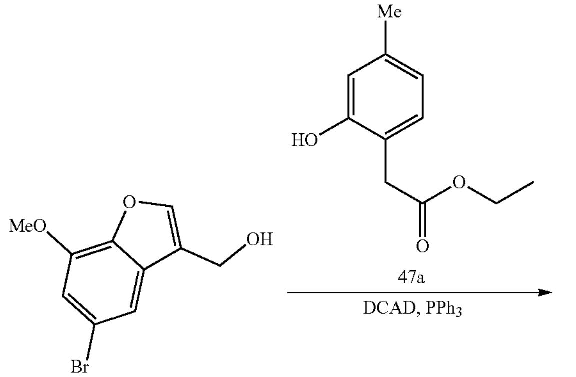

47a

18b

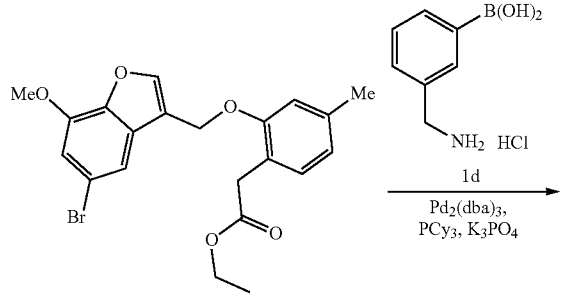

1d

252a

-continued

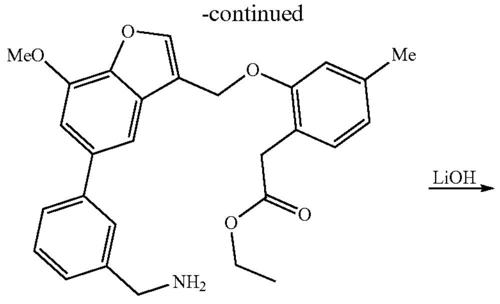

252b

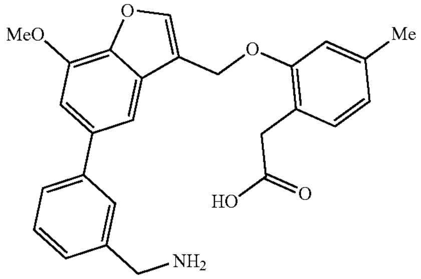

252c

Preparation of 2-(2-((5-(3-(aminomethyl)phenyl)-7-methoxybenzofuran-3-yl)methoxy)-4-methylphenyl) acetic acid (252c)

Step-1: Preparation of ethyl 2-(2-((5-bromo-7-methoxybenzofuran-3-yl)methoxy)-4-methylphenyl) acetate (252a)

Compound 252a was prepared according to the procedure reported in step-3 of scheme 7, from (5-bromo-7-methoxybenzofuran-3-yl)methanol (18b) (300 mg, 1.167 mmol) in DCM (10 mL) using ethyl 2-(2-hydroxy-4-methylphenyl) acetate (47a) (249 mg, 1.284 mmol), triphenylphosphine (352 mg, 1.342 mmol), bis(4-chlorobenzyl) diazene-1,2-dicarboxylate (DCAD, 493 mg, 1.342 mmol) in DCM (5 mL) stirring at RT for 1 h. This gave after workup and purification using flash column chromatography [silica gel (24 g), eluting with EtOAc in hexane from 0-25%] ethyl 2-(2-((5-bromo-7-methoxybenzofuran-3-yl)methoxy)-4-methylphenyl)acetate (252a) (375 mg, 74% yield) as a white solid; MS (ES+): 433.0/435.0 (M+1); 455.0/457.0 (M+Na).

Step-2: Preparation of ethyl 2-(2-((5-(3-(aminomethyl)phenyl)-7-methoxybenzofuran-3-yl)methoxy)-4-methylphenyl)acetate (252b)

Compound 252b was prepared according to the procedure reported in step-2 of scheme 1, from ethyl 2-(2-((5-bromo-7-methoxybenzofuran-3-yl)methoxy)-4-methylphenyl)acetate (252a) (300 mg, 0.692 mmol) in dioxane (22 mL) using 3-(aminomethyl)phenylboronic acid hydrochloride (1d) (162 mg, 0.865 mmol), 4M solution of $K_3PO_4$ (0.692 mL, 2.77 mmol), tricyclohexylphosphine (0.058 g, 0.208 mmol), $Pd_2(dba)_3$ (95 mg, 0.104 mmol) and heating at 115° C. for 3 h. This gave after workup and purification using flash column chromatography [silica gel (24 g), eluting with DMA-80 in DCM from 0-70%] ethyl 2-(2-((5-(3-(aminomethyl)phenyl)-7-methoxybenzofuran-3-yl)methoxy)-4-methylphenyl)acetate (252b) (175 mg, 55% yield) as a colorless oil; MS (ES+): 460.2 (M+1).

Step-3: Preparation of 2-(2-((5-(3-(aminomethyl) phenyl)-7-methoxybenzofuran-3-yl)methoxy)-4-methylphenyl)acetic acid (252c)

Compound 252c was prepared according to the procedure reported in step-3 of scheme 1, from ethyl 2-(2-((5-(3-(aminomethyl)phenyl)-7-methoxybenzofuran-3-yl) methoxy)-4-methylphenyl)acetate (252b) (160 mg, 0.348 mmol) in THF (2.1 mL), acetonitrile (1.05 mL) using lithium hydroxide monohydrate, 1N (1.045 mL, 1.045 mmol) and stirring at RT for 25 h. This gave after workup and purification using reverse phase column chromatography [C18 column (50 g), eluting with ACN in water (containing 0.1% HCl) from 0-100%] 2-(2-((5-(3-(aminomethyl) phenyl)-7-methoxybenzofuran-3-yl)methoxy)-4-methylphenyl)acetic acid (252c) (95 mg, 63% yield) HCl salt as a white solid; $^1$H NMR (300 MHz, DMSO-$d_6$) δ 8.45 (s, 2H, $D_2O$ exchangeable), 8.08 (s, 1H), 7.93 (s, 1H), 7.77 (dt, J=7.6, 1.7 Hz, 1H), 7.58 (d, J=1.5 Hz, 1H), 7.54-7.43 (m, 2H), 7.29 (d, J=1.5 Hz, 1H), 7.10-7.03 (m, 2H), 6.74 (d, J=7.5 Hz, 1H), 5.27 (s, 2H), 4.11 (s, 2H), 4.06 (s, 3H), 3.48 (s, 2H), 2.31 (s, 3H). MS (ES+): 432.2 (M+1); (ES−): 430.1 (M−1); Analysis calculated for $C_{26}H_{25}NO_5H_2O\cdot1.05HCl$: C, 64.02; H, 5.80; Cl, 7.63; N, 2.87. Found: C, 64.29; H, 5.79; Cl, 7.74; N, 3.04.

Scheme 253

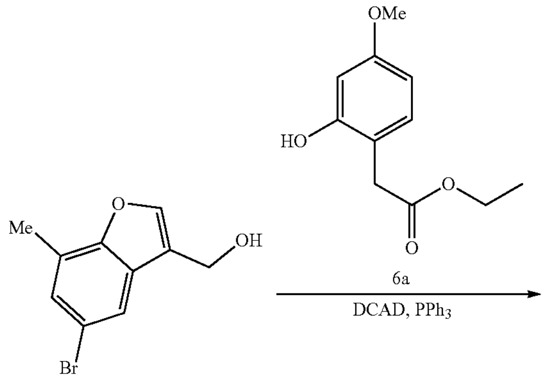

17b

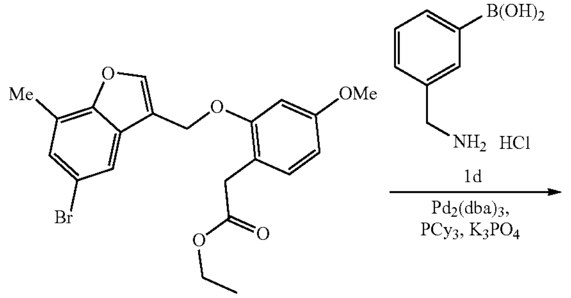

253a

-continued

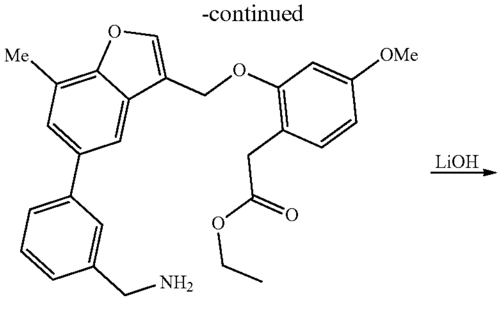

253b

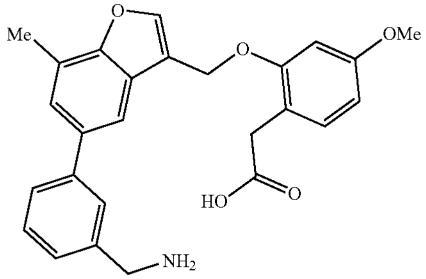

253c

Preparation of 2-(2-((5-(3-(aminomethyl)phenyl)-7-methylbenzofuran-3-yl)methoxy)-4-methoxyphenyl) acetic acid (253c)

Step-1: Preparation of ethyl 2-(2-((5-bromo-7-methylbenzofuran-3-yl)methoxy)-4-methoxyphenyl)acetate (253a)

Compound 253a was prepared according to the procedure reported in step-3 of scheme 7, from (5-bromo-7-methylbenzofuran-3-yl)methanol (17b) (240 mg, 0.996 mmol) in DCM (8 mL) using ethyl 2-(2-hydroxy-4-methoxyphenyl) acetate (6a) (230 mg, 1.095 mmol), triphenylphosphine (300 mg, 1.145 mmol), bis(4-chlorobenzyl) diazene-1,2-dicarboxylate (DCAD, 420 mg, 1.145 mmol) in DCM (4 mL) and stirring at RT for 1 h. This gave after workup and purification using flash column chromatography [silica gel (24 g), eluting with EtOAc in hexane from 0-25%] ethyl 2-(2-((5-bromo-7-methylbenzofuran-3-yl)methoxy)-4-methoxyphenyl)acetate (253a) (265 mg, 61% yield) as a colorless gum; MS (ES+): 455.0/457.0 (M+Na).

Step-2: Preparation of ethyl 2-(2-((5-(3-(aminomethyl)phenyl)-7-methylbenzofuran-3-yl)methoxy)-4-methoxyphenyl)acetate (253b)

Compound 253b was prepared according to the procedure reported in step-2 of scheme 1, from ethyl 2-(2-((5-bromo-7-methylbenzofuran-3-yl)methoxy)-4-methoxyphenyl)acetate (253a) (260 mg, 0.6 mmol) in dioxane (20 mL) using 3-(aminomethyl)phenylboronic acid hydrochloride (1d) (141 mg, 0.75 mmol), 4M solution of $K_3PO_4$ (0.6 mL, 2.4 mmol), tricyclohexylphosphine (50.5 mg, 0.18 mmol), $Pd_2(dba)_3$ (82 mg, 0.09 mmol) and heating at 115° C. for 3 h. This gave after workup and purification using flash column chromatography [silica gel (24 g), eluting with DMA-80 in DCM from 0-70%] ethyl 2-(2-((5-(3-(aminomethyl)phenyl)-7-methylbenzofuran-3-yl)methoxy)-4-methoxyphenyl) acetate (253b) (160 mg, 58% yield) as a colorless oil; MS (ES+): 460.2 (M+1).

Step-3: Preparation of 2-(2-((5-(3-(aminomethyl) phenyl)-7-methylbenzofuran-3-yl)methoxy)-4-methoxyphenyl)acetic acid (253c)

Compound 253c was prepared according to the procedure reported in step-3 of scheme 1, from ethyl 2-(2-((5-(3-(aminomethyl)phenyl)-7-methylbenzofuran-3-yl)methoxy)-4-methoxyphenyl)acetate (253b) (150 mg, 0.326 mmol) in THF (2 mL), acetonitrile (1 mL) using lithium hydroxide monohydrate, 1N (0.979 mL, 0.979 mmol) and stirring at RT for 25 h. This gave after workup and purification using reverse phase column chromatography [C18 column (50 g), eluting with ACN in water (containing 0.1% HCl) from 0-100%] 2-(2-((5-(3-(aminomethyl)phenyl)-7-methylbenzofuran-3-yl)methoxy)-4-methoxyphenyl)acetic acid (253c) (85 mg, 60% yield) HCl salt as a white solid; $^1$H NMR (300 MHz, DMSO-$d_6$) δ 8.33 (s, 2H, $D_2O$ exchangeable), 8.13 (s, 1H), 7.86 (s, 1H), 7.83 (d, J=1.8 Hz, 1H), 7.74 (dt, J=7.7, 1.5 Hz, 1H), 7.57-7.42 (m, 3H), 7.10 (d, J=8.3 Hz, 1H), 6.80 (d, J=2.4 Hz, 1H), 6.51 (dd, J=8.3, 2.4 Hz, 1H), 5.31 (s, 2H), 4.11 (s, 2H), 3.77 (s, 3H), 3.45 (s, 2H), 2.56 (s, 3H).

MS (ES+): 432.2 (M+1); (ES−): 430.1 (M−1); Analysis calculated for $C_{26}H_{25}NO_5 \cdot 0.5H_2O \cdot HCl$: C, 65.47; H, 5.71; Cl, 7.43; N, 2.94. Found: C, 65.52; H, 5.44; Cl, 7.82; N, 3.04.

Scheme 254

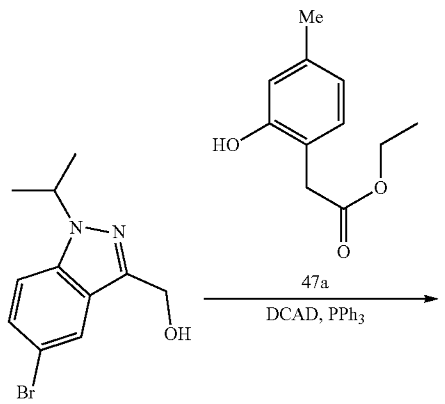

182b

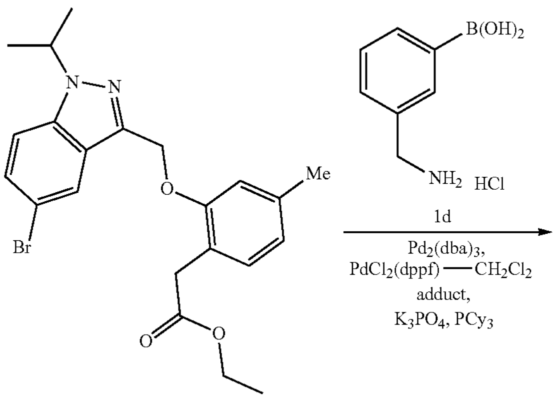

254a

-continued

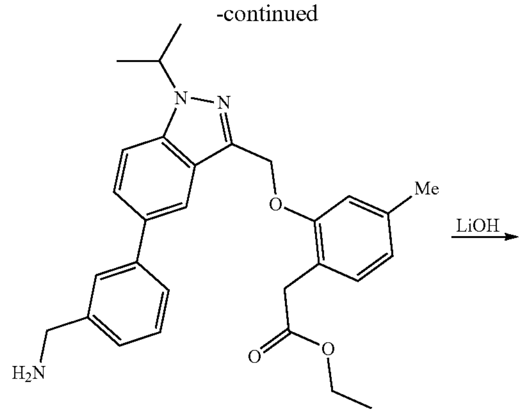

254b

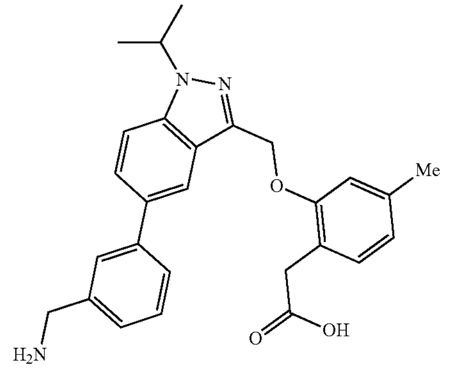

254c

Preparation of 2-(2-((5-(3-(aminomethyl)phenyl)-1-isopropyl-1H-indazol-3-yl)methoxy)-4-methylphenyl)acetic acid (254c)

Step-1: Preparation of ethyl 2-(2-((5-bromo-1-isopropyl-1H-indazol-3-yl)methoxy)-4-methylphenyl) acetate (254a)

Compound 254a was prepared according to the procedure reported in step-2 of scheme 65, from (5-bromo-1-isopropyl-1H-indazol-3-yl)methanol (182b) (320 mg, 1.189 mmol) in DCM (20 mL) using triphenylphosphine (374 mg, 1.427 mmol), ethyl 2-(2-hydroxy-4-methylphenyl)acetate (47a) (242 mg, 1.248 mmol), a solution of DCAD (524 mg, 1.427 mmol) in DCM (10 mL) and stirring at RT for 30 min. This gave after workup and purification using flash column chromatography [silica gel (12 g), eluting with EtOAc in hexane from 0-60%] ethyl 2-(2-((5-bromo-1-isopropyl-1H-indazol-3-yl)methoxy)-4-methylphenyl)acetate (254a) (400 mg, 76% yield) as a light yellow oil; MS (ES+): 445.10 & 447.10 (M+1); 467.05 & 469.10 (M+Na); MS (ES−): 443.10 & 445.05 (M−1).

Step-2: Preparation of ethyl 2-(2-((5-(3-(aminomethyl)phenyl)-1-isopropyl-1H-indazol-3-yl) methoxy)-4-methylphenyl)acetate (254b)

Compound 254b was prepared according to the procedure reported in step-2 of scheme 1, from ethyl 2-(2-((5-bromo-1-isopropyl-1H-indazol-3-yl)methoxy)-4-methylphenyl)acetate (254a) (400 mg, 0.898 mmol) in dioxane (4 mL) and THF (4 mL) using (3-(aminomethyl)phenyl)boronic acid hydrochloride (1d) (337 mg, 1.796 mmol), 2 M solution of $K_3PO_4$ (1.796 mL, 3.59 mmol), tricyclohexylphosphine (50.4 mg, 0.180 mmol), $Pd_2(dba)_3$ (82 mg, 0.090 mmol), $PdCl_2(dppf)$-$CH_2Cl_2$ adduct (73.3 mg, 0.090 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-isopropyl-1H-indazol-3-yl)methoxy)-4-methylphenyl)acetate (254b) (270 mg, 64% yield) as a clear oil; MS (ES+): 472.20 (M+1); MS (ES−): 470.20 (M−1).

Step-3: Preparation of 2-(2-((5-(3-(aminomethyl) phenyl)-1-isopropyl-1H-indazol-3-yl)methoxy)-4-methylphenyl)acetic acid (254c)

Compound 254c was prepared according to the procedure reported in step-3 of scheme 1, from ethyl 2-(2-((5-(3-(aminomethyl)phenyl)-1-isopropyl-1H-indazol-3-yl) methoxy)-4-methylphenyl)acetate (254b) (270 mg, 0.573 mmol) in THF (2 mL) and MeOH (2 mL) using lithium hydroxide hydrate (72.1 mg, 1.718 mmol) in water (1 mL) and stirring at RT for 15 h.

This gave after workup and purification using reverse phase column chromatography [C18 column (50 g), eluting with ACN in water (containing 0.1% HCl) from 0-100%] 2-(2-((5-(3-(aminomethyl)phenyl)-1-isopropyl-1H-indazol-3-yl)methoxy)-4-methylphenyl)acetic acid (254c) (95 mg, 37% yield) HCl salt as a white solid; $^1H$ NMR (300 MHz, DMSO-$d_6$) δ 12.08 (s, 1H, $D_2O$ exchangeable), 8.41 (s, 3H, $D_2O$ exchangeable), 8.07 (s, 1H), 7.87 (s, 1H), 7.84 (d, J=8.9 Hz, 1H), 7.79-7.69 (m, 2H), 7.51 (t, J=7.6 Hz, 1H), 7.47-7.41 (m, 1H), 7.13 (s, 1H), 7.05 (d, J=7.6 Hz, 1H), 6.72 (d, J=7.5 Hz, 1H), 5.44 (s, 2H), 5.04 (h, J=6.5 Hz, 1H), 4.10 (s, 2H), 3.47 (s, 2H), 2.29 (s, 3H), 1.52 (d, J=6.6 Hz, 6H); MS (ES+): 444.20 (M+1); MS (ES−): 442.20 (M−1); Analysis calculated for $C_{27}H_{29}N_3O_3$·HCl·$H_2O$: C, 65.12; H, 6.48; Cl, 7.12; N, 8.44. Found: C, 65.41; H, 6.35; Cl, 6.97; N, 8.50.

Scheme 255

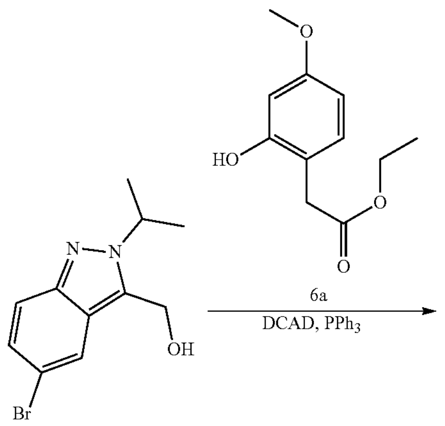

183b

-continued

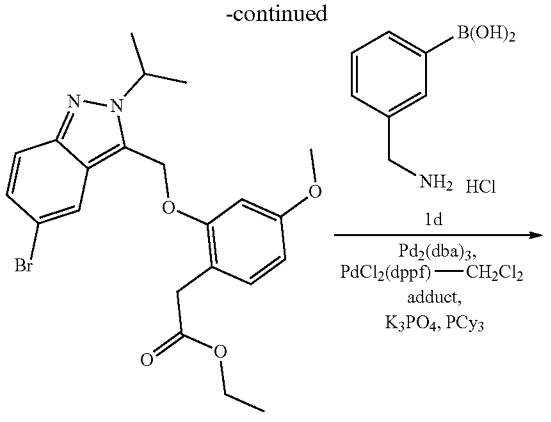

255a

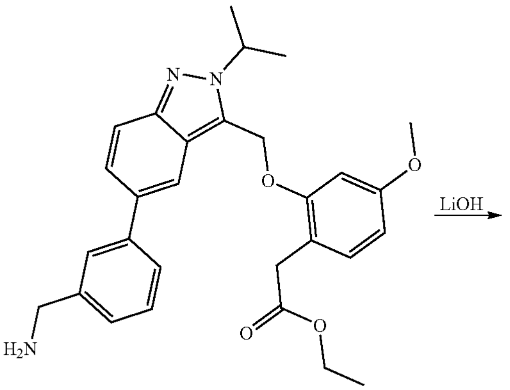

255b

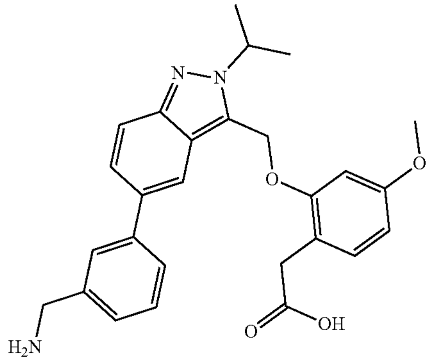

255c

Preparation of 2-(2-((5-(3-(aminomethyl)phenyl)-2-isopropyl-2H-indazol-3-yl)methoxy)-4-methoxyphenyl)acetic acid (255c)

Step-1: Preparation of ethyl 2-(2-((5-bromo-2-isopropyl-2H-indazol-3-yl)methoxy)-4-methoxyphenyl) acetate (255a)

Compound 255a was prepared according to the procedure reported in step-2 of scheme 65, from (5-bromo-2-isopropyl-2H-indazol-3-yl)methanol (183b) (550 mg, 2.044 mmol) in DCM (20 mL) using triphenylphosphine (643 mg, 2.452 mmol), ethyl 2-(2-hydroxy-4-methoxyphenyl)acetate (6a) (451 mg, 2.146 mmol), a solution of DCAD (900 mg, 2.452 mmol) in DCM (10 mL) and stirring at RT for 30 min. This gave after workup and purification using flash column chromatography [silica gel (12 g), eluting with EtOAc in hexane from 0-60%] ethyl 2-(2-((5-bromo-2-isopropyl-2H- indazol-3-yl)methoxy)-4-methoxyphenyl)acetate (255a) (220 mg, 23% yield) as a light yellow oil; MS (ES+): 461.10 & 463.05 (M+1).

Step-2: Preparation of ethyl 2-(2-((5-(3-(aminomethyl)phenyl)-2-isopropyl-2H-indazol-3-yl) methoxy)-4-methoxyphenyl)acetate (255b)

Compound 255b was prepared according to the procedure reported in step-2 of scheme 1, from ethyl 2-(2-((5-bromo-2-isopropyl-2H-indazol-3-yl)methoxy)-4-methoxyphenyl) acetate (255a) (220 mg, 0.477 mmol) in dioxane (3 mL) and THF (3 mL) using (3-(aminomethyl)phenyl)boronic acid hydrochloride (1d) (179 mg, 0.954 mmol), 2 M solution of $K_3PO_4$ (0.954 mL, 1.907 mmol), tricyclohexylphosphine (26.7 mg, 0.095 mmol), $Pd_2(dba)_3$ (43.7 mg, 0.048 mmol), $PdCl_2(dppf)\text{-}CH_2Cl_2$ adduct (38.9 mg, 0.048 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-2-isopropyl-2H-indazol-3-yl)methoxy)-4-methoxyphenyl)acetate (255b) (70 mg, 30% yield) as a clear oil; MS (ES+): 488.20 (M+1).

Step-3: Preparation of 2-(2-((5-(3-(aminomethyl) phenyl)-2-isopropyl-2H-indazol-3-yl)methoxy)-4-methoxyphenyl)acetic acid (255c)

Compound 255c was prepared according to the procedure reported in step-3 of scheme 1, from ethyl 2-(2-((5-(3-(aminomethyl)phenyl)-2-isopropyl-2H-indazol-3-yl) methoxy)-4-methoxyphenyl)acetate (255b) (70 mg, 0.144 mmol) in THF (2 mL) and MeOH (2 mL) using lithium hydroxide hydrate (18.07 mg, 0.431 mmol) in water (1 mL) and stirring at 50° C. for 1 h. This gave after workup and purification using reverse phase column chromatography [C18 column (50 g), eluting with ACN in water (containing 0.1% HCl) from 0-100%] 2-(2-((5-(3-(aminomethyl)phenyl)-2-isopropyl-2H-indazol-3-yl)methoxy)-4-methoxyphenyl)acetic acid (255c) (40 mg, 61% yield) HCl salt as a white solid; $^1H$ NMR (300 MHz, DMSO-$d_6$) δ 8.34 (s, 3H, $D_2O$ exchangeable), 8.24 (s, 1H), 7.90 (s, 1H), 7.77 (d, J=9.0 Hz, 2H), 7.66 (dd, J=9.0, 1.7 Hz, 1H), 7.51 (t, J=7.6 Hz, 1H), 7.43 (d, J=7.7 Hz, 1H), 7.11 (d, J=8.3 Hz, 1H), 6.93 (d, J=2.4 Hz, 1H), 6.53 (dd, J=8.3, 2.3 Hz, 1H), 5.64 (s, 2H), 5.11-4.83 (m, 1H), 4.20-4.03 (m, 2H), 3.77 (s, 3H), 3.40 (s, 2H), 1.55 (d, J=6.4 Hz, 6H); MS (ES+): 460.80 (M+1); (ES−): 458.80 (M−1); Analysis calculated for $C_{27}H_{29}N_3O_4\cdot1.5HCl\cdot2H_2O$: C, 58.93; H, 6.32; Cl, 9.66; N, 7.64. Found: C, 59.10; H, 6.10; Cl, 9.95; N, 7.42.

Scheme 256

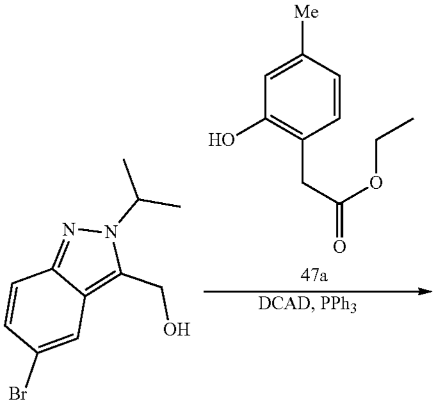

183b

-continued

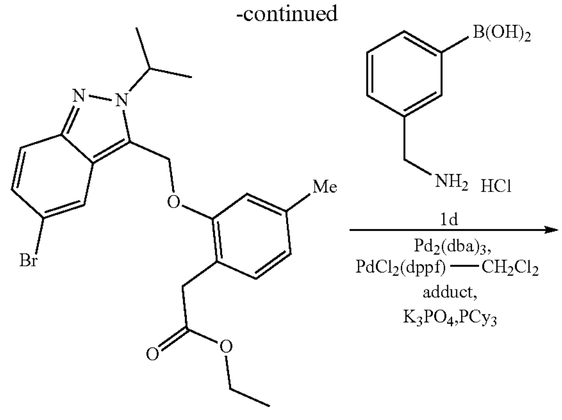

256a

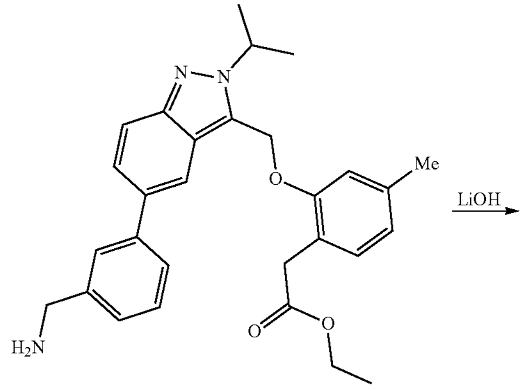

256b

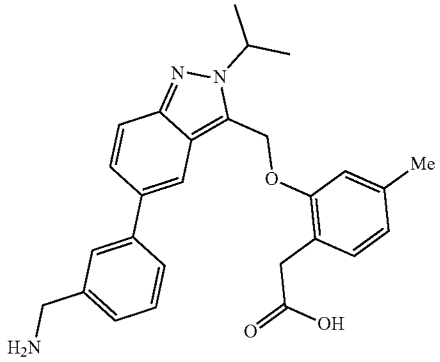

256c

Preparation of 2-(2-((5-(3-(aminomethyl)phenyl)-2-isopropyl-2H-indazol-3-yl)methoxy)-4-methylphenyl)acetic acid (256c)

Step-1: Preparation of ethyl 2-(2-((5-bromo-2-isopropyl-2H-indazol-3-yl)methoxy)-4-methylphenyl) acetate (256a)

Compound 256a was prepared according to the procedure reported in step-2 of scheme 65, from (5-bromo-2-isopropyl-2H-indazol-3-yl)methanol (183b) (550 mg, 2.044 mmol) in DCM (20 mL) using triphenylphosphine (643 mg, 2.452 mmol), ethyl 2-(2-hydroxy-4-methylphenyl)acetate (47a) (417 mg, 2.146 mmol), a solution of DCAD (900 mg, 2.452 mmol) in DCM (10 mL) and stirring at RT for 30 min. This gave after workup and purification using flash column chromatography [silica gel (12 g), eluting with EtOAc in hexane from 0-60%] ethyl 2-(2-((5-bromo-2-isopropyl-2H-indazol-3-yl)methoxy)-4-methylphenyl)acetate (256a) (190 mg, 21% yield) as a light yellow oil; $^1H$ NMR (300 MHz, DMSO-$d_6$) δ 8.14 (d, J=1.8 Hz, 1H), 7.63 (d, J=9.1 Hz, 1H), 7.33 (dd, J=9.1, 1.9 Hz, 1H), 7.15 (s, 1H), 7.08 (d, J=7.5 Hz, 1H), 6.77 (d, J=7.6 Hz, 1H), 5.55 (s, 2H), 4.98 (p, J=6.5 Hz, 1H), 3.80 (q, J=7.1 Hz, 2H), 3.45 (s, 2H), 2.33 (s, 3H), 1.53 (d, J=6.5 Hz, 6H), 0.88 (t, J=7.1 Hz, 3H); MS (ES+): 445.10 & 447.10 (M+1).

Step-2: Preparation of ethyl 2-(2-((5-(3-(aminomethyl)phenyl)-2-isopropyl-2H-indazol-3-yl)methoxy)-4-methylphenyl)acetate (256b)

Compound 256b was prepared according to the procedure reported in step-2 of scheme 1, from ethyl 2-(2-((5-bromo-2-isopropyl-2H-indazol-3-yl)methoxy)-4-methylphenyl)acetate (256a) (190 mg, 0.427 mmol) in dioxane (3 mL) and THF (3 mL) using (3-(aminomethyl)phenyl)boronic acid hydrochloride (1d) (160 mg, 0.853 mmol), 2 M solution of $K_3PO_4$ (0.853 mL, 1.707 mmol), tricyclohexylphosphine (23.93 mg, 0.085 mmol), $Pd_2(dba)_3$ (39.1 mg, 0.043 mmol), $PdCl_2(dppf)$-$CH_2Cl_2$ adduct (34.8 mg, 0.043 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-2-isopropyl-2H-indazol-3-yl)methoxy)-4-methylphenyl)acetate (256b) (130 mg, 65% yield) as a clear oil; MS (ES+): 472.20 (M+1).

Step-3: Preparation of 2-(2-((5-(3-(aminomethyl)phenyl)-2-isopropyl-2H-indazol-3-yl)methoxy)-4-methylphenyl)acetic acid (256c)

Compound 256c was prepared according to the procedure reported in step-3 of scheme 1, from ethyl 2-(2-((5-(3-(aminomethyl)phenyl)-2-isopropyl-2H-indazol-3-yl)methoxy)-4-methylphenyl)acetate (256b) (130 mg, 0.276 mmol) in THF (2 mL) and MeOH (2 mL) using lithium hydroxide hydrate (34.7 mg, 0.827 mmol) in water (1 mL) and stirring at 50° C. for 2 h. This gave after workup and purification using reverse phase column chromatography [C18 column (50 g), eluting with ACN in water (containing 0.1% HCl) from 0-100%] 2-(2-((5-(3-(aminomethyl)phenyl)-2-isopropyl-2H-indazol-3-yl)methoxy)-4-methylphenyl)acetic acid (256c) (80 mg, 65% yield) HCl salt as a white solid; $^1H$ NMR (300 MHz, DMSO-$d_6$) δ 8.37 (s, 3H, $D_2O$ exchangeable), 8.23 (s, 1H), 7.91 (s, 1H), 7.78 (dd, J=9.2, 2.9 Hz, 2H), 7.66 (dd, J=9.1, 1.7 Hz, 1H), 7.51 (t, J=7.6 Hz, 1H), 7.43 (d, J=7.6 Hz, 1H), 7.20 (s, 1H), 7.08 (d, J=7.5 Hz, 1H), 6.77 (d, J=7.5 Hz, 1H), 5.61 (s, 2H), 5.17-4.89 (m, 1H), 4.14-4.07 (m, 2H), 3.43 (s, 2H), 2.34 (s, 3H), 1.55 (d, J=6.4 Hz, 6H); MS (ES+): 444.20 (M+1); MS (ES−): 442.20 (M−1); Analysis calculated for $C_{27}H_{29}N_3O_3 \cdot 1.25HCl \cdot 1.5H_2O$: C, 62.83; H, 6.49; Cl, 8.59; N, 8.14. Found: C, 62.52; H, 6.36; Cl, 9.00; N, 8.01.

Scheme 257

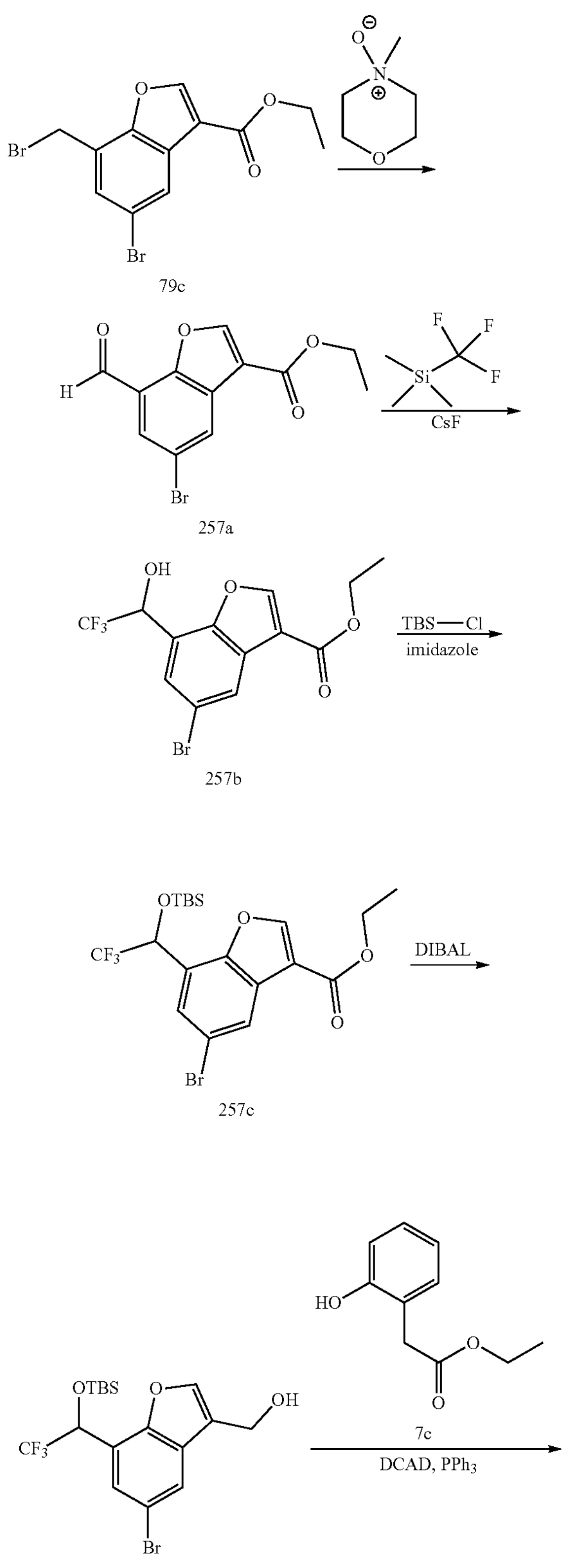

79c

257a

257b

257c

7c

257d

-continued

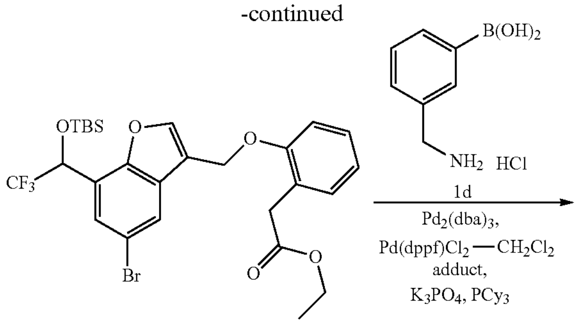

257e

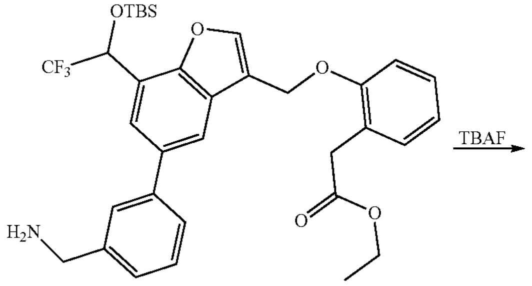

257f

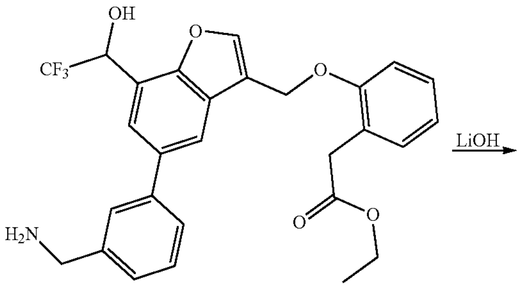

257g

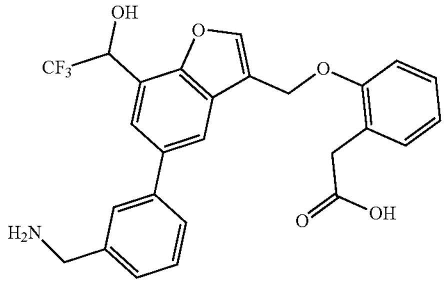

257h

Preparation of 2-(2-((5-(3-(aminomethyl)phenyl)-7-(2,2,2-trifluoro-1-hydroxyethyl)benzofuran-3-yl)methoxy)phenyl)acetic acid (257 h)

Step-1: Preparation of ethyl 5-bromo-7-formylbenzofuran-3-carboxylate (257a)

To a solution of ethyl 5-bromo-7-(bromomethyl)benzofuran-3-carboxylate (79c) (500 mg, 1.381 mmol) in EtOH (10 mL) was added 4-methylmorpholine 4-oxide (485 mg, 4.14 mmol) and heated at 80° C. for 6 h. The reaction mixture was cooled to room temperature, diluted with water (20 mL) and extracted with ethyl acetate (50 mL×3). The combined organics were washed with water, brine, dried, filtered and evaporated to dryness. The residue obtained was purified using flash column chromatography [silica gel (24 g), eluting with EtOAc in Hexane from 0-70%] to furnish ethyl 5-bromo-7-formylbenzofuran-3-carboxylate (257a) (150 mg, 37% yield) as a white solid; $^1$H NMR (300 MHz, DMSO-$d_6$) δ 10.24 (s, 1H), 9.00 (s, 1H), 8.33 (d, J=2.1 Hz, 1H), 8.12 (d, J=2.1 Hz, 1H), 4.38 (q, J=7.1 Hz, 2H), 1.36 (t, J=7.1 Hz, 3H); MS (ES+): 296.90 (M+1).

Step-2: Preparation of ethyl 5-bromo-7-(2,2,2-trifluoro-1-hydroxyethyl)benzofuran-3-carboxylate (257b)

Compound 257b was prepared according to the procedure reported in step-1 of scheme 140, from ethyl 5-bromo-7-formylbenzofuran-3-carboxylate (257a) (0.45 g, 1.515 mmol) in anhydrous THF (20 mL) using trimethyl(trifluoromethyl)silane (0.280 g, 1.969 mmol), CsF (0.230 g, 1.515 mmol) and stirring at RT for 12 h. This gave after workup and purification using flash column chromatography [silica gel (24 g), eluting with EtOAc in hexane from 0-60%] ethyl 5-bromo-7-(2,2,2-trifluoro-1-hydroxyethyl)benzofuran-3-carboxylate (257b) (800 mg, 69% yield) as a yellow oil; $^1$H NMR (300 MHz, DMSO-$d_6$) δ 8.92 (s, 1H), 8.12 (d, J=2.0 Hz, 1H), 7.72 (d, J=2.1 Hz, 1H), 7.33 (d, J=5.8 Hz, 1H, $D_2O$ exchangeable), 5.65 (p, J=6.8 Hz, 1H), 4.36 (q, J=7.1 Hz, 2H), 1.34 (t, J=7.1 Hz, 3H).

Step-3: Preparation of ethyl 5-bromo-7-(1-((tert-butyldimethylsilyl)oxy)-2,2,2-trifluoroethyl)benzofuran-3-carboxylate (257c)

Compound 257c was prepared according to the procedure reported in step-1 of scheme 140, from ethyl 5-bromo-7-(2,2,2-trifluoro-1-hydroxyethyl)benzofuran-3-carboxylate (257b) (400 mg, 1.09 mmol) in anhydrous DCM (10 mL) using TBS-$C_1$ (246 mg, 1.634 mmol), imidazole (148 mg, 2.179 mmol) and stirring at RT for 18 h. This gave after workup and purification using flash column chromatography [silica gel (12 g), eluting with EtOAc in hexane from 0-70%] ethyl 5-bromo-7-(1-((tert-butyldimethylsilyl)oxy)-2,2,2-trifluoroethyl)benzofuran-3-carboxylate (257c) (270 mg, 52% yield) as a clear oil; $^1$H NMR (300 MHz, DMSO-$d_6$) δ 8.96 (s, 1H), 8.15 (d, J=2.0 Hz, 1H), 7.73 (d, J=2.0 Hz, 1H), 5.83 (q, J=6.5 Hz, 1H), 4.36 (q, J=7.1 Hz, 2H), 1.34 (t, J=7.1 Hz, 3H), 0.84 (s, 9H), 0.13 (s, 3H), −0.08 (s, 3H).

Step-4: Preparation of (5-bromo-7-(1-((tert-butyldimethylsilyl)oxy)-2,2,2-trifluoroethyl)benzofuran-3-yl)methanol (257d)

Compound 257d was prepared according to the procedure reported in step-2 of scheme 69, from ethyl 5-bromo-7-(1-((tert-butyldimethylsilyl)oxy)-2,2,2-trifluoroethyl)benzofuran-3-carboxylate (257c) (270 mg, 0.561 mmol) in THF (10 mL) using 1.0 M solution of DIBAL in THE (1.402 mL, 1.402 mmol) and stirring at −78° C. for 30 min. This gave after work up and purification using flash column chromatography [silica gel (24 g), eluting with DMA-80 in DCM from 0-100%) (5-bromo-7-(1-((tert-butyldimethylsilyl)oxy)-2,2,2-trifluoroethyl)benzofuran-3-yl)methanol (257d) (105 mg, 43% yield) as a light yellow oil; $^1$H NMR (300 MHz, DMSO-$d_6$) δ 8.04 (s, 1H), 7.98 (d, J=2.0 Hz, 1H), 7.58 (d, J=2.0 Hz, 1H), 5.79-5.72 (m, 1H), 5.26 (t, J=5.6 Hz, 1H), 4.61 (dd, J=5.6, 1.1 Hz, 2H), 0.84 (s, 9H), 0.12 (s, 3H), −0.07 (s, 3H).

Step-5: Preparation of ethyl 2-(2-((5-bromo-7-(1-((tert-butyldimethylsilyl)oxy)-2,2,2-trifluoroethyl)benzofuran-3-yl)methoxy)phenyl)acetate (257e)

Compound 257e was prepared according to the procedure reported in step-2 of scheme 65, from (5-bromo-7-(1-((tert-butyldimethylsilyl)oxy)-2,2,2-trifluoroethyl)benzofuran-3-yl)methanol (257d) (100 mg, 0.228 mmol) in DCM (10 mL) using triphenylphosphine (71.6 mg, 0.273 mmol), ethyl 2-(2-hydroxyphenyl)acetate (7c) (43.1 mg, 0.239 mmol) a solution of DCAD (100 mg, 0.273 mmol) in DCM (5 mL) and stirring at RT for 60 min. This gave after workup and purification using flash column chromatography [silica gel (24 g), eluting with EtOAc in hexane from 0-80%] ethyl 2-(2-((5-bromo-7-(1-((tert-butyldimethylsilyl)oxy)-2,2,2-trifluoroethyl)benzofuran-3-yl)methoxy)phenyl)acetate (257e) (100 mg, 73% yield) as a white solid; $^1$H NMR (300 MHz, DMSO-$d_6$) δ 8.25 (s, 1H), 7.92 (d, J=2.0 Hz, 1H), 7.62 (d, J=2.0 Hz, 1H), 7.34-7.25 (m, 1H), 7.25-7.16 (m, 2H), 6.93 (td, J=7.4, 1.2 Hz, 1H), 5.84-5.74 (m, 1H), 5.24 (s, 2H), 3.87 (q, J=7.1 Hz, 2H), 3.55 (s, 2H), 0.92-0.86 (m, 3H), 0.85 (s, 9H), 0.14 (s, 3H), −0.06 (s, 3H).

Step-6: Preparation of ethyl 2-(2-((5-(3-(aminomethyl)phenyl)-7-(1-((tert-butyldimethylsilyl)oxy)-2,2,2-trifluoroethyl)benzofuran-3-yl)methoxy)phenyl)acetate (257f)

Compound 257f was prepared according to the procedure reported in step-2 of scheme 1, from ethyl 2-(2-((5-bromo-7-(1-((tert-butyldimethylsilyl)oxy)-2,2,2-trifluoroethyl)benzofuran-3-yl)methoxy)phenyl)acetate (257e) (100 mg, 0.166 mmol) in dioxane (2 mL) and THF (2 mL) using (3-(aminomethyl)phenyl)boronic acid hydrochloride (1d) (62.3 mg, 0.332 mmol), 2 M solution of $K_3PO_4$ (0.332 mL, 0.665 mmol), tricyclohexylphosphine (9.32 mg, 0.033 mmol), $Pd_2(dba)_3$ (15.22 mg, 0.017 mmol), $PdCl_2$(dppf)-$CH_2Cl_2$ adduct (13.58 mg, 0.017 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-7-(1-((tert-butyldimethylsilyl)oxy)-2,2,2-trifluoroethyl)benzofuran-3-yl)methoxy)phenyl)acetate (257f) (80 mg, 77% yield) as a clear oil; MS (ES+): 628.70 (M+1).

Step-7: Preparation of ethyl 2-(2-((5-(3-(aminomethyl)phenyl)-7-(2,2,2-trifluoro-1-hydroxyethyl)benzofuran-3-yl)methoxy)phenyl)acetate (257g)

Compound 257g was prepared according to the procedure reported in step-2 of scheme 3, from ethyl 2-(2-((5-(3-(aminomethyl)phenyl)-7-(1-((tert-butyldimethylsilyl)oxy)-2,2,2-trifluoroethyl)benzofuran-3-yl)methoxy)phenyl)acetate (257f) (80 g, 0.127 mmol) in THF (5 mL) using 1M TBAF in THF (0.191 mL, 0.191 mmol) and stirring at RT for 3 h. This gave after workup and purification using flash column chromatography [silica gel, eluting with EtOAc in hexane from 0-100%] ethyl 2-(2-((5-(3-(aminomethyl)phenyl)-7-(2,2,2-trifluoro-1-hydroxyethyl)benzofuran-3-yl)methoxy)phenyl)acetate (257g) (60 mg, 92% yield) as a clear oil; MS (ES+): 514.70 (M+1).

Step-8: Preparation of 2-(2-((5-(3-(aminomethyl)phenyl)-7-(2,2,2-trifluoro-1-hydroxyethyl)benzofuran-3-yl)methoxy)phenyl)acetic acid (257 h)

Compound 257h was prepared according to the procedure reported in step-3 of scheme 1, from ethyl 2-(2-((5-(3-(aminomethyl)phenyl)-7-(2,2,2-trifluoro-1-hydroxyethyl)benzofuran-3-yl)methoxy)phenyl)acetate (257g) (60 mg, 0.117 mmol) in THF (2 mL) and MeOH (2 mL) using lithium hydroxide hydrate (14.71 mg, 0.351 mmol) in water (1 mL) and stirring at 50° C. for 2 h. This gave after workup and purification using reverse phase column chromatography [C18 column (50 g), eluting with ACN in water (containing 0.1% HCl) from 0-100%] 2-(2-((5-(3-(aminomethyl)phenyl)-7-(2,2,2-trifluoro-1-hydroxyethyl)benzofuran-3-yl)methoxy)phenyl)acetic acid (257 h) (20 mg, 35% yield) HCl salt as a white solid; $^1$H NMR (300 MHz, DMSO-$d_6$) δ 12.13 (s, 1H, $D_2O$ exchangeable), 8.24 (s, 2H, $D_2O$ exchangeable), 8.20 (s, 1H), 8.04 (s, 1H), 7.87-7.79 (m, 2H), 7.74 (d, J=7.8 Hz, 1H), 7.55 (t, J=7.6 Hz, 1H), 7.51-7.43 (m, 1H), 7.28 (t, J=8.0 Hz, 1H), 7.25-7.17 (m, 3H), 6.93 (t, J=7.2 Hz, 1H), 5.73-5.61 (m, 1H), 5.34 (s, 2H), 4.13 (s, 2H), 3.54 (s, 2H); $^{19}$F NMR (282 MHz, DMSO-$d_6$) δ −76.59; MS (ES+): 486.10 (M+1); (ES−): 484.10 (M−1).

Scheme 258

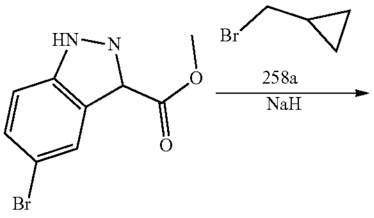

144a

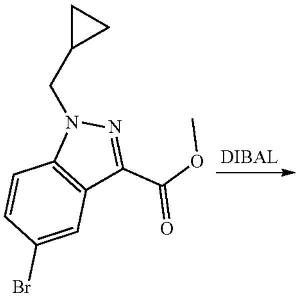

258b

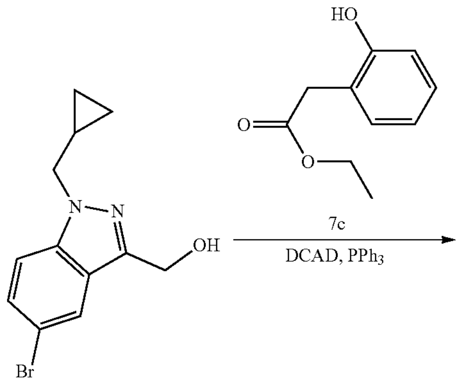

258c

-continued

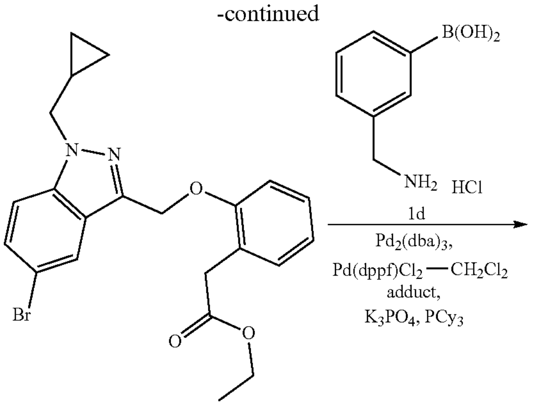

258d

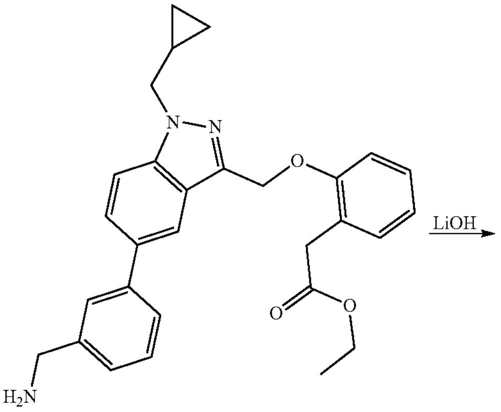

258e

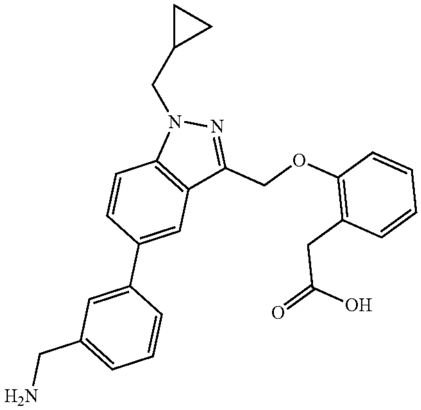

258f

Preparation of 2-(2-((5-(3-(aminomethyl)phenyl)-1-(cyclopropylmethyl)-1H-indazol-3-yl)methoxy)phenyl)acetic acid (258f)

Step-1: Preparation of methyl 5-bromo-1-(cyclopropylmethyl)-1H-indazole-3-carboxylate (258b)

Compound 258b was prepared according to the procedure reported in step-1 of scheme 67, from methyl 5-bromo-1H-indazole-3-carboxylate (144a) (3 g, 11.76 mmol) in DMF (40 mL) using (bromomethyl) cyclopropane (258a) (4.76 g, 35.3 mmol; CAS #7051-34-5), sodium hydride (941 mg, 23.52 mmol) and stirring at RT for 15 h. This gave after work up and purification using flash column chromatography [silica gel (80 g), eluting with EtOAc in Hexane from 0-50%]methyl 5-bromo-1-(cyclopropylmethyl)-1H-indazole-3-carboxylate (258b) (0.810 g, 22% yield) as a white solid; $^1$H NMR (300 MHz, DMSO-$d_6$) δ 8.21 (d, J=1.8, 0.7 Hz, 1H), 7.90 (d, J=9.0, 0.7 Hz, 1H), 7.63 (dd, J=9.0, 1.9 Hz, 1H), 4.43 (d, J=7.2 Hz, 2H), 3.93 (s, 3H), 1.40-1.23 (m, 1H), 0.56-0.39 (m, 4H).

Step-2: Preparation of (5-bromo-1-(cyclopropylmethyl)-1H-indazol-3-yl)methanol (258c)

Compound 258c was prepared according to the procedure reported in step-2 of scheme 69, from methyl 5-bromo-1-(cyclopropylmethyl)-1H-indazole-3-carboxylate (258b) (0.8 g, 2.59 mmol) in THF (10 mL) using 1.0 M solution of DIBAL in THF (6.47 mL, 6.47 mmol) and stirring at −78° C. for 30 min. This gave after workup and purification using flash column chromatography [silica gel (24 g), eluting with DMA-80 in DCM from 0-100%] (5-bromo-1-(cyclopropylmethyl)-1H-indazol-3-yl)methanol (258c) (0.53 g, 73% yield) as a light yellow oil; $^1$H NMR (300 MHz, DMSO-$d_6$) δ 8.05 (d, J=1.8 Hz, 1H), 7.67 (d, J=8.9 Hz, 1H), 7.47 (dd, J=8.9, 1.9 Hz, 1H), 5.33 (d, J=5.9 Hz, 1H), 4.75 (d, J=3.8 Hz, 2H), 4.24 (d, J=7.0 Hz, 2H), 1.30-1.18 (m, 1H), 0.50-0.34 (m, 4H).

Step-3: Preparation of ethyl 2-(2-((5-bromo-1-(cyclopropylmethyl)-1H-indazol-3-yl)methoxy)phenyl) acetate (258d)

Compound 258d was prepared according to the procedure reported in step-2 of scheme 65, from (5-bromo-1-(cyclopropylmethyl)-1H-indazol-3-yl)methanol (258c) (150 mg, 0.534 mmol) in DCM (10 mL) using triphenylphosphine (358 mg, 1.365 mmol), ethyl 2-(2-hydroxyphenyl)acetate (7c) (246 mg, 1.365 mmol), a solution of DCAD (168 mg, 0.640 mmol) in DCM (5 mL) and stirring at RT for 60 min. This gave after workup and purification using flash column chromatography [silica gel (24 g), eluting with EtOAc in hexane from 0-80%] ethyl 2-(2-((5-bromo-1-(cyclopropylmethyl)-1H-indazol-3-yl)methoxy)phenyl)acetate (258d) (120 mg, 51% yield) as a white solid; $^1$H NMR (300 MHz, DMSO-$d_6$) δ 7.95 (d, J=1.8 Hz, 1H), 7.74 (d, J=8.9 Hz, 1H), 7.53 (dd, J=8.9, 1.8 Hz, 1H), 7.33-7.17 (m, 3H), 6.93 (td, J=7.1, 1.8 Hz, 1H), 5.38 (s, 2H), 4.32 (d, J=7.0 Hz, 2H), 3.93 (q, J=7.1 Hz, 2H), 3.54 (s, 2H), 1.33-1.21 (m, 1H), 0.95 (t, J=7.1 Hz, 3H), 0.50-0.37 (m, 4H).

Step-4: Preparation of ethyl 2-(2-((5-(3-(aminomethyl)phenyl)-1-(cyclopropylmethyl)-1H-indazol-3-yl)methoxy)phenyl)acetate (258e)

Compound 258e was prepared according to the procedure reported in step-2 of scheme 1, from ethyl 2-(2-((5-bromo-1-(cyclopropylmethyl)-1H-indazol-3-yl)methoxy)phenyl) acetate (258d) (120 mg, 0.271 mmol) in dioxane (2 mL) and THF (2 mL) using (3-(aminomethyl)phenyl)boronic acid hydrochloride (1d) (101 mg, 0.541 mmol), 2 M solution of $K_3PO_4$ (0.541 mL, 1.083 mmol), tricyclohexylphosphine (15.18 mg, 0.054 mmol), $Pd_2(dba)_3$ (24.79 mg, 0.027 mmol), $PdCl_2$(dppf)-$CH_2Cl_2$ adduct (22.1 mg, 0.027 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-(cyclopropylmethyl)-

1H-indazol-3-yl)methoxy)phenyl)acetate (258e) (100 mg, 79% yield) as a clear oil; MS (ES+): 470.30 (M+1).

Step-5: Preparation of 2-(2-((5-(3-(aminomethyl)phenyl)-1-(cyclopropylmethyl)-1H-indazol-3-yl)methoxy)phenyl)acetic acid (258f)

Compound 258f was prepared according to the procedure reported in step-3 of scheme 1, from ethyl 2-(2-((5-(3-(aminomethyl)phenyl)-1-(cyclopropylmethyl)-1H-indazol-3-yl)methoxy)phenyl)acetate (258e) (100 mg, 0.213 mmol) in THF (2 mL) and MeOH (2 mL) using lithium hydroxide hydrate (26.8 mg, 0.639 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-1-(cyclopropylmethyl)-1H-indazol-3-yl)methoxy)phenyl)acetic acid (258f) (40 mg, 43% yield) HCl salt as a white solid; $^1$H NMR (300 MHz, DMSO-$d_6$) δ 8.46 (s, 3H, $D_2O$ exchangeable), 8.09 (s, 1H), 7.90 (s, 1H), 7.85 (d, J=8.8 Hz, 1H), 7.80-7.71 (m, 2H), 7.55-7.42 (m, 2H), 7.32-7.24 (m, 2H), 7.24-7.14 (m, 1H), 6.92 (ddd, J=7.8, 6.3, 2.1 Hz, 1H), 5.46 (s, 2H), 4.35 (d, J=6.9 Hz, 2H), 4.15-4.04 (m, 2H), 3.53 (s, 2H), 1.39-1.14 (m, 1H), 0.57-0.33 (m, 4H); MS (ES+): 442.20 (M+1); (ES−): 440.20 (M−1); Analysis calculated for $C_{27}H_{27}N_3O_3\cdot1.5HCl\cdot1.25H_2O$: C, 62.52; H, 6.02; Cl, 10.25; N, 8.10. Found: C, 62.77; H, 6.00; Cl, 10.70; N, 8.31.

Scheme 259

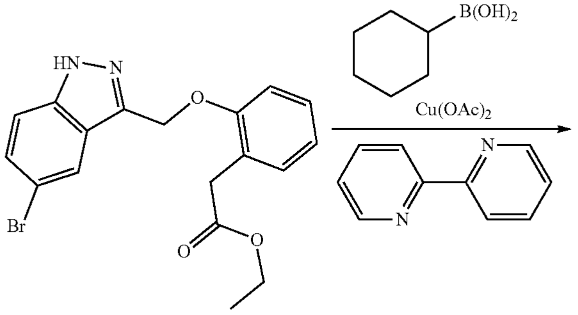

144e

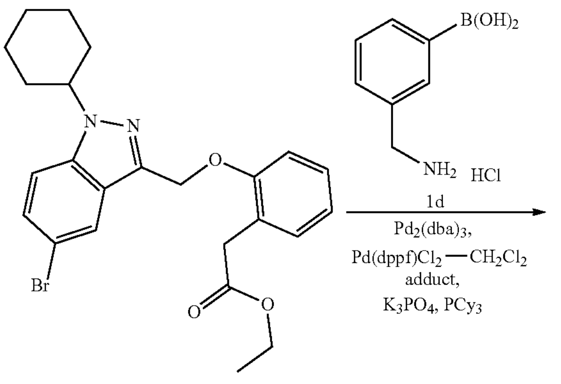

259a

-continued

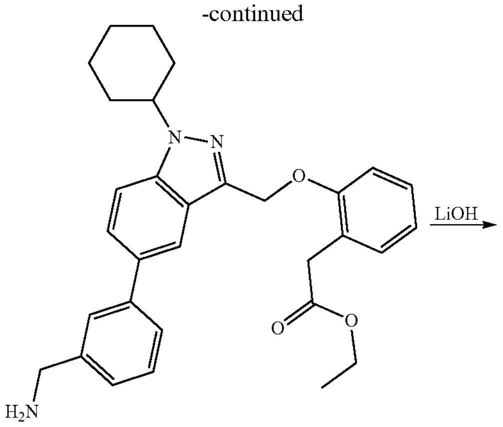

259b

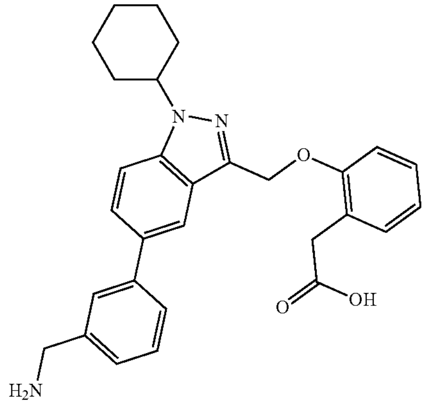

259c

Preparation of 2-(2-((5-(3-(aminomethyl)phenyl)-1-cyclohexyl-1H-indazol-3-yl)methoxy)phenyl)acetic acid (259c)

Step-1: Preparation of ethyl 2-(2-((5-bromo-1-cyclohexyl-1H-indazol-3-yl)methoxy)phenyl)acetate (259a)

Compound 259a was prepared according to the procedure reported in step-2 of scheme 1, from ethyl 2-(2-((5-bromo-1H-indazol-3-yl)methoxy)phenyl)acetate (144e) (0.500 g, 1.285 mmol) in DCE (10 mL) using cyclohexyl boronic acid (0.329 g, 2.57 mmol), 2,2'-bipyridine (201 mg, 1.285 mmol), copper (II) acetate (0.233 g, 1.285 mmol) and heating at 70° C. for 6 h. This gave after workup and purification using flash column chromatography [silica gel (24 g), eluting with EtOAc in hexane from 0-50%] ethyl 2-(2-((5-bromo-1-cyclohexyl-1H-indazol-3-yl)methoxy)phenyl)acetate (259a) (0.330 g, 55% yield) as a clear oil; MS (ES+): 471.10 & 473.10 (M+1); 493.10 & 495.10 (M+Na).

Step-2: Preparation of ethyl 2-(2-((5-(3-(aminomethyl)phenyl)-1-cyclohexyl-1H-indazol-3-yl)methoxy)phenyl)acetate (259b)

Compound 259b was prepared according to the procedure reported in step-2 of scheme 1, from ethyl 2-(2-((5-bromo-1-cyclohexyl-1H-indazol-3-yl)methoxy)phenyl)acetate (259a) (0.33 g, 0.7 mmol) in dioxane (2 mL) and THF (2 mL) using 3-(aminomethyl)phenylboronic acid hydrochloride (1d) (262 mg, 1.4 mmol), 2 M solution of $K_3PO_4$ (1.4 mL, 2.8 mmol), tricyclohexylphosphine (39.3 mg, 0.14 mmol), $Pd_2(dba)_3$ (64.1 mg, 0.07 mmol), $PdCl_2$(dppf)-$CH_2Cl_2$ adduct (57.2 mg, 0.07 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-cyclohexyl-1H-indazol-3-yl)methoxy)phenyl)acetate (259b) (0.200 g, 57% yield) as a clear oil; MS (ES+): 498.30 (M+1).

Step-3: Preparation of 2-(2-((5-(3-(aminomethyl) phenyl)-1-cyclohexyl-1H-indazol-3-yl)methoxy) phenyl)acetic acid (259c)

Compound 259c was prepared according to the procedure reported in step-3 of scheme 1, from ethyl 2-(2-((5-(3-(aminomethyl)phenyl)-1-cyclohexyl-1H-indazol-3-yl) methoxy)phenyl)acetate (259b) (200 mg, 0.402 mmol) in THF (2 mL) and MeOH (2 mL) using lithium hydroxide hydrate (101 mg, 2.411 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-1-cyclohexyl-1H-indazol-3-yl)methoxy)phenyl)acetic acid (259c) (65 mg, 34% yield) HCl salt as a white solid; $^1$H NMR (300 MHz, DMSO-$d_6$) δ 12.16 (s, 1H, $D_2O$ exchangeable), 8.58 (s, 3H, $D_2O$ exchangeable), 8.08 (s, 1H), 7.91 (s, 1H), 7.86 (d, J=8.9 Hz, 1H), 7.79 (d, J=1.6 Hz, 1H), 7.77-7.69 (m, 1H), 7.53-7.43 (m, 2H), 7.32-7.24 (m, 2H), 7.24-7.16 (m, 1H), 6.96-6.88 (m, 1H), 5.44 (s, 2H), 4.80-4.53 (m, 1H), 4.25-3.97 (m, 2H), 3.54 (s, 2H), 2.06-1.79 (m, 6H), 1.79-1.64 (m, 1H), 1.64-1.41 (m, 2H), 1.41-1.15 (m, 1H); MS (ES+): 470.30 (M+1); MS (ES−): 468.20 (M−1); Analysis calculated for $C_{29}H_{31}N_3O_3 \cdot HCl \cdot H_2O$: C, 66.47; H, 6.54; Cl, 6.76; N, 8.02. Found: C, 66.29; H, 6.40; Cl, 6.99; N, 7.87.

Scheme 260

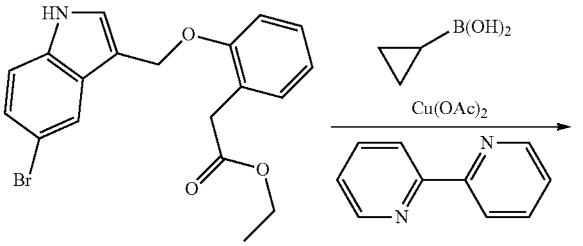

144e

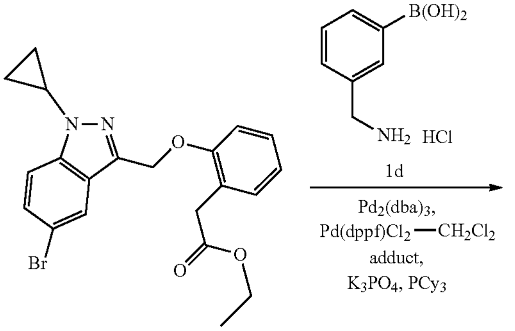

260a

-continued

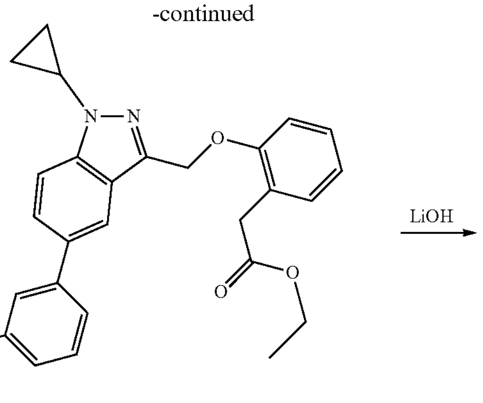

260b

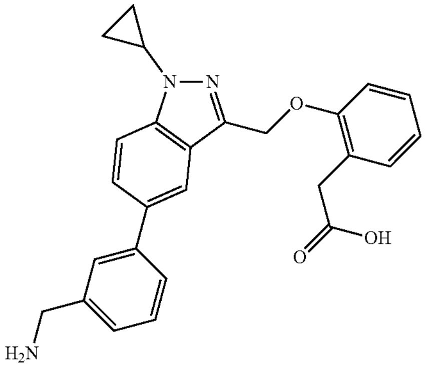

260c

Preparation of 2-(2-((5-(3-(aminomethyl)phenyl)-1-cyclopropyl-1H-indazol-3-yl)methoxy)phenyl)acetic acid (260c)

Step-1: Preparation of ethyl 2-(2-((5-bromo-1-cyclopropyl-1H-indazol-3-yl)methoxy)phenyl)acetate (260a)

Compound 260a was prepared according to the procedure reported in step-2 of scheme 1, from ethyl 2-(2-((5-bromo-1H-indazol-3-yl)methoxy)phenyl)acetate (144e) (500 mg, 1.285 mmol) in DCE (10 mL) using cyclopropyl boronic acid (221 mg, 2.57 mmol), 2,2'-bipyridine (201 mg, 1.285 mmol), copper (II) acetate (233 mg, 1.285 mmol), sodium carbonate (272 mg, 2.57 mmol) and stirring for 15 h at RT followed by heating at 70° C. for 3 h. This gave after workup and purification using flash column chromatography [silica gel (24 g), eluting with EtOAc in hexane from 0-50%] ethyl 2-(2-((5-bromo-1-cyclopropyl-1H-indazol-3-yl)methoxy) phenyl)acetate (260a) (220 mg, 40% yield) as a clear oil; $^1$H NMR (300 MHz, DMSO-$d_6$) δ 7.95 (dd, J=1.9, 0.7 Hz, 1H), 7.69 (dd, J=8.9, 0.7 Hz, 1H), 7.57 (dd, J=8.9, 1.8 Hz, 1H), 7.28 (td, J=7.7, 7.1, 1.7 Hz, 1H), 7.21 (ddt, J=7.2, 5.5, 2.4 Hz, 2H), 6.92 (td, J=7.3, 1.3 Hz, 1H), 5.34 (s, 2H), 3.92 (q, J=7.1 Hz, 2H), 3.83-3.72 (m, 1H), 3.53 (s, 2H), 1.19-1.08 (m, 4H), 0.95 (t, J=7.1 Hz, 3H).

Step-2: Preparation of ethyl 2-(2-((5-(3-(aminomethyl)phenyl)-1-cyclopropyl-1H-indazol-3-yl) methoxy)phenyl)acetate (260b)

Compound 260b was prepared according to the procedure reported in step-2 of scheme 1, from ethyl 2-(2-((5-bromo- 1-cyclopropyl-1H-indazol-3-yl)methoxy)phenyl)acetate (260a) (200 mg, 0.466 mmol) in dioxane (2 mL) and THF (2 mL) using 3-(aminomethyl)phenylboronic acid hydrochloride (1d) (175 mg, 0.932 mmol), 2 M solution of $K_3PO_4$ (0.932 mL, 1.863 mmol), tricyclohexylphosphine (26.1 mg, 0.093 mmol) and $Pd_2(dba)_3$ (42.7 mg, 0.047 mmol), $PdCl_2$ (dppf)-$CH_2Cl_2$ adduct (38 mg, 0.047 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-cyclopropyl-1H-indazol-3-yl) methoxy)phenyl)acetate (260b) (150 mg, 71% yield) as a clear oil; MS (ES+): 456.30 (M+1).

Step-3: Preparation of 2-(2-((5-(3-(aminomethyl) phenyl)-1-cyclopropyl-1H-indazol-3-yl)methoxy) phenyl)acetic acid (260c)

Compound 260c was prepared according to the procedure reported in step-3 of scheme 1, from ethyl 2-(2-((5-(3-(aminomethyl)phenyl)-1-cyclopropyl-1H-indazol-3-yl) methoxy)phenyl)acetate (260b) (150 mg, 0.329 mmol) in THF (2 mL) and MeOH (2 mL) using a solution of lithium hydroxide hydrate (41.5 mg, 0.988 mmol) in water (1 mL) and stirring at RT for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-1-cyclopropyl-1H-indazol-3-yl)methoxy)phenyl)acetic acid (260c) (60 mg, 43% yield) HCl salt as a white solid; $^1H$ NMR (300 MHz, DMSO-$d_6$) δ 8.40 (s, 3H, $D_2O$ exchangeable), 8.09 (s, 1H), 7.88 (s, 1H), 7.81 (d, J=1.2 Hz, 2H), 7.74 (dt, J=7.5, 1.7 Hz, 1H), 7.51 (t, J=7.6 Hz, 1H), 7.45 (d, J=7.8 Hz, 1H), 7.29-7.23 (m, 2H), 7.20 (d, J=7.4 Hz, 1H), 6.98-6.87 (m, 1H), 5.42 (s, 2H), 4.16-4.06 (m, 2H), 3.86-3.74 (m, 1H), 3.52 (s, 2H), 1.20-1.11 (m, 4H); MS (ES+): 428.20 (M+1); (ES−): 426.10 (M−1); Analysis calculated for $C_{26}H_{25}N_3O_3 \cdot 1.2HCl \cdot 0.25H_2O$: C, 65.64; H, 5.66; Cl, 8.94; N, 8.83. Found: C, 65.48; H, 5.52; Cl, 8.70; N, 8.85.

Scheme 261

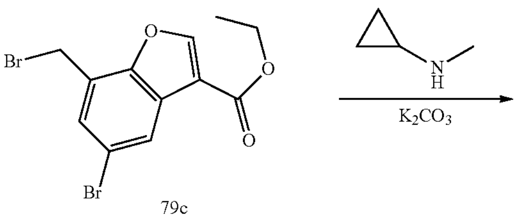

79c

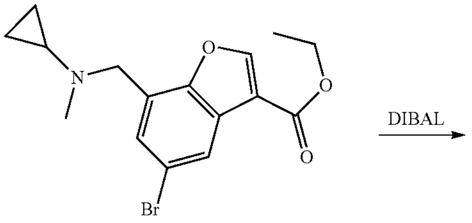

261a

-continued

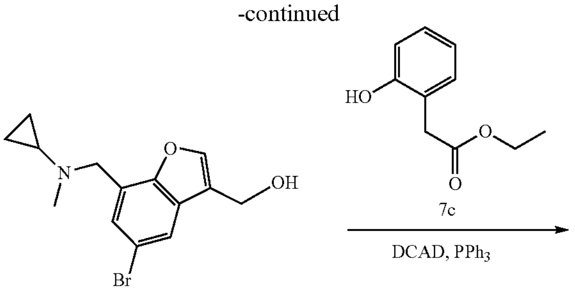

261b

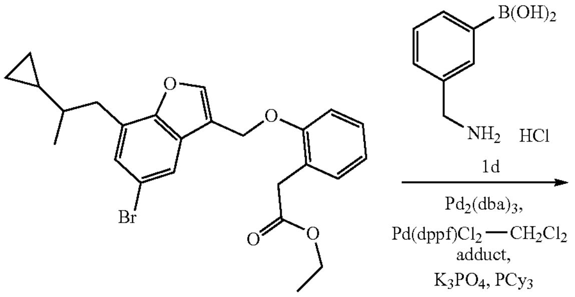

261c

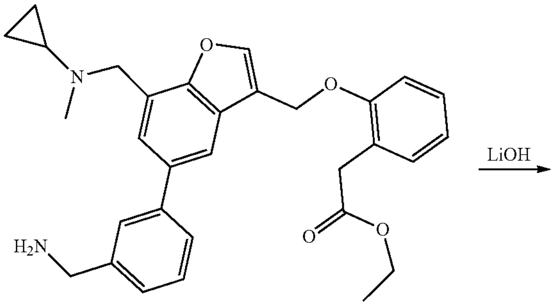

261d

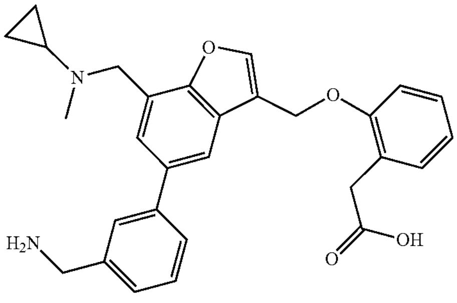

261e

Preparation of 2-(2-((5-(3-(aminomethyl)phenyl)-7-((cyclopropyl(methyl)amino)methyl)benzofuran-3-yl)methoxy)phenyl)acetic acid (261e)

Step-1: Preparation of ethyl 5-bromo-7-((cyclopropyl(methyl)amino)methyl)benzofuran-3-carboxylate (261a)

Compound 261a was prepared according to the procedure reported in step-3 of scheme 7, from ethyl 5-bromo-7-(bromomethyl)benzofuran-3-carboxylate (79c) (500 mg, 1.381 mmol) in DMF (5 mL) using N-methylcyclopropanamine (196 mg, 2.76 mmol; CAS #5163-20-2) potassium carbonate (573 mg, 4.14 mmol) and stirring at RT for 15 h. This gave after workup and purification using flash column chromatography [silica gel (24 g), eluting with DMA-80 in DCM from 0-50%] ethyl 5-bromo-7-((cyclopropyl(methyl)amino)methyl)benzofuran-3-carboxylate (261a) (450 mg, 93% yield) as a yellow oil; MS (ES+): 352.05 (M+1).

Step-2: Preparation of (5-bromo-7-((cyclopropyl(methyl)amino)methyl)benzofuran-3-yl)methanol (261b)

Compound 261b was prepared according to the procedure reported in step-2 of scheme 69, from ethyl 5-bromo-7-((cyclopropyl(methyl)amino)methyl)benzofuran-3-carboxylate (261a) (450 mg, 1.278 mmol) in THF (10 mL) using 1.0 M solution of DIBAL in THF (3.19 mL, 3.19 mmol) and stirring at −78° C. for 30 min. This gave after work up and purification using flash column chromatography [silica gel (24 g), eluting with DMA-80 in DCM from 0-100%](5-bromo-7-((cyclopropyl(methyl)amino)methyl)benzofuran-3-yl)methanol (261b) (240 mg, 61% yield) as a light yellow oil; $^1$H NMR (300 MHz, DMSO-$d_6$) δ 7.92 (s, 1H), 7.78 (d, J=2.1 Hz, 1H), 7.33 (d, J=2.1 Hz, 1H), 5.25-5.12 (m, 1H), 4.63-4.53 (m, 2H), 3.88 (s, 2H), 2.19 (s, 3H), 1.81-1.71 (m, 1H), 0.45-0.34 (m, 4H); MS (ES+): 310.10 & 312.15 (M+1).

Step-3: Preparation of ethyl 2-(2-((5-bromo-7-((cyclopropyl(methyl)amino)methyl)benzofuran-3-yl)methoxy)phenyl)acetate (261c)

Compound 261c was prepared according to the procedure reported in step-2 of scheme 65, from (5-bromo-7-((cyclopropyl(methyl)amino)methyl)benzofuran-3-yl)methanol (261b) (240 mg, 0.774 mmol) in DCM (10 mL) using triphenylphosphine (244 mg, 0.928 mmol), ethyl 2-(2-hydroxyphenyl)acetate (7c) (146 mg, 0.812 mmol) in DCM (5 mL), a solution of DCAD (341 mg, 0.928 mmol) in DCM (5 mL) and stirring at RT for 60 min. This gave after workup and purification using flash column chromatography [silica gel (24 g), eluting with DMA80 in DCM from 0-60%] ethyl 2-(2-((5-bromo-7-((cyclopropyl(methyl)amino)methyl)benzofuran-3-yl)methoxy)phenyl)acetate (261c) (350 mg, 96% yield) as a white solid; MS (ES+): 472.10 & 474.10 (M+1); (ES−): 470.10 & 472.10 (M−1).

Step-4: Preparation of ethyl 2-(2-((5-(3-(aminomethyl)phenyl)-7-((cyclopropyl(methyl)amino)methyl)benzofuran-3-yl)methoxy)phenyl)acetate (261d)

Compound 261d was prepared according to the procedure reported in step-2 of scheme 1, from ethyl 2-(2-((5-bromo-7-((cyclopropyl(methyl)amino)methyl)benzofuran-3-yl)methoxy)phenyl)acetate (261c) (350 mg, 0.741 mmol) in dioxane (2 mL) and THF (2 ML) using 3-(aminomethyl)phenylboronic acid hydrochloride (1d) (278 mg, 1.482 mmol), 2 M solution of $K_3PO_4$ (1.482 mL, 2.96 mmol), tricyclohexylphosphine (41.6 mg, 0.148 mmol), $Pd_2(dba)_3$ (67.8 mg, 0.074 mmol), $PdCl_2(dppf)$-$CH_2Cl_2$ adduct (60.5 mg, 0.074 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-7-((cyclopropyl(methyl)amino)methyl)benzofuran-3-yl)methoxy)phenyl)acetate (261d) (200 mg, 54% yield) as a clear oil; MS (ES+): 499.25 (M+1); (ES−): 497.20 (M−1).

Step-5: Preparation of 2-(2-((5-(3-(aminomethyl)phenyl)-7-((cyclopropyl(methyl)amino)methyl)benzofuran-3-yl)methoxy)phenyl)acetic acid (261e)

Compound 261e was prepared according to the procedure reported in step-3 of scheme 1, from ethyl 2-(2-((5-(3-(aminomethyl)phenyl)-7-((cyclopropyl(methyl)amino)methyl)benzofuran-3-yl)methoxy)phenyl)acetate (261d) (200 mg, 0.401 mmol) in THF (2 mL) and MeOH (2 mL) using a solution of lithium hydroxide hydrate (67.3 mg, 1.604 mmol) in water (1 mL) and stirring at 50° C. for 3 h. This gave after workup and purification using reverse phase column chromatography [C18 column (50 g), eluting with ACN in water (containing 0.1% HCl) from 0-100%] 2-(2-((5-(3-(aminomethyl)phenyl)-7-((cyclopropyl(methyl)amino)methyl)benzofuran-3-yl)methoxy)phenyl)acetic acid (261e) (55 mg, 29% yield) HCl salt as a white solid; $^1$H NMR (300 MHz, DMSO-$d_6$) δ 12.18 (s, 1H, $D_2O$ exchangeable), 11.09 (s, 1H, $D_2O$ exchangeable), 8.51 (s, 3H, $D_2O$ exchangeable), 8.22 (s, 1H), 8.11 (d, J=8.1 Hz, 2H), 8.01 (s, 1H), 7.83 (d, J=7.2 Hz, 1H), 7.59-7.45 (m, 2H), 7.28 (td, J=7.7, 7.1, 1.7 Hz, 1H), 7.22 (dd, J=7.2, 1.6 Hz, 2H), 6.98-6.88 (m, 1H), 5.35 (s, 2H), 4.74 (s, 2H), 4.22-4.00 (m, 2H), 3.55 (s, 2H), 3.05-2.91 (m, 1H), 2.85 (s, 3H), 1.17-0.63 (m, 4H); MS (ES+): 471.20 (M+1); (ES−): 469.20 (M−1); Analysis calculated for $C_{29}H_{30}N_2O_4 \cdot 2HCl \cdot 1.75H_2O$: C, 60.58; H, 6.22; Cl, 12.33; N, 4.87. Found: C, 60.79; H, 6.16; Cl, 12.57; N, 5.03.

Scheme 262

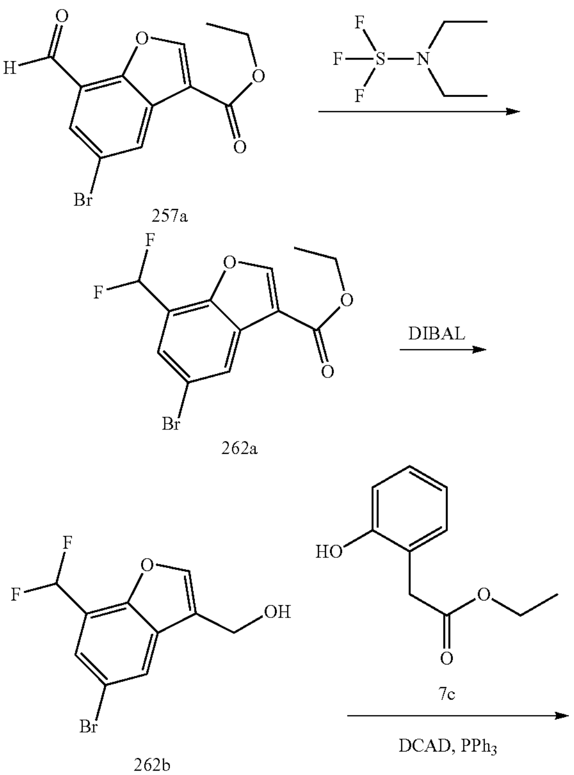

257a

262a

7c

262b

-continued

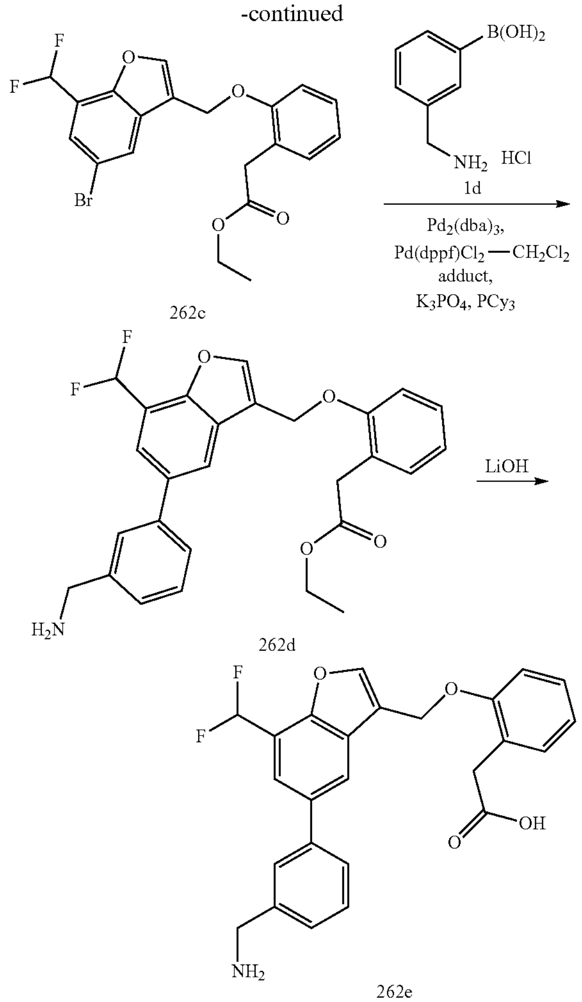

262c

262d

262e

Preparation of 2-(2-((5-(3-(aminomethyl)phenyl)-7-(difluoromethyl)benzofuran-3-yl)methoxy)phenyl) acetic acid (262e)

Step-1: Preparation of ethyl 5-bromo-7-(difluoromethyl)benzofuran-3-carboxylate (262a)

Compound 262a was prepared according to the procedure reported in step-1 of scheme 139, from ethyl 5-bromo-7-formylbenzofuran-3-carboxylate (257a) (750 mg, 2.52 mmol) in DCM (20 mL) using diethylamino sulfur trifluoride (DAST) (0.434 mL, 3.28 mmol) and stirring at RT for 3 h. This gave after work up and purification using flash column chromatography [silica gel, eluting with EtOAc in hexane from 0-100%] ethyl 5-bromo-7-(difluoromethyl) benzofuran-3-carboxylate (262a) (520 mg, 65% yield) as a white solid; MS (ES+): 318.20 (M+1).

Step-2: Preparation of (5-bromo-7-(difluoromethyl) benzofuran-3-yl)methanol (262b)

Compound 262b was prepared according to the procedure reported in step-2 of scheme 69, from ethyl 5-bromo-7-(difluoromethyl)benzofuran-3-carboxylate (262a) (520 mg, 1.630 mmol) in THF (10 mL using 1.0 M solution of DIBAL in THF (4.07 mL, 4.07 mmol) and stirring at −78° C. for 30 min. This gave after work up and purification using flash column chromatography [silica gel (24 g), eluting with DMA-80 in DCM from 0-100%] (5-bromo-7-(difluoromethyl)benzofuran-3-yl)methanol (262b) (230 mg, 51% yield) as a light yellow oil; $^1$H NMR (300 MHz, DMSO-$d_6$) δ 8.10 (dt, J=2.2, 1.2 Hz, 1H), 8.07 (d, J=1.1 Hz, 1H), 7.68 (q, J=1.5 Hz, 1H), 7.44-7.11 (m, 1H), 5.30 (t, J=5.6 Hz, 1H), 4.63 (dd, J=5.6, 1.1 Hz, 2H); $^{19}$F NMR (282 MHz, DMSO-$d_6$) δ −110.41--115.12 (m).

Step-3: Preparation of ethyl 2-(2-((5-bromo-7-(difluoromethyl)benzofuran-3-yl)methoxy)phenyl)acetate (262c)

Compound 262c was prepared according to the procedure reported in step-2 of scheme 65, from (5-bromo-7-(difluoromethyl)benzofuran-3-yl)methanol (262b) (230 mg, 0.830 mmol) in DCM (10 mL) using triphenylphosphine (261 mg, 0.996 mmol), ethyl 2-(2-hydroxyphenyl)acetate (7c) (157 mg, 0.872 mmol) in DCM (5 mL) a solution of DCAD (366 mg, 0.996 mmol) in DCM (5 mL) and stirring at RT for 60 min. This gave after workup and purification using flash column chromatography [silica gel (24 g), eluting with EtOAc in Hexane from 0-80%] ethyl 2-(2-((5-bromo-7-(difluoromethyl)benzofuran-3-yl)methoxy)phenyl)acetate (262c) (0.2 g, 55% yield) as a white solid; MS (ES+): 439.00 (M+1).

Step-4: Preparation of ethyl 2-(2-((5-(3-(aminomethyl)phenyl)-7-(difluoromethyl)benzofuran-3-yl) methoxy)phenyl)acetate (262d)

Compound 262d was prepared according to the procedure reported in step-2 of scheme 1, from ethyl 2-(2-((5-bromo-7-(difluoromethyl)benzofuran-3-yl)methoxy)phenyl)acetate (262c) (200 mg, 0.455 mmol) in dioxane (2 mL) and THF (2 ML) using 3-(aminomethyl)phenylboronic acid hydrochloride (1d) (171 mg, 0.911 mmol), 2 M solution of $K_3PO_4$ (0.911 mL, 1.821 mmol), tricyclohexylphosphine (25.5 mg, 0.091 mmol), $Pd_2(dba)_3$ (41.7 mg, 0.046 mmol), $PdCl_2$(dppf)-$CH_2Cl_2$ adduct (37.2 mg, 0.046 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-7-(difluoromethyl)benzofuran-3-yl) methoxy)phenyl)acetate (262d) (150 mg, 71% yield) as a clear oil; MS (ES+): 466.20 (M+1); MS (ES−): 464.10 (M−1).

Step-5: Preparation of 2-(2-((5-(3-(aminomethyl) phenyl)-7-(difluoromethyl)benzofuran-3-yl) methoxy)phenyl)acetic acid (262e)

Compound 262e was prepared according to the procedure reported in step-3 of scheme 1, from ethyl 2-(2-((5-(3-(aminomethyl)phenyl)-7-(difluoromethyl)benzofuran-3-yl) methoxy)phenyl)acetate (262d) (150 mg, 0.322 mmol) in THF (2 mL) and MeOH (2 mL) using a solution of lithium hydroxide hydrate (54.1 mg, 1.289 mmol) in water (1 mL) and heating at 50° C. for 3 h. This gave after workup and purification using reverse phase column chromatography [C18 column (50 g), eluting with ACN in water (containing 0.1% HCl) from 0-100%] 2-(2-((5-(3-(aminomethyl)phenyl)-7-(difluoromethyl)benzofuran-3-yl)methoxy)phenyl) acetic acid (262e) (35 mg, 25% yield) HCl salt as a white solid; $^1$H NMR (300 MHz, DMSO-$d_6$) δ 12.11 (s, 1H, $D_2O$ exchangeable), 8.40 (s, 2H, $D_2O$ exchangeable), 8.26 (s, 1H), 8.21 (s, 1H), 7.91 (d, J=11.5 Hz, 2H), 7.83-7.72 (m, 1H), 7.67-7.41 (m, 3H), 7.28 (td, J=7.3, 1.6 Hz, 1H), 7.25-7.13 (m, 2H), 6.98-6.88 (m, 1H), 5.36 (s, 2H), 4.12 (s, 2H), 3.54 (s, 2H); $^{19}$F NMR (282 MHz, DMSO-$d_6$) δ −112.01 (d, J=54.6 Hz); MS (ES+): 438.15 (M+1); (ES−): 436.10 (M−1); Analysis calculated for $C_{25}H_{21}F_2NO_4$·HCl·0.25$H_2O$: C, 62.77; H, 4.74; Cl, 7.41; N, 2.93. Found: C, 62.61; H, 4.77; Cl, 7.15; N, 2.92.
Scheme 263
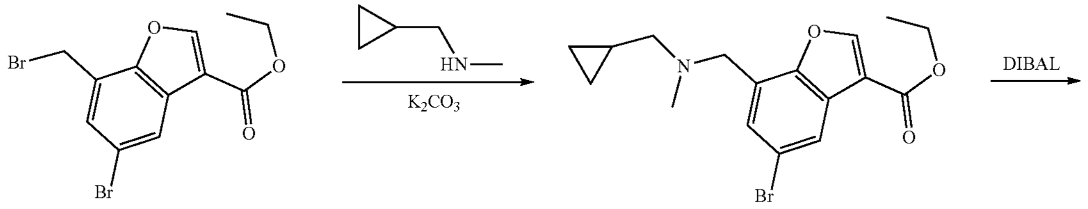
79c 263a
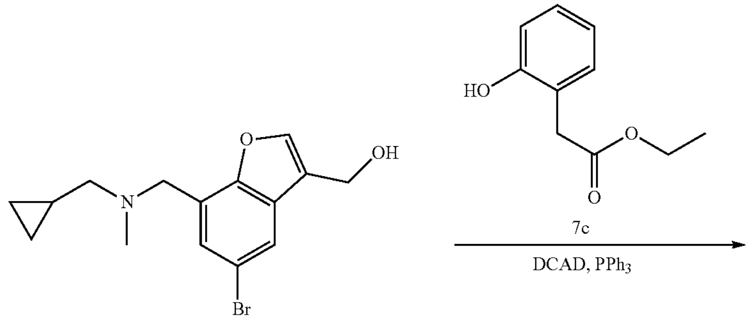
263b
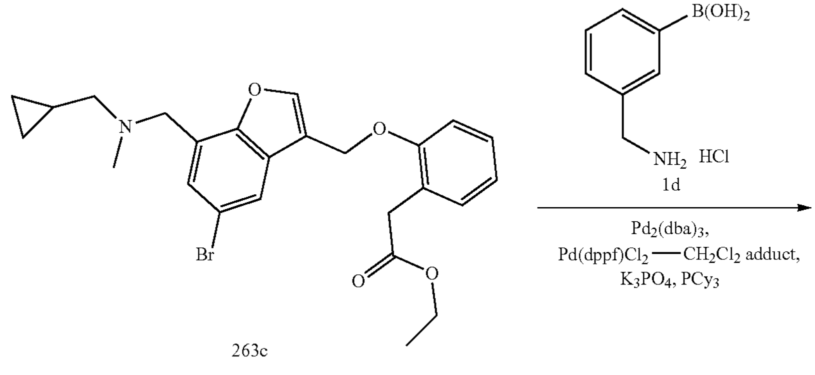
263c
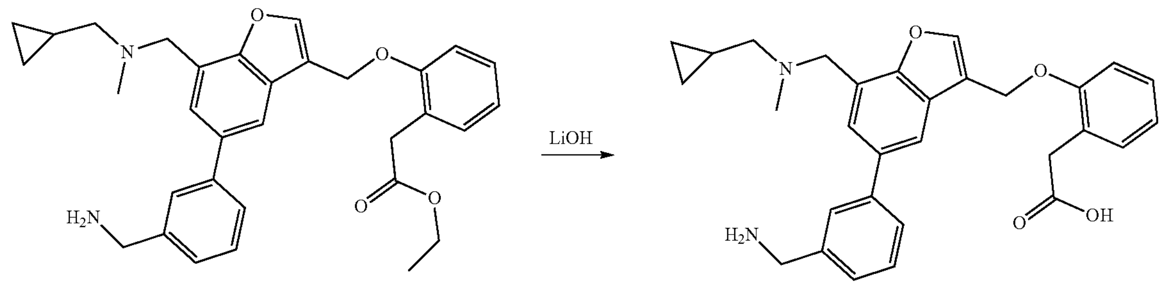
263d 263e

Preparation of 2-(2-((5-(3-(aminomethyl)phenyl)-7-(((cyclopropylmethyl)(methyl)amino)methyl)benzofuran-3-yl)methoxy)phenyl)acetic acid (263e)

Step-1: Preparation of ethyl 5-bromo-7-(((cyclopropylmethyl)(methyl)amino)methyl)benzofuran-3-carboxylate (263a)

Compound 263a was prepared according to the procedure reported in step-3 of scheme 7, from ethyl 5-bromo-7-(bromomethyl)benzofuran-3-carboxylate (79c) (500 mg, 1.381 mmol) in DMF (5 mL) using 1-cyclopropyl-N-methylmethanamine (235 mg, 2.76 mmol; CAS #18977-45-2), potassium carbonate (573 mg, 4.14 mmol) and stirring at RT for 15 h. This gave after workup and purification using flash column chromatography [silica gel (24 g), eluting with DMA-80 in DCM from 0-50%] ethyl 5-bromo-7-(((cyclopropylmethyl)(methyl)amino)methyl)benzofuran-3-carboxylate (263a) (380 mg, 75% yield) as a yellow oil; MS (ES+): 366.10 (M+1).

Step-2: Preparation of (5-bromo-7-(((cyclopropylmethyl)(methyl)amino)methyl)benzofuran-3-yl)methanol (263b)

Compound 263b was prepared according to the procedure reported in step-2 of scheme 69, from ethyl 5-bromo-7-(((cyclopropylmethyl)(methyl)amino)methyl)benzofuran-3-carboxylate (263a) (380 mg, 1.038 mmol) in THF (10 mL) using 1.0 M solution of DIBAL in THE (2.59 mL, 2.59 mmol) and stirring at −78° C. for 30 min. This gave after work up and purification using flash column chromatography [silica gel (24 g), eluting with DMA80 in DCM from 0-100%] (5-bromo-7-(((cyclopropylmethyl)(methyl)amino)methyl)benzofuran-3-yl)methanol (263b) (150 mg, 45% yield) as a light yellow oil; MS (ES+): 324.10 & 326.10 (M+1).

Step-3: Preparation of ethyl 2-(2-((5-bromo-7-(((cyclopropylmethyl)(methyl)amino)methyl)benzofuran-3-yl)methoxy)phenyl)acetate (263c)

Compound 263c was prepared according to the procedure reported in step-2 of scheme 65, from (5-bromo-7-(((cyclopropylmethyl)(methyl)amino)methyl)benzofuran-3-yl)methanol (263b) (150 mg, 0.463 mmol) in DCM (10 mL) using triphenylphosphine (146 mg, 0.555 mmol), ethyl 2-(2-hydroxyphenyl)acetate (7c) (88 mg, 0.486 mmol) a solution of DCAD (204 mg, 0.555 mmol) in DCM (5 mL) and stirring at RT for 60 min. This gave after workup and purification using flash column chromatography [silica gel (24 g), eluting with DMA-80 in DCM from 0-60%] ethyl 2-(2-((5-bromo-7-(((cyclopropylmethyl)(methyl)amino)methyl)benzofuran-3-yl)methoxy)phenyl)acetate (263c) (200 mg, 89% yield) as a white solid; MS (ES+): 486.10 & 488.10 (M+1); (ES−): 484.10 & 486.10 (M−1).

Step-4: Preparation of ethyl 2-(2-((5-(3-(aminomethyl)phenyl)-7-(((cyclopropylmethyl)(methyl)amino)methyl)benzofuran-3-yl)methoxy)phenyl)acetate (263d)

Compound 263d was prepared according to the procedure reported in step-2 of scheme 1, from ethyl 2-(2-((5-bromo-7-(((cyclopropylmethyl)(methyl)amino)methyl)benzofuran-3-yl)methoxy)phenyl)acetate (263c) (200 mg, 0.411 mmol) in dioxane (2 mL) and THF (2 ML) using 3-(aminomethyl)phenylboronic acid hydrochloride (1d) (154 mg, 0.822 mmol), 2 M solution of $K_3PO_4$ (0.822 mL, 1.645 mmol), tricyclohexylphosphine (23.06 mg, 0.082 mmol), $Pd_2(dba)_3$ (37.7 mg, 0.041 mmol), $PdCl_2(dppf)$-$CH_2Cl_2$ adduct (33.6 mg, 0.041 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-7-(((cyclopropylmethyl)(methyl)amino)methyl)benzofuran-3-yl)methoxy)phenyl)acetate (263d) (60 mg, 29% yield) as a clear oil; MS (ES+): 513.30 (M+1); (ES−): 511.20 (M−1).

Step-5: Preparation of 2-(2-((5-(3-(aminomethyl)phenyl)-7-(((cyclopropylmethyl)(methyl)amino)methyl)benzofuran-3-yl)methoxy)phenyl)acetic acid (263e)

Compound 263e was prepared according to the procedure reported in step-3 of scheme 1, from ethyl 2-(2-((5-(3-(aminomethyl)phenyl)-7-(((cyclopropylmethyl)(methyl)amino)methyl)benzofuran-3-yl)methoxy)phenyl)acetate (263d) (60 mg, 0.117 mmol) in THF (2 mL) and MeOH (2 mL) using a solution of lithium hydroxide hydrate (29.5 mg, 0.702 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-7-(((cyclopropylmethyl)(methyl)amino)methyl)benzofuran-3-yl)methoxy)phenyl)acetic acid (263e) (20 mg, 35% yield) HCl salt as a white solid; $^1H$ NMR (300 MHz, DMSO-$d_6$) δ 10.84 (s, 1H, $D_2O$ exchangeable), 8.48 (s, 3H, $D_2O$ exchangeable), 8.24 (s, 1H), 8.17-8.10 (m, 2H), 8.01 (s, 1H), 7.84 (d, J=7.5 Hz, 1H), 7.58-7.46 (m, 2H), 7.32-7.25 (m, 1H), 7.25-7.17 (m, 2H), 6.97-6.89 (m, 1H), 5.35 (s, 2H), 4.84-4.51 (m, 2H), 4.16-4.06 (m, 2H), 3.55 (s, 2H), 3.29-2.91 (m, 2H), 2.79 (d, J=4.7 Hz, 3H), 1.34-1.18 (m, 1H), 0.71-0.62 (m, 2H), 0.51-0.36 (m, 2H); MS (ES+): 485.25 (M+1); MS (ES−): 483.20 (M−1).

Scheme 264

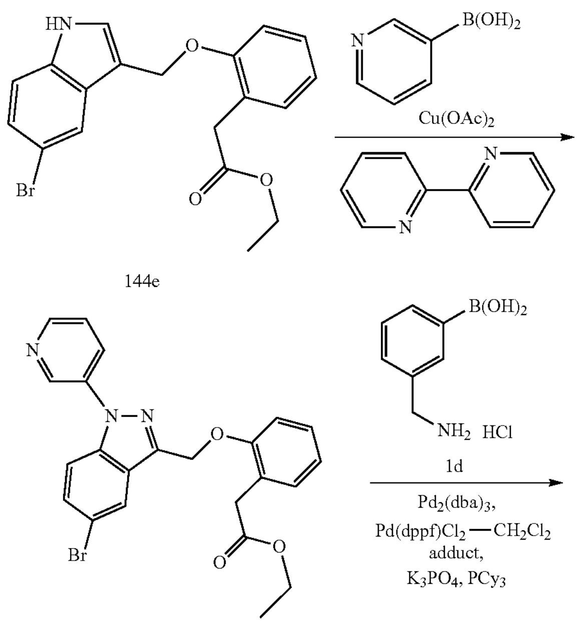

144e

264a

-continued

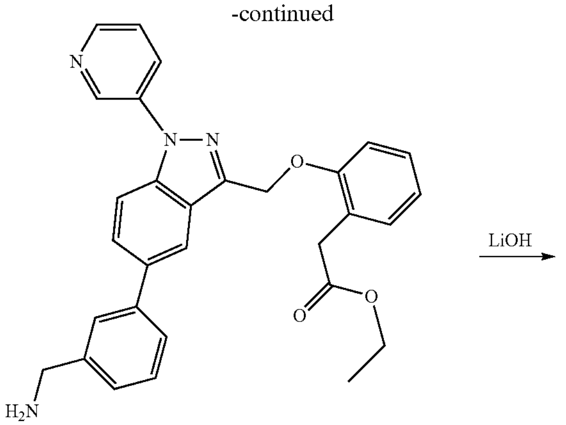

264b

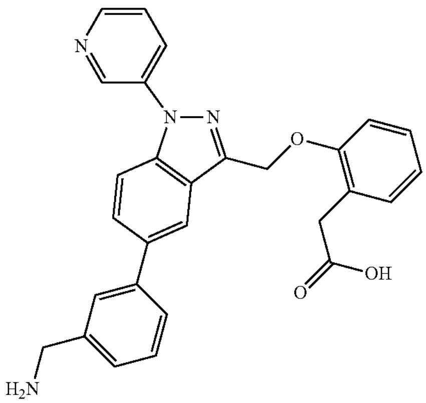

264c

Preparation of 2-(2-((5-(3-(aminomethyl)phenyl)-1-(pyridin-3-yl)-1H-indazol-3-yl)methoxy)phenyl)acetic acid (264c)

Step-1: Preparation of ethyl 2-(2-((5-bromo-1-(pyridin-3-yl)-1H-indazol-3-yl)methoxy)phenyl)acetate (264a)

Compound 264a was prepared according to the procedure reported in step-2 of scheme 1, from ethyl 2-(2-((5-bromo-1H-indazol-3-yl)methoxy)phenyl)acetate (144e) (500 mg, 1.285 mmol) in DCE (8 mL) using pyridin-3-ylboronic acid (395 mg, 3.21 mmol), 2,2'-bipyridine (201 mg, 1.285 mmol), copper (II) acetate (233 mg, 1.285 mmol), potassium carbonate (355 mg, 2.57 mmol) and heating at 70° C. for 3 h. This gave after workup and purification using flash column chromatography [silica gel (24 g), eluting with DMA-80 in DCM from 0-50%]ethyl 2-(2-((5-bromo-1-(pyridin-3-yl)-1H-indazol-3-yl)methoxy)phenyl)acetate (264a) (250 mg, 42% yield) as a clear oil; MS (ES+): 466.10 & 468.05 (M+1); MS (ES−): 464.90 (M−1).

Step-2: Preparation of ethyl 2-(2-((5-(3-(aminomethyl)phenyl)-1-(pyridin-3-yl)-1H-indazol-3-yl)methoxy)phenyl)acetate (264b)

Compound 264b was prepared according to the procedure reported in step-2 of scheme 1, from ethyl 2-(2-((5-bromo-1-(pyridin-3-yl)-1H-indazol-3-yl)methoxy)phenyl)acetate (264a) (250 mg, 0.536 mmol) in dioxane (2 mL) and THF (2 mL) using 3-(aminomethyl)phenylboronic acid hydrochloride (1d) (201 mg, 1.072 mmol), 2 M solution of $K_3PO_4$ (1.072 mL, 2.144 mmol), tricyclohexylphosphine (30.1 mg, 0.107 mmol), $Pd_2(dba)_3$ (49.1 mg, 0.054 mmol), $PdCl_2$(dppf)-$CH_2Cl_2$ adduct (43.8 mg, 0.054 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-(pyridin-3-yl)-1H-indazol-3-yl)methoxy)phenyl)acetate (264b) (100 mg, 38% yield) as a clear oil; MS (ES+): 493.20 (M+1).

Step-3: Preparation of 2-(2-((5-(3-(aminomethyl)phenyl)-1-(pyridin-3-yl)-1H-indazol-3-yl)methoxy)phenyl)acetic acid (264c)

Compound 264c was prepared according to the procedure reported in step-3 of scheme 1, from ethyl 2-(2-((5-(3-(aminomethyl)phenyl)-1-(pyridin-3-yl)-1H-indazol-3-yl)methoxy)phenyl)acetate (264b) (100 mg, 0.203 mmol) in THF (6 mL) and MeOH (2 mL) using a solution of lithium hydroxide hydrate (51.1 mg, 1.218 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-1-(pyridin-3-yl)-1H-indazol-3-yl)methoxy)phenyl)acetic acid (264c) (55 mg, 58% yield) HCl salt as a white solid; $^1H$ NMR (300 MHz, DMSO-$d_6$) δ 9.17 (d, J=2.6 Hz, 1H), 8.69 (dd, J=4.9, 1.4 Hz, 1H), 8.53-8.37 (m, 4H, 3H $D_2O$ exchangeable), 8.28 (d, J=1.6 Hz, 1H), 8.09 (d, J=8.9 Hz, 1H), 7.99-7.89 (m, 2H), 7.84-7.72 (m, 2H), 7.55 (t, J=7.5 Hz, 1H), 7.49 (dt, J=7.7, 1.6 Hz, 1H), 7.37-7.25 (m, 2H), 7.23 (dd, J=7.5, 1.5 Hz, 1H), 6.95 (td, J=7.0, 1.9 Hz, 1H), 5.60 (s, 2H), 4.14-4.10 (m, 2H), 3.57 (s, 2H); MS (ES+): 465.20 (M+1); MS (ES−): 463.20 (M−1); Analysis calculated for $C_{28}H_{24}N_4O_3 \cdot 2HCl \cdot 2H_2O$: C, 58.64; H, 5.27; N, 9.77. Found: C, 58.30; H, 5.27; N, 9.64.

Scheme 265

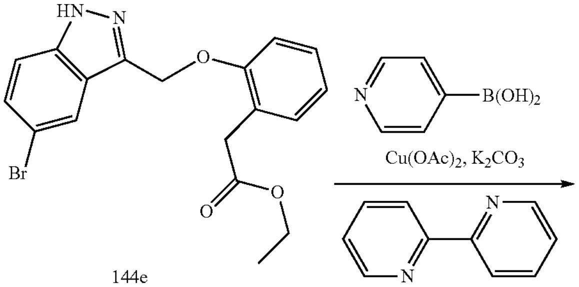

144e

-continued

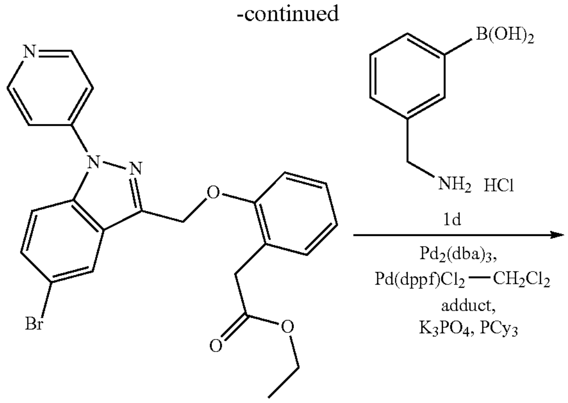

265a

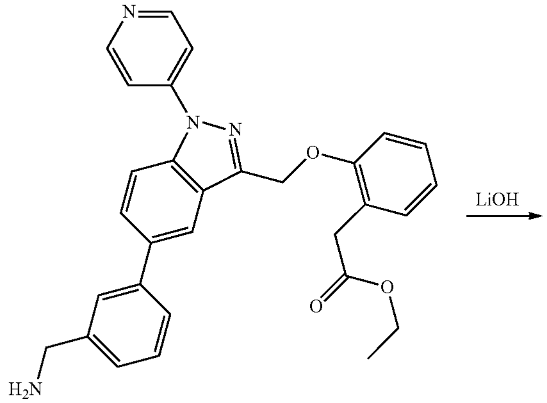

265b

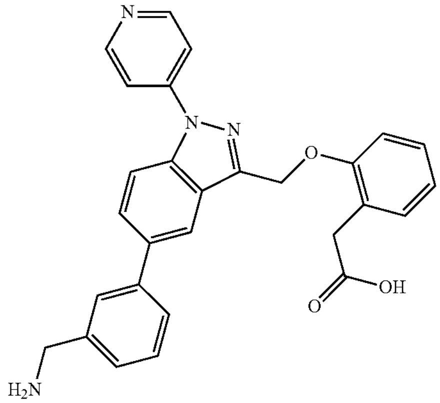

265c

Preparation of 2-(2-((5-(3-(aminomethyl)phenyl)-1-(pyridin-4-yl)-1H-indazol-3-yl)methoxy)phenyl) acetic acid (265c)

Step-1: Preparation of ethyl 2-(2-((5-bromo-1-(pyridin-4-yl)-1H-indazol-3-yl)methoxy)phenyl)acetate (265a)

Compound 265a was prepared according to the procedure reported in step-2 of scheme 1, from ethyl 2-(2-((5-bromo-1H-indazol-3-yl)methoxy)phenyl)acetate (144e) (500 mg, 1.285 mmol) in DCE (8 mL) using pyridin-4-ylboronic acid (395 mg, 3.21 mmol), 2,2'-bipyridine (201 mg, 1.285 mmol), copper (II) acetate (233 mg, 1.285 mmol), potassium carbonate (355 mg, 2.57 mmol) and heating at 70° C. for 6 h. This gave after workup and purification using flash column chromatography [silica gel (24 g), eluting with DMA-80 in DCM from 0-50%]ethyl 2-(2-((5-bromo-1-(pyridin-4-yl)-1H-indazol-3-yl)methoxy)phenyl)acetate (265a) (330 mg, 55% yield) as a clear oil; MS (ES+): 466.10 & 468.10 (M+1); (ES−): 464.95 (M−1).

Step-2: Preparation of ethyl 2-(2-((5-(3-(aminomethyl)phenyl)-1-(pyridin-4-yl)-1H-indazol-3-yl) methoxy)phenyl)acetate (265b)

Compound 265b was prepared according to the procedure reported in step-2 of scheme 1, from ethyl 2-(2-((5-bromo-1-(pyridin-4-yl)-1H-indazol-3-yl)methoxy)phenyl)acetate (265a) (330 mg, 0.708 mmol) in dioxane (2 mL) and THF (2 mL) using 3-(aminomethyl)phenylboronic acid hydrochloride (1d) (265 mg, 1.415 mmol), 2 M solution of $K_3PO_4$ (1.415 mL, 2.83 mmol), tricyclohexylphosphine (39.7 mg, 0.142 mmol), $Pd_2(dba)_3$ (64.8 mg, 0.071 mmol), $PdCl_2$(dppf)-$CH_2Cl_2$ adduct (43.8 mg, 0.054 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-(pyridin-4-yl)-1H-indazol-3-yl) methoxy)phenyl)acetate (265b) (150 mg, 43% yield) as a clear oil; MS (ES+): 493.30 (M+1).

Step-3: Preparation of 2-(2-((5-(3-(aminomethyl) phenyl)-1-(pyridin-4-yl)-1H-indazol-3-yl)methoxy) phenyl)acetic acid (265c)

Compound 265c was prepared according to the procedure reported in step-3 of scheme 1, from ethyl 2-(2-((5-(3-(aminomethyl)phenyl)-1-(pyridin-4-yl)-1H-indazol-3-yl) methoxy)phenyl)acetate (265b) (150 mg, 0.305 mmol) in THF (2 mL) and MeOH (2 mL) using a solution of lithium hydroxide hydrate (77 mg, 1.827 mmol) in water (1 mL) and stirring at RT for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-1-(pyridin-4-yl)-1H-indazol-3-yl)methoxy)phenyl)acetic acid (265c) (85 mg, 60% yield) HCl salt as a white solid; $^1$H NMR (300 MHz, DMSO-$d_6$) δ 8.96-8.87 (m, 2H), 8.48 (s, 2H, $D_2O$ exchangeable), 8.46-8.40 (m, 2H), 8.40-8.35 (m, 2H), 8.09 (dd, J=8.9, 1.8 Hz, 1H), 8.00 (s, 1H), 7.84 (dt, J=7.6, 1.7 Hz, 1H), 7.61-7.48 (m, 2H), 7.34-7.28 (m, 2H), 7.28-7.19 (m, 1H), 6.96 (ddd, J=7.8, 5.6, 2.8 Hz, 1H), 5.65 (s, 2H), 4.17-4.09 (m, 2H), 3.58 (s, 2H); MS (ES+): 465.20 (M+1); MS (ES−): 463.10 (M−1); Analysis calculated for $C_{28}H_{24}N_4O_3 \cdot 2HCl \cdot 2.5H_2O$: C, 57.74; H, 5.36; Cl, 12.17; N, 9.62. Found: C, 57.88; H, 5.19; Cl, 11.90; N, 9.62.

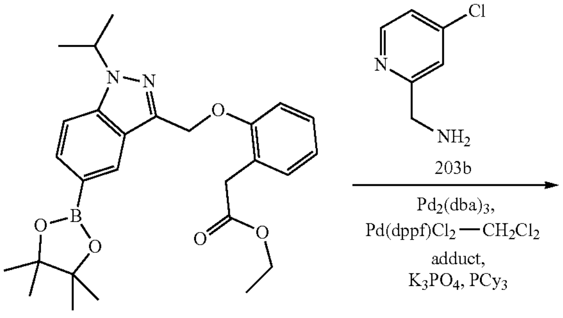

243c

-continued

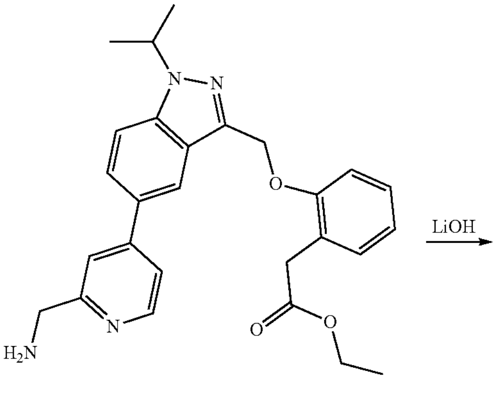

266a

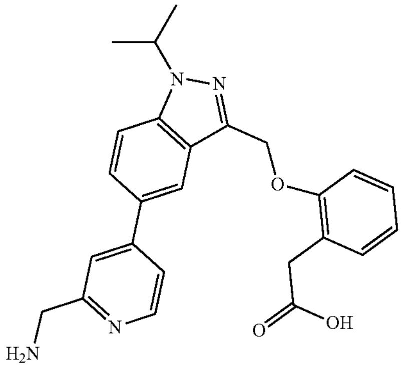

266b

Preparation of 2-(2-((5-(2-(aminomethyl)pyridin-4-yl)-1-isopropyl-1H-indazol-3-yl)methoxy)phenyl) acetic acid (266b)

Step-1: Preparation of ethyl 2-(2-((5-(2-(aminomethyl)pyridin-4-yl)-1-isopropyl-1H-indazol-3-yl) methoxy)phenyl)acetate (266a)

Compound 266a was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (3 mL) and THF (3 mL) using (4-chloropyridin-2-yl)methanamine (203b) (119 mg, 0.836 mmol), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2(dppf)$-$CH_2Cl_2$ adduct (34.1 mg, 0.042 mmol) and heating at 100° C. for 2 h. This gave after workup and purification using flash column chromatography [silica gel (24 g), eluting with DMA-80 in DCM from 0-70%] ethyl 2-(2-((5-(2-(aminomethyl)pyridin-4-yl)-1-isopropyl-1H-indazol-3-yl)methoxy)phenyl)acetate (266a) (150 mg, 0.327 mmol, 78% yield) as a clear oil; $^1$H NMR (300 MHz, DMSO-$d_6$) δ 8.76-8.25 (m, 1H), 8.25-7.95 (m, 1H), 7.94-7.69 (m, 2H), 7.69-7.46 (m, 1H), 7.47-7.07 (m, 4H), 6.98-6.84 (m, 1H), 5.46 (d, J=8.3 Hz, 2H), 5.16-4.76 (m, 1H), 4.05-3.72 (m, 2H), 3.67 (p, J=6.6, 6.1 Hz, 2H), 3.57-3.49 (m, 2H), 1.51 (d, J=6.5 Hz, 6H), 0.75 (dt, J=15.8, 7.2 Hz, 3H); MS (ES+): 459.20 (M+1).

Step-2: Preparation of 2-(2-((5-(2-(aminomethyl) pyridin-4-yl)-1-isopropyl-1H-indazol-3-yl)methoxy) phenyl)acetic acid (266b)

Compound 266b was prepared according to the procedure reported in step-3 of scheme 1, from ethyl 2-(2-((5-(2-(aminomethyl)pyridin-4-yl)-1-isopropyl-1H-indazol-3-yl) methoxy)phenyl)acetate (266a) (150 mg, 0.327 mmol) in THF (2 mL) and MeOH (2 mL) using a solution of lithium hydroxide hydrate (82 mg, 1.963 mmol) in water (1 mL) and heating at 50° C. for 1 h. This gave after workup and purification using reverse phase column chromatography [C18 column (50 g), eluting with ACN in water (containing 0.1% HCl) from 0-100%] 2-(2-((5-(2-(aminomethyl)pyridin-4-yl)-1-isopropyl-1H-indazol-3-yl)methoxy)phenyl) acetic acid (266b) (45 mg, 32% yield) HCl salt as a white solid; $^1$H NMR (300 MHz, DMSO-$d_6$) δ 8.84-8.72 (m, 4H, 3H $D_2O$ exchangeable), 8.39 (s, 1H), 8.28 (s, 1H), 8.05 (d, J=5.8 Hz, 1H), 8.01-7.90 (m, 2H), 7.33-7.25 (m, 2H), 7.21 (d, J=7.3 Hz, 1H), 6.98-6.87 (m, 1H), 5.47 (s, 2H), 5.21-4.96 (m, 1H), 4.36 (s, 2H), 3.54 (s, 2H), 1.52 (d, J=6.5 Hz, 6H); MS (ES+): 431.20 (M+1); (ES−): 429.10 (M−1); Analysis calculated for $C_{25}H_{26}N_4O_3 \cdot 2.3HCl \cdot 1.5H_2O$: C, 55.46; H, 5.83; Cl, 15.06; N, 10.35. Found: C, 55.44; H, 5.67; Cl, 15.42; N, 10.45.

Scheme 267

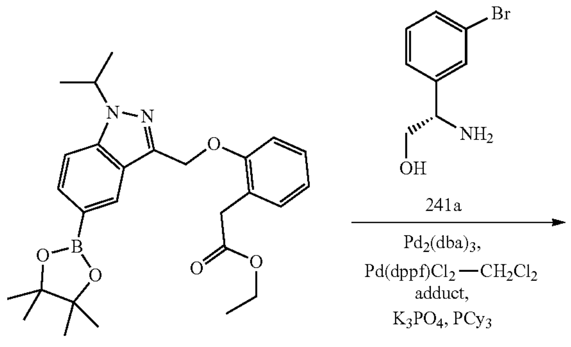

243c

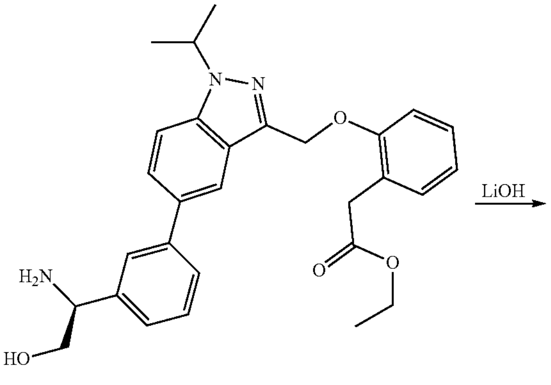

267a

-continued

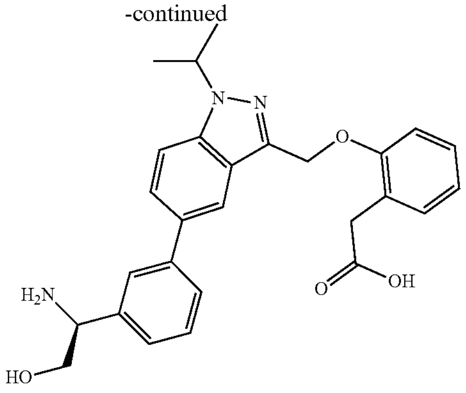

267b

Preparation of (S)-2-(2-((5-(3-(1-amino-2-hydroxyethyl)phenyl)-1-isopropyl-1H-indazol-3-yl)methoxy)phenyl)acetic acid (267b)

Step-1: Preparation of (S)-ethyl 2-(2-((5-(3-(1-amino-2-hydroxyethyl)phenyl)-1-isopropyl-1H-indazol-3-yl)methoxy)phenyl)acetate (267a)

Compound 267a was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (3 mL) and THF (3 mL) using (S)-2-amino-2-(3-bromophenyl)ethanol (241a) (181 mg, 0.836 mmol; CAS #209963-05-3), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2$(dppf)-$CH_2Cl_2$ adduct (34.1 mg, 0.042 mmol) and heating at 100° C. for 2 h. This gave after workup and purification using flash column chromatography [silica gel (24 g), eluting with DMA-80 in DCM from 0-70%](S)-ethyl 2-(2-((5-(3-(1-amino-2-hydroxyethyl)phenyl)-1-isopropyl-1H-indazol-3-yl)methoxy)phenyl)acetate (267a) (160 mg, 78% yield) as a clear oil; MS (ES+): 488.25 (M+1); (ES−): 486.20 (M−1); Optical rotation: $[\alpha]_D$=(+) 32.0 [$CH_3OH$, 0.05].

Step-2: Preparation of (S)-2-(2-((5-(3-(1-amino-2-hydroxyethyl)phenyl)-1-isopropyl-1H-indazol-3-yl)methoxy)phenyl)acetic acid (267b)

Compound 267b was prepared according to the procedure reported in step-3 of scheme 1, from (S)-ethyl 2-(2-((5-(3-(1-amino-2-hydroxyethyl)phenyl)-1-isopropyl-1H-indazol-3-yl)methoxy)phenyl)acetate (267a) (160 mg, 0.328 mmol) in THF (2 mL) and MeOH (2 mL) using a solution of lithium hydroxide hydrate (83 mg, 1.969 mmol) in water (1 mL) and heating at 50° C. for 1 h. This gave after workup and purification using reverse phase column chromatography [C18 column (50 g), eluting with ACN in water (containing 0.1% HCl) from 0-100%](S)-2-(2-((5-(3-(1-amino-2-hydroxyethyl)phenyl)-1-isopropyl-1H-indazol-3-yl)methoxy)phenyl)acetic acid (267b) (55 mg, 37% yield) HCl salt as a white solid; $^1$H NMR (300 MHz, DMSO-$d_6$) δ 12.11 (s, 1H, $D_2O$ exchangeable), 8.52 (s, 3H, $D_2O$ exchangeable), 8.08 (s, 1H), 7.91-7.80 (m, 2H), 7.80-7.67 (m, 2H), 7.56-7.40 (m, 2H), 7.33-7.23 (m, 2H), 7.23-7.14 (m, 1H), 6.97-6.87 (m, 1H), 5.67-5.53 (m, 1H, $D_2O$ exchangeable), 5.45 (s, 2H), 5.11-4.93 (m, 1H), 4.36 (s, 1H), 3.78 (s, 2H), 3.53 (s, 2H), 1.52 (d, J=6.5 Hz, 6H); MS (ES+): 460.20 (M+1); (ES−): 458.20 (M−1).

Optical rotation: $[\alpha]_D$=(+) 7.179 [$CH_3OH$, 0.195].

Scheme 268

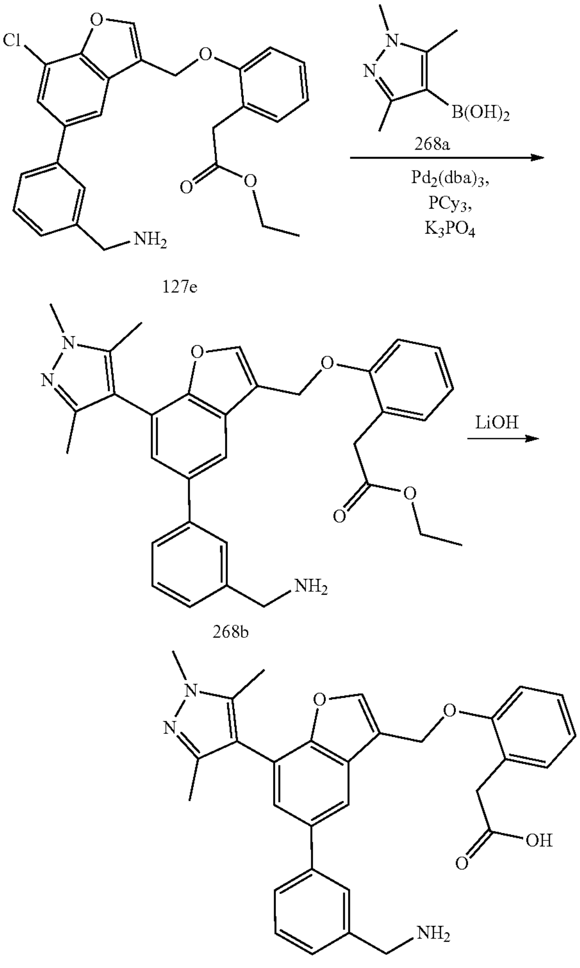

127e, 268a, 268b, 268c

Preparation of 2-(2-((5-(3-(aminomethyl)phenyl)-7-(1,3,5-trimethyl-1H-pyrazol-4-yl)benzofuran-3-yl)methoxy)phenyl)acetic acid (268c)

Step-1: Preparation of ethyl 2-(2-((5-(3-(aminomethyl)phenyl)-7-(1,3,5-trimethyl-1H-pyrazol-4-yl)benzofuran-3-yl)methoxy)phenyl)acetate (268b)

Compound 268b was prepared according to the procedure reported in step-2 of scheme 1, from ethyl 2-(2-((5-(3-(aminomethyl)phenyl)-7-chlorobenzofuran-3-yl)methoxy)phenyl)acetate (127e) (500 mg, 1.111 mmol) in dioxane (40 mL) using (1,3,5-trimethyl-1H-pyrazol-4-yl)boronic acid (268a) (257 mg, 1.667 mmol; CAS #847818-62-6), 4 M solution of $K_3PO_4$ (1.111 mL, 4.45 mmol), tricyclohexylphosphine (62.3 mg, 0.222 mmol), $Pd_2(dba)_3$ (102 mg, 0.111 mmol) and heating at 130° C. for 6 h. This gave after workup and purification using flash column chromatography [silica gel (40 g), eluting with DMA-80 in DCM from 0-50%] ethyl 2-(2-((5-(3-(aminomethyl)phenyl)-7-(1,3,5-trimethyl-1H-pyrazol-4-yl)benzofuran-3-yl)methoxy)phenyl)acetate (268b) (151 mg, 0.288 mmol, 25.9% yield) as a clear gel; $^1$H NMR (300 MHz, DMSO-$d_6$) δ 8.11 (s, 1H), 7.84 (d, J=1.8 Hz, 1H), 7.68 (s, 1H), 7.55 (d, J=7.7 Hz, 1H), 7.44-7.18 (m, 6H), 6.94 (t, J=7.3 Hz, 1H), 5.31 (s, 2H), 3.83-3.66 (m, 7H), 3.58 (s, 2H), 2.19 (s, 3H), 2.10 (s, 3H), 0.83 (t, J=7.1 Hz, 3H); MS (ES+): 524.3 (M+1).

Step-2: Preparation of 2-(2-((5-(3-(aminomethyl)phenyl)-7-(1,3,5-trimethyl-1H-pyrazol-4-yl)benzofuran-3-yl)methoxy)phenyl)acetic acid (268c)

Compound 268c was prepared according to the procedure reported in step-3 of scheme 1, from ethyl 2-(2-((5-(3-(aminomethyl)phenyl)-7-(1,3,5-trimethyl-1H-pyrazol-4-yl)benzofuran-3-yl)methoxy)phenyl)acetate (268b) (140 mg, 0.267 mmol) in THF (1.6 mL), acetonitrile (0.8 mL) using lithium hydroxide monohydrate, 1N (0.802 mL, 0.802 mmol) and stirring the reaction for 25 hours at RT. This gave after workup and purification by reverse phase column chromatography [C18 column (30 g), eluting with ACN in water (containing 0.1% HCl) from 0-100%] 2-(2-((5-(3-(aminomethyl)phenyl)-7-(1,3,5-trimethyl-1H-pyrazol-4-yl)benzofuran-3-yl)methoxy)phenyl)acetic acid (268c) (71 mg, 54% yield) HCl salt as a white solid; $^1$H NMR (300 MHz, DMSO-$d_6$) δ 8.28 (s, 3H, $D_2O$ exchangeable), 8.13 (s, 1H), 7.95 (d, J=1.8 Hz, 1H), 7.87 (s, 1H), 7.79 (d, J=7.7 Hz, 1H), 7.60-7.40 (m, 3H), 7.33-7.19 (m, 3H), 6.99-6.90 (m, 1H), 5.35 (s, 2H), 4.20-4.03 (m, 2H), 3.77 (s, 3H), 3.57 (s, 2H), 2.21 (s, 3H), 2.12 (s, 3H). MS (ES+): 496.2 (M+1); (ES−): 494.2 (M−1); Analysis calculated for $C_{30}H_{29}N_3O_4 \cdot 2.5H_2O \cdot 1.75$ HCl·: C, 59.61; H, 5.96; Cl, 10.26; N, 6.95. Found: C, 59.60; H, 5.83; Cl, 10.42; N, 6.76.

Scheme 269

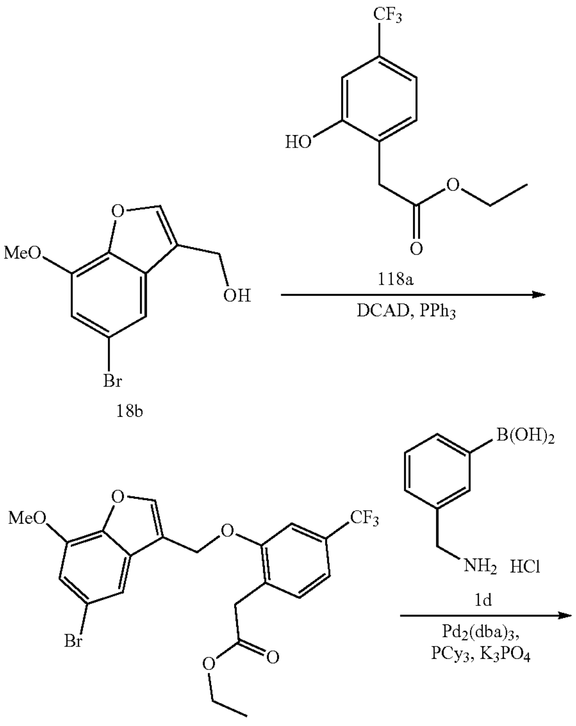

118a

18b

1d

269a

-continued

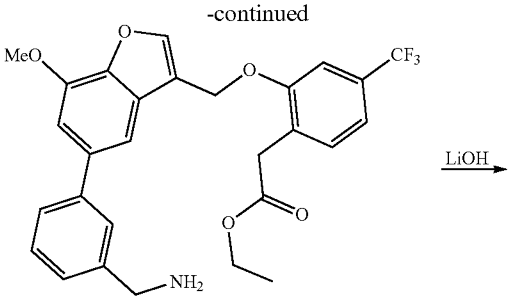

269b

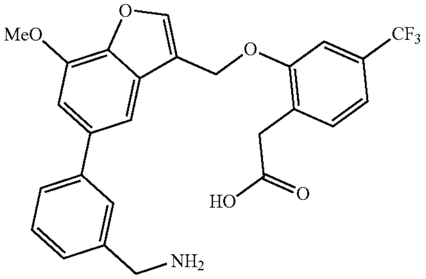

269c

Preparation of 2-(2-((5-(3-(aminomethyl)phenyl)-7-methoxybenzofuran-3-yl)methoxy)-4-(trifluoromethyl)phenyl)acetic acid (269c)

Step-1: Preparation of ethyl 2-(2-((5-bromo-7-methoxybenzofuran-3-yl)methoxy)-4-(trifluoromethyl)phenyl)acetate (269a)

Compound 269a was prepared according to the procedure reported in step-3 of scheme 7, from (5-bromo-7-methoxybenzofuran-3-yl)methanol (18b) (300 mg, 1.167 mmol) in DCM (10 mL) using triphenylphosphine (352 mg, 1.342 mmol), ethyl 2-(2-hydroxy-4-(trifluoromethyl)phenyl)acetate (118a) (319 mg, 1.284 mmol), bis(4-chlorobenzyl) diazene-1,2-dicarboxylate (DCAD, 493 mg, 1.342 mmol) in DCM (5 mL) and stirring the reaction mixture at RT for 1 h. This gave after workup and purification using flash column chromatography [silica gel (24 g), eluting with EtOAc in hexane from 0-25%] ethyl 2-(2-((5-bromo-7-methoxybenzofuran-3-yl)methoxy)-4-(trifluoromethyl)phenyl)acetate (269a) (452 mg, 79% yield) as a white solid; $^1$H NMR (300 MHz, DMSO-$d_6$) δ 8.20-8.05 (m, 1H), 7.48 (d, J=17.0 Hz, 3H), 7.32 (d, J=7.8 Hz, 1H), 7.16 (s, 1H), 5.33 (s, 2H), 4.05-3.90 (m, 5H), 3.67 (s, 2H), 1.07-0.92 (m, 3H); MS (ES+): 509.1/511.1 (M+Na).

Step-2: Preparation of ethyl 2-(2-((5-(3-(aminomethyl)phenyl)-7-methoxybenzofuran-3-yl)methoxy)-4-(trifluoromethyl)phenyl)acetate (269b)

Compound 269b was prepared according to the procedure reported in step-2 of scheme 1, from ethyl 2-(2-((5-bromo-7-methoxybenzofuran-3-yl)methoxy)-4-(trifluoromethyl)phenyl)acetate (269a) (200 mg, 0.410 mmol) in dioxane (15 mL) using 3-(aminomethyl)phenylboronic acid hydrochloride (1d) (96 mg, 0.513 mmol), 4M solution of $K_3PO_4$ (0.410 mL, 1.642 mmol), tricyclohexylphosphine (34.5 mg, 0.123 mmol), $Pd_2(dba)_3$ (56.4 mg, 0.062 mmol) and heating at 115° C. for 3 h. This gave after workup and purification using flash column chromatography [silica gel (24 g), eluting with DMA-80 in DCM from 0-70%] ethyl 2-(2-((5-(3-(aminomethyl)phenyl)-7-methoxybenzofuran-3-yl)methoxy)-4-(trifluoromethyl)phenyl)acetate (269b) (129 mg, 61% yield) as a clear oil; $^1$H NMR (300 MHz, DMSO-$d_6$) δ 8.10 (s, 1H), 7.70 (s, 1H), 7.62-7.52 (m, 2H), 7.52-7.37 (m, 3H), 7.37-7.28 (m, 2H), 7.22 (d, J=1.5 Hz, 1H), 5.40 (s, 2H), 4.04 (s, 3H), 3.82 (s, 2H), 3.75 (q, J=7.1 Hz, 2H), 3.67 (s, 2H), 0.87 (t, J=7.1 Hz, 3H); MS (ES+): 514.2 (M+1).

Step-3: Preparation of 2-(2-((5-(3-(aminomethyl)phenyl)-7-methoxybenzofuran-3-yl)methoxy)-4-(trifluoromethyl)phenyl)acetic acid (269c)

Compound 269c was prepared according to the procedure reported in step-3 of scheme 1, from ethyl 2-(2-((5-(3-(aminomethyl)phenyl)-7-methoxybenzofuran-3-yl)methoxy)-4-(trifluoromethyl)phenyl)acetate (269b) (120 mg, 0.234 mmol) in THF (1.5 mL), acetonitrile (0.75 mL) using lithium hydroxide monohydrate, 1N (0.701 mL, 0.701 mmol) and stirring the reaction for 25 hours at RT. This gave after workup and purification by reverse phase column chromatography [C18 column (50 g), eluting with ACN in water (containing 0.1% HCl) from 0-100%] 2-(2-((5-(3-(aminomethyl)phenyl)-7-methoxybenzofuran-3-yl)methoxy)-4-(trifluoromethyl)phenyl)acetic acid (269c) (99 mg, 87% yield) HCl salt as a white solid; $^1$H NMR (300 MHz, DMSO-$d_6$) δ 12.33 (s, 1H, $D_2O$ exchangeable), 8.40 (s, 3H, $D_2O$ exchangeable), 8.11 (s, 1H), 7.93 (t, J=1.7 Hz, 1H), 7.78 (dt, J=7.6, 1.6 Hz, 1H), 7.61 (d, J=1.5 Hz, 1H), 7.56-7.45 (m, 4H), 7.35-7.27 (m, 2H), 5.42 (s, 2H), 4.12 (s, 2H), 4.06 (s, 3H), 3.64 (s, 2H); $^{19}$F NMR (282 MHz, DMSO) δ −60.66. MS (ES+): 486.1 (M+1); Analysis calculated for $C_{26}H_{22}F_3NO_5 \cdot 0.5H_2O \cdot 1.1HCl$: C, 58.42; H, 4.54; Cl, 7.30; N, 2.62. Found: C, 58.11; H, 4.57; Cl, 7.30; N, 2.73.

Scheme 270

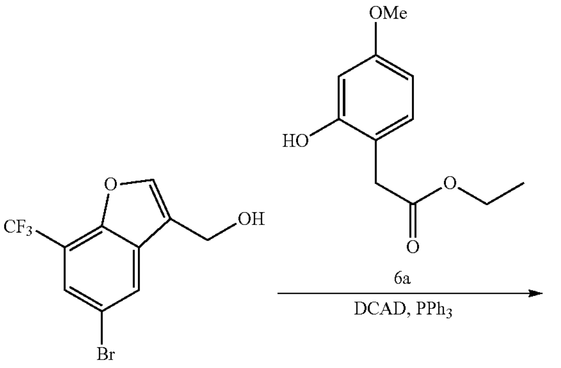

6a

113d

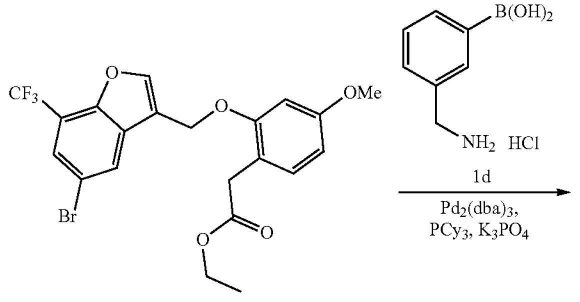

1d

270a

-continued

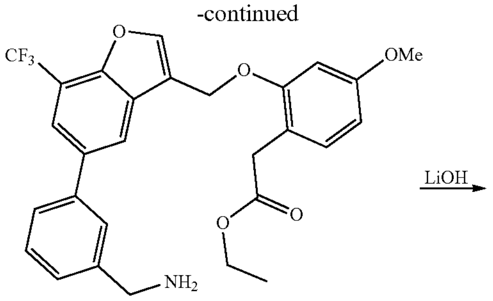

270b

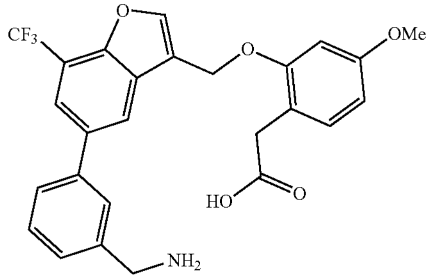

270c

Preparation of 2-(2-((5-(3-(aminomethyl)phenyl)-7-(trifluoromethyl)benzofuran-3-yl)methoxy)-4-methoxyphenyl)acetic acid (270c)

Step-1: Preparation of ethyl 2-(2-((5-bromo-7-(trifluoromethyl)benzofuran-3-yl)methoxy)-4-methoxyphenyl)acetate (270a)

Compound 270a was prepared according to the procedure reported in step-3 of scheme 7, from (5-bromo-7-(trifluoromethyl)benzofuran-3-yl)methanol (113d) (300 mg, 1.017 mmol) in DCM (10 mL) triphenylphosphine (307 mg, 1.169 mmol), ethyl 2-(2-hydroxy-4-methoxyphenyl)acetate (6a) (257 mg, 1.220 mmol), bis(4-chlorobenzyl) diazene-1,2-dicarboxylate (DCAD, 429 mg, 1.169 mmol) in DCM (5 mL) and stirring the reaction mixture at RT for 1 h. This gave after workup and purification using flash column chromatography [silica gel (24 g), eluting with EtOAc in hexane from 0-25%] ethyl 2-(2-((5-bromo-7-(trifluoromethyl)benzofuran-3-yl)methoxy)-4-methoxyphenyl)acetate (270a) (404 mg, 0.829 mmol, 82% yield) as a white solid; $^1$H NMR (300 MHz, DMSO-$d_6$) δ 8.35 (s, 1H), 8.22 (s, 1H), 7.91 (s, 1H), 7.11 (d, J=8.2 Hz, 1H), 6.79 (s, 1H), 6.52 (d, J=8.3 Hz, 1H), 5.29 (s, 2H), 3.91 (q, J=7.0 Hz, 2H), 3.78 (s, 3H), 3.48 (s, 2H), 0.95 (t, J=7.1 Hz, 3H); MS (ES+): 509.0/511.0 (M+Na).

Step-2: Preparation of ethyl 2-(2-((5-(3-(aminomethyl)phenyl)-7-(trifluoromethyl)benzofuran-3-yl)methoxy)-4-methoxyphenyl)acetate (270b)

Compound 270b was prepared according to the procedure reported in step-2 of scheme 1, from ethyl 2-(2-((5-bromo-7-(trifluoromethyl)benzofuran-3-yl)methoxy)-4-methoxyphenyl)acetate (270a) (200 mg, 0.410 mmol) in dioxane (15 mL) using 3-(aminomethyl)phenylboronic acid hydrochloride (1d) (96 mg, 0.513 mmol), 4M solution of $K_3PO_4$ (0.410 mL, 1.642 mmol), tricyclohexylphosphine (34.5 mg, 0.123 mmol) and $Pd_2(dba)_3$ (56.4 mg, 0.062 mmol) and heating at 115° C. for 3 h. This gave after workup and purification using flash column chromatography [silica gel (24 g), eluting with DMA-80 in DCM from 0-70%] ethyl 2-(2-((5-(3-(aminomethyl)phenyl)-7-(trifluoromethyl)benzofuran-3-yl)methoxy)-4-methoxyphenyl)acetate (270b) (125 mg, 0.243 mmol, 59.3% yield) as a clear oil; $^1$H NMR (300 MHz, DMSO-$d_6$) δ 8.34 (s, 1H), 8.24 (d, J=1.8 Hz, 1H), 7.94 (s, 1H), 7.75 (s, 1H), 7.63 (dt, J=7.5, 1.7 Hz, 1H), 7.42 (dt, J=14.7, 7.5 Hz, 2H), 7.10 (d, J=8.3 Hz, 1H), 6.83 (d, J=2.4 Hz, 1H), 6.52 (dd, J=8.3, 2.4 Hz, 1H), 5.35 (s, 2H), 3.82 (s, 2H), 3.78 (s, 3H), 3.68 (q, J=7.1 Hz, 2H), 3.47 (s, 2H), 0.82 (t, J=7.1 Hz, 3H); MS (ES+): 514.2 (M+1).

Step-3: Preparation of 2-(2-((5-(3-(aminomethyl)phenyl)-7-(trifluoromethyl)benzofuran-3-yl)methoxy)-4-methoxyphenyl)acetic acid (270c)

Compound 270c was prepared according to the procedure reported in step-3 of scheme 1, from ethyl 2-(2-((5-(3-(aminomethyl)phenyl)-7-(trifluoromethyl)benzofuran-3-yl)methoxy)-4-methoxyphenyl)acetate (270b) (120 mg, 0.234 mmol) in THF (1.5 mL), acetonitrile (0.75 mL) using lithium hydroxide monohydrate, 1N (0.701 mL, 0.701 mmol) and stirring the reaction for 25 hours at RT. This gave after workup and purification by reverse phase column chromatography [C18 column (50 g), eluting with ACN in water (containing 0.1% HCl) from 0-100%] 2-(2-((5-(3-(aminomethyl)phenyl)-7-(trifluoromethyl)benzofuran-3-yl)methoxy)-4-methoxyphenyl)acetic acid (270c) (82 mg, 72% yield) HCl salt as a white solid; $^1$H NMR (300 MHz, DMSO-$d_6$) δ 8.47-8.21 (m, 4H, 2H $D_2O$ exchangeable), 8.04-7.93 (m, 2H), 7.85 (dt, J=7.6, 1.7 Hz, 1H), 7.64-7.43 (m, 2H), 7.11 (d, J=8.3 Hz, 1H), 6.82 (d, J=2.4 Hz, 1H), 6.52 (dd, J=8.3, 2.4 Hz, 1H), 5.38 (s, 2H), 4.14 (s, 2H), 3.77 (s, 3H), 3.46 (s, 2H). $^{19}$F NMR (282 MHz, DMSO) δ -59.56. MS (ES+): 486.1 (M+1); (ES−): 484.1 (M−1); Analysis calculated for $C_{26}H_{22}F_3NO_5 \cdot 1.25H_2O \cdot HCl$: C, 57.36; H, 4.72; Cl, 6.51; N, 2.57. Found: C, 57.35; H, 4.63; Cl, 6.48; N, 2.60.

Scheme 271

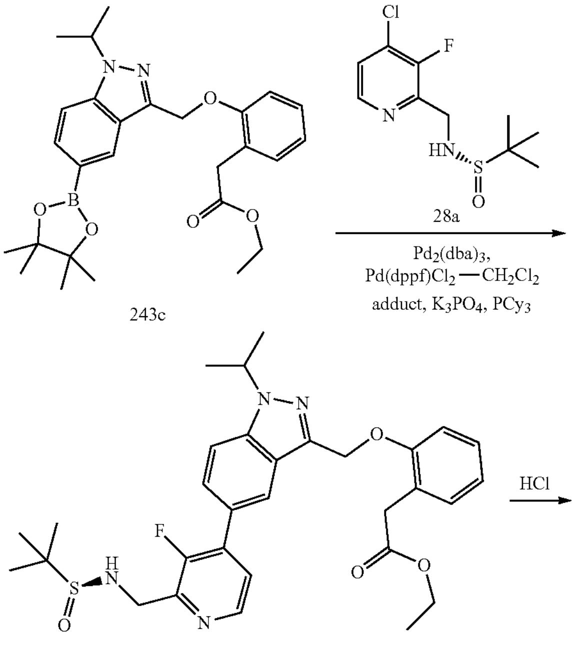

243c

28a

271a

-continued

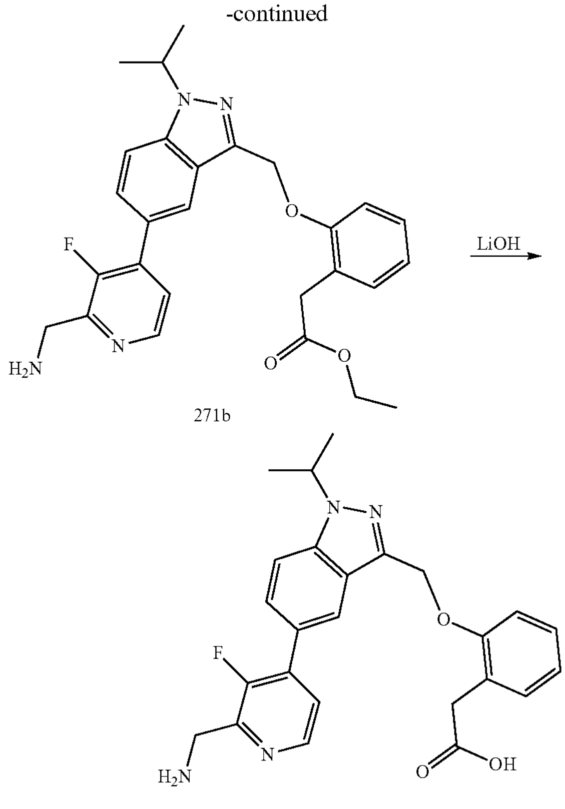

271b

271c

Preparation of 2-(2-((5-(2-(aminomethyl)-3-fluoropyridin-4-yl)-1-isopropyl-1H-indazol-3-yl)methoxy)phenyl)acetic acid (271c)

Step-1: Preparation of (−)-ethyl 2-(2-((5-(2-((1,1-dimethylethylsulfinamido)methyl)-3-fluoropyridin-4-yl)-1-isopropyl-1H-indazol-3-yl)methoxy)phenyl)acetate (271a)

Compound 271a was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (3 mL) and 2Me-THF (3 mL) using (+)-N-((4-chloro-3-fluoropyridin-2-yl)methyl)-2-methylpropane-2-sulfinamide (28a) (221 mg, 0.836 mmol), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2(dppf)$-$CH_2Cl_2$ adduct (34.1 mg, 0.042 mmol) and heating at 100° C. for 3 h. This gave after workup and purification by flash column chromatography [silica gel (24 g), eluting with DMA-80 in DCM from 0-70%](−)-ethyl 2-(2-((5-(2-((1,1-dimethylethylsulfinamido)methyl)-3-fluoropyridin-4-yl)-1-isopropyl-1H-indazol-3-yl)methoxy)phenyl)acetate (271a) (160 mg, 66% yield) as a clear oil; MS (ES+): 581.30 (M+1); Optical rotation: $[\alpha]_D$=(−) 6.107 [$CH_3OH$, 0.655].

Step-2: Preparation of ethyl 2-(2-((5-(2-(aminomethyl)-3-fluoropyridin-4-yl)-1-isopropyl-1H-indazol-3-yl)methoxy)phenyl)acetate (271b)

Compound 271b was prepared according to the procedure reported in step-2 of scheme 7, from (−)-ethyl 2-(2-((5-(2-

((1,1-dimethylethylsulfinamido)methyl)-3-fluoropyridin-4-yl)-1-isopropyl-1H-indazol-3-yl)methoxy)phenyl)acetate (271a) (180 mg, 0.310 mmol) in THF (5 mL) using HCl (4 M in 1,4-dioxane) (0.232 mL, 0.93 mmol) and stirring the reaction for 30 min. This gave after workup ethyl 2-(2-((5-(2-(aminomethyl)-3-fluoropyridin-4-yl)-1-isopropyl-1H-indazol-3-yl)methoxy)phenyl)acetate (271b) (148 mg, 100% yield) as a light yellow oil which was used as such for the next step; $^1$H NMR (300 MHz, DMSO-$d_6$) δ 8.54 (d, J=5.0 Hz, 1H), 8.47-8.44 (m, 2H), 8.10 (s, 1H), 7.92 (d, J=8.9 Hz, 1H), 7.82-7.69 (m, 2H), 7.35-7.24 (m, 2H), 7.22-7.14 (m, 1H), 7.02-6.89 (m, 1H), 5.43 (s, 2H), 5.17-4.95 (m, 1H), 4.34-4.26 (m, 2H), 3.66 (q, J=7.2 Hz, 2H), 3.53 (s, 2H), 1.52 (d, J=6.6 Hz, 6H), 0.78 (t, J=7.1 Hz, 3H); MS (ES+): 477.20 (M+1); (ES−): 475.15 (M−1).

Step-3: Preparation of 2-(2-((5-(2-(aminomethyl)-3-fluoropyridin-4-yl)-1-isopropyl-1H-indazol-3-yl)methoxy)phenyl)acetic acid (271c)

Compound 271c was prepared according to the procedure reported in step-3 of scheme 1, from ethyl 2-(2-((5-(2-(aminomethyl)-3-fluoropyridin-4-yl)-1-isopropyl-1H-indazol-3-yl)methoxy)phenyl)acetate (271b) (150 mg, 0.315 mmol) in THF (2 mL) and MeOH (2 mL) using a solution of lithium hydroxide hydrate (79 mg, 1.889 mmol) in water (1 mL) and heating at 50° C. for 1 h. This gave after workup and purification by reverse phase column chromatography [C18 column (50 g), eluting with ACN in water (containing 0.1% HCl) from 0-100%] 2-(2-((5-(2-(aminomethyl)-3-fluoropyridin-4-yl)-1-isopropyl-1H-indazol-3-yl)methoxy)phenyl)acetic acid (271c) (50 mg, 35% yield) HCl salt as a white solid; $^1$H NMR (300 MHz, DMSO-$d_6$) δ 8.58-8.44 (m, 4H, 3H $D_2O$ exchangeable), 8.15 (s, 1H), 7.91 (d, J=8.9 Hz, 1H), 7.80-7.66 (m, 2H), 7.26 (d, J=3.9 Hz, 2H), 7.20 (d, J=7.3 Hz, 1H), 6.98-6.84 (m, 1H), 5.46 (s, 2H), 5.21-4.90 (m, 1H), 4.47-4.24 (m, 2H), 3.52 (s, 2H), 1.52 (d, J=6.6 Hz, 6H); $^{19}$F NMR (282 MHz, DMSO-$d_6$) δ −132.92; MS (ES+): 449.20 (M+1); MS (ES−): 447.15 (M−1).

Scheme 272

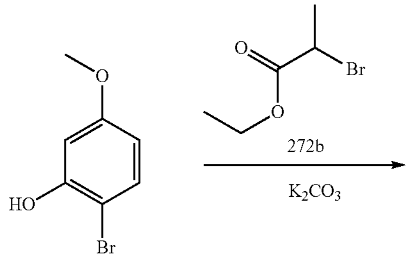

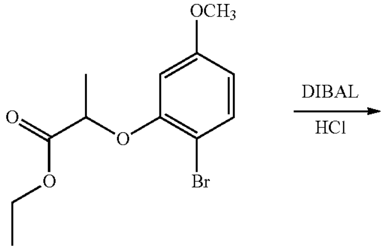

272c

-continued

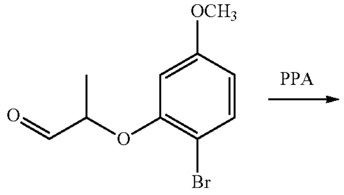

272d

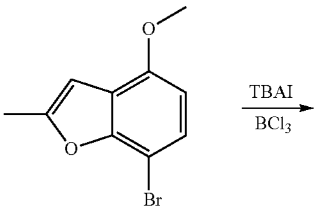

272e

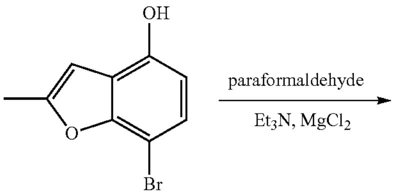

272f

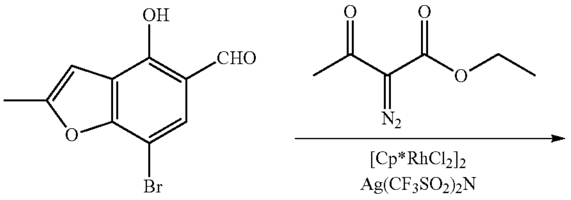

272g

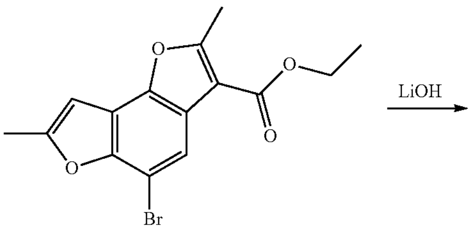

272h

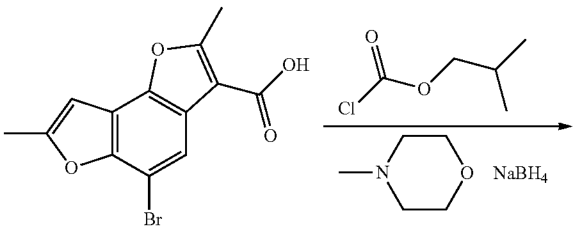

272i

-continued

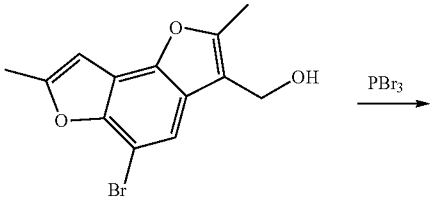

272j

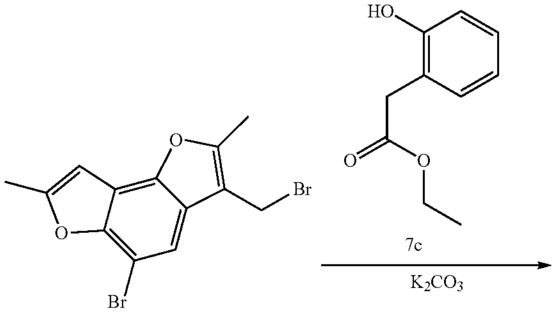

272k

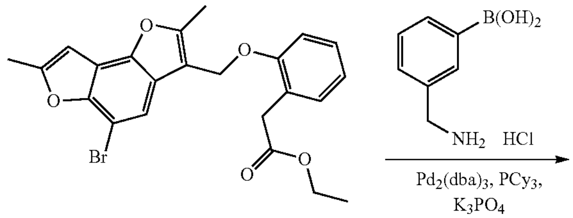

2721

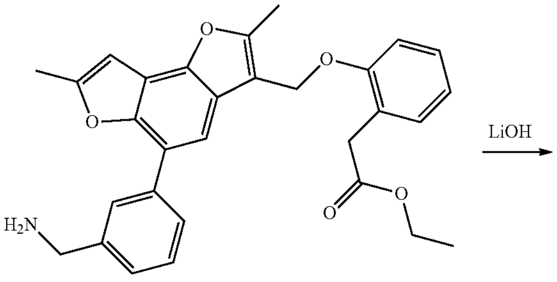

272m

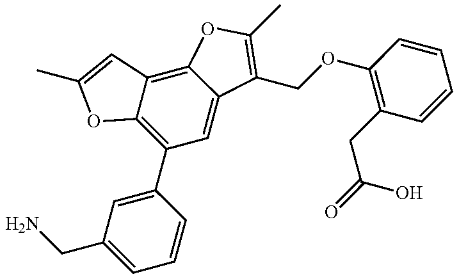

272n

Preparation of 2-(2-((5-(3-(aminomethyl)phenyl)-2,7-dimethylbenzo[1,2-b:3,4-b']difuran-3-yl)methoxy)phenyl)acetic acid (272n)

Step-1: Preparation of ethyl 2-(2-bromo-5-methoxyphenoxy)propanoate (272c)

Compound 272c was prepared according to the procedure reported in step-3 of scheme 7, from 2-bromo-5-methoxyphenol (272a) (3 g, 14.78 mmol; CAS #63604-94-4) in acetone (30 mL) using ethyl 2-bromopropanoate (272b) (5.35 g, 29.6 mmol; CAS #535-11-5), potassium carbonate (6.13 g, 44.3 mmol) and stirring overnight at RT. This gave after workup and purification using flash column chromatography [silica gel (40 g) eluting with ethyl acetate and hexanes from 0-50%] ethyl 2-(2-bromo-5-methoxyphenoxy)propanoate (272c) (4.48 g, 100% yield) as a colorless oil; $^{1}H$ NMR (300 MHz, DMSO-$d_6$) δ 7.47 (d, J=8.4 Hz, 1H), 6.59-6.48 (m, 2H), 5.08 (q, J=6.7 Hz, 1H), 4.16 (q, J=7.1 Hz, 2H), 3.73 (s, 3H), 1.53 (d, J=6.7 Hz, 3H), 1.18 (t, J=7.1 Hz, 3H).

Step-2: Preparation of 2-(2-bromo-5-methoxyphenoxy)propanal (272d)

Compound 272d was prepared according to the procedure reported in step-4 of scheme 3, from ethyl 2-(2-bromo-5-methoxyphenoxy)propanoate (272c) (4.4 g, 14.51 mmol) in DCM (60 mL) using DIBAL (1M in DCM) (17.42 mL, 17.42 mmol) and stirring at −78° C. for 2 h. This gave after workup and purification by flash column chromatography [silica gel (40 g), eluting with EA/MeOH (9:1) in hexane from 0-50%] 2-(2-bromo-5-methoxyphenoxy)propanal (272d) (3.4 g, 90% yield) as a colorless oil; $^{1}H$ NMR (300 MHz, DMSO-$d_6$) δ 9.66 (s, 1H), 7.48 (d, J=8.7 Hz, 1H), 6.66 (d, J=2.7 Hz, 1H), 6.55 (dd, J=8.8, 2.7 Hz, 1H), 5.13 (q, J=7.0 Hz, 1H), 3.74 (s, 3H), 1.43 (d, J=7.0 Hz, 3H).

Step-3: Preparation of 7-bromo-4-methoxy-2-methylbenzofuran (272e)

Compound 272e was prepared according to the procedure reported in step-1 of scheme 123, from 2-(2-bromo-5-methoxyphenoxy)propanal (272d) (3.4 g, 13.12 mmol) in chlorobenzene (10 mL) using polyphosphoric acid (PPA) (3.9 g, 13.12 mmol) in chlorobenzene (50 mL) and heating at 80° C. for 90 min followed by 120° C. for 2 h. This gave after workup and purification using flash column chromatography [silica gel (24 g) eluting with ethyl acetate in hexanes from 0-35%] 7-bromo-4-methoxy-2-methylbenzofuran (272e) (3.01 g, 95% yield) as a white yellow solid; $^{1}H$ NMR (300 MHz, DMSO-$d_6$) δ 7.37 (d, J=8.5 Hz, 1H), 6.74 (d, J=8.6 Hz, 1H), 6.69 (q, J=1.0 Hz, 1H), 3.88 (s, 3H), 2.46 (d, J=1.1 Hz, 3H).

Step-4: Preparation of 7-bromo-2-methylbenzofuran-4-ol (272f)

To a solution of 7-bromo-4-methoxy-2-methylbenzofuran (272e) (3.01 g, 12.49 mmol) and tetrabutylammonium iodide (TBAI, 4.61 g, 12.49 mmol) in DCM (50 mL) was added a solution of boron trichloride in 1 M DCM (24.97 mL, 24.97 mmol) dropwise at −78° C. and was stirred for 30 min and then warmed to RT and stirred for 1 h. The mixture was diluted with saturated $NaHCO_3$ and was extracted with DCM. The combined organics were washed with brine, dried, filtered and concentrated in vacuo. The residue obtained was purified using flash column chromatography [silica gel (24 g), eluting with EtOAc in hexane from 0-80%] to afford 7-bromo-2-methylbenzofuran-4-ol (272f) (2.63 g, 93% yield) as a white yellow solid; $^1$H NMR (300 MHz, DMSO-$d_6$) δ 10.07 (s, 1H), 7.20 (d, J=8.4 Hz, 1H), 6.68 (q, J=1.1 Hz, 1H), 6.55 (d, J=8.4 Hz, 1H), 2.44 (d, J=1.1 Hz, 3H).

Step-5: Preparation of 7-bromo-4-hydroxy-2-methylbenzofuran-5-carbaldehyde (272g)

To a solution of 7-bromo-2-methylbenzofuran-4-ol (272f) (2.62 g, 11.54 mmol), magnesium chloride (2.197 g, 23.08 mmol), triethylamine (8.04 mL, 57.7 mmol) in acetonitrile (80 mL) was added paraformaldehyde (2.079 g, 69.2 mmol) and heated at reflux for 5 h. The mixture was cooled and quenched by the addition of water. The reaction mixture was acidified using HCl (5.5 N) and extracted using ethyl acetate (3×30 mL). The combined organics were dried, filtered and concentrated in vacuo. The residue obtained was purified using flash column chromatography [silica gel (12 g), EtOAc in hexanes from 0-50%) to afford 7-bromo-4-hydroxy-2-methylbenzofuran-5-carbaldehyde (272g) (1.38 g, 47% yield) as a white solid; $^1$H NMR (300 MHz, DMSO-$d_6$) δ 1.46 (s, 1H), 10.21 (s, 1H), 7.72 (s, 1H), 6.97 (d, J=1.2 Hz, 1H), 2.50 (s, 3H).

Step-6: Preparation of ethyl 5-bromo-2,7-dimethylbenzo[1,2-b:3,4-b']difuran-3-carboxylate (272h)

Compound 272h was prepared according to the procedure reported in step-1 of scheme 233, from 7-bromo-4-hydroxy-2-methylbenzofuran-5-carbaldehyde (272g) (255 mg, 1.00 mmol) in DCE (5 mL) using pentamethylcyclopentadienylrhodium chloride dimer (65.3 mg, 0.106 mmol), silver bis(trifluoromethanesulfonyl)imide (164 mg, 0.422 mmol), ethyl 2-diazo-3-oxobutanoate (659 mg, 4.22 mmol) and stirring vigorously in a sealed tube at 50° C. for 14 h. This gave after workup and purification using flash column chromatography [silica gel (12 g), eluting with EtOAc in hexane from 0-40%] ethyl 5-bromo-2,7-dimethylbenzo[1,2-b:3,4-b']difuran-3-carboxylate (272 h) (181 mg, 54% yield) as a white solid; $^1$H NMR (300 MHz, DMSO-$d_6$) δ 7.89 (s, 1H), 7.03 (d, J=1.2 Hz, 1H), 4.38 (q, J=7.1 Hz, 2H), 2.79 (s, 3H), 2.55 (d, J=1.1 Hz, 3H), 1.38 (t, J=7.1 Hz, 3H).

Step-7: Preparation of 5-bromo-2,7-dimethylbenzo[1,2-b:3,4-b']difuran-3-carboxylic acid (272i)

Compound 272i was prepared according to the procedure reported in step-3 of scheme 1, from ethyl 5-bromo-2,7-dimethylbenzo[1,2-b:3,4-b']difuran-3-carboxylate (272 h) (179 mg, 0.531 mmol) in MeOH (3 mL) and THF (3 mL) using a solution of lithium hydroxide (89 mg, 2.124 mmol) in water (2 mL) and stirring at RT for 48 h. This gave after workup 5-bromo-2,7-dimethylbenzo[1,2-b:3,4-b']difuran-3-carboxylic acid (272i) (164 mg, 100% yield), which was used as such in the next step; MS (ES−): 307.0, 309.0 (M−H).

Step-8: Preparation of (5-bromo-2,7-dimethylbenzo[1,2-b:3,4-b']difuran-3-yl)methanol (272j)

Compound 272j was prepared according to the procedure reported in step-1 of scheme 8, from 5-bromo-2,7-dimethylbenzo[1,2-b:3,4-b']difuran-3-carboxylic acid (272i) (164 mg, 0.531 mmol) in THF (10 mL) using N-methylmorpholine (0.07 mL, 0.637 mmol), isobutyl chloroformate (0.084 mL, 0.637 mmol) and $NaBH_4$ (60.2 mg, 1.592 mmol) in water (1 mL).

This gave after workup and purification using flash column chromatography [silica gel (12 g), eluting with EtOAc in hexane from 0-80%] (5-bromo-2,7-dimethylbenzo[1,2-b:3,4-b']difuran-3-yl)methanol (272j) (157 mg, 100% yield) as a white solid; $^1$H NMR (300 MHz, DMSO-$d_6$) δ 7.68 (s, 1H), 6.94 (d, J=1.2 Hz, 1H), 5.07 (t, J=5.6 Hz, 1H), 4.58 (d, J=5.6 Hz, 2H), 2.59 (s, 3H), 2.46 (s, 3H).

Step-9: Preparation of 5-bromo-3-(bromomethyl)-2,7-dimethylbenzo[1,2-b:3,4-b']difuran (272k)

Compound 272k was prepared according to the procedure reported in step-3 of scheme 228, from (5-bromo-2,7-dimethylbenzo[1,2-b:3,4-b']difuran-3-yl)methanol (272j) (157 mg, 0.532 mmol) in dry DCM (8 mL) using $PBr_3$ (0.060 mL, 0.638 mmol) and stirring for 90 min. This gave after work up 5-bromo-3-(bromomethyl)-2,7-dimethylbenzo[1,2-b:3,4-b']difuran (272k) (190 mg, 100% yield), which was used as such for the next step.

Step-10: Preparation of ethyl 2-(2-((5-bromo-2,7-dimethylbenzo[1,2-b:3,4-b']difuran-3-yl)methoxy)phenyl)acetate (2721)

Compound 2721 was prepared according to the procedure reported in step-3 of scheme 7, from 5-bromo-3-(bromomethyl)-2,7-dimethylbenzo[1,2-b:3,4-b']difuran (272k) (190 mg, 0.531 mmol) in acetone (10 mL) using ethyl 2-(2-hydroxyphenyl)acetate (7c) (143 mg, 0.796 mmol), potassium carbonate (220 mg, 1.592 mmol) and stirring overnight at RT. This gave after workup and purification using flash column chromatography [silica gel (12 g), eluting with ethyl acetate in hexanes from 0-50%] ethyl 2-(2-((5-bromo-2,7-dimethylbenzo[1,2-b:3,4-b']difuran-3-yl)methoxy)phenyl)acetate (2721) (131 mg, 54.0% yield) as a pale yellow oil; $^1$H NMR (300 MHz, DMSO-$d_6$) δ 7.62 (s, 1H), 7.36-7.27 (m, 1H), 7.25-7.17 (m, 2H), 6.99-6.89 (m, 2H), 5.22 (s, 2H), 3.90 (q, J=7.1 Hz, 2H), 3.52 (s, 2H), 2.56-2.53 (m, 6H), 0.93 (t, J=7.1 Hz, 3H).

Step-11: Preparation of ethyl 2-(2-((5-(3-(aminomethyl)phenyl)-2,7-dimethylbenzo[1,2-b:3,4-b']difuran-3-yl)methoxy)phenyl)acetate (272m)

Compound 272m was prepared according to the procedure reported in step-2 of scheme 1, from ethyl 2-(2-((5-bromo-2,7-dimethylbenzo[1,2-b:3,4-b']difuran-3-yl)methoxy)phenyl)acetate (2721) (130 mg, 0.284 mmol) in dioxane/2Me-THF (12 mL, ratio 2:1) using 3-(aminomethyl)phenylboronic acid hydrochloride (1d) (133 mg, 0.711 mmol), 4M solution of $K_3PO_4$ (0.284 mL, 1.137 mmol), tricyclohexylphosphine (31.9 mg, 0.114 mmol), $Pd_2(dba)_3$ (52.1 mg, 0.057 mmol) and heating at 115° C. for 3 h. This gave after workup and purification using flash column chromatography [silica gel (12 g), eluting with DMA-80 in DCM from 0-80%] ethyl 2-(2-((5-(3-(aminomethyl)phenyl)-2,7-dimethylbenzo[1,2-b:3,4-b']difuran-3-yl)methoxy)phenyl)acetate (272m) (118 mg, 86% yield) as a yellow oil; $^1$H NMR (300 MHz, DMSO-$d_6$) δ 7.76 (s, 1H), 7.68 (d, J=7.6 Hz, 1H), 7.52 (s, 1H), 7.44 (t, J=7.6 Hz, 1H), 7.37 (d, J=7.7 Hz, 1H), 7.30 (dd, J=7.2, 1.6 Hz, 1H), 7.25 (d, J=8.0 Hz, 1H), 7.19 (dd, J=7.5, 1.6 Hz, 1H), 6.97-6.87 (m, 2H), 5.27 (s, 2H), 3.81 (s, 2H), 3.70 (q, J=7.1 Hz, 2H), 3.52 (s, 2H), 2.55 (s, 3H), 2.51 (s, 3H), 0.81 (t, J=7.1 Hz, 3H); MS (ES+) 484.2 (M+1).

Step-12: Preparation of 2-(2-((5-(3-(aminomethyl)phenyl)-2,7-dimethylbenzo[1,2-b:3,4-b']difuran-3-yl)methoxy)phenyl)acetic acid (272n)

Compound 272n was prepared according to the procedure reported in step-3 of scheme 1, from ethyl 2-(2-((5-(3-(aminomethyl)phenyl)-2,7-dimethylbenzo[1,2-b:3,4-b']difuran-3-yl)methoxy)phenyl)acetate (272m) (116 mg, 0.240 mmol) in MeOH (3 mL) THF (3 mL) using a solution of lithium hydroxide monohydrate (80 mg, 1.907 mmol) in water (2 mL) and stirring overnight at RT. This gave after workup and purification using reverse phase column chromatography [C18 column (50 g), eluting with ACN in water (containing 0.1% HCl) from 0-100%] 2-(2-((5-(3-(aminomethyl)phenyl)-2,7-dimethylbenzo[1,2-b:3,4-b']difuran-3-yl)methoxy)phenyl)acetic acid (272n) (95 mg, 87% yield) HCl salt as a white solid; $^1$H NMR (300 MHz, DMSO-$d_6$) δ 12.11 (s, 1H, $D_2O$ exchangeable), 8.35 (s, 3H, $D_2O$ exchangeable), 7.94 (s, 1H), 7.89 (d, J=7.7 Hz, 1H), 7.67-7.46 (m, 3H), 7.34-7.16 (m, 3H), 6.94 (d, J=9.4 Hz, 2H), 5.28 (s, 2H), 4.14 (s, 2H), 3.50 (s, 2H), 2.56 (s, 3H), 2.53 (s, 3H); MS (ES+): 456.2 (M+1); (ES−): 454.1 (M−1); Analysis calculated for: $C_{28}H_{25}NO_5$·1.05HCl·0.75$H_2O$: C, 66.29; H, 5.47; Cl, 7.34; N, 2.76. Found: C, 66.41; H, 5.35; N, 3.10; Cl, 7.54.

Scheme 273

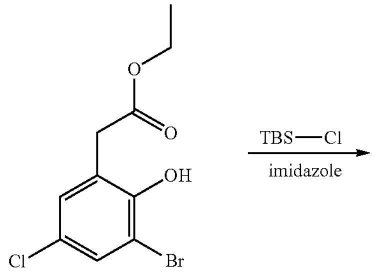

273a

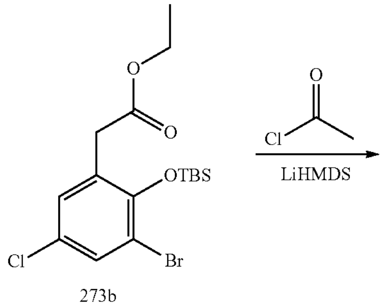

273b

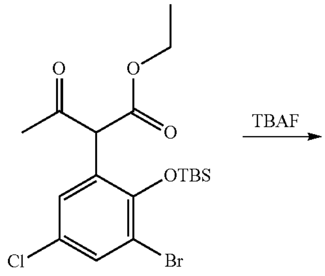

273c

-continued

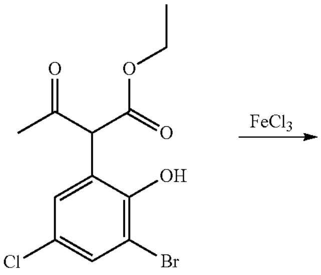

273d

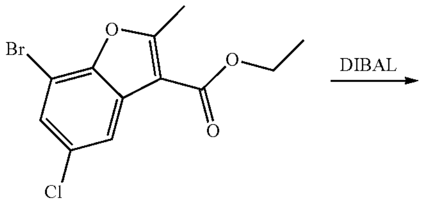

273e

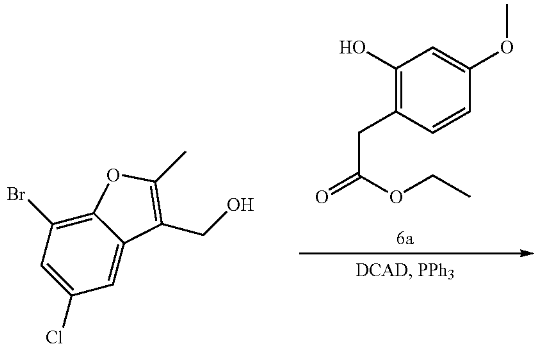

273f

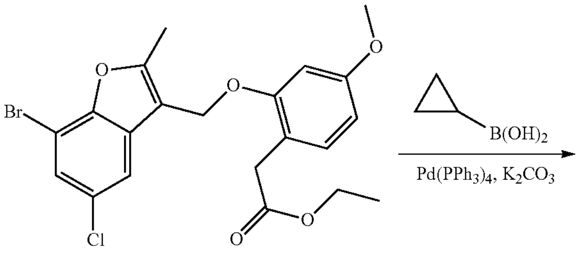

273g

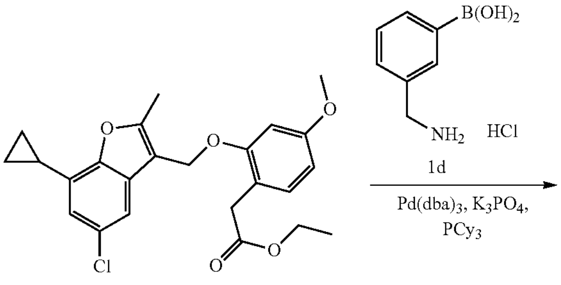

273h

-continued

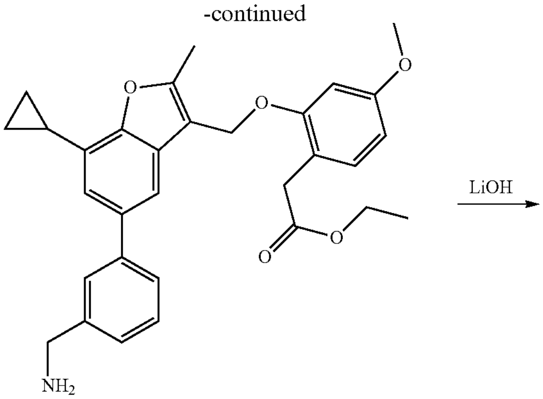

273i

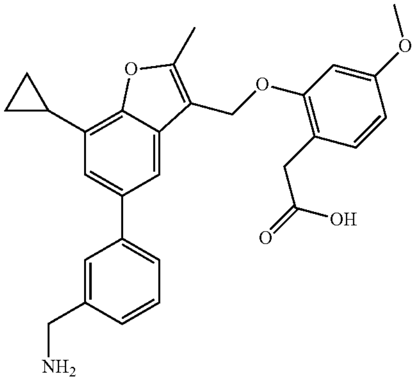

273j

Preparation of 2-(2-((5-(3-(aminomethyl)phenyl)-7-cyclopropyl-2-methylbenzofuran-3-yl)methoxy)-4-methoxyphenyl)acetic acid (273j)

Step-1: Preparation of ethyl 2-(3-bromo-2-((tert-butyldimethylsilyl)oxy)-5-chlorophenyl)acetate (273b)

Compound 273b was prepared according to the procedure reported in step-1 of scheme 171, from ethyl 2-(3-bromo-5-chloro-2-hydroxyphenyl)acetate (273a) (50.0 g, 170.33 mmol) in DMF (500 mL) using TBS-$C_1$ (51.34 g, 340.66 mmol), imidazole (23.18 g, 340.66 mmol) and stirring at 60° C. for 1 h. This gave after workup and purification using flash column chromatography [silica gel, eluting with EtOAc in n-heptane from 0-20%] ethyl 2-(3-bromo-2-((tert-butyldimethylsilyl)oxy)-5-chlorophenyl)acetate (273b) (69.0 g, 99% yield) as an oily mass; MS (ES+): 429.0 (M+Na).

Step-2: Preparation of ethyl 2-(3-bromo-2-((tert-butyldimethylsilyl)oxy)-5-chlorophenyl)-3-oxobutanoate (273c)

Compound 273c was prepared according to the procedure reported in step-1 of scheme 171, from ethyl 2-(3-bromo-2-((tert-butyldimethylsilyl)oxy)-5-chlorophenyl)acetate (273b) (5 g, 12.26 mmol) in THF (50 mL) using LiHMDS (1N in THF) (14.71 mL, 14.71 mmol), acetyl chloride (1.002 mL, 14.1 mmol) in THF (3 mL) and stirring at −78° C. for 1 h followed at 0° C. for 1 h. This gave after workup and purification using flash column chromatography [silica gel (80 g), eluting with EtOAc in hexane from 0-100%] ethyl 2-(3-bromo-2-((tert-butyldimethylsilyl)oxy)-5-chlorophenyl)-3-oxobutanoate (273c) ((3.518 g, 64% yield) as a clear oil; $^1$H NMR (300 MHz, DMSO-$d_6$) δ 13.09 (d, J=0.9 Hz, 1H), 7.65 (d, J=2.7 Hz, 1H), 7.29 (d, J=2.7 Hz, 1H), 4.24-4.01 (m, 2H), 1.82 (s, 3H), 1.11 (t, J=7.1 Hz, 3H), 0.94 (s, 9H), 0.09 (s, 3H), 0.06 (s, 3H).

Step-3: Preparation of ethyl 2-(3-bromo-5-chloro-2-hydroxyphenyl)-3-oxobutanoate (273d)

Compound 273d was prepared according to the procedure reported in step-2 of scheme 3, from ethyl 2-(3-bromo-2-((tert-butyldimethylsilyl)oxy)-5-chlorophenyl)-3-oxobutanoate (273c) (3.518 g, 7.82 mmol) in THF (25 mL) using TBAF (9.78 mL, 9.78 mmol) and stirring at 0° C. for 1 h. This gave after workup and purification using flash column chromatography [silica gel (80 g), eluting with EtOAc in hexane from 0-100%] ethyl 2-(3-bromo-5-chloro-2-hydroxyphenyl)-3-oxobutanoate (273d) (0.859 g, 33% yield) as a clear oil; MS (ES+): 356.90 (M+Na).

Step-4: Preparation of ethyl 7-bromo-5-chloro-2-methylbenzofuran-3-carboxylate (273e)

Compound 273e was prepared according to the procedure reported in step-3 of scheme 171, from ethyl 2-(3-bromo-5-chloro-2-hydroxyphenyl)-3-oxobutanoate (273d) (0.859 g, 2.61 mmol) in DCE (10 mL) using iron(III) chloride (0.071 g, 0.261 mmol) and stirring for 2 days at RT. This gave after workup and purification using flash column chromatography [silica gel (40 g), eluting with EtOAc in hexane from 0-100%] ethyl 7-bromo-5-chloro-2-methylbenzofuran-3-carboxylate (273e) (455 mg, 55% yield) as a white solid; $^1$H NMR (300 MHz, DMSO-$d_6$) δ 7.85 (d, J=2.1 Hz, 1H), 7.75 (d, J=2.0 Hz, 1H), 4.37 (q, J=7.1 Hz, 2H), 2.80 (s, 3H), 1.37 (t, J=7.1 Hz, 3H).

Step-5: Preparation of (7-bromo-5-chloro-2-methylbenzofuran-3-yl)methanol (273f)

Compound 273f was prepared according to the procedure reported in step-2 of scheme 69, from ethyl 7-bromo-5-chloro-2-methylbenzofuran-3-carboxylate (273e) (455 mg, 1.433 mmol) in DCM (10 mL) using 1.0 M solution of DIBAL in DCM (3.58 mL, 3.58 mmol) and stirring at 0° C. for 2 h. This gave after workup and purification using flash column chromatography [silica gel (24 g), eluting with EtOAc in hexane from 0-50%] (7-bromo-5-chloro-2-methylbenzofuran-3-yl)methanol (273f) (317 mg, 80% yield) as a white solid; $^1$H NMR (300 MHz, DMSO-$d_6$) δ 7.70 (d, J=2.0 Hz, 1H), 7.58 (d, J=2.0 Hz, 1H), 5.13 (t, J=5.6 Hz, 1H), 4.55 (d, J=5.6 Hz, 2H), 2.48 (s, 3H).

Step-6: Preparation of ethyl 2-(2-((7-bromo-5-chloro-2-methylbenzofuran-3-yl)methoxy)-4-methoxyphenyl)acetate (273g)

Compound 273g was prepared according to the procedure reported in step-2 of scheme 65, from (7-bromo-5-chloro-2-methylbenzofuran-3-yl)methanol (273f) (317 mg, 1.151 mmol) in DCM (7 mL) using triphenylphosphine (392 mg, 1.496 mmol), ethyl 2-(2-hydroxy-4-methoxyphenyl)acetate (6a) (363 mg, 1.726 mmol), DCAD (549 mg, 1.496 mmol) in DCM (3 mL) and stirring at RT for 3 h. This gave after workup and purification using flash column chromatography [silica gel (12 g), eluting with EtOAc in hexane from 0-50%]

ethyl 2-(2-((7-bromo-5-chloro-2-methylbenzofuran-3-yl)methoxy)-4-methoxyphenyl)acetate (273g) (209 mg, 39% yield) as a white solid; MS (ES+): 489.0 (M+Na).

Step-7: Preparation of ethyl 2-(2-((5-chloro-7-cyclopropyl-2-methylbenzofuran-3-yl)methoxy)-4-methoxyphenyl)acetate (273 h)

Compound 273h was prepared according to the procedure reported in step-2 of scheme 111, from ethyl 2-(2-((7-bromo-5-chloro-2-methylbenzofuran-3-yl)methoxy)-4-methoxyphenyl)acetate (273g) (209 mg, 0.447 mmol) in THF (2.5 mL) using cyclopropyl boronic acid (57.6 mg, 0.670 mmol), a solution of potassium carbonate (93 mg, 0.670 mmol) in water (1.25 mL), $Pd(PPh_3)_4$ (51.6 mg, 0.045 mmol) and heating at 80° C. for 4 h. This gave after workup and purification using flash column chromatography [silica gel (12 g), eluting with EtOAc in hexane from 0-50%] ethyl 2-(2-((5-chloro-7-cyclopropyl-2-methylbenzofuran-3-yl)methoxy)-4-methoxyphenyl)acetate (273 h) (108 mg, 58% yield) as a clear gum; MS (ES+): 451.0 (M+Na).

Step-8: Preparation of ethyl 2-(2-((5-(3-(aminomethyl)phenyl)-7-cyclopropyl-2-methylbenzofuran-3-yl)methoxy)-4-methoxyphenyl)acetate (273i)

Compound 273i was prepared according to the procedure reported in step-2 of scheme 1, from ethyl 2-(2-((5-chloro-7-cyclopropyl-2-methylbenzofuran-3-yl)methoxy)-4-methoxyphenyl)acetate (273 h) (102 mg, 0.238 mmol) in dioxane (6 mL) and 2-Me THF (3 mL) using (3-(aminomethyl)phenyl)boronic acid hydrochloride (1d) (111 mg, 0.595 mmol), 4 M solution of $K_3PO_4$ (0.238 mL, 0.951 mmol), tricyclohexylphosphine (53.4 mg, 0.190 mmol), $Pd_2(dba)_3$ (87 mg, 0.095 mmol) and heating at 115° C. for 16 h. This gave after workup ethyl 2-(2-((5-(3-(aminomethyl)phenyl)-7-cyclopropyl-2-methylbenzofuran-3-yl)methoxy)-4-methoxyphenyl)acetate (273i) which was used as such for the next step.

Step-9: Preparation of 2-(2-((5-(3-(aminomethyl)phenyl)-7-cyclopropyl-2-methylbenzofuran-3-yl)methoxy)-4-methoxyphenyl)acetic acid (273j)

Compound 273j was prepared according to the procedure reported in step-3 of scheme 1, from ethyl 2-(2-((5-(3-(aminomethyl)phenyl)-7-cyclopropyl-2-methylbenzofuran-3-yl)methoxy)-4-methoxyphenyl)acetate (273i) (119 mg, 0.238 mmol) in THF (2 mL), methanol (0.2 mL) and water (0.2 mL) using lithium hydroxide monohydrate (22.82 mg, 0.953 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-cyclopropyl-2-methylbenzofuran-3-yl)methoxy)-4-methoxyphenyl)acetic acid (273j) (30 mg, 27% yield) HCl salt as a white solid; $^1H$ NMR (300 MHz, DMSO-$d_6$) δ 8.23 (s, 3H, $D_2O$ exchangeable), 7.81 (s, 1H), 7.72 (d, J=7.6 Hz, 1H), 7.69 (d, J=1.7 Hz, 1H), 7.50 (t, J=7.6 Hz, 1H), 7.41 (d, J=7.7 Hz, 1H), 7.13 (d, J=1.7 Hz, 1H), 7.08 (d, J=8.3 Hz, 1H), 6.82 (d, J=2.4 Hz, 1H), 6.50 (dd, J=8.3, 2.4 Hz, 1H), 5.24 (s, 2H), 4.11 (s, 2H), 3.76 (s, 3H), 3.40 (s, 2H), 2.54 (s, 3H), 2.34-2.22 (m, 1H), 1.19-1.03 (m, 2H), 1.03-0.93 (m, 2H); MS (ES+): 472.2 (M+1); Analysis calculated for $C_{29}H_{29}NO_5 \cdot HCl \cdot 1.5H_2O$: C, 65.10; H, 6.22; Cl, 6.63; N, 2.62. Found: C, 64.94; H, 6.18; Cl, 6.48; N, 2.58.

Scheme 274

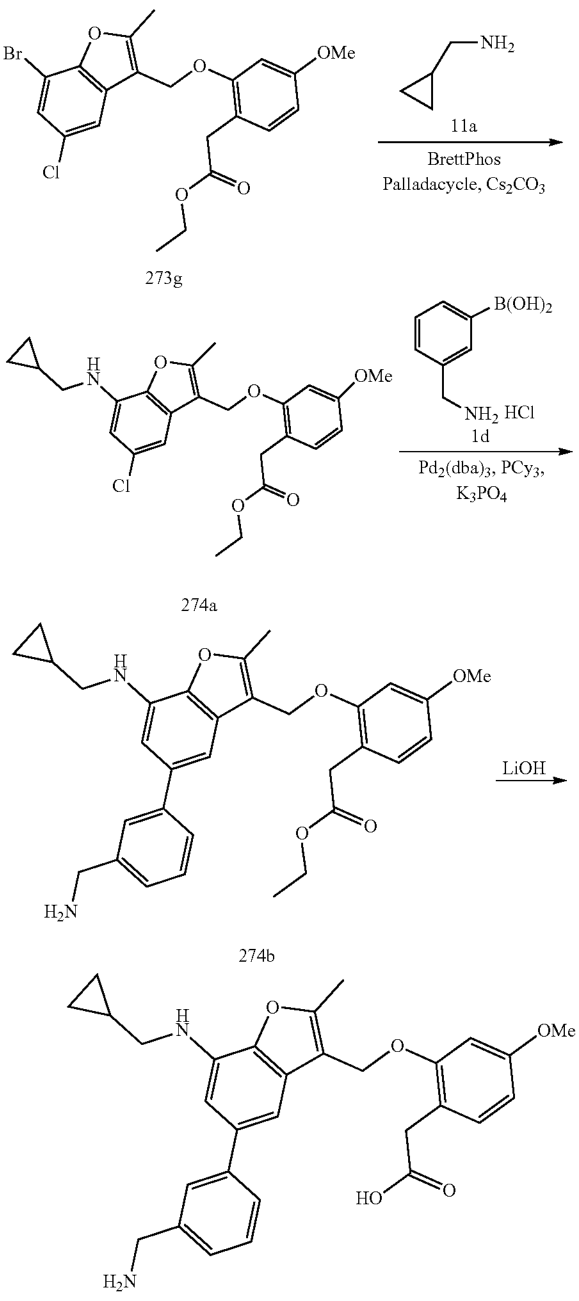

273g

274a

274b

274c

Preparation of 2-(2-((5-(3-(aminomethyl)phenyl)-7-((cyclopropylmethyl)amino)-2-methylbenzofuran-3-yl)methoxy)-4-methoxyphenyl)acetic acid (274c)

Step-1: Preparation of ethyl 2-(2-((5-chloro-7-((cyclopropylmethyl)amino)-2-methylbenzofuran-3-yl)methoxy)-4-methoxyphenyl)acetate (274a)

Compound 274a was prepared according to the procedure reported in step-8 of scheme 3, from ethyl 2-(2-((7-bromo-5-chloro-2-methylbenzofuran-3-yl)methoxy)-4-methoxyphenyl)acetate (273g) (679 mg, 1.452 mmol) in acetonitrile (2 mL) using cyclopropylmethanamine (11a) (0.249 mL, 2.90 mmol), BrettPhos Palladacycle (57.9 mg, 0.073 mmol), cesium carbonate (1419 mg, 4.36 mmol) and stirring at 90° C. for 2 h in microwave. This gave after workup and purification using flash column chromatography [silica gel (12 g), eluting with EtOAc in hexanes from 0-50%] ethyl 2-(2-((5-chloro-7-((cyclopropylmethyl)amino)-2-methylbenzofuran-3-yl)methoxy)-4-methoxyphenyl)acetate (274a) (367 mg, 55% yield); MS (ES+): 457.70 (M+1).

Step-2: Preparation of ethyl 2-(2-((5-(3-(aminomethyl)phenyl)-7-((cyclopropylmethyl)amino)-2-methylbenzofuran-3-yl)methoxy)-4-methoxyphenyl) acetate (274b)

Compound 274b was prepared according to the procedure reported in step-2 of scheme 1, from ethyl 2-(2-((5-chloro-7-((cyclopropylmethyl)amino)-2-methylbenzofuran-3-yl) methoxy)-4-methoxyphenyl)acetate (274a) (367 mg, 0.801 mmol) in dioxane (4 mL) and 2-methyltetrahydrofuran (2 mL) using (3-(aminomethyl)phenyl)boronic acid hydrochloride (1d) (376 mg, 2.004 mmol), 4M solution of $K_3PO_4$ (0.801 mL, 3.21 mmol), tricyclohexylphosphine (180 mg, 0.641 mmol), $Pd_2(dba)_3$ (294 mg, 0.321 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-((cyclopropylmethyl)amino)-2-methylbenzofuran-3-yl)methoxy)-4-methoxyphenyl)acetate (274b) (102 mg, 24% yield); MS (ES+): 528.80 (M+1).

Step-3: Preparation of 2-(2-((5-(3-(aminomethyl)phenyl)-7-((cyclopropylmethyl)amino)-2-methylbenzofuran-3-yl)methoxy)-4-methoxyphenyl)acetic acid (274c)

Compound 274c was prepared according to the procedure reported in step-3 of scheme 1, from ethyl 2-(2-((5-(3-(aminomethyl)phenyl)-7-((cyclopropylmethyl)amino)-2-methylbenzofuran-3-yl)methoxy)-4-methoxyphenyl)acetate (274b) (102 mg, 0.193 mmol) in THF (2 mL), methanol (0.2 mL) and water (0.2 mL) using lithium hydroxide monohydrate (18.48 mg, 0.772 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-((cyclopropylmethyl) amino)-2-methylbenzofuran-3-yl)methoxy)-4-methoxyphenyl)acetic acid (274c) (27 mg, 28% yield) HCl salt as a white solid; $^1H$ NMR (300 MHz, DMSO-$d_6$) δ 8.34 (s, 4H, $D_2O$ exchangeable), 7.80 (s, 1H), 7.68 (d, J=7.6 Hz, 1H), 7.48 (t, J=7.6 Hz, 1H), 7.41 (d, J=7.5 Hz, 1H), 7.17 (s, 1H), 7.08 (d, J=8.3 Hz, 1H), 6.83 (s, 1H), 6.81 (d, J=2.4 Hz, 1H), 6.49 (dd, J=8.2, 2.3 Hz, 1H), 5.20 (s, 2H), 4.16-4.04 (m, 2H), 3.76 (s, 3H), 3.41 (s, 2H), 3.18 (d, J=6.7 Hz, 2H), 2.51 (s, 3H), 1.26-1.09 (m, 1H), 0.53-0.43 (m, 2H), 0.36-0.18 (m, 2H); MS (ES+): 501.2 (M+1); (ES−): 499.2 (M−1); Analysis calculated for $C_{30}H_{32}N_2O_5 \cdot 2HCl \cdot 2H_2O$: C, 59.11; H, 6.28; N, 4.60. Found: C, 58.82; H, 6.08; N, 4.55.

Scheme 275

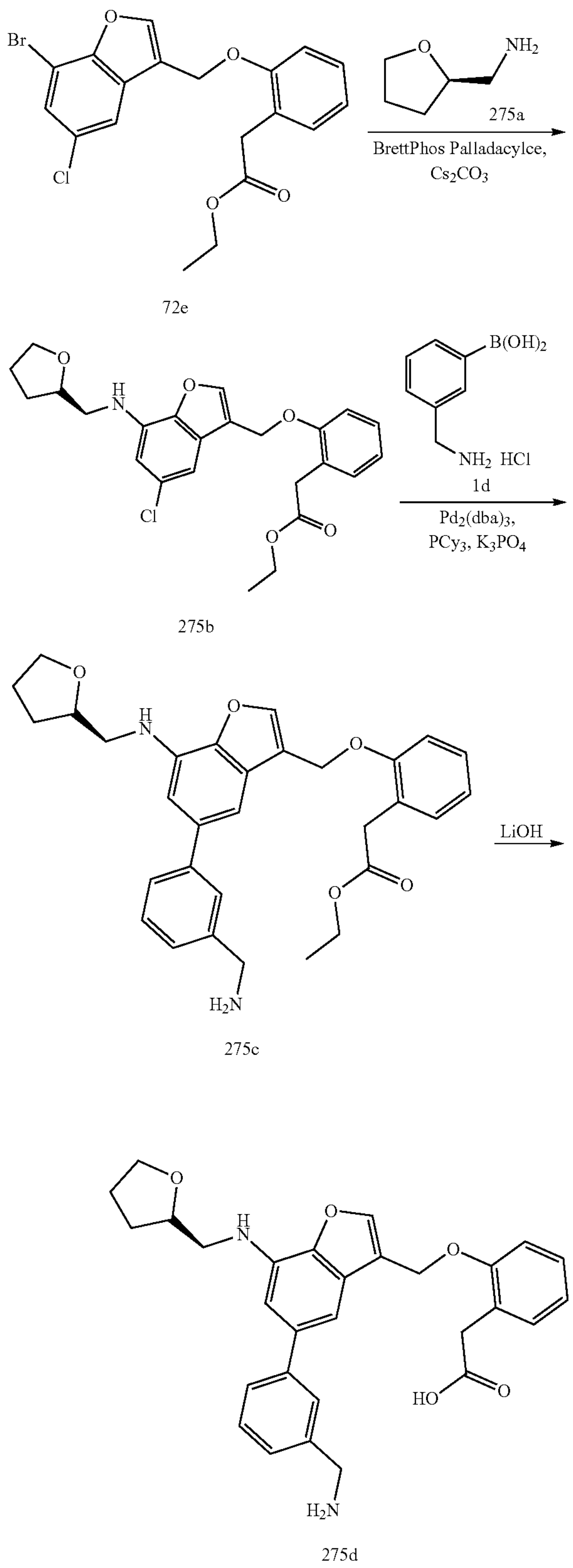

72e

275b

275c

275d

Preparation of (S)-2-(2-((5-(3-(aminomethyl)phenyl)-7-(((tetrahydrofuran-2-yl)methyl)amino)benzofuran-3-yl)methoxy)phenyl)acetic acid (275d)

Step-1: Preparation of (S)-ethyl 2-(2-((5-chloro-7-(((tetrahydrofuran-2-yl)methyl)amino)benzofuran-3-yl)methoxy)phenyl)acetate (275b)

Compound 275b was prepared according to the procedure reported in step-8 of scheme 3, from ethyl 2-(2-((7-bromo-5-chlorobenzofuran-3-yl)methoxy)phenyl)acetate (72e) (2 g, 4.72 mmol) in acetonitrile (3 mL) using (S)-(tetrahydrofuran-2-yl)methanamine (275a) (0.249 mL, 2.90 mmol; CAS #7202-43-9), BrettPhos Palladacycle (0.188 g, 0.236 mmol), cesium carbonate (4.61 g, 14.16 mmol) and stirring at 90° C. for 2 h in microwave. This gave after workup and purification using flash column chromatography [silica gel (12 g), eluting with DMA-80 in DCM from 0-50%](S)-ethyl 2-(2-((5-chloro-7-(((tetrahydrofuran-2-yl)methyl)amino) benzofuran-3-yl)methoxy)phenyl)acetate (275b) (0.896 g, 43% yield); MS (ES+): 443.70 (M+1).

Step-2: Preparation of (S)-ethyl 2-(2-((5-(3-(aminomethyl)phenyl)-7-(((tetrahydrofuran-2-yl)methyl) amino)benzofuran-3-yl)methoxy)phenyl)acetate (275c)

Compound 275c was prepared according to the procedure reported in step-2 of scheme 1, from (S)-ethyl 2-(2-((5-chloro-7-(((tetrahydrofuran-2-yl)methyl)amino)benzofuran-3-yl)methoxy)phenyl)acetate (275b) (896 mg, 2.018 mmol) in dioxane (8 mL) and 2-methyltetrahydrofuran (4 mL) using (3-(aminomethyl)phenyl)boronic acid hydrochloride (1d) (946 mg, 5.05 mmol), 4M solution of $K_3PO_4$ (2.018 mL, 8.07 mmol), tricyclohexylphosphine (453 mg, 1.615 mmol), $Pd_2(dba)_3$ (739 mg, 0.807 mmol) and heating at 115° C. for 16 h. This gave after workup and purification by flash column chromatography [silica gel (24 g), eluting with DMA-80 in DCM from 0-70%](S)-ethyl 2-(2-((5-(3-(aminomethyl)phenyl)-7-(((tetrahydrofuran-2-yl)methyl)amino) benzofuran-3-yl)methoxy)phenyl)acetate (275c) (1.039 g, 100% yield); MS (ES+): 514.80 (M+1).

Step-3: Preparation of (S)-2-(2-((5-(3-(aminomethyl)phenyl)-7-(((tetrahydrofuran-2-yl)methyl) amino)benzofuran-3-yl)methoxy)phenyl)acetic acid (275d)

Compound 275d was prepared according to the procedure reported in step-3 of scheme 1, from (S)-ethyl 2-(2-((5-(3-(aminomethyl)phenyl)-7-(((tetrahydrofuran-2-yl)methyl) amino)benzofuran-3-yl)methoxy)phenyl)acetate (275c) (1.039 g, 2.019 mmol) in THE (6 mL), methanol (0.6 mL) and water (0.6 mL) using lithium hydroxide monohydrate (0.193 g, 8.08 mmol) and stirring for 10 h at RT. This gave after workup and purification using reverse phase column chromatography [C18 column (40 g), eluting with ACN in water (containing 0.1% HCl) from 0-100%](S)-2-(2-((5-(3-(aminomethyl)phenyl)-7-(((tetrahydrofuran-2-yl)methyl) amino)benzofuran-3-yl)methoxy)phenyl)acetic acid (275d) (14 mg, 1.4% yield) HCl salt as a white solid; $^1H$ NMR (300 MHz, DMSO-$d_6$) δ 8.29 (s, 3H, $D_2O$ exchangeable), 8.04 (s, 1H), 7.80 (s, 1H), 7.70 (d, 1H), 7.50 (t, J=7.6 Hz, 1H), 7.42 (d, J=7.8 Hz, 1H), 7.34-7.24 (m, 1H), 7.24-7.14 (m, 4H), 6.93 (t, J=7.5 Hz, 1H), 6.87 (s, 1H), 5.26 (s, 2H), 4.20-4.03 (m, 3H), 3.86-3.74 (m, 1H), 3.73-3.65 (m, 1H), 3.64 (m, 2H), 3.38-3.30 (m, 2H), 2.06-1.90 (m, 1H), 1.92-1.75 (m, 2H), 1.75-1.61 (m, 1H); MS (ES+): 487.3 (M+1); (ES−): 485.2 (M−1).

Scheme 276

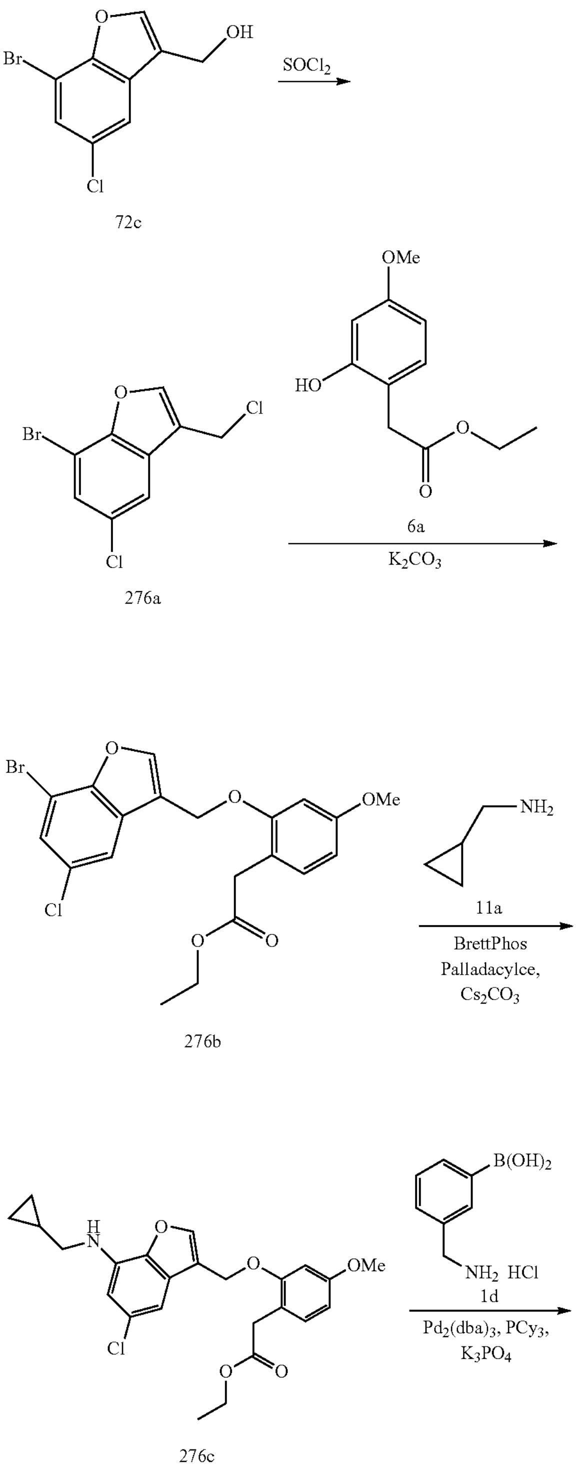

72c 276a 6a 276b 11a 276c 1d

-continued

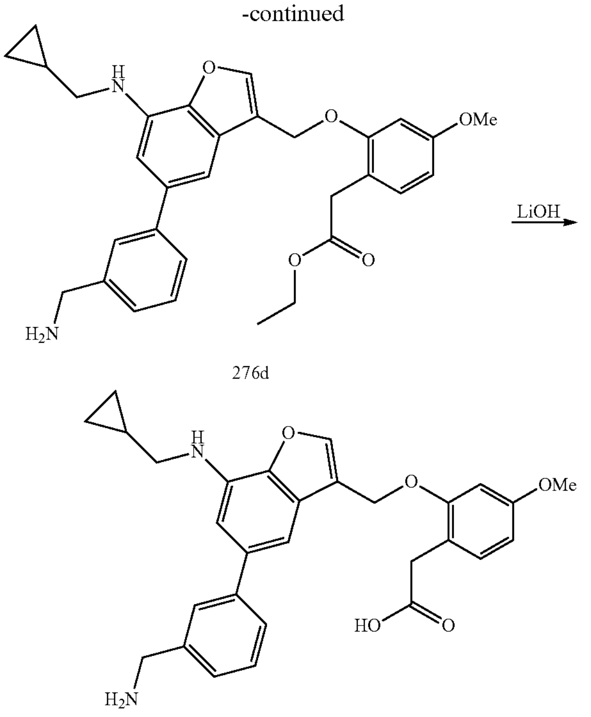

276d

276e

Preparation of 2-(2-((5-(3-(aminomethyl)phenyl)-7-((cyclopropylmethyl)amino)benzofuran-3-yl)methoxy)-4-methoxyphenyl)acetic acid (276e)

Step-1: Preparation of 7-bromo-5-chloro-3-(chloromethyl)benzofuran (276a)

Compound 276a was prepared according to the procedure reported in step-2 of scheme 39, from (7-bromo-5-chlorobenzofuran-3-yl)methanol (72c) (88.0 g, 336.52 mmol) in DCM (3080 mL) using thionyl chloride (48.8 mL, 673.04 mmol), DMF (11.5 mL) at 10° C. and stirring at RT for 4 h. This gave after workup 7-bromo-5-chloro-3-(chloromethyl) benzofuran (276a) (84.0 g, 89.2%); $^1H$ NMR (300 MHz, DMSO-$d_6$) δ 8.34 (s, 1H), 7.86 (d, J=1.9 Hz, 1H), 7.75 (d, J=2.0 Hz, 1H), 4.98 (s, 2H).

Step-2: Preparation of ethyl 2-(2-((7-bromo-5-chlorobenzofuran-3-yl)methoxy)-4-methoxyphenyl)acetate (276b)

Compound 276b was prepared according to the procedure reported in step-1 of scheme 1, from 7-bromo-5-chloro-3-(chloromethyl)benzofuran (276a) (10 g, 35.7 mmol) in acetone (10 mL) using ethyl 2-(2-hydroxy-4-methoxyphenyl)acetate (6a) (6.83 g, 32.5 mmol), $K_2CO_3$ (13.46 g, 97 mmol) and stirring overnight at RT. This gave after workup and purification using flash column chromatography [silica gel (12 g), eluting with EtOAc in hexane from 0-50%] ethyl 2-(2-((7-bromo-5-chlorobenzofuran-3-yl)methoxy)-4-methoxyphenyl)acetate (276b) (9.972 g, 68% yield); $^1H$ NMR (300 MHz, DMSO-$d_6$) δ 9.51 (s, 1H), 8.29 (s, 1H), 7.75 (q, J=2.0 Hz, 2H), 7.11 (d, J=8.3 Hz, 1H), 6.99 (d, J=8.2 Hz, 1H), 5.24 (s, 2H), 3.92 (q, J=7.1 Hz, 2H), 3.77 (s, 3H), 3.45 (s, 2H), 0.99 (t, J=7.1 Hz, 3H).

Step-3: Preparation of ethyl 2-(2-((5-chloro-7-((cyclopropylmethyl)amino)benzofuran-3-yl)methoxy)-4-methoxyphenyl)acetate (276c)

Compound 276c was prepared according to the procedure reported in step-8 of scheme 3, from ethyl 2-(2-((7-bromo-5-chlorobenzofuran-3-yl)methoxy)-4-methoxyphenyl)acetate (276b) (2 g, 4.41 mmol) in acetonitrile (2 mL) using cyclopropylmethanamine (11a) (0.755 mL, 8.82 mmol), BrettPhos Palladacycle (0.176 g, 0.220 mmol) and cesium carbonate (4.31 g, 13.22 mmol) and stirring at 90° C. for 2 h in microwave. This gave after workup and purification using flash column chromatography [silica gel (12 g), eluting with EtOAc in hexanes from 0-50%] ethyl 2-(2-((5-chloro-7-((cyclopropylmethyl)amino)benzofuran-3-yl) methoxy)-4-methoxyphenyl)acetate (276c) (407 mg, 21% yield); MS (ES+): 444.20 (M+1).

Step-4: Preparation of ethyl 2-(2-((5-(3-(aminomethyl)phenyl)-7-((cyclopropylmethyl)amino)benzofuran-3-yl)methoxy)-4-methoxyphenyl)acetate (276d)

Compound 276d was prepared according to the procedure reported in step-2 of scheme 1, from ethyl 2-(2-((5-chloro-7-((cyclopropylmethyl)amino)benzofuran-3-yl)methoxy)-4-methoxyphenyl)acetate (276c) (407 mg, 0.917 mmol) in dioxane (6 mL) and 2-methyltetrahydrofuran (3 mL) using (3-(aminomethyl) phenyl)boronic acid hydrochloride (1d) (430 mg, 2.292 mmol), 4M solution of $K_3PO_4$ (0.917 mL, 3.67 mmol), tricyclohexylphosphine (206 mg, 0.733 mmol), $Pd_2(dba)_3$ (336 mg, 0.367 mmol) and heating at 115° C. for 16 h. This gave after workup ethyl 2-(2-((5-(3-(aminomethyl)phenyl)-7-((cyclopropylmethyl)amino)benzofuran-3-yl)methoxy)-4-methoxyphenyl)acetate (276d) (338 mg) and was used as such for the next step; MS (ES+): 515.30 (M+1).

Step-5: Preparation of 2-(2-((5-(3-(aminomethyl) phenyl)-7-((cyclopropylmethyl)amino)benzofuran-3-yl)methoxy)-4-methoxyphenyl)acetic acid (276e)

Compound 276e was prepared according to the procedure reported in step-3 of scheme 1, from ethyl 2-(2-((5-(3-(aminomethyl)phenyl)-7-((cyclopropylmethyl)amino)benzofuran-3-yl)methoxy)-4-methoxyphenyl)acetate (276d) (338 mg, 0.657 mmol) in THF (6 mL), MeOH (0.6 mL), water (0.6 mL) using a solution of lithium hydroxide monohydrate (62.9 mg, 2.63 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-((cyclopropylmethyl) amino)benzofuran-3-yl)methoxy)-4-methoxyphenyl)acetic acid (276e) (41 mg, 13% yield) HCl salt as a light brown solid; $^1H$ NMR (300 MHz, DMSO-$d_6$) δ 8.20 (s, 4H, $D_2O$ exchangeable), 7.97 (s, 1H), 7.72 (s, 1H), 7.62 (d, J=7.3 Hz, 1H), 7.42 (t, J=7.6 Hz, 1H), 7.35 (d, J=7.4 Hz, 1H), 7.10 (d, J=1.6 Hz, 1H), 7.03 (d, J=8.3 Hz, 1H), 6.76 (s, 1H), 6.71 (d, J=2.4 Hz, 1H), 6.43 (dd, J=8.3, 2.4 Hz, 1H), 5.18 (s, 2H), 4.11-3.93 (m, 2H), 3.69 (s, 3H), 3.39 (s, 2H), 3.11 (d, J=6.7 Hz, 2H), 1.27-1.03 (m, 1H), 0.46-0.36 (m, 2H), 0.25-0.17 (m, 2H); MS (ES+): 487.2 (M+1); (ES−): 485.2 (M−1).

Scheme 277

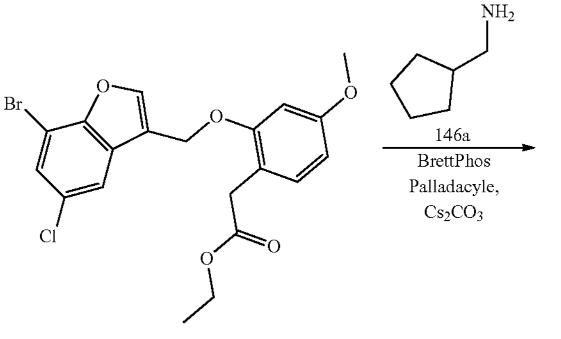

276b

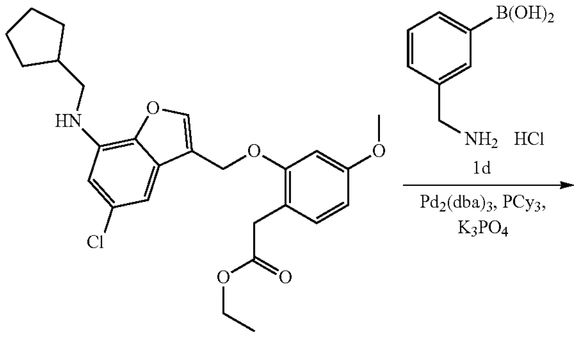

277a

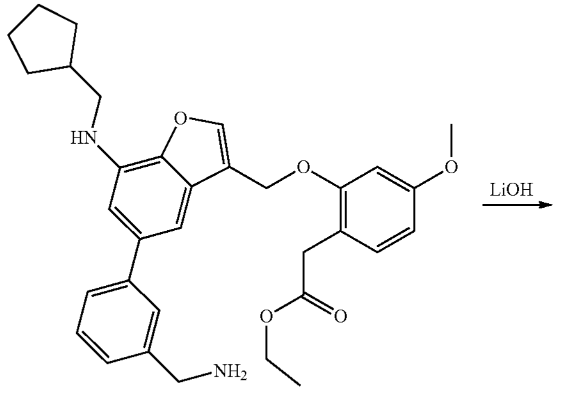

277b

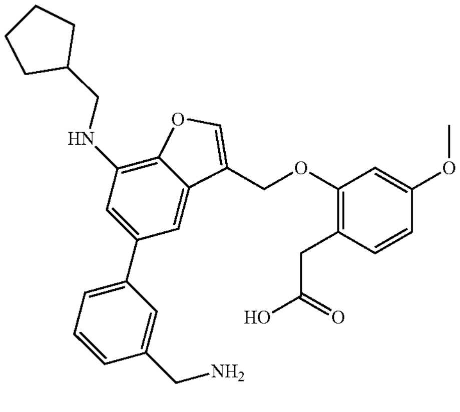

277c

Preparation of 2-(2-((5-(3-(aminomethyl)phenyl)-7-((cyclopentylmethyl)amino)benzofuran-3-yl) methoxy)-4-methoxyphenyl)acetic acid (277c)

Step-1: Preparation of ethyl 2-(2-((5-chloro-7-((cyclopentylmethyl)amino)benzofuran-3-yl)methoxy)-4-methoxyphenyl)acetate (277a)

Compound 277a was prepared according to the procedure reported in step-8 of schemes 3, from ethyl 2-(2-((7-bromo-5-chlorobenzofuran-3-yl)methoxy)-4-methoxyphenyl)acetate (276b) (2 g, 4.41 mmol) in acetonitrile (2 mL) using cyclopentylmethanamine (146a) (1.053 mL, 8.82 mmol), BrettPhos Palladacycle (0.176 g, 0.220 mmol), cesium carbonate (4.31 g, 13.22 mmol) and stirring at 90° C. for 2 h in microwave. This gave after workup and purification by flash column chromatography [silica gel (12 g), eluting with EtOAc in hexanes from 0-50%] ethyl 2-(2-((5-chloro-7-((cyclopentylmethyl)amino)benzofuran-3-yl)methoxy)-4-methoxyphenyl)acetate (277a) (0.845 g, 41% yield); $^1$H NMR (300 MHz, DMSO-$d_6$) δ 8.04 (s, 1H), 7.75 (q, J=2.0 Hz, 1H), 7.09 (dd, J=2.9 Hz, 1H), 6.78-6.74 (m, 1H), 6.48 (d, J=2.1 Hz, 1H), 6.13 (t, J=5.8 Hz, 1H), 5.16 (s, 2H), 3.98-3.92 (m, 2H), 3.77 (s, 3H), 3.47 (s, 2H), 3.15-3.05 (m, 2H), 2.34-2.15 (m, 1H), 1.81-1.66 (m, 2H), 1.66-1.44 (m, 2H), 1.35-1.21 (m, 2H), 1.06-1.00 (m, 3H), 0.99-0.94 (m, 2H).

Step-2: Preparation of ethyl 2-(2-((5-(3-(aminomethyl)phenyl)-7-((cyclopentylmethyl)amino)benzofuran-3-yl)methoxy)-4-methoxyphenyl)acetate (277b)

Compound 277b was prepared according to the procedure reported in step-2 of scheme 1, from ethyl 2-(2-((5-chloro-7-((cyclopentylmethyl)amino)benzofuran-3-yl)methoxy)-4-methoxyphenyl)acetate (277a) (845 mg, 1.790 mmol) in dioxane (6 mL) and 2-methyltetrahydrofuran (3 mL) using (3-(aminomethyl) phenyl)boronic acid hydrochloride (1d) (839 mg, 4.48 mmol), 4M solution of $K_3PO_4$ (1.790 mL, 7.16 mmol), tricyclohexylphosphine (402 mg, 1.432 mmol), $Pd_2(dba)_3$ (656 mg, 0.716 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-((cyclopentylmethyl)amino)benzofuran-3-yl)methoxy)-4-methoxyphenyl)acetate (277b) (247 mg, 25% yield); MS (ES+): 543.30 (M+1).

Step-3: Preparation of 2-(2-((5-(3-(aminomethyl) phenyl)-7-((cyclopentylmethyl)amino)benzofuran-3-yl)methoxy)-4-methoxyphenyl)acetic acid (277c)

Compound 277c was prepared according to the procedure reported in step-3 of scheme 1, from ethyl 2-(2-((5-(3-(aminomethyl)phenyl)-7-((cyclopentylmethyl)amino)benzofuran-3-yl)methoxy)-4-methoxyphenyl)acetate (277b) (247 mg, 0.455 mmol) in THF (2 mL), MeOH (0.2 mL), water (0.2 mL) and using a solution of lithium hydroxide monohydrate (43.6 mg, 1.821 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-((cyclopentylmethyl) amino)benzofuran-3-yl)methoxy)-4-methoxyphenyl)acetic acid (277c) (20 mg, 9% yield) HCl salt as a light brown solid; $^1$H NMR (300 MHz, DMSO-$d_6$) δ 8.26 (s, 3H, $D_2O$ exchangeable), 8.03 (s, 1H), 7.78 (s, 1H), 7.68 (d, J=7.7 Hz, 1H), 7.50 (t, J=7.6 Hz, 1H), 7.42 (d, J=7.8 Hz, 1H), 7.15 (d, J=1.5 Hz, 1H), 7.10 (d, J=8.3 Hz, 1H), 6.78 (s, 2H), 6.50 (dd, J=8.3, 2.3 Hz, 1H), 5.25 (s, 2H), 4.17-4.05 (m, 2H), 3.76 (s, 3H), 3.45 (s, 2H), 3.20 (d, J=7.2 Hz, 2H), 2.35-2.24 (m, 1H), 1.78 (s, 3H), 1.69-1.44 (m, 2H), 1.44-1.21 (m, 3H). MS (ES+): 515.3 (M+1); (ES−): 513.2 (M−1).

Scheme 278

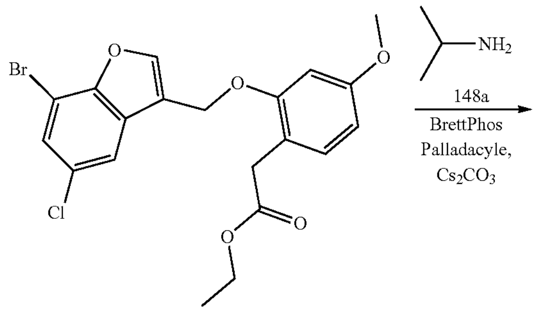

276b

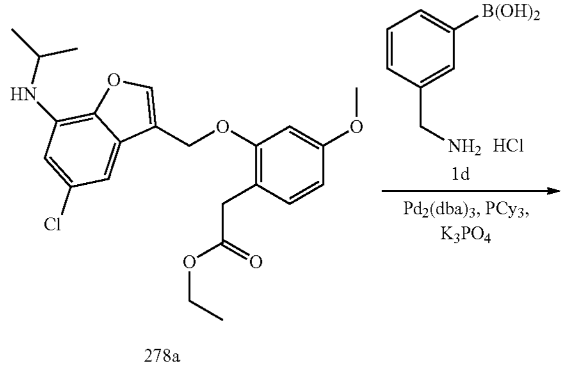

278a

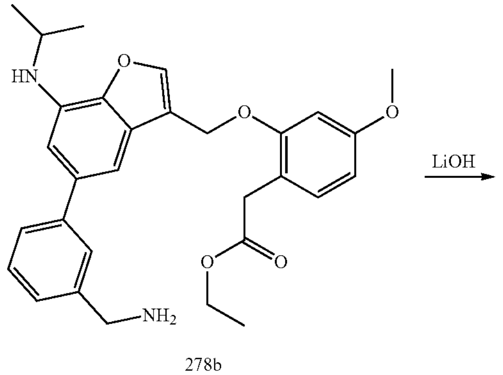

278b

-continued

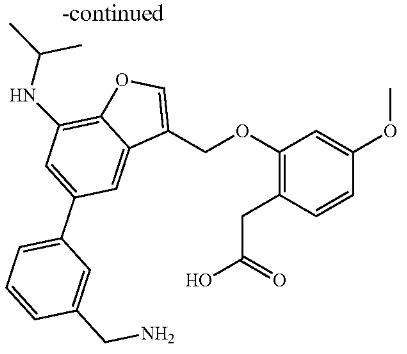

278c

Preparation of 2-(2-((5-(3-(aminomethyl)phenyl)-7-(isopropylamino)benzofuran-3-yl)methoxy)-4-methoxyphenyl)acetic acid (278c)

Step-1: Preparation of ethyl 2-(2-((5-chloro-7-(isopropylamino)benzofuran-3-yl)methoxy)-4-methoxyphenyl)acetate (278a)

Compound 278a was prepared according to the procedure reported in step-8 of scheme 3, from ethyl 2-(2-((7-bromo-5-chlorobenzofuran-3-yl)methoxy)-4-methoxyphenyl)acetate (276b) (2 g, 4.41 mmol) in acetonitrile (2 mL) using propan-2-amine (148a) (0.722 mL, 8.82 mmol), BrettPhos Palladacycle (0.176 g, 0.220 mmol), cesium carbonate (4.31 g, 13.22 mmol) and heating at 90° C. for 2 h in microwave. This gave after workup and purification using flash column chromatography [silica gel (24 g), eluting with EtOAc in hexanes from 0-50%] ethyl 2-(2-((5-chloro-7-(isopropylamino)benzofuran-3-yl)methoxy)-4-methoxyphenyl)acetate (278a) (596 mg, 31% yield); MS (ES+): 432.20 (M+1).

Step-2: Preparation of ethyl 2-(2-((5-(3-(aminomethyl)phenyl)-7-(isopropylamino)benzofuran-3-yl)methoxy)-4-methoxyphenyl)acetate (278b)

Compound 278b was prepared according to the procedure reported in step-2 of scheme 1, from ethyl 2-(2-((5-chloro-7-(isopropylamino)benzofuran-3-yl)methoxy)-4-methoxyphenyl)acetate (278a) (596 mg, 1.380 mmol) in dioxane (24 mL) and 2-Me THF (12 mL) using 3-(aminomethyl)phenylboronic acid hydrochloride (1d) (647 mg, 3.45 mmol), 4M solution of $K_3PO_4$ (1.38 mL, 5.52 mmol), tricyclohexylphosphine (310 mg, 1.104 mmol), $Pd_2(dba)_3$ (505 mg, 0.552 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-(isopropylamino)benzofuran-3-yl)methoxy)-4-methoxyphenyl)acetate (278b) (224 mg, 32% yield); MS (ES+): 503.3 (M+1).

Step-3: Preparation of 2-(2-((5-(3-(aminomethyl)phenyl)-7-(isopropylamino)benzofuran-3-yl)methoxy)-4-methoxyphenyl)acetic acid (278c)

Compound 278c was prepared according to the procedure reported in step-3 of scheme 1, from ethyl 2-(2-((5-(3-(aminomethyl)phenyl)-7-(isopropylamino)benzofuran-3-yl)methoxy)-4-methoxyphenyl)acetate (278b) (224 mg, 0.446 mmol) in THF (4 mL), MeOH (0.4 mL), water (0.4 mL) and using a solution of lithium hydroxide monohydrate (42.7 mg, 1.783 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(isopropylamino)benzofuran-3-yl)methoxy)-4-methoxyphenyl)acetic acid (278c) (53 mg, 25% yield) HCl salt as a light brown solid; $^1H$ NMR (300 MHz, DMSO-$d_6$) δ 8.43 (s, 4H, $D_2O$ exchangeable), 8.08 (s, 1H), 7.83 (s, 1H), 7.76-7.65 (m, 1H), 7.52 (d, J=7.6 Hz, 1H), 7.49-7.41 (m, 1H), 7.37 (s, 1H), 7.10 (d, J=8.3 Hz, 1H), 7.06 (s, 1H), 6.79 (d, J=2.4 Hz, 1H), 6.51 (dd, J=8.3, 2.3 Hz, 1H), 5.27 (s, 2H), 4.15-4.06 (m, 2H), 4.03-3.87 (m, 1H), 3.76 (s, 3H), 3.46 (s, 2H), 1.27 (d, J=6.3 Hz, 6H); MS (ES+): 475.2 (M+1); (ES−): 473.2 (M−1).

Scheme 279

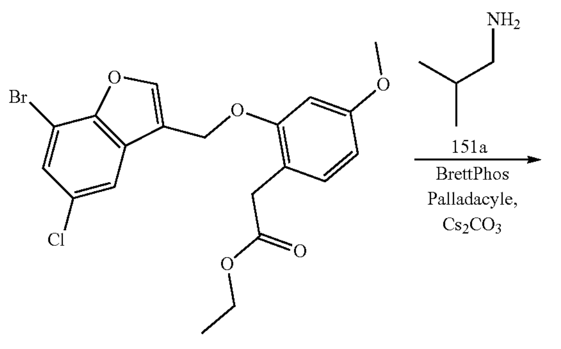

276b

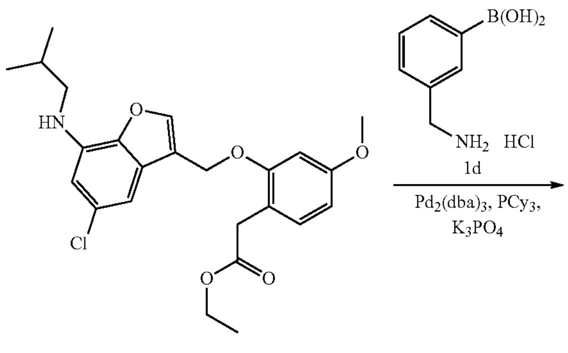

279a

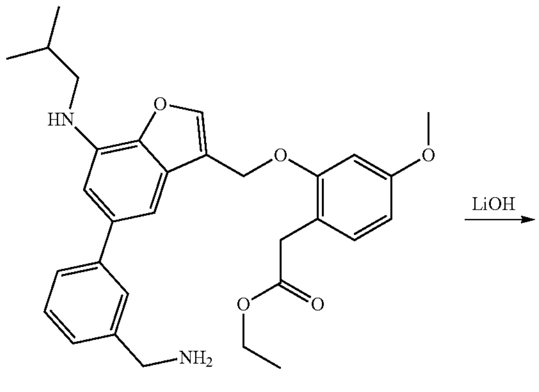

279b

-continued

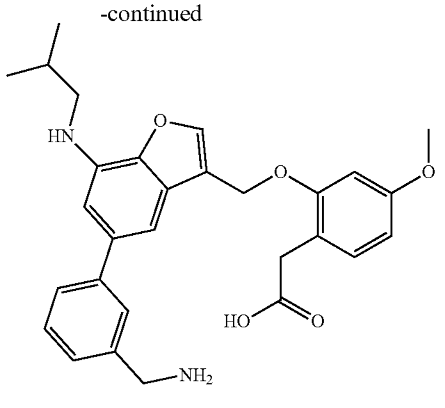

279c

Preparation of 2-(2-((5-(3-(aminomethyl)phenyl)-7-(isobutylamino)benzofuran-3-yl)methoxy)-4-methoxyphenyl)acetic acid (279c)

Step-1: Preparation of ethyl 2-(2-((5-chloro-7-(isobutylamino)benzofuran-3-yl)methoxy)-4-methoxyphenyl)acetate (279a)

Compound 279a was prepared according to the procedure reported in step-8 of scheme 3, from ethyl 2-(2-((7-bromo-5-chlorobenzofuran-3-yl)methoxy)-4-methoxyphenyl)acetate (276b) (2 g, 4.41 mmol) in acetonitrile (2 mL) using 2-methylpropan-1-amine (151a) (0.876 mL, 8.82 mmol), BrettPhos Palladacycle (0.176 g, 0.220 mmol), cesium carbonate (4.31 g, 13.22 mmol) and heating at 90° C. for 2 h in microwave. This gave after workup and purification using flash column chromatography [silica gel (12 g), eluting with EtOAc in hexanes from 0-50%] ethyl 2-(2-((5-chloro-7-(isobutylamino)benzofuran-3-yl)methoxy)-4-methoxyphenyl)acetate (279a) (648 mg, 33% yield); MS (ES+): 446.2 (M+1).

Step-2: Preparation of ethyl 2-(2-((5-(3-(aminomethyl)phenyl)-7-(isobutylamino)benzofuran-3-yl)methoxy)-4-methoxyphenyl)acetate (279b)

Compound 279b was prepared according to the procedure reported in step-2 of scheme 1, from ethyl 2-(2-((5-chloro-7-(isobutylamino)benzofuran-3-yl)methoxy)-4-methoxyphenyl)acetate (279a) (648 mg, 1.453 mmol) in dioxane (36 mL) and 2-Me THF (18 mL) using 3-(aminomethyl)phenylboronic acid hydrochloride (1d) (681 mg, 3.63 mmol), 4M solution of $K_3PO_4$ (1.453 mL, 5.81 mmol), tricyclohexylphosphine (326 mg, 1.162 mmol), $Pd_2(dba)_3$ (532 mg, 0.581 mmol) and heating at 115° C. for 16 h. This gave after workup and purification using flash column chromatography [silica gel (24 g), eluting with DMA80 in DCM from 0-70%] ethyl 2-(2-((5-(3-(aminomethyl)phenyl)-7-(isobutylamino)benzofuran-3-yl)methoxy)-4-methoxyphenyl)acetate (279b) (379 mg, 51% yield); MS (ES+): 517.30 (M+1).

Step-3: Preparation of 2-(2-((5-(3-(aminomethyl)phenyl)-7-(isobutylamino)benzofuran-3-yl)methoxy)-4-methoxyphenyl)acetic acid (279c)

Compound 279c was prepared according to the procedure reported in step-3 of scheme 1, from ethyl 2-(2-((5-(3-(aminomethyl)phenyl)-7-(isobutylamino)benzofuran-3-yl)

methoxy)-4-methoxyphenyl)acetate (279b) (379 mg, 0.734 mmol) in THF (4 mL), methanol (0.4 mL) and water (0.4 mL) using lithium hydroxide monohydrate (70.3 mg, 2.93 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(isobutylamino)benzofuran-3-yl)methoxy)-4-methoxyphenyl)acetic acid (279c) (63 mg, 18% yield) HCl salt as a light brown solid; $^1H$ NMR (300 MHz, DMSO-$d_6$) δ 8.38 (s, 3H, $D_2O$ exchangeable), 8.03 (s, 1H), 7.80 (s, 1H), 7.67 (d, J=7.6 Hz, 1H), 7.49 (t, J=7.6 Hz, 1H), 7.43 (d, J=7.6 Hz, 1H), 7.16 (d, J=1.5 Hz, 1H), 7.10 (d, J=8.3 Hz, 1H), 6.78 (d, J=2.1 Hz, 2H), 6.50 (dd, J=8.3, 2.4 Hz, 1H), 5.25 (s, 2H), 4.20-4.04 (m, 2H), 3.76 (s, 3H), 3.46 (s, 2H), 3.11 (d, J=6.9 Hz, 2H), 2.11-1.92 (m, 1H), 0.98 (d, J=6.6 Hz, 6H). MS (ES+): 489.3 (M+1): (ES−): 487.2 (M−1); Analysis calculated for $C_{29}H_{32}N_2O_5 \cdot 1.5H_2O \cdot 1.5HCl$: C, 61.08; H, 6.45; Cl, 9.33; N, 4.91. Found: C, 60.83; H, 6.57; Cl, 9.20; N, 4.70.

Scheme 280

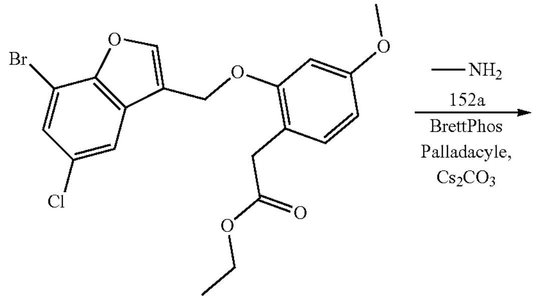

276b

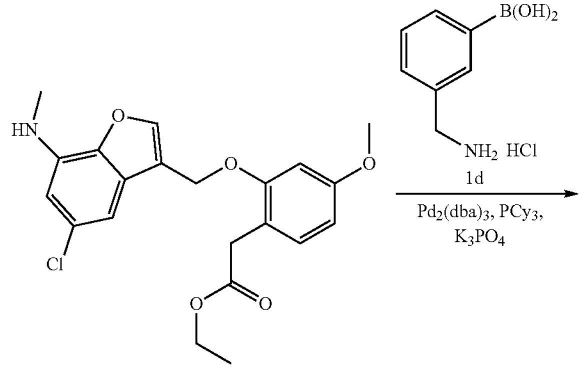

280a

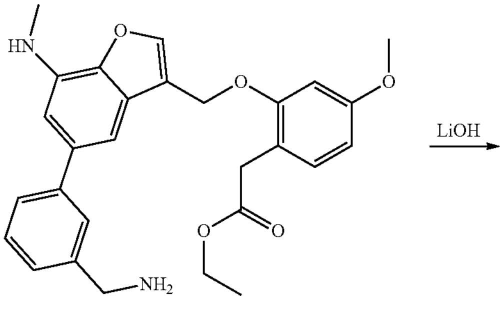

280b

-continued

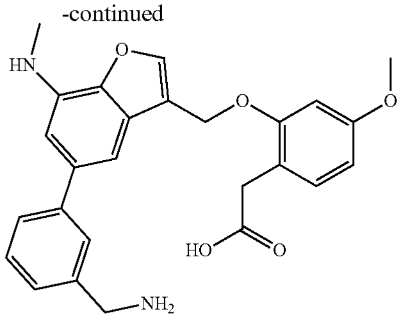

280c

Preparation of 2-(2-((5-(3-(aminomethyl)phenyl)-7-(methylamino)benzofuran-3-yl)methoxy)-4-methoxyphenyl)acetic acid (280c)

Step-1: Preparation of ethyl 2-(2-((5-chloro-7-(methylamino)benzofuran-3-yl)methoxy)-4-methoxyphenyl)acetate (280a)

Compound 280a was prepared according to the procedure reported in step-8 of scheme 3, from ethyl 2-(2-((7-bromo-5-chlorobenzofuran-3-yl)methoxy)-4-methoxyphenyl)acetate (276b) (2 g, 4.41 mmol) in acetonitrile (2 mL) using methanamine (152a) (4.41 mL, 8.82 mmol), BrettPhos Palladacycle (0.176 g, 0.220 mmol), cesium carbonate (4.31 g, 13.22 mmol) and heating at 90° C. for 2 h in microwave. This gave after workup and purification using flash column chromatography [silica gel (12 g), eluting with EtOAc in hexanes from 0-50%] ethyl 2-(2-((5-chloro-7-(methylamino)benzofuran-3-yl)methoxy)-4-methoxyphenyl)acetate (280a) (467 mg, 26% yield); MS (ES+): 404.10 (M+1).

Step-2: Preparation of ethyl 2-(2-((5-(3-(aminomethyl)phenyl)-7-(methylamino)benzofuran-3-yl)methoxy)-4-methoxyphenyl)acetate (280b)

Compound 280b was prepared according to the procedure reported in step-2 of scheme 1, from ethyl 2-(2-((5-chloro-7-(methylamino)benzofuran-3-yl)methoxy)-4-methoxyphenyl)acetate (280a) (467 mg, 1.156 mmol) in dioxane (24 mL) and 2-Me THF (12 mL) using 3-(aminomethyl)phenylboronic acid hydrochloride (1d) (542 mg, 2.89 mmol), 4M solution of $K_3PO_4$ (1.156 mL, 4.63 mmol), tricyclohexylphosphine (259 mg, 0.925 mmol), $Pd_2(dba)_3$ (424 mg, 0.463 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-(methylamino)benzofuran-3-yl)methoxy)-4-methoxyphenyl)acetate (280b) (252 mg, 46% yield); MS (ES+): 475.20 (M+1).

Step-3: Preparation of 2-(2-((5-(3-(aminomethyl)phenyl)-7-(methylamino)benzofuran-3-yl)methoxy)-4-methoxyphenyl)acetic acid (280c)

Compound 280c was prepared according to the procedure reported in step-3 of scheme 1, from ethyl 2-(2-((5-(3-(aminomethyl)phenyl)-7-(methylamino)benzofuran-3-yl)methoxy)-4-methoxyphenyl)acetate (280b) (252 mg, 0.531 mmol) in THF (4 mL), methanol (0.4 mL) and water (0.4 mL) using lithium hydroxide monohydrate (50.9 mg, 2.124 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-(methylamino)benzofuran-3-yl)methoxy)-4-methoxyphenyl)acetic acid (280c) (100 mg, 42% yield) HCl salt as a white solid; $^1$H NMR (300 MHz, DMSO-$d_6$) δ 8.32 (s, 4H, $D_2O$ exchangeable), 8.03 (s, 1H), 7.83 (s, 1H), 7.71 (d, J=7.8 Hz, 1H), 7.50 (t, J=7.6 Hz, 1H), 7.42 (d, J=7.6 Hz, 1H), 7.19 (d, J=1.6 Hz, 1H), 7.10 (d, J=8.3 Hz, 1H), 6.78 (d, J=2.4 Hz, 1H), 6.75 (d, J=1.5 Hz, 1H), 6.50 (dd, J=8.3, 2.3 Hz, 1H), 5.26 (s, 2H), 4.16-4.06 (m, 2H), 3.76 (s, 3H), 3.45 (s, 2H), 2.91 (s, 3H); MS (ES+): 447.2 (M+1); (ES−): 445.2 (M−1); Analysis calculated for $C_{26}H_{26}N_2O_5\cdot 2HCl\cdot 0.5H_2O$: C, 59.10; H, 5.53; Cl, 13.42; N, 5.30. Found: C, 59.03; H, 5.60; Cl, 13.15; N, 5.60.

Scheme 281

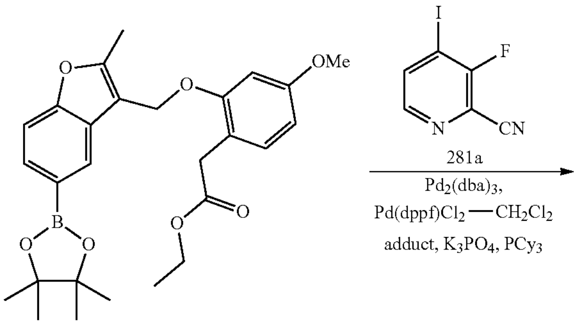

203a

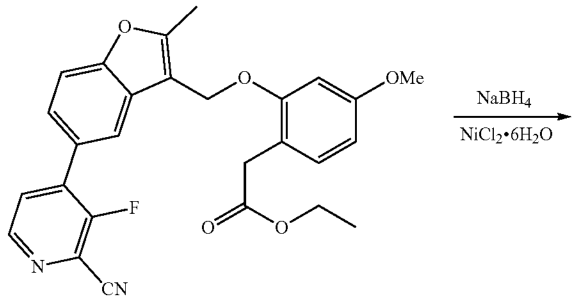

281b

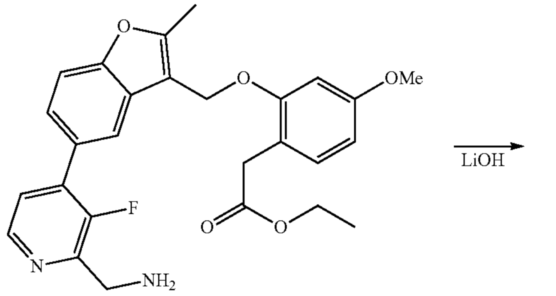

281c

-continued

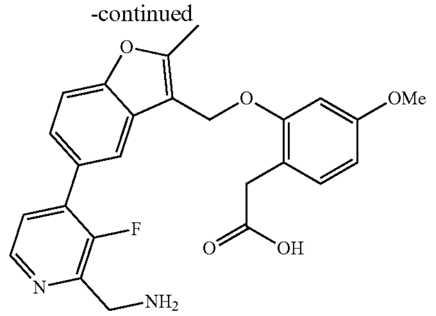

281d

Preparation of 2-(2-((5-(2-(aminomethyl)-3-fluoropyridin-4-yl)-2-methylbenzofuran-3-yl)methoxy)-4-methoxyphenyl)acetic acid (281d)

Step-1: Preparation of ethyl 2-(2-((5-(2-cyano-3-fluoropyridin-4-yl)-2-methylbenzofuran-3-yl)methoxy)-4-methoxyphenyl)acetate (281b)

Compound 281a was prepared according to the procedure reported in step-2 of scheme 1, from ethyl 2-(4-methoxy-2-((2-methyl-5-(4,4,5,5-tetramethyl-1,3,2-dioxaborolan-2-yl)benzofuran-3-yl)methoxy)phenyl)acetate (203a) (350 mg, 0.729 mmol) in dioxane (20 mL) using 3-fluoro-4-iodopicolinonitrile (281a) (361 mg, 1.457 mmol; CAS #669066-35-7), 4 M solution of $K_3PO_4$ (0.729 mL, 2.91 mmol), tricyclohexylphosphine (61.3 mg, 0.219 mmol), $Pd_2(dba)_3$ (133 mg, 0.146 mmol), $Pd(dppf)Cl_2$—$CH_2Cl_2$ adduct (119 mg, 0.146 mmol) and heating at 110° C. for overnight. This gave after workup and purification using flash column chromatography [silica gel (24 g), eluting with DMA-80 in DCM from 0-70%] ethyl 2-(2-((5-(2-cyano-3-fluoropyridin-4-yl)-2-methylbenzofuran-3-yl)methoxy)-4-methoxyphenyl)acetate (281b) (145 mg, 42% yield) as a clear oil; $^1$H NMR (300 MHz, DMSO-$d_6$) δ 8.67 (d, J=4.9 Hz, 1H), 8.10-8.02 (m, 1H), 7.96-7.91 (m, 1H), 7.73 (d, J=8.6 Hz, 1H), 7.62 (dt, J=8.5, 1.8 Hz, 1H), 7.08 (d, J=8.3 Hz, 1H), 6.81 (d, J=2.4 Hz, 1H), 6.49 (dd, J=8.3, 2.4 Hz, 1H), 5.24 (s, 2H), 3.77 (s, 3H), 3.69 (q, J=7.1 Hz, 2H), 3.42 (s, 2H), 2.55 (s, 3H), 0.85 (t, J=7.1 Hz, 3H); $^{19}$F NMR (282 MHz, DMSO-$d_6$) δ −123.21; MS (ES+): 497.10 (M+Na).

Step-2: Preparation of ethyl 2-(2-((5-(2-(aminomethyl)-3-fluoropyridin-4-yl)-2-methylbenzofuran-3-yl)methoxy)-4-methoxyphenyl)acetate (281c)

Compound 281c was prepared according to the procedure reported in step-2 of scheme 145, from ethyl 2-(2-((5-(2-cyano-3-fluoropyridin-4-yl)-2-methylbenzofuran-3-yl)methoxy)-4-methoxyphenyl)acetate (281b) (145 mg, 0.306 mmol) in dry EtOH (5 mL) using nickel(II) chloride (72.6 mg, 0.306 mmol) and sodium borohydride (69.4 mg, 1.834 mmol). This gave after workup and purification using flash column chromatography [silica gel, eluting with DMA-80 in DCM from 0-100%] ethyl 2-(2-((5-(2-(aminomethyl)-3-fluoropyridin-4-yl)-2-methylbenzofuran-3-yl)methoxy)-4-methoxyphenyl)acetate (281c) (82 mg, 56% yield) as a clear oil; $^1$H NMR (300 MHz, DMSO-$d_6$) δ $^1$H NMR (300 MHz, DMSO-$d_6$) δ 8.42 (d, J=4.9 Hz, 1H), 7.84 (s, 1H), 7.67 (d, J=8.6 Hz, 1H), 7.58-7.48 (m, 2H), 7.07 (d, J=8.3 Hz, 1H), 6.81 (d, J=2.4 Hz, 1H), 6.49 (dd, J=8.3, 2.4 Hz, 1H), 5.23 (s, 2H), 3.91 (d, J=2.2 Hz, 2H), 3.77 (s, 3H), 3.67 (q, J=7.1 Hz, 2H), 3.41 (s, 2H), 2.54 (s, 3H), 2.26 (s, 2H), 0.83 (t, J=7.1 Hz, 3H); $^{19}$F NMR (282 MHz, DMSO-$d_6$) δ −134.95.

Step-3: Preparation of 2-(2-((5-(2-(aminomethyl)-3-fluoropyridin-4-yl)-2-methylbenzofuran-3-yl)methoxy)-4-methoxyphenyl)acetic acid (281d)

Compound 281d was prepared according to the procedure reported in step-3 of scheme 1, from ethyl 2-(2-((5-(2-(aminomethyl)-3-fluoropyridin-4-yl)-2-methylbenzofuran-3-yl)methoxy)-4-methoxyphenyl)acetate (281c) (82 mg, 0.171 mmol) in THF (3 mL) using lithium hydroxide hydrate (21.57 mg, 0.514 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(2-(aminomethyl)-3-fluoropyridin-4-yl)-2-methylbenzofuran-3-yl)methoxy)-4-methoxyphenyl)acetic acid (281d) (45 mg, 58% yield) HCl salt as a white solid; $^{1}$H NMR (300 MHz, DMSO-$d_6$) δ 8.59 (t, J=6.0 Hz, 3H, $D_2O$ exchangeable), 8.54 (d, J=5.0 Hz, 1H), 7.95 (s, 1H), 7.79-7.68 (m, 2H), 7.58 (dt, J=8.5, 1.8 Hz, 1H), 7.08 (d, J=8.3 Hz, 1H), 6.82 (d, J=2.4 Hz, 1H), 6.50 (dd, J=8.3, 2.4 Hz, 1H), 5.26 (s, 2H), 4.42-4.16 (m, 2H), 3.76 (s, 3H), 3.40 (s, 2H), 2.55 (s, 3H); $^{19}$F NMR (282 MHz, DMSO-$d_6$) δ −132.75; MS (ES+) 451.2 (M+1); (ES−) 449.1 (M−1); Analysis calculated for $C_{25}H_{23}FN_2O_5 \cdot 1.5HCl \cdot 0.75H_2O$: C, 57.89; H, 5.05; Cl, 10.25; N, 5.40. Found: C, 58.04; H, 4.97; Cl, 10.25; N, 5.52.

Scheme 282

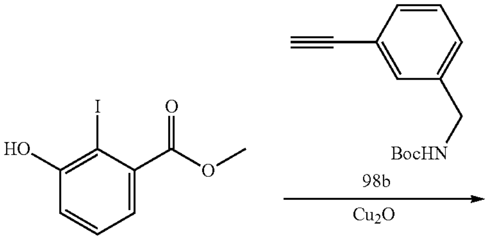

282a

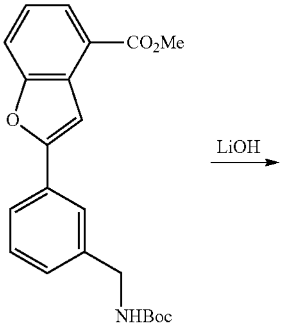

282b

-continued

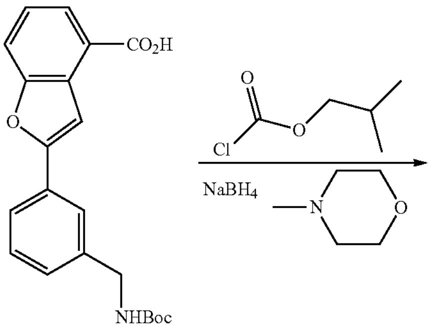

282c

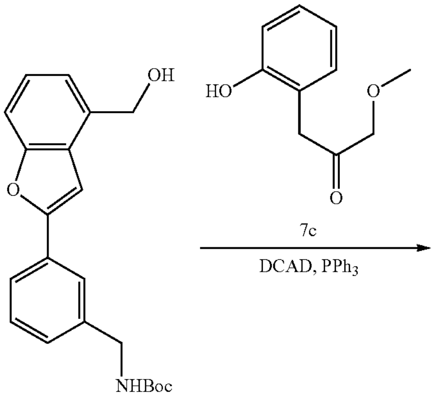

282d

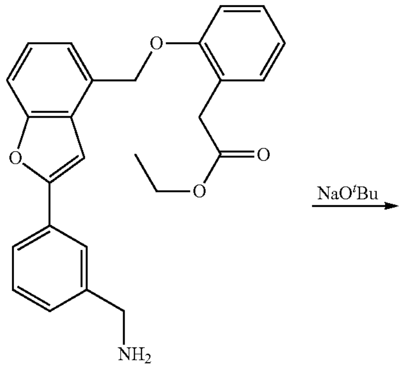

282e

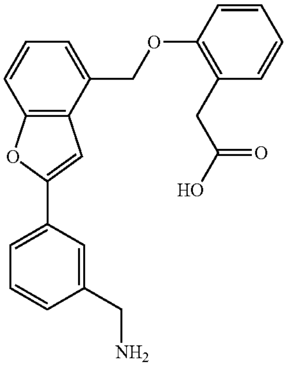

282f

Preparation of 2-(2-((2-(3-(aminomethyl)phenyl) benzofuran-4-yl)methoxy)phenyl)acetic acid (282f)

Step-1: Preparation of methyl 2-(3-(((tert-butoxycarbonyl)amino)methyl)phenyl)benzofuran-4-carboxylate (282b)

Compound 282b was prepared according to the procedure reported in step-1 of scheme 3, from methyl 3-hydroxy-2-iodobenzoate (282a) (358 mg, 1.287 mmol; CAS #1823056-63-8) in pyridine (6 mL) using tert-butyl 3-ethynylbenzylcarbamate (98b) (248 mg, 1.072 mmol), copper(I) oxide (153 mg, 1.072 mmol) and stirring at RT for 10 min and 125° C. for 3 h. This gave after workup and purification using flash column chromatography [silica (12 g), eluting with EtOAc in hexane from 0-70%]methyl 2-(3-(((tert-butoxycarbonyl)amino)methyl)phenyl)benzofuran-4-carboxylate (282b) (409 mg, 100% yield) as a yellow oil; $^1$H NMR (300 MHz, DMSO-$d_6$) δ 7.98-7.86 (m, 4H), 7.78 (d, J=1.0 Hz, 1H), 7.58-7.42 (m, 3H), 7.37-7.30 (m, 1H), 4.23 (d, J=6.2 Hz, 2H), 3.97 (s, 3H), 1.43 (s, 9H).

Step-2: Preparation of 2-(3-(((tert-butoxycarbonyl) amino)methyl)phenyl)benzofuran-4-carboxylic acid (282c)

Compound 282c was prepared according to the procedure reported in step-3 of scheme 1, from methyl 2-(3-(((tert-butoxycarbonyl)amino)methyl)phenyl)benzofuran-4-carboxylate (282b) (409 mg, 1.072 mmol) in MeOH/THF (4.5 mL each) using a solution of lithium hydroxide monohydrate (180 mg, 4.29 mmol) in water (3 mL) and stirring overnight at RT.

This gave after work up 2-(3-(((tert-butoxycarbonyl) amino)methyl)phenyl)benzofuran-4-carboxylic acid (282c) (394 mg, 100% yield) as a white solid; MS (ES−): 366.1 (M−H).

Step-3: Preparation of tert-butyl 3-(4-(hydroxymethyl)benzofuran-2-yl)benzylcarbamate (282d)

Compound 282d was prepared according to the procedure reported in step-1 of scheme 8, from 2-(3-(((tert-butoxycarbonyl)amino)methyl)phenyl)benzofuran-4-carboxylic acid (282c) (394 mg, 1.072 mmol) in THF (12 mL) using N-Methylmorpholine (0.141 mL, 1.287 mmol), isobutyl chloroformate (0.169 mL, 1.287 mmol), $NaBH_4$ (122 mg, 3.22 mmol) in water (1 mL). This gave after workup and purification using flash column chromatography [silica gel (12 g), eluting with EtOAc in hexane from 0-80%] tert-butyl 3-(4-(hydroxymethyl)benzofuran-2-yl)benzylcarbamate (282d) (348 mg, 92% yield) as a colorless oil; $^1$H NMR (300 MHz, DMSO-$d_6$) δ 7.85-7.77 (m, 2H), 7.56-7.48 (m, 3H), 7.45 (d, J=7.9 Hz, 1H), 7.33-7.23 (m, 3H), 5.33 (t, J=5.7 Hz, 1H), 4.79 (d, J=5.7 Hz, 2H), 4.21 (d, J=6.2 Hz, 2H), 1.42 (s, 9H).

Step-4: Preparation of ethyl 2-(2-((2-(3-(((tert-butoxycarbonyl)amino)methyl)phenyl)benzofuran-4-yl)methoxy)phenyl)acetate (282e)

Compound 282e was prepared according to the procedure reported in step-3 of scheme 7, from tert-butyl 3-(4-(hydroxymethyl)benzofuran-2-yl)benzylcarbamate (282d) (348 mg, 0.985 mmol) in DCM (10 mL), triphenylphosphine (387 mg, 1.477 mmol), ethyl 2-(2-hydroxyphenyl)acetate (7c) (266 mg, 1.477 mmol) using bis(4-chlorobenzyl) diazene-1,2-dicarboxylate (DCAD, 542 mg, 1.477 mmol) in DCM (5 mL) and stirring at RT for 1 h. This gave after workup and purification by flash column chromatography [silica gel (12 g), eluting with EtOAc in hexane from 0-50%] ethyl 2-(2-((2-(3-(((tert-butoxycarbonyl)amino)methyl)phenyl)benzofuran-4-yl)methoxy)phenyl)acetate (282e) (315 mg, 0.611 mmol, 62.0% yield) as a colorless oil; $^1$H NMR (300 MHz, DMSO-$d_6$) δ 7.87-7.76 (m, 2H), 7.65-7.57 (m, 1H), 7.56-7.48 (m, 2H), 7.48-7.43 (m, 1H), 7.39-7.32 (m, 2H), 7.32-7.25 (m, 2H), 7.24 (dd, J=7.5, 1.7 Hz, 1H), 7.18 (d, J=8.1 Hz, 1H), 6.94 (td, J=7.4, 1.1 Hz, 1H), 5.38 (s, 2H), 4.21 (d, J=6.2 Hz, 2H), 3.90 (q, J=7.1 Hz, 2H), 3.63 (s, 2H), 1.41 (s, 9H), 0.97 (t, J=7.1 Hz, 3H).

Step-5: Preparation of 2-(2-((2-(3-(aminomethyl) phenyl)benzofuran-4-yl)methoxy)phenyl)acetic acid (282f)

To a solution of ethyl 2-(2-((2-(3-(((tert-butoxycarbonyl) amino)methyl)phenyl)benzofuran-4-yl)methoxy)phenyl)acetate (282e) (135 mg, 0.262 mmol) in THF (4 mL) was added sodium tert-butoxide (160 mg, 1.665 mmol) followed by water (0.015 mL, 0.833 mmol). The mixture was heated to 67° C. for 66 h. The solvent was removed in vacuo, and the residue obtained was dissolved in water and purified using reverse phase column chromatography [C-18 column (50 g), eluting with ACN in water (containing 0.1% HCl) from 0-100%] to provide 2-(2-((2-(3-(aminomethyl)phenyl) benzofuran-4-yl)methoxy)phenyl)acetic acid (282f) (52 mg, 51% yield) HCl salt as a white solid; $^1$H NMR (300 MHz, DMSO-$d_6$) δ 8.60 (s, 1H), 7.77 (d, J=21.0 Hz, 2H), 7.60 (s, 1H), 7.45 (s, 1H), 7.32 (s, 3H), 7.16 (s, 2H), 7.03 (s, 1H), 6.88 (s, 1H), 5.36 (s, 2H), 3.98 (s, 2H), 3.44 (s, 2H); MS (ES+): 388.1 (M+1); (ES−): 386.1 (M−1); Analysis calculated for: $C_{24}H_{21}NO_4{\cdot}0.25H_2O$: C, 73.55; H, 5.53; N, 3.57. Found: C, 73.37; H, 5.35; N, 3.69.

Scheme 283

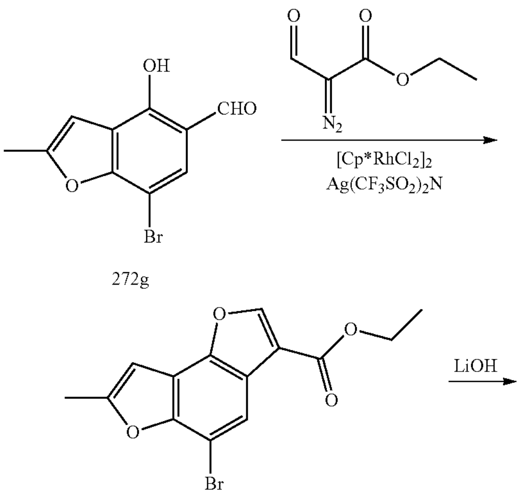

272g

283a

-continued

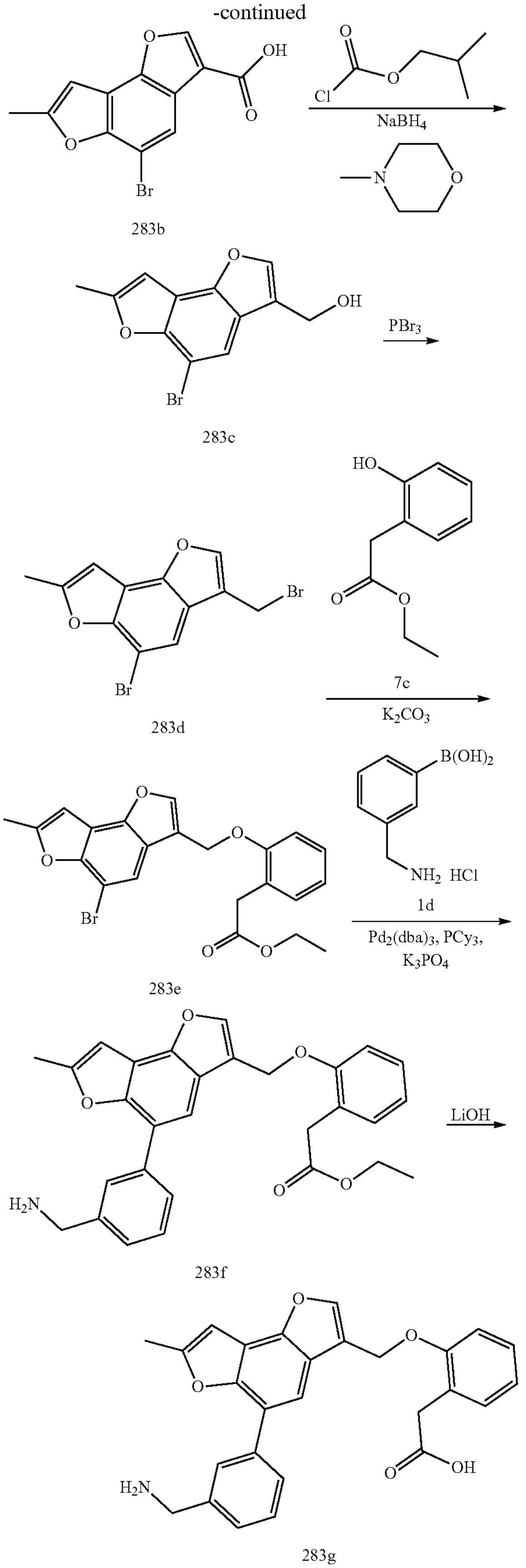

Preparation of 2-(2-((5-(3-(aminomethyl)phenyl)-7-methylbenzo[1,2-b:3,4-b']difuran-3-yl)methoxy)phenyl)acetic acid (283g)

Step-1: Preparation of ethyl 5-bromo-7-methylbenzo[1,2-b:3,4-b']difuran-3-carboxylate (283a)

Compound 283a was prepared according to the procedure reported in step-1 of scheme 233, from 7-bromo-4-hydroxy-2-methylbenzofuran-5-carbaldehyde (272g) (300 mg, 1.176 mmol) in DCE (3 mL) using pentamethylcyclopentadienylrhodium chloride dimer (36.3 mg, 0.059 mmol), silver bis(trifluoromethanesulfonyl)imide (91 mg, 0.235 mmol), ethyl 2-diazo-3-oxopropanoate (334 mg, 2.352 mmol; CAS #14762-48-2) and heating at 50° C. for 20 h. This gave after workup and purification using flash column chromatography [silica gel (12 g), eluting with EtOAc in hexane from 0-40%] ethyl 5-bromo-7-methylbenzo[1,2-b:3,4-b']difuran-3-carboxylate (283a) (105 mg, 28% yield) as a white solid; $^1H$ NMR (300 MHz, DMSO-$d_6$) δ 8.84 (s, 1H), 7.97 (s, 1H), 7.08 (d, J=1.2 Hz, 1H), 4.38 (q, J=7.1 Hz, 2H), 2.57 (d, J=1.1 Hz, 3H), 1.37 (t, J=7.1 Hz, 3H).

Step-2: Preparation of 5-bromo-7-methylbenzo[1,2-b:3,4-b']difuran-3-carboxylic acid (283b)

Compound 283b was prepared according to the procedure reported in step-3 of scheme 1, from ethyl 5-bromo-7-methylbenzo[1,2-b:3,4-b']difuran-3-carboxylate (283a) (104 mg, 0.322 mmol) in MeOH (3 mL) and THF (3 mL) using a solution of lithium hydroxide (54.0 mg, 1.287 mmol) in water (2 mL) and stirring at RT overnight. This gave after workup 5-bromo-7-methylbenzo[1,2-b:3,4-b']difuran-3-carboxylic acid (283b) (95 mg, 100% yield) as a white solid; MS (ES−): 292.9 and 294.9 (M−1).

Step-3: Preparation of (5-bromo-7-methylbenzo[1,2-b:3,4-b']difuran-3-yl)methanol (283c)

Compound 283c was prepared according to the procedure reported in step-1 of scheme 8, from 5-bromo-7-methylbenzo[1,2-b:3,4-b']difuran-3-carboxylic acid (283b) (95 mg, 0.322 mmol) in THF (8 mL) using N-methylmorpholine (0.042 mL, 0.386 mmol), isobutyl chloroformate (0.051 mL, 0.386 mmol) and $NaBH_4$ (36.5 mg, 0.966 mmol) in water (1 mL). This gave after workup and purification using flash column chromatography [silica gel (12 g), eluting with EtOAc in hexane from 0-80%] (5-bromo-7-methylbenzo[1,2-b:3,4-b']difuran-3-yl)methanol (283c) (80 mg, 88% yield) as a white solid; $^1H$ NMR (300 MHz, DMSO-$d_6$) δ 7.93 (d, J=1.1 Hz, 1H), 7.77 (s, 1H), 6.99 (d, J=1.3 Hz, 1H), 5.24 (t, J=5.6 Hz, 1H), 4.65 (d, J=5.6, 1.1 Hz, 2H), 2.54 (d, J=1.1 Hz, 3H).

Step-4: Preparation of 5-bromo-3-(bromomethyl)-7-methylbenzo[1,2-b:3,4-b']difuran (283d)

Compound 283d was prepared according to the procedure reported in step-3 of scheme 228, from (5-bromo-7-methylbenzo[1,2-b:3,4-b']difuran-3-yl)methanol (283c) (79 mg, 0.281 mmol) in dry Ether (8 mL) using $PBr_3$ (0.040 mL, 0.422 mmol) and stirring for 90 min. This gave after work up 5-bromo-3-(bromomethyl)-7-methylbenzo[1,2-b:3,4-b'] difuran (283d), which was used as such for the next step.

Step-5: Preparation of ethyl 2-(2-((5-bromo-7-methylbenzo[1,2-b:3,4-b']difuran-3-yl)methoxy)phenyl) acetate (283e)

Compound 283e was prepared according to the procedure reported in step-3 of scheme 7, from 5-bromo-3-(bromomethyl)-7-methylbenzo[1,2-b:3,4-b']difuran (283d) (97 mg, 0.282 mmol) in acetone (10 mL) using ethyl 2-(2-hydroxyphenyl)acetate (7c) (76 mg, 0.423 mmol), potassium carbonate (117 mg, 0.846 mmol) and stirring overnight at RT. This gave after workup and purification using flash column chromatography [silica gel (12 g), eluting with ethyl acetate in hexanes from 0-50%] ethyl 2-(2-((5-bromo-7-methylbenzo[1,2-b:3,4-b']difuran-3-yl)methoxy)phenyl)acetate (283e) (68 mg, 54% yield) as a colorless oil; $^1$H NMR (300 MHz, DMSO-$d_6$) δ 8.14 (s, 1H), 7.72 (s, 1H), 7.30 (td, J=7.8, 7.2, 1.7 Hz, 1H), 7.21 (dt, J=7.2, 2.1 Hz, 2H), 7.02 (d, J=1.2 Hz, 1H), 6.98-6.90 (m, 1H), 5.28 (s, 2H), 3.94 (q, J=7.1 Hz, 2H), 3.57 (s, 2H), 2.55 (d, J=1.1 Hz, 3H), 0.96 (t, J=7.1 Hz, 3H).

Step-6: Preparation of ethyl 2-(2-((5-(3-(aminomethyl)phenyl)-7-methylbenzo[1,2-b:3,4-b']difuran-3-yl)methoxy)phenyl)acetate (283f)

Compound 283f was prepared according to the procedure reported in step-2 of scheme 1, from ethyl 2-(2-((5-bromo-7-methylbenzo[1,2-b:3,4-b']difuran-3-yl)methoxy)phenyl) acetate (283e) (67 mg, 0.151 mmol) in dioxane/2Me-THF (12 mL, ratio 2:1) using 3-(aminomethyl)phenylboronic acid hydrochloride (1d) (70.8 mg, 0.378 mmol), 4M solution of $K_3PO_4$ (0.151 mL, 0.605 mmol), tricyclohexylphosphine (16.95 mg, 0.060 mmol), $Pd_2(dba)_3$ (27.7 mg, 0.030 mmol) and heating at 115° C. for 3 h. This gave after workup and purification using flash column chromatography [silica gel (12 g), eluting with DMA-80 in DCM from 0-80%] ethyl 2-(2-((5-(3-(aminomethyl)phenyl)-7-methylbenzo[1,2-b:3,4-b']difuran-3-yl)methoxy)phenyl)acetate (283f) (49 mg, 69% yield) as a yellow oil; MS (ES+) 470.2 (M+1).

Step-7: Preparation of 2-(2-((5-(3-(aminomethyl) phenyl)-7-methylbenzo[1,2-b:3,4-b']difuran-3-yl) methoxy)phenyl)acetic acid (283g)

Compound 283g was prepared according to the procedure reported in step-3 of scheme 1, from ethyl 2-(2-((5-(3-(aminomethyl)phenyl)-7-methylbenzo[1,2-b:3,4-b']difuran-3-yl)methoxy)phenyl)acetate (283f) (49 mg, 0.104 mmol) in MeOH/THF (3 mL each) using a solution of lithium hydroxide monohydrate (50 mg, 1.192 mmol) in water (2 mL) and stirring overnight at RT. This gave after workup and purification by reverse phase column chromatography [C18 column (50 g), eluting with ACN in water (containing 0.1% HCl) from 0-100%] 2-(2-((5-(3-(aminomethyl)phenyl)-7-methylbenzo[1,2-b:3,4-b']difuran-3-yl)methoxy)phenyl) acetic acid (283g) (35 mg, 76% yield) HCl salt as a white solid; $^1$H NMR (300 MHz, DMSO-$d_6$) δ 8.64 (s, 2H, $D_2O$ exchangeable), 8.11 (s, 1H), 7.99 (s, 1H), 7.89 (dt, J=4.7, 2.3 Hz, 1H), 7.73 (s, 1H), 7.62-7.49 (m, 2H), 7.33-7.17 (m, 3H), 6.94 (d, J=7.9 Hz, 2H), 5.35 (s, 2H), 4.13 (s, 2H), 3.55 (s, 2H), 2.53 (s, 3H); MS (ES+): 442.2 (M+1); (ES−): 440.1 (M−1); Analysis calculated for $C_{27}H_{23}NO_5 \cdot HCl \cdot H_2O$: C, 65.39; H, 5.28; N, 2.82. Found: C, 65.17; H, 5.21; N, 3.03.

Scheme 284

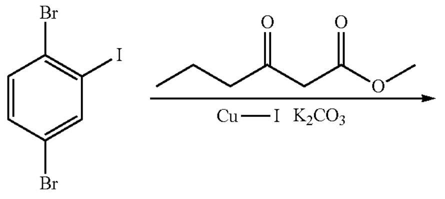

124a

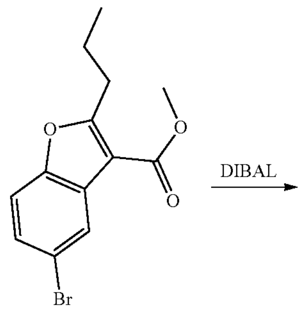

284a

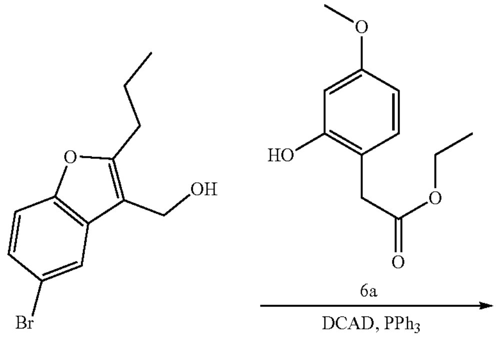

284b

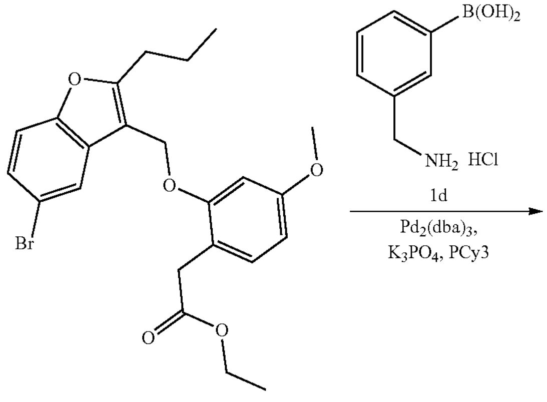

284c

-continued

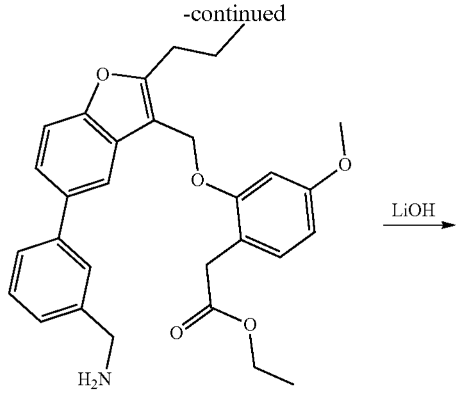

284d

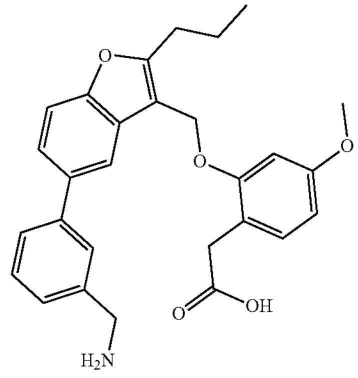

284e

Preparation of 2-(2-((5-(3-(aminomethyl)phenyl)-2-propylbenzofuran-3-yl)methoxy)-4-methoxyphenyl) acetic acid (284e)

Step-1: Preparation of methyl 5-bromo-2-propylbenzofuran-3-carboxylate (284a)

Compound 284a was prepared according to the procedure reported in step-1 of scheme 124, from 1,4-dibromo-2-iodobenzene (124a) (25 g, 69.1 mmol) in THF (250 mL) using methyl 3-oxohexanoate (14.41 mL, 104 mmol), copper(I) iodide (2.63 g, 13.82 mmol), potassium carbonate (47.7 g, 345 mmol) and heating at 80° C. for 15 h under an argon atmosphere. This gave after workup and purification using flash column chromatography [silica gel (80 g), eluting with EtOAc in hexane from 0-100%]methyl 5-bromo-2-propylbenzofuran-3-carboxylate (284a) (880 mg, 4% yield) as a white solid; MS (ES+): 297.25 (M+1).

Step-2: Preparation of (5-bromo-2-propylbenzofuran-3-yl)methanol (284b)

Compound 284b was prepared according to the procedure reported in step-4 of scheme 3, from methyl 5-bromo-2-propylbenzofuran-3-carboxylate (284a) (4.25 g, 14.30 mmol) in DCM (45 mL) using 1.0 M DIBAL in DCM (35.8 mL, 35.8 mmol) and stirring at 0° C. for 2 h. This gave after workup and purification by flash column chromatography [silica gel (24 g), eluting with EtOAc in hexane from 0-100%] (5-bromo-2-propylbenzofuran-3-yl)methanol (284b) (2.805 g, 73% yield) as a white solid; $^{1}H$ NMR (300 MHz, DMSO-$d_6$) δ 7.81 (d, J=2.1 Hz, 1H), 7.47 (d, J=8.6 Hz, 1H), 7.37 (dd, J=8.6, 2.1 Hz, 1H), 5.07 (t, J=5.6 Hz, 1H), 4.55 (d, J=5.6 Hz, 2H), 2.77 (t, J=7.3 Hz, 2H), 1.75-1.60 (m, 2H), 0.91 (t, J=7.4 Hz, 3H).

Step-3: Preparation of ethyl 2-(2-((5-bromo-2-propylbenzofuran-3-yl)methoxy)-4-methoxyphenyl) acetate (284c)

Compound 284c was prepared according to the procedure reported in step-3 of scheme 7, from (5-bromo-2-propylbenzofuran-3-yl)methanol (284b) (1 g, 3.72 mmol) in DCM (80 mL) using triphenylphosphine (1.072 g, 4.09 mmol), ethyl 2-(2-hydroxy-4-methoxyphenyl)acetate (6a) (0.859 g, 4.09 mmol) using bis(4-chlorobenzyl) diazene-1,2-dicarboxylate (DCAD, 1.501 g, 4.09 mmol) in DCM (10 mL) and stirring the reaction mixture at RT for 30 min. This gave after workup and purification by flash column chromatography [silica gel (40 g), eluting with EtOAc in hexane from 0-50%] ethyl 2-(2-((5-bromo-2-propylbenzofuran-3-yl) methoxy)-4-methoxyphenyl)acetate (284c) (750 mg, 44% yield) as a clear oil. (ES+): 483.10 (M+Na).

Step-4: Preparation of ethyl 2-(2-((5-(3-(aminomethyl)phenyl)-2-propylbenzofuran-3-yl)methoxy)-4-methoxyphenyl)acetate (284d)

Compound 284d was prepared according to the procedure reported in step-2 of scheme 1, from ethyl 2-(2-((5-bromo-2-propylbenzofuran-3-yl)methoxy)-4-methoxyphenyl)acetate (284c) (300 mg, 0.650 mmol) in dioxane (12 mL) using 3-(aminomethyl)phenylboronic acid hydrochloride (1d) (123 mg, 0.813 mmol), 4 M solution of $K_3PO_4$ (0.650 mL, 2.60 mmol), tricyclohexylphosphine (36.5 mg, 0.130 mmol), $Pd_2(dba)_3$ (59.5 mg, 0.065 mmol) and heating at 115° C. for 12 h. This gave after workup and purification by flash column chromatography [silica gel (12 g), eluting with EtOAc in hexane from 0-100%] ethyl 2-(2-((5-(3-(aminomethyl)phenyl)-2-propylbenzofuran-3-yl)methoxy)-4-methoxyphenyl)acetate (284d) (145 mg, 46% yield); MS (ES+): 488.2 (M+1).

Step-5: Preparation of 2-(2-((5-(3-(aminomethyl) phenyl)-2-propylbenzofuran-3-yl)methoxy)-4-methoxyphenyl)acetic acid (284e)

Compound 284e was prepared according to the procedure reported in step-3 of scheme 1, from ethyl 2-(2-((5-(3-(aminomethyl)phenyl)-2-propylbenzofuran-3-yl)methoxy)-4-methoxyphenyl)acetate (284d) (140 mg, 0.287 mmol) in THF (3 mL) using a solution of lithium hydroxide hydrate (36.1 mg, 0.861 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)-2-propylbenzofuran-3-yl)methoxy)-4-methoxyphenyl)acetic acid (284e) (92.9 mg, 70% yield) HCl salt as a white solid; $^{1}H$ NMR (300 MHz, DMSO-$d_6$) δ 11.96 (s, 1H, $D_2O$ exchangeable), 8.41 (s, 2H, $D_2O$ exchangeable), 7.93 (d, J=1.7 Hz, 1H), 7.87 (s, 1H), 7.72 (dt, J=7.6, 1.6 Hz, 1H), 7.67-7.55 (m, 2H), 7.55-7.40 (m, 2H), 7.08 (d, J=8.3 Hz, 1H), 6.84 (d, J=2.4 Hz, 1H), 6.50 (dd, J=8.3, 2.4 Hz, 1H), 5.25 (s, 2H), 4.10 (s, 2H), 3.76 (s, 3H), 3.39 (s, 2H), 2.87 (t, J=7.3 Hz, 2H), 1.79-1.62 (m, 2H), 0.93 (t, J=7.4 Hz, 3H); MS (ES+): 460.20 (M+1); (ES−) 458.20 (M−1).

Scheme 285

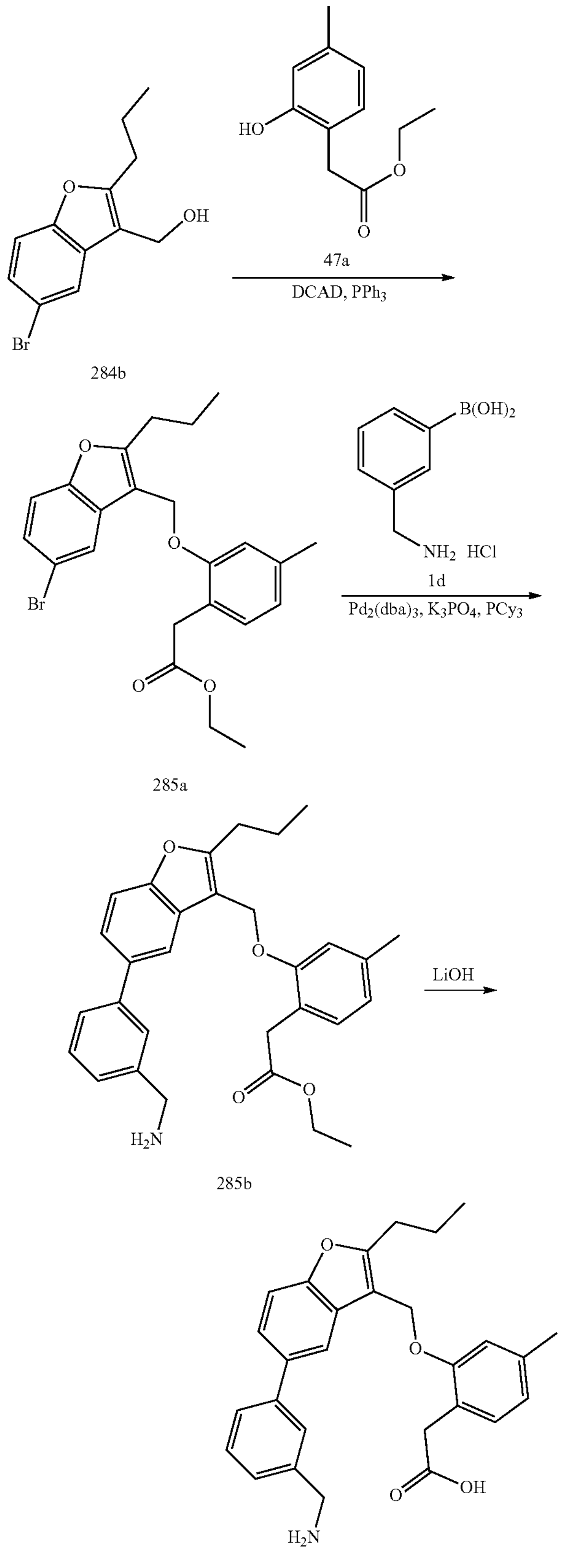

284b

285a

285b

285c

Preparation of 2-(2-((5-(3-(aminomethyl)phenyl)-2-propylbenzofuran-3-yl)methoxy)-4-methylphenyl) acetic acid (285c)

Step-1: Preparation of ethyl 2-(2-((5-bromo-2-propylbenzofuran-3-yl)methoxy)-4-methylphenyl)acetate (285a)

Compound 285a was prepared according to the procedure reported in step-3 of scheme 7, from (5-bromo-2-propylbenzofuran-3-yl)methanol (284b) (0.5 g, 1.858 mmol) in DCM (40 mL) using triphenylphosphine (0.536 g, 2.044 mmol), ethyl 2-(2-hydroxy-4-methylphenyl)acetate (47a) (0.397 g, 2.044 mmol) using bis(4-chlorobenzyl) diazene-1,2-dicarboxylate (DCAD, 0.75 g, 2.044 mmol) in DCM (10 mL) and stirring the reaction mixture at RT for 30 min. This gave after workup and purification by flash column chromatography [silica gel (40 g), eluting with EtOAc in hexane from 0-50%] ethyl 2-(2-((5-bromo-2-propylbenzofuran-3-yl)methoxy)-4-methylphenyl)acetate (285a) (460 mg, 56% yield) as a clear oil; (ES+): 467.05 (M+Na).

Step-2: Preparation of ethyl 2-(2-((5-(3-(aminomethyl)phenyl)-2-propylbenzofuran-3-yl)methoxy)-4-methylphenyl)acetate (285b)

Compound 285b was prepared according to the procedure reported in step-2 of scheme 1, from ethyl 2-(2-((5-bromo-2-propylbenzofuran-3-yl)methoxy)-4-methylphenyl)acetate (285a) (450 mg, 1.01 mmol) in dioxane (12 mL) using 3-(aminomethyl)phenylboronic acid hydrochloride (1d) (191 mg, 1.263 mmol), 4 M solution of $K_3PO_4$ (1.01 mL, 4.04 mmol), tricyclohexylphosphine (56.7 mg, 0.202 mmol), $Pd_2(dba)_3$ (93 mg, 0.101 mmol) and heating at 115° C. for 12 h. This gave after workup and purification by flash column chromatography [silica gel (12 g), eluting with EtOAc in hexane from 0-100%] ethyl 2-(2-((5-(3-(aminomethyl)phenyl)-2-propylbenzofuran-3-yl)methoxy)-4-methylphenyl)acetate (285b) (145 mg, 0.307 mmol, 30.4% yield); MS (ES+): 472.20 (M+1).

Step-3: Preparation of 2-(2-((5-(3-(aminomethyl) phenyl)-2-propylbenzofuran-3-yl)methoxy)-4-methylphenyl)acetic acid (285c)

Compound 285c was prepared according to the procedure reported in step-3 of scheme 1, from ethyl 2-(2-((5-(3-(aminomethyl)phenyl)-2-propylbenzofuran-3-yl)methoxy)-4-methylphenyl)acetate (285b) (140 mg, 0.297 mmol) in THF (3 mL) using a solution of lithium hydroxide hydrate (37.4 mg, 0.891 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-propylbenzofuran-3-yl)methoxy)-4-methylphenyl)acetic acid (285c) (74 mg, 0.167 mmol, 56.2% yield) HCl salt as a white solid; $^1H$ NMR (300 MHz, DMSO-$d_6$) δ 12.03 (s, 1H, $D_2O$ exchangeable), 8.34 (s, 3H, $D_2O$ exchangeable), 7.92 (d, J=1.7 Hz, 1H), 7.85 (t, J=1.8 Hz, 1H), 7.73 (dt, J=7.7, 1.6 Hz, 1H), 7.68-7.55 (m, 2H), 7.50 (t, J=7.6 Hz, 1H), 7.47-7.40 (m, 1H), 7.10 (s, 1H), 7.05 (d, J=7.5 Hz, 1H), 6.74 (d, J=7.5 Hz, 1H), 5.23 (s, 2H), 4.10 (s, 2H), 3.42 (s, 2H), 2.87 (t, J=7.3 Hz, 2H), 2.32 (s, 3H), 1.78-1.59 (m, 2H), 0.94 (t, J=7.3 Hz, 3H); (ES+): 444.20 (M+1); (ES−): 442.20 (M−1).

Scheme 286

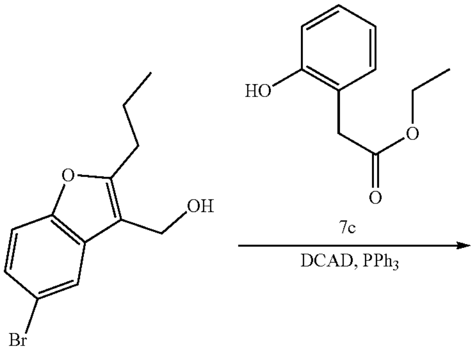

284b

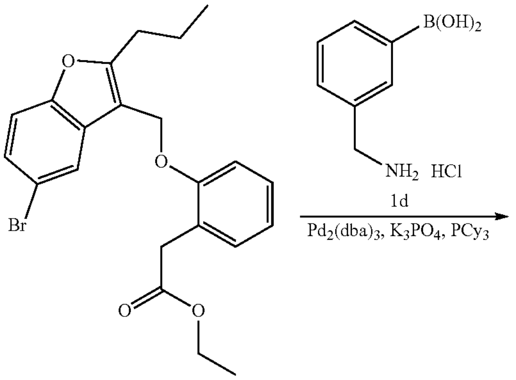

286a

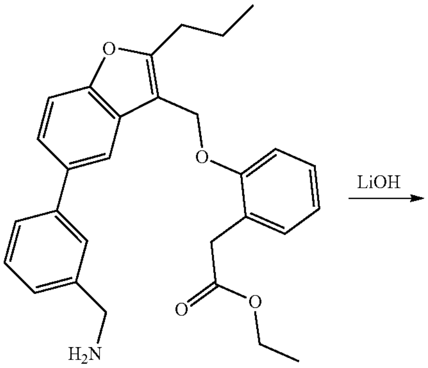

286b

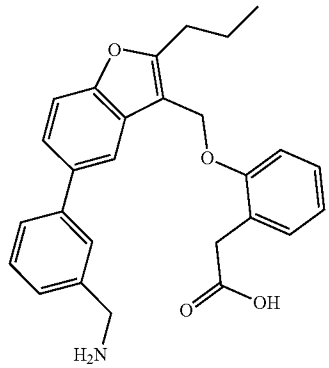

286c

Preparation of 2-(2-((-(3-(aminomethyl)phenyl)-2-propylbenzofuran-3-yl)methoxy)phenyl)acetic acid (286c)

Step-1: Preparation of ethyl 2-(2-((5-bromo-2-propylbenzofuran-3-yl)methoxy)phenyl)acetate (286a)

Compound 286a was prepared according to the procedure reported in step-3 of scheme 7, from (5-bromo-2-propylbenzofuran-3-yl)methanol (284b) (0.5 g, 1.858 mmol) in DCM (20 mL) using triphenylphosphine (0.536 g, 2.044 mmol), ethyl 2-(2-hydroxyphenyl)acetate (7c) (0.368 g, 2.044 mmol), bis(4-chlorobenzyl) diazene-1,2-dicarboxylate (DCAD, 0.750 g, 2.044 mmol) in DCM (10 mL) and stirring the reaction mixture at RT for 30 min. This gave after workup and purification by flash column chromatography [silica gel (40 g), eluting with EtOAc in hexane from 0-50%] ethyl 2-(2-((5-bromo-2-propylbenzofuran-3-yl)methoxy)phenyl)acetate (286a) (290 mg, 36% yield) as a clear oil; $^1$H NMR (300 MHz, DMSO-$d_6$) δ 7.75 (d, J=2.0 Hz, 1H), 7.53 (d, J=8.7 Hz, 1H), 7.42 (dd, J=8.7, 2.1 Hz, 1H), 7.32-7.27 (m, 1H), 7.24-7.18 (m, 2H), 6.97-6.91 (m, 1H), 5.18 (s, 2H), 3.93-3.83 (m, 2H), 3.50 (s, 2H), 2.84 (t, J=7.3 Hz, 2H), 1.72-1.63 (m, 2H), 0.96-0.89 (m, 6H); MS (ES−): 431.00 (M−1).

Step-2: Preparation of ethyl 2-(2-((5-(3-(aminomethyl)phenyl)-2-propylbenzofuran-3-yl)methoxy)phenyl)acetate (286b)

Compound 286b was prepared according to the procedure reported in step-2 of scheme 1, from ethyl 2-(2-((5-bromo-2-propylbenzofuran-3-yl)methoxy)phenyl)acetate (286a) (280 mg, 0.649 mmol) in dioxane (12 mL) using 3-(aminomethyl)phenylboronic acid hydrochloride (1d) (123 mg, 0.811 mmol), 4 M solution of $K_3PO_4$ (0.649 mL, 2.60 mmol), tricyclohexylphosphine (36.4 mg, 0.130 mmol), $Pd_2(dba)_3$ (59.4 mg, 0.065 mmol) and heating at 115° C. for 12 h. This gave after workup and purification by flash column chromatography [silica gel (12 g), eluting with EtOAc in hexane from 0-100%] ethyl 2-(2-((5-(3-(aminomethyl)phenyl)-2-propylbenzofuran-3-yl)methoxy)phenyl)acetate (286b) 145 mg, 0.317 mmol, 48.8% yield); MS (ES+): 458.20 (M+1).

Step-3: Preparation of 2-(2-((5-(3-(aminomethyl)phenyl)-2-propylbenzofuran-3-yl)methoxy)phenyl)acetic acid (286c)

Compound 286c was prepared according to the procedure reported in step-3 of scheme 1, from ethyl 2-(2-((5-(3-(aminomethyl)phenyl)-2-propylbenzofuran-3-yl)methoxy)phenyl)acetate (286b) (140 mg, 0.306 mmol) in THF (3 mL) using a solution of lithium hydroxide hydrate (38.5 mg, 0.918 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-propylbenzofuran-3-yl)methoxy)phenyl)acetic acid (286c) (69 mg, 0.161 mmol, 52.5% yield) HCl salt as a white solid; $^1$H NMR (300 MHz, DMSO-$d_6$) δ 12.06 (s, 1H, $D_2O$ exchangeable), 8.31 (s, 3H, $D_2O$ exchangeable), 7.92 (d, J=1.8 Hz, 1H), 7.85 (s, 1H), 7.75-7.69 (m, 1H), 7.68-7.56 (m, 2H), 7.51 (t, J=7.6 Hz, 1H), 7.43 (d, J=7.6 Hz, 1H), 7.32-7.22 (m, 2H), 7.19 (dd, J=7.3, 1.5 Hz, 1H), 6.93 (td, J=6.8, 2.0 Hz, 1H), 5.25 (s, 2H), 4.10 (s, 2H), 3.48 (s, 2H), 2.86 (t, J=7.3 Hz, 2H), 1.79-1.61 (m, 2H), 0.93 (t, J=7.4 Hz, 3H); MS (ES+): 430.20 (M+1); (ES−): 428.20 (M−1).

Scheme 287

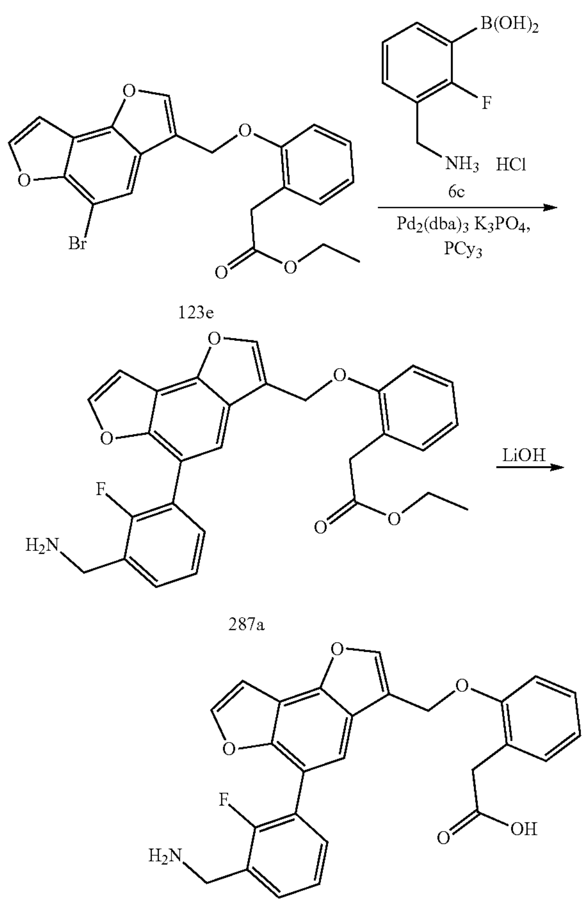

123e

287a

287b

Preparation of 2-(2-((5-(3-(aminomethyl)-2-fluorophenyl)benzo[1,2-b:3,4-b']difuran-3-yl)methoxy)phenyl)acetic acid (287b)

Step-1: Preparation of ethyl 2-(2-((5-(3-(aminomethyl)-2-fluorophenyl)benzo[1,2-b:3,4-b']difuran-3-yl)methoxy)phenyl)acetate (287a)

Compound 287a was prepared according to the procedure reported in step-2 of scheme 1, from ethyl 2-(2-((5-bromobenzo[1,2-b:3,4-b']difuran-3-yl)methoxy)phenyl)acetate (123e) (123 mg, 0.287 mmol) in dioxane/2Me-THF (12 mL, ratio 2:1) using 3-(aminomethyl)-2-fluorophenylboronic acid hydrochloride (6c) (147 mg, 0.716 mmol), 4M solution of $K_3PO_4$ (0.287 mL, 1.146 mmol), tricyclohexylphosphine (32.1 mg, 0.115 mmol), $Pd_2(dba)_3$ (52.5 mg, 0.057 mmol) and heating at 115° C. for 3 h. This gave after workup and purification by flash column chromatography [silica gel (12 g), eluting with DMA-80 in DCM from 0-80%]ethyl 2-(2-((5-(3-(aminomethyl)-2-fluorophenyl)benzo[1,2-b:3,4-b']difuran-3-yl)methoxy)phenyl)acetate (287a) (136 mg, 100% yield) as a yellow oil; MS (ES+) 474.2 (M+1).

Step-2: Preparation of 2-(2-((5-(3-(aminomethyl)-2-fluorophenyl)benzo[1,2-b:3,4-b']difuran-3-yl)methoxy)phenyl)acetic acid (287b)

Compound 287b was prepared according to the procedure reported in step-3 of scheme 1, from ethyl 2-(2-((5-(3-(aminomethyl)-2-fluorophenyl)benzo[1,2-b:3,4-b']difuran-3-yl)methoxy)phenyl)acetate (287a) (137 mg, 0.289 mmol) in MeOH/THF (3 mL each) using a solution of lithium hydroxide monohydrate (67 mg, 1.597 mmol) in water (2 mL) and stirring overnight at RT. This gave after workup and purification by reverse phase column chromatography [C18 column (50 g), eluting with ACN in water (containing 0.1% HCl) from 0-100%] 2-(2-((5-(3-(aminomethyl)-2-fluorophenyl)benzo[1,2-b:3,4-b']difuran-3-yl)methoxy)phenyl)acetic acid (287b) (79 mg, 61% yield) HCl salt as a white solid; $^{1}H$ NMR (300 MHz, DMSO-$d_6$) δ 9.25-8.31 (m, 2H, $D_2O$ exchangeable), 8.17 (d, J=9.8 Hz, 2H), 7.71 (d, J=10.3 Hz, 3H), 7.54-7.10 (m, 5H), 6.92 (t, J=7.1 Hz, 1H), 5.36 (s, 2H), 4.18 (s, 2H), 3.55 (s, 2H); $^{19}F$ NMR (282 MHz, DMSO-$d_6$) δ −118.71; MS (ES+): 446.1 (M+1); (ES−): 444.1 (M−1); Analysis calculated for: $C_{26}H_{20}FNO_5 \cdot HCl \cdot 1.25H_2O$: C, 61.91; H, 4.70; N, 2.78; Cl, 7.03. Found: C, 62.21; H, 4.53; N, 2.90; Cl, 6.94.

Scheme 288

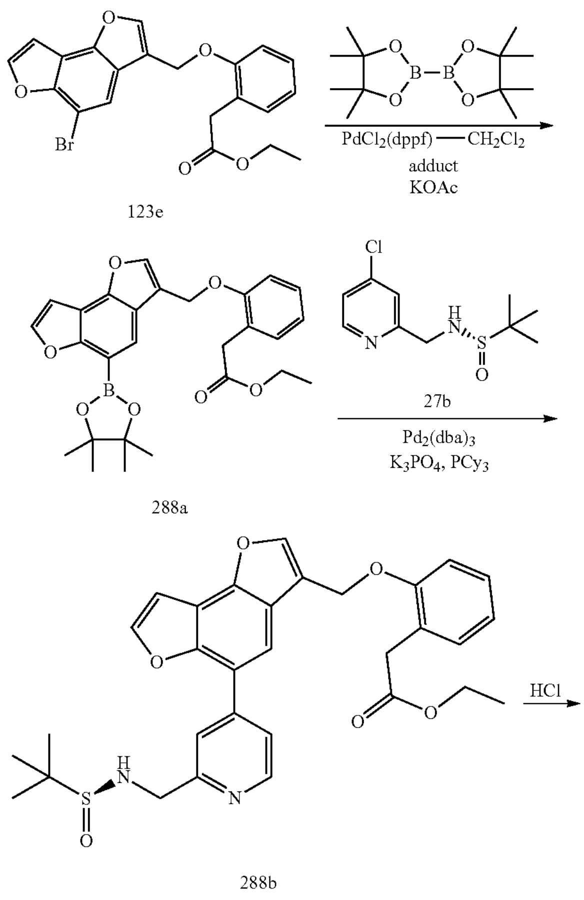

123e

288a

288b

-continued

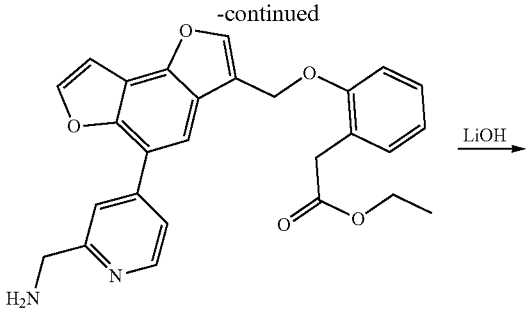

288c

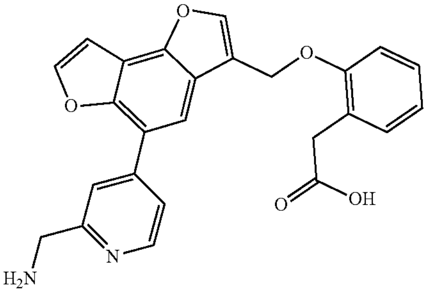

288d

Preparation of 2-(2-((5-(2-(aminomethyl)pyridin-4-yl)benzo[1,2-b:3,4-b']difuran-3-yl)methoxy)phenyl) acetic acid (288d)

Step-1: Preparation of ethyl 2-(2-((5-(4,4,5,5-tetramethyl-1,3,2-dioxaborolan-2-yl)benzo[1,2-b:3,4-b']difuran-3-yl)methoxy)phenyl)acetate (288a)

Compound 288a was prepared according to the procedure reported in step-1 of scheme 27, from ethyl 2-(2-((5-bromobenzo[1,2-b:3,4-b']difuran-3-yl)methoxy)phenyl)acetate (123e) (245 mg, 0.571 mmol) in anhydrous dioxane (10 mL) using BisPin (217 mg, 0.856 mmol), potassium acetate (168 mg, 1.712 mmol), $PdCl_2(dppf)$-$CH_2Cl_2$ adduct (69.9 mg, 0.086 mmol) and heating at 95° C. overnight. This gave after work up and purification using flash column chromatography [silica gel (12 g), eluting with EtOAc in hexane from 0-40%] ethyl 2-(2-((5-(4,4,5,5-tetramethyl-1,3,2-dioxaborolan-2-yl)benzo[1,2-b:3,4-b']difuran-3-yl)methoxy)phenyl) acetate (288a) (185 mg, 68% yield) as a white solid; $^1$H NMR (300 MHz, DMSO-$d_6$) δ 8.17 (d, J=2.3 Hz, 1H), 8.12 (s, 1H), 7.94 (s, 1H), 7.34-7.18 (m, 4H), 6.94 (t, J=6.9 Hz, 1H), 5.34 (s, 2H), 3.90 (q, J=7.1 Hz, 2H), 3.57 (s, 2H), 1.35 (s, 12H), 0.93 (t, J=7.1 Hz, 3H).

Step-2: Preparation of ethyl 2-(2-((5-(2-((1,1-dimethylethylsulfinamido)methyl)pyridin-4-yl)benzo[1,2-b:3,4-b']difuran-3-yl)methoxy)phenyl)acetate (288b)

Compound 288b was prepared according to the procedure reported in step-2 of scheme 1, from ethyl 2-(2-((5-(4,4,5,5-tetramethyl-1,3,2-dioxaborolan-2-yl)benzo[1,2-b:3,4-b'] difuran-3-yl)methoxy)phenyl)acetate (288a) (95 mg, 0.199 mmol) in dioxane (6 mL) and 2Me-THF (3 mL) using (+)-N-((4-chloropyridin-2-yl)methyl)-2-methylpropane-2-sulfinamide (27b) (123 mg, 0.499 mmol), 4 M solution of $K_3PO_4$ (0.199 mL, 0.798 mmol), tricyclohexylphosphine (22.37 mg, 0.080 mmol), $Pd_2(dba)_3$ (36.5 mg, 0.04 mmol) and heating at 115° C. for 3 h. This gave after workup and purification by flash column chromatography [silica gel (12 g), eluting with EtOAc: MeOH (9:1) in hexanes from 0-100%] ethyl 2-(2-((5-(2-((1,1-dimethylethylsulfinamido) methyl)pyridin-4-yl)benzo[1,2-b:3,4-b']difuran-3-yl) methoxy)phenyl)acetate (288b) (112 mg, 100% yield) as a yellow oil; MS (ES+): 561.2 (M+1).

Step-3: Preparation of ethyl 2-(2-((5-(2-(aminomethyl)pyridin-4-yl)benzo[1,2-b:3,4-b']difuran-3-yl) methoxy)phenyl)acetate (288c)

Compound 288c was prepared according to the procedure reported in step-2 of scheme 7, from ethyl 2-(2-((5-(2-((1,1-dimethylethylsulfinamido)methyl)pyridin-4-yl)benzo[1,2-b:3,4-b']difuran-3-yl)methoxy)phenyl)acetate (288b) (112 mg, 0.200 mmol) in MeOH (6 mL) using HCl (4M in dioxane) (0.3 mL, 1.2 mmol) and stirring the reaction mixture at RT for 1 h. This gave after workup ethyl 2-(2-((5-(2-(aminomethyl)pyridin-4-yl)benzo[1,2-b:3,4-b']difuran-3-yl)methoxy)phenyl)acetate (288c) (91 mg, 100% yield) as a yellow solid and used as such for the next step; MS (ES+): 457.2 (M+1).

Step-4: Preparation of 2-(2-((5-(2-(aminomethyl) pyridin-4-yl)benzo[1,2-b:3,4-b']difuran-3-yl) methoxy)phenyl)acetic acid (288d)

Compound 288d was prepared according to the procedure reported in step-3 of scheme 1, from ethyl 2-(2-((5-(2-(aminomethyl)pyridin-4-yl)benzo[1,2-b:3,4-b']difuran-3-yl) methoxy)phenyl)acetate (288c) (91 mg, 0.199 mmol) in MeOH (3 mL) and THF (3 mL) using a solution of lithium hydroxide monohydrate (79 mg, 1.883 mmol) in water (2 mL) and stirring at RT overnight. This gave after workup and purification by reverse phase column chromatography [C18 column (50 g), eluting with ACN in water (containing 0.1% HCl) from 0-100%] 2-(2-((5-(2-(aminomethyl)pyridin-4-yl)benzo[1,2-b:3,4-b']difuran-3-yl)methoxy)phenyl) acetic acid (288d) (45 mg, 53% yield) HCl salt as a white solid; $^1$H NMR (300 MHz, DMSO-$d_6$) δ 8.79 (d, J=5.3 Hz, 1H), 8.58 (s, 3H, $D_2O$ exchangeable), 8.28 (d, J=2.2 Hz, 1H), 8.22 (s, 1H), 8.16 (s, 1H), 8.10-8.00 (m, 2H), 7.42 (d, J=2.2 Hz, 1H), 7.35-7.18 (m, 3H), 6.94 (td, J=7.2, 1.4 Hz, 1H), 5.39 (s, 2H), 4.42-4.27 (m, 2H), 3.56 (s, 2H); H NMR (300 MHz, DMSO-$d_6$/$D_2O$) δ 8.76 (d, J=5.3 Hz, 1H), 8.22-8.14 (m, 2H), 8.06 (s, 1H), 8.03-7.93 (m, 2H), 7.37 (s, 1H), 7.28 (t, J=7.7 Hz, 1H), 7.25-7.16 (m, 2H), 6.93 (t, J=7.3 Hz, 1H), 5.36 (s, 2H), 4.30 (s, 2H), 3.53 (s, 2H); MS (ES+): 429.2 (M+1); (ES−): 427.1 (M−1); Analysis calculated for: $C_{25}H_{20}N205.1.8HCl\cdot 3.5H_2O$: C, 53.90; H, 5.21; N, 5.03; Cl, 11.45. Found: C, 53.92; H, 4.95; N, 5.02; Cl, 11.66.

Scheme 289

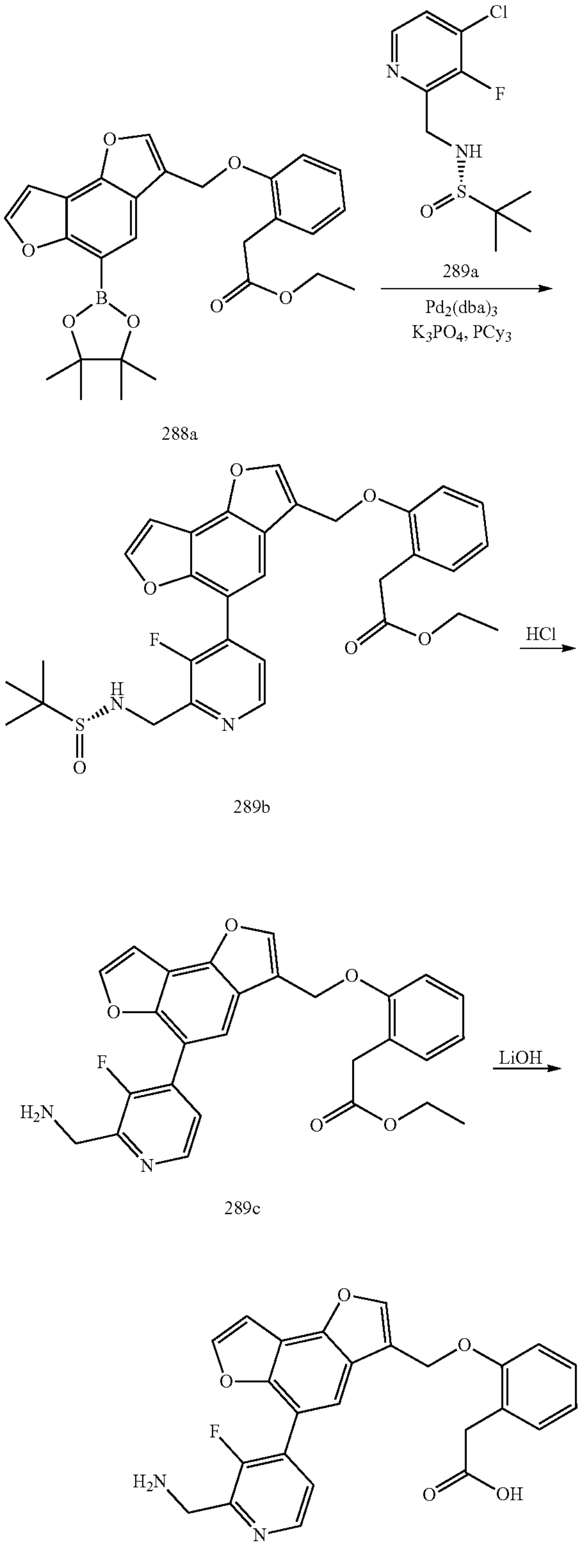

288a

289b

289c

289d

Preparation of 2-(2-((5-(2-(aminomethyl)-3-fluoropyridin-4-yl)benzo[1,2-b:3,4-b']difuran-3-yl)methoxy)phenyl)acetic acid (289d)

Step-1: Preparation of ethyl 2-(2-((5-(2-((1,1-dimethylethylsulfinamido)methyl)-3-fluoropyridin-4-yl)benzo[1,2-b:3,4-b']difuran-3-yl)methoxy)phenyl)acetate (289b)

Compound 289b was prepared according to the procedure reported in step-2 of scheme 1, from ethyl 2-(2-((5-(4,4,5,5-tetramethyl-1,3,2-dioxaborolan-2-yl)benzo[1,2-b:3,4-b']difuran-3-yl)methoxy)phenyl) acetate (288a) (93 mg, 0.195 mmol) in dioxane (6 mL) and 2Me-THF (3 mL) using (+)-N-((4-chloro-3-fluoropyridin-2-yl)methyl)-2-methylpropane-2-sulfinamide (289a) (129 mg, 0.488 mmol), 4 M solution of $K_3PO_4$ (0.195 mL, 0.781 mmol), tricyclohexylphosphine (21.90 mg, 0.078 mmol), $Pd_2(dba)_3$ (35.8 mg, 0.039 mmol) and heating at 115° C. for 3 h. This gave after workup and purification by flash column chromatography [silica gel (12 g), eluting with DMA80 in DCM from 0-80%] ethyl 2-(2-((5-(2-((1,1-dimethylethylsulfinamido)methyl)-3-fluoropyridin-4-yl)benzo[1,2-b:3,4-b']difuran-3-yl)methoxy)phenyl)acetate (289b) (113 mg, 100% yield) as a yellow oil; MS (ES+): 579.2 (M+1).

Step-2: Preparation of ethyl 2-(2-((5-(2-(aminomethyl)-3-fluoropyridin-4-yl)benzo[1,2-b:3,4-b']difuran-3-yl)methoxy)phenyl)acetate (289c)

Compound 289c was prepared according to the procedure reported in step-2 of scheme 7, from ethyl 2-(2-((5-(2-((1,1-dimethylethylsulfinamido)methyl)-3-fluoropyridin-4-yl)benzo[1,2-b:3,4-b']difuran-3-yl)methoxy)phenyl)acetate (289b) (113 mg, 0.195 mmol) in MeOH (6 mL) using HCl (4M in dioxane) (0.4 mL, 1.600 mmol) and stirring the reaction mixture at RT for 1.5 h. This gave after workup ethyl 2-(2-((5-(2-(aminomethyl)-3-fluoropyridin-4-yl)benzo[1,2-b:3,4-b']difuran-3-yl)methoxy)phenyl)acetate (289c) (93 mg, 100% yield) as a brown oil and was used as such for the next step; MS (ES+): 475.1 (M+1).

Step-3: Preparation of 2-(2-((5-(2-(aminomethyl)-3-fluoropyridin-4-yl)benzo[1,2-b:3,4-b']difuran-3-yl)methoxy)phenyl)acetic acid (289d)

Compound 289d was prepared according to the procedure reported in step-3 of scheme 1, from ethyl 2-(2-((5-(2-(aminomethyl)-3-fluoropyridin-4-yl)benzo[1,2-b:3,4-b']difuran-3-yl)methoxy)phenyl)acetate (289c) (93 mg, 0.196 mmol) in MeOH/THF (3 mL each) using a solution of lithium hydroxide monohydrate (77 mg, 1.835 mmol) in water (2 mL) and stirring at RT overnight. This gave after workup and purification by reverse phase column chromatography [C18 column (50 g), eluting with ACN in water (containing 0.1% HCl) from 0-100%] 2-(2-((5-(2-(aminomethyl)-3-fluoropyridin-4-yl)benzo[1,2-b:3,4-b']difuran-3-yl)methoxy)phenyl)acetic acid (289d) (53 mg, 61% yield) HCl salt as a white solid; $^1H$ NMR (300 MHz, DMSO-$d_6$) δ 8.76-8.51 (m, 4H, 3H $D_2O$ exchangeable), 8.34-8.16 (m, 2H), 7.92-7.77 (m, 2H), 7.39 (d, J=2.2 Hz, 1H), 7.33-7.15 (m, 3H), 6.92 (t, J=7.2 Hz, 1H), 5.36 (s, 2H), 4.46-4.29 (m, 2H), 3.54 (s, 2H); $^1H$ NMR (300 MHz, DMSO-$d_6$/$D_2O$) δ 8.61 (d, J=4.9 Hz, 1H), 8.18 (d, J=10.0 Hz, 2H), 7.88-7.74 (m, 2H), 7.37 (s, 1H), 7.32-7.13 (m, 3H), 6.92 (t, J=7.3 Hz, 1H), 5.34 (s, 2H), 4.37 (s, 2H), 3.52 (s, 2H); $^{19}F$ NMR (282 MHz, DMSO-$d_6$) δ −128.67. MS (ES+): 447.1 (M+1);

(ES−): 445.1 (M−1); Analysis calculated for: $C_{25}H_{19}FN_2O_5 \cdot 1.25HCl \cdot 2.25H_2O$: C, 56.38; H, 4.68; N, 5.26; Cl, 8.32. Found: C, 56.32; H, 4.40; N, 5.43; Cl, 8.40.

Scheme 290

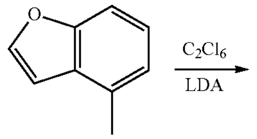

290a

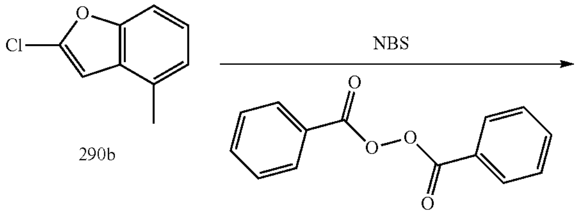

290b

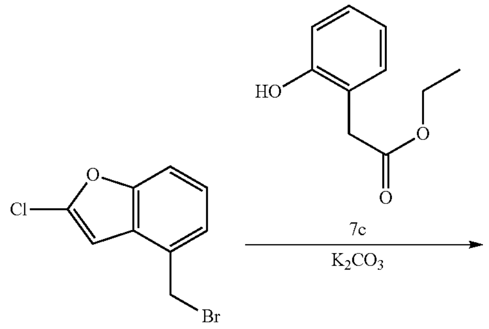

290c

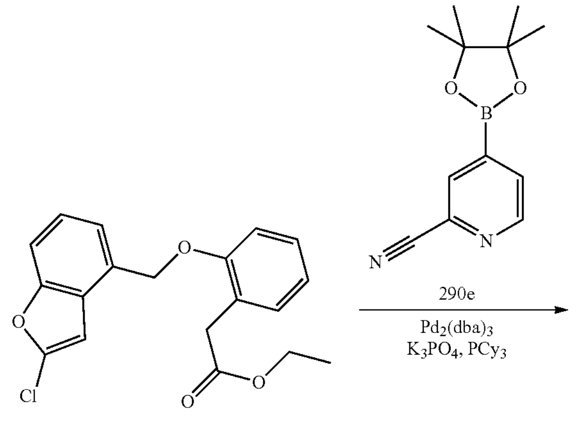

290d

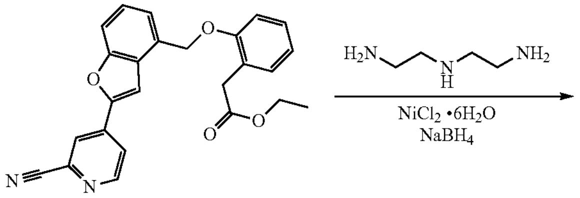

290f

-continued

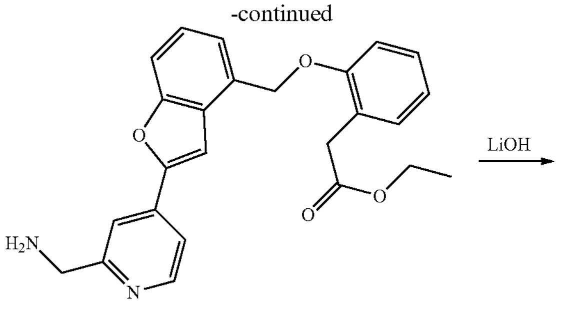

290g

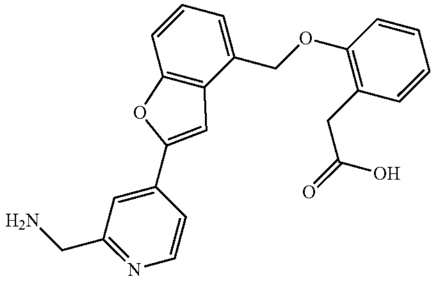

290h

Preparation of 2-(2-((2-(2-(aminomethyl)pyridin-4-yl)benzofuran-4-yl)methoxy)phenyl)acetic acid (290 h)

Step-1: Preparation of 2-chloro-4-methylbenzofuran (290b)

To a solution of 4-methylbenzofuran (290a) (2.2 g, 16.65 mmol; CAS #5670-23-5) in dry THE (24 mL), was added LDA (1.5 M in hexanes, 16.65 mL, 24.97 mmol) dropwise at −78° C. under a $N_2$ atmosphere. The mixture was kept at −78° C. for 1.5 h and a solution of perchloroethane (5.91 g, 24.97 mmol) in dry THF (5 mL) was added at −78° C. and the mixture was slowly warmed to RT overnight. The reaction mixture was concentrated in vacuum and the residue obtained was quenched with 2 M HCl, extracted with MTBE. Combined organics were washed with brine, dried, filtered and concentrated in vacuo. Residue obtained was further purified using flash column chromatography [silica gel (40 g), eluting with EtOAc in hexane from 0-20%] to afford 2-chloro-4-methylbenzofuran (290b) (2.77 g, 100%) as an orange oil.

Step-2: Preparation of 4-(bromomethyl)-2-chlorobenzofuran (290c)

Compound 290c was prepared according to the procedure reported in step-2 of scheme 58, from 2-chloro-4-methylbenzofuran (290b) (2.7 g, 16.21 mmol) in carbon tetrachloride (40 mL) using NBS (3.17 g, 17.83 mmol), benzoyl peroxide (0.589 g, 2.431 mmol) and refluxing overnight. This gave after workup 4-(bromomethyl)-2-chlorobenzofuran (290c) (3.98 g, 100% yield) as a yellow oil which was used as such for the next step.

Step-3: Preparation of ethyl 2-(2-((2-chlorobenzofuran-4-yl)methoxy)phenyl)acetate (290d)

Compound 290d was prepared according to the procedure reported in step-1 of scheme 58, from 4-(bromomethyl)-2- chlorobenzofuran (290c) (3.9 g, 15.89 mmol) in acetone (30 mL) using ethyl 2-(2-hydroxyphenyl)acetate (7c) (3.15 g, 17.47 mmol), $K_2CO_3$ (6.59 g, 47.7 mmol) and stirring overnight at RT. This gave after workup and purification by flash column chromatography [silica (80 g), eluting with EtOAc in hexane from 0-30%] ethyl 2-(2-((2-chlorobenzofuran-4-yl)methoxy)phenyl)acetate (290d) (1.70 g, 31% yield) as a yellow oil; $^1H$ NMR (300 MHz, DMSO-$d_6$) δ 7.63-7.55 (m, 1H), 7.42-7.35 (m, 2H), 7.24 (ddd, J=9.3, 7.5, 1.7 Hz, 2H), 7.13 (dd, J=8.9, 1.0 Hz, 2H), 6.93 (td, J=7.4, 1.1 Hz, 1H), 5.32 (s, 2H), 3.97 (q, J=7.1 Hz, 2H), 3.61 (s, 2H), 1.06 (t, J=7.1 Hz, 3H).

Step-4: Preparation of ethyl 2-(2-((2-(2-cyanopyridin-4-yl)benzofuran-4-yl)methoxy)phenyl)acetate (290f)

Compound 290f was prepared according to the procedure reported in step-8 of scheme 3, from ethyl 2-(2-((2-chlorobenzofuran-4-yl)methoxy)phenyl)acetate (290d) (201 mg, 0.583 mmol) in dioxane (6 mL) and 2Me-THF (3 mL) using 4-(4,4,5,5-tetramethyl-1,3,2-dioxaborolan-2-yl)picolinonitrile (290e) (201 mg, 0.874 mmol), $Pd_2(dba)_3$ (107 mg, 0.117 mmol), tripotassium phosphate (4M aqueous, 0.583 mL, 2.332 mmol) and heating at 115° C. for 4.5 h. This gave after workup and purification using flash column chromatography [silica gel (12 g), eluting with EtOAc in hexanes from 0-60%] ethyl 2-(2-((2-(2-cyanopyridin-4-yl)benzofuran-4-yl)methoxy)phenyl)acetate (290f) (139 mg, 58% yield) as a yellow solid; $^1H$ NMR (300 MHz, DMSO-$d_6$) δ 8.87 (dd, J=5.2, 0.8 Hz, 1H), 8.58 (dd, J=1.8, 0.8 Hz, 1H), 8.17 (dd, J=5.2, 1.7 Hz, 1H), 8.13 (d, J=1.0 Hz, 1H), 7.71 (d, J=7.9 Hz, 1H), 7.53-7.40 (m, 2H), 7.34-7.22 (m, 2H), 7.16 (d, J=8.2 Hz, 1H), 6.99-6.90 (m, 1H), 5.40 (s, 2H), 3.88 (q, J=7.1 Hz, 2H), 3.65 (s, 2H), 0.95 (t, J=7.1 Hz, 3H); MS (ES+): 413.1 (M+1).

Step-5: Preparation of ethyl 2-(2-((2-(2-(aminomethyl)pyridin-4-yl)benzofuran-4-yl)methoxy)phenyl) acetate (290 g)

Compound 290g was prepared according to the procedure reported in step-2 of scheme 1, from ethyl 2-(2-((2-(2-cyanopyridin-4-yl)benzofuran-4-yl)methoxy)phenyl)acetate (290f) (135 mg, 0.327 mmol) in anhydrous methanol (10 mL) using nickel(II) chloride hexahydrate (19.45 mg, 0.082 mmol), sodium borohydride (37.2 mg, 0.982 mmol), N1-(2-aminoethyl)ethane-1,2-diamine (0.071 mL, 0.655 mmol). The residue obtained was purified using flash column chromatography [silica gel (12 g), eluting with MeOH in DCM from 0 to 20%)] to furnish ethyl 2-(2-((2-(2-(aminomethyl) pyridin-4-yl)benzofuran-4-yl)methoxy)phenyl)acetate (290 g) (78 mg, 57% yield) as a yellow oil; MS (ES+): 417.2 (M+1).

Step-6: Preparation of 2-(2-((2-(2-(aminomethyl) pyridin-4-yl)benzofuran-4-yl)methoxy)phenyl)acetic acid (290 h)

Compound 290h was prepared according to the procedure reported in step-3 of scheme 1, from ethyl 2-(2-((2-(2-(aminomethyl)pyridin-4-yl)benzofuran-4-yl)methoxy)phenyl)acetate (290 g) (78 mg, 0.187 mmol) in MeOH/THF (3 mL each) using a solution of lithium hydroxide monohydrate (50 mg, 1.192 mmol) in water (2 mL) and stirring overnight at RT. This gave after workup and purification by reverse phase column chromatography [C18 column (50 g), eluting with ACN in water (containing 0.1% HCl) from 0-100%] 2-(2-((2-(2-(aminomethyl)pyridin-4-yl)benzofuran-4-yl) methoxy)phenyl)acetic acid (290 h) (69 mg, 95% yield) HCl salt as a yellow solid; $^1H$ NMR (300 MHz, DMSO-$d_6$) δ 8.76 (d, J=5.4 Hz, 1H), 8.64 (s, 3H, $D_2O$ exchangeable), 8.11 (s, 1H), 8.00 (s, 1H), 7.96 (d, J=5.4 Hz, 1H), 7.74-7.63 (m, 1H), 7.46 (d, J=4.7 Hz, 2H), 7.33-7.19 (m, 2H), 7.14 (d, J=8.1 Hz, 1H), 6.93 (t, J=7.4 Hz, 1H), 5.43 (s, 2H), 4.34-4.27 (m, 2H), 3.61 (s, 2H); MS (ES+): 389.1 (M+1); (ES−): 387.1 (M−1).

Scheme 291

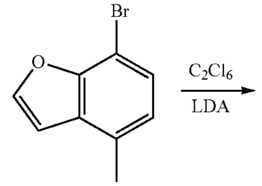

291a

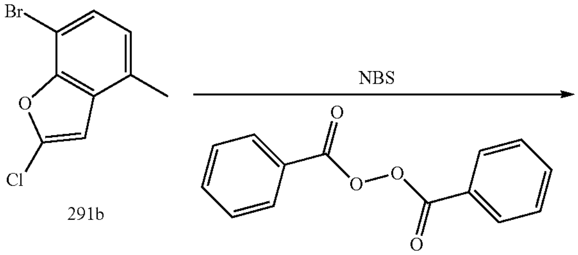

291b

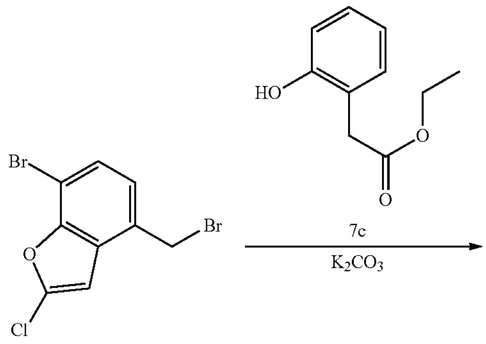

291c

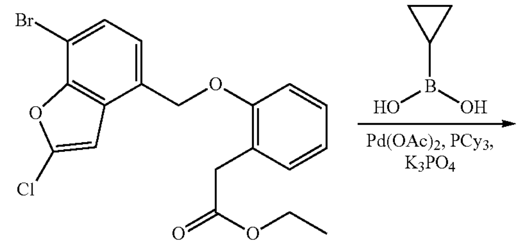

291d

-continued

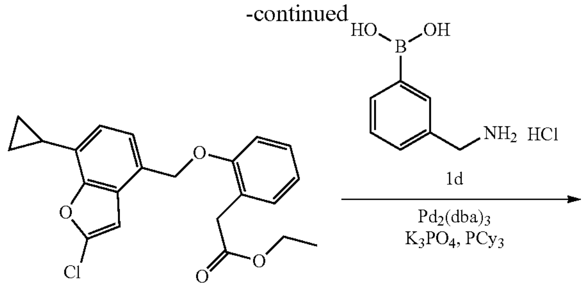

291e

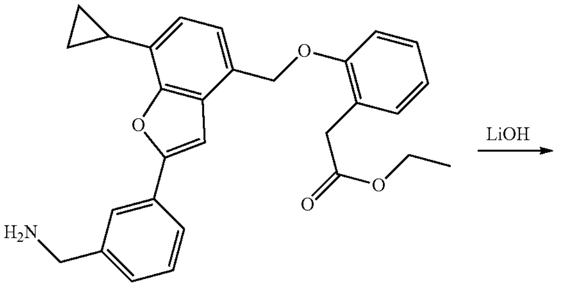

291f

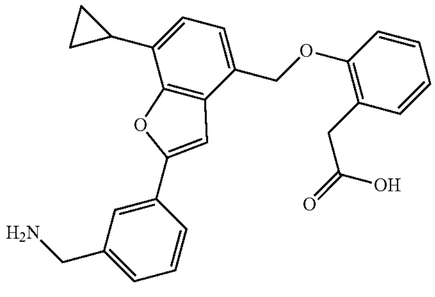

291g

Preparation of 2-(2-((2-(3-(aminomethyl)phenyl)-7-cyclopropylbenzofuran-4-yl)methoxy)phenyl)acetic acid (291g)

Step-1: Preparation of 7-bromo-2-chloro-4-methylbenzofuran (291b)

Compound 291b was prepared according to the procedure reported in step-1 of scheme 290, from 7-bromo-4-methylbenzofuran (291a) (615 mg, 2.91 mmol; CAS #799766-13-5) in dry THE (12 mL) using LDA (1.5 M in hexanes, 2.91 mL, 4.37 mmol), perchloroethane (1035 g, 4.37 mmol). This gave after workup and purification using flash column chromatography [silica gel (12 g), eluting with EtOAc in hexane from 0-20%] 7-bromo-2-chloro-4-methylbenzofuran (291b) (715 mg, 100% yield) as a colorless oil; $^1H$ NMR (300 MHz, DMSO-$d_6$) δ 7.46 (d, J=8.0 Hz, 1H), 7.29 (s, 1H), 7.07 (dd, J=8.0, 1.0 Hz, 1H), 2.43 (d, J=0.8 Hz, 3H).

Step-2: Preparation of 7-bromo-4-(bromomethyl)-2-chlorobenzofuran (291c)

Compound 291c was prepared according to the procedure reported in step-2 of scheme 58, from 7-bromo-2-chloro-4-methylbenzofuran (291b) (710 mg, 2.89 mmol) in carbon tetrachloride (8 mL) using NBS (566 mg, 3.18 mmol), benzoyl peroxide (105 mg, 0.434 mmol) and refluxing overnight. This gave after workup 7-bromo-4-(bromomethyl)-2-chlorobenzofuran (291c) (938 mg, 100% yield) as a yellow oil, which was used as such for the next step.

Step-3: Preparation of ethyl 2-(2-((7-bromo-2-chlorobenzofuran-4-yl)methoxy)phenyl)acetate (291d)

Compound 291d was prepared according to the procedure reported in step-1 of scheme 58, from 7-bromo-4-(bromomethyl)-2-chlorobenzofuran (291c) (936 mg, 2.89 mmol) in acetone (10 mL) using ethyl 2-(2-hydroxyphenyl)acetate (7c) (624 mg, 3.46 mmol), $K_2CO_3$ (1196 mg, 8.66 mmol) and stirring overnight at RT. This gave after workup and purification by flash column chromatography [silica gel (12 g), eluting with EtOAc in hexane from 0-30%]ethyl 2-(2-((7-bromo-2-chlorobenzofuran-4-yl)methoxy)phenyl)acetate (291d) (409 mg, 34% yield) as a pale yellow oil; $^1H$ NMR (300 MHz, DMSO-$d_6$) δ 7.61 (d, J=8.0 Hz, 1H), 7.34 (d, J=8.0 Hz, 1H), 7.31-7.19 (m, 3H), 7.11 (d, J=8.2 Hz, 1H), 6.99-6.87 (m, 1H), 5.30 (s, 2H), 3.96 (q, J=7.1 Hz, 2H), 3.61 (s, 2H), 1.05 (t, J=7.1 Hz, 3H).

Step-4: Preparation of ethyl 2-(2-((2-chloro-7-cyclopropylbenzofuran-4-yl)methoxy)phenyl)acetate (291e)

Compound 291e was prepared according to the procedure reported in step-2 of scheme 111, from ethyl 2-(2-((7-bromo-2-chlorobenzofuran-4-yl)methoxy)phenyl)acetate (291d) (360 mg, 0.850 mmol) in toluene (10 mL) using cyclopropyl boronic acid (95 mg, 1.105 mmol), a solution of $K_3PO_4$ (541 mg, 2.55 mmol) in water (1 mL), palladium(II) acetate (9.54 mg, 0.042 mmol) and heating at 100° C. for 5 h. This gave after workup and purification using flash column chromatography [silica gel (24 g), eluting with EtOAc in hexane from 0-35%]ethyl 2-(2-((2-chloro-7-cyclopropylbenzofuran-4-yl)methoxy)phenyl)acetate (291e) (278 mg, 0.722 mmol, 85% yield) as a yellow oil; $^1H$ NMR (300 MHz, DMSO-$d_6$) δ 7.30-7.18 (m, 3H), 7.16-7.05 (m, 2H), 6.96-6.87 (m, 2H), 5.24 (s, 2H), 3.96 (q, J=7.1 Hz, 2H), 3.58 (s, 2H), 2.30-2.16 (m, 1H), 1.11-0.99 (m, 5H), 0.91-0.82 (m, 2H).

Step-5: Preparation of ethyl 2-(2-((2-(3-(aminomethyl)phenyl)-7-cyclopropylbenzofuran-4-yl)methoxy)phenyl)acetate (291f)

Compound 291f was prepared according to the procedure reported in step-2 of scheme 1, from ethyl 2-(2-((2-chloro-7-cyclopropylbenzofuran-4-yl)methoxy)phenyl)acetate (291e) (140 mg, 0.364 mmol) in dioxane (6 mL) and 2-methyltetrahydrofuran (3 mL) using 3-(aminomethyl)phenylboronic acid hydrochloride (1d) (102 mg, 0.546 mmol), 4M solution of $K_3PO_4$ (0.364 mL, 1.455 mmol), tricyclohexylphosphine (40.8 mg, 0.146 mmol), $Pd_2(dba)_3$ (66.6 mg, 0.073 mmol) and heating at 115° C. for 4.5 h. This gave after workup and purification by flash column chromatography [silica gel (12 g), eluting with DMA-80 in DCM from 0-90%] ethyl 2-(2-((2-(3-(aminomethyl)phenyl)-7-cyclopropylbenzofuran-4-yl)methoxy)phenyl)acetate (291f) (91 mg, 0.200 mmol, 54.9% yield) as a yellow solid; MS (ES+): 478.2 (M+Na), 911.3 (2M+1).

Step-6: Preparation of 2-(2-((2-(3-(aminomethyl)phenyl)-7-cyclopropylbenzofuran-4-yl)methoxy)phenyl)acetic acid (291g)

Compound 291g was prepared according to the procedure reported in step-3 of scheme 1, from ethyl 2-(2-((2-(3-

(aminomethyl)phenyl)-7-cyclopropylbenzofuran-4-yl) methoxy)phenyl)acetate (291f) (88 mg, 0.193 mmol) in MeOH/THF (3 mL each) using a solution of lithium hydroxide monohydrate (55 mg, 1.311 mmol) in water (2 mL) and stirring overnight at RT. This gave after workup and purification by reverse phase column chromatography [C18 column (50 g), eluting with ACN in water (containing 0.1% HCl) from 0-100%] 2-(2-((2-(3-(aminomethyl)phenyl)-7-cyclopropylbenzofuran-4-yl)methoxy)phenyl)acetic acid (291g) (61 mg, 74% yield) HCl salt as a white solid; $^1$H NMR (300 MHz, DMSO-$d_6$) δ 12.21 (s, 1H, $D_2O$ exchangeable), 8.51 (s, 3H, $D_2O$ exchangeable), 8.00 (d, J=8.1 Hz, 2H), 7.70-7.59 (m, 3H), 7.31-7.19 (m, 3H), 7.13 (d, J=8.1 Hz, 1H), 6.97-6.87 (m, 2H), 5.34 (s, 2H), 4.09 (s, 2H), 3.58 (s, 2H), 2.46-2.31 (m, 1H), 1.18-1.04 (m, 2H), 1.04-0.91 (m, 2H); MS (ES−): 426.1 (M−1).

Scheme 292

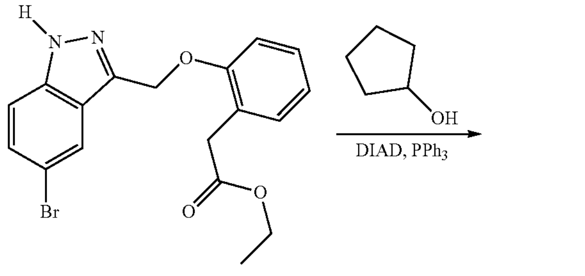

144e

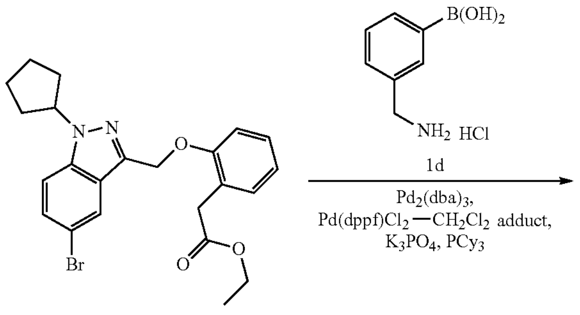

292a

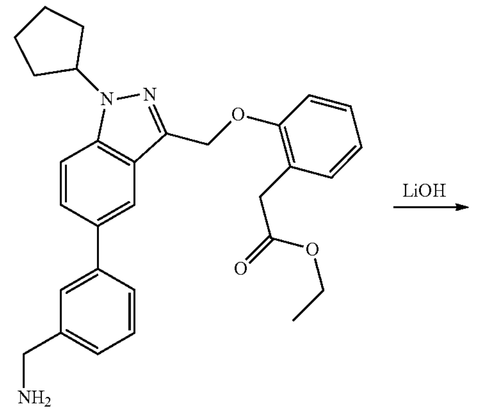

292b

-continued

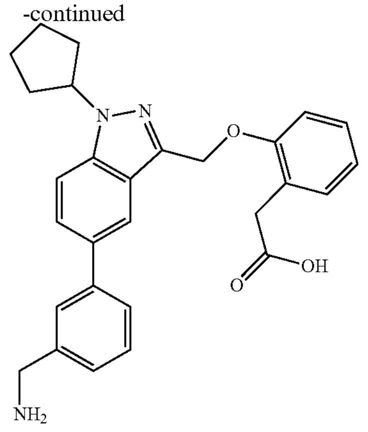

292c

Preparation of 2-(2-((5-(3-(aminomethyl)phenyl)-1-cyclopentyl-1H-indazol-3-yl)methoxy)phenyl)acetic acid (292c)

Step-1: Preparation of ethyl 2-(2-((5-bromo-1-cyclopentyl-1H-indazol-3-yl)methoxy)phenyl)acetate (292a)

Compound 292a was prepared according to the procedure reported in step-2 of scheme 65, from ethyl 2-(2-((5-bromo-1H-indazol-3-yl)methoxy)phenyl)acetate (144e) (500 mg, 1.285 mmol) in THF (20 mL) using cyclopentanol (199 mg, 2.312 mmol), triphenylphosphine (606 mg, 2.312 mmol), diisopropyl azodicarboxylate (DIAD, 0.450 mL, 2.312 mmol). This gave after workup and purification using flash column chromatography [silica gel (24 g), eluting with EtOAc in hexane from 0-60%] ethyl 2-(2-((5-bromo-1-cyclopentyl-1H-indazol-3-yl)methoxy)phenyl)acetate (292a) (200 mg, 34% yield) as a clear oil; $^1$H NMR (300 MHz, DMSO-$d_6$) δ 7.94 (d, J=1.8 Hz, 1H), 7.72 (d, J=9.0 Hz, 1H), 7.52 (dd, J=8.9, 1.9 Hz, 1H), 7.31-7.15 (m, 3H), 6.97-6.84 (m, 1H), 5.36 (s, 2H), 5.24-5.08 (m, 1H), 3.91 (q, J=7.1 Hz, 2H), 3.53 (s, 2H), 2.21-2.06 (m, 2H), 2.04-1.82 (m, 4H), 1.76-1.61 (m, 2H), 0.94 (t, J=7.1 Hz, 3H); MS (ES+): 457.10 & 459.10 (M+1); 479.10 & 481.10 (M+Na).

Step-2: Preparation of ethyl 2-(2-((5-(3-(aminomethyl)phenyl)-1-cyclopentyl-1H-indazol-3-yl) methoxy)phenyl)acetate (292b)

Compound 292b was prepared according to the procedure reported in step-2 of scheme 1, from ethyl 2-(2-((5-bromo-1-cyclopentyl-1H-indazol-3-yl)methoxy)phenyl)acetate (292a) (200 mg, 0.437 mmol) in dioxane (2 mL) and THF (2 mL) using 3-(aminomethyl)phenylboronic acid hydrochloride (1d) (164 mg, 0.875 mmol), 2 M solution of $K_3PO_4$ (0.875 mL, 1.749 mmol), tricyclohexylphosphine (24.53 mg, 0.087 mmol), $Pd_2(dba)_3$ (40.0 mg, 0.044 mmol), $PdCl_2$ (dppf)-$CH_2Cl_2$ adduct (35.7 mg, 0.044 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-cyclopentyl-1H-indazol-3-yl) methoxy)phenyl)acetate (292b) (150 mg, 71% yield) as a clear oil; $^1$H NMR (300 MHz, DMSO-$d_6$) δ 7.98 (s, 1H), 7.81-7.64 (m, 3H), 7.58-7.51 (m, 1H), 7.40-7.24 (m, 4H), 7.22-7.14 (m, 1H), 7.00-6.79 (m, 1H), 5.42 (s, 2H), 5.28-5.08 (m, 1H), 3.80 (s, 2H), 3.71-3.63 (m, 2H), 3.53 (s, 2H), 2.07-1.76 (m, 6H), 1.39-1.14 (m, 2H), 0.86-0.65 (m, 3H); MS (ES+): 484.20 (M+1); 506.20 (M+Na).

Step-3: Preparation of 2-(2-((5-(3-(aminomethyl)phenyl)-1-cyclopentyl-1H-indazol-3-yl)methoxy)phenyl)acetic acid (292c)

Compound 292c was prepared according to the procedure reported in step-3 of scheme 1, from ethyl 2-(2-((5-(3-(aminomethyl)phenyl)-1-cyclopentyl-1H-indazol-3-yl)methoxy)phenyl)acetate (292b) (150 mg, 0.310 mmol) in THF (2 mL) and MeOH (2 mL) using a solution of lithium hydroxide hydrate (78 mg, 1.861 mmol) in water (1 mL) and stirring at RT for 15 h. This gave after workup and purification by reverse phase column chromatography [C18 column (50 g), eluting with ACN in water (containing 0.1% HCl) from 0-100%] 2-(2-((5-(3-(aminomethyl)phenyl)-1-cyclopentyl-1H-indazol-3-yl)methoxy)phenyl)acetic acid (292c) (105 mg, 74% yield) HCl salt as a white solid; $^1$H NMR (300 MHz, DMSO-$d_6$) δ 12.11 (s, 1H, $D_2O$ exchangeable), 8.45 (s, 3H, $D_2O$ exchangeable), 8.08 (s, 1H), 7.89 (s, 1H), 7.84 (d, J=8.9 Hz, 1H), 7.80-7.70 (m, 2H), 7.55-7.40 (m, 2H), 7.33-7.23 (m, 2H), 7.23-7.15 (m, 1H), 6.96-6.86 (m, 1H), 5.45 (s, 2H), 5.32-5.07 (m, 1H), 4.23-3.98 (m, 2H), 3.53 (s, 2H), 2.22-2.10 (m, 2H), 2.10-2.00 (m, 2H), 1.96-1.84 (m, 2H), 1.78-1.67 (m, 2H); MS (ES+): 456.20 (M+1); (ES−): 454.20 (M−1).

Scheme 293

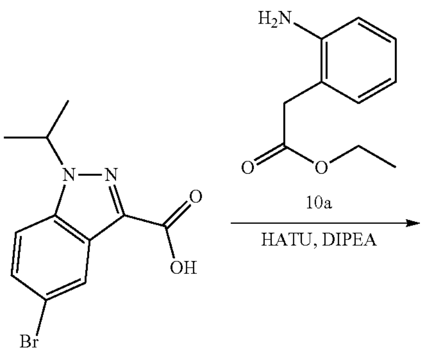

314a

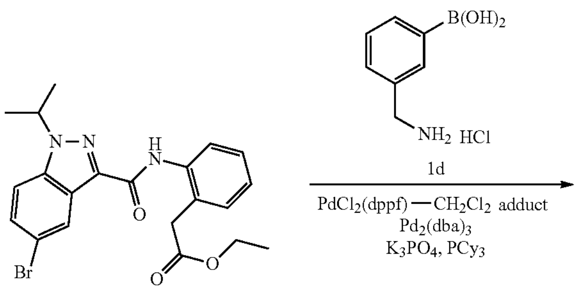

293a

-continued

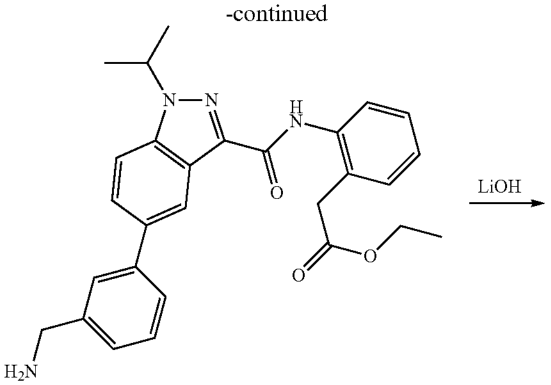

293b

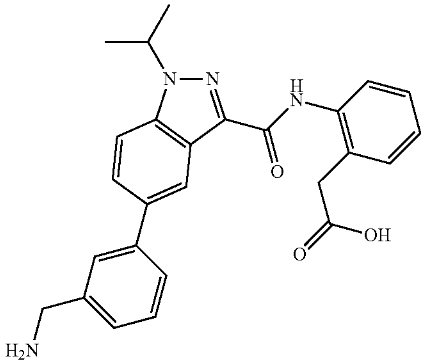

293c

Preparation of 2-(2-(5-(3-(aminomethyl)phenyl)-1-isopropyl-1H-indazole-3-carboxamido)phenyl)acetic acid (293c)

Step-1: Preparation of ethyl 2-(2-(5-bromo-1-isopropyl-1H-indazole-3-carboxamido)phenyl)acetate (293a)

Compound 293a was prepared according to the procedure reported in step-1 of scheme 10, from 5-bromo-1-isopropyl-1H-indazole-3-carboxylic acid (314a) (400 mg, 1.413 mmol) in DMF (8 mL) using ethyl 2-(2-aminophenyl)acetate (10a) (266 mg, 1.483 mmol), N-ethyl-N-isopropylpropan-2-amine (DIPEA, 0.984 mL, 5.65 mmol), and 2-(3H-[1,2,3]triazolo[4,5-b]pyridin-3-yl)-1,1,3,3-tetramethylisouronium hexafluorophosphate(V) (HATU, 806 mg, 2.119 mmol) and stirring at RT for 16 h. This gave after workup and purification by flash column chromatography [silica gel (24 g), eluting with EtOAc in hexane from 0-60%] ethyl 2-(2-(5-bromo-1-isopropyl-1H-indazole-3-carboxamido)phenyl)acetate (293a) (450 mg, 72% yield) as a white solid; $^1$H NMR (300 MHz, DMSO-$d_6$) δ 9.87 (s, 1H), 8.32 (d, J=1.9 Hz, 1H), 7.88 (d, J=9.0 Hz, 1H), 7.68 (d, J=7.8 Hz, 1H), 7.61 (dd, J=9.0, 1.9 Hz, 1H), 7.34 (td, J=6.9, 6.2, 1.7 Hz, 2H), 7.28-7.17 (m, 1H), 5.24-5.02 (m, 1H), 4.06-3.98 (m, 2H), 3.79 (s, 2H), 1.56 (d, J=6.6 Hz, 6H), 1.05 (t, J=7.1 Hz, 3H); MS (ES+): 444.10 & 446.10 (M+1); (ES−): 442.00 & 444.00 (M−1).

Step-2: Preparation of ethyl 2-(2-(5-(3-(aminomethyl)phenyl)-1-isopropyl-1H-indazole-3-carboxamido)phenyl)acetate (293b)

Compound 293b was prepared according to the procedure reported in step-2 of scheme 1, from ethyl 2-(2-(5-bromo- 1-isopropyl-1H-indazole-3-carboxamido)phenyl)acetate (293a) (150 mg, 0.338 mmol) in dioxane (2 mL) and THF (2 mL) using 3-(aminomethyl)phenylboronic acid hydrochloride (1d) (127 mg, 0.675 mmol), 2 M solution of $K_3PO_4$ (0.675 mL, 1.350 mmol), tricyclohexylphosphine (18.93 mg, 0.068 mmol), $Pd_2(dba)_3$ (30.9 mg, 0.034 mmol), $PdCl_2$ (dppf)-$CH_2Cl_2$ adduct (27.6 mg, 0.034 mmol) and heating at 100° C. for 2 h. This gave after workup and purification using flash column chromatography [silica gel (24 g), eluting with DMA-80 in DCM from 0-70%] ethyl 2-(2-(5-(3-(aminomethyl)phenyl)-1-isopropyl-1H-indazole-3-carboxamido)phenyl)acetate (293b) (100 mg, 63% yield) as a clear oil; $^1H$ NMR (300 MHz, DMSO-$d_6$) δ 9.84 (s, 1H), 8.44 (d, J=1.7 Hz, 1H), 7.97 (d, J=8.9 Hz, 1H), 7.85-7.70 (m, 3H), 7.64-7.55 (m, 1H), 7.46 (t, J=7.6 Hz, 1H), 7.35 (t, J=7.1 Hz, 3H), 7.25-7.15 (m, 1H), 5.25-5.08 (m, 1H), 4.05 (q, J=7.1 Hz, 2H), 3.90 (s, 2H), 3.81 (s, 2H), 1.59 (d, J=6.6 Hz, 6H), 1.08 (t, J=7.1 Hz, 3H); MS (ES+): 471.20 (M+1).

Step-3: Preparation of 2-(2-(5-(3-(aminomethyl)phenyl)-1-isopropyl-1H-indazole-3-carboxamido)phenyl)acetic acid (293c)

Compound 293c was prepared according to the procedure reported in step-3 of scheme 1, from ethyl 2-(2-(5-(3-(aminomethyl)phenyl)-1-isopropyl-1H-indazole-3-carboxamido)phenyl)acetate (293b) (100 mg, 0.213 mmol) in THF (2 mL) and MeOH (2 mL) using a solution of lithium hydroxide hydrate (53.5 mg, 1.275 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-(5-(3-(aminomethyl)phenyl)-1-isopropyl-1H-indazole-3-carboxamido)phenyl)acetic acid (293c) (55 mg, 59% yield) HCl salt as a white solid; $^1H$ NMR (300 MHz, DMSO-$d_6$) δ 10.05 (s, 1H, $D_2O$ exchangeable), 8.50 (d, J=1.7 Hz, 1H), 8.41 (s, 2H, $D_2O$ exchangeable), 8.00 (d, J=8.9 Hz, 1H), 7.91 (s, 1H), 7.89-7.81 (m, 2H), 7.77-7.71 (m, 1H), 7.55 (t, J=7.6 Hz, 1H), 7.48 (d, J=7.6 Hz, 1H), 7.35 (t, J=7.4 Hz, 2H), 7.22-7.14 (m, 1H), 5.26-5.09 (m, 1H), 4.13 (s, 2H), 3.72 (s, 2H), 1.59 (d, J=6.6 Hz, 6H); MS (ES+): 443.20 (M+1); (ES−): 441.20 (M−1); Analysis calculated for $C_{26}H_{26}N_4O_3 \cdot HCl \cdot 1.5H_2O$: C, 61.72; H, 5.98; Cl, 7.01; N, 11.07. Found: C, 61.73; H, 5.93; Cl, 6.84; N, 11.09.

Scheme 294

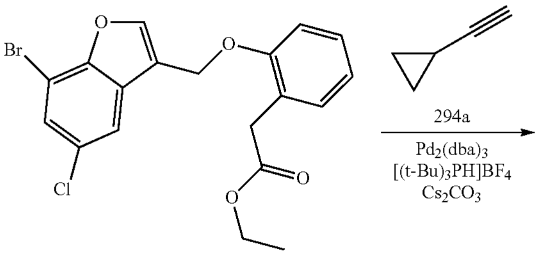

72e

-continued

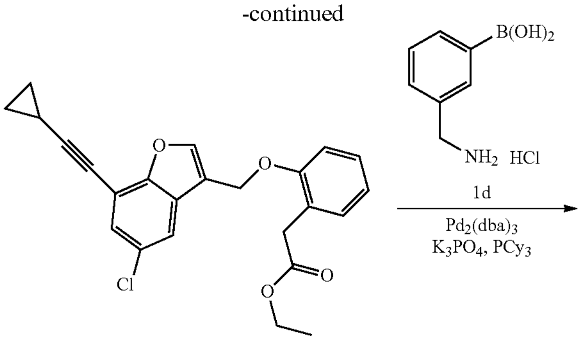

294b

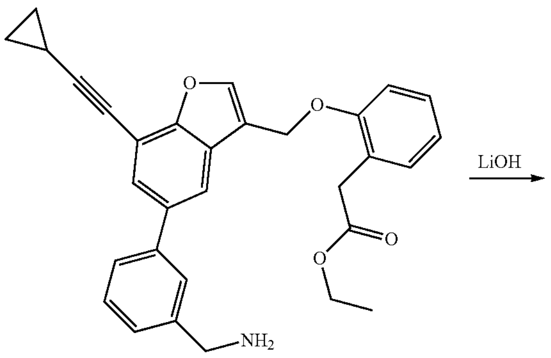

294c

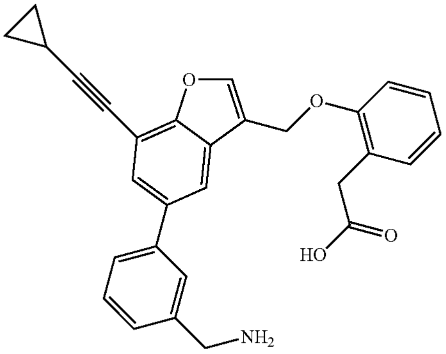

294d

Preparation of 2-(2-((5-(3-(aminomethyl)phenyl)-7-(cyclopropylethynyl)benzofuran-3-yl)methoxy)phenyl)acetic acid (294d)

Step-1: Preparation of ethyl 2-(2-((5-chloro-7-(cyclopropylethynyl)benzofuran-3-yl)methoxy)phenyl) acetate (294b)

To a solution of ethyl 2-(2-((7-bromo-5-chlorobenzofuran-3-yl)methoxy)phenyl)acetate (72e) (500 mg, 1.18 mmol), cesium carbonate (441 mg, 1.354 mmol), $Pd_2(dba)_3$ (22.69 mg, 0.025 mmol), and tri-tert-butylphosphonium tetrafluoroborate (28.1 mg, 0.097 mmol) in dioxane (5 mL) was added ethynyl cyclopropane (294a) (122 mg, 1.840 mmol; CAS #6746-94-7) and heated at 60° C. for 6 h. The reaction mixture was concentrated and the residue obtained was purified using flash column chromatography [silica gel (12 g), eluting with EtOAc in hexanes from 0-70%] to afford ethyl 2-(2-((5-chloro-7-(cyclopropylethynyl)benzofuran-3-yl)methoxy)phenyl)acetate (294b) (327 mg, 68% yield); MS (ES+): 431.1 (M+Na).

Step-2: Preparation of ethyl 2-(2-((5-(3-(aminomethyl)phenyl)-7-(cyclopropylethynyl)benzofuran-3-yl)methoxy)phenyl)acetate (294c)

Compound 294c was prepared according to the procedure reported in step-2 of scheme 1, from ethyl 2-(2-((5-chloro-7-(cyclopropylethynyl)benzofuran-3-yl)methoxy)phenyl) acetate (294b) (200 mg, 0.489 mmol) in dioxane (20 mL) using 3-(aminomethyl)phenylboronic acid hydrochloride (1d) (115 mg, 0.611 mmol), 4 M solution of $K_3PO_4$ (0.489 mL, 1.957 mmol), tricyclohexylphosphine (27.4 mg, 0.098 mmol), $Pd_2(dba)_3$ (44.8 mg, 0.049 mmol) and heating at 100° C. overnight. This gave after workup and purification using flash column chromatography [silica gel (12 g), eluting with DMA-80 in DCM from 0-50%] ethyl 2-(2-((5-(3-(aminomethyl)phenyl)-7-(cyclopropylethynyl)benzofuran-3-yl)methoxy)phenyl)acetate (294c) (55 mg, 23% yield) as a clear oil; MS (ES+): 480.3 (M+1).

Step-3: Preparation of 2-(2-((5-(3-(aminomethyl) phenyl)-7-(cyclopropylethynyl)benzofuran-3-yl) methoxy)phenyl)acetic acid (294d)

Compound 294d was prepared according to the procedure reported in step-3 of scheme 1, from ethyl 2-(2-((5-(3-(aminomethyl)phenyl)-7-(cyclopropylethynyl)benzofuran-3-yl)methoxy)phenyl)acetate (294c) (55 mg, 0.115 mmol) in THF (3 mL) using a solution of lithium hydroxide hydrate (14.44 mg, 0.344 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)phenyl)-7-(cyclopropylethynyl)benzofuran-3-yl)methoxy)phenyl)acetic acid (294d) (12.1 mg, 0.027 mmol, 23.37% yield) HCl salt as a white solid; $^1H$ NMR (300 MHz, DMSO-$d_6$) δ 12.16 (s, 1H), 8.29 (s, 3H), 8.17 (s, 1H), 7.98 (d, J=1.8 Hz, 1H), 7.88 (s, 1H), 7.77 (d, J=7.7 Hz, 1H), 7.70 (d, J=1.8 Hz, 1H), 7.52 (t, J=7.6 Hz, 1H), 7.45 (d, J=7.7 Hz, 1H), 7.32-7.24 (m, 1H), 7.24-7.17 (m, 2H), 6.93 (t, J=7.0 Hz, 1H), 5.31 (s, 2H), 4.11 (s, 2H), 3.53 (s, 2H), 1.70-1.64 (m, 1H), 1.03-0.91 (m, 2H), 0.90-0.74 (m, 2H); MS (ES+): 452.2 (M+1); (ES−): 450.1 (M−1).

Scheme 295

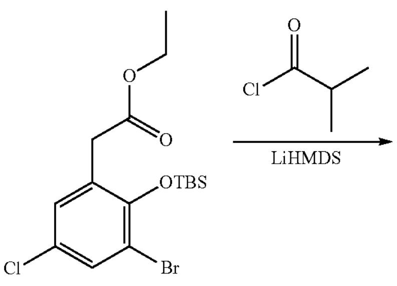

273b

-continued

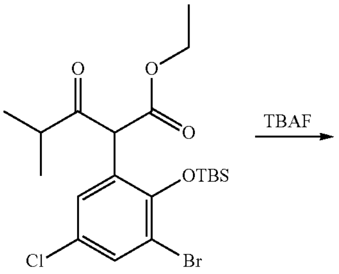

295a

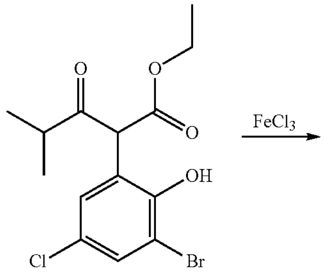

295b

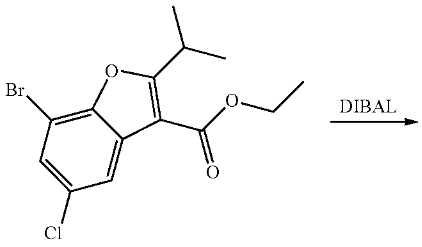

295c

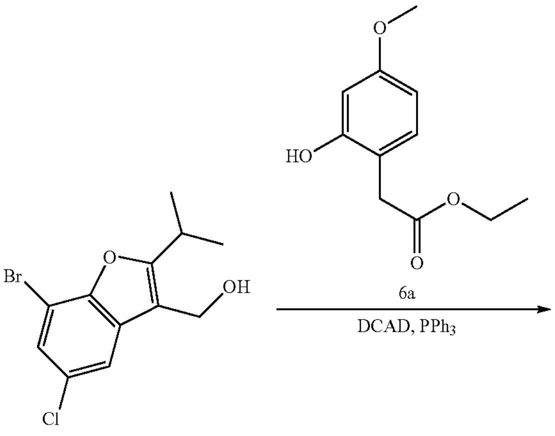

295d

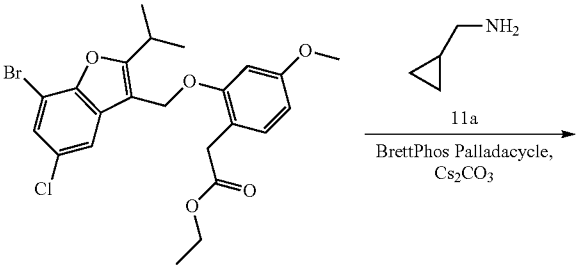

295e

-continued

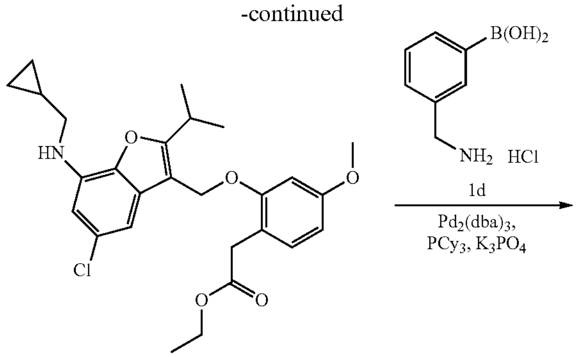

295f

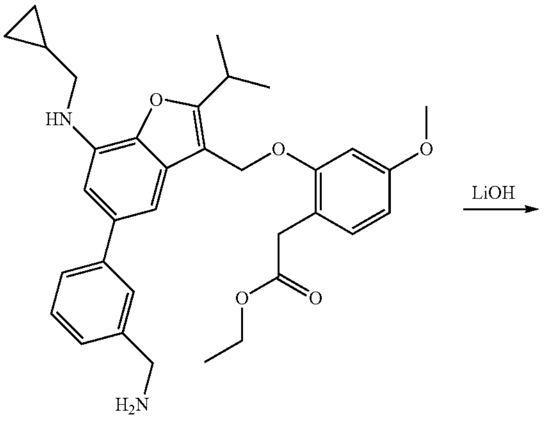

295g

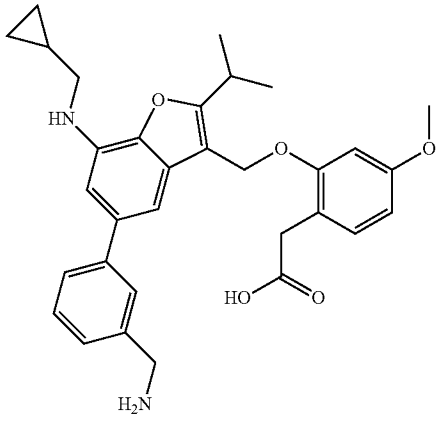

295h

Preparation of 2-(2-((5-(3-(aminomethyl)phenyl)-7-((cyclopropylmethyl)amino)-2-isopropylbenzofuran-3-yl)methoxy)-4-methoxyphenyl)acetic acid (295 h)

Step-1: Preparation of ethyl 2-(3-bromo-2-((tert-butyldimethylsilyl)oxy)-5-chlorophenyl)-4-methyl-3-oxopentanoate (295a)

Compound 295a was prepared according to the procedure reported in step-1 of scheme 171, from ethyl 2-(3-bromo-2-((tert-butyldimethylsilyl)oxy)-5-chlorophenyl)acetate (273b) (10 g, 24.52 mmol) in THF (75 mL) using LiHMDS (1N in THF, 29.4 mL, 29.4 mmol), isobutyryl chloride (2.98 mL, 28.2 mmol) in THF (3 mL) and stirring at −78° C. for 1 h and at 0° C. for 1 h. This gave after workup and purification using flash column chromatography [silica gel (80 g), eluting with EtOAc in hexane from 0-100%] ethyl 2-(3-bromo-2-((tert-butyldimethylsilyl)oxy)-5-chlorophenyl)-4-methyl-3-oxopentanoate (295a) (10.002 g, 85% yield) as a clear oil.

Step-2: Preparation of ethyl 2-(3-bromo-5-chloro-2-hydroxyphenyl)-4-methyl-3-oxopentanoate (295b)

Compound 295b was prepared according to the procedure reported in step-2 of scheme 3, from ethyl 2-(3-bromo-2-((tert-butyldimethylsilyl)oxy)-5-chlorophenyl)-4-methyl-3-oxopentanoate (295a) (10.002 g, 22.23 mmol) in THF (60 mL) using TBAF (27.8 mL, 27.8 mmol) and stirring at 0° C. for 1 h. This gave after workup and purification using flash column chromatography [silica gel (80 g), eluting with EtOAc in hexane from 0-100%] ethyl 2-(3-bromo-5-chloro-2-hydroxyphenyl)-4-methyl-3-oxopentanoate (295b) (4.778 g, 59% yield).

Step-3: Preparation of ethyl 7-bromo-5-chloro-2-isopropylbenzofuran-3-carboxylate (295c)

Compound 295c was prepared according to the procedure reported in step-3 of scheme 171, from ethyl 2-(3-bromo-5-chloro-2-hydroxyphenyl)-4-methyl-3-oxopentanoate (295b) (4.778 g, 13.14 mmol) in DCE (40 mL) using iron(III) chloride (0.355 g, 1.314 mmol) and stirring for 2 days at RT. This gave after workup and purification using flash column chromatography [silica gel (40 g), eluting with EtOAc in hexane from 0-100%] ethyl 7-bromo-5-chloro-2-isopropylbenzofuran-3-carboxylate (295c) (3.81 g, 84% yield) as a white solid; $^1H$ NMR (300 MHz, DMSO-$d_6$) δ 7.85 (d, J=2.0 Hz, 1H), 7.75 (d, J=2.1 Hz, 1H), 4.37 (q, J=7.1 Hz, 2H), 3.93 (p, J=7.0 Hz, 1H), 1.36 (dd, J=11.1, 7.0 Hz, 9H).

Step-4: Preparation of (7-bromo-5-chloro-2-isopropylbenzofuran-3-yl)methanol (295d)

Compound 295d was prepared according to the procedure reported in step-2 of scheme 69, from ethyl 7-bromo-5-chloro-2-isopropylbenzofuran-3-carboxylate (295c) (3.81 g, 11.02 mmol) in DCM (10 mL) using 1.0 M solution of DIBAL in DCM (27.6 mL, 27.6 mmol) and stirring at 0° C. for 2 h. This gave after workup and purification using flash column chromatography [silica gel (120 g), eluting with EtOAc in hexane from 0-50%] (7-bromo-5-chloro-2-isopropylbenzofuran-3-yl)methanol (295d) (2.133 g, 64% yield) as a white solid; $^1H$ NMR (300 MHz, DMSO-$d_6$) δ 7.70 (d, J=2.0 Hz, 1H), 7.57 (d, J=2.0 Hz, 1H), 5.12 (t, J=5.6 Hz, 1H), 4.56 (d, J=5.7 Hz, 2H), 3.41-3.28 (m, 1H), 1.29 (d, J=6.9 Hz, 6H).

Step-5: Preparation of ethyl 2-(2-((7-bromo-5-chloro-2-isopropylbenzofuran-3-yl)methoxy)-4-methoxyphenyl)acetate (295e)

Compound 295e was prepared according to the procedure reported in step-2 of scheme 65, from (7-bromo-5-chloro-2-isopropylbenzofuran-3-yl)methanol (295d) (1.07 g, 3.52 mmol) in DCM (15 mL) using triphenylphosphine (1.202 g, 4.58 mmol), ethyl 2-(2-hydroxy-4-methoxyphenyl)acetate (6a) (1.111 g, 5.29 mmol), a solution of DCAD (1.682 g, 4.58 mmol) in DCM (5 mL) and stirring at RT for 3 h. This gave after workup and purification using flash column chromatography [silica gel (12 g), eluting with EtOAc in hexane from 0-50%]ethyl 2-(2-((7-bromo-5-chloro-2-isopropylbenzofuran-3-yl)methoxy)-4-methoxyphenyl)acetate (295e) (529 mg, 30% yield) as a white solid; $^1$H NMR (300 MHz, DMSO-$d_6$) δ 7.69 (d, J=2.0 Hz, 1H), 7.63 (d, J=1.9 Hz, 1H), 7.08 (d, J=8.3 Hz, 1H), 6.79 (d, J=2.4 Hz, 1H), 6.50 (dd, J=8.3, 2.4 Hz, 1H), 5.20 (s, 2H), 3.85 (q, J=7.1 Hz, 2H), 3.77 (s, 3H), 3.49-3.37 (m, 3H), 1.29 (d, J=6.9 Hz, 6H), 0.94 (t, J=7.1 Hz, 3H).

Step-6: Preparation of ethyl 2-(2-((5-chloro-7-((cyclopropylmethyl)amino)-2-isopropylbenzofuran-3-yl)methoxy)-4-methoxyphenyl)acetate (295f)

Compound 295f was prepared according to the procedure reported in step-2 of scheme 111, from ethyl 2-(2-((7-bromo-5-chloro-2-isopropylbenzofuran-3-yl)methoxy)-4-methoxyphenyl)acetate (295e) (529 mg, 1.067 mmol) in MeCN (2 mL) using cyclopropylmethanamine (11a) (0.183 mL, 2.134 mmol), cesium carbonate (1043 mg, 3.20 mmol), BrettPhos Palladacycle (42.6 mg, 0.053 mmol) and heating at 90° C. for 2 h. This gave after workup and purification using flash column chromatography [silica gel (12 g), eluting with EtOAc in hexane from 0-50%] ethyl 2-(2-((5-chloro-7-((cyclopropylmethyl)amino)-2-isopropylbenzofuran-3-yl)methoxy)-4-methoxyphenyl)acetate (295f) (341 mg, 66% yield); $^1$H NMR (300 MHz, DMSO-$d_6$) δ 7.07 (d, J=8.3 Hz, 1H), 6.81-6.74 (m, 2H), 6.53-6.41 (m, 2H), 5.96 (t, J=5.9 Hz, 1H), 5.12 (s, 2H), 3.91 (q, J=7.1 Hz, 2H), 3.80-3.74 (m, 3H), 3.41 (s, 2H), 3.38-3.27 (m, 2H), 3.09 (t, J=6.3 Hz, 2H), 1.31-1.26 (m, 6H), 1.18-1.07 (m, OH), 1.00 (t, J=7.1 Hz, 3H), 0.55-0.42 (m, 2H), 0.31-0.20 (m, 2H).

Step-7: Preparation of ethyl 2-(2-((5-(3-(aminomethyl)phenyl)-7-((cyclopropylmethyl)amino)-2-isopropylbenzofuran-3-yl)methoxy)-4-methoxyphenyl) acetate (295g)

Compound 295g was prepared according to the procedure reported in step-2 of scheme 1, from ethyl 2-(2-((5-chloro-7-((cyclopropylmethyl)amino)-2-isopropylbenzofuran-3-yl) methoxy)-4-methoxyphenyl)acetate (295f) (341 mg, 0.702 mmol) in dioxane (12 mL) and THE (6 mL) using 3-(aminomethyl)phenylboronic acid hydrochloride (1d) (329 mg, 1.754 mmol), 4 M solution of $K_3PO_4$ (0.702 mL, 2.81 mmol), tricyclohexylphosphine (157 mg, 0.561 mmol), $Pd_2(dba)_3$ (257 mg, 0.281 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-((cyclopropylmethyl)amino)-2-isopropylbenzofuran-3-yl)methoxy)-4-methoxyphenyl)acetate (295g) (321 mg, 82% yield); MS (ES+): 557.30 (M+1).

Step-8: Preparation of 2-(2-((5-(3-(aminomethyl) phenyl)-7-((cyclopropylmethyl)amino)-2-isopropylbenzofuran-3-yl)methoxy)-4-methoxyphenyl)acetic acid (295 h)

Compound 295h was prepared according to the procedure reported in step-3 of scheme 1, from ethyl 2-(2-((5-(3-(aminomethyl)phenyl)-7-((cyclopropylmethyl)amino)-2-isopropylbenzofuran-3-yl)methoxy)-4-methoxyphenyl)acetate (295g) (321 mg, 0.577 mmol) in THF (6 mL), methanol (0.6 mL) and water (0.6 mL) using lithium hydroxide monohydrate (55.2 mg, 2.306 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-((cyclopropylmethyl)amino)-2-isopropylbenzofuran-3-yl)methoxy)-4-methoxyphenyl)acetic acid (295 h) (73 mg, 24% yield) HCl salt as a white solid; $^1$H NMR (300 MHz, DMSO-$d_6$) δ 8.30 (s, 3H, $D_2O$ exchangeable), 7.79 (s, 1H), 7.68 (d, J=7.8 Hz, 1H), 7.48 (t, J=7.6 Hz, 1H), 7.41 (d, J=7.6 Hz, 1H), 7.17 (s, 1H), 7.07 (d, J=8.3 Hz, 1H), 6.81 (d, J=2.5 Hz, 2H), 6.49 (dd, J=8.3, 2.4 Hz, 1H), 5.21 (s, 2H), 4.16-4.05 (m, 2H), 3.76 (s, 3H), 3.50-3.39 (m, 1H), 3.39 (s, 2H), 3.19 (d, J=6.7 Hz, 2H), 1.32 (d, J=6.9 Hz, 6H), 1.28-1.08 (m, 1H), 0.58-0.43 (m, 2H), 0.36-0.24 (m, 2H). MS (ES+): 529.3 (M+1); MS (ES−): 527.2 (M−1).

Scheme 296

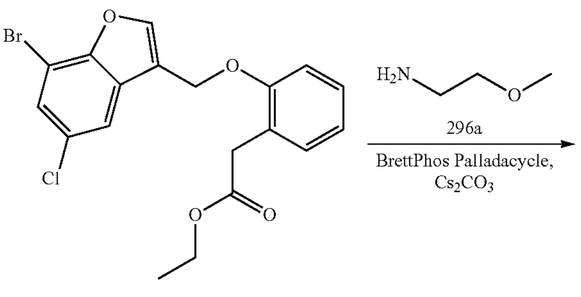

72e

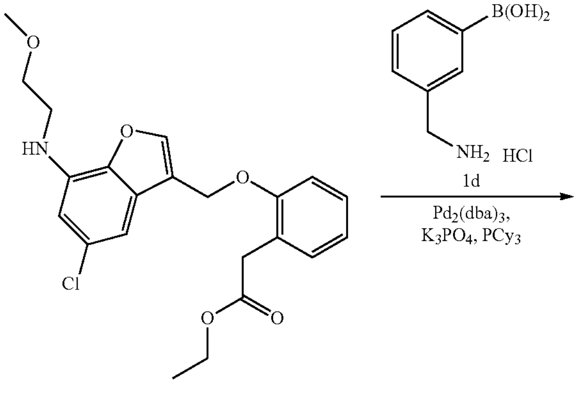

296b

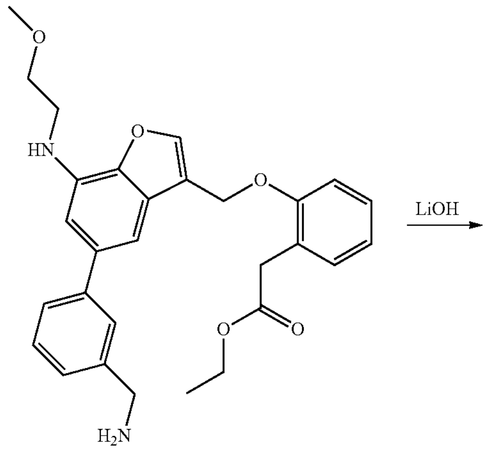

296c

-continued

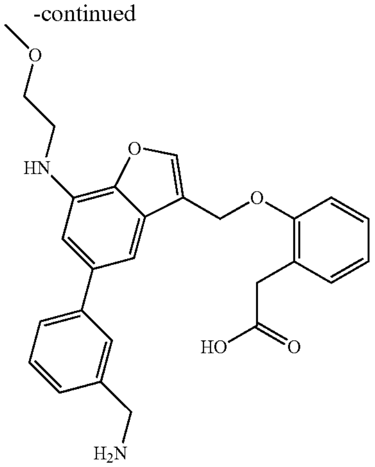

296d

Preparation of 2-(2-((5-(3-(aminomethyl)phenyl)-7-((2-methoxyethyl)amino)benzofuran-3-yl)methoxy)phenyl)acetic acid (296d)

Step-1: Preparation of ethyl 2-(2-((5-chloro-7-((2-methoxyethyl)amino)benzofuran-3-yl)methoxy)phenyl)acetate (296b)

Compound 296b was prepared according to the procedure reported in step-2 of scheme 111, from ethyl 2-(2-((7-bromo-5-chlorobenzofuran-3-yl)methoxy)phenyl)acetate (72e) (2 g, 4.72 mmol) in MeCN (2 mL) using 2-methoxyethanamine (296a) (0.832 mL, 9.44 mmol), cesium carbonate (4.61 g, 14.16 mmol), BrettPhos Palladacycle (0.188 g, 0.236 mmol) and heating at 90° C. for 2 h. This gave after workup and purification using flash column chromatography [silica gel (12 g), eluting with EtOAc in hexane from 0-50%] ethyl 2-(2-((5-chloro-7-((2-methoxyethyl)amino)benzofuran-3-yl)methoxy)phenyl)acetate (296b) (811 mg, 41% yield); MS (ES+): 418.10 (M+1).

Step-2: Preparation of ethyl 2-(2-((5-(3-(aminomethyl)phenyl)-7-((2-methoxyethyl)amino)benzofuran-3-yl)methoxy)phenyl)acetate (296c)

Compound 296c was prepared according to the procedure reported in step-2 of scheme 1, from ethyl 2-(2-((5-chloro-7-((2-methoxyethyl)amino)benzofuran-3-yl)methoxy)phenyl)acetate (296b) (811 mg, 1.941 mmol) in dioxane (24 mL) and THF (12 mL) using 3-(aminomethyl)phenylboronic acid hydrochloride (1d) (909 mg, 4.85 mmol), 4 M solution of $K_3PO_4$ (1.941 mL, 7.76 mmol), tricyclohexylphosphine (435 mg, 1.553 mmol), $Pd_2(dba)_3$ (711 mg, 0.776 mmol) and heating at 115° C. for 16 h. This gave after workup and purification using flash column chromatography [silica gel (24 g), eluting with DMA-80 in DCM from 0-70%] ethyl 2-(2-((5-(3-(aminomethyl)phenyl)-7-((2-methoxyethyl)amino)benzofuran-3-yl)methoxy)phenyl)acetate (296c) (925 mg, 98% yield); MS (ES+): 489.30 (M+1).

Step-3: Preparation of 2-(2-((5-(3-(aminomethyl)phenyl)-7-((2-methoxyethyl)amino)benzofuran-3-yl)methoxy)phenyl)acetic acid (296d)

Compound 296d was prepared according to the procedure reported in step-3 of scheme 1, from ethyl 2-(2-((5-(3-(aminomethyl)phenyl)-7-((2-methoxyethyl)amino)benzofuran-3-yl)methoxy)phenyl)acetate (296c) (925 mg, 1.662 mmol) in THF (6 mL), methanol (0.6 mL) and water (0.6 mL) using lithium hydroxide monohydrate (159 mg, 6.65 mmol) and stirring for 10 h at RT. This gave after workup and purification using reverse phase column chromatography [C18 column (40 g), eluting with ACN in water (containing 0.1% HCl) from 0-100%] 2-(2-((5-(3-(aminomethyl)phenyl)-7-((2-methoxyethyl)amino)benzofuran-3-yl)methoxy)phenyl)acetic acid (296d) (82 mg, 9% yield) HCl salt as a light brown solid; $^1H$ NMR (300 MHz, DMSO-$d_6$) δ 8.50 (s, 4H, $D_2O$ exchangeable), 8.04 (s, 1H), 7.85 (s, 1H), 7.69 (dt, J=7.2, 1.8 Hz, 1H), 7.52-7.41 (m, 2H), 7.30-7.20 (m, 3H), 7.23-7.15 (m, 1H), 6.96-6.88 (m, 2H), 5.27 (s, 2H), 4.14-4.04 (m, 2H), 3.60 (t, J=5.6 Hz, 2H), 3.55 (s, 2H), 3.50 (t, J=5.6 Hz, 2H), 3.31 (s, 3H). MS (ES+): 461.1 (M+1); MS (ES−): 459.1 (M−1).

Scheme 297

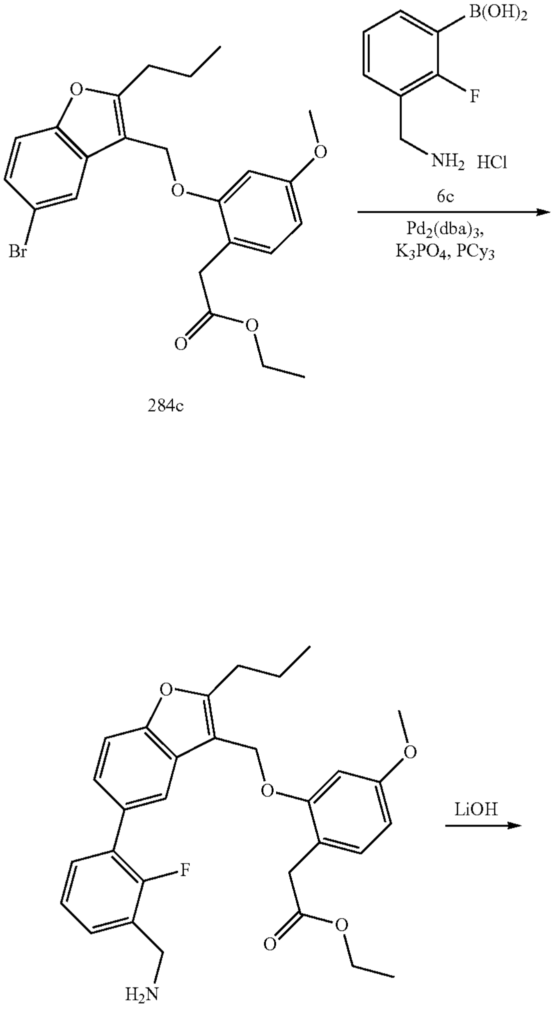

284c

6c

297a

-continued

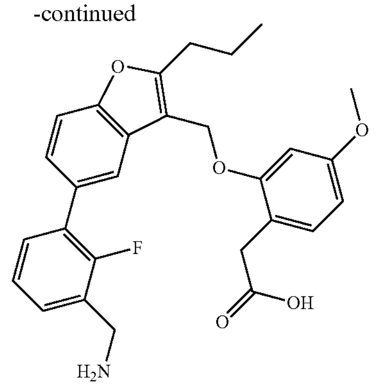

297b

Scheme 298

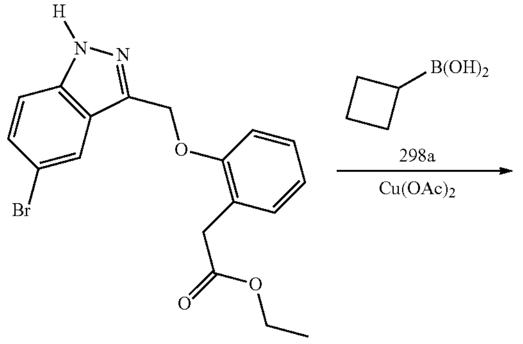

144e

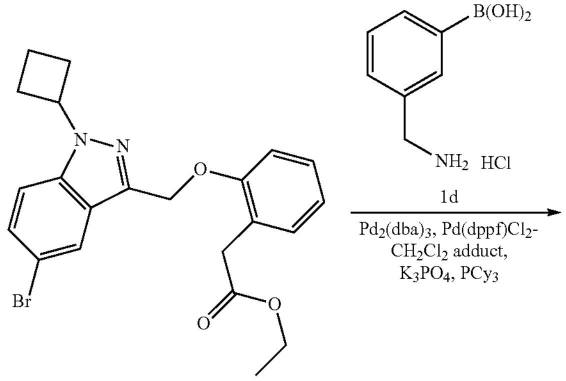

298b

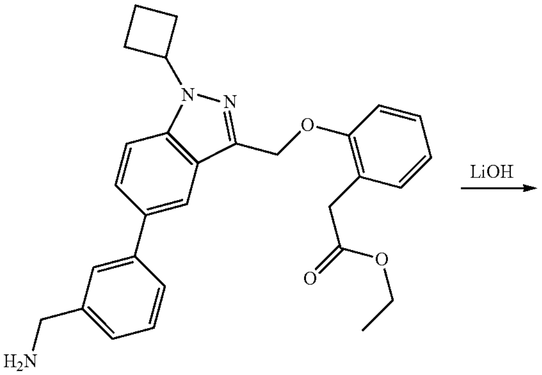

298c

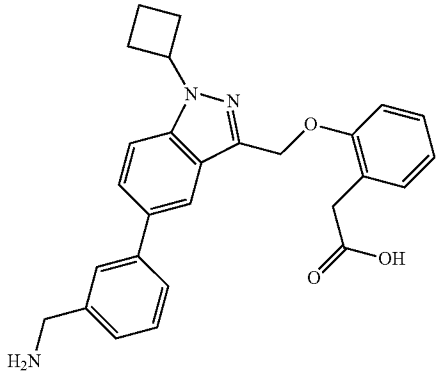

298d

Preparation of 2-(2-((5-(3-(aminomethyl)-2-fluorophenyl)-2-propylbenzofuran-3-yl)methoxy)-4-methoxyphenyl)acetic acid (297b)

Step-1: Preparation of ethyl 2-(2-((5-(3-(aminomethyl)-2-fluorophenyl)-2-propylbenzofuran-3-yl)methoxy)-4-methoxyphenyl)acetate (297a)

Compound 297a was prepared according to the procedure reported in step-2 of scheme 1, from ethyl 2-(2-((5-bromo-2-propylbenzofuran-3-yl)methoxy)-4-methoxyphenyl)acetate (284c) (300 mg, 0.650 mmol) in dioxane (12 mL) using (3-(aminomethyl)-2-fluorophenyl)boronic acid hydrochloride (6c) (137 mg, 0.813 mmol), 4 M solution of $K_3PO_4$ (0.650 mL, 2.60 mmol), tricyclohexylphosphine (36.5 mg, 0.130 mmol) and $Pd_2(dba)_3$ (59.5 mg, 0.065 mmol) and heating at 115° C. for 12 h. This gave after workup and purification by flash column chromatography [silica gel (12 g), eluting with EtOAc in hexane from 0-100%]ethyl 2-(2-((5-(3-(aminomethyl)-2-fluorophenyl)-2-propylbenzofuran-3-yl)methoxy)-4-methoxyphenyl)acetate (297a) (250 mg, 76% yield); (ES+): 506.20 (M+1).

Step-2: Preparation of 2-(2-((5-(3-(aminomethyl)-2-fluorophenyl)-2-propylbenzofuran-3-yl)methoxy)-4-methoxyphenyl)acetic acid (297b)

Compound 297b was prepared according to the procedure reported in step-3 of scheme 1, from ethyl 2-(2-((5-(3-(aminomethyl)-2-fluorophenyl)-2-propylbenzofuran-3-yl)methoxy)-4-methoxyphenyl)acetate (297a) (244 mg, 0.483 mmol) in THF (3 mL) using a solution of lithium hydroxide hydrate (60.8 mg, 1.448 mmol) in water (1 mL) and stirring overnight at RT. This gave after workup and purification by reverse phase column chromatography [C18 column (30 g), eluting with ACN in water (containing 0.1% HCl) from 0-100%] 2-(2-((5-(3-(aminomethyl)-2-fluorophenyl)-2-propylbenzofuran-3-yl)methoxy)-4-methoxyphenyl)acetic acid (297b) (138.8 mg, 0.291 mmol, 60.2% yield) HCl salt as a white solid; $^1H$ NMR (300 MHz, DMSO-$d_6$) δ 8.69 (s, 1H, $D_2O$ exchangeable), 7.79 (s, 1H), 7.69-7.61 (m, 1H), 7.61-7.51 (m, 2H), 7.44 (dt, J=8.5, 1.9 Hz, 1H), 7.35 (t, J=7.7 Hz, 1H), 7.07 (d, J=8.3 Hz, 1H), 6.81 (d, J=2.4 Hz, 1H), 6.50 (dd, J=8.3, 2.4 Hz, 1H), 5.23 (s, 2H), 4.13 (s, 2H), 3.75 (s, 3H), 3.38 (s, 2H), 2.87 (t, J=7.3 Hz, 2H), 1.76-1.61 (m, 2H), 0.93 (t, J=7.4 Hz, 3H); $^{19}F$ NMR (282 MHz, DMSO) δ −122.29; MS (ES+): 478.20 (M+1); (ES−): 476.20 (M−1).

Preparation of 2-(2-((5-(3-(aminomethyl)phenyl)-1-cyclobutyl-1H-indazol-3-yl)methoxy)phenyl)acetic acid (298d)

Step-1: Preparation of ethyl 2-(2-((5-bromo-1-cyclobutyl-1H-indazol-3-yl)methoxy)phenyl)acetate (298b)

Compound 298b was prepared according to the procedure reported in step-5 of scheme 144, from ethyl 2-(2-((5-bromo-1H-indazol-3-yl)methoxy)phenyl)acetate (144e) (0.500 g, 1.285 mmol) in DCM (8 mL) using cyclobutyl boronic acid (298a) (0.321 g, 3.21 mmol; CAS #849052-26-2), 2,2'-bipyridine (201 mg, 1.285 mmol), copper (II) acetate (0.233 g, 1.285 mmol) and heating at 70° C. for 6 h. This gave after work up and purification using flash column chromatography [silica gel (24 g), eluting with DMA-80 in DCM from 0-50%] ethyl 2-(2-((5-bromo-1-cyclobutyl-1H-indazol-3-yl)methoxy)phenyl)acetate (298b) (0.180 g, 32% yield) as a clear oil; $^1$H NMR (300 MHz, DMSO-$d_6$) δ 7.94 (d, J=1.8 Hz, 1H), 7.70 (d, J=8.9 Hz, 1H), 7.52 (dd, J=8.9, 1.8 Hz, 1H), 7.30-7.18 (m, 3H), 6.93 (td, J=7.1, 1.7 Hz, 1H), 5.39 (s, 2H), 5.29 (p, J=8.3 Hz, 1H), 3.91 (q, J=7.1 Hz, 2H), 3.56 (s, 2H), 2.69-2.55 (m, 2H), 2.47-2.40 (m, 2H), 1.94-1.78 (m, 2H), 0.93 (t, J=7.1 Hz, 3H); MS (ES+): 443.10 & 445.10 (M+1); (ES−): 441.00 (M−1).

Step-2: Preparation of ethyl 2-(2-((5-(3-(aminomethyl)phenyl)-1-cyclobutyl-1H-indazol-3-yl)methoxy)phenyl)acetate (298c)

Compound 298c was prepared according to the procedure reported in step-2 of scheme 1, from ethyl 2-(2-((5-bromo-1-cyclobutyl-1H-indazol-3-yl)methoxy)phenyl)acetate (298b) (180 mg, 0.406 mmol) in dioxane (2 mL) and THF (2 mL) using 3-(aminomethyl)phenylboronic acid hydrochloride (1d) (152 mg, 0.812 mmol), 2 M solution of $K_3PO_4$ (0.812 mL, 1.624 mmol), tricyclohexylphosphine (22.77 mg, 0.081 mmol), $Pd_2(dba)_3$ (37.2 mg, 0.041 mmol), $PdCl_2$(dppf)-$CH_2Cl_2$ adduct (33.2 mg, 0.041 mmol) and heating at 100° C. for 2 h. This gave after workup and purification by flash column chromatography [silica gel (24 g), eluting with DMA-80 in DCM from 0-70%] ethyl 2-(2-((5-(3-(aminomethyl)phenyl)-1-cyclobutyl-1H-indazol-3-yl)methoxy)phenyl)acetate (298c) (120 mg, 63% yield) as a clear oil; MS (ES+): 470.20 (M+1).

Step-3: Preparation of 2-(2-((5-(3-(aminomethyl)phenyl)-1-cyclobutyl-1H-indazol-3-yl)methoxy)phenyl)acetic acid (298d)

Compound 298d was prepared according to the procedure reported in step-3 of scheme 1, from ethyl 2-(2-((5-(3-(aminomethyl)phenyl)-1-cyclobutyl-1H-indazol-3-yl)methoxy)phenyl)acetate (298c) (120 mg, 0.256 mmol) in THF (2 mL) and MeOH (2 mL) using a solution of lithium hydroxide hydrate (64.3 mg, 1.533 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-1-cyclobutyl-1H-indazol-3-yl)methoxy)phenyl)acetic acid (298d) (45 mg, 40% yield) HCl salt as a white solid; $^1$H NMR (300 MHz, DMSO-$d_6$) δ 12.12 (s, 1H, $D_2O$ exchangeable), 8.39 (s, 3H, $D_2O$ exchangeable), 8.08 (s, 1H), 7.87 (s, 1H), 7.83 (d, J=8.8 Hz, 1H), 7.79-7.69 (m, 2H), 7.55-7.39 (m, 2H), 7.32-7.23 (m, 2H), 7.23-7.17 (m, 1H), 6.92 (ddd, J=8.1, 6.1, 2.4 Hz, 1H), 5.47 (s, 2H), 5.33 (p, J=8.3 Hz, 1H), 4.17-4.03 (m, 2H), 3.53 (s, 2H), 2.76-2.56 (m, 2H), 2.49-2.38 (m, 2H), 1.98-1.80 (m, 2H); MS (ES+): 442.20 (M+1); MS (ES−): 440.20 (M−1); Analysis calculated for $C_{27}H_{27}N_3O_3 \cdot HCl \cdot H_2O$: C, 65.38; H, 6.10; Cl, 7.15; N, 8.47. Found: C, 65.62; H, 5.98; Cl, 7.03; N, 8.46.

Scheme 299

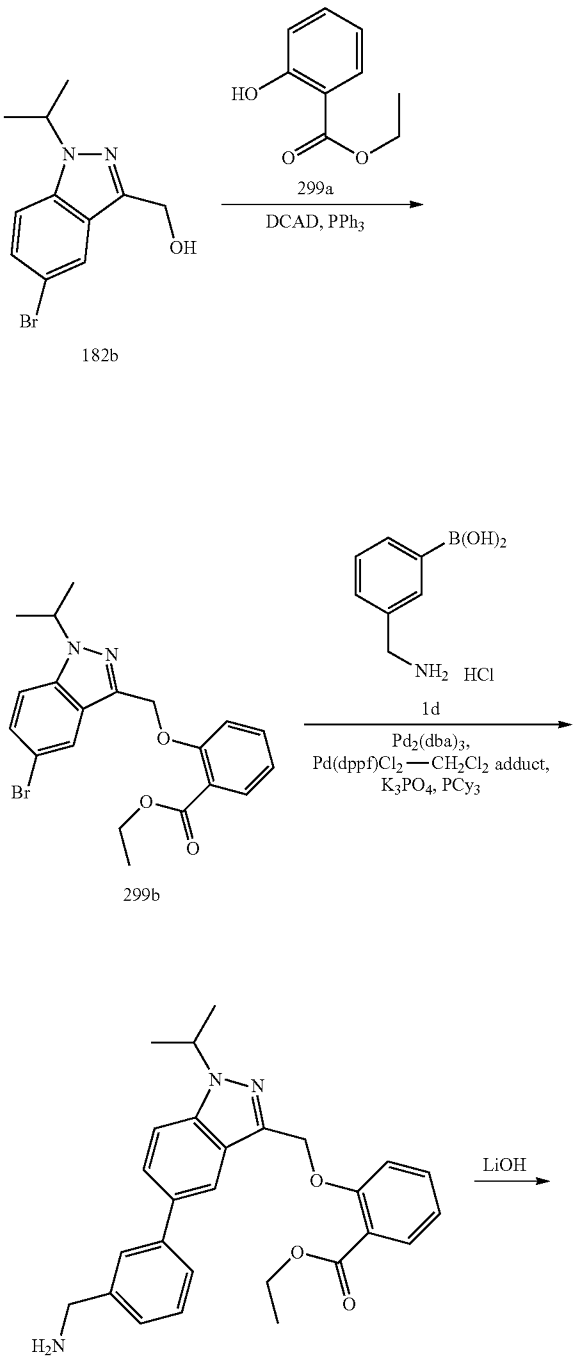

182b

299b

299c

-continued

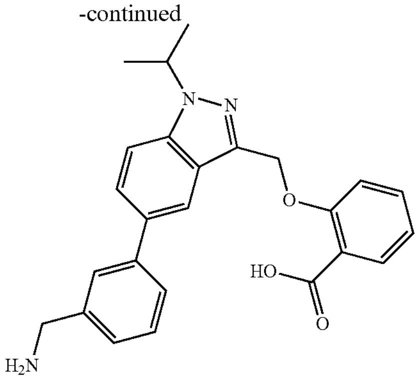

299d

Preparation of 2-((5-(3-(aminomethyl)phenyl)-1-isopropyl-1H-indazol-3-yl)methoxy)benzoic acid (299d)

Step-1: Preparation of ethyl 2-((5-bromo-1-isopropyl-1H-indazol-3-yl)methoxy)benzoate (299b)

Compound 299b was prepared according to the procedure reported in step-3 of scheme 7, from (5-bromo-1-isopropyl-1H-indazol-3-yl)methanol (182b) (550 mg, 2.044 mmol) in DCM (10 mL) using triphenylphosphine (643 mg, 2.452 mmol), ethyl 2-hydroxybenzoate (299a)(357 mg, 2.146 mmol; CAS #118-61-6), a solution of bis(4-chlorobenzyl) diazene-1,2-dicarboxylate (DCAD, 900 mg, 2.452 mmol) in DCM (5 mL) and stirring at RT for 60 min. This gave after workup and purification using flash column chromatography [silica gel (24 g), eluting with DMA80 in DCM from 0-60%] ethyl 2-((5-bromo-1-isopropyl-1H-indazol-3-yl)methoxy) benzoate (299b) (150 mg, 18% yield) as a white solid; MS (ES+): 417.10 & 419.05 (M+1).

Step-2: Preparation of ethyl 2-((5-(3-(aminomethyl) phenyl)-1-isopropyl-1H-indazol-3-yl)methoxy)benzoate (299c)

Compound 299c was prepared according to the procedure reported in step-2 of scheme 1, from ethyl 2-((5-bromo-1-isopropyl-1H-indazol-3-yl)methoxy)benzoate (299b) (300 mg, 0.719 mmol) in dioxane (2 mL) and THF (2 mL) using 3-(aminomethyl)phenylboronic acid hydrochloride (1d) (269 mg, 1.438 mmol), 2 M solution of $K_3PO_4$ (1.438 mL, 2.88 mmol), tricyclohexylphosphine (40.3 mg, 0.144 mmol), $Pd_2(dba)_3$ (65.8 mg, 0.072 mmol), $PdCl_2$(dppf)-$CH_2Cl_2$ adduct (58.7 mg, 0.072 mmol) and heating at 100° C. for 2 h. This gave after workup and purification using flash column chromatography [silica gel (24 g), eluting with DMA-80 in DCM from 0-70%] ethyl 2-((5-(3-(aminomethyl)phenyl)-1-isopropyl-1H-indazol-3-yl)methoxy)benzoate (299c) (50 mg, 16% yield) as a clear oil; MS (ES+): 444.20 (M+1).

Step-3: Preparation of 2-((5-(3-(aminomethyl)phenyl)-1-isopropyl-1H-indazol-3-yl)methoxy)benzoic acid (299d)

Compound 299d was prepared according to the procedure reported in step-3 of scheme 1, from ethyl 2-((5-(3-(aminomethyl)phenyl)-1-isopropyl-1H-indazol-3-yl)methoxy) benzoate (299c) (50 mg, 0.113 mmol) in THF (2 mL) and MeOH (2 mL) using a solution of lithium hydroxide hydrate (18.92 mg, 0.451 mmol) in water (1 mL) and stirring at RT for 15 h. This gave after workup and purification using reverse phase column chromatography [C18 column (50 g), eluting with ACN in water (containing 0.1% HCl) from 0-100%] 2-((5-(3-(aminomethyl)phenyl)-1-isopropyl-1H-indazol-3-yl)methoxy)benzoic acid (299d) (6 mg, 13% yield) HCl salt as a white solid; $^1$H NMR (300 MHz, DMSO-$d_6$) δ 12.58 (s, 1H, $D_2O$ exchangeable), 8.52 (s, 2H, $D_2O$ exchangeable), 8.24 (s, 1H), 7.88 (s, 1H), 7.83 (d, J=8.8 Hz, 1H), 7.79-7.71 (m, 2H), 7.60 (d, J=7.6 Hz, 1H), 7.50 (td, J=7.8, 4.2 Hz, 2H), 7.42 (d, J=7.7 Hz, 1H), 7.35 (d, J=8.4 Hz, 1H), 7.01 (t, J=7.5 Hz, 1H), 5.54 (s, 2H), 5.16-4.92 (m, 1H), 4.11 (s, 2H), 1.51 (d, J=6.5 Hz, 6H); MS (ES+): 416.20 (M+1); MS (ES−): 414.10 (M−1).

Scheme 300

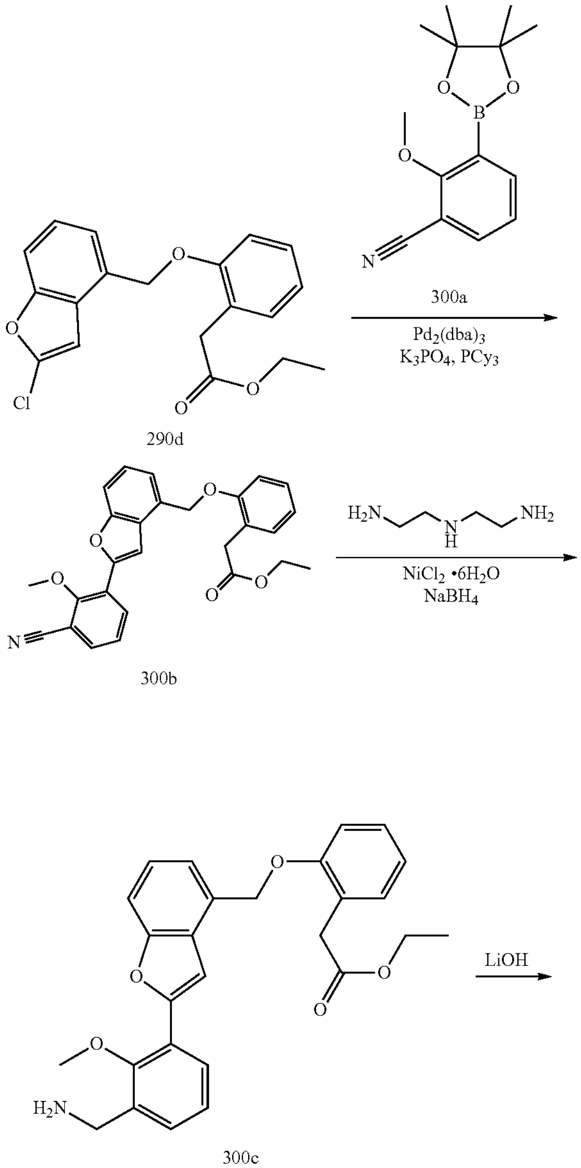

-continued

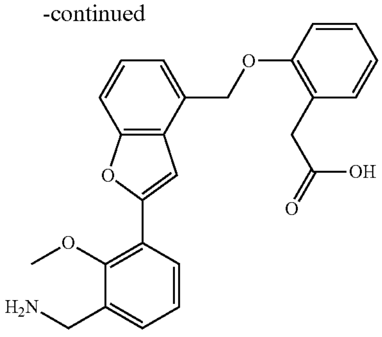

300d

Preparation of 2-(2-((2-(3-(aminomethyl)-2-methoxyphenyl)benzofuran-4-yl)methoxy)phenyl) acetic acid (300d)

Step-1: Preparation of ethyl 2-(2-((2-(3-cyano-2-methoxyphenyl)benzofuran-4-yl)methoxy)phenyl) acetate (300b)

Compound 300b was prepared according to the procedure reported in step-8 of scheme 3, from ethyl 2-(2-((2-chlorobenzofuran-4-yl)methoxy)phenyl)acetate (290d) (150 mg, 0.435 mmol) in dioxane (6 mL) and 2Me-THF (3 mL) using 2-methoxy-3-(4,4,5,5-tetramethyl-1,3,2-dioxaborolan-2-yl) benzonitrile (300a) (322 mg, 0.870 mmol; CAS #874472-84-1), $Pd_2(dba)_3$ (80 mg, 0.087 mmol), tripotassium phosphate (4M) (0.435 mL, 1.740 mmol), tricyclohexylphosphine (48.8 mg, 0.174 mmol) and heating at 115° C. for 4.5 h. This gave after workup and purification using flash column chromatography [silica gel (12 g), eluting with EtOAc in hexanes from 0-50%] ethyl 2-(2-((2-(3-cyano-2-methoxyphenyl)benzofuran-4-yl)methoxy)phenyl) acetate (300b) (162 mg, 84% yield) as a yellow semi-solid; MS (ES+): 464.1 (M+Na).

Step-2: Preparation of ethyl 2-(2-((2-(3-(aminomethyl)-2-methoxyphenyl)benzofuran-4-yl)methoxy) phenyl)acetate (300c)

Compound 300c was prepared according to the procedure reported in step-2 of scheme 1, from ethyl 2-(2-((2-(3-cyano-2-methoxyphenyl)benzofuran-4-yl)methoxy)phenyl) acetate (300b) (160 mg, 0.362 mmol) in anhydrous methanol (10 mL) using nickel(II) chloride hexahydrate (21.54 mg, 0.091 mmol), sodium borohydride (200 mg, 5.29 mmol) and N1-(2-aminoethyl)ethane-1,2-diamine (0.078 mL, 0.725 mmol). This gave after workup and purification by flash column chromatography [silica gel (12 g), eluting with MeOH in DCM from 0 to 20%)] to furnish ethyl 2-(2-((2-(3-(aminomethyl)-2-methoxyphenyl)benzofuran-4-yl) methoxy)phenyl)acetate (300c) (64 mg, 40% yield) as a yellow oil; MS (ES+): 446.2 (M+1).

Step-3: Preparation of 2-(2-((2-(3-(aminomethyl)-2-methoxyphenyl)benzofuran-4-yl)methoxy)phenyl) acetic acid (300d)

Compound 300d was prepared according to the procedure reported in step-3 of scheme 1, from ethyl 2-(2-((2-(3-(aminomethyl)-2-methoxyphenyl)benzofuran-4-yl) methoxy)phenyl)acetate (300c) (65 mg, 0.146 mmol) in MeOH/THF (3 mL each) using a solution of lithium hydroxide monohydrate (50 mg, 1.192 mmol) in water (2 mL) and stirring at RT for 5 h. This gave after workup and purification by reverse phase column chromatography [C18 column (50 g), eluting with ACN in water (containing 0.1% HCl) from 0-100%] 2-(2-((2-(3-(aminomethyl)-2-methoxyphenyl)benzofuran-4-yl)methoxy)phenyl)acetic acid (300d) (49 mg, 80% yield) HCl salt as a white solid; $^1H$ NMR (300 MHz, DMSO-$d_6$) δ 12.19 (s, 1H), 8.58 (s, 3H), 7.98 (dd, J=7.9, 1.7 Hz, 1H), 7.69-7.59 (m, 2H), 7.57 (s, 1H), 7.45-7.33 (m, 3H), 7.29-7.15 (m, 3H), 6.92 (t, J=7.2 Hz, 1H), 5.44 (s, 2H), 4.15 (q, J=5.8 Hz, 2H), 3.77 (s, 3H), 3.59 (s, 2H); MS (ES+): 418.1 (M+1); (ES−): 416.1 (M−1).

Scheme 301

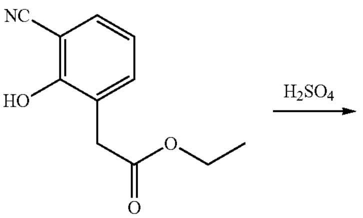

114b (ethyl analog)

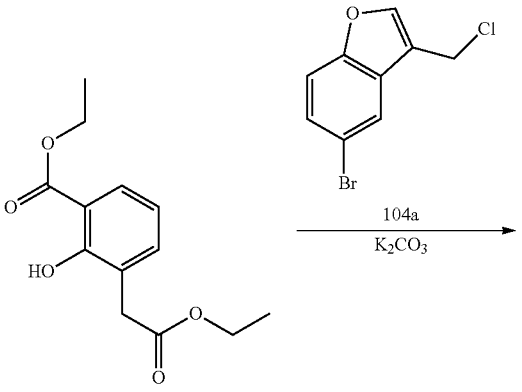

301a

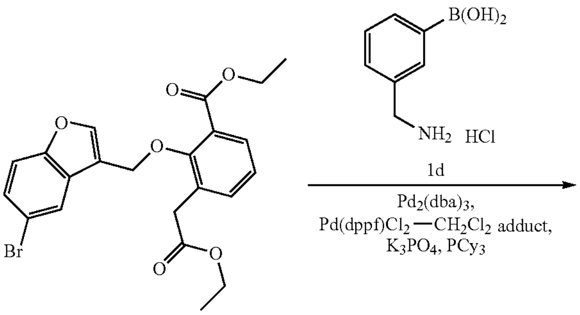

301b

-continued

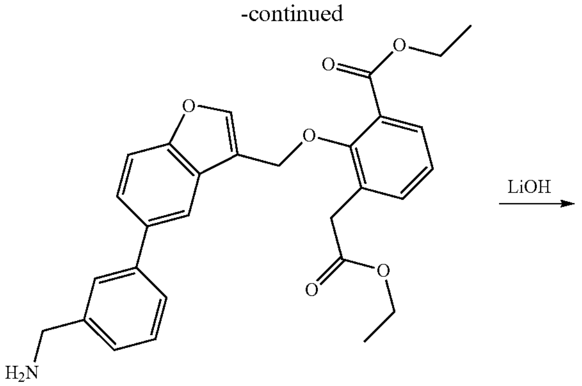

301c

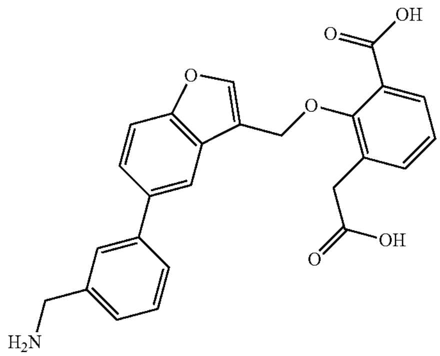

301d

Preparation of 2-((5-(3-(aminomethyl)phenyl)benzofuran-3-yl)methoxy)-3-(carboxymethyl)benzoic acid (301d)

Step-1: Preparation of ethyl 3-(2-ethoxy-2-oxoethyl)-2-hydroxybenzoate (301a)

To a solution of ethyl 2-(3-cyano-2-hydroxyphenyl)acetate (114b, ethyl analog) (1 g, 4.87 mmol) in ethanol (20 mL) was added conc. sulfuric acid (2.60 mL, 48.7 mmol) and heated at reflux for 48 h. This gave after work up and purification using flash column chromatography [silica gel (24 g) eluting with EtOAc in hexane from 0-80%] ethyl 3-(2-ethoxy-2-oxoethyl)-2-hydroxybenzoate (301a) (0.34 g, 28% yield) as a white oil; $^1$H NMR (300 MHz, DMSO-$d_6$) δ 10.94 (s, 1H), 7.75 (dd, J=8.0, 1.7 Hz, 1H), 7.50 (dd, J=7.4, 1.7 Hz, 1H), 6.93 (t, J=7.7 Hz, 1H), 4.38 (q, J=7.1 Hz, 2H), 4.07 (q, J=7.1 Hz, 2H), 3.66 (s, 2H), 1.34 (t, J=7.1 Hz, 3H), 1.17 (t, J=7.1 Hz, 3H).

Step-2: Preparation of ethyl 2-((5-bromobenzofuran-3-yl)methoxy)-3-(2-ethoxy-2-oxoethyl)benzoate (301b)

Compound 301b was prepared according to the procedure reported in step-1 of scheme 1, from 5-bromo-3-(chloromethyl)benzofuran (104a) (331 mg, 1.348 mmol) in DMF (10 mL) using ethyl 3-(2-ethoxy-2-oxoethyl)-2-hydroxybenzoate (301a) (340 mg, 1.348 mmol), $K_2CO_3$ (559 mg, 4.04 mmol) and stirring at RT for 3 h under an Ar atmosphere. This gave after workup and purification using flash column chromatography [silica gel (24 g) eluting with EtOAc in hexane from 0-80%] ethyl 2-((5-bromobenzofuran-3-yl)methoxy)-3-(2-ethoxy-2-oxoethyl)benzoate (301b) (560 mg, 90% yield) as a white oil; $^1$H NMR (300 MHz, DMSO-$d_6$) δ 8.07 (s, 1H), 7.91 (d, J=2.1 Hz, 1H), 7.71 (dd, J=7.8, 1.8 Hz, 1H), 7.62 (d, J=8.7 Hz, 1H), 7.51 (td, J=8.7, 7.9, 1.9 Hz, 2H), 7.24 (t, J=7.7 Hz, 1H), 5.12-4.99 (m, 2H), 4.28 (q, J=7.1 Hz, 2H), 3.96 (q, J=7.1 Hz, 2H), 3.68 (d, J=12.3 Hz, 2H), 1.28 (t, J=7.1 Hz, 3H), 1.04 (t, J=7.1 Hz, 3H).

Step-3: Preparation of ethyl 2-((5-(3-(aminomethyl)phenyl)benzofuran-3-yl)methoxy)-3-(2-ethoxy-2-oxoethyl)benzoate (301c)

Compound 301c was prepared according to the procedure reported in step-2 of scheme 1, from ethyl 2-((5-bromobenzofuran-3-yl)methoxy)-3-(2-ethoxy-2-oxoethyl)benzoate (301b) (280 mg, 0.607 mmol) in dioxane (3 mL) and THF (3 mL) using 3-(aminomethyl)phenylboronic acid hydrochloride (1d) (228 mg, 1.214 mmol), 2 M solution of $K_3PO_4$ (1.214 mL, 2.428 mmol), tricyclohexylphosphine (34.0 mg, 0.121 mmol), $Pd_2(dba)_3$ (55.6 mg, 0.061 mmol), Pd(dppf)$Cl_2$—$CH_2Cl_2$ adduct (49.6 mg, 0.061 mmol) and heating at 90° C. for 1 h. This gave after workup and purification using flash column chromatography [silica gel (12 g), eluting with DMA-80 in DCM from 0-70%] ethyl 2-((5-(3-(aminomethyl)phenyl)benzofuran-3-yl)methoxy)-3-(2-ethoxy-2-oxoethyl)benzoate (301c) (40 mg, 14% yield) as a clear oil; MS (ES+): 488.20 (M+1).

Step-4: Preparation of 2-((5-(3-(aminomethyl)phenyl)benzofuran-3-yl)methoxy)-3-(carboxymethyl)benzoic acid (301d)

Compound 301d was prepared according to the procedure reported in step-3 of scheme 1, from ethyl 2-((5-(3-(aminomethyl)phenyl)benzofuran-3-yl)methoxy)-3-(2-ethoxy-2-oxoethyl)benzoate (301c) (40 mg, 0.082 mmol) in THF (2 mL) and MeOH (2 mL) using a solution of lithium hydroxide hydrate (20.66 mg, 0.492 mmol) in water (1 mL) and stirring at RT for 15 h. This gave after workup and purification by reverse phase column chromatography [C18 column (50 g), eluting with ACN in water (containing 0.1% HCl) from 0-100%] 2-((5-(3-(aminomethyl)phenyl)benzofuran-3-yl)methoxy)-3-(carboxymethyl)benzoic acid (301d) (8 mg, 23% yield) HCl salt as a white solid; $^1$H NMR (300 MHz, DMSO-$d_6$) δ 13.05 (s, 1H, $D_2O$ exchangeable), 12.37 (s, 1H, $D_2O$ exchangeable), 8.28 (s, 3H, $D_2O$ exchangeable), 8.09 (d, J=1.8 Hz, 1H), 8.06 (s, 1H), 7.84 (s, 1H), 7.78-7.71 (m, 2H), 7.68 (dd, J=8.7, 1.8 Hz, 1H), 7.58-7.50 (m, 2H), 7.50-7.42 (m, 2H), 7.21 (t, J=7.6 Hz, 1H), 5.15 (s, 2H), 4.12 (s, 2H), 3.62 (s, 2H); MS (ES+): 432.10 (M+1); (ES−): 430.10 (M−1).

Scheme 302

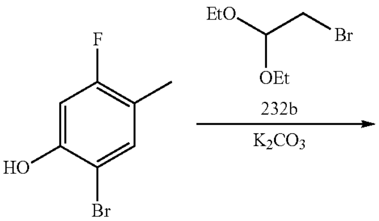

302a

-continued
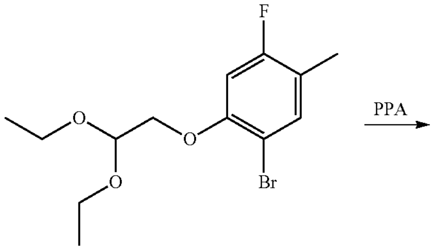
302b
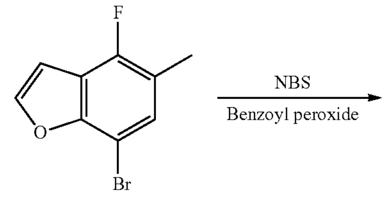
302c
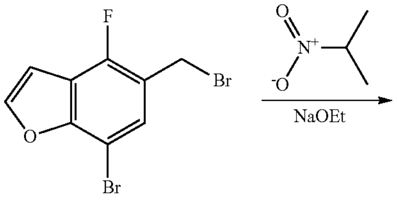
302d
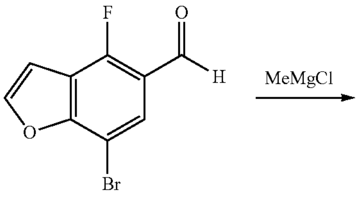
302e
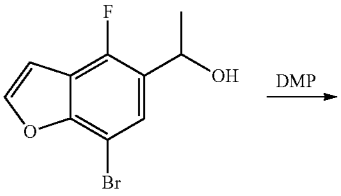
302f
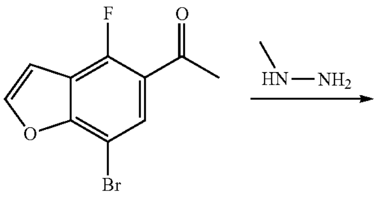
302g
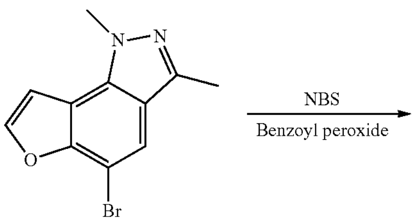
302h
-continued
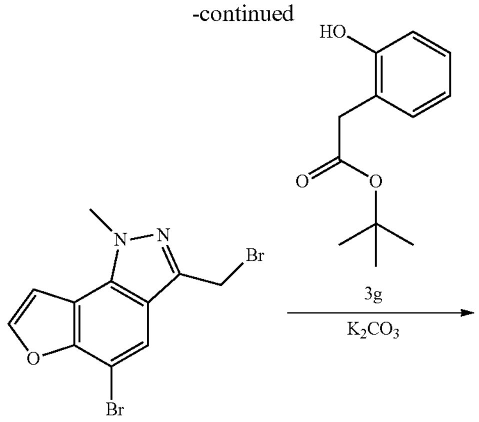
302i
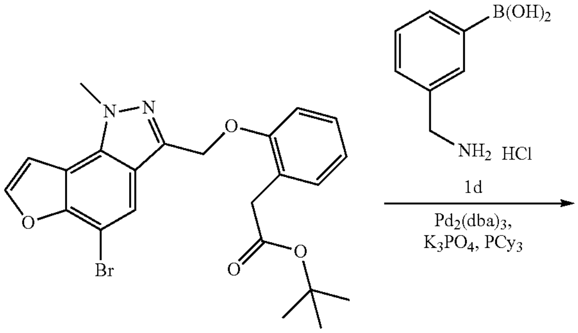
302j
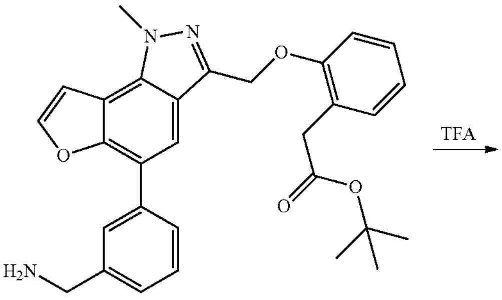
302k
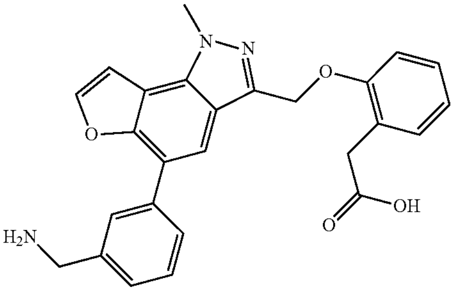
302l
Preparation of 2-(2-((5-(3-(aminomethyl)phenyl)-1-methyl-1H-furo[2,3-g]indazol-3-yl)methoxy)phenyl) acetic acid (3021)
Step-1: Preparation of 1-bromo-2-(2,2-diethoxy-ethoxy)-4-fluoro-5-methylbenzene (302b)
Compound 302b was prepared according to the procedure reported in step-1 of scheme 123, from 2-bromo-5-fluoro- 4-methylphenol (302a) (16.4 g, 80 mmol; CAS #1268511-85-8) in DMF (60 mL) using potassium carbonate (22.11 g, 160 mmol), 2-bromo-1,1-diethoxyethane (232b) (23.65 g, 120 mmol) and heating at 120° C. in a sealed tube overnight. This gave after workup and purification using flash column chromatography [silica gel (220 g), eluting with EtOAc in hexanes from 0-20%] 1-bromo-2-(2,2-diethoxyethoxy)-4-fluoro-5-methylbenzene (302b) (25.5 g, 99% yield) as a colorless oil; $^1$H NMR (300 MHz, DMSO-$d_6$) δ 7.52 (d, J=8.3 Hz, 1H), 7.08 (d, J=11.6 Hz, 1H), 4.81 (t, J=5.3 Hz, 1H), 4.01 (d, J=5.3 Hz, 2H), 3.76-3.44 (m, 4H), 2.15 (d, J=1.9 Hz, 3H), 1.19-1.09 (m, 6H); $^{19}$F NMR (282 MHz, DMSO-$d_6$) δ −115.19; MS (ES+): 321.10 (M+1).

Step-2: Preparation of 7-bromo-4-fluoro-5-methylbenzofuran (302c)

Compound 302c was prepared according to the procedure reported in step-1 of scheme 123, from 1-bromo-2-(2,2-diethoxyethoxy)-4-fluoro-5-methylbenzene (302b) (25.5 g, 79 mmol) in chlorobenzene (50 mL) using polyphosphoric acid (PPA) (26 g, 79 mmol) in chlorobenzene (500 mL) and heating at 80° C. for 90 min and then at 120° C. for 3 h. This gave after workup and purification using flash column chromatography [silica gel (120 g) eluting with ethyl acetate in hexanes from 0-20%] 7-bromo-4-fluoro-5-methylbenzofuran (302c) (6.7 g, 37% yield) as a colorless oil; $^1$H NMR (300 MHz, DMSO-$d_6$) δ 8.14 (d, J=2.3 Hz, 1H), 7.52 (d, J=6.6 Hz, 1H), 7.17 (d, J=2.2 Hz, 1H), 2.32 (d, J=2.3 Hz, 3H); $^{19}$F NMR (282 MHz, DMSO-$d_6$) δ −124.69.

Step-3: Preparation of 7-bromo-5-(bromomethyl)-4-fluorobenzofuran (302d)

Compound 302d was prepared according to the procedure reported in step-2 of scheme 58, from 7-bromo-4-fluoro-5-methylbenzofuran (302c) (6.7 g, 29.3 mmol) in carbon tetrachloride (100 mL) using NBS (5.21 g, 29.3 mmol), benzoyl peroxide (1.063 g, 4.39 mmol) and refluxing overnight. The reaction mixture was concentrated to give 7-bromo-5-(bromomethyl)-4-fluorobenzofuran (302d) (9.01 g, 100% yield) as a yellow solid, which was used as such for the next step;

Step-4: Preparation of 7-bromo-4-fluorobenzofuran-5-carbaldehyde (302e)

To a solution of sodium ethoxide (10.42 g, 32.1 mmol) in EtOH (80 mL) was added 2-nitropropane (2.89 mL, 32.1 mmol) followed by 7-bromo-5-(bromomethyl)-4-fluorobenzofuran (302d) (9.0 g, 29.2 mmol) and stirred for 20 h at RT. The reaction mixture was concentrated in vacuum and the residue obtained was purified using flash column chromatography [silica gel (120 g), eluting with ethyl acetate in hexanes from 0-30%] to give 7-bromo-4-fluorobenzofuran-5-carbaldehyde (302e) (2.62 g, 37% yield) as a white solid; $^1$H NMR (300 MHz, DMSO-$d_6$) δ 10.24 (s, 1H), 8.35 (d, J=2.3 Hz, 1H), 7.97 (d, J=5.9 Hz, 1H), 7.45 (d, J=2.3 Hz, 1H); $^{19}$F NMR (282 MHz, DMSO-$d_6$) δ −125.87.

Step-5: Preparation of 1-(7-bromo-4-fluorobenzofuran-5-yl)ethanol (302f)

Compound 302f was prepared according to the procedure reported in step-7 of scheme 3, from 7-bromo-4-fluorobenzofuran-5-carbaldehyde (302e) (2 g, 8.23 mmol) in THF (45 mL) using methyl magnesium chloride (2.88 mL, 8.64 mmol; 3 M in THF) and stirring at 0° C. for 45 min. This gave after work up and purification by flash column chromatography [silica gel (40 g), eluting with EtOAc in hexane from 0-50%] 1-(7-bromo-4-fluorobenzofuran-5-yl)ethanol (302f) (1.77 g, 83% yield) as a colorless oil which solidified to a white solid on standing; $^1$H NMR (300 MHz, DMSO-$d_6$) δ 8.17 (d, J=2.3 Hz, 1H), 7.64 (d, J=6.2 Hz, 1H), 7.20 (d, J=2.3 Hz, 1H), 5.48 (d, J=4.6 Hz, 1H), 5.09 (p, J=6.2 Hz, 1H), 1.38 (d, J=6.4 Hz, 3H); $^{19}$F NMR (282 MHz, DMSO-$d_6$) δ −127.24.

Step-6: Preparation of 1-(7-bromo-4-fluorobenzofuran-5-yl)ethanone (302g)

Compound 302g was prepared according to the procedure reported in step-1 of scheme 141, from 1-(7-bromo-4-fluorobenzofuran-5-yl)ethanol (302f) (1.77 g, 6.83 mmol) in DCM (60 mL) using Dess-Martin periodinane (DMP, 4.58 g, 10.25 mmol) and stirring at RT for 16 h.

This gave after workup and purification using flash column chromatography [silica gel (80 g), eluting with EtOAc in hexane from 0-40%] 1-(7-bromo-4-fluorobenzofuran-5-yl)ethanone (302g) (1.69 g, 96% yield) as a white needles; $^1$H NMR (300 MHz, DMSO-$d_6$) δ 8.30 (d, J=2.3 Hz, 1H), 7.96 (d, J=6.2 Hz, 1H), 7.40 (d, J=2.3 Hz, 1H), 2.65 (d, J=4.6 Hz, 3H); $^{19}$F NMR (282 MHz, DMSO-$d_6$) δ −115.22.

Step-7: Preparation of 5-bromo-1,3-dimethyl-1H-furo[2,3-g]indazole (302 h)

A solution of 1-(7-bromo-4-fluorobenzofuran-5-yl)ethanone (302g) (150 mg, 0.584 mmol) in methylhydrazine (2 mL, 0.584 mmol) was heated at 80° C. for 1 h and then 130° C. for 2 h. The reaction mixture was diluted with water, and the solid obtained was collected by filtration to provide on drying 5-bromo-1,3-dimethyl-1H-furo[2,3-g]indazole (302 h) (148 mg, 96% yield) as a pink solid; $^1$H NMR (300 MHz, DMSO-$d_6$) δ 8.24 (d, J=2.2 Hz, 1H), 7.91 (s, 1H), 7.64 (d, J=2.2 Hz, 1H), 4.17 (s, 3H), 2.49 (s, 3H); MS (ES+): 265.0 and 267.0 (M+1).

Step-8: Preparation of 5-bromo-3-(bromomethyl)-1-methyl-1H-furo[2,3-g]indazole (302i)

Compound 302i was prepared according to the procedure reported in step-2 of scheme 58, from 5-bromo-1,3-dimethyl-1H-furo[2,3-g]indazole (302 h) (146 mg, 0.551 mmol) in carbon tetrachloride (8 mL) using NBS (118 mg, 0.661 mmol), benzoyl peroxide (20.01 mg, 0.083 mmol) and refluxing overnight. This gave after workup and purification using flash column chromatography [silica gel (12 g), eluting with EtOAc in hexane from 0-70%] 5-bromo-3-(bromomethyl)-1-methyl-1H-furo[2,3-g]indazole (302i) (109 mg, 58% yield) as a white solid; $^1$H NMR (300 MHz, DMSO-$d_6$) δ 8.30 (d, J=2.2 Hz, 1H), 8.08 (s, 1H), 7.68 (d, J=2.2 Hz, 1H), 5.08 (s, 2H), 4.25 (s, 3H).

Step-9: Preparation of tert-butyl 2-(2-((5-bromo-1-methyl-1H-furo[2,3-g]indazol-3-yl)methoxy)phenyl) acetate (302j)

Compound 302j was prepared according to the procedure reported in step-3 of scheme 7, from 5-bromo-3-(bromomethyl)-1-methyl-1H-furo[2,3-g]indazole (302i) (107 mg, 0.311 mmol) in acetone (6 mL) using tert-butyl 2-(2-hydroxyphenyl)acetate (3g) (97 mg, 0.467 mmol), potassium carbonate (86 mg, 0.622 mmol) and stirring at RT for 72 h. This gave after workup and purification using flash column chromatography [silica gel (12 g), eluting with ethyl acetate in hexanes from 0-60%] tert-butyl 2-(2-((5-bromo-1-methyl-1H-furo[2,3-g]indazol-3-yl)methoxy)phenyl)acetate (302j) (98 mg, 67% yield) as colorless oil, which slowly solidified on standing to a white solid; $^{1}H$ NMR (300 MHz, DMSO-$d_6$) δ 8.29 (d, J=2.3 Hz, 1H), 7.99 (s, 1H), 7.69 (d, J=2.2 Hz, 1H), 7.32-7.21 (m, 2H), 7.21-7.14 (m, 1H), 6.96-6.85 (m, 1H), 5.40 (s, 2H), 4.26 (s, 3H), 3.46 (s, 2H), 1.17 (s, 9H); MS (ES+) 471.1, 473.0 (M+1).

Step-10: Preparation of tert-butyl 2-(2-((5-(3-(aminomethyl)phenyl)-1-methyl-1H-furo[2,3-g]indazol-3-yl)methoxy)phenyl)acetate (302k)

Compound 302k was prepared according to the procedure reported in step-2 of scheme 1, from tert-butyl 2-(2-((5-bromo-1-methyl-1H-furo[2,3-g]indazol-3-yl)methoxy)phenyl)acetate (302j) (98 mg, 0.208 mmol) in dioxane/2Me-THF (9 mL, ratio 2:1) using 3-(aminomethyl)phenylboronic acid hydrochloride (1d) (97 mg, 0.520 mmol), 4 M solution of $K_3PO_4$ (0.208 mL, 0.832 mmol), tricyclohexylphosphine (23.32 mg, 0.083 mmol), $Pd_2(dba)_3$ (38.1 mg, 0.042 mmol) and heating at 115° C. for 3 h. This gave after workup and purification using flash column chromatography [silica gel (12 g), eluting with DMA-80 in DCM from 0-80%] tert-butyl 2-(2-((5-(3-(aminomethyl)phenyl)-1-methyl-1H-furo[2,3-g]indazol-3-yl)methoxy)phenyl)acetate (302k) (64 mg, 62% yield) as a yellow foam; MS (ES+): 498.2 (M+1).

Step-11: Preparation of 2-(2-((5-(3-(aminomethyl)phenyl)-1-methyl-1H-furo[2,3-g]indazol-3-yl)methoxy)phenyl)acetic acid (3021)

Compound 3021 was prepared according to the procedure reported in step-9 of scheme 3, from tert-butyl 2-(2-((5-(3-(aminomethyl)phenyl)-1-methyl-1H-furo[2,3-g]indazol-3-yl)methoxy)phenyl)acetate (302k) (64 mg, 0.129 mmol) in DCM (4 mL) using TFA (0.4 mL, 5.19 mmol) and stirring overnight at RT. This gave after workup and purification by reverse phase column chromatography [C18 (50 g), eluting with ACN in water (containing 0.1% HCl) from 0-100%] 2-(2-((5-(3-(aminomethyl)phenyl)-1-methyl-1H-furo[2,3-g]indazol-3-yl)methoxy)phenyl)acetic acid (3021) (37 mg, 65% yield) HCl salt as a white solid; $^{1}H$ NMR (300 MHz, DMSO-$d_6$) δ 8.52 (s, 3H, $D_2O$ exchangeable), 8.24 (d, J=2.2 Hz, 1H), 7.97 (s, 1H), 7.93-7.84 (m, 2H), 7.64 (d, J=2.2 Hz, 1H), 7.60-7.53 (m, 2H), 7.33-7.25 (m, 2H), 7.25-7.17 (m, 1H), 6.98-6.86 (m, 1H), 5.46 (s, 2H), 4.30 (s, 3H), 4.17-4.09 (m, 2H), 3.52 (s, 2H); MS (ES+): 442.2 (M+1); (ES−): 440.1 (M−1); Analysis calculated for: $C_{26}H_{23}N_3O_4 \cdot 1.65HCl \cdot 2.2H_2O$: C, 57.69; H, 5.41; N, 7.76; Cl, 10.81. Found: C, 57.74; H, 5.24; N, 8.01; Cl, 10.98.

Scheme 303

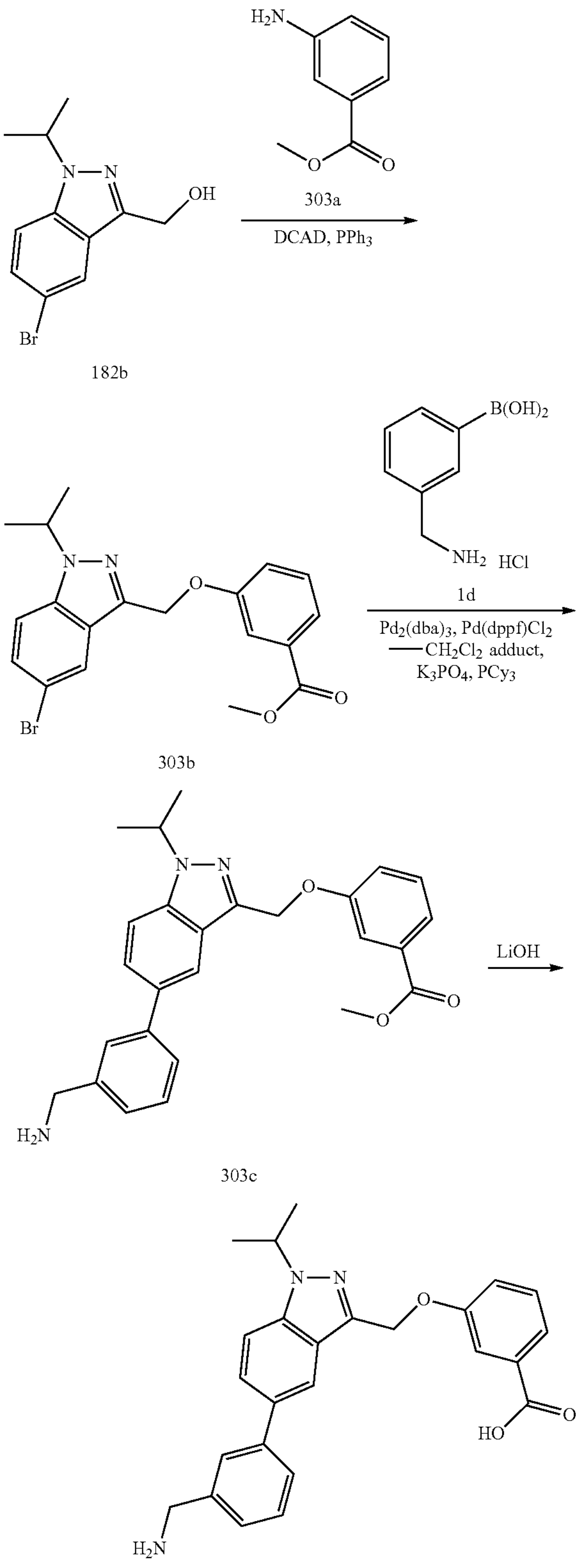

182b

303a

303b

1d

303c

303d

Preparation of 3-((5-(3-(aminomethyl)phenyl)-1-isopropyl-1H-indazol-3-yl)methoxy)benzoic acid (303d)

Step-1: Preparation of methyl 3-((5-bromo-1-isopropyl-1H-indazol-3-yl)methoxy)benzoate (303b)

Compound 303b was prepared according to the procedure reported in step-3 of scheme 7, from (5-bromo-1-isopropyl-1H-indazol-3-yl)methanol (182b) (300 mg, 1.115 mmol) in DCM (10 mL) using triphenylphosphine (351 mg, 1.338 mmol), methyl 3-hydroxybenzoate (303a) (204 mg, 1.338 mmol; CAS #19438-10-9), bis(4-chlorobenzyl) diazene-1,2-dicarboxylate (DCAD, 491 mg, 1.338 mmol) in DCM (5 mL) and stirring at RT for 60 min. This gave after workup and purification using flash column chromatography [silica gel (24 g), eluting with DMA-80 in DCM from 0-80%] methyl 3-((5-bromo-1-isopropyl-1H-indazol-3-yl)methoxy)benzoate (303b) (180 mg, 40% yield) as a white solid; MS (ES+): 403.00 & 405.10 (M+1); 425.00 & 427.05 (M+Na); (ES−): 401.15 (M−1).

Step-2: Preparation of methyl 3-((5-(3-(aminomethyl)phenyl)-1-isopropyl-1H-indazol-3-yl)methoxy)benzoate (303c)

Compound 303c was prepared according to the procedure reported in step-2 of scheme 1, from methyl 3-((5-bromo-1-isopropyl-1H-indazol-3-yl)methoxy)benzoate (303b) (180 mg, 0.446 mmol) in dioxane (2 mL) and THF (2 mL) using 3-(aminomethyl)phenylboronic acid hydrochloride (1d) (167 mg, 0.893 mmol), 2 M solution of $K_3PO_4$ (0.893 mL, 1.785 mmol), tricyclohexylphosphine (25.03 mg, 0.089 mmol), $Pd_2(dba)_3$ (40.9 mg, 0.045 mmol), $PdCl_2$(dppf)-$CH_2Cl_2$ adduct (36.5 mg, 0.045 mmol) and heating at 100° C. for 2 h. This gave after workup and purification using flash column chromatography [silica gel (24 g), eluting with DMA-80 in DCM from 0-70%]methyl 3-((5-(3-(aminomethyl)phenyl)-1-isopropyl-1H-indazol-3-yl)methoxy)benzoate (303c) (150 mg, 78% yield) as a clear oil; MS (ES+): 430.20 (M+1).

Step-3: Preparation of 3-((5-(3-(aminomethyl)phenyl)-1-isopropyl-1H-indazol-3-yl)methoxy)benzoic acid (303d)

Compound 303d was prepared according to the procedure reported in step-3 of scheme 1, from methyl 3-((5-(3-(aminomethyl)phenyl)-1-isopropyl-1H-indazol-3-yl)methoxy)benzoate (303c) (150 mg, 0.349 mmol) in THF (2 mL) and MeOH (2 mL) using a solution of lithium hydroxide hydrate (88 mg, 2.095 mmol) in water (1 mL) and stirring at 50° C. for 5 h. This gave after workup and purification using reverse phase column chromatography [C18 column (50 g), eluting with ACN in water (containing 0.1% HCl) from 0-100%] 3-((5-(3-(aminomethyl)phenyl)-1-isopropyl-1H-indazol-3-yl)methoxy)benzoic acid (303d) (50 mg, 35% yield) HCl salt as a white solid; $^1H$ NMR (300 MHz, DMSO-$d_6$) δ 13.00 (s, 1H, $D_2O$ exchangeable), 8.40 (s, 3H, $D_2O$ exchangeable), 8.12 (s, 1H), 7.90-7.81 (m, 2H), 7.80-7.69 (m, 2H), 7.69-7.63 (m, 1H), 7.57-7.47 (m, 2H), 7.47-7.38 (m, 2H), 7.38-7.30 (m, 1H), 5.53 (s, 2H), 5.17-4.90 (m, 1H), 4.18-4.02 (m, 2H), 1.51 (d, J=6.6 Hz, 6H); MS (ES+): 416.20 (M+1); (ES−): 414.20 (M−1).

Scheme 304

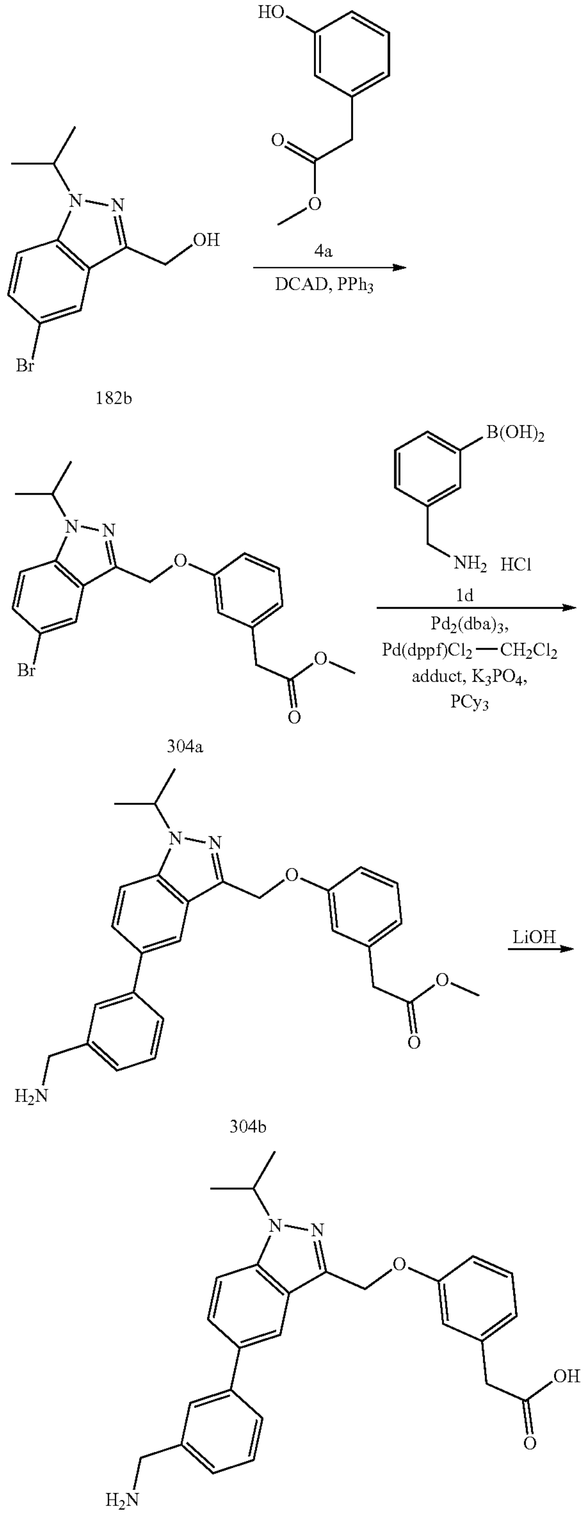

182b

304a

304b

304c

Preparation of 2-(3-((5-(3-(aminomethyl)phenyl)-1-isopropyl-1H-indazol-3-yl)methoxy)phenyl)acetic acid (304c)

Step-1: Preparation of methyl 2-(3-((5-bromo-1-isopropyl-1H-indazol-3-yl)methoxy)phenyl)acetate (304a)

Compound 304a was prepared according to the procedure reported in step-3 of scheme 7, from (5-bromo-1-isopropyl-1H-indazol-3-yl)methanol (182b) (300 mg, 1.115 mmol) in DCM (10 mL) using triphenylphosphine (351 mg, 1.338 mmol), methyl 2-(3-hydroxyphenyl)acetate (4a) (204 mg, 1.338 mmol), bis(4-chlorobenzyl) diazene-1,2-dicarboxylate (DCAD, 491 mg, 1.338 mmol) in DCM (5 mL) and stirring at RT for 60 min.

This gave after workup and purification using flash column chromatography [silica gel (24 g), eluting with EtOAc in hexane from 0-80%]methyl 2-(3-((5-bromo-1-isopropyl-1H-indazol-3-yl)methoxy)phenyl)acetate (304a) (120 mg, 26% yield) as a white solid; MS (ES+): 417.10 & 419.10 (M+1); 439.10 & 441.05 (M+Na); (ES−): 415.05 (M−1).

Step-2: Preparation of methyl 2-(3-((5-(3-(aminomethyl)phenyl)-1-isopropyl-1H-indazol-3-yl)methoxy)phenyl)acetate (304b)

Compound 304b was prepared according to the procedure reported in step-2 of scheme 1, from methyl 2-(3-((5-bromo-1-isopropyl-1H-indazol-3-yl)methoxy)phenyl)acetate (304a) (120 mg, 0.288 mmol) in dioxane (2 mL) and THF (2 mL) using 3-(aminomethyl)phenylboronic acid hydrochloride (1d) (108 mg, 0.575 mmol), 2 M solution of $K_3PO_4$ (0.575 mL, 1.150 mmol), tricyclohexylphosphine (16.13 mg, 0.058 mmol), $Pd_2(dba)_3$ (26.3 mg, 0.029 mmol), $PdCl_2$ (dppf)-$CH_2Cl_2$ adduct (23.48 mg, 0.029 mmol) and heating at 100° C. for 2 h. This gave after workup and purification using flash column chromatography [silica gel (24 g), eluting with DMA-80 in DCM from 0-70%]methyl 2-(3-((5-(3-(aminomethyl)phenyl)-1-isopropyl-1H-indazol-3-yl)methoxy)phenyl)acetate (304b) (100 mg, 78% yield) as a clear oil; MS (ES+): 444.30 (M+1).

Step-3: Preparation of 2-(3-((5-(3-(aminomethyl)phenyl)-1-isopropyl-1H-indazol-3-yl)methoxy)phenyl)acetic acid (304c)

Compound 304c was prepared according to the procedure reported in step-3 of scheme 1, from methyl 2-(3-((5-(3-(aminomethyl)phenyl)-1-isopropyl-1H-indazol-3-yl)methoxy)phenyl)acetate (304b) (100 mg, 0.225 mmol) in THF (2 mL) and MeOH (2 mL) using a solution of lithium hydroxide hydrate (56.8 mg, 1.353 mmol) in water (1 mL) and stirring at 50° C. for 5 h. This gave after workup and purification using reverse phase column chromatography [C18 column (50 g), eluting with ACN in water (containing 0.1% HCl) from 0-100%] 2-(3-((5-(3-(aminomethyl)phenyl)-1-isopropyl-1H-indazol-3-yl)methoxy)phenyl)acetic acid (304c) (8 mg, 8% yield) HCl salt as a white solid; $^1H$ NMR (300 MHz, DMSO-$d_6$) δ 7.97 (d, J=1.6 Hz, 1H), 7.83-7.73 (m, 2H), 7.73-7.59 (m, 2H), 7.46 (t, J=7.6 Hz, 1H), 7.35 (d, J=7.6 Hz, 1H), 7.26 (t, J=2.0 Hz, 1H), 7.14 (t, J=7.9 Hz, 1H), 6.87 (dd, J=8.1, 2.6 Hz, 1H), 6.76 (d, J=7.5 Hz, 1H), 5.48 (s, 2H), 5.09-4.94 (m, 1H), 4.03 (s, 2H), 3.35 (s, 2H), 1.51 (d, J=6.6 Hz, 6H); MS (ES+): 430.20 (M+1); (ES−): 428.20 (M−1).

Scheme 305

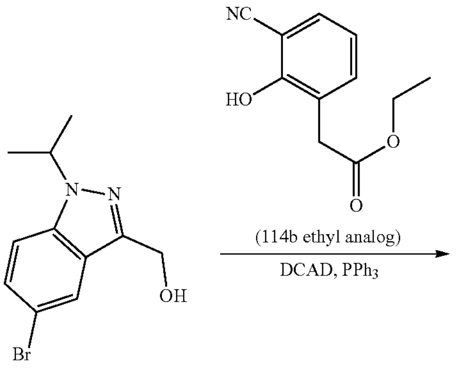

182b

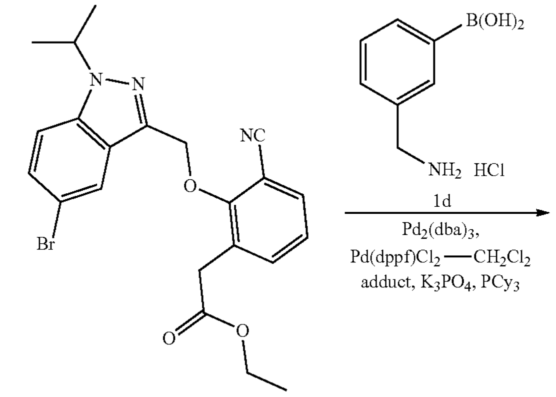

305a

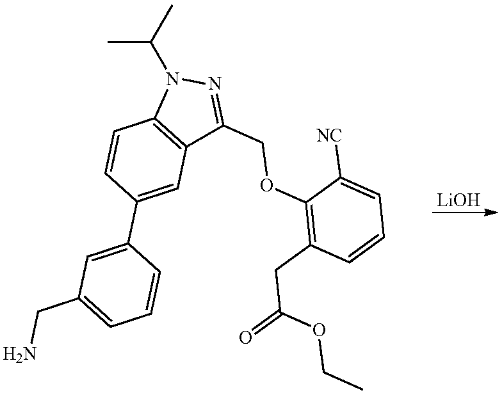

305b

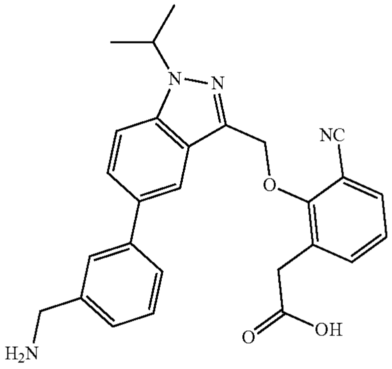

305c

Preparation of 2-(2-((5-(3-(aminomethyl)phenyl)-1-isopropyl-1H-indazol-3-yl)methoxy)-3-cyanophenyl) acetic acid (305c)

Step-1: Preparation of ethyl 2-(2-((5-bromo-1-isopropyl-1H-indazol-3-yl)methoxy)-3-cyanophenyl) acetate (305a)

Compound 305a was prepared according to the procedure reported in step-3 of scheme 7, from (5-bromo-1-isopropyl-1H-indazol-3-yl)methanol (182b) (300 mg, 1.115 mmol) in DCM (10 mL) using triphenylphosphine (351 mg, 1.338 mmol), ethyl 2-(3-cyano-2-hydroxyphenyl)acetate ((114b, ethyl analog) (204 mg, 1.338 mmol), bis(4-chlorobenzyl) diazene-1,2-dicarboxylate (DCAD, 491 mg, 1.338 mmol) in DCM (5 mL) and stirring at RT for 60 min. This gave after workup and purification using flash column chromatography [silica gel (24 g), eluting with EtOAc in hexane from 0-80%] ethyl 2-(2-((5-bromo-1-isopropyl-1H-indazol-3-yl) methoxy)-3-cyanophenyl)acetate (305a) (360 mg, 71% yield) as a white solid; MS (ES+): 456.10 & 458.10 (M+1); 478.05 & 480.10 (M+Na); (ES−): 454.05 & 456.05 (M−1).

Step-2: Preparation of ethyl 2-(2-((5-(3-(aminomethyl)phenyl)-1-isopropyl-1H-indazol-3-yl) methoxy)-3-cyanophenyl)acetate (305b)

Compound 305b was prepared according to the procedure reported in step-2 of scheme 1, from ethyl 2-(2-((5-bromo-1-isopropyl-1H-indazol-3-yl)methoxy)-3-cyanophenyl)acetate (305a) (160 mg, 0.351 mmol) in dioxane (2 mL) and THF (2 mL) using 3-(aminomethyl)phenylboronic acid hydrochloride (1d) (131 mg, 0.701 mmol), 2 M solution of $K_3PO_4$ (0.701 mL, 1.402 mmol), tricyclohexylphosphine (19.66 mg, 0.070 mmol), $Pd_2(dba)_3$ (32.1 mg, 0.035 mmol), $PdCl_2(dppf)$-$CH_2Cl_2$ adduct (28.6 mg, 0.035 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-isopropyl-1H-indazol-3-yl)methoxy)-3-cyanophenyl)acetate (305b) (50 mg, 30% yield) as a clear oil; MS (ES+): 483.25 (M+1).

Step-3: Preparation of 2-(2-((5-(3-(aminomethyl) phenyl)-1-isopropyl-1H-indazol-3-yl)methoxy)-3-cyanophenyl)acetic acid (305c)

Compound 305c was prepared according to the procedure reported in step-3 of scheme 1, from ethyl 2-(2-((5-(3-(aminomethyl)phenyl)-1-isopropyl-1H-indazol-3-yl) methoxy)-3-cyanophenyl)acetate (305b) (50 mg, 0.104 mmol) in THF (2 mL) and MeOH (2 mL) using a solution of lithium hydroxide hydrate (26.1 mg, 0.622 mmol) in water (1 mL) and stirring at 50° C. for 5 h. This gave after workup and purification using reverse phase column chromatography [C18 column (50 g), eluting with ACN in water (containing 0.1% HCl) from 0-100%] 2-(2-((5-(3-(aminomethyl)phenyl)-1-isopropyl-1H-indazol-3-yl)methoxy)-3-cyanophenyl)acetic acid (305c) (22 mg, 47% yield) HCl salt as a white solid; $^1H$ NMR (300 MHz, DMSO-$d_6$) δ 8.50 (s, 3H, $D_2O$ exchangeable), 8.11 (s, 1H), 7.85 (d, J=9.2 Hz, 2H), 7.81-7.68 (m, 3H), 7.63 (dd, J=7.8, 1.7 Hz, 1H), 7.55-7.44 (m, 2H), 7.29 (t, J=7.7 Hz, 1H), 5.51 (s, 2H), 5.03 (h, J=6.6 Hz, 1H), 4.14-4.05 (m, 2H), 3.60 (s, 2H), 1.49 (d, J=6.5 Hz, 6H); MS (ES+): 455.20 (M+1); MS (ES−): 453.20 (M−1).

Scheme 306

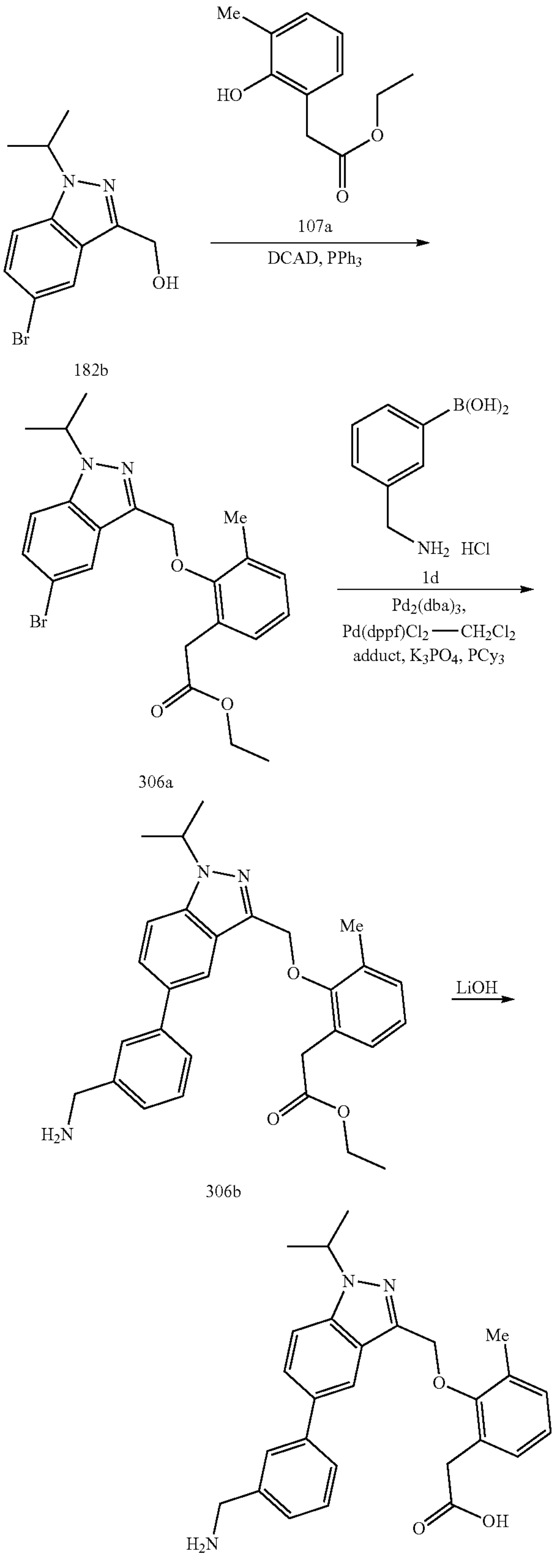

107a

182b

1d

306a

306b

306c

Preparation of 2-(2-((5-(3-(aminomethyl)phenyl)-1-isopropyl-1H-indazol-3-yl)methoxy)-3-methylphenyl)acetic acid (306c)

Step-1: Preparation of ethyl 2-(2-((5-bromo-1-isopropyl-1H-indazol-3-yl)methoxy)-3-methylphenyl) acetate (306a)

Compound 306a was prepared according to the procedure reported in step-3 of scheme 7, from (5-bromo-1-isopropyl-1H-indazol-3-yl)methanol (182b) (300 mg, 1.115 mmol) in DCM (10 mL) using triphenylphosphine (351 mg, 1.338 mmol), ethyl 2-(2-hydroxy-3-methylphenyl)acetate (107a) (238 mg, 1.226 mmol), bis(4-chlorobenzyl) diazene-1,2-dicarboxylate (DCAD, 491 mg, 1.338 mmol) in DCM (5 mL) and stirring at RT for 60 min.

This gave after workup and purification using flash column chromatography [silica gel (24 g), eluting with EtOAc in hexane from 0-80%] ethyl 2-(2-((5-bromo-1-isopropyl-1H-indazol-3-yl)methoxy)-3-methylphenyl)acetate (306a) (110 mg, 0.247 mmol, 22.16% yield) as a white solid; MS (ES+): 445.10 & 447.10 (M+1); 467.10 & 469.10 (M+Na).

Step-2: Preparation of ethyl 2-(2-((5-(3-(aminomethyl)phenyl)-1-isopropyl-1H-indazol-3-yl) methoxy)-3-methylphenyl)acetate (306b)

Compound 306b was prepared according to the procedure reported in step-2 of scheme 1, from ethyl 2-(2-((5-bromo-1-isopropyl-1H-indazol-3-yl)methoxy)-3-methylphenyl)acetate (306a) (110 mg, 0.247 mmol) in dioxane (2 mL) and THF (2 mL) using 3-(aminomethyl)phenylboronic acid hydrochloride (1d) (93 mg, 0.494 mmol), 2 M solution of $K_3PO_4$ (0.494 mL, 0.988 mmol), tricyclohexylphosphine (13.85 mg, 0.049 mmol), $Pd_2(dba)_3$ (22.62 mg, 0.025 mmol), $PdCl_2(dppf)-CH_2Cl_2$ adduct (20.17 mg, 0.025 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)phenyl)-1-isopropyl-1H-indazol-3-yl)methoxy)-3-methylphenyl)acetate (306b) (60 mg, 0.127 mmol, 51.5% yield) as a clear oil; MS (ES+): 472.30 (M+1).

Step-3: Preparation of 2-(2-((5-(3-(aminomethyl) phenyl)-1-isopropyl-1H-indazol-3-yl)methoxy)-3-methylphenyl)acetic acid (306c)

Compound 306c was prepared according to the procedure reported in step-3 of scheme 1, from ethyl 2-(2-((5-(3-(aminomethyl)phenyl)-1-isopropyl-1H-indazol-3-yl) methoxy)-3-methylphenyl)acetate (306b) (60 mg, 0.127 mmol) in THF (2 mL) and MeOH (2 mL) using a solution of lithium hydroxide hydrate (32.0 mg, 0.763 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)phenyl)-1-isopropyl-1H-indazol-3-yl)methoxy)-3-methylphenyl)acetic acid (306c) (30 mg, 53% yield) HCl salt as a white solid; $^1H$ NMR (300 MHz, DMSO-$d_6$) δ 8.47 (s, 3H, $D_2O$ exchangeable), 8.20-7.89 (m, 1H), 7.89-7.80 (m, 2H), 7.80-7.65 (m, 2H), 7.58-7.42 (m, 2H), 7.20-7.05 (m, 2H), 7.05-6.91 (m, 1H), 5.19 (d, J=3.8 Hz, 2H), 5.11-4.94 (m, 1H), 4.15-4.07 (m, 2H), 3.62 (s, 2H), 2.25 (s, 3H), 1.54-1.46 (m, 6H).; MS (ES+): 444.20 (M+1); (ES−): 442.20 (M−1).

Scheme 307

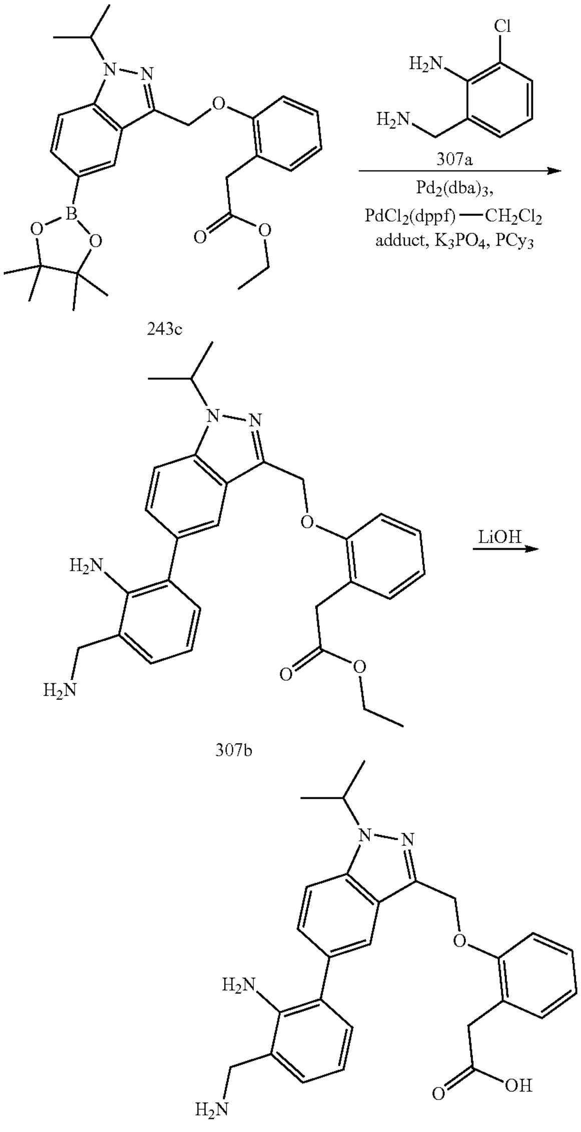

243c

307b

307c

Preparation of 2-(2-((5-(2-amino-3-(aminomethyl) phenyl)-1-isopropyl-1H-indazol-3-yl)methoxy)phenyl)acetic acid (307c)

Step-1: Preparation of ethyl 2-(2-((5-(2-amino-3-(aminomethyl)phenyl)-1-isopropyl-1H-indazol-3-yl) methoxy)phenyl)acetate (307b)

Compound 307b was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl) acetate (243c) (200 mg, 0.418 mmol) in dioxane (2 mL) and THF (2 mL) using 2-(aminomethyl)-6-chloroaniline (307a) (98 mg, 0.627 mmol; CAS #1261497-89-5), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2(dppf)$-$CH_2Cl_2$ adduct (34.1 mg, 0.042 mmol) and heating at 100°

C. for 2 h. This gave after workup and purification using flash column chromatography [silica gel (24 g), eluting with EtOAc in Hexane from 0-70%] ethyl 2-(2-((5-(2-amino-3-(aminomethyl)phenyl)-1-isopropyl-1H-indazol-3-yl)methoxy)phenyl)acetate (307b) (150 mg, 76% yield) as a clear oil; MS (ES+): 473.20 (M+1).

Step-2: Preparation of 2-(2-((5-(2-amino-3-(aminomethyl)phenyl)-1-isopropyl-1H-indazol-3-yl)methoxy)phenyl)acetic acid (307c)

Compound 307c was prepared according to the procedure reported in step-3 of scheme 1, from ethyl 2-(2-((5-(2-amino-3-(aminomethyl)phenyl)-1-isopropyl-1H-indazol-3-yl)methoxy)phenyl)acetate (307b) (150 mg, 0.317 mmol) in THF (3 mL) and MeOH (3 mL) using lithium hydroxide hydrate (80 mg, 1.904 mmol) in water (2 mL) and stirring at RT for 15 h. This gave after workup and purification using reverse phase column chromatography [C18 column (50 g), eluting with ACN in water (containing 0.1% HCl) from 0-100%] 2-(2-((5-(2-amino-3-(aminomethyl)phenyl)-1-isopropyl-1H-indazol-3-yl)methoxy)phenyl)acetic acid (307c) (26 mg, 18% yield) HCl salt as a white solid; $^1$H NMR (300 MHz, DMSO-$d_6$) δ 8.30 (s, 2H, $D_2O$ exchangeable), 7.83 (d, J=8.8 Hz, 1H), 7.78 (s, 1H), 7.39 (d, J=8.7 Hz, 1H), 7.34-7.22 (m, 3H), 7.18 (d, J=7.5 Hz, 2H), 6.97-6.83 (m, 2H), 5.43 (s, 2H), 5.12-4.96 (m, 1H), 4.08 (s, 2H), 3.49 (s, 2H), 1.52 (d, J=6.5 Hz, 6H).; MS (ES+): 445.20 (M+1); MS (ES−): 443.10 (M−1).

Scheme 308

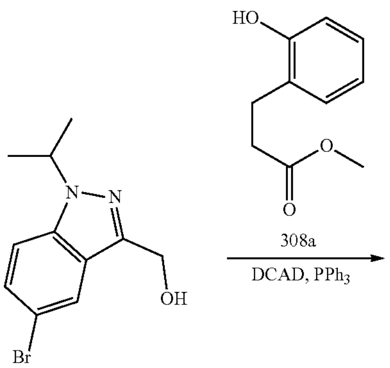

182b

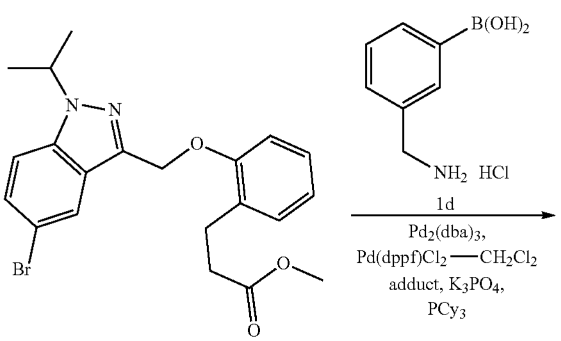

308b

-continued

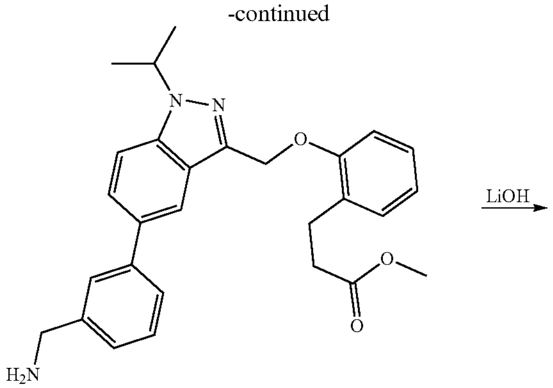

308c

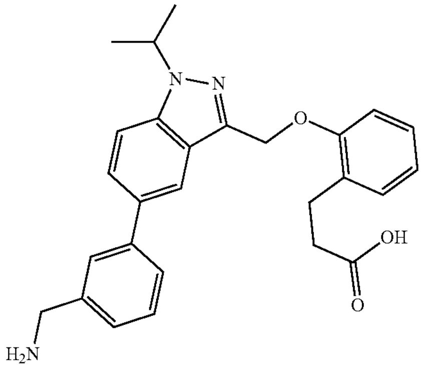

308d

Preparation of 3-(2-((5-(3-(aminomethyl)phenyl)-1-isopropyl-1H-indazol-3-yl)methoxy)phenyl)propanoic acid (308d)

Step-1: Preparation of methyl 3-(2-((5-bromo-1-isopropyl-1H-indazol-3-yl)methoxy)phenyl)propanoate (308b)

Compound 308b was prepared according to the procedure reported in step-3 of scheme 7, from (5-bromo-1-isopropyl-1H-indazol-3-yl)methanol (182b) (300 mg, 1.115 mmol) in DCM (10 mL) using triphenylphosphine (241 mg, 1.338 mmol), methyl 3-(2-hydroxyphenyl)propanoate (308a) (238 mg, 1.226 mmol; CAS #20349-89-7), bis(4-chlorobenzyl) diazene-1,2-dicarboxylate (DCAD, 491 mg, 1.338 mmol) in DCM (5 mL) and stirring at RT for 60 min. This gave after workup and purification using flash column chromatography [silica gel (24 g), eluting with EtOAc in hexane from 0-80%]methyl 3-(2-((5-bromo-1-isopropyl-1H-indazol-3-yl)methoxy)phenyl)propanoate (308b) (300 mg, 62% yield) as a white solid; MS (ES+): 431.10 & 433.10 (M+1); (ES−): 429.10 & 431.10 (M−1).

Step-2: Preparation of methyl 3-(2-((5-(3-(aminomethyl)phenyl)-1-isopropyl-1H-indazol-3-yl)methoxy)phenyl)propanoate (308c)

Compound 308c was prepared according to the procedure reported in step-2 of scheme 1, from methyl 3-(2-((5-bromo-1-isopropyl-1H-indazol-3-yl)methoxy)phenyl)propanoate (308b) (300 mg, 0.696 mmol) in dioxane (2 mL) and THF (2 mL) using 3-(aminomethyl)phenylboronic acid hydrochloride (1d) (261 mg, 1.391 mmol), 2 M solution of $K_3PO_4$ (1.391 mL, 2.78 mmol), tricyclohexylphosphine (39.0 mg, 0.139 mmol), $Pd_2(dba)_3$ (63.7 mg, 0.070 mmol), $PdCl_2$(dppf)-$CH_2Cl_2$ adduct (56.8 mg, 0.070 mmol) and heating at 100° C. for 2 h. This gave after workup and purification using flash column chromatography [silica gel (24 g), eluting with DMA-80 in DCM from 0-70%]methyl 3-(2-((5-(3-(aminomethyl)phenyl)-1-isopropyl-1H-indazol-3-yl)methoxy)phenyl)propanoate (308c) (100 mg, 0.219 mmol, 31.4% yield) as a clear oil; MS (ES+): 458.20 (M+1).

Step-3: Preparation of 3-(2-((5-(3-(aminomethyl)phenyl)-1-isopropyl-1H-indazol-3-yl)methoxy)phenyl)propanoic acid (308d)

Compound 308d was prepared according to the procedure reported in step-3 of scheme 1, from methyl 3-(2-((5-(3-(aminomethyl)phenyl)-1-isopropyl-1H-indazol-3-yl)methoxy)phenyl)propanoate (308c) (100 mg, 0.219 mmol) in THF (2 mL) and MeOH (2 mL) using a solution of lithium hydroxide hydrate (55 mg, 1.311 mmol) in water (1 mL) and stirring at RT for 15 h. This gave after workup and purification using reverse phase column chromatography [C18 column (50 g), eluting with ACN in water (containing 0.1% HCl) from 0-100%] 3-(2-((5-(3-(aminomethyl)phenyl)-1-isopropyl-1H-indazol-3-yl)methoxy)phenyl)propanoic acid (308d) (30 mg, 31% yield) HCl salt as a white solid; $^1$H NMR (300 MHz, DMSO-$d_6$) δ 8.58 (s, 3H, $D_2O$ exchangeable), 8.15 (d, J=19.5, 1.5 Hz, 1H), 7.97-7.66 (m, 4H), 7.54-7.43 (m, 2H), 7.31-6.96 (m, 3H), 6.93-6.77 (m, 1H), 5.48 (s, 2H), 5.04 (hept, J=6.4 Hz, 1H), 4.14-4.03 (m, 2H), 3.02-2.92 (m, 1H), 2.84-2.68 (m, 2H), 2.48-2.41 (m, 1H), 1.56-1.45 (m, 6H); MS (ES+): 444.20 (M+1); MS (ES−): 442.20 (M−1).

Scheme 309

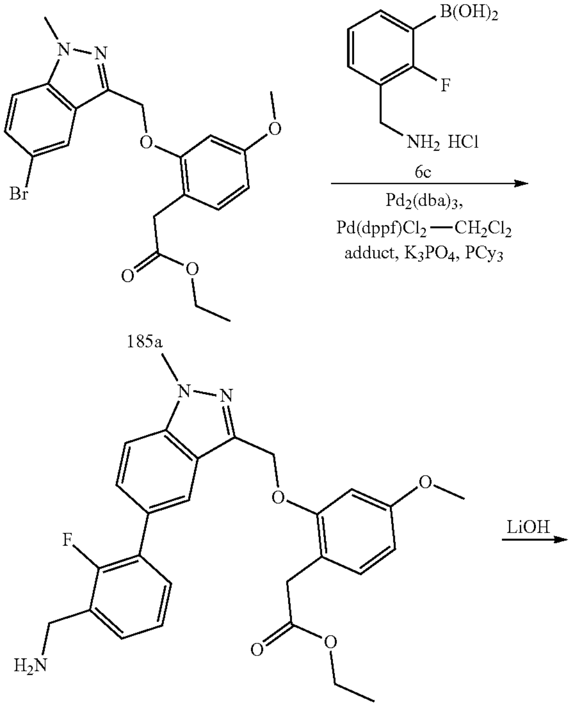

185a

6c

309a

-continued

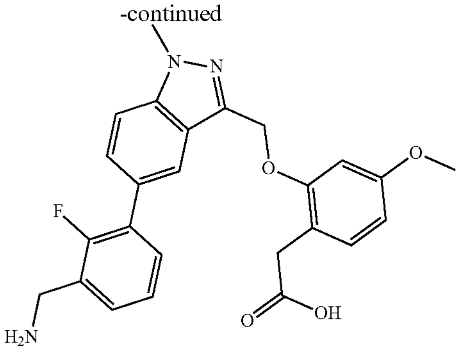

309b

Preparation of 2-(2-((5-(3-(aminomethyl)-2-fluorophenyl)-1-methyl-1H-indazol-3-yl)methoxy)-4-methoxyphenyl)acetic acid (309b)

Step-1: Preparation of ethyl 2-(2-((5-(3-(aminomethyl)-2-fluorophenyl)-1-methyl-1H-indazol-3-yl)methoxy)-4-methoxyphenyl)acetate (309a)

Compound 309a was prepared according to the procedure reported in step-2 of scheme 1, from ethyl 2-(2-((5-bromo-1-methyl-1H-indazol-3-yl)methoxy)-4-methoxyphenyl)acetate (185a) (200 mg, 0.462 mmol) in dioxane (2 mL) and THF (2 mL) using 3-(aminomethyl)-2-fluorophenylboronic acid hydrochloride (6c) (190 mg, 0.923 mmol), 2 M solution of $K_3PO_4$ (0.923 mL, 1.846 mmol), tricyclohexylphosphine (25.9 mg, 0.092 mmol), $Pd_2(dba)_3$ (42.3 mg, 0.046 mmol), $PdCl_2$(dppf)-$CH_2Cl_2$ adduct (37.7 mg, 0.046 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)-2-fluorophenyl)-1-methyl-1H-indazol-3-yl)methoxy)-4-methoxyphenyl)acetate (309a) (150 mg, 68% yield) as a clear oil; MS (ES+): 478.20 (M+1); (ES−): 476.10 (M−1).

Step-2: Preparation of 2-(2-((5-(3-(aminomethyl)-2-fluorophenyl)-1-methyl-1H-indazol-3-yl)methoxy)-4-methoxyphenyl)acetic acid (309b)

Compound 309b was prepared according to the procedure reported in step-3 of scheme 1, from ethyl 2-(2-((5-(3-(aminomethyl)-2-fluorophenyl)-1-methyl-1H-indazol-3-yl)methoxy)-4-methoxyphenyl)acetate (309a) (150 mg, 0.314 mmol) in THF (2 mL) and MeOH (2 mL) using a solution of lithium hydroxide hydrate (79 mg, 1.885 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-2-fluorophenyl)-1-methyl-1H-indazol-3-yl)methoxy)-4-methoxyphenyl)acetic acid (309b) (65 mg, 46% yield) HCl salt as a white solid; $^1$H NMR (300 MHz, DMSO-$d_6$) δ 8.56 (s, 3H, $D_2O$ exchangeable), 7.97 (s, 1H), 7.78 (d, J=8.8 Hz, 1H), 7.68-7.54 (m, 3H), 7.36 (t, J=7.6 Hz, 1H), 7.08 (d, J=8.3 Hz, 1H), 6.85 (d, J=2.4 Hz, 1H), 6.49 (dd, J=8.3, 2.4 Hz, 1H), 5.42 (s, 2H), 4.19-4.11 (m, 2H), 4.09 (s, 3H), 3.75 (s, 3H), 3.41 (s, 2H); $^{19}$F NMR (282 MHz, DMSO-$d_6$) δ −122.32; MS (ES+): 450.20 (M+1); (ES−): 448.20 (M−1); Analysis calculated for $C_{25}H_{24}FN_3O_4 \cdot HCl \cdot 0.5H_2O$: C, 60.67; H, 5.30; Cl, 7.16; N, 8.49. Found: C, 60.74; H, 5.34; Cl, 6.99; N, 8.52.

Scheme 310

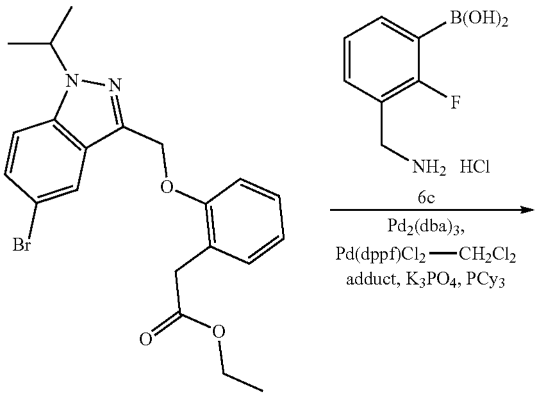

182c

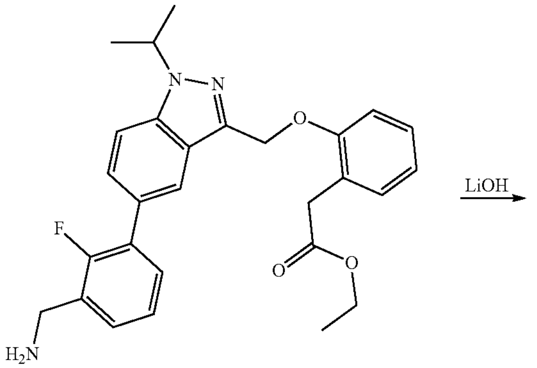

310a

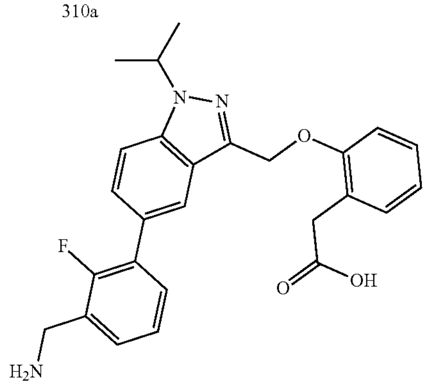

310b

Preparation of 2-(2-((5-(3-(aminomethyl)-2-fluorophenyl)-1-isopropyl-1H-indazol-3-yl)methoxy)phenyl)acetic acid (310b)

Step-1: Preparation of ethyl 2-(2-((5-(3-(aminomethyl)-2-fluorophenyl)-1-isopropyl-1H-indazol-3-yl)methoxy)phenyl)acetate (310a)

Compound 310a was prepared according to the procedure reported in step-2 of scheme 1, from ethyl 2-(2-((5-bromo-1-isopropyl-1H-indazol-3-yl)methoxy)phenyl)acetate (182c) (200 mg, 0.464 mmol) in dioxane (2 mL) and THF (2 mL) using (3-(aminomethyl)-2-fluorophenyl)boronic acid hydrochloride (6c) (191 mg, 0.927 mmol), 2 M solution of $K_3PO_4$ (0.927 mL, 1.855 mmol), tricyclohexylphosphine (26.0 mg, 0.093 mmol), $Pd_2(dba)_3$ (42.5 mg, 0.046 mmol), $PdCl_2(dppf)$-$CH_2Cl_2$ adduct (37.9 mg, 0.046 mmol) and heating at 100° C. for 2 h. This gave after workup and purification using flash column chromatography [silica gel (24 g), eluting with DMA-80 in DCM from 0-70%] ethyl 2-(2-((5-(3-(aminomethyl)-2-fluorophenyl)-1-isopropyl-1H-indazol-3-yl)methoxy)phenyl)acetate (310a) (130 mg, 59% yield) as a clear oil; $^1$H NMR (300 MHz, DMSO-$d_6$) δ 7.87 (s, 1H), 7.80 (d, J=8.8 Hz, 1H), 7.57 (dt, J=8.7, 1.9 Hz, 1H), 7.47 (dt, J=7.4, 3.6 Hz, 1H), 7.41 (td, J=7.7, 1.9 Hz, 1H), 7.27 (d, J=3.7 Hz, 2H), 7.21-7.10 (m, 2H), 6.96-6.86 (m, 1H), 5.41 (s, 2H), 5.04 (p, J=6.5 Hz, 1H), 3.81 (s, 2H), 3.65 (q, J=7.2 Hz, 2H), 3.52 (s, 2H), 1.52 (d, J=6.6 Hz, 6H), 0.80 (t, J=7.1 Hz, 3H); MS (ES+): 476.20 (M+1); (ES−): 474.20 (M−1).

Step-2: Preparation of 2-(2-((5-(3-(aminomethyl)-2-fluorophenyl)-1-isopropyl-1H-indazol-3-yl)methoxy)phenyl)acetic acid (310b)

Compound 310b was prepared according to the procedure reported in step-3 of scheme 1, from ethyl 2-(2-((5-(3-(aminomethyl)-2-fluorophenyl)-1-isopropyl-1H-indazol-3-yl)methoxy)phenyl)acetate (310a) (120 mg, 0.256 mmol) in THF (2 mL) and MeOH (2 mL) using a solution of lithium hydroxide hydrate (64.3 mg, 1.533 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-2-fluorophenyl)-1-isopropyl-1H-indazol-3-yl)methoxy)phenyl)acetic acid (310b) (45 mg, 40% yield) HCl salt as a white solid; $^1$H NMR (300 MHz, DMSO-$d_6$) δ 12.11 (s, 1H, $D_2O$ exchangeable), 8.48 (s, 3H, $D_2O$ exchangeable), 7.97 (s, 1H), 7.85 (d, J=8.8 Hz, 1H), 7.60 (m, 3H), 7.36 (t, J=7.6 Hz, 1H), 7.30-7.23 (m, 2H), 7.23-7.15 (m, 1H), 6.96-6.87 (m, 1H), 5.44 (s, 2H), 5.16-4.92 (m, 1H), 4.19-4.08 (m, 2H), 3.51 (s, 2H), 1.52 (d, J=6.6 Hz, 6H); $^{19}$F NMR (282 MHz, DMSO-$d_6$) δ −122.44; MS (ES+): 448.20 (M+1); (ES−): 446.20 (M−1).

Scheme 311

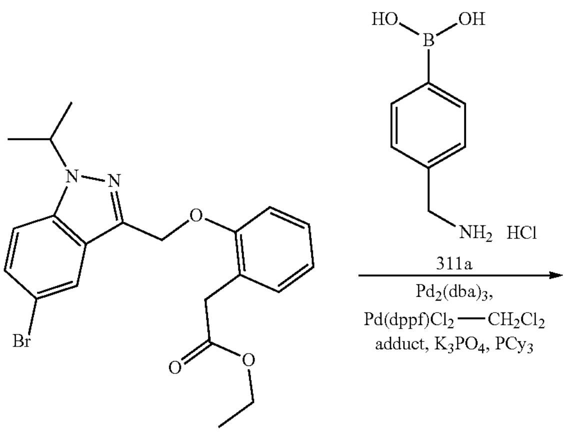

182c

-continued

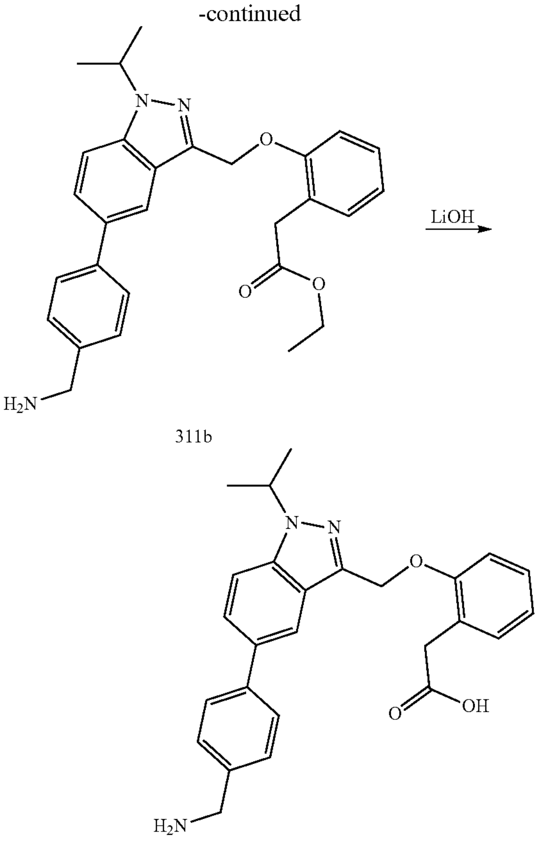

311b

311c

Preparation of 2-(2-((5-(4-(aminomethyl)phenyl)-1-isopropyl-1H-indazol-3-yl)methoxy)phenyl)acetic acid (311c)

Step-1: Preparation of ethyl 2-(2-((5-(4-(aminomethyl)phenyl)-1-isopropyl-1H-indazol-3-yl)methoxy)phenyl)acetate (311b)

Compound 311b was prepared according to the procedure reported in step-2 of scheme 1, from ethyl 2-(2-((5-bromo-1-isopropyl-1H-indazol-3-yl)methoxy)phenyl)acetate (182c) (200 mg, 0.464 mmol) in dioxane (2 mL) and THF (2 mL) using 4-(aminomethyl)phenylboronic acid hydrochloride (311a) (174 mg, 0.927 mmol; CAS #75705-21-4), 2 M solution of $K_3PO_4$ (0.927 mL, 1.855 mmol), tricyclohexylphosphine (26.0 mg, 0.093 mmol), $Pd_2(dba)_3$ (42.5 mg, 0.046 mmol), $PdCl_2(dppf)$-$CH_2Cl_2$ adduct (37.9 mg, 0.046 mmol) and heating at 100° C. for 2 h. This gave after workup and purification using flash column chromatography [silica gel (24 g), eluting with DMA-80 in DCM from 0-70%] ethyl 2-(2-((5-(4-(aminomethyl)phenyl)-1-isopropyl-1H-indazol-3-yl)methoxy)phenyl)acetate (311b) (110 mg, 52% yield) as a clear oil; $^1$H NMR (300 MHz, DMSO-$d_6$) δ 7.96 (d, J=1.5 Hz, 1H), 7.78 (d, J=8.8 Hz, 1H), 7.70 (dd, J=8.8, 1.6 Hz, 1H), 7.64 (d, J=8.0 Hz, 2H), 7.40 (d, J=8.0 Hz, 2H), 7.29 (h, J=4.3 Hz, 2H), 7.19 (d, J=7.3 Hz, 1H), 6.97-6.85 (m, 1H), 5.42 (s, 2H), 5.12-4.89 (m, 1H), 3.75 (s, 2H), 3.68 (q, J=7.1 Hz, 2H), 3.53 (s, 2H), 1.51 (d, J=6.6 Hz, 6H), 0.78 (t, J=7.1 Hz, 3H); MS (ES+): 458.20 (M+1); (ES−): 456.30 (M−1).

Step-2: Preparation of 2-(2-((5-(4-(aminomethyl)phenyl)-1-isopropyl-1H-indazol-3-yl)methoxy)phenyl)acetic acid (311c)

Compound 311c was prepared according to the procedure reported in step-3 of scheme 1, from ethyl 2-(2-((5-(4-(aminomethyl)phenyl)-1-isopropyl-1H-indazol-3-yl)methoxy)phenyl)acetate (311b) (110 mg, 0.240 mmol) in THF (2 mL) and MeOH (2 mL) using a solution of lithium hydroxide hydrate (60.5 mg, 1.442 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(4-(aminomethyl)phenyl)-1-isopropyl-1H-indazol-3-yl)methoxy)phenyl)acetic acid (311c) (65 mg, 63% yield) HCl salt as a white solid; $^1$H NMR (300 MHz, DMSO-$d_6$) δ 12.12 (s, 1H, $D_2O$ exchangeable), 8.40 (s, 3H, $D_2O$ exchangeable), 8.07 (d, J=1.5 Hz, 1H), 7.85-7.78 (m, 2H), 7.78-7.71 (m, 2H), 7.57 (d, J=8.1 Hz, 2H), 7.31-7.22 (m, 2H), 7.22-7.16 (m, 1H), 6.95-6.88 (m, 1H), 5.46 (s, 2H), 5.11-4.94 (m, J=6.4 Hz, 1H), 4.10-3.99 (m, 2H), 3.52 (s, 2H), 1.51 (d, J=6.6 Hz, 6H); MS (ES+): 430.20 (M+1); (ES−): 428.20 (M−1).

Scheme 312

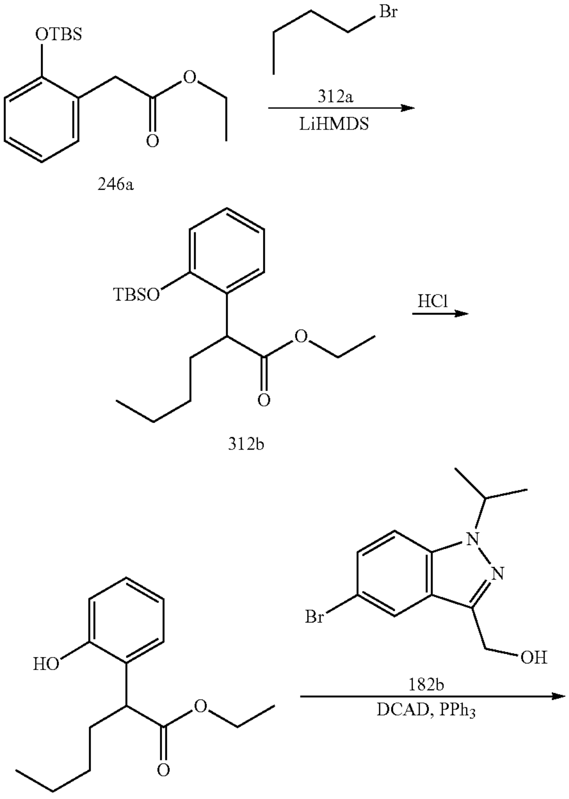

246a

312b

312c

-continued

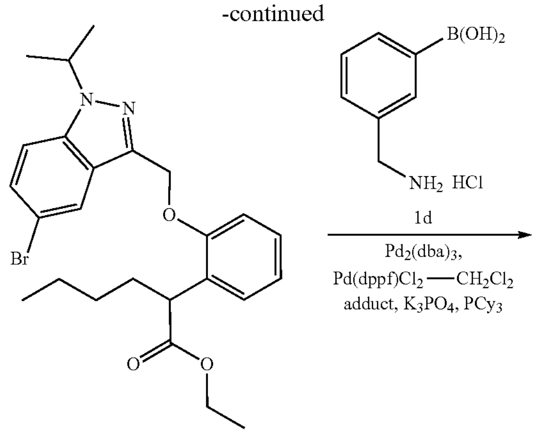

312d

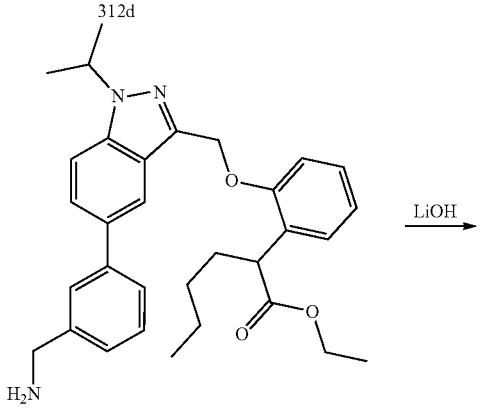

312e

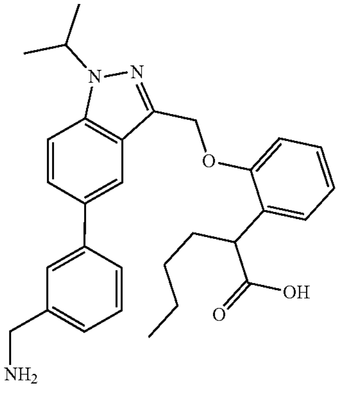

312f

Preparation of 2-(2-((5-(3-(aminomethyl)phenyl)-1-isopropyl-1H-indazol-3-yl)methoxy)phenyl) hexanoic acid (312f)

Step-1: Preparation of ethyl 2-(2-((tert-butyldimethylsilyl)oxy)phenyl)hexanoate (312b)

Compound 312b was prepared according to the procedure reported in step-1 of scheme 171, from ethyl 2-(2-(tert-butyldimethylsilyloxy)phenyl)acetate (246a) (5 g, 16.98 mmol) in THF (50 mL) using LiHMDS (1N in THF, 18.68 mL, 18.68 mmol), 1-bromobutane (312a) (2.56 g, 18.68 mmol) in THF (3 mL) and stirring at −78° C. for 1 h and at 0° C. for 1 h. This gave after workup and purification using flash column chromatography [silica gel (80 g), eluting with EtOAc in hexane from 0-100%] ethyl 2-(2-((tert-butyldimethylsilyl)oxy)phenyl)hexanoate (312b) (2.69 g, 45% yield) as a clear oil; $^1$H NMR (300 MHz, DMSO-$d_6$) δ 7.07-6.94 (m, 1H), 6.94-6.85 (m, 1H), 6.76-6.65 (m, 1H), 6.65-6.55 (m, 1H), 3.92-3.64 (m, 3H), 1.77-1.61 (m, 1H), 1.49-1.31 (m, 1H), 1.16-0.90 (m, 4H), 0.87 (t, J=7.1 Hz, 3H), 0.70 (s, 9H), 0.58 (t, J=7.0 Hz, 3H), −0.15 (s, 6H); MS (ES+): 351.2 (M+1).

Step-2: Preparation of ethyl 2-(2-hydroxyphenyl)hexanoate (312c)

Compound 312c was prepared according to the procedure reported in step-2 of scheme 7, from ethyl 2-(2-((tert-butyldimethylsilyl)oxy)phenyl)hexanoate (312b) (2.3 g, 4.20 mmol) in THE (10 mL) using HCl (aqueous 4 N, 5 mL) and stirring the reaction mixture at RT for 3 h.

This gave after workup and purification by flash column chromatography [silica gel, eluting with EtOAc in hexane from 0-100%] ethyl 2-(2-hydroxyphenyl)hexanoate (312c) (2.1 g, 52% yield) as a clear oil; $^1$H NMR (300 MHz, DMSO-$d_6$) δ 9.54 (s, 1H, $D_2O$ exchangeable), 7.17-7.11 (m, 1H), 7.11-7.03 (m, 1H), 6.86-6.73 (m, 2H), 4.15-3.99 (m, 2H), 3.92 (t, J=7.5 Hz, 1H), 1.98-1.84 (m, 1H), 1.73-1.58 (m, 1H), 1.39-1.19 (m, 4H), 1.16 (t, J=7.1 Hz, 3H), 0.88-0.81 (m, 3H).

Step-3: Preparation of ethyl 2-(2-((5-bromo-1-isopropyl-1H-indazol-3-yl)methoxy)phenyl)hexanoate (312d)

Compound 312d was prepared according to the procedure reported in step-3 of scheme 7, from (5-bromo-1-isopropyl-1H-indazol-3-yl)methanol (182b) (500 mg, 1.858 mmol) in DCM (20 mL) using ethyl 2-(2-hydroxyphenyl)hexanoate (312c) (483 mg, 2.044 mmol), triphenylphosphine (536 mg, 2.044 mmol), bis(4-chlorobenzyl) diazene-1,2-dicarboxylate (DCAD) (750 mg, 2.044 mmol) in DCM (10 mL) and stirring at RT for 30 min. This gave after workup and purification using flash column chromatography [silica gel (40 g), eluting with EtOAc in hexane from 0-50%] ethyl 2-(2-((5-bromo-1-isopropyl-1H-indazol-3-yl)methoxy)phenyl)hexanoate (312d) (250 mg, 28% yield) as a clear oil; MS (ES+): 487.2 (M+1).

Step-4: Preparation of ethyl 2-(2-((5-(3-(aminomethyl)phenyl)-1-isopropyl-1H-indazol-3-yl)methoxy) phenyl)hexanoate (312e)

Compound 312e was prepared according to the procedure reported in step-2 of scheme 1, from ethyl 2-(2-((5-bromo-1-isopropyl-1H-indazol-3-yl)methoxy)phenyl)hexanoate (312d) (250 mg, 0.513 mmol) in dioxane (20 mL) using 3-(aminomethyl)phenylboronic acid hydrochloride (1d) (192 mg, 1.026 mmol), 4 M solution of $K_3PO_4$ (0.513 mL, 2.052 mmol), tricyclohexylphosphine (43.1 mg, 0.154 mmol) and $Pd_2(dba)_3$ (47.0 mg, 0.051 mmol), $PdCl_2(dppf)$-$CH_2Cl_2$ adduct (41.9 mg, 0.051 mmol) and heating at 110° C. for 3 h. This gave after workup and purification using flash column chromatography [silica gel (40 g), eluting with DMA-80 in DCM from 0-100%] ethyl 2-(2-((5-(3-(aminomethyl)phenyl)-1-isopropyl-1H-indazol-3-yl)methoxy)phenyl)hexanoate (312e) (104 mg, 40% yield) as a yellow oil; MS (ES+): 514.3 (M+1).

Step-5: Preparation of 2-(2-((5-(3-(aminomethyl) phenyl)-1-isopropyl-1H-indazol-3-yl)methoxy)phenyl)hexanoic acid (312f)

Compound 312f was prepared according to the procedure reported in step-3 of scheme 1, from ethyl 2-(2-((5-(3-

(aminomethyl)phenyl)-1-isopropyl-1H-indazol-3-yl) methoxy)phenyl)hexanoate (312e) (104 mg, 0.202 mmol) in THF (3 mL) using a solution of lithium hydroxide hydrate (64.6 mg, 1.539 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-1-isopropyl-1H-indazol-3-yl)methoxy)phenyl)hexanoic acid (312f) (55 mg, 22% yield) as a white solid; $^1H$ NMR (300 MHz, DMSO-$d_6$) δ 12.17 (s, 1H, $D_2O$ exchangeable), 8.45 (s, 3H, $D_2O$ exchangeable), 8.10 (s, 1H), 7.90-7.81 (m, 2H), 7.77 (dd, J=8.9, 1.6 Hz, 1H), 7.71 (dt, J=7.4, 1.8 Hz, 1H), 7.53-7.40 (m, 2H), 7.36-7.17 (m, 3H), 6.95 (td, J=7.3, 1.4 Hz, 1H), 5.55-5.37 (m, 2H), 5.13-4.93 (m, 1H), 4.09 (q, J=5.8 Hz, 2H), 3.89 (t, J=7.5 Hz, 1H), 1.87-1.68 (m, 1H), 1.52 (dd, J=6.6, 3.8 Hz, 7H), 1.10-0.81 (m, 4H), 0.66-0.43 (m, 3H); MS (ES+): 486.2 (M+1); (ES−): 484.3 (M−1).

Scheme 313

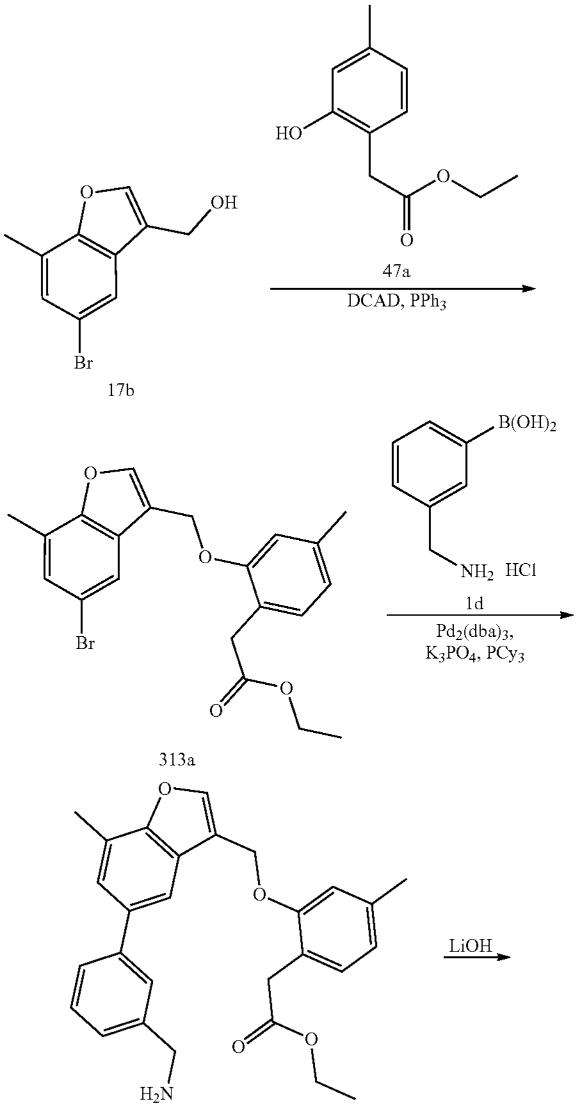

47a

17b

1d

313a

313b

-continued

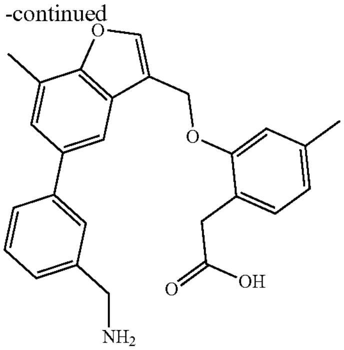

313c

Preparation of 2-(2-((5-(3-(aminomethyl)phenyl)-7-methylbenzofuran-3-yl)methoxy)-4-methylphenyl) acetic acid (313c)

Step-1, Preparation of ethyl 2-(2-((5-bromo-7-methylbenzofuran-3-yl)methoxy)-4-methylphenyl)acetate (313a)

Compound 313a was prepared according to the procedure reported in step-3 of scheme 7, from (5-bromo-7-methylbenzofuran-3-yl)methanol (17b) (240 mg, 0.996 mmol) in DCM (8 mL) using triphenylphosphine (300 mg, 1.145 mmol), ethyl 2-(2-hydroxy-4-methylphenyl)acetate (47a) (213 mg, 1.095 mmol), bis(4-chlorobenzyl) diazene-1,2-dicarboxylate (DCAD, 420 mg, 1.145 mmol) in DCM (4 mL) and stirring at RT for 1 h. This gave after workup and purification using flash column chromatography [silica gel (24 g), eluting with EtOAc in hexane from 0-25%] ethyl 2-(2-((5-bromo-7-methylbenzofuran-3-yl)methoxy)-4-methylphenyl)acetate (313a) (300 mg, 72% yield) as a colorless gum; $^1H$ NMR (300 MHz, DMSO-$d_6$) δ 8.19 (s, 1H), 7.72 (d, J=2.0 Hz, 1H), 7.44 (dd, J=2.1, 1.0 Hz, 1H), 7.13 (d, J=7.6 Hz, 1H), 7.09 (d, J=1.6 Hz, 1H), 6.86-6.75 (m, 1H), 5.26 (s, 2H), 4.00 (q, J=7.2 Hz, 2H), 3.56 (s, 2H), 2.53 (s, 3H), 2.38 (s, 3H), 1.06 (t, J=7.1 Hz, 3H); MS (ES+): 439.0/441.1 (M+Na).

Step-2: Preparation of ethyl 2-(2-((5-(3-(aminomethyl)phenyl)-7-methylbenzofuran-3-yl)methoxy)-4-methylphenyl)acetate (313b)

Compound 313b was prepared according to the procedure reported in step-2 of scheme 1, from ethyl 2-(2-((5-bromo-7-methylbenzofuran-3-yl)methoxy)-4-methylphenyl)acetate (313a) (260 mg, 0.623 mmol) in dioxane (20 mL) using 3-(aminomethyl)phenylboronic acid hydrochloride (1d) (146 mg, 0.779 mmol), 4 M solution of $K_3PO_4$ (0.623 mL, 2.492 mmol), tricyclohexylphosphine (52.4 mg, 0.187 mmol) and $Pd_2(dba)_3$ (86 mg, 0.093 mmol) and heating at 115° C. for 3 h. This gave after workup and purification using flash column chromatography [silica gel (24 g), eluting with DMA-80 in DCM from 0-70%] ethyl 2-(2-((5-(3-(aminomethyl)phenyl)-7-methylbenzofuran-3-yl)methoxy)-4-methylphenyl)acetate (313b) (145 mg, 53% yield) as a clear oil; MS (ES+): 444.2 (M+1).

Step-3: Preparation of 2-(2-((5-(3-(aminomethyl) phenyl)-7-methylbenzofuran-3-yl)methoxy)-4-methylphenyl)acetic acid (313c)

Compound 313c was prepared according to the procedure reported in step-3 of scheme 1, from ethyl 2-(2-((5-(3-

(aminomethyl)phenyl)-7-methylbenzofuran-3-yl)methoxy)-4-methylphenyl)acetate (313b) (95 mg, 0.208 mmol) in THF (2 mL) and acetonitrile (1 mL) using a solution of lithium hydroxide monohydrate, (aqueous 1N, 0.947 mL, 0.947 mmol) and stirring at RT for 25 h. This gave after workup and purification using reverse phase column chromatography [C18 column (50 g), eluting with ACN in water (containing 0.1% HCl) from 0-100%] 2-(2-((5-(3-(aminomethyl)phenyl)-7-methylbenzofuran-3-yl)methoxy)-4-methylphenyl)acetic acid (313c) (75 mg, 57% yield) HCl salt as a white solid; $^1$H NMR (300 MHz, DMSO-$d_6$) δ 8.36 (s, 1H, $D_2O$ exchangeable), 8.13 (s, 1H), 7.87 (s, 1H), 7.83 (d, J=1.8 Hz, 1H), 7.79-7.70 (m, 1H), 7.57-7.39 (m, 3H), 7.12-7.01 (m, 2H), 6.74 (d, J=7.5 Hz, 1H), 5.29 (s, 2H), 4.11 (s, 2H), 3.48 (s, 2H), 2.56 (s, 3H), 2.32 (s, 3H). MS (ES+): 416.2 (M+1); (ES−): 414.1 (M−1); Analysis calculated for $C_{26}H_{25}NO_4 \cdot 0.5H_2O \cdot HCl$: C, 67.75; H, 5.90; Cl, 7.69; N, 3.04. Found: C, 68.08; H, 5.79; Cl, 7.78; N, 3.16.

Scheme 314

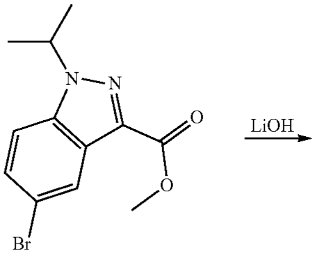

182a

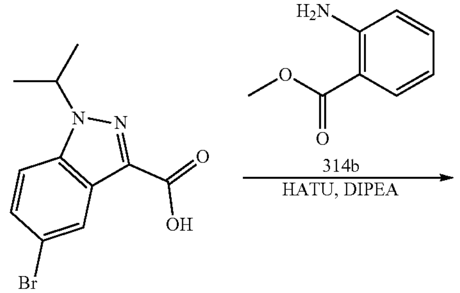

314a

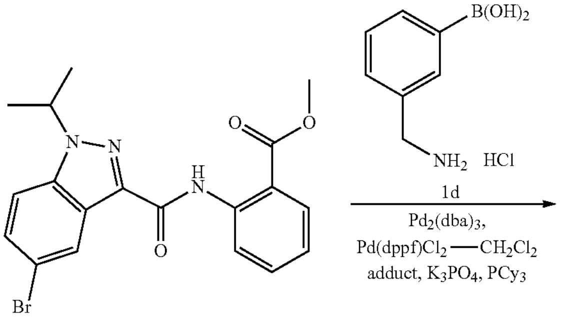

314c

-continued

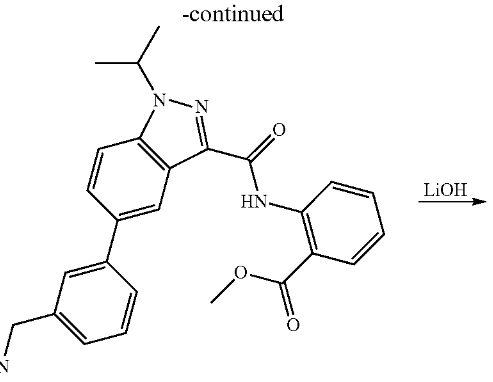

314d

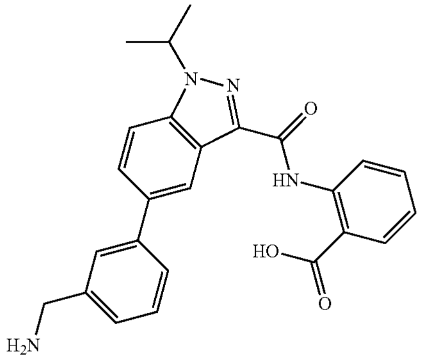

314e

Preparation of 2-(5-(3-(aminomethyl)phenyl)-1-isopropyl-1H-indazole-3-carboxamido)benzoic acid (314e)

Step-1: Preparation of 5-bromo-1-isopropyl-1H-indazole-3-carboxylic acid (314a)

Compound 314a was prepared according to the procedure reported in step-3 of scheme 1, from methyl 5-bromo-1-isopropyl-1H-indazole-3-carboxylate (182a) (1.4 g, 4.71 mmol) in MeOH/THF (5 mL each) using a solution of lithium hydroxide hydrate (0.593 g, 14.13 mmol) in water (3 mL) and stirring at RT for 15 h. This gave after workup and purification using flash column chromatography [C18 column (50 g), eluting with ACN in water (containing 0.1% HCl) from 0-100%] 5-bromo-1-isopropyl-1H-indazole-3-carboxylic acid (314a) (1.2 g, 90% yield) as a white solid; $^1$H NMR (300 MHz, DMSO-$d_6$) δ 8.32 (d, J=1.9 Hz, 1H), 7.76 (d, J=8.9 Hz, 1H), 7.52 (dd, J=8.9, 1.9 Hz, 1H), 5.05 (hept, J=6.5 Hz, 1H), 1.48 (d, J=6.6 Hz, 6H); MS (ES+): 283.00 & 285.00 (M+1).

Step-2: Preparation of methyl 2-(5-bromo-1-isopropyl-1H-indazole-3-carboxamido)benzoate (314c)

Compound 314c was prepared according to the procedure reported in step-1 of scheme 10, from 5-bromo-1-isopropyl-1H-indazole-3-carboxylic acid (314a) (500 mg, 1.766 mmol) in DMF (10 mL) using methyl 2-aminobenzoate (314b) (0.251 mL, 1.943 mmol; CAS #134-20-3), N-ethyl-N-isopropylpropan-2-amine (DIPEA, 1.230 mL, 7.06 mmol), 2-(3H-[1,2,3]triazolo[4,5-b]pyridin-3-yl)-1,1,3,3-tetramethylisouronium hexafluorophosphate(V) (HATU, 1007 mg, 2.65 mmol) and stirring at RT for 16 h. This gave after workup and purification using flash column chromatography [silica gel (24 g), eluting with MeOH in DCM from 0-100%] methyl 2-(5-bromo-1-isopropyl-1H-indazole-3-carboxamido)benzoate (314c) (600 mg, 82% yield) as a white solid; $^1$H NMR (300 MHz, DMSO-$d_6$) δ 12.27 (s, 1H), 8.82 (dd, J=8.5, 1.2 Hz, 1H), 8.38 (d, J=1.8 Hz, 1H), 8.07 (dd, J=8.0, 1.6 Hz, 1H), 7.92 (d, J=9.0 Hz, 1H), 7.75-7.61 (m, 2H), 7.23 (td, J=7.6, 1.2 Hz, 1H), 5.18 (p, J=6.6 Hz, 1H), 3.95 (s, 3H), 1.59 (d, J=6.6 Hz, 6H); MS (ES+): 416.00 & 418.00 (M+1).

Step-3: Preparation of methyl 2-(5-(3-(aminomethyl)phenyl)-1-isopropyl-1H-indazole-3-carboxamido)benzoate (314d)

Compound 314d was prepared according to the procedure reported in step-2 of scheme 1, from methyl 2-(5-bromo-1-isopropyl-1H-indazole-3-carboxamido)benzoate (314c) (43.2 mg, 0.53 mmol) in dioxane (2 mL) and THF (2 mL) using 3-(aminomethyl)phenylboronic acid hydrochloride (1d) (198 mg, 1.057 mmol), 2 M solution of $K_3PO_4$ (1.057 mL, 2.114 mmol), tricyclohexylphosphine (29.6 mg, 0.106 mmol), $Pd_2(dba)_3$ (48.4 mg, 0.053 mmol), $PdCl_2(dppf)$-$CH_2Cl_2$ adduct (43.2 mg, 0.053 mmol) and heating at 100° C. for 2 h. This gave after workup and purification by flash column chromatography [silica gel (24 g), eluting with DMA-80 in DCM from 0-70%]methyl 2-(5-(3-(aminomethyl)phenyl)-1-isopropyl-1H-indazole-3-carboxamido) benzoate (314d) (150 mg, 64% yield) as a clear oil; $^1$H NMR (300 MHz, DMSO-$d_6$) δ 12.31 (s, 1H), 8.93-8.82 (m, 1H), 8.47 (d, J=1.6 Hz, 1H), 8.13-7.96 (m, 2H), 7.83 (dd, J=8.9, 1.7 Hz, 1H), 7.75-7.65 (m, 2H), 7.56 (d, J=7.5 Hz, 1H), 7.44 (t, J=7.5 Hz, 1H), 7.35 (d, J=7.5 Hz, 1H), 7.26-7.19 (m, 1H), 5.31-5.11 (m, 1H), 3.97 (s, 3H), 3.83 (s, 2H), 1.63 (d, J=6.6 Hz, 6H); MS (ES+): 443.20 (M+1).

Step-2: Preparation of 2-(5-(3-(aminomethyl)phenyl)-1-isopropyl-1H-indazole-3-carboxamido)benzoic acid (314e)

Compound 314e was prepared according to the procedure reported in step-3 of scheme 1, from methyl 2-(5-(3-(aminomethyl)phenyl)-1-isopropyl-1H-indazole-3-carboxamido)benzoate (314d) (150 mg, 0.339 mmol) in THF (2 mL) and MeOH (2 mL) using a solution of lithium hydroxide hydrate (85 mg, 2.034 mmol) in water (1 mL) and stirring at RT for 15 h. This gave after workup and purification by reverse phase column chromatography [C18 column (50 g), eluting with ACN in water (containing 0.1% HCl) from 0-100%] 2-(5-(3-(aminomethyl)phenyl)-1-isopropyl-1H-indazole-3-carboxamido)benzoic acid (314e) (75 mg, 52% yield) HCl salt as a white solid; $^1$H NMR (300 MHz, DMSO-$d_6$) δ 13.82 (s, 1H, $D_2O$ exchangeable), 12.81 (s, 1H, $D_2O$ exchangeable), 8.90 (dd, J=8.5, 1.1 Hz, 1H), 8.54 (d, J=1.6 Hz, 1H), 8.47-8.33 (m, 3H, $D_2O$ exchangeable), 8.08 (dd, J=8.0, 1.7 Hz, 1H), 8.02 (d, J=8.9 Hz, 1H), 7.93 (s, 1H), 7.86 (dd, J=8.9, 1.7 Hz, 1H), 7.76 (dt, J=7.7, 1.6 Hz, 1H), 7.67 (ddd, J=8.7, 7.2, 1.7 Hz, 1H), 7.56 (t, J=7.6 Hz, 1H), 7.52-7.45 (m, 1H), 7.25-7.13 (m, 1H), 5.34-5.05 (m, 1H), 4.15 (s, 2H), 1.61 (d, J=6.5 Hz, 6H); MS (ES+): 429.20 (M+1); (ES−): 427.20 (M−1).

Scheme 315

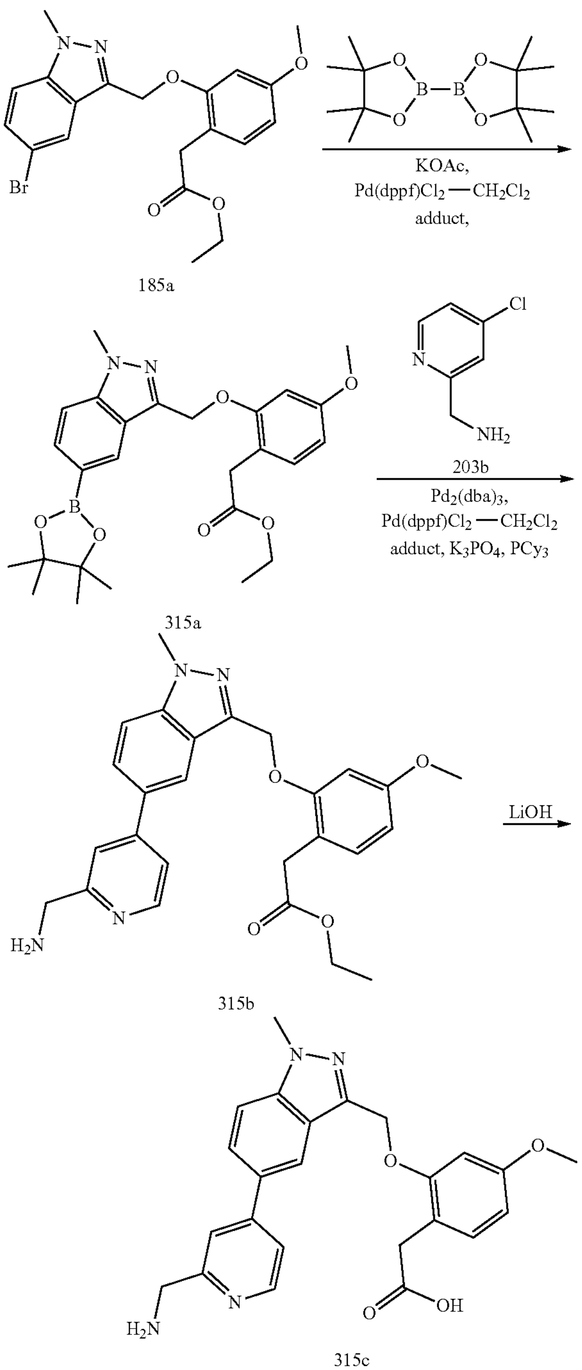

Preparation of 2-(2-((5-(2-(aminomethyl)pyridin-4-yl)-1-methyl-1H-indazol-3-yl)methoxy)-4-methoxyphenyl)acetic acid (315c)

Step-1: Preparation of ethyl 2-(4-methoxy-2-((1-methyl-5-(4,4,5,5-tetramethyl-1,3,2-dioxaborolan-2-yl)-1H-indazol-3-yl)methoxy)phenyl)acetate (315a)

Compound 315a was prepared according to the procedure reported in step-1 of scheme 27, from ethyl 2-(2-((5-bromo-1-methyl-1H-indazol-3-yl)methoxy)-4-methoxyphenyl)acetate (185a) (2 g, 4.62 mmol) in anhydrous dioxane (40 mL) using BisPin (2.344 g, 9.23 mmol), potassium acetate (1.133 g, 11.54 mmol), $PdCl_2(dppf)$-$CH_2Cl_2$ adduct (0.226 g, 0.277 mmol) and stirring at 100° C. for 3 h. This gave after work up and purification using flash column chromatography [silica gel (40 g), eluting with EtOAc in hexane from 0-40%] ethyl 2-(4-methoxy-2-((1-methyl-5-(4,4,5,5-tetramethyl-1,3,2-dioxaborolan-2-yl)-1H-indazol-3-yl)methoxy)phenyl) acetate (315a) (1.7 g, 77% yield) as a clear oil; $^1$H NMR (300 MHz, DMSO-$d_6$) δ 8.17 (t, J=1.0 Hz, 1H), 7.72-7.57 (m, 2H), 7.08 (d, J=8.3 Hz, 1H), 6.88 (d, J=2.4 Hz, 1H), 6.49 (dd, J=8.3, 2.4 Hz, 1H), 5.38 (s, 2H), 4.05 (s, 3H), 3.85 (q, J=7.1 Hz, 2H), 3.77 (s, 3H), 3.41 (s, 2H), 1.30 (s, 12H), 0.89 (t, J=7.1 Hz, 3H); MS (ES+): 481.30 (M+1).

Step-2: Preparation of ethyl 2-(2-((5-(2-(aminomethyl)pyridin-4-yl)-1-methyl-1H-indazol-3-yl) methoxy)-4-methoxyphenyl)acetate (315b)

Compound 315b was prepared according to the procedure reported in step-2 of scheme 1, from ethyl 2-(4-methoxy-2-((1-methyl-5-(4,4,5,5-tetramethyl-1,3,2-dioxaborolan-2-yl)-1H-indazol-3-yl)methoxy)phenyl)acetate (315a) (300 mg, 0.625 mmol) in dioxane (3 mL) and THE (3 mL) using (4-chloropyridin-2-yl)methanamine (203b) (178 mg, 1.249 mmol), 2 M solution of $K_3PO_4$ (1.249 mL, 2.498 mmol), tricyclohexylphosphine (35.0 mg, 0.125 mmol), $Pd_2(dba)_3$ (57.2 mg, 0.062 mmol), $PdCl_2(dppf)$-$CH_2Cl_2$ adduct (51 mg, 0.062 mmol) and heating at 100° C. for 2 h. This gave after workup and purification using flash column chromatography [silica gel (24 g), eluting with DMA-80 in DCM from 0-70%] ethyl 2-(2-((5-(2-(aminomethyl)pyridin-4-yl)-1-methyl-1H-indazol-3-yl)methoxy)-4-methoxyphenyl)acetate (315b) (200 mg, 70% yield) as a clear oil; MS (ES+): 461.25 (M+1).

Step-3: Preparation of 2-(2-((5-(2-(aminomethyl) pyridin-4-yl)-1-methyl-1H-indazol-3-yl)methoxy)-4-methoxyphenyl)acetic acid (315c)

Compound 315c was prepared according to the procedure reported in step-3 of scheme 1, from ethyl 2-(2-((5-(2-(aminomethyl)pyridin-4-yl)-1-methyl-1H-indazol-3-yl) methoxy)-4-methoxyphenyl)acetate (315b) (200 mg, 0.434 mmol) in THF (2 mL) and MeOH (2 mL) using a solution of lithium hydroxide hydrate (109 mg, 2.61 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(2-(aminomethyl) pyridin-4-yl)-1-methyl-1H-indazol-3-yl)methoxy)-4-methoxyphenyl)acetic acid (315c) (70 mg, 37% yield) HCl salt as a white solid; $^1$H NMR (300 MHz, DMSO-$d_6$) δ 8.72 (d, J=5.5 Hz, 1H), 8.64 (s, 3H, $D_2O$ exchangeable), 8.37 (s, 1H), 8.16 (s, 1H), 7.97 (dt, J=7.6, 1.6 Hz, 2H), 7.86 (d, J=8.9 Hz, 1H), 7.09 (d, J=8.3 Hz, 1H), 6.86 (d, J=2.4 Hz, 1H), 6.50 (dd, J=8.3, 2.4 Hz, 1H), 5.46 (s, 2H), 4.32 (s, 2H), 4.11 (s, 3H), 3.76 (s, 3H), 3.43 (s, 2H); MS (ES+): 433.20 (M+1); (ES−): 431.10 (M−1); Analysis calculated for $C_{24}H_{24}N_4O_4 \cdot 2.25HCl \cdot 1.25H_2O$: C, 53.68; H, 5.40; Cl, 14.85; N, 10.43. Found: C, 53.87; H, 5.29; Cl, 14.75; N, 10.72.

Scheme 316

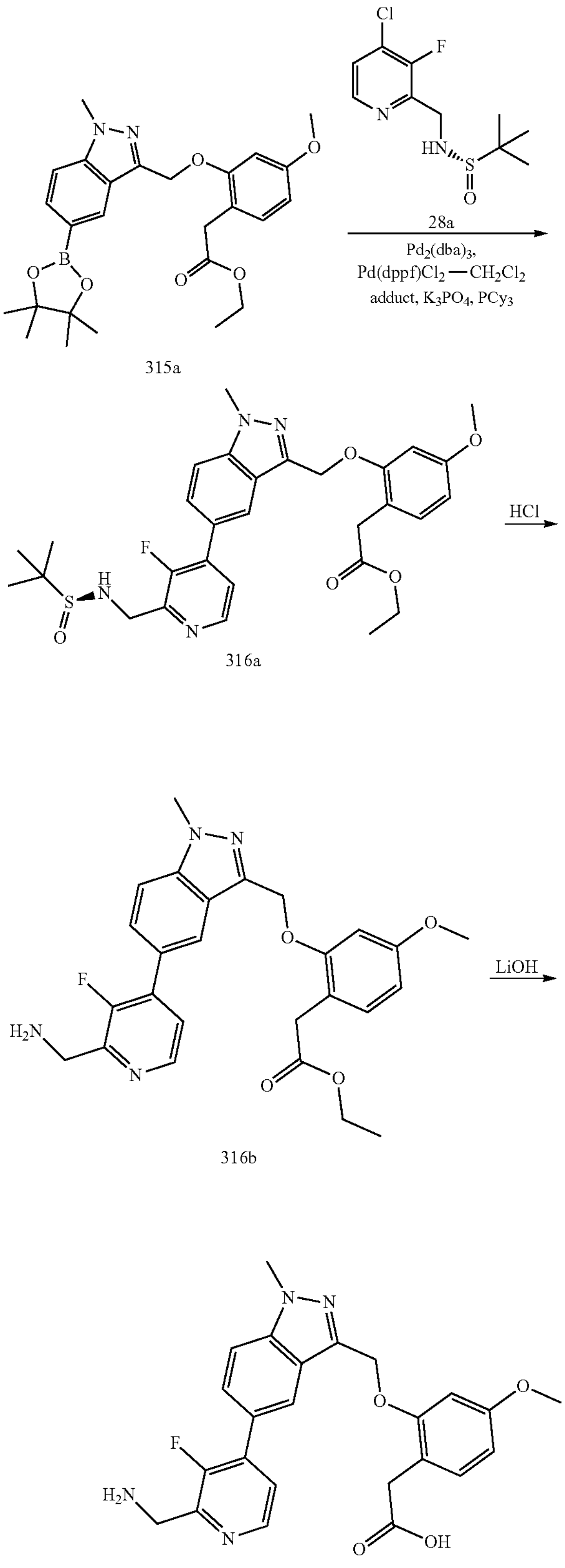

315a

316a

316b

316c

Preparation of 2-(2-((5-(2-(aminomethyl)-3-fluoropyridin-4-yl)-1-methyl-1H-indazol-3-yl)methoxy)-4-methoxyphenyl)acetic acid (316c)

Step-1: Preparation of (+)-ethyl 2-(2-((5-(2-((1,1-dimethylethylsulfinamido)methyl)-3-fluoropyridin-4-yl)-1-methyl-1H-indazol-3-yl)methoxy)-4-methoxyphenyl)acetate (316a)

Compound 316a was prepared according to the procedure reported in step-2 of scheme 1, from ethyl 2-(4-methoxy-2-((1-methyl-5-(4,4,5,5-tetramethyl-1,3,2-dioxaborolan-2-yl)-1H-indazol-3-yl)methoxy)phenyl)acetate (315a) (300 mg, 0.625 mmol) in dioxane (3 mL) and THE (3 mL) using (+)-N-((4-chloro-3-fluoropyridin-2-yl)methyl)-2-methyl-propane-2-sulfinamide (28a) (331 mg, 1.249 mmol), 2 M solution of $K_3PO_4$ (1.249 mL, 2.498 mmol), tricyclohexylphosphine (35.0 mg, 0.125 mmol), $Pd_2(dba)_3$ (57.2 mg, 0.062 mmol), $PdCl_2(dppf)$-$CH_2Cl_2$ adduct (51 mg, 0.062 mmol) and heating at 100° C. for 2 h. This gave after workup and purification using flash column chromatography [silica gel (24 g), eluting with DMA80 in DCM from 0-70%](+)-ethyl 2-(2-((5-(2-((1,1-dimethylethylsulfinamido)methyl)-3-fluoropyridin-4-yl)-1-methyl-1H-indazol-3-yl)methoxy)-4-methoxyphenyl)acetate (316a) (250 mg, 69% yield) as a clear oil; MS (ES+): 583.20 (M+1); (ES−): 581.00 (M−1); Optical rotation: $[\alpha]_D$=(+) 21.62 [$CH_3OH$, 0.555].

Step-2: Preparation of ethyl 2-(2-((5-(2-(aminomethyl)-3-fluoropyridin-4-yl)-1-methyl-1H-indazol-3-yl)methoxy)-4-methoxyphenyl)acetate (316b)

Compound 316b was prepared according to the procedure reported in step-2 of scheme 7, from (+)-ethyl 2-(2-((5-(2-((1,1-dimethylethylsulfinamido)methyl)-3-fluoropyridin-4-yl)-1-methyl-1H-indazol-3-yl)methoxy)-4-methoxyphenyl) acetate (316a) (250 mg, 0.429 mmol) in THE (5 mL) using HCl (4M in 1,4-dioxane) (0.215 mL, 0.858 mmol) and stirring at RT for 30 min. This gave after workup ethyl 2-(2-((5-(2-(aminomethyl)-3-fluoropyridin-4-yl)-1-methyl-1H-indazol-3-yl)methoxy)-4-methoxyphenyl)acetate (316b) (205 mg, 100% yield) as a light yellow oil; MS (ES+): 479.20 (M+1).

Step-3: Preparation of 2-(2-((5-(2-(aminomethyl)-3-fluoropyridin-4-yl)-1-methyl-1H-indazol-3-yl) methoxy)-4-methoxyphenyl)acetic acid (316c)

Compound 316c was prepared according to the procedure reported in step-3 of scheme 1, from ethyl 2-(2-((5-(2-(aminomethyl)-3-fluoropyridin-4-yl)-1-methyl-1H-indazol-3-yl)methoxy)-4-methoxyphenyl)acetate (316b) (200 mg, 0.418 mmol) in THF (2 mL) and MeOH (2 mL) using a solution of lithium hydroxide hydrate (105 mg, 2.508 mmol) in water (1 mL) and stirring at RT for 15 h. This gave after workup and purification by reverse phase column chromatography [C18 column (50 g), eluting with ACN in water (containing 0.1% HCl) from 0-100%] 2-(2-((5-(2-(aminomethyl)-3-fluoropyridin-4-yl)-1-methyl-1H-indazol-3-yl) methoxy)-4-methoxyphenyl)acetic acid (316c) (80 mg, 43% yield) HCl salt as a white solid; $^1H$ NMR (300 MHz, DMSO-$d_6$) δ 8.53 (d, J=5.0 Hz, 1H), 8.50 (s, 2H, $D_2O$ exchangeable), 8.15 (s, 1H), 7.85 (d, J=8.8 Hz, 1H), 7.80-7.68 (m, 2H), 7.08 (d, J=8.3 Hz, 1H), 6.85 (d, J=2.4 Hz, 1H), 6.49 (dd, J=8.3, 2.4 Hz, 1H), 5.44 (s, 2H), 4.37-4.30 (m, 2H), 4.11 (s, 3H), 3.75 (s, 3H), 3.41 (s, 2H); $^{19}F$ NMR (282 MHz, DMSO-$d_6$) δ −132.82; MS (ES+): 451.20 (M+1); MS (ES−): 449.10 (M−1); Analysis calculated for $C_{24}H_{23}FN_4O_4 \cdot 1.1HCl \cdot 1.75H_2O$: C, 55.21; H, 5.33; Cl, 7.47; N, 10.73. Found: C, 55.39; H, 5.02; Cl, 7.60; N, 10.75.

Scheme 317

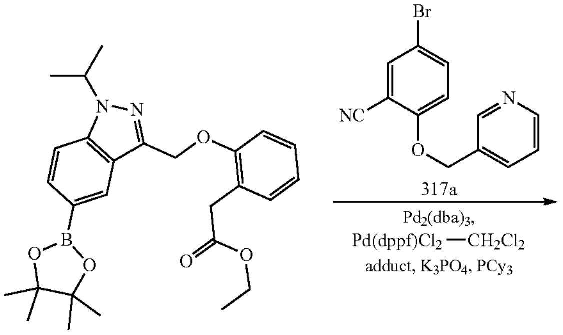

243c

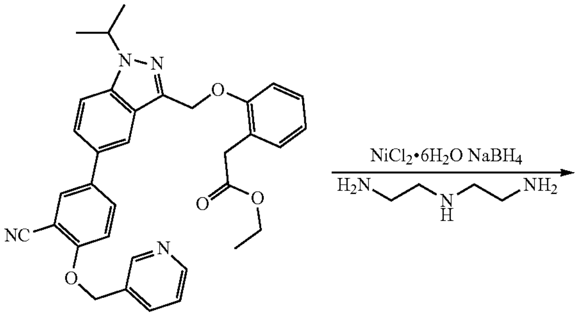

317b

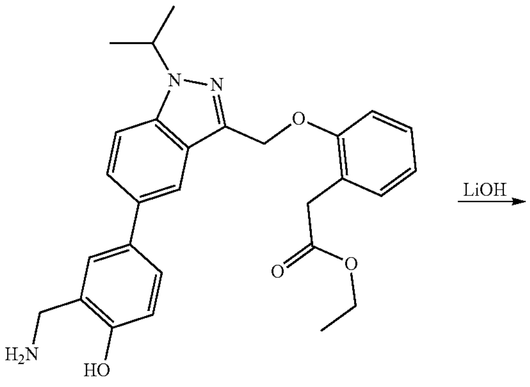

317c

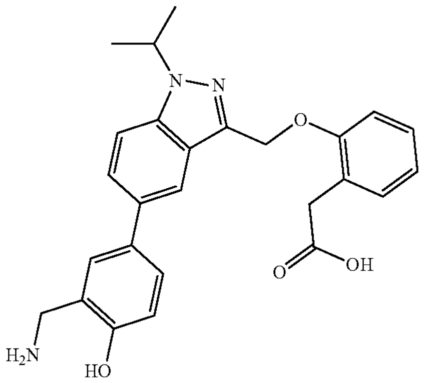

317d

Preparation of 2-2-5-3-aminomethyl)-4-hydroxyphenyl-1-isopropyl-1H-indazol-3-yl)methoxy)phenyl) acetic acid (317d)

Step-1: Preparation of ethyl 2-(2-((5-(3-cyano-4-(pyridin-3-ylmethoxy)phenyl)-1-isopropyl-1H-indazol-3-yl)methoxy)phenyl)acetate (317b)

Compound 317b was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (2 mL) and THF (2 mL) using 5-bromo-2-(pyridin-3-ylmethoxy)benzonitrile (317a) (181 mg, 0.627 mmol; CAS #1557149-05-9), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2(dppf)$-$CH_2Cl_2$ adduct (34.1 mg, 0.042 mmol) and heating at 100° C. for 2 h. This gave after workup and purification using flash column chromatography [silica gel (24 g), eluting with EtOAc/MeOH (9:1) in hexane from 0-100%] ethyl 2-(2-((5-(3-cyano-4-(pyridin-3-ylmethoxy)phenyl)-1-isopropyl-1H-indazol-3-yl)methoxy)phenyl)acetate (317b) (220 mg, 0.392 mmol, 94% yield) as a clear oil; MS (ES+): 561.30 (M+1); (ES−): 559.15 (M−1).

Step-2: Preparation of ethyl 2-(2-((5-(3-(aminomethyl)-4-hydroxyphenyl)-1-isopropyl-1H-indazol-3-yl)methoxy)phenyl)acetate (317c)

Compound 317c was prepared according to the procedure reported in step-2 of scheme 1, from ethyl 2-(2-((5-(3-cyano-4-(pyridin-3-ylmethoxy)phenyl)-1-isopropyl-1H-indazol-3-yl)methoxy)phenyl)acetate (317b) (200 mg, 0.357 mmol) in anhydrous ethanol (10 mL) using nickel(II) chloride hexahydrate (42.4 mg, 0.178 mmol), sodium borohydride (60.7 mg, 1.605 mmol), N1-(2-aminoethyl)ethane-1,2-diamine (0.077 mL, 0.713 mmol). This gave after workup and purification using flash column chromatography [silica gel (24 g), eluting with DMA-80 in DCM from 0 to 60%)]ethyl 2-(2-((5-(3-(aminomethyl)-4-hydroxyphenyl)-1-isopropyl-1H-indazol-3-yl)methoxy)phenyl)acetate (317c) (0.030 g, 18% yield) as a white solid; MS (ES+): 474.20 (M+1); (ES−): 472.20 (M−1).

Step-3: Preparation of 2-(2-((5-(3-(aminomethyl)-4-hydroxyphenyl)-1-isopropyl-1H-indazol-3-yl) methoxy)phenyl)acetic acid (317d)

Compound 317d was prepared according to the procedure reported in step-3 of scheme 1, from ethyl 2-(2-((5-(3-(aminomethyl)-4-hydroxyphenyl)-1-isopropyl-1H-indazol-3-yl)methoxy)phenyl)acetate (317c) (30 mg, 0.063 mmol) in THF (2 mL) and MeOH (2 mL) using a solution of lithium hydroxide hydrate (15.95 mg, 0.38 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-4-hydroxyphenyl)-1-isopropyl-1H-indazol-3-yl)methoxy)phenyl)acetic acid (317d) (11 mg, 39% yield) HCl salt as a white solid; $^1H$ NMR (300 MHz, DMSO-$d_6$) δ 12.12 (s, 1H, $D_2O$ exchangeable), 10.27 (s, 1H, $D_2O$ exchangeable), 8.13 (s, 2H, $D_2O$ exchangeable), 7.94 (s, 1H), 7.79 (d, J=8.8 Hz, 1H), 7.73-7.63 (m, 2H), 7.57 (dd, J=8.4, 2.3 Hz, 1H), 7.30-7.22 (m, 2H), 7.22-7.16 (m, 1H), 7.01 (d, J=8.4 Hz, 1H), 6.97-6.86 (m, 1H), 5.43 (s, 2H), 5.12-4.89 (m, 1H), 4.02 (s, 2H), 3.53 (s, 2H), 1.51 (d, J=6.6 Hz, 6H); MS (ES+): 446.20 (M+1); (ES−): 444.20 (M−1).

Scheme 318

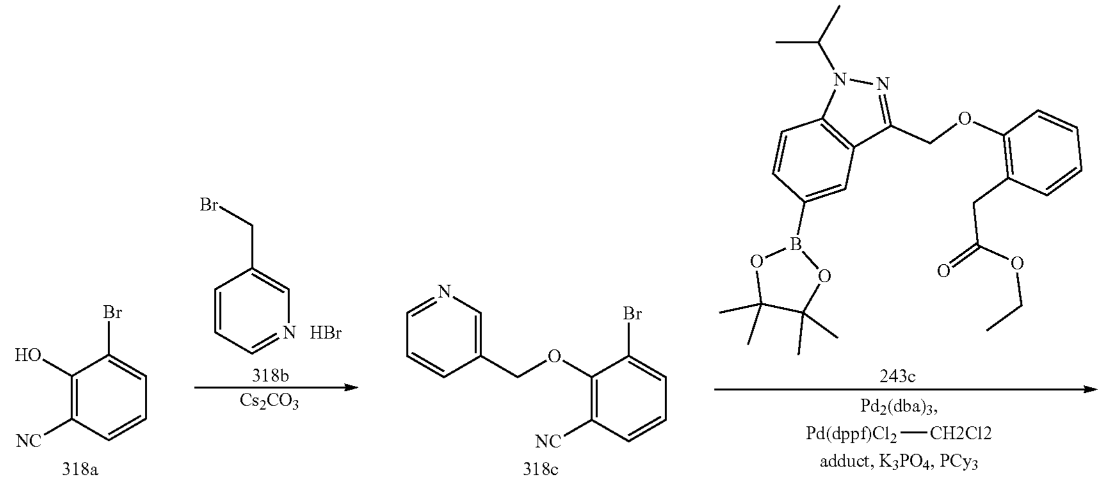

318a 318c

-continued

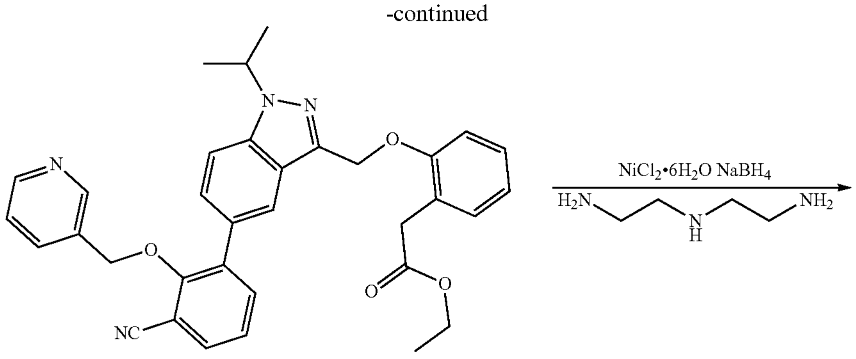

318d

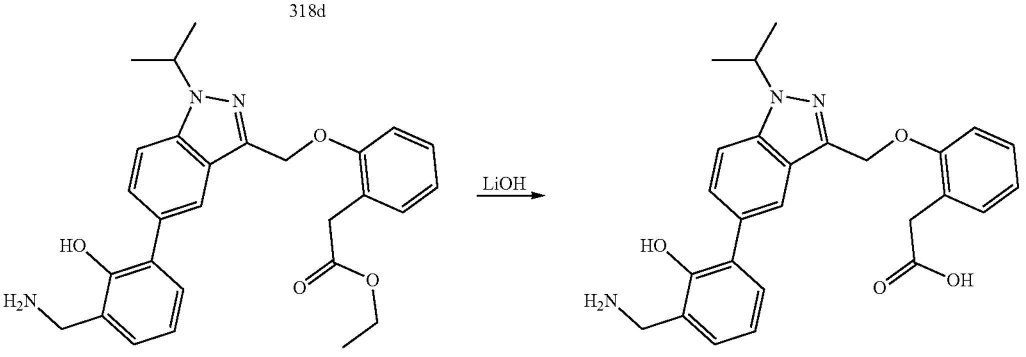

318e 318f

Preparation of 2-(2-((5-(3-(aminomethyl)-2-hydroxyphenyl)-1-isopropyl-1H-indazol-3-yl)methoxy)phenyl)acetic acid (318f)

Step-1: Preparation of 3-bromo-2-(pyridin-3-ylmethoxy)benzonitrile (318c)

Compound 318c was prepared according to the procedure reported in step-3 of scheme 7, from 3-bromo-2-hydroxybenzonitrile (318a) (1 g, 5.05 mmol) in DMF (15 mL) using 3-(bromomethyl)pyridine hydrobromide (318b) (1.277 g, 5.05 mmol), cesium carbonate (4.94 g, 15.15 mmol) and stirring for 15 h at RT. This gave after workup and purification using flash column chromatography [silica (40 g), eluting with Hexane in EtOAc from 0-80%] 3-bromo-2-(pyridin-3-ylmethoxy)benzonitrile (318c) (1.3 g, 4.50 mmol, 89% yield) as a white solid; $^1H$ NMR (300 MHz, DMSO-$d_6$) δ 8.71 (d, J=2.3 Hz, 1H), 8.61 (dd, J=4.8, 1.7 Hz, 1H), 8.05 (dd, J=8.1, 1.5 Hz, 1H), 7.95 (dt, J=7.8, 2.0 Hz, 1H), 7.89 (dd, J=7.8, 1.5 Hz, 1H), 7.53-7.42 (m, 1H), 7.30 (t, J=7.9 Hz, 1H), 5.25 (s, 2H); MS (ES+): 289.00 & 291.00 (M+1).

Step-2: Preparation of ethyl 2-(2-((5-(3-cyano-2-(pyridin-3-ylmethoxy)phenyl)-1-isopropyl-1H-indazol-3-yl)methoxy)phenyl)acetate (318d)

Compound 318d was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (2 mL) and THF (2 mL) using 3-bromo-2-(pyridin-3-ylmethoxy)benzonitrile (318c) (181 mg, 0.627 mmol), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2(dppf)$-$CH_2Cl_2$ adduct (34.1 mg, 0.042 mmol) and heating at 100° C. for 2 h. This gave after workup and purification using flash column chromatography [silica gel (24 g), eluting with EtOAc/MeOH (9:1) in hexane from 0-100%]ethyl 2-(2-((5-(3-cyano-2-(pyridin-3-ylmethoxy)phenyl)-1-isopropyl-1H-indazol-3-yl)methoxy)phenyl)acetate (318d) (200 mg, 85% yield) as a clear oil; MS (ES+): 561.25 (M+1); (ES−): 559.20 (M−1).

Step-3: Preparation of ethyl 2-(2-((5-(3-(aminomethyl)-2-hydroxyphenyl)-1-isopropyl-1H-indazol-3-yl)methoxy)phenyl)acetate (318e)

Compound 318e was prepared according to the procedure reported in step-2 of scheme 1, from ethyl 2-(2-((5-(3-cyano-2-(pyridin-3-ylmethoxy)phenyl)-1-isopropyl-1H-indazol-3-yl)methoxy)phenyl)acetate (318d) (200 mg, 0.357 mmol) in anhydrous ethanol (10 mL) using nickel(II) chloride hexahydrate (42.4 mg, 0.178 mmol), sodium borohydride (67.5 mg, 1.784 mmol), N1-(2-aminoethyl)ethane-1,2-diamine (0.077 mL, 0.713 mmol). This gave after workup and purification using flash column chromatography [silica gel (24 g), eluting with DMA-80 in DCM from 0 to 60%)]ethyl 2-(2-((5-(3-(aminomethyl)-2-hydroxyphenyl)-1-isopropyl-1H-indazol-3-yl)methoxy)phenyl)acetate (318e) (60 mg, 36% yield) as a white solid; MS (ES+): 474.20 (M+1).

Step-4: Preparation of 2-(2-((5-(3-(aminomethyl)-2-hydroxyphenyl)-1-isopropyl-1H-indazol-3-yl)methoxy)phenyl)acetic acid (318f)

Compound 318f was prepared according to the procedure reported in step-3 of scheme 1, from ethyl 2-(2-((5-(3-(aminomethyl)-2-hydroxyphenyl)-1-isopropyl-1H-indazol-3-yl)methoxy)phenyl)acetate (318e) (60 mg, 0.127 mmol) in THF (2 mL) and MeOH (2 mL) using a solution of lithium hydroxide hydrate (31.9 mg, 0.760 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-2-hydroxyphenyl)-1-isopropyl-1H-indazol-3-yl)methoxy)phenyl)acetic acid (318f) (11 mg, 19% yield) HCl salt as a white solid; $^1$H NMR (300 MHz, DMSO-$d_6$) δ 12.08 (s, 1H, $D_2O$ exchangeable), 9.01 (s, 1H, $D_2O$ exchangeable), 8.10 (s, 3H, $D_2O$ exchangeable), 7.85 (s, 1H), 7.78 (d, J=8.8 Hz, 1H), 7.56-7.47 (m, 1H), 7.36-7.28 (m, 2H), 7.28-7.21 (m, 2H), 7.21-7.15 (m, 1H), 7.01 (t, J=7.6 Hz, 1H), 6.95-6.84 (m, 1H), 5.42 (s, 2H), 5.11-4.95 (m, 1H), 4.11-4.02 (m, 2H), 3.50 (s, 2H), 1.52 (d, J=6.6 Hz, 6H); MS (ES+): 446.20 (M+1); (ES−): 444.20 (M−1).

Scheme 319

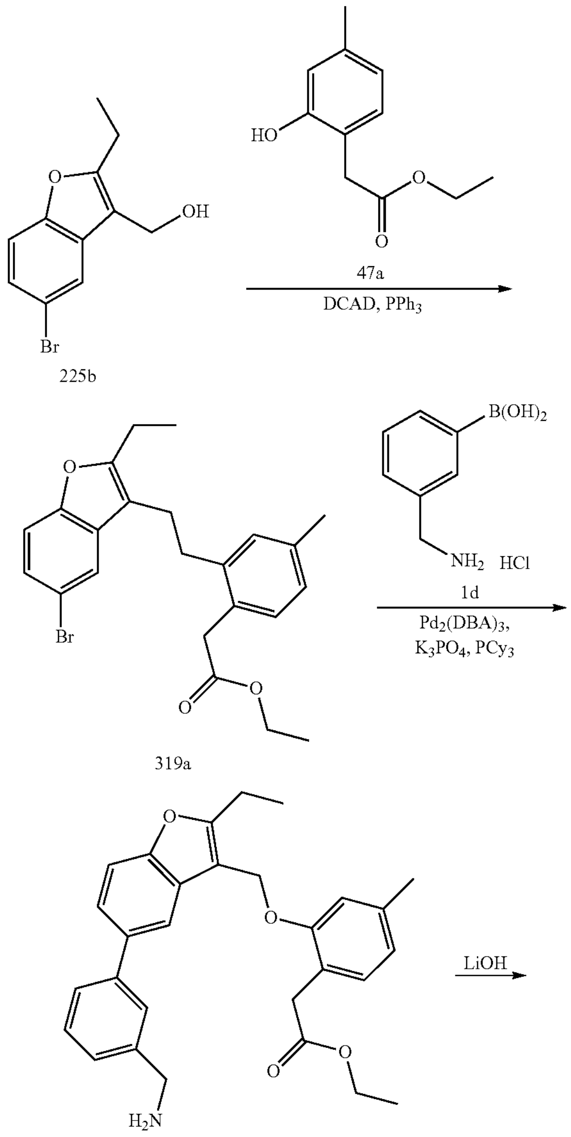

225b

319a

319b

-continued

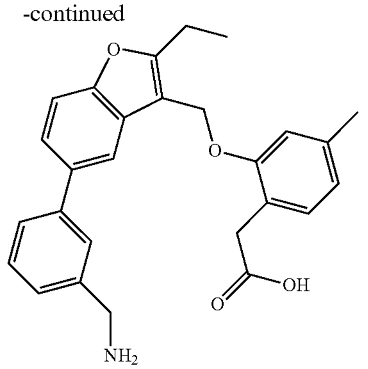

319c

Preparation of 2-(2-((5-(3-(aminomethyl)phenyl)-2-ethylbenzofuran-3-yl)methoxy)-4-methylphenyl) acetic acid (319c)

Step-1, Preparation of ethyl 2-(2-((5-bromo-2-ethylbenzofuran-3-yl)methoxy)-4-methylphenyl)acetate (319a)

Compound 319a was prepared according to the procedure reported in step-3 of scheme 7, from (5-bromo-2-ethylbenzofuran-3-yl)methanol (225b) (1 g, 3.92 mmol) in DCM (40 mL) using triphenylphosphine (1.131 g, 4.31 mmol), ethyl 2-(2-hydroxy-4-methylphenyl)acetate (47a) (0.837 g, 4.31 mmol), bis(4-chlorobenzyl) diazene-1,2-dicarboxylate (DCAD, 1.583 g, 4.31 mmol) in DCM (10 mL) and stirring at RT for 30 min. This gave after workup and purification using flash column chromatography [silica gel (40 g), eluting with EtOAc in hexane from 0-50%] ethyl 2-(2-((5-bromo-2-ethylbenzofuran-3-yl)methoxy)-4-methylphenyl) acetate (319a) (860 mg, 51% yield) as a clear oil; MS (ES+): 431.05 (M+1).

Step-2: Preparation of ethyl 2-(2-((5-(3-(aminomethyl)phenyl)-2-ethylbenzofuran-3-yl)methoxy)-4-methylphenyl)acetate (319b)

Compound 319b was prepared according to the procedure reported in step-2 of scheme 1, from ethyl 2-(2-((5-bromo-2-ethylbenzofuran-3-yl)methoxy)-4-methylphenyl)acetate (319a) (850 mg, 1.971 mmol) in dioxane (12 mL) using 3-(aminomethyl)phenylboronic acid hydrochloride (1d) (372 mg, 2.463 mmol), 4 M solution of $K_3PO_4$ (1.971 mL, 7.88 mmol), tricyclohexylphosphine (111 mg, 0.394 mmol), $Pd_2(dba)_3$ (180 mg, 0.197 mmol) and heating at 115° C. for 12 h. This gave after workup and purification using flash column chromatography [silica gel (12 g), eluting with EtOAc in hexane from 0-100%] ethyl 2-(2-((5-(3-(aminomethyl)phenyl)-2-ethylbenzofuran-3-yl)methoxy)-4-methylphenyl)acetate (319b) (100 mg, 0.219 mmol, 11.09% yield) (ES+): 458.20 (M+1).

Step-3: Preparation of 2-(2-((5-(3-(aminomethyl) phenyl)-2-ethylbenzofuran-3-yl)methoxy)-4-methylphenyl)acetic acid (319c)

Compound 319c was prepared according to the procedure reported in step-3 of scheme 1, from ethyl 2-(2-((5-(3-(aminomethyl)phenyl)-2-ethylbenzofuran-3-yl)methoxy)-4-methylphenyl)acetate (319b) (95 mg, 0.208 mmol) in THF (3 mL) using a solution of lithium hydroxide hydrate (26.1 mg, 0.623 mmol) in water (1 mL) and stirring overnight at RT. This gave after workup and purification using reverse phase column chromatography [C18 column (30 g), eluting with ACN in water (containing 0.1% HCl) from 0-100%] 2-(2-((5-(3-(aminomethyl)phenyl)-2-ethylbenzofuran-3-yl)methoxy)-4-methylphenyl)acetic acid (319c) (85 mg, 0.198 mmol, 95% yield) as a white solid. $^1$H NMR (300 MHz, DMSO-$d_6$) δ 8.29 (s, 2H, $D_2O$ exchangeable), 7.94 (d, J=1.7 Hz, 1H), 7.89 (s, 1H), 7.73 (dt, J=7.6, 1.6 Hz, 1H), 7.68-7.55 (m, 2H), 7.54-7.39 (m, 2H), 7.12-6.99 (m, 2H), 6.73 (d, J=7.5 Hz, 1H), 5.24 (s, 2H), 4.09 (s, 2H), 3.42 (s, 2H), 2.91 (q, J=7.5 Hz, 2H), 2.31 (s, 3H), 1.26 (t, J=7.5 Hz, 3H); MS (ES+): 430.20 (M+1); (ES−): 428.20 (M−1).

Scheme 320

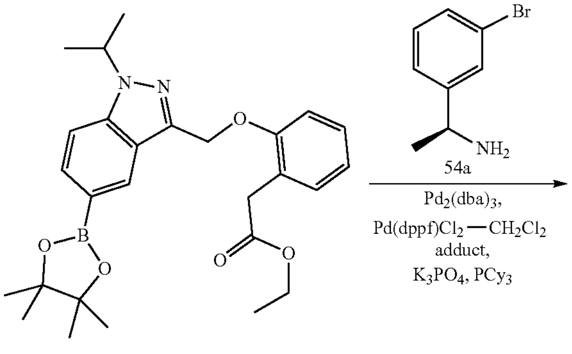

243c

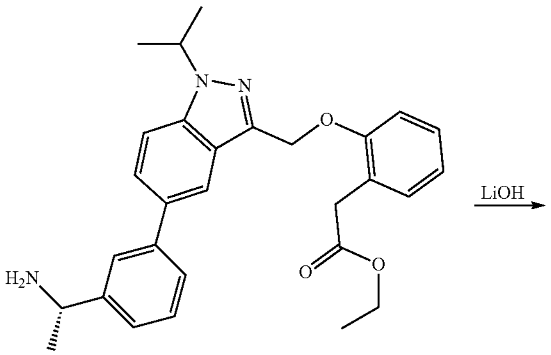

320a

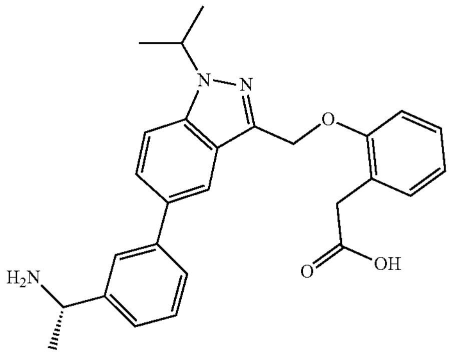

320b

Preparation of (S)-2-(2-((5-(3-(1-aminoethyl)phenyl)-1-isopropyl-1H-indazol-3-yl)methoxy)phenyl)acetic acid (320b)

Step-1: Preparation of (S)-ethyl 2-(2-((5-(3-(1-aminoethyl)phenyl)-1-isopropyl-1H-indazol-3-yl)methoxy)phenyl)acetate (320a)

Compound 320a was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (2 mL) and THF (2 mL) using (S)-1-(3-bromophenyl)ethanamine (54a) (167 mg, 0.836 mmol), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2(dppf)$-$CH_2Cl_2$ adduct (34.1 mg, 0.042 mmol) and heating at 100° C. for 2 h. This gave after workup and purification using flash column chromatography [silica gel (24 g), eluting with DMA-80 in DCM from 0-100%] (S)-ethyl 2-(2-((5-(3-(1-aminoethyl)phenyl)-1-isopropyl-1H-indazol-3-yl)methoxy)phenyl)acetate (320a) (110 mg, 56% yield) as a clear oil; MS (ES+): 472.30 (M+1).

Step-2: Preparation of (S)-2-(2-((5-(3-(1-aminoethyl)phenyl)-1-isopropyl-1H-indazol-3-yl)methoxy)phenyl)acetic acid (320b)

Compound 320b was prepared according to the procedure reported in step-3 of scheme 1, from (S)-ethyl 2-(2-((5-(3-(1-aminoethyl)phenyl)-1-isopropyl-1H-indazol-3-yl)methoxy)phenyl)acetate (320a) (110 mg, 0.233 mmol) in THF (2 mL) and MeOH (2 mL) using a solution of lithium hydroxide hydrate (58.7 mg, 1.4 mmol) in water (1 mL) and heating at 50° C. for 1 h. This gave after workup and purification using reverse phase column chromatography [C18 column (50 g), eluting with ACN in water (containing 0.1% HCl) from 0-100%](S)-2-(2-((5-(3-(1-aminoethyl)phenyl)-1-isopropyl-1H-indazol-3-yl)methoxy)phenyl)acetic acid (320b) (50 mg, 48% yield) HCl salt as a white solid; $^1$H NMR (300 MHz, DMSO-$d_6$) δ 8.54 (s, 3H, $D_2O$ exchangeable), 8.09 (s, 1H), 7.90 (s, 1H), 7.87-7.77 (m, 2H), 7.77-7.69 (m, 1H), 7.56-7.40 (m, 2H), 7.31-7.24 (m, 2H), 7.24-7.15 (m, 1H), 6.96-6.87 (m, 1H), 5.45 (s, 2H), 5.14-4.90 (m, 1H), 4.56-4.36 (m, 1H), 3.53 (s, 2H), 1.58 (d, J=6.8 Hz, 3H), 1.52 (d, J=6.6 Hz, 6H); MS (ES+): 444.30 (M+1); (ES−): 442.20 (M−1); Optical rotation: $[\alpha]_D$=(+) 3.158 [$CH_3OH$, 0.19].

Scheme 321

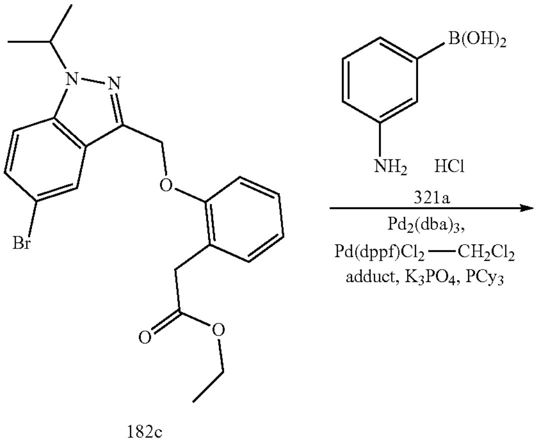

182c

-continued

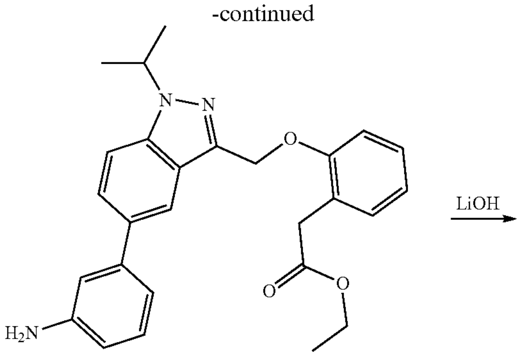

321b

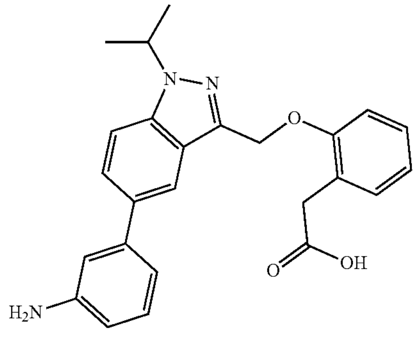

321c

Preparation of 2-(2-((5-(3-aminophenyl)-1-isopropyl-1H-indazol-3-yl)methoxy)phenyl)acetic acid (321c)

Step-1: Preparation of ethyl 2-(2-((5-(3-aminophenyl)-1-isopropyl-1H-indazol-3-yl)methoxy)phenyl) acetate (321b)

Compound 321b was prepared according to the procedure reported in step-2 of scheme 1, from ethyl 2-(2-((5-bromo-1-isopropyl-1H-indazol-3-yl)methoxy)phenyl)acetate (182c) (200 mg, 0.464 mmol) in dioxane (2 mL) and THF (2 mL) using (3-aminophenyl)boronic acid hydrochloride (321a) (161 mg, 0.927 mmol), 2 M solution of $K_3PO_4$ (0.927 mL, 1.855 mmol), tricyclohexylphosphine (26.0 mg, 0.093 mmol), $Pd_2(dba)_3$ (42.5 mg, 0.046 mmol), $PdCl_2$(dppf)-$CH_2Cl_2$ adduct (37.9 mg, 0.046 mmol) and heating at 100° C. for 2 h. This gave after workup and purification using flash column chromatography [silica gel (24 g), eluting with DMA-80 in DCM from 0-70%] ethyl 2-(2-((5-(3-aminophenyl)-1-isopropyl-1H-indazol-3-yl)methoxy)phenyl)acetate (321b) (100 mg, 49% yield) as a clear oil; 1H NMR (300 MHz, DMSO-$d_6$) δ 7.88 (d, J=1.6 Hz, 1H), 7.76 (d, J=8.8 Hz, 1H), 7.61 (dd, J=8.8, 1.7 Hz, 1H), 7.29 (q, J=4.4, 3.2 Hz, 2H), 7.20 (d, J=7.4 Hz, 1H), 7.13-7.05 (m, 1H), 6.96-6.89 (m, 1H), 6.88 (t, J=2.1 Hz, 1H), 6.82 (d, J=7.4 Hz, 1H), 6.54 (dd, J=7.7, 2.2 Hz, 1H), 5.41 (s, 2H), 5.13 (s, 3H), 5.03 (dq, J=13.1, 6.6 Hz, 1H), 3.70 (q, J=7.1 Hz, 2H), 3.53 (s, 2H), 1.51 (d, J=6.5 Hz, 6H), 0.80 (t, J=7.1 Hz, 3H); MS (ES+): 444.20 (M+1); 466.20 (M+Na); (ES−): 442.20 (M−1).

Step-2: Preparation of 2-(2-((5-(3-aminophenyl)-1-isopropyl-1H-indazol-3-yl)methoxy)phenyl)acetic acid (321c)

Compound 321c was prepared according to the procedure reported in step-3 of scheme 1, from ethyl 2-(2-((5-(3-aminophenyl)-1-isopropyl-1H-indazol-3-yl)methoxy)phenyl)acetate (321b) (100 mg, 0.225 mmol) in THF (2 mL) and MeOH (2 mL) using a solution of lithium hydroxide hydrate (56.8 mg, 1.353 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(3-aminophenyl)-1-isopropyl-1H-indazol-3-yl)methoxy)phenyl)acetic acid (321c) (25 mg, 27% yield) HCl salt as a light yellow solid; $^1$H NMR (300 MHz, DMSO-$d_6$) δ 8.02 (d, J=1.6 Hz, 1H), 7.84 (d, J=8.8 Hz, 1H), 7.72-7.58 (m, 2H), 7.58-7.45 (m, 2H), 7.31-7.24 (m, 2H), 7.24-7.15 (m, 2H), 6.97-6.86 (m, 1H), 5.45 (s, 2H), 5.13-4.93 (m, 1H), 3.52 (s, 2H), 1.52 (d, J=6.6 Hz, 6H); MS (ES+): 416.20 (M+1); (ES−): 414.20 (M−1).

Scheme 322

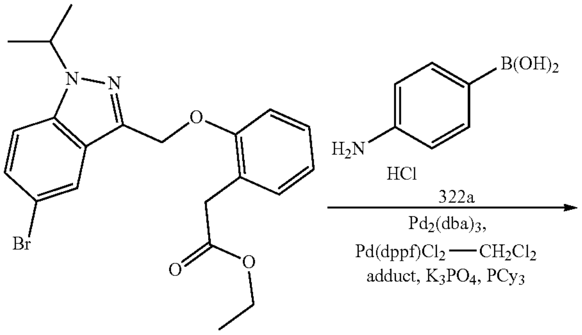

182c

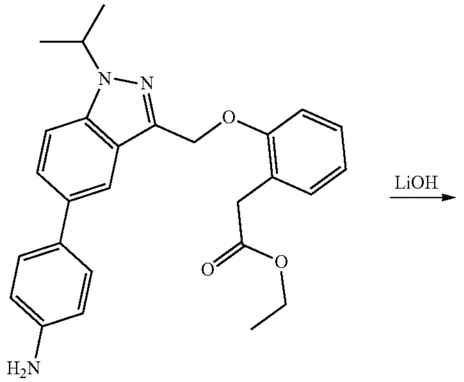

322b

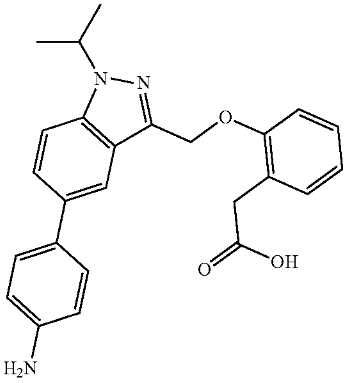

322c

Preparation of 2-(2-((5-(4-aminophenyl)-1-isopropyl-1H-indazol-3-yl)methoxy)phenyl)acetic acid (322c)

Step-1: Preparation of ethyl 2-(2-((5-(4-aminophenyl)-1-isopropyl-1H-indazol-3-yl)methoxy)phenyl) acetate (322b)

Compound 322b was prepared according to the procedure reported in step-2 of scheme 1, from ethyl 2-(2-((5-bromo-1-isopropyl-1H-indazol-3-yl)methoxy)phenyl)acetate (182c) (200 mg, 0.464 mmol) in dioxane (2 mL) and THF (2 mL) using (4-aminophenyl)boronic acid hydrochloride (322a) (161 mg, 0.927 mmol), 2 M solution of $K_3PO_4$ (0.927 mL, 1.855 mmol), tricyclohexylphosphine (3926.0 mg, 0.093 mmol), $Pd_2(dba)_3$ (42.5 mg, 0.046 mmol), $PdCl_2$ (dppf)-$CH_2Cl_2$ adduct (37.9 mg, 0.046 mmol) and heating at 100° C. for 2 h. This gave after workup and purification using flash column chromatography [silica gel (24 g), eluting with DMA-80 in DCM from 0-70%] ethyl 2-(2-((5-(4-aminophenyl)-1-isopropyl-1H-indazol-3-yl)methoxy)phenyl)acetate (322b) (100 mg, 49% yield) as a clear oil; 1H NMR (300 MHz, DMSO-$d_6$) δ 7.80 (s, 1H), 7.69 (d, J=8.8 Hz, 1H), 7.63-7.60 (m, 1H), 7.37 (d, J=8.1 Hz, 2H), 7.28 (d, J=4.0 Hz, 2H), 7.19 (d, J=7.4 Hz, 1H), 6.99-6.85 (m, 1H), 6.69-6.56 (m, 2H), 5.39 (s, 2H), 5.16 (s, 2H), 4.97 (dq, J=12.6, 6.4 Hz, 1H), 3.71 (q, J=7.1 Hz, 2H), 3.53 (s, 2H), 1.49 (d, J=6.6 Hz, 6H), 0.81 (t, J=7.1 Hz, 3H); MS (ES+): 444.20 (M+1); 466.20 (M+Na); (ES−): 442.20 (M−1).

Step-2: Preparation of 2-(2-((5-(4-aminophenyl)-1-isopropyl-1H-indazol-3-yl)methoxy)phenyl)acetic acid (322c)

Compound 322c was prepared according to the procedure reported in step-3 of scheme 1, from ethyl 2-(2-((5-(4-aminophenyl)-1-isopropyl-1H-indazol-3-yl)methoxy)phenyl)acetate (322b) (100 mg, 0.225 mmol) in THF (2 mL) and MeOH (2 mL) using a solution of lithium hydroxide hydrate (56.8 mg, 1.353 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(4-aminophenyl)-1-isopropyl-1H-indazol-3-yl)methoxy)phenyl)acetic acid (322c) (35 mg, 37% yield) HCl salt as a light yellow solid; $^1H$ NMR (300 MHz, DMSO-$d_6$) δ 10.10 (s, 2H, $D_2O$ exchangeable), 8.04 (d, J=1.6 Hz, 1H), 7.85-7.76 (m, 3H), 7.71 (dd, J=8.8, 1.7 Hz, 1H), 7.45-7.34 (m, 2H), 7.32-7.23 (m, 2H), 7.23-7.16 (m, 1H), 6.97-6.85 (m, 1H), 5.45 (s, 2H), 5.15-4.89 (m, 1H), 3.53 (s, 2H), 1.51 (d, J=6.6 Hz, 6H); MS (ES+): 416.20 (M+1); (ES−): 414.10 (M−1).

Scheme 323

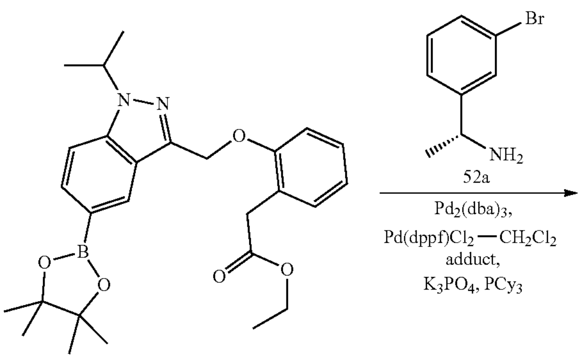

52a

243c

-continued

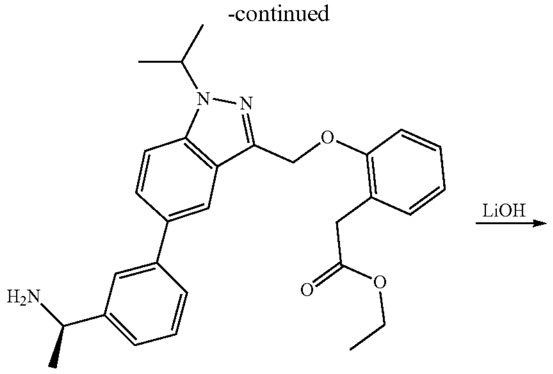

323a

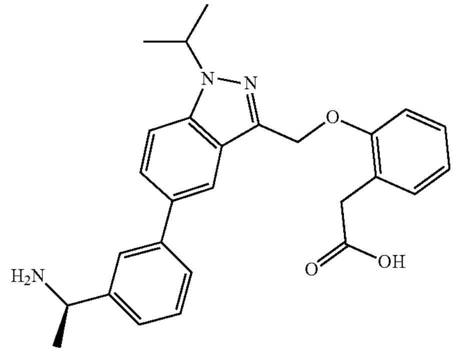

323b

Step-1: Preparation of (R)-ethyl 2-(2-((5-(3-(1-aminoethyl)phenyl)-1-isopropyl-1H-indazol-3-yl) methoxy)phenyl)acetate (323a)

Compound 323a was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (2 mL) and THF (2 mL) using (R)-1-(3-bromophenyl)ethanamine (52a) (167 mg, 0.836 mmol), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2$(dppf)-$CH_2Cl_2$ adduct (34.1 mg, 0.042 mmol) and heating at 100° C. for 2 h. This gave after workup and purification using flash column chromatography [silica gel (24 g), eluting with DMA-80 in DCM from 0-100%] (R)-ethyl 2-(2-((5-(3-(1-aminoethyl)phenyl)-1-isopropyl-1H-indazol-3-yl)methoxy)phenyl)acetate (323a) (160 mg, 81% yield) as a clear oil; MS (ES+): 472.30 (M+1); (ES−): 470.20 (M−1); Optical rotation: $[\alpha]_D$=(−) 1.18 [$CH_3OH$, 1.015].

Step-2: Preparation of (R)-2-(2-((5-(3-(1-aminoethyl)phenyl)-1-isopropyl-1H-indazol-3-yl)methoxy) phenyl)acetic acid (323b)

Compound 323b was prepared according to the procedure reported in step-3 of scheme 1, from (R)-ethyl 2-(2-((5-(3-(1-aminoethyl)phenyl)-1-isopropyl-1H-indazol-3-yl) methoxy)phenyl)acetate (323a) (160 mg, 0.339 mmol) in THF (2 mL) and MeOH (2 mL) using a solution of lithium hydroxide hydrate (85 mg, 2.036 mmol) in water (1 mL) and heating at 50° C. for 1 h. This gave after workup and purification using reverse phase column chromatography

[C18 column (50 g), eluting with ACN in water (containing 0.1% HCl) from 0-100%](R)-2-(2-((5-(3-(1-aminoethyl) phenyl)-1-isopropyl-1H-indazol-3-yl)methoxy)phenyl)acetic acid (323b) (60 mg, 40% yield) HCl salt as a white solid; $^1$H NMR (300 MHz, DMSO-$d_6$) δ 12.12 (s, 1H, $D_2O$ exchangeable), 8.55 (s, 3H, $D_2O$ exchangeable), 8.09 (s, 1H), 7.91 (s, 1H), 7.87-7.77 (m, 2H), 7.77-7.67 (m, 1H), 7.57-7.43 (m, 2H), 7.27 (dd, J=5.8, 1.8 Hz, 2H), 7.23-7.14 (m, 1H), 6.97-6.85 (m, 1H), 5.45 (s, 2H), 5.03 (h, J=6.5 Hz, 1H), 4.63-4.23 (m, 1H), 3.54 (s, 2H), 1.58 (d, J=6.8 Hz, 3H), 1.52 (d, J=6.6 Hz, 6H); MS (ES+): 444.20 (M+1); (ES−): 442.20 (M−1); Optical rotation: $[\alpha]_D$=(−) 1.905 [$CH_3OH$, 0.21].

Scheme 324

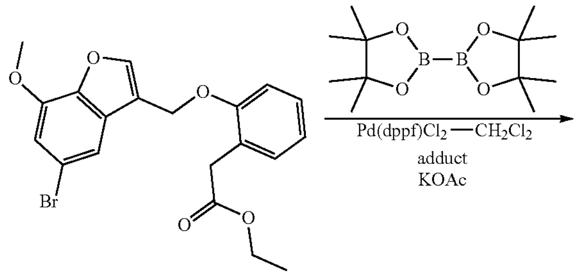

18c

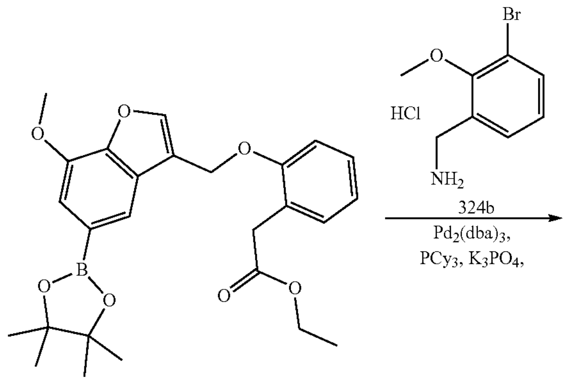

324a

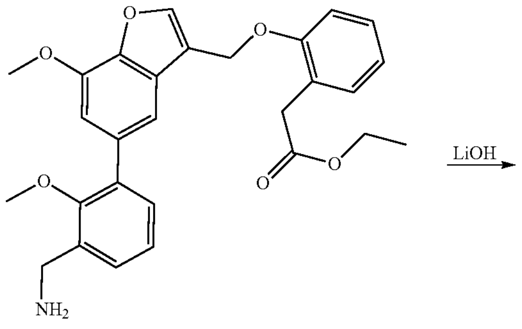

324c

-continued

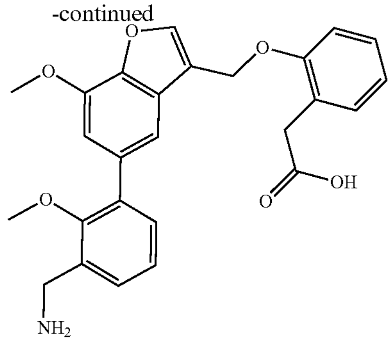

324d

Preparation of 2-(2-((5-(3-(aminomethyl)-2-methoxyphenyl)-7-methoxybenzofuran-3-yl)methoxy)phenyl)acetic acid (324d)

Step-1: Preparation of ethyl 2-(2-((7-methoxy-5-(4,4,5,5-tetramethyl-1,3,2-dioxaborolan-2-yl)benzofuran-3-yl)methoxy)phenyl)acetate (324a)

Compound 324a was prepared according to the procedure reported in step-1 of scheme 27, from ethyl 2-(2-((5-bromo-7-methoxybenzofuran-3-yl)methoxy)phenyl)acetate (18c) (700 mg, 1.670 mmol) in anhydrous dioxane (60 mL) using BisPin (848 mg, 3.34 mmol), potassium acetate (492 mg, 5.01 mmol), $PdCl_2$(dppf)-$CH_2Cl_2$ adduct (205 mg, 0.250 mmol) and heating at 90° C. for 14 h. This gave after work up and purification using flash column chromatography [silica gel (40 g), eluting with EtOAc in hexane from 0-30%] ethyl 2-(2-((7-methoxy-5-(4,4,5,5-tetramethyl-1,3,2-dioxaborolan-2-yl)benzofuran-3-yl)methoxy)phenyl)acetate (324a) (0.72 g, 92% yield) as a clear oil; MS (ES+): 489.2 (M+Na).

Step-2: Preparation of ethyl 2-(2-((5-(3-(aminomethyl)-2-methoxyphenyl)-7-methoxybenzofuran-3-yl)methoxy)phenyl)acetate (324c)

Compound 324c was prepared according to the procedure reported in step-2 of scheme 1, from ethyl 2-(2-((7-methoxy-5-(4,4,5,5-tetramethyl-1,3,2-dioxaborolan-2-yl)benzofuran-3-yl)methoxy)phenyl)acetate (324a) (0.24 g, 0.515 mmol) in dioxane (18 mL) using (3-bromo-2-methoxyphenyl)methanamine hydrochloride (324b) (0.195 g, 0.772 mmol), 4 M solution of $K_3PO_4$ (0.515 mL, 2.059 mmol), tricyclohexylphosphine (0.043 g, 0.154 mmol), $Pd_2(dba)_3$ (0.071 g, 0.077 mmol) and heating at 115° C. for 3 h. This gave after workup and purification by flash column chromatography [silica gel (24 g), eluting with DMA-80 in DCM from 0-50%] ethyl 2-(2-((5-(3-(aminomethyl)-2-methoxyphenyl)-7-methoxybenzofuran-3-yl)methoxy)phenyl)acetate (324c) (166 mg, 68% yield) as a clear oil; MS (ES+): 476.2 (M+1).

Step-3: Preparation of 2-(2-((5-(3-(aminomethyl)-2-methoxyphenyl)-7-methoxybenzofuran-3-yl)methoxy)phenyl)acetic acid (324d)

Compound 324d was prepared according to the procedure reported in step-3 of scheme 1, from ethyl 2-(2-((5-(3-(aminomethyl)-2-methoxyphenyl)-7-methoxybenzofuran-3-yl)methoxy)phenyl)acetate (324c) (160 mg, 0.336 mmol) in THF (2 mL) and acetonitrile (1 mL) using a 1N solution of lithium hydroxide monohydrate (1.009 mL, 1.009 mmol) and stirring for 25 h at RT. This gave after workup and purification using reverse phase column chromatography [C18 column (50 g), eluting with ACN in water (containing 0.1% HCl) from 0-100%] 2-(2-((5-(3-(aminomethyl)-2-methoxyphenyl)-7-methoxybenzofuran-3-yl)methoxy)phenyl)acetic acid (324d) (73 mg, 49% yield) HCl salt as an off-white solid; $^{1}H$ NMR (300 MHz, DMSO-$d_6$) δ 12.11 (s, 1H, $D_2O$ exchangeable), 8.36 (s, 3H, $D_2O$ exchangeable), 8.11 (s, 1H), 7.55-7.47 (m, 2H), 7.45 (d, J=1.4 Hz, 1H), 7.33-7.13 (m, 5H), 6.92 (td, J=7.3, 1.2 Hz, 1H), 5.28 (s, 2H), 4.10 (s, 2H), 3.98 (s, 3H), 3.53 (s, 2H), 3.37 (s, 3H); MS (ES+): 448.1 (M+1); (ES−): 446.1 (M−1).

Scheme 325

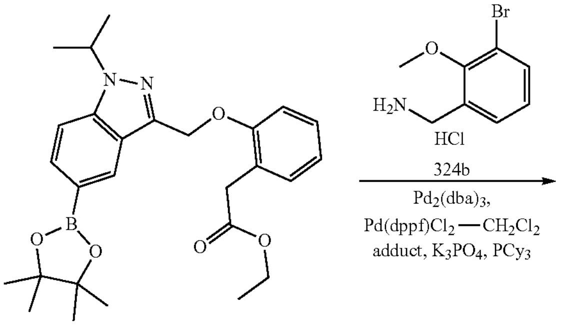

243c

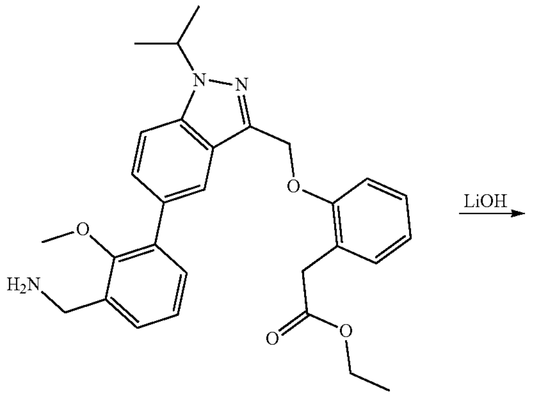

325a

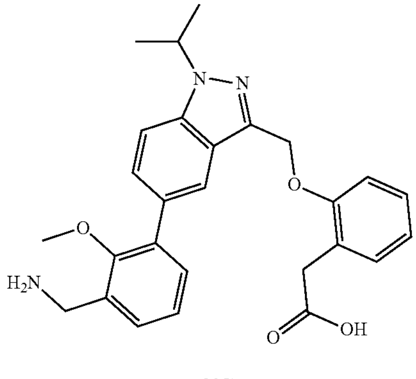

325b

Preparation of 2-(2-((5-(3-(aminomethyl)-2-methoxyphenyl)-1-isopropyl-1H-indazol-3-yl)methoxy)phenyl)acetic acid (325b)

Step-1: Preparation of ethyl 2-(2-((5-(3-(aminomethyl)-2-methoxyphenyl)-1-isopropyl-1H-indazol-3-yl)methoxy)phenyl)acetate (325a)

Compound 325a was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (200 mg, 0.418 mmol) in dioxane (2 mL) and THF (2 mL) using (3-bromo-2-methoxyphenyl)methanamine hydrochloride (324b) (211 mg, 0.836 mmol), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2(dppf)$-$CH_2Cl_2$ adduct (34.1 mg, 0.042 mmol) and heating at 100° C. for 2 h. This gave after workup and purification using flash column chromatography [silica gel (24 g), eluting with DCM in DMA-80 from 0-100%] ethyl 2-(2-((5-(3-(aminomethyl)-2-methoxyphenyl)-1-isopropyl-1H-indazol-3-yl)methoxy)phenyl)acetate (325a) (150 mg, 74% yield) as a clear oil; $^{1}H$ NMR (300 MHz, DMSO-$d_6$) δ 7.88 (s, 1H), 7.77 (d, J=8.9 Hz, 1H), 7.62 (t, J=7.8 Hz, 1H), 7.49-7.44 (m, 2H), 7.27 (d, J=3.9 Hz, 1H), 7.20-7.14 (m, 2H), 7.06 (t, J=7.6 Hz, 1H), 6.95-6.85 (m, 1H), 5.42 (s, 2H), 5.12-4.95 (m, 1H), 3.83-3.81 (m, 2H), 3.75 (s, 3H), 3.72-3.62 (m, 2H), 3.52 (s, 2H), 1.52 (d, J=6.5 Hz, 6H), 0.86-0.75 (m, 3H); MS (ES+): 488.30 (M+1).

Step-2: Preparation of 2-(2-((5-(3-(aminomethyl)-2-methoxyphenyl)-1-isopropyl-1H-indazol-3-yl)methoxy)phenyl)acetic acid (325b)

Compound 325b was prepared according to the procedure reported in step-3 of scheme 1, from ethyl 2-(2-((5-(3-(aminomethyl)-2-methoxyphenyl)-1-isopropyl-1H-indazol-3-yl)methoxy)phenyl)acetate (325a) (150 mg, 0.308 mmol) in THF (2 mL) and MeOH (2 mL) using lithium hydroxide hydrate (77 mg, 1.846 mmol) in water (1 mL) and stirring at RT for 15 h. This gave after workup and purification using reverse phase column chromatography [C18 column (30 g), eluting with ACN in water (containing 0.1% HCl) from 0-100%] 2-(2-((5-(3-(aminomethyl)-2-methoxyphenyl)-1-isopropyl-1H-indazol-3-yl)methoxy)phenyl)acetic acid (325b) (55 mg, 39% yield) HCl salt as a white solid; $^{1}H$ NMR (300 MHz, DMSO-$d_6$) δ 12.07 (s, 1H, $D_2O$ exchangeable), 8.33 (s, 3H, $D_2O$ exchangeable), 7.95 (s, 1H), 7.81 (d, J=8.8 Hz, 1H), 7.61 (dd, J=8.8, 1.6 Hz, 1H), 7.47 (td, J=7.7, 1.7 Hz, 2H), 7.32-7.23 (m, 3H), 7.23-7.14 (m, 1H), 6.97-6.86 (m, 1H), 5.43 (s, 2H), 5.11-4.95 (m, 1H), 4.15-4.04 (m, 2H), 3.51 (s, 2H), 3.31 (s, 3H), 1.53 (d, J=6.6 Hz, 6H); MS (ES+): 460.20 (M+1); (ES−): 458.20 (M−1).

Scheme 326

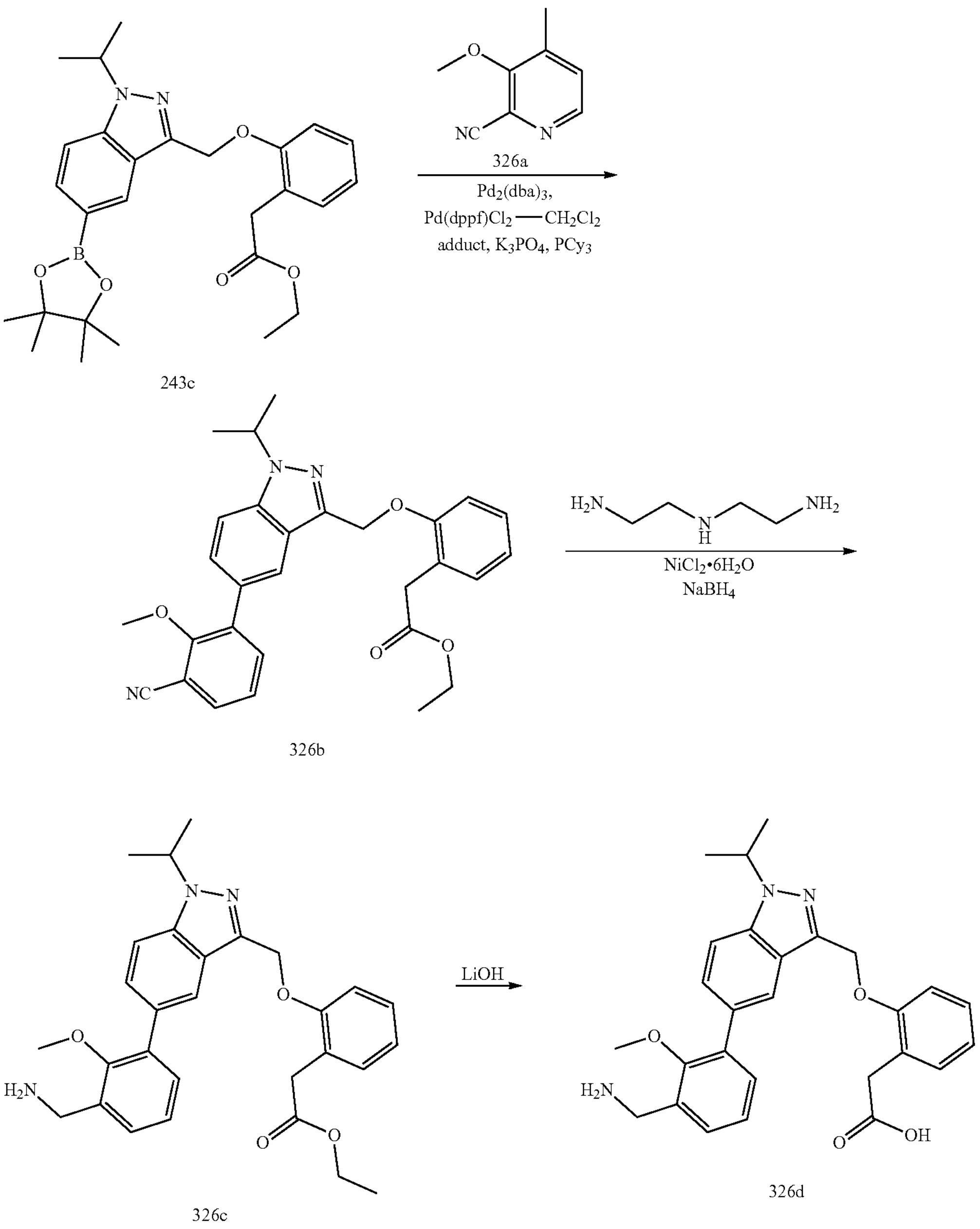

Preparation of 2-(2-((5-(2-(aminomethyl)-3-methoxypyridin-4-yl)-1-isopropyl-1H-indazol-3-yl)methoxy)phenyl)acetic acid (326d)

Step-1: Preparation of ethyl 2-(2-((5-(2-cyano-3-methoxypyridin-4-yl)-1-isopropyl-1H-indazol-3-yl)methoxy)phenyl)acetate (326b)

Compound 326b was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (300 mg, 0.627 mmol) in dioxane (2 mL) and THF (2 mL) using 4-iodo-3-methoxypicolinonitrile (326a) (196 mg, 0.753 mmol), 2 M solution of $K_3PO_4$ (1.254 mL, 2.508 mmol), tricyclohexylphosphine (35.2 mg, 0.125 mmol), $Pd_2(dba)_3$ (57.4 mg, 0.063 mmol), $PdCl_2(dppf)$-$CH_2Cl_2$ adduct (51.2 mg, 0.063 mmol) and heating at 100° C. for 2 h. This gave after workup and purification using flash column chromatography [silica gel (24 g), eluting with EtOAc in Hexane from 0-70%] ethyl 2-(2-((5-(2-cyano-3-methoxypyridin-4-yl)-1-isopropyl-1H-indazol-3-yl)methoxy)phenyl)acetate (326b) (180 mg, 59% yield) as a clear oil; $^1H$ NMR (300 MHz, DMSO-$d_6$) δ 8.55 (d, J=4.9 Hz, 1H), 8.12-8.04 (m, 1H), 7.93-7.87 (m, 1H), 7.84 (d, J=4.9 Hz, 1H), 7.70 (dd, J=8.8, 1.6 Hz, 1H), 7.33-7.23 (m, 2H), 7.23-7.15 (m, 1H), 6.99-6.84 (m, 1H), 5.44 (s, 2H), 5.14-4.99 (m, 1H), 3.72-3.66 (m, 2H), 3.65 (s, 3H), 3.54 (s, 2H), 1.52 (d, J=6.6 Hz, 6H), 0.80 (t, J=7.1 Hz, 3H); MS (ES+): 485.20 (M+1); (ES−): 483.05 (M−1).

Step-2: Preparation of ethyl 2-(2-((5-(2-(aminomethyl)-3-methoxypyridin-4-yl)-1-isopropyl-1H-indazol-3-yl)methoxy)phenyl)acetate (326c)

Compound 326c was prepared according to the procedure reported in step-2 of scheme 1, from ethyl 2-(2-((5-(2-cyano-3-methoxypyridin-4-yl)-1-isopropyl-1H-indazol-3-yl)methoxy)phenyl)acetate (326b) (180 mg, 0.371 mmol) in anhydrous ethanol (10 mL) using nickel(II) chloride hexahydrate (22.07 mg, 0.093 mmol), sodium borohydride (42.2 mg, 1.114 mmol), N1-(2-aminoethyl)ethane-1,2-diamine (0.080 mL, 0.743 mmol). This gave after work up and purification using flash column chromatography [silica gel (24 g), eluting with DMA-80 in DCM from 0 to 60%] ethyl 2-(2-((5-(2-(aminomethyl)-3-methoxypyridin-4-yl)-1-isopropyl-1H-indazol-3-yl)methoxy)phenyl)acetate (326c) (60 mg, 33% yield) as a white solid; $^{1}$H NMR (300 MHz, DMSO-$d_6$) δ 8.35 (d, J=4.9 Hz, 1H), 8.07-7.98 (m, 1H), 7.84 (d, J=8.8 Hz, 1H), 7.74-7.65 (m, 1H), 7.37 (d, J=5.0 Hz, 1H), 7.31-7.23 (m, 2H), 7.18 (d, J=7.4 Hz, 1H), 6.95-6.85 (m, 1H), 5.43 (s, 2H), 5.11-4.97 (m, 1H), 3.90 (s, 2H), 3.67 (q, J=7.2 Hz, 2H), 3.56-3.50 (m, 2H), 3.37 (s, 3H), 1.52 (d, J=6.6 Hz, 6H), 0.78 (t, J=7.2 Hz, 3H); MS (ES+): 489.30 (M+1).

Step-3: Preparation of 2-(2-((5-(2-(aminomethyl)-3-methoxypyridin-4-yl)-1-isopropyl-1H-indazol-3-yl)methoxy)phenyl)acetic acid (326d)

Compound 326d was prepared according to the procedure reported in step-3 of scheme 1, from ethyl 2-(2-((5-(2-(aminomethyl)-3-methoxypyridin-4-yl)-1-isopropyl-1H-indazol-3-yl)methoxy)phenyl)acetate (326c) (60 mg, 0.123 mmol) in THF (2 mL) and MeOH (2 mL) using lithium hydroxide hydrate (30.9 mg, 0.737 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(2-(aminomethyl)-3-methoxypyridin-4-yl)-1-isopropyl-1H-indazol-3-yl)methoxy)phenyl)acetic acid (326d) (25 mg, 44% yield) HCl salt as a light yellow solid; $^{1}$H NMR (300 MHz, DMSO-$d_6$) δ 8.45 (d, J=5.0 Hz, 1H), 8.42-8.29 (m, 3H, $D_2O$ exchangeable), 8.10 (d, J=1.5 Hz, 1H), 7.88 (d, J=8.9 Hz, 1H), 7.70 (dd, J=8.8, 1.6 Hz, 1H), 7.55 (d, J=5.0 Hz, 1H), 7.30-7.23 (m, 2H), 7.20 (d, J=7.3 Hz, 1H), 6.98-6.86 (m, 1H), 5.45 (s, 2H), 5.14-4.98 (m, 1H), 4.34-4.24 (m, 2H), 3.52 (s, 2H), 3.39 (s, 3H), 1.53 (d, J=6.6 Hz, 6H); MS (ES+): 461.20 (M+1); (ES−): 459.20 (M−1).

Scheme 327

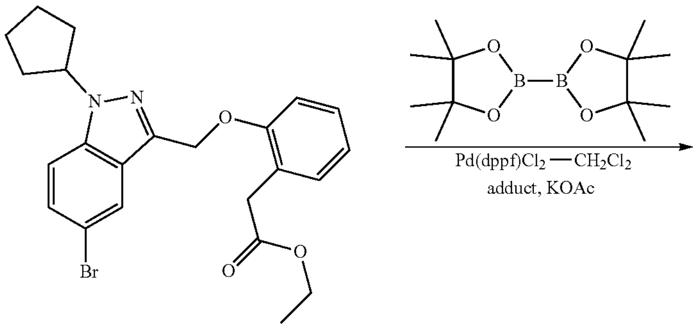

292a

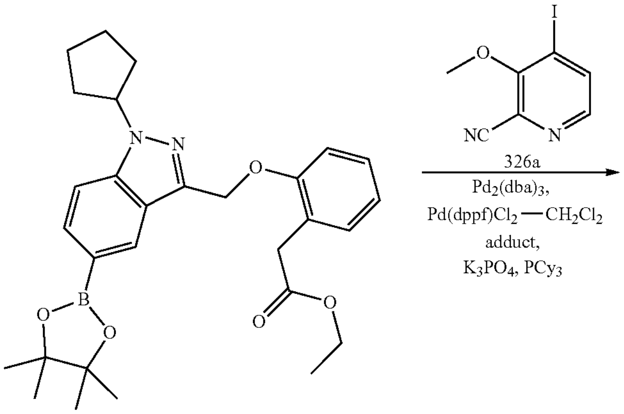

327a

-continued

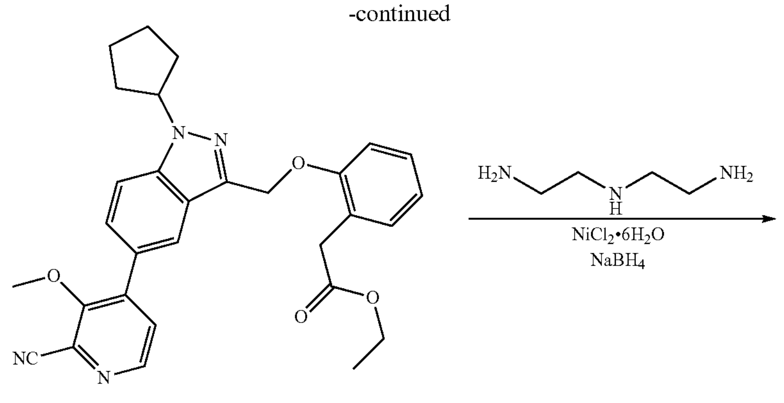

327b

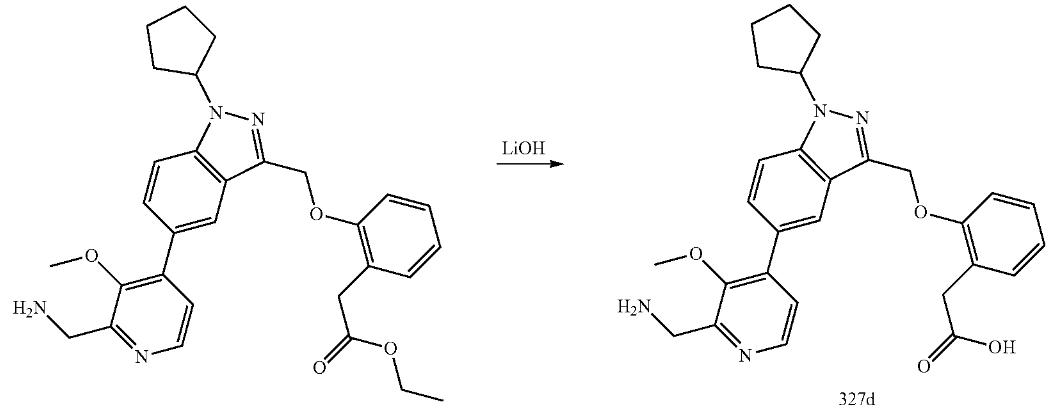

327c

327d

Preparation of 2-(2-((5-(2-(aminomethyl)-3-methoxypyridin-4-yl)-1-cyclopentyl-1H-indazol-3-yl)methoxy)phenyl)acetic acid (327d)

Step-1: Preparation of ethyl 2-(2-((1-cyclopentyl-5-(4,4,5,5-tetramethyl-1,3,2-dioxaborolan-2-yl)-1H-indazol-3-yl)methoxy)phenyl)acetate (327a)

Compound 327a was prepared according to the procedure reported in step-1 of scheme 27, from ethyl 2-(2-((5-bromo-1-cyclopentyl-1H-indazol-3-yl)methoxy)phenyl)acetate (292a) (650 mg, 1.421 mmol) in anhydrous dioxane (20 mL) using BisPin (722 mg, 2.84 mmol), potassium acetate (349 mg, 3.55 mmol), $PdCl_2$(dppf)-$CH_2Cl_2$ adduct (69.6 mg, 0.085 mmol) and stirring at 100° C. for 15 h. This gave after work up and purification using flash column chromatography [silica gel (12 g), eluting with EtOAc in hexane from 0-40%] ethyl 2-(2-((1-cyclopentyl-5-(4,4,5,5-tetramethyl-1,3,2-dioxaborolan-2-yl)-1H-indazol-3-yl)methoxy)phenyl) acetate (327a) (580 mg, 81% yield) as a clear oil; $^1$H NMR (300 MHz, DMSO-$d_6$) δ 8.15 (d, J=1.0 Hz, 1H), 7.74-7.60 (m, 2H), 7.33-7.23 (m, 2H), 7.19 (d, J=7.3 Hz, 1H), 6.97-6.85 (m, 1H), 5.39 (s, 2H), 5.25-5.05 (m, 1H), 3.86 (q, J=7.1 Hz, 2H), 3.50 (s, 2H), 2.20-2.07 (m, 2H), 2.07-1.94 (m, 2H), 1.94-1.78 (m, 2H), 1.78-1.63 (m, 2H), 1.29 (s, 12H), 0.88 (t, J=7.1 Hz, 3H); MS (ES+): 505.30 (M+1).

Step-2: Preparation of ethyl 2-(2-((5-(2-cyano-3-methoxypyridin-4-yl)-1-cyclopentyl-1H-indazol-3-yl)methoxy)phenyl)acetate (327b)

Compound 327b was prepared according to the procedure reported in step-2 of scheme 1, from ethyl 2-(2-((1-cyclopentyl-5-(4,4,5,5-tetramethyl-1,3,2-dioxaborolan-2-yl)-1H-indazol-3-yl)methoxy)phenyl)acetate (327a) (300 mg, 0.595 mmol) in dioxane (2 mL) and THF (2 mL) using 4-iodo-3-methoxypicolinonitrile (326a) (186 mg, 0.714 mmol), 2 M solution of $K_3PO_4$ (1.189 mL, 2.379 mmol), tricyclohexylphosphine (33.4 mg, 0.119 mmol), $Pd_2(dba)_3$ (54.5 mg, 0.059 mmol)), $PdCl_2$(dppf)-$CH_2Cl_2$ adduct (48.6 mg, 0.059 mmol) and heating at 100° C. for 2 h. This gave after workup and purification using flash column chromatography [silica gel (24 g), eluting with EtOAc in Hexane from 0-70%] ethyl 2-(2-((5-(2-cyano-3-methoxypyridin-4-yl)-1-cyclopentyl-1H-indazol-3-yl)methoxy)phenyl)acetate (327b) (200 mg, 66% yield) as a clear oil; $^1$H NMR (300 MHz, DMSO-$d_6$) δ 8.55 (d, J=4.9 Hz, 1H), 8.08 (d, J=1.7, 0.8 Hz, 1H), 7.93-7.80 (m, 2H), 7.70 (dd, J=8.8, 1.6 Hz, 1H), 7.34-7.22 (m, 2H), 7.22-7.13 (m, 1H), 6.97-6.84 (m, 1H), 5.44 (s, 2H), 5.31-5.16 (m, 1H), 3.69 (q, J=7.1 Hz, 2H), 3.64 (s, 3H), 3.54 (s, 2H), 2.24-2.10 (m, 2H), 2.10-1.96 (m, 2H), 1.96-1.81 (m, 2H), 1.81-1.60 (m, 2H), 0.81 (t, J=7.1 Hz, 3H); MS (ES+): 511.20 (M+1); (ES−): 509.05 (M−1).

Step-3: Preparation of ethyl 2-(2-((5-(2-(aminomethyl)-3-methoxypyridin-4-yl)-1-cyclopentyl-1H-indazol-3-yl)methoxy)phenyl)acetate (327c)

Compound 327c was prepared according to the procedure reported in step-2 of scheme 1, from ethyl 2-(2-((5-(2-cyano-3-methoxypyridin-4-yl)-1-cyclopentyl-1H-indazol-3-yl)methoxy)phenyl)acetate (327b) (200 mg, 0.392 mmol) in anhydrous ethanol (10 mL) using nickel(II) chloride hexahydrate (23.28 mg, 0.098 mmol), sodium borohydride (44.5 mg, 1.175 mmol), N1-(2-aminoethyl)ethane-1,2-diamine (81 mg, 0.783 mmol). This gave after work up and purification using flash column chromatography [silica gel (24 g), eluting with DMA-80 in DCM from 0 to 60%] ethyl 2-(2-((5-(2-(aminomethyl)-3-methoxypyridin-4-yl)-1-cyclopentyl-1H-indazol-3-yl)methoxy)phenyl)acetate (327c) (60 mg, 30% yield) as a white solid; $^1H$ NMR (300 MHz, DMSO-$d_6$) δ 8.35 (d, J=4.9 Hz, 1H), 8.02 (s, 1H), 7.83 (d, J=8.8 Hz, 1H), 7.69 (dd, J=8.8, 1.6 Hz, 1H), 7.36 (d, J=5.0 Hz, 1H), 7.27 (d, J=4.0 Hz, 2H), 7.18 (d, J=7.3 Hz, 1H), 6.95-6.86 (m, 1H), 5.43 (s, 2H), 5.29-5.15 (m, 1H), 3.90 (s, 2H), 3.67 (q, J=7.1 Hz, 2H), 3.53 (s, 2H), 3.36 (s, 3H), 2.22-2.11 (m, 2H), 2.09-1.99 (m, 2H), 1.94-1.84 (m, 2H), 1.79-1.65 (m, 2H), 0.80 (t, J=7.1 Hz, 3H); MS (ES+): 515.30 (M+1).

Step-3: Preparation of 2-(2-((5-(2-(aminomethyl)-3-methoxypyridin-4-yl)-1-cyclopentyl-1H-indazol-3-yl)methoxy)phenyl)acetic acid (327d)

Compound 327d was prepared according to the procedure reported in step-3 of scheme 1, from ethyl 2-(2-((5-(2-(aminomethyl)-3-methoxypyridin-4-yl)-1-cyclopentyl-1H-indazol-3-yl)methoxy)phenyl)acetate (327c) (60 mg, 0.117 mmol) in THF (2 mL) and MeOH (2 mL) using a solution of lithium hydroxide hydrate (29.4 mg, 0.7 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(2-(aminomethyl)-3-methoxypyridin-4-yl)-1-cyclopentyl-1H-indazol-3-yl)methoxy)phenyl)acetic acid (327d) (28 mg, 49% yield) HCl salt as a light yellow solid; $^1H$ NMR (300 MHz, DMSO-$d_6$) δ 8.45 (d, J=5.0 Hz, 1H), 8.30 (s, 2H, $D_2O$ exchangeable), 8.10 (s, 1H), 7.87 (d, J=8.8 Hz, 1H), 7.73-7.66 (m, 1H), 7.56 (d, J=5.0 Hz, 1H), 7.30-7.23 (m, 2H), 7.19 (d, J=7.2 Hz, 1H), 6.97-6.86 (m, 1H), 5.45 (s, 2H), 5.29-5.16 (m, 1H), 4.33-4.27 (m, 2H), 3.51 (s, 2H), 3.39 (s, 3H), 2.24-2.10 (m, 2H), 2.10-1.96 (m, 2H), 1.96-1.84 (m, 2H), 1.80-1.66 (m, 2H).; MS (ES+): 487.20 (M+1); (ES−): 485.20 (M−1).

Scheme 328

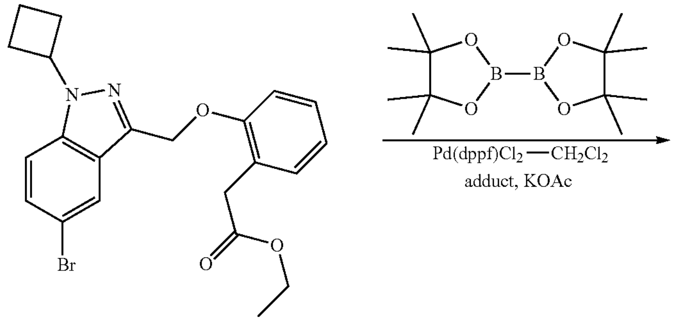

298b

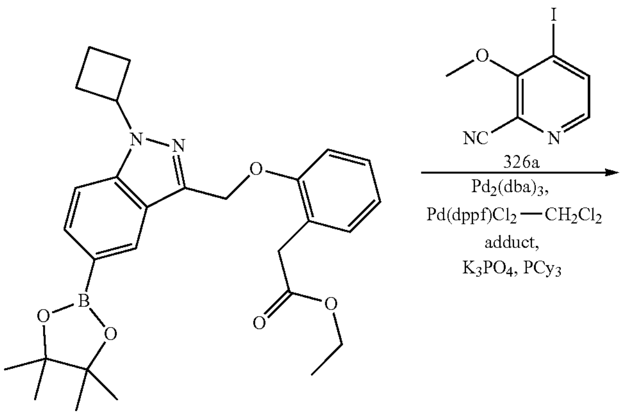

328a

-continued

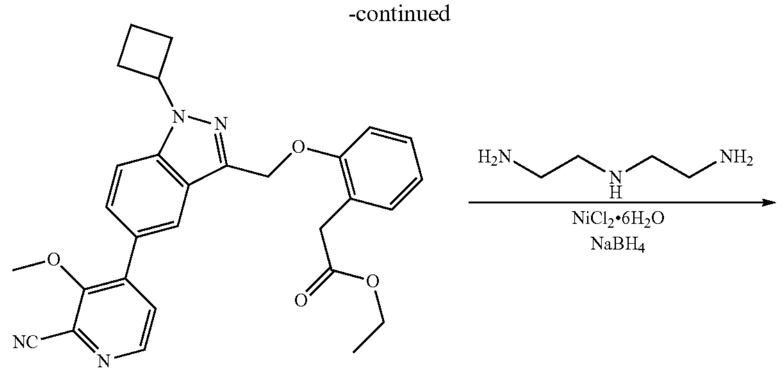

328b

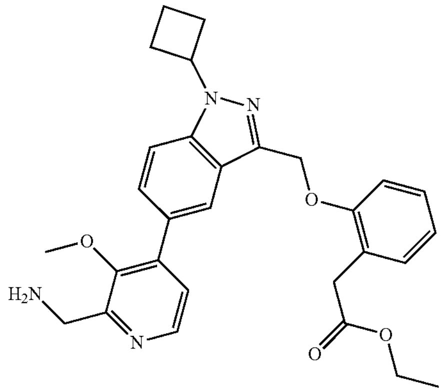

328c

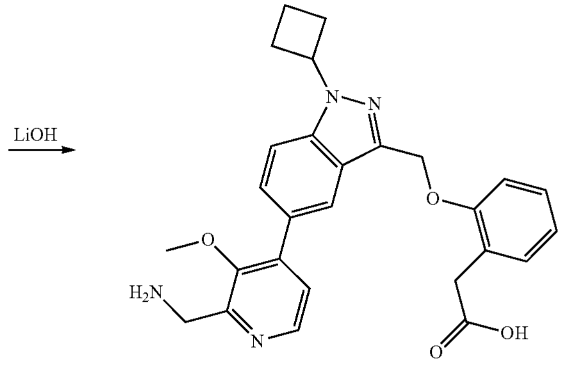

328d

Preparation of 2-(2-((5-(2-(aminomethyl)-3-methoxypyridin-4-yl)-1-cyclobutyl-1H-indazol-3-yl)methoxy)phenyl)acetic acid (328d)

Step-1: Preparation of ethyl 2-(2-((1-cyclobutyl-5-(4,4,5,5-tetramethyl-1,3,2-dioxaborolan-2-yl)-1H-indazol-3-yl)methoxy)phenyl)acetate (328a)

Compound 328a was prepared according to the procedure reported in step-1 of scheme 27, from ethyl 2-(2-((5-bromo-1-cyclobutyl-1H-indazol-3-yl)methoxy)phenyl)acetate (298b) (800 mg, 1.805 mmol) in anhydrous dioxane (15 mL) using BisPin (916 mg, 3.61 mmol), potassium acetate (443 mg, 4.51 mmol), $PdCl_2$(dppf)-$CH_2Cl_2$ adduct (88 mg, 0.108 mmol) and heating at 100° C. for 3 h. This gave after work up and purification using flash column chromatography [silica gel (24 g), eluting with EtOAc in hexane from 0-40%] ethyl 2-(2-((1-cyclobutyl-5-(4,4,5,5-tetramethyl-1,3,2-dioxaborolan-2-yl)-1H-indazol-3-yl)methoxy)phenyl)acetate (328a) (840 mg, 95% yield) as a clear oil; $^1$H NMR (300 MHz, DMSO-$d_6$) δ 8.15 (s, 1H), 7.72-7.58 (m, 2H), 7.35-7.25 (m, 2H), 7.20 (d, J=7.3 Hz, 1H), 7.00-6.83 (m, 1H), 5.42 (s, 2H), 5.36-5.20 (m, 1H), 3.85 (q, J=7.1 Hz, 2H), 3.51 (s, 2H), 2.71-2.56 (m, 2H), 2.19-2.04 (m, 2H), 1.95-1.85 (m, 2H), 1.29 (s, 12H), 0.87 (t, J=7.1 Hz, 3H); MS (ES+): 491.30 (M+1).

Step-2: Preparation of ethyl 2-(2-((5-(2-cyano-3-methoxypyridin-4-yl)-1-cyclobutyl-1H-indazol-3-yl)methoxy)phenyl)acetate (328b)

Compound 328b was prepared according to the procedure reported in step-2 of scheme 1, from ethyl 2-(2-((1-cyclobutyl-5-(4,4,5,5-tetramethyl-1,3,2-dioxaborolan-2-yl)-1H-indazol-3-yl)methoxy)phenyl)acetate (328a) (500 mg, 1.020 mmol) in dioxane (3 mL) and THF (3 mL) using 4-iodo-3-methoxypicolinonitrile (326a) (398 mg, 1.529 mmol), 2 M solution of $K_3PO_4$ (2.039 mL, 4.08 mmol), tricyclohexylphosphine (57.2 mg, 0.204 mmol), $Pd_2(dba)_3$ (93 mg, 0.102 mmol)), $PdCl_2$(dppf)-$CH_2Cl_2$ adduct (83 mg, 0.102 mmol) and heating at 100° C. for 2 h. This gave after workup and purification using flash column chromatography [silica gel (24 g), eluting with EtOAc in Hexane from 0-70%] ethyl 2-(2-((5-(2-cyano-3-methoxypyridin-4-yl)-1-cyclobutyl-1H-indazol-3-yl)methoxy)phenyl)acetate (328b) (350 mg, 69% yield) as a clear oil; $^1$H NMR (300 MHz, DMSO-$d_6$) δ 8.55 (d, J=4.9 Hz, 1H), 8.09 (d, J=1.7, 0.8 Hz, 1H), 7.90-7.80 (m, 2H), 7.70 (dd, J=8.9, 1.6 Hz, 1H), 7.32-7.24 (m, 2H), 7.22-7.15 (m, 1H), 6.96-6.86 (m, 1H), 5.46 (s, 2H), 5.43-5.27 (m, 1H), 3.68 (q, J=7.0 Hz, 2H), 3.63 (s, 3H), 3.54 (s, 2H), 2.77-2.58 (m, 2H), 2.50-2.42 (m, 2H), 1.97-1.82 (m, 2H), 0.81 (t, J=7.1 Hz, 3H); MS (ES+): 497.20 (M+1); (ES−): 495.05 (M−1).

Step-3: Preparation of ethyl 2-(2-((5-(2-(aminomethyl)-3-methoxypyridin-4-yl)-1-cyclobutyl-1H-indazol-3-yl)methoxy)phenyl)acetate (328c)

Compound 328c was prepared according to the procedure reported in step-2 of scheme 1, from ethyl 2-(2-((5-(2-cyano-3-methoxypyridin-4-yl)-1-cyclobutyl-1H-indazol-3-yl)methoxy)phenyl)acetate (328b) (350 mg, 0.705 mmol) in anhydrous ethanol (10 mL) using nickel(II) chloride hexahydrate (41.9 mg, 0.176 mmol), sodium borohydride (80 mg, 2.115 mmol), N1-(2-aminoethyl)ethane-1,2-diamine (145 mg, 1.41 mmol). This gave after work up and purification using flash column chromatography [silica gel (24 g), eluting with DMA80 in DCM from 0 to 60%] ethyl 2-(2-((5-(2-(aminomethyl)-3-methoxypyridin-4-yl)-1-cyclobutyl-1H-indazol-3-yl)methoxy)phenyl)acetate (328c) (100 mg, 28% yield) as a white solid; MS (ES+): 501.20 (M+1).

Step-3: Preparation of 2-(2-((5-(2-(aminomethyl)-3-methoxypyridin-4-yl)-1-cyclobutyl-1H-indazol-3-yl)methoxy)phenyl)acetic acid (328d)

Compound 328d was prepared according to the procedure reported in step-3 of scheme 1, from ethyl 2-(2-((5-(2-(aminomethyl)-3-methoxypyridin-4-yl)-1-cyclobutyl-1H-indazol-3-yl)methoxy)phenyl)acetate (328c) (100 mg, 0.200 mmol) in THF (2 mL) and MeOH (2 mL) using a solution of lithium hydroxide hydrate (50.3 mg, 1.199 mmol) in water (1 mL) and stirring at RT for 15 h. This gave after workup and purification using reverse phase column chromatography [C18 column (50 g), eluting with ACN in water (containing 0.1% HCl) from 0-100%] 2-(2-((5-(2-(aminomethyl)-3-methoxypyridin-4-yl)-1-cyclobutyl-1H-indazol-3-yl)methoxy)phenyl)acetic acid (328d) (35 mg, 37% yield) HCl salt as a yellow solid; $^1$H NMR (300 MHz, DMSO-$d_6$) δ 8.52-8.45 (m, 2H, $D_2O$ exchangeable), 8.44 (d, J=5.3 Hz, 1H), 8.10 (s, 1H), 7.85 (d, J=8.8 Hz, 1H), 7.70 (d, J=8.8 Hz, 1H), 7.55 (d, J=5.1 Hz, 1H), 7.27 (d, J=4.2 Hz, 2H), 7.20 (d, J=7.3 Hz, 1H), 6.98-6.85 (m, 1H), 5.48 (s, 2H), 5.41-5.27 (m, 1H), 4.33-4.23 (m, 2H), 3.52 (s, 2H), 3.37 (s, 3H), 2.76-2.58 (m, 2H), 2.58-2.51 (m, 2H), 2.01-1.80 (m, 2H); MS (ES+): 473.20 (M+1); (ES−): 471.20 (M−1); Analysis calculated for $C_{27}H_{28}N_4O_4 \cdot 2.25HCl \cdot 2.75H_2O$: C, 53.68; H, 5.97; N, 9.27. Found: C, 53.73; H, 5.79; N, 9.29.

Scheme 329

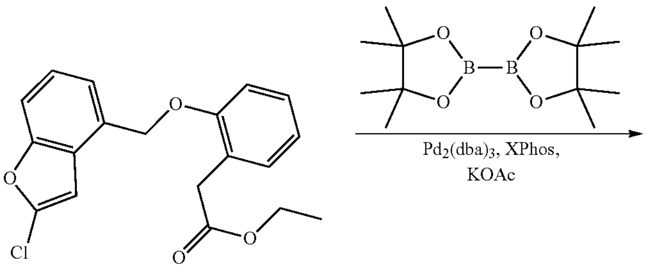

290d

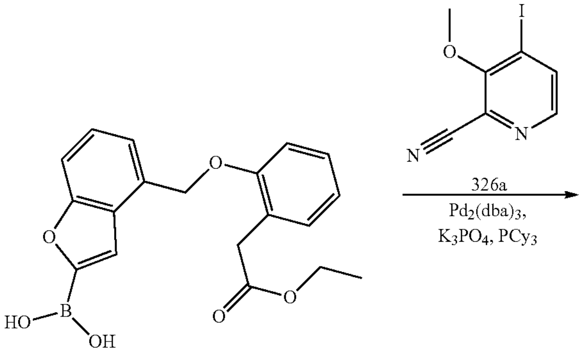

329a

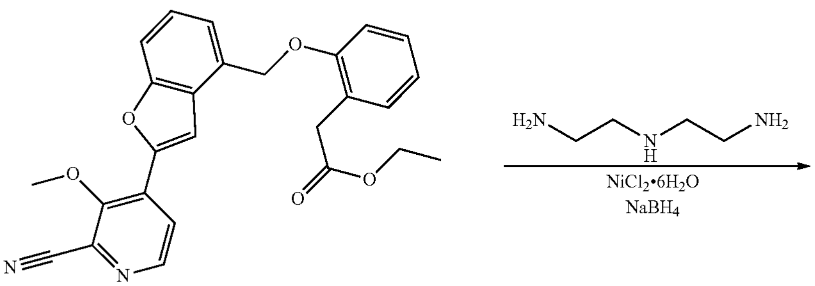

329b

-continued

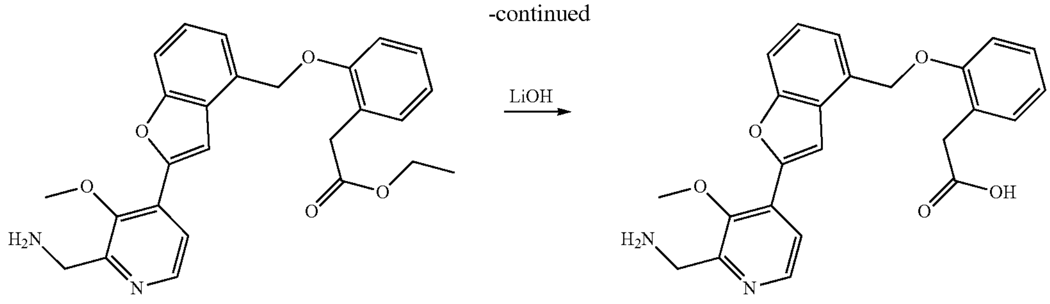

329c 329d

Preparation of 2-(2-((2-(2-(aminomethyl)-3-methoxypyridin-4-yl)benzofuran-4-yl)methoxy)phenyl)acetic acid (329d)

Step-1: Preparation of (4-((2-(2-ethoxy-2-oxoethyl)phenoxy)methyl)benzofuran-2-yl)boronic acid (329a)

Compound 329a was prepared according to the procedure reported in step-1 of scheme 27 from ethyl 2-(2-((2-chlorobenzofuran-4-yl)methoxy)phenyl)acetate (290d) (200 mg, 0.580 mmol) in anhydrous dioxane (10 mL) using BisPin (295 mg, 1.160 mmol), potassium acetate (228 mg, 2.320 mmol), $Pd_2(dba)_3$ (53.1 mg, 0.058 mmol), X-Phos (55.3 mg, 0.116 mmol) and heating at 90° C. overnight. This gave after work up and purification using flash column chromatography [silica gel (12 g), eluting with EtOAc/MeOH (9:1) in hexane from 0-100%](4-((2-(2-ethoxy-2-oxoethyl)phenoxy)methyl)benzofuran-2-yl)boronic acid (329a)(205 mg, 100% yield) as a dark oil; MS (ES+): 377.1 (M+Na); (ES−): 389.0 ($M+C_1$).

Step-2: Preparation of ethyl 2-(2-((2-(2-cyano-3-methoxypyridin-4-yl)benzofuran-4-yl)methoxy)phenyl)acetate (329b)

Compound 329b was prepared according to the procedure reported in step-8 of scheme 3, from (4-((2-(2-ethoxy-2-oxoethyl)phenoxy)methyl)benzofuran-2-yl)boronic acid (329a) (205 mg, 0.579 mmol) in dioxane (6 mL) and 2Me-THF (3 mL) using 4-iodo-3-methoxypicolinonitrile (326a) (176 mg, 0.677 mmol), $Pd_2(dba)_3$ (106 mg, 0.116 mmol), tripotassium phosphate (4M) (0.579 mL, 2.315 mmol), tricyclohexylphosphine (64.9 mg, 0.232 mmol) and heating at 115° C. for 4.5 h. This gave after workup and purification using flash column chromatography [silica gel (12 g), eluting with EtOAc in hexanes from 0-60%]ethyl 2-(2-((2-(2-cyano-3-methoxypyridin-4-yl)benzofuran-4-yl)methoxy)phenyl)acetate (329b) (100 mg, 0.226 mmol, 39.0% yield) as a yellow oil; MS (ES+): 443.1 (M+H).

Step-3: Preparation of ethyl 2-(2-((2-(2-(aminomethyl)-3-methoxypyridin-4-yl)benzofuran-4-yl)methoxy)phenyl)acetate (329c)

Compound 329c was prepared according to the procedure reported in step-2 of scheme 1, from ethyl 2-(2-((2-(2-cyano-3-methoxypyridin-4-yl)benzofuran-4-yl)methoxy)phenyl)acetate (329b) (100 mg, 0.226 mmol) in anhydrous methanol (10 mL) using nickel(II) chloride hexahydrate (21.49 mg, 0.090 mmol), sodium borohydride (90 mg, 2.379 mmol), N1-(2-aminoethyl)ethane-1,2-diamine (0.073 mL, 0.678 mmol). This gave after workup and purification using flash column chromatography [silica gel (12 g), eluting with DMA-80 in DCM from 0 to 80%] ethyl 2-(2-((2-(2-(aminomethyl)-3-methoxypyridin-4-yl)benzofuran-4-yl)methoxy)phenyl)acetate (329c) (51 mg, 51% yield) as a yellow oil; MS (ES+): 447.2 (M+1).

Step-6: Preparation of 2-(2-((2-(2-(aminomethyl)-3-methoxypyridin-4-yl)benzofuran-4-yl)methoxy)phenyl)acetic acid (329d)

Compound 329d was prepared according to the procedure reported in step-3 of scheme 1, from ethyl 2-(2-((2-(2-(aminomethyl)-3-methoxypyridin-4-yl)benzofuran-4-yl)methoxy)phenyl)acetate (329c) (51 mg, 0.114 mmol) in MeOH/THF (3 mL each) using a solution of lithium hydroxide monohydrate (40 mg, 0.953 mmol) in water (2 mL) and stirring at RT for 5 h. This gave after workup and purification by reverse phase column chromatography [C18 column (50 g), eluting with ACN in water (containing 0.1% HCl) from 0-100%] 2-(2-((2-(2-(aminomethyl)-3-methoxypyridin-4-yl)benzofuran-4-yl)methoxy)phenyl)acetic acid (329d) (42 mg, 88% yield) HCl salt as a yellow solid; $^1H$ NMR (300 MHz, DMSO-$d_6$) δ 8.72-8.43 (m, 4H, 3H $D_2O$ exchangeable), 7.95 (d, J=5.1 Hz, 1H), 7.85 (s, 1H), 7.69 (dd, J=6.9, 2.2 Hz, 1H), 7.59-7.42 (m, 2H), 7.33-7.15 (m, 3H), 6.93 (td, J=7.3, 1.4 Hz, 1H), 5.49 (s, 2H), 4.41-4.28 (m, 2H), 3.87 (s, 3H), 3.60 (s, 2H); MS (ES+): 419.10 (M+1); MS (ES−): 417.10 (M−1).

Scheme 330

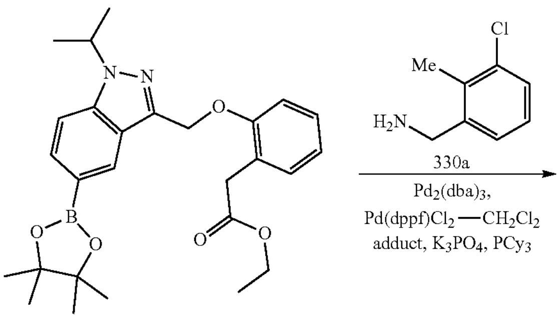

243c

-continued

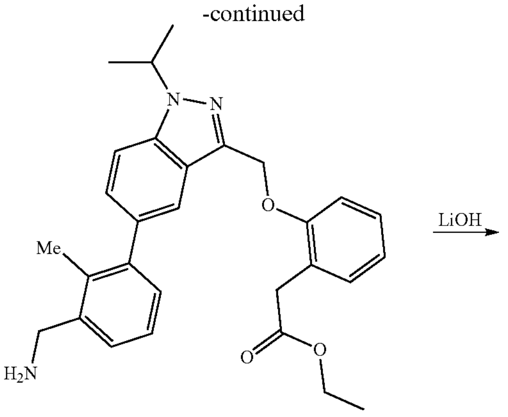

330b

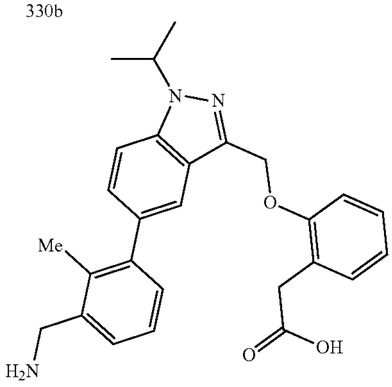

330c

Preparation of 2-(2-((5-(3-(aminomethyl)-2-methylphenyl)-1-isopropyl-1H-indazol-3-yl)methoxy)phenyl)acetic acid (330c)

Step-1: Preparation of ethyl 2-(2-((5-(3-(aminomethyl)-2-methylphenyl)-1-isopropyl-1H-indazol-3-yl)methoxy)phenyl)acetate (330b)

Compound 330b was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl) acetate (243c) (200 mg, 0.418 mmol) in dioxane (2 mL) and THF (2 mL) using (3-chloro-2-methylphenyl)methanamine (330a) (98 mg, 0.627 mmol), 2 M solution of $K_3PO_4$ (0.836 mL, 1.672 mmol), tricyclohexylphosphine (23.45 mg, 0.084 mmol), $Pd_2(dba)_3$ (38.3 mg, 0.042 mmol), $PdCl_2$(dppf)-$CH_2Cl_2$ adduct (34.1 mg, 0.042 mmol) and heating at 100° C. for 2 h. This gave after workup and purification using flash column chromatography [silica gel (24 g), eluting with EtOAc in Hexane from 0-70%] ethyl 2-(2-((5-(3-(aminomethyl)-2-methylphenyl)-1-isopropyl-1H-indazol-3-yl)methoxy)phenyl)acetate (330b) (150 mg, 76% yield) as a clear oil; MS (ES+): 472.30 (M+1).

Step-2: Preparation of 2-(2-((5-(3-(aminomethyl)-2-methylphenyl)-1-isopropyl-1H-indazol-3-yl) methoxy)phenyl)acetic acid (330c)

Compound 330c was prepared according to the procedure reported in step-3 of scheme 1, from ethyl 2-(2-((5-(3-(aminomethyl)-2-methylphenyl)-1-isopropyl-1H-indazol-3-yl)methoxy)phenyl)acetate (330b) (150 mg, 0.318 mmol) in THF (3 mL) and MeOH (3 mL) using lithium hydroxide hydrate (80 mg, 1.908 mmol) in water (2 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-2-methylphenyl)-1-isopropyl-1H-indazol-3-yl)methoxy)phenyl)acetic acid (330c) (55 mg, 39% yield) HCl salt as a white solid; $^1$H NMR (300 MHz, DMSO-$d_6$) δ 12.07 (s, 1H, $D_2O$ exchangeable), 8.28 (s, 3H, $D_2O$ exchangeable), 7.79 (d, J=8.7 Hz, 1H), 7.66 (s, 1H), 7.40 (d, J=7.2 Hz, 1H), 7.36-7.27 (m, 3H), 7.27-7.22 (m, 2H), 7.18 (d, J=7.4 Hz, 1H), 6.90 (t, J=7.4 Hz, 1H), 5.43 (s, 2H), 5.13-4.88 (m, 1H), 4.20-3.98 (m, 2H), 3.48 (s, 2H), 2.23 (s, 3H), 1.53 (d, J=6.5 Hz, 6H).; MS (ES+): 444.20 (M+1); MS (ES−): 442.10 (M−1).

Scheme 331

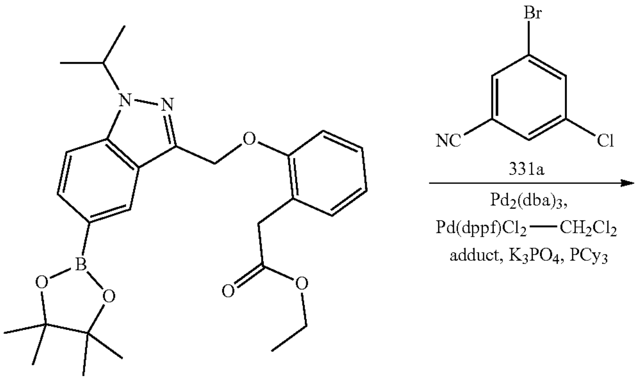

243c

-continued

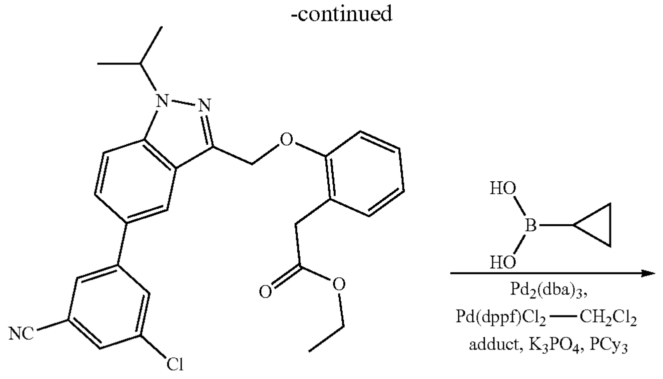

331b

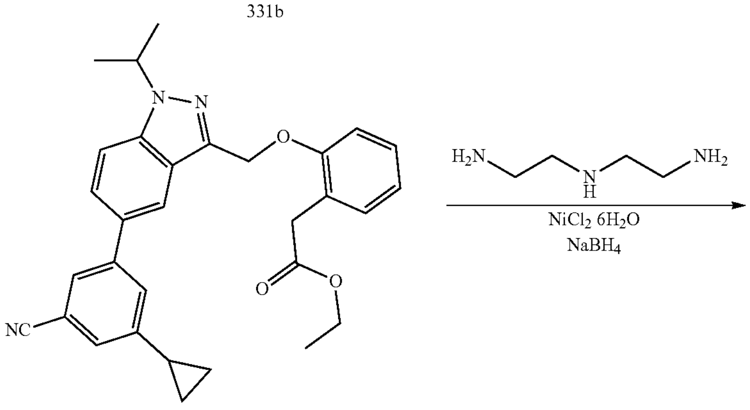

331c

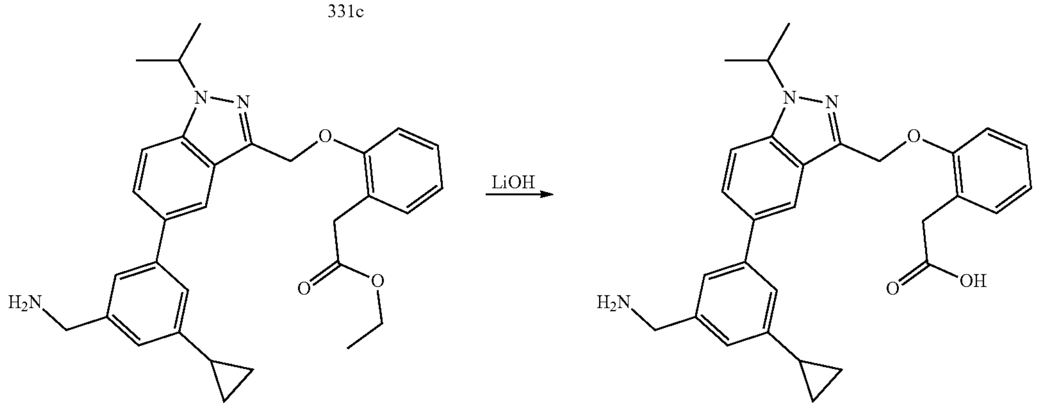

331d 331e

Preparation of 2-(2-((5-(3-(aminomethyl)-5-cyclopropylphenyl)-1-isopropyl-1H-indazol-3-yl)methoxy)phenyl)acetic acid (331e)

Step-1: Preparation of ethyl 2-(2-((5-(3-chloro-5-cyanophenyl)-1-isopropyl-1H-indazol-3-yl)methoxy)phenyl)acetate (331b)

Compound 331b was prepared according to the procedure reported in step-2 of scheme 1, from ethyl 2-(2-((1-isopropyl-5-(4,4,5,5-tetramethyl-1,3,2-dioxaborolan-2-yl)-1H-indazol-3-yl)methoxy)phenyl)acetate (243c) (450 mg, 0.941 mmol) in dioxane (3 mL) and THF (3 mL) using 3-bromo-5-chlorobenzonitrile (331a) (204 mg, 0.941 mmol), 2 M solution of $K_3PO_4$ (1.881 mL, 3.76 mmol), tricyclohexylphosphine (52.8 mg, 0.188 mmol), $Pd_2(dba)_3$ (86 mg, 0.094 mmol), $Pd(dppf)Cl_2$—$CH_2Cl_2$ adduct (77 mg, 0.094 mmol) and heating at 90° C. for 90 min. This gave after workup and purification using flash column chromatography [silica gel (24 g), eluting with EtOAc in Hexane from 0-70%] ethyl 2-(2-((5-(3-chloro-5-cyanophenyl)-1-isopropyl-1H-indazol-3-yl)methoxy)phenyl)acetate (331b) (300 mg, 65% yield) as a clear oil; MS (ES+): 488.10 & 490.00 (M+1).

Step-2: Preparation of ethyl 2-(2-((5-(3-cyano-5-cyclopropylphenyl)-1-isopropyl-1H-indazol-3-yl)methoxy)phenyl)acetate (331c)

Compound 331c was prepared according to the procedure reported in step-2 of scheme 1, from ethyl 2-(2-((5-(3-chloro-5-cyanophenyl)-1-isopropyl-1H-indazol-3-yl)methoxy)phenyl)acetate (331b) (260 mg, 0.533 mmol) in dioxane (3 mL) and THF (3 mL) using cyclopropyl boronic acid (92 mg, 1.066 mmol), 2 M solution of $K_3PO_4$ (1.066 mL, 2.131 mmol), tricyclohexylphosphine (29.9 mg, 0.107 mmol), $Pd_2(dba)_3$ (48.8 mg, 0.053 mmol), $Pd(dppf)Cl_2$—$CH_2Cl_2$ adduct (43.5 mg, 0.053 mmol) and heating at 100° C. for 3 h.

This gave after workup and purification using flash column chromatography [silica gel (24 g), eluting with EtOAc in Hexane from 0-70%] ethyl 2-(2-((5-(3-cyano-5-cyclopropylphenyl)-1-isopropyl-1H-indazol-3-yl)methoxy)phenyl)acetate (331c) (150 mg, 57% yield) as a clear oil; $^1$H NMR (300 MHz, DMSO-$d_6$) δ 8.07 (s, 1H), 7.94 (s, 1H), 7.83-7.73 (m, 3H), 7.51-7.46 (m, 1H), 7.34-7.24 (m, 2H), 7.24-7.16 (m, 1H), 6.98-6.91 (m, 1H), 5.43 (s, 2H), 5.13-4.97 (m, 1H), 3.71-3.59 (m, 2H), 3.54 (s, 2H), 2.14-2.04 (m, 1H), 1.52 (d, J=5.7 Hz, 6H), 1.08-0.98 (m, 2H), 0.90-0.82 (m, 2H), 0.81-0.72 (m, 3H); MS (ES+): 494.20 (M+1).

Step-3: Preparation of ethyl 2-(2-((5-(3-(aminomethyl)-5-cyclopropylphenyl)-1-isopropyl-1H-indazol-3-yl)methoxy)phenyl)acetate (331d)

Compound 331d was prepared according to the procedure reported in step-2 of scheme 1, from ethyl 2-(2-((5-(3-cyano-5-cyclopropylphenyl)-1-isopropyl-1H-indazol-3-yl)methoxy)phenyl)acetate (331c) (150 mg, 0.304 mmol) in anhydrous ethanol (10 mL) using nickel(II) chloride hexahydrate (18.06 mg, 0.076 mmol), sodium borohydride (34.5 mg, 0.912 mmol) and N1-(2-aminoethyl)ethane-1,2-diamine (0.066 mL, 0.608 mmol) for quenching. This gave after workup and purification using flash column chromatography [silica gel (24 g), eluting with DMA-80 in DCM from 0 to 60%] ethyl 2-(2-((5-(3-(aminomethyl)-5-cyclopropylphenyl)-1-isopropyl-1H-indazol-3-yl)methoxy)phenyl)acetate (331d) (100 mg, 66% yield) as a white solid; MS (ES+): 498.30 (M+1).

Step-4: Preparation of 2-(2-((5-(3-(aminomethyl)-5-cyclopropylphenyl)-1-isopropyl-1H-indazol-3-yl)methoxy)phenyl)acetic acid (331e)

Compound 331e was prepared according to the procedure reported in step-3 of scheme 1, from ethyl 2-(2-((5-(3-(aminomethyl)-5-cyclopropylphenyl)-1-isopropyl-1H-indazol-3-yl)methoxy)phenyl)acetate (331d) (100 mg, 0.201 mmol) in THF (3 mL) and MeOH (3 mL) using lithium hydroxide hydrate (50.6 mg, 1.206 mmol) in water (2 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-5-cyclopropylphenyl)-1-isopropyl-1H-indazol-3-yl)methoxy)phenyl)acetic acid (331e) (65 mg, 69% yield) HCl salt as a white solid; $^1$H NMR (300 MHz, DMSO-$d_6$) δ 12.12 (s, 1H, $D_2O$ exchangeable), 8.41 (s, 3H, $D_2O$ exchangeable), 8.05 (s, 1H), 7.89-7.68 (m, 2H), 7.67-7.54 (m, 1H), 7.46 (s, 1H), 7.34-7.24 (m, 2H), 7.24-7.17 (m, 1H), 7.14 (s, 1H), 6.97-6.81 (m, 1H), 5.45 (s, 2H), 5.12-4.91 (m, 1H), 4.04 (s, 2H), 3.54 (s, 2H), 2.09-1.94 (m, 1H), 1.59-1.42 (m, 6H), 1.07-0.93 (m, 2H), 0.88-0.68 (m, 2H); MS (ES+): 470.2 (M+1); MS (ES−): 468.15 (M−1).

Scheme 332

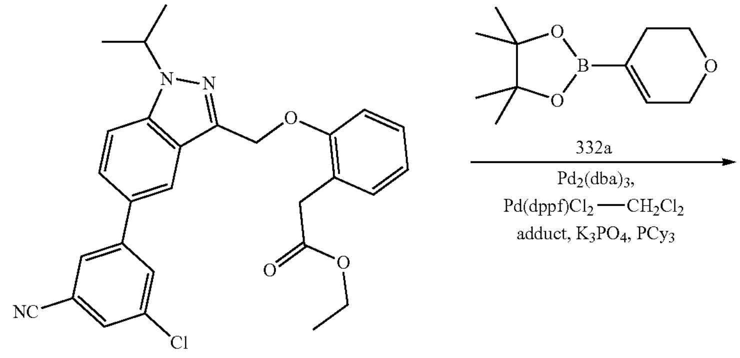

331b

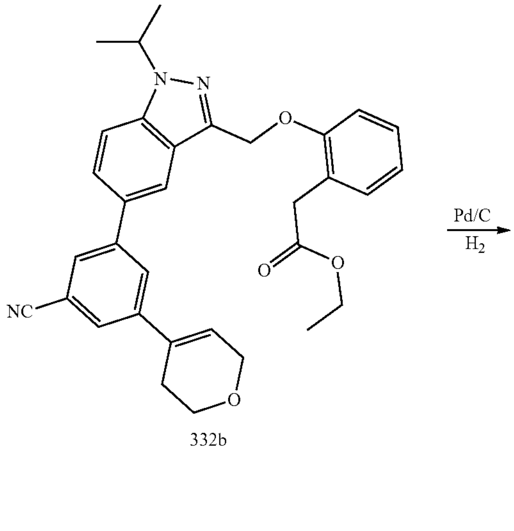

332b

-continued

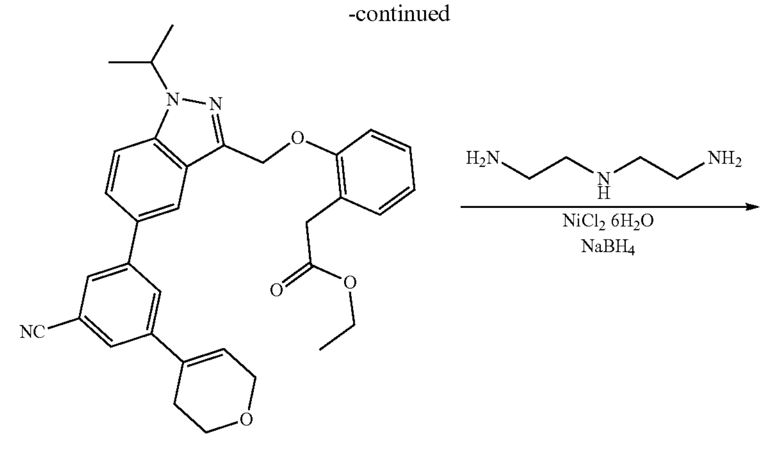

332c

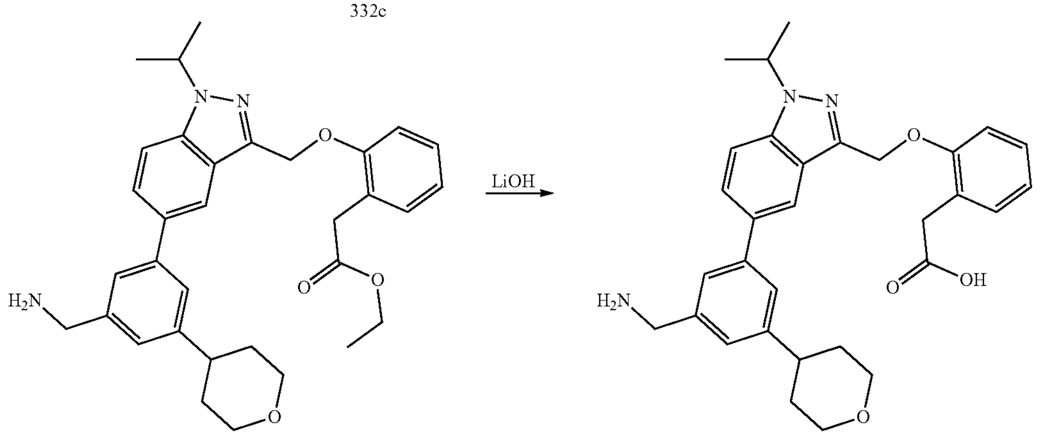

332d 331e

Preparation of 2-(2-((5-(3-(aminomethyl)-5-(tetrahydro-2H-pyran-4-yl)phenyl)-1-isopropyl-1H-indazol-3-yl)methoxy)phenyl)acetic acid (332e)

Step-1: Preparation of ethyl 2-(2-((5-(3-cyano-5-(3,6-dihydro-2H-pyran-4-yl)phenyl)-1-isopropyl-1H-indazol-3-yl)methoxy)phenyl)acetate (332b)

Compound 332b was prepared according to the procedure reported in step-2 of scheme 1, from ethyl 2-(2-((5-(3-chloro-5-cyanophenyl)-1-isopropyl-1H-indazol-3-yl)methoxy)phenyl)acetate (331b) (450 mg, 0.922 mmol) in dioxane (3 mL) and THF (3 mL) using 2-(3,6-dihydro-2H-pyran-4-yl)-4,4,5,5-tetramethyl-1,3,2-dioxaborolane (332a) (291 mg, 1.383 mmol; CAS #287944-16-5), 2 M solution of $K_3PO_4$ (1.844 mL, 3.69 mmol), tricyclohexylphosphine (51.7 mg, 0.184 mmol), $Pd_2(dba)_3$ (84 mg, 0.092 mmol), $Pd(dppf)Cl_2$—$CH_2Cl_2$ adduct (75 mg, 0.092 mmol) and heating at 100° C. for 90 min. This gave after workup and purification using flash column chromatography [silica gel (24 g), eluting with EtOAc in Hexane from 0-70%] ethyl 2-(2-((5-(3-cyano-5-(3,6-dihydro-2H-pyran-4-yl)phenyl)-1-isopropyl-1H-indazol-3-yl)methoxy)phenyl)acetate (332b) (230 mg, 47% yield) as a clear oil; MS (ES+): 558.85 (M+Na).

Step-2: Preparation of ethyl 2-(2-((5-(3-cyano-5-(tetrahydro-2H-pyran-4-yl)phenyl)-1-isopropyl-1H-indazol-3-yl)methoxy)phenyl)acetate (332c)

Compound 332c was prepared according to the procedure reported in step-2 of scheme 1, from ethyl 2-(2-((5-(3-cyano-5-(3,6-dihydro-2H-pyran-4-yl)phenyl)-1-isopropyl-1H-indazol-3-yl)methoxy)phenyl)acetate (332b) (230 mg, 0.429 mmol) in EtOH (10 mL) using 10% palladium on carbon (45.7 mg, 0.043 mmol) and hydrogenating for 6 h. This gave after work up ethyl 2-(2-((5-(3-cyano-5-(tetrahydro-2H-pyran-4-yl)phenyl)-1-isopropyl-1H-indazol-3-yl)methoxy)phenyl)acetate (332c) (180 mg, 78% yield) as a light yellow oil; MS (ES+): 538.30 (M+1).

Step-3: Preparation of ethyl 2-(2-((5-(3-(aminomethyl)-5-(tetrahydro-2H-pyran-4-yl)phenyl)-1-isopropyl-1H-indazol-3-yl)methoxy)phenyl)acetate (332d)

Compound 332d was prepared according to the procedure reported in step-2 of scheme 1, from ethyl 2-(2-((5-(3-cyano-5-(tetrahydro-2H-pyran-4-yl)phenyl)-1-isopropyl-1H-indazol-3-yl)methoxy)phenyl)acetate (332c) (180 mg, 0.335 mmol) in anhydrous ethanol (10 mL) using nickel(II) chloride hexahydrate (19.89 mg, 0.084 mmol), sodium borohydride (38.0 mg, 1.004 mmol), N1-(2-aminoethyl)ethane-1,2-diamine (0.072 mL, 0.670 mmol) and stirring for 4 h. The residue obtained was purified using flash column chromatography [silica gel (24 g), eluting with DMA-80 in DCM from 0 to 60%] ethyl 2-(2-((5-(3-(aminomethyl)-5-(tetrahydro-2H-pyran-4-yl)phenyl)-1-isopropyl-1H-indazol-3-yl)methoxy)phenyl)acetate (332d) (80 mg, 44% yield) as a white solid; MS (ES+): 542.30 (M+1).

Step-4: Preparation of 2-(2-((5-(3-(aminomethyl)-5-(tetrahydro-2H-pyran-4-yl)phenyl)-1-isopropyl-1H-indazol-3-yl)methoxy)phenyl)acetic acid (332e)

Compound 332e was prepared according to the procedure reported in step-3 of scheme 1, from ethyl 2-(2-((5-(3-(aminomethyl)-5-(tetrahydro-2H-pyran-4-yl)phenyl)-1-isopropyl-1H-indazol-3-yl)methoxy)phenyl)acetate (332d) (80 mg, 0.148 mmol) in THF (3 mL) and MeOH (3 mL) using lithium hydroxide hydrate (37.2 mg, 0.886 mmol) in water (2 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-5-(tetrahydro-2H-pyran-4-yl)phenyl)-1-isopropyl-1H-indazol-3-yl)methoxy)phenyl)acetic acid (332e) (20 mg, 26% yield) HCl salt as a white solid; H NMR (300 MHz, DMSO-$d_6$) δ 12.10 (s, 1H, $D_2O$ exchangeable), 8.31 (s, 3H, $D_2O$ exchangeable), 8.07 (s, 1H), 7.87-7.79 (m, 1H), 7.79-7.72 (m, 1H), 7.69 (s, 1H), 7.61 (s, 1H), 7.36 (s, 1H), 7.28 (s, 2H), 7.24-7.16 (m, 1H), 6.97-6.84 (m, 1H), 5.46 (s, 2H), 5.14-4.90 (m, 1H), 4.09 (s, 2H), 3.99 (d, J=11.1 Hz, 2H), 3.54 (s, 2H), 3.51-3.44 (m, 2H), 2.96-2.76 (m, 1H), 1.85-1.66 (m, 4H), 1.51 (d, J=5.6 Hz, 6H); MS (ES+): 514.25 (M+1); MS (ES−): 512.20 (M−1).

Scheme 333

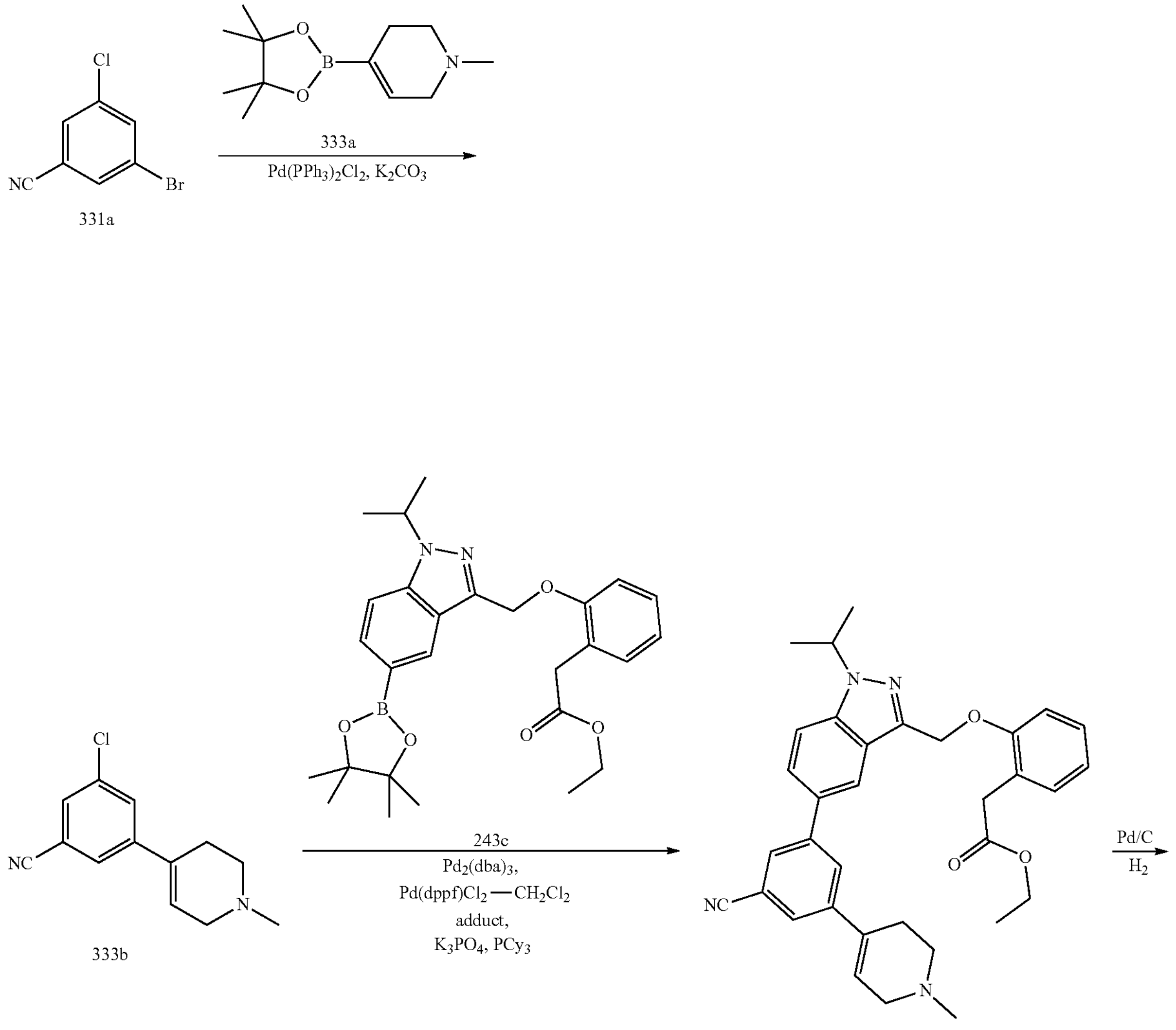

333c

-continued

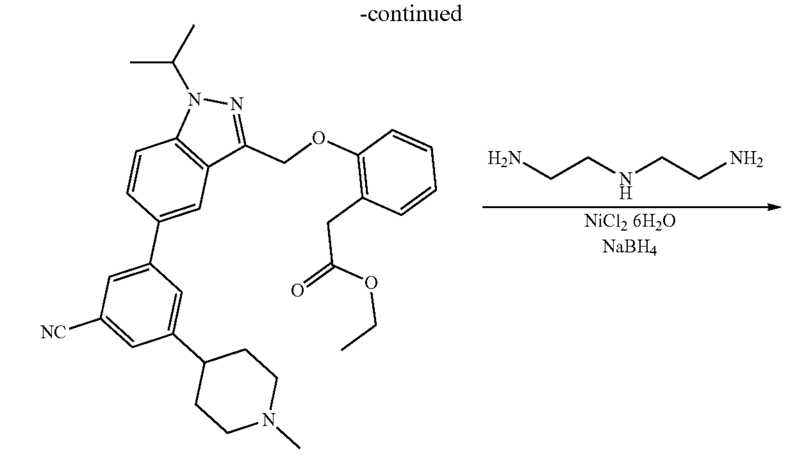

333d

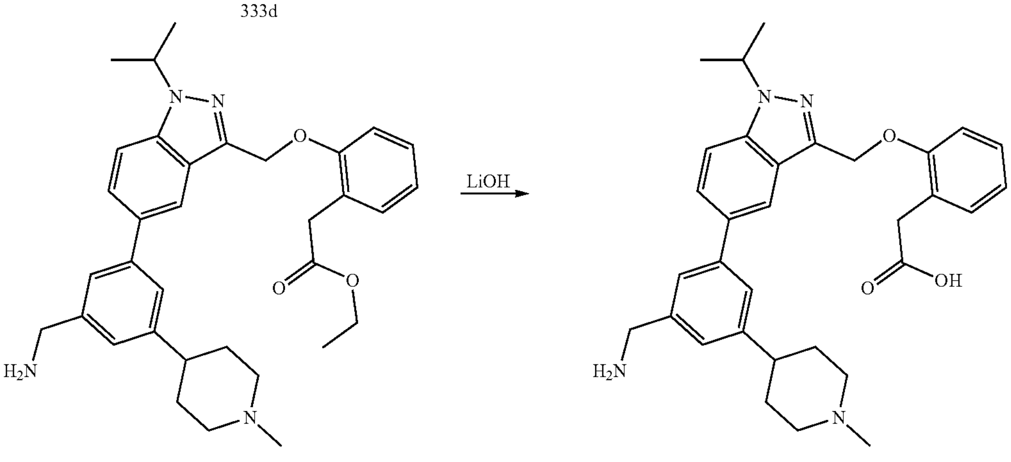

333e

333f

Preparation of 2-(2-((5-(3-(aminomethyl)-5-(1-methylpiperidin-4-yl)phenyl)-1-isopropyl-1H-indazol-3-yl)methoxy)phenyl)acetic acid (333f)

Step-1: Preparation of 3-chloro-5-(1-methyl-1,2,3,6-tetrahydropyridin-4-yl)benzonitrile (333b)

Compound 333b was prepared according to the procedure reported in step-2 of scheme 1, from 3-bromo-5-chlorobenzonitrile (331a) (300 mg, 1.386 mmol) in dioxane (10 mL) using 1-methyl-4-(4,4,5,5-tetramethyl-1,3,2-dioxaborolan-2-yl)-1,2,3,6-tetrahydropyridine (333a) (309 mg, 1.386 mmol; CAS #454482-11-2), $Pd(PPh_3)_2C_{12}$ (146 mg, 0.208 mmol), a solution of $K_2CO_3$ (575 mg, 4.16 mmol) in water (3 mL) and heating at 90° C. for 1 h. This gave after workup and purification by flash column chromatography [silica gel (24 g), eluting with DMA80 in DCM from 0-100%] 3-chloro-5-(1-methyl-1,2,3,6-tetrahydropyridin-4-yl)benzonitrile (333b) (250 mg, 78% yield) as a light yellow oil; $^1H$ NMR (300 MHz, DMSO-$d_6$) δ 7.83 (s, 2H), 7.75 (s, 1H), 6.38 (s, 1H), 3.44 (m, 2H), 3.03-2.93 (m, 2H), 2.44 (s, 3H), 2.30-2.19 (m, 2H); MS (ES+): 233.10 & 235.00 (M+1).

Step-2: Preparation of ethyl 2-(2-((5-(3-cyano-5-(1-methyl-1,2,3,6-tetrahydropyridin-4-yl)phenyl)-1-isopropyl-1H-indazol-3-yl)methoxy)phenyl)acetate (333c)

Compound 333c was prepared according to the procedure reported in step-2 of scheme 1, from 3-chloro-5-(1-methyl-1,2,3,6-tetrahydropyridin-4-yl)benzonitrile (333b) (233 mg, 1.003 mmol) in dioxane (3 mL) and THF (3 mL) using ethyl 2-(2-((1-isopropyl-5-(4,4,5,5-tetramethyl-1,3,2-dioxaborolan-2-yl)-1H-indazol-3-yl)methoxy)phenyl)acetate (243c) (400 mg, 0.836 mmol), 2 M solution of $K_3PO_4$ (1.672 mL, 3.34 mmol), tricyclohexylphosphine (46.9 mg, 0.167 mmol), $Pd_2(dba)_3$ (77 mg, 0.084 mmol), $Pd(dppf)Cl_2$—$CH_2Cl_2$ adduct (68.3 mg, 0.084 mmol) and heating at 100° C. for 2 h. This gave after workup and purification using flash column chromatography [silica gel (24 g), eluting with EtOAc in Hexane from 0-70%] ethyl 2-(2-((5-(3-cyano-5-(1-methyl-1,2,3,6-tetrahydropyridin-4-yl)phenyl)-1-isopropyl-1H-indazol-3-yl)methoxy)phenyl)acetate (333c) (360 mg, 78% yield) as a clear oil; $^1H$ NMR (300 MHz, DMSO-$d_6$) δ 8.11 (s, 1H), 8.03 (d, J=8.5 Hz, 2H), 7.82 (s, 3H), 7.27 (s, 2H), 7.24-7.12 (m, 1H), 6.99-6.75 (m, 1H), 6.42 (s, 1H), 5.44 (s, 2H), 5.14-4.96 (m, 1H), 3.73-3.61 (m, 2H), 3.54 (s, 2H), 3.04 (s, 2H), 2.57 (s, 4H), 2.28 (d, J=3.6 Hz, 3H), 1.51 (d, J=4.8 Hz, 6H), 0.77 (q, J=6.0 Hz, 3H); MS (ES+): 549.30 (M+1).

Step-3: Preparation of ethyl 2-(2-((5-(3-cyano-5-(1-methylpiperidin-4-yl)phenyl)-1-isopropyl-1H-indazol-3-yl)methoxy)phenyl)acetate (333d)

Compound 333d was prepared according to the procedure reported in step-2 of scheme 1, from ethyl 2-(2-((5-(3-cyano-5-(1-methyl-1,2,3,6-tetrahydropyridin-4-yl)phenyl)-1-isopropyl-1H-indazol-3-yl)methoxy)phenyl)acetate (333c) (180 mg, 0.328 mmol) in EtOH (10 mL) using 10% palladium on carbon (34.9 mg, 0.033 mmol) and hydrogenating for 6 h. This gave after work up ethyl 2-(2-((5-(3-cyano-5-(1-methylpiperidin-4-yl)phenyl)-1-isopropyl-1H-indazol-3-yl)methoxy)phenyl)acetate (333d) (150 mg, 83% yield) as a light yellow oil; MS (ES+): 551.30 (M+1).

Step-4: Preparation of ethyl 2-(2-((5-(3-(aminomethyl)-5-(1-methylpiperidin-4-yl)phenyl)-1-isopropyl-1H-indazol-3-yl)methoxy)phenyl)acetate (333e)

Compound 333e was prepared according to the procedure reported in step-2 of scheme 1, from ethyl 2-(2-((5-(3-cyano-5-(1-methylpiperidin-4-yl)phenyl)-1-isopropyl-1H-indazol-3-yl)methoxy)phenyl)acetate (333d) (150 mg, 0.272 mmol) in anhydrous ethanol (10 mL) using nickel(II) chloride hexahydrate (16.19 mg, 0.068 mmol), sodium borohydride (30.9 mg, 0.817 mmol) and N1-(2-aminoethyl)ethane-1,2-diamine (0.059 mL, 0.545 mmol) for quenching. This gave after workup and purification using flash column chromatography [silica gel (24 g), eluting with DMA-80 in DCM from 0 to 60%] ethyl 2-(2-((5-(3-(aminomethyl)-5-(1-methylpiperidin-4-yl)phenyl)-1-isopropyl-1H-indazol-3-yl)methoxy)phenyl)acetate (333e) (20 mg, 13% yield) as a white solid; MS (ES+): 555.30 (M+1).

Step-5: Preparation of 2-(2-((5-(3-(aminomethyl)-5-(1-methylpiperidin-4-yl)phenyl)-1-isopropyl-1H-indazol-3-yl)methoxy)phenyl)acetic acid (333f)

Compound 333f was prepared according to the procedure reported in step-3 of scheme 1, from ethyl 2-(2-((5-(3-(aminomethyl)-5-(1-methylpiperidin-4-yl)phenyl)-1-isopropyl-1H-indazol-3-yl)methoxy)phenyl)acetate (333e) (20 mg, 0.036 mmol) in THF (3 mL) and MeOH (3 mL) using lithium hydroxide hydrate (9.08 mg, 0.216 mmol) in water (2 mL) and stirring at RT for 15 h. This gave after workup and purification using reverse phase column chromatography [C18 column (50 g), eluting with ACN in water (containing 0.1% HCl) from 0-100%] 2-(2-((5-(3-(aminomethyl)-5-(1-methylpiperidin-4-yl)phenyl)-1-isopropyl-1H-indazol-3-yl)methoxy)phenyl)acetic acid (333f) (5 mg, 26% yield) HCl salt as a white solid; H NMR (300 MHz, DMSO-$d_6$) δ 12.12 (s, 1H, $D_2O$ exchangeable), 10.52 (s, 1H, $D_2O$ exchangeable), 8.38 (s, 3H, $D_2O$ exchangeable), 8.06 (s, 1H), 7.89-7.81 (m, 1H), 7.80-7.69 (m, 2H), 7.63-7.56 (m, 1H), 7.36-7.31 (m, 1H), 7.31-7.24 (m, 2H), 7.24-7.17 (m, 1H), 6.97-6.85 (m, 1H), 5.46 (s, 2H), 5.11-4.96 (m, 1H), 4.10 (s, 2H), 3.58-3.51 (m, 4H), 3.51-3.47 (m, 2H), 2.98-2.85 (m, 1H), 2.78 (s, 3H), 2.14-1.98 (m, 4H), 1.52 (d, J=5.6 Hz, 6H); MS (ES+): 527.30 (M+1).

Example 334

The $IC_{50}$ value of a compound (i.e., the concentration of the compound that inhibits 50% of the enzymatic activity) was calculated according to the procedure reported in U.S. Pat. No. 6,653,340 B1, e.g., column 74 (incorporated by reference).

Specifically, the compounds were dissolved in a stock solution of DMSO at 10.0 or 100 mM. A portion of this stock solution was added to assay buffer in a final volume of 50 μL. Controls included buffer alone and enzyme solutions to which DMSO was added. Substrate was added to the reaction wells immediately or after incubation at room temperature. The reaction rates were measured spectrophotometrically by the generation of product at 405 nm for 600 sec. Background absorbance at 690 nm was measured and subtracted from the absorbance at 405 nm for each well.

The reaction rate for enzyme alone was compared to the rate of enzyme in the presence of inhibitor and the percent inhibition was calculated as shown below:

$$\text{Percent Inhibition} = [\text{Rate without inhibitor} - \text{Rate with inhibitor})/(\text{Rate wihtout inhibitor})] \times 100$$

Factor D Esterolytic Assay:

An established esterolytic assay for the measurement of Factor D activity and inhibition of Factor D activity was used (Kam, C. M.; McRae, B. J.; Harper, J. W.; Niemann, M. A.; Volanakis, J. E.; Powers, J. C. Human complement proteins D, C2, and B Active site mapping with peptide thioester substrates. J Biol. Chem. 1987, 262, 3444-3451). For this assay Z-Lys-SBzl, 1.29 mM (Kim, S.; Narayana, S. V. L; Volanakis, J. E. Mutational analysis of the substrate binding site of human complement Factor D. Biochemistry. 1994, 33, 14393-14399.) was used as the substrate for Factor D (104 mM). Hydrolysis of this compound by Factor D liberated a free sulfhydryl group which is then reacted with 5,5'-dithiobis(2nitrobenzoic acid) producing an intense yellow color (Habeeb, A. F. S. A. Reaction of protein sulfhydryl groups with Ellman's Reagent. Methods in Enzymol. 1976, 25, 457-464.). The assays were performed in 96 well microtiter plates and rates of hydrolysis were monitored at 405 nm on a Biotek Synergy $H_1$ plate reader. Hydrolysis rates were reported as change in mOD/min. The assay was conducted in 100 mM HEPES, 500 mM NaCl, pH 7.5 containing 10% DMSO in a final volume of 50 μL per well.

An $IC_{50}$, a compound concentration which inhibits 50% of the enzymatic activity, was calculated. Compounds in the examples were tested a minimum of three times. In the table below, three plus symbols (+++) are used to indicate compounds with an $IC_{50}$ value of less than 1 micromolar; two plus symbols (++) indicate compounds with an $IC_{50}$ value between 1 and 10 micromolar; and one plus symbol (+) indicates compounds with an $IC_{50}$ value greater than 10 micromolar.

TABLE 1

Measured Ki ($IC_{50}$) Value for Compounds.

| Compound | $IC_{50}$ | Compound | $IC_{50}$ | Compound | $IC_{50}$ |
|---|---|---|---|---|---|
| 7f | +++ | 29b | +++ | 39f | +++ |
| 13b | +++ | 33f | +++ | 42b | +++ |
| 19e | +++ | 34c | + | 42c | +++ |
| 20j | +++ | 35c | + | 47d | +++ |
| 21b | ++ | 8e | +++ | 40d | ++ |
| 41d | + | 9e | +++ | 40c | +++ |
| 22e | +++ | 36e | + | 31 | +++ |
| 30d | +++ | 37b | ++ | 44d | +++ |
| 43c | + | 10c | +++ | 45b | +++ |
| 23c | +++ | 11d | +++ | 5d | +++ |
| 24a | +++ | 38e | +++ | 46b | +++ |
| 99d | + | 14c | +++ | 6e | +++ |
| 27e | +++ | 15e | +++ | 48b | +++ |
| 26a | +++ | 16e | +++ | 1f | +++ |
| 28d | +++ | 100d | +++ | 4d | ++ |
| 25c | + | 17e | +++ | 2d | ++ |
| 31f | +++ | 18e | +++ | 12g | +++ |
| 32d | +++ | 101d | +++ | 49b | +++ |
| 73f | ++ | 69f | +++ | 86b | +++ |
| 50d | +++ | 70f | ++ | 82e | +++ |
| 57d | +++ | 77d | + | 83h | +++ |
| 51c | +++ | 61d | +++ | 84b | +++ |

TABLE 1-continued

Measured Ki ($IC_{50}$) Value for Compounds.

| Compound | $IC_{50}$ | Compound | $IC_{50}$ | Compound | $IC_{50}$ |
|---|---|---|---|---|---|
| 75d | +++ | 62c | +++ | 59g | +++ |
| 75e | + | 96e | + | 60d | +++ |
| 74d | +++ | 97h | + | 98g | +++ |
| 52c | +++ | 71d | +++ | 105d | +++ |
| 53b | +++ | 78e | +++ | 87c | +++ |
| 54c | +++ | 58f | +++ | 88e | +++ |
| 56d | +++ | 63c | +++ | 106c | +++ |
| 55d | +++ | 85c | +++ | 107d | +++ |
| 66f | +++ | 72h | +++ | 102c | +++ |
| 65e | +++ | 79h | +++ | 108d | +++ |
| 67e | +++ | 80d | +++ | 76i | +++ |
| 68e | +++ | 104e | +++ | 103c | +++ |
| 94d | + | 81a | +++ | 109d | ++ |
| 95b | + | 64h | +++ | 113g | +++ |
| 110d | +++ | 115c | +++ | 124f | +++ |
| 90h | +++ | 116d | +++ | 125d | +++ |
| 91a | +++ | 117d | +++ | 128c | +++ |
| 111d | +++ | 118d | +++ | 129c | +++ |
| 89e | +++ | 119d | +++ | 127f | +++ |
| 92e | +++ | 120c | +++ | 130c | +++ |
| 93e | +++ | 121f | +++ | 126f | +++ |
| 112c | +++ | 122b | +++ | | |
| 114i | ++ | 123g | +++ | | |
| 134c | +++ | 141c | +++ | 142e | +++ |
| 135c | +++ | 155e | +++ | 167e | +++ |
| 138c | +++ | 156c | +++ | 188d | +++ |
| 131c | +++ | 157e | +++ | 229g | +++ |
| 143f | +++ | 158d | +++ | 179b | +++ |
| 133f | +++ | 151d | +++ | 182e | +++ |
| 146d | +++ | 152d | +++ | 183e | +++ |
| 147d | +++ | 153d | +++ | 162c | +++ |
| 136d | +++ | 159f | +++ | 165c | +++ |
| 137c | +++ | 163e | +++ | 168c | +++ |
| 132d | +++ | 154c | +++ | 169c | +++ |
| 144h | +++ | 301d | +++ | 189c | +++ |
| 148d | +++ | 177g | +++ | 190f | +++ |
| 149d | +++ | 178f | +++ | 191c | +++ |
| 150d | +++ | 181f | +++ | 192c | +++ |
| 139c | +++ | 164e | +++ | 170b | +++ |
| 140c | +++ | 186c | +++ | 184e | +++ |
| 145c | +++ | 187d | +++ | 185c | +++ |
| 230c | +++ | 210c | +++ | 199f | +++ |
| 231c | +++ | 211c | +++ | 250f | +++ |
| 205d | +++ | 174c | +++ | 213c | +++ |
| 166f | +++ | 175h | +++ | 254c | +++ |
| 195f | +++ | 176c | +++ | 194f | +++ |
| 196f | +++ | 200c | +++ | 255c | +++ |
| 180d | +++ | 238c | +++ | 256c | +++ |
| 206c | +++ | 273j | +++ | 201b | +++ |
| 212d | +++ | 234d | +++ | 235g | + |
| 193b | ++ | 248f | +++ | 236c | +++ |
| 172f | +++ | 249f | +++ | 202c | +++ |
| 171i | +++ | 214c | +++ | 257h | +++ |
| 197c | +++ | 215d | +++ | 258f | +++ |
| 232h | +++ | 216c | +++ | 203d | +++ |
| 173c | +++ | 217c | +++ | 204c | +++ |
| 207d | +++ | 218c | +++ | 274c | +++ |
| 208d | +++ | 233h | +++ | 239c | +++ |
| 209c | +++ | 198f | +++ | 240b | +++ |
| 241c | +++ | 276e | +++ | 303d | + |
| 242b | +++ | 224c | +++ | 247c | +++ |
| 260c | +++ | 265c | +++ | 312f | ++ |
| 272n | +++ | 298d | +++ | 304c | + |
| 219c | +++ | 244d | +++ | 305c | +++ |
| 220c | +++ | 314e | + | 228e | + |
| 221c | +++ | 283g | +++ | 278c | +++ |
| 282f | +++ | 277c | +++ | 225e | +++ |
| 281d | +++ | 294d | +++ | 226c | +++ |
| 222c | +++ | 245d | +++ | 284e | +++ |
| 223c | +++ | 299d | +++ | 297b | +++ |
| 275d | +++ | 295h | +++ | 306c | +++ |
| 268c | +++ | 296d | +++ | 3021 | +++ |
| 259c | +++ | 287b | +++ | 308d | ++ |
| 262e | +++ | 288d | +++ | 319c | +++ |
| 261e | +++ | 289d | +++ | 227b | +++ |
| 263e | +++ | 160c | +++ | 286c | +++ |

TABLE 1-continued

Measured Ki ($IC_{50}$) Value for Compounds.

| Compound | $IC_{50}$ | Compound | $IC_{50}$ | Compound | $IC_{50}$ |
|---|---|---|---|---|---|
| 264c | +++ | 246f | ++ | 285c | +++ |
| 279c | +++ | 267b | +++ | 237c | +++ |
| 280c | +++ | 271c | +++ | 330c | +++ |
| 309b | +++ | 253c | +++ | 307c | +++ |
| 310b | +++ | 313c | +++ | 331e | ++ |
| 311c | + | 292c | +++ | 333f | + |
| 243g | +++ | 269c | +++ | 332e | + |
| 315b | +++ | 270c | +++ | 323b | +++ |
| 161c | +++ | 293c | +++ | 320b | +++ |
| 316c | +++ | 290h | +++ | 266b | +++ |
| 317d | ++ | 291g | ++ | 324d | +++ |
| 318f | +++ | 243h | + | 300d | ++ |
| 321c | ++ | 325b | ++ | 329d | ++ |
| 322c | + | 326d | ++ | 252c | +++ |
| 251c | +++ | 327d | ++ | 328d | + |

Three (+++) is used to denote compounds with an $IC_{50}$ value of less than 1 micromolar concentration; Two (++) indicates compounds with an $IC_{50}$ value between 1 and 10 micromolar concentration; One (+) indicate compounds with an $IC_{50}$ value greater than 10 micromolar concentration.

INCORPORATION BY REFERENCE

All of the U.S. patents and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of formula (Ia), or a pharmaceutically acceptable salt thereof:

(Ia)

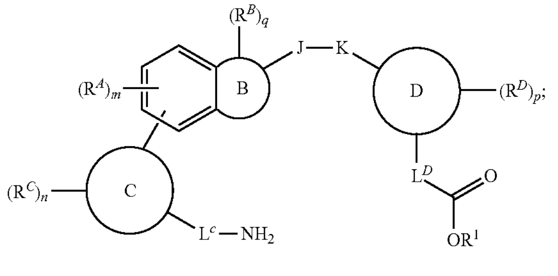

wherein:

ring

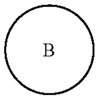

is arylene or heteroarylene;

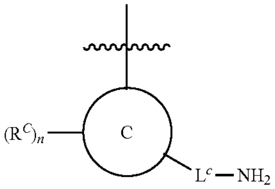

represents

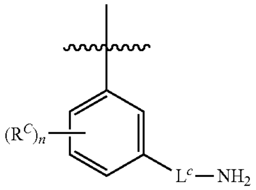

or

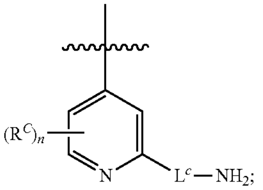

ring

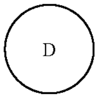

is aryl or heteroaryl;

J represents —$CH_2$—, —NH—, —$CH_2CH_2$—, —C(O)—, —O—, —S—, —S(O)—, —$SO_2$—, —N(alkyl)-, —CH(alkyl)-, —CH(aryl)-, —$C(alkyl)_2$-, —CH(cycloalkyl)-, or

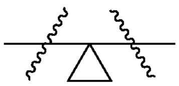

;

K represents a bond, —O—, —NH—, —C(O)—, —$CH_2$—, —S—, —S(O)—, —$SO_2$—, —N(alkyl)-, —CH(alkyl)-, or —CH(cycloalkyl)-;

wherein at least one of J and K is a bond, —C(O)—, —$CH_2$—, —$CH_2CH_2$—, —CH(alkyl)-, or —CH (aryl)-;

$L^C$ represents a bond, —$CH_2$—, —CH(alkyl)-, —CH (cycloalkyl)-, —CH(hydroxyalkyl)-, —CH(haloalkyl)-, —$CH_2CH_2$—, —$CF_2$—, —CH(F)—, —CF(alkyl)-, —C(O)—, —$CD_2$-, or —CH(D)-;

$L^D$ represents —$CH_2$—, —$CH_2CH_2$—, —$CF_2$—, —CH (F)—, —$CD_2$-, —CH(D)-, —CH(alkyl)-, —CH(cycloalkyl)-, —$CHNH_2$—, —CH(NH(alkyl))-, —CH (NH(cycloalkyl))-, or a bond;

$R^A$ represents H, halo, hydroxyl, cyano, amino, alkyl, alkoxyl, hydroxyalkyl, optionally substituted aryloxy, (aryloxy)alkyl, (cycloalkyl)alkoxy, (heterocycloalkyl) alkoxy, optionally substituted (heteroaryl)alkoxy, haloalkyl, haloalkoxy, (hydroxy)haloalkyl, alkoxyalkyl, optionally substituted aminoalkyl, optionally substituted alkynyl, optionally substituted aryl, optionally substituted heteroaryl, optionally substituted heteroarylalkyl, optionally substituted cycloalkyl, optionally substituted (cycloalkyl)alkyl, optionally substituted (cycloalkyl)alkenyl, optionally substituted heterocycloalkyl, optionally substituted (heterocycloalkyl)alkyl, —C(O)OH, —C(O)$NH_2$—, —C(O)$N(alkyl)_2$-, —$CH_2$C(O)OH, —$NO_2$, —$CH_2$NH(optionally substituted alkyl), —$CH_2$N(Boc)(optionally substituted alkyl), —$CH_2$NH((cycloalkyl)alkyl), —$CH_2$N(alkyl) (cycloalkyl), —$CH_2$N(alkyl)((cycloalkyl)alkyl), —NH (optionally substituted alkyl), —NH(cycloalkyl), —NH((cycloalkyl)alkyl), —NH((heterocycloalkyl)alkyl), —$N(alkyl)_2$, —N(alkyl)((cycloalkyl)alkyl, —N(alkyl)((heterocycloalkyl)alkyl, —NH(heteroarylalkyl), —$CH_2$O(optionally substituted aryl), —C(O)O (alkyl), —C(O)NH(optionally substituted alkyl), —C(O)NH((cycloalkyl)alkyl), —NHC(O)O(alkyl), or —$CH_2N(alkyl)_2$;

$R^B$ represents H, —C(O)O(alkyl), halogen, cyano, amino, —C(O)OH, —$CH_2$C(O)OH, —C(O)$NH_2$, —C(O)NH (cycloalkyl), —C(O)NH(alkyl), —C(O)NH(aryl), —C(O)NH(heteroaryl), —C(O)(alkyl), alkylaminoalkyl, alkylaminocycloalkyl, alkoxyalkyl, hydroxyalkyl, haloalkyl, (hydroxy)haloalkyl, or tosyl, or is optionally substituted alkyl, aryl, heteroaryl, cycloalkyl, (cycloalkyl)alkyl, or heterocycloalkyl;

$R^C$ represents H, halo, —OH, or amino, or is optionally substituted alkoxy, alkyl, cycloalkyl, heterocycloalkyl, or (heteroaryl)alkoxy;

$R^D$ represents H, halo, hydroxyl, cyano, —$NH_2$, —NH (Ac), —NH(alkyl), —$N(alkyl)_2$, —NH(CO)(alkyl), —$CH_2NH_2$, —$CH_2$NHC(O)(alkyl), —C(O)$NH_2$, —C(O)OH, or —NHC(O)O(alkyl), or is optionally substituted alkyl, alkoxyl, cycloalkyl, (cycloalkyl)alkyl, hydroxyalkyl, aminoalkyl, haloalkoxyl, or haloalkyl;

$R^1$ represents H or optionally substituted alkyl; and m, n, p, and q are each independently 0, 1, or 2.

2. The compound of claim 1, wherein:

J represents —$CH_2$—, —NH—, —$CH_2CH_2$—, or —C(O)—;

K represents a bond, —O—, —NH—, or —C(O)—;

wherein if J represents —NH—, then K is a bond or —C(O)—;

$L^C$ represents —$CH_2$—, —CH(alkyl)-, or —CH(hydroxyalkyl)-;

$R^A$ represents H, halo, hydroxyl, alkyl, alkoxyl, hydroxyalkyl, optionally substituted aryloxy, (aryloxy)alkyl, (heterocycloalkyl)alkoxy, optionally substituted aryl, optionally substituted heteroaryl, optionally substituted heterocycloalkyl, optionally substituted (heterocycloalkyl)alkyl, —C(O)OH, —$NO_2$, —$CH_2$NH(optionally substituted alkyl), —$CH_2$NH((cycloalkyl)alkyl), —NH ((cycloalkyl)alkyl), —$CH_2$O(optionally substituted aryl), —C(O)O(alkyl), —C(O)NH(optionally substituted alkyl), —C(O)NH((cycloalkyl)alkyl), —NHC(O) O(alkyl), or —$CH_2N(alkyl)_2$;

$R^B$ represents H, —C(O)O(alkyl), alkyl, —C(O)OH, hydroxyalkyl, tosyl, heterocycloalkyl, —C(O)$NH_2$, or —C(O)NH(cycloalkyl);

$R^C$ represents H or halo;

$R^D$ represents H or halo, hydroxyl, alkyl, alkoxyl, —$NH_2$, —C(O)$NH_2$, —NHC(O)O(alkyl), or haloalkoxyl; and $R^1$ represents H or alkyl.

3. The compound of claim 1, having the structure of formula (Ia-1):

(Ia-1)

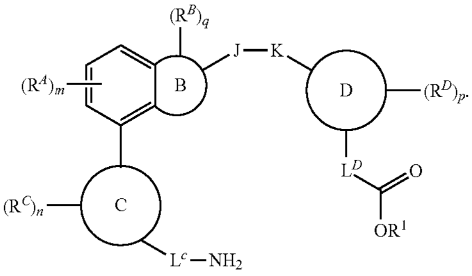

4. The compound of claim 1, having the structure of formula (Ia-2):

(Ia-2)

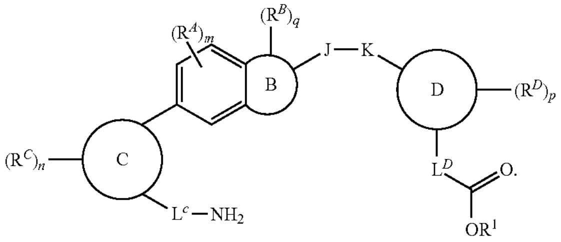

5. The compound of claim 1, wherein

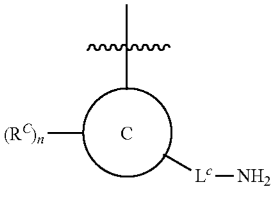

represents

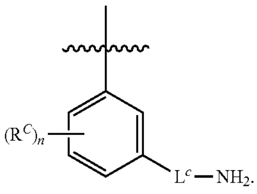

6. The compound of claim 1, wherein

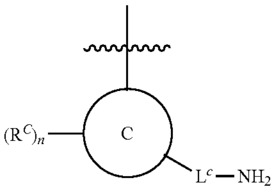

represents

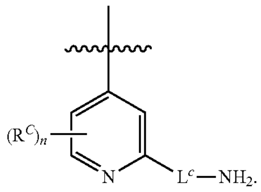

7. The compound of claim 1, wherein $L^C$ represents —$CH_2$—.

8. The compound of claim 1, wherein $R^C$ represents H.

9. The compound of claim 1, wherein $R^C$ represents halo.

10. The compound of claim 1, wherein -J-K— represents —$CH_2$—, —NH—, —$CH_2$—O—, —$CH_2CH_2$—O—, —C(O)—NH—, or —NHC(O)—.

11. The compound of claim 1, wherein -J-K— represents —$CH_2$—O— or —C(O)—NH—.

12. The compound of claim 1, wherein ring

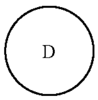

is aryl.

13. The compound of claim 1, wherein

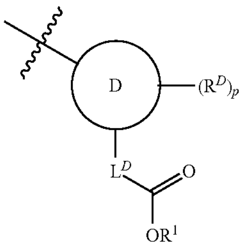

represents

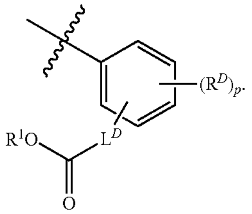

14. The compound of claim 1, wherein

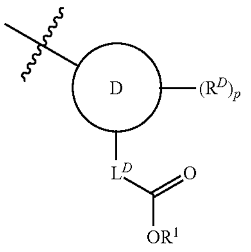

represents

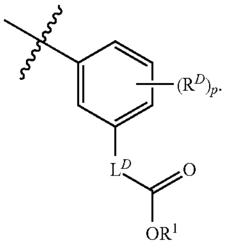

15. The compound of claim 1, wherein

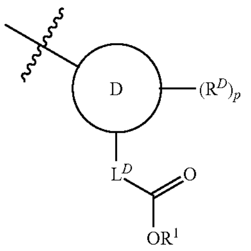

represents

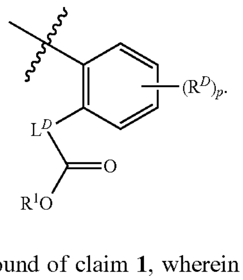

16. The compound of claim 1, wherein $R^1$ is H.

17. The compound of claim 1, wherein $L^D$ represents $—CH_2—$, $—CH_2CH_2—$, or a bond.

18. The compound of claim 1, wherein $L^D$ represents $—CH_2—$.

19. The compound of claim 1, wherein $R^D$ represents H, halo, hydroxyl, alkyl, or alkoxyl.

20. The compound of claim 1, wherein $R^D$ represents H.

21. The compound of claim 1, wherein $R^B$ represents H, alkyl, or —C(O)OH.

22. The compound of claim 1, wherein $R^B$ represents H.

23. The compound of claim 1, wherein $R^A$ represents H, alkyl, alkoxyl, or $—CH_2O$(optionally substituted aryl).

24. The compound of claim 1, wherein $R^A$ represents H.

25. The compound of claim 1, wherein the compound is selected from the group consisting of:

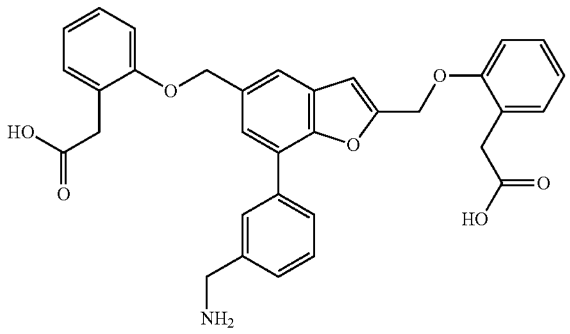

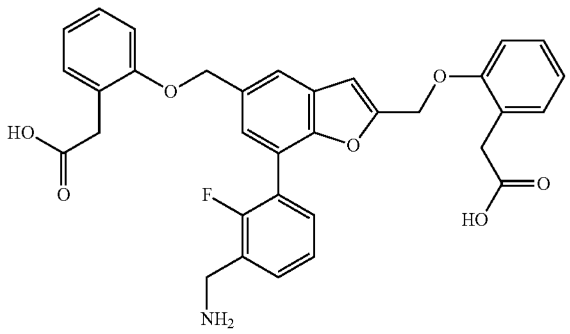

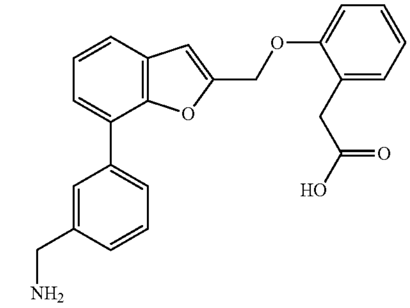

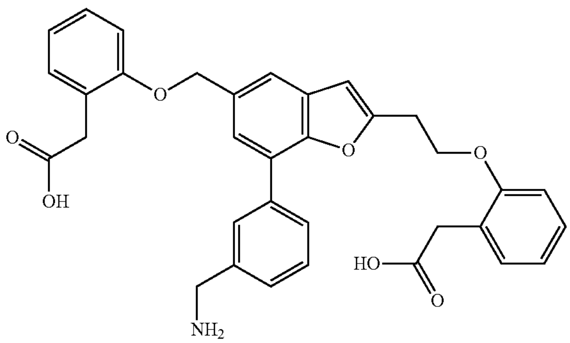

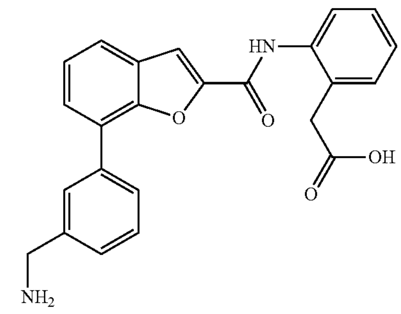

-continued
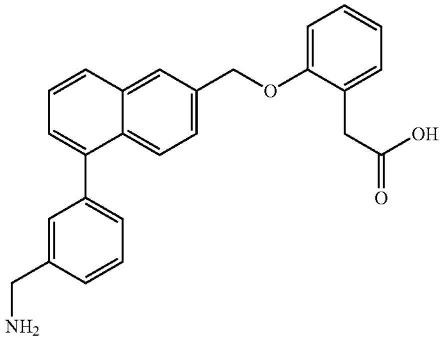
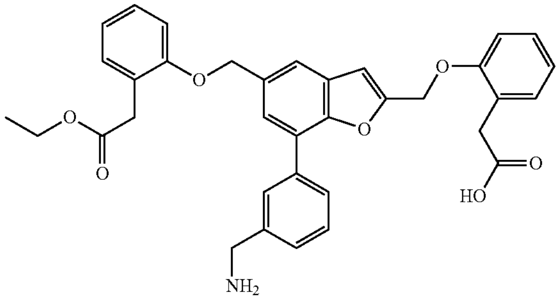
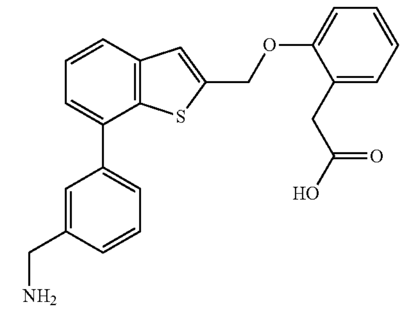
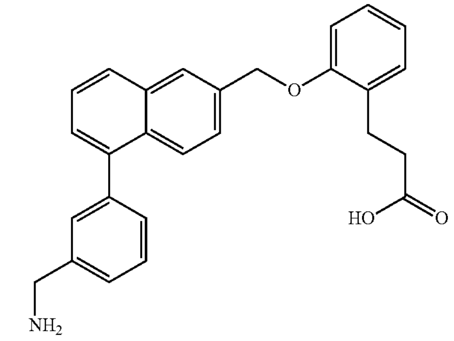
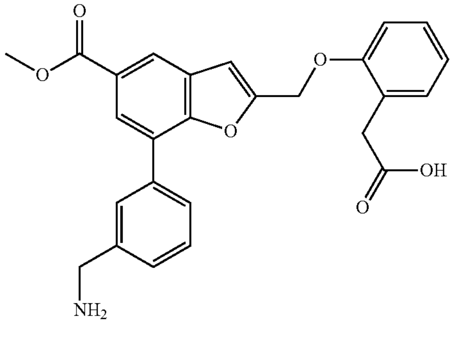
-continued
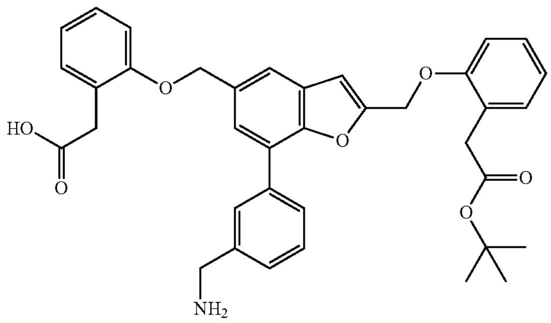
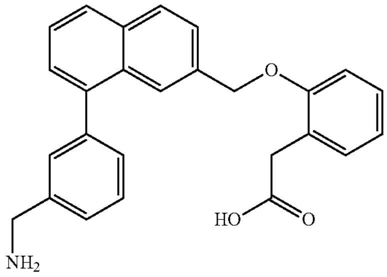
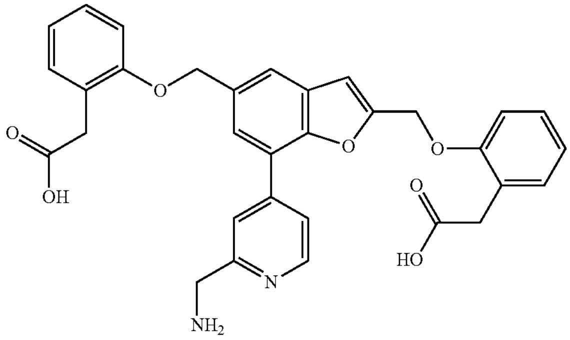
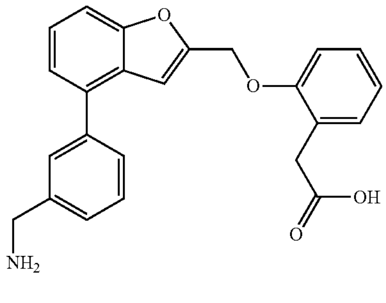
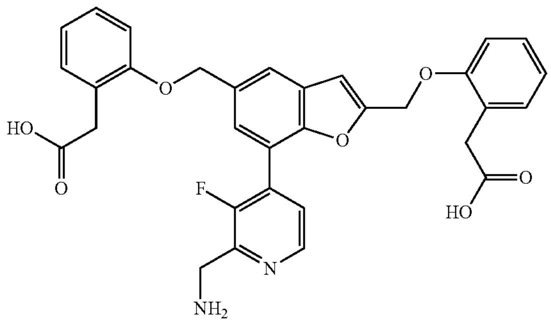

-continued
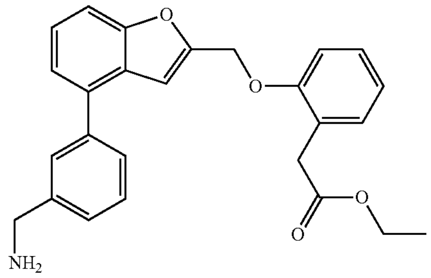
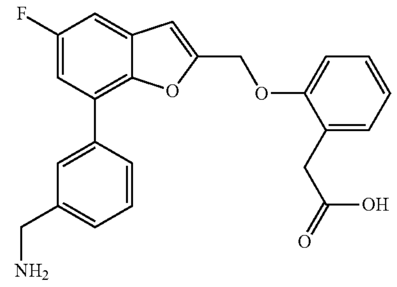
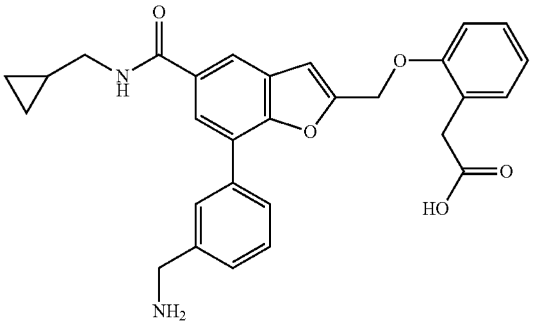
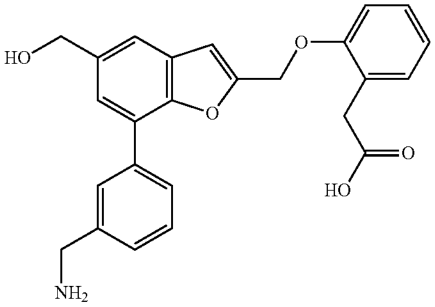
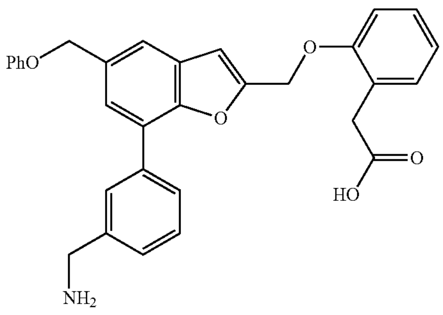
-continued
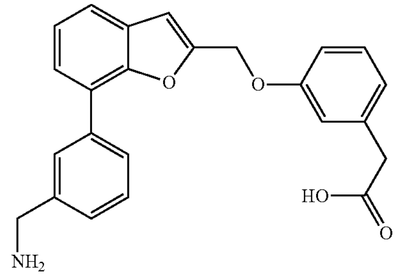
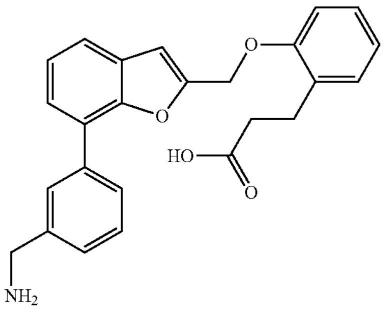
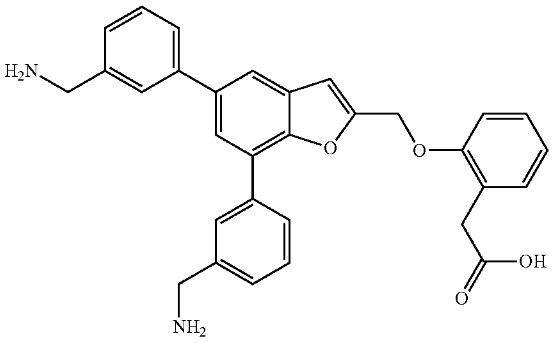
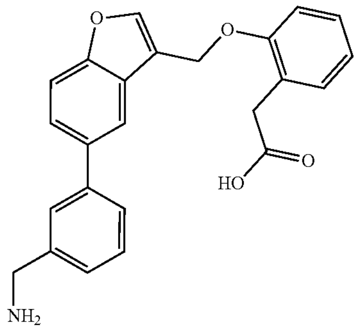
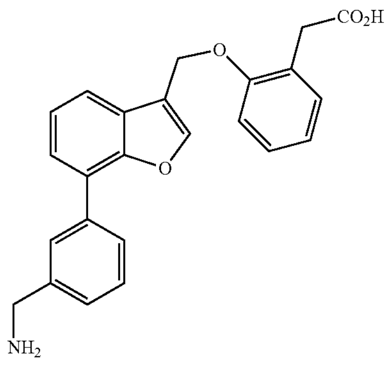

-continued
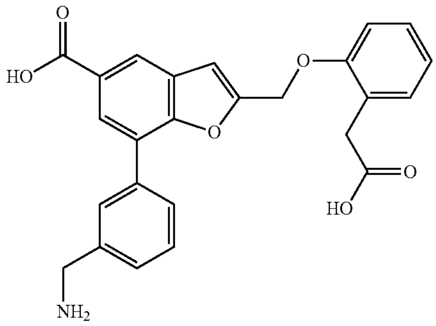
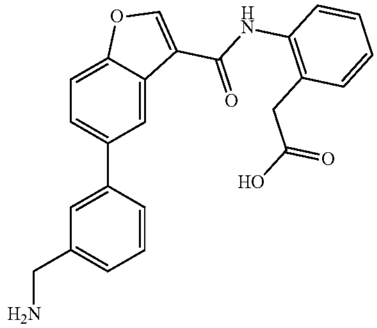
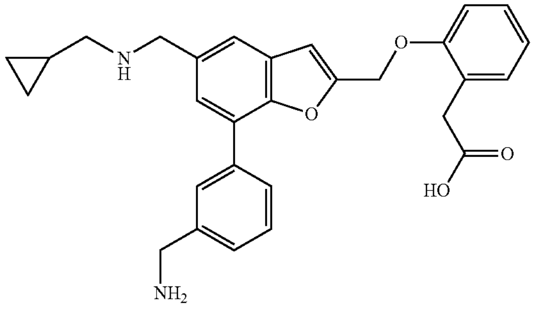
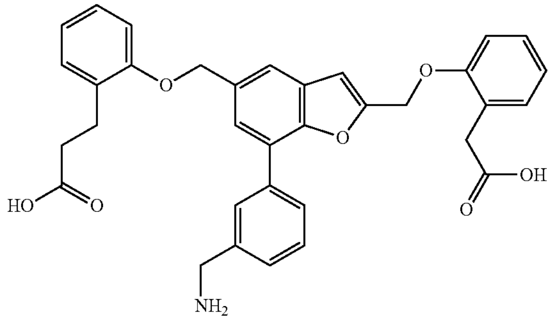
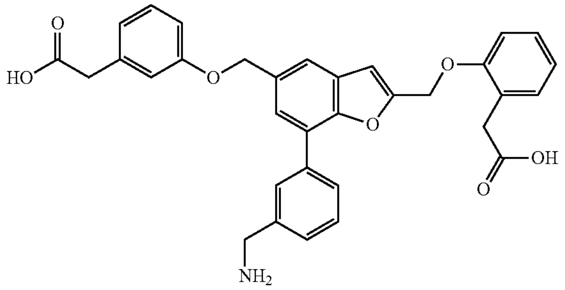
-continued
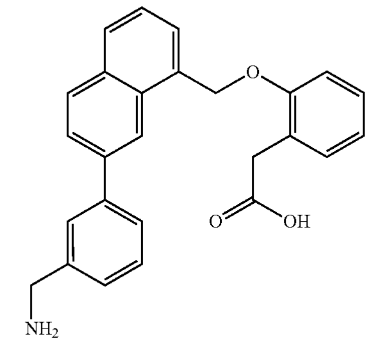
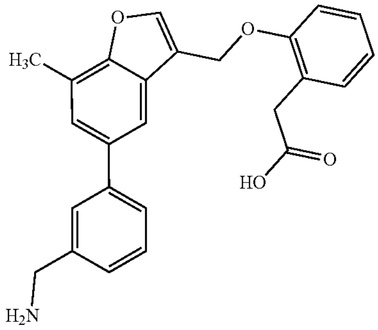
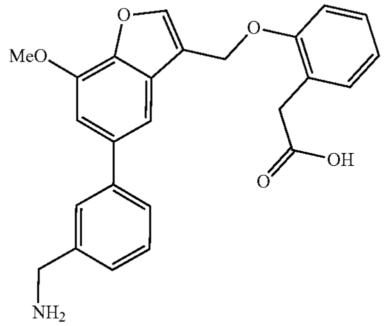
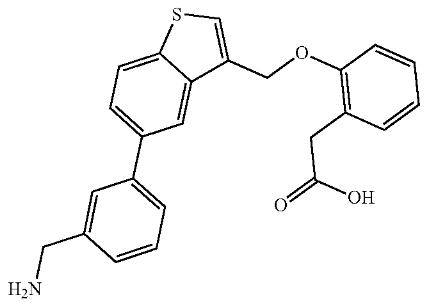
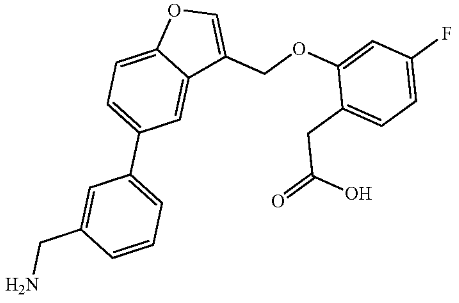

-continued
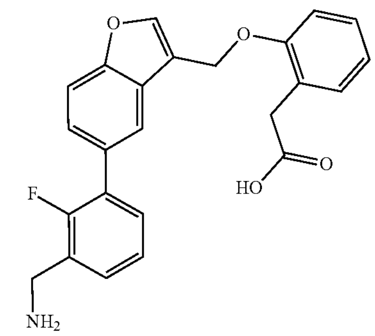
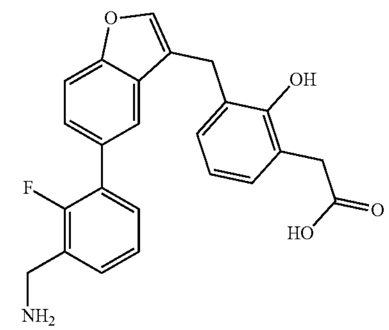
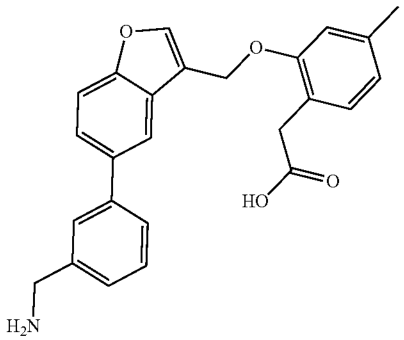
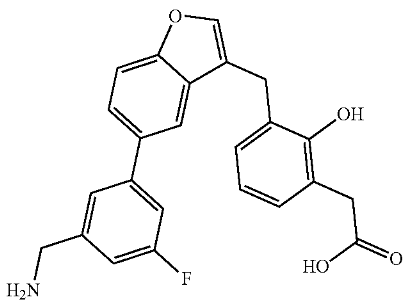
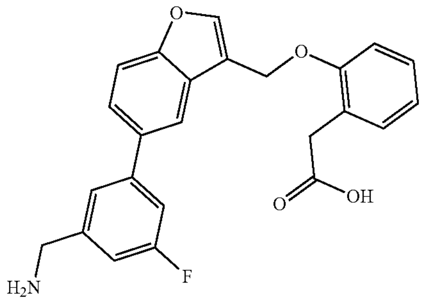
-continued
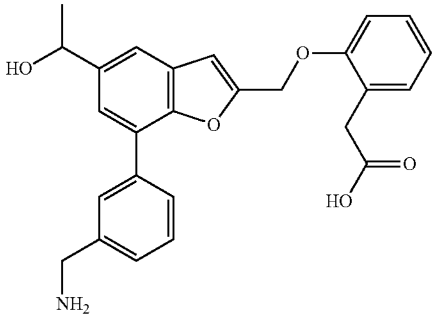
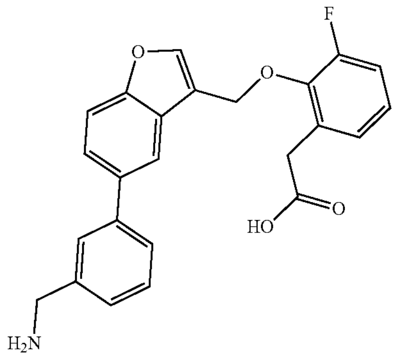
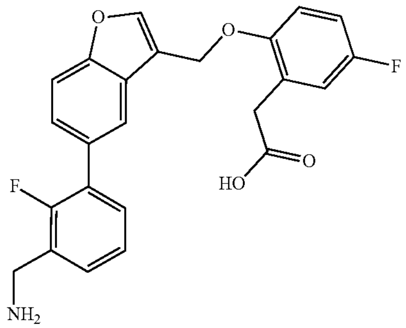
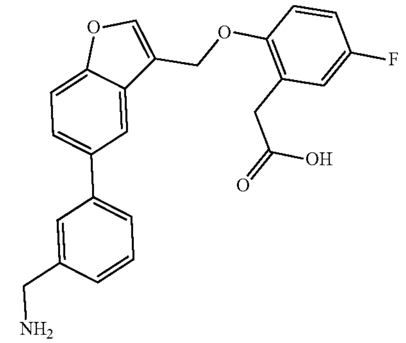
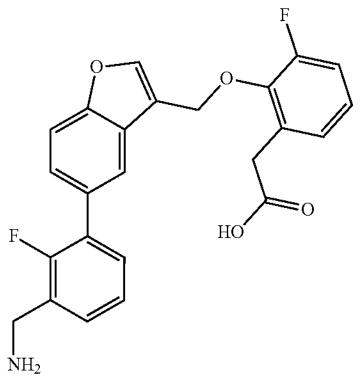

-continued
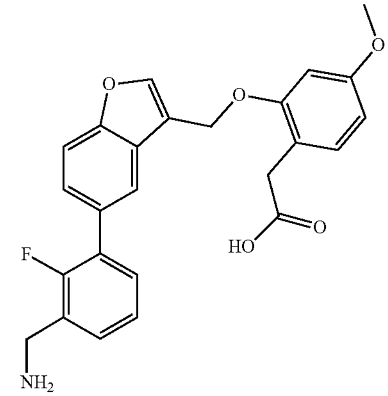
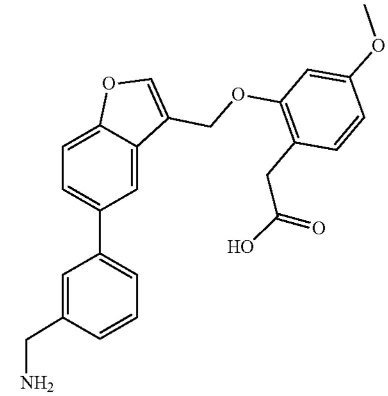
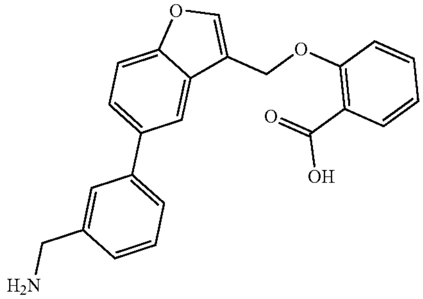
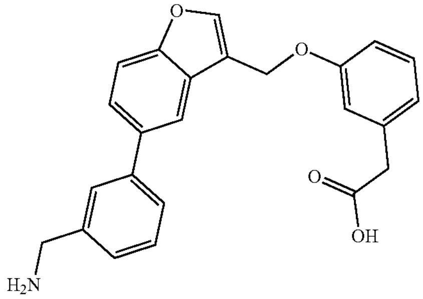
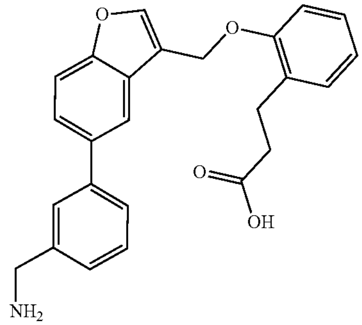
-continued
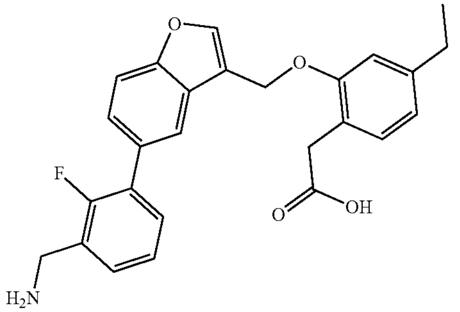
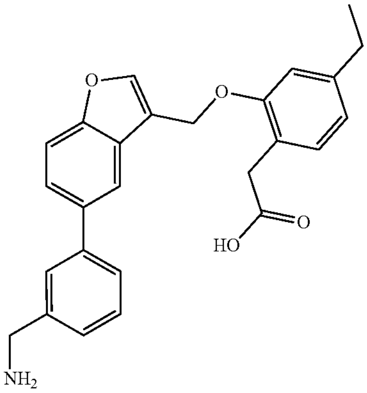
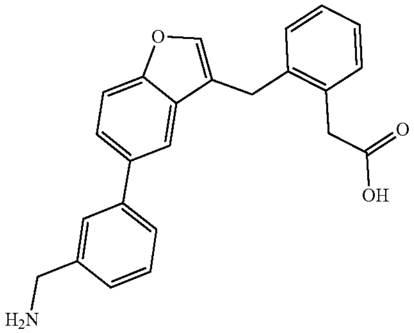
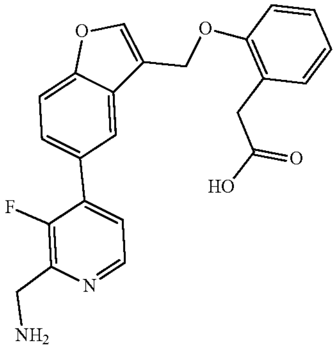

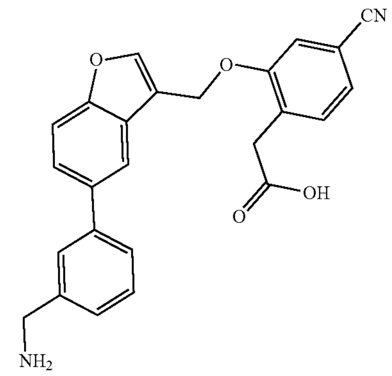
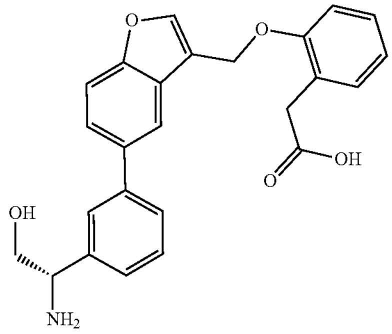
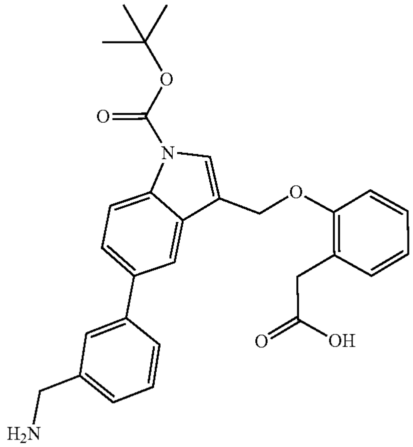
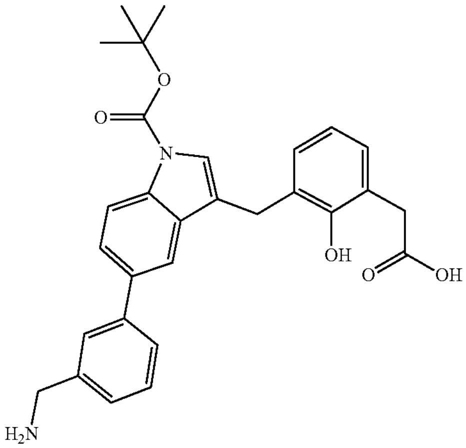
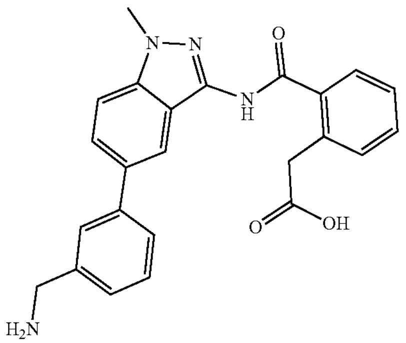
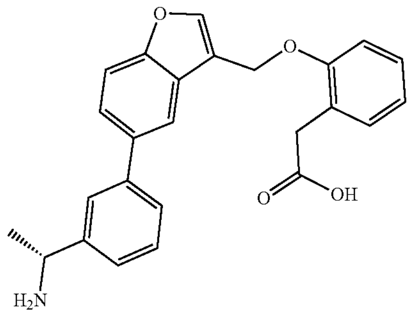
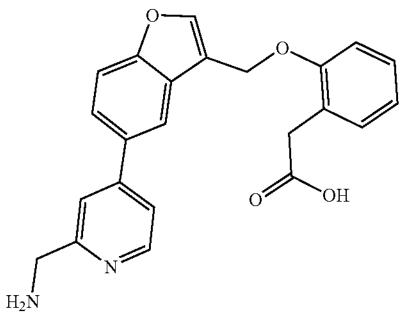
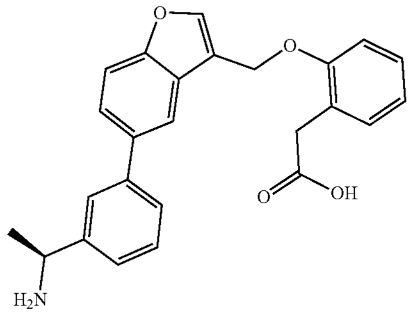
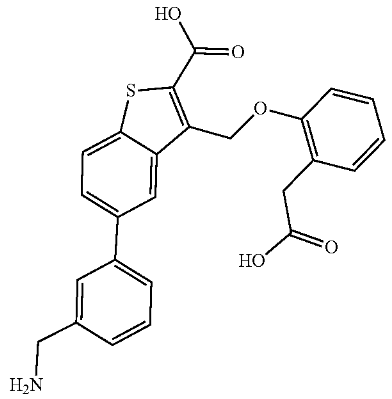

-continued
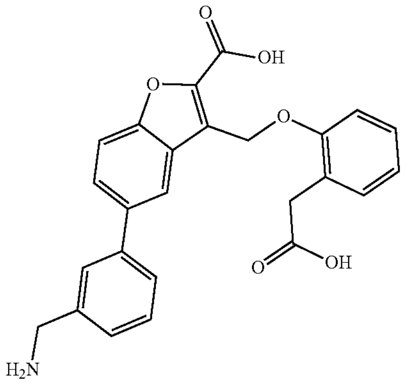
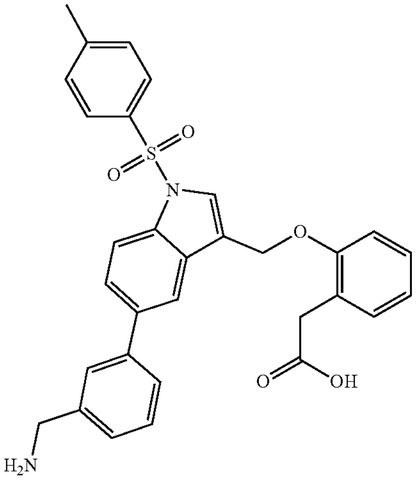
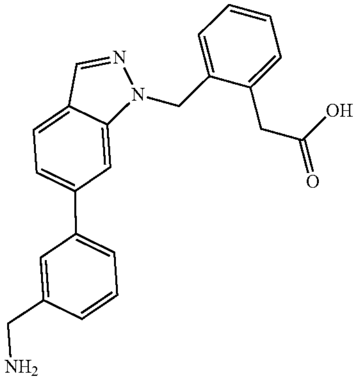
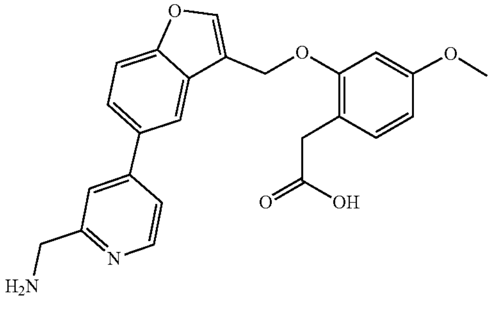
-continued
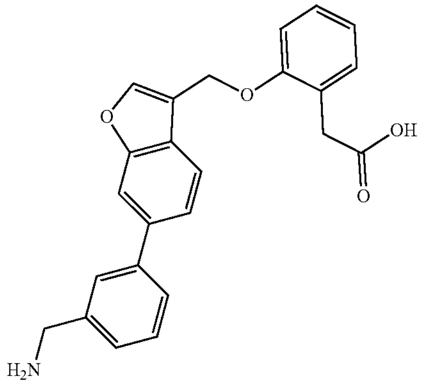
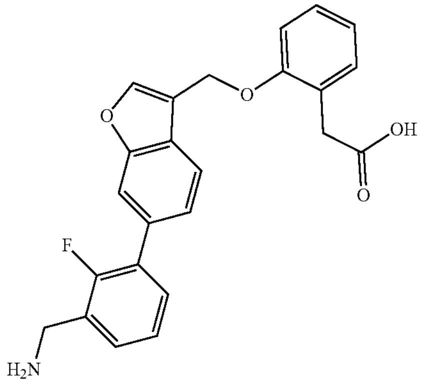
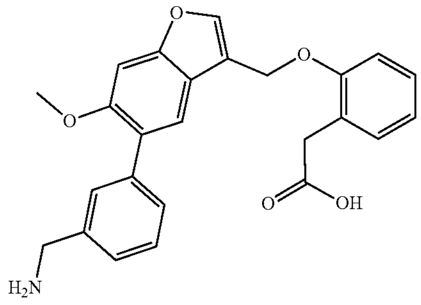
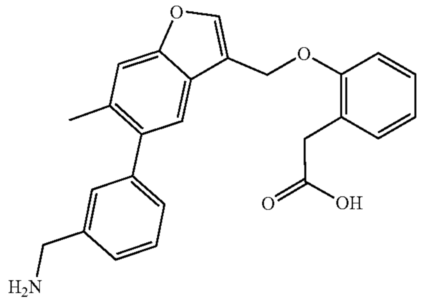

-continued
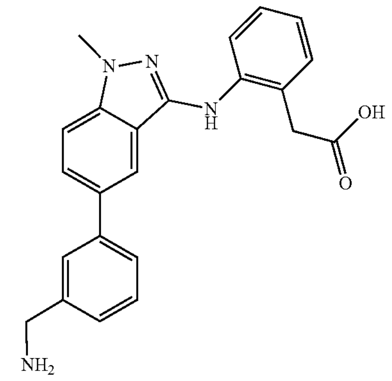
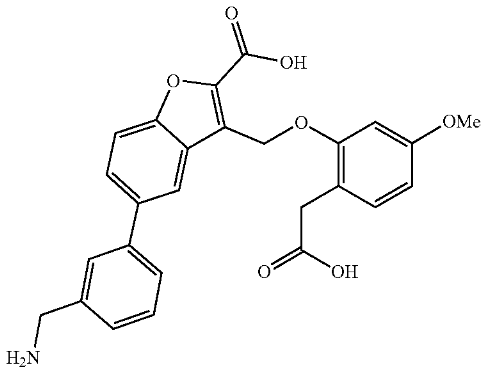
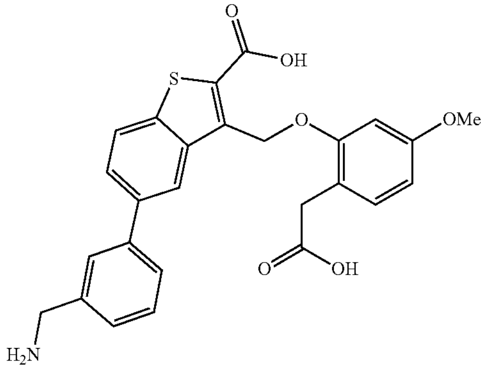
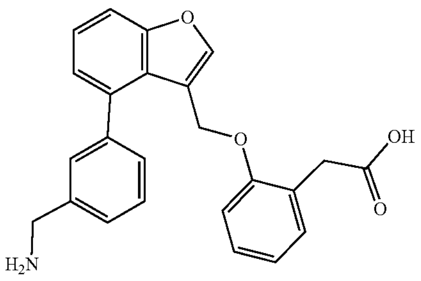
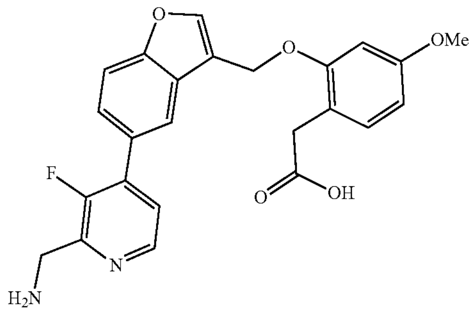
-continued
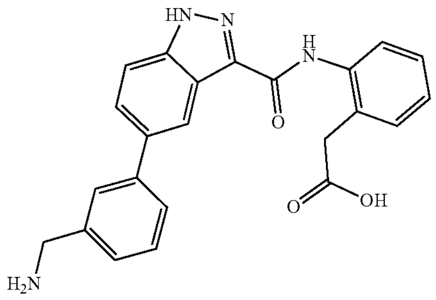
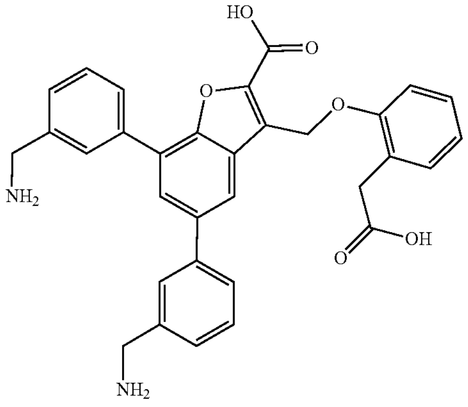
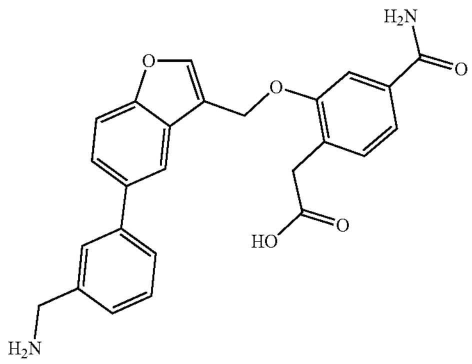
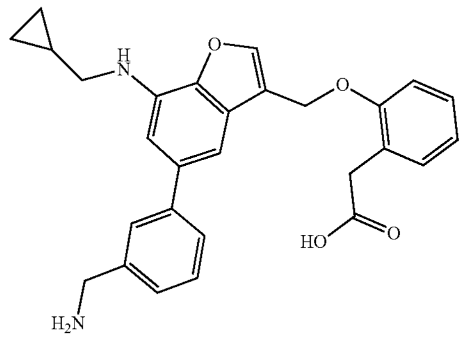

-continued
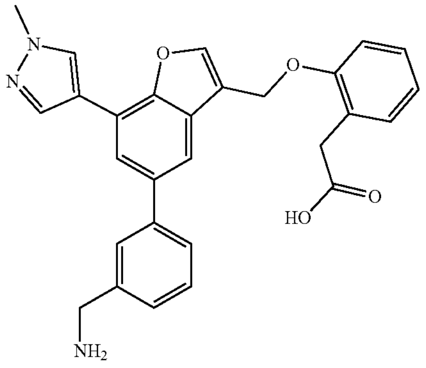
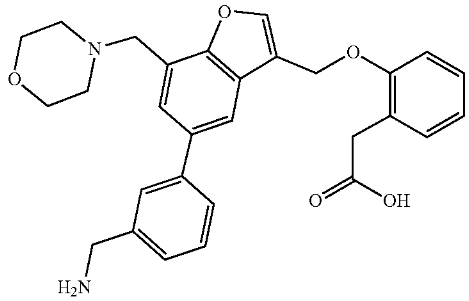
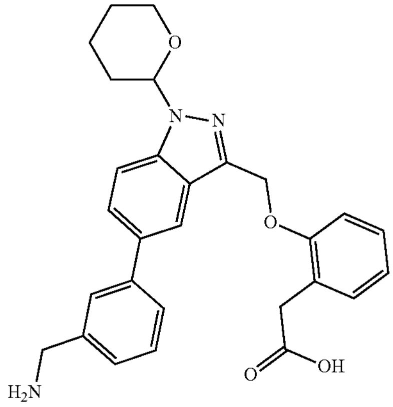
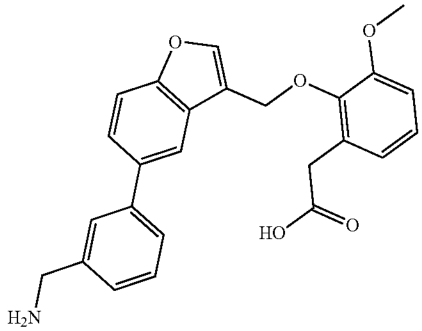
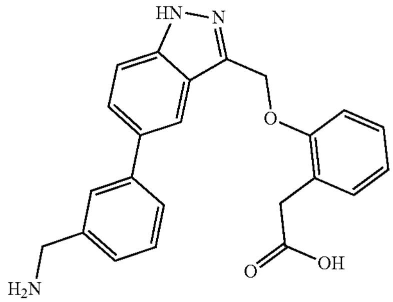
-continued
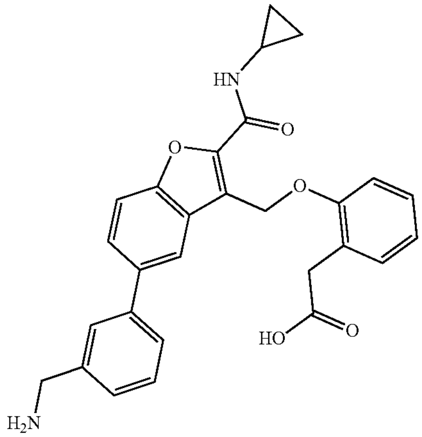
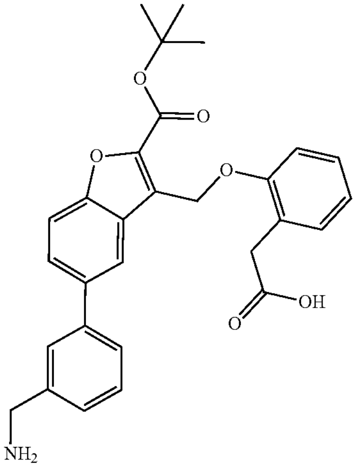
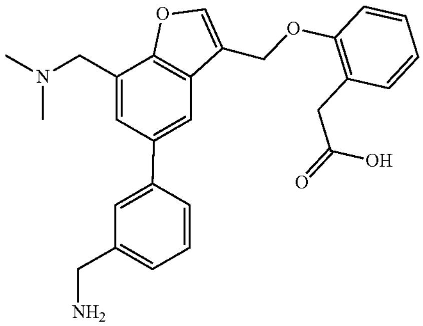
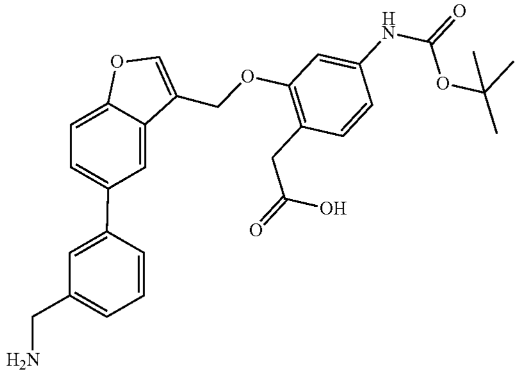

-continued
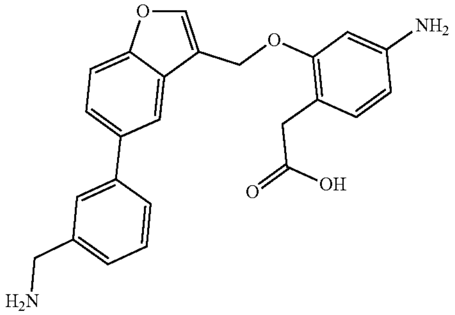
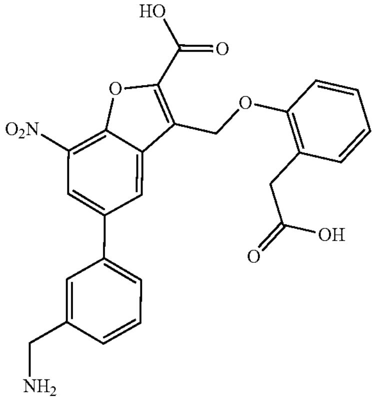
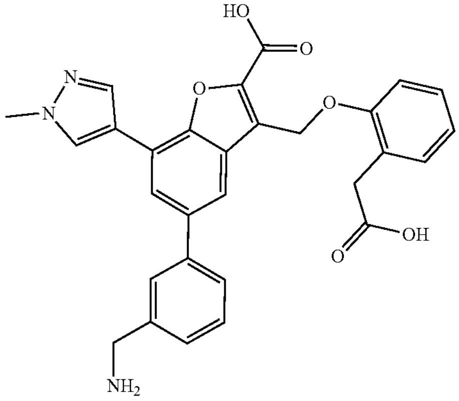
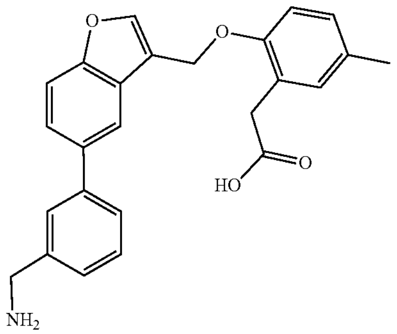
-continued
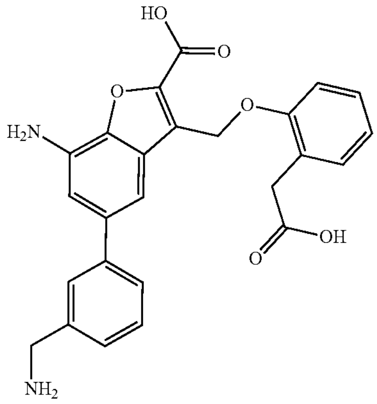
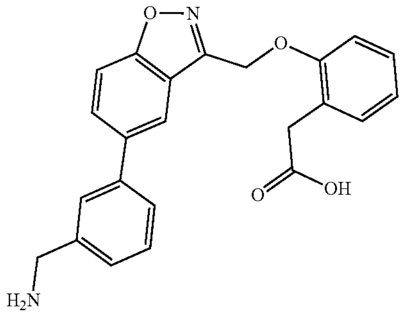
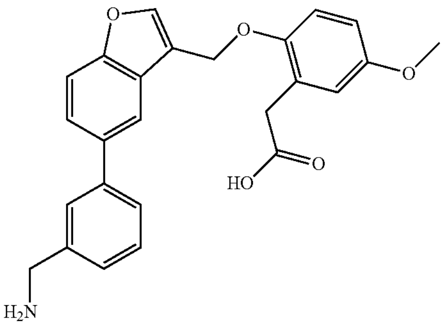
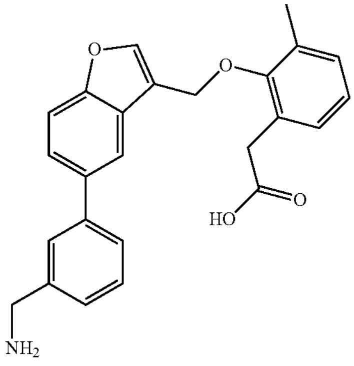

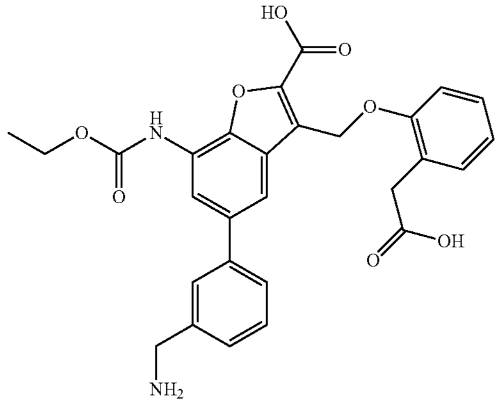
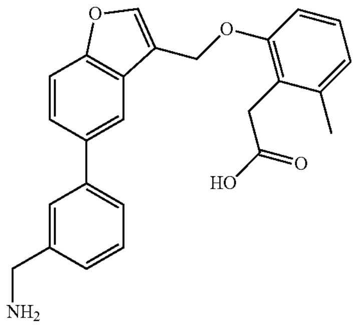
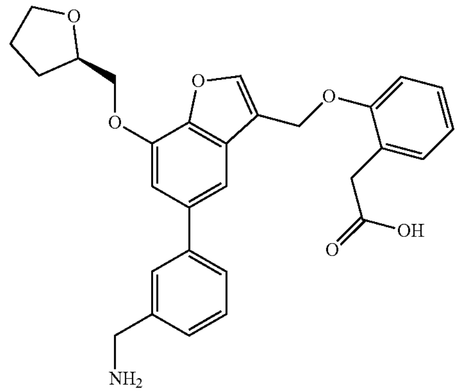
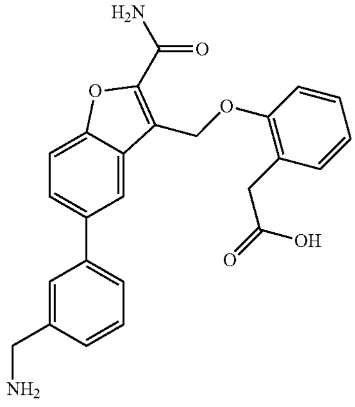
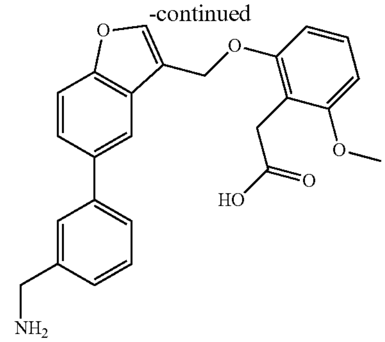
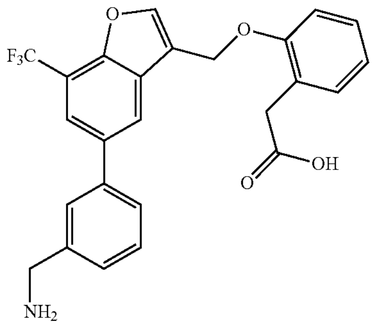
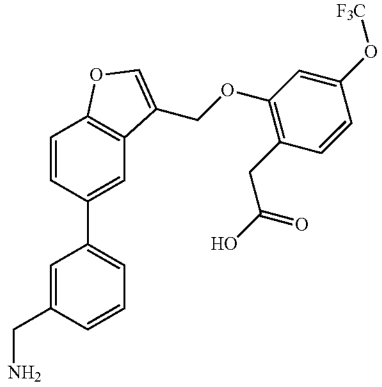
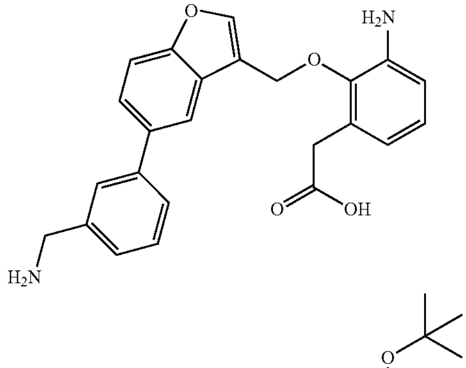
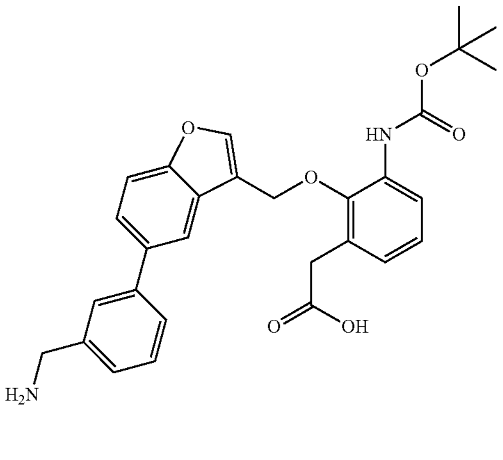

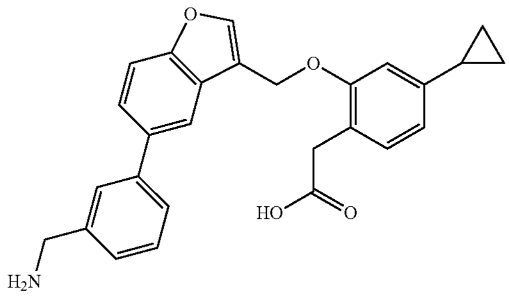
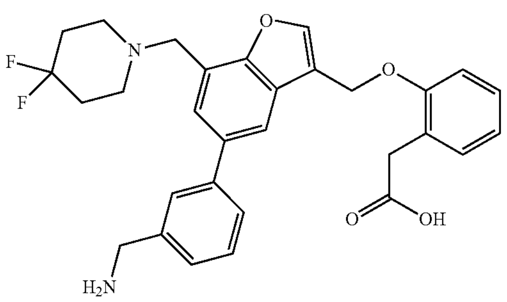
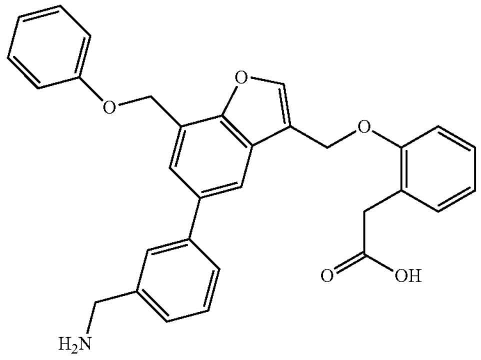
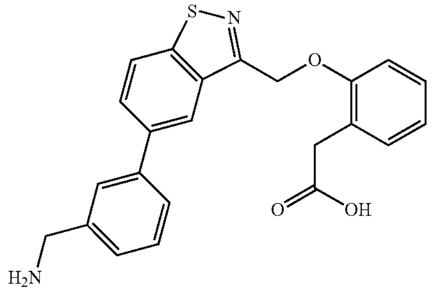
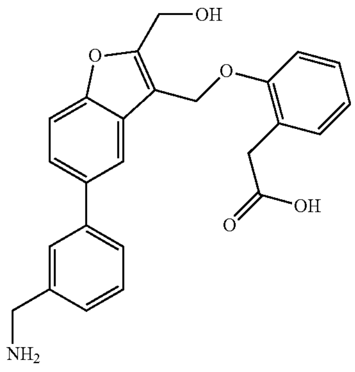
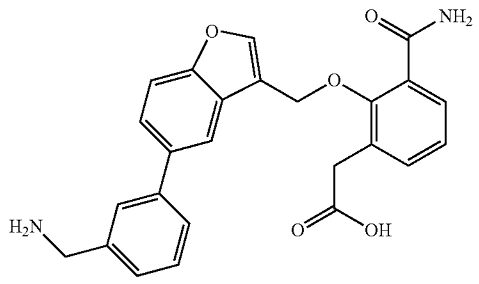
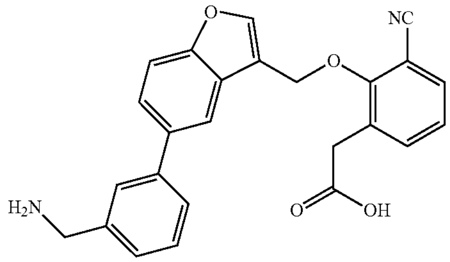
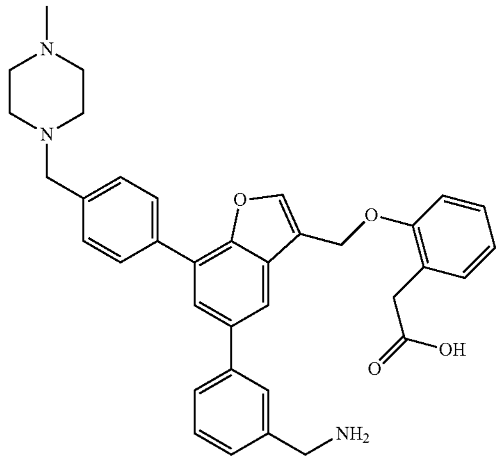
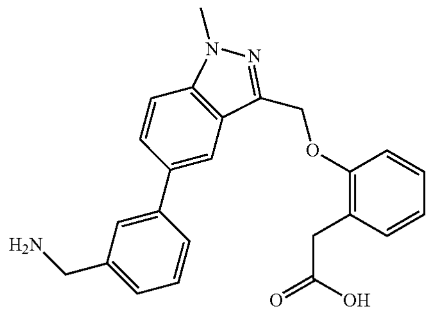
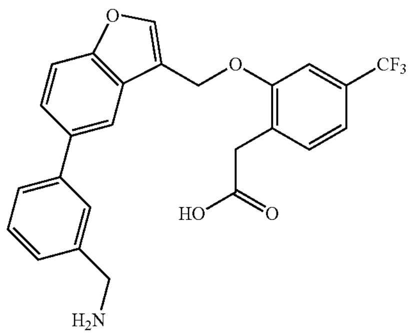

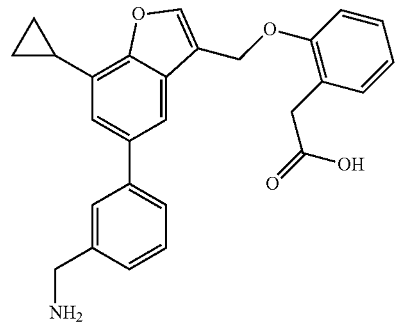
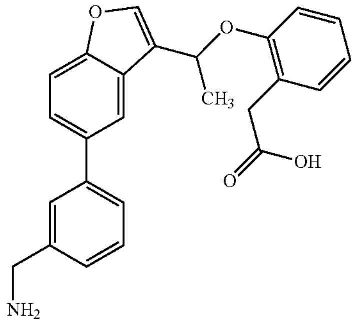
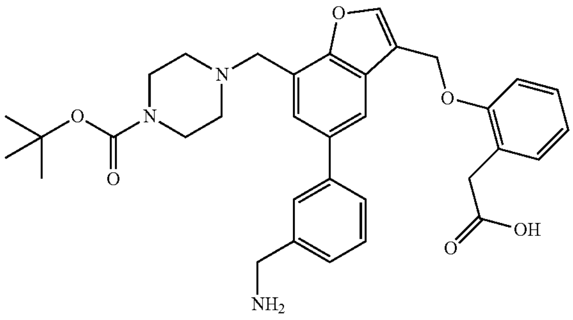
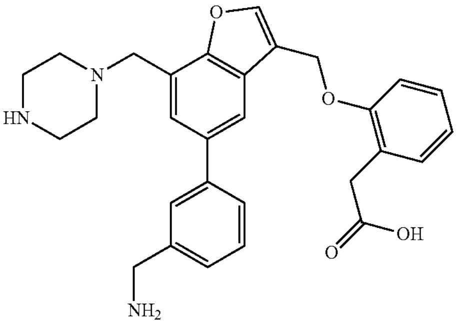
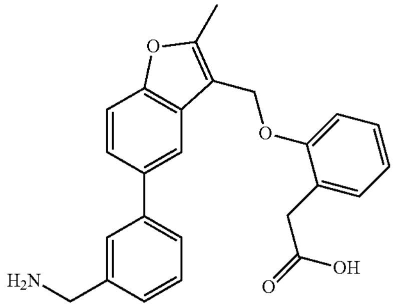
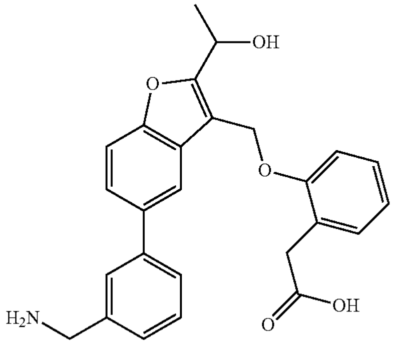
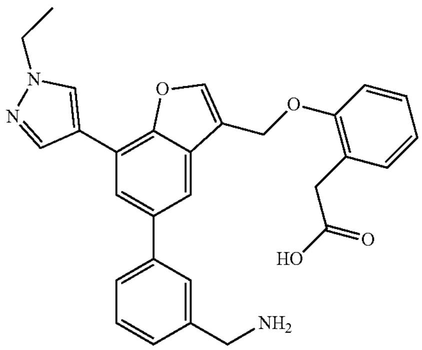
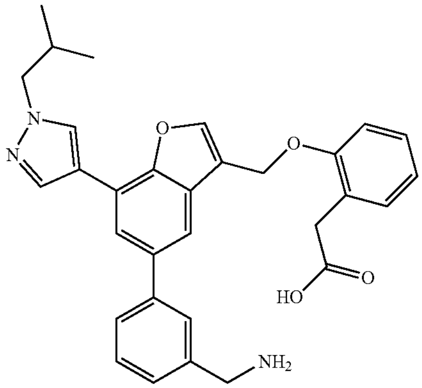
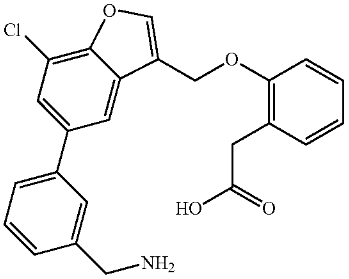
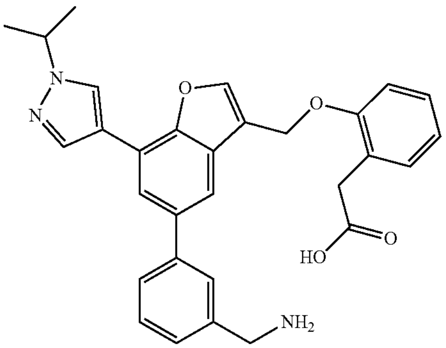

-continued
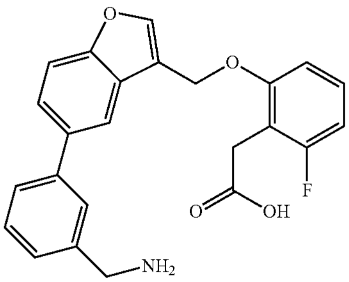
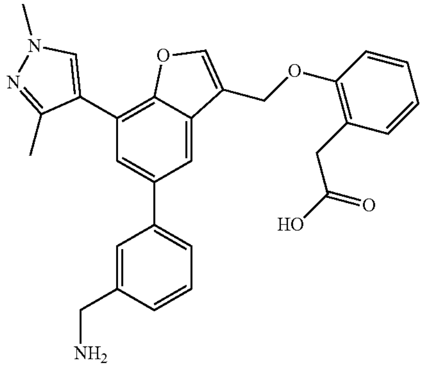
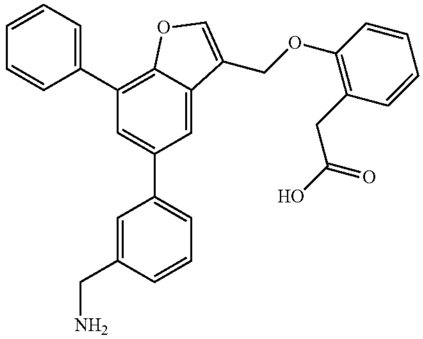
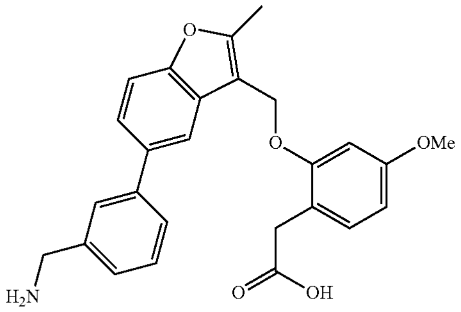
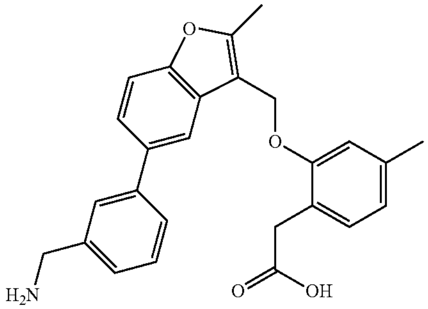
-continued
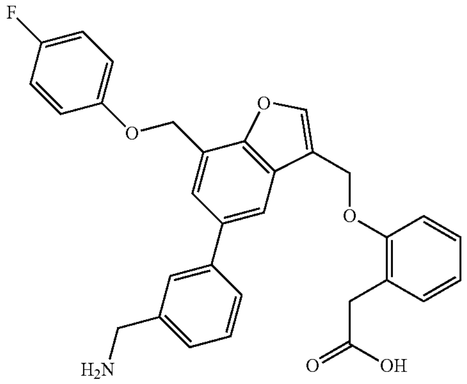
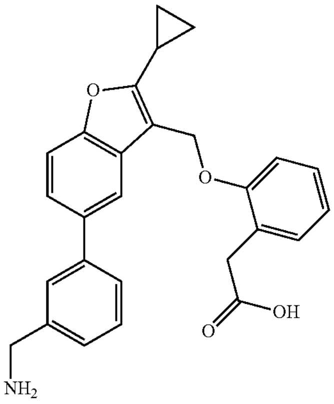
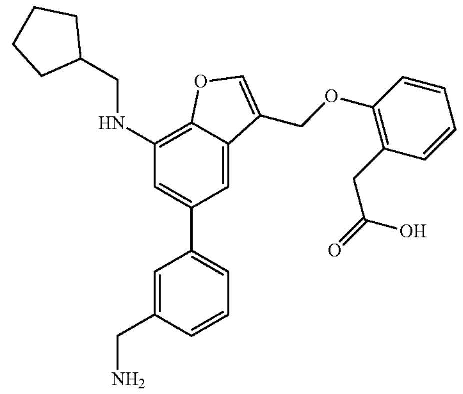
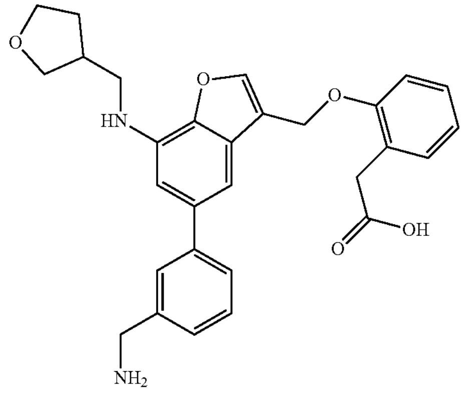

-continued
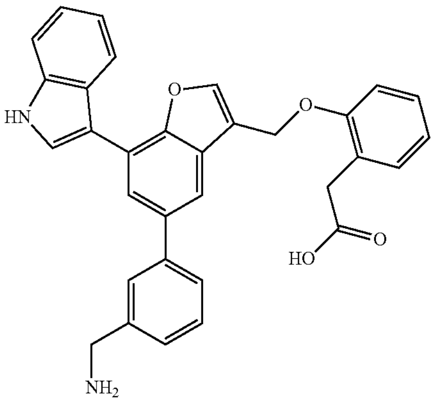
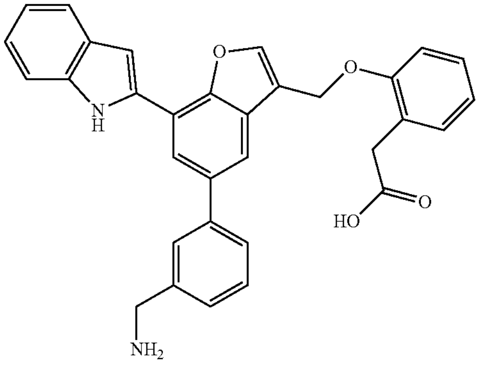
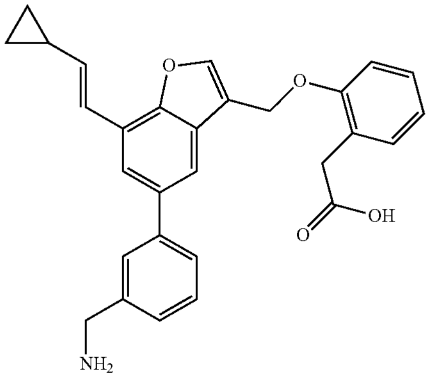
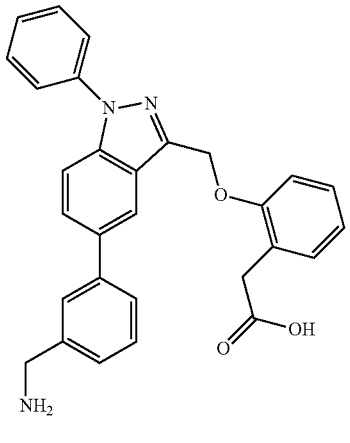
-continued
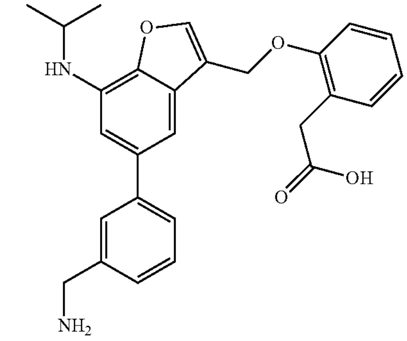
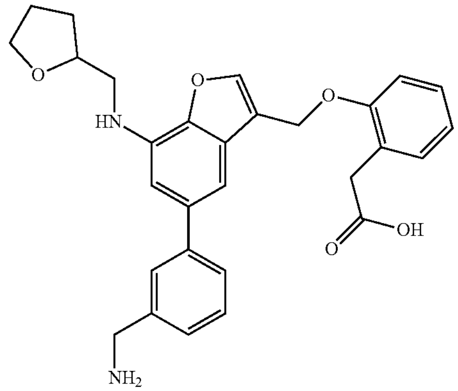
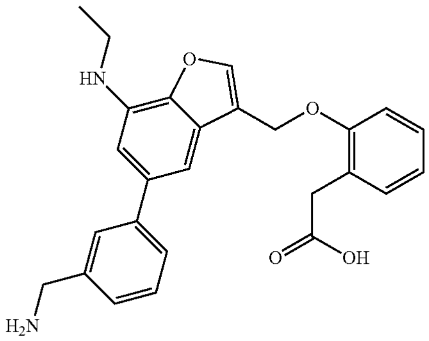
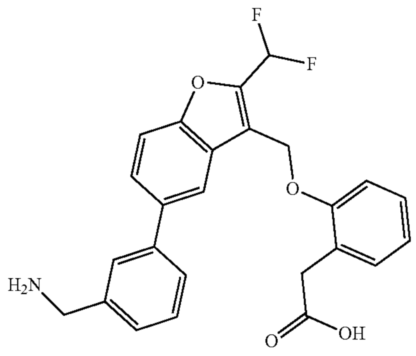

-continued
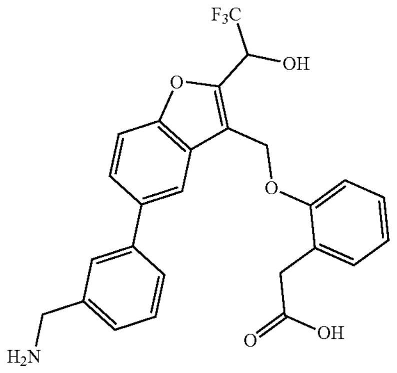
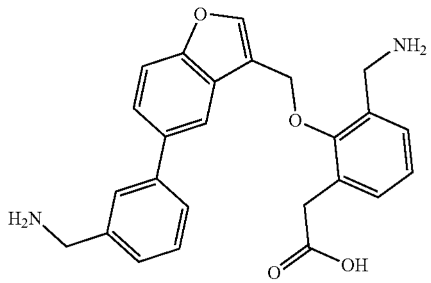
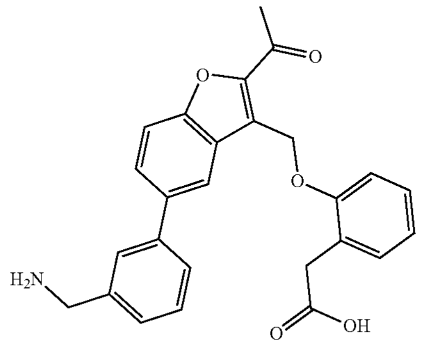
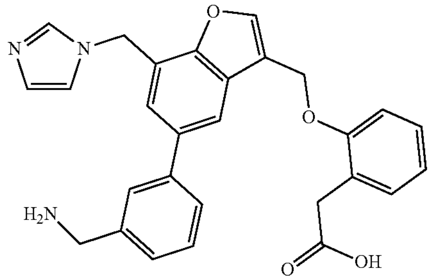
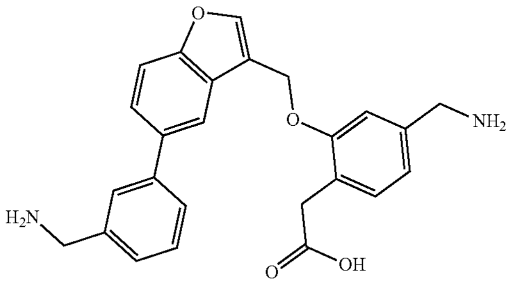
-continued
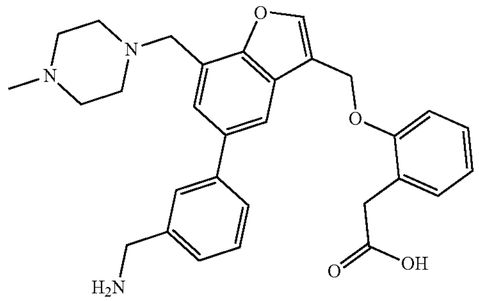
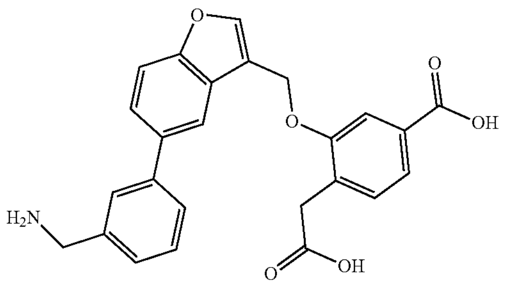
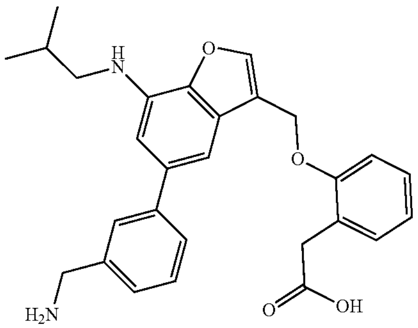
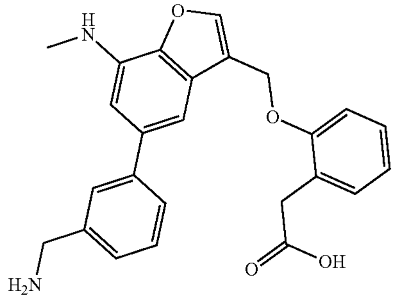
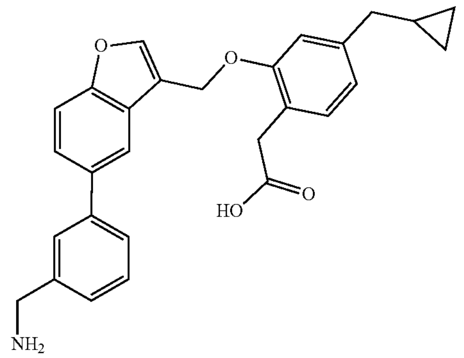

-continued
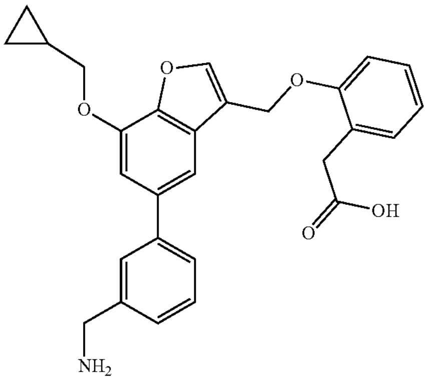
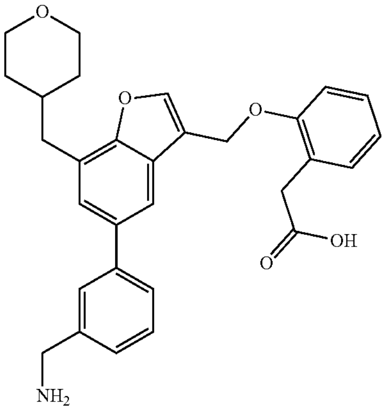
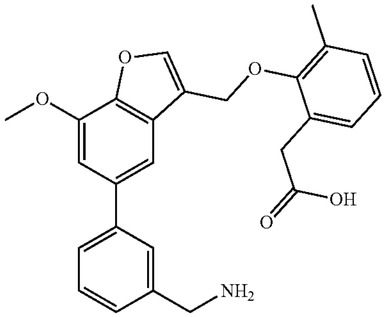
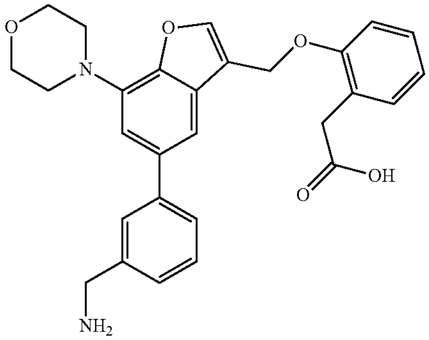
-continued
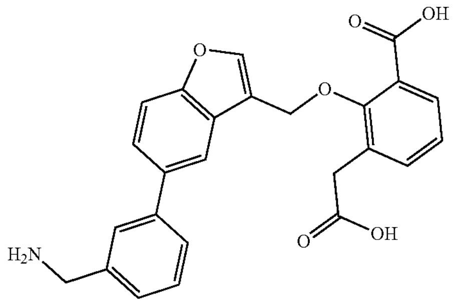
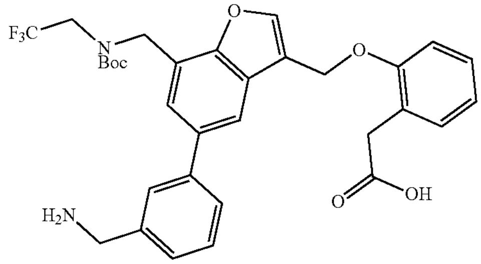
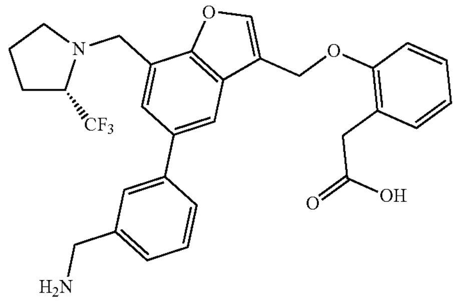
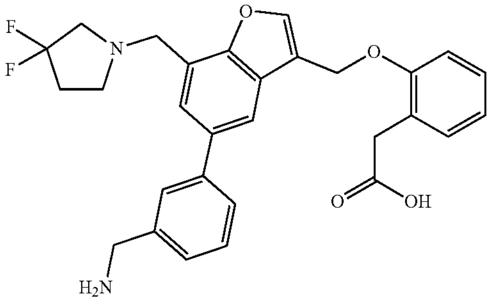
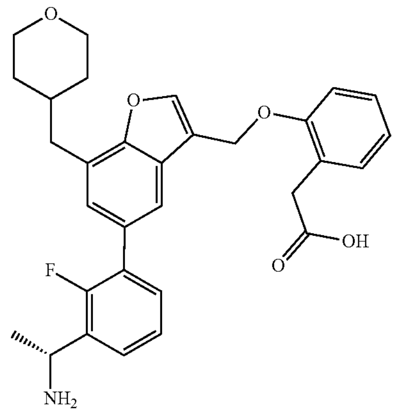

-continued
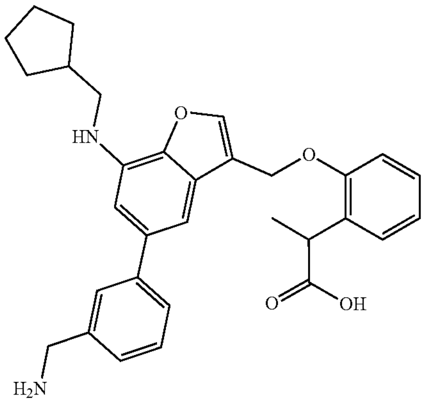
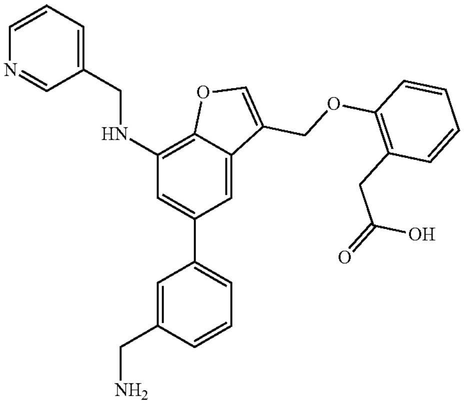
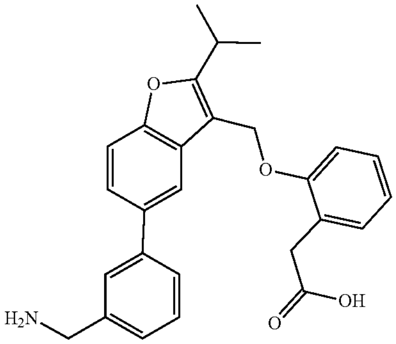
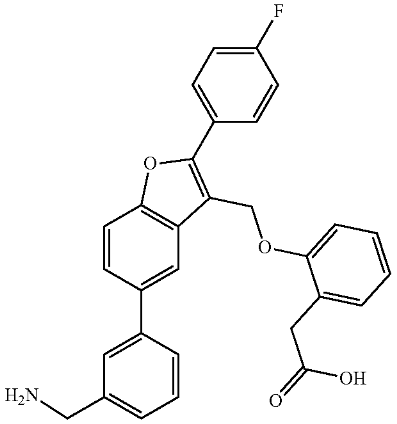
-continued
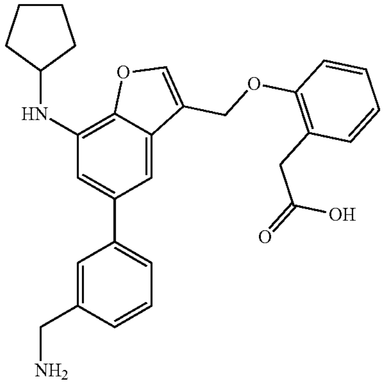
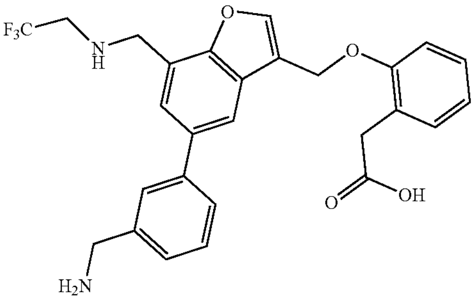
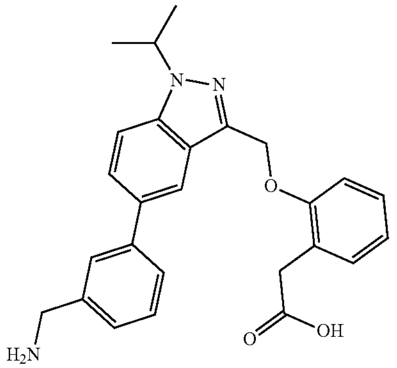
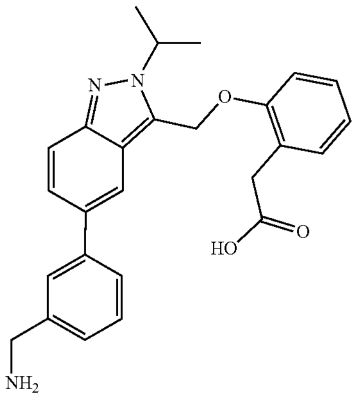

-continued
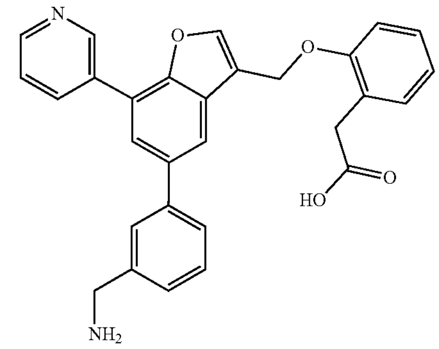
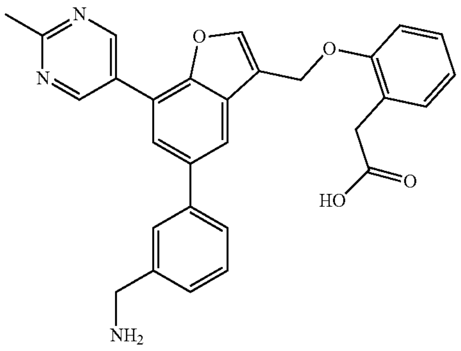
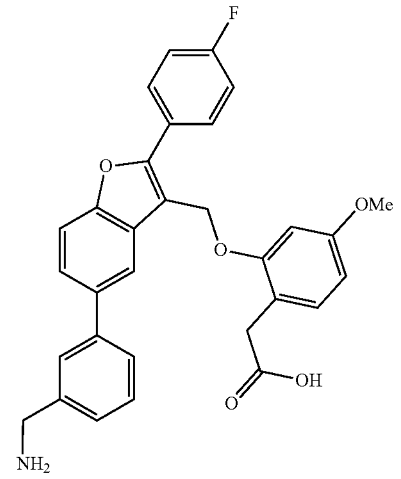
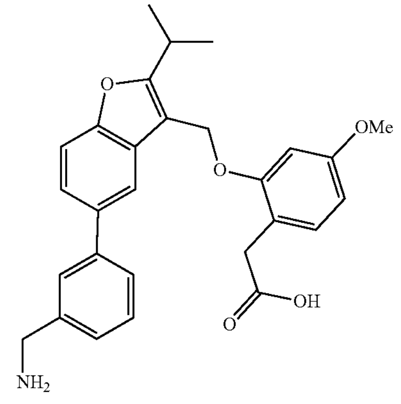
-continued
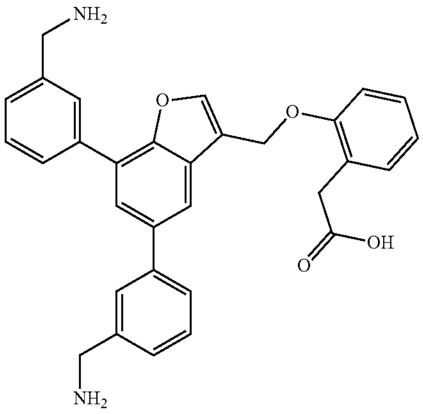
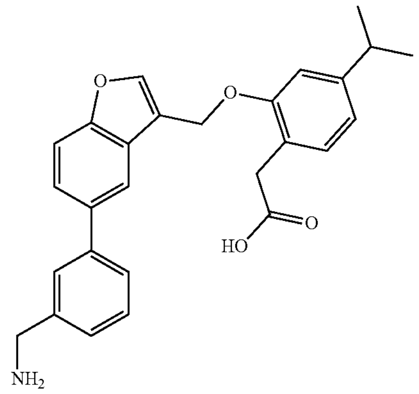
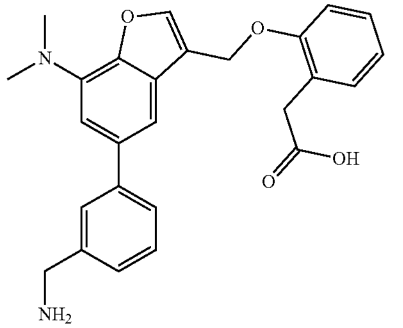
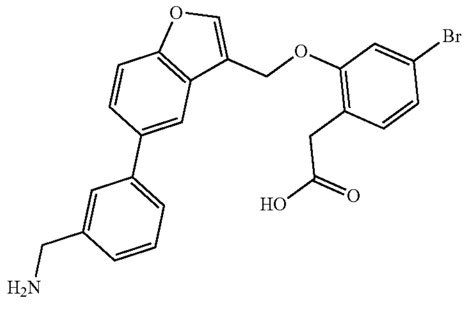

-continued
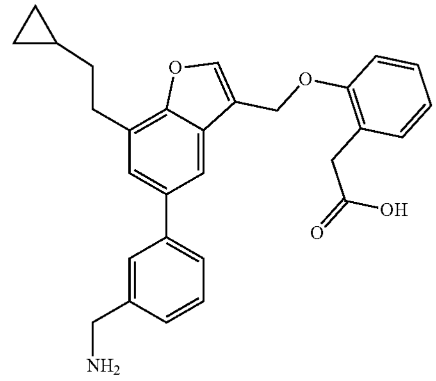
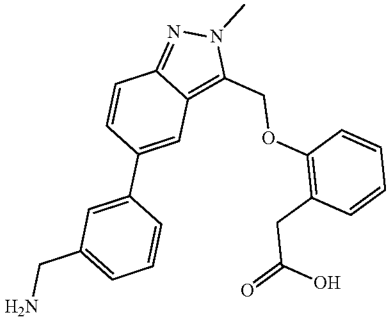
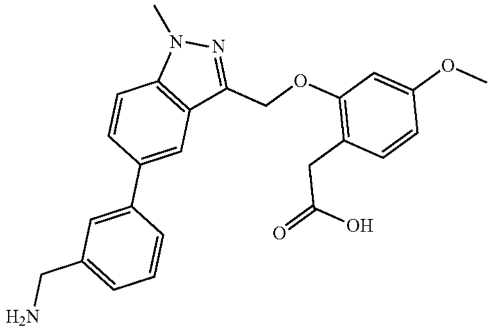
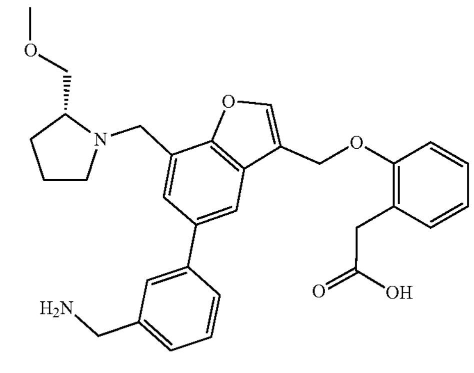
-continued
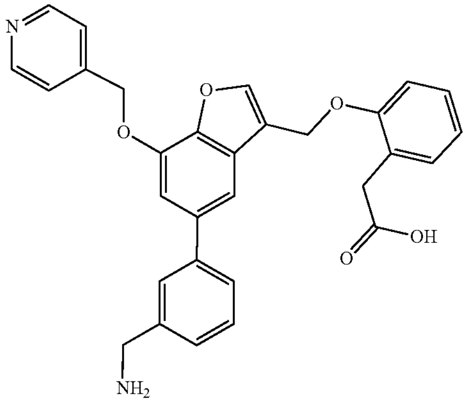
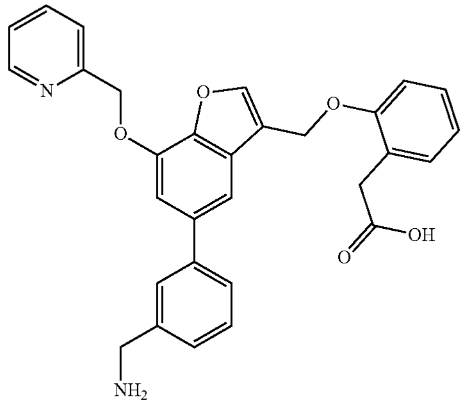
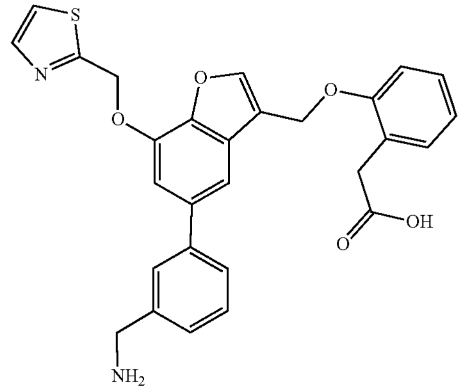
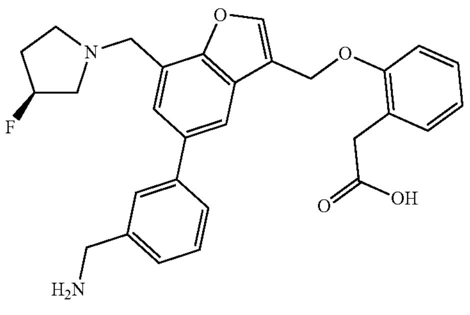

-continued
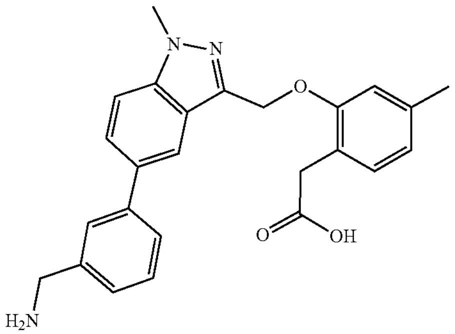
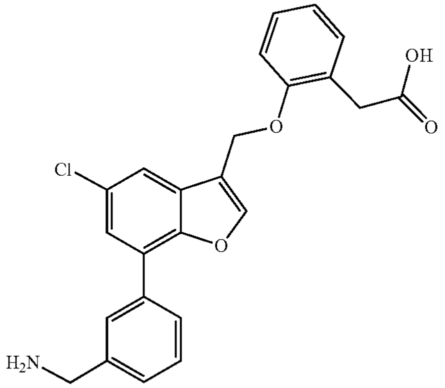
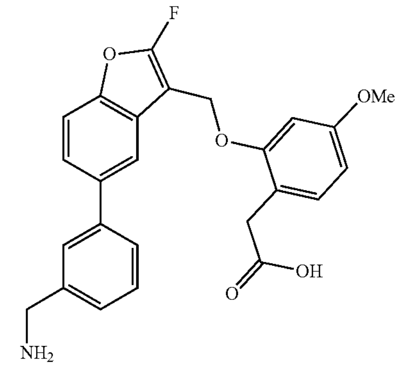
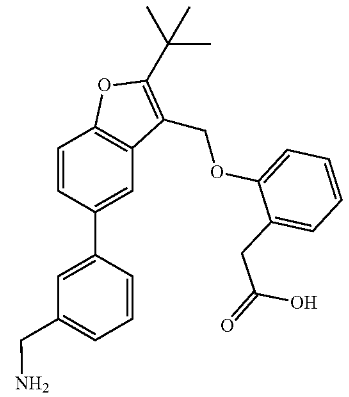
-continued
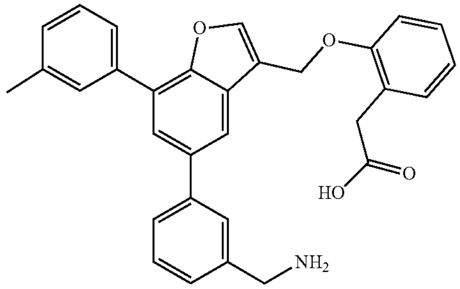
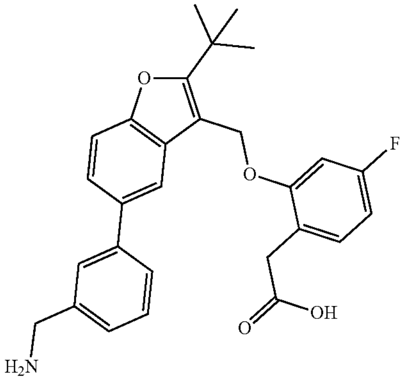
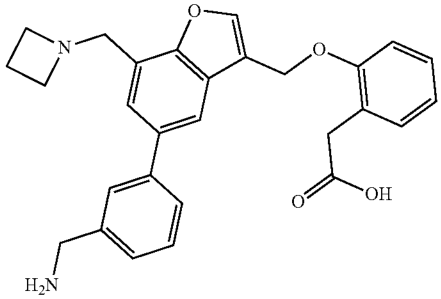
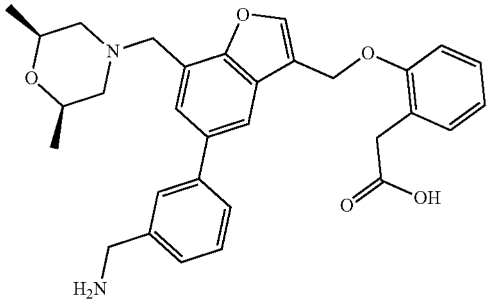
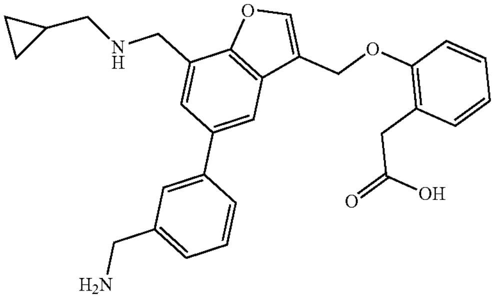

-continued
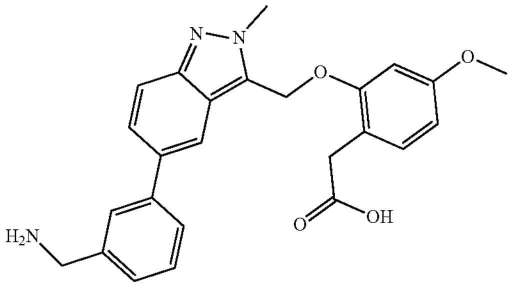
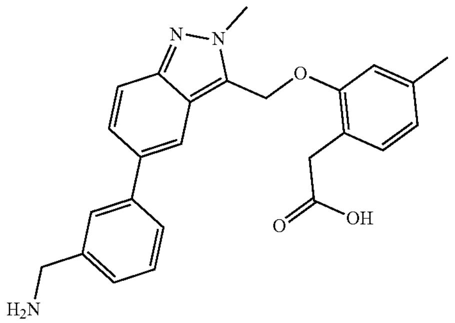
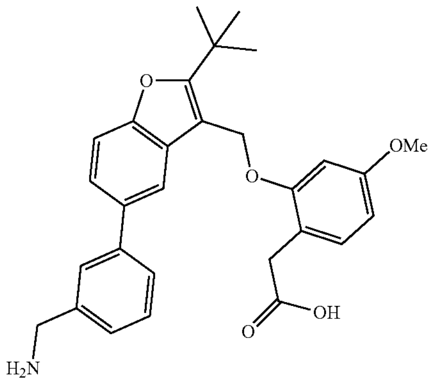
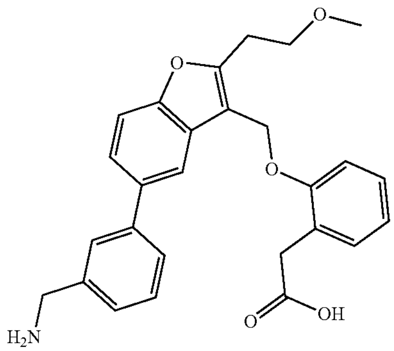
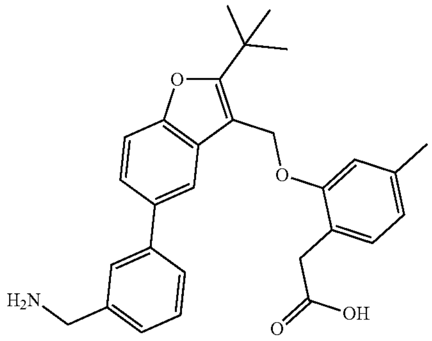
-continued
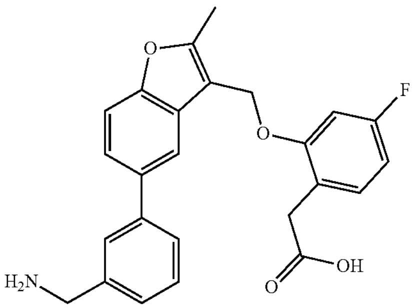
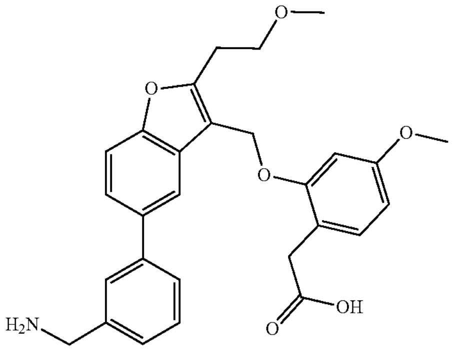
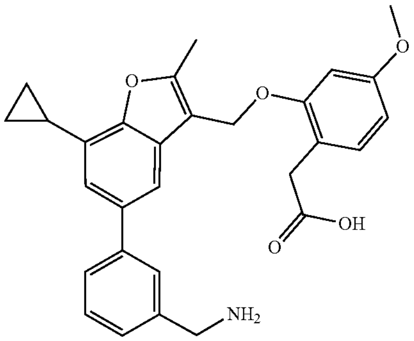
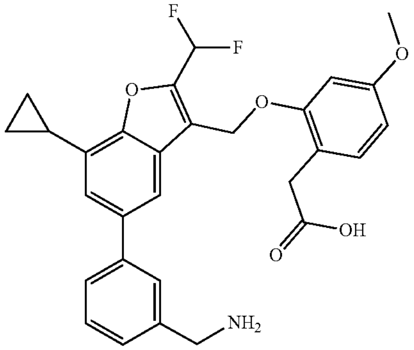
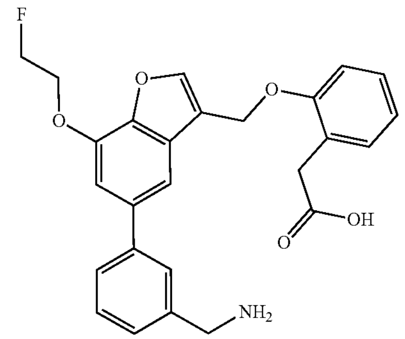

-continued
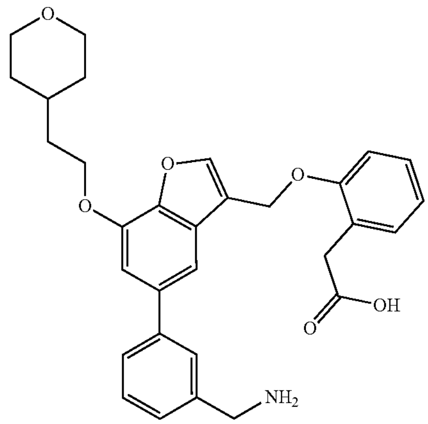
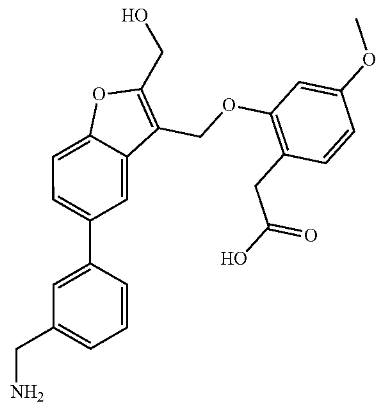
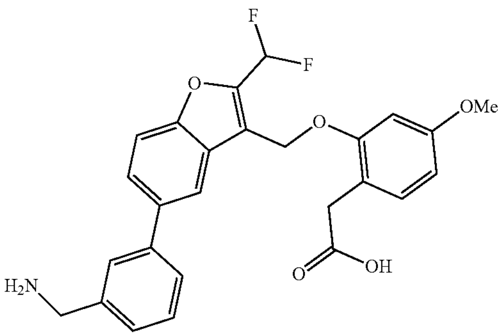
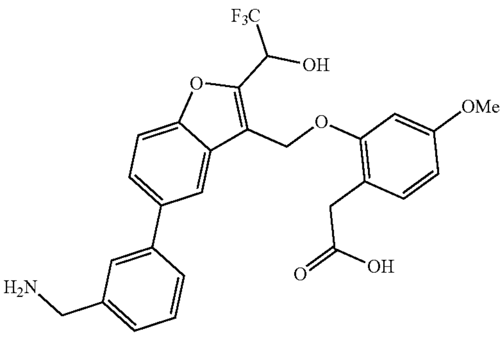
-continued
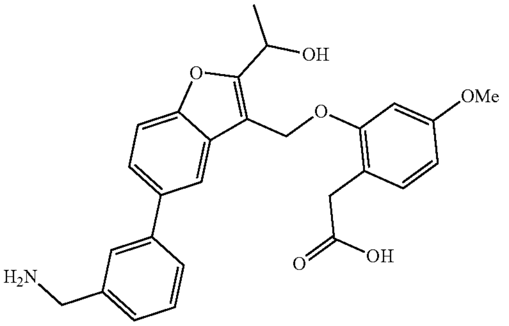
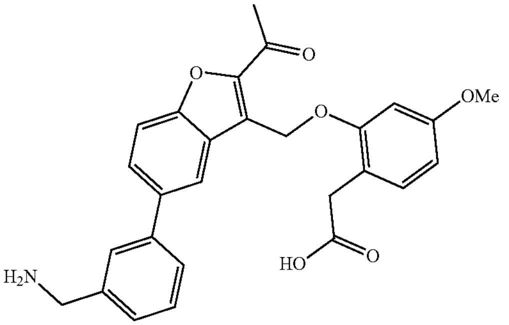
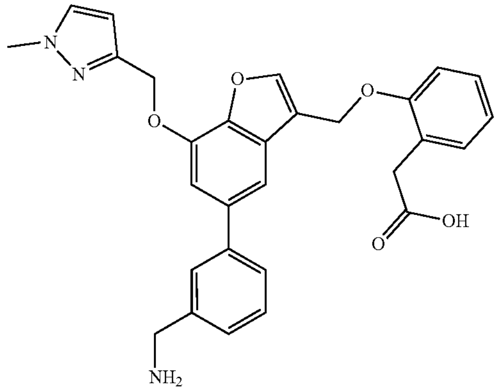
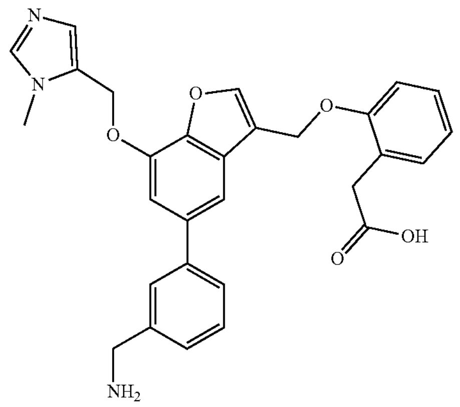

-continued
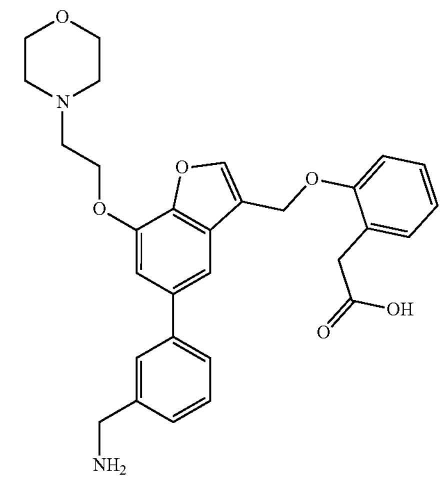
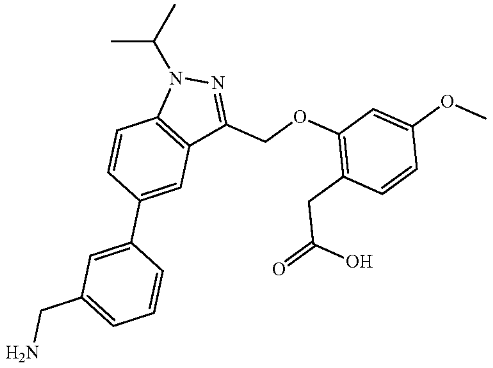
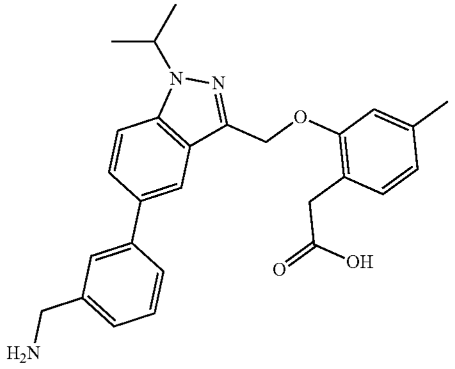
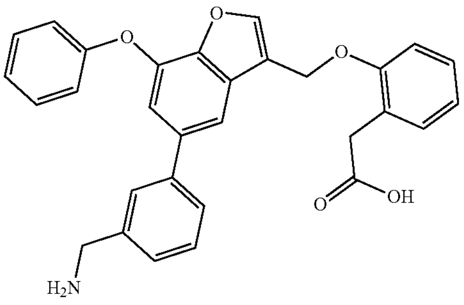
-continued
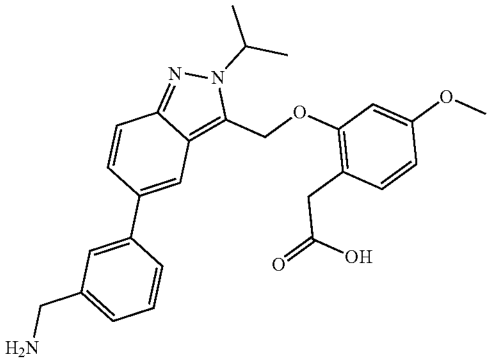
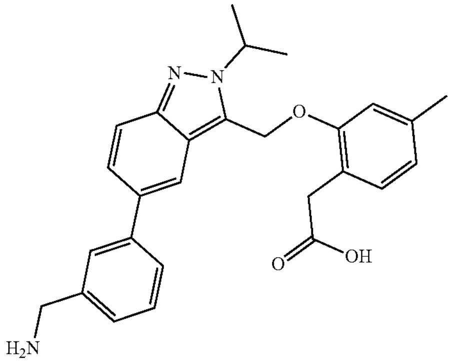
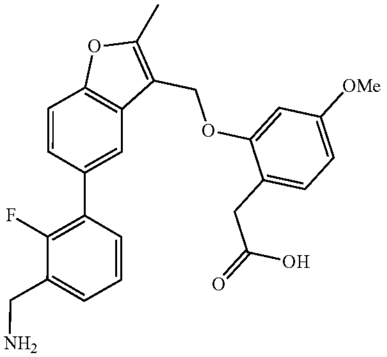
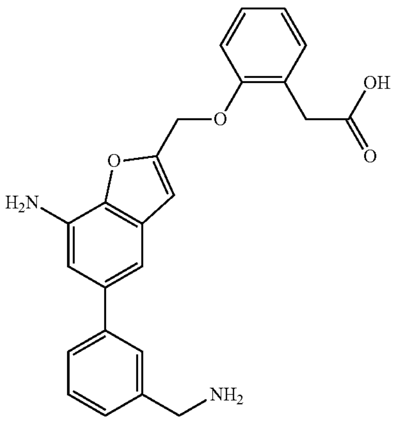

-continued
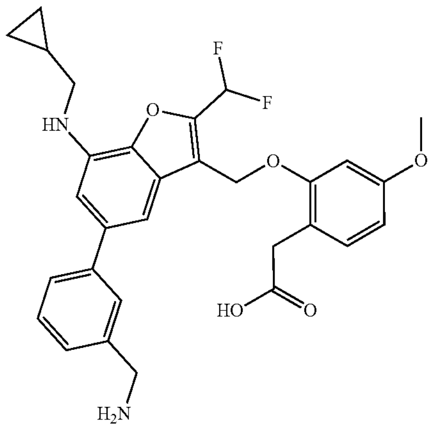
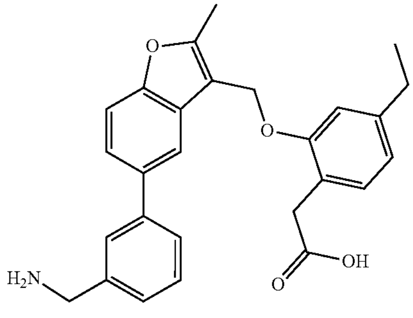
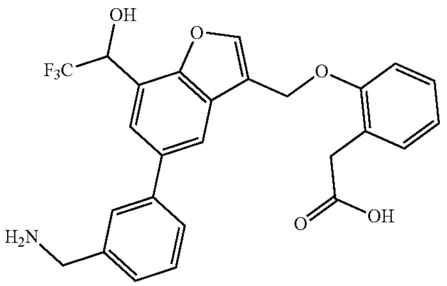
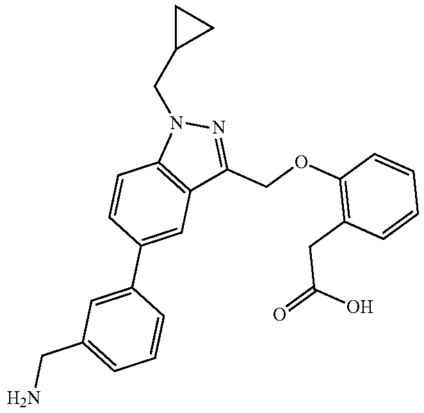
-continued
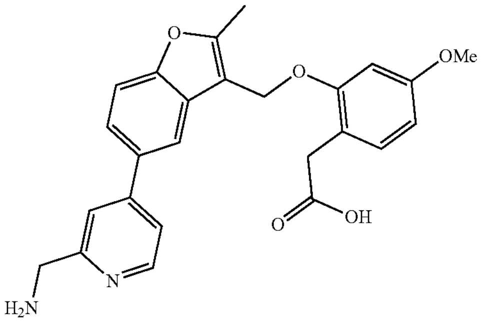
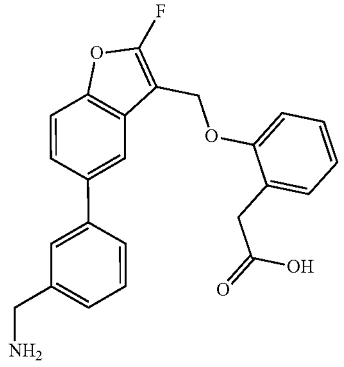
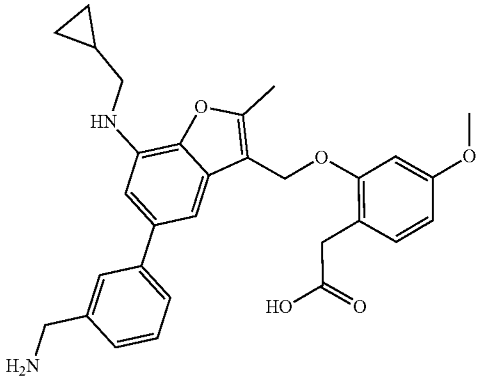
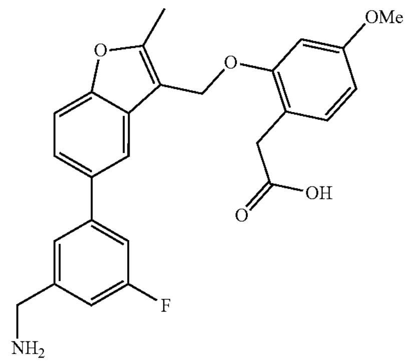

-continued
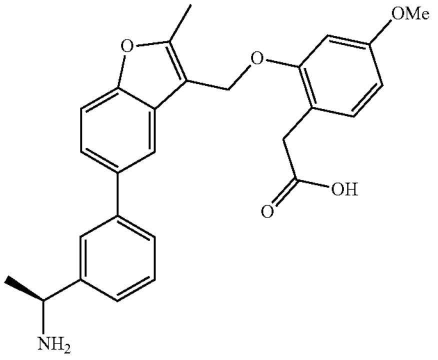
(+)-isomer
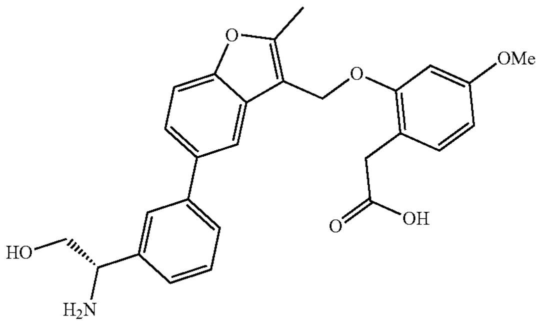
(+)-isomer
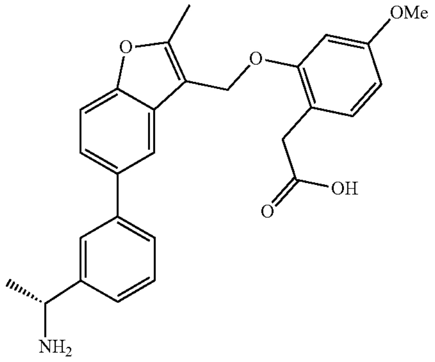
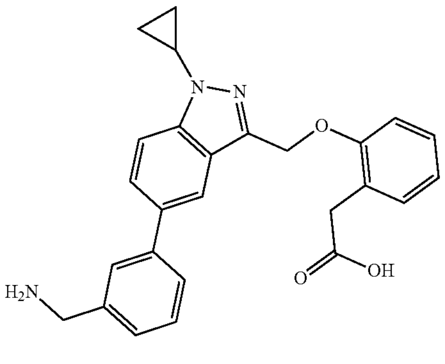
-continued
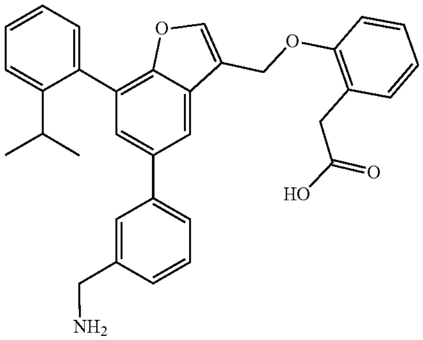
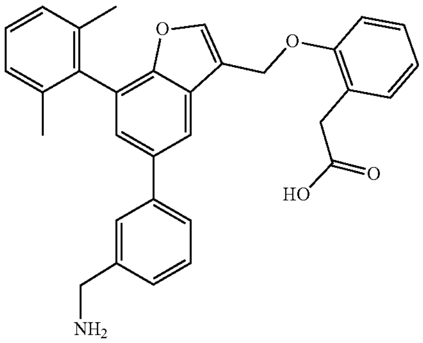
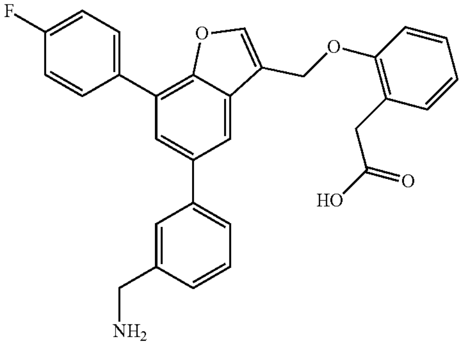
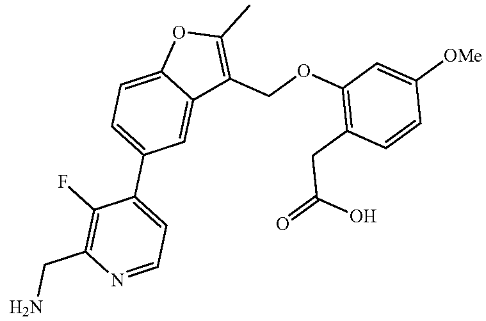

-continued
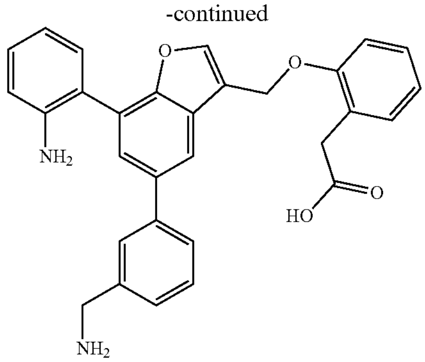
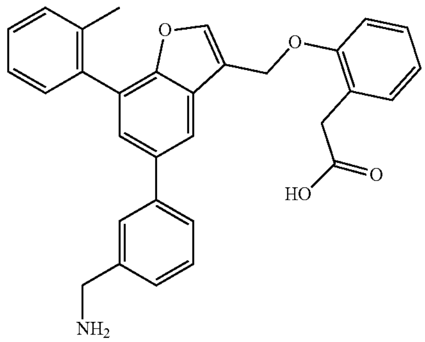
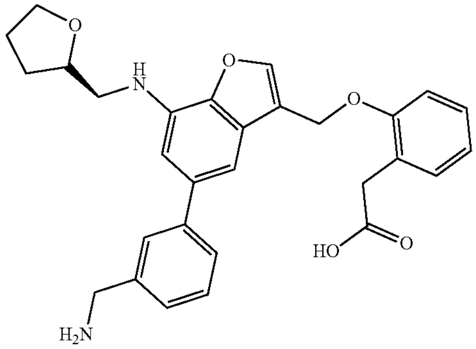
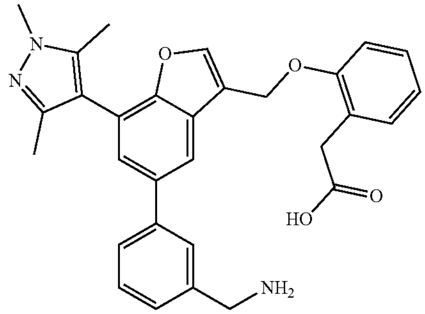
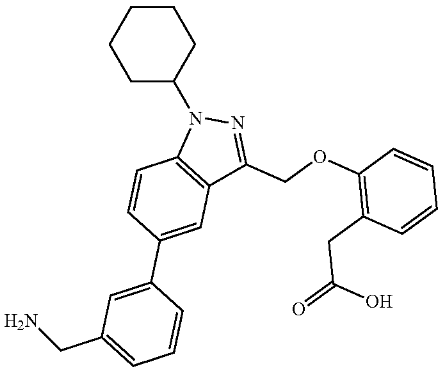
-continued
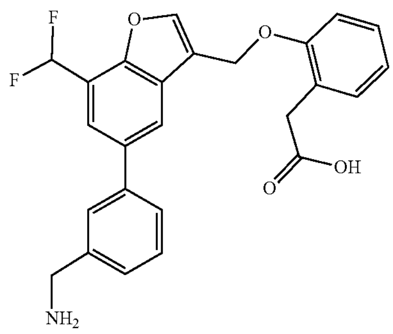
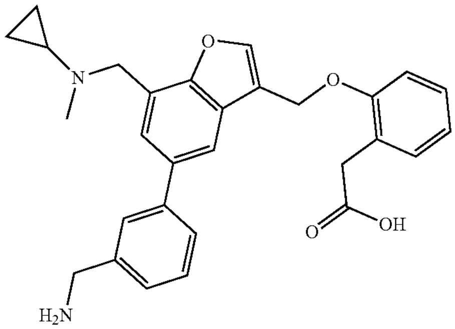
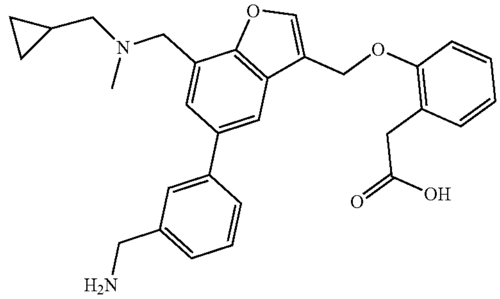
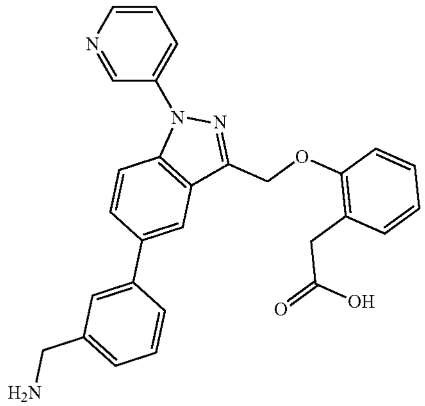

-continued
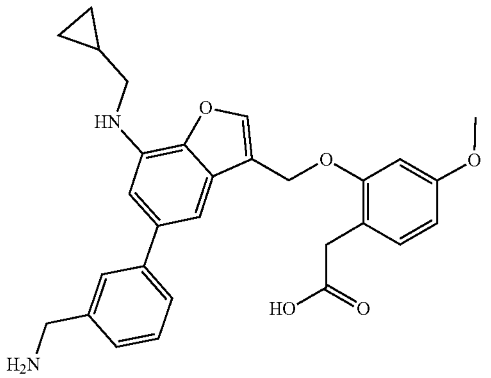
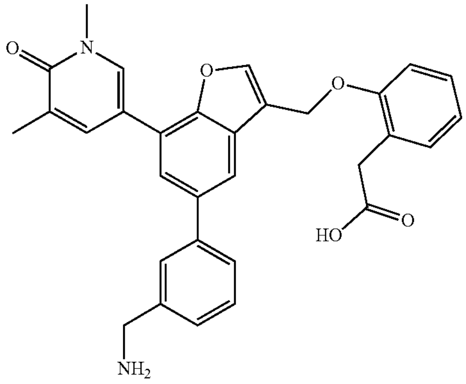
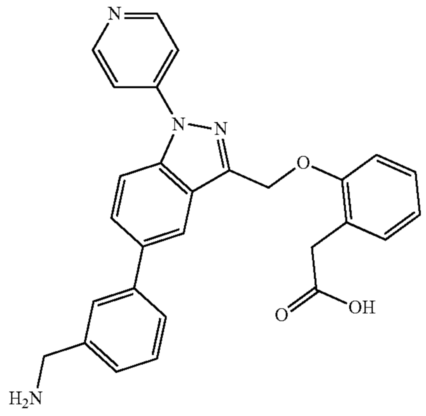
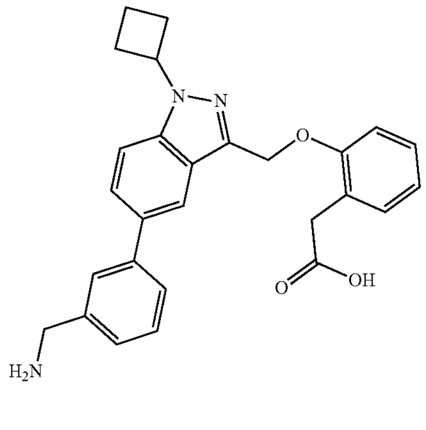
-continued
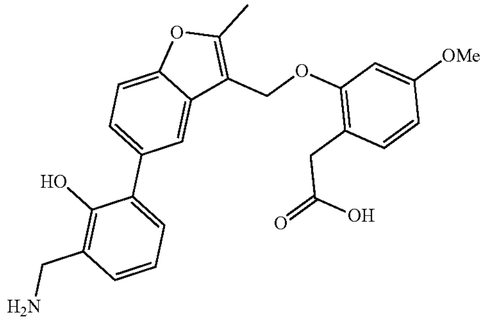
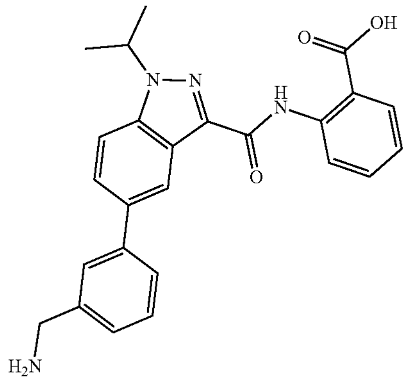
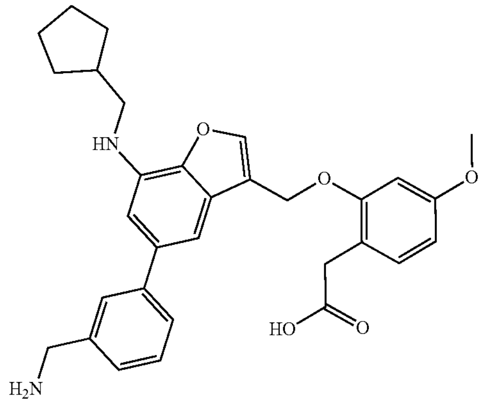
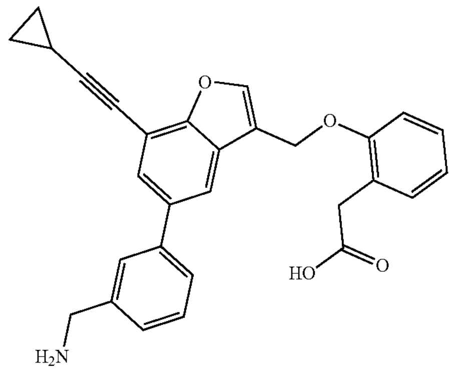

-continued
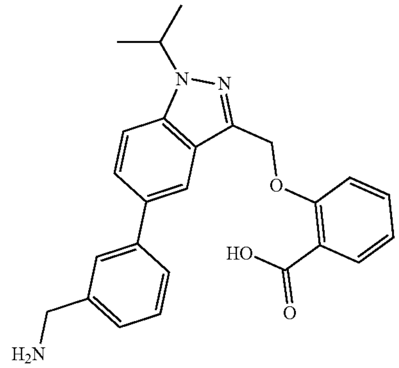
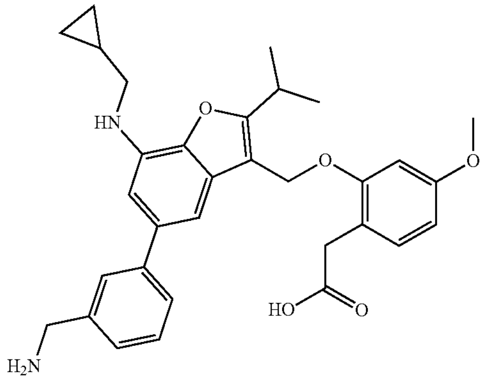
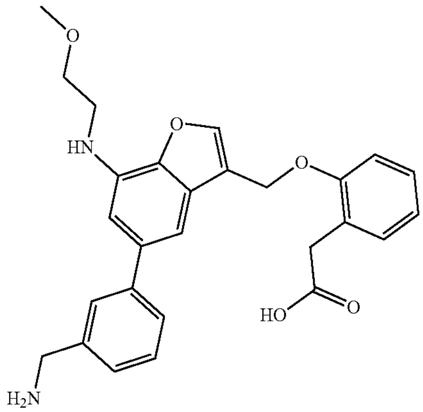 [SMILES: COCCNc1cc(-c2cccc(CN)c2)cc2c(COc3ccccc3CC(=O)O)coc12]
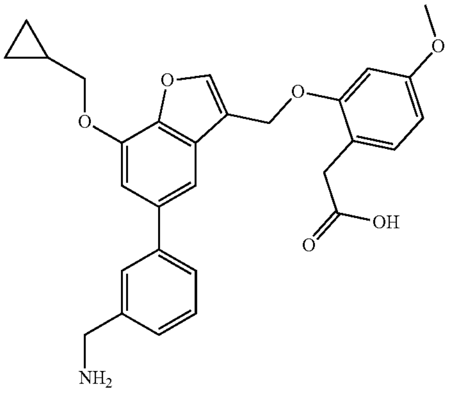
-continued
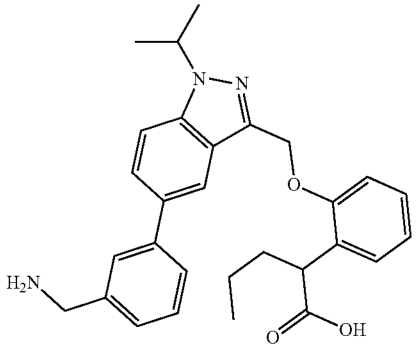
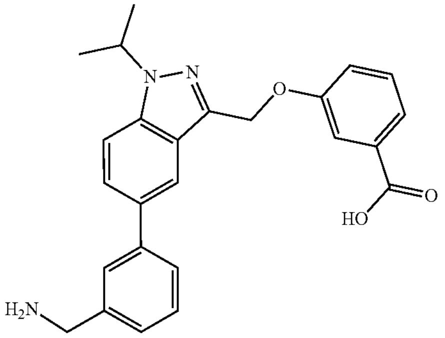
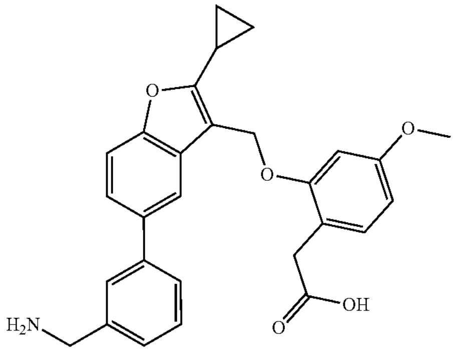
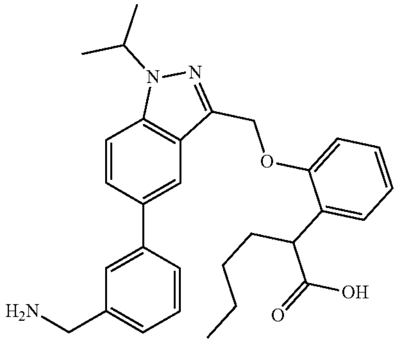
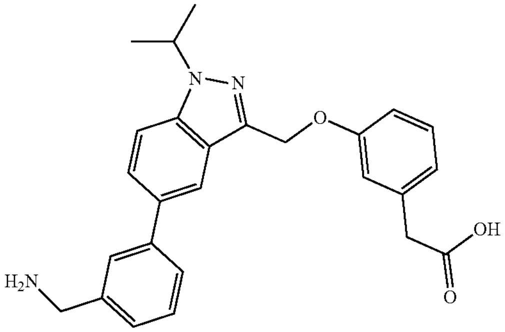

-continued
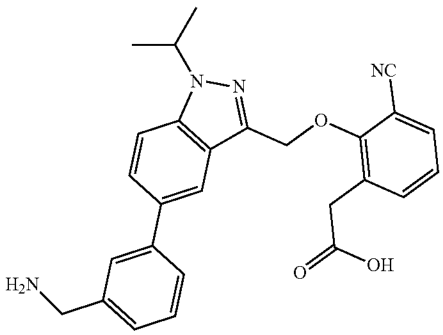
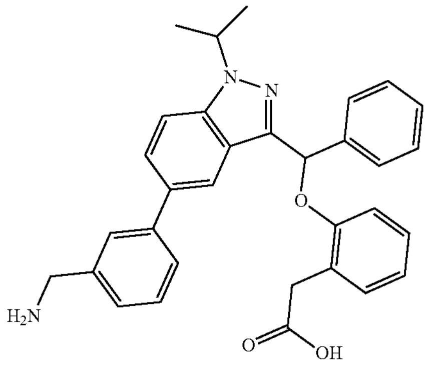
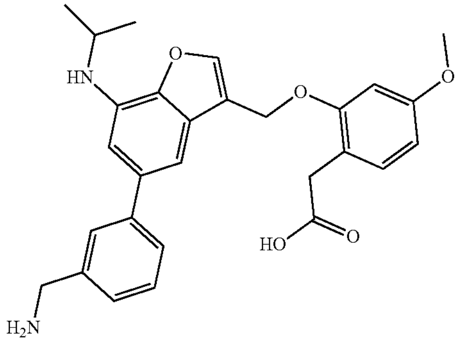
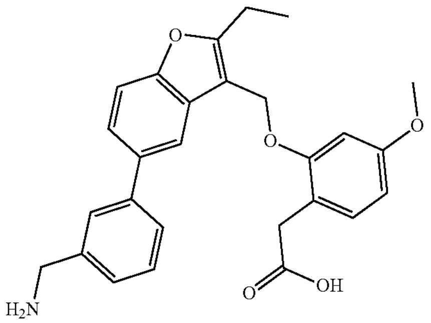
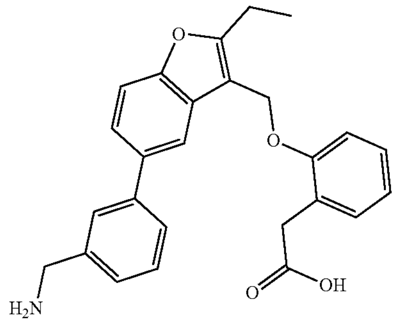
-continued
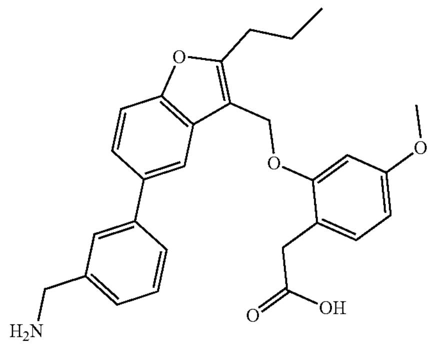
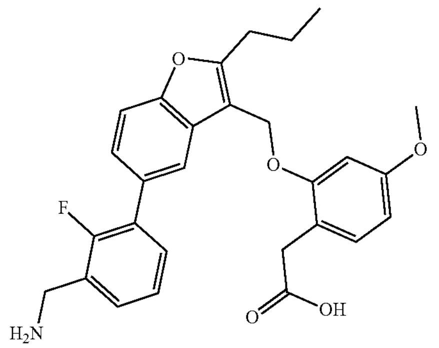
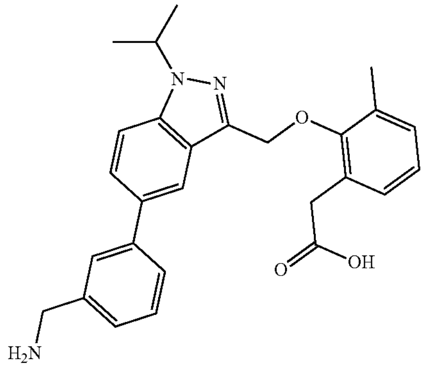
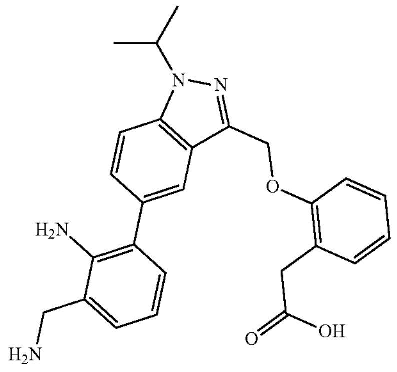

-continued
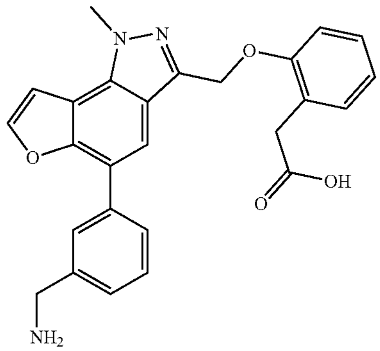
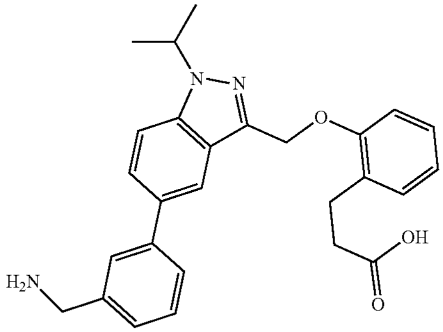
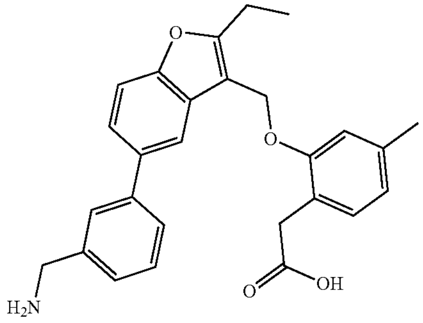
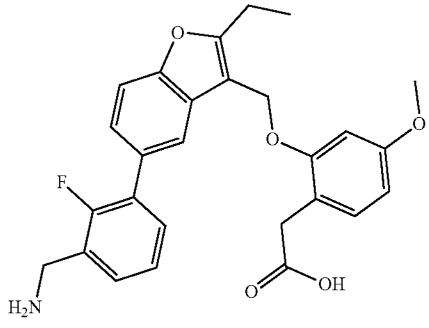
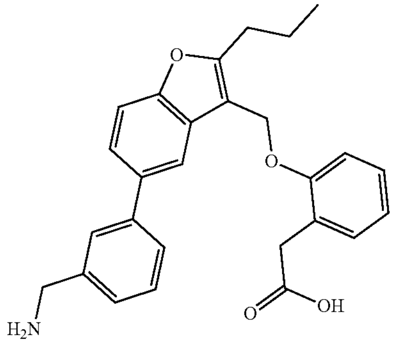
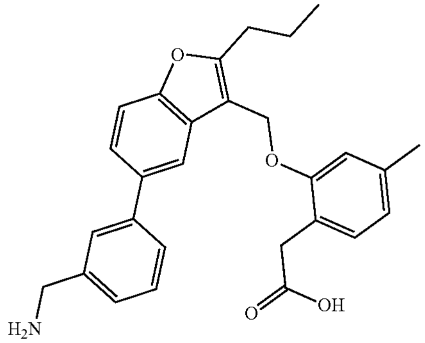
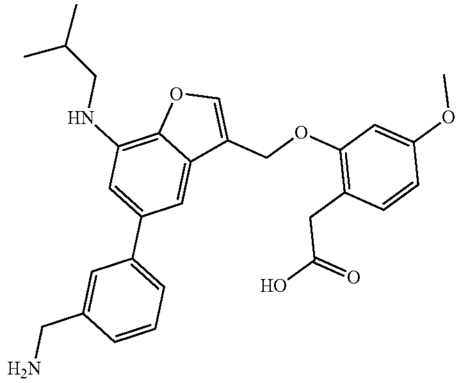
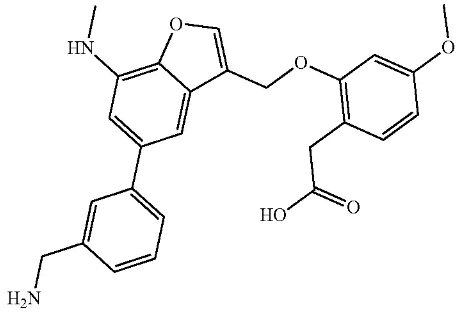
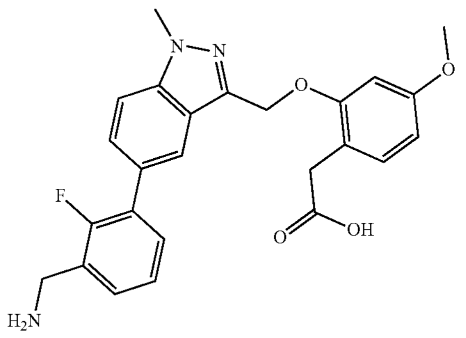

-continued
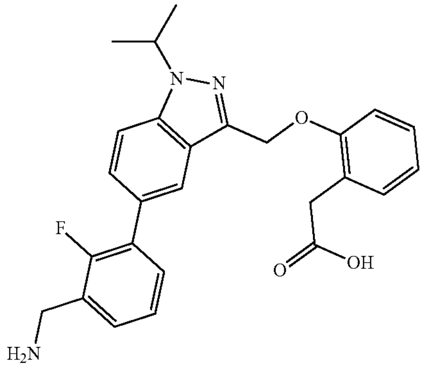
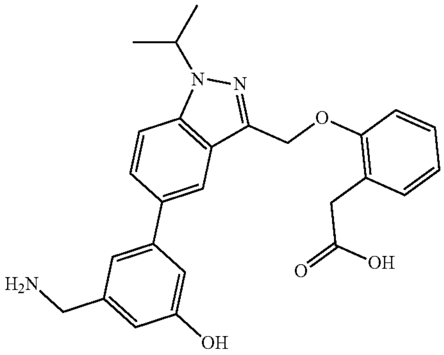
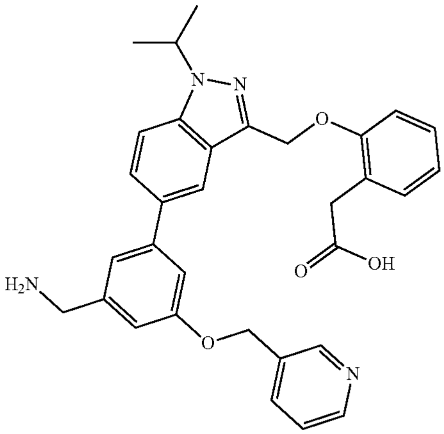
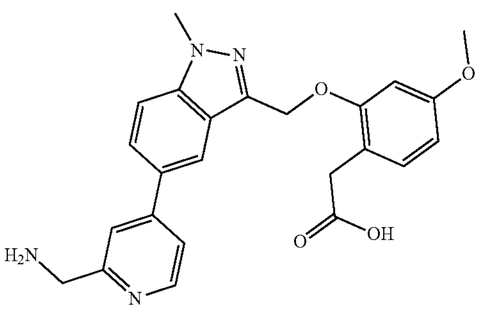
-continued
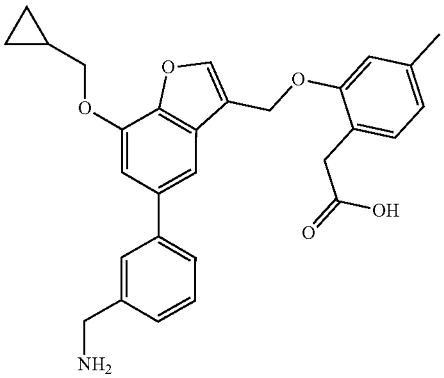
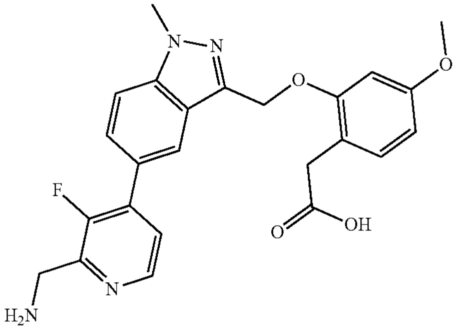
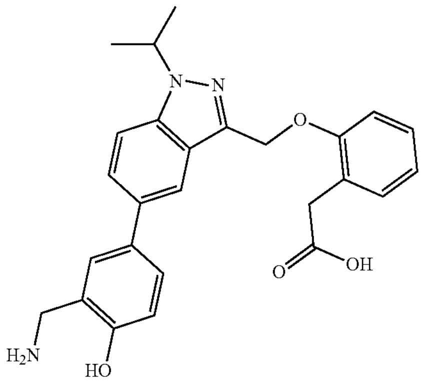
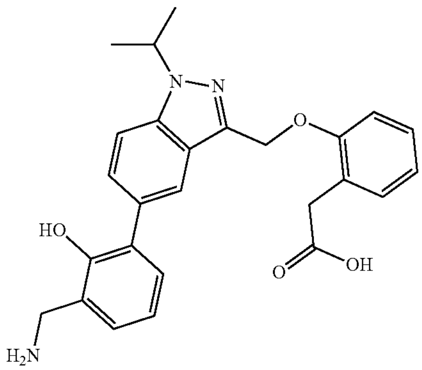

-continued
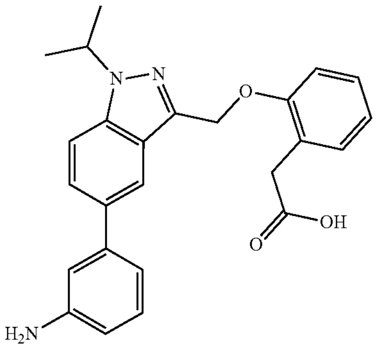
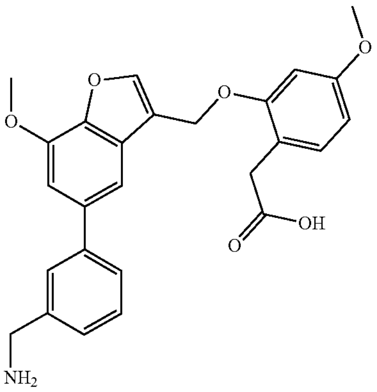
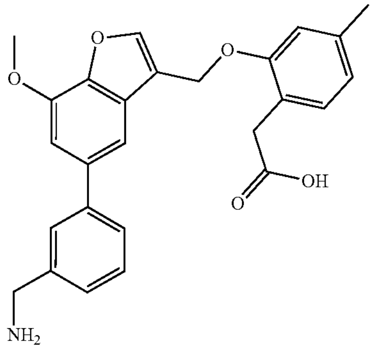
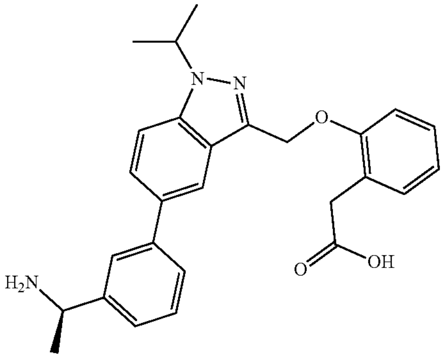
-continued
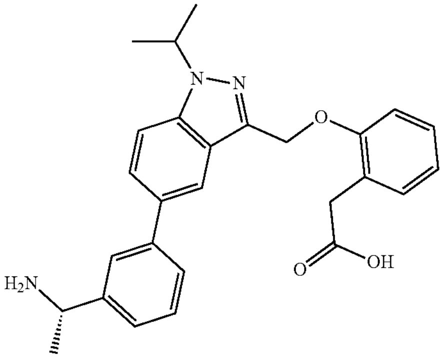
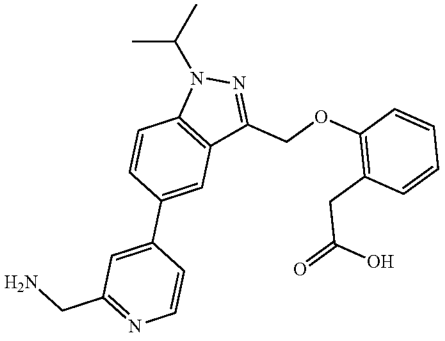
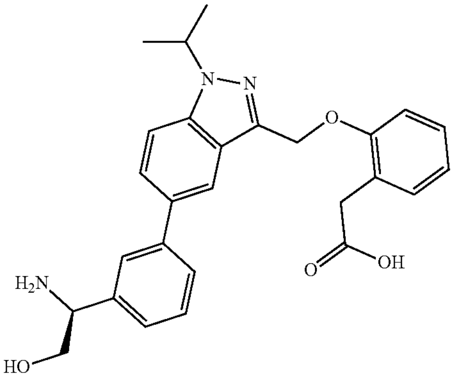
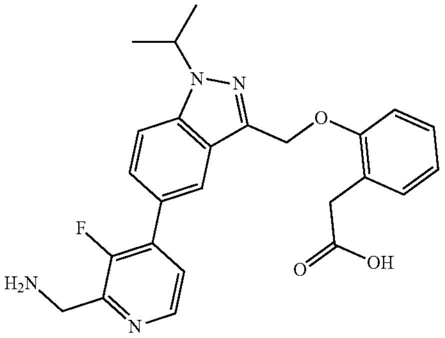
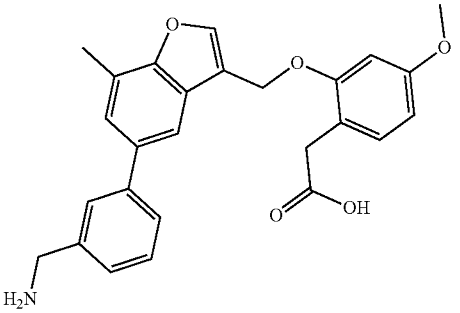

-continued
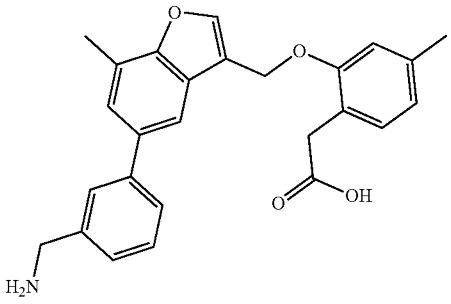
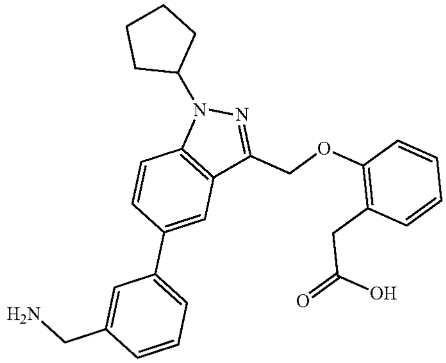
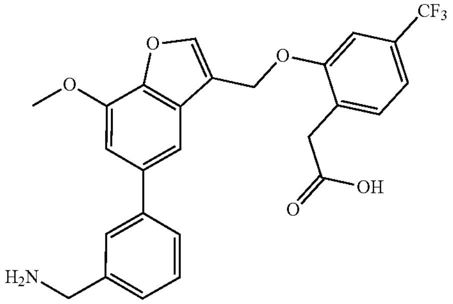
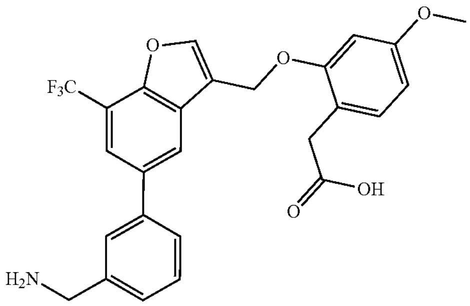
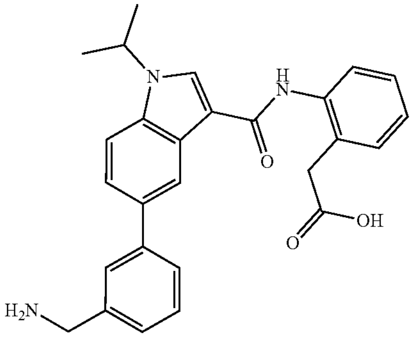
-continued
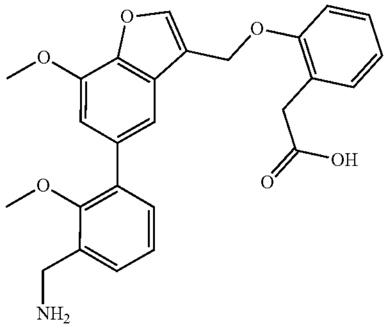
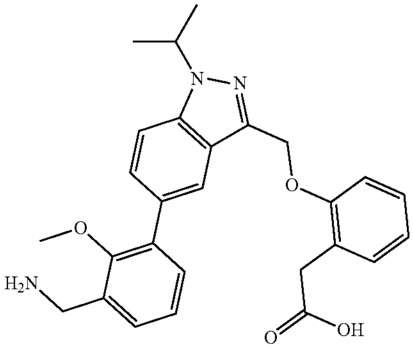
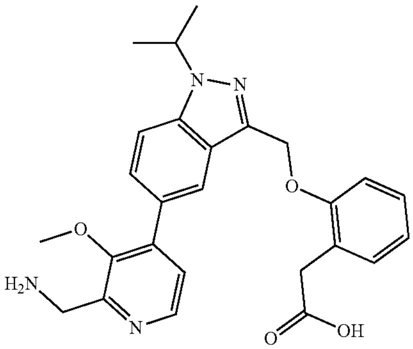
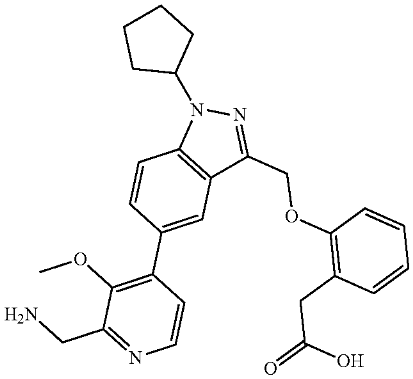

-continued

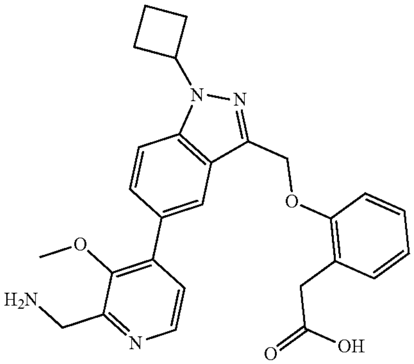

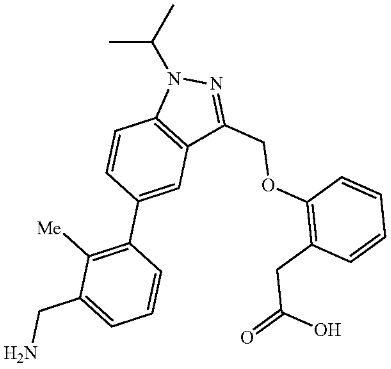

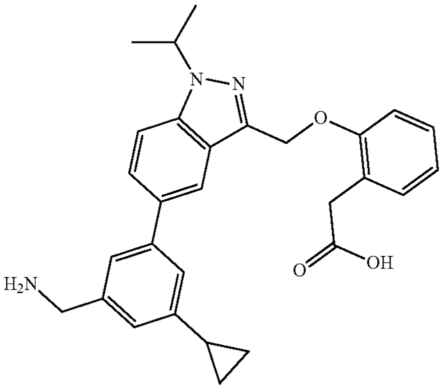

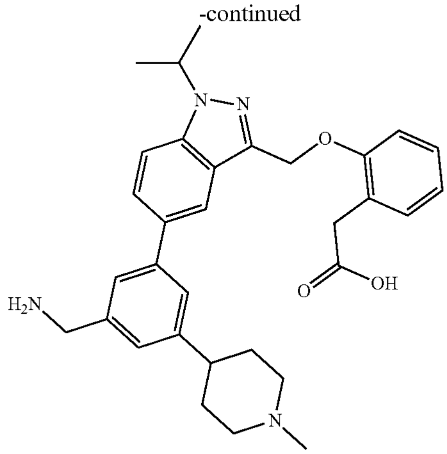

and

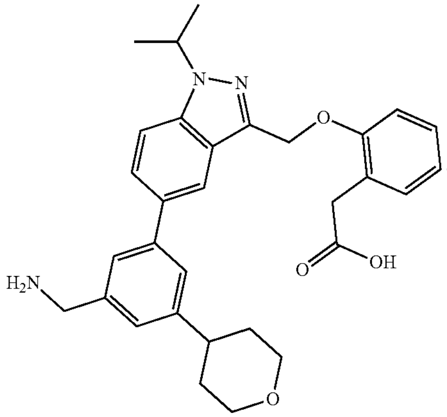

.

26. A pharmaceutical composition, comprising a compound of claim 1, or a pharmaceutically acceptable salt thereof; and a pharmaceutically acceptable carrier.

27. A method of treating or preventing a disease or condition characterized by aberrant complement system activity, comprising administering to a subject in need thereof a therapeutically effective amount of a compound of claim 1, or a pharmaceutically acceptable salt thereof.

28. The compound of claim 1, wherein $R^C$ represents F.

* * * * *